US008415469B2

(12) United States Patent
Ibrahim et al.

(10) Patent No.: US 8,415,469 B2
(45) Date of Patent: Apr. 9, 2013

(54) COMPOUNDS AND METHODS FOR KINASE MODULATION, AND INDICATIONS THEREFOR

(75) Inventors: Prabha N. Ibrahim, Mountain View, CA (US); Dean R. Artis, Kensington, CA (US); Ryan Bremer, Oakland, CA (US); Gaston Habets, Pleasant Hill, CA (US); Shumeye Mamo, Oakland, CA (US); Marika Nespi, Berkeley, CA (US); Chao Zhang, Moraga, CA (US); Jiazhong Zhang, Foster City, CA (US); Yong-Liang Zhu, Fremont, CA (US); Rebecca Zuckerman, Alameda, CA (US); Brian West, San Francisco, CA (US); Yoshisa Suzuki, El Sobrante, CA (US); Jianming Tsai, Vallejo, CA (US); Klaus-Peter Hirth, San Francisco, CA (US); Gideon Bollag, Orinda, CA (US); Wayne Spevak, Berkeley, CA (US); Hanna Cho, Oakland, CA (US); Samuel J. Gillette, Oakland, CA (US); Guoxian Wu, Palo Alto, CA (US); Hongyao Zhu, Berkeley, CA (US); Shenghua Shi, San Diego, CA (US)

(73) Assignee: Plexxikon Inc., Berkeley, CA (US)

( * ) Notice: Subject to any disclaimer, the term of this patent is extended or adjusted under 35 U.S.C. 154(b) by 420 days.

(21) Appl. No.: 12/616,079

(22) Filed: Nov. 10, 2009

(65) Prior Publication Data

US 2010/0256365 A1 Oct. 7, 2010

Related U.S. Application Data

(62) Division of application No. 11/473,347, filed on Jun. 21, 2006, now Pat. No. 7,863,288.

(60) Provisional application No. 60/692,960, filed on Jun. 22, 2005, provisional application No. 60/731,528, filed on Oct. 28, 2005.

(51) Int. Cl.
*C07D 413/14* (2006.01)
*C07D 401/14* (2006.01)
*C07D 471/04* (2006.01)
*C07F 7/02* (2006.01)

(52) U.S. Cl. ......... 544/127; 544/362; 546/14; 546/113
(58) Field of Classification Search .............. 546/14, 546/113; 544/127, 362
See application file for complete search history.

(56) References Cited

U.S. PATENT DOCUMENTS

| 2,234,705 | A | | 3/1941 | Normington et al. |
|---|---|---|---|---|
| 2,413,258 | A | | 12/1946 | Soday et al. |
| 4,150,949 | A | | 4/1979 | Smith |
| 4,301,159 | A | * | 11/1981 | Ogata et al. ............... 514/166 |
| 4,439,444 | A | * | 3/1984 | Nisato et al. .............. 514/444 |
| 4,568,649 | A | | 2/1986 | Bertoglio-Matte |
| 4,595,780 | A | * | 6/1986 | Ogata et al. ................ 564/79 |
| 4,626,513 | A | | 12/1986 | Burton et al. |
| 4,634,701 | A | | 1/1987 | De Vincentiis |
| 4,714,693 | A | | 12/1987 | Targos |
| 4,727,395 | A | | 2/1988 | Oda et al. |
| 5,120,782 | A | | 6/1992 | Hubsch et al. |
| 5,143,854 | A | | 9/1992 | Pirrung et al. |
| 5,338,849 | A | | 8/1994 | Festal et al. |
| 5,360,822 | A | * | 11/1994 | Morino et al. ............. 514/605 |
| 5,426,039 | A | | 6/1995 | Wallace et al. |
| 5,432,177 | A | | 7/1995 | Baker et al. |
| 5,434,049 | A | | 7/1995 | Okano et al. |
| 5,449,614 | A | | 9/1995 | Danos et al. |
| 5,474,935 | A | | 12/1995 | Chatterjee et al. |
| 5,486,525 | A | | 1/1996 | Summers et al. |
| 5,556,752 | A | | 9/1996 | Lockhart et al. |
| 5,576,319 | A | | 11/1996 | Baker et al. |
| 5,580,859 | A | | 12/1996 | Felgner et al. |
| 5,631,236 | A | | 5/1997 | Woo et al. |
| 5,632,957 | A | | 5/1997 | Heller et al. |
| 5,658,775 | A | | 8/1997 | Gilboa |
| 5,681,959 | A | | 10/1997 | Bishop et al. |
| 5,700,637 | A | | 12/1997 | Southern |
| 5,700,809 | A | | 12/1997 | Leeson et al. |
| 5,712,285 | A | | 1/1998 | Curtis et al. |
| 5,721,118 | A | | 2/1998 | Scheffler |
| 5,744,305 | A | | 4/1998 | Fodor et al. |
| 5,747,276 | A | | 5/1998 | Hoch et al. |
| 5,763,198 | A | | 6/1998 | Hirth et al. |
| 5,770,456 | A | | 6/1998 | Holmes |
| 5,800,992 | A | | 9/1998 | Fodor et al. |
| 5,807,522 | A | | 9/1998 | Brown et al. |
| 5,830,645 | A | | 11/1998 | Pinkel et al. |
| 5,840,485 | A | | 11/1998 | Lebl et al. |
| 5,856,174 | A | | 1/1999 | Lipshutz et al. |
| 5,877,007 | A | | 3/1999 | Housey |
| 5,959,098 | A | | 9/1999 | Goldberg et al. |
| 5,965,452 | A | | 10/1999 | Kovacs |
| 6,013,440 | A | | 1/2000 | Lipshutz et al. |
| 6,022,963 | A | | 2/2000 | McGall et al. |
| 6,025,155 | A | | 2/2000 | Hadlaczky et al. |
| 6,045,996 | A | | 4/2000 | Cronin et al. |
| 6,048,695 | A | | 4/2000 | Bradley et al. |
| 6,054,270 | A | | 4/2000 | Southern |
| 6,090,912 | A | | 7/2000 | Lebl et al. |
| 6,096,718 | A | | 8/2000 | Weitzman et al. |

(Continued)

FOREIGN PATENT DOCUMENTS

CA 2550361 7/2005
DE 24 13 258 A1 10/1975

(Continued)

OTHER PUBLICATIONS

Das-Gupta et al., Journal of the Indian Chemical Society, (1941), 18, 25-8.*

(Continued)

*Primary Examiner* — Niloofar Rahmani
(74) *Attorney, Agent, or Firm* — Foley & Lardner LLP

(57) ABSTRACT

Compounds active on protein kinases are described, as well as methods of using such compounds to treat diseases and conditions associated with aberrant activity of protein kinases.

18 Claims, No Drawings

U.S. PATENT DOCUMENTS

| | | | |
|---|---|---|---|
| 6,107,478 | A | 8/2000 | Pedersen et al. |
| 6,110,456 | A | 8/2000 | During |
| 6,110,458 | A | 8/2000 | Freeman et al. |
| 6,113,913 | A | 9/2000 | Brough et al. |
| 6,117,681 | A | 9/2000 | Salmons et al. |
| 6,161,776 | A | 12/2000 | Byles |
| 6,178,384 | B1 | 1/2001 | Kolossvary |
| 6,235,769 | B1 | 5/2001 | Clary |
| 6,243,980 | B1 | 6/2001 | Bronstein et al. |
| 6,258,606 | B1 | 7/2001 | Kovacs |
| 6,261,776 | B1 | 7/2001 | Pirrung et al. |
| 6,277,489 | B1 | 8/2001 | Abbott et al. |
| 6,277,628 | B1 | 8/2001 | Johann et al. |
| 6,288,234 | B1 | 9/2001 | Griffin |
| 6,294,330 | B1 | 9/2001 | Michnick et al. |
| 6,310,074 | B1 | 10/2001 | Depreux et al. |
| 6,350,786 | B1 | 2/2002 | Albano et al. |
| 6,545,014 | B2 | 4/2003 | Verner |
| 6,858,860 | B2 | 2/2005 | Hosono et al. |
| 7,259,165 | B2 | 8/2007 | Bernotas et al. |
| 7,361,763 | B2 | 4/2008 | Arnold et al. |
| 7,361,764 | B2 | 4/2008 | Arnold et al. |
| 7,452,993 | B2 | 11/2008 | Arnold et al. |
| 7,498,342 | B2 | 3/2009 | Ibrahim et al. |
| 7,504,509 | B2 | 3/2009 | Ibrahim et al. |
| 7,582,637 | B2 | 9/2009 | Arnold et al. |
| 7,601,839 | B2 | 10/2009 | Arnold et al. |
| 7,626,021 | B2 | 12/2009 | Arnold et al. |
| 7,846,941 | B2 | 12/2010 | Zhang et al. |
| 7,863,288 | B2 | 1/2011 | Ibrahim et al. |
| 7,863,289 | B2 | 1/2011 | Spevak et al. |
| 7,893,075 | B2 | 2/2011 | Zhang et al. |
| 2001/0001449 | A1 | 5/2001 | Kiliany et al. |
| 2001/0008765 | A1 | 7/2001 | Shinoki et al. |
| 2001/0012537 | A1 | 8/2001 | Anderson et al. |
| 2001/0014448 | A1 | 8/2001 | Chappa et al. |
| 2001/0016322 | A1 | 8/2001 | Caren et al. |
| 2001/0018642 | A1 | 8/2001 | Balaban et al. |
| 2001/0019827 | A1 | 9/2001 | Dawson et al. |
| 2003/0003004 | A1 | 1/2003 | Stones et al. |
| 2004/0002534 | A1 | 1/2004 | Lipson et al. |
| 2004/0022534 | A1 | 2/2004 | Amano et al. |
| 2004/0077595 | A1 | 4/2004 | Cheng et al. |
| 2004/0142864 | A1 | 7/2004 | Bremer et al. |
| 2004/0167030 | A1 | 8/2004 | Bernotas et al. |
| 2005/0085463 | A1 | 4/2005 | Weiner et al. |
| 2005/0154014 | A1 | 7/2005 | Bloxham et al. |
| 2005/0164300 | A1 | 7/2005 | Artis et al. |
| 2005/0170431 | A1 | 8/2005 | Ibrahim et al. |
| 2005/0256151 | A1 | 11/2005 | Salom et al. |
| 2006/0035898 | A1 | 2/2006 | Arnold et al. |
| 2006/0058339 | A1 | 3/2006 | Ibrahim et al. |
| 2006/0058340 | A1 | 3/2006 | Ibrahim et al. |
| 2007/0032519 | A1 | 2/2007 | Zhang et al. |
| 2007/0049615 | A1 | 3/2007 | Ibrahim et al. |
| 2007/0218138 | A1 | 9/2007 | Bittorf et al. |
| 2007/0287711 | A1 | 12/2007 | Arnold et al. |
| 2008/0167338 | A1 | 7/2008 | Spevak et al. |
| 2008/0188514 | A1 | 8/2008 | Wu et al. |
| 2009/0005356 | A1 | 1/2009 | Blaney et al. |
| 2009/0076046 | A1 | 3/2009 | Zhang et al. |
| 2009/0143352 | A1 | 6/2009 | Arnold et al. |
| 2009/0306056 | A1 | 12/2009 | Arnold et al. |

FOREIGN PATENT DOCUMENTS

| | | |
|---|---|---|
| EP | 0 154 734 | 8/1990 |
| EP | 0 465 970 | 1/1992 |
| EP | 1 057 826 | 12/2000 |
| EP | 0 870 768 | 5/2002 |
| EP | 1 749 829 | 2/2007 |
| GB | 2 292 143 | 2/1996 |
| GB | 2 292 145 | 2/1996 |
| GB | 2 298 198 | 8/1996 |
| GB | 2 299 581 | 10/1996 |
| JP | 06-135946 | 5/1994 |
| JP | 10-130269 | 5/1998 |
| JP | 2001278886 * | 10/2001 |
| JP | 15-073357 | 3/2003 |
| WO | WO-93/13099 | 7/1993 |
| WO | WO-94/14808 | 7/1994 |
| WO | WO-94/20459 | 9/1994 |
| WO | WO-94/20497 | 9/1994 |
| WO | WO-95/04742 | 2/1995 |
| WO | WO-95/07910 | 3/1995 |
| WO | WO-95/28387 | 10/1995 |
| WO | WO-96/00226 | 1/1996 |
| WO | WO-96/11929 | 2/1996 |
| WO | WO-96/05200 | 4/1996 |
| WO | WO-96/17958 | 6/1996 |
| WO | WO-96/18738 | 6/1996 |
| WO | WO-96/38131 | 12/1996 |
| WO | WO-97/46313 | 12/1997 |
| WO | WO-97/46558 | 12/1997 |
| WO | WO-97/49703 | 12/1997 |
| WO | WO-98/06433 | 2/1998 |
| WO | WO-98/22457 | 5/1998 |
| WO | WO-98/47899 | 10/1998 |
| WO | WO-99/00386 | 1/1999 |
| WO | WO-99/09217 | 2/1999 |
| WO | WO-99/51231 | 10/1999 |
| WO | WO-99/51232 | 10/1999 |
| WO | WO-99/51233 | 10/1999 |
| WO | WO-99/51234 | 10/1999 |
| WO | WO-99/51595 | 10/1999 |
| WO | WO-99/51596 | 10/1999 |
| WO | WO-99/51773 | 10/1999 |
| WO | WO-00/09162 | 2/2000 |
| WO | WO-00/12074 | 3/2000 |
| WO | WO-00/12514 | 3/2000 |
| WO | WO-00/29411 | 5/2000 |
| WO | 0055153 * | 9/2000 |
| WO | WO-00/53582 | 9/2000 |
| WO | WO-00/64898 | 11/2000 |
| WO | WO-00/71537 | 11/2000 |
| WO | WO-00/75139 | 12/2000 |
| WO | WO-01/09121 | 2/2001 |
| WO | WO-01/24236 | 4/2001 |
| WO | WO-01/29036 | 4/2001 |
| WO | WO-01/46196 | 6/2001 |
| WO | WO-01/60822 | 8/2001 |
| WO | WO-01/62255 | 8/2001 |
| WO | 0174786 * | 11/2001 |
| WO | WO-01/98299 | 12/2001 |
| WO | WO-02/00657 | 1/2002 |
| WO | WO-02/18346 | 3/2002 |
| WO | WO-02/083175 | 10/2002 |
| WO | WO-02/085896 | 10/2002 |
| WO | WO-02/102783 | 12/2002 |
| WO | WO-03/000258 | 1/2003 |
| WO | WO-03/003004 A2 | 1/2003 |
| WO | WO-03/006459 | 1/2003 |
| WO | WO-03/008422 | 1/2003 |
| WO | WO-03/011868 | 2/2003 |
| WO | WO-03/020698 | 3/2003 |
| WO | WO-03/028724 | 4/2003 |
| WO | WO 03/037862 | 5/2003 |
| WO | WO-03/064413 | 8/2003 |
| WO | WO-03/068221 | 8/2003 |
| WO | WO-03/082289 | 10/2003 |
| WO | WO-03/082868 | 10/2003 |
| WO | WO-03/082869 | 10/2003 |
| WO | WO-03/087087 | 10/2003 |
| WO | WO-03/101990 | 12/2003 |
| WO | 2004054581 * | 1/2004 |
| WO | WO-2004/009600 | 1/2004 |
| WO | WO-2004/009601 | 1/2004 |
| WO | WO-2004/016609 | 2/2004 |
| WO | WO-2004/016610 | 2/2004 |
| WO | WO-2004/024895 | 3/2004 |
| WO | WO-2004/065393 | 8/2004 |
| WO | WO-2004/065394 | 8/2004 |
| WO | WO-2004/069138 | 8/2004 |
| WO | WO-2004/074286 | 9/2004 |
| WO | WO-2004/078756 | 9/2004 |
| WO | WO-2004/078923 | 9/2004 |
| WO | WO-2004/101565 | 11/2004 |

| | | |
|---|---|---|
| WO | WO-2005/028475 | 3/2005 |
| WO | WO-2005/028624 | 3/2005 |
| WO | WO-2005/044181 | 5/2005 |
| WO | WO-2005/058891 | 6/2005 |
| WO | WO-2005/062795 | 7/2005 |
| WO | WO-2005/063746 | 7/2005 |
| WO | WO-2005/063747 | 7/2005 |
| WO | WO-2005/066347 | 7/2005 |
| WO | WO-2005/082367 | 9/2005 |
| WO | WO-2005/085244 | 9/2005 |
| WO | WO-2005/095400 | 10/2005 |
| WO | WO-2005/103050 | 11/2005 |
| WO | WO-2005/115363 | 12/2005 |
| WO | WO-2006/004984 | 1/2006 |
| WO | WO-2006/009755 | 1/2006 |
| WO | WO-2006/009797 | 1/2006 |
| WO | WO-2006/015123 | 2/2006 |
| WO | WO-2006/015124 | 2/2006 |
| WO | WO-03/051838 | 6/2006 |
| WO | WO-2006/114180 | 11/2006 |
| WO | WO-2006/127587 | 11/2006 |
| WO | WO-2007/002325 | 1/2007 |
| WO | WO-2007/002433 | 1/2007 |
| WO | WO-2007/013896 | 2/2007 |
| WO | WO-2007/106236 | 9/2007 |
| WO | WO-2008/079906 | 7/2008 |

OTHER PUBLICATIONS

Joule et al., Science of Synthesis (2001), 10, 361-652.*
Patani et al., Chem. Rev. (1996), 96, 3147-3176.*
Alfthan, K., Surface Plasmon Resonance Biosensors as a Tool in Antibody Engineering, Biosensors & Bioelectronics 13:653-663 (1998).
Al-Obeidi, et al., Peptide and Peptidomimetic Libraries, Mol Biotechnol 9:205-223, 1998.
Amersdorfer and Marks, Phage Libraries for Generation of Anti-Botulinum scFv Antibodies, Methods in Molecular Biology 145:219-240, 2000.
Ashman et al., The biology of stem cell factor and its receptor C-kit, The International Journal of Biochemistry & Cell Biology, 31:1037-1051, 1999.
Baghestanian, et al., A Case of Malignant Mastocytosis with Circulating Mast Cell Precursors: Biologic and Phenotypic Characterization of the Malignant Clone, Leuk. 10:159-166 (1996).
Bagshawe, Antibody-Directed Enzyme Prodrug Therapy: A Review; 1995, Drug Dev, Res., 34:220-230.
Balak, et. al., Novel D761Y and common secondary T790M mutations in epidermal growth factor receptor-mutant lung adenocarcinomas with acquired resistance to kinase inhibitors. Clin. Cancer Res. 12:6494-501 (2006).
Bancalari, et al., Blood Markers of Early and Late Airway Responses to Allergen in Asthmatic Subjects. Relationship with Functional Findings Allergy 52:32-40, 1997.
Bartlett, et al., CAVEAT: A Program to Facilitate the Structure-Derived Design of Biologically Active Molecules Royal Society of Chemistry 78:I80-I96, 1989.
Barton et al, The chemistry of pentavalent organobismuth reagants. Part X. Studies on the phenylation and oxidation of phenols, Tetrahedron, vol. 43, No. 2, 1987, pp. 323-332.
Bashford and Harris, Measurement of Ligand Binding to Proteins, Spectrophotometry and Spectrofluorimetry: A Practical Approach 4:91-113 (1987).
Basta et al, High-dose Intravenous Immunoglobulin Exerts Its Beneficial Effect in Patients with Dermatomyositis by Blocking Endomysial Deposition of Activated Complement Fragments; J Clin Invest 1994, 94:1729-1735.
Bedi, et al., BCR-ABL-Mediated Inhibition of Apoptosis With Delay of G2/M Transition After DNA Damage: A Mechanism of Resistance to Multiple Anticancer Agents; Blood 1995, 86:1148-1158.
Bell, Fluorescence: Solution Studies,(1981), Spectroscopy in Biochemistry, vol. I, pp. 155-194, CRC Press.
Bellone, et at, Growth Stimulation of Colorectal Carcinoma Cells Via the c-Kit Receptor is Inhibited by TGF-β1, J. Cell Physiol. 172:1-11 (1997).
Berdel, et at, Recombinant Human Stem Cell Factor Stimulates Growth of a Human Glioblastoma Cell Line Expressing c-kit Protooncogene, Canc. Res. 52:3498-3502 (1992).
Bertolini et al., A new Rational Hypothesis for the Pharmacophore of the Active Metabolite of Leflunomide, a Potent Immunosuppressive Drug; 1997, J. Med. Chem., 40:2011-2016.
Bjorntorp, Neuroendocrine Pertuirbations as a Cause of Insulin Resistance; Diabetes Metab. Res. Rev., 1999, 15: 427-441.
Bloom, A. and Day. A.R., The Preparation of 2-Alkylaminobenzimidazoles, J. Org. Chem. 14, 17 (1939).
Blundell et al., Knowledge-Based Protein Modelling and Design Eur. J. Biochem. 172:513-520 1988.
Böhm, H., On the Use of LUDI to Search the Fine Chemicals Directory for Ligands of Proteins of Known Three-Dimensional Structure, J. Comp. Aided Molec. Design 8:623-632, 1994.
Bokenmeyer, et al., Expression of Stem-Cell Factor and Its Receptor c-kit Protein in Normal Testicular Tissue and Malignant Germ-Cell Tumours, J. Cancer Res. Clin. Oncol. 122:301-306 (1996).
Bolger et al., Computer Modeling of Combining Site Structure of Anti-Hapten Monoclonal Antibodies, Methods Enz., 203:21-45, 1991.
Bothwell, M., Keeping Track of Neurotrophin Receptors Cell, 65:915-918, 1991.
Bouzakri, K. and Zierath, J.R., MAP4K4 Gene silencing in Human Skeletal Muscle Prevents Tumor Necrosis Factor-a-induced Insulin Resistance, J. Biol. Chem. 282:7783-7789 (2007).
Bowtell, D., Options Available From Start to Finish for Obtaining Expression Data by Microarray, Nature Genetics Supp. 21:25-32 (1999).
Brenner et al., Encoded Combinatorial Chemistry, Proc. Natl. Acad. Sci. USA 89:5381-5383, 1992.
Broudy, V., Stem Cell Factor and Hematopoiesis, Blood 90:1345-1364 (1997).
Brünger, A., Free R Value: a Novel Statistical Quantity for Assessing the Accuracy of Crystal Structures Nature 355:472-475 (1992).
Buchschacher, Human Immunodeficiency Virus Vectors for Inducible Expression of Foreign Genes; (1992) J. Virol. 66:2731-2739.
Capon, et al., Designing CD4 Immunoadhesins for AIDS Therapy, Nature 337:525-531 (1989).
Carell et al., New Promise in Combinatorial Chemistry: Synthesis, Characterization, and Screening of Small-Molecule Libraries in Solution, Chem. Biol. 2:171-183 (1995).
Carpino, et al., p62dok: A Constitutively Tyrosine-Phosphorylated, GAP-Associated Protein in Chronic Myelogenous Leukemia Progenitor Cells; Cell 1997, 88:197-204.
Castells, et al., The Presence of Membrane-Bound Stem Cell Factor on Highly Immature Nonmetachromatic Mast Cells in the Peripheral Blood of a Patient with Aggressive Systemic Mastocytosis, J. Aller. Clin. Immunol. 98:831-840 (1996).
Chabala, J., Solid-Phase Combinatorial Chemistry and Novel Tagging Methods for Identifying, Leads, Curr Opin Biotechnol 6:632-639 (1995).
Checovich, et al., Fluorescence Polarization—A New Tool for Cell and Molecular Biology, Nature 375:254-256 (1995).
Chou et al., Computerized Quantitation of Synergism and Antagonism of Taxol, Topotecan, and Cisplatin Against Human Teratocarcinoma Cell Growth: a Rational Approach to Clinical Protocol Design, J. Natl. Cancer Inst. 86:1517-24 (1994).
Chou, T. and Talalay, P., Quantitative analysis of Dose-Effect Relationships: The Combined Effects of Multiple Drugs or Enzyme Inhibitors, Adv. Enzyme Regul. 22:27-55 (1984).
Chou, T. et al., Chemotherapeutic Synergism, Potentiation and Antagonism, Encyclopedia of Human Biology, Academic Press, 2:371-9 (1991).
Chou, T.C. and Rideout, D.C., editors: Synergism and Antagonism in Chemotherapy, San Diego, CA: Academic Press, Chapter 2, 61-102 (1991).
Clark, et al., PRO_LIGAND: An Approach to De Novo Molecular Design. 1. Application to the Design of Organic Molecules, J. Comp. Aided Molec. Design 9:13-32 (1995).
Clohisy et al, Review of Cellular Mechanisms of Tumor Osteolysis; Clin. Orthop. 2000, 373: 104-14.

Coe, et al., Solution-Phase Combinatorial Chemistry, Mol Divers. 4:31-38 (1999).

Cohen, et al., Expression of Stem Cell Factor and C-Kit in Human Neuroblastoma; 1994, Blood 84:3465-3472.

Collins et al., A small interfereing RNA screen for modulators of tumor cell motility identifies MAP4K4 as a prommigratory kinase, Proc. Natl. Acad. Sci. USA, 103:3775-3780 (2006).

Collioud et al., Oriented and Covalent Immobilization of Target Molecules to Solid Supports: Synthesis and Application of a Light-Activatable and Thiol-Reactive Cross-Linking Reagent; (1993) Bioconjugate Chem. 4:528-536.

Columbo, et al., The Human Recombinant c-kit Receptor Ligand, rhSCF, Induces Mediator Release From Human Cutaneous Mast Cells and Enhances IgE-Dependent Mediator Release From Both Skin Mast Cells and Peripheral Blood Basophils, J. Immunol 149:599-608 (1992).

Costa, et al., The Cells of the Allergic Response, JAMA 278:1815-1822 (1997).

Coulie et al, Recombinant Human Neurotropic Factors Accelerate Colonic Transit and Relieve Constipation in Humans, Gastroenterology 119:41-50 (2000).

Creighton, T., An Empirical Approach to Protein Conformation Stability and Flexibility, Biopolymers 22(1):49-58 (1983).

Crouch et al., The use of ATP bioluminescence as a measure of cell proliferation and cytotoxicity. Journal of Immunological Methods, 160:81-8 (1993).

Crump, M., Inhibition of Raf Kinase in the Treatment of Acute Myeloid Leukemia, Curr. Pharm. Design 8(25):2243-8 (2002).

Curtin et al., Discovery and Evaluation of a Series of 3-Acylindole Imidazopyridine Platelet-Activating Factor Antagonists, J. Med. Chem., vol. 41, 1998, pp. 74-95.

Cwirla et al., Peptides on Phage: A Vast Library of Peptides for Identifying Ligands, Biochemistry 87:6378-6382 (1990).

Dai et al., Targeted disruption of the mouse colony-stimulating factor 1 receptor gene results in osteopetrosis, mononuclear phagocyte deficiency, increased primitive progenitor cell frequencies, and reproductive defects; Blood, 2002, 99: 111-120.

Dandliker, et al., Equilibrium and Kinetic Inhibition Assays Based Upon Fluorescence Polarization, Methods in Enzymology 74:3-28 (1981).

Dastych, et al., Stem Cell Factor Induces Mast Cell Adhesion to Fibronectin; 1994, J. Immunol. 152:213-219.

Demetri, Targeting c-kit mutations in solid tumors: Scientific rationale and novel therapeutic options, Seminars in Oncology, 28(5), Supp. 17, 19-26, 2001.

Dewar et al., Inhibition of c-fms by Imatinib Expanding the Spectrum of Treatment; Cell Cycle 2005, 4(7):851-3.

Dobeli, H., et al., Recombinant Fusion Proteins for the Industrial Production of Disulfide Bridge containing Peptides: Purification, Oxidation without Cancatamer Formation, and Selective Cleavage; (1998) Protein Expr. Purif. 12:404-414.

Dolle et al., Comprehensive Survey of Combinatorial Library Synthesis: 1998, J Comb Chem 1:235-282 (1999).

Douma, S. et al, Suppression of anoikis and induction of metastasis by the neurotropic receptor TrkB, Nature 430:1034-9 (2004).

Doyle and Bryker, Alkyl Nitrite-metal halide Deamination Reactions. 6. Direct Synthesis of Arenediazonium Tetrafluoroborate Salts from Aromatic Amines, tert-Butyl Nitrite, and Boron Trifluoride Etherate in Anhydrous Media; J. Org. Chem. 1979, 44:1572.

Dyson, et al., The Human Papilloma Virus 13 16 E7 Oncoprotein is Able to Bind to the Retinoblastoma Gene Product, Science 243:934-937 (1989).

Eklund and Joensuu, Treatment of rheumatoid arthritis with imatinib mesylate: clinical improvements in three refractory cases, Annals of Medicine, 35:362-367, 2003.

Eliseev et al, Dynamic Combinatorial Chemistry: Evolutionary Formation and Screening of Molecular Libraries, Current Topics in Microbiology & Immunology 243:159-172 (1999).

Enjalbal, et al., Mass Spectrometry in Combinatorial Chemistry, Mass Spectrometry Reviews. 19:139-161 (2000).

Escribano, et al., Expression of the c-kit (CD117) Molecule in Normal and Malignant Hematopoiesis, Leuk. Lymph. 30:459-466 (1998).

Feng et al, Tyrosines 559 and 807 in the Cytoplasmic Tail of the Macrophage colony-Stimulating Factor Receptor Play Distinct Roles in Osteoclast Differentiation and Function; Endocrinology 2002, 143: 4868-74.

Feng, et al., Stable in Vivo Gene Transduction Via a Novel Adenoviral/Retroviral Chimeric Vector, Nature Biotechnology 15:866-870 (1997).

Finotto, et al., Glucocorticoids Disease Tissue Mast Cell Number by Reducing the Production of the c-kit Ligand, Stem Cell Factor, by Resident Cells, J. Clin. Invest. 99:1721-1728 (1997).

Fivash et al., BIAcore for macromolecular interaction; (1998) BIAcore for macromolecular interaction, Current Opinion in Biotechnology. 9:97-101.

Flanagan & Lader, Macrophages and the various isoforms of macrophage colony-stimulating factor; Curr Opin Hematol. 1998, 5:181-5.

Furitsu, et al., Identification of Mutations in the Coding Sequence of the Proto-oncogene c-kit in a Human Mast Cell Leukemia Cell Line Causing Ligand-independent Activation of the c-kit Product; 1993, J. Clin. Invest. 92:1736-1744.

Furuta, et al., Stem Cell Factor Influences Mast Cell Mediator Release in Response to Eosinophil-Derived Granule Major Basic Protein, Blood 92:1055-1061 (1998).

Gallop et al., Applications of Combinatorial Technologies to Drug Discovery. 1. Background and Peptide Combinatorial Libraries, J. Med. Chem. 37:1233-1251 (1994).

Gassman et al., Specific Ortho Substitution of Aromatic Heterocyclic Amines, J American Chemical Society, (1973), 95(13), pp. 4453-4455.

Girgis, N. et.al., The Synthesis of 5-Azaindoles by Substitution-Rearrangement of 7-Azaindoles upon Treatment with Certain Primary Amines; J. Heterocyclic. Chem. 1989, 26:317-325.

Golkar, et al., Mastocytosis, Lancet 349:1379-1385 (1997).

Goodford, P.J., A Computational Procedure for Determining Energetically Favorable Binding Sites on Biologically Important Macromolecules, J. Med. Chem. 28:849-857 (1985).

Goodsell et al, Automated Docking of Substrates to Proteins by Simulated Annealing, Proteins: Structure, Function, and Genetics 8:195-202 (1990).

Gordon et al., Applications of Combinatorial Technologies to Drug Discovery. 2. Combinatorial Organic Synthesis, Library Screening Strategies, and Future Directions, J. Med. Chem. 37:1384-1401 (1994).

Gram H., Phage Display in Proteolysis and Signal Transduction, Combinatorial Chemistry & High Throughput Screening 2:19-28 (1999).

Gravert et al, Synthesis on Soluble Polymers: New Reactions and the Construction of Small Molecules, Curr Opin Chem Biol 1:107-113 (1997).

Greer, J., Model Structure for the Inflammatory Protein C5a, Science 228:1055-1060 (1985).

Hafner, et al., Isothermal Amplification and Mu t merization of DNA by Bst DNA Polymerase, Biotechniques Apr. 2001;30(4):852-867.

Hallek, et al., Interaction of the Receptor Tyrosine Kinase p145c-kit with the p210bcr/abl Kinase in Myeloid Cells, Brit. J Haem. 94:5-16 (1996).

Halvorson, K.G. et al., A Blocking Antibody to Nerve Growth Factor Attenuates Skeletal Pain Induced by Prostate Tumor Cells Growing in Bone, Cancer Res. 65:9426-35 (2005).

Hamel, et al., The Road Less Traveled: c-kit and Stem Cell Factor, J. Neuro-Onc. 35:327-333 (1997).

Hands et. al., A convenient Method for the Preparation of 5-, 6- and 7-Azaindoles and Their Derivatives; Synthesis 1996, 877-882.

Hanselman, et al., A cDNA-Dependent Scintillation Proximity Assay for Quantifying Apolipoprotein A-1, J. Lipid Res. 38:2365-2373 (1997).

Hassan and Zander, Stem Cell Factor as a Survival and Growth Factor in Human Normal and Malignant Hematopoiesis, Acta. Hem. 95:257-262 (1996).

Hassan, et al., Expression of Protooncogene c-kit and Its Ligand Stem Cell Factor (SCF) in Gastric Carcinoma Cell Lines; 1998, Digest. Dis. Science 43:8-14.

Heacock et al., Orientation and Relative Reaction rate Factors in aromatic Substitution by the Benzensulfonimido Radical, J. Am. Chem. Soc., vol. 82, 1960, pp. 3460-3463.

Heim, et al., Engineering Green Fluorescent Protein for Improved Brightness, Longer Wavelengths and Fluorescence Resonance Energy Transfer, Curr. Biol. 6:178-182 (1996).

Heinrich et al., PDGFRA Activating Mutations in Gastrointestinal Stromal Tumors; (Science 2003, 299:708-10).

Herbst, et al., Differential Effects of W Mutations on p145c-kit Tyrosine Kinase Activity and Substrate Interaction, J. Biol. Chem. 267:13210-13216 (1992).

Hibi, et al., Coexpression of the stem cell factor and the c-kit genes in small-cell lung cancer; 1991, Oncogene 6:2291-2296.

Hirota, et al., Gain-of-function Mutations of c-kit in Human Gastrointestinal Stromal Tumors; 1998, Science 279:577-580.

Hoffmann, m-Trifluoromethylbenzenesulfonyl Chloride, Organic Syntheses, Coll. vol. 60, p. 121-126, 1981.

Hogaboam, et al., Novel Role of Transmembrane SCF for Mast Cell Activation and Eotaxin Production in Mast Cell-Fibroblast Interactions, J. Immunol. 160:6166-6171 (1998).

Hood, J.D. et al., Tumor Regression by Targeted Gene Delivery to the Neovasculature, Science 296, 2404 (2002).

Houghten, et al., Generation and Use of Synthetic Peptide Combinatorial Libraries for Basic Research and Drug Discovery, Nature 354:84-86 (1991).

Houghten, R., Parallel Array and Mixture-Based Synthetic Combinatorial Chemistry: Tools for the Next Millennium, Annu Rev Pharmacol Toxicol 40:273-282 (2000).

Houghten, R., Peptide Libraries: Criteria and Trends, Trends Genet. 9:235-239 (1993).

Hudson, P. B. et al., A Simple Method for the Determination of Serum Acid Phosphatase, Journal of Urology 58:89-92 (1947).

Hughes-Jones, et al., Synthesis of Rh Fv Phage-Antibodies Using VH and VL Germline Genes, British Journal of Haematology 105:811-816 (1999).

Iemura, et al., The c-kit Ligand, Stem Cell Factor, Promotes Mast Cell Survival by Suppressing Apoptosis, Amer. J. Pathol 144:321-328 (1994).

Inoue, et al., Coexpression of the c-kit Receptor and the Stem Cell Factor in Gynecological Tumors, Cancer Res. 54:3049-3053 (1994).

International Search Report and Written Opinion of the ISA dated Oct. 24, 2006 for PCT Application No. PCT/US2006/024524.

International Search Report and Written Opinion of the ISA dated Apr. 4, 2007 for PCT Application No. PCT/US2006/018726.

International Search Report and Written Opinion of the ISA dated Apr. 20, 2006 for PCT Application No. PCT/US2005/021231.

International Search Report and Written Opinion of the ISA dated Jun. 4, 2008 for PCT Application No. PCT/US2007/088231.

International Search Report and Written Opinion of the ISA dated Jun. 4, 2008 for PCT Application No. PCT/U52007/088237.

International Search Report and Written Opinion of the ISA dated Jun. 5, 2008 for PCT Application No. PCT/US2007/083910.

International Search Report and Written Opinion of the ISA dated Jun. 5, 2008 for PCT Application No. PCT/US2007/085289.

International Search Report and Written Opinion of the ISA dated Jun. 5, 2008 for PCT Application No. PCT/US2007/088243.

International Search Report and Written Opinion of the ISA dated Jul. 25, 2008 for PCT Application No. PCT/US2007/088443.

International Search Report and Written Opinion of the ISA dated Jul. 28, 2008 for PCT Application No. PCT/US2007/085299.

International Search Report and Written Opinion of the ISA dated Oct. 24, 2006 for PCT Application No. PCT/US2006/024361.

International Search Report and Written Opinion of the ISA dated Nov. 17, 2008 for PCT Application No. PCT/US07/088412.

International Search Report and Written Opinion of the ISA dated Nov. 25, 2005 for PCT Application No. PCT/U504/42470.

Isbel et al., Local macrophage proliferation correlates with increased renal M-CSF expression in human glomerulonephritis; Nephrol Dial Transplant 2001, 16: 1638-1647.

Isozaki, et al., Deficiency of c-kit cells in patients with a myopathic form of chronic idiopathic intestinal pseudo-obstruction; 1997, Amer. J. of Gast. 9 332-334.

Iwane, et al., Myosin Subfragment-1 is Fully Equipped with Factors Essential for Motor Function, Biochem. and Biophys. Res. Comm. 230:76-80 (1997).

Izquierdo, et al., Differential Expression of the c-kit Proto-Oncogene in Germ Cel Tumours, J. Pathol. 177:253-258 (1995).

Jarugula et al., Nonlinear pharmacokinetics of 5-fluorouracil in rats. 1997, J Pharm Sci 86(7):756-757.

Johann, S., et al., GLVR1, a Receptor for gibbon Ape Leukemia Virus, Is Homologous to a Phosphate Permease of Neurospora crassa and is Expressed at High Levels in the Brain and Thymus; (1992) J. Virol. 66:1635-1640.

Johnston, M., Gene Chips: Array of hope for understanding gene regulation; (1998) Curr. Biol. 8:R171-R174.

Jones, Jones, R., Biology and Treatment of Chronic Myeloid Leukemia, Curr. Opin. Onc. 9:3-7 (1997).

Jones, T., Interactive Computer Graphics: FRODO, Methods in Enzymology 115:157-171 (1985).

Jose et al., Blockade or Macrophage colony-Stimulating Factor Reduces Macrophage Proliferation and Accumulation in Renal Allograft Rejection; Am J Transplant 2003, 3(3):294-300.

Joseph-McCarthy, D., Computational Approaches to Structure-Based Ligand Design, Pharmacology & Therapeutics 84:179-191 (1999).

Kahl, et al., A Multiple-Approach Scintillation Proximity Assay to Measure the Association Between Ras and Raf, Anal. Biochem. 243:282-283 (1996).

Kassel, O. et al., Local increase in the number of mast cells and expression of nerve growth factor in the bronchus of asthmatic patients after repeated inhalation of allergen at low-dose, Clin. Exp. Allergy 31:1432-40 (2001).

Kay, et al., Eosinophils and Eosinophil-Associated Cytokines in Allergic Inflammation, Int. Arch, Aller. Immunol. 113:196-199 (1997).

Kern and Hampton, Direct Hybridization of Large-Insert Genomic Clones on High-Density Gridded cDNA Filter Arrays, Biotechniques 23:120-124 (1997).

Kim et al, A Merger of Rational Drug Design and Combinatorial Chemistry: Development and Application of Peptide Secondary Structure Mimetics, Combinatorial Chemistry & High Throughput Screening 3:167-183 (2000).

Kim et al, Database CAS on STN (Columbus, OH, USA) No. 138:55974, Preparation of 2-anilino-4-indolyl pyrimidines as tyrosine kinase inhibitors, abstract, 2002) see whole article.

Kinashi and Springer, Steel Factor and c-kit Cell-Matrix Adhesion; Blood 83:1033-1038 (1994).

Kirkpatrick, et al., Structure-Based Drug Design: Combinatorial Chemistry and Molecular Modeling, Combinatorial Chemistry & High Throughput Screening 2:211-221 (1999).

Kitamura, et al., Synthesis of Quinolines and 2H-Dihydropyrroles by Nucleophilic Substitution at the Nitrogen Atom of Oxime Derivatives, Synthesis 15:2415-2426 (2003).

Kline et al., Studies by 1H Nuclear Magnetic Resonance and Distance Geometry of the Solution Conformation of the x-Amylase Inhibitor Tendamistat, J. Mol. Biol. 189:377-382 (1986).

Knighton, et al., Structural Basis of the Intrasteric Regulation of Myosin Light Chain Kinases, Science 258:130-135 (1992).

Kodama et al, Congenital Osteoclast Deficiency in Osteopetrotic (op/op) Mice Is Cured by Injections of Macrophage colony-stimulating Factor; J. Exp,. Med. 1991, 173: 269-72.

Kolaskar et al, A Semi-Empirical Method for Prediction of Antigenic Determinants on Protein Antigens, FEBS Lett. 276:172-174 (1990).

Komoyira, S. et. al., Design, synthesis and biological activity of amidinobicyclic compounds (derivatives of DX-9065a) as a factor Xa inhibitors: SAR study of S1 and aryl binding sites, Bioorg. Med. Chem. 12, 2099 (2004).

Kondoh, et al., An in vivo model for receptor tyrosine kinase autocrine/paracrine activation: auto-stimulated Kit receptor acts as a tumor promoting factor in papillomavirus-induced tumorigenesis; 1995, Oncogene 10:341-347.

Kondoh, et al., Establishment and Further Characterization of a Line of Transgenic Mice Showing Testicular Tumorigenesis at 100% Incidence, J. Urol. 152:2151-2154 (1994).

Kondoh, et al., Very High Incidence of Germ Cell tumorigenesis (Seminomagenesis) in Human Papillomavirus Type 16 Transgenic Mice; 1991, J. Virol. 65:3335-3339.

Kroll, David J., et al., A Malfunctional Prokaryotic Protein Expression System: Overproduction, Affinity Purification, and Selective Detection; (1993) DNA Cell. Biol. 12:441-53.

Kundu, et al., Combinatorial Chemistry: Polymer Supported Synthesis of Peptide and Non-Peptide Libraries, Progress in Drug Research 53:89-156 (1999).

Kunisada, et al., Murine Cutaneous Mastocytosis and Epidermal Melanocytosis Induced by II Keratinocyte Expression of Transgenic Stem Cell Factor; 1998, J. Exp. Med. 187:1565-1573.

Kunkel, T., Rapid and Efficient Site-Specific Mutagenesis Without Phenotypic Selection, Proc. Natl. Acad. Sci. USA 82:488-492 (1985).

Kunnimalaiyaan, M. and Chen, H. et al., The Raf-1 pathway: a molecular target for treatment of select neuroendocrine tumors? Anticancer Drugs 17(2):139-42 (2006).

Kuntz, et al., A Geometric Approach to Macromolecule-Ligand Interactions, J. Mol. Biol. 161:269-288 (1982).

Kuntz, et al., Structure-Based Molecular Design, Acc. Chem. Res. 27:117-123 (1994).

Lahm, et al., Interleukin 4 Down-Regulates Expression of c-kit and Autocrine Stem Cell Factor in Human Colorectal Carcinoma Cells, Cell Growth & Differ 6:1111-1118 (1995).

Lam et al., A new type of synthetic peptide library for identifying ligand-binding activity, Nature, 354: 82-84, 1991.

Langham et al., Metalation of Halogen-Metal Interconversion Reactions of Some Halogenated Phenyl Ethers, J. Am. Chem. Soc., vol. 63, 1941, pp. 545-549.

Iftawicki et al., The pretreratment plasma level and disgnostic utility of M-CSF in benign breast tumor and breast cancer patients, Clinica Chimica Acta, 371: 112-116, 2006.

Le Meur et.al., Macrophage accumulation at a site of renal inflammation is dependent on the M-CSF/c-fms pathway; J Leukocyte Biology, 2002, 72: 530-537.

Lebl, et al., One-Bead-One-Structure Combinatorial Libraries, Biopolymers 37:177-198 (1995).

Lee, et al., HLA-DR-Triggered Inhibition of Hemopoiesis Involves Fas/Fas Ligand Interactions and is Prevented by c-kit Ligand, J. Immunol. 159:3211-3219 (1997).

Lee, et al., Mast Cells: A Cellular Link Between Autoantibodies and Inflammatory Arthritis, Science 297:1689-1692 (2002).

Levin, et al., Neoplasms of the Central Nervous System, Cancer Principles & Practice of Oncology 2:2022-2082 (1997).

Li, et al., Abrogation of c-kit/Steel Factor-Dependent Tumorigenesis by Kinase Defective Mutants of the c-kit Receptor: c-kit Kinase Defective Mutants as Candidate Tools for Cancer Gene Therapy, Canc. Res. 56:4343-4346 (1996).

Libby, Inflammation in atherosclerosis, Nature, 2002;420:868-874

Liparoto, et al., Biosensor Analysis of the Interleukin-2 Receptor Complex, Journal of Molecular Recognition 12:316-321 (1999).

Lipinski, et al., Experimental and Computational Approaches to Estimate Solubility and Permeability in Drug Discovery and Development Settings, Advanced Drug Delivery Reviews 23:3-25 (1997).

Lipschultz et al., Experimental design for analysis of complex kinetics using surface plasmon resonance, Methods; (2000) 20(3):310-318.

London, et al., Expression of Stem Cell Factor Receptor (c-kit) by the Malignant Mast Cells from Spontaneous Canine Mast Cell Tumors, 1996, J. Compar. Pathol. 115:399-414.

Longley, et al., Altered Metabolism of Mast-cell Growth Factor (c-kit Ligand) in Cutaneous Mastocytosis, 1993, New Engl. J. Med. 328:1302-1307.

Longley, et al., Chymase Cleavage of Stem Cell Factor Yields a Bioactive Soluble Product, Proc. Natl. Acad. Sci. 94:9017-9021 (1997).

Longley, et al., Somatic c-Kit Activating Mutation in Urticaria Pigmentosa and Aggressive Mastocytosis: Establishment of Clonality in a Human Mast Cell Neoplasm, Nat. Gen. 12:312-314 (1996).

Loveland, et al., Stem Cell Factor and c-kit in the Mammalian Testis: Lessons Originating from Mother Nature 19s Gene Knockouts, J. Endocrinol 153:337-344 (1997).

Lu, et al., Oriented Immobilization of Fab 19 Fragments on Silica Surfaces, Anal. Chem. 67:83-87 (1995).

Lukacs, et al., Stem Cell Factor (c-kit Ligand) Influences Eosinophil Recruitment and Histamine 1 Levels in Allergic Airway Inflammation, J. Immunol. 156:3945-3951 (1996).

Lyman, et al., c-kit Ligand and Flt3 Ligand: Stem/Progenitor Cell Factors With Overlapping Yet Distinct Activities, Blood 91:1101-1134 (1998).

Ma et al., Indolinone Derivatives Inhibit Constitutively Activated KIT Mutants and Kill Neoplastic Mast Cells, 2000, J Invest Dermatol. 114:392-394.

Ma, et al., The c-KIT Mutation Causing Human Mastocytosis is Resistant to ST1571 and Other KIT Kinase Inhibitors; Kinases with Enzymatic Site Mutations Show Different Inhibitor Sensitivity Profiles Than Wild-type Kinases and Those With Regulatory-Type Mutations, Blood 99:1741-1744 (2002).

Machida, N. et al., Mitogen-activated Protein Kinase Kinase Kinase Kinase 4 as a Putative Effector of Rap2 to Activate the c-Jun N-terminal Kinase, J. Biol. Chem. 279: 15711-15714 (2004).

Mack, K.D. et al., Functional identification of kinases essential for T-cell activation through a genetic suppression screen, Immunol. Lett. 96, 129-145 (2005).

Madden, et al., Synthetic Combinatorial Libraries: Views on Techniques and Their Application Perspectives in Drug Discovery and Design 2:269-285 (1994).

Malmborg, et al., BIAcore as a Tool in Antibody Engineering, Journal of Immunological Methods 183:7-13 (1995).

Malmqvist, et al., Biomolecular Interaction Analysis: Affinity Biosensor Technologies for Functional Analysis of Proteins, Current Opinion in Chemical Biology 1:378-383 (1997).

Malmqvist., BIACORE: an affinity biosensor system for characterization of biomolecular interactions, (1999) Biochemical Society Transactions 27:335-40.

Markiewicz, et al., Synthetic Oligonucleotide Combinatorial Libraries and Their Applications, II Farmaco 55:174-177 (2000).

Martin, Y., Computer-Assisted Rational Drug Design, Methods Enz. 203:587-613 (1991).

Matayoshi, S. et al, Actions of brain-derived neurotrophic factor on spinal nociceptive transmission during inflammation in the rat, J Physiol. 569:685-95 (2005).

Mazeas, et. al., Synthesis of new melatoninergic ligands including azaindole moiety. Heterocycles, 50:1065 (1999).

McCall, et al., Characterization of Anti-Mouse FcγRII Single-Chain Fv Fragments Derived from Phage Display Libraries, Immunotechnology 4:71-87 (1998).

McPherson, A., Current Approaches to Macromolecule Crystallization, Eur. J. Biochem. 189:1-23 (1990).

Mekori, et al., Transforming Growth Factor-β Prevents Stem Cell Factor-Mediated Rescue of Mast Cells from Apoptosis After IL-3 Deprivation, 1994, J. Immunol 153:2194-2203.

Mekori, et al., The Role of c-Kit and Its Ligand, Stem Cell Factor, in Mast Cell Apoptosis, 1995, Int. Immunol. 107:136-138.

Meltzer, The pharmacological basis for the treatment of perennial allergic rhinitis and non-allergic rhinitis with topical corticosteroids, 1997, Aller. 52:33-40.

Meng, et al., Automated Docking with Grid-Based Energy Evaluation, J. Compt. Chem. 13:505-524 (1992).

Merour and Joseph, Synthesis and Reactivity of 7-Azaindoles (1H-Pyrrolo[2,3-b]pyridine), Curr. Org. Chem. 2001, 5:471-506.

Merritt, A., Solution Phase Combinatorial Chemistry, Comb Chem High Throughput Screen 1:57-72 (1998).

Metcalf, D., Lineage Commitment in the Progeny of Murine Hematopoietic Preprogenitor Cells: Influence of Thrombopoietin and Interleukin 5, Proc. Natl. Acad. Sci. USA 95:6408-6412 (1998).

Metcalfe, Classification and Diagnosis of Mastocytosis: Current Status, 1991, J. Invest. Derm 93:2S-4S.

Metcalfe et al., Mast Cells, Physiol. Rev. 77:1033-1079 (1997).

Miller, et al., FLOG: A System to Select Quasi-Flexible Ligands Complementary to a Receptor of Known Three-Dimensional Structure, J. Comp. Aided Molec. Design 8:153-174 (1994).

Minakata et al., Functionalization of 1H-Pyrrolo[2,3-b]pyridine, Bulletin of the Chemical Society of Japan (1992), 65(11): 2992-2997.

Miranker et al, Functionality Maps of Binding Sites: A Multiple Copy Simultaneous Search Method, Proteins: Structure, Function, and Genetics 11:29-34 (1991).

Mitra, et al., Fluorescence Resonance Energy Transfer Between Blue-Emitting and Red-Shifted Excitation Derivatives of the Green Fluorescent Protein, Gene 173:13-17 (1996).

Miyaura and Suzuki, Palladium-Catalyzed Cross-Coupling Reactions of Organoboron Compounds, Chem. Rev. 1995, 95:2457.

Mol, et al. Structural Basis for the Autoinhibition and STI-571 Inhibition of c-Kit Tyrosine Kinase, J. Biol. Chem. 279:31655-31663 (2004).

Mol, et al., Structure of a c-Kit Product Complex Reveals the Basis for Kinase Transactivation, J. Biol. Chem. 278:31461-31464 (2003).

Morgan, C., Pollard, J.W., and Stanley, E.R., Isolation and Characterization of a Cloned Growth Factor Dependent Macrophage Cell Line, BAC1.2F5, Journal of Cellular Physiology, 130:420-427 (1987).

Motoyoshi, Biological activities and clinical application of M-CSF, Int J Hematol. 1998, 67:109-22.

Murty, et al., A Genetic Perspective of Male Germ Cell tumors, 1998, Sem. Oncol. 25:133-144.

Naclerio, et al., Rhinitis and Inhalant Allergens, JAMA 278:1842-1848 (1997).

Nagata, et al., Elevated Expression of the Proto-Oncogene c-kit in Patients with Mastocytosis, Leukemia 12:175-181 (1998).

Nakagawara, A. et al., Expression and Function of TRK-B an BDNF in Human Neuroblastomas, Mol. Cell Biol. 14:759-767 (1994).

Nassentein, C. et al, The Neurotrophins Nerve Growth Factor, Brain-derived Neurotrophic Factor, Neurotrophin-3, and Neurotrophin-4 Are Survival and Activation Factors for Eosinophils in Patients with Allergic Bronchial Asthma, J. Exp. Med. 198:455-467 (2003).

Navaza, J., AMoRe: an Automated Package for Molecular Replacement, Acta Cryst. A50:157-163 (1994).

Neidle, et al., Molecular Modeling to Study DNA Intercalation by Anti-Tumor Drugs, Methods Enz. 203:433-458 (1991).

Ng, et al., Engineering Protein-Lipid Interactions: Targeting of Histidine-Tagged Proteins to Metal-Chelating Lipid Monolayers, Langmuir 11:4048-4055 (1995).

Nicholls, et al., Protein Folding and Association: Insights From the Interfacial and Thermodynamic Properties of Hydrocarbons, Proteins 11:281-296 (1991).

Nichols, et al., Development of a Scintillation Proximity Assay for Peroxisome Proliferator-Activated Receptor y Ligand Binding Domain, Anal. Biochem. 257:112-119 (1998).

Niihori, T. et al., Germline KRAS and BRAF mutations in cardio-facio-cutaneous syndrome, Nature Genet. 38(3):294-6 (2006).

Notice of Allowance dated Dec. 26, 2007 for U.S. Appl. No. 11/016,350.

Notice of Allowance dated Jun. 6, 2008 for U.S. Appl. No. 11/154,988.

Ochs, G. et al, A phase I/II trial of recombinant methionyl human brain derived neurotrophic factor administered by intrathecal infusion to patients with amyotrophic lateral sclerosis, Amyotroph Lateral Scler Other Motor Neuron Disord. 1:201-6 (2000).

Okada, et al., Gene Therapy Against an Experimental Glioma Using Adeno-Associated Virus Vectors, Gene Ther. 3:957-964 (1996).

Okayama, et al., Human Lung Mast Cells are Enriched in the Capacity to Produce Granulocyte-Macrophage Colony-Stimulating Factor in Response to IgE-Dependent Stimulation, Eur. J. Immunol. 28:708-715 (1998).

Okayama, et at., Activation of Eosinophils with Cytokines Produced by Lung Mast Cells, Int. Arch. Aller. Immunol. 114(suppl. 1):75-77 (1997).

O'Shannessy and Winzor, Interpretation of Deviations from Pseudo-First-Order Kinetic Behavior in the Characterization of Ligand Binding by Biosensor Technology, Analytical Biochemistry 236:275-283 (1996).

O'Shannessy, Determination of kinetic rate and equilibrium binding constants for macromolecular interactions: a critique of the surface plasmon resonance literature, (1994) Current Opinions in Biotechnology, 5:65-71.

Otwinowski, Z. Maximum Likelihood Refinement of Heavy Atom Parameters, Dept. of Molecular Biophysics and Biochemistry pp. 80-86 (1991).

Owicki et al., Application of Fluorescence Polarization Assays in High-Throughput Screening, (1997), Genetic Engineering News, 17:27.

Parker, et al., Development of High Throughput Screening Assays Using Fluorescence Polarization: Nuclear Receptor-Ligand-Binding and Kinase/Phosphatase Assays, J Biomol Screen 5:77-88 (2000).

Perrin, D., Nucleic Acids for Recognition and Catalysis: Landmarks, Limitations, and Looking to the Future, Combinatorial Chemistry & High Throughput Screening 3:243-269 (2000).

Petty et al, The effect of systemically administered recombinant human nerve growth factor in healthy human subjects. Ann Neurol. 36:244-6 (1994).

Pflugrath, et al., Crystal Structure Determination, Refinement and the Molecular Model of the x-Amylase Inhibitor Hoe-467A, J. Mol. Biol. 189:383-386 (1986).

Pierce et al., Local anaesthetics. I. beta-Monoaklylaminoethyl Esters of Alkoxybenzoic Acids, J. Am. Chem. Soc., vol. 64, 1942, pp. 1691-1694.

Pignon, J.M., C-kit mutations and mast cell disorders A model of activating mutations of growth factor receptors, Hermatol Cell Ther 39:114-116 (1997).

Plunkett et al, A Silicon-Based Linker for Traceless Solid-Phase Synthesis, J. Org. Chem. 60:6006-6007 (1995).

Poul, et al., Selection of Tumor-Specific Internalizing Human Antibodies from Phage Libraries, J. Mol. Biol. 301:1149-1161 (2000).

Price et al., Summary report on the ISOBM TD-4 Workshop: analysis of 56 monoclonal antibodies against the MUC1 mucin, (1998) Tumour Biology 19 Suppl 1:1-20.

Qiao, et. al., Role of Macrophage Colony-Stimulating Factor in Atherosclerosis, Am. J. Path. 1997;150:1687-1699.

Rajavashisth, et. al., Heterozygous Osteopetrotic (op) Mutation Reduces Atherosclerosis in LDL Receptor-deficient Mice, J. Clin. Invest. 1998;101:2702-2710.

Rajpert-de Meyts, et al., Expression of the c-kit Protein Product in Carcinoma-in-situ and Invasive Testicular Germ Cell Tumours, Int. J. Androl. 17:85-92 (1994).

Ricotti, et al., c-kit Is Expressed in Soft Tissue Sarcoma of Neuroectodermic Origin and Its Ligand Prevents Apoptosis of Neoplastic Cells, Blood 91:2397-2405 (1998).

Ridge et al, FMS mutations in myelodysplastic, leukemic, and normal subjects, Proc. Nat. Acad. Sci., 1990, 87:1377-1380.

Roberts, S., et al., Generation of an antibody with enhanced affinity and specificity for its antigen by protein engineering, (1987) Nature 328:731-734.

Robinson et al., Stimulation of Bone Marrow Colony Growth in Vitro by Human Urine; Blood, 1969, 33:396-9.

Robison et al, 7-Azaindole. I. Synthesis and Conversion to 7-Azatryptophan and Other Derivatives, J. Am. Chem. Soc. 77:457-460 (1955).

Rodan, G., et al., Therapeutic Approaches to Bone Diseases, Science. 2000;289:1508.

Rosenfeld, Human artificial chromosomes get real, (1997) Nat. Genet. 15:333-335.

Ryan, et al., Role for the Stem Cell Factor/KIT Complex in Schwann Cell Neoplasia and Mast Cell Proliferation Associated with Neurofibromatosis, 1994, J. Neuro. Res. 37:415-432.

Saify et al, Database CAS on STN (Columbus, OH, USA) No. 124:170379, Synthesis of some 2-azaindole derivatives: their cyctotoxicity and antibacterial activity, abstract, (1996), See RN 271-63-6.

Saify et al., Synthesis of some 7-azaindole derivatives: Their cytotoxicity and antibacterial activity, Pakistan Journal of Scientific and Industrial Research, 37(10): 439-441, 1994.

Saiki, Amplification of Genomic DNA, in PCR Protocols, Innis et al., Eds., Academic Press, San Diego, CA 1990, pp. 13-20.

Sambrook et al, Molecular Cloning: A Laboratory Manual, 1989, Cold Spring Harbor Laboratory Press, Cold Spring Harbor N.Y, pp. 16.30-16.37.

Sandlow, et al., Expression of c-KIT and its Ligand, Stem Cell Factor, in Normal and Subfertile Human Testicular Tissue, 1996, J. Androl. 17:403-408.
Sawada et al., 4-(Benzoylindolizinyl)butyric acids; Novel nonsteroidal inhibitors of steroid 5;1-reductase. III, Chemical and Pharmaceutical Bulletin (2001), 49(7): 799-813.
Sawada, et al., Role of Cytokines in Leukemic type Growth of Myelodysplastic CD34+ Cells, 1996, Blood 88:319-327.
Sawai, et al., Aberrant growth of granulocyte-macrophage progenitors in juvenile chronic myelogenous leukemia in serum-free culture, 1996, Exp. Hem. 2:116-122.
Scheffner, et al., The E6 Oncoprotein Encoded by Human Papillomavirus Types 16 and 18 Promotes the Degredation of p53, Cell 63:1129-1136 (1990).
Schiemann and Winkelmüller, p-Fluorobenzoic Acid, Org. Syn. Coll. vol. 2:299, 1943.
Schneider, et al., Functional Purification of a Bacterial ATP-Binding Cassette Transporter Protein (MaIK) from the Cytoplasmic Fraction of an Overproducing Strain, (1995) Protein Expr. Purif. 6435:10.
Schneller et. al., Synthesis of 4-Amino-1 H-pyrrolo[2,3-b]pyridine {1,7-Dideazaadenine) and 1H-Pyrrolo[2,3-b]pyridine-4-ol (1,7-Dideazahypoxanthine), J. Org. Chem. 1980, 45:4045.
Schuhmann, et al., Immobilization of Enzymes on Langmuir-Blodgett Films via a Membrane-Bound Receptor. Possible Applications for Amperometric Biosensors, Adv. Mater. 3:388-391 (1991).
Schummer, et al., Inexpensive Handheld Device for the Construction of High-Density Nucleic Acid Arrays, Biotechniques 23:1087-1092 (1997).
Schweizer, et al., Combinatorial Synthesis of Carbohydrates, Curr Opin. Chem. Biol., 3:291-298 (1999).
Sclabas, G.M. et al, Overexpression of Tropomysin-Related Kinase B in Metastatic Human Pancreatic Cancer Cells, Clin. Cancer. Res. V11:440-449 (2005).
Secor, et al., Mast cells are essential for early onset and severe disease in a murine model of multiple sclerosis. J. Exp. Med. 5:813-821 (2000).
Selvin, P., Fluorescence Resonance Energy Transfer, Meth. Enzymol. 246:300-345 (1995).
Sheets, et al., Efficient Construction of a Large Nonimmune Phage Antibody Library: The Production of High-Affinity Human Single-Chain Antibodies to Protein Antigens, Proc Natl Acad Sci USA 95:6157-6162 (1998).
Shibata et al, Alveolar macrophage deficiency in osteopetrotic mice deficient in macrophage colony-stimulating factor is spontaneously corrected with age and associated with matrix metalloproteinase expression and emphysema, Blood 2001, 98: pp. 2845-2852.
Siegel, et al., Mass Spectral Analysis of a Protein Complex Using Single-Chain Antibodies Selected on a Peptide Target: Applications to Functional Genomics, Journal of Molecular Biology 302:285-293 (2000).
Sigal, et al., A Self-Assembled Monolayer for the Binding and Study of histidine-Tagged Proteins by Surface Plasmon Resonance, (1996) Anal. Chem. 68:490-497.
Smalley et al., c-Kit signaling as the driving oncogenic event in sub-groups of melanomas. Histol Histopathol, 24:643-650, 2009.
Solinas-Toldo, et al., Matrix-Based Comparative Genomic Hybridization Biochips to Screen for Genomic Imbalances, Genes, Chromosomes & Cancer 20:399-407 (1997).
Song et al., Isomerism of Bis(7-azaindolyl)methane, Organic Letters (2002), 4:23, 4049-4052, Table of content p. 1-16 and Supporting information p. 1-15.
Sperling, et al., Expression of the Stem Cell Factor Receptor C-Kit (CD117) in Acute Leukemias, Haemat 82:617-621 (1997).
Stanulla, et al., Coexpression of Stem Cell Factor and Its Receptor c-Kit in Human Malignant Glioma Cell Lines, Act Neuropath 89:158-165 (1995).
Steinman, Multiple sclerosis: A coordinated immunological attack against myelin in the central nervous system. Cell 85:299-302 (1996).
Strohmeyer, et al., Expression of the C-kit Proto-Oncogene and its Ligand Stem Cell Factor (SCF) in Normal and Malignant Human Testicular Tissue, 1995, J. Urol. 153:511-515.
Strohmeyer, et al. Expression of the hst-1 and c-kit Protooncogenes in Human Testicular Germ Cell Tumors, Canc. Res. 51:1811-1816 (1991).
Su & Tsou, Synthesis of bromo-substituted Idoxyl Esters for Cytochemical Demonstration of Enzyme Activity, J. Am. Chem. Soc.,82, 1960, 1187.
Sun, et al., Design, Synthesis, and Evaluations of Substituted 3-[(3- or 4-Carboxyethylpyrrol-2-yl) Methylidenyl]indolin-2-Ones as Inhibitors of VEGF, PGF, and PDGF Receptor Tyrosine Kinases, J. Med. Chem. 42:5120-5130 (1999).
Supplemental Notice of Allowance dated Jul. 23, 2008 for U.S. Appl. No. 11/154,988.
Supplemental Notice of Allowance dated Sep. 8, 2008 for U.S. Appl. No. 11/154,988.
Supplementary Search Report dated Aug. 4, 2009 for European Application No. 04814626.0.
Tada, et al., Analysis of Cytokine Receptor Messenger RNA Expression in Human Glioblastoma Cells and Normal Astrocytes by Reverse-Transcription Polymerase Chain Reaction, J. Neuro 80:1063-1073 1994.
Takahashi et al, ret Transforming Gene Encodes a Fusion Protein Homologous to Tyrosine Kinases, Mol Cell Biol. 7:1378-1385 (1987).
Tang, X. et al., An RNA interference-based screen identifies MAP4K4/NIK as a negative regulator of PPARy, adipogenesis, and insulin-responsive hexose transport, Proc. Natl. Acad. Sci. U. S. A. 103:2087-2092 (2006).
Taylor et al. The Rapid Generation of Oligonucleotide-directed Mutations at High Frequency Using Phosphorothloate-Modified DNA: (1985) Nucl. Acids Res. 13:8764-8785.
Teitelbaum, Bone Resorption by Osteoclasts, Science. 2000;289:1504.
Thibault et. al., Concise and Efficient Synthesis of 4-fluoro-1H-pyrrolo[2,3-b] pyridine, Org. Lett. 2003, 5:5023-5025.
Thomas et al, The Eosinophil and its Role in Asthma, Gen. Pharmac 27:593-597 (1996).
Toyota, et al., Expression of c-kit and kit Ligand in Human Colon Carcinoma Cells, 1993, Turn Biol 14:295-302.
Tsujimura, et al., Substitution of an Aspartic Acid Results in Constitutive Activation of c-kit Receptor Tyrosine Kinase in a Rat Tumor Mast Cell Line RBL-2H3, 1995, Int. Arch. Aller. Immunol 106:377-385.
Tsujimura, et al.,Ligand-Independent Activation of c-kit Receptor Tyrosine Kinase in a Murine Mastocytoma Cell Line P-815 Generated by a Point Mutation, Blood 9:2619-2626 (1994).
Tsujimura, T., Role of c-kit Receptor Tyrosine Kinase in the Development, Survival and Neoplastic Transformation of Mast Cells, Pathol Int 46:933-938 (1996).
Turner, et al., Nonhematopoeietic Tumor Cell Lines Express Stern Cell Factor and Display c-kit Receptors, 1992, Blood 80:374-381.
Undenfriend, et al., Scintillation Proximity Assay: A Sensitive and Continuous Isotopic Method for Monitoring Ligand/Receptor and Antigen/Antibody Interactions, Anal. Biochem., 161:494-500 (1987).
Uritskaya et al., STN Accession No. 1974-27133; Document No. 08:27133; Abstract of Khimiya Geterotsiklicheskikh Soedinenii (1973, (10), 1370-3).
US Office Action dated Jan. 4, 2008 for U.S. Appl. No. 11/154,988.
US Office Action dated Jun. 6, 2007 for U.S. Appl. No. 11/016,350.
US Office Action dated Aug. 22, 2007 for U.S. Appl. No. 11/487,134.
US Office Action dated Sep. 22, 2009 for U.S. Appl. No. 11/986,667.
US Office Action dated Sep. 23, 2009 for U.S. Appl. No. 11/962,044.
US Office Action dated Oct. 19, 2007 for U.S. Appl. No. 11/154,988.
US Office Action dated Oct. 26, 2007 for U.S. Appl. No. 11/016,350.
i US Office Action dated Feb. 17, 2010 for U.S. Appl. No. 11/962,044.
US Office Action dated Feb. 19, 2010 for U.S. Appl. No. 11/435,381.
US Office Action dated Feb. 26, 2010 for U.S. Appl. No. 11/986,667.
US Office Action dated Jun. 1, 2009 for U.S. Appl. No. 11/435,381.
US Office Action dated Mar. 4, 2009 for U.S. Appl. No. 11/435,381.
Valent, P., Biology, Classification and Treatment of Human Mastocytosis, Wein/Klin Wochenschr 108:385-397 (1996).

Van Regenmortel, Use of biosensors to characterize recombinant proteins, (1994), Developments in Biological Standardization, 83:143-51.

Vely F. et al., BIAcore® analysis to test phosphopeptide-SH2 domain interactions, (2000), Methods in Molecular Biology, 121:313-21.

Verfaillie, Chronic myelogenous leukemia: too much or too little growth, or both?; Leukemia, 1998, 12:136-138.

Viskochil, D., It Takes Two to Tango: Mast Cell and Schwann Cell Interactions in Neurofibromas, J Clin Invest., 112:1791-1793 (2003).

Vliagoftis, et al., The protooncogene c-kit and c-kit ligand in human disease, Journ. Clin. Immunol, 100:435-440 (1997).

Weber, P., Physical Principles of Protein Crystallization, Adv. Protein Chem., 41:1-36 (1991).

Wendt, et al, Identification of novel binding interactions in the development of potent, selective 2-naphthamidine inhibitors of urokinase, synthesis, structural analysis, and SAR of y-Phenyl amide 6-substitution. J. Med. Chem., 47(2):303 (2004).

Werness, et al., Association of Human Papillomavirus Types 16 and 18 E6 Proteins with p53, Science 248:76-79 (1990).

Wessjohann, L., Synthesis of Natural-Product-Based Compound Libraries, Curr Opin Chem Biol., 4:303-309 (2000).

Wharam, et al., Specific Detection of DNA and RNA Targets Using a Novel Isothermal Nucleic Acid Amplification Assay Based on the Formation of a Three-Way Junction Structure, Nucleic Acids Res., 29:1-8 (2001).

Wild, K.D. et al, Antibodies to Nerve Growth Factor Reverse Established Tactile Allodynia in Rodent Models of Neuropathic Pain without Tolerance, J. Pharmacol. Exp. Ther. 322:282-287 (2007).

Williams et al., Dissection of the Extracellular Human Interferon y Receptor a-Chain into two Immunoglobulin-like domains. Production in an *Escherichia coli* Thioredoxin Gene Fusion Expression system and Recognition by Neutralizing Antibodies, (1995) Biochemistry 34:1787-1797.

Woon, et al., Contruction and Characterization of a 10-Fold Genome Equivalent Rat P1-Derived Artificial Chromosome Library, Genomics, 50:306-316 (1998).

Wright, J.H. et al., The STE20 Kinase KGK Is Broadly Expressed in Human tumor Cells and Can Modulate Cellular Transformation, Invasion, and Adhesion, Mol. Cell. Biol. 23:2068-2082 (2003).

Wuthrich, K., Chapter 10: Three-Dimensional Protein Structures by NMR, NMR of Proteins and Nucleic Acids, 10:176-199 (1986).

Wyckoff et al., Direct visualization of macrophage-assisted tumor cell intravasation in mammary tumors. Cancer Research, 67(6): 2649-2656, 2007.

Xu et al, Modulation of Endothelial Cell function by Normal Polyspecific Human Intraveneous immunoglobulins, Am. J. Path. 1998;153:1257-1266.

Yakhontov et al., Derivatives of 7-azaindole. XV. Electrophilic substitution of 4-methyl-7-azaindole and its derivatives, Zhurnal Obshchei Khimii (1965), 1(11): 2032-2040. (English abstract only).

Yang et al., Nf1-Dependent tumors require a microenvironment containing Nf1+/_ -and c-kit-Dependent bone marrow, Cell, 135:437-448, 2008.

Yang et. al., Synthesis of some 5-substituted indoles. Heterocycles, 34:1169 (1992).

Yang, et al., Neurofibromin-Deficient Schwann Cells Secrete a Potent Migratory Stimulus for NF1+/− Mast Cells, J Clin Invest., 112:1851-1861 (2003).

Yang, Z.F. et al, Identification of Brain-Derived Neurotrophic Factor as a Novel Functional Protein in Hepatocellular Carcinoma, Cancer Res. 65:219-225 (2005).

Yao, Z. et al., A Novel Human STE20-related Protein Kinase, HGK, That Specifically Activates the c-Jun N-terminal Kinase Signaling Pathway, J. Biol. Chem. 274:2118-2125 (1999).

Yee, et al., Role of kit-Ligand in Proliferation and Suppression of Apoptosis in Mast Cells: Basis for Radiosensitivity of White Spotting and Steel Mutant Mice, J. Exp. Med., 179:1777-1787 (1994).

Yeung et al., Friedel-Crafts acylation of indoles in acidic imidazolium chloroaluminate ionic liquid at room temperature, Tetrahedron Letters, (2002), 43(33), 5793-5795.

Yuan, et al., Human Peripheral Blood Eosinophils Express a Functional c-kit Receptor for Stem Cell Factor that Stimulates Very Late Antigen 4 (VLA-4)-Mediated Cell Adhesion to Fibronectin and Vascular Cell Adhesion Molecule 1 (VCAM-1), J. Exp. Med. 186:313-323 (1997).

Zhang et al., An effective procedure for the acylation of azaindoles at C-3, Journal of Organic Chemistry (2002), 67(17): 6226-6227 and p. S1-S30.

Allegretti, et al., Palladium-Catalysed Functionalisation at 4- and 6-Position of the 7-Azaindole System, Synlett 5:609-612 (2001).

Alvarez, et al., Synthesis of 3-Aryl- and 3-Heteroaryl-7-Azaindoles, Synthesis 4:615-620 (1999).

Amiel, et al., Hirschsprung disease, associated syndromes and genetics: a review, J Med Genet, (2008), 45:1-14.

Anderson, et al., Cooperative Catalyst Effects in Palladium-Mediated Cyanation Reactions of Aryl Halides and Triflates, J. Org. Chem. 63:8224-8228 (1998).

Antonini, et al., Synthesis of 4-Amino-1-β-D-Ribofuranosy1-1H-pyrrolo[2,3-b]pyridine (1-Deazatubercidin) as a Potential Antitumor Agent, J. Med. Chem. 25:1258-1261 (1982).

Barton, et al., The chemistry of pentavalent organobismuth reagents. Part X. Studies on the phenylation and oxidation of phenols, Tetrahedron, 43:323-332 (1987).

Bode, et al, Mutations in the tyrosine kinase domain of the EGFR gene are rare in synovial sarcoma, Modem Pathology, (2006), 19:541-547.

Bongarzone, et al., High Frequency of Activation of Tyrosine Kinase Oncogenes in Human Papillary Thyroid Carcinoma, Oncogene 4(12):1457-1462 (1989).

Castellone, et al., A novel de novo germ-line V292M mutation in the extracellular region of RET in a patient with phaeochromocytoma and medullary thyroid carcinoma: functional characterization, Clinical Endocrinology, (2010), 73:529-534.

Chayer, et al., Synthesis of Carboranylpyrroles, Tetrahedron Lett. 42(44):7759-7761 (2001).

Coelho, et al., Studies of RET gene expression and acetylcholinesterase activity in a series of sporadic Hirschsprung's disease, Pediatr Surg Int, (2008), 24:1017-21.

Colman, P.M., Structure-Based Drug Design, Current Opinion in Struc. Biol. 4: 868-874 (1994).

Communication Pursuant to Article 94(3) EPC dated Feb. 15, 2010 for EP Application No. 05789913.0.

Communication pursuant to Article 94(3) EPC dated Dec. 15, 2009 for European Application No. 04814626.0.

Communication pursuant to Article 94(3) EPC dated Jun. 6, 2011 in EP application 04814626.

Communication Pursuant to Article 94(3)EPC dated Jul. 9, 2009 for European Application No. 06773861.7.

Communication Pursuant to Article 94(3)EPC dated Sep. 15, 2009 for European Application No. 06813186.1.

Communication Pursuant to Article 94(3)EPC dated Dec. 2, 2009 for EP Application No. 07864681.7.

Communication Pursuant to Article 94(3)EPC dated Dec. 21, 2009 for European Application No. 06773861.7.

Coste, et al., Coupling N-Methylated Amino Acids Using PyBroP1 and PyCloP Halogenophosphonium Salts: Mechanism and Fields of Application, Journal of Organic Chemistry 59:2437-2446 (1994).

Donis-Keller, et al., Mutations in the RET Proto-Oncogene are Associated with MEN 2A and FMTC, Hum Mol Genet. 2(7):851-856 (1993).

Dube and Scholte, Reductive N-Alkylation of Amides, Carbamates and Ureas, Tetrahedron Lett. 40:2295-2298 (1999).

Durbec, et al., GDNF Signalling Through the RET Receptor Tyrosine Kinase, Nature 381:789-793 (1996).

Extended European Search Report dated Mar. 6, 2012 in related EP Application No. 1117370.1.

Felder, E.R., The Challenge of Preparing and Testing Combinatorial Compound Libraries in the Fast Lane, at the Front End of Drug Development, Chimia 48:531-541 (1994).

Franz and Martin, Sulfuranes. X. A Reagent for the Facile Cleavage of Secondary Amides, JACS, 95(6):2017-2019 (1973).

Galofre, et al., Evaluation and Treatment of Thyroid Nodules: A Clinical Guide, (2008), Mt Sinai J Med, 75:299-311.

Gordon, and Ford, Detection of Peroxides and Their Removal, The Chemist's Companion: A Handbook of Practical Data, Techniques, and References p. 437 (1972).

Grieco, et al., PTC is a Novel Rearranged Form of the ret Proto-Oncogene and is Frequently Detected in Vivo in Human Thyroid Papillary Carcinomas, Cell 60(4):557-563 (1990).

Guida, W., Software for Structure-Based Drug Design, Current Opinion in Struc. Biol. 4:777-781 (1994).

Hayashi, et al., Dichloro[1,1 19-bis(diphenylophosphino)ferrocene]palladium-(II), An Effective Catalyst for Cross-Coupling of Secondary and Primary Alkyl Grignard and Alkylzinc Reagents with Organic Halides, J. Am. Chem. Soc. 106:158-163(1984).

Haydock, et al., Analogues of clofibrate and clobuzarit containing fluorine in the side chains, European Journal of Medicinal Chemistry, 19:205-214 (1984).

Heinrich, M. C. et al., "Inhibition of KIT Tyrosine Kinase Activity: A Novel Molecular Approach to the Treatment of KIT-Positive Malignancies," J. Clin. Oncol., vol. 20, No. 6, pp. 1692-1703, Mar. 15, 2002.

International Search Report dated Oct. 5, 2010 for PCT Application No. PCT/US2010/029489.

Ishizaka, et al., Human ret Proto-Oncogene Mapped to Chromsome 10q11.2, Oncogene 4(12):1519-1521 (1989).

Jensen et al, Pharmacological targeting of the KIT growth factor receptor: a therapeutic consideration for mast cell disorders, Brit J Pharmacology, (2008), 154:1572-1582.

Jing, et al., GDNF-Induced Activation of the Ret Protein Tyrosine Kinase is Mediated by GDNFR-a, a Novel Receptor for GDNF, Cell 85:1113-1124 (1996).

Jones, et al., Antiestrogens. 2. Structure-Activity Studies in a Series of 3-Aroyl-2-arylbenzo[b]thiophene Derivatives Leading to [6-Hydroxy-2-(4-hydroxyphenyl)benzo(b)thien-3-yl](4-[2-(1-piperidiny)ethoxy]-phenyl]methanone Hydrochloride (LY156758), a Remarkably Effective Estrogen Antagonist with Only Minimal Intrinsic Estrogenicity, J.Med.Chem., 27:1057-1066 (1984).

Katritzky, et al., Regiospecific C-Acylation of Pyrroles and Indoles Using N-Acylbenzotriazoles, J. Org. Chem. 68:5720-5723 (2003).

Konishi, et al, Overexpression of leucocyte common antigen (LAR) P-subunit in thyroid carcinomas, Brit J Cancer, (2003), 88:1223-1228.

Leuner, C. et al., "Improving drug solubility for oral delivery using solid dispersions", European J. of Pharm. Biopharm., (2000), 50, pp. 47-60.

Luo, et al., Close Linkage with the RET Proto-Oncogene and Boundaries of Deletion Mutations in Autosomal Dominant Hirschsprung Disease, Hum Mol Genet. 2(11):1803-1808 (1993).

Machens, et al., Modification of multiple endocrine neoplasia 2A phenotype by cell membrane proximity of RET mutations in exon 10, Endocrine-Related Cancer, (2009), 16:171-177.

Matsumoto and Zografi, Physical properties of solid molecular dispersions of indomethacin with poly(vinylpyrrolindone) and poly(vinylpyrrolidone-co-vinyl-acetate) in relation to indomethacin crystallization. Pharmaceutical Research, 16:11, 1722-1728, 1999.

Minakata et al., Regioselective Funtionalization of 1H-Pyrrolo[2,3-b]pyridine Via its N-Oxide, Synthesis pp. 661-663 (1992).

Mokhtari, et al, Potential utility of small tyrosine kinase inhibitors in the treatment of diabetes, Clinical Science, (2010), 118(4):241-247.

Nagafuji and Cushman, A General Synthesis of Pyrroles and Fused Pyrrole Systems from Ketones and Amino Acids, J. Org. Chem. 61:4999-5003 (1996).

Nahm and Weinreb, N-Methoxy-N-Methylamides as Effective Acylating Agents, Tetrahedron Lett. 22(39):3815-3818 (1981).

Nakai, et al., New Potent Antagonists of Leukotrienes C4 and D4. 1. Synthesis and Structure-Activity Relationships, J.Med.Chem, 31:84-91 (1988).

Non Final Office Action dated Apr. 18, 2012 in related U.S. Appl. No. 12/958,376.

Office Communication dated Apr. 22, 2010 from related application EP 06773861.

Olah, et al., Synthetic Methods and Reactions: Part 209. Improved Preparation of Aldehydes and Ketones from N,N-Dimethylamides and Grignard Reagents, Synthesis pp. 228-230 (1984).

Ottoni, et al., Efficient and Simple Methods for the Introduction of the Sulfonyl, Acyl and Alkyl Protecting Groups on the Nitrogen of Indole and its Derivatives, Tetrahedron 54:13915-13928 (1998).

Partial European Search Report dated Oct. 26, 2011 for EP Patent Application No. 11173701.1.

Santoro, et al., The ret Proto-Oncogene is Consistently Expressed in Human Pheochromocytomas and Thyroid Medullary Carcinomas, Oncogene, 5(10):1595-1598 (1990).

Shan et al., Prodrug strategies based on intramolecular cyclization reactions. Journal of Pharmaceutical Sciences, 86:7, 765-767, 1997.

Sun, C., Recent Advances in Liquid-Phase Combinatorial Chemistry, Comb. Chem. & High Throughput Screening 2:299-318 (1999).

Supplemental Notice of Allowance dated Sep. 8, 2010 in U.S. Appl. No. 11/473,347.

Takahashi, et al., Activation of a Novel Human Transforming Gene, ret, by DNA Rearrangement, Cell 42(2):581-588 (1985).

Takahashi, et al., Cloning and Expression of the ret Proto-Oncogene Encoding a Tyrosine Kinase with Two Potential Transmembrane Domains, Oncogene 3(5):571-578 (1988).

Thomas, et. al., Light-Emitting Carbazole Derivatives: Potential Electroluminescent Materials, J. Am. Chem. Soc. 123:9404-9411 (2001).

Toste, et al., A Versatile Procedure for the Preparation of Aryl Thiocyanates Using N-Thiocyanatosuccinimide (NTSs), Synth. Comm. 25(8):1277-1286 (1995).

Trupp, et al., Functional Receptor for GDNF Encoded by the c-ret Proto-Oncogene, Nature 381:785-789 (1996).

US Notice of Allowance dated May 27, 2010 in related U.S. Appl. No. 11/435,381.

US Notice of Allowance dated Jun. 6, 2008 for U.S. Appl. No. 11/154,988.

US Notice of Allowance dated Jan. 6, 2011 in U.S. Appl. No. 12/244,730.

US Notice of Allowance dated Jun. 18, 2010 in U.S. Appl. No. 11/473,347.

US Notice of Allowance dated Jul. 27, 2010 in related U.S. Appl. No. 11/435,381.

US Notice of Allowance dated Aug. 11, 2010 in U.S. Appl. No. 11/960,590.

US Notice of Allowance dated Aug. 13, 2010 in related U.S. Appl. No. 11/962,044.

US Notice of Allowance dated Aug. 6, 2010 in U.S. Appl. No. 11/986,667.

US Notice of Allowance dated Dec. 8, 2011 in related U.S. Appl. No. 13/216,200.

US Notice of Allowance dated May 17, 2012 in related U.S. Appl. No. 11/961,901.

US Office Action dated Nov. 8, 2010 in U.S. Appl. No. 12/082,665.

US Office Action dated Jul. 22, 2010 in related U.S. Appl. No. 12/244,730.

US Office Action dated Aug. 2, 2007 in related U.S. Appl. No. 11/016,350.

US Office Action dated Feb. 29, 2012 in related U.S. Appl. No. 12/906,980.

US Office Action dated May 15, 2008 in related U.S. Appl. No. 11/487,134.

US Office Action Dec. 18, 2009 for US Appl. No. 11/473,347.

US Supplemental Notice of Allowance dated Jul. 23, 2008 for U.S. Appl. No. 11/154,988.

US Supplemental Notice of Allowance dated Sep. 8, 2008 for U.S. Appl. No. 11/154,988.

Vachon and Nairn, The influence of microencapsulation using Eudragit RS100 on the hydrolysis kinetics of acetylsalicylic acid. J. Microencapsulation, 14:281-301 (1997).

Van Heyningen,V., One Gene—Four Syndromes, Nature 367:319-320 (1994).

Vandelli et al., Analysis of release data in the evaluation of the physical state of progesterone in matrix systems. J. Microencapsulation, 10:1, 55-65, 1993.

Wells, et al, Targeting the RET Pathway in Thyroid Cancer, Clin Cancer Res, (2009), 15(23):7119-7123.

Zanon, et. al., Copper-Catalyzed Domino Halide Exchange-Cyanation of Aryl Bromides, J. Am. Chem. Soc. 125:2890-2891 (2003).

Calabresi, et al., Section IX, "Chemotherapy of neoplastic diseases in Goodman & Gilman's The Pharmacological Basis of Therapeutics," Tenth Edition, McGraw-Hill Medical Publishing Division, (2001), p. 1381, 1383-1385 and 1388 (2001).

He, et al., "Gamma-secretase activating protein, a therapeutic target for Alzheimer's disease," Nature, (2010), 467(7311):95-98.

Holmes, et al., "Long-term effects of AB42 immunisation in Alzheimer's disease: follow-up of a randomised, placebo-controlled phase I trail," The Lancet, (2008), 372:216-233.

Malaysian Examination Report dated Aug. 15, 2012 in related Malaysian Appl Serial No. PI 20092547.

Malaysian Substantive Examination Report dated Aug. 15, 2012 in related Malaysian Appl No. PI 20092040.

Natali, et al., "Breast cancer is associated wuth loss of the c-kit oncogene product," Int. J. Cancer, (1992), 52:713-717.

Norwegian Office Action dated Aug. 15, 2012 in related Norwegian Patent Appl No. 20076659 (With English Translation).

Office Action (with English Translation) dated Apr. 23, 2012 in related Israeli Patent Application No. 199194.

Philippines Office Action dated Jul. 27, 2012 in related Philippines Appl. No. 1-2009-501241.

Philippines Office Action dated Jul. 27, 2012 in related Philippines Patent Appl No. 12009501009.

Taiwanese Office Action dated Jun. 26, 2012 in related Taiwan Appl Serial No. 099110011 (With English Translation).

Toste, et al., "A Versatile Procedure for the Preparation of Aryl Thiocyanates Using N-Thiocyanatosuccinimide (NTS)," Synth. Comm., (1995), 25(8):1277-1286.

US Office Action dated Sep. 18, 2012 in related U.S. Appl. No. 13/546,923.

US Office Action dated Oct. 3, 2012 in related U.S. Appl. No. 12/752,035.

US Office Action dated Jul. 17, 2012 in related U.S. Appl. No. 12/958,379.

U.S. Office Action dated Oct. 17, 2012 in related U.S. Appl. No. 12/906,980.

Rapp, et al., Raf kinases in lung tumor development, Advan. Enzyme Regul., 43:183-195 (2003).

* cited by examiner

COMPOUNDS AND METHODS FOR KINASE MODULATION, AND INDICATIONS THEREFOR

RELATED PATENT APPLICATIONS

This application is a U.S. Divisional Application of U.S. application Ser. No. 11/473,347 filed Jun. 21, 2006, which claims the benefit of U.S. Prov. App. No. 60/692,960, filed Jun. 22, 2005, and U.S. Prov. App. No. 60/731,528, filed Oct. 28, 2005, which are incorporated herein by reference in their entireties and for all purposes.

FIELD OF THE INVENTION

The present invention relates to kinases and compounds which modulate kinases, and uses therefor. Particular embodiments contemplate disease indications which are amenable to treatment by modulation of kinase activity by the compounds of the present invention.

BACKGROUND OF THE INVENTION

The information provided herein is intended solely to assist the understanding of the reader. None of the information provided nor references cited is admitted to be prior art to the present invention. Each of the references cited herein is incorporated in its entirety.

Receptor protein kinases regulate key signal transduction cascades that control or are involved in the control of a plethora of physiological functions including cellular growth and proliferation, cell differentiation, cellular development, cell division, cell adhesion, stress response, short-range contact-mediated axonal guidance, transcription regulation, aberrant mitogenesis, angiogenesis, abnormal endothelial cell-cell or cell-matrix interactions during vascular development, inflammation, lymphohematopoietic stem cell activity, protective immunity against specific bacteria, allergic asthma, aberrant tissue-specific responses to the activation of the INK signal transduction pathway, cell transformation, memory, apoptosis, competitive activity-dependent synapse modification at the neuromuscular synapse, immunological mediation of disease, and calcium regulation.

Specific disease states associated with aberrant regulation of protein kinases include, for example without limitation, acrocephalo-syndactyly type I, acute myeloid leukemia, AIDS-induced non-Hodgkin's lymphoma, Alzheimer's disease, amyotrophic lateral sclerosis, arthritis, asthma, atherosclerosis, atopic dermatitis, autoimmune diseases, bacterial infection, bladder cancer, cancer of the breast, cancer of the central nervous system, cancer of the colon, cancer of the endometrium, cancer of the fallopian tube, cancer of the gastrointestinal tract, cancer of the ovary, heart failure, chronic myeloid leukemia, colon carcinoma, colorectal cancer, chronic obstructive pulmonary disease (COPD), Crouzon Syndrome, diabetes, diabetic nephropathy, emphysema, endometriosis, epidermoid cancer, fibrotic disorders, gastrointestinal stromal tumor (GIST), glomerulonephritis, Graves' disease, head injury, hepatocellular carcinoma, Hirschsprung's disease, human gliomas, immunodeficiency diseases, inflammatory disorders, ischemic stroke, Jackson-Weiss syndrome, leiomyosarcoma, leukemias, lupus nephritis, malignant melanoma, malignant nephrosclerosis, mastocytosis, mast cell tumors, melanoma of the colon, MEN2 syndromes, metabolic disorders, migraine, multiple sclerosis, myeloproliferative disorders, nephritis, neurodegenerative diseases, neurotraumatic diseases, non small cell lung cancer, organ transplant rejection, osteoporosis, pain, Parkinson's disease, Pfeiffer Syndrome, polycystic kidney disease, primary lymphoedema, prostate cancer, psoriasis, vascular restenosis, rheumatoid arthritis, dermal and tissue scarring, selective T-cell defect (STD), severe combined immunodeficiency (SCID), small cell lung cancer, spinal cord injury, squamous cell carcinoma, systemic lupus erythematosis, testicular cancer, thrombotic microangiopathy syndromes, Wegener's granulomatosis, X-linked agammaglobulinemia, viral infection, diabetic retinopathy, alopecia, erectile dysfunction, macular degeneration, chronic lymphocytic leukemia (CLL), myelodysplastic syndrome (MDS), neurofibromatosis, and tuberous sclerosis. Accordingly, there is a need in the art for additional compounds and methods of use thereof for the modulation of receptor protein kinases.

This application is related to the following published patent applications: WO 2004024895, US 20040142864, WO 2004078923, US 20050170431, WO 2005028624, US 20050164300, and WO 2005062795, each of which are hereby incorporated by reference herein in their entireties including all specifications, figures, and tables, and for all purposes.

SUMMARY OF THE INVENTION

The present invention concerns compounds active on protein kinases in general, including, but not limited to, Abl, Akt1, Akt2, Akt3, ALK, Alk5, B-Raf, Brk, Btk, Cdk2, CDK4, CDK5, CDK6, CHK1, c-Raf-1, Csk, EGFR, EphA1, EphA2, EphB2, EphB4, Erk2, Fak, FGFR1, FGFR2, FGFR3, FGFR4, Flt1, Flt3, Flt4, Fms, Frk, Fyn, Gsk3α, Gsk3β, HCK, Her2/Erbb2, Her4/Erbb4, IGF1R, IKK beta, Irak4, Itk, Jak1, Jak2, Jak3, Jnk1, Jnk2, Jnk3, Kdr, Kit, LCK, MAP2K1, MAP2K2, MAP4K4, MAPKAPK2, Met, Mnk1, MLK1, p38, PDGFRA, PDGFRB, PDPK1, Pim1, Pim2, Pim3, PKC alpha, PKC beta, PKC theta, Plk1, Pyk2, Ret, ROCK1, ROCK2, Ron, Src, Stk6, Syk, TEC, Tie2, TrkA, Yes, and/or Zap70, including any mutations of these kinases, and the use thereof in treating disease and conditions associated with regulation of the activity of the kinase. In particular, the invention concerns compounds of Formula I as described below. Thus, the invention provides novel use of compounds for therapeutic methods involving modulation of protein kinases, as well as novel compounds that can be used for therapeutic methods involving modulation of protein kinases.

The compounds of Formula I have the following structure:

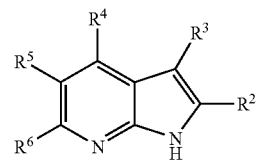

Formula I all salts, prodrugs, tautomers, and isomers thereof,
wherein:
$R^2$, $R^4$, $R^5$, and $R^6$ are independently selected from the group consisting of hydrogen, halogen, optionally substituted lower alkyl, optionally substituted lower alkenyl, optionally substituted lower alkynyl, optionally substituted cycloalkyl, optionally substituted heterocycloalkyl, optionally substituted aryl, optionally substituted heteroaryl, —CN, —NO$_2$, —CR$^a$R$^b$R$^{26}$, and -LR$^{26}$;

$R^3$ is selected from the group consisting of hydrogen, halogen, optionally substituted lower alkyl, optionally substituted lower alkenyl, optionally substituted lower alkynyl, optionally substituted cycloalkyl, optionally substituted heterocycloalkyl, optionally substituted aryl, optionally substituted heteroaryl, —CN, —NO$_2$, —CR$^a$R$^b$R$^{26}$, -LR$^{26}$ and -A-Ar-L$_1$-R$^{24}$;

A is selected from the group consisting of —O—, —S—, —CR$^a$R$^b$—, —NR$^1$—, —C(O)—, —C(S)—, —S(O)—, and —S(O)$_2$—;

$R^1$ is selected from the group consisting of hydrogen, lower alkyl, cycloalkyl, heterocycloalkyl, aryl, heteroaryl, —C(O)R$^7$, —C(S)R$^7$, —S(O)$_2$R$^7$, —C(O)NHR$^7$, —C(S)NHR$^7$, and —S(O)$_2$NHR$^7$, wherein lower alkyl is optionally substituted with one or more substituents selected from the group consisting of fluoro, —OH, —NH$_2$, lower alkoxy, lower alkylthio, mono-alkylamino, di-alkylamino, and —NR$^8$R$^9$, wherein the alkyl chain(s) of lower alkoxy, lower alkylthio, mono-alkylamino, or di-alkylamino are optionally substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino, and cycloalkylamino, provided, however, that any substitution of the alkyl chain carbon bound to O of alkoxy, S of thioalkyl or N of mono- or di-alkylamino is fluoro, further provided, however, that when R$^1$ is lower alkyl, any substitution on the lower alkyl carbon bound to the N of —NR$^1$— is fluoro, and wherein cycloalkyl, heterocycloalkyl, aryl or heteroaryl are optionally substituted with one or more substituents selected from the group consisting of halogen, —OH, —NH$_2$, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino;

$R^7$ is selected from the group consisting of lower alkyl, cycloalkyl, heterocycloalkyl, aryl, and heteroaryl, wherein lower alkyl is optionally substituted with one or more substituents selected from the group consisting of fluoro, —OH, —NH$_2$, lower alkoxy, lower alklylthio, mono-alkylamino, di-alkylamino, and —NR$^8$R$^9$, provided, however, that any substitution of the alkyl carbon bound to the N of —C(O)NHR$^7$, —C(S)NHR$^7$ or —S(O)$_2$NHR$^7$ is fluoro, wherein the alkyl chain(s) of lower alkoxy, lower alkylthio, mono-alkylamino, or di-alkylamino are optionally substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino, and cycloalkylamino, provided, however, that any substitution of the alkyl chain carbon bound to O of alkoxy, S of thioalkyl or N of mono- or di-alkylamino is fluoro, and wherein cycloalkyl, heterocycloalkyl, aryl and heteroaryl are optionally substituted with one or more substituents selected from the group consisting of halogen, —OH, —NH$_2$, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino;

Ar is selected from the group consisting of optionally substituted arylene and optionally substituted heteroarylene;

L at each occurrence is independently selected from the group consisting of -(alk)$_a$-S-(alk)$_b$-, -(alk)$_a$-O-(alk)$_b$-, -(alk)$_a$-NR$^{25}$-(alk)$_b$-, -(alk)$_a$-C(O)-(alk)$_b$-, -(alk)$_a$-C(S)-(alk)$_b$-, -(alk)$_a$-S(O)-(alk)$_b$-, -(alk)$_a$-S(O)$_2$-(alk)$_b$-, -(alk)$_a$-OC(O)-(alk)$_b$-, -(alk)$_a$-C(O)O-(alk)$_b$-, -(alk)$_a$-OC(S)-(alk)$_b$-, -(alk)$_a$-C(S)O-(alk)$_b$-, -(alk)$_a$-C(O)NR$^{25}$-(alk)$_b$-, -(alk)$_a$-C(S)NR$^{25}$-(alk)$_b$-, -(alk)$_a$-S(O)$_2$NR$^{25}$-(alk)$_b$-, -(alk)$_a$-NR$^{25}$C(O)-(alk)$_b$-, -(alk)$_a$-NR$^{25}$C(S)-(alk)$_b$-, -(alk)$_a$-NR$^{25}$S(O)$_2$-(alk)$_b$-, -(alk)$_a$-NR$^{25}$C(O)O-(alk)$_b$-, -(alk)$_a$-NR$^{25}$C(S)O-(alk)$_b$-, -(alk)$_a$-OC(O)NR$^{25}$-(alk)$_b$-, -(alk)$_a$-OC(S)NR$^{25}$-(alk)$_b$-, -(alk)$_a$-NR$^{25}$C(O)NR$^{25}$-(alk)$_b$-, -(alk)$_a$-NR$^{25}$C(S)NR$^{25}$-(alk)$_b$-, and -(alk)$_a$-NR$^{25}$S(O)$_2$NR$^{25}$-(alk)$_b$-;

a and b are independently 0 or 1;

alk is C$_{1-3}$ alkylene or C$_{1-3}$ alkylene substituted with one or more substituents selected from the group consisting of fluoro, —OH, —NH$_2$, lower alkyl, lower alkoxy, lower alkylthio, mono-alkylamino, di-alkylamino, and —NR$^8$R$^9$, wherein lower alkyl or the alkyl chain(s) of lower alkoxy, lower alkylthio, mono-alkylamino or di-alkylamino are optionally substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino and cycloalkylamino, provided, however, that any substitution of the alkyl chain carbon bound to O of alkoxy, S of thioalkyl or N of mono- or di-alkylamino is fluoro;

L$_1$ is —(CR$^a$R$^b$)$_v$- or L, wherein v is 1, 2, or 3;

wherein R$^a$ and R$^b$ at each occurrence are independently selected from the group consisting of hydrogen, fluoro, —OH, —NH$_2$, lower alkyl, lower alkoxy, lower alklythio, mono-alkylamino, di-alkylamino, and —NR$^8$R$^9$, wherein the alkyl chain(s) of lower alkyl, lower alkoxy, lower alkylthio, mono-alkylamino, or di-alkylamino are optionally substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino, and cycloalkylamino, provided, however, that any substitution of the alkyl chain carbon bound to O of alkoxy, S of thioalkyl or N of mono- or di-alkylamino is fluoro; or any two of R$^a$ and R$^b$ on the same or different carbons combine to form a 3-7 membered monocyclic cycloalkyl or 5-7 membered monocyclic heterocycloalkyl and any others of R$^a$ and R$^b$ are independently selected from the group consisting of hydrogen, fluoro, —OH, —NH$_2$, lower alkyl, lower alkoxy, lower alklylthio, mono-alkylamino, di-alkylamino, and —NR$^8$R$^9$, wherein the alkyl chain(s) of lower alkyl, lower alkoxy, lower alkylthio, mono-alkylamino, or di-alkylamino are optionally substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino, and cycloalkylamino, provided, however, that any substitution of the alkyl chain carbon bound to O of alkoxy, S of thioalkyl or N of mono- or di-alkylamino is fluoro, and wherein the 3-7 membered monocyclic cycloalkyl or 5-7 membered monocyclic heterocycloalkyl are optionally substituted with one or more substituents selected from the group consisting of halogen, —OH, —NH$_2$, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino;

$R^8$ and $R^9$ combine with the nitrogen to which they are attached to form a 5-7 membered heterocycloalkyl optionally substituted with one or more substituents selected from the group consisting of fluoro, —OH, —NH$_2$, lower alkyl, fluoro substituted lower alkyl, lower alkoxy, fluoro substituted lower alkoxy, lower alkylthio, and fluoro substituted lower alkylthio;

$R^{25}$ at each occurrence is independently selected from the group consisting of hydrogen, optionally substituted lower alkyl, optionally substituted cycloalkyl, optionally substituted heterocycloalkyl, optionally substituted aryl, and optionally substituted heteroaryl; and $R^{24}$ and $R^{26}$ at each occurrence are independently selected from the group consisting of hydrogen, provided, however, that hydrogen is not bound to any of S(O), S(O)$_2$, C(O) or C(S) of L or L$_1$, optionally substituted lower alkyl, optionally substituted lower alkenyl, provided, however, that when $R^{24}$ or $R^{26}$ is optionally substituted lower alkenyl, no alkene carbon thereof is bound to N, S, O, S(O), S(O)$_2$, C(O) or C(S) of L or L$_1$, optionally substituted lower alkynyl, provided, however, that when $R^{24}$ or $R^{26}$ is optionally substituted lower alkynyl, no alkyne carbon thereof is bound to N, S, O, S(O), S(O)$_2$, C(O) or C(S) of L or L$_1$, optionally substituted cycloalkyl, optionally substituted heterocycloalkyl, optionally substituted aryl, and optionally substituted heteroaryl.

The description above of substituents in Formula I includes descriptions of each combination of the specified substituents. $R^2$, $R^3$, $R^4$, $R^5$, and $R^6$. In some embodiments, at least one of $R^2$, $R^3$, $R^4$, $R^5$ and $R^6$ is other than hydrogen.

In some embodiments involving compounds of Formula I, $R^2$ and $R^6$ are hydrogen, or $R^2$ and $R^5$ are hydrogen, or $R^2$ and $R^4$ are hydrogen, or $R^2$ and $R^3$ are hydrogen, or $R^3$ and $R^6$ are hydrogen, or $R^3$ and $R^5$ are hydrogen, or $R^3$ and $R^4$ are hydrogen, or $R^4$ and $R^6$ are hydrogen, or $R^4$ and $R^5$ are hydrogen, or $R^5$ and $R^6$ are hydrogen, wherein the substitutions at the other positions are non-hydrogen. In some embodiments, $R^2$, $R^3$ and $R^4$ are hydrogen, or $R^2$, $R^3$ and $R^5$ are hydrogen, or $R^2$, $R^3$ and $R^6$ are hydrogen, or $R^2$, $R^4$ and $R^5$ are hydrogen, or $R^2$, $R^4$ and $R^6$ are hydrogen, or $R^2$, $R^5$ and $R^6$ are hydrogen, or $R^3$, $R^4$ and $R^5$ are hydrogen, or $R^3$, $R^4$ and $R^6$ are hydrogen, or $R^3$, $R^5$ and $R^6$ are hydrogen, or $R^4$, $R^5$ and $R^6$ are hydrogen, wherein the substitutions at the other positions are non-hydrogen. In some embodiments, the compounds are mono-substituted with non-hydrogen at one of $R^2$, $R^3$, $R^4$, $R^5$ or $R^6$ (i.e. hydrogen at the other four positions). In some embodiments, compounds of Formula I have non-hydrogen substitution at $R^3$; non-hydrogen substitution at $R^4$; non-hydrogen substitution at $R^5$; non-hydrogen substitution at $R^3$ and $R^4$; non-hydrogen substitution at $R^3$ and $R^5$. In some embodiments, the substitutions as listed are the only substitutions; the substitutions as listed are combined with $R^2$ and $R^6$ as H; the substitutions as listed are combined with substitution at one other of the substitution positions shown in Formula I. The compounds of Formula I, and all sub-embodiments detailed herein, may be used to treat a subject suffering from or at risk for any of the protein kinase mediated diseases or conditions contemplated herein.

In some embodiments, the compound of Formula I has a structure according to the following sub-generic structure Formula Ia:

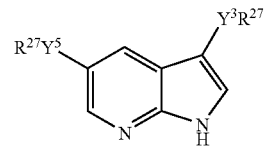

Formula Ia all salts, prodrugs, tautomers, and isomers thereof, wherein $Y^3$ is a bond, —CR$^a$R$^b$, -A-Ar-L$_1$-, or L, and $Y^5$ is a bond. —CR$^a$R$^b$—, or L, and each $R^{27}$ is independently halogen, provided that $Y^3$ or $Y^5$ is a bond, or $R^{26}$, provided, however, that neither of $Y^3R^{27}$ and $Y^5R^{27}$ are hydrogen, wherein $R^a$, $R^b$, L, L$_1$, A, Ar and $R^{26}$ are as defined with reference to Formula I.

In some embodiments of compounds of Formula Ia, $Y^3$ and $Y^5$ are bonds. In some embodiments, $Y^3$ and $Y^5$ are independently —CR$^a$R$^b$— or L. In some embodiments, $Y^3$ and $Y^5$ are independently L. In some embodiments, $Y^3$ and $Y^5$ are independently —CR$^a$R$^b$—. In some embodiments, $Y^3$ is a bond, and $Y^5$ is —CR$^a$R$^b$— or L. In some embodiments, $Y^3$ is a bond, and $Y^5$ is L. In some embodiments, $Y^3$ is a bond, and $Y^5$ is —CR$^a$R$^b$—. In some embodiments, $Y^5$ is a bond, and $Y^3$ is —CR$^a$R$^b$— or L. In some embodiments, $Y^5$ is a bond, and $Y^3$ is L. In some embodiments, $Y^5$ is a bond, and $Y^3$ is —CR$^a$R$^b$—.

In some embodiments of any of the above embodiments of compounds of Formula Ia, each $R^{27}$ is independently optionally substituted cycloalkyl, optionally substituted heterocycloalkyl, optionally substituted aryl, or optionally substituted heteroaryl, or $R^{27}$ is halogen, provided that $Y^3$ or $Y^5$ is a bond. In some embodiments, $Y^5$ is a bond, —CR$^a$R$^b$—, or L, $Y^3$ is —CR$^a$R$^b$—, —O—, —S—, —NR$^{25}$—, —C(O)—, —C(S)—, —S(O)—, or —S(O)$_2$—, wherein $R^{25}$ is as defined for Formula I, and each $R^{27}$ is independently $R^{26}$ or $Y^5R^{27}$ is halogen; in further embodiments, $Y^3$ is —CR$^a$R$^b$— or —C(O)—; in further embodiments, —CR$^a$R$^b$— is —CH$_2$—. In some embodiments, $Y^5$ is a bond, —CR$^a$R$^b$—, or L, $R^{27}$ bound to $Y^5$ is $R^{26}$ or $Y^5R^{27}$ is halogen, $Y^3$ is —CR$^a$R$^b$— or —C(O)—, and $R^{27}$ bound to $Y^3$ is optionally substituted aryl or optionally substituted heteroaryl.

In some embodiments of any of the above embodiments of compounds of Formula Ia, $Y^3R^{27}$ is -A-Ar-L$_1$-R$^{24}$, wherein A, Ar, and L$_1$ are as defined for Formula I, and $R^{24}$ is substituted methyl, optionally substituted C$_{2-6}$ alkyl, optionally substituted lower alkenyl, provided, however, that when $R^{24}$ is optionally substituted lower alkenyl, no alkene carbon thereof is bound to N, S, O, S(O), S(O)$_2$, C(O) or C(S) of L$_1$, optionally substituted lower alkynyl, provided, however, that when $R^{24}$ is optionally substituted lower alkynyl, no alkyne carbon thereof is bound to N, S, O, S(O), S(O)$_2$, C(O) or C(S) of L$_1$, optionally substituted cycloalkyl, optionally substituted heterocycloalkyl, optionally substituted aryl, or optionally substituted heteroaryl, provided, however, that -A-Ar-L$_1$-R$^{24}$ is not

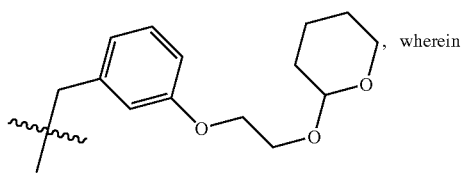

, wherein

-continued

indicates the point of attachment to the 3 position of the azaindole ring; in further embodiments, $R^{24}$ is optionally substituted $C_{2-6}$ alkyl, optionally substituted cycloalkyl, optionally substituted heterocycloalkyl, optionally substituted aryl, optionally substituted heteroaryl, or substituted methyl, wherein methyl is substituted with optionally substituted cycloalkyl, optionally substituted heterocycloalkyl, optionally substituted aryl, or optionally substituted heteroaryl; in further embodiments, when Ar is optionally substituted heteroarylene, the heteroarylene ring is not a five or six membered ring having the structure

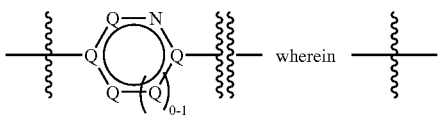

indicates the point of attachment to A and

indicates the point of attachment to $L_1$, and wherein the indicated N is either =N— or —N=, and wherein each Q is independently a heteroaryl ring atom that may be optionally substituted. The term "heteroaryl ring atom" refers to any atom that can be part of a heteroaryl ring structure (i.e., C, N, O, or S).

In some embodiments of any of the above embodiments of compounds of Formula Ia, $Y^3$ and $Y^5$ are independently —O—, —S—, —$CR^aR^b$—, —$NR^{25}$—, —C(O)—, —C(S)—, —S(O)—, or —S(O)$_2$—, where $R^a$, $R^b$ and $R^{25}$ are as defined in Formula I, and each $R^{27}$ is independently optionally substituted lower alkyl, optionally substituted cycloalkyl, optionally substituted heterocycloalkyl, optionally substituted aryl, or optionally substituted heteroaryl; in further embodiments, $Y^5$ is —O—, —$NR^{25}$—, or —S(O)$_2$—, preferably wherein $R^{25}$ is hydrogen or lower alkyl, and $R^{27}$ bound to $Y^3$ is optionally substituted cycloalkyl, optionally substituted heterocycloalkyl, optionally substituted aryl, or optionally substituted heteroaryl, preferably optionally substituted aryl, or optionally substituted heteroaryl; in further embodiments, $Y^3$ is —$CR^aR^b$—, or —C(O)—, preferably —CH$_2$— or —C(O)—, $Y^5$ is —O—, —$NR^{25}$—, or —S(O)$_2$—, preferably —$NR^{25}$—, wherein $R^{25}$ is hydrogen or lower alkyl, and each $R^{27}$ is optionally substituted cycloalkyl, optionally substituted heterocycloalkyl, optionally substituted aryl, or optionally substituted heteroaryl, preferably optionally substituted aryl, or optionally substituted heteroaryl, provided, however, that $Y^3R^{27}$ is not

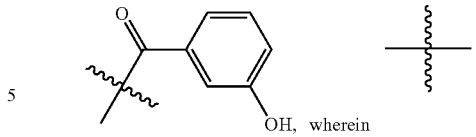

indicates the bond to the 3 position of the 7-azaindole ring, and $Y^5R^{27}$ is not

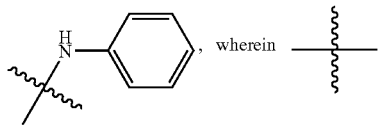

indicates the bond to the 5 position of the 7-azaindole ring, i.e. the compound is not (3-hydroxy-phenyl)-(5-phenylamino-1H-pyrrolo[2,3-b]pyridin-3-yl)-methanone; in further embodiments, when $R^{27}$ bound to $Y^3$ is optionally substituted heteroaryl, the heteroaryl ring is not a five or six membered ring having the structure

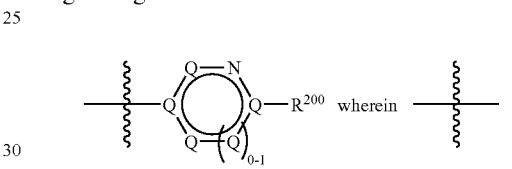

indicates the point of attachment to $Y^3$, and wherein the indicated N is either =N— or —N=, and wherein each Q is independently a heteroaryl ring atom that may be appropriately optionally substituted and wherein $R^{200}$ is other than hydrogen. The term "other than hydrogen" and like terms refer to substituents contemplated herein which are not hydrogen. For example without limitation, if substituent $R^{ex}$ were defined as selected from the group consisting of hydrogen and optionally substituted lower alkyl, then the phrase "$R^{ex}$ is other than hydrogen" would contemplate only optionally substituted lower alkyl, i.e., all options of the substituent, excluding hydrogen.

In some embodiments, the compound of Formula I has a structure according to the following sub-generic structure Formula Ib:

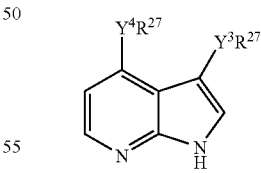

Formula Ib all salts, prodrugs, tautomers, and isomers thereof, wherein $Y^3$ and $Y^4$ are independently a bond, —$CR^aR^b$—, or L, and each $R^{27}$ is independently halogen, provided that $Y^3$ or $Y^4$ is a bond, or $R^{26}$, provided, however, that neither of $Y^3R^{27}$ and $Y^4R^{27}$ are hydrogen, wherein $R^a$, $R^b$, L and $R^{26}$ are as defined with reference to Formula I.

In some embodiments of compounds of Formula Ib, $Y^3$ and $Y^4$ are bonds. In some embodiments, $Y^3$ and $Y^4$ are independently —$CR^aR^b$— or L. In some embodiments, $Y^3$ and $Y^4$ are independently L. In some embodiments, $Y^3$ and $Y^4$ are independently —CR$^a$R$^b$—. In some embodiments, Y$^3$ is a bond and Y$^4$ is —CR$^a$R$^b$— or L. In some embodiments, Y$^3$ is a bond and Y$^4$ is L. In some embodiments, Y$^3$ is a bond and Y$^4$ is —CR$^a$R$^b$—. In some embodiments, Y$^4$ is a bond, and Y$^3$ is —CR$^a$R$^b$— or L. In some embodiments, Y$^4$ is a bond and Y$^3$ is L. In some embodiments, Y$^4$ is a bond and Y$^3$ is —CR$^a$R$^b$—.

In some embodiments of any of the above embodiments of compounds of Formula Ib, each R$^{27}$ is independently optionally substituted cycloalkyl, optionally substituted heterocycloalkyl, optionally substituted aryl, or optionally substituted heteroaryl, or R$^{27}$ is halogen, provided that Y$^3$ or Y$^4$ is a bond. In some embodiments, Y$^4$ is a bond, —CR$^a$R$^b$—, or L, Y$^3$ is —CR$^a$R$^b$—, —O—, —S—, —NR$^{25}$—, —C(O)—, —C(S)—, —S(O)—, or —S(O)$_2$—, wherein R$^{25}$ is as defined for Formula I, and R$^{27}$ is independently R$^{26}$ or Y$^4$R$^{27}$ is halogen; in further embodiments, Y$^3$ is —CR$^a$R$^b$— or —C(O)—; in further embodiments, —CR$^a$R$^b$— is —CH$_2$—. In some embodiments, Y$^4$ is a bond, —CR$^a$R$^b$—, or L, R$^{27}$ bound to Y$^4$ is R$^{26}$ or Y$^4$R$^{27}$ is halogen, Y$^3$ is —CR$^a$R$^b$— or —C(O)—, and R$^{27}$ bound to Y$^3$ is optionally substituted aryl or optionally substituted heteroaryl.

In some embodiments of any of the above embodiments of compounds of Formula Ib, Y$^3$ and Y$^4$ are independently —O—, —S—, —CR$^a$R$^b$—, —NR$^{25}$—, —C(O)—, —C(S)—, —S(O)—, or —S(O)$_2$—, where R$^a$, R$^b$ and R$^{25}$ are as defined in Formula I, and each R$^{27}$ is independently optionally substituted lower alkyl, optionally substituted cycloalkyl, optionally substituted heterocycloalkyl, optionally substituted aryl, or optionally substituted heteroaryl; in a further embodiment Y$^4$ is —O—, —NR$^{23}$—, or —S(O)$_2$—, preferably wherein R$^{25}$ is hydrogen or lower alkyl, and R$^{27}$ bound to Y$^3$ is optionally substituted cycloalkyl, optionally substituted heterocycloalkyl, optionally substituted aryl, or optionally substituted heteroaryl, preferably optionally substituted aryl, or optionally substituted heteroaryl; in a further embodiment Y$^3$ is —CR$^a$R$^b$—, or —C(O)—, preferably —CH$_2$— or —C(O)—, Y$^4$ is —O—, —NR$^{25}$—, or —S(O)$_2$—, preferably —NR$^{25}$—, wherein R$^{25}$ is hydrogen or lower alkyl, and each R$^{27}$ is optionally substituted cycloalkyl, optionally substituted heterocycloalkyl, optionally substituted aryl, or optionally substituted heteroaryl, preferably optionally substituted aryl, or optionally substituted heteroaryl.

In some embodiments, the compound of Formula I has a structure according to the following sub-generic structure Formula Ic:

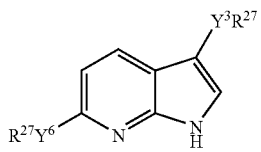

Formula Ic all salts, prodrugs, tautomers, and isomers thereof, wherein Y$^3$ and Y$^6$ are independently a bond, —CR$^a$R$^b$—, or L, and each R$^{27}$ is independently halogen, provided that Y$^3$ or Y$^6$ is a bond, or R$^{26}$, provided, however, that neither of Y$^3$R$^{27}$ and Y$^6$R$^{27}$ are hydrogen, wherein R$^a$, R$^b$, L and R$^{26}$ are as defined with reference to Formula I.

In some embodiments of compounds of Formula Ic, Y$^3$ and Y$^6$ are bonds. In some embodiments, Y$^3$ and Y$^6$ are independently —CR$^a$R$^b$— or L. In some embodiments, Y$^3$ and Y$^6$ are independently L. In some embodiments, Y$^3$ and Y$^6$ are independently —CR$^a$R$^b$—. In some embodiments, Y$^3$ is a bond, and Y$^6$ is —CR$^a$R$^b$— or L. In some embodiments, Y$^3$ is a bond, and Y$^6$ is L. In some embodiments, Y$^3$ is a bond, and Y$^6$ is —CR$^a$R$^b$—. In some embodiments, Y$^6$ is a bond, and Y$^3$ is —CR$^a$R$^b$— or L. In some embodiments, Y$^6$ is a bond, and Y$^3$ is L. In some embodiments, Y$^6$ is a bond, and Y$^3$ is —CR$^a$R$^b$—.

In some embodiments of any of the above embodiments of compounds of Formula Ic, each R$^{27}$ is independently optionally substituted cycloalkyl, optionally substituted heterocycloalkyl, optionally substituted aryl, or optionally substituted heteroaryl, or R$^{27}$ halogen, provided that Y$^3$ or Y$^6$ is a bond.

In some embodiments of any of the above embodiments of compounds of Formula Ia, Y$^3$ and Y$^6$ are independently —O—, —S—, —CR$^a$R$^b$—, —C(O)—, —C(S)—, —S(O)—, or —S(O)$_2$—, where R$^a$, R$^b$ and R$^{25}$ are as defined in Formula I, and each R$^{27}$ is independently optionally substituted lower alkyl, optionally substituted cycloalkyl, optionally substituted heterocycloalkyl, optionally substituted aryl, or optionally substituted heteroaryl; in further embodiments. Y$^6$ is —O—, —NR$^{25}$—, or —S(O)$_2$—, preferably wherein R$^{25}$ is hydrogen or lower alkyl, and R$^{27}$ bound to Y$^3$ is optionally substituted cycloalkyl, optionally substituted heterocycloalkyl, optionally substituted aryl, or optionally substituted heteroaryl, preferably optionally substituted aryl, or optionally substituted heteroaryl; in further embodiments, Y$^3$ is —CR$^a$R$^b$—, or —C(O)—, preferably —CH$_2$— or —C(O)—, Y$^6$ is —O—, —NR$^{25}$—, or —S(O)$_2$—, preferably —NR$^{25}$—, wherein R$^{25}$ is hydrogen or lower alkyl, and each R$^{27}$ is optionally substituted cycloalkyl, optionally substituted heterocycloalkyl, optionally substituted aryl, or optionally substituted heteroaryl, preferably optionally substituted aryl, or optionally substituted heteroaryl.

In some embodiments, the compound of Formula I has a structure according to the following sub-generic structure Formula Id:

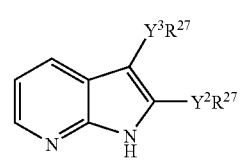

Formula Id all salts, prodrugs, tautomers, and isomers thereof, wherein Y$^3$ and Y$^2$ are independently a bond, —CR$^a$R$^b$—, or L, and each R$^{27}$ is independently halogen, provided that Y$^3$ or Y$^2$ is a bond, or R$^{26}$, provided, however, that neither of Y$^2$R$^{27}$ and Y$^3$R$^{27}$ are hydrogen, wherein R$^a$, R$^b$, L and R$^{26}$ are as defined with reference to Formula I.

In some embodiments of compounds of Formula Id, Y$^3$ and Y$^2$ are bonds. In some embodiments, Y$^3$ and Y$^2$ are independently —CR$^a$R$^b$— or L. In some embodiments, Y$^3$ and Y$^2$ are independently L. In some embodiments, Y$^3$ and Y$^2$ are independently —CR$^a$R$^b$—. In some embodiments, Y$^3$ is a bond, and Y$^2$ is —CR$^a$R$^b$— or L. In some embodiments, Y$^3$ is a bond, and Y$^2$ is L. In some embodiments, Y$^3$ is a bond, and Y$^2$ is —CR$^a$R$^b$—. In some embodiments, Y$^2$ is a bond, and Y$^3$ is —CR$^a$R$^b$— or L. In some embodiments, Y$^2$ is a bond, and Y$^3$ is L. In some embodiments, Y$^2$ is a bond, and Y$^3$ is —CR$^a$R$^b$—.

In some embodiments of any of the above embodiments of compounds of Formula Id, each R$^{27}$ is independently optionally substituted cycloalkyl, optionally substituted heterocycloalkyl, optionally substituted aryl, or optionally substituted heteroaryl, or R$^{27}$ is halogen, provided that Y$^3$ or Y$^2$ is a bond.

In some embodiments, the compound of Formula I has a structure according to the following sub-generic structure Formula Ie:

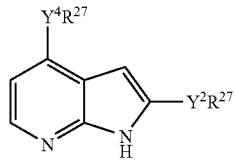

Formula Ie all salts, prodrugs, tautomers, and isomers thereof, wherein $Y^4$ and $Y^2$ are independently a bond, —$CR^aR^b$—, or L, and each $R^{27}$ is independently halogen, provided that $Y^4$ or $Y^2$ is a bond, or $R^{26}$, provided, however, that neither of $Y^2R^{27}$ and $Y^4R^{27}$ are hydrogen, wherein $R^a$, $R^b$, L and $R^{26}$ are as defined with reference to Formula I.

In some embodiments of compounds of Formula Ie, $Y^4$ and $Y^2$ are bonds. In some embodiments, $Y^4$ and $Y^2$ are independently —$CR^aR^b$— or L. In some embodiments, $Y^4$ and $Y^2$ are independently L. In some embodiments, $Y^4$ and $Y^2$ are independently —$CR^aR^b$—. In some embodiments, $Y^4$ is a bond, and $Y^2$ is —$CR^aR^b$— or L. In some embodiments, $Y^4$ is a bond, and $Y^2$ is L. In some embodiments, $Y^4$ is a bond, and $Y^2$ is —$CR^aR^b$—. In some embodiments, $Y^2$ is a bond and $Y^4$ is —$CR^aR^b$— or L. In some embodiments, $Y^2$ is a bond, and $Y^4$ is L. In some embodiments, $Y^2$ is a bond, and $Y^4$ is —$CR^aR^b$—.

In some embodiments of any of the above embodiments of compounds of Formula Id, each $R^{27}$ is independently optionally substituted cycloalkyl, optionally substituted heterocycloalkyl, optionally substituted aryl, or optionally substituted heteroaryl, or $R^{27}$ is halogen, provided that $Y^4$ or $Y^2$ is a bond.

In some embodiments, the compound of Formula I has a structure according to the following sub-generic structure Formula If:

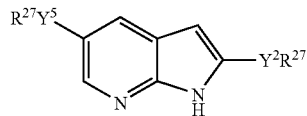

Formula If all salts, prodrugs, tautomers, and isomers thereof, wherein $Y^5$ and $Y^2$ are independently a bond, —$CR^aR^b$—, or L, and each $R^{27}$ is independently halogen, provided that $Y^5$ or $Y^2$ is a bond, or $R^{26}$, provided, however, that neither of $Y^2R^{27}$ and $Y^5R^{27}$ are hydrogen, wherein $R^a$, $R^b$, L and $R^{26}$ are as defined with reference to Formula I.

In some embodiments of compounds of Formula If, $Y^5$ and $Y^2$ are bonds. In some embodiments, $Y^5$ and $Y^2$ are independently —$CR^aR^b$— or L. In some embodiments, $Y^5$ and $Y^2$ are independently L. In some embodiments, $Y^5$ and $Y^2$ are independently —$CR^aR^b$—. In some embodiments, $Y^5$ is a bond, and $Y^2$ is —$CR^aR^b$— or L. In some embodiments, $Y^5$ is a bond, and $Y^2$ is L. In some embodiments, $Y^5$ is a bond, and $Y^2$ is —$CR^aR^b$—. In some embodiments, $Y^2$ is a bond, and $Y^5$ is —$CR^aR^b$— or L. In some embodiments, $Y^2$ is a bond, and $Y^5$ is L. In some embodiments, $Y^2$ is a bond, and $Y^5$ is —$CR^aR^b$—.

In some embodiments of any of the above embodiments of compounds of Formula If, each $R^{27}$ is independently optionally substituted cycloalkyl, optionally substituted heterocycloalkyl, optionally substituted aryl, or optionally substituted heteroaryl, or $R^{27}$ is halogen, provided that $Y^5$ or $Y^2$ is a bond.

In some embodiments, the compound of Formula I has a structure according to the following sub-generic structure Formula Ig:

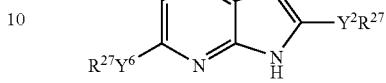

Formula Ig all salts, prodrugs, tautomers, and isomers thereof, wherein $Y^6$ and $Y^2$ are independently a bond, —$CR^aR^b$—, or L, and each $R^{27}$ is independently halogen, provided that $Y^6$ or $Y^2$ is a bond, or $R^{26}$, provided, however, that neither of $Y^2R^{27}$ and $Y^6R^{27}$ are hydrogen, wherein $R^a$, $R^b$, L and $R^{26}$ are as defined with reference to Formula I.

In some embodiments of compounds of Formula Ig, $Y^6$ and $Y^2$ are bonds. In some embodiments, $Y^6$ and $Y^2$ are independently —$CR^aR^b$— or L. In some embodiments, $Y^6$ and $Y^2$ are independently L. In some embodiments, $Y^6$ and $Y^2$ are independently —$CR^aR^b$—. In some embodiments, $Y^6$ is a bond, and $Y^7$ is —$CR^aR^b$— or L. In some embodiments. $Y^6$ is a bond, and $Y^2$ is L. In some embodiments, $Y^6$ is a bond, and $Y^2$ is —$CR^aR^b$—. In some embodiments, $Y^2$ is a bond, and $Y^6$ is —$CR^aR^b$— or L. In some embodiments, $Y^2$ is a bond, and $Y^6$ is L. In some embodiments, $Y^2$ is a bond, and $Y^6$ is —$CR^aR^b$—.

In some embodiments of any of the above embodiments of compounds of Formula Ig, each $R^{27}$ is independently optionally substituted cycloalkyl, optionally substituted heterocycloalkyl, optionally substituted aryl, or optionally substituted heteroaryl, or $R^{27}$ is halogen, provided that $Y^6$ or $Y^2$ is a bond.

In some embodiments, the compound of Formula I has a structure according to the following sub-generic structure Formula Ih:

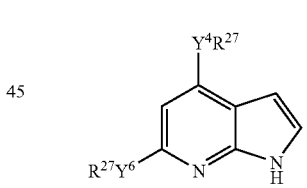

Formula Ih all salts, prodrugs, tautomers, and isomers thereof, wherein $Y^6$ and $Y^4$ are independently a bond, —$CR^aR^b$—, or L, and each $R^{27}$ is independently halogen, provided that $Y^6$ or $Y^4$ is a bond, or $R^{26}$, provided, however, that neither of $Y^4R^{27}$ and $Y^6R^{27}$ are hydrogen, wherein $R^a$, $R^b$, L and $R^{26}$ are as defined with reference to Formula I.

In some embodiments of compounds of Formula Ih, $Y^6$ and $Y^4$ are bonds. In some embodiments, $Y^6$ and $Y^4$ are independently —$CR^aR^b$— or L. In some embodiments, $Y^6$ and $Y^4$ are independently L. In some embodiments, $Y^6$ and $Y^4$ are independently —$CR^aR^b$—. In some embodiments, $Y^6$ is a bond, and $Y^4$ is —$CR^aR^b$— or L. In some embodiments, $Y^6$ is a bond, and $Y^4$ is L. In some embodiments, $Y^6$ is a bond, and $Y^4$ is —$CR^aR^b$—. In some embodiments, $Y^4$ is a bond and $Y^6$ is —$CR^aR^b$— or L. In some embodiments, $Y^4$ is a bond, and $Y^6$ is L. In some embodiments, $Y^4$ is a bond, and $Y^6$ is —$CR^aR^b$—.

In some embodiments of any of the above embodiments of compounds of Formula Ih, each $R^{27}$ is independently optionally substituted cycloalkyl, optionally substituted heterocycloalkyl, optionally substituted aryl, or optionally substituted heteroaryl, or $R^{27}$ is halogen, provided that $Y^6$ or $Y^4$ is a bond.

In some embodiments, the compound of Formula I has a structure according to the following sub-generic structure Formula Ii:

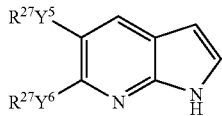

Formula Ii all salts, prodrugs, tautomers, and isomers thereof, wherein $Y^6$ and $Y^5$ are independently a bond, $-CR^aR^b-$, or L, and each $R^{27}$ is independently halogen, provided that $Y^6$ or $Y^5$ is a bond, or $R^{26}$, provided, however, that neither of $Y^5R^{27}$ and $Y^6R^{27}$ are hydrogen, wherein $R^a$, $R^b$, L and $R^{26}$ are as defined with reference to Formula I.

In some embodiments of compounds of Formula Ii, $Y^6$ and $Y^5$ are bonds. In some embodiments, $Y^6$ and $Y^5$ are independently $-CR^aR^b-$ or L. In some embodiments, $Y^6$ and $Y^5$ are independently L. In some embodiments, $Y^6$ and $Y^5$ are independently $-CR^aR^b-$. In some embodiments, $Y^6$ is a bond, and $Y^5$ is $-CR^aR^b-$ or L. In some embodiments, $Y^6$ is a bond, and $Y^5$ is L. In some embodiments, $Y^6$ is a bond, and $Y^5$ is $-CR^aR^b-$. In some embodiments, $Y^5$ is a bond, and $Y^6$ is $-CR^aR^b-$ or L. In some embodiments, $Y^5$ is a bond, and $Y^6$ is L. In some embodiments, $Y^5$ is a bond, and $Y^6$ is $-CR^aR^b-$.

In some embodiments of any of the above embodiments of compounds of Formula Ii, each $R^{27}$ is independently optionally substituted cycloalkyl, optionally substituted heterocycloalkyl, optionally substituted aryl, or optionally substituted heteroaryl, or $R^{27}$ is halogen, provided that $Y^6$ or $Y^5$ is a bond.

In some embodiments, the compound of Formula I has a structure according to the following sub-generic structure Formula Ij:

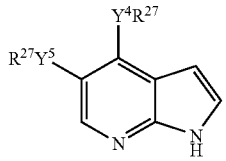

Formula Ij all salts, prodrugs, tautomers, and isomers thereof, wherein $Y^4$ and $Y^5$ are independently a bond, $-CR^aR^b-$, or L, and each $R^{27}$ is independently halogen, provided that $Y^4$ or $Y^5$ is a bond, or $R^{26}$, provided, however, that neither of $Y^4R^{27}$ and $Y^5R^{27}$ are hydrogen, wherein $R^a$, $R^b$, L and $R^{26}$ are as defined with reference to Formula I.

In some embodiments of compounds of Formula Ij, $Y^4$ and $Y^5$ are bonds. In some embodiments, $Y^4$ and $Y^5$ are independently $-CR^aR^b-$ or L. In some embodiments, $Y^4$ and $Y^5$ are independently L. In some embodiments, $Y^4$ and $Y^5$ are independently $-CR^aR^b-$. In some embodiments, $Y^4$ is a bond, and $Y^5$ is $-CR^aR^b-$ or L. In some embodiments, $Y^4$ is a bond, and $Y^5$ is L. In some embodiments, $Y^4$ is a bond, and $Y^5$ is $-CR^aR^b-$. In some embodiments, $Y^5$ is a bond, and $Y^4$ is $-CR^aR^b-$ or L. In some embodiments, $Y^5$ is a bond, and $Y^4$ is L. In some embodiments, $Y^5$ is a bond, and $Y^4$ is $-CR^aR^b-$.

In some embodiments of any of the above embodiments of compounds of Formula Ij, each $R^{27}$ is independently optionally substituted cycloalkyl, optionally substituted heterocycloalkyl, optionally substituted aryl, or optionally substituted heteroaryl, or $R^{27}$ is halogen, provided that $Y^4$ or $Y^5$ is a bond.

In some embodiments, compounds of Formula I have the structure according to the following sub-generic structure Formula Ik:

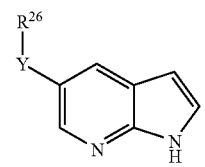

Formula Ik all salts, prodrugs, tautomers, and isomers thereof, wherein $R^{26}$ is as defined in Formula I, and Y is selected from the group consisting of a bond, $-CR^aR^b-$ and L, where $R^a$, $R^b$ and L are as defined with reference to Formula I, provided that $YR^{26}$ is not hydrogen.

In some embodiments of compounds of Formula Ik, Y is -(alk)$_a$-S-(alk)$_b$-, -(alk)$_a$-O-(alk)$_b$-, -(alk)$_a$-OC(O)-(alk)$_b$-, -(alk)$_a$-C(O)O-(alk)$_b$-, -(alk)$_a$-OC(S)-(alk)$_b$-, -(alk)$_a$-C(S)O-(alk)$_b$-, -(alk)$_a$-C(O)-(alk)$_b$-, -(alk)$_a$-C(S)-(alk)$_b$-, -(alk)$_a$-C(O)NR$^{25}$-(alk)$_b$-, -(alk)$_a$-OC(O)NR$^{25}$-(alk)$_b$-, -(alk)$_a$-OC(S)NR$^{25}$-(alk)$_b$-, -(alk)$_a$-C(S)NR$^{25}$-(alk)$_b$-, -(alk)$_a$-S(O)-(alk)$_b$-, -(alk)$_a$-S(O)$_2$-(alk)$_b$-, -(alk)$_a$-S(O)$_2$NR$^{25}$-(alk)$_b$-, -(alk)$_a$-NR$^{25}$-(alk)$_b$-, -(alk)$_a$-NR$^{25}$C(O)-(alk)$_b$-, -(alk)$_a$-NR$^{25}$C(S)-(alk)$_b$-, -(alk)$_a$-NR$^{25}$C(O)NR$^{25}$-(alk)$_b$-, -(alk)$_a$-NR$^{25}$C(S)NR$^{25}$-(alk)$_b$-, -(alk)$_a$-NR$^{25}$C(O)O-(alk)$_b$-, -(alk)$_a$-NR$^{25}$C(S)O-(alk)$_b$-, -(alk)$_a$-NR$^{25}$S(O)$_2$-(alk)$_b$-, or -(alk)$_a$-NR$^{25}$S(O)$_2$NR$^{25}$-(alk)$_b$-, wherein alk, a, b, and $R^{25}$ are as defined for Formula I.

In some embodiments of compounds of Formula Ik, Y is $-S-(alk)_b-$, $-O-(alk)_b-$, $-OC(O)-(alk)_b-$, $-C(O)O-(alk)_b-$, $-OC(S)-(alk)_b-$, $-C(S)O-(alk)_b-$, $-C(O)-(alk)_b-$, $-C(S)-(alk)_b-$, $-C(O)NR^{25}-(alk)_b-$, $-OC(O)NR^{25}-(alk)_b-$, $-OC(S)NR^{25}-(alk)_b-$, $-C(S)NR^{25}-(alk)_b-$, $-S(O)-(alk)_b-$, $-S(O)_2-(alk)_b-$, $S(O)_2NR^{25}-(alk)_b-$, $-NR^{25}-(alk)_b-$, $-NR^{25}C(O)-(alk)_b-$, $-NR^{25}C(S)-(alk)_b-$, $-NR^{25}C(O)NR^{25}-(alk)_b-$, $-NR^{25}C(S)NR^{25}-(alk)_b-$, $-NR^{25}C(O)O-(alk)_b-$, $-NR^{25}C(S)O-(alk)_b-$, $-NR^{25}S(O)_2-(alk)_b-$, or $-NR^{25}S(O)_2NR^{25}-(alk)_b-$, wherein alk, b and $R^{25}$ are as defined for Formula I.

In some embodiments of compounds of Formula IIk, Y is $-S-(alk)_b-$, $-O-(alk)_b-$, $-OC(O)-(alk)_b-$, $-OC(S)-(alk)_b-$, $-OC(O)NR^{25}-(alk)_b-$, $-OC(S)NR^{25}-(alk)_b-$, $-S(O)-(alk)_b-$, $-S(O)_2-(alk)_b-$, $S(O)_2NR^{25}-(alk)_b-$, $-NR^{25}-(alk)_b-$, $-NR^{25}C(O)-(alk)_b-$, $-NR^{25}C(S)-(alk)_b-$, $-NR^{25}C(O)NR^{25}-(alk)_b-$, $-NR^{25}C(S)NR^{25}-(alk)_b-$, $-NR^{25}C(O)O-(alk)_b-$, $-NR^{25}C(S)O-(alk)_b-$, $-NR^{25}S(O)_2-(alk)_b-$, or $-NR^{25}S(O)_2NR^{25}-(alk)_b-$, wherein alk, b and $R^{25}$ are as defined for Formula I.

In some embodiments of compounds of Formula Ik, $R^{26}$ is optionally substituted cycloalkyl, optionally substituted heterocycloalkyl, optionally substituted aryl, or optionally substituted heteroaryl. In some embodiments, Y is $-O-$, $-S-$, $-NR^{25}-$, $-C(O)-$, $-C(S)-$, $-S(O)-$, or —S(O)$_2$— and R$^{26}$ is optionally substituted cycloalkyl, optionally substituted heterocycloalkyl, optionally substituted aryl, or optionally substituted heteroaryl. In some embodiments, Y is —NR$^{25}$—, preferably wherein R$^{25}$ is hydrogen or lower alkyl, preferably wherein Y is —NH—; in further embodiments, R$^{26}$ is optionally substituted lower alkyl, optionally substituted cycloalkyl, optionally substituted heterocycloalkyl, optionally substituted aryl, or optionally substituted heteroaryl; in further embodiments, lower alkyl is substituted with optionally substituted cycloalkyl, optionally substituted heterocycloalkyl, optionally substituted aryl, or optionally substituted heteroaryl; in further embodiments, heteroaryl is monocyclic. In some embodiments, Y is —NH—; in further embodiments, R$^{26}$ is substituted phenyl or optionally substituted heteroaryl, provided that heteroaryl is monocyclic.

In some embodiments of any of the above embodiments of compounds of Formula Ik, YR$^{26}$ is not optionally substituted cycloalkyl, optionally substituted heterocycloalkyl, optionally substituted aryl, optionally substituted heteroaryl, —C≡CCH$_2$N(CH$_3$)$_2$, —C(O)H, —CH$_2$N(CH$_3$)$_2$, —C(O)OCH$_3$, —CH$_2$OH, —OH, —OCH$_3$, —NHCH$_2$=CH$_2$, —NHCH$_3$, —NHCH$_2$CH$_3$, —NHphenyl,

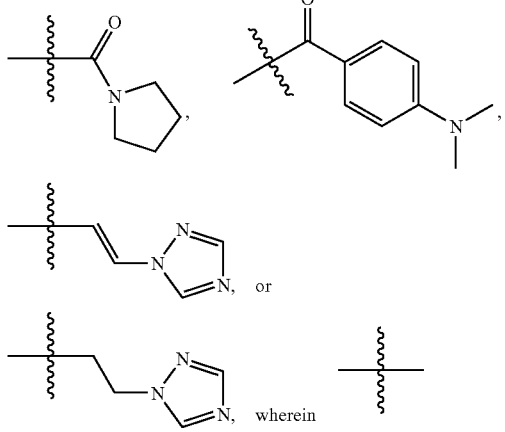

indicates the bond attached to the 5-position of the 7-azaindole ring; and when Y is —O— or —NR$^{25}$—, then R$^{26}$ is not

which is optionally substituted, wherein

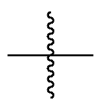

indicates the bond attached to Y; and when Y is —O—, then R$^{26}$ is not

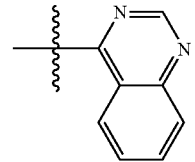 [SMILES: *c1ncnc2ccccc12]

which is optionally substituted, wherein

indicates the bond attached Y.

In some embodiments, compounds of Formula I have the structure according to the following sub-generic structure Formula Im:

Formula Im

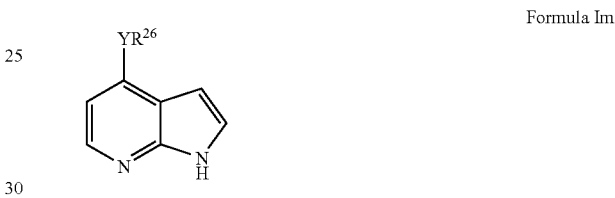

all salts, prodrugs, tautomers, and isomers thereof, wherein R$^{26}$ and Y are as defined for Formula Ik.

In some embodiments of compounds of Formula Im, Y is —OC(O)-(alk)$_b$-, —C(O)O-(alk)$_b$-, —OC(S)-(alk)$_b$-, —C(S)O-(alk)$_b$-, —C(O)-(alk)$_b$-, —C(S)-(alk)$_b$-, —C(O)NR$^{25}$-(alk)$_b$-, —OC(O)NR$^{25}$-(alk)$_b$-, —OC(S)NR$^{25}$-(alk)$_b$-, —C(S)NR$^{25}$-(alk)$_b$-, —S(O)-(alk)$_b$-, —S(O)$_2$-(alk)$_b$-, S(O)$_2$NR$^{25}$-(alk)$_b$-, —NR$^{25}$C(S)-(alk)$_b$-, —NR$^{25}$C(O)NR$^{25}$-(alk)$_b$-, —NR$^{25}$C(S)NR$^{25}$-(alk)$_b$-, —NR$^{25}$C(O)O-(alk)$_b$-, —NR$^{25}$C(S)O-(alk)$_b$-, —NR$^{25}$S(O)$_2$-(alk)$_b$-, or —NR$^{25}$S(O)$_2$NR$^{25}$-(alk)$_b$-, wherein alk, b and R$^{25}$ are as defined for Formula I.

In other embodiments of compounds of Formula Im, Y is —S-(alk)$_b$-, —O-(alk)$_b$-, —OC(O)-(alk)$_b$-, —C(O)O-(alk)$_b$-, —OC(S)-(alk)$_b$-, —C(S)O-(alk)$_b$-, —C(O)-(alk)$_b$-, —C(S)-(alk)$_b$-, —C(O)NR$^{25}$-(alk)$_b$-, —OC(O)NR$^{25}$-(alk)$_b$-, —OC(S)NR$^{25}$-(alk)$_b$-, —C(S)NR$^{25}$-(alk)$_b$-, —S(O)-(alk)$_b$-, —S(O)$_2$-(alk)$_b$-, —S(O)$_2$NR$^{25}$-(alk)$_b$-, —NR$^{25}$-(alk)$_b$-, —NR$^{25}$C(O)-(alk)$_b$-, —NR$^{25}$C(S)-(alk)$_b$-, —NR$^{25}$C(O)NR$^{25}$-(alk)$_b$-, —NR$^{25}$C(S)NR$^{25}$-(alk)$_b$-, —NR$^{25}$C(O)O-(alk)$_b$-, —NR$^{25}$C(S)O-(alk)$_b$-, —NR$^{25}$S(O)$_2$-(alk)$_b$-, or —NR$^{25}$S(O)$_2$NR$^{25}$-(alk)$_b$-, wherein alk, b and R$^{25}$ are as defined for Formula I.

In other embodiments of compounds of Formula Im, Y is —S-(alk)$_b$-, —O-(alk)$_b$-, —OC(O)-(alk)$_b$-, —OC(S)-(alk)$_b$-, —OC(O)NR$^{25}$-(alk)$_b$-, —OC(S)NR$^{25}$-(alk)$_b$-, —S(O)$_2$-(alk)$_b$-, —S(O)$_2$NR$^{25}$-(alk)$_b$-, —NR$^{25}$-(alk)$_b$-, —NR$^{25}$C(O)-(alk)$_b$-, —NR$^{25}$C(S)-(alk)$_b$-, —NR$^{25}$C(O)NR$^{25}$-(alk)$_b$-, —NR$^{25}$C(S)NR$^{25}$-(alk)$_b$-, —NR$^{25}$C(O)O-(alk)$_b$-, —NR$^{25}$C(S)O-(alk)$_b$-, —NR$^{25}$S(O)$_2$-(alk)$_b$-, or —NR$^{25}$S(O)$_2$NR$^{25}$-(alk)$_b$-, wherein alk, b and R$^{25}$ are as defined for Formula I.

In some embodiments of compounds of Formula Im, R$^{26}$ is optionally substituted cycloalkyl, optionally substituted heterocycloalkyl, optionally substituted aryl, or optionally substituted heteroaryl. In some embodiments, Y is —O—, —S—, —NR$^{25}$—, —C(O)—, —C(S)—, —S(O)—, or —S(O)$_2$— and R$^{26}$ is optionally substituted cycloalkyl, optionally substituted heterocycloalkyl, optionally substituted aryl, or optionally substituted heteroaryl. In some embodiments, Y is —NR$^{25}$—, preferably wherein R$^{25}$ is hydrogen or lower alkyl, preferably wherein Y is —NH—; in further embodiments, R$^{26}$ is optionally substituted lower alkyl, optionally substituted cycloalkyl, optionally substituted heterocycloalkyl, optionally substituted aryl, or optionally substituted heteroaryl; in further embodiments, lower alkyl is substituted with optionally substituted cycloalkyl, optionally substituted heterocycloalkyl, optionally substituted aryl, or optionally substituted heteroaryl; in further embodiments, heteroaryl is monocyclic.

In some embodiments of any of the above embodiments of compounds of Formula Im, when Y is —CH$_2$NH—, then R$^{26}$ is not optionally substituted thiophene or optionally substituted pyridine; when Y is —O— or —NH—, then R$^{26}$ is not optionally substituted bicyclic heteroaryl; when Y is —O—, then R$^{26}$ is not optionally substituted phenyl; when Y is —NH— or —N(CH$_3$)— and R$^{26}$ is substituted phenyl, the phenyl is not substituted by halogen ortho to Y and optionally substituted amine para to Y, Y is not —NH—C(O)— or —C(O)—NH—, and YR$^{26}$ is not optionally substituted cycloalkyl, optionally substituted heterocycloalkyl, optionally substituted aryl, optionally substituted heteroaryl, optionally substituted —CH=CH$_2$, —C(O)OH, —C(O)OCH$_3$, —C(O)OtBu, —OH, —NHCH$_2$CH=CH$_2$, —N(CH$_3$)$_2$, —NH$_2$, —NHCH$_2$C(O)OCH$_2$CH$_3$, —N(CH$_3$)phenyl,

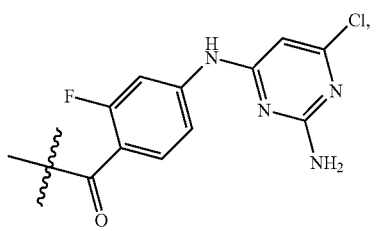

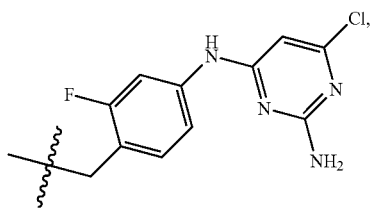

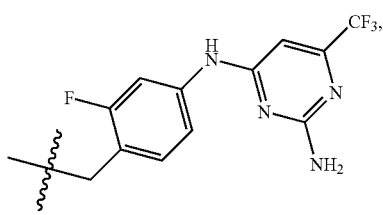

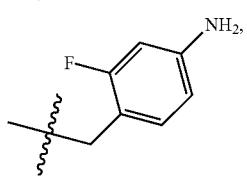

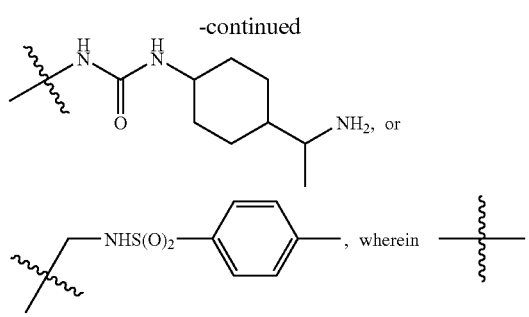

indicates the bond attached to the 4-position of the 7-azaindole ring.

In some embodiments, compounds of Formula I have the structure according to the following sub-generic structure Formula In:

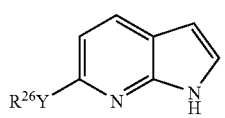

Formula In all salts, prodrugs, tautomers, and isomers thereof, wherein R$^{26}$ and Y are as defined for Formula Ik.

In other embodiments of compounds of Formula In, Y is —S-(alk)$_b$-, —O-(alk)$_b$-, —OC(O)-(alk)$_b$-, —C(O)O-(alk)$_b$-, —OC(S)-(alk)$_b$-, —C(S)O-(alk)$_b$-, —C(O)-(alk)$_b$-, —C(S)-(alk)-$_b$-, —C(O)NR$^{25}$-(alk)$_b$-, —OC(O)NR$^{25}$-(alk)$_b$-, —OC(S)NR$^{25}$-(alk)$_b$-, —C(S)NR$^{25}$-(alk)$_b$-, —S(O)-(alk)$_b$-, —S(O)$_2$-(alk)$_b$-, —S(O)$_2$NR$^{25}$-(alk)$_b$-, —NR$^{25}$-(alk)$_b$-, —NR$^{25}$C(O)-(alk)$_b$-, —NR$^{25}$C(S)-(alk)$_b$-, —NR$^{25}$C(O)NR$^{25}$-(alk)$_b$-, —NR$^{25}$C(S)NR$^{25}$-(alk)$_b$-, —NR$^{25}$C(O)O-(alk)$_b$-, —NR$^{25}$C(S)O-(alk)$_b$-, —NR$^{25}$S(O)$_2$-(alk)$_b$-, or —NR$^{25}$S(O)$_2$NR$^{25}$-(alk)$_b$-, wherein alk, b and R$^{25}$ are as defined for Formula I.

In other embodiments of compounds of Formula In, Y is —S-(alk)$_b$-, —O-(alk)$_b$-, —OC(O)-(alk)$_b$-, —OC(S)-(alk)$_b$-, —OC(O)NR$^{25}$-(alk)$_b$-, —OC(S)NR$^{25}$-(alk)$_b$-, —S(O)-(alk)-$_b$-, —S(O)$_2$-(alk)$_b$-, —S(O)$_2$NR$^{25}$-(alk)$_b$-, —NR$^{25}$-(alk)$_b$-, —NR$^{25}$C(O)-(alk)$_b$-, —NR$^{25}$C(S)-(alk)$_b$-, —NR$^{25}$C(O)NR$^{25}$-(alk)$_b$-, —NR$^{25}$C(S)NR$^{25}$-(alk)$_b$-, —NR$^{25}$C(O)O-(alk)$_b$-, —NR$^{25}$C(S)O-(alk)$_b$-, —NR$^{25}$S(O)$_2$-(alk)$_b$-, or —NR$^{25}$S(O)$_2$NR$^{25}$-(alk)$_b$-, wherein alk, b and R$^{25}$ are as defined for Formula I.

In some embodiments of compounds of Formula In, R$^{26}$ is optionally substituted cycloalkyl, optionally substituted heterocycloalkyl, optionally substituted aryl, or optionally substituted heteroaryl. In some embodiments, Y is —NR$^{25}$—, preferably wherein R$^{25}$ is hydrogen or lower alkyl, preferably wherein Y is —NH—; in further embodiments, R$^{26}$ is optionally substituted lower alkyl, optionally substituted cycloalkyl, optionally substituted heterocycloalkyl, optionally substituted aryl, or optionally substituted heteroaryl; in further embodiments, lower alkyl is substituted with optionally substituted cycloalkyl, optionally substituted heterocycloalkyl, optionally substituted aryl, or optionally substituted heteroaryl.

In some embodiments of any of the above embodiments of compounds of Formula In, compounds are excluded where Y is —O— and R$^{26}$ is optionally substituted

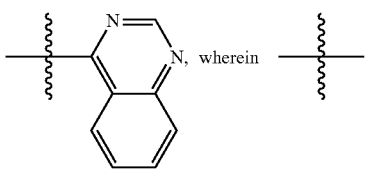

indicates the bond attached to Y; and where YR$^{26}$ is —NH$_2$, —CH$_3$, —OC(O)phenyl,

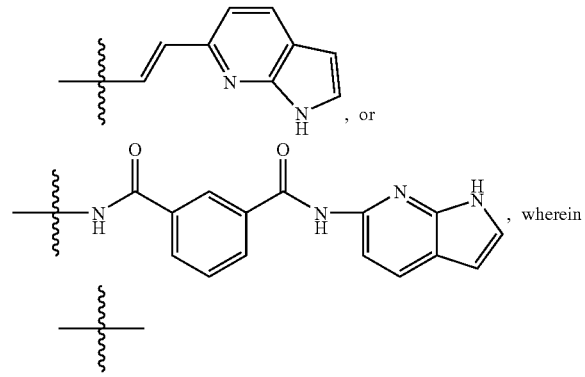

indicates the bond attached to the 6-position of the 7-azaindole ring.

In some embodiments, compounds of Formula I have the structure according to the following sub-generic structure Formula Io:

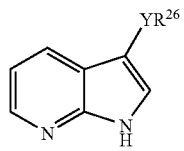

Formula Io all salts, prodrugs, tautomers, and isomers thereof, wherein R$^{26}$ and Y are as defined for Formula Ik.

In other embodiments of compounds of Formula Io, Y is —S-(alk)$_b$-, —O-(alk)$_b$-, —OC(O)-(alk)$_b$-, —C(O)O-(alk)$_b$-, —OC(S)-(alk)$_b$-, —C(S)O-(alk)$_b$-, —C(O)-(alk)$_b$-, —C(S)-(alk)$_b$-, —C(O)NR$^{25}$-(alk)$_b$, —OC(O)NR$^{25}$-(alk)$_b$-, —OC(S)NR$^{25}$-(alk)$_b$-, —C(S)NR$^{25}$-(alk)$_b$-, —S(O)-(alk)$_b$-, —S(O)$_2$-(alk)$_b$-, —S(O)$_2$NR$^{25}$-(alk)$_b$-, —NR$^{25}$-(alk)$_b$-, —NR$^{25}$C(O)-(alk)$_b$-, —NR$^{25}$C(S)-(alk)$_b$-, —NR$^{25}$C(O)NR$^{25}$-(alk)$_b$-, —NR$^{25}$C(S)NR$^{25}$-(alk)$_b$-, —NR$^{25}$C(O)O-(alk)$_b$-, —NR$^{25}$C(SO)O-(alk)$_b$-, —NR$^{25}$S(O)$_2$-(alk)$_b$-, or —NR$^{25}$S(O)$_2$NR$^{25}$-(alk)$_b$-, wherein alk, b and R$^{25}$ are as defined for Formula I.

In other embodiments of compounds of Formula Io, Y is —S-(alk)$_b$-, —O-(alk)$_b$-, —OC(O)-(alk)$_b$-, —OC(S)-(alk)$_b$-, —OC(O)NR$^{25}$-(alk)$_b$-, —OC(S)NR$^{25}$-(alk)$_b$-, —S(O)-(alk)$_b$-, —S(O)$_2$-(alk)$_b$-, —S(O)$_2$NR$^{25}$-(alk)$_b$-, —NR$^{25}$-(alk)$_b$, —NR$^{25}$C(O)-(alk)$_b$-, —NR$^{25}$C(S)-(alk)$_b$-, —NR$^{25}$C(O)NR$^{25}$-(alk)$_b$-, —NR$^{25}$C(S)NR$^{25}$-(alk)$_b$-, —NR$^{25}$C(O)O-(alk)$_b$-, —NR$^{25}$C(S)O-(alk)$_b$-, —NR$^{25}$S(O)$_2$-(alk)$_b$-, or —NR$^{25}$S(O)$_2$NR$^{25}$-(alk)$_b$-, wherein alk, b and R$^{25}$ are as defined for Formula I.

In some embodiments of compounds of Formula Io, R$^{26}$ is optionally substituted cycloalkyl, optionally substituted heterocycloalkyl, optionally substituted aryl, or optionally substituted heteroaryl. In some embodiments, Y is —NR$^{25}$—, preferably wherein R$^{25}$ is hydrogen or lower alkyl, preferably wherein Y is —NH—; in further embodiments, R$^{26}$ is optionally substituted lower alkyl, optionally substituted cycloalkyl, optionally substituted heterocycloalkyl, optionally substituted aryl, or optionally substituted heteroaryl; in further embodiments, lower alkyl is substituted with optionally substituted cycloalkyl, optionally substituted heterocycloalkyl, optionally substituted aryl, or optionally substituted heteroaryl.

In some embodiments of any of the above embodiments of compounds of Formula Io, compounds are excluded when —YR$^{26}$ is optionally substituted cycloalkyl, optionally substituted heterocycloalkyl, optionally substituted aryl, optionally substituted heteroaryl, —CH$_2$NR'R", wherein NR'R" is optionally substituted heterocycloalkyl or optionally substituted heteroaryl, —C(O)NR'R", wherein NR'R" is optionally substituted heterocycloalkyl or optionally substituted heteroaryl, or R' is H and R" is optionally substituted cycloalkyl, optionally substituted aryl or optionally substituted heteroaryl, optionally substituted —CH═CH$_2$, —CH$_3$, —CH$_2$CH$_2$NHCH$_3$, —CH$_2$CH(NH$_2$)C(O)OH, —CH$_2$CH(NH$_2$)C(O)OCH$_3$, —CH$_2$CH(C(O)OH)NHCH$_3$, —C(O)C(O)OCH$_3$, —CH$_2$C(O)OCH$_2$CH$_3$, —CH$_2$C(O)NH$_2$, —CH$_2$CN, —NH$_2$, —N(CH$_3$)$_2$, —SCH$_3$, —N═C(CH$_3$)NHOAc, —C(O)CCl$_3$, —C(O)OCH$_3$, —C(O)CH$_2$Br, —C(O)NH$_2$, —C(S)NH$_2$, —CH$_2$NH-thiophene, wherein thiophene is optionally substituted,

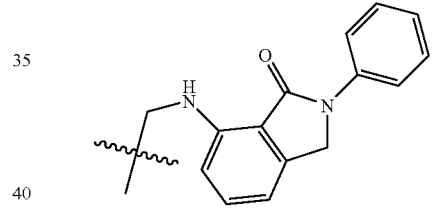

wherein the phenyl ring is optionally substituted

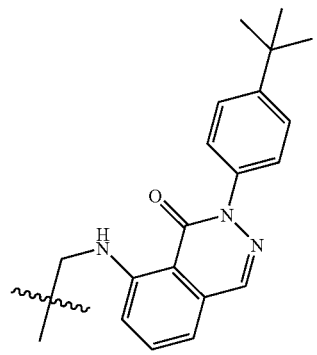

,

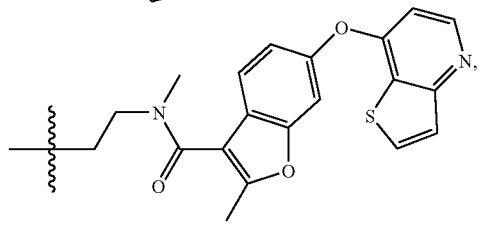

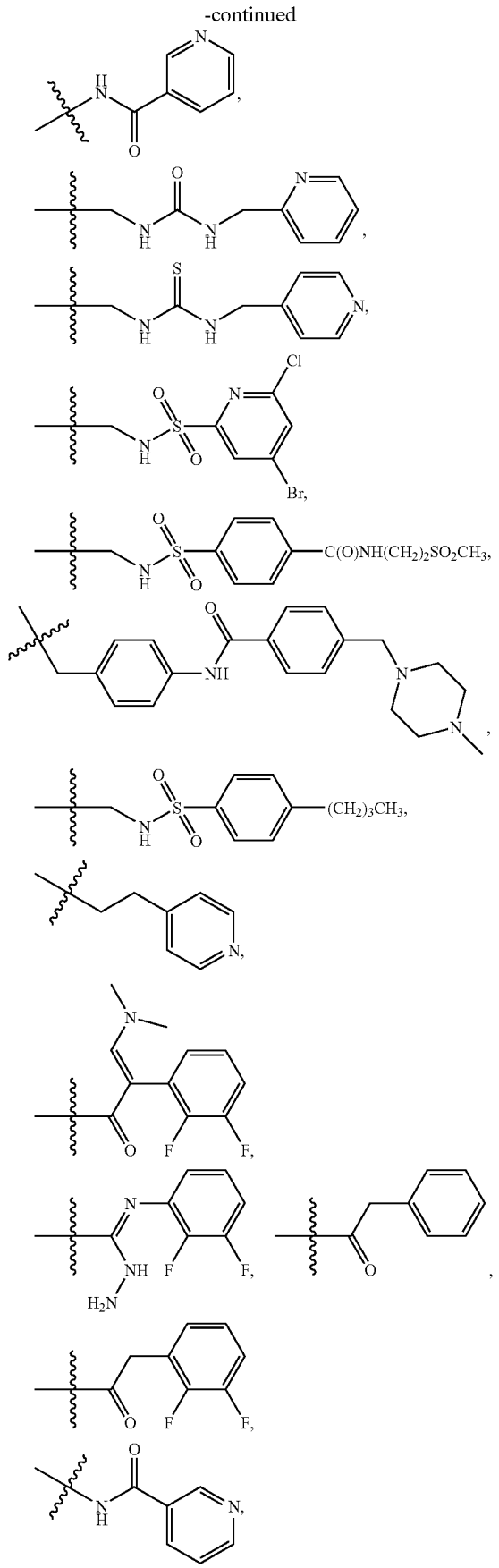
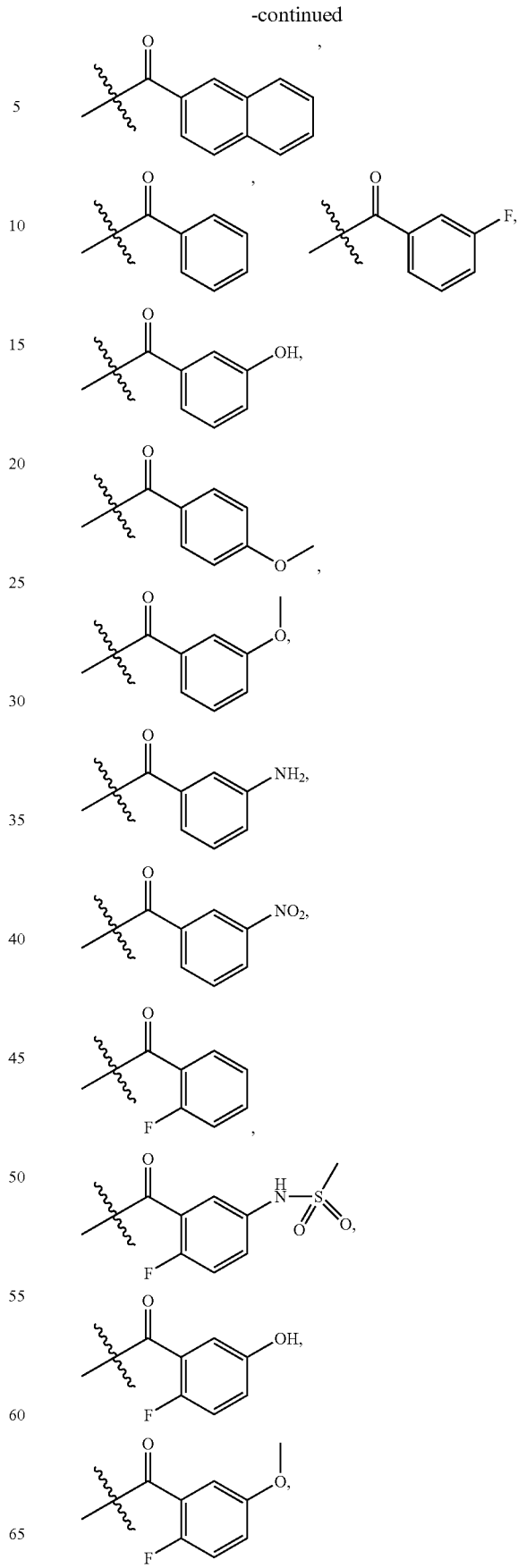

-continued
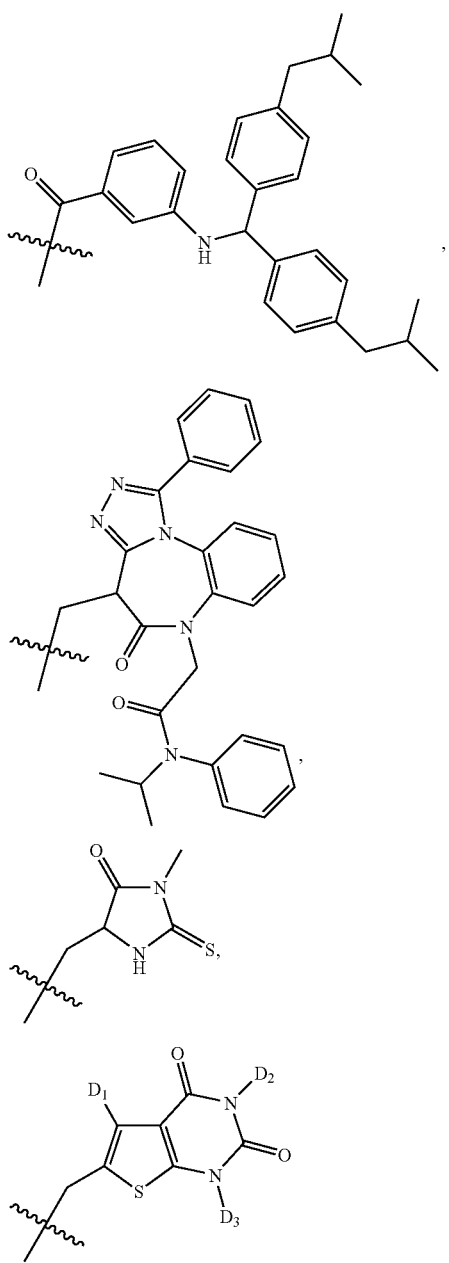
wherein the ring is optionally substituted at $D_1$, $D_2$ and $D_3$,
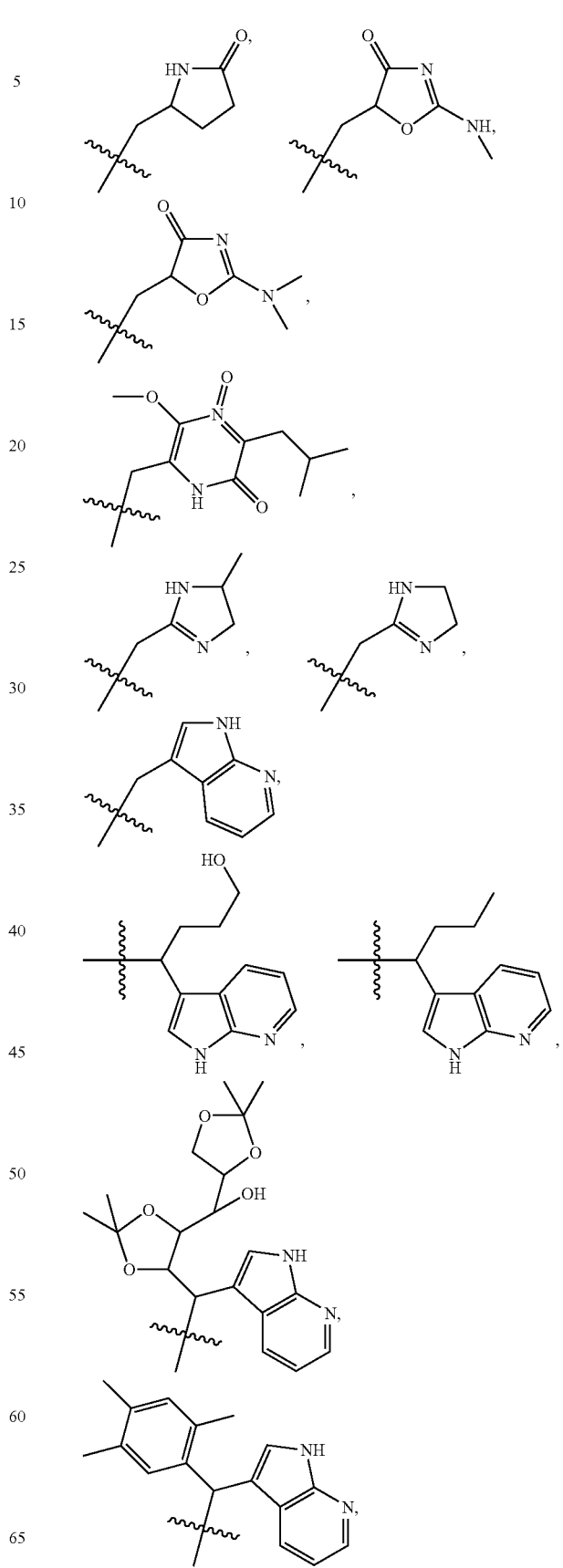
wherein the ring is optionally substituted at $D_1$, $D_2$ and $D_3$,

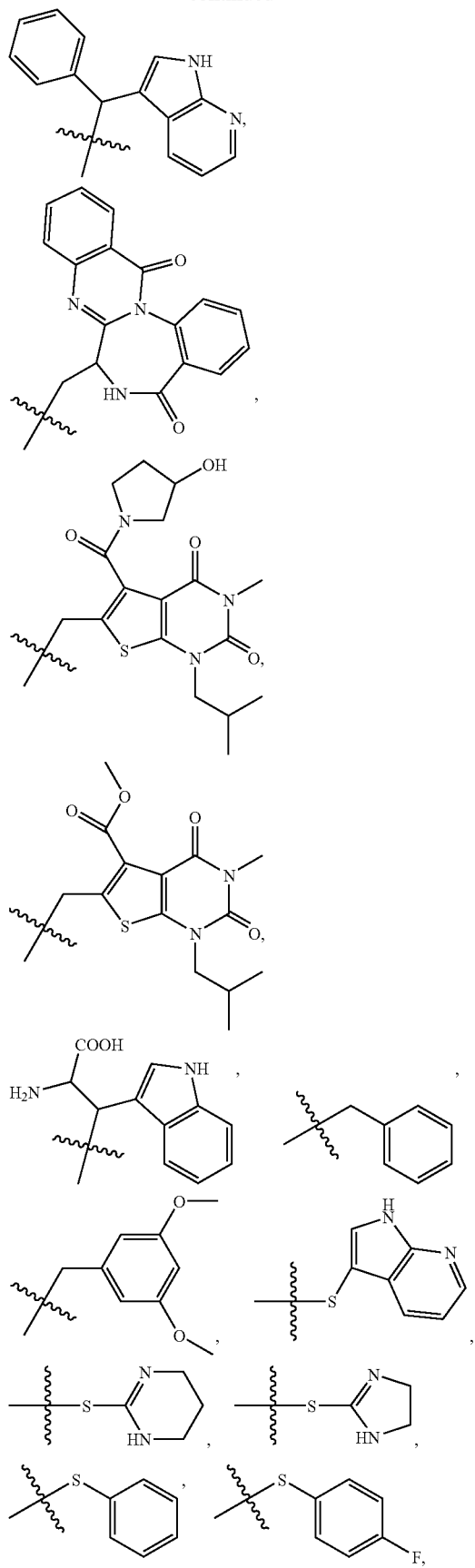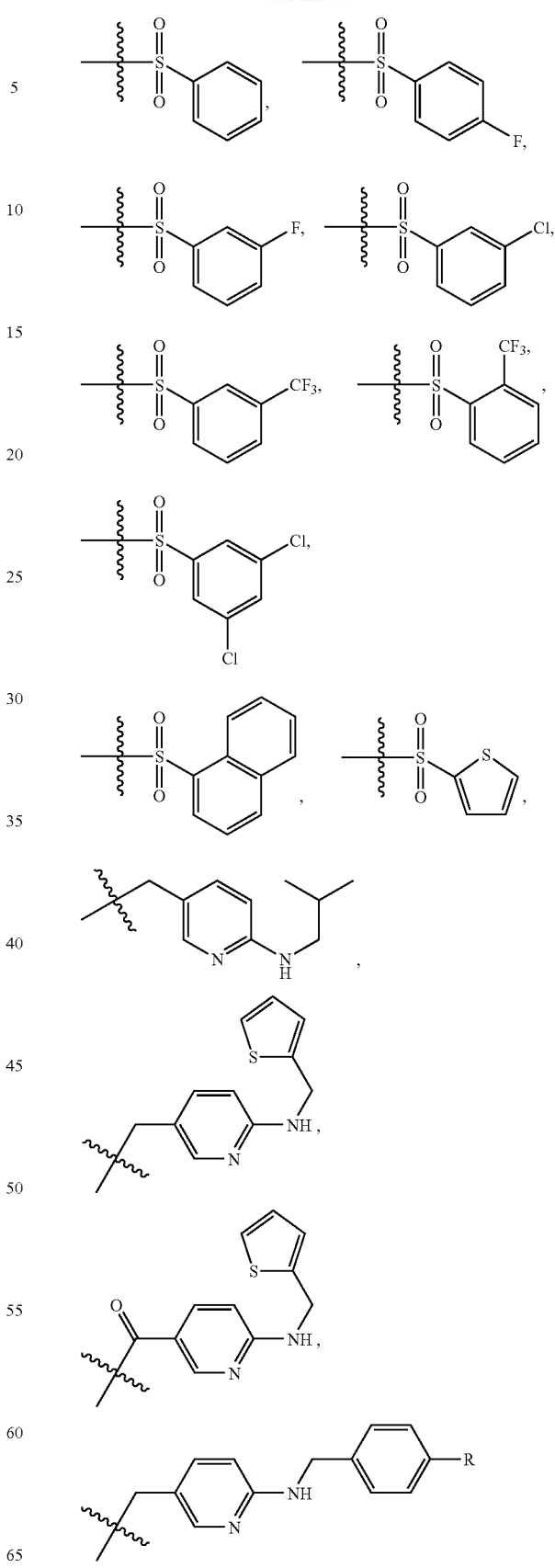

when R is H, F, Cl, CH₃, CF₃ or OCH₃,

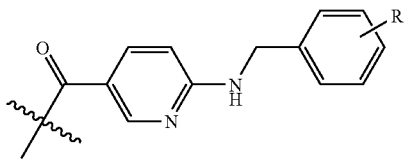

when R is H, 4-F, 4-CF₃ or 3-F, or

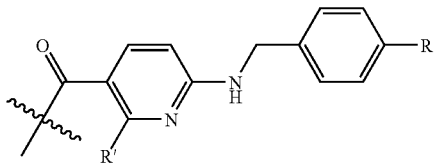

when R' is OCH₃ or CH₃ and R is CF₃, or when R' is CH₃ and R is Cl, wherein

indicates the bond attached to the 3-position of the 7-azaindole ring.

In some embodiments, compounds of Formula I have the structure according to the following sub-generic structure Formula Ip:

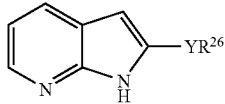

Formula Ip all salts, prodrugs, tautomers, and isomers thereof, wherein $R^{26}$ and Y are as defined for Formula Ik.

In other embodiments of compounds of Formula Ip, Y is —S-(alk)$_b$-, —O-(alk)$_b$-, —OC(O)-(alk)$_b$-, —C(O)O-(alk)$_b$-, —OC(S)-(alk)$_b$-, —C(S)O-(alk)$_b$-, —C(O)-(alk)$_b$-, —C(S)-(alk)$_b$-, —C(O)NR$^{25}$-(alk)$_b$-, —OC(O)NR$^{25}$-(alk)$_b$-, —OC(S)NR$^{25}$-(alk)$_b$-, —C(S)NR$^{25}$-(alk)$_b$-, —S(O)-(alk)$_b$-, —S(O)$_2$-(alk)$_b$-, —S(O)$_2$NR$^{25}$-(alk)$_b$-, —NR$^{25}$-(alk)$_b$-, —NR$^{25}$C(O)-(alk)$_b$-, —NR$^{25}$C(S)-(alk)$_b$-, —NR$^{25}$C(O)NR$^{25}$-(alk)$_b$-, —NR$^{25}$C(S)NR$^{25}$-(alk)$_b$-, —NR$^{25}$C(O)O-(alk)$_b$-, —NR$^{25}$C(S)O-(alk)$_b$-, —NR$^{25}$S(O)$_2$-(alk)$_b$-, or —NR$^{25}$S(O)$_2$NR$^{25}$-(alk)$_b$-, wherein alk, b and $R^{25}$ are as defined for Formula I.

In other embodiments of compounds of Formula Ip, Y is —S-(alk)$_b$-, —O-(alk)$_b$-, —OC(O)-(alk)$_b$-, —OC(S)-(alk)$_b$-, —OC(O)NR$^{25}$-(alk)$_b$-, —OC(S)NR$^{25}$-(alk)$_b$-, —S(O)-(alk)$_b$-, —S(O)$_2$-(alk)$_b$-, —S(O)$_2$NR$^{25}$-(alk)$_b$-, —NR$^{25}$-(alk)$_b$-, —NR$^{25}$C(O)-(alk)$_b$-, —NR$^{25}$C(S)-(alk)$_b$-, —NR$^{25}$C(O)NR$^{25}$-(alk)$_b$-, —NR$^{25}$C(S)NR$^{25}$-(alk)$_b$-, —NR$^{25}$C(O)O-(alk)$_b$-, —NR$^{25}$C(S)O-(alk)$_b$-, —NR$^{25}$S(O)$_2$-(alk)$_b$-, or —NR$^{25}$S(O)$_2$NR$^{25}$-(alk)$_b$-, wherein alk, b and $R^{25}$ are as defined for Formula I.

In some embodiments of compounds of Formula Ip, $R^{26}$ is optionally substituted cycloalkyl, optionally substituted heterocycloalkyl, optionally substituted aryl, or optionally substituted heteroaryl. In some embodiments, Y is —NR$^{25}$—, preferably wherein $R^{25}$ is hydrogen or lower alkyl, preferably wherein Y is —NH—; in further embodiments, $R^{26}$ is optionally substituted lower alkyl, optionally substituted cycloalkyl, optionally substituted heterocycloalkyl, optionally substituted aryl, and optionally substituted heteroaryl; in further embodiments, lower alkyl is substituted with optionally substituted cycloalkyl, optionally substituted heterocycloalkyl, optionally substituted aryl, or optionally substituted heteroaryl.

In some embodiments of any of the above embodiments of compounds of Formula Ip above, compounds are excluded when YR$^{26}$ is —CH₃, optionally substituted cycloalkyl,

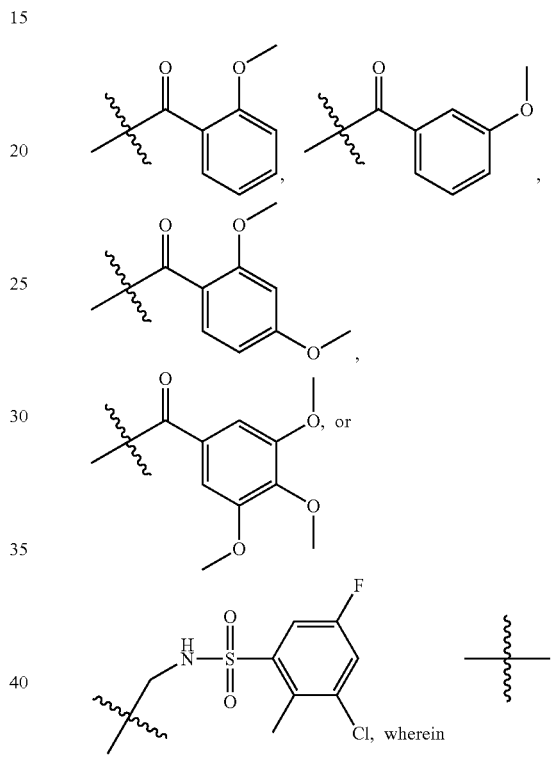

indicates the bond attached to the 2-position of the 7-azaindole ring.

In some embodiments, the compound of Formula I has a structure according to the following sub-generic structure Formula Iq:

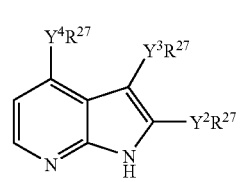

Formula Iq all salts, prodrugs, tautomers, and isomers thereof, wherein $Y^2 Y^3$ and $Y^4$ are independently a bond, —CR$^a$R$^b$— or L, and each $R^{27}$ is independently halogen, provided that $Y^2$, $Y^3$ or $Y^4$ is a bond, or $R^{26}$ provided, however, that none of $Y^2R^{27}$, $Y^3R^{27}$, and $Y^4R^{27}$ are hydrogen, wherein $R^a$, $R^b$, L and $R^{26}$ are as defined with reference to Formula I.

In some embodiments of compounds of Formula Iq, $Y^2$, $Y^3$ and $Y^4$ are bonds. In some embodiments, $Y^2$, $Y^3$ and $Y^4$ are independently —CR$^a$R$^b$— or L. In some embodiments, Y$^2$, Y$^3$ and Y$^4$ are independently L. In some embodiments, one of Y$^2$, Y$^3$ and Y$^4$ is a bond, and the others are independently —CR$^a$R$^b$— or L. In some embodiments, one of Y$^2$, Y$^3$ and Y$^4$ is a bond, and the others are independently L. In some embodiments, two of Y$^2$, Y$^3$ and Y$^4$ are bonds, and the other is —CR$^a$R$^b$— or L. In some embodiments, two of Y$^2$, Y$^3$ and Y$^4$ are bonds and the other is L.

In some embodiments of any of the above embodiments of compounds of Formula Iq, each R$^{27}$ is independently optionally substituted cycloalkyl, optionally substituted heterocycloalkyl, optionally substituted aryl, or optionally substituted heteroaryl, or R$^{27}$ is halogen, provided that Y$^2$, Y$^3$ or Y$^4$ is a bond.

In some embodiments, the compound of Formula I has a structure according to the following sub-generic structure Formula Ir:

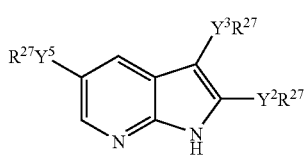

Formula Ir all salts, prodrugs, tautomers, and isomers thereof; wherein Y$^2$Y$^3$ and Y$^5$ are independently a bond, —CR$^a$R$^b$— or L, and each R$^{27}$ is independently halogen, provided that Y$^2$, Y$^3$ or Y$^5$ is a bond, or R$^{26}$, provided, however, that none of Y$^2$R$^{27}$, Y$^3$R$^{27}$, and Y$^5$R$^{27}$ are hydrogen, wherein R$^a$, R$^b$, L and R$^{26}$ are as defined with reference to Formula I.

In some embodiments of compounds of Formula Ir, Y$^2$, Y$^3$ and Y$^5$ are bonds. In some embodiments, Y$^2$, Y$^3$ and Y$^5$ are independently —CR$^a$R$^b$— or L. In some embodiments, Y$^2$, Y$^3$ and Y$^5$ are independently L. In some embodiments, any one of Y$^2$, Y$^3$ and Y$^5$ is a bond, and the remaining of Y$^2$, Y$^3$ and Y$^5$ are independently —CR$^a$R$^b$— or L. In some embodiments, any one of Y$^2$, Y$^3$ and Y$^5$ is a bond, and the remaining of Y$^2$, Y$^3$ and Y$^5$ are independently L. In some embodiments, any two of Y$^2$, Y$^3$ and Y$^5$ are bonds, and the remaining of Y$^2$, Y$^3$ and Y$^5$ is —CR$^a$R$^b$— or L. In some embodiments, any two of Y$^2$, Y$^3$ and Y$^5$ are bonds, and the remaining of Y$^2$, Y$^3$ and Y$^5$ is L.

In some embodiments of any of the above embodiments of compounds of Formula Ir, each R$^{27}$ is independently optionally substituted cycloalkyl, optionally substituted heterocycloalkyl, optionally substituted aryl, or optionally substituted heteroaryl, or R$^{27}$ is halogen, provided that Y$^2$, Y$^3$ or Y$^5$ is a bond.

In some embodiments, the compound of Formula I has a structure according to the following sub-generic structure Formula Is:

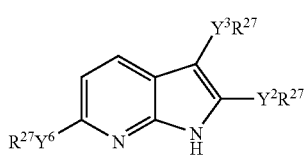

Formula Is all salts, prodrugs, tautomers, and isomers thereof, wherein Y$^2$Y$^3$ and Y$^6$ are independently a bond, —CR$^a$R$^b$—, or L, and each R$^{27}$ is independently halogen, provided that Y$^2$, Y$^3$ or Y$^6$ is a bond, or R$^{26}$, provided, however, that none of Y$^2$R$^{27}$, Y$^3$R$^{27}$, and Y$^6$R$^{27}$ are hydrogen, wherein R$^a$, R$^b$, L and R$^{26}$ are as defined with reference to Formula I.

In some embodiments of compounds of Formula Is, Y$^2$, Y$^3$ and Y$^6$ are bonds. In some embodiments, Y$^2$, Y$^3$ and Y$^6$ are independently —CR$^a$R$^b$— or L. In some embodiments, Y$^2$, Y$^3$ and Y$^6$ are independently L. In some embodiments, any one of Y$^2$, Y$^3$ and Y$^6$ is a bond, and the remaining of Y$^2$, Y$^3$ and Y$^6$ are independently —CR$^a$R$^b$— or L. In some embodiments, any one of Y$^2$, Y$^3$ and Y$^6$ is a bond, and the remaining of Y$^2$, Y$^3$ and Y$^6$ are independently L. In some embodiments, any two of Y$^2$, Y$^3$ and Y$^6$ are bonds, and the remaining of Y$^2$, Y$^3$ and Y$^6$ is —CR$^a$R$^b$— or L. In some embodiments, any two of Y$^2$, Y$^3$ and Y$^6$ are bonds, and the remaining of Y$^2$, Y$^3$ and Y$^6$ is L.

In some embodiments of any of the above embodiments of compounds of Formula Is, each R$^{27}$ is independently optionally substituted cycloalkyl, optionally substituted heterocycloalkyl, optionally substituted aryl, or optionally substituted heteroaryl, or R$^{27}$ is halogen, provided that Y$^2$, Y$^3$ or Y$^6$ is a bond.

In some embodiments, the compound of Formula I has a structure according to the following sub-generic structure Formula It:

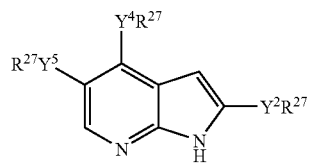

Formula It all salts, prodrugs, tautomers, and isomers thereof, wherein Y$^2$Y$^4$ and Y$^5$ are independently a bond, —CR$^a$R$^b$—, or L, and each R$^{27}$ is independently halogen, provided that Y$^2$, Y$^4$ or Y$^5$ is a bond, or R$^{26}$, provided, however, that none of Y$^2$R$^{27}$, Y$^4$R$^{27}$, and Y$^5$R$^{27}$ are hydrogen, wherein R$^a$, R$^b$, L and R$^{26}$ are as defined with reference to Formula I.

In some embodiments of compounds of Formula It, Y$^2$, Y$^4$ and Y$^5$ are bonds. In some embodiments, Y$^2$, Y$^4$ and Y$^5$ are independently —CR$^a$R$^b$— or L. In some embodiments, Y$^2$, Y$^4$ and Y$^5$ are independently L. In some embodiments, any one of Y$^2$, Y$^4$ and Y$^5$ is a bond, and the remaining of Y$^2$, Y$^4$ and Y$^5$ are independently —CR$^a$R$^b$— or L. In some embodiments, any one of Y$^2$, Y$^4$ and Y$^5$ is a bond, and the remaining of Y$^2$, Y$^4$ and Y$^5$ are independently L. In some embodiments, any two of Y$^2$, Y$^4$ and Y$^5$ are bonds, and the remaining of Y$^2$, Y$^4$ and Y$^5$ is —CR$^a$R$^b$— or L. In some embodiments, any two of Y$^2$, Y$^4$ and Y$^5$ are bonds, and the remaining of Y$^2$, Y$^4$ and Y$^5$ is L.

In some embodiments of any of the above embodiments of compounds of Formula It, each R$^{27}$ is independently optionally substituted cycloalkyl, optionally substituted heterocycloalkyl, optionally substituted aryl, or optionally substituted heteroaryl, or R$^{27}$ is halogen, provided that Y$^2$, Y$^4$ or Y$^5$ is a bond.

In some embodiments, the compound of Formula I has a structure according to the following sub-generic structure Formula Iu:

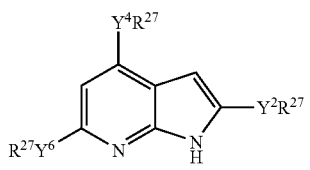

Formula Iu all salts, prodrugs, tautomers, and isomers thereof, wherein $Y^2 Y^4$ and $Y^6$ are independently a bond, —$CR^aR^b$—, or L, and each $R^{27}$ is independently halogen, provided that $Y^2$, $Y^4$ or $Y^6$ is a bond, or $R^{26}$, provided, however, that none of $Y^2R^{27}$, $Y^4R^{27}$, and $Y^6R^{27}$ are hydrogen, wherein $R^a$, $R^b$, L and $R^{26}$ are as defined with reference to Formula I.

In some embodiments of compounds of Formula Iu, $Y^2$, $Y^4$ and $Y^6$ are bonds. In some embodiments, $Y^2$, $Y^4$ and $Y^6$ are independently —$CR^aR^b$— or L. In some embodiments, $Y^2$, $Y^4$ and $Y^6$ are independently L. In some embodiments, any one of $Y^2$, $Y^4$ and $Y^6$ is a bond, and the remaining of $Y^2$, $Y^4$ and $Y^6$ are independently —$CR^aR^b$— or L. In some embodiments, any one of $Y^2$, $Y^4$ and $Y^6$ is a bond, and the remaining of $Y^2$, $Y^4$ and $Y^6$ are independently L. In some embodiments, any two of $Y^2$, $Y^4$ and $Y^6$ are bonds, and the remaining of $Y^2$, $Y^4$ and $Y^6$ is —$CR^aR^b$— or L. In some embodiments, any two of $Y^2$, $Y^4$ and $Y^6$ are bonds, and the remaining of $Y^2$, $Y^4$ and $Y^6$ is L.

In some embodiments of any of the above embodiments of compounds of Formula Iu, each $R^{27}$ is independently optionally substituted cycloalkyl, optionally substituted heterocycloalkyl, optionally substituted aryl, or optionally substituted heteroaryl, or $R^{27}$ is halogen, provided that $Y^2$, $Y^4$ or $Y^6$ is a bond.

In some embodiments, the compound of Formula I has a structure according to the following sub-generic structure Formula Iv:

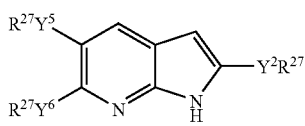

Formula Iv all salts, prodrugs, tautomers, and isomers thereof, wherein $Y^2 Y^5$ and $Y^6$ are independently a bond, —$CR^aR^b$—, or L, and each $R^{27}$ is independently halogen, provided that $Y^2$, $Y^5$ or $Y^6$ is a bond, or $R^{26}$, provided, however, that none of $Y^2R^{27}$, $Y^5R^{27}$, and $Y^6R^{27}$ are hydrogen, wherein $R^a$, $R^b$, L and $R^{26}$ are as defined with reference to Formula I.

In some embodiments of compounds of Formula Iv, $Y^2$, $Y^5$ and $Y^6$ are bonds. In some embodiments, $Y^2$, $Y^5$ and $Y^6$ are independently —$CR^aR^b$— or L. In some embodiments, $Y^2$, $Y^5$ and $Y^6$ are independently L. In some embodiments, any one of $Y^2$, $Y^5$ and $Y^6$ is a bond, and the remaining of $Y^2$, $Y^5$ and $Y^6$ are independently —$CR^aR^b$— or L. In some embodiments, any one of $Y^2$, $Y^5$ and $Y^6$ is a bond, and the remaining of $Y^2$, $Y^5$ and $Y^6$ are independently L. In some embodiments, any two of $Y^2$, $Y^5$ and $Y^6$ are bonds, and the remaining of $Y^2$, $Y^5$ and $Y^6$ is —$CR^aR^b$— or L. In some embodiments, any two of $Y^2$, $Y^5$ and $Y^6$ are bonds, and the remaining of $Y^2$, $Y^5$ and $Y^6$ is L.

In some embodiments of any of the above embodiments of compounds of Formula Iv, each $R^{27}$ is independently optionally substituted cycloalkyl, optionally substituted heterocycloalkyl, optionally substituted aryl, or optionally substituted heteroaryl, or $R^{27}$ is halogen, provided that $Y^2$, $Y^5$ or $Y^6$ is a bond.

In some embodiments, the compound of Formula I has a structure according to the following sub-generic structure Formula Iw:

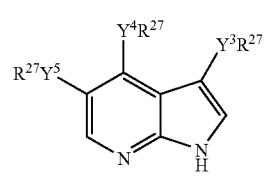

Formula Iw all salts, prodrugs, tautomers, and isomers thereof, wherein $Y^3 Y^4$ and $Y^5$ are independently a bond, —$CR^aR^b$—, or L, and each $R^{27}$ is independently halogen, provided that $Y^3$, $Y^4$ or $Y^5$ is a bond, or $R^{26}$, provided, however, that none of $Y^3R^{27}$, $Y^4R^{27}$, and $Y^5R^{27}$ are hydrogen, wherein $R^a$, $R^b$, L and $R^{26}$ are as defined with reference to Formula I.

In some embodiments of compounds of Formula Iw, $Y^3$, $Y^4$ and $Y^5$ are bonds. In some embodiments, $Y^3$, $Y^4$ and $Y^5$ are independently —$CR^aR^b$— or L. In some embodiments, $Y^3$, $Y^4$ and $Y^5$ are independently L. In some embodiments, any one of $Y^3$, $Y^4$ and $Y^5$ is a bond, and the remaining of $Y^3$, $Y^4$ and $Y^5$ are independently —$CR^aR^b$— or L. In some embodiments, any one of $Y^3$, $Y^4$ and $Y^5$ is a bond, and the remaining of $Y^3$, $Y^4$ and $Y^5$ are independently L. In some embodiments, any two of $Y^3$, $Y^4$ and $Y^5$ are bonds, and the remaining of $Y^3$, $Y^4$ and $Y^5$ is —$CR^aR^b$— or L. In some embodiments, any two of $Y^3$, $Y^4$ and $Y^5$ are bonds, and the remaining of $Y^3$, $Y^4$ and $Y^5$ is L.

In some embodiments of any of the above embodiments of compounds of Formula Iw, each $R^{27}$ is independently optionally substituted cycloalkyl, optionally substituted heterocycloalkyl, optionally substituted aryl, or optionally substituted heteroaryl, or $R^{27}$ is halogen, provided that $Y^3$, $Y^4$ or $Y^5$ is a bond.

In some embodiments, the compound of Formula I has a structure according to the following sub-generic structure Formula Ix:

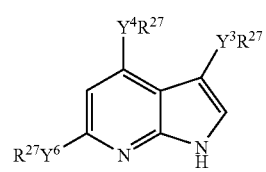

Formula Ix all salts, prodrugs, tautomers, and isomers thereof, wherein $Y^3 Y^4$ and $Y^6$ are independently a bond, —$CR^aR^b$— or L, and each $R^{27}$ is independently halogen, provided that $Y^3$, $Y^4$ or $Y^6$ is a bond, or $R^{26}$, provided, however, that none of $Y^3R^{27}$, $Y^4R^{27}$ and $Y^6R^{27}$ are hydrogen, wherein $R^a$, $R^b$, L and $R^{26}$ are as defined with reference to Formula I.

In some embodiments of compounds of Formula Ix, $Y^3$, $Y^4$ and $Y^6$ are bonds. In some embodiments, $Y^3$, $Y^4$ and $Y^6$ are independently —$CR^aR^b$— or L. In some embodiments, $Y^3$, $Y^4$ and $Y^6$ are independently L. In some embodiments, any one of $Y^3$, $Y^4$ and $Y^6$ is a bond, and the remaining of $Y^3$, $Y^4$ and $Y^6$ are independently —$CR^aR^b$— or L. In some embodiments, any one of $Y^3$, $Y^4$ and $Y^6$ is a bond, and the remaining of $Y^3$, $Y^4$ and $Y^6$ are independently L. In some embodiments, any two of $Y^3$, $Y^4$ and $Y^6$ are bonds, and the remaining of $Y^3$, $Y^4$ and $Y^6$ is —$CR^aR^b$— or L. In some embodiments, any two of $Y^3$, $Y^4$ and $Y^6$ are bonds, and the remaining of $Y^3$, $Y^4$ and $Y^6$ is L.

In some embodiments of any of the above embodiments of compounds of Formula Ix, each $R^{27}$ is independently optionally substituted cycloalkyl, optionally substituted heterocycloalkyl, optionally substituted aryl, or optionally substituted heteroaryl, or $R^{27}$ is halogen, provided that $Y^3$, $Y^4$ or $Y^6$ is a bond.

In some embodiments, the compound of Formula I has a structure according to the following sub-generic structure Formula Iy:

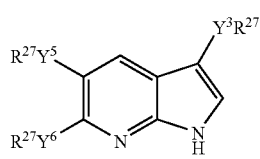

Formula Iy all salts, prodrugs, tautomers, and isomers thereof, wherein $Y^3Y^5$ and $Y^6$ are independently a bond, —$CR^aR^b$—, or L, and each $R^{27}$ is independently halogen, provided that $Y^3$, $Y^5$ or $Y^6$ is a bond, or $R^{26}$, provided, however, that none of $Y^3R^{27}$, $Y^5R^{27}$, and $Y^6R^{27}$ are hydrogen, wherein $R^a$, $R^b$, L and $R^{26}$ are as defined with reference to Formula I.

In some embodiments of compounds of Formula Iy, $Y^3$, $Y^5$ and $Y^6$ are bonds. In some embodiments, $Y^3$, $Y^5$ and $Y^6$ are independently —$CR^aR^b$— or L. In some embodiments, $Y^3$, $Y^5$ and $Y^6$ are independently L. In some embodiments, any one of $Y^3$, $Y^5$ and $Y^6$ is a bond, and the remaining of $Y^3$, $Y^5$ and $Y^6$ are independently —$CR^aR^b$— or L. In some embodiments, any one of $Y^3$, $Y^5$ and $Y^6$ is a bond, and the remaining of $Y^3$, $Y^5$ and $Y^6$ are independently L. In some embodiments, any two of $Y^3$, $Y^5$ and $Y^6$ are bonds, and the remaining of $Y^3$, $Y^5$ and $Y^6$ is —$CR^aR^b$— or L. In some embodiments, any two of $Y^3$, $Y^5$ and $Y^6$ are bonds, and the remaining of $Y^3$, $Y^5$ and $Y^6$ is L.

In some embodiments of any of the above embodiments of compounds of Formula Iy, each $R^{27}$ is independently optionally substituted cycloalkyl, optionally substituted heterocycloalkyl, optionally substituted aryl, or optionally substituted heteroaryl, or $R^{27}$ is halogen, provided that $Y^3$, $Y^5$ or $Y^6$ is a bond.

In some embodiments, the compound of Formula I has a structure according to the following sub-generic structure Formula Iz:

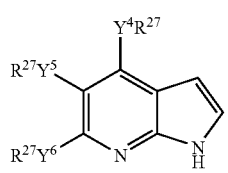

Formula Iz all salts, prodrugs, tautomers, and isomers thereof, wherein $Y^4Y^5$ and $Y^6$ are independently a bond, —$CR^aR^b$—, or L, and each $R^{27}$ is independently halogen, provided that $Y^4$, $Y^5$ or $Y^6$ is a bond, or $R^{26}$, provided, however, that none of $Y^4R^{27}$, $Y^5R^{27}$, and $Y^6R^{27}$ are hydrogen, wherein $R^a$, $R^b$, L and $R^{26}$ are as defined with reference to Formula I.

In some embodiments of compounds of Formula Iz, $Y^4$, $Y^5$ and $Y^6$ are bonds. In some embodiments, $Y^4$, $Y^5$ and $Y^6$ are independently —$CR^aR^b$— or L. In some embodiments, $Y^4$, $Y^5$ and $Y^6$ are independently L. In some embodiments, any one of $Y^4$, $Y^5$ and $Y^6$ is a bond, and the remaining of $Y^4$, $Y^5$ and $Y^6$ are independently —$CR^aR^b$— or L. In some embodiments, any one of $Y^4$, $Y^5$ and $Y^6$ is a bond, and the remaining of $Y^4$, $Y^5$ and $Y^6$ are independently L. In some embodiments, any two of $Y^4$, $Y^5$ and $Y^6$ are bonds, and the remaining of $Y^4$, $Y^5$ and $Y^6$ is —$CR^aR^b$— or L. In some embodiments, any two of $Y^4$, $Y^5$ and $Y^6$ are bonds, and the remaining of $Y^4$, $Y^5$ and $Y^6$ is L.

In some embodiments, of any of the above embodiments of compounds of Formula Iz, each $R^{27}$ is independently optionally substituted cycloalkyl, optionally substituted heterocycloalkyl, optionally substituted aryl, or optionally substituted heteroaryl, or $R^{27}$ is halogen, provided that $Y^4$, $Y^5$ or $Y^6$ is a bond.

The compounds of Formulae Ia-Iz, and all sub-embodiments detailed herein, may be used to treat a subject suffering from or at risk for any of the protein kinase mediated diseases or conditions contemplated herein.

In some embodiments, compounds of Formula I have the structure according to the following sub-generic structure Formula II:

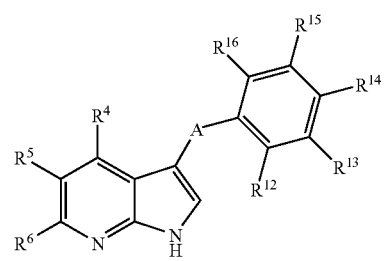

Formula II all salts, prodrugs, tautomers and isomers thereof,
wherein:
A, $R^4$, $R^5$ and $R^6$ are as defined with reference to Formula I; and
$R^{12}$, $R^{13}$, $R^{14}$, $R^{15}$ and $R^{16}$ are independently selected from the group consisting of hydrogen, halogen, optionally substituted lower alkyl, optionally substituted lower alkenyl, optionally substituted lower alkynyl, optionally substituted cycloalkyl, optionally substituted heterocycloalkyl, optionally substituted aryl, optionally substituted heteroaryl, —CN, —$NO_2$, —$CR^aR^bR^{24}$, and -L$R^{24}$, where L and $R^{24}$ are as defined for Formula I.

In some embodiments of compounds of Formula II, at least one of $R^{12}$, $R^{13}$, $R^{14}$, $R^{15}$ and $R^{16}$ is other than hydrogen. In some embodiments, at least two of $R^{12}$, $R^{13}$, $R^{14}$, $R^{15}$ and $R^{16}$ are other than hydrogen. In some embodiments, at least three of $R^{12}$, $R^{13}$, $R^{14}$, $R^{15}$ and $R^{16}$ are other than hydrogen. In some embodiments, at least four of $R^{12}$, $R^{13}$, $R^{14}$, $R^{15}$ and $R^{16}$ are other than hydrogen. In some embodiments, $R^{12}$, $R^{13}$, $R^{14}$, $R^{15}$ and $R^{16}$ are other than hydrogen.

In some embodiments of compounds of Formula II, one of $R^{12}$, $R^{13}$, $R^{14}$, $R^{15}$ and $R^{16}$ is other than hydrogen, and the others of $R^{12}$, $R^{13}$, $R^{14}$, $R^{15}$ and $R^{16}$ are each independently hydrogen, halogen, optionally fluoro substituted lower alkyl, optionally fluoro substituted lower alkoxy, or optionally fluoro substituted lower alkylthio. In some embodiments, $R^{12}$ is other than hydrogen and $R^{13}$, $R^{14}$, $R^{15}$ and $R^{16}$ are each independently hydrogen, halogen, optionally fluoro substituted lower alkyl, optionally fluoro substituted lower alkoxy, or optionally fluoro substituted lower alkylthio. In some embodiments, $R^{13}$ is other than hydrogen, and $R^{12}$, $R^{14}$, $R^{15}$ and $R^{16}$ are each independently hydrogen, halogen, optionally fluoro substituted lower alkyl, optionally fluoro substituted lower alkoxy, or optionally fluoro substituted lower alkylthio. In some embodiments, $R^{14}$ is other than hydrogen, and $R^{12}$, $R^{13}$, $R^{15}$ and $R^{16}$ are each independently hydrogen, halogen, optionally fluoro substituted lower alkyl, optionally fluoro substituted lower alkoxy, or optionally fluoro substituted lower alkylthio.

In some embodiments of compounds of Formula II, any two of $R^{12}$, $R^{13}$, $R^{14}$, $R^{15}$ and $R^{16}$ are independently other than hydrogen, and the others of $R^{12}$, $R^{13}$, $R^{14}$, $R^{15}$ and $R^{16}$ are each independently hydrogen, halogen, optionally fluoro substituted lower alkyl, optionally fluoro substituted lower alkoxy, or optionally fluoro substituted lower alkylthio. In some embodiments, $R^{12}$ and $R^{13}$ are each independently other than hydrogen, and $R^{14}$, $R^{15}$ and $R^{16}$ are each independently hydrogen, halogen, optionally fluoro substituted lower alkyl, optionally fluoro substituted lower alkoxy, or optionally fluoro substituted lower alkylthio. In some embodiments, $R^{12}$ and $R^{14}$ are each independently other than hydrogen, and $R^{13}$, $R^{15}$ and $R^{16}$ are each independently hydrogen, halogen, optionally fluoro substituted lower alkyl, optionally fluoro substituted lower alkoxy, or optionally fluoro substituted lower alkylthio. In some embodiments, $R^{12}$ and $R^{15}$ are each independently other than hydrogen, and $R^{13}$, $R^{14}$ and $R^{16}$ are each independently hydrogen, halogen, optionally fluoro substituted lower alkyl, optionally fluoro substituted lower alkoxy, or optionally fluoro substituted lower alkylthio. In some embodiments, $R^{12}$ and $R^{16}$ are each independently other than hydrogen, and $R^{13}$, $R^{14}$ and $R^{15}$ are each independently hydrogen, halogen, optionally fluoro substituted lower alkyl, optionally fluoro substituted lower alkoxy, or optionally fluoro substituted lower alkylthio. In some embodiments, $R^{13}$ and $R^{14}$ are each independently other than hydrogen, and $R^{12}$, $R^{15}$ and $R^{16}$ are each independently hydrogen, halogen, optionally fluoro substituted lower alkyl, optionally fluoro substituted lower alkoxy, or optionally fluoro substituted lower alkylthio. In some embodiments, $R^{13}$ and $R^{15}$ are each independently other than hydrogen, and $R^{12}$, $R^{14}$ and $R^{16}$ are each independently hydrogen, halogen, optionally fluoro substituted lower alkyl, optionally fluoro substituted lower alkoxy, or optionally fluoro substituted lower alkylthio.

In some embodiments of any of the above embodiments of compounds of Formula II, wherein any of $R^{12}$, $R^{13}$, $R^{14}$, $R^{15}$, and $R^{16}$ is designated as other than hydrogen, each such $R^{12}$, $R^{13}$, $R^{14}$, $R^{15}$, or $R^{16}$ is independently -$LR^{24}$.

In some embodiments of any of the above embodiments of compounds of Formula II, $R^5$ is other than hydrogen, and $R^4$ and $R^6$ are hydrogen, or $R^4$ is other than hydrogen, and $R^5$ and $R^6$ are hydrogen, or $R^6$ is other than hydrogen, and $R^4$ and $R^5$ are hydrogen, or $R^4$ and $R^5$ are other than hydrogen, and $R^6$ is hydrogen, or $R^4$ and $R^6$ are other than hydrogen, and $R^5$ is hydrogen, or $R^5$ and $R^6$ are other than hydrogen, and $R^4$ is hydrogen, or $R^4$, $R^5$ and $R^6$ are other than hydrogen.

In some embodiments of compounds of Formula II, the following compounds are excluded:

$R^4$, $R^5$, $R^6$, $R^{12}$, $R^{13}$, $R^{14}$, $R^{15}$ and $R^{16}$ are hydrogen and A is —$CH_2$—, —S— or —$S(O)_2$—;

$R^4$, $R^6$, $R^{12}$, $R^{13}$, $R^{14}$, $R^{15}$ and $R^{16}$ are hydrogen, $R^5$ is —Br or thiophen-3-yl, and A is —C(O)—;

$R^4$ is 3,5 di-fluorophenyl, —$NH_2$, or —$NO_2$, $R^5$, $R^6$, $R^{12}$, $R^{13}$, $R^{14}$, $R^{15}$ and $R^{16}$ are hydrogen, and A is —C(O)—;

$R^4$ is $NO_2$, $R^5$ is Br, $R^{12}$, $R^{13}$, $R^{14}$, $R^{15}$ and $R^{16}$ are hydrogen, and A is —C(O)—;

$R^5$ is —Br, $R^4$, $R^6$, $R^{12}$, $R^{13}$, $R^{14}$, $R^{15}$ and $R^{16}$ are hydrogen, and A is —S(O)—;

$R^{12}$ is —$CH_3$ or —F, $R^6$, $R^{13}$, $R^{14}$, $R^{15}$ and $R^{16}$ are hydrogen, and A is —C(O)—;

$R^{12}$ is —OH, $R^4$, $R^6$, $R^{13}$, $R^{14}$, $R^{15}$ and $R^{16}$ are hydrogen, $R^5$ is thiophen-2-yl, and A is —C(O)—;

$R^{12}$ is —$CF_3$, $R^4$, $R^5$, $R^6$, $R^{13}$, $R^{14}$, $R^{15}$ and $R^{16}$ are hydrogen, and A is —$S(O)_2$;

$R^{13}$ is —OH or —$OCH_3$, $R^4$, $R^6$, $R^{12}$, $R^{14}$, $R^{15}$ and $R^{16}$ are hydrogen, and A is —$CH_2$—;

$R^{13}$ is —$OCH_3$, $R^5$, $R^6$, $R^{12}$, $R^{14}$, $R^{15}$ and $R^{16}$ are hydrogen, $R^4$ is —Br, and A is —$CH_2$—;

$R^{13}$ is —OH or —$OCH_3$, $R^4$, $R^6$, $R^{12}$, $R^{14}$, $R^{15}$ and $R^{16}$ are hydrogen, $R^5$ is thiophen-2-yl, and A is —CHOH—;

$R^{13}$ is

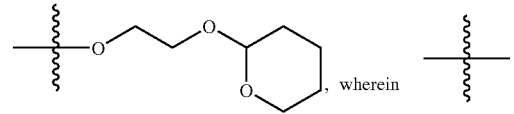, wherein indicates the bond to the phenyl ring, $R^4$, $R^6$, $R^{12}$, $R^{14}$, $R^{15}$ and $R^{16}$ are hydrogen, $R^5$ is thiophen-3-yl, and A is —$CH_2$—;

$R^{13}$ is —F, —OH or —$OCH_3$, $R^6$, $R^{12}$, $R^{14}$, $R^{15}$ and $R^{16}$ are hydrogen, and A is —C(O)—;

$R^{13}$, is —$NO_2$, —$NH_2$, or

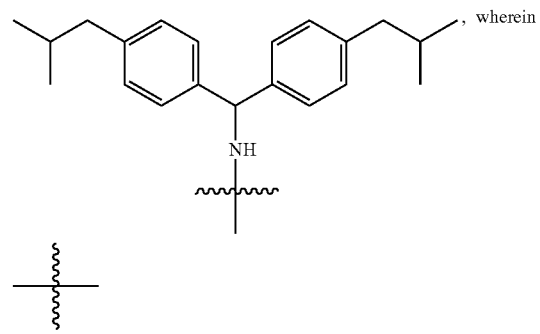, wherein indicates the bond to the phenyl ring, $R^4$, $R^5$, $R^6$, $R^{12}$, $R^{14}$, $R^{15}$ and $R^{16}$ are hydrogen, and A is —C(O)—;

$R^{13}$ is —F, —Cl, or —$CF_3$, $R^4$, $R^5$, $R^6$, $R^{12}$, $R^{14}$, $R^{15}$ and $R^{16}$ are hydrogen, and A is —$S(O)_2$—;

$R^{13}$ and $R^{14}$ are —OH, $R^4$, $R^6$, $R^{12}$, $R^{15}$ and $R^{16}$ are hydrogen, $R^5$ is thiophen-3-yl, and A is —$CH_2$—;

$R^{14}$ is —OH or —$OCH_3$, $R^4$, $R^6$, $R^{12}$, $R^{13}$, $R^{15}$ and $R^{16}$ are hydrogen, $R^5$ is thiophen-2-yl, and A is —C(O)—;

$R^{14}$ is —$OCH_3$, $R^4$, $R^5$, $R^6$, $R^{12}$, $R^{13}$, $R^{15}$ and $R^{16}$ are hydrogen, and A is —C(O)—;

$R^{14}$ is —Cl, $R^6$, $R^{12}$, $R^{13}$, $R^{15}$ and $R^{16}$ are hydrogen, and A is —C(O)—;

$R^{14}$ is

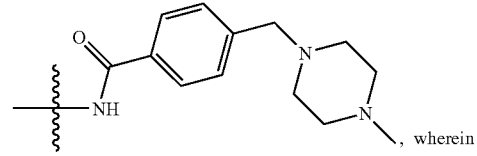, wherein

indicates the bond to the phenyl ring, $R^4$, $R^5$, $R^6$, $R^{12}$, $R^{13}$, $R^{15}$ and $R^{16}$ are hydrogen, and A is —$CH_2$—;

$R^{14}$ is —F, $R^4$, $R^5$, $R^6$, $R^{12}$, $R^{13}$, $R^{15}$ and $R^{16}$ are hydrogen, and A is —S— or —$S(O)_2$—;

$R^{14}$ is —$CH_3$, $R^5$, $R^6$, $R^{12}$, $R^{13}$, $R^{15}$ and $R^{16}$ are hydrogen, $R^4$ is 3-(hydroxymethyl)phenyl, and A is —S—;

$R^{12}$ and $R^{16}$ are —F, $R^5$, $R^6$, $R^{13}$, $R^{14}$ and $R^{15}$ are hydrogen, $R^4$ is 3,5 difluorophenyl, and A is —C(O)—;

$R^{12}$ is —Cl, $R^{13}$ is —Cl, $R^6$, $R^{14}$, $R^{15}$ and $R^{16}$ are hydrogen, and A is —C(O)—;

$R^{12}$ is —F, $R^{13}$ is —F, $R^5$, $R^6$, $R^{14}$, $R^{15}$ and $R^{16}$ are hydrogen, $R^4$ is 3,5 difluorophenyl, and A is —C(O)—;

$R^{12}$ is —F, $R^{13}$ is —OH or —$OCH_3$, $R^4$, $R^6$, $R^{14}$, $R^{15}$ and $R^{16}$ are hydrogen, $R^5$ is thiophen-2-yl, and A is —C(O)—;

$R^{12}$ is —F, $R^{13}$ is —$OCH_3$, $R^4$, $R^6$, $R^{14}$, $R^{15}$ and $R^{16}$ are hydrogen, $R^5$ is —Br, and A is —C(O)—;

$R^{12}$ and $R^{14}$ are —F, $R^5$, $R^6$, $R^{13}$, $R^{15}$ and $R^{16}$ are hydrogen, $R^4$ is 3,5 difluorophenyl, and A is —C(O)—;

$R^{12}$ is —$CH_3$, $R^{15}$ is —F, $R^6$, $R^{13}$, $R^{14}$ and $R^{16}$ are hydrogen and A is —C(O)—;

$R^{12}$ is —F, $R^{15}$ is —Cl, $R^4$, $R^6$, $R^{13}$, $R^{14}$ and $R^{16}$ are hydrogen, $R^5$ is thiophen-2-yl and A is —C(O)—;

$R^{12}$ and $R^{15}$ are —F, $R^6$, $R^{13}$, $R^{14}$ and $R^{16}$ are hydrogen, and A is —C(O)—;

$R^{12}$ is halogen, $R^{15}$ is —OH or —$OCH_3$, $R^6$, $R^{13}$, $R^{14}$ and $R^{16}$ are hydrogen and A is —C(O)—;

$R^{12}$ is —F, $R^{15}$ is —$NHS(O)_2CH_3$, $R^4$, $R^5$, $R^6$, $R^{13}$, $R^{14}$ and $R^{16}$ are hydrogen and A is —C(O)—;

$R^{13}$ and $R^{15}$ are —$OCH_3$, $R^4$, $R^5$, $R^6$, $R^{12}$, $R^{14}$ and $R^{16}$ are hydrogen, and A is —$CH_2$—;

$R^{13}$ and $R^{15}$ are —Cl, $R^4$, $R^5$, $R^6$, $R^{12}$, $R^{14}$ and $R^{16}$ are hydrogen, and A is —$S(O)_2$—;

$R^{13}$ is —OH and $R^{15}$ is —OH or —$OCH_3$, $R^4$, $R^6$, $R^{12}$, $R^{14}$ and $R^{16}$ are hydrogen, $R^5$ is thiophen-3-yl, and A is —$CH_2$—;

$R^4$, $R^6$, $R^{12}$, $R^{13}$, $R^{14}$, $R^{15}$ and $R^{16}$ are hydrogen, A is —$S(O)_2$—, and $R^5$ is

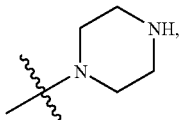

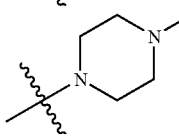

indicates the bond to the 5-position of the 7-azaindole ring; $R^5$, $R^6$, $R^{12}$, $R^{13}$, $R^{14}$, $R^{15}$ and $R^{16}$ are hydrogen, A is —$S(O)_2$—, and $R^4$ is

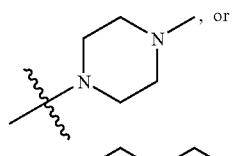

indicates the bond to the 4-position of the 7-azaindole ring; $R^4$, $R^5$, $R^{12}$, $R^{13}$, $R^{14}$, $R^{15}$ and $R^{16}$ are hydrogen, A is —$S(O)_2$—, and $R^6$ is

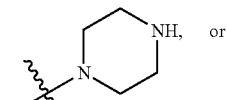

indicates the bond to the 6-position of the 7-azaindole ring; $R^{13}$ is —CN, $R^4$, $R^6$, $R^{12}$, $R^{14}$, $R^{15}$ and $R^{16}$ are hydrogen, A is —$S(O)_2$—, and $R^5$ is

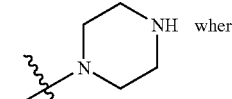

indicates the bond to the 5-position of the 7-azaindole ring; $R^{12}$ is —Cl, $R^{14}$ is —F or hydrogen, $R^4$, $R^6$, $R^{13}$, $R^{15}$ and $R^{16}$ are hydrogen, A is —$S(O)_2$—, and $R^5$ is

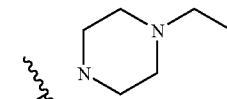

indicates the bond to the 5-position of the 7-azaindole ring; $R^{14}$ is —$NH_2$, $R^4$, $R^6$, $R^{12}$, $R^{13}$, $R^{15}$ and $R^{16}$ are hydrogen, A is —$S(O)_2$—, and $R^5$ is

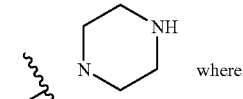

indicates the bond to the 5-position of the 7-azaindole ring; $R^6$, $R^{12}$, $R^{13}$, $R^{14}$, $R^{15}$ and $R^{16}$ are hydrogen, A is —$S(O)_2$—, $R^4$ is —Cl, and $R^5$ is

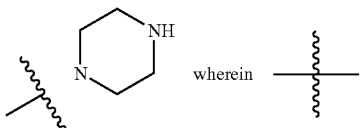

indicates the bond to the 5-position of the 7-azaindole ring;
$R^{13}$ is —F, $R^4$, $R^6$, $R^{12}$, $R^{14}$, $R^{15}$ and $R^{16}$ are hydrogen, A is —CH and and $R^5$ is 3-hydroxy-phenyl;
$R^{14}$ is —N(CH$_3$)$_2$, $R^4$, $R^6$, $R^{12}$, $R^{13}$, $R^{15}$ and $R^{16}$ are hydrogen, A is —CH$_2$—, and $R^5$ is 3-hydroxy-phenyl;
$R^{14}$ is hydrogen or —Br, $R^4$, $R^6$, $R^{12}$, $R^{13}$, $R^{15}$ and $R^{16}$ are hydrogen, A is —S—, and $R^5$ is 3-hydroxy-phenyl; and
$R^4$, $R^6$, $R^{12}$, $R^{13}$, $R^{14}$, $R^{15}$ and $R^{16}$ are hydrogen, A is —C(O)—, and $R^5$ is 3-hydroxy-phenyl.

In some embodiments of compounds of Formula II, at least one of $R^{12}$, $R^{13}$, $R^{14}$, $R^{15}$ and $R^{16}$ is -L$R^{24}$, wherein $R^{24}$ is substituted methyl, optionally substituted alkyl, optionally substituted lower alkenyl, provided, however, that when $R^{24}$ is optionally substituted lower alkenyl, no alkene carbon thereof is bound to N, S, O, S(O), S(O)$_2$, C(O) or C(S) of L, optionally substituted lower alkynyl, provided, however, that when $R^{24}$ is optionally substituted lower alkynyl, no alkyne carbon thereof is bound to N, S, O, S(O), S(O)$_2$, C(O) or C(S) of L, optionally substituted cycloalkyl, optionally substituted heterocycloalkyl, optionally substituted aryl, or optionally substituted heteroaryl, provided, however, that $R^{13}$ is not and

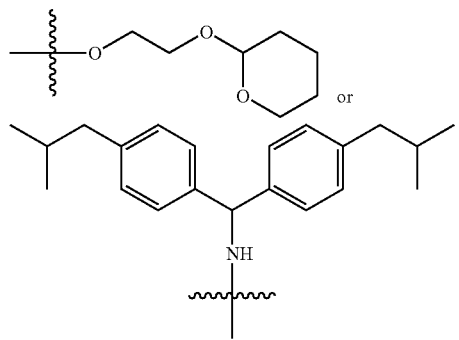

and that $R^{14}$ is not

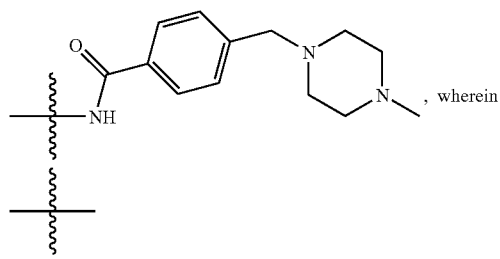

indicates the bond to the phenyl ring; in further embodiments, $R^{24}$ is optionally substituted C$_{2-6}$ alkyl, optionally substituted cycloalkyl, optionally substituted heterocycloalkyl, optionally substituted aryl, optionally substituted heteroaryl, or substituted methyl, wherein methyl is substituted with optionally substituted cycloalkyl, optionally substituted heterocycloalkyl, optionally substituted aryl, or optionally substituted heteroaryl; in further embodiments, $R^5$ is other than hydrogen; in further embodiments, $R^4$ and $R^6$ are hydrogen.

In some embodiments of compounds of Formula II, $R^{12}$ is other than hydrogen. In some embodiments, $R^{12}$ is -L$R^{24}$. In some embodiments, $R^{12}$ is other than hydrogen and $R^{13}$, $R^{14}$, $R^{15}$ and $R^{16}$ are each independently hydrogen, halogen, optionally fluoro substituted lower alkyl, optionally fluoro substituted lower alkoxy, or optionally fluoro substituted lower alkylthio. In some embodiments, $R^{12}$ is -L$R^{24}$ and $R^{13}$, $R^{15}$, $R^{15}$ and $R^{16}$ are independently hydrogen, halogen, optionally fluoro substituted lower alkyl, optionally fluoro substituted lower alkoxy, or optionally fluoro substituted lower alkylthio. In some embodiments, R is -L$R^{24}$, any three of $R^{13}$, $R^{14}$, $R^{15}$ and $R^{16}$ are independently hydrogen, halogen, optionally fluoro substituted lower alkyl, optionally fluoro substituted lower alkoxy, or optionally fluoro substituted lower alkylthio and the remaining of $R^{13}$, $R^{14}$, $R^{15}$ and $R^{16}$ is hydrogen. In some embodiments, $R^{12}$ is -L$R^{24}$, any two of $R^{13}$, $R^{14}$, $R^{15}$ and $R^{16}$ are independently hydrogen, halogen, optionally fluoro substituted lower alkyl, optionally fluoro substituted lower alkoxy, or optionally fluoro substituted lower alkylthio and the remaining of $R^{13}$, $R^{14}$, $R^{15}$ and $R^{16}$ are hydrogen. In some embodiments, $R^{12}$ is -L$R^{24}$, any one of $R^{13}$, $R^{14}$, $R^{15}$ and $R^{16}$ is hydrogen, halogen, optionally fluoro substituted lower alkyl, optionally fluoro substituted lower alkoxy, or optionally fluoro substituted lower alkylthio and the remaining of $R^{13}$, $R^{14}$, $R^{15}$ and $R^{16}$ are hydrogen. In some embodiments, $R^{12}$ is -L$R^{24}$, and $R^{13}$, $R^{14}$, $R^{15}$ and $R^{16}$ are hydrogen. In some embodiments, $R^{12}$ is other than hydrogen, and $R^{13}$, $R^{14}$, $R^{15}$ and $R^{16}$ are hydrogen.

In other embodiments of compounds of Formula II, wherein $R^{12}$ is other than hydrogen, when $R^{13}$, $R^{14}$, $R^{15}$ and $R^{16}$ are hydrogen and A is —C(O)—, then $R^{12}$ is not —CH$_3$, —F, or —OH; and when $R^4$, $R^5$, $R^6$, $R^{13}$, $R^{14}$, $R^{15}$ and $R^{16}$ are hydrogen, and A is —S(O)$_2$—, then $R^{12}$ is not —CF$_3$; and when $R^{12}$ and $R^{16}$ are —F, $R^5$, $R^6$, $R^{13}$, $R^{14}$ and $R^{15}$ are hydrogen, and A is —C(O)—, $R^4$ is not 3,5 difluorophenyl; and when $R^{12}$ is halogen, $R^6$, $R^{14}$, $R^{15}$ and $R^{16}$ are hydrogen, and A is —C(O)—, $R^{13}$ is not halogen, —OH, or —OCH$_3$; and when $R^{12}$ and $R^{14}$ are —F, $R^5$, $R^6$, $R^{13}$, $R^{15}$ and $R^{16}$ are hydrogen, and A is —C(O)—, $R^4$ is not 3,5 difluorophenyl; and when $R^{15}$ is halogen, —OH or —OCH$_3$, $R^6$, $R^{13}$, $R^{14}$ and $R^{15}$ are hydrogen, and A is —C(O)—, $R^{12}$ is not halogen; and when $R^{15}$ is —F, $R^6$, $R^{13}$, $R^{14}$ and $R^{16}$ are hydrogen and A is —C(O)—, $R^{12}$ is not —CH$_3$; and when $R^{12}$ is —F, $R^4$, $R^5$, $R^6$, $R^{13}$, $R^{14}$ and hydrogen and A is —C(O)—, $R^{15}$ is not —NHS(O)$_2$CH$_3$; and when $R^{12}$ is —Cl, $R^{14}$ is —F or hydrogen, $R^4$, $R^6$, $R^{13}$, $R^{15}$ and $R^{16}$ are hydrogen, and A is —S(O)$_2$—, $R^5$ is not

indicates the bond to the 5-position of the 7-azaindole ring.

In some embodiments of any of the above embodiments of compounds of Formula II wherein $R^{12}$ is other than hydrogen, $R^5$ is other than hydrogen and $R^4$ and $R^6$ are hydrogen; or $R^4$ is other than hydrogen and $R^5$ and $R^6$ are hydrogen; or $R^6$ is other than hydrogen and $R^4$ and $R^5$ are hydrogen; or $R^4$ and $R^5$ are other than hydrogen and $R^6$ is hydrogen; or $R^4$ and $R^5$ are other than hydrogen and $R^5$ is hydrogen; or $R^5$ and $R^6$ are other than hydrogen and $R^4$ is hydrogen; or $R^4$, $R^5$ and $R^6$ are all other than hydrogen.

In some embodiments of compounds of Formula II, $R^{13}$ is other than hydrogen. In some embodiments, $R^{13}$ is -$LR^{24}$. In some embodiments, $R^{13}$ is other than hydrogen and $R^{12}$, $R^{14}$, $R^{15}$ and $R^{16}$ are each independently hydrogen, halogen, optionally fluoro substituted lower alkyl, optionally fluoro substituted lower alkoxy, or optionally fluoro substituted lower alkylthio. In some embodiments, $R^{13}$ is -$LR^{24}$ and $R^{12}$, $R^{14}$, $R^{15}$ and $R^{16}$ are each independently hydrogen, halogen, optionally fluoro substituted lower alkyl, optionally fluoro substituted lower alkoxy, or optionally fluoro substituted lower alkylthio. In some embodiments, $R^{13}$ is -$LR^{24}$, any three of $R^{12}$, $R^{14}$, $R^{15}$ and $R^{16}$ are independently hydrogen, halogen, optionally fluoro substituted lower alkyl, optionally fluoro substituted lower alkoxy, or optionally fluoro substituted lower alkylthio and the remaining of $R^{12}$, $R^{14}$, $R^{15}$ and $R^{16}$ is hydrogen. In some embodiments, $R^{13}$ is -$LR^{24}$, any two of $R^{12}$, $R^{14}$, $R^{15}$ and $R^{16}$ are independently hydrogen, halogen, optionally fluoro substituted lower alkyl, optionally fluoro substituted lower alkoxy, or optionally fluoro substituted lower alkylthio and the remaining of $R^{12}$, $R^{14}$ $R^{15}$ and $R^{16}$ are hydrogen. In some embodiments, $R^{13}$ is -$LR^{24}$, any one of $R^{12}$, $R^{14}$, $R^{15}$ and $R^{16}$ is independently hydrogen, halogen, optionally fluoro substituted lower alkyl, optionally fluoro substituted lower alkoxy, or optionally fluoro substituted lower alkylthio, and the remaining of $R^{12}$, $R^{14}$, $R^{15}$ and $R^{16}$ are hydrogen. In some embodiments, $R^{13}$ is -$LR^{24}$, and $R^{12}$, $R^{14}$, $R^{15}$ and $R^{16}$ are hydrogen. In some embodiments, $R^{13}$ is other than hydrogen, and $R^{12}$, $R^{14}$, $R^{15}$ and $R^{16}$ are hydrogen.

In other embodiments of compounds of Formula II, wherein $R^{13}$ is other than hydrogen, when $R^4$, $R^6$, $R^{12}$, $R^{14}$, $R^{15}$ and $R^{16}$ are hydrogen, and A is —$CH_2$— or —CH(OH)—, then $R^{13}$ is not —OH or —$OCH_3$; and when $R^5$, $R^6$, $R^{12}$, $R^{14}$, $R^{15}$ and $R^{16}$ are hydrogen, and A is —$CH_2$—, then $R^{13}$ is not —$OCH_3$; and when $R^{13}$ is

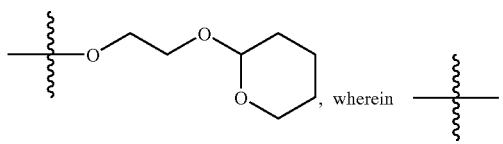, wherein indicates the bond to the phenyl ring, $R^4$, $R^6$, $R^{12}$, $R^{14}$, $R^{15}$ and $R^{16}$ are hydrogen, and A is —$CH_2$—, then $R^5$ is not thiophen-3-yl; and when $R^6$, $R^{12}$, $R^{14}$, $R^{15}$ and $R^{16}$ are hydrogen, and A is —C(O)—, then $R^{13}$ is not —F, —OH, or —$OCH_3$; and when $R^4$, $R^5$, $R^6$, $R^{12}$, $R^{14}$, $R^{15}$ and $R^{16}$ are hydrogen, and A is —C(O)—, then $R^{13}$ is not —$NO_2$, —$NH_2$, or

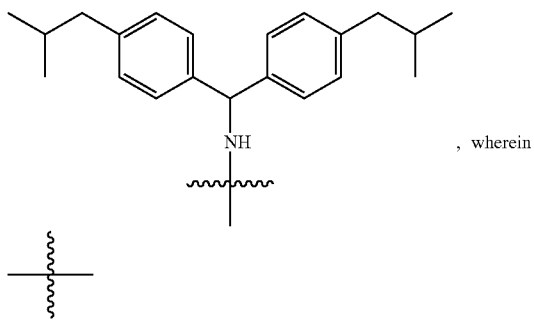, wherein indicates the bond to the phenyl ring; and when $R^4$, $R^5$, $R^6$, $R^{12}$, $R^{14}$, $R^{15}$ and $R^{16}$ are hydrogen, and A is —$S(O)_2$—, then $R^{13}$ is not —F, —Cl, or —$CF_3$; and when $R^{13}$ and $R^{14}$ are —OH, $R^4$, $R^6$, $R^{12}$, $R^{15}$ and $R^{16}$ are hydrogen and A is —$CH_2$—, $R^5$ is not thiophen-3-yl; and when $R^6$, $R^{14}$, $R^{15}$ and $R^{16}$ are hydrogen and A is —C(O)—, then $R^{13}$ and $R^{12}$ are not both Cl; and when $R^{12}$ and $R^{13}$ are both —F, $R^5$, $R^6$, $R^{14}$, $R^{15}$ and $R^{16}$ are hydrogen and A is —C(O)—, then $R^4$ is not 3,5-difluorophenyl; and when $R^{13}$ is —OH or —$OCH_3$, $R^{12}$ is —F, $R^4$, $R^6$, $R^{14}$, $R^{15}$ and $R^{16}$ are hydrogen, and A is —C(O)—, then $R^5$ is not thiophen-2-yl; and when $R^{13}$ is —$OCH_3$, $R^{12}$ is —F, $R^4$, $R^6$, $R^{14}$, $R^{15}$ and $R^{16}$ are hydrogen, and A is —C(O)—, then $R^5$ is not —Br; and when $R^6$, $R^{12}$, $R^{14}$ and $R^{15}$ are hydrogen, $R^{16}$ is —$CH_3$ and A is —C(O)—, then $R^{13}$ is not —F; and when $R^{13}$ is —Cl, $R^{16}$ is —F, $R^4$, $R^6$, $R^{12}$, $R^{14}$ and $R^{15}$ are hydrogen, and A is —C(O)—, then $R^5$ is not thiophen-2-yl; and when $R^6$, $R^{12}$, $R^{14}$ and $R^{15}$ are hydrogen and A is —C(O)—, then $R^{43}$ and $R^{16}$ are not both —F; and when $R^6$, $R^{12}$, $R^{14}$ and $R^{15}$ are hydrogen, $R^{16}$ is halogen, and A is —C(O)—, then $R^{13}$ is not —OH or —$OCH_3$; and when $R^4$, $R^5$, $R^6$, $R^{12}$, $R^{14}$ and $R^{15}$ are hydrogen, $R^{13}$ is —$NHS(O)_2CH_3$, and A is —C(O)—, then $R^{16}$ is not F; and when $R^4$, $R^5$, $R^6$, $R^{12}$, $R^{14}$ and $R^{15}$ are hydrogen, and A is —$CH_2$—, then $R^{13}$ and $R^{15}$ are not both —$OCH_3$; and when $R^4$, $R^5$, $R^6$, $R^{12}$, $R^{14}$ and $R^{16}$ are hydrogen, and A is —$S(O)_2$—, then $R^{13}$ and $R^{15}$ are not both —Cl; and when $R^{13}$ is —OH, $R^{15}$ is —OH or —$OCH_3$, $R^4$, $R^6$, $R^{12}$, $R^{14}$ and $R^{16}$ are hydrogen, and A is —$CH_2$—, then $R^5$ is not thiophen-3-yl; and when $R^{13}$ is —F, $R^4$, $R^6$, $R^{12}$, $R^{14}$, $R^{15}$ and $R^{16}$ are hydrogen, and A is —$CH_2$—, then $R^5$ is not 3-hydroxy-phenyl; and when $R^{13}$ is —CN, $R^4$, $R^6$, $R^{12}$, $R^{14}$, $R^{15}$ and $R^{16}$ are hydrogen, A is —$S(O)_2$—, then $R^5$ is not

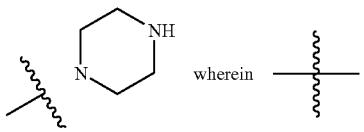 wherein indicates the bond to the 5-position of the 7-azaindole ring.

In some embodiments of any of the above embodiments of compounds of Formula II wherein $R^{13}$ is other than hydrogen, $R^5$ is other than hydrogen and $R^4$ and $R^6$ are hydrogen, or $R^4$ is other than hydrogen and $R^5$ and $R^6$ are hydrogen, or $R^6$ is other than hydrogen and $R^4$ and $R^5$ are hydrogen, or $R^4$ and $R^5$ are other than hydrogen and $R^6$ is hydrogen, or $R^4$ and $R^6$ are other than hydrogen and $R^5$ is hydrogen, or $R^5$ and $R^6$ are other than hydrogen and $R^4$ is hydrogen, or $R^4$, $R^5$ and $R^6$ are other than hydrogen.

In some embodiments of compounds of Formula II, $R^{14}$ is other than hydrogen. In some embodiments, $R^{14}$ is -$LR^{24}$. In some embodiments, $R^{14}$ is other than hydrogen and $R^{12}$, $R^{13}$, $R^{15}$ and $R^{16}$ are each independently hydrogen, halogen, optionally fluoro substituted lower alkyl, optionally fluoro substituted lower alkoxy, or optionally fluoro substituted lower alkylthio. In some embodiments, $R^{14}$ is -$LR^{24}$, and $R^{12}$, $R^{13}$, $R^{15}$ and $R^{16}$ are independently hydrogen, halogen, optionally fluoro substituted lower alkyl, optionally fluoro substituted lower alkoxy, or optionally fluoro substituted lower alkylthio. In some embodiments, $R^{14}$ is -$LR^{24}$, any three of $R^{12}$, $R^{13}$, $R^{15}$ and $R^{16}$ are independently hydrogen, halogen, optionally fluoro substituted lower alkyl, optionally fluoro substituted lower alkoxy, or optionally fluoro substituted lower alkylthio, and the remaining of $R^{12}$, $R^{13}$, $R^{15}$ and $R^{16}$ is hydrogen. In some embodiments, $R^{14}$ is -$LR^{24}$, any two of $R^{12}$, $R^{13}$, $R^{15}$ and $R^{16}$ are independently hydrogen, halogen, optionally fluoro substituted lower alkyl, optionally fluoro substituted lower alkyl, or optionally fluoro substituted lower alkoxy, or optionally fluoro substituted lower alkylthio, and the remaining of $R^{12}$, $R^{13}$, $R^{15}$ and $R^{16}$ are hydrogen. In some embodiments, $R^{14}$ is -$LR^{24}$, any one of $R^{12}$, $R^{13}$, $R^{15}$ and $R^{16}$ are independently hydrogen, halogen, optionally fluoro substituted lower alkyl, optionally fluoro substituted lower alkoxy, or optionally fluoro substituted lower alkylthio, and the remaining of $R^{12}$, $R^{13}$, $R^{15}$ and $R^{16}$ are hydrogen. In some embodiments, $R^{14}$ is -$LR^{24}$, and $R^{12}$, $R^{13}$, $R^{15}$ and $R^{16}$ are hydrogen. In some embodiments, $R^{14}$ is other than hydrogen, and $R^{12}$, $R^{13}$, $R^{15}$ and $R^{16}$ are hydrogen.

In other embodiments of compounds of Formula II, wherein $R^{14}$ is other than hydrogen, when $R^4$, $R^6$, $R^{12}$, $R^{13}$, $R^{15}$ and $R^{16}$ are hydrogen, $R^5$ is thiophen-2-yl and A is —C(O)—, then $R^{14}$ is not —OH, or —OCH$_3$; and when $R^4$, $R^5$, $R^6$, $R^{12}$, $R^{13}$, $R^{15}$ and $R^{16}$ are hydrogen and A is —C(O)—, then $R^{14}$ is not —OCH$_3$; and when $R^6$, $R^{12}$, $R^{13}$, $R^{15}$ and $R^{16}$ are hydrogen and A is —C(O)—, then $R^{14}$ is not —Cl; and when $R^4$, $R^5$, $R^6$, $R^{12}$, $R^{13}$, $R^{15}$ and $R^{16}$ are hydrogen and A is —CH$_2$—, then $R^{14}$ is not

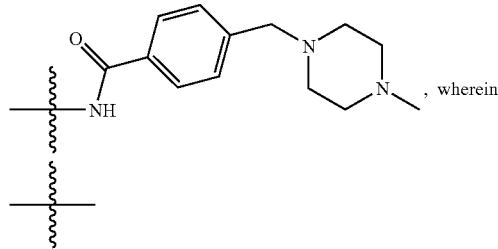

indicates the bond to the phenyl ring; and when $R^4$, $R^5$, $R^6$, $R^{12}$, $R^{13}$, $R^{15}$ and $R^{16}$ are hydrogen and A is —S— or —S(O)$_2$—, then $R^{14}$ is not —F; and when $R^5$, $R^6$, $R^{12}$, $R^{13}$, $R^{15}$ and $R^{16}$ are hydrogen, $R^4$ is 3-(hydroxymethyl)phenyl and A is —S—, then $R^{14}$ is not —CH$_3$; and when $R^5$, $R^6$, $R^{12}$, $R^{13}$, $R^{15}$ and $R^{16}$ are hydrogen, $R^4$ is 3,5-difluorophenyl and A is —C(O)—, $R^{12}$ and $R^{14}$ are not both —F; and when $R^{14}$ is —N(CH$_3$)$_2$, $R^4$, $R^6$, $R^{12}$, $R^{13}$, $R^{15}$ and $R^{16}$ and hydrogen, and A is —CH$_2$—, then $R^5$ is not 3-hydroxy-phenyl; and when $R^{14}$ is —Br, $R^4$, $R^6$, $R^{12}$, $R^{13}$, $R^{15}$ and $R^{16}$ are hydrogen, and A is hydrogen, and A is —S—, then $R^5$ is not 3-hydroxy-phenyl; and when $R^{12}$ is —Cl, $R^{14}$ is —F, $R^4$, $R^6$, $R^{13}$, $R^{15}$ and $R^{16}$ are hydrogen, and A is —S(O)$_2$—, then $R^5$ is not

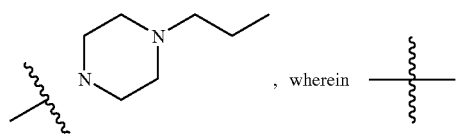

indicates the bond to the 5-position of the 7-azaindole ring; and when $R^{14}$ is —NH$_2$, $R^4$, $R^6$, $R^{12}$, $R^{13}$, $R^{15}$ and $R^{16}$ are hydrogen, and A is —S(O)$_2$—, then $R^5$ is not

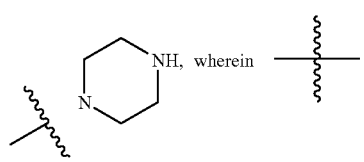

indicates the bond to the 5-position of the 7-azaindole ring; and when $R^4$, $R^6$, $R^{12}$, $R^{15}$ and $R^{16}$ are hydrogen, $R^{13}$ and $R^{14}$ are —OH, and A is —CH$_2$—, then $R^5$ is not thiophen-3-yl.

In some embodiments of any of the above embodiments of compounds of Formula II wherein $R^{14}$ is other than hydrogen, $R^5$ is other than hydrogen and $R^4$ and $R^6$ are hydrogen, or $R^4$ is other than hydrogen and $R^5$ and $R^6$ are hydrogen, or $R^6$ is other than hydrogen and $R^4$ and $R^5$ are hydrogen, or $R^4$ and $R^5$ are other than hydrogen and $R^6$ is hydrogen, or $R^4$ and $R^6$ are other than hydrogen and $R^5$ is hydrogen, or $R^5$ and $R^6$ are other than hydrogen and $R^4$ is hydrogen, or $R^4$, $R^5$ and $R^6$ are other than hydrogen.

In some embodiments of compounds of Formula II, $R^{12}$ and $R^{16}$ are other than hydrogen. In some embodiments, $R^{12}$ and $R^{16}$ are independently -$LR^{24}$. In some embodiments, $R^{12}$ and $R^{16}$ are other than hydrogen and $R^{13}$, $R^{14}$ and $R^{15}$ are independently hydrogen, halogen, optionally fluoro substituted lower alkyl, optionally fluoro substituted lower alkoxy, or optionally fluoro substituted lower alkylthio. In some embodiments, $R^{12}$ and $R^{16}$ are independently -$LR^{24}$ and $R^{13}$, $R^{14}$ and $R^{15}$ are independently hydrogen, halogen, optionally fluoro substituted lower alkyl, optionally fluoro substituted lower alkoxy, or optionally fluoro substituted lower alkylthio. In some embodiments, $R^{12}$ and $R^{16}$ are independently -$LR^{24}$, any two of $R^{13}$, $R^{14}$ and $R^{15}$ are independently hydrogen, halogen, optionally fluoro substituted lower alkyl, optionally fluoro substituted lower alkoxy, or optionally fluoro substituted lower alkylthio, and the remaining of $R^{13}$, $R^{14}$ and $R^{15}$ is hydrogen. In some embodiments, $R^{12}$ and $R^{16}$ are independently -$LR^{24}$, any one of $R^{13}$, $R^{14}$ and $R^{15}$ is independently hydrogen, halogen, optionally fluoro substituted lower alkyl, optionally fluoro substituted lower alkoxy, or optionally fluoro substituted lower alkylthio, and the remaining of $R^{13}$, $R^{14}$ and $R^{15}$ are hydrogen. In some embodiments, $R^{12}$ and $R^{16}$ are independently -$LR^{24}$, and $R^{13}$, $R^{14}$ and $R^{15}$ are hydrogen. In some embodiments, $R^{12}$ and $R^{16}$ are other than hydrogen, and $R^{13}$, $R^{14}$ and $R^{15}$ are hydrogen. In other embodiments, wherein $R^{12}$ and $R^{16}$ are other than hydrogen, when $R^5$, $R^6$, $R^{13}$, $R^{14}$ and $R^{15}$ are hydrogen and A is —C(O)—, then $R^{12}$ and $R^{16}$ are not both —F.

In some embodiments of any of the above embodiments of compounds of Formula II wherein $R^{12}$ and $R^{16}$ is other than hydrogen, $R^5$ is other than hydrogen and $R^4$ and $R^6$ are hydrogen, or $R^4$ is other than hydrogen and $R^5$ and $R^6$ are hydrogen, or $R^6$ is other than hydrogen and $R^4$ and $R^5$ are hydrogen, or $R^4$ and $R^5$ are other than hydrogen and $R^6$ is hydrogen, or $R^4$ and $R^6$ are other than hydrogen and $R^5$ is hydrogen, or $R^5$ and $R^6$ are other than hydrogen and $R^4$ is hydrogen, or $R^4$, $R^5$ and $R^6$ are other than hydrogen.

In some embodiments of compounds of Formula II, $R^{12}$ and $R^{13}$ are other than hydrogen. In some embodiments, $R^{12}$ and $R^{13}$ are independently -$LR^{24}$. In some embodiments, $R^{12}$ and $R^{13}$ are other than hydrogen and $R^{14}$, $R^{15}$ and $R^{16}$ are independently hydrogen, halogen, optionally fluoro substituted lower alkyl, optionally fluoro substituted lower alkoxy, or optionally fluoro substituted lower alkylthio. In some embodiments, $R^{12}$ and $R^{13}$ are independently -$LR^{24}$, and $R^{14}$, $R^{15}$ and $R^{16}$ are independently hydrogen, halogen, optionally fluoro substituted lower alkyl, optionally fluoro substituted lower alkoxy, or optionally fluoro substituted lower alkylthio. In some embodiments, $R^{12}$ and $R^{13}$ are independently -$LR^{24}$, any two of $R^{14}$, $R^{15}$ and $R^{16}$ are independently hydrogen, halogen, optionally fluoro substituted lower alkyl, optionally fluoro substituted lower alkoxy, or optionally fluoro substituted lower alkylthio, and the remaining of $R^{14}$, $R^{15}$ and $R^{16}$ is hydrogen. In some embodiments, $R^{12}$ and $R^{13}$ are independently -$LR^{24}$, any one of $R^{14}$, $R^{15}$ and $R^{16}$ is independently hydrogen, halogen, optionally fluoro substituted lower alkyl, optionally fluoro substituted lower alkoxy, or optionally fluoro substituted lower alkylthio, and the remaining of $R^{14}$, $R^{15}$ and $R^{16}$ are hydrogen. In some embodiments, $R^{12}$ and $R^{13}$ are independently -$LR^{24}$, and $R^{14}$, $R^{15}$ and $R^{16}$ are hydrogen. In some embodiments, $R^{12}$ and $R^{13}$ are other than hydrogen and $R^{14}$, $R^{15}$ and $R^{16}$ are hydrogen. In other embodiments, wherein $R^{12}$ and $R^{13}$ are other than hydrogen, when $R^6$, $R^{14}$, $R^{15}$ and $R^{16}$ are hydrogen, A is —C(O)—, and $R^{13}$ is halogen, —OH, or —OCH$_3$, then $R^{12}$ is not halogen. In alternate embodiments, when $R^{12}$ and $R^{13}$ are other than hydrogen, $R^6$, $R^{14}$, $R^{15}$ and $R^{16}$ are hydrogen and A is —C(O)—, then both $R^{12}$ and $R^{13}$ are not halogen; and when $R^{12}$ and $R^{13}$ are other than hydrogen, $R^4$, $R^6$, $R^{14}$, $R^{15}$ and $R^{16}$ are hydrogen, and A is —C(O)—, $R^{12}$ is —F and $R^{13}$ is —OH or —OCH$_3$, then $R^5$ is not —Br or thiophen-2-yl.

In some embodiments of any of the above embodiments of compounds of Formula II wherein $R^{12}$ and $R^{13}$ is other than hydrogen, $R^5$ is other than hydrogen and $R^4$ and $R^6$ are hydrogen, or $R^4$ is other than hydrogen and $R^5$ and $R^6$ are hydrogen, or $R^6$ is other than hydrogen and $R^4$ and $R^5$ are hydrogen, or $R^4$ and $R^5$ are other than hydrogen and $R^6$ is hydrogen, or $R^4$ and $R^6$ are other than hydrogen and $R^5$ is hydrogen, or $R^5$ and $R^6$ are other than hydrogen and $R^4$ is hydrogen, or $R^4$, $R^4$ and $R^6$ are other than hydrogen.

In some embodiments of compounds of Formula II, $R^{13}$ and $R^{14}$ are other than hydrogen. In some embodiments, $R^{12}$ and $R^{14}$ are independently -$LR^{24}$. In some embodiments, $R^{12}$ and $R^{14}$ are other than hydrogen and $R^{13}$, $R^{15}$ and $R^{16}$ are independently hydrogen, halogen, optionally fluoro substituted lower alkyl, optionally fluoro substituted lower alkoxy, or optionally fluoro substituted lower alkylthio. In some embodiments, $R^{12}$ and $R^{14}$ are independently -$LR^{24}$, and $R^{13}$, $R^{15}$ and $R^{16}$ are independently hydrogen, halogen, optionally fluoro substituted lower alkyl, optionally fluoro substituted lower alkoxy, or optionally fluoro substituted lower alkylthio. In some embodiments, $R^{12}$ and $R^{14}$ are independently -$LR^{24}$, and any one of $R^{13}$, $R^{15}$ and $R^{16}$ is independently hydrogen, halogen, optionally fluoro substituted lower alkyl, optionally fluoro substituted lower alkoxy, or optionally fluoro substituted lower alkylthio, and the remaining of $R^{13}$, $R^{15}$ and $R^{16}$ is hydrogen. In some embodiments, $R^{13}$ and $R^{14}$ are independently -$LR^{24}$, and any two of $R^{13}$, $R^{15}$ and $R^{16}$ are independently hydrogen, halogen, optionally fluoro substituted lower alkyl, optionally fluoro substituted lower alkoxy, or optionally fluoro substituted lower alkylthio and the remaining of $R^{13}$, $R^{15}$ and $R^{16}$ is hydrogen. In some embodiments, $R^{12}$ and $R^{14}$ are independently -$LR^{24}$ and $R^{13}$, $R^{15}$ and $R^{16}$ are hydrogen. In some embodiments, $R^{12}$ and $R^{14}$ are other than hydrogen and $R^{13}$, $R^{15}$ and $R^{16}$ are hydrogen. In some embodiments, wherein $R^{12}$ and $R^{14}$ are other than hydrogen, when $R^5$, $R^6$, $R^{13}$, $R^{15}$ and $R^{16}$ are hydrogen, A is —C(O)—, and $R^4$ is 3,5 difluorophenyl, then $R^{12}$ and $R^{14}$ are not both —F; and when $R^{12}$ is —Cl, $R^{14}$ is —F, $R^4$, $R^6$, $R^{13}$, $R^{15}$ and $R^{16}$ are hydrogen, and A is —S(O)$_2$—, then $R^5$ is not

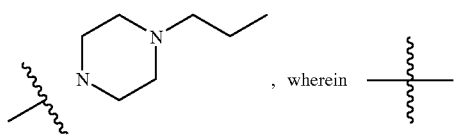, wherein indicates the bond to the 5-position of the 7-azaindole ring.

In some embodiments of any of the above embodiments of compounds of Formula II wherein $R^{12}$ and $R^{14}$ is other than hydrogen, $R^5$ is other than hydrogen and $R^4$ and $R^6$ are hydrogen, or $R^4$ is other than hydrogen and $R^5$ and $R^6$ are hydrogen, or $R^6$ is other than hydrogen and $R^4$ and $R^5$ are hydrogen, or $R^4$ and $R^5$ are other than hydrogen and $R^6$ is hydrogen, or $R^4$ and $R^6$ are other than hydrogen and $R^5$ is hydrogen, or $R^5$ and $R^6$ are other than hydrogen and $R^4$ is hydrogen, or $R^4$, $R^5$ and $R^6$ are other than hydrogen.

In some embodiments of compounds of Formula II, $R^{12}$ and $R^{15}$ are other than hydrogen. In some embodiments, $R^{12}$ and $R^{15}$ are independently -$LR^{24}$. In some embodiments, $R^{12}$ and $R^{15}$ are other than hydrogen and $R^{13}$, $R^{14}$ and $R^{16}$ are independently hydrogen, halogen, optionally fluoro substituted lower alkyl, optionally fluoro substituted lower alkoxy, or optionally fluoro substituted lower alkylthio. In some embodiments, $R^{12}$ and $R^{15}$ are independently -$LR^{24}$ and $R^{13}$, $R^{14}$ and $R^{16}$ are independently hydrogen, halogen, optionally fluoro substituted lower alkyl, optionally fluoro substituted lower alkoxy, or optionally fluoro substituted lower alkylthio. In some embodiments, $R^{12}$ and $R^{15}$ are independently -$LR^{24}$, any two of $R^{13}$, $R^{14}$ and $R^{16}$ are independently hydrogen, halogen, optionally fluoro substituted lower alkyl, optionally fluoro substituted lower alkoxy, or optionally fluoro substituted lower alkylthio and the remaining of $R^{13}$, $R^{14}$ and $R^{16}$ is hydrogen. In some embodiments, $R^{12}$ and $R^{15}$ are independently -$LR^{24}$, any one of $R^{13}$, $R^{14}$ and $R^{16}$ is hydrogen, halogen, optionally fluoro substituted lower alkyl, optionally fluoro substituted lower alkoxy, or optionally fluoro substituted lower alkylthio and the remaining of $R^{13}$, $R^{14}$ and $R^{16}$ are hydrogen. In some embodiments, $R^{12}$ and $R^{15}$ are independently -$LR^{24}$ and $R^{13}$, $R^{14}$ and $R^{16}$ are hydrogen. In some embodiments, $R^{12}$ and $R^{15}$ are other than hydrogen and $R^{13}$, $R^{14}$ and $R^{16}$ are hydrogen. In other embodiments, wherein $R^{12}$ and $R^{15}$ are other than hydrogen, when $R^6$, $R^{13}$, $R^{14}$ and $R^{16}$ are hydrogen and A is —C(O)—, then $R^{12}$ and $R^{15}$ are not both halogen; and when $R^6$, $R^{13}$, $R^{14}$ and $R^{16}$ are hydrogen, A is —C(O)—, and $R^{12}$ is —CH$_3$, then $R^{15}$ is not —F; and when $R^6$, $R^{13}$, $R^{14}$ and $R^{16}$ are hydrogen, A is —C(O)—, and $R^{12}$ is halogen, then $R^{15}$ is not —OH or —OCH$_3$; and when $R^4$, $R^5$, $R^6$, $R^{13}$, $R^{14}$ and $R^{16}$ are hydrogen, A is —C(O)—, and $R^{12}$ is —F then $R^{15}$ is not NHS(O)$_2$CH$_3$.

In some embodiments of any of the above embodiments of compounds of Formula II wherein $R^{12}$ and $R^{15}$ is other than hydrogen, $R^5$ is other than hydrogen and $R^4$ and $R^6$ are hydrogen, or $R^4$ is other than hydrogen and $R^5$ and $R^6$ are hydrogen, or $R^6$ is other than hydrogen and $R^4$ and $R^5$ are hydrogen, or $R^4$ and $R^5$ are other than hydrogen and $R^6$ is hydrogen, or $R^4$ and $R^6$ are other than hydrogen and $R^5$ is hydrogen, or $R^5$ and $R^6$ are other than hydrogen and $R^4$ is hydrogen, or $R^4$, $R^5$ and $R^6$ are other than hydrogen.

In some embodiments of compounds of Formula II, $R^{13}$ and $R^{14}$ are other than hydrogen. In some embodiments, $R^{13}$ and $R^{14}$ are independently -$LR^{24}$. In some embodiments, $R^{13}$ and $R^{14}$ are other than hydrogen and $R^{12}$, $R^{15}$ and $R^{16}$ are independently hydrogen, halogen, optionally fluoro substituted lower alkyl, optionally fluoro substituted lower alkoxy, or optionally fluoro substituted lower alkylthio. In some embodiments, $R^{13}$ and $R^{14}$ are independently -$LR^{24}$ and $R^{12}$, $R^{15}$ and $R^{16}$ are independently hydrogen, halogen, optionally fluoro substituted lower alkyl, optionally fluoro substituted lower alkoxy, or optionally fluoro substituted lower alkylthio. In some embodiments, $R^{13}$ and $R^{14}$ are independently -$LR^{24}$, any two of $R^{12}$, $R^{15}$ and $R^{16}$ are independently hydrogen, halogen, optionally fluoro substituted lower alkyl, optionally fluoro substituted lower alkoxy, or optionally fluoro substituted lower alkylthio and the remaining of $R^{12}$, $R^{15}$ and $R^{16}$ is hydrogen. In some embodiments, $R^{13}$ and $R^{14}$ are independently -$LR^{24}$, any one of $R^{12}$, $R^{15}$ and $R^{16}$ is hydrogen, halogen, optionally fluoro substituted lower alkyl, optionally fluoro substituted lower alkoxy, or optionally fluoro substituted lower alkylthio and the remaining of $R^{12}$, $R^{15}$ and $R^{16}$ are hydrogen. In some embodiments, $R^{13}$ and $R^{14}$ are independently -$LR^{24}$ and $R^{12}$, $R^{15}$ and $R^{16}$ are hydrogen. In some embodiments, $R^{13}$ and $R^{14}$ are other than hydrogen and $R^{12}$, $R^{15}$ and $R^{16}$ are hydrogen. In other embodiments, wherein $R^{13}$ and $R^{14}$ are other than hydrogen, when $R^4$, $R^6$, $R^{12}$, $R^{15}$ and $R^{16}$ are hydrogen, A is —$CH_2$—, and $R^5$ is thiophen-3-yl, then $R^{13}$ and $R^{14}$ are both —OH.

In some embodiments of any of the above embodiments of compounds of Formula II wherein $R^{13}$ and $R^{14}$ is other than hydrogen, $R^5$ is other than hydrogen and $R^4$ and $R^6$ are hydrogen, or $R^4$ is other than hydrogen and $R^5$ and $R^6$ are hydrogen, or $R^6$ is other than hydrogen and $R^4$ and $R^5$ are hydrogen, or $R^4$ and $R^5$ are other than hydrogen and $R^6$ is hydrogen, or $R^4$ and $R^6$ are other than hydrogen and $R^5$ is hydrogen, or $R^5$ and $R^6$ are other than hydrogen and $R^4$ is hydrogen, or $R^4$, $R^5$ and $R^6$ are other than hydrogen.

In some embodiments of compounds of Formula II, $R^{13}$ and $R^{15}$ are other than hydrogen. In some embodiments, $R^{13}$ and $R^{15}$ are independently -$LR^{24}$. In some embodiments, $R^{13}$ and $R^{15}$ are other than hydrogen and $R^{12}$, $R^{14}$ and $R^{16}$ are independently hydrogen, halogen, optionally fluoro substituted lower alkyl, optionally fluoro substituted lower alkoxy, or optionally fluoro substituted lower alkylthio. In some embodiments, $R^{13}$ and $R^{15}$ are independently -$LR^{24}$ and $R^{12}$, $R^{14}$ and $R^{16}$ are independently hydrogen, halogen, optionally fluoro substituted lower alkyl, optionally fluoro substituted lower alkoxy, or optionally fluoro substituted lower alkylthio. In some embodiments, $R^{13}$ and $R^{15}$ are independently -$LR^{24}$, two of $R^{12}$, $R^{14}$ and $R^{16}$ are independently hydrogen, halogen, optionally fluoro substituted lower alkyl, optionally fluoro substituted lower alkoxy, or optionally fluoro substituted lower alkylthio and the remaining of $R^{12}$, $R^{14}$ and $R^{16}$ is hydrogen. In some embodiments, $R^{13}$ and $R^{15}$ are independently -$LR^{24}$, one of $R^{12}$, $R^{14}$ and $R^{16}$ is hydrogen, halogen, optionally fluoro substituted lower alkyl, optionally fluoro substituted lower alkoxy, or optionally fluoro substituted lower alkylthio and the remaining of $R^{12}$, $R^{14}$ and $R^{16}$ are hydrogen. In some embodiments, $R^{13}$ and $R^{15}$ are independently -$LR^{24}$ and $R^{12}$, $R^{14}$ and $R^{16}$ are hydrogen, some embodiments, $R^{13}$ and $R^{15}$ are other than hydrogen and $R^{12}$, $R^{14}$ and $R^{16}$ are hydrogen. In other embodiments, wherein $R^{13}$ and $R^{15}$ are other than hydrogen, when $R^4$, $R^5$, $R^6$, $R^{12}$, $R^{14}$ and $R^{16}$ are hydrogen and A is —$CH_2$—, then $R^{13}$ and $R^{15}$ are not both —$OCH_3$; and when $R^4$, $R^5$, $R^6$, $R^{12}$, $R^{14}$ and $R^{16}$ are hydrogen and A is —$S(O)_2$—, then $R^{13}$ and $R^{15}$ are not both —Cl; and when $R^4$, $R^6$, $R^{12}$, $R^{14}$ and $R^{16}$ are hydrogen, A is —$CH_2$—, $R^{13}$ is —OH and $R^{15}$ is —OH or —$OCH_3$, then $R^5$ is not thiophen-3-yl.

In some embodiments of any of the above embodiments of compounds of Formula II wherein $R^{13}$ and $R^{15}$ is other than hydrogen, $R^5$ is other than hydrogen and $R^4$ and $R^6$ are hydrogen, or $R^4$ is other than hydrogen and $R^5$ and $R^6$ are hydrogen, or $R^6$ is other than hydrogen and $R^4$ and $R^5$ are hydrogen, or $R^4$ and $R^5$ are other than hydrogen and $R^6$ is hydrogen, or $R^4$ and $R^6$ are other than hydrogen and $R^5$ is hydrogen, or $R^5$ and $R^6$ are other than hydrogen and $R^4$ is hydrogen, or $R^4$, $R^5$ and $R^6$ are other than hydrogen.

In some embodiments of compounds of Formula II, $R^{13}$ is -$LR^{24}$, provided, however, that when A is —$CH_2$—, —CH(OH)— or —C(O)—, and $R^{12}$, $R^{14}$, $R^{15}$, $R^{16}$ are hydrogen, then $R^{13}$ is not —OH, —$OCH_3$, or

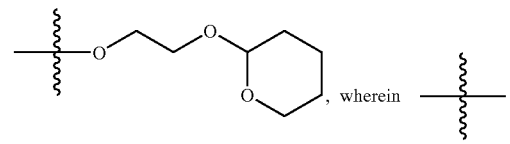, wherein indicates the bond to the phenyl ring; and when $R^4$, $R^5$, $R^6$, $R^{12}$, $R^{14}$, $R^{15}$, and $R^{16}$ are hydrogen and A is —C(O)—, $R^{13}$ is not $NH_2$, or

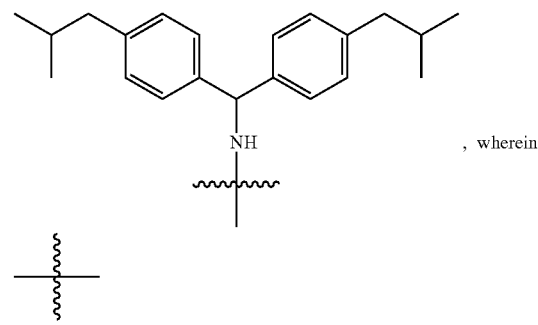, wherein indicates the bond to the phenyl ring; and when $R^4$, $R^5$, $R^6$, $R^{12}$, $R^{14}$ and $R^{16}$ are hydrogen and A is —$CH_2$—, $R^{13}$ and $R^{15}$ are not both —$OCH_3$; and when $R^4$, $R^6$, $R^{12}$, $R^{14}$ and $R^{16}$ are hydrogen, A is —$CH_2$—, $R^5$ is thiophen-3-yl, $R^{13}$ is —OH, $R^{15}$ is not —OH or —$OCH_3$; and when $R^4$, $R^6$, $R^{12}$, $R^{15}$ and $R^{16}$ are hydrogen, A is —$CH_2$—, and $R^5$ is thiophen-3-yl, $R^{13}$ and $R^{14}$ are not both —OH; and when $R^4$, $R^6$, $R^{14}$, $R^{15}$ and $R^{16}$ are hydrogen and A is —C(O)—, $R^{12}$ is —F, $R^5$ is —Br or thiophen-2-yl, $R^{13}$ is not —OH or —$OCH_3$; and when $R^{12}$, $R^{14}$, and $R^{15}$ are hydrogen, A is —C(O)—, and $R^{16}$ is halogen, $R^{13}$ is not —OH or —$OCH_3$; and when $R^4$, $R^5$, $R^6$, $R^{12}$, $R^{14}$ and $R^{15}$ are hydrogen, A is —C(O)—, and $R^{16}$ is —F, $R^{13}$ is not —$NHS(O)_2CH_3$. In further embodiments, $R^{13}$ is -$LR^{24}$ and L is —$NHS(O)_2CH_3$—, —O—, or —O—$CH_2$—, $R^{24}$ is not H, or when L is —$NHS(O)_2$— or —O—, $R^{24}$ is not $CH_3$. In further embodiments, where $R^{13}$ is -$LR^{24}$, one of $R^{12}$, $R^{14}$, $R^{15}$, and $R^{16}$ is other than hydrogen and the remaining of $R^{12}$, $R^{14}$, $R^{15}$, and $R^{16}$ are hydrogen. In further embodiments, where $R^{13}$ is -$LR^{24}$, two of $R^{12}$, $R^{14}$, $R^{15}$, and $R^{16}$ are independently other than hydrogen and the remaining two of $R^{12}$, $R^{14}$, $R^{15}$, and $R^{16}$ are hydrogen. In some embodiments where $R^{13}$ is -$LR^{24}$, $R^{14}$ and $R^{15}$ are hydrogen, and at least one of $R^{12}$ and $R^{16}$ is other than hydrogen. In further embodiments, where $R^{13}$ is -$LR^{24}$, $R^{14}$ and $R^{15}$ are hydrogen, and at least one of $R^{12}$ and $R^{16}$ is other than hydrogen, L is -(alk)$_a$-$NR^{25}$-(alk)$_b$-, -(alk)$_a$-C(O)$NR^{25}$-(alk)$_b$-, -(alk)$_a$-OC(O)$NR^{25}$-(alk)$_b$-, -(alk)$_a$-OC(S)$NR^{25}$-(alk)$_b$-, -(alk)$_a$-C(S)$NR^{25}$-(alk)$_b$-, -(alk)$_a$-S(O)$_2$$NR^{25}$-(alk)$_b$-, -(alk)$_a$-$NR^{25}$C(O)-(alk)$_b$-, -(alk)$_a$-$NR^{25}$C(S)-(alk)$_b$-, -(alk)$_a$-$NR^{25}$C(O)$NR^{25}$-(alk)$_b$-, -(alk)$_a$-$NR^{25}$C(S)$NR^{25}$-(alk)$_b$-, -(alk)$_a$$NR^{25}$C(O)O-(alk)$_b$-, -(alk)$_a$-$NR^{25}$C(S)O-(alk)$_b$-, -(alk)$_a$-$NR^{25}$S(O)$_2$-(alk)$_b$-, or -(alk)$_a$-$NR^{25}$S(O)$_2$$NR^{25}$-(alk)$_b$-, wherein a, b, $R^{35}$ and alk are as defined for Formula I.

In further embodiments of compounds of Formula II, where $R^{13}$ is -$LR^{24}$, $R^{14}$ and $R^{15}$ are hydrogen, and at least one of $R^{12}$ and $R^{16}$ is other than hydrogen, L is —$NR^{25}$—, —$NR^{25}$-(alk)$_b$-, —C(O)$NR^{25}$-(alk)$_b$-, —OC(O)$NR^{25}$-(alk)$_b$-, —OC(S)$NR^{25}$-(alk)$_b$-, —C(S)$NR^{25}$-(alk)$_b$-, —S(O)$_2$$NR^{25}$-(alk)$_b$-, —$NR^{25}$C(O)-(alk)$_b$-, —$NR^{25}$C(S)-(alk)$_b$-, —$NR^{25}$C(O)$NR^{25}$-(alk)$_b$-, —$NR^{25}$C(S)$NR^{25}$-(alk)$_b$-, —$NR^{25}C(O)O$-$(alk)_b$-, —$NR^{25}C(S)O$-$(alk)_b$-, —$NR^{25}S(O)_2$-$(alk)_b$-, or —$NR^{25}S(O)_2NR^{25}$-$(alk)_b$-.

In further embodiments of compounds of Formula II, where $R^{13}$ is -$LR^{24}$, $R^{14}$ and $R^{15}$ are hydrogen, and at least one of $R^{12}$ and $R^{16}$ is other than hydrogen, L is —$NR^{25}$-$(alk)_b$-, —$NR^{25}C(O)$-$(alk)_b$-, —$NR^{25}C(S)$-$(alk)_b$-, —$NR^{25}C(O)NR^{25}$-$(alk)_b$-, —$NR^{25}C(S)NR^{25}$-$(alk)_b$-, —$NR^{25}C(O)O$-$(alk)_b$-, —$NR^{25}C(S)O$-$(alk)_b$-, —$NR^{25}S(O)_2$-$(alk)_b$-, or —$NR^{25}S(O)_2NR^{25}$-$(alk)_b$-. In further embodiments where $R^{13}$ is -$LR^{24}$, $R^{14}$ and $R^{15}$ are hydrogen, and at least one of $R^{12}$ and $R^{16}$ is other than hydrogen, L is —$NR^{25}C(O)$-$(alk)_b$-, —$NR^{25}C(S)$-$(alk)_b$-, —$NR^{25}S(O)_2$-$(alk)_b$-, —$NR^{25}C(O)NR^{25}$-$(alk)_b$-, —$NR^{25}C(S)NR^{25}$-$(alk)_b$-, or —$NR^{25}S(O)_2NR^{25}$-$(alk)_b$-. In further embodiments where $R^{13}$ is -$LR^{24}$, $R^{14}$ and $R^{15}$ are hydrogen, and at least one of $R^{12}$ and $R^{16}$ is other than hydrogen, L is —$NR^{25}C(O)O$-$(alk)_b$-, —$NR^{25}C(S)O$-$(alk)_b$-, —$OC(O)NR^{25}$-$(alk)_b$-, or —$OC(S)NR^{25}$-$(alk)_b$-. In some embodiments of any of the above embodiments where $R^{13}$-$LR^{24}$, $R^5$ is other than hydrogen and $R^4$ and $R^6$ are hydrogen, or $R^4$ is other than hydrogen and $R^5$ and $R^6$ are hydrogen, or $R^6$ is other than hydrogen and $R^4$ and $R^5$ are hydrogen, or $R^4$ and $R^5$ are other than hydrogen and $R^6$ is hydrogen, or $R^4$ and $R^6$ are other than hydrogen and $R^5$ is hydrogen, or $R^5$ and $R^6$ are other than hydrogen and $R^4$ is hydrogen, or $R^4$, $R^5$ and $R^6$ are other than hydrogen.

In some embodiments of compounds of Formula II, A is —$CR^aR^b$— or —$C(O)$—, $R^{13}$ is -$LR^{24}$, $R^{14}$ and $R^{15}$ are hydrogen, $R^{12}$ and $R^{16}$ are independently hydrogen, halogen, optionally fluoro substituted lower alkyl, optionally fluoro substituted lower alkoxy, or optionally fluoro substituted lower alkylthio, wherein one of $R^{12}$ and $R^{16}$ is other than hydrogen, and wherein L is —$NR^{25}$-$(alk)_b$-, —$C(O)NR^{25}$-$(alk)_b$-, —$OC(O)NR^{25}$-$(alk)_b$-, —$OC(S)NR^{25}$-$(alk)_b$-, —$C(S)NR^{25}$-$(alk)_b$-, —$S(O)_2NR^{25}$-$(alk)_b$-, —$NR^{25}C(O)$-$(alk)_b$-, —$NR^{25}C(S)$-$(alk)_b$-, —$NR^{25}C(O)NR^{25}$-$(alk)_b$-, —$NR^{25}C(S)NR^{25}$-$(alk)_b$-, —$NR^{25}C(O)O$-$(alk)_b$-, —$NR^{25}C(S)O$-$(alk)_b$-, —$NR^{25}S(O)_2$-$(alk)_b$-, or —$NR^{25}S(O)_2NR^{25}$-$(alk)_b$-, wherein b and $R^{25}$ are as defined for Formula I, alk is $C_{1-3}$ alkylene optionally substituted with fluoro or optionally fluoro substituted lower alkyl, and $R^{24}$ is hydrogen, provided, however, that said hydrogen would not be attached to $S(O)_2$—, optionally fluoro substituted lower alkyl, cycloalkyl, heterocycloalkyl, aryl or heteroaryl, wherein cycloalkyl, heterocycloalkyl, aryl and heteroaryl are optionally substituted with halogen, optionally fluoro substituted lower alkyl, optionally fluoro substituted lower alkoxy, or optionally fluoro substituted lower alkylthio, and $R^a$ and $R^b$ are independently hydrogen, halogen, optionally fluoro substituted lower alkyl or optionally fluoro substituted lower alkoxy, provided, however, that when $R^4$, $R^5$, $R^6$, $R^{12}$, $R^{14}$ and $R^{15}$ are hydrogen, A is —$C(O)$—, and $R^{16}$ is —F, then $R^{13}$ is not —$NHS(O)_2CH_3$. In other embodiments, $R^{12}$ and $R^{16}$ are independently halogen, optionally fluoro substituted lower alkyl, optionally fluoro substituted lower alkoxy, or optionally fluoro substituted lower alkylthio. In other embodiments, A is —$CH_2$—. In other embodiments, A is —$C(O)$—. In other embodiments, $R^4$ is other than hydrogen and $R^5$ and $R^6$ are hydrogen. In other embodiments, A is —$CH_2$—, $R^4$ is other than hydrogen and $R^5$ and $R^6$ are hydrogen. In other embodiments, A is —$C(O)$—, $R^4$ is other than hydrogen and $R^5$ and $R^6$ are hydrogen. In other embodiments, $R^5$ is other than hydrogen and $R^4$ and $R^6$ are hydrogen. In other embodiments, A is —$CH_2$—, $R^5$ is other than hydrogen and $R^4$ and $R^6$ are hydrogen. In other embodiments, A is —$C(O)$—, $R^5$ is other than hydrogen and $R^4$ and $R^6$ are hydrogen. In other embodiments, $R^6$ is other than hydrogen and $R^4$ and $R^5$ are hydrogen. In other embodiments, A is —$CH_2$—, $R^6$ is other than hydrogen and $R^4$ and $R^5$ are hydrogen and $R^4$ and $R^5$ are hydrogen. In other embodiments, $R^4$ and $R^5$ are hydrogen. In other embodiments, $R^4$ and $R^5$ are other than hydrogen and $R^6$ is hydrogen. In other embodiments, $R^4$ and $R^6$ are other than hydrogen, and $R^5$ is hydrogen. In other embodiments, $R^4$ and $R^5$ are hydrogen, and $R^6$ is other than hydrogen. In other embodiments, $R^4$, $R^5$, and $R^6$ are other than hydrogen.

In some embodiments of compounds of Formula II, A is —$CR^aR^b$— or —$C(O)$—, $R^{13}$ is -$LR^{24}$, $R^{14}$ and $R^{15}$ are hydrogen, $R^{12}$ and $R^{16}$ are independently hydrogen, halogen, optionally fluoro substituted lower alkyl, optionally fluoro substituted lower alkoxy, or optionally fluoro substituted lower alkylthio, wherein one of $R^{12}$ and $R^{16}$ is other than hydrogen, and wherein L is —$NR^{25}$-$(alk)_b$-, —$NR^{25}C(O)$-$(alk)_b$-, —$NR^{25}C(S)$-$(alk)_b$-, —$NR^{25}C(O)NR^{25}$-$(alk)_b$-, —$NR^{25}C(S)NR^{25}$-$(alk)_b$-, —$NR^{25}C(O)O$-$(alk)_b$-, —$NR^{25}C(S)O$-$(alk)_b$-, —$NR^{25}S(O)_2$-$(alk)_b$-, or —$NR^{25}S(O)_2NR^{25}$-$(alk)_b$-, wherein b and $R^{25}$ are as defined for Formula I, alk is $C_{1-3}$ alkylene optionally substituted with fluoro or optionally fluoro substituted lower alkyl, $R^{24}$ is hydrogen provided, however, that said hydrogen would not be attached to $S(O)_2$—, optionally fluoro substituted lower alkyl, cycloalkyl, heterocycloalkyl, aryl or heteroaryl, wherein cycloalkyl, heterocycloalkyl, aryl and heteroaryl are optionally substituted with halogen, optionally fluoro substituted lower alkyl, optionally fluoro substituted lower alkoxy, and optionally fluoro substituted lower alkylthio, $R^a$ and $R^b$ are independently hydrogen, halogen, optionally fluoro substituted lower alkyl, or optionally fluoro substituted lower alkoxy, one of $R^4$ and $R^5$ is other than hydrogen and $R^6$ is hydrogen. In other embodiments, $R^{16}$ is hydrogen. In other embodiments, $R^{12}$ is hydrogen. In other embodiments, $R^{12}$ and $R^{16}$ are independently halogen, optionally fluoro substituted lower alkyl, optionally fluoro substituted lower alkoxy, or optionally fluoro substituted lower alkylthio. In other embodiments, A is —$CH_2$—. In other embodiments, A is —$C(O)$—. In other embodiments, $R^4$ is other than hydrogen and $R^5$ and $R^6$ are hydrogen. In other embodiments, A is —$CH_2$—, $R^4$ is other than hydrogen and $R^5$ and $R^6$ are hydrogen. In other embodiments, A is —$C(O)$—, $R^4$ is other than hydrogen and $R^5$ and $R^6$ are hydrogen. In other embodiments, $R^5$ is other than hydrogen and $R^4$ and $R^6$ are hydrogen. In other embodiments, A is —$CH_2$—, $R^5$ is other than hydrogen and $R^4$ and $R^6$ are hydrogen. In other embodiments, A is —$C(O)$—, $R^5$ is other than hydrogen and $R^4$ and $R^6$ are hydrogen. In other embodiments, $R^6$ is other than hydrogen and $R^4$ and $R^5$ are hydrogen. In other embodiments, A is —$CH_2$—, $R^6$ is other than hydrogen and $R^4$ and $R^5$ are hydrogen. In other embodiments, A is —$C(O)$—, $R^6$ is other than hydrogen and $R^4$ and $R^5$ are hydrogen. In other embodiments, $R^4$ and $R^5$ are other than hydrogen and $R^6$ is hydrogen. In other embodiments, $R^4$ and $R^6$ are other than hydrogen and $R^5$ is hydrogen. In other embodiments, $R^4$ and $R^5$ are hydrogen and $R^6$ is other than hydrogen. In other embodiments, $R^4$, $R^5$, and $R^6$ are other than hydrogen.

In some embodiments of compounds of Formula II, A is —$CR^aR^b$— or —$C(O)$—, $R^{13}$ is -$LR^{24}$, $R^{13}$ is halogen, optionally fluoro substituted lower alkyl, optionally fluoro substituted lower alkoxy, or optionally fluoro substituted lower alkylthio, one of $R^{14}$, $R^{15}$ and $R^{16}$ are halogen, optionally fluoro substituted lower alkyl, optionally fluoro substituted lower alkoxy, or optionally fluoro substituted lower alkylthio and the other two are hydrogen, L is —$NR^{25}$-$(alk)_b$-, —$NR^{25}C(O)$-$(alk)_b$-, —$NR^{25}C(S)$-$(alk)_b$-, —$NR^{25}C(O)NR^{25}$-$(alk)_b$-, —$NR^{25}C(S)NR^{25}$-$(alk)_b$-, —$NR^{25}C(O)O$-$(alk)_b$-, —$NR^{25}C(S)O$-$(alk)_b$-, —$NR^{25}S(O)_2$-$(alk)_b$-, or —NR$^{25}$S(O)$_2$NR$^{25}$-(alk)$_b$-, wherein b and R$^{25}$ are as defined for Formula I, alk is C$_{1-3}$ alkylene optionally substituted with fluoro or optionally fluoro substituted lower alkyl, R$^{24}$ is hydrogen provided, however, that said hydrogen would not be attached to S(O) or S(O)$_2$, optionally substituted lower alkyl, optionally substituted cycloalkyl, optionally substituted heterocycloalkyl, optionally substituted aryl, or optionally substituted heteroaryl, R$^a$ and R$^b$ are independently hydrogen, halogen, optionally fluoro substituted lower alkyl, or optionally fluoro substituted lower alkoxy, one of R$^4$ and R$^5$ is other than hydrogen and R$^6$ is hydrogen. In other embodiments, R$^4$ is hydrogen and R$^5$ is other than hydrogen. In other embodiments, R$^5$ is hydrogen and R$^4$ is other than hydrogen. In other embodiments, A is —CH$_2$—, R$^5$ is hydrogen and R$^4$ is other than hydrogen. In other embodiments, A is —C(O)—, R$^5$ is hydrogen and R$^4$ is other than hydrogen. In other embodiments, A is —CH$_2$—, R$^4$ is hydrogen and R$^5$ is other than hydrogen. In other embodiments, A is —C(O)—, R$^4$ is hydrogen and R$^5$ is other than hydrogen.

In some embodiments of compounds of Formula II, A is —CR$^a$R$^b$— or —C(O)—, R$^{13}$ is -LR$^{24}$, R$^{12}$, R$^{14}$, R$^{15}$ and R$^{16}$ are independently hydrogen, halogen, optionally fluoro substituted lower alkyl, optionally fluoro substituted lower alkoxy, or optionally fluoro substituted lower alkylthio, where at least one of R$^{12}$, R$^{14}$, R$^{15}$ and R$^{16}$ is other than hydrogen, L is —NR$^{25}$C(O)-(alk)$_b$-, —NR$^{25}$C(S)-(alk)$_b$-, —NR$^{25}$S(O)$_2$-(alk)$_b$-, —NR$^{25}$C(O)NR$^{25}$-(alk)$_b$-, —NR$^{25}$C(S)NR$^{25}$-(alk)$_b$-, or —NR$^{25}$S(O)$_2$NR$^{25}$-(alk)$_b$-, wherein b and R$^{25}$ are as defined for Formula I, alk is C$_{1-3}$ alkylene optionally substituted with fluoro or optionally fluoro substituted lower alkyl, R$^{24}$ is hydrogen provided, however, that said hydrogen would not be attached to S(O)$_2$, optionally substituted lower alkyl, optionally substituted cycloalkyl, optionally substituted heterocycloalkyl, optionally substituted aryl, or optionally substituted heteroaryl, R$^a$ and R$^b$ are independently hydrogen, halogen, optionally fluoro substituted lower alkyl, or optionally fluoro substituted lower alkoxy, provided, however, that when R$^4$, R$^5$, R$^6$, R$^{12}$, R$^{14}$, and R$^{15}$ are hydrogen, A is —C(O)—, and R$^{16}$ is —F, then R$^{13}$ is not —NHS(O)$_2$CH$_3$. In further embodiments, R$^{12}$ is other than hydrogen and R$^{14}$, R$^{15}$ and R$^{16}$ are hydrogen. In further embodiments, R$^{16}$ is other than hydrogen and R$^{12}$, R$^{14}$ and R$^{15}$ are hydrogen. In further embodiments, at least two of R$^{12}$, R$^{14}$, R$^{15}$ and R$^{16}$ are other than hydrogen. In further embodiments, R$^{12}$ and R$^{16}$ are other than hydrogen and R$^{14}$ and R$^{15}$ are hydrogen. In further embodiments, R$^5$ is other than hydrogen and R$^4$ and R$^6$ are hydrogen. In further embodiments, R$^4$ is other than hydrogen and R$^5$ and R$^6$ are hydrogen.

In some embodiments of compounds of Formula II, A is —CR$^a$R$^b$— or —C(O)—, R$^{13}$ is -LR$^{24}$, R$^{12}$, R$^{14}$, R$^{15}$ and R$^{16}$ are independently hydrogen, halogen, optionally fluoro substituted lower alkyl, optionally fluoro substituted lower alkoxy, or optionally fluoro substituted lower alkylthio, where at least one of R$^{12}$, R$^{14}$, R$^{15}$ and R$^{16}$ is other than hydrogen, L is —NR$^{25}$C(O)O-(alk)$_b$-, —NR$^{25}$C(S)O-(alk)$_b$-, —OC(O)NR$^{25}$-(alk)$_b$-, or —OC(S)NR$^{25}$-(alk)$_b$-, wherein b and R$^{25}$ are as defined for Formula I, alk is C$_{1-3}$ alkylene optionally substituted with fluoro or optionally fluoro substituted lower alkyl, R$^{24}$ is hydrogen, optionally substituted lower alkyl, optionally substituted cycloalkyl, optionally substituted heterocycloalkyl, optionally substituted aryl, or optionally substituted heteroaryl, R$^a$ and R$^b$ are independently hydrogen, halogen, optionally fluoro substituted lower alkyl, and optionally fluoro substituted lower alkoxy. In further embodiments, R$^{12}$ is other than hydrogen and R$^{14}$, R$^{15}$ and R$^{16}$ are hydrogen. In further embodiments, R$^{16}$ is other than hydrogen and R$^{12}$, R$^{15}$ and R$^{16}$ are hydrogen.

In further embodiments, at least two of R$^{12}$, R$^{14}$, R$^{15}$ and R$^{16}$ are other than hydrogen. In further embodiments, R$^{12}$ and R$^{16}$ are other than hydrogen and R$^{14}$ and R$^{15}$ are hydrogen. In further embodiments, R$^5$ is other than hydrogen and R$^4$ and R$^6$ are hydrogen. In further embodiments, R$^4$ is other than hydrogen and R$^5$ and R$^6$ are hydrogen.

In some embodiments of any of the above embodiments of compounds of Formula II wherein R$^{13}$ is -LR$^{24}$, -LR$^{24}$ is not —NH$_2$, —OH, —OCH$_3$, —NHS(O)$_2$CH$_3$,

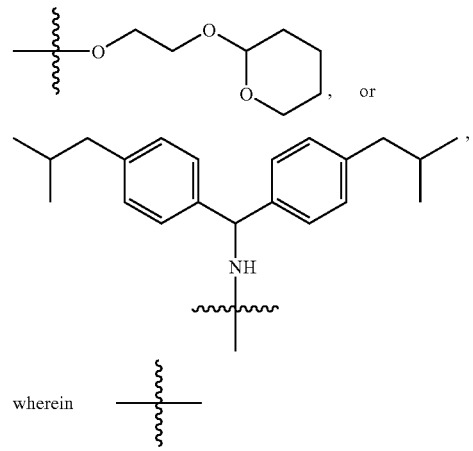

indicates the bond to the phenyl ring.

In some embodiments of compounds of Formula II, R$^{14}$ is -LR$^{24}$, provided, however, that when R$^4$, R$^6$, R$^{12}$, R$^{13}$, R$^{15}$ and R$^{16}$ are hydrogen, R$^5$ is hydrogen or thiophen-2-yl and A is —C(O)—, then R$^{14}$ is not —OH, or —OCH$_3$; and when R$^4$, R$^5$, R$^6$, R$^{12}$, R$^{13}$, R$^{15}$ and R$^{16}$ are hydrogen and A is —CH$_2$—, R$^{14}$ is not

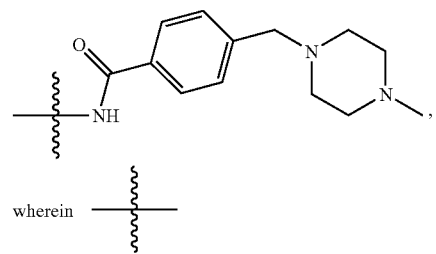

indicates the bond to the phenyl ring, when R$^4$, R$^6$, R$^{12}$, R$^{15}$ and R$^{16}$ are hydrogen, A is —CH$_2$—, and R$^5$ is thiophen-3-yl, R$^{13}$ and R$^{14}$ are not both —OH; and when R$^5$, R$^6$, R$^{12}$, R$^{13}$, R$^{15}$ and R$^{16}$ are hydrogen and A is —S—, R$^{14}$ is not —CH$_3$; and when R$^{14}$ is —N(CH$_3$)$_2$, R$^4$, R$^6$, R$^{12}$, R$^{13}$, R$^{15}$ and R$^{16}$ are hydrogen, and A is —CH$_2$—, then R$^5$ is not 3-hydroxy-phenyl; and when R$^{14}$ is —NH$_2$, R$^4$, R$^6$, R$^{12}$, R$^{13}$, R$^{15}$ and R$^{16}$ are hydrogen, and A is —S(O)$_2$—, then R$^5$ is not

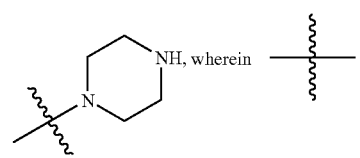

indicates the bond to the 5-position of the 7-azaindole ring. In further embodiments, when L is —O—, $R^{24}$ is not H or $CH_3$; and when L is —$OCH_2$—, $R^{24}$ is not H. In some embodiments, one of $R^{12}$, $R^{13}$, $R^{15}$, and $R^{16}$ is other than hydrogen and the others are hydrogen. In some embodiments, at least one of $R^{12}$, $R^{13}$, $R^{15}$, and $R^{16}$ are other than hydrogen. In some embodiments, two of $R^{12}$, $R^{13}$, $R^{15}$, and $R^{16}$ are other than hydrogen and the others are hydrogen. In some embodiments, at least two of $R^{12}$, $R^{13}$, $R^{15}$, and $R^{16}$ are other than hydrogen. In a some embodiments, at least three of $R^{13}$, $R^{13}$, $R^{15}$, and $R^{16}$ are other than hydrogen. In some embodiments, $R^{12}$, $R^{13}$, $R^{15}$, and $R^{16}$ are other than hydrogen. In some embodiments, one of $R^{12}$, $R^{13}$, $R^{15}$ and $R^{16}$ is hydrogen, halogen, optionally fluoro substituted lower alkyl, optionally fluoro substituted lower alkoxy, or optionally fluoro substituted lower alkylthio, and the others of $R^{12}$, $R^{13}$, $R^{15}$ and $R^{16}$ are hydrogen. In some embodiments, any two of $R^{12}$, $R^{13}$, $R^{15}$ and $R^{16}$ is hydrogen, halogen, optionally fluoro substituted lower alkyl, optionally fluoro substituted lower alkoxy, or optionally fluoro substituted lower alkylthio and the remaining of $R^{12}$, $R^{13}$, $R^{15}$ and $R^{16}$ are hydrogen. In some embodiments, $R^{14}$ is —$OR^{24}$, where $R^{24}$ is optionally substituted $C_{2-6}$ alkyl, optionally substituted lower alkenyl, optionally substituted lower alkynyl, optionally substituted cycloalkyl, optionally substituted heterocycloalkyl, optionally substituted aryl, or optionally substituted heteroaryl, or $R^{14}$ is —O-alk-$R^{24}$, where $R^{24}$ is optionally substituted cycloalkyl, optionally substituted heterocycloalkyl, optionally substituted aryl, or optionally substituted heteroaryl. In some embodiments, $R^{14}$ is —$SR^{24}$, where $R^{24}$ is hydrogen, optionally substituted lower alkyl, optionally substituted lower alkenyl, optionally substituted lower alkynyl, optionally substituted cycloalkyl, optionally substituted heterocycloalkyl, optionally substituted aryl, or optionally substituted heteroaryl, or $R^{14}$ is —S-alk-$R^{24}$, where $R^{24}$ is optionally substituted cycloalkyl, optionally substituted heterocycloalkyl, optionally substituted aryl, or optionally substituted heteroaryl. In some embodiments. $R^{14}$ is —$NHR^{24}$, where $R^{24}$ is hydrogen, optionally substituted lower alkyl, optionally substituted lower alkenyl, optionally substituted lower alkynyl, optionally substituted cycloalkyl, optionally substituted heterocycloalkyl, optionally substituted aryl, or optionally substituted heteroaryl, or $R^{14}$ is —NH-alk-$R^{24}$, where $R^{24}$ is optionally substituted cycloalkyl, optionally substituted heterocycloalkyl, optionally substituted aryl, or optionally substituted heteroaryl. In some embodiments, A is —$CH_2$— or —C(O)—. In some embodiments, $R^5$ is other than hydrogen and $R^4$ and $R^6$ are hydrogen. In some embodiments, $R^4$ is other than hydrogen and $R^5$ and $R^6$ are hydrogen. In some embodiments, $R^6$ is other than hydrogen and $R^4$ and $R^5$ are hydrogen. In some embodiments, A is —$CH_2$—, $R^5$ is other than hydrogen and $R^4$ and $R^6$ are hydrogen. In some embodiments, A is —$CH_2$—, $R^4$ is other than hydrogen and $R^5$ and $R^6$ are hydrogen. In some embodiments, A is —$CH_2$—, $R^6$ is other than hydrogen and $R^4$ and $R^5$ are hydrogen. In some embodiments, A is —C(O)—, $R^5$ is other than hydrogen and $R^4$ and $R^6$ are hydrogen. In some embodiments, A is —C(O)—, $R^4$ is other than hydrogen and $R^5$ and $R^6$ are hydrogen. In some embodiments, A is —C(O)—, $R^6$ is other than hydrogen and $R^4$ and $R^5$ are hydrogen.

In some embodiments of compounds of Formula II, $R^{14}$ is —$OR^{24}$ where $R^{24}$ is optionally substituted $C_{2-6}$ alkyl, optionally substituted cycloalkyl, optionally substituted heterocycloalkyl, optionally substituted aryl, or optionally substituted heteroaryl, or $R^{14}$ is —$SR^{24}$ where $R^{24}$ is hydrogen, optionally substituted lower alkyl, optionally substituted cycloalkyl, optionally substituted heterocycloalkyl, optionally substituted aryl, or optionally substituted heteroaryl, or $R^{14}$ is —$NHR^{24}$, where $R^{24}$ is hydrogen, optionally substituted lower alkyl, optionally substituted cycloalkyl, optionally substituted heterocycloalkyl, optionally substituted aryl, or optionally substituted heteroaryl. In some embodiments, any one of $R^{12}$, $R^{13}$, $R^{15}$ and $R^{16}$ is hydrogen, halogen, optionally fluoro substituted lower alkyl, optionally fluoro substituted lower alkoxy, or optionally fluoro substituted lower alkylthio and the remaining of $R^{12}$, $R^{13}$, $R^{15}$ and $R^{16}$ are hydrogen. In some embodiments, two of $R^{12}$, $R^{13}$, $R^{15}$ and $R^{16}$ are independently hydrogen, halogen, optionally fluoro substituted lower alkyl, optionally fluoro substituted lower alkoxy, or optionally fluoro substituted lower alkylthio and the remaining two of $R^{12}$, $R^{13}$, $R^{15}$ and $R^{16}$ are hydrogen. In some embodiments, $R^{12}$ is hydrogen, halogen, optionally fluoro substituted lower alkyl, optionally fluoro substituted lower alkoxy, or optionally fluoro substituted lower alkylthio and $R^{13}$, $R^{15}$ and $R^{16}$ are hydrogen. In some embodiments, A is —$CH_2$— or —C(O)—. In some embodiments, $R^5$ is other than hydrogen and $R^4$ and $R^6$ are hydrogen. In some embodiments, $R^4$ is other than hydrogen and $R^5$ and $R^6$ are hydrogen. In some embodiments, $R^6$ is other than hydrogen and $R^4$ and $R^5$ are hydrogen. In some embodiments, A is —$CH_2$—, $R^5$ is other than hydrogen and $R^4$ and $R^6$ are hydrogen. In some embodiments, A is —$CH_2$—, $R^4$ is other than hydrogen and $R^5$ and $R^6$ are hydrogen. In some embodiments, A is —$CH_2$—, $R^6$ is other than hydrogen and $R^4$ and $R^5$ are hydrogen. In some embodiments, A is —C(O)—, $R^5$ is other than hydrogen and $R^4$ and $R^6$ are hydrogen. In some embodiments, A is —C(O)—, $R^4$ is other than hydrogen and $R^5$ and $R^6$ are hydrogen. In some embodiments, A is —C(O)—, $R^6$ is other than hydrogen and $R^4$ and $R^5$ are hydrogen.

In some embodiments of compounds of Formula II, $R^{14}$ is -$LR^{24}$, where L is —$NR^{25}$-(alk)$_b$-, —C(O)$NR^{25}$-(alk)$_b$-, —OC(O)$NR^{25}$-(alk)$_b$-, —OC(S)$NR^{25}$-(alk)$_b$-, —C(S)$NR^{25}$-(alk)$_b$-, —S(O)$_2NR^{25}$-(alk)$_b$-, —$NR^{25}$C(O)-(alk)$_b$-, —$NR^{25}$C(S)-(alk)$_b$-, —$NR^{25}$C(O)$NR^{25}$-(alk)$_b$-, —$NR^{25}$C(S)$NR^{25}$-(alk)$_b$-, —$NR^{25}$C(O)O-(alk)$_b$-, —$NR^{25}$C(S)O-(alk)$_b$-, —$NR^{25}$S(O)$_2$-(alk)$_b$-, or —$NR^{25}$S(O)$_2NR^{25}$-(alk)$_b$-, wherein b, alk and $R^{25}$ are as defined for Formula I, and $R^{24}$ is optionally substituted cycloalkyl, optionally substituted heterocycloalkyl, optionally substituted aryl, or optionally substituted heteroaryl. In some embodiments, any one of $R^{12}$, $R^{13}$, $R^{15}$, and $R^{16}$ is other than hydrogen and the remaining of $R^{12}$, $R^{13}$, $R^{15}$, and $R^{16}$ are hydrogen. In some embodiments, at least one of $R^{12}$, $R^{13}$, $R^{15}$, and $R^{16}$ are other than hydrogen. In some embodiments, any two of $R^{12}$, $R^{13}$, $R^{15}$, and $R^{16}$ are other than hydrogen and the remaining of $R^{12}$, $R^{13}$, $R^{15}$, and $R^{16}$ are hydrogen. In some embodiments, at least two of $R^{12}$, $R^{13}$, $R^{15}$, and $R^{16}$ are other than hydrogen. In a some embodiments, at least three of $R^{12}$, $R^{13}$, $R^{15}$, and $R^{16}$ are other than hydrogen. In a some embodiments, $R^{12}$, $R^{13}$, $R^{15}$, and $R^{16}$ are other than hydrogen. In some embodiments, any one of $R^{12}$, $R^{13}$, $R^{15}$ and $R^{16}$ is hydrogen, halogen, optionally fluoro substituted lower alkyl, optionally fluoro substituted lower alkoxy, or optionally fluoro substituted lower alkylthio, and the remaining of $R^{12}$, $R^{13}$, $R^{15}$, and $R^{16}$ are hydrogen. In some embodiments, two of $R^{12}$, $R^{13}$, $R^{15}$ and $R^{16}$ are independently hydrogen, halogen, optionally fluoro substituted lower alkyl, optionally fluoro substituted lower alkoxy, or optionally fluoro substituted lower alkylthio and the others of $R^{12}$, $R^{13}$, $R^{15}$ and $R^{16}$ are hydrogen. In some embodiments, A is selected from —$CH_2$— and —C(O)—. In some embodiments, $R^5$ is other than hydrogen and $R^4$ and $R^6$ are hydrogen. In some embodiments, $R^4$ is other than hydrogen and $R^5$ and $R^6$ are hydrogen. In some embodiments, $R^6$ is other than hydrogen and $R^4$ and $R^5$ are hydrogen. In some embodiments, A is —CH$_2$—, R$^5$ is other than hydrogen and R$^4$ and R$^6$ are hydrogen. In some embodiments, A is —CH$_2$—, R$^4$ is other than hydrogen and R$^5$ and R$^6$ are hydrogen. In some embodiments, A is —CH$_2$—, R$^6$ is other than hydrogen and R$^4$ and R$^5$ are hydrogen. In some embodiments, A is —C(O)—, R$^5$ is other than hydrogen and R$^4$ and R$^6$ are hydrogen. In some embodiments, A is —C(O)—, R$^4$ is other than hydrogen and R$^5$ and R$^6$ are hydrogen. In some embodiments, A is —C(O)—, R$^6$ is other than hydrogen and R$^4$ and R$^5$ are hydrogen.

In some embodiments of any of the above embodiments of compounds of Formula II wherein R$^{14}$ is -LR$^{24}$, -LR$^{24}$ is not —NH$_2$, —OH, —OCH$_3$, —N(CH$_3$)$_2$, or

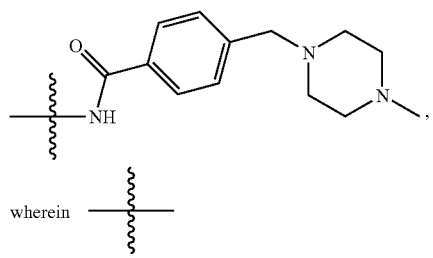

wherein indicates the bond to the phenyl ring.

In some embodiments of compounds of Formula II, R$^{13}$ and R$^{15}$ are halogen, optionally fluoro substituted lower alkyl, —OR$^{24}$, where R$^{24}$ is optionally substituted C$_{2-6}$, alkyl, optionally substituted lower alkenyl, optionally substituted lower alkynyl, optionally substituted cycloalkyl, optionally substituted heterocycloalkyl, optionally substituted aryl, or optionally substituted heteroaryl, —O-alk-R$^{24}$, where R$^{24}$ is optionally substituted cycloalkyl, optionally substituted heterocycloalkyl, optionally substituted aryl, or optionally substituted heteroaryl, —SR$^{24}$, where R$^{24}$ is hydrogen, optionally substituted lower alkyl, optionally substituted lower alkenyl, optionally substituted lower alkynyl, optionally substituted cycloalkyl, optionally substituted heterocycloalkyl, optionally substituted aryl, or optionally substituted heteroaryl, —S-alk-R$^{24}$, where R$^{24}$ is optionally substituted cycloalkyl, optionally substituted heterocycloalkyl, optionally substituted aryl, or optionally substituted heteroaryl, —NHR$^{24}$, where R$^{24}$ is hydrogen, optionally substituted lower alkyl, optionally substituted lower alkenyl, optionally substituted lower alkynyl, optionally substituted cycloalkyl, optionally substituted heterocycloalkyl, optionally substituted aryl, or optionally substituted heteroaryl, or —NH-alk-R$^{24}$, where R$^{24}$ is optionally substituted cycloalkyl, optionally substituted heterocycloalkyl, optionally substituted aryl, or optionally substituted heteroaryl. In some embodiments, at least one of R$^{12}$, R$^{14}$ and R$^{16}$ is other than hydrogen. In some embodiments, at least two of R$^{12}$, R$^{14}$ and R$^{16}$ are other than hydrogen. In some embodiments, R$^{12}$, R$^{14}$ and R$^{16}$ are other than hydrogen. In some embodiments, any one of R$^{12}$, R$^{14}$ and R$^{16}$ is hydrogen, halogen, optionally fluoro substituted lower alkyl, optionally fluoro substituted lower alkoxy, or optionally fluoro substituted lower alkylthio and the remaining of R$^{12}$, R$^{14}$ and R$^{16}$ are hydrogen. In some embodiments, any two of R$^{12}$, R$^{14}$ and R$^{16}$ are independently hydrogen, halogen, optionally fluoro substituted lower alkyl, optionally fluoro substituted lower alkoxy, or optionally fluoro substituted lower alkylthio and the remaining of R$^{12}$, R$^{14}$ and R$^{16}$ is hydrogen. In some embodiments, R$^{12}$, R$^{14}$ and R$^{16}$ are independently hydrogen, halogen, optionally fluoro substituted lower alkyl, optionally fluoro substituted lower alkoxy, or optionally fluoro substituted lower alkylthio. In some embodiments, A is —CH$_2$— or —C(O)—. In some embodiments, R$^5$ is other than hydrogen and R$^4$ and R$^6$ are hydrogen. In some embodiments, R$^4$ is other than hydrogen and R$^5$ and R$^6$ are hydrogen. In some embodiments, R$^6$ is other than hydrogen and R$^4$ and R$^5$ are hydrogen. In some embodiments, A is —CH$_2$—, R$^5$ is other than hydrogen and R$^4$ and R$^5$ are hydrogen. In some embodiments, A is —CH$_2$—, R$^4$ is other than hydrogen and R$^5$ and R$^6$ are hydrogen. In some embodiments, A is —CH$_2$—, R$^6$ is other than hydrogen and R$^4$ and R$^5$ are hydrogen. In some embodiments, A is —C(O)—, R$^5$ is other than hydrogen and R$^4$ and R$^6$ are hydrogen. In some embodiments, A is —C(O)—, R$^4$ is other than hydrogen and R$^5$ and R$^6$ are hydrogen. In some embodiments, A is —C(O)—R$^6$ is other than hydrogen and R$^4$ and R$^5$ are hydrogen.

The compounds of Formula II, and all sub-embodiments detailed herein, may be used to treat a subject suffering from or at risk for any of the protein kinase mediated diseases or conditions contemplated herein.

In some embodiments, compounds of Formula II have the structure according to the following sub-generic structure Formula IIa:

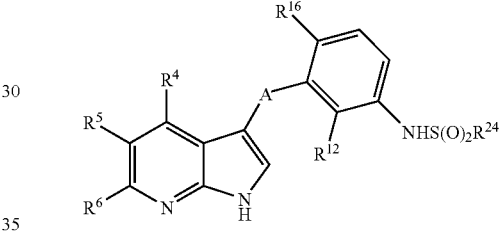

Formula IIa all salts, prodrugs, tautomers and isomers thereof, wherein A, R$^4$, R$^5$, R$^6$, R$^{12}$, R$^{16}$ and R$^{24}$ are as defined for Formula II, provided, however, that when A is C(O), R$^4$, R$^5$, R$^6$, and R$^{12}$ are hydrogen and R$^{16}$ is fluoro, then R$^{24}$ is not CH$_3$.

In some embodiments of compounds of Formula IIa, A is —CH$_2$— or —C(O)—.

In other embodiments of compounds of Formula IIa, A is —CH$_2$— or —C(O)— and R$^{12}$ and R$^{16}$ are independently hydrogen, halogen, optionally fluoro substituted lower alkyl, optionally fluoro substituted lower alkoxy, or optionally fluoro substituted lower alkylthio; in further embodiments, R$^{12}$ and R$^{16}$ are independently hydrogen, halogen, optionally fluoro substituted C$_{1-3}$alkyl, optionally fluoro substituted C$_{1-3}$alkoxy, or optionally fluoro substituted C$_{1-3}$alkylthio. In some embodiments, A is —CH$_2$— or —C(O)—, and R$^{12}$ and R$^{16}$ are independently halogen, optionally fluoro substituted lower alkyl, optionally fluoro substituted lower alkoxy, or optionally fluoro substituted lower alkylthio; in further embodiments, R$^{12}$ and R$^{16}$ are independently halogen, optionally fluoro substituted C$_{1-3}$alkyl, optionally fluoro substituted C$_{1-3}$alkoxy, or optionally fluoro substituted C$_{1-3}$alkylthio.

In other embodiments of compounds of Formula IIa, A is —CH$_2$—, R$^{12}$ is hydrogen and R$^{16}$ is halogen, optionally fluoro substituted lower alkyl, optionally fluoro substituted lower alkoxy, or optionally fluoro substituted lower alkylthio; in further embodiments, R$^{16}$ is halogen, optionally fluoro substituted C$_{1-3}$alkyl, optionally fluoro substituted C$_{1-3}$alkoxy, or optionally fluoro substituted C$_{1-3}$alkylthio. In some embodiments, A is —CH$_2$—, R$^{16}$ is hydrogen and R$^{12}$ is halogen, optionally fluoro substituted lower alkyl, optionally fluoro substituted lower alkoxy, or optionally fluoro substituted lower alkylthio; in further embodiments, $R^{12}$ is halogen, optionally fluoro substituted $C_{1-3}$alkyl, optionally fluoro substituted $C_{1-3}$alkoxy, or optionally fluoro substituted $C_{1-3}$alkylthio.

In some embodiments of compounds of Formula IIa, A is —$CH_2$— and $R^{12}$ and $R^{16}$ are independently halogen, optionally fluoro substituted lower alkyl, optionally fluoro substituted lower alkoxy, or optionally fluoro substituted lower alkylthio; in further embodiments, $R^{12}$ and $R^{16}$ are independently halogen, optionally fluoro substituted $C_{1-3}$alkyl, optionally fluoro substituted $C_{1-3}$alkoxy, and optionally fluoro substituted $C_{1-3}$alkylthio.

In other embodiments of compounds of Formula IIa, A is —C(O)—, $R^{12}$ is hydrogen and $R^{16}$ is halogen, optionally fluoro substituted lower alkyl, optionally fluoro substituted lower alkoxy, or optionally fluoro substituted lower alkylthio; in further embodiments, $R^{16}$ is halogen, optionally fluoro substituted $C_{1-3}$alkyl, optionally fluoro substituted $C_{1-3}$alkoxy, or optionally fluoro substituted $C_{1-3}$alkylthio. In some embodiments, A is —C(O)—, $R^{16}$ is hydrogen and $R^{12}$ is halogen, optionally fluoro substituted lower alkyl, optionally fluoro substituted lower alkoxy, or optionally fluoro substituted lower alkylthio; in further embodiments, $R^{12}$ is halogen, optionally fluoro substituted $C_{1-3}$alkyl, optionally fluoro substituted $C_{1-3}$alkoxy, or optionally fluoro substituted $C_{1-3}$alkylthio.

In some embodiments of compounds of Formula IIa, A is —C(O)— and $R^{12}$ and $R^{16}$ are independently halogen, optionally fluoro substituted lower alkyl, optionally fluoro substituted lower alkoxy, or optionally fluoro substituted lower alkylthio; in further embodiments, $R^{12}$ and $R^{16}$ are independently hydrogen, halogen, optionally fluoro substituted $C_{1-3}$alkyl, optionally fluoro substituted $C_{1-3}$alkoxy, or optionally fluoro substituted $C_{1-3}$alklylthio.

In some embodiments of any of the above embodiments of compounds of Formula IIa, $R^4$ and $R^6$ are hydrogen, or $R^5$ and $R^6$ are hydrogen, or $R^4$ and $R^5$ are hydrogen.

In some embodiments of any of the above embodiments of compounds of Formula IIa, $R^{24}$ is substituted methyl, optionally substituted $C_{2-6}$ alkyl, optionally substituted cycloalkyl, optionally substituted heterocycloalkyl, optionally substituted aryl, or optionally substituted heteroaryl; in further embodiments, $R^{24}$ is $C_{2-6}$ lower alkyl, aryl or heteroaryl, wherein aryl and heteroaryl are optionally substituted with halogen, lower alkyl or lower alkoxy; in further embodiments, $R^{24}$ is n-propyl, i-propyl, or phenyl, wherein phenyl is optionally substituted with halogen, lower alkyl or lower alkoxy.

In some embodiments, compounds of Formula II have the structure according to the following sub-generic structure Formula IIb:

Formula IIb

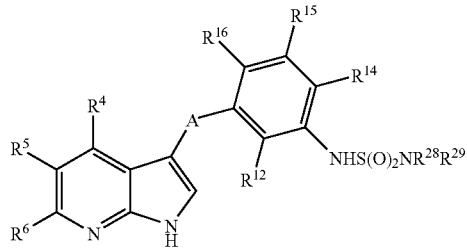

all salts, prodrugs, tautomers and isomers thereof, wherein A, $R^4$, $R^5$, $R^6$, $R^{12}$, $R^{14}$, $R^{15}$ and $R^{16}$, are as defined for Formula II, $R^{28}$ is hydrogen, lower alkyl, or lower alkyl substituted with fluoro, hydroxyl, lower alkoxy, thiol, lower alkylthio, or —$NR^8R^9$, wherein $R^9$ and $R^9$ are as defined for Formula I, provided, however, that when $R^{28}$ is substituted lower alkyl, any substitution of the alkyl carbon bound to the nitrogen of $NR^{29}$ is fluoro, and $R^{29}$ is hydrogen, optionally substituted lower alkyl, optionally substituted lower alkenyl, provided, however, that nitrogen of $NR^{29}$ is not bound to any alkene carbon thereof, optionally substituted lower alkynyl, provided, however, that nitrogen of $NR^{29}$ is not bound to any alkyne carbon thereof, optionally substituted cycloalkyl, optionally substituted heterocycloalkyl, optionally substituted aryl, or optionally substituted heteroaryl, or $R^{28}$ and $R^{29}$ combine with the nitrogen to which they are attached form optionally substituted 5-7 membered heterocycloalkyl or optionally substituted 5 or 7 membered nitrogen containing heteroaryl. In some embodiments of compounds of Formula IIb, A is —$CH_2$— or —C(O)—, $R^{12}$, $R^{14}$, $R^{15}$ and $R^{16}$ are independently hydrogen, halogen, optionally fluoro substituted lower alkyl, optionally fluoro substituted lower alkoxy, or optionally fluoro substituted lower alkylthio, $R^{28}$ is hydrogen or lower alkyl and $R^{29}$ is optionally substituted cycloalkyl, optionally substituted heterocycloalkyl, optionally substituted aryl, or optionally substituted heteroaryl, or $R^{28}$ and $R^{29}$ combine with the nitrogen to which they are attached form optionally substituted 5-7 membered heterocycloalkyl or optionally substituted 5 or 7 membered nitrogen containing heteroaryl.

In some embodiments of compounds of Formula IIb, A is —$CH_2$—, one of $R^{12}$, $R^{14}$, $R^{15}$ and $R^{16}$ is halogen, optionally fluoro substituted lower alkyl, optionally fluoro substituted lower alkoxy, or optionally fluoro substituted lower alkylthio and the remaining of $R^{12}$, $R^{14}$, $R^{15}$ and $R^{16}$ are hydrogen.

In other embodiments of compounds of Formula IIb, A is —$CH_2$—, $R^{12}$, $R^{14}$ and $R^{15}$ are hydrogen and $R^{16}$ is halogen, optionally fluoro substituted lower alkyl, optionally fluoro substituted lower alkoxy, or optionally fluoro substituted lower alkylthio.

In other embodiments of compounds of Formula IIb, A is —$CH_2$—, $R^{14}$, $R^{15}$ and $R^{16}$ are hydrogen and $R^{12}$ is halogen, optionally fluoro substituted lower alkyl, optionally fluoro substituted lower alkoxy, or optionally fluoro substituted lower alkylthio.

In some embodiments of compounds of Formula IIb, A is —$CH_2$—, two of $R^{12}$, $R^{14}$, $R^{15}$ and $R^{16}$ are independently halogen, optionally fluoro substituted lower alkyl, optionally fluoro substituted lower alkoxy, or optionally fluoro substituted lower alkylthio and the other two of $R^{12}$, $R^{14}$, $R^{15}$ and $R^{16}$ are hydrogen.

In some embodiments of compounds of Formula IIb, A is —$CH_2$—, $R^{14}$ and $R^{15}$ are hydrogen and $R^{12}$ and $R^{16}$ are independently halogen, optionally fluoro substituted lower alkyl, optionally fluoro substituted lower alkoxy, or optionally fluoro substituted lower alkylthio.

In some embodiments of compounds of Formula IIb, A is —C(O)—, one of $R^{12}$, $R^{14}$, $R^{15}$ and $R^{16}$ is halogen, optionally fluoro substituted lower alkyl, optionally fluoro substituted lower alkoxy, or optionally fluoro substituted lower alkylthio and the others of $R^{12}$, $R^{14}$, $R^{15}$ and $R^{16}$ are hydrogen.

In some embodiments of compounds of Formula IIb, A is —C(O)—, $R^{12}$, $R^{14}$ and $R^{15}$ are hydrogen and $R^{16}$ is halogen, optionally fluoro substituted lower alkyl, optionally fluoro substituted lower alkoxy, or optionally fluoro substituted lower alkylthio.

In some embodiments of compounds of Formula IIb, A is —C(O)—, $R^{14}$, $R^{15}$ and $R^{16}$ are hydrogen and $R^{12}$ is halogen, optionally fluoro substituted lower alkyl, optionally fluoro substituted lower alkoxy, or optionally fluoro substituted lower alkylthio.

In some embodiments of compounds of Formula IIb, A is —C(O)—, two of $R^{12}$, $R^{14}$, $R^{15}$ and $R^{16}$ are independently halogen, optionally fluoro substituted lower alkyl, optionally fluoro substituted lower alkoxy, or optionally fluoro substituted lower alkylthio and the other two of $R^{12}$, $R^{14}$, $R^{15}$ and $R^{16}$ are hydrogen.

In some embodiments of compounds of Formula IIb, A is —C(O)—, $R^{14}$ and $R^{15}$ are hydrogen and $R^{12}$ and $R^{16}$ are independently halogen, optionally fluoro substituted lower alkyl, optionally fluoro substituted lower alkoxy, or optionally fluoro substituted lower alkylthio.

In some embodiments of any of the above embodiments of compounds of Formula IIb, $R^4$ and $R^6$ are hydrogen, or $R^5$ and $R^6$ are hydrogen, or $R^4$ and $R^5$ are hydrogen. In some embodiments of any of the above embodiments of compounds of Formula IIb, $R^{28}$ and $R^{29}$ are both lower alkyl, or $R^{28}$ and $R^{29}$ combine with the nitrogen to which they are attached to form optionally substituted 5-7 membered heterocycloalkyl, further wherein the heterocycloalkyl is pyrrolidine, piperidine, piperazine or morpholine.

In some embodiments, compounds of Formula II have the structure according to the following sub-generic structures Formulae IIc, IId, IIe, IIf, or IIg:

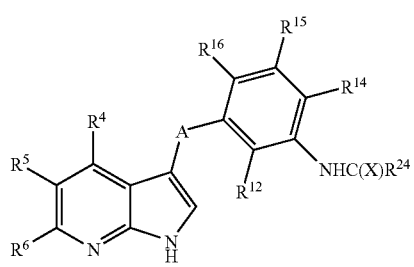

Formula IIc

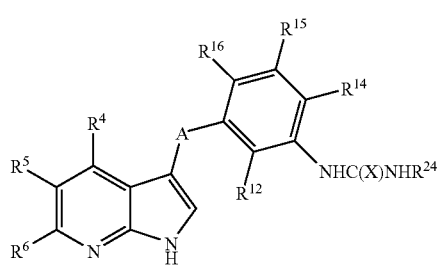

Formula IId

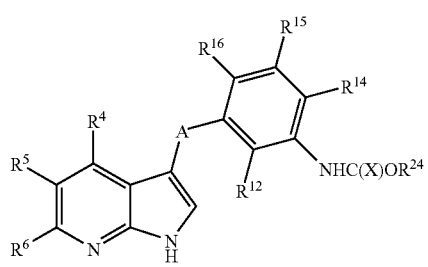

Formula IIe

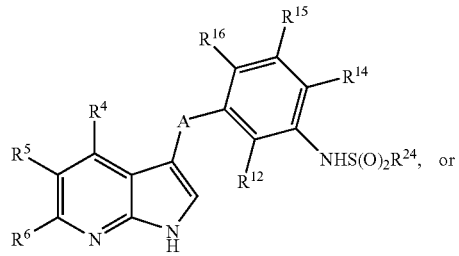

Formula IIf

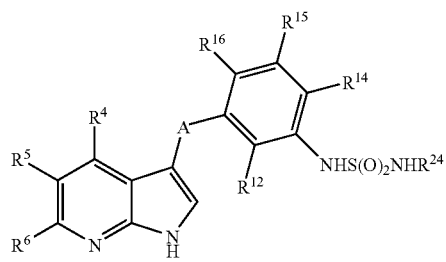

Formula IIg all salts, prodrugs, tautomers and isomers thereof, wherein A, X, $R^4$, $R^5$, $R^6$, $R^{12}$, $R^{14}$, $R^{15}$, $R^{16}$ and $R^{24}$ are as defined for Formula II. In some embodiments of compounds of Formulae IIc, IId, IIe, IIf, or IIg, A is —CH$_2$— or —C(O)—. In some embodiments, any one of $R^{12}$, $R^{14}$, $R^{15}$, and $R^{16}$ is other than hydrogen. In some embodiments, any two of $R^{12}$, $R^{14}$, $R^{15}$, and $R^{16}$ are other than hydrogen. In some embodiments, any three of $R^{12}$, $R^{14}$, $R^{15}$, and $R^{16}$ are other than hydrogen. In some embodiments, $R^{12}$, $R^{14}$, $R^{15}$, and $R^{16}$ are other than hydrogen. In some embodiments, A is —CH$_2$— or —C(O)— and $R^{12}$, $R^{14}$, $R^{15}$, and $R^{16}$ are independently hydrogen, halogen, optionally fluoro substituted lower alkyl, optionally fluoro substituted lower alkoxy, or optionally fluoro substituted lower alkylthio. In some embodiments, A is —CH$_2$—, any one of $R^{12}$, $R^{14}$, $R^{15}$ and $R^{16}$ is halogen, optionally fluoro substituted lower alkyl, optionally fluoro substituted lower alkoxy, or optionally fluoro substituted lower alkylthio and the remaining of $R^{12}$, $R^{14}$, $R^{15}$ and $R^{16}$ are hydrogen. In some embodiments, A is —CH$_2$—, $R^{12}$, $R^{14}$ and $R^{15}$ are hydrogen and $R^{16}$ is halogen, optionally fluoro substituted lower alkyl, optionally fluoro substituted lower alkoxy, or optionally fluoro substituted lower alkylthio. In some embodiments, A is —CH$_2$—, $R^{14}$, $R^{15}$ and $R^{16}$ are hydrogen and $R^{12}$ is halogen, optionally fluoro substituted lower alkyl, optionally fluoro substituted lower alkoxy, or optionally fluoro substituted lower alkylthio. In some embodiments, A is —CH$_2$—, any two of $R^{12}$, $R^{14}$, $R^{15}$ and $R^{16}$ are independently halogen, optionally fluoro substituted lower alkyl, optionally fluoro substituted lower alkoxy, or optionally fluoro substituted lower alkylthio and the remaining two of $R^{12}$, $R^{14}$, $R^{15}$ and $R^{16}$ are hydrogen. In some embodiments, A is —CH$_2$—, $R^{14}$ and $R^{15}$ are hydrogen and $R^{12}$ and $R^{16}$ are independently halogen, optionally fluoro substituted lower alkyl, optionally fluoro substituted lower alkoxy, or optionally fluoro substituted lower alkylthio. In some embodiments. A is —C(O)—, any one of $R^{12}$, $R^{14}$, $R^{15}$ and $R^{16}$ is halogen, optionally fluoro substituted lower alkyl, optionally fluoro substituted lower alkoxy, or optionally fluoro substituted lower alkylthio and the remaining of $R^{12}$, $R^{14}$, $R^{15}$ and $R^{16}$ are hydrogen. In some embodiments, A is —C(O)—, $R^{12}$, $R^{14}$ and $R^{15}$ are hydrogen and $R^{16}$ is halogen, optionally fluoro substituted lower alkyl, optionally fluoro substituted lower alkoxy, or optionally fluoro substituted lower alkylthio. In some embodiments, A is —C(O)—, $R^{14}$, $R^{15}$ and $R^{16}$ are hydrogen and $R^{12}$ is halogen, optionally fluoro substituted lower alkyl, optionally fluoro substituted lower alkoxy, or optionally fluoro substituted lower alkylthio. In some embodiments, A is —C(O)—, any two of $R^{12}$, $R^{14}$, $R^{15}$ and $R^{16}$ are independently halogen, optionally fluoro substituted lower alkyl, optionally fluoro substituted lower alkoxy, or optionally fluoro substituted lower alkylthio and the remaining two of $R^{12}$, $R^{14}$, $R^{15}$ and $R^{16}$ are hydrogen. In some embodiments, A is —C(O)—, $R^{14}$ and $R^{15}$ are hydrogen and $R^{12}$ and $R^{16}$ are independently halogen, optionally fluoro substituted lower alkyl, optionally fluoro substituted lower alkoxy, or optionally fluoro substituted lower alkylthio. In some embodiments of any of the above embodiments of compounds of Formula IIc, IId, IIe, IIf, and IIg, $R^4$ and $R^6$ are hydrogen or $R^5$ and $R^6$ are hydrogen, or $R^4$ and $R^5$ are hydrogen.

In some embodiments, compounds of Formula II have the structure according to the following sub-generic structure Formula IIh:

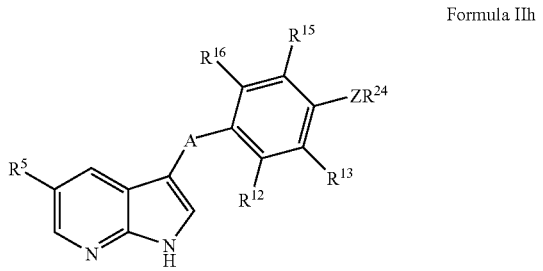

Formula IIh all salts, prodrugs, tautomers and isomers thereof, wherein A, $R^5$, $R^{12}$, $R^{13}$, $R^{15}$, $R^{16}$ and $R^{24}$ are as defined for Formula II, and Z is —O—, —S— or —NH—. In some embodiments of compounds of Formula IIh, $R^{24}$ is hydrogen, optionally substituted lower alkyl, optionally substituted cycloalkyl, optionally substituted heterocycloalkyl, optionally substituted aryl, or optionally substituted heteroaryl. In some embodiments, $R^{24}$ is hydrogen, optionally substituted lower alkyl, optionally substituted cycloalkyl, optionally substituted heterocycloalkyl, optionally substituted aryl, or optionally substituted heteroaryl and at least one of $R^{12}$, $R^{13}$, $R^{15}$ and $R^{16}$ is halogen, optionally fluoro substituted lower alkyl, optionally fluoro substituted lower alkoxy, or optionally fluoro substituted lower alkylthio and the others of $R^{12}$, $R^{13}$, $R^{15}$ and $R^{16}$ are hydrogen; in further embodiments, $R^{13}$ is halogen, optionally fluoro substituted lower alkyl, optionally fluoro substituted lower alkoxy, or optionally fluoro substituted lower alkylthio and $R^{12}$, $R^{15}$ and $R^{16}$ are hydrogen; in further embodiments, A is —CH$_2$— or —C(O)—.

In some embodiments of compounds of Formula IIh, Z is —O— or —NH—, $R^{24}$ is hydrogen, optionally substituted cycloalkyl, optionally substituted heterocycloalkyl, optionally substituted aryl, optionally substituted heteroaryl, or lower alkyl optionally substituted with optionally substituted aryl or optionally substituted heteroaryl, and at least one of $R^{12}$, $R^{13}$, $R^{15}$ and $R^{16}$ is halogen, optionally fluoro substituted lower alkyl, or optionally fluoro substituted lower alkoxy and the others of $R^{12}$, $R^{13}$, $R^{15}$ and $R^{16}$ are hydrogen; in further embodiments, $R^{13}$ is halogen, optionally fluoro substituted lower alkyl, or optionally fluoro substituted lower alkoxy and $R^{12}$, $R^{15}$ and $R^{16}$ are hydrogen; in further embodiments, A is —CH$_2$— or —C(O)—.

In some embodiments of compounds of Formula IIh, Z is —O— or —NH—, $R^{24}$ is hydrogen, optionally substituted cycloalkyl, optionally substituted heterocycloalkyl, optionally substituted aryl, optionally substituted heteroaryl, or lower alkyl optionally substituted with optionally substituted aryl or optionally substituted heteroaryl, $R^{13}$ is halogen, optionally fluoro substituted lower alkyl, or optionally fluoro substituted lower alkoxy and one of $R^{12}$, $R^{15}$ and $R^{16}$ is halogen, optionally fluoro substituted lower alkyl, or optionally fluoro substituted lower alkoxy and the others of $R^{12}$, $R^{15}$ and $R^{16}$ are hydrogen; in further embodiments, A is —CH$_2$— or —C(O)—.

In some embodiments of compounds of Formula IIh, Z is —O— or —NH—, $R^{24}$ is hydrogen, optionally substituted cycloalkyl, optionally substituted heterocycloalkyl, optionally substituted aryl, optionally substituted heteroaryl, or lower alkyl optionally substituted with optionally substituted aryl or optionally substituted heteroaryl, $R^{13}$ is halogen, optionally fluoro substituted lower alkyl, or optionally fluoro substituted lower alkoxy and two of $R^{12}$, $R^{15}$ and $R^{16}$ are independently halogen, optionally fluoro substituted lower alkyl, or optionally fluoro substituted lower alkoxy and the other of $R^{12}$, $R^{15}$ and $R^{16}$ is hydrogen; in further embodiments, A is —CH$_2$— or —C(O)—.

In some embodiments of compounds of Formula IIh, Z is —O— or —NH—, $R^{24}$ is hydrogen, optionally substituted cycloalkyl, optionally substituted heterocycloalkyl, optionally substituted aryl, optionally substituted heteroaryl, or lower alkyl optionally substituted with optionally substituted aryl or optionally substituted heteroaryl, $R^{12}$, $R^{13}$, $R^{15}$ and $R^{16}$ are independently hydrogen, halogen, optionally fluoro substituted lower alkyl, or optionally fluoro substituted lower alkoxy; in further embodiments, A is —CH$_2$— or —C(O)—.

In some embodiments, compounds of Formula II have the structure according to the following sub-generic structures Formulae IIi, IIj, IIk, IIm, or IIn:

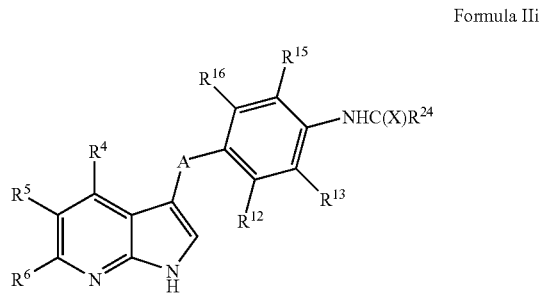

Formula IIi

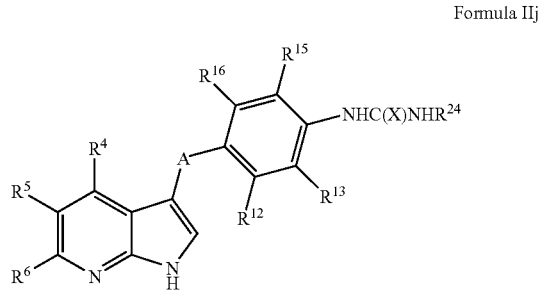

Formula IIj

-continued

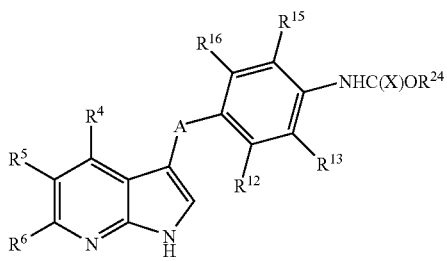

Formula IIk

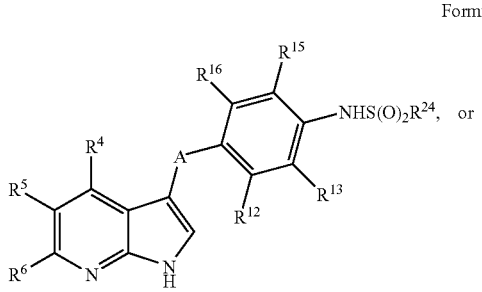

Formula IIm

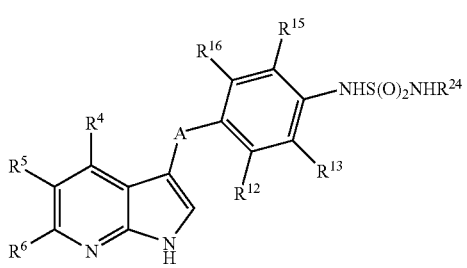

Formula IIn all salts, prodrugs, tautomers and isomers thereof, wherein A, X, $R^4$, $R^5$, $R^6$, $R^{12}$, $R^{13}$, $R^{15}$, $R^{16}$ and $R^{24}$ are as defined for Formula II. In some embodiments of compounds of Formulae IIi, IIj, IIk, IIm, or IIn, A is —$CH_2$— or —C(O)—. In some embodiments, one of $R^{12}$, $R^{13}$, $R^{15}$, and $R^{16}$ is other than hydrogen. In some embodiments, two of $R^{12}$, $R^{13}$, $R^{15}$, and $R^{16}$ are other than hydrogen. In one embodiment, three of $R^{12}$, $R^{13}$, $R^{15}$, and $R^{16}$ are other than hydrogen. In some embodiments, $R^{12}$, $R^{13}$, $R^{15}$, and $R^{16}$ are other than hydrogen.

In some embodiments of compounds of Formulae IIi, IIj, IIk, IIm, or IIn, A is —$CH_2$— or —C(O)—, $R^{12}$, $R^{13}$, $R^{15}$, and $R^{16}$ are independently hydrogen, halogen, optionally fluoro substituted lower alkyl, optionally fluoro substituted lower alkoxy, or optionally fluoro substituted lower alkylthio. In some embodiments, A is —$CH_2$—, any one of $R^{12}$, $R^{13}$, $R^{15}$ and $R^{16}$ is halogen, optionally fluoro substituted lower alkyl, optionally fluoro substituted lower alkoxy, or optionally fluoro substituted lower alkylthio and the remaining of $R^{12}$, $R^{13}$, $R^{15}$ and $R^{16}$ are hydrogen. In some embodiments, A is —$CH_2$—, $R^{13}$, $R^{15}$ and $R^{16}$ are hydrogen and $R^{12}$ is halogen, optionally fluoro substituted lower alkyl, optionally fluoro substituted lower alkoxy, or optionally fluoro substituted lower alkylthio. In some embodiments, A is —$CH_2$—, $R^{12}$, $R^{15}$ and $R^{16}$ are hydrogen and $R^{13}$ is halogen, optionally fluoro substituted lower alkyl, optionally fluoro substituted lower alkoxy, or optionally fluoro substituted lower alkylthio. In some embodiments, A is —$CH_2$—, any two of $R^{12}$, $R^{13}$, $R^{15}$ and $R^{16}$ are independently halogen, optionally fluoro substituted lower alkyl, optionally fluoro substituted lower alkoxy, or optionally fluoro substituted lower alkylthio and the remaining two of $R^{12}$, $R^{13}$, $R^{15}$ and $R^{16}$ are hydrogen. In some embodiments, A is —$CH_2$—, $R^{15}$ and $R^{16}$ are hydrogen and $R^{12}$ and $R^{13}$ are independently halogen, optionally fluoro substituted lower alkyl, optionally fluoro substituted lower alkoxy, or optionally fluoro substituted lower alkylthio. In some embodiments, A is —$CH_2$—, $R^{13}$ and $R^{16}$ are hydrogen and $R^{12}$ and $R^{15}$ are independently halogen, optionally fluoro substituted lower alkyl, optionally fluoro substituted lower alkoxy, or optionally fluoro substituted lower alkylthio. In some embodiments, A is —$CH_2$—, $R^{13}$ and $R^{15}$ are hydrogen and $R^{12}$ and $R^{16}$ are independently halogen, optionally fluoro substituted lower alkyl, optionally fluoro substituted lower alkoxy, or optionally fluoro substituted lower alkylthio. In some embodiments, A is —$CH_2$—, $R^{12}$ and $R^{16}$ are hydrogen and $R^{13}$ and $R^{15}$ are independently halogen, optionally fluoro substituted lower alkyl, optionally fluoro substituted lower alkylthio.

In some embodiments of compounds of Formulae IIi, IIj, IIk, IIm, or IIn, A is —C(O)—, any one of $R^{12}$, $R^{13}$, $R^{15}$ and $R^{16}$ is halogen, optionally fluoro substituted lower alkyl, optionally fluoro substituted lower alkoxy, or optionally fluoro substituted lower alkylthio and the remaining of $R^{12}$, $R^{13}$, $R^{15}$ and $R^{16}$ are hydrogen. In some embodiments, A is —C(O)—, $R^{13}$, $R^{15}$ and $R^{16}$ are hydrogen and $R^{12}$ is halogen, optionally fluoro substituted lower alkyl, optionally fluoro substituted lower alkoxy, or optionally fluoro substituted lower alkylthio. In some embodiments, A is —C(O)—, $R^{13}$, $R^{15}$ and $R^{16}$ are hydrogen and $R^{13}$ is halogen, optionally fluoro substituted lower alkyl, optionally fluoro substituted lower alkoxy, or optionally fluoro substituted lower alkylthio. In some embodiments, A is —C(O)—, two of $R^{12}$, $R^{13}$, $R^{15}$ and $R^{16}$ are independently halogen, optionally fluoro substituted lower alkyl, optionally fluoro substituted lower alkoxy, or optionally fluoro substituted lower alkylthio and the remaining two of $R^{12}$, $R^{13}$, $R^{15}$ and $R^{16}$ are hydrogen. In some embodiments, A is —C(O)—, $R^{15}$ and $R^{16}$ are hydrogen and $R^{12}$ and $R^{13}$ are independently halogen, optionally fluoro substituted lower alkyl, optionally fluoro substituted lower alkoxy, or optionally fluoro substituted lower alkylthio. In some embodiments, A is —C(O)—, $R^{13}$ and $R^{16}$ are hydrogen and $R^{12}$ and $R^{15}$ are independently halogen, optionally fluoro substituted lower alkyl, optionally fluoro substituted lower alkoxy, or optionally fluoro substituted lower alkylthio. In some embodiments, A is —C(O)—, $R^{13}$ and $R^{15}$ are hydrogen and $R^{12}$ and $R^{16}$ are independently halogen, optionally fluoro substituted lower alkyl, optionally fluoro substituted lower alkoxy, or optionally fluoro substituted lower alkylthio. In some embodiments, A is —C(O)—, $R^{12}$ and $R^{16}$ are hydrogen and $R^{13}$ and $R^{15}$ are independently halogen, optionally fluoro substituted lower alkyl, optionally fluoro substituted lower alkoxy, or optionally fluoro substituted lower alkylthio. In some embodiments of any of the above embodiments of compounds of Formula IIa, $R^4$ and $R^6$ are hydrogen or $R^5$ and $R^6$ are hydrogen, or $R^4$ and $R^5$ are hydrogen.

In some embodiments, compounds of Formula II have the structure according to the following sub-generic structure Formula IIo:

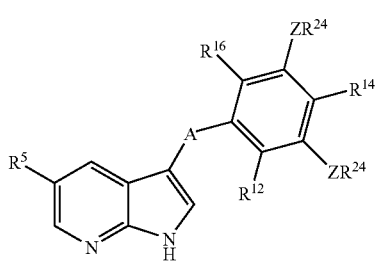

Formula IIo all salts, prodrugs, tautomers and isomers thereof, wherein A, $R^5$, $R^{12}$, $R^{14}$, $R^{16}$ and $R^{24}$ are as defined for Formula II, where each $R^{24}$ is selected independently, and each Z is independently —O—, —S— or —NH—. In some embodiments of compounds of Formula IIo, each $R^{24}$ is independently hydrogen, optionally substituted lower alkyl, optionally substituted cycloalkyl, optionally substituted heterocycloalkyl, optionally substituted aryl, or optionally substituted heteroaryl. In some embodiments, each $R^{24}$ is independently hydrogen, optionally substituted lower alkyl, optionally substituted cycloalkyl, optionally substituted heterocycloalkyl, optionally substituted aryl, or optionally substituted heteroaryl and $R^{12}$, $R^{14}$ and $R^{16}$ are hydrogen.

In some embodiments of compounds of Formula IIo, each $R^{24}$ is independently hydrogen, optionally substituted lower alkyl, optionally substituted cycloalkyl, optionally substituted heterocycloalkyl, optionally substituted aryl, or optionally substituted heteroaryl and at least one of $R^{12}$, $R^{14}$ and $R^{16}$ is hydrogen, halogen, optionally fluoro substituted lower alkyl, optionally fluoro substituted lower alkoxy, or optionally fluoro substituted lower alkylthio, and the others of $R^{12}$, $R^{14}$, and $R^{16}$ are hydrogen; in further embodiments, $R^{12}$ is hydrogen, halogen, optionally fluoro substituted lower alkyl, optionally fluoro substituted lower alkoxy, or optionally fluoro substituted lower alkylthio and $R^{14}$ and $R^{16}$ are hydrogen: in further embodiments, A is —CH$_2$— or —C(O)—.

In some embodiments of compounds of Formula IIo, each $R^{24}$ is independently hydrogen, optionally substituted lower alkyl, optionally substituted cycloalkyl, optionally substituted heterocycloalkyl, optionally substituted aryl, or optionally substituted heteroaryl and at least two of $R^{12}$, $R^{14}$ and $R^{16}$ are independently hydrogen, halogen, optionally fluoro substituted lower alkyl, optionally fluoro substituted lower alkoxy, or optionally fluoro substituted lower alkylthio, and the other of $R^{12}$, $R^{14}$ and $R^{16}$ is hydrogen; in further embodiments, $R^{12}$ and $R^{16}$ are independently hydrogen, halogen, optionally fluoro substituted lower alkyl, optionally fluoro substituted lower alkoxy, or optionally fluoro substituted lower alkylthio and $R^{14}$ is hydrogen; in further embodiments, A is —CH$_2$— or —C(O)—.

In some embodiments of compounds of Formula IIo, L is —O— or —NH—, each $R^{24}$ is independently hydrogen, optionally substituted lower alkyl, optionally substituted cycloalkyl, optionally substituted heterocycloalkyl, optionally substituted aryl, or optionally substituted heteroaryl, $R^{12}$ and $R^{16}$ are independently hydrogen, halogen, optionally fluoro substituted lower alkyl, optionally fluoro substituted lower alkoxy, or optionally fluoro substituted lower alkylthio and $R^{14}$ is hydrogen; in further embodiments, A is —CH$_2$— or —C(O)—.

The compounds of Formulae IIa-IIo, and all sub-embodiments detailed herein, may be used to treat a subject suffering from or at risk for any of the protein kinase mediated diseases or conditions contemplated herein.

In some embodiments, compounds of Formula I have the structure according to the following sub-generic structure Formula III:

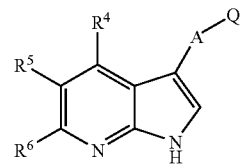

Formula III all salts, prodrugs, tautomers, and isomers thereof,
wherein:
Q has a structure selected from the group consisting of

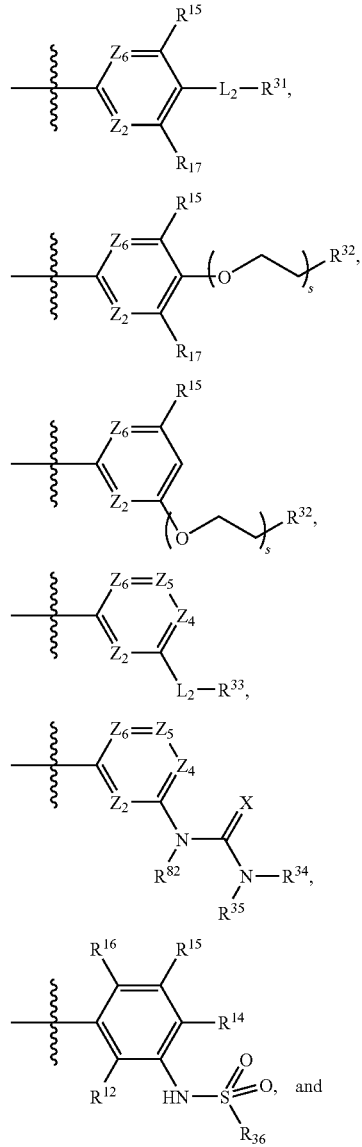

-continued

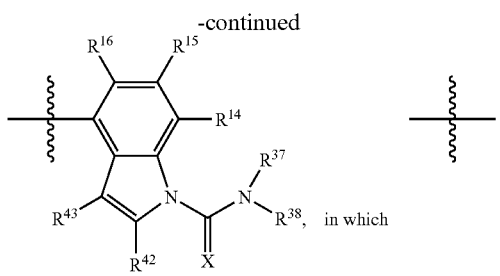

in which indicates the attachment point of Q to A of Formula III;

$Z_2$ is N or $CR^{12}$; $Z_4$ is N or $CR^{14}$; $Z_5$ is N or $CR^{15}$; $Z_6$ is N or $CR^{16}$;

$L_2$ is selected from the group consisting of $-(CR^{10}R^{11})_p-NR^{25}-(CR^{10}R^{11})_q-$, $-(CR^{10}R^{11})_p-O-(CR^{10}R^{11})_q-$, $-(CR^{10}R^{11})_p-S-(CR^{10}R^{11})_q-$, $-(CR^{10}R^{11})_p-C(O)-(CR^{10}R^{11})_q-$, $-(CR^{10}R^{11})_p-C(S)-(CR^{10}R^{11})_q-$, $-(CR^{10}R^{11})_p-S(O)-(CR^{10}R^{11})_q-$, $-(CR^{10}R^{11})_p-S(O)_2-(CR^{10}R^{11})_q-$, $-(CR^{10}R^{11})_p-C(O)NR^{25}-(CR^{10}R^{11})_q-$, $-(CR^{10}R^{11})_p-C(S)NR^{25}-(CR^{10}R^{11})_q-$, $-(CR^{10}R^{11})_p-S(O)_2NR^{25}-(CR^{10}R^{11})_q-$, $-(CR^{10}R^{11})_p-NR^{25}C(O)-(CR^{10}R^{11})_q-$, $-(CR^{10}R^{11})_p-NR^{25}C(S)-(CR^{10}R^{11})_q-$, and $-(CR^{10}R^{11})_p-NR^{25}S(O)_2-(CR^{10}R^{11})_q-$;

p and q are independently 0, 1, or 2 provided, however, that at least one of p and q is 0;

s is 1 or 2;

X is O or S;

A is selected from the group consisting of $-O-$, $-S-$, $-CR^aR^b-$, $-NR^1-$, $-C(O)-$, $-C(S)-$, $-S(O)-$, and $-S(O)_2-$;

$R^a$ and $R^b$ at each occurrence are independently selected from the group consisting of hydrogen, fluoro, $-OH$, $-NH_2$, lower alkyl, lower alkoxy, lower alkylthio, mono-alkylamino, di-alkylamino, and $-NR^8R^9$, wherein the alkyl chain(s) of lower alkyl, lower alkoxy, lower alkylthio, mono-alkylamino, or di-alkylamino are optionally substituted with one or more substituents selected from the group consisting of fluoro, $-OH$, $-NH_2$, lower alkoxy, fluoro substituted lower alkoxy, lower alkylthio, fluoro substituted lower alkylthio, mono-alkylamino, di-alkylamino, and cycloalkylamino, provided, however, that any substitution of the alkyl chain carbon bound to O of alkoxy, S of thioalkyl or N of mono- or di-alkylamino is fluoro; or $R^a$ and $R^b$ combine to form a 3-7 membered monocyclic cycloalkyl or 5-7 membered monocyclic heterocycloalkyl, wherein the monocyclic cycloalkyl or monocyclic heterocycloalkyl are optionally substituted with one or more substituents selected from the group consisting of halogen, $-OH$, $-NH_2$, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino;

$R^1$ is selected from the group consisting of hydrogen, lower alkyl, cycloalkyl, heterocycloalkyl, aryl, heteroaryl, $-C(O)R^7$, $-C(S)R^7$, $-S(O)_2R^7$, $-C(O)NHR^7$, $-C(S)NHR^7$, and $-S(O)_2NHR^7$, wherein lower alkyl is optionally substituted with one or more substituents selected from the group consisting of fluoro, $-OH$, $-NH_2$, lower alkoxy, lower alkylthio, mono-alkylamino, di-alkylamino, and $-NR^8R^9$, wherein the alkyl chain(s) of lower alkoxy, lower alkylthio, mono-alkylamino, or di-alkylamino are optionally substituted with one or more substituents selected from the group consisting of fluoro, $-OH$, $-NH_2$, lower alkoxy, fluoro substituted lower alkoxy, lower alkylthio, fluoro substituted lower alkylthio, mono-alkylamino, di-alkylamino, and cycloalkylamino, provided, however, that any substitution of the alkyl chain carbon bound to O of alkoxy, S of thioalkyl or N of mono- or di-alkylamino is fluoro, further provided that when $R^1$ is lower alkyl, any substitution on the lower alkyl carbon bound to the N of $-NR^1-$ is fluoro, and wherein cycloalkyl, heterocycloalkyl, aryl or heteroaryl are optionally substituted with one or more substituents selected from the group consisting of halogen, $-OH$, $-NH_2$, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino;

$R^7$ is selected from the group consisting of lower alkyl, cycloalkyl, heterocycloalkyl, aryl, and heteroaryl, wherein lower alkyl is optionally substituted with one or more substituents selected from the group consisting of fluoro, $-OH$, $-NH_2$, lower alkoxy, lower alkylthio, mono-alkylamino, di-alkylamino, and $-NR^8R^9$, provided, however, that any substitution of the alkyl carbon bound to the N of $-C(O)NHR^7$, $-C(S)NHR^7$ or $-S(O)_2NHR^7$ is fluoro, wherein the alkyl chain(s) of lower alkoxy, lower alkylthio, mono-alkylamino, or di-alkylamino are optionally substituted with one or more substituents selected from the group consisting of fluoro, $-OH$, $-NH_2$, lower alkoxy, fluoro substituted lower alkoxy, lower alkylthio, fluoro substituted lower alkylthio, mono-alkylamino, di-alkylamino, and cycloalkylamino, provided, however, that any substitution of the alkyl chain carbon bound to O of alkoxy, S of thioalkyl or N of mono- or di-alkylamino is fluoro, and wherein cycloalkyl, heterocycloalkyl, aryl and heteroaryl are optionally substituted with one or more substituents selected from the group consisting of halogen, $-OH$, $-NH_2$, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino;

$R^4$, $R^5$, $R^6$, $R^{12}$, $R^{14}$, $R^{15}$, $R^{16}$, $R^{42}$, $R^{43}$, $R^{45}$, $R^{46}$ and $R^{47}$ are independently selected from the group consisting of hydrogen, halogen, optionally substituted lower alkyl, optionally substituted lower alkenyl, optionally substituted lower alkynyl, optionally substituted cycloalkyl, optionally substituted heterocycloalkyl, optionally substituted aryl, optionally substituted heteroaryl, $-CN$, $-NO_2$, $-CR^aR^bR^{26}$, and $-LR^{26}$;

L at each occurrence is independently selected from the group consisting of $-(alk)_a-S-(alk)_b-$, $-(alk)_a-O-(alk)_b-$, $-(alk)_a-NR^{25}-(alk)_b-$, $-(alk)_a-C(O)-(alk)_b-$, $-(alk)_a-C(S)-(alk)_b-$, $-(alk)_a-S(O)-(alk)_b-$, $-(alk)_a-S(O)_2-(alk)_b-$, $-(alk)_a-OC(O)-(alk)_b-$, $-(alk)_a-C(O)O-(alk)_b-$, $-(alk)_a-OC(S)-(alk)_b-$, $-(alk)_a-C(S)O-(alk)_b-$, $-(alk)_a-C(O)NR^{25}-(alk)_b$, $-(alk)_a-C(S)NR^{25}-(alk)_b-$, $-(alk)_a-S(O)_2NR^{25}-(alk)_b-$, $-(alk)_a-NR^{25}C(O)-(alk)_b-$, $-(alk)_a-NR^{25}C(S)-(alk)_b-$, $-(alk)_a-NR^{25}S(O)_2-(alk)_b-$, $-(alk)_a-NR^{25}C(O)O-(alk)_b-$, $-(alk)_a-NR^{25}C(S)O-(alk)_b-$, $-(alk)_a-OC(O)NR^{25}-(alk)_b-$, $-(alk)_a-OC(S)NR^{25}-(alk)_b-$, $-(alk)_a-NR^{25}C(O)NR^{25}-(alk)_b-$, $-(alk)_a-NR^{25}C(S)NR^{25}-(alk)_b-$, and $-(alk)_a-NR^{25}S(O)_2NR^{25}-(alk)_b-$;

a and b are independently 0 or 1;

alk is $C_{1-3}$ alkylene or $C_{1-3}$ alkylene substituted with one or more substituents selected from the group consisting of fluoro, —OH, —NH$_2$, lower alkyl, lower alkoxy, lower alkylthio, mono-alkylamino, di-alkylamino, and —NR$^8$R$^9$, wherein lower alkyl or the alkyl chain(s) of lower alkoxy, lower alkylthio, mono-alkylamino or di-alkylamino are optionally substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino and cycloalkylamino, provided, however, that any substitution of the alkyl chain carbon bound to O of alkoxy, S of thioalkyl or N of mono- or di-alkylamino is fluoro;

R$^{25}$ at each occurrence is independently selected from the group consisting of hydrogen, optionally substituted lower alkyl, optionally substituted cycloalkyl, optionally substituted heterocycloalkyl, optionally substituted aryl, and optionally substituted heteroaryl;

R$^{26}$ at each occurrence is independently selected from the group consisting of hydrogen, provided, however, that hydrogen is not bound to any of S(O), S(O)$_2$, C(O) or C(S) of L, optionally substituted lower alkyl, optionally substituted lower alkenyl, provided, however, that when R$^{26}$ is optionally substituted lower alkenyl, no alkene carbon thereof is bound to N, S, O, S(O), S(O)$_2$, C(O) or C(S) of L, optionally substituted lower alkynyl, provided, however, that when R$^{26}$ is optionally substituted lower alkynyl, no alkyne carbon thereof is bound to N, S, O, S(O), S(O)$_2$, C(O) or C(S) of L, optionally substituted cycloalkyl, optionally substituted heterocycloalkyl, optionally substituted aryl, and optionally substituted heteroaryl;

R$^{10}$ and R$^{11}$ at each occurrence are independently selected from the group consisting of hydrogen, fluoro, lower alkyl, and lower alkyl optionally substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino, and cycloalkylamino; or any two of R$^{10}$ and R$^{11}$ on the same or adjacent carbon atoms combine to form a 3-7 membered monocyclic cycloalkyl or 5-7 membered monocyclic heterocycloalkyl, and any others of R$^{10}$ and R$^{11}$ are independently selected from the group consisting of hydrogen, fluoro, lower alkyl, and lower alkyl optionally substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino, and cycloalkylamino, and wherein the monocyclic cycloalkyl or monocyclic heterocycloalkyl are optionally substituted with one or more substituents selected from the group consisting of halogen, —OH, —NH$_2$, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino;

R$^8$ and R$^9$ combine with the nitrogen to which they are attached to form a 5-7 membered heterocycloalkyl optionally substituted with one or more substituents selected from the group consisting of fluoro, —OH, —NH$_2$, lower alkyl, fluoro substituted lower alkyl, lower alkoxy, fluoro substituted lower alkoxy, lower alkylthio, and fluoro substituted lower alkylthio;

R$^{17}$ is selected from the group consisting of hydrogen, halogen, optionally substituted lower alkyl and —OR$^{18}$;

R$^{31}$ and R$^{33}$ are independently selected from the group consisting of optionally substituted aryl, optionally substituted heteroaryl, optionally substituted cycloalkyl, and optionally substituted heterocycloalkyl;

R$^{36}$ is selected from the group consisting of substituted methyl, optionally substituted $C_{2-6}$ alkyl, optionally substituted lower alkenyl, provided, however, that when R$^{36}$ is optionally substituted lower alkenyl, no alkene carbon thereof is bound to the S(O)$_2$ of S(O)$_2$R$^{36}$, optionally substituted lower alkynyl, provided, however, that when R$^{36}$ is optionally substituted lower alkynyl, no alkyne carbon thereof is bound to the S(O)$_2$ of S(O)$_2$R$^{36}$, optionally substituted cycloalkyl, optionally substituted heterocycloalkyl, optionally substituted aryl, optionally substituted heteroaryl, and —NR$^{19}$R$^{20}$;

R$^{19}$, R$^{20}$, R$^{34}$, R$^{35}$, R$^{37}$, and R$^{38}$ are independently selected from the group consisting of hydrogen, optionally substituted lower alkyl, optionally substituted lower alkenyl, provided, however, that when R$^{19}$, R$^{20}$, R$^{34}$, R$^{35}$, R$^{37}$, or R$^{38}$ is optionally substituted lower alkenyl, no alkene carbon thereof is bound to the N of NR$^{19}$R$^{20}$, NR$^{34}$R$^{35}$ or NR$^{37}$R$^{38}$, optionally substituted lower alkynyl, provided, however, that when R$^{19}$, R$^{20}$, R$^{34}$, R$^{35}$, R$^{37}$, or R$^{38}$ is optionally substituted lower alkynyl, no alkyne carbon thereof is bound to the N of NR$^{19}$R$^{20}$, NR$^{34}$R$^{35}$ or NR$^{37}$R$^{38}$, optionally substituted cycloalkyl, optionally substituted heterocycloalkyl, optionally substituted aryl and optionally substituted heteroaryl; or R$^{34}$ and R$^{35}$ together with the nitrogen to which they are attached form optionally substituted 5-7 membered heterocycloalkyl or optionally substituted 5 or 7 membered nitrogen containing heteroaryl; or R$^{37}$ and R$^{38}$ together with the nitrogen to which they are attached form optionally substituted 5-7 membered heterocycloalkyl or optionally substituted 5 or 7 membered nitrogen containing heteroaryl;

R$^{32}$ is selected from the group consisting of hydrogen, optionally substituted lower alkyl, optionally substituted cycloalkyl, optionally substituted heterocycloalkyl, optionally substituted aryl, optionally substituted heteroaryl, and —OR$^{18}$;

R$^{82}$ is selected from hydrogen or lower alkyl; and

R$^{18}$ is hydrogen or optionally substituted lower alkyl;

provided, however, that the compound is not 3-{3-[2-(tetrahydropyran-2-yloxy)-ethoxy]-benzyl}-5-thiophen-3-yl-1H-pyrrolo[2,3-b]pyridine, which has the structure

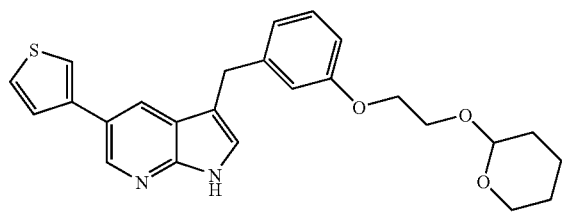 [SMILES: c1cc(Cc2c[nH]c3ncc(-c4ccsc4)cc23)cc(OCCOC2CCCCO2)c1]

or 4-(4-Methyl-piperazin-1-ylmethyl)-N-[4-(1H-pyrrolo[2,3-b]pyridin-3-ylmethyl)-phenyl]-benzamide, which has the structure

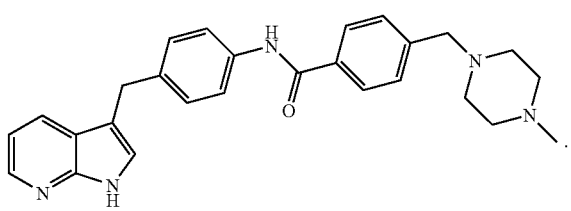 [SMILES: CN1CCN(Cc2ccc(C(=O)Nc3ccc(Cc4c[nH]c5ncccc45)cc3)cc2)CC1]

The compounds of Formula III, and all sub-embodiments detailed herein, may be used to treat a subject suffering from or at risk for any of the protein kinase mediated diseases or conditions contemplated herein.

In some embodiments, compounds of Formula III have the structure according to the following sub-generic structure Formula IIIc:

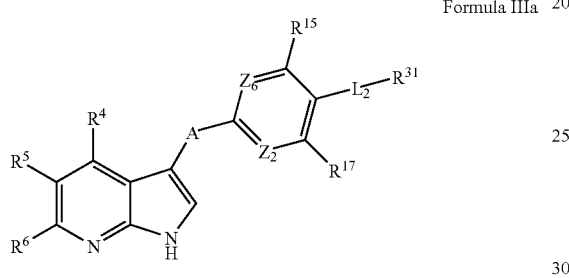

Formula IIIa all salts, prodrugs, tautomers and isomers thereof, wherein A, $L_2$, $Z_2$, $Z_6$, $R^4$, $R^5$, $R^6$, $R^{15}$, $R^{17}$ and $R^{31}$ are as defined for Formula III.

In some embodiments of compounds of Formula IIIa, $R^4$ and $R^6$ are hydrogen, A is —O—, —CR$^a$R$^b$—, —NR$^1$—, or —C(O)—, preferably —CH$_2$— or —C(O)—, more preferably —CH$_2$—, $R^{17}$ is selected from the group consisting of hydrogen, halogen, lower alkyl and lower alkoxy, wherein the alkyl chain of lower alkyl or lower alkoxy is optionally substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino and cycloalkylamino, provided, however, that any substitution on the alkyl carbon bound to the —O— of lower alkoxy is fluoro, and $R^{15}$ is selected from the group consisting of hydrogen, halogen, lower alkyl, fluoro substituted lower alkyl, lower alkoxy, and fluoro substituted lower alkoxy.

In some embodiments of compounds of Formula IIIa, $R^4$ and $R^6$ are hydrogen, A is —O—, —CR$^a$R$^b$—, —NR$^1$—, or —C(O)—, preferably —CH$_2$— or —C(O)—, $R^{17}$ is selected from the group consisting of hydrogen, halogen, lower alkyl and lower alkoxy, wherein the alkyl chain of lower alkyl or lower alkoxy is optionally substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino and cycloalkylamino, provided, however, that any substitution on the alkyl carbon bound to the —O— of lower alkoxy is fluoro, $R^{15}$ is selected from the group consisting of hydrogen, halogen, lower alkyl, fluoro substituted lower alkyl, lower alkoxy, and fluoro substituted lower alkoxy, $Z_2$ is N or CR$^{12}$, $Z_6$ is N or CR$^{16}$, $R^{12}$ and $R^{16}$ are independently selected from the group consisting of hydrogen, halogen, lower alkyl, fluoro substituted lower alkyl, lower alkoxy, and fluoro substituted lower alkoxy, and $R^5$ is selected from the group consisting of hydrogen, halogen, lower alkyl, lower alkoxy, optionally substituted aryl, optionally substituted heteroaryl, and NR$^{21}$R$^{22}$, wherein R$^{21}$ is hydrogen or lower alkyl, and R$^{22}$ is hydrogen, lower alkyl, optionally substituted aryl or optionally substituted heteroaryl, and wherein the alkyl chain of R$^5$, R$^{21}$ or R$^{22}$, when lower alkyl, or the alkyl chain of lower alkoxy is optionally substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino and cycloalkylamino.

In some embodiments, compounds of Formula III have the structure according to the following sub-generic structure Formula IIIb:

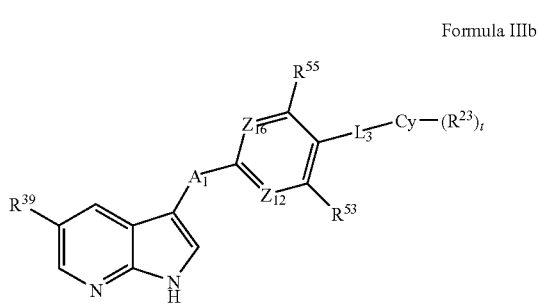

Formula IIIb all salts, prodrugs, tautomers, and isomers thereof,
wherein;
$A_1$ is —O—, —CR$^{40}$R$^{41}$, —C(O)— or —R$^{48}$—;
$Z_{12}$ is N or CR$^{52}$;
$Z_{16}$ is N or CR$^{56}$;
$R^{40}$ and $R^{41}$ are independently selected from the group consisting of hydrogen, fluoro, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino; or
$R^{40}$ and $R^{41}$ combine to form a 3-7 membered monocyclic cycloalkyl or 5-7 membered monocyclic heterocycloalkyl, wherein the monocyclic cycloalkyl or monocyclic heterocycloalkyl is optionally substituted with one or more substituents selected from the group consisting of halogen, —OH, —NH$_2$, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino;
$L_3$ is selected from the group consisting of —NR$^{48}$—, —S—, —O—, —NR$^{48}$CH(R$^{49}$)—, —SCH(R$^{49}$)—, —OCH(R$^{49}$)—, —C(O)NR$^{48}$—, —S(O)$_2$NR$^{48}$, —CH(R$^{49}$)NR$^{48}$—, —CH(R$^{49}$)O—, —CH(R$^{49}$)S—, —NR$^{48}$C(O)—, and —NR$^{48}$S(O)$_2$—;
$R^{53}$ and $R^{55}$ are independently selected from the group consisting of hydrogen, halogen, lower alkyl and lower alkoxy, wherein the alkyl chain of lower alkyl or lower alkoxy is optionally substituted with fluoro, —OH, —NH$_2$, lower alkoxy, fluoro substituted lower alkoxy, lower alkylthio, fluoro substituted lower alkylthio, mono-alkylamino, di-alkylamino or cycloalkylamino, provided, however, that any substitution on the alkyl carbon bound to the —O— of lower alkoxy is fluoro;
$R^{52}$ and $R^{56}$ are independently selected from the group consisting of hydrogen, halogen, lower alkyl, fluoro substituted lower alkyl, lower alkoxy, and fluoro substituted lower alkoxy;

$R^{49}$ is selected from the group consisting of hydrogen, lower alkyl, and fluoro substituted lower alkyl;

Cy is selected from the group consisting of aryl, heteroaryl, cycloalkyl, and heterocycloalkyl;

$R^{39}$ is selected from the group consisting of hydrogen, halogen, lower alkyl, lower alkoxy, aryl, heteroaryl, and $NR^{50}R^{51}$, wherein the alkyl chain of lower alkyl or lower alkoxy is optionally substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino and cycloalkylamino, and wherein aryl and heteroaryl are optionally substituted with one or more independent substituents $R^{23}$;

$R^{50}$ is hydrogen or lower alkyl optionally substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino and cycloalkylamino;

$R^{51}$ is aryl or heteroaryl, wherein aryl and heteroaryl are optionally substituted with one or more independent substituents $R^{23}$;

$R^{23}$ at each occurrence is independently selected from the group consisting of —OH, —NH$_2$, —CN, —NO$_2$, —C(O)OH, —S(O)$_2$NH$_2$, —C(O)NH$_2$, —OR$^{57}$, —SR$^{57}$, —NR$^{48}$R$^{57}$, —NR$^{48}$C(O)R$^{57}$, —NR$^{48}$S(O)$_2$R$^{57}$, —S(O)$_2$R$^{57}$, —C(O)R$^{57}$, —C(O)OR$^{57}$, —C(O)NR$^{48}$R$^{57}$, —S(O)$_2$NR$^{48}$R$^{57}$, halogen, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, wherein cycloalkyl, heterocycloalkyl, aryl, and heteroaryl as $R^{23}$, or as substituents of lower alkyl, are optionally substituted with one or more substituents selected from the group consisting of —OH, —NH$_2$, —CN, —NO$_2$, —C(O)OH, —S(O)$_2$NH$_2$, —C(O)NH$_2$, —OR$^{58}$, —SR$^{58}$, —NR$^{48}$R$^{58}$, —NR$^{48}$C(O)R$^{58}$, —NR$^{48}$S(O)$_2$R$^{58}$, —S(O)$_2$R$^{58}$, —C(O)R$^{58}$, —C(O)OR$^{58}$, —C(O)NR$^{48}$R$^{58}$, —S(O)$_2$NR$^{48}$R$^{58}$, halogen, lower alkyl, fluoro substituted lower alkyl, and cycloalkylamino;

$R^{57}$ is selected from the group consisting of lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, provided, however, that any substitution of the alkyl carbon bound to O, S, or N of —OR$^{57}$, —SR$^{57}$, —NR$^{48}$R$^{57}$, —C(O)OR$^{57}$, —C(O)NR$^{48}$R$^{57}$, or —S(O)$_2$NR$^{48}$R$^{57}$ is fluoro, cycloalkyl, heterocycloalkyl, aryl or heteroaryl, wherein cycloalkyl, heterocycloalkyl, aryl, and heteroaryl as $R^{57}$ or as substituents of lower alkyl are optionally substituted with one or more substituents selected from the group consisting of —OH, —NH$_2$, —CN, —NO$_2$, —C(O)OH, —S(O)$_2$NH$_2$, —C(O)NH$_2$, —OR$^{58}$, —SR$^{58}$, —NR$^{48}$R$^{58}$, —NR$^{48}$C(O)R$^{58}$, —NR$^{48}$S(O)$_2$R$^{58}$, —S(O)$_2$R$^{58}$, —C(O)R$^{58}$, —C(O)OR$^{58}$, —C(O)NR$^{48}$R$^{58}$, —S(O)$_2$NR$^{48}$R$^{58}$, halogen, lower alkyl, fluoro substituted lower alkyl, and cycloalkylamino;

$R^{58}$ at each occurrence is independently selected from the group consisting of lower alkyl, heterocycloalkyl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, and cycloalkylamino, provided, however, that any substitution of the alkyl carbon bound to O, S, or N of —OR$^{58}$, —SR$^{58}$, —NR$^{48}$R$^{58}$, —C(O)OR$^{58}$, —C(O)NR$^{48}$R$^{58}$, or —S(O)$_2$NR$^{48}$R$^{58}$ is fluoro;

$R^{48}$ at each occurrence is independently hydrogen or lower alkyl; and t is 0, 1, 2, or 3.

In some embodiments of compounds of Formula IIIb, $A_1$ is —CR$^{40}$R$^{41}$— or —C(O)—, preferably —CH$_2$— or —C(O)—, more preferably —CH$_2$—. In some embodiments, $A_1$ is —CR$^{40}$R$^{41}$— or —C(O)—, preferably —CH$_2$— or —C(O)—, more preferably —CH$_2$—, and $R^{53}$ and $R^{55}$ are independently selected from the group consisting of hydrogen, halogen, lower alkyl, fluoro substituted lower alkyl, lower alkoxy, and fluoro substituted lower alkoxy. In some embodiments, $L_3$ is —NR$^{48}$CH(R$^{49}$)—, —SCH(R$^{49}$)—, or —OCH(R$^{49}$)—, preferably —OCH(R$^{49}$)—. In some embodiments, $A_1$ is —CR$^{40}$R$^{41}$— or —C(O)—, preferably —CH$_2$— or —C(O)—, more preferably —CH$_2$—, and $L_3$ is —NR$^{48}$CH(R$^{49}$)—, —SCH(R$^{49}$)—, or —OCH(R$^{49}$)—, preferably —OCH(R$^{49}$)—.

In some embodiments, compounds of Formula III have the structure according to the following sub-generic structure Formula IIIp:

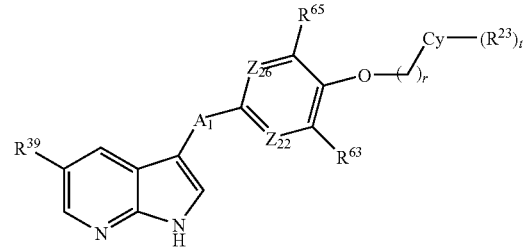

Formula IIIp all salts, prodrugs, tautomers, and isomers thereof,
wherein:
$A_1$ is —O—, —CR$^{40}$R$^{41}$, —C(O)— or —NR$^{48}$—;
$Z_{22}$ is N or CR$^{62}$;
$Z_{26}$ is N or CR$^{66}$;
r is 0, 1, or 2;
$R^{40}$ and $R^{41}$ are independently selected from the group consisting of hydrogen, fluoro, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino; or
$R^{40}$ and $R^{41}$ combine to form a 3-7 membered monocyclic cycloalkyl or 5-7 membered monocyclic heterocycloalkyl, wherein the monocyclic cycloalkyl or monocyclic heterocycloalkyl is optionally substituted with one or more substituents selected from the group consisting of halogen, —OH, —NH$_2$, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino;

$R^{62}$, $R^{63}$, $R^{65}$ and $R^{66}$ are independently selected from the group consisting of hydrogen, halogen, lower alkyl and lower alkoxy, wherein the alkyl chain of lower alkyl or lower alkoxy is optionally substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino and cycloalkylamino, provided, however, that any substitution on the alkyl carbon bound to the —O— of lower alkoxy is fluoro;

Cy is selected from the group consisting of aryl, heteroaryl, cycloalkyl, and heterocycloalkyl;

$R^{39}$ is selected from the group consisting of hydrogen, halogen, lower alkyl, lower alkoxy, aryl, heteroaryl, and NR$^{50}$R$^{51}$, wherein the alkyl chain of lower alkyl or lower alkoxy is optionally substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino and cycloalkylamino, and wherein aryl and heteroaryl are optionally substituted with one or more independent substituents $R^{23}$;

$R^{50}$ is hydrogen or lower alkyl optionally substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino and cycloalkylamino;

$R^{51}$ is aryl or heteroaryl, wherein aryl and heteroaryl are optionally substituted with one or more independent substituents $R^{23}$;

$R^{23}$ at each occurrence is independently selected from the group consisting of —OH, —NH$_2$, —CN, —NO$_2$, —C(O)OH, —S(O)$_2$NH$_2$, —C(O)NH$_2$, —OR$^{57}$, —SR$^{57}$, —NR$^{48}$R$^{57}$, —NR$^{48}$C(O)R$^{57}$, —NR$^{48}$S(O)$_2$R$^{57}$, —S(O)$_2$R$^{57}$, —C(O)R$^{57}$, —C(O)OR$^{57}$, —C(O)NR$^{48}$R$^{57}$, —S(O)$_2$NR$^{48}$R$^{57}$, halogen, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, wherein cycloalkyl, heterocycloalkyl, aryl, and heteroaryl as $R^{23}$, or as substituents of lower alkyl, are optionally substituted with one or more substituents selected from the group consisting of —OH, —NH$_2$, —CN, —NO$_2$, —C(O)OH, —S(O)$_2$NH$_2$, —C(O)NH$_2$, —OR$^{58}$, —SR$^{58}$, —NR$^{48}$R$^{58}$, —NR$^{48}$C(O)R$^{58}$, —NR$^{48}$S(O)$_2$R$^{58}$, —S(O)$_2$R$^{58}$, —C(O)R$^{58}$, —C(O)R$^{58}$, —C(O)OR$^{58}$, —C(O)NR$^{48}$R$^{58}$, —S(O)$_2$NR$^{18}$R$^{58}$, halogen, lower alkyl, fluoro substituted lower alkyl, and cycloalkylamino;

$R^{57}$ is selected from the group consisting of lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, provided, however, that any substitution of the alkyl carbon bound to O, S, or N of —OR$^{57}$, —SR$^{57}$, —NR$^{48}$R$^{57}$, —C(O)OR$^{57}$, —C(O)NR$^{48}$R$^{57}$, or —S(O)$_2$NR$^{48}$R$^{57}$ is fluoro, cycloalkyl, heterocycloalkyl, aryl or heteroaryl, wherein cycloalkyl, heterocycloalkyl, aryl, and heteroaryl as $R^{57}$ or as substituents of lower alkyl are optionally substituted with one or more substituents selected from the group consisting of —OH, —NH$_2$, —CN, —NO$_2$, —C(O)OH, —S(O)$_2$NH$_2$, —C(O)NH$_2$, —OR$^{58}$, —SR$^{58}$, —NR$^{48}$R$^{58}$, —NR$^{48}$C(O)R$^{58}$, —NR$^{48}$S(O)$_2$R$^{58}$, —S(O)$_2$R$^{58}$, —C(O)R$^{58}$, —C(O)OR$^{58}$, —C(O)NR$^{48}$R$^{58}$, —S(O)$_2$NR$^{48}$R$^{58}$, halogen, lower alkyl, fluoro substituted lower alkyl, and cycloalkylamino;

$R^{58}$ at each occurrence is independently selected from the group consisting of lower alkyl, heterocycloalkyl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, and cycloalkylamino, provided, however, that any substitution of the alkyl carbon bound to O, S, or N of —OR$^{58}$, —SR$^{58}$, —NR$^{48}$R$^{58}$, —C(O)OR$^{58}$, —C(O)NR$^{48}$R$^{58}$, or —S(O)$_2$NR$^{48}$R$^{58}$ is fluoro;

$R^{48}$ at each occurrence is independently hydrogen or lower alkyl; and t is 0, 1, 2, or 3.

In some embodiments of compounds of Formula IIIp, A$_1$ is —CR$^{40}$R$^{41}$— or —C(O)—, preferably —CH$_2$— or —C(O)—. In some embodiments, A$_1$ is —CR$^{40}$R$^{41}$— or —C(O)—, preferably —CH$_2$— or —C(O)—, and $R^{62}$, $R^{64}$, $R^{65}$ and $R^{66}$ are independently selected from the group consisting of hydrogen, halogen, lower alkyl, fluoro substituted lower alkyl, lower alkoxy, and fluoro substituted lower alkoxy.

In some embodiments, compounds of Formula III have the structure according to the following sub-generic structure Formula IIIc:

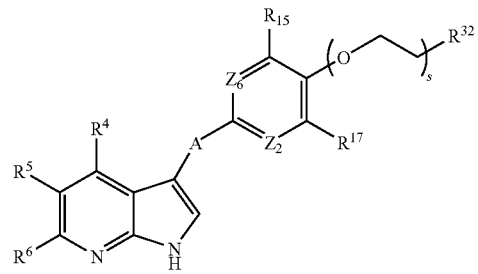

Formula IIIc all salts, prodrugs, tautomers and isomers thereof, wherein A, s, $Z_2$, $Z_6$, $R^4$, $R^5$, $R^6$, $R^{15}$, $R^{17}$, and $R^{32}$ are as defined for Formula III.

In some embodiments of compounds of Formula IIIc, $R^4$ and $R^6$ are hydrogen, A is —O—, —CR$^a$R$^b$, —NR$^1$—, or —C(O)—, preferably —CH$_2$— or —C(O)—, more preferably —CH$_2$—, $R^{17}$ is selected from the group consisting of hydrogen, halogen, lower alkyl and lower alkoxy, wherein the alkyl chain of lower alkyl or lower alkoxy is optionally substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino and cycloalkylamino, provided, however, that any substitution on the alkyl carbon bound to the —O— of lower alkoxy is fluoro, and $R^{15}$ is selected from the group consisting of hydrogen, halogen, lower alkyl, fluoro substituted lower alkyl, lower alkoxy, and fluoro substituted lower alkoxy.

In some embodiments of compounds of Formula IIIc, $R^4$ and $R^6$ are hydrogen, A is —O—, —$CR^aR^b$—, —$NR^1$—, or —C(O)—, preferably —$CH_2$— or —C(O)—, $R^{17}$ is selected from the group consisting of hydrogen, halogen, lower alkyl and lower alkoxy, wherein the alkyl chain of lower alkyl or lower alkoxy is optionally substituted with one or more substituents selected from the group consisting of fluoro, —OH, —$NH_2$, lower alkoxy, fluoro substituted lower alkoxy, lower alkylthio, fluoro substituted lower alkylthio, mono-alkylamino, di-alkylamino and cycloalkylamino, provided, however, that any substitution on the alkyl carbon bound to the —O— of lower alkoxy is fluoro, $R^{15}$ is selected from the group consisting of hydrogen, halogen, lower alkyl, fluoro substituted lower alkyl, lower alkoxy, and fluoro substituted lower alkoxy, $Z_2$ is N or $CR^{12}$, $Z_6$ is N or $CR^{16}$, $R^{12}$ and $R^{16}$ are independently selected from the group consisting of hydrogen, halogen, lower alkyl, fluoro substituted lower alkyl, lower alkoxy, and fluoro substituted lower alkoxy, and $R^5$ is selected from the group consisting of hydrogen, halogen, lower alkyl, lower alkoxy, optionally substituted aryl, optionally substituted heteroaryl, and —$NR^{21}R^{22}$, wherein $R^{21}$ is hydrogen or lower alkyl, and $R^{22}$ is hydrogen, lower alkyl, optionally substituted aryl or optionally substituted heteroaryl, and wherein the alkyl chain of $R^5$, $R^{21}$ or $R^{22}$, when lower alkyl, or the alkyl chain of lower alkoxy is optionally substituted with one or more substituents selected from the group consisting of fluoro, —OH, —$NH_2$, lower alkoxy, fluoro substituted lower alkoxy, lower alkylthio, fluoro substituted lower alkylthio, mono-alkylamino, di-alkylamino and cycloalkylamino, further wherein $R^{32}$ is optionally substituted lower alkyl or —$OR^{18}$, where $R^{18}$ is as defined for Formula III.

In some embodiments, compounds of Formula III have the structure according to the following sub-generic structure Formula IIIn:

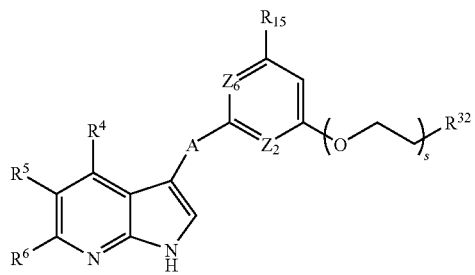

Formula IIIn all salts, prodrugs, tautomers and isomers thereof, wherein A, s, $Z_2$, $Z_6$, $R^4$, $R^5$, $R^6$, $R^{15}$, and $R^{32}$ are as defined for Formula III.

In some embodiments of compounds of Formula IIIn, $R^4$ and $R^6$ are hydrogen, A is —O—, —$CR^aR^b$—, —$NR^1$—, or —C(O)—, preferably —$CH_2$— or —C(O)—, more preferably —$CH_2$—, and $R^{15}$ is selected from the group consisting of hydrogen, halogen, lower alkyl, fluoro substituted lower alkyl, lower alkoxy, and fluoro substituted lower alkoxy.

In some embodiments of compounds of Formula IIIc, $R^4$ and $R^6$ are hydrogen, A is —O—, —$CR^aR^b$—, —$NR^1$—, or —C(O)—, preferably —$CH_2$— or —C(O)—, $R^{15}$ is selected from the group consisting of hydrogen, halogen, lower alkyl, fluoro substituted lower alkyl, lower alkoxy, and fluoro substituted lower alkoxy, $Z_2$ is N or $CR^{12}$, $Z_6$ is N or $CR^{16}$, $R^{12}$ and $R^{16}$ are independently selected from the group consisting of hydrogen, halogen, lower alkyl, fluoro substituted lower alkyl, lower alkoxy, and fluoro substituted lower alkoxy, and $R^5$ is selected from the group consisting of hydrogen, halogen, lower alkyl, lower alkoxy, optionally substituted aryl, optionally substituted heteroaryl, and —$NR^{21}R^{22}$, wherein $R^{21}$ is hydrogen or lower alkyl, and $R^{22}$ is hydrogen, lower alkyl, optionally substituted aryl or optionally substituted heteroaryl, and wherein the alkyl chain of $R^5$, $R^{21}$ or $R^{22}$, when lower alkyl, or the alkyl chain of lower alkoxy is optionally substituted with one or more substituents selected from the group consisting of fluoro, —OH, —$NH_2$, lower alkoxy, fluoro substituted lower alkoxy, lower alkylthio, fluoro substituted lower alkylthio, mono-alkylamino, di-alkylamino and cycloalkylamino, further wherein $R^{32}$ is optionally substituted lower alkyl or —$OR^{18}$, where $R^{18}$ is as defined for Formula III.

In some embodiments, compounds of Formula III have the structure according to the following sub-generic structure Formula IIIo:

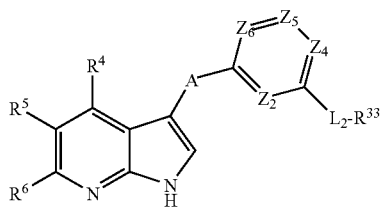

Formula IIIo all salts, prodrugs, tautomers and isomers thereof, wherein A, $L_2$, $Z_2$, $Z_4$, $Z_5$, $Z_6$, $R^4$, $R^5$, $R^6$, and $R^{33}$ are as defined for Formula III.

In some embodiments of compounds of Formula IIIo, $R^4$ and $R^6$ are hydrogen, A is —O—, —$CR^aR^b$—, —$NR^1$—, or —C(O)—, preferably —$CH_2$—, or —C(O)—, $Z_2$ is N or $CR^{12}$, $Z_4$ is N or $CR^{14}$, $Z_5$ is N or $CR^{15}$, $Z_6$ is N or $CR^{16}$, and $R^{12}$, $R^{14}$, $R^{15}$ and $R^{16}$ are independently selected from the group consisting of hydrogen, halogen, lower alkyl and lower alkoxy, wherein the alkyl chain of lower alkyl or lower alkoxy is optionally substituted with one or more substituents selected from the group consisting of fluoro, —OH, —$NH_2$, lower alkoxy, fluoro substituted lower alkoxy, lower alkylthio, fluoro substituted lower alkylthio, mono-alkylamino, di-alkylamino and cycloalkylamino, provided, however, that any substitution on the alkyl carbon bound to the —O— of lower alkoxy is fluoro.

In some embodiments of compounds of Formula IIIo, $R^4$ and $R^6$ are hydrogen, A is —O—, —$CR^aR^b$—, —$NR^1$—, or —C(O)—, preferably —$CH_2$—, or —C(O)—, $Z_2$ is N or $CR^{12}$, $Z_4$ is N or $CR^{14}$, $Z_5$ is N or $CR^{15}$, $Z_6$ is N or $CR^{16}$, $R^{12}$, $R^{14}$, $R^{15}$ and $R^{16}$ are independently selected from the group consisting of hydrogen, halogen, lower alkyl and lower alkoxy, wherein the alkyl chain of lower alkyl or lower alkoxy is optionally substituted with one or more substituents selected from the group consisting of fluoro, —OH, —$NH_2$, lower alkoxy, fluoro substituted lower alkoxy, lower alkylthio, fluoro substituted lower alkylthio, mono-alkylamino, di-alkylamino and cycloalkylamino, provided, however, that any substitution on the alkyl carbon bound to the —O— of lower alkoxy is fluoro, and $R^5$ is selected from the group consisting of hydrogen, halogen, lower alkyl, lower alkoxy, optionally substituted aryl, optionally substituted heteroaryl, and $NR^{21}R^{22}$, wherein $R^{21}$ is hydrogen or lower alkyl, and $R^{22}$ is hydrogen, lower alkyl, optionally substituted aryl or optionally substituted heteroaryl, and wherein the alkyl chain of $R^5$, $R^{21}$ or $R^{22}$, when lower alkyl, or the alkyl chain of lower alkoxy is optionally substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino and cycloalkylamino.

In some embodiments of compounds of Formula IIIo, $R^4$ and $R^6$ are hydrogen, A is —O—, —$CR^aR^b$—, —$NR^1$—, or —C(O)—, preferably —CH$_2$— or —C(O)—, $Z_2$ is N or $CR^{12}$, $Z_4$ is N or $CR^{14}$, $Z_5$ is N or $CR^{15}$, $Z_6$ is N or $CR^{16}$, $R^{12}$, $R^{14}$, $R^{15}$ and $R^{16}$ are independently selected from the group consisting of hydrogen, halogen, lower alkyl, fluoro substituted lower alkyl, lower alkoxy, and fluoro substituted lower alkoxy, and $R^5$ is selected from the group consisting of hydrogen, halogen, lower alkyl, lower alkoxy, optionally substituted aryl, optionally substituted heteroaryl, and $NR^{21}R^{22}$, wherein $R^{21}$ is hydrogen or lower alkyl, and $R^{22}$ is hydrogen, lower alkyl, optionally substituted aryl or optionally substituted heteroaryl, and wherein the alkyl chain of $R^5$, $R^{21}$ or $R^{22}$, when lower alkyl, or the alkyl chain of lower alkoxy is optionally substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino and cycloalkylamino.

In some embodiments, compounds of Formula III have the structure according to the following sub-generic structure Formula IIIq:

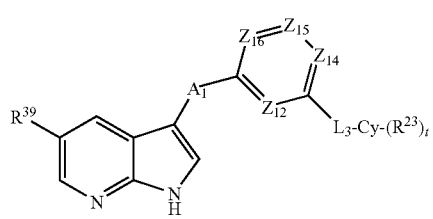

Formula IIIq all salts, prodrugs, tautomers, and isomers thereof, wherein:
$A_1$ is —O—, —$CR^{40}R^{41}$—, —C(O)— or —$NR^{48}$—;
$Z_{12}$ is N or $CR^{52}$;
$Z_{14}$ is N or $CR^{54}$;
$Z_{15}$ is N or $CR^{55}$;
$Z_{16}$ is N or $CR^{56}$;
$R^{40}$ and $R^{41}$ are independently selected from the group consisting of hydrogen, fluoro, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino; or
$R^{40}$ and $R^{41}$ combine to form a 3-7 membered monocyclic cycloalkyl or 5-7 membered monocyclic heterocycloalkyl, wherein the monocyclic cycloalkyl or monocyclic heterocycloalkyl is optionally substituted with one or more substituents selected from the group consisting of halogen, —OH, —NH$_2$, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino;
$L_3$ is selected from the group consisting of —$NR^{48}$—, —S—, —O—, —$NR^{48}CH(R^{49})$—, —$SCH(R^{49})$—, —$OCH(R^{49})$—, —$C(O)NR^{48}$—, —$S(O)_2NR^{48}$—, —$CH(R^{49})NR^{48}$—, —$CH(R^{49})O$—, —$CH(R^{49})S$—, —$NR^{48}C(O)$—, and —$NR^{48}S(O)_2$—;
$R^{54}$ and $R^{55}$ are independently selected from the group consisting of hydrogen, halogen, lower alkyl and lower alkoxy, wherein the alkyl chain of lower alkyl or lower alkoxy is optionally substituted with fluoro, —OH, —NH$_2$, lower alkoxy, fluoro substituted lower alkoxy, lower alkylthio, fluoro substituted lower alkylthio, mono-alkylamino, di-alkylamino or cycloalkylamino, provided, however, that any substitution on the alkyl carbon bound to the —O— of lower alkoxy is fluoro:
$R^{52}$ and $R^{56}$ are independently selected from the group consisting of hydrogen, halogen, lower alkyl, fluoro substituted lower alkyl, lower alkoxy, and fluoro substituted lower alkoxy;
$R^{49}$ is selected from the group consisting of hydrogen, lower alkyl, and fluoro substituted lower alkyl;
Cy is selected from the group consisting of aryl, heteroaryl, cycloalkyl, and heterocycloalkyl;
$R^{39}$ is selected from the group consisting of hydrogen, halogen, lower alkyl, lower alkoxy, aryl, heteroaryl, and $NR^{50}R^{51}$, wherein the alkyl chain of lower alkyl or lower alkoxy is optionally substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino and cycloalkylamino, and wherein aryl and heteroaryl are optionally substituted with one or more independent substituents $R^{23}$;
$R^{50}$ is hydrogen or lower alkyl optionally substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino and cycloalkylamino;
$R^{51}$ is aryl or heteroaryl, wherein aryl and heteroaryl are optionally substituted with one or more independent substituents $R^{23}$;
$R^{23}$ at each occurrence is independently selected from the group consisting of —OH, —NH$_2$, —CN, —NO$_2$, —C(O)OH, —S(O)$_2$NH$_2$, —C(O)NH$_2$, —$OR^{57}$, —$SR^{57}$, —$NR^{48}R^{57}$, —$NR^{48}C(O)R^{57}$, —$NR^{48}S(O)_2R^{57}$, —$S(O)_2R^{57}$, —$C(O)R^{57}$, —$C(O)OR^{57}$, —$C(O)NR^{48}R^{57}$, —$S(O)_2NR^{48}R^{57}$, halogen lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, wherein cycloalkyl, heterocycloalkyl, aryl, and heteroaryl as $R^{23}$, or as substituents of lower alkyl, are optionally substituted with one or more substituents selected from the group consisting of —OH, —NH$_2$, —CN, —NO$_2$, —C(O)OH, —S(O)$_2$NH$_2$, —C(O)NH$_2$, —$OR^{58}$, —$SR^{58}$, —$NR^{48}R^{58}$, —$NR^{48}C(O)R^{58}$, —$NR^{48}S(O)_2R^{58}$, —$S(O)_2R^{58}$, —$C(O)R^{58}$, —$C(O)OR^{58}$, —$C(O)NR^{48}R^{58}$, —$S(O)_2NR^{48}R^{58}$, halogen, lower alkyl, fluoro substituted lower alkyl, and cycloalkylamino;
$R^{57}$ is selected from the group consisting of lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, provided, however, that any substitution of the alkyl carbon bound to O, S, or N of —OR$^{57}$, —SR$^{57}$, —NR$^{48}$R$^{57}$, —C(O)OR$^{57}$, —C(O)NR$^{48}$R$^{57}$, or —S(O)$_2$NR$^{48}$R$^{57}$ is fluoro, cycloalkyl, heterocycloalkyl, aryl or heteroaryl, wherein cycloalkyl, heterocycloalkyl, aryl, and heteroaryl as R$^{57}$ or as substituents of lower alkyl are optionally substituted with one or more substituents selected from the group consisting of —OH, —NH$_2$, —CN, —NO$_2$, —C(O)OH, —S(O)$_2$NH$_2$, —C(O)NH$_2$, —OR$^{58}$, —SR$^{58}$, —NR$^{48}$R$^{58}$, —NR$^{48}$C(O)R$^{58}$, —NR$^{48}$S(O)$_2$R$^{58}$, —S(O)$_2$R$^{58}$, —C(O)R$^{58}$, —C(O)OR$^{58}$, —C(O)NR$^{48}$R$^{58}$, —S(O)$_2$NR$^{48}$R$^{58}$, halogen, lower alkyl, fluoro substituted lower alkyl, and cycloalkylamino;

R$^{58}$ at each occurrence is independently selected from the group consisting of lower alkyl, heterocycloalkyl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, and cycloalkylamino, provided, however, that any substitution of the alkyl carbon bound to O, S, or N of —OR$^{58}$, —SR$^{58}$, —NR$^{48}$R$^{58}$, —C(O)OR$^{58}$, —C(O)NR$^{48}$R$^{58}$, or —S(O)$_2$NR$^{48}$R$^{58}$ is fluoro;

R$^{48}$ at each occurrence is independently hydrogen or lower alkyl; and t is 0, 1, 2, or 3.

In some embodiments of compounds of Formula IIIg, A$_1$ is —CR$^{40}$R$^{41}$— or —C(O)—, preferably —CH$_2$— or —C(O)—, more preferably —CH$_2$—. In some embodiments, A$_1$ is —CR$^{40}$R$^{41}$— or —C(O)—, preferably —CH$_2$— or —C(O)—, more preferably —CH$_2$—, and R$^{54}$ and R$^{55}$ are independently selected from the group consisting of hydrogen, halogen, lower alkyl, fluoro substituted lower alkyl, lower alkoxy, and fluoro substituted lower alkoxy. In some embodiments, L$_3$ is —NR$^{48}$CH(R$^{49}$)—, —SCH(R$^{49}$)—, or —OCH(R$^{49}$)—, preferably —OCH(R$^{49}$)—. In some embodiments, A$_1$ is —CR$^{40}$R$^{41}$— or —C(O)—, preferably —CH$_2$— or —C(O)—, more preferably —CH$_2$—, and L$_3$ is —NR$^{48}$CH(R$^{49}$)—, —SCH(R$^{49}$)—, or —OCH(R$^{49}$)—, preferably —OCH(R$^{49}$)—.

In some embodiments, compounds of Formula III have the structure according to the following sub-generic structure Formula IIId:

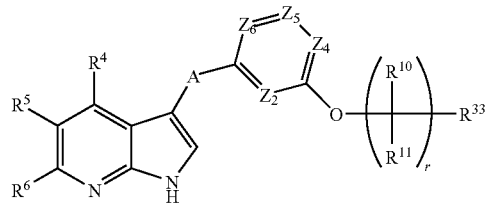

Formula IIId all salts, prodrugs, tautomers and isomers thereof, wherein A, Z$_2$, Z$_4$, Z$_5$, Z$_6$, R$^4$, R$^5$, R$^6$, R$^{10}$, R$^{11}$ and R$^{33}$ are as defined for Formula III, and r is 0, 1, or 2.

In some embodiments of compounds of Formula IIId, R$^4$ and R$^5$ are hydrogen, A is —O—, —CR$^a$R$^b$—, —NR$^1$—, or —C(O)—, preferably —CH$_2$— or —C(O)—, Z$_2$ is N or CR$^{12}$, Z$_4$ is N or CR$^{14}$, Z$_5$ is N or CR$^{15}$, Z$_6$ is N or CR$^{16}$, and R$^{12}$, R$^{14}$, R$^{15}$ and R$^{16}$ are independently selected from the group consisting of hydrogen, halogen, lower alkyl and lower alkoxy, wherein the alkyl chain of lower alkyl or lower alkoxy is optionally substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino and cycloalkylamino, provided, however, that any substitution on the alkyl carbon bound to the —O— of lower alkoxy is fluoro.

In some embodiments of compounds of Formula IIId, R$^4$ and R$^6$ are hydrogen, A is —O—, —CR$^a$R$^b$—, —NR$^1$—, or —C(O)—, preferably —CH$_2$— or —C(O)—, Z$_2$ is N or CR$^{12}$, Z$_4$ is N or CR$^{14}$, Z$_5$ is N or CR$^{15}$, Z$_6$ is N or CR$^{16}$, R$^{12}$, R$^{14}$, R$^{15}$ and R$^{16}$ are independently selected from the group consisting of hydrogen, halogen, lower alkyl and lower alkoxy, wherein the alkyl chain of lower alkyl or lower alkoxy is optionally substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino and cycloalkylamino, provided, however, that any substitution on the alkyl carbon bound to the —O— of lower alkoxy is fluoro, R$^{10}$ and R$^{11}$ are independently selected from the group consisting of hydrogen, fluoro, lower alkyl, and fluoro substituted lower alkyl, and R$^5$ is selected from the group consisting of hydrogen, halogen, lower alkyl, lower alkoxy, optionally substituted aryl, optionally substituted heteroaryl, and NR$^{21}$R$^{22}$, wherein R$^{21}$ is hydrogen or lower alkyl, and R$^{22}$ is hydrogen, lower alkyl, optionally substituted aryl or optionally substituted heteroaryl, and wherein the alkyl chain of R$^5$, R$^{21}$ or R$^{22}$, when lower alkyl, or the alkyl chain of lower alkoxy is optionally substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino and cycloalkylamino.

In some embodiments of compounds of Formula IIId, R$^4$ and R$^6$ are hydrogen, A is —O—, —CR$^a$R$^b$—, —NR$^1$—, or —C(O)—, preferably —CH$_2$— or —C(O)—, Z$_2$ is N or CR$^{12}$, Z$_4$ is N or CR$^{14}$, Z$_5$ is N or CR$^{15}$, R$_6$ is N or CR$^{16}$, R$^{12}$, R$^{14}$, R$^{15}$ and R$^{16}$ are independently selected from the group consisting of hydrogen, halogen, lower alkyl, fluoro substituted lower alkyl, lower alkoxy, and fluoro substituted lower alkoxy, R$^{10}$ and R$^{11}$ are independently selected from the group consisting of hydrogen, fluoro, lower alkyl, and fluoro substituted lower alkyl, and R$^5$ is selected from the group consisting of hydrogen, halogen, lower alkyl, lower alkoxy, optionally substituted aryl, optionally substituted heteroaryl, and NR$^{21}$R$^{22}$, wherein R$^{21}$ is hydrogen or lower alkyl, and R$^{22}$ is hydrogen, lower alkyl, optionally substituted aryl or optionally substituted heteroaryl, and wherein the alkyl chain of R$^5$, R$^{21}$ or R$^{22}$, when lower alkyl, or the alkyl chain of lower alkoxy is optionally substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino and cycloalkylamino.

In some embodiments, compounds of Formula III have the structure according to the following sub-generic structure Formula IIIe:

Formula IIIe

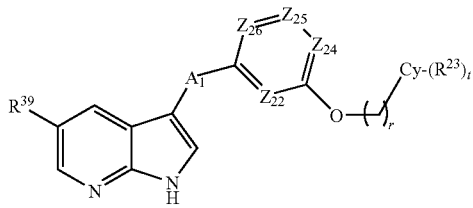

all salts, prodrugs, tautomers, and isomers thereof,
wherein:
$A_1$ is —O—, —$CR^{40}R^{41}$—, —C(O)— or —$NR^{48}$—;
$Z_{22}$ is N or $CR^{62}$;
$Z_{24}$ is N or $CR^{64}$;
$Z_{25}$ is N or $CR^{65}$;
$Z_{26}$ is N or $CR^{66}$;
r is 0, 1, or 2;
$R^{40}$ and $R^{41}$ are independently selected from the group consisting of hydrogen, fluoro, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino; or
$R^{40}$ and $R^{41}$ combine to form a 3-7 membered monocyclic cycloalkyl or 5-7 membered monocyclic heterocycloalkyl, wherein the monocyclic cycloalkyl or monocyclic heterocycloalkyl is optionally substituted with one or more substituents selected from the group consisting of halogen, —OH, —$NH_2$, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino;
$R^{62}$, $R^{64}$, $R^{65}$ and $R^{66}$ are independently selected from the group consisting of hydrogen, halogen, lower alkyl and lower alkoxy, wherein the alkyl chain of lower alkyl or lower alkoxy is optionally substituted with one or more substituents selected from the group consisting of fluoro, —OH, —$NH_2$, lower alkoxy, fluoro substituted lower alkoxy, lower alkylthio, fluoro substituted lower alkylthio, mono-alkylamino, di-alkylamino and cycloalkylamino, provided, however, that any substitution on the alkyl carbon bound to the —O— of lower alkoxy is fluoro;
Cy is selected from the group consisting of aryl, heteroaryl, cycloalkyl, and heterocycloalkyl;
$R^{39}$ is selected from the group consisting of hydrogen, halogen, lower alkyl, lower alkoxy, aryl, heteroaryl, and $NR^{50}R^{51}$, wherein the alkyl chain of lower alkyl or lower alkoxy is optionally substituted with one or more substituents selected from the group consisting of fluoro, —OH, —$NH_2$, lower alkoxy, fluoro substituted lower alkoxy, lower alkylthio, fluoro substituted lower alkylthio, mono-alkylamino, di-alkylamino and cycloalkylamino, and wherein aryl and heteroaryl are optionally substituted with one or more independent substituents $R^{23}$;
$R^{50}$ is hydrogen or lower alkyl optionally substituted with one or more substituents selected from the group consisting of fluoro, —OH, —$NH_2$, lower alkoxy, fluoro substituted lower alkoxy, lower alkylthio, fluoro substituted lower alkylthio, mono-alkylamino, di-alkylamino and cycloalkylamino;
$R^{51}$ is aryl or heteroaryl, wherein aryl and heteroaryl are optionally substituted with one or more independent substituents $R^{23}$;
$R^{23}$ at each occurrence is independently selected from the group consisting of —OH, —$NH_2$, —CN, —$NO_2$, —C(O)OH, —$S(O)_2NH_2$, —C(O)$NH_2$, —$OR^{57}$, —$SR^{57}$, —$NR^{48}R^{57}$, —$NR^{48}C(O)R^{57}$, —$NR^{48}S(O)_2R^{57}$, —$S(O)_2R^{57}$, —$C(O)R^{57}$, —$C(O)OR^{57}$, —$C(O)NR^{48}R^{57}$, —$S(O)_2NR^{48}R^{57}$, halogen, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, wherein cycloalkyl, heterocycloalkyl, aryl, and heteroaryl as $R^{23}$, or as substituents of lower alkyl, are optionally substituted with one or more substituents selected from the group consisting of —OH, —$NH_2$, —CN, —$NO_2$, —C(O)OH, —$S(O)_2NH_2$, —C(O)$NH_2$, —$OR^{58}$, —$SR^{58}$, —$NR^{48}R^{58}$, —$NR^{48}C(O)R^{58}$, —$NR^{48}S(O)_2R^{58}$, —$S(O)_2R^{58}$, —$C(O)R^{58}$, —$C(O)OR^{58}$, —$C(O)NR^{48}R^{58}$, —$S(O)_2NR^{48}R^{58}$, halogen, lower alkyl, fluoro substituted lower alkyl, and cycloalkylamino;
$R^{57}$ is selected from the group consisting of lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, provided, however, that any substitution of the alkyl carbon bound to O, S, or N of —$OR^{57}$, —$SR^{57}$, —$NR^{48}R^{57}$, —$C(O)OR^{57}$, —$C(O)NR^{48}R^{57}$, or —$S(O)_2NR^{48}R^{57}$ is fluoro, cycloalkyl, heterocycloalkyl, aryl or heteroaryl, wherein cycloalkyl, heterocycloalkyl, aryl, and heteroaryl as $R^{57}$ or as substituents of lower alkyl are optionally substituted with one or more substituents selected from the group consisting of —OH, —$NH_2$, —CN, —$NO_2$, —C(O)OH, —$S(O)_2NH_2$, —C(O)$NH_2$, —$OR^{58}$, —$SR^{58}$, —$NR^{48}R^{58}$, —$NR^{48}C(O)R^{58}$, —$NR^{48}S(O)_2R^{58}$, —$S(O)_2R^{58}$, —$C(O)R^{58}$, —$C(O)OR^{58}$, —$C(O)NR^{48}R^{58}$, —$S(O)_2NR^{48}R^{58}$, halogen, lower alkyl, fluoro substituted lower alkyl, and cycloalkylamino;
$R^{58}$ at each occurrence is independently selected from the group consisting of lower alkyl, heterocycloalkyl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, and cycloalkylamino, provided, however, that any substitution of the alkyl carbon bound to O, S, or N of —$OR^{58}$, —$SR^{58}$, —$NR^{48}R^{58}$, —$C(O)OR^{58}$, —$C(O)NR^{48}R^{58}$, or —$S(O)_2NR^{48}R^{58}$ is fluoro;
$R^{48}$ at each occurrence is independently hydrogen or lower alkyl; and
t is 0, 1, 2, or 3.
In some embodiments of compounds of Formula IIIe, $A_1$ is —$CR^{40}R^{41}$— or —C(O)—, preferably —$CH_2$— or —C(O)—. In some embodiments, $A_1$ is —$CR^{40}R^{41}$— or —C(O)—, preferably —$CH_2$— or —C(O)—, and $R^{62}$, $R^{64}$, $R^{65}$ and $R^{66}$ are independently selected from the group consisting of hydrogen, halogen, lower alkyl, fluoro substituted lower alkyl, lower alkoxy, and fluoro substituted lower alkoxy.

In some embodiments, compounds of Formula III have the structure according to the following sub-generic structure Formula IIIf:

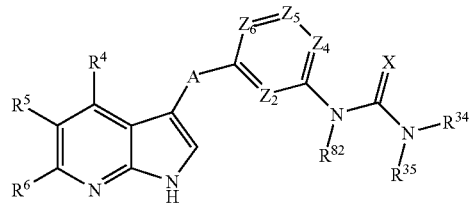

Formula IIIf all salts, prodrugs, tautomers and isomers thereof, wherein A, $Z_2$, $Z_4$, $Z_5$, $Z_6$, X, $R^4$, $R^5$, $R^6$, $R^{34}$, $R^{35}$ and $R^{82}$ are as defined for Formula III.

In some embodiments of compounds of Formula IIIf, $R^4$ and $R^6$ are hydrogen, A is —O—, —$CR^aR^b$—, —$NR^1$—, or —C(O)—, preferably —$CH_2$— or —C(O)—, $Z_2$ is N or $CR^{12}$, $Z_4$ is N or $CR^{14}$, $Z_5$ is N or $CR^{15}$, $Z_6$ is N or $CR^{16}$, and $R^{12}$, $R^{14}$, $R^{15}$ and $R^{16}$ are independently selected from the group consisting of hydrogen, halogen, lower alkyl and lower alkoxy, wherein the alkyl chain of lower alkyl or lower alkoxy is optionally substituted with one or more substituents selected from the group consisting of fluoro, —OH, —$NH_2$, lower alkoxy, fluoro substituted lower alkoxy, lower alkylthio, fluoro substituted lower alkylthio, mono-alkylamino, di-alkylamino and cycloalkylamino, provided, however, that any substitution on the alkyl carbon bound to the —O— of lower alkoxy is fluoro.

In some embodiments of compounds of Formula IIIf, $R^4$ and $R^6$ are hydrogen, A is —O—, —$CR^aR^b$—, —$NR^1$—, or —C(O)—, preferably —$CH_2$— or —C(O)—, $Z_2$ is N or $CR^{12}$, $Z_4$ is N or $CR^{14}$, $Z_5$ is N or $CR^{15}$, $Z_6$ is N or $CR^{16}$, $R^{12}$, $R^{14}$, $R^{15}$ and $R^{16}$ are independently selected from the group consisting of hydrogen, halogen, lower alkyl and lower alkoxy, wherein the alkyl chain of lower alkyl or lower alkoxy is optionally substituted with one or more substituents selected from the group consisting of fluoro, —OH, —$NH_2$, lower alkoxy, fluoro substituted lower alkoxy, lower alkylthio, fluoro substituted lower alkylthio, mono-alkylamino, di-alkylamino and cycloalkylamino, provided, however, that any substitution on the alkyl carbon bound to the —O— of lower alkoxy is fluoro, and one of $R^{34}$ and $R^{35}$ is selected from the group consisting of optionally substituted lower alkyl, optionally substituted cycloalkyl, optionally substituted heterocycloalkyl, optionally substituted aryl and optionally substituted heteroaryl, and the other of $R^{34}$ and $R^{35}$ is hydrogen or lower alkyl, or $R^{34}$ and $R^{35}$ together with the nitrogen to which they are attached form optionally substituted 5-7 membered heterocycloalkyl or optionally substituted 5 or 7 membered nitrogen containing heteroaryl.

In some embodiments, compounds of Formula III have the structure according to the following sub-generic structure Formula IIIg:

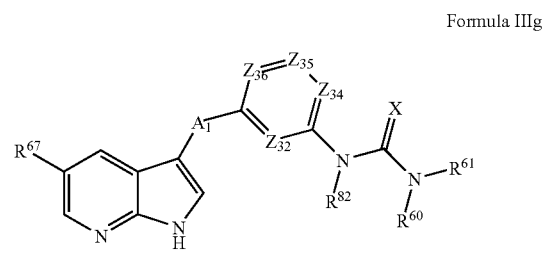

Formula IIIg all salts, prodrugs, tautomers, and isomers thereof, wherein:
$A_1$ is —O—, —$CR^{40}R^{41}$, —C(O)— or —$NR^{48}$—;
$Z_{32}$ is N or $CR^{72}$;
$Z_{34}$ is N or $CR^{74}$;
$Z_{35}$ is N or $CR^{75}$;
$Z_{36}$ is N or $CR^{76}$;
X is O or S;
$R^{48}$ at each occurrence is independently hydrogen or lower alkyl;
$R^{40}$ and $R^{41}$ are independently selected from the group consisting of hydrogen, fluoro, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino; or
$R^{40}$ and $R^{41}$ combine to form a 3-7 membered monocyclic cycloalkyl or 5-7 membered monocyclic heterocycloalkyl, wherein the monocyclic cycloalkyl or monocyclic heterocycloalkyl is optionally substituted with one or more substituents selected from the group consisting of halogen, —OH, —$NH_2$, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino;
$R^{72}$, $R^{74}$, $R^{75}$ and $R^{76}$ are independently selected from the group consisting of hydrogen, halogen, lower alkyl and lower alkoxy, wherein the alkyl chain of lower alkyl and lower alkoxy is optionally substituted with one or more substituents selected from the group consisting of fluoro, —OH, —$NH_2$, lower alkoxy, fluoro substituted lower alkoxy, lower alkylthio, fluoro substituted lower alkylthio, mono-alkylamino, di-alkylamino and cycloalkylamino, provided, however, that any substitution on the alkyl carbon bound to the —O— of lower alkoxy is fluoro;
$R^{67}$ is selected from the group consisting of hydrogen, halogen, optionally substituted lower alkyl, optionally substituted lower alkenyl, optionally substituted lower alkenyl, optionally substituted cycloalkyl, optionally substituted heterocycloalkyl, optionally substituted aryl, optionally substituted heteroaryl, —OH, —$NH_2$, —CN, —$NO_2$, —C(O)OH, —$S(O)_2NH_2$, —$C(O)NH_2$, —$C(S)NH_2$, —$NHC(O)NH_2$, —$NHC(S)NH_2$, —$NHS(O)_2NH_2$, —$OR^{68}$, —$SR^{68}$, —$NR^{69}R^{68}$, —$C(O)R^{68}$, —$C(S)R^{68}$, —$C(O)OR^{68}$, —$C(O)NR^{69}R^{68}$, —$C(S)NR^{69}R^{68}$, —$S(O)_2NR^{69}R^{68}$, —$NR^{69}C(O)R^{68}$, —$NR^{69}C(S)NR^{69}R^{68}$, —$NR^{69}S(O)_2R^{68}$, —$NR^{69}C(O)NH_2$, —$NR^{69}C(O)NR^{69}R^{68}$, —$NR^{69}C(S)NH_2$, —$NR^{69}C(S)NR^{69}R^{68}$, —$NR^{69}S(O)_2NH_2$, —$NR^{69}S(O)_2NR^{69}R^{68}$, —$S(O)R^{68}$, and —$S(O)_2R^{68}$;
one of $R^{60}$ and $R^{61}$ is lower alkyl, fluoro substituted lower alkyl, or —$(CH_2)_{0-2}R^{70}$, and the other of $R^{60}$ and $R^{61}$ is hydrogen or lower alkyl;

or R$^{60}$ and R$^{61}$ together with the nitrogen to which they are attached form optionally substituted 5-7 membered heterocycloalkyl or optionally substituted 5 or 7 membered nitrogen containing heteroaryl;

R$^{68}$ is selected from the group consisting of optionally substituted lower alkyl, optionally substituted lower alkenyl, provided, however, that when R$^{68}$ is optionally substituted lower alkenyl, no alkene carbon thereof is bound to N, S, O, S(O), S(O)$_2$, C(O) or C(S) of —OR$^{68}$, —SR$^{68}$, —NR$^{69}$R$^{68}$, —C(O)R$^{68}$, —C(S)R$^{68}$, —C(O)OR$^{68}$, —C(O)NR$^{69}$R$^{68}$, —C(S)NR$^{69}$R$^{68}$, —S(O)$_2$NR$^{69}$R$^{68}$, —NR$^{69}$C(O)R$^{68}$, —NR$^{69}$C(S)R$^{68}$, —NR$^{69}$S(O)$_2$R$^{68}$, —NR$^{69}$C(O)NH$_2$, —NR$^{69}$C(O)NR$^{69}$R$^{68}$, —NR$^{69}$C(S)NH$_2$, —NR$^{69}$C(S)NR$^{69}$R$^{68}$, —NR$^{69}$S(O)$_2$NH$_2$, —NR$^{69}$S(O)$_2$NR$^{69}$R$^{68}$, —S(O)R$^{68}$, or —S(O)$_2$R$^{68}$, optionally substituted lower alkynyl, provided, however, that when R$^{68}$ is optionally substituted lower alkynyl, no alkyne carbon thereof is bound to N, S, O, S(O), S(O)$_2$, C(O) or C(S) of —OR$^{68}$, —SR$^{68}$, —NR$^{69}$R$^{68}$, —C(O)R$^{68}$, —C(S)R$^{68}$, —C(O)OR$^{68}$, —C(O)NR$^{69}$R$^{68}$, —C(S)NR$^{69}$R$^{68}$, —S(O)$_2$NR$^{69}$R$^{68}$, —NR$^{69}$C(O)R$^{68}$, —NR$^{69}$C(S)R$^{68}$, —NR$^{69}$S(O)$_2$R$^{68}$, —NR$^{69}$C(O)NH$_2$, —NR$^{69}$C(O)NR$^{69}$R$^{68}$, —NR$^{69}$C(S)NH$_2$, —NR$^{69}$C(S)NR$^{69}$R$^{68}$, —NR$^{69}$S(O)$_2$NH$_2$, —NR$^{69}$S(O)$_2$NR$^{69}$R$^{68}$, —S(O)R$^{68}$, or —S(O)$_2$R$^{68}$, optionally substituted cycloalkyl, optionally substituted heterocycloalkyl, optionally substituted aryl, and optionally substituted heteroaryl;

R$^{69}$ is hydrogen or optionally substituted lower alkyl;

R$^{70}$ is selected from the group consisting of optionally substituted cycloalkyl, optionally substituted heterocycloalkyl, optionally substituted aryl, and optionally substituted heteroaryl; and R$^{82}$ is hydrogen or lower alkyl.

In some embodiments of compounds of Formula IIIg, A$_1$ is —CR$^{40}$R$^{41}$— or —C(O)—, preferably —CH$_2$— or —C(O)—.

In some embodiments of compounds of Formula IIIg, A$_1$ is —CR$^{40}$R$^{41}$— or —C(O)—, preferably —CH$_2$— or —C(O)—, and R$^{67}$ is selected from the group consisting of hydrogen, halogen, optionally substituted lower alkyl, optionally substituted lower alkenyl, optionally substituted lower alkynyl, optionally substituted cycloalkyl, optionally substituted heterocycloalkyl, optionally substituted aryl, optionally substituted heteroaryl, —CN, —S(O)$_2$NH$_2$, —C(O)NH$_2$, —OR$^{68}$, —SR$^{68}$, —NR$^{69}$R$^{68}$, —C(O)R$^{68}$, —C(S)R$^{68}$, —C(O)NR$^{69}$R$^{68}$, —S(O)$_2$NR$^{69}$R$^{68}$, —NR$^{69}$C(O)R$^{68}$, —NR$^{69}$S(O)$_2$R$^{68}$, —S(O)R$^{68}$, and —S(O)$_2$R$^{68}$.

In some embodiments, compounds of Formula III have the structure according to the following sub-generic structure Formula IIIh:

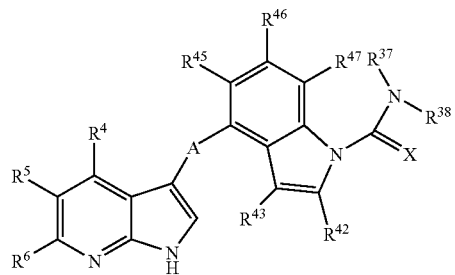

Formula IIIh all salts, prodrugs, tautomers and isomers thereof, wherein A, X, R$^4$, R$^5$, R$^6$, R$^{37}$, R$^{38}$, R$^{42}$, R$^{43}$, R$^{45}$, R$^{46}$, and R$^{47}$ are as defined for Formula III.

In some embodiments of compounds of Formula IIIh, R$^4$ and R$^6$ are hydrogen, A is —O—, —CR$^a$R$^b$—, —NR$^1$—, or —C(O)—, preferably —CH$_2$— or —C(O)—, and R$^{42}$, R$^{43}$, R$^{45}$, R$^{46}$ and R$^{47}$ are independently selected from the group consisting of hydrogen, halogen, —OH, —CN, —NO$_2$, —NH$_2$, lower alkyl, fluoro substituted lower alkyl, lower alkoxy, fluoro substituted lower alkoxy, lower alkylthio, fluoro substituted lower alkyl, mono-alkylamino, di-alkylamino, and cycloalkylamino, further wherein at least one of, at least two of, at least three of, at least four of, or preferably all of R$^{42}$, R$^{43}$, R$^{45}$, R$^{46}$ and R$^7$ are hydrogen.

In some embodiments, compounds of Formula III have the structure according to the following sub-generic structure Formula IIIi:

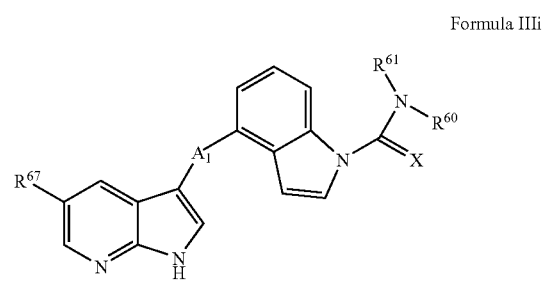

Formula IIIi all salts, prodrugs, tautomers, and isomers thereof, wherein:

A$_1$ is —O—, —CR$^{40}$R$^{41}$—, —C(O)— or —NR$^{48}$—;

X is O or S;

R$^{48}$ at each occurrence is independently hydrogen or lower alkyl;

R$^{40}$ and R$^{41}$ are independently selected from the group consisting of hydrogen, fluoro, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino; or R$^{40}$ and R$^{41}$ combine to form a 3-7 membered monocyclic cycloalkyl or 5-7 membered monocyclic heterocycloalkyl, wherein the monocyclic cycloalkyl or monocyclic heterocycloalkyl is optionally substituted with one or more substituents selected from the group consisting of halogen, —OH, —NH$_2$, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino;

R$^{67}$ is selected from the group consisting of hydrogen, halogen, optionally substituted lower alkyl, optionally substituted lower alkenyl, optionally substituted lower alkynyl, optionally substituted cycloalkyl, optionally substituted heterocycloalkyl, optionally substituted aryl, optionally substituted heteroaryl, —OH, —NH$_2$, —CN, —NO$_2$, —C(O)OH, —S(O)$_2$NH$_2$, —C(O)NH$_2$, —C(S)NH$_2$, —NHC(O)NH$_2$, —NHC(S)NH$_2$, —NHS(O)$_2$NH$_2$, —OR$^{68}$, —SR$^{68}$, —NR$^{69}$R$^{68}$, —C(O)R$^{68}$, —C(S)R$^{68}$, —C(O)OR$^{68}$, —C(O)NR$^{69}$R$^{68}$, —C(S)NR$^{69}$R$^{68}$, —S(O)$_2$NR$^{69}$R$^{68}$, —NR$^{69}$C(O)R$^{68}$, —NR$^{69}$C(S)R$^{68}$, —NR$^{69}$S(O)$_2$R$^{68}$, —NR$^{69}$C(O)NH$_2$, —NR$^{69}$C(O)NR$^{69}$R$^{68}$, —NR$^{69}$C(S)NH$_2$, —NR$^{69}$C(S)

$NR^{69}R^{68}$, $-NR^{69}S(O)_2NH_2$, $-NR^{69}S(O)_2NR^{69}R^{68}$, $-S(O)R^{68}$, and $-S(O)_2R^{68}$;

one of $R^{60}$ and $R^{61}$ is lower alkyl, fluoro substituted lower alkyl, or $-(CH_2)_{0-2}R^{70}$ and the other of $R^{60}$ and $R^{61}$ is hydrogen or lower alkyl;

or $R^{60}$ and $R^{61}$ together with the nitrogen to which they are attached form optionally substituted 5-7 membered heterocycloalkyl or optionally substituted 5 or 7 membered nitrogen containing heteroaryl;

$R^{68}$ is selected from the group consisting of optionally substituted lower alkyl, optionally substituted lower alkenyl, provided, however, that when $R^{68}$ is optionally substituted lower alkenyl, no alkene carbon thereof is bound to N, S, O, S(O), S(O)$_2$, C(O) or C(S) of $-OR^{68}$, $-SR^{68}$, $-NR^{69}R^{68}$, $-C(O)R^{68}$, $-C(S)R^{68}$, $-C(O)OR^{68}$, $-C(O)NR^{69}R^{68}$, $-C(S)NR^{69}R^{68}$, $-S(O)_2NR^{69}R^{68}$, $-NR^{69}C(O)R^{68}$, $-NR^{69}C(S)R^{68}$, $-NR^{69}S(O)_2R^{68}$, $-NR^{69}C(O)NH_2$, $-NR^{69}C(O)NR^{69}R^{68}$, $-NR^{69}C(S)NH_2$, $-NR^{69}C(S)NR^{69}R^{68}$, $-NR^{69}S(O)_2NH_2$, $-NR^{69}S(O)_2NR^{69}R^{68}$, $-S(O)R^{68}$, or $-S(O)_2R^{68}$, optionally substituted lower alkynyl, provided, however, that when $R^{68}$ is optionally substituted lower alkynyl, no alkyne carbon thereof is bound to N, S, O, S(O), S(O)$_2$, C(O) or C(S) of $-OR^{68}$, $-SR^{68}$, $-NR^{69}R^{68}$, $-C(O)R^{68}$, $-C(S)R^{68}$, $-C(O)OR^{68}$, $-C(O)NR^{69}R^{68}$, $-C(S)NR^{69}R^{68}$, $-S(O)_2NR^{69}R^{68}$, $-NR^{69}C(O)R^{68}$, $-NR^{69}C(S)R^{68}$, $-NR^{69}S(O)_2R^{68}$, $-NR^{69}C(O)NH_2$, $-NR^{69}C(O)NR^{69}R^{68}$, $-NR^{69}C(S)NH_2$, $-NR^{69}C(S)NR^{69}R^{68}$, $-NR^{69}S(O)_2NH_2$, $-NR^{69}S(O)_2NR^{69}R^{68}$, $-S(O)R^{68}$, or $-S(O)_2R^{68}$, optionally substituted cycloalkyl, optionally substituted heterocycloalkyl, optionally substituted aryl, and optionally substituted heteroaryl;

$R^{69}$ is hydrogen or optionally substituted lower alkyl; and $R^{20}$ is selected from the group consisting of optionally substituted cycloalkyl, optionally substituted heterocycloalkyl, optionally substituted aryl, and optionally substituted heteroaryl.

In some embodiments of compounds of Formula IIIi, $A_1$ is $-CR^{41}R^{41}-$ or $-C(O)-$, preferably $-CH_2-$ or $-C(O)-$.

In some embodiments of compounds of Formula IIIi, $A_1$ is $-CR^{40}R^{41}-$ or $-C(O)-$, preferably $-CH_2-$ or $-C(O)-$, and $R^{67}$ is selected from the group consisting of hydrogen, halogen, optionally substituted lower alkyl, optionally substituted lower alkenyl, optionally substituted lower alkynyl, optionally substituted cycloalkyl, optionally substituted heterocycloalkyl, optionally substituted aryl, optionally substituted heteroaryl, $-CN$, $-S(O)_2NH_2$, $-C(O)NH_2$, $-OR^{68}$, $-SR^{68}$, $-NR^{69}R^{68}$, $-C(O)R^{68}$, $-C(S)R^{68}$, $-C(O)NR^{69}R^{68}$, $-S(O)_2NR^{69}R^{68}$, $-NR^{69}C(O)R^{68}$, $-NR^{69}S(O)_2R^{68}$, $-S(O)R^{68}$, and $-S(O)_2R^{68}$.

In some embodiments of compounds of Formula IIIi, $A_1$ is $-CR^{40}R^{41}-$ or $-C(O)-$, preferably $-CH_2-$ or $-C(O)-$, more preferably $-C(O)-$, $R^{67}$ is selected from the group consisting of hydrogen, halogen, lower alkyl, lower alkoxy, optionally substituted aryl, optionally substituted heteroaryl, and $NR^{21}R^{22}$, wherein $R^{21}$ is hydrogen or lower alkyl, and $R^{22}$ is hydrogen, lower alkyl, optionally substituted aryl or optionally substituted heteroaryl, and wherein the alkyl chain of $R^{67}$, $R^{21}$ or $R^{22}$, when lower alkyl, or the alkyl chain of lower alkoxy is optionally substituted with one or more substituents selected from the group consisting of fluoro, $-OH$, $-NH_2$, lower alkoxy, fluoro substituted lower alkoxy, lower alkylthio, fluoro substituted lower alkylthio, mono-alkylamino, di-alkylamino and cycloalkylamino, and one of $R^{60}$ and $R^{61}$ is lower alkyl or fluoro substituted lower alkyl, and the other of $R^{60}$ and $R^{61}$ is hydrogen or lower alkyl. In some embodiments, $A_1$ is $-C(O)-$, $R^{67}$ is optionally substituted aryl or optionally substituted heteroaryl, and one of $R^{60}$ and $R^{61}$ is lower alkyl or fluoro substituted lower alkyl, and the other of $R^{60}$ and $R^{61}$ is hydrogen or lower alkyl.

In some embodiments, compounds of Formula III have the structure according to the following sub-generic structure Formula IIIj:

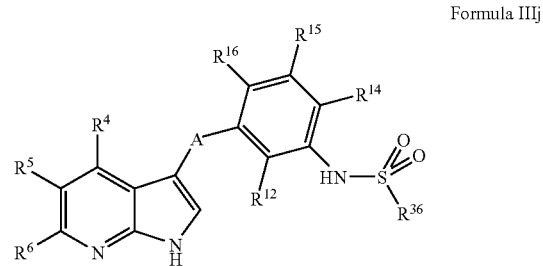

Formula IIIj all salts, prodrugs, tautomers and isomers thereof, wherein A, $R^4$, $R^5$, $R^6$, $R^{12}$, $R^{14}$, $R^{15}$, $R^{16}$, and $R^{36}$ are as defined for Formula III.

In some embodiments of compounds of Formula IIIj, $R^4$ and $R^6$ are hydrogen, A is $-O-$, $-CR^aR^b-$, $-NR^1-$, or $-C(O)-$, preferably $-CH_2-$ or $-C(O)-$, and $R^{12}$, $R^{14}$, $R^{15}$ and $R^{16}$ are independently selected from the group consisting of hydrogen, halogen, lower alkyl and lower alkoxy, wherein the alkyl chain of lower alkyl or lower alkoxy is optionally substituted with one or more substituents selected from the group consisting of fluoro, $-OH$, $-NH_2$, lower alkoxy, fluoro substituted lower alkoxy, lower alkylthio, fluoro substituted lower alkylthio, mono-alkylamino, di-alkylamino and cycloalkylamino, provided, however, that any substitution on the alkyl carbon bound to the $-O-$ of lower alkoxy is fluoro, preferably wherein $R^{14}$ and $R^{15}$ are hydrogen, more preferably wherein $R^{12}$ is fluoro, $R^{16}$ is hydrogen, fluoro or chloro, and $R^{14}$ and $R^{15}$ are hydrogen.

In some embodiments of compounds of Formula IIIj, $R^4$ and $R^6$ are hydrogen, A is $-O-$, $-CR^aR^b-$, $-NR^1-$, or $-C(O)-$, preferably $-CH_2-$ or $-C(O)-$, $R^{12}$, $R^{14}$, $R^{15}$ and $R^{16}$ are independently selected from the group consisting of hydrogen, halogen, lower alkyl and lower alkoxy, wherein the alkyl chain of lower alkyl or lower alkoxy is optionally substituted with one or more substituents selected from the group consisting of fluoro, $-OH$, $-NH_2$, lower alkoxy, fluoro substituted lower alkoxy, lower alkylthio, fluoro substituted lower alkylthio, mono-alkylamino, di-alkylamino and cycloalkylamino, provided, however, that any substitution on the alkyl carbon bound to the $-O-$ of lower alkoxy is fluoro, preferably wherein $R^{14}$ and $R^{15}$ are hydrogen, more preferably wherein $R^{12}$ is fluoro, $R^{16}$ is hydrogen, fluoro or chloro, and $R^{14}$ and $R^{15}$ are hydrogen, and $R^{36}$ is selected from the group consisting of optionally substituted $C_{2-6}$alkyl, optionally substituted cycloalkyl, optionally substituted heterocycloalkyl, optionally substituted aryl, optionally substituted heteroaryl, and $-NR^{19}R^{20}$, where $R^{19}$ and $R^{20}$ are as defined for Formula III, further wherein one of $R^{19}$ and $R^{20}$ is hydrogen or optionally substituted lower alkyl, and the other of $R^{19}$ and $R^{20}$ is selected from the group consisting of hydrogen, optionally substituted lower alkyl, optionally substituted cycloalkyl, optionally substituted heterocycloalkyl, optionally substituted aryl and optionally substituted heteroaryl.

In some embodiments, compounds of Formula III have the structure according to the following sub-generic structure Formula IIIk:

Formula IIIk

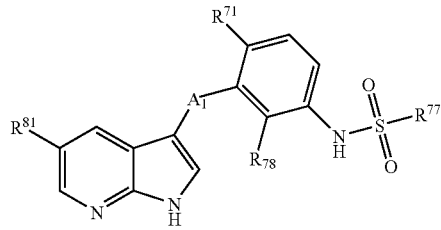

all salts, prodrugs, tautomers and isomers thereof,
wherein:
$A_1$ is —O—, —$CR^{40}R^{41}$—, —C(O)— or —$NR^{48}$—;
$R^{81}$ is selected from the group consisting of hydrogen, halogen, optionally substituted lower alkyl, optionally substituted lower alkenyl, optionally substituted lower alkynyl, optionally substituted cycloalkyl, optionally substituted heterocycloalkyl, optionally substituted aryl, optionally substituted heteroaryl, —OH, —$NH_2$, —CN, —$NO_2$, —C(O)OH, —$S(O)_2NH_2$, —$C(O)NH_2$, —$C(S)NH_2$, —$NHC(O)NH_2$, —$NHC(S)NH_2$, —$NHS(O)_2NH_2$, —$OR^{68}$, —$SR^{68}$, —$NR^{69}R^{68}$, —$C(O)R^{68}$, —$C(S)R^{68}$, —$C(O)OR^{68}$, —$C(O)NR^{69}R^{68}$, —$C(S)NR^{69}R^{68}$, $S(O)_2NR^{69}R^{68}$, —$NR^{69}C(O)R^{68}$, —$NR^{69}C(S)R^{68}$, —$NR^{69}S(O)_2R^{68}$, —$NR^{69}C(O)NH_2$, —$NR^{69}C(O)NR^{69}R^{68}$, —$NR^{69}C(S)NH_2$, —$NR^{69}C(S)NR^{69}R^{68}$, —$NR^{69}S(O)_2NH_2$, —$NR^{69}S(O)_2NR^{69}R^{68}$, —$S(O)R^{68}$, and —$S(O)_2R^{68}$;

$R^{71}$ and $R^{78}$ are independently selected from the group consisting of hydrogen, halogen, $C_{1-3}$ alkyl, and fluoro substituted $C_{1-3}$ alkyl;

$R^{77}$ is selected from the group consisting of substituted methyl, optionally substituted $C_{2-6}$ alkyl, optionally substituted aryl, optionally substituted heteroaryl, and —$NR^{79}R^{80}$, wherein methyl is substituted with one or more substituents selected from the group consisting of optionally substituted aryl and optionally substituted heteroaryl;

$R^{68}$ is selected from the group consisting of optionally substituted lower alkyl, optionally substituted lower alkenyl, provided, however, that when $R^{68}$ is optionally substituted lower alkenyl, no alkene carbon thereof is bound to N, S, O, S(O), $S(O)_2$, C(O) or C(S) of —$OR^{68}$, —$SR^{68}$, —$NR^{69}R^{68}$, —$C(O)R^{68}$, —$C(S)R^{68}$, —$C(O)OR^{68}$, —$C(O)NR^{69}R^{68}$, —$C(S)NR^{69}R^{68}$, —$S(O)_2NR^{69}R^{68}$, —$NR^{69}C(O)R^{68}$, —$NR^{69}C(S)R^{68}$, —$NR^{69}S(O)_2R^{68}$, —$NR^{69}C(O)NH_2$, —$NR^{69}C(O)NR^{69}R^{68}$, —$NR^{69}C(S)NH_2$, —$NR^{69}C(S)NR^{69}R^{68}$, —$NR^{69}S(O)_2NH^2$, —$NR^{69}S(O)_2NR^{69}R^{68}$, —$S(O)R^{68}$, or —$S(O)_2R^{68}$, optionally substituted lower alkynyl, provided, however, that when $R^{68}$ is optionally substituted lower alkynyl, no alkyne carbon thereof is bound to N, S, O, S(O), $S(O)_2$, C(O) or C(S) of —$OR^{68}$, —$SR^{68}$, —$NR^{69}R^{68}$, —$C(O)R^{68}$, —$C(S)R^{68}$, —$C(O)OR^{68}$, —$C(O)NR^{69}R^{68}$, —$C(S)NR^{69}R^{68}$, —$S(O)_2NR^{69}R^{68}$, —$NR^{69}C(O)R^{68}$, —$NR^{69}C(S)R^{68}$, —$NR^{69}S(O)_2R^{68}$, —$NR^{69}C(O)NH_2$, —$NR^{69}C(O)NR^{69}R^{68}$, —$NR^{69}C(S)NH_2$, —$NR^{69}C(S)NR^{69}R^{68}$, —$NR^{69}S(O)_2NH_2$, —$NR^{69}S(O)_2NR^{69}R^{68}$, —$S(O)R^{68}$, or —$S(O)_2R^{68}$, optionally substituted cycloalkyl, optionally substituted heterocycloalkyl, optionally substituted aryl, and optionally substituted heteroaryl;

$R^{69}$ is hydrogen or optionally substituted lower alkyl; and
$R^{79}$ and $R^{80}$ are independently hydrogen or optionally substituted lower alkyl, or $R^{79}$ and $R^{80}$ combine with the nitrogen to which they are attached to form optionally substituted 5-7 membered heterocycloalkyl.

In some embodiments of compounds of Formula IIIk, $A_1$ is —$CR^{40}R^{41}$— or —C(O)—, preferably —$CH_2$— or —C(O)—, more preferably —C(O)—.

In some embodiments of compounds of Formula IIIk, $A_1$ is —$CR^{40}R^{41}$— or —C(O)—, preferably —$CH_2$— or —C(O)—, more preferably —C(O)—, and $R^{81}$ is selected from the group consisting of hydrogen, halogen, optionally substituted lower alkyl, optionally substituted lower alkenyl, optionally substituted lower alkynyl, optionally substituted cycloalkyl, optionally substituted heterocycloalkyl, optionally substituted aryl, optionally substituted heteroaryl, —CN, —$S(O)_2NH_2$, —$C(O)NH_2$, —$OR^{68}$, —$SR^{68}$, —$NR^{69}R^{68}$, —$C(O)R^{68}$, —$C(S)R^{68}$, —$C(O)NR^{69}R^{68}$, —$S(O)_2NR^{69}R^{68}$, —$NR^{69}C(O)R^{68}$, —$NR^{69}S(O)_2R^{68}$, —$S(O)R^{68}$, and —$S(O)_2R^{68}$.

In some embodiments, compounds of Formula III have the structure according to the following sub-generic structure Formula IIIm:

Formula IIIm

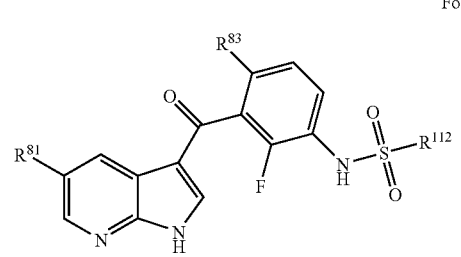

all salts, prodrugs, tautomers and isomers thereof,
wherein:
$R^{81}$ is selected from the group consisting of hydrogen, halogen, optionally substituted lower alkyl, optionally substituted lower alkenyl, optionally substituted lower alkynyl, optionally substituted cycloalkyl, optionally substituted heterocycloalkyl, optionally substituted aryl, optionally substituted heteroaryl, —OH, —$NH_2$, —CN, —$NO_2$, —C(O)OH, —$S(O)_2NH_2$, —$C(O)NH_2$, —$C(S)NH_2$, —$NHC(O)NH_2$, —$NHC(S)NH_2$, —$NHS(O)_2NH_2$, —$OR^{68}$, —$SR^{68}$, —$NR^{69}R^{68}$, —$C(O)R^{68}$, —$C(S)R^{68}$, —$C(O)OR^{68}$, —$C(O)NR^{69}R^{68}$, —$C(S)NR^{69}R^{68}$, —$S(O)_2NR^{69}R^{68}$, —$NR^{69}C(O)R^{68}$, —$NR^{69}C(S)R^{68}$, —$NR^{69}S(O)_2R^{68}$, —$NR^{69}C(O)NH_2$, —$NR^{69}C(O)NR^{69}R^{68}$, —$NR^{69}C(S)NH_2$, —$NR^{69}C(S)NR^{69}R^{68}$, —$NR^{69}S(O)_2NH_2$, —$NR^{69}S(O)_2NR^{69}R^{68}$, —$S(O)R^{68}$, and —$S(O)_2R^{68}$;

$R^{83}$ is selected from the group consisting of hydrogen, fluoro and chloro;

$R^{112}$ is selected from the group consisting of optionally substituted $C_{2-6}$ alkyl, optionally substituted aryl, optionally substituted heteroaryl, and —$NR^{79}R^{80}$;

$R^{68}$ is selected from the group consisting of optionally substituted lower alkyl, optionally substituted lower alkenyl, provided, however, that when $R^{68}$ is optionally substituted lower alkenyl, no alkene carbon thereof is bound to N, S, O, S(O), $S(O)_2$, C(O) or C(S) of —$OR^{68}$, —$SR^{68}$, —$NR^{69}R^{68}$, —$C(O)R^{68}$, —$C(S)R^{68}$, —$C(O)$ OR$^{68}$, —C(O)NR$^{69}$R$^{68}$, —C(S)NR$^{69}$R$^{68}$, —S(O)$_2$NR$^{69}$R$^{68}$, —NR$^{69}$C(O)R$^{68}$, —NR$^{69}$C(S)R$^{68}$, —NR$^{69}$S(O)$_2$R$^{68}$, —NR$^{69}$C(O)NR$_2$, —NR$^{69}$C(O)NR$^{69}$R$^{68}$, —NR$^{69}$C(S)NH$_2$, —NR$^{69}$C(S)NR$^{69}$R$^{68}$, —NR$^{69}$S(O)$_2$NH$_2$, —NR$^{69}$S(O)$_2$NR$^{69}$R$^{68}$, —S(O)R$^{68}$, or —S(O)$_2$R$^{68}$, optionally substituted lower alkynyl, provided, however, that when R$^{68}$ is optionally substituted lower alkynyl, no alkyne carbon thereof is bound to N, S, O, S(O), S(O)$_2$, C(O) or C(S) of —OR$^{68}$, —SR$^{68}$, —NR$^{69}$R$^{68}$, —C(O)R$^{68}$, —C(S)R$^{68}$, —C(O)OR$^{68}$, —C(O)NR$^{69}$R$^{68}$, —C(S)NR$^{69}$R$^{68}$, —S(O)$_2$NR$^{69}$R$^{68}$, —NR$^{69}$C(O)R$^{68}$, —NR$^{69}$C(S)R$^{68}$, —NR$^{69}$S(O)$_2$R$^{68}$, —NR$^{69}$C(O)NH$_2$, —NR$^{69}$C(O)NR$^{69}$R$^{68}$, —NR$^{69}$C(S)NH$_2$, —NR$^{69}$C(S)NR$^{69}$R$^{68}$, —NR$^{69}$S(O)$_2$NH$_2$, —NR$^{69}$S(O)$_2$NR$^{69}$R$^{68}$, —S(O)R$^{68}$, or —S(O)$_2$R$^{68}$, optionally substituted cycloalkyl, optionally substituted heterocycloalkyl, optionally substituted aryl, and optionally substituted heteroaryl;

R$^{69}$ is selected from the group consisting of hydrogen and optionally substituted lower alkyl; and R$^{79}$ and R$^{80}$ are independently hydrogen or optionally substituted lower alkyl, or R$^{79}$ and R$^{80}$ combine with the nitrogen to which they are attached to form optionally substituted 5-7 membered heterocycloalkyl.

In some embodiments of compounds of Formula IIIm, R$^{81}$ is selected from the group consisting of hydrogen, halogen, optionally substituted lower alkyl, optionally substituted lower alkenyl, optionally substituted lower alkynyl, optionally substituted cycloalkyl, optionally substituted heterocycloalkyl, optionally substituted aryl, optionally substituted heteroaryl, —CN, —S(O)$_2$NH$_2$, —C(O)NH$_2$, —OR$^{68}$, —NR$^{69}$R$^{68}$, —C(O)R$^{68}$, —C(S)R$^{68}$, —C(O)NR$^{69}$R$^{68}$, —S(O)$_2$NR$^{69}$R$^{68}$, —NR$^{69}$C(O)R$^{68}$, —NR$^{69}$S(O)$_2$R$^{68}$, —S(O)R$^{68}$, and —S(O)$_2$R$^{68}$.

The compounds of Formulae IIIa-IIIq, and all sub-embodiments detailed herein, may be used to treat a subject suffering from or at risk for any of the protein kinase mediated diseases or conditions contemplated herein.

In one aspect, the present invention includes compounds that are useful as intermediates in the preparation of compounds of Formula III, the compounds having a structure selected from the group consisting of Formula IV, Formula V, Formula VI, Formula VII, Formula VIII, and Formula IX as follows:

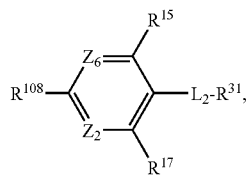

Formula IV

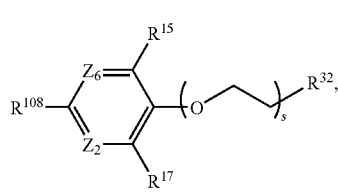

Formula V

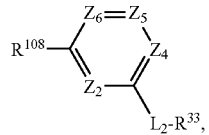

Formula VI

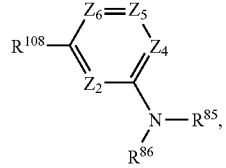

Formula VII

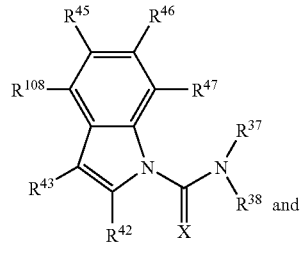

Formula VIII

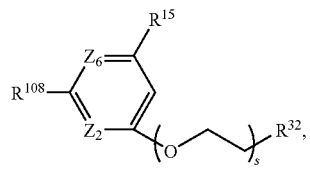

Formula IX wherein:
Z$_2$, Z$_4$, Z$_5$, Z$_6$, L$_2$, X, s, R$^{15}$, R$^{17}$, R$^{31}$, R$^{32}$, R$^{33}$, R$^{37}$, R$^{38}$, R$^{42}$, R$^{43}$, R$^{45}$, R$^{46}$, and R$^{47}$ are as defined for Formula III;

R$^{108}$ is selected from the group consisting of —C(O)R$^{84}$, —CH$_2$I, —CH$_2$Cl, —CH$_2$Br, —CH$_2$OH, and —CH$_2$OS(O)$_2$R$^{109}$;

R$^{109}$ is selected from the group consisting of lower alkyl and aryl;

R$^{84}$ is selected from the group consisting of hydrogen, lower alkoxy, —OH, and —Cl;

R$^{85}$ is selected from the group consisting of hydrogen, a nitrogen protecting group, —S(O)$_2$R$^{87}$, —C(O)NR$^{88}$R$^{89}$, and —C(S)NR$^{88}$R$^{89}$;

R$^{86}$ is selected from the group consisting of hydrogen, lower alkyl, and a nitrogen protecting group;

R$^{87}$ is selected from the group consisting of optionally substituted lower alkyl, optionally substituted lower alkenyl, provided, however, that when R$^{87}$ is optionally substituted lower alkenyl, no alkene carbon thereof is bound to S(O)$_2$, optionally substituted lower alkynyl, provided, however, that when R$^{87}$ is optionally substituted lower alkynyl, no alkyne carbon thereof is bound to S(O)$_2$, optionally substituted cycloalkyl, optionally substituted heterocycloalkyl, optionally substituted aryl, optionally substituted heteroaryl, and —NR$^{90}$R$^{91}$; and R$^{88}$, R$^{89}$, R$^{90}$ and R$^{91}$ are independently selected from the group consisting of hydrogen, optionally substituted lower alkyl, optionally substituted cycloalkyl, optionally substituted heterocycloalkyl, optionally substituted aryl and optionally substituted heteroaryl; or R$^{88}$ and R$^{89}$ together with the nitrogen to which they are attached form optionally substituted 5-7 membered heterocycloalkyl or optionally substituted 5 or 7 membered nitrogen containing heteroaryl.

In some embodiments of compounds of Formulae IV, V, VI, VII, or VIII, $R^{108}$ is —C(O)$R^{84}$, preferably wherein $R^{84}$ is hydrogen. In some embodiments of compounds of Formulae IV, V, VI, VII, or VIII, $Z_2$ is N or $CR^{12}$, $Z_4$ is N or $CR^{14}$, $Z_5$ is N or $CR^{15}$, and $Z_6$ is N or $CR^{16}$ and $R^{12}$, $R^{14}$, $R^{15}$, $R^{16}$, $R^{17}$, $R^{42}$, $R^{43}$, $R^{45}$, $R^{46}$ and $R^{47}$ are independently selected from the group consisting of hydrogen, halogen, lower alkyl, fluoro substituted lower alkyl, lower alkoxy, and fluoro substituted lower alkoxy.

In some embodiments, compounds of Formula IV have the structure according to the following sub-generic structure Formula IVa:

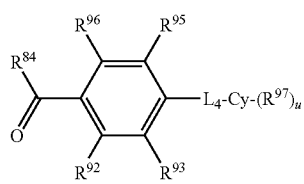

Formula IVa wherein:

$R^{84}$ is selected from the group consisting of hydrogen, lower alkoxy, —OH, and —Cl;

$R^{92}$, $R^{93}$, $R^{95}$, and $R^{96}$ are independently selected from the group consisting of hydrogen, halogen, lower alkyl, fluoro substituted lower alkyl, lower alkoxy, and fluoro substituted lower alkoxy;

$L_4$ is selected from the group consisting of —$NR^{48}$—, —S—, —O—, —$NR^{48}CH(R^{49})$—, —$SCH(R^{49})$—, —$OCH(R^{49})$—, —$C(O)NR^{48}$—, —$S(O)_2NR^{48}$—, —$CH(R^{49})NR^{48}$—, —$CH(R^{49})O$—, —$CH(R^{49})S$—, —$NR^{48}C(O)$—, and —$NR^{48}S(O)_2$—;

Cy is selected from the group consisting of cycloalkyl, heterocycloalkyl, aryl and heteroaryl;

$R^{97}$ at each occurrence is independently selected from the group consisting of —OH, —$NH_2$, —CN, —$NO_2$, —C(O)OH, —$S(O)_2NH_2$, —$C(O)NH_2$, —$OR^{57}$, —$SR^{57}$, —$NR^{48}R^{57}$, —$NR^{48}C(O)R^{57}$, —$NR^{48}S(O)_2R^{57}$, —$S(O)_2R^{57}$, —$C(O)R^{57}$, —$C(O)OR^{57}$, —$C(O)NR^{48}R^{57}$, —$S(O)_2NR^{48}R^{57}$, halogen, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, wherein cycloalkyl, heterocycloalkyl, aryl, and heteroaryl as $R^{97}$, or as substituents of lower alkyl, are optionally substituted with one or more substituents selected from the group consisting of —OH, —$NH_2$, —CN, —$NO_2$, —C(O)OH, —$S(O)_2NH_2$, —$C(O)NH_2$, —$OR^{58}$, —$SR^{58}$, —$NR^{48}R^{58}$, —$NR^{48}C(O)R^{58}$, —$NR^{48}S(O)_2R^{58}$, —$S(O)_2R^{58}$, —$C(O)R^{58}$, —$C(O)OR^{58}$, —$C(O)NR^{48}R^{58}$, —$S(O)_2NR^{48}R^{58}$, halogen, lower alkyl, fluoro substituted lower alkyl, and cycloalkylamino;

$R^{49}$ is selected from the group consisting of hydrogen, lower alkyl, and fluoro substituted lower alkyl;

$R^{57}$ is selected from the group consisting of lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, provided, however, that any substitution of the alkyl carbon bound to O, S, or N of —$OR^{57}$, —$SR^{57}$, —$NR^{48}R^{57}$, —$C(O)OR^{57}$, —$C(O)NR^{48}R^{57}$, or —$S(O)_2NR^{48}R^{57}$ is fluoro, cycloalkyl, heterocycloalkyl, aryl or heteroaryl, wherein cycloalkyl, heterocycloalkyl, aryl, and heteroaryl as $R^{57}$ or as substituents of lower alkyl are optionally substituted with one or more substituents selected from the group consisting of —OH, —$NH_2$, —CN, —$NO_2$, —C(O)OH, —$S(O)_2NH_2$, —$C(O)NH_2$, —$OR^{58}$, —$SR^{58}$, —$NR^{48}R^{58}$, —$NR^{48}C(O)R^{58}$, —$NR^{48}S(O)_2R^{58}$, —$S(O)_2R^{58}$, —$C(O)R^{58}$, —$C(O)OR^{58}$, —$C(O)NR^{48}R^{58}$, —$S(O)_2NR^{48}R^{58}$, halogen, lower alkyl, fluoro substituted lower alkyl, and cycloalkylamino; and $R^{58}$ at each occurrence is independently selected from the group consisting of lower alkyl, heterocycloalkyl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, and cycloalkylamino, provided, however, that any substitution of the alkyl carbon bound to O, S, or N of —$OR^{58}$, —$SR^{58}$, —$NR^{48}R^{58}$, —$C(O)OR^{58}$, —$C(O)NR^{48}R^{58}$, or —$S(O)_2NR^{48}R^{58}$ is fluoro;

$R^{48}$ at each occurrence is independently hydrogen or lower alkyl; and u is 0, 1, 2, or 3.

In one embodiment of compounds of Formula IVa, at least two of $R^{92}$, $R^{93}$, $R^{95}$ and $R^{96}$ are hydrogen. In one embodiment, at least two of $R^{92}$, $R^{93}$, $R^{95}$ and $R^{96}$ are hydrogen, $L_1$ is —$NR^{48}CH(R^{49})$—, —$SCH(R^{49})$—, or —$OCH(R^{49})$—, preferably $L_4$ is —$OCH_2$—, Cy is aryl or heteroaryl, and each $R^{97}$ is independently selected from the group consisting of halogen, lower alkyl, fluoro substituted lower alkyl, lower alkoxy, and fluoro substituted lower alkoxy.

In some embodiments, compounds of Formula IV have the structure according to the following sub-generic structure Formula IVb:

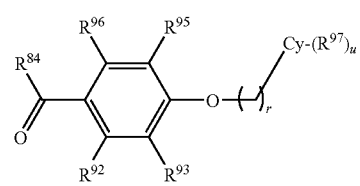

Formula IVb wherein $R^{84}$, $R^{92}$, $R^{93}$, $R^{95}$, $R^{96}$, $R^{97}$, Cy and u are as defined for Formula IVa and r is 0, 1 or 2.

In some embodiments of compounds of Formula IVb, at least two of $R^{92}$, $R^{93}$, $R^{95}$ and $R^{96}$ are hydrogen. In some embodiments, at least two of $R^{92}$, $R^{93}$, $R^{95}$ and $R^{96}$ are hydrogen, Cy is aryl or heteroaryl, and each $R^{97}$ is independently selected from the group consisting of halogen, lower alkyl, fluoro substituted lower alkyl, lower alkoxy, and fluoro substituted lower alkoxy.

In some embodiments, compounds of Formula V have the structure according to the following sub-generic structure Formula Va:

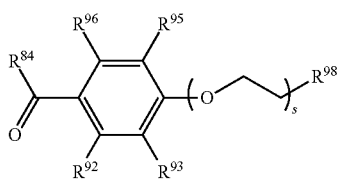

Formula Va wherein:
$R^{84}$ is selected from the group consisting of hydrogen, lower alkoxy, —OH, and —Cl;
$R^{92}$, $R^{93}$, $R^{95}$, and $R^{96}$ are independently selected from the group consisting of hydrogen, halogen, lower alkyl, fluoro substituted lower alkyl, lower alkoxy, and fluoro substituted lower alkoxy;
$R^{98}$ is selected from the group consisting of hydrogen, lower alkyl, fluoro substituted lower alkyl, lower alkoxy, and fluoro substituted lower alkoxy; and
s is 0, 1, or 2;

In some embodiments, compounds of Formula VI have the structure according to the following sub-generic structure Formula VIa:

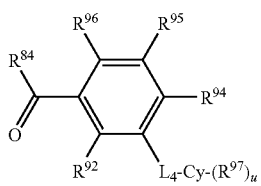

Formula VIa wherein:
$R^{84}$ is selected from the group consisting of hydrogen, lower alkoxy, —OH, and —Cl;
$R^{92}$, $R^{94}$, $R^{95}$, and $R^{96}$ are independently selected from the group consisting of hydrogen, halogen, lower alkyl, fluoro substituted lower alkyl, lower alkoxy, and fluoro substituted lower alkoxy;
$L_4$ is selected from the group consisting of —$NR^{48}$—, —S—, —O—, —$NR^{48}CH(R^{49})$—, —$SCH(R^{49})$—, —$OCH(R^{49})$—, —$C(O)NR^{48}$—, —$S(O)_2NR^{48}$—, —$CH(R^{49})NR^{48}$—, —$CH(R^{49})O$—, —$CH(R^{49})S$—, —$NR^{48}C(O)$—, and —$NR^{48}S(O)_2$—;
Cy is selected from the group consisting of cycloalkyl, heterocycloalkyl, aryl and heteroaryl;
$R^{97}$ at each occurrence is independently selected from the group consisting of —OH, —$NH_2$, —CN, —$NO_2$, —C(O)OH, —$S(O)_2NH_2$, —$C(O)NH_2$, —$OR^{57}$, —$SR^{57}$, —$NR^{48}R^{57}$, —$NR^{48}C(O)R^{57}$, —$NR^{48}S(O)_2R^{57}$, —$S(O)_2R^{57}$, —$C(O)R^{57}$, —$C(O)OR^{57}$, —$C(O)NR^{48}R^{57}$, —$S(O)_2NR^{48}R^{57}$, halogen, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, wherein cycloalkyl, heterocycloalkyl, aryl, and heteroaryl as $R^{97}$, or as substituents of lower alkyl, are optionally substituted with one or more substituents selected from the group consisting of —OH, —$NH_2$, —CN, —$NO_2$, —C(O)OH, —$S(O)_2NH_2$, —$C(O)NH_2$, —$OR^{58}$, —$SR^{58}$, —$NR^{48}R^{58}$, —$NR^{48}C(O)R^{58}$, —$NR^{48}S(O)_2R^{58}$, —$S(O)_2R^{58}$, —$C(O)R^{58}$, —$C(O)NR^{48}R^{58}$, —$S(O)_2NR^{48}R^{58}$, halogen, lower alkyl, fluoro substituted lower alkyl, and cycloalkylamino;

$R^{49}$ is selected from the group consisting of hydrogen, lower alkyl, and fluoro substituted lower alkyl;
$R^{57}$ is selected from the group consisting of lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, provided, however, that any substitution of the alkyl carbon bound to O, S, or N of —$OR^{57}$, —$SR^{57}$, —$NR^{48}R^{57}$, —$C(O)OR^{57}$, —$C(O)NR^{48}R^{57}$, or —$S(O)_2NR^{48}R^{57}$ is fluoro, cycloalkyl, heterocycloalkyl, aryl or heteroaryl, wherein cycloalkyl, heterocycloalkyl, aryl, and heteroaryl as $R^{57}$ or as substituents of lower alkyl are optionally substituted with one or more substituents selected from the group consisting of —OH, —$NH_2$, —CN, —$NO_2$, —C(O)OH, —$S(O)_2NH_2$, —$C(O)NH_2$, —$OR^{58}$, —$SR^{58}$, —$NR^{48}R^{58}$, —$NR^{48}C(O)R^{58}$, —$NR^{48}S(O)_2R^{58}$, —$S(O)_2R^{58}$, —$C(O)R^{58}$, —$C(O)OR^{58}$, —$C(O)NR^{48}R^{58}$, —$S(O)_2NR^{48}R^{58}$, halogen, lower alkyl, fluoro substituted lower alkyl, and cycloalkylamino;

$R^{58}$ at each occurrence is independently selected from the group consisting of lower alkyl, heterocycloalkyl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, and cycloalkylamino, provided, however, that any substitution of the alkyl carbon bound to O, S, or N of —$OR^{58}$, —$SR^{58}$, —$NR^{48}R^{58}$, —$C(O)OR^{58}$, —$C(O)NR^{48}R^{58}$, or —$S(O)_2NR^{48}R^{58}$ is fluoro;

$R^{48}$ at each occurrence is independently hydrogen or lower alkyl; and
u is 0, 1, 2 or 3.

In some embodiments of compounds of Formula VIa, at least two of $R^{92}$, $R^{94}$, $R^{95}$ and $R^{96}$ are hydrogen. In some embodiments, at least two of $R^{92}$, $R^{94}$, $R^{95}$ and $R^{96}$ are hydrogen, $L_4$ is —$NR^{48}CH(R^{49})$—, —$SCH(R^{49})$—, or —$OCH(R^{49})$—, preferably $L_4$ is —$OCH_2$—, Cy is aryl or heteroaryl, and each $R^{97}$ is independently selected from the group consisting of halogen, lower alkyl, fluoro substituted lower alkyl, lower alkoxy, and fluoro substituted lower alkoxy.

In some embodiments, compounds of Formula VI have the structure according to the following sub-generic structure Formula VIb:

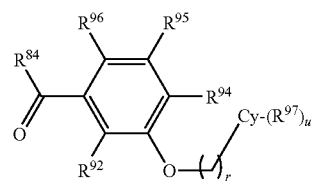

Formula VIb wherein $R^{84}$, $R^{92}$, $R^{94}$, $R^{95}$, $R^{96}$, $R^{97}$, Cy and u are as defined for Formula VIa and r is 0, 1 or 2.

In some embodiments of compounds of Formula VIb, at least two of $R^{92}$, $R^{94}$, $R^{95}$ and $R^{96}$ are hydrogen. In some embodiments, at least two of $R^{92}$, $R^{94}$, $R^{95}$ and $R^{96}$ are hydrogen, Cy is aryl or heteroaryl, and each $R^{97}$ is independently selected from the group consisting of halogen, lower alkyl, fluoro substituted lower alkyl, lower alkoxy, and fluoro substituted lower alkoxy.

In some embodiments, compounds of Formula VII have the structure according to the following sub-generic structure Formula VIIa:

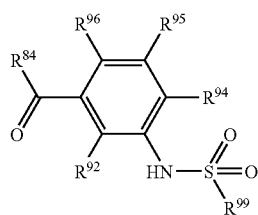

Formula VIIa wherein:

$R^{84}$ is selected from the group consisting of hydrogen, lower alkoxy, —OH, and —Cl;

$R^{92}$, $R^{94}$, $R^{95}$, and $R^{96}$ are independently selected from the group consisting of hydrogen, halogen, lower alkyl, fluoro substituted lower alkyl, lower alkoxy, and fluoro substituted lower alkoxy;

$R^{99}$ is selected from the group consisting of optionally substituted lower alkyl, optionally substituted aryl, optionally substituted heteroaryl, and —$NR^{79}R^{80}$; and $R^{79}$ and $R^{80}$ are independently hydrogen or optionally substituted lower alkyl, or $R^{79}$ and $R^{80}$ combine with the nitrogen to which they are attached to form optionally substituted 5-7 membered heterocycloalkyl.

In some embodiments of compounds of Formula VIIa, one of $R^{92}$ and $R^{96}$ is selected from the group consisting of hydrogen, halogen, lower alkyl, fluoro substituted lower alkyl, lower alkoxy, and fluoro substituted lower alkoxy, and the other of $R^{92}$ and $R^{96}$ is selected from the group consisting of halogen, lower alkyl, fluoro substituted lower alkyl, lower alkoxy, and fluoro substituted lower alkoxy; in further embodiments, one of $R^{92}$ and $R^{96}$ is hydrogen, fluoro or chloro, and the other of $R^{92}$ and $R^{96}$ is fluoro or chloro; in further embodiments, $R^{92}$ is fluoro and $R^{96}$ is hydrogen, fluoro, or chloro; in further embodiments, $R^{92}$ and $R^{96}$ are both fluoro.

In some embodiments of compounds of Formula VIIa, $R^{94}$ and $R^{95}$ are hydrogen; in further embodiments, one of $R^{92}$ and $R^{96}$ is selected from the group consisting of hydrogen, halogen, lower alkyl, fluoro substituted lower alkyl, lower alkoxy, and fluoro substituted lower alkoxy and the other of $R^{92}$ and $R^{96}$ is selected from the group consisting of halogen, lower alkyl, fluoro substituted lower alkyl, lower alkoxy, and fluoro substituted lower alkoxy; in further embodiments, one of $R^{92}$ and $R^{96}$ is selected from hydrogen, fluoro or chloro and the other of $R^{92}$ and $R^{96}$ is selected from fluoro or chloro; in further embodiments, $R^{92}$ is fluoro and $R^{96}$ is selected from hydrogen, fluoro, or chloro; in further embodiments, $R^{92}$ and $R^{96}$ are both fluoro.

In some embodiments, compounds of Formula VII have the structure according to the following sub-generic structure Formula VIIb:

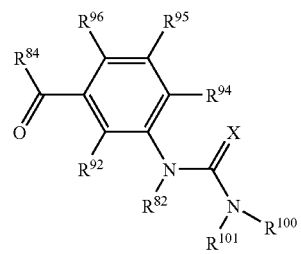

Formula VIIb wherein:

X is O or S;

$R^{84}$ is selected from the group consisting of hydrogen, lower alkoxy, —OH, and —Cl;

$R^{92}$, $R^{94}$, $R^{95}$, and $R^{96}$ are independently selected from the group consisting of hydrogen, halogen, lower alkyl, fluoro substituted lower alkyl, lower alkoxy, and fluoro substituted lower alkoxy;

$R^{82}$ is hydrogen or lower alkyl;

one of $R^{100}$ and $R^{101}$ is lower alkyl, fluoro substituted lower alkyl, or —$(CH_2)_{0-7}R^{70}$, and the other of $R^{100}$ and $R^{101}$ is hydrogen or lower alkyl; or $R^{100}$ and $R^{101}$ together with the nitrogen to which they are attached form optionally substituted 5-7 membered heterocycloalkyl or optionally substituted 5 or 7 membered nitrogen containing heteroaryl; and $R^{70}$ is selected from the group consisting of optionally substituted cycloalkyl, optionally substituted heterocycloalkyl, optionally substituted aryl, and optionally substituted heteroaryl.

In some embodiments of compounds of Formula VIIb, at least two of $R^{92}$, $R^{94}$, $R^{95}$ and $R^{96}$ are hydrogen. In some embodiments, at least two of $R^{92}$, $R^{94}$, $R^{55}$ and $R^{96}$ are hydrogen, and $R^{70}$ is aryl or heteroaryl, wherein aryl and heteroaryl are optionally substituted with one or more substituents selected from the group consisting of halogen, lower alkyl, fluoro substituted lower alkyl, lower alkoxy, and fluoro substituted lower alkoxy.

In some embodiments, compounds of Formula VIII have the structure according to the following sub-generic structure Formula VIIIa:

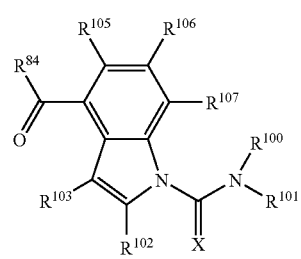

Formula VIIIa wherein:

X is O or S;

$R^{84}$ is selected from the group consisting of hydrogen, lower alkoxy, —OH, and —Cl;

$R^{102}$, $R^{103}$, $R^{105}$, $R^{106}$, and $R^{107}$ are independently selected from the group consisting of hydrogen, halogen, lower alkyl, fluoro substituted lower alkyl, lower alkoxy, and fluoro substituted lower alkoxy;

one of $R^{100}$ and $R^{101}$ is lower alkyl, fluoro substituted lower alkyl, or —$(CH_2)_{0-2}R^{70}$ and the other of $R^{100}$ and $R^{101}$ is hydrogen or lower alkyl;

or $R^{100}$ and $R^{101}$ together with the nitrogen to which they are attached form optionally substituted 5-7 membered heterocycloalkyl or optionally substituted 5 or 7 membered nitrogen containing heteroaryl; and $R^{70}$ is selected from the group consisting of optionally substituted cycloalkyl, optionally substituted heterocycloalkyl, optionally substituted aryl, and optionally substituted heteroaryl.

In some embodiments of compounds of Formula VIIIa, at least two, also at least three, also at least four, or all of $R^{102}$, $R^{103}$, $R^{105}$, $R^{106}$, and $R^{107}$ are hydrogen. In some embodiments, at least two, also at least three, also at least four, or all of $R^{102}$, $R^{103}$, $R^{105}$, $R^{106}$, and $R^{107}$ are hydrogen, and $R^{70}$ is aryl or heteroaryl, wherein aryl and heteroaryl are optionally substituted with one or more substituents selected from the group consisting of halogen, lower alkyl, fluoro substituted lower alkyl, lower alkoxy, and fluoro substituted lower alkoxy.

In some embodiments, compounds of Formula IX have the structure according to the following sub-generic structure Formula IXa:

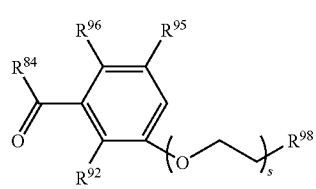

Formula IXa wherein:
$R^{84}$ is selected from the group consisting of hydrogen, lower alkoxy, —OH, and —Cl;
$R^{92}$, $R^{95}$, and $R^{96}$ are independently selected from the group consisting of hydrogen, halogen, lower alkyl, fluoro substituted lower alkyl, lower alkoxy, and fluoro substituted lower alkoxy;
$R^{98}$ is selected from the group consisting of hydrogen, lower alkyl, fluoro substituted lower alkyl, lower alkoxy, and fluoro substituted lower alkoxy; and
s is 0, 1, or 2;

In some embodiments of any of the above embodiments of compounds of Formula IVa, IVb, Va, VIa, VIb, VIIa, VIIb, VIIIa, or IXa, $R^{84}$ is hydrogen.

In some embodiments of the above compounds, compounds are excluded where N (except where N is a heteroaryl ring atom), O, or S is bound to a carbon that is also bound to N (except where N is a heteroaryl ring atom), O, or S; or where N (except where N is a heteroaryl ring atom), O, C(S), C(O), or S(O)$_n$, (n is 0-2) is bound to an alkene carbon of an alkenyl group or bound to an alkyne carbon of an alkynyl group; accordingly, in some embodiments compounds which include linkages such as the following are excluded from the present invention: —NR—CH$_2$—NR—, —O—CH$_2$—NR—, —S—CH$_2$—NR—, —NR—CH$_2$—O—, —O—CH$_2$—O—, —S—CH$_2$—O—, —NR—CH$_2$—S—, —O—CH$_2$—S—, —S—CH$_2$—S—, —NR—CH=CH—, —CH=CH—NR—, —NR—C≡C—, —C≡C—NR—, —O—CH=CH—, —CH=CH—O—, —O—C≡C—, —C≡C—O—, —S(O)$_{0-2}$—CH=CH—, —CH=CH—S(O)$_{0-2}$—, —S(O)$_{0-2}$—C≡C—, —C≡C—S(O)$_{0-2}$—, —C(O)—CH=CH—, —CH=CH—C(O)—, —C≡C—C(O)—, or —C(O)—C≡C—, —C(S)—CH=CH—, —CH=CH—C(S)—, —C≡C—C(S)—, or —C(S)—C≡C—.

In reference to compounds herein, specification of a compound or group of compounds includes pharmaceutically acceptable salts of such compound(s) unless clearly indicated to the contrary, prodrug(s), and all stereoisomers. In reference to compositions, kits, methods of use, etc. of compounds of Formula I described herein, it is understood that a compound of Formula I includes compounds of Formulae Ia-Iz, and all sub-embodiments thereof, compounds of Formula II, including Formulae IIa-IIo, and all sub-embodiments thereof, and compounds of Formula III, including Formulae IIIc-IIIq, and all sub-embodiments thereof, unless indicated otherwise. In reference to compositions, kits, methods of use, etc. of compounds of Formula II described herein, it is understood that this includes compounds of Formulae IIa-IIo, and all sub-embodiments thereof, unless indicated otherwise. In reference to compositions, kits, methods of use, etc. of compounds of Formula III described herein, it is understood that this includes compounds of Formulae II and all sub-embodiments thereof, unless indicated otherwise.

In one aspect, the invention provides methods for treating a protein kinase mediated disease or condition in an animal subject, wherein the method involves administering to the subject an effective amount of a compound of Formula I. The terms "treat," "therapy," and like terms refer to the administration of material, e.g., compound of Formula I, in an amount effective to prevent, alleviate, or ameliorate one or more symptoms of a disease or condition, i.e., indication, and/or to prolong the survival of the subject being treated. The term "protein kinase mediated disease or condition" refers to a disease or condition in which the biological function of a protein kinase affects the development and/or course of the disease or condition, and/or in which modulation of the protein kinase alters the development, course, and/or symptoms of the disease or condition. A protein kinase mediated disease or condition includes a disease or condition for which modulation provides a therapeutic benefit, e.g. wherein treatment with protein kinase inhibitors, including compounds described herein, provides a therapeutic benefit to the subject suffering from or at risk of the disease or condition. In one aspect, the method involves administering to the subject an effective amount of a compound of Formula I in combination with one or more other therapies for the disease or condition.

In one aspect, the invention provides methods for treating a protein kinase mediated disease or condition in an animal subject, wherein the method involves administering to the subject an effective amount of a compound of any one or more of Formula Ia through Formula Iz, and all sub-embodiments thereof.

In another aspect, the invention provides methods for treating a protein kinase mediated disease or condition in an animal subject, wherein the method involves administering to the subject an effective amount of a compound of Formula II.

In another aspect, the invention provides methods for treating a protein kinase mediated disease or condition in an animal subject, wherein the method involves administering to the subject an effective amount of a compound of any one or more of Formula IIa through Formula IIo, and all sub-embodiments thereof.

In another aspect, the invention provides methods for treating a protein kinase mediated disease or condition in an animal subject, wherein the method involves administering to the subject an effective amount of a compound of Formula III.

In another aspect, the invention provides methods for treating a protein kinase mediated disease or condition in an animal subject, wherein the method involves administering to the subject an effective amount of a compound of any one or more of Formula IIIa through Formula IIIq, and all sub-embodiments thereof.

In one aspect, the invention provides methods for treating a Raf protein kinase mediated disease or condition in an animal subject, wherein the method involves administering to the subject an effective amount of a compound of Formula I. The terms "Raf protein kinase mediated disease or condition," "Raf mediated disease or condition," and the like refer to a disease or condition in which the biological function of a Raf kinase, including any mutations thereof, affects the development and/or course of the disease or condition, and/or in which modulation of the Raf protein kinase alters the development, course, and/or symptoms of the disease or condition. The Raf protein kinase includes, but is not limited to, B-Raf, mutations of B-Raf, c-Raf-1 and mutations of c-Raf-1. In some embodiments, the Raf protein kinase is B-Raf mutation V600E. In further embodiments, the disease or condition is a cancer that is amenable to treatment by an inhibitor of the V600E mutant B-Raf. A Raf protein kinase mediated disease or condition includes a disease or condition for which Raf inhibition provides a therapeutic benefit, e.g. wherein treatment with Raf inhibitors, including compounds described herein, provides a therapeutic benefit to the subject suffering from or at risk of the disease or condition. In one aspect, the method involves administering to the subject an effective amount of a compound of Formula I in combination with one or more other therapies for the disease or condition.

In one aspect, the invention provides methods for treating a Raf protein kinase mediated disease or condition in an animal subject, wherein the method involves administering to the subject an effective amount of a compound of Formula IIa or III. In one aspect, the method involves administering to the subject an effective amount of a compound of Formula IIa or III in combination with one or more other therapies for the disease, further wherein the compound is of Formula IIIj, IIIk, or IIIm. The Raf protein kinase includes, but is not limited to, B-Raf, mutations of B-Raf, c-Raf-1 and mutations of c-Raf-1. In some embodiments, the Raf protein kinase is B-Raf mutation V600E. In further embodiments, the disease or condition is a cancer that is amenable to treatment by an inhibitor of the V600E mutant B-Raf.

In one aspect, the invention provides methods for treating a Fms protein kinase mediated disease or condition in an animal subject, wherein the method involves administering to the subject an effective amount of a compound of Formula I. The terms "Fms protein kinase mediated disease or condition," "Fms mediated disease or condition," and the like refer to a disease or condition in which the biological function of a Fms protein kinase, including any mutations thereof, affects the development and/or course of the disease or condition, and/or in which modulation of Fms alters the development, course, and/or symptoms of the disease or condition. A Fms mediated disease or condition includes a disease or condition for which Fms inhibition provides a therapeutic benefit, e.g. wherein treatment with Fms inhibitors, including compounds described herein, provides a therapeutic benefit to the subject suffering from or at risk of the disease or condition. In one aspect, the method involves administering to the subject an effective amount of a compound of Formula I in combination with one or more other therapies for the disease or condition.

In one aspect, the invention provides methods for treating a Kit protein kinase mediated disease or condition in an animal subject, wherein the method involves administering to the subject an effective amount of a compound of Formula I. The terms "Kit mediated disease or condition," "Kit protein kinase mediated disease or condition," and the like refer to a disease or condition in which the biological function of a Kit protein kinase, including any mutation thereof, affects the development and/or course of the disease or condition, and/or in which modulation of Kit alters the development, course, and/or symptoms of the disease or condition. A Kit mediated disease or condition includes a disease or condition for which Kit inhibition provides a therapeutic benefit, e.g. wherein treatment with Kit inhibitors, including compounds described herein, provides a therapeutic benefit to the subject suffering from or at risk of the disease or condition. In one aspect, the method involves administering to the subject an effective amount of a compound of Formula I in combination with one or more other therapies for the disease or condition.

In one aspect, the invention provides methods for treating a Jnk protein kinase mediated disease or condition in an animal subject, wherein the method involves administering to the subject an effective amount of a compound of Formula I. The terms "Jnk mediated disease or condition," "Jnk protein kinase mediated disease or condition," and the like refer to a disease or condition in which the biological function of a Jnk kinase, e.g. Jnk1, Jnk2, Jnk3, or any mutation thereof, affects the development and/or course of the disease or condition, and/or in which modulation of the Jnk kinase alters the development, course, and/or symptoms of the disease or condition. A Jnk mediated disease or condition includes a disease or condition for which Jnk inhibition provides a therapeutic benefit, e.g. wherein treatment with ink inhibitors, including compounds described herein, provides a therapeutic benefit to the subject suffering from or at risk of the disease or condition. In one aspect, the method involves administering to the subject an effective amount of a compound of Formula I in combination with one or more other therapies for the disease or condition. The Jnk protein kinase includes, but is not limited to, Jnk1, Jnk2, or Jnk3.

In some embodiments, a compound of Formula I will have an $IC_{50}$ of less than 500 nm, less than 100 nM, less than 50 nM, less than 20 nM, less than 10 nM, less than 5 nM, or less than 1 nM as determined in a generally accepted kinase activity assay. In some embodiments, a compound of any of Formula I will have an $IC_{50}$ of less than 500 nm, less than 100 nM, less than 50 nM, less than 20 nM, less than 10 nM, less than 5 nM, or less than 1 nM with respect to at least one kinase selected from the group consisting of Abl, Akt1, Akt2, Akt3, ALK, Alk5, B-Raf, Brk, Btk, Cdk2, CDK4, CDK5, CDK6, CHK1, c-Raf-1, Csk, EGFR, EphA1, EphA2, EphB2, EphB4, Erk2, Fak, FGFR1, FGFR2, FGFR3, FGFR4, Flt1, Flt3, Flt4, Fms, Frk, Fyn, Gsk3α, Gsk3β, HCK, Her2/Erbb2, Her4/Erbb4, IGF1R, IKK beta, Irak4, Itk, Jak1, Jak2, Jak3, Jnk1, Jnk2, Jnk3, Kdr, Kit, LCK, MAP2K1, MAP2K2, MAP4K4, MAPKAPK2, Met, Mnk1, MLK1, p38, PDGFRA, PDGFRB, PDPK1, Pim1, Pim2, Pim3, PKC alpha, PKC beta, PKC theta, Plk1, Pyk2, ROCK1, ROCK2, Ron, Src, Stk6, Syk, TEC, Tie2, TrkA, Yes, and Zap70, including any mutations thereof.

In some embodiments, a compound of Formula I will have an $IC_{50}$ of less than 500 nm, less than 100 nM, less than 50 nM, less than 20 nM, less than 10 nM, less than 5 nM, or less than 1 nM with respect to at least one kinase selected from the group consisting of Abl, Akt 1, Akt2, Akt3, ALK, Alk5, B-Raf, Btk, Cdk2, CDK4, CDK5, CDK6, CHK1, c-Raf-1, Csk, EGFR, EphA1, EphA2, EphB2, EphB4, Erk2, Fak, Fms, Fyn, Gsk3α, Gsk3β, HCK, Her2/Erbb2, Her4/Erbb4, IGF1R, IKK beta, Irak4, Itk, Jak1, Jak2, Jak3, Jnk1, Jnk2, Jnk3, Kit, LCK, MAP2K1, MAP2K2, MAP4K4, MAPKAPK2, Met, Mnk1, MLK1, p38, PDPK1, Pim1, Pim2, Pim3, PKC alpha, PKC beta, PKC theta, Plk1, Pyk2, Ron, Src, Stk6, Syk, TEC, Tie2, TrkA, Yes, and Zap70, including any mutations thereof.

In some embodiments, a compound of Formula I will have an $IC_{50}$ of less than 500 nm, less than 100 nM, less than 50 nM, less than 20 nM, less than 10 nM, less than 5 nM, or less than 1 nM with respect to at least one kinase selected from the group consisting of Abl, B-Raf, Btk, c-Raf-1, EGFR, EphB2, Erk2, Fak, FGFR1, Flt1, Flt3, Flt4, Fms, Irak4, Jnk1, Jnk2, Jnk3, Kdr, Kit, MAP2K1, MAPKAP kinase 2, Met, p38, PDGFRB, Pim1, PKC theta, Pyk2, Ret, Src, Stk6, Yes, and Zap70, including any mutations thereof.

In some embodiments, a compound of Formula I will have an $IC_{50}$ of less than 500 nm, less than 100 nM, less than 50 nM, less than 20 nM, less than 10 nM, less than 5 nM, or less than 1 nM with respect to at least one kinase selected from the group consisting of Abl, B-Raf, Btk, c-Raf-1, EGFR, EphB2, Erk2, Fak, Fms, Irak4, Jnk1, Jnk2, Jnk3, Kit, MAP2K1, MAPKAP kinase 2, Met, p38, Pim1, PKC theta, Pyk2, Src, Stk6, Yes, and Zap70, including any mutations thereof.

In some embodiments, a compound of Formula II will have an $IC_{50}$ of less than 500 nm, less than 100 nM, less than 50 nM, less than 20 nM, less than 10 nM, less than 5 nM, or less than 1 nM with respect to at least one kinase selected from the group consisting of B-Raf, B-Raf V600E mutant, c-Raf-1, FGFR1, FGFR2, FGFR3, FGFR4, Jnk1, Jnk2, Jnk3, Met, Pim1, Pim2, Pim3, Pyk2, Kdr and Ret, including any mutations thereof.

In some embodiments, a compound of Formula III will have an $IC_{50}$ of less than 500 nm, less than 100 nM, less than 50 nM, less than 20 nM, less than 10 nM, less than 5 nM, or less than 1 nM with respect to at least one kinase selected from the group consisting of B-Raf, c-Raf-1, Fms, Jnk1, Jnk2, Jnk3, and Kit, and any mutations thereof. In some embodiments, a compound of any of Formula III will have an $IC_{50}$ of less than 500 nm, less than 100 nM, less than 50 nM, less than 20 nM, less than 10 nM, less than 5 nM, or less than 1 nM with respect to at least one kinase selected from the group consisting of B-Raf, B-Raf V600E mutant, c-Raf-1, Fms, Jnk1, Jnk2, Jnk3, and Kit, preferably B-Raf, B-Raf V600E mutant or c-Raf-1.

In some embodiments, a compound of Formula III is an inhibitor of a Raf kinase and has an $IC_{50}$ of less than 500 nm, less than 100 nM, less than 50 nM, less than 20 nM, less than 10 nM, less than 5 nM, or less than 1 nM as determined in a generally accepted Raf kinase activity assay. In some embodiments, a compound of Formula III will have an $IC_{50}$ of less than 500 nm, less than 100 nM, less than 50 nM, less than 20 nM, less than 10 nM, less than 5 nM, or less than 1 nM with respect to B-Raf, c-Raf-1, or B-Raf V600E mutant. In some embodiments, a compound of Formula III will selectively inhibit one Raf kinase relative to one or more other Raf kinases. In some embodiments, the compound of Formula III will selectively inhibit a mutation of the Raf kinase relative to the wild type kinase, for example B-Raf V600E relative to wild type B-Raf.

In some embodiments, a compound of Formula III is an inhibitor of a Fms kinase and has an $IC_{50}$ of less than 500 nm, less than 100 nM, less than 50 nM, less than 20 nM, less than 10 nM, less than 5 nM, or less than 1 nM as determined in a generally accepted Fms kinase activity assay. In some embodiments, a compound of Formula III will selectively inhibit Fms kinase relative to Kit kinase.

In some embodiments, a compound of Formula III is an inhibitor of a Kit kinase and has an $IC_{50}$ of less than 500 nm, less than 100 nM, less than 50 nM, less than 20 nM, less than 10 nM, less than 5 nM, or less than 1 nM as determined in a generally accepted Kit kinase activity assay.

In some embodiments, a compound of Formula III is an inhibitor of a Jnk kinase and has an $IC_{50}$ of less than 500 nm, less than 100 nM, less than 50 nM, less than 20 nM, less than 10 nM, less than 5 nM, or less than 1 nM as determined in a generally accepted Jnk kinase activity assay. In some embodiments, a compound of Formula III is an inhibitor of a Jnk1 kinase and has an $IC_{50}$ of less than 500 nm, less than 100 nM, less than 50 nM, less than 20 nM, less than 10 nM, less than 5 nM, or less than 1 nM as determined in a generally accepted Jnk1 kinase activity assay. In some embodiments, a compound of Formula III is an inhibitor of a Jnk2 kinase and has an $IC_{50}$ of less than 500 nm, less than 100 nM, less than 50 nM, less than 20 nM, less than 10 nM, less than 5 nM, or less than 1 nM as determined in a generally accepted Jnk2 kinase activity assay. In some embodiments, a compound of Formula III is an inhibitor of a Jnk3 kinase and has an $IC_{50}$ of less than 500 nm, less than 100 nM, less than 50 nM, less than 20 nM, less than 10 nM, less than 5 nM, or less than 1 nM as determined in a generally accepted Jnk3 kinase activity assay. In some embodiments, a compound of Formula III will selectively inhibit one ink kinase relative to one or more other Jnk kinases, such as selectively inhibiting Jnk 1 relative to Jnk 2 and/or Jnk3, selectively inhibiting Jnk2 relative to Jnk3 and/or Jnk1, or selectively inhibiting Jnk3 relative to Jnk1 and/or Jnk 2.

Further to any of the above mentioned embodiments, a compound of the invention will also inhibit the effects of a mutation of the kinase, including, but not limited to, a mutation that is related to a disease state, such as a cancer. For example, B-Raf V600E mutant is present in a high percentage of some cancers, such as melanoma, and compounds of the invention will inhibit the kinase activity of this mutant.

Further to any of the above embodiments, a compound of the invention may selectively inhibit one kinase relative to one or more other kinases, where preferably inhibition is selective with respect to any of the other kinases, whether a kinase discussed herein, or other kinases. In some embodiments, the compound may selectively inhibit the effects of a mutation of the kinase relative to the wild type kinase, for example B-Raf V600E relative to wild type B-Raf. In some embodiments, the compound may selectively inhibit Fms relative to Kit. Selective inhibition of one kinase relative to another is such that the $IC_{50}$ for the one kinase may be at least about 2-fold, also 5-fold, also 10-fold, also 20-fold, also 50-fold, or at least about 100-fold less than the $IC_{50}$ for any of the other kinases as determined in a generally accepted kinase activity assay.

In another aspect, the invention provides compositions that include a therapeutically effective amount of a compound of Formula I and at least one pharmaceutically acceptable carrier, excipient, and/or diluent. The composition can include a plurality of different pharmacologically active compounds, which can include a plurality of compounds of Formula I. In another aspect, the composition can include one or more compounds of Formula I, Formula II, or Formula III along with one or more compounds that are therapeutically effective for the same disease indication. In one aspect, the composition includes one or more compounds of Formula I, Formula II, or Formula III along with one or more compounds that are therapeutically effective for the same disease indication, wherein the compounds have a synergistic effect on the disease indication.

In another aspect, the invention provides compositions that include a therapeutically effective amount of at least one compound of Formula III and at least one pharmaceutically acceptable carrier, excipient, and/or diluent. The composition can include a plurality of different pharmacologically active compounds, which can include a plurality of compounds of Formula III, or can include at least one compound of Formula III along with at least one compound that is therapeutically effective for the same disease indication. In one aspect, the at least one compound of Formula III and the at least one compound that is therapeutically effective for the same disease indication have a synergistic effect on the disease indication. In one aspect, the composition includes one or more compounds of Formula III effective in treating a cancer and one or more other compounds that are effective in treating the cancer, further wherein the compounds are synergistically effective in treating the cancer.

In another aspect, the invention provides a method for modulating the activity of a protein kinase selected from the group consisting of Abl, Akt1, Akt2, Akt3, ALK, Alk5, B-Raf, Brk, Btk, Cdk2, CDK4, CDK5, CDK6, CHK1, c-Raf-1, Csk, EGFR, EphA1, EphA2, EphB2, EphB4, Erk2, Fak, FGFR1, FGFR2, FGFR3, FGFR4, Flt1, Flt3, Flt4, Fms, Frk, Fyn, Gsk3α, Gsk3β, HCK, Her2/Erbb2, Her4/Erbb4, IGF1R, IKK beta, Irak4, Itk, Jak1, Jak2, Jak3, Jnk1, Jnk2, Jnk3, Kdr, Kit, LCK, MAP2K1, MAP2K2, MAP4K4, MAPKAPK2, Met, Mnk1, MLK1, p38, PDGFRA, PDGFRB, PDPK1, Pim1, Pim2, Pim3, PKC alpha, PKC beta, PKC theta, Plk1, Pyk2, ROCK1, ROCK2, Ron, Src, Stk6, Syk, TEC, Tie2, TrkA, Yes, or Zap70 by contacting the protein kinase with an effective amount of a compound of Formula I.

In another aspect, the invention provides methods for treating a protein kinase mediated disease or condition in an animal subject, wherein the method involves administering to the subject an effective amount of a composition including a compound of Formula I.

In one aspect, the invention provides methods for treating a disease or condition mediated by a protein kinase selected from the group consisting of Abl, Akt 1, Akt2, Akt3, ALK, Alk5, B-Raf, Btk, Cdk2, CDK4, CDK5, CDK6, CHK1, c-Raf-1, Csk, EGFR, EphA1, EphA2, EphB2, EphB4, Erk2, Fak, FGFR1, FGFR2, FGFR3, FGFR4, Flt1, Flt3, Flt4, Fms, Fyn, Gsk3α, Gsk3β, HCK, Her2/Erbb2, Her4/Erbb4, IGF1R, IKK beta, Irak4, Itk, Jak1, Jak2, Jak3, Jnk1, Jnk2, Jnk3, Kdr, Kit, LCK, MAP2K1, MAP2K2, MAP4K4, MAPKAPK2, Met, Mnk1, MLK1, p38, PDGFRA, PDGFRB, PDPK1, Pim1, Pim2, Pim3, PKC alpha, PKC beta, PKC theta, Plk1, Pyk2, ROCK1, ROCK2, Ron, Src, Stk6, Syk, TEC, Tie2, TrkA, Yes, and Zap70 by administering to the subject an effective amount of a composition including a compound of Formula I.

In one aspect, the invention provides methods for treating a disease or condition mediated by a protein kinase selected from the group consisting of Abl, Akt 1, Akt2, Akt3, ALK, Alk5, B-Raf, Btk, Cdk2, CDK4, CDK5, CDK6, CHK1, c-Raf-1, Csk, EGFR, EphA1, EphA2, EphB2, EphB4, Erk2, Fak, Fms, Fyn, Gsk3α, Gsk3β, HCK, Her4/Erbb4, IGF1R, IKK beta, Irak4, Itk, Jak1, Jak2, Jak3, Jnk1, Jnk2, Jnk3, Kit, LCK, MAP2K1, MAP2K2, MAP4K4, MAPKAPK2, Met, Mnk1, MLK1, p38, PDPK1, Pim1, Pim2, Pim3, PKC alpha, PKC beta, PKC theta, Plk1, Pyk2, Ron, Src, Stk6, Syk, TEC, Tie2, TrkA, Yes, and Zap70 by administering to the subject an effective amount of a composition including a compound of Formula I.

In one aspect, the invention provides methods for treating a disease or condition mediated by a protein kinase selected from the group consisting of Abl, B-Raf, Btk, c-Raf-1, EGFR, EphB2, Erk2, Fak, FGFR1, Flt1, Flt3, Flt4, Fms, Irak4, Jnk1, Jnk2, Jnk3, Kdr, Kit, MAP2K1, MAPKAPK2, Met, p38, PDGFRB, Pim1, PKC theta, Pyk2, Rct, Src, Stk6, Yes, and Zap70 by administering to the subject an effective amount of a composition including a compound of Formula I.

In one aspect, the invention provides methods for treating a disease or condition mediated by a protein kinase selected from the group consisting of Abl, B-Raf, Btk, c-Raf-1, EGFR, EphB2, Erk2, Fak, Fms, Irak4, Jnk1, Jnk2, Jnk3, Kit, MAP2K1, MAPKAPK2, Met, p38, Pim1, PKC theta, Pyk2, Src, Stk6, Yes, and Zap70 by administering to the subject an effective amount of a composition including a compound of Formula I.

In one aspect, the invention provides methods for treating a disease or condition mediated by a protein kinase selected from the group consisting of B-Raf, B-Raf V600E mutant, c-Raf-1, FGFR1, FGFR2, FGFR3, FGFR4, Jnk1, Jnk2, Jnk3, Met, Pim1, Pim2, Pim3, Pyk2, Kdr and Ret by administering to the subject an effective amount of a composition including a compound of Formula I.

In one aspect, the invention provides methods for treating a disease or condition mediated by a protein kinase selected from the group consisting of B-Raf, c-Raf-1, Fms, Jnk1, Jnk2, Jnk3, and Kit, and any mutations thereof, by administering to the subject an effective amount of a composition including a compound of Formula III.

In one aspect, the invention provides methods for treating a disease or condition mediated by B-Raf, c-Raf-1, or B-Raf V600E by administering to the subject an effective amount of a composition including a compound of Formula II or Formula III, where in further embodiments, the compound is of Formula IIa or Formula III. In one aspect, the invention provides methods for treating a disease or condition mediated by B-Raf, c-Raf-1, or B-Raf V600E by administering to the subject an effective amount of a composition including a compound of Formula IIIj, IIIk, or IIIm in combination with one or more other suitable therapies for treating the disease. In one aspect, the invention provides methods for treating a cancer mediated by B-Raf V600E mutant by administering to the subject an effective amount of a composition of Formula IIIj, IIIk, or IIIm in combination with one or more suitable anticancer therapies, such as one or more chemotherapeutic drugs.

In one aspect, the invention provides a method of treating a cancer by administering to the subject an effective amount of a composition including a compound of Formula I, or where the compound is of Formula III, or where the compound is of Formula IIIj, IIIk, or IIIm, in combination with one or more other therapies or medical procedures effective in treating the cancer. Other therapies or medical procedures include suitable anticancer therapy (e.g. drug therapy, vaccine therapy, gene therapy, photodynamic therapy) or medical procedure (e.g. surgery, radiation treatment, hyperthermia heating, bone marrow or stem cell transplant). In one aspect, the one or more suitable anticancer therapies or medical procedures is selected from treatment with a chemotherapeutic agent (e.g. chemotherapeutic drug), radiation treatment (e.g. x-ray, γ-ray, or electron, proton, neutron, or α particle beam), hyperthermia heating (e.g. microwave, ultrasound, radiofrequency ablation), Vaccine therapy (e.g. AFP gene hepatocellular carcinoma vaccine, AFP adenoviral vector vaccine, AG-858, allogeneic GM-CSF-secretion breast cancer vaccine, dendritic cell peptide vaccines), gene therapy (e.g. Ad5CMV-p53 vector, adenovector encoding MDA7, adenovirus 5-tumor necrosis factor alpha), photodynamic therapy (e.g. aminolevulinic acid, motexafin lutetium), surgery, and bone marrow and stem cell transplantation.

In a preferred embodiment, the invention provides a method of treating a cancer by administering to the subject an effective amount of a composition including a compound of Formula I, or wherein the compound is of Formula II, or wherein the compound is of Formula IIIj, IIIk, or IIIm, in combination with one or more suitable chemotherapeutic agents. In one aspect, the one or more suitable chemotherapeutic agents is selected from an alkylating agent, including, but not limited to, adozelesin, altretamine, bizelesin, busulfan, carboplatin, carboquone, carmustine, chlorambucil, cisplatin, cyclophosphamide, dacarbazine, estramustine, fotemustine, hepsulfam, ifosfamide, improsulfan, irofulven, lomustine, mechlorethamine, melphalan, oxaliplatin, piposulfan, semustine, streptozocin, temozolomide, thiotepa, and treosulfan; an antibiotic, including, but not limited to, bleomycin, dactinomycin, daunorubicin, doxorubicin, epirubicin, idarubicin, menogaril, mitomycin, mitoxantrone, neocarzinostatin, pentostatin, and plicamycin; an antimetabolite, including, but not limited to, azacitidine, capecitabine, cladribine, clofarabine, cytarabine, decitabine, floxuridine, fludarabine, 5-fluorouracil, ftorafur, gemcitabine, hydroxyurea, mercaptopurine, methotrexate, nelarabine, pemeterxed, raltitrexed, thioguanine, and trimeterxate; an immunotherapy, including, but not limited to, alemtuzumab, bevacizumab, cetuximab, galiximab, gemtuzumab, panitumumab, pertuzumab, rituximab, tositumomab, trastuzumab, and 90 Y ibritumomab tiuxetan; a hormone or hormone antagonist, including, but not limited to, anastrozole, androgens, buserelin, diethylstilbestrol, exemestane, flutamide, fulvestrant, goserelin, idoxifene, letrozole, leuprolide, magestrol, raloxifene, tamoxifen, and toremifene; a taxane, including, but not limited to, DJ-927, docetaxel, TPI 287, paclitaxel and DHA-paclitaxel; a retinoid, including, but not limited to, alitertinoin, bexarotene, fenretinide, isotretinoin, and tretinoin; an alkaloid, including, but not limited to, etoposide, homoharringtonine, teniposide, vinblastine, vincristine, vindesine, and vinorelbine; an antiangiogenic agent, including, but not limited to, AE-941 (GW786034, Neovastat), ABT-510, 2-methoxyestradiol, lenalidomide, and thalidomide; a topoisomerase inhibitor, including, but not limited to, amsacrine, edotecarin, exatecan, irinotecan (also active metabolite SN-38 (7-ethyl-10-hydroxy-camptothecin)), rubitecan, topotecan, and 9-aminocamptothecin; a kinase inhibitor, including, but not limited to, erlotinib, gefitinib, flavopiridol, imatinib mesylate, lapatinib, sorafenib, sunitinib malate, AEE-788, AG-013736, AMG 706, AMN107, BMS-354825, BMS-599626, UCN-01 (7-hydroxystaurosporine), and vatalanib; a targeted signal transduction inhibitor including, but not limited to bortezomib, geldanamycin, and rapamycin; a biological response modifier, including, but not limited to, imiquimod, interferon-α, and interleukin-2; and other chemotherapeutics, including, but not limited to 3-AP (3-amino-2-carboxyaldehyde thiosemicarbazone), aminoglutethimide, asparaginase, bryostatin-1, cilengitide. E7389, ixabepilone, procarbazine, sulindac, temsirolimus, tipifarnib. Preferably, the method of treating a cancer involves administering to the subject an effective amount of a composition of Formula I (more preferably Formula III, and even more preferably Formulae IIIj, IIIk, or IIIm) in combination with a chemotherapeutic agent selected from 5-fluorouracil, carboplatin, dacarbazinc, gefitinib, oxaliplatin, paclitaxel, SN-38, temozolomide, vinblastine, bevacizumab, cetuximab, or erlotinib.

In another aspect, the invention provides a method of treating or prophylaxis of a disease or condition in a mammal, by administering to the mammal a therapeutically effective amount of a compound of Formula I, a prodrug of such compound, or a pharmaceutically acceptable salt of such compound or prodrug. The compound can be alone or can be part of a composition. In another aspect, the invention provides a method of treating or prophylaxis of a disease or condition in a mammal, by administering to the mammal a therapeutically effective amount of a compound of Formula III, a prodrug of such compound, or a pharmaceutically acceptable salt of such compound or prodrug in combination with one or more other suitable therapies for the disease or condition.

In another aspect, the invention provides compositions that include a therapeutically effective amount of a compound of Formula III and at least one pharmaceutically acceptable carrier, excipient, and/or diluent. The composition can include a plurality of different pharmacologically active compounds, which can include a plurality of compounds of Formula III.

In a related aspect, the invention provides kits that include a composition as described herein. In some embodiments, the composition is packaged, e.g., in a vial, bottle, flask, which may be further packaged, e.g., within a box, envelope, or bag; the composition is approved by the U.S. Food and Drug Administration or similar regulatory agency for administration to a mammal, e.g., a human; the composition is approved for administration to a mammal, e.g., a human, for a protein kinase mediated disease or condition; the invention kit includes written instructions for use and/or other indication that the composition is suitable or approved for administration to a mammal, e.g., a human, for a protein kinase-mediated disease or condition; and the composition is packaged in unit dose or single dose form, e.g., single dose pills, capsules, or the like.

In aspects involving treatment or prophylaxis of a disease or condition with the compounds of Formula I, the disease or condition is, for example without limitation, neurologic diseases such as ischemic stroke, cerebrovascular ischemia, multi-infarct dementia, head injury, spinal cord injury, Alzheimer's disease (AD), Parkinson's disease, amyotrophic lateral sclerosis, dementia, senile chorea, and Huntington's disease; neoplastic diseases and associated complications, including chemotherapy-induced hypoxia, gastrointestinal stromal tumors (GISTs), prostate tumors, mast cell tumors (including canine mast cell tumors), acute myeloid leukemia, acute lymphocytic leukemia, chronic myeloid leukemia, chronic lymphocytic leukemia, multiple myeloma, melanoma, mastocytosis, gliomas, glioblastoma, astrocytoma, neuroblastoma, sarcomas (e.g. sarcomas of neuroectodermal origin, leiomyosarcoma), carcinomas (e.g. lung, breast, pancreatic, colon, hepatocellular, renal, female genital tract, squamous cell, carcinoma in situ), lymphoma (e.g. histiocytic lymphoma, non-Hodgkin's lymphoma), MEN2 syndromes, neurofibromatosis (including Schwann cell neoplasia), myelodysplastic syndrome, leukemia, tumor angiogenesis, and cancers of the thyroid, liver, bone, skin, brain, central nervous system, pancreas, lung (e.g. small cell lung cancer, non small cell lung cancer), breast, colon, bladder, prostate, gastrointestinal tract, endometrium, fallopian tube, testes and ovary; pain of neuropathic or inflammatory origin, including acute pain, chronic pain, and migraine; cardiovascular diseases including heart failure, cardiac hypertrophy, thrombosis (e.g. thrombotic microangiopathy syndromes), atherosclerosis, reperfusion injury and ischemia (e.g. cerebrovascular ischemia, liver ischemia); inflammation including, but not limited to, polycystic kidney disease (PKI)), age-related macular degeneration, rheumatoid arthritis, allergic rhinitis, inflammatory bowel disease (IBD), ulcerative colitis, Crohn's disease, systemic lupus erythematosis, Sjogren's Syndrome, Wegener's granulomatosis, psoriasis, scleroderma, chronic thyroiditis, Grave's disease, myasthenia gravis, multiple sclerosis, osteoarthritis, endometriosis, scarring (e.g. dermal, tissue), vascular restenosis, fibrotic disorders, hypereosinophilia, CNS inflammation, pancreatitis, nephritis, atopic dermatitis, and hepatitis; immunodeficiency diseases (e.g. severe combined immunodeficiency (SCID)), organ transplant rejection, graft versus host disease; renal or prostatic diseases including diabetic nephropathy, nephrosclerosis, glomerulonephritis, interstitial nephritis, Lupus nephritis, prostate hyperplasia, chronic renal failure, tubular necrosis, diabetes-associated renal complications, and hypertrophy; metabolic diseases including type 1 diabetes, type 2 diabetes, metabolic syndrome, obesity, hepatic steatosis, insulin resistance, hyperglycemia, lipolysis and obesity; infection, including, but not limited to *Helicobacter pylori* and *Influenza* virus, fever, sepsis; pulmonary diseases including chronic obstructive pulmonary disease (COPD), acute respiratory distress syndrome (ARDS), asthma, allergy, bronchitis, emphysema, and pulmonary fibrosis; genetic developmental diseases such as Noonan's syndrome, Crouzon syndrome, acrocephalo-syndactyly type I, Pfeiffer's syndrome, Jackson-Weiss syndrome, Costello syndrome, (faciocutaneoskeletal syndrome), leopard syndrome, cardio-faciocutaneous syndrome (CFC) and neural crest syndrome abnormalities causing cardiovascular, skeletal, intestinal, skin, hair and endocrine diseases; disorders of bone structure or mineralization, including osteoporosis, increased risk of fracture, hypercalcemia, and bone metastases; Grave's disease; Hirschsprung's disease; lymphoedema; selective T-cell defect (STD); X-linked agammaglobulinemia; diabetic retinopathy; alopecia; erectile dysfunction; and tuberous sclerosis.

In a related aspect, compounds of Formula I, further where the compound is of Formula can be used in the preparation of a medicament for the treatment of a B-Raf-mediated disease or condition, selected from the group consisting of neurologic diseases such as ischemic stroke, multi-infarct dementia, head injury, spinal cord injury, Alzheimer's disease (AD), Parkinson's disease; neoplastic diseases including, but not limited to, melanoma, glioma, sarcoma, carcinoma (e.g. lung, breast, pancreatic, renal), lymphoma (e.g. histiocytic lymphoma) and cancer of the thyroid, lung (e.g. small cell lung cancer), liver, breast, ovary and colon, neurofibromatosis, myelodysplastic syndrome, leukemia, tumor angiogenesis; pain of neuropathic or inflammatory origin, including acute pain, chronic pain, and migraine; cardiovascular diseases including heart failure, cardiac hypertrophy, thrombosis (e.g. thrombotic microangiopathy syndromes), atherosclerosis, reperfusion injury; inflammation including, but not limited to, psoriasis, polycystic kidney disease (PKD), arthritis and autoimmune diseases and conditions, osteoarthritis, endometriosis, scarring, vascular restenosis, fibrotic disorders, rheumatoid arthritis, inflammatory bowel disease (IBD); immunodeficiency diseases, organ transplant rejection, graft versus host disease; renal or prostatic diseases including diabetic nephropathy, nephrosclerosis, glomerulonephritis, prostate hyperplasia; metabolic disorders, obesity; infection, including, but not limited to *Helicobacter pylori* and *Influenza* virus, fever, sepsis; pulmonary diseases including chronic obstructive pulmonary disease (COPD) and acute respiratory distress syndrome (ARDS); genetic developmental diseases such as Noonan's syndrome, Costello syndrome, (faciocutaneoskelctal syndrome), leopard syndrome, cardio-faciocutaneous syndrome (CFC), and neural crest syndrome abnormalities causing cardiovascular, skeletal, intestinal, skin, hair and endocrine diseases.

In a related aspect, compounds of Formula III, further where the compound is of Formula III, can be used in the preparation of a medicament for the treatment of a c-Raf-1-mediated disease or condition selected from the group consisting of colorectal, ovarian, lung and renal cell carcinoma, acute myeloid leukemia, myelodysplastic syndromes, tumor angiogenesis, and neuroendocrine tumors such as medullary thyroid cancer, carcinoid, small cell lung cancer and pheochromocytoma.

In a related aspect, compounds of Formula III, further where the compound is of Formula III, can be used in the preparation of a medicament for the treatment of a Fms-mediated disease or condition selected from the group consisting of immune disorders, including rheumatoid arthritis, systemic lupus erythematosis (SLE), Wegener's granulomatosis, and transplant rejection, inflammatory diseases including Chronic Obstructive Pulmonary Disease (COPD), emphysema, and atherosclerosis, metabolic disorders, including insulin resistance, hyperglycemia, and lipolysis, disorders of bone structure or mineralization, including osteoporosis, increased risk of fracture, hypercalcemia, and bone metastases, kidney diseases, including nephritis (e.g. glomerulonephritis, interstitial nephritis, Lupus nephritis), tubular necrosis, diabetes-associated renal complications, and hypertrophy and cancers, including multiple myeloma, acute myeloid leukemia, chronic myeloid leukemia (CML), breast cancer, and ovarian cancer.

In a related aspect, compounds of Formula III, further where the compound is of Formula III, can be used in the preparation of a medicament for the treatment of a Jnk-mediated disease or condition selected from the group consisting of metabolic diseases including type 1 diabetes, type 2 diabetes, metabolic syndrome, obesity, and hepatic steatosis; cardiovascular diseases such as atherosclerosis, ischemia (e.g. cerebrovascular ischemia, liver ischemia), reperfusion injury, cardiac hypertrophy; renal diseases such as chronic renal failure; neoplastic diseases and associated complications, including chemotherapy-induced hypoxia, prostate tumors, myeloid leukemia and cancers of the liver, bone, skin, brain, pancreas, lung breast, colon, prostate and ovary; transplant rejection; pain of neuropathic or inflammatory origin including acute and chronic pain; inflammatory and autoimmune diseases including age-related macular degeneration, rheumatoid arthritis, inflammatory bowel disease, ulcerative colitis, Crohn's disease, systemic lupus erythematosis, Sjogren's Syndrome, psoriasis, scleroderma, chronic thyroiditis, Grave's disease, myasthenia gravis, and multiple sclerosis, and inflammation in other organs including CNS inflammation, pancreatitis, nephritis, atopic dermatitis, and hepatitis; airway inflammatory diseases such as asthma, allergy, bronchitis, pulmonary fibrosis, chronic obstructive pulmonary disease; neurologic diseases such as stroke, cerebrovascular ischemia, neurodegenerative diseases such as Parkinson's disease, Alzheimer's disease, amyotrophic lateral sclerosis, dementia, senile chorea, head and spinal cord trauma, and Huntington's disease.

In a related aspect, compounds of Formula III, further where the compound is of Formula III, can be used in the preparation of a medicament for the treatment of a Jnk1-mediated disease or condition selected from the group consisting of type 1 diabetes, type 2 diabetes, metabolic syndrome, obesity and hepatic steatosis.

In a related aspect, compounds of Formula III, further where the compound is of Formula III, can be used in the preparation of a medicament for the treatment of a Jnk2-mediated disease or condition, such as atherosclerosis.

In a related aspect, compounds of Formula III, further where the compound is of Formula III, can be used in the preparation of a medicament for the treatment of a Jnk3-mediated disease or condition selected from the group consisting of inflammatory diseases including autoimmune diseases such as rheumatoid arthritis, inflammatory bowel syndrome, Crohn's disease, systemic lupus erythematosis, Sjogren's Syndrome, psoriasis and multiple sclerosis, airway inflammatory diseases such as asthma, allergy, pulmonary fibrosis, and chronic obstructive pulmonary disease, and inflammation in other organs, such as CNS inflammation, pancreatitis, nephritis, and hepatitis; neurologic diseases such as stroke, cerebrovascular ischemia, and neurodegenerative diseases such as Parkinson's disease, Alzheimer's disease, and Huntington's disease; and neoplastic diseases such as prostate tumors and myeloid leukemia.

In a related aspect, compounds of Formula III, further where the compound is of Formula III, can be used in the preparation of a medicament for the treatment of a Kit-mediated disease or condition selected from the group consisting of malignancies, including mast cell tumors, small cell lung cancer, testicular cancer, gastrointestinal stromal tumors (GISTs), glioblastoma, astrocytoma, neuroblastoma, carcinomas of the female genital tract, sarcomas of neuroectodermal origin, colorectal carcinoma, carcinoma in situ, Schwann cell neoplasia associated with neurofibromatosis, acute myelocytic leukemia, acute lymphocytic leukemia, chronic myelogenous leukemia, mastocytosis, melanoma, and canine mast cell tumors, and inflammatory diseases, including asthma, rheumatoid arthritis, allergic rhinitis, multiple sclerosis, inflammatory bowel syndrome, transplant rejection, and hypereosinophilia.

The compounds of Formula I with kinase activity $IC_{50}$ less than 10 μM as determined in a standard assay described herein can be used to treat protein kinase mediated diseases and conditions related to the following protein kinases, for example without limitation:

Abl, related to chronic myeloid leukemia (CML), acute lymphoblastic leukemia (ALL) and acute myelogenous leukemia (AML);

Akt1, related to gastric, prostate, colorectal, ovarian, pancreatic and breast cancer, glioblastoma and leukemia, as well as schizophrenia and bipolar disorders, and also use in combination with other chemotherapeutic drugs;

Akt2, related to hyperglycemia due to peripheral insulin resistance and nonsuppressible hepatic glucose production accompanied by inadequate compensatory hyperinsulinemia, also related to pancreatic, ovarian and breast cancer;

Akt3, related to melanoma, prostate and breast cancer;

ALK, related to non-Hodgkin lymphomas such as diffuse large B-cell lymphoma and anaplastic large cell lymphoma;

Alk5, related to pancreatic and biliary cancers, and cutaneous T-cell lymphoma;

B-Raf, related to neurologic diseases such as ischemic stroke, multi-infarct dementia, head injury, spinal cord injury, Alzheimer's disease (AD), Parkinson's disease; neoplastic diseases including, but not limited to, melanoma, glioma, sarcoma, carcinoma (e.g. lung, breast, pancreatic, renal), lymphoma (e.g. histiocytic lymphoma) and cancer of the thyroid, lung (e.g. small cell lung cancer), liver, breast, ovary and colon, neurofibromatosis, myelodysplastic syndrome, leukemia, tumor angiogenesis; pain of neuropathic or inflammatory origin, including acute pain, chronic pain, and migraine; cardiovascular diseases including heart failure, cardiac hypertrophy, thrombosis (e.g. thrombotic microangiopathy syndromes), atherosclerosis, reperfusion injury; inflammation including, but not limited to, psoriasis, polycystic kidney disease (PKD), arthritis and autoimmune diseases and conditions, osteoarthritis, endometriosis, scarring, vascular restenosis, fibrotic disorders, rheumatoid arthritis, inflammatory bowel disease (IBD); immunodeficiency diseases, organ transplant rejection, graft versus host disease; renal or prostatic diseases including diabetic nephropathy, nephrosclerosis, glomerulonephritis, prostate hyperplasia; metabolic disorders, obesity; infection, including, but not limited to *Helicobacter pylori* and *Influenza* virus, fever, sepsis; pulmonary diseases including chronic obstructive pulmonary disease (COPD) and acute respiratory distress syndrome (ARDS); genetic developmental diseases such as Noonan's syndrome, Costello syndrome, (faciocutaneoskeletal syndrome), leopard syndrome, cardio-faciocutaneous syndrome (CFC), and neural crest syndrome abnormalities causing cardiovascular, skeletal, intestinal, skin, hair and endocrine diseases;

c-Raf-1, related to colorectal, ovarian, lung and renal cell carcinoma, acute myeloid leukemia, myelodysplastic syndromes, tumor angiogenesis, and neuroendocrine tumors such as medullary thyroid cancer, carcinoid, small cell lung cancer and pheochromocytoma;

Brk, related to breast and colon cancer, and head and neck squamous cell carcinoma;

Btk, related to X-linked agammaglobulinemia, acute lymphocytic leukemia, autoimmune diseases such as multiple sclerosis, systemic lupus erythematosis, rheumatoid arthritis, and Graves' disease, immune suppression in organ transplant, and drug sensitivity of B-lineage cells;

Cdk2, related to prostate, breast, colorectal and ovarian cancer;

Cdk4, related to glioblastoma (e.g. glioblastoma multiforme), anaplastic astrocytoma, and breast cancer;

Cdk5, related to Alzheimer's disease, amyotrophic lateral sclerosis and Lewy body disease;

Cdk6, related to glioblastoma multiforme, non-Hodgkin's lymphoma, splenic marginal zone lymphoma, T-cell lymphoblastic lymphoma (T-LBL) and T-cell acute lymphoblastic leukemia (T-ALL);

CHK1, related to DNA damage repair, sensitizes cells to chemotherapeutic agents;

Csk, related to colon and pancreatic carcinomas and autoimmune pathology such as type 1 diabetes, rheumatoid arthritis and systemic lupus erythematosus;

EGFR, related to breast, colorectal, bladder, prostate and non small cell lung cancer, squamous cell carcinomas of the head and neck cancer, oral cavity, and esophagus, and glioblastoma multiforme;

EphA1, related to bead and neck squamous cell carcinoma, hepatoma and lung cancer;

EphA2, related to aberrant short-range contact-mediated axonal guidance, bladder, breast, prostate, colon, skin, cervical, ovarian, pancreatic and lung cancers, and metastatic melanoma;

EphB2, related to angiogenesis disorder (e.g. ocular angiogenesis disease such as retinopathy), and cancer (e.g. glioblastoma, breast and liver cancer);

EphB4, related to colorectal cancer (CRC), head and neck squamous cell carcinoma, and tumours of the prostate, breast, endometrium, and bladder;

Erk2, related to aberrant proliferation, differentiation, transcription regulation and development, and may be useful in treating inflammation, for example inflammation associated with Lyme neuroborreliosis, and in treating cancers, such as gastric cancer;

Fak, related to colon and breast tumors, and is also related to esophageal squamous cell carcinoma, melanoma, anaplastic astrocytoma, glioblastoma, ductal carcinoma in situ, prostate and hepatocellular carcinoma, and tumor metastases, and may also provide synergistic effects when used with other chemotherapeutic drugs;

FGFR1, related to 8p11 myeloproliferative syndrome;

FGFR2, related to Crouzon Syndrome, Jackson-Weiss Syndrome, Apert Syndrome, craniosynostosis, Pfeiffer Syndrome, acrocephalo syndactyly type V, and Beare-Stevenson Cutis Gyrata Syndrome;

FGFR3, related to angiogenesis, wound healing, achondroplasia, Muenke craniosynostosis, Crouzon syndrome, acanthosis nigricans, thanatophoric dysplasia, bladder carcinomas, and multiple myeloma;

FGFR4, related to cancer of the breast, lung, colon, medullary thyroid, pancreas, ovary, prostate, endometrium, and fallopian tube, head and neck squamous cell carcinomas and leiomyosarcoma;

Flt1, related to non-small cell lung carcinoma, prostate carcinoma, and colorectal cancer;

Flt3, related to acute myeloid leukemia, myelodysplastic syndrome, acute lymphoblastic leukemia;

Flt4, related to primary lymphoedema;

Fms, related to immune disorders, including rheumatoid arthritis, systemic lupus erythematosis (SLE), Wegener's granulomatosis, and transplant rejection, inflammatory diseases including Chronic Obstructive Pulmonary Disease (COPD), emphysema, and atherosclerosis, metabolic disorders, including insulin resistance, hyperglycemia, and lipolysis, disorders of bone structure or mineralization, including osteoporosis, increased risk of fracture, hypercalcemia, and bone metastases, kidney diseases, including nephritis (e.g. glomerulonephritis, interstitial nephritis, Lupus nephritis), tubular necrosis, diabetes-associated renal complications, and hypertrophy and cancers, including multiple myeloma, acute myeloid leukemia, chronic myeloid leukemia (CML), breast cancer, and ovarian cancer;

Frk, related to acute myeloid leukemia and type I diabetes;

Fyn, related to Alzheimer's disease, schizophrenia and prevention of metastases, e.g. in melanoma and squamous cell carcinoma;

GSK3 (Gsk3α and/or Gsk3β), related to CNS disorders such as Alzheimer's disease, Parkinson's disease, amyotrophic lateral sclerosis, diabetes type II, bipolar disorders, stroke, cancer, chronic inflammatory disease, leucopenia, schizophrenia, chronic pain, neuropathic pain, and traumatic head injury;

HCK, related to chronic myelogenous leukemia and acute lymphocytic leukemia;

Her2/Erbb2, related to prostate and breast cancer;

Her4/Erbb4, related to childhood medulloblastoma;

IGF1R, related to prostate cancer, hepatocellular carcinoma;

IKK beta, related to leukemia of T-cells, necrosis, insulin resistance, and malignant neoplasms;

Irak4, related to bacterial infections, immunodeficiency syndrome, Crohn's disease, ulcerative colitis, asthma, chronic bronchitis, cardio hypertrophy, and kidney hypertension;

Itk, related to allergic asthma;

Jak1, related to Hepatitis C virus infection;

Jak2, related to myeloproliferative disorders such as polycythaemia vera, myelofibrosis, essential thrombocythemia, myeloid metaplasia and leukemias, including acute lymphoblastic leukemia, chronic neutrophilic leukemia, juvenile myelomonocytic leukemia, CMML, Philadelphia chromosome-negative CML, megakaryocytic leukemia, and acute erythroid leukemia;

Jak3, related to X-linked severe combined immunodeficiency, myeloproliferative disorders, transplant rejection and autoimmune diseases such as rheumatoid arthritis, inflammatory bowel syndrome, Crohn's disease, systemic lupus erythematosis, ulcerative colitis, psoriasis and multiple sclerosis;

Jnk (Jnk1, Jnk2, Jnk3), related to metabolic diseases including type 1 diabetes, type 2 diabetes, metabolic syndrome, obesity, and hepatic steatosis; cardiovascular diseases such as atherosclerosis, ischemia (e.g. cerebrovascular ischemia, liver ischemia), reperfusion injury, cardiac hypertrophy; renal diseases such as chronic renal failure; neoplastic diseases and associated complications, including chemotherapy-induced hypoxia, prostate tumors, myeloid leukemia and cancers of the liver, bone, skin, brain, pancreas, lung breast, colon, prostate and ovary; transplant rejection; pain of neuropathic or inflammatory origin including acute and chronic pain; inflammatory and autoimmune diseases including age-related macular degeneration, rheumatoid arthritis, inflammatory bowel disease, ulcerative colitis, Crohn's disease, systemic lupus erythematosis, Sjogren's Syndrome, psoriasis, scleroderma, chronic thyroiditis, Grave's disease, myasthenia gravis, and multiple sclerosis, and inflammation in other organs including CNS inflammation, pancreatitis, nephritis, atopic dermatitis, and hepatitis; airway inflammatory diseases such as asthma, allergy, bronchitis, pulmonary fibrosis, chronic obstructive pulmonary disease; neurologic diseases such as stroke, cerebrovascular ischemia, neurodegenerative diseases such as Parkinson's disease, Alzheimer's disease, amyotrophic lateral sclerosis, dementia, senile chorea, head and spinal cord trauma, and Huntington's disease. More particularly, Jnk1 is related to type 1 diabetes, type 2 diabetes, metabolic syndrome, obesity and hepatic steatosis, Jnk2 is related to atherosclerosis, and Jnk3 is related to inflammatory diseases including autoimmune diseases such as rheumatoid arthritis, inflammatory bowel syndrome, Crohn's disease, systemic lupus erythematosis, Sjogren's Syndrome, psoriasis and multiple sclerosis, airway inflammatory diseases such as asthma, allergy, pulmonary fibrosis, and chronic obstructive pulmonary disease, and inflammation in other organs, such as CNS inflammation, pancreatitis, nephritis, and hepatitis; neurologic diseases such as stroke, cerebrovascular ischemia, and neurodegenerative diseases such as Parkinson's disease, Alzheimer's disease, and Huntington's disease; and neoplastic diseases such as prostate tumors and myeloid leukemia;

Kdr, related to anti-angiogenesis for treating solid tumor growth (e.g. ovarian, lung, breast, prancreatic, prostate, colon, gastrointestinal stromal tumor, non small cell lung cancer, and epidermoid cancer), metastasis, psoriasis, rheumatoid arthritis, diabetic retinopathy and age related macular degeneration;

Kit, related to malignancies, including mast cell tumors, small cell lung cancer, testicular cancer, gastrointestinal stromal tumors (GISTs), glioblastoma, astrocytoma, neuroblastoma, carcinomas of the female genital tract, sarcomas of neuroectodermal origin, colorectal carcinoma, carcinoma in situ, Schwann cell neoplasia associated with neurofibromatosis, acute myelocytic leukemia, acute lymphocytic leukemia, chronic myelogenous leukemia, mastocytosis, melanoma, and canine mast cell tumors, and inflammatory diseases, including asthma, rheumatoid arthritis, allergic rhinitis, multiple sclerosis, inflammatory bowel syndrome, transplant rejection, and hypereosinophilia;

LCK, related to acute lymphoblastic leukemia, T-cell lymphoma, lymphopenia, renal carcinoma, colon carcinoma, severe combined immunodeficiency, multiple sclerosis, inflammatory bowel and type I diabetes;

MAP2K1, related to acute myeloid leukemia, breast, ovarian and liver cancer;

MAP2K2, related to cancer and inflammation;

MAP4K4, related to cancer and tumor metastasis, diabetes and metabolic syndrome;

MAPKAPK2, cancer (e.g. prostate, breast), stroke, menengitis, and inflammatory disorders;

Met, related to kidney, breast, bladder, non-small-cell lung, colorectal, and bladder cancers, and hepatocellular carcinoma;

Mnk1, related to conditions associated with heat shock, nutrient deprivation, oxidative or osmotic stress, and infection of mammalian cells (e.g. with viruses such as adenovirus (Ad) or influenza virus), and autoimmune diseases;

MLK1, related to neurodegenerative diseases such as Alzheimer's disease and Parkinson's disease, and inflammatory disorders;

p38, related to acute coronary syndrome, stroke, atherosclerosis, and inflammatory autoimmune diseases such as rheumatoid arthritis, inflammatory bowel disease, and Crohn's disease;

PDGFR (PDGFRA, PDGFRB), related to idiopathic hypereosinophilic syndrome, chronic eosinophilic leukemia, glioma, gastrointestinal stromal tumors (GISTs), juvenile myelomonocytic leukemia, metastatic medulloblastoma, atherogenesis, and restenosis. More particularly, PDGFRA related to idiopathic hypereosinophilic syndrome, chronic eosinophilic leukemia, glioma, gastrointestinal stromal tumors (GISTs), juvenile myelomonocytic leukemia, metastatic medulloblastoma, atherogenesis, and restenosis, and PDGFRB related to idiopathic hypereosinophilic syndrome, chronic eosinophilic leukemia, juvenile myelomonocytic leukemia, and metastatic medulloblastoma;

PDPK1, related to cancer and diabetes;

Pim1, related to cancers such as hematopoietic (e.g. acute myeloid and acute lymphoid leukemias) and prostate cancers, and non-Hodgkin's lymphomas;

Pim2, related to lymphomas;

Pim3, related to hepatocellular carcinoma;

PKC alpha, related to pituitary tumors and prefrontal cortical dysfunction such as distractibility, impaired judgment, impulsivity, and thought disorder, also may be used to sensitize chemotherapy in breast, colon, and non small cell lung cancers;

PKC beta, related to diabetic retinopathy; PKC-theta, related to insulin resistance, T-cell lymphoma;

Plk1, related to cancers (e.g. lymphoma of the thyroid, non-Hodgkin's lymphomas, colorectal cancers, leukemias and melanoma), also useful as sensitizer in chemotherapy;

Pyk2, related to inflammation (e.g. osteoporosis, polycystic kidney disease, rheumatoid arthiritis and inflammatory bowel disease), CNS disease (e.g. Parkinson's disease and Alzheimer's disease), stroke and cancers (e.g. gliomas, breast cancer, and pancreatic cancer);

Ret, related to cancer of the thyroid, neuroblastoma, familial medullary thyroid carcinoma (FMTC), multiple endocrine neoplasia type IIA and IIB (MEN2A, MEN2B), and neurodegenerative disorders (e.g. Hirschsprung's disease, Parkinson's disease, Alzheimer's disease, and amyotrophic lateral sclerosis);

ROCK (ROCK-1, ROCK-2), related to cancers (e.g. ovarian cancer, hepatocellular carcinoma, pancreatic cancer), ocular disease (e.g. glaucoma), cardiac hypertrophy, improved renal perfusion, transplant rejection, and acute respiratory distress syndrome;

Ron, related to cancer and inflammation;

Src, related to cancer and osteoporosis;

Stk6, related to gastric, bladder, breast, lung, CNS, ovarian, kidney, colon, prostate, pancreas, and cervical cancers, melanoma, leukemia, and neuroblastoma;

Syk, related to lymphomas (e.g. mantle cell lymphoma);

TEC, related to sepsis, septic shock, inflammation, rheumatoid arthritis, Crohn's disease, irritable bowel disease (IBD), and ulcerative colitis;

Tie2 (TEK), related to cancer, arthritis (e.g. rheumatoid arthritis), and atherosclerosis;

TrkA, related to pain (e.g. chronic pain, neuropathic pain), cancer, arthritis, diabetic retinopathy, macular degeneration and psoriasis;

Yes, related to various cancers including esophageal squamous cell carcinoma; and Zap70, related to AIDS, systemic lupus erythematosus, myasthenia gravis, atherosclerosis, rejection of transplanted organs or tissues, allograft rejection including acute and chronic allograft rejection, graft versus host disease, rheumathoid arthritis, psoriasis, systemic sclerosis, atopic dermatitis, eczematous dermatitis, alopecia, and inflammation of the nasal mucus membrane, including all forms of rhinitis.

Additional aspects and embodiments will be apparent from the following Detailed Description and from the claims.

DETAILED DESCRIPTION OF THE PREFERRED EMBODIMENTS

As used herein the following definitions apply unless clearly indicated otherwise:

"Halogen" refer to all halogens, that is, chloro (Cl), fluoro (F), bromo (Br), or iodo (I).

"Hydroxyl" or "hydroxy" refer to the group —OH.

"Thiol" refers to the group —SH.

"Lower alkyl" alone or in combination means au alkane-derived radical containing from 1 to 6 carbon atoms (unless specifically defined) that includes a straight chain alkyl or branched alkyl. The straight chain or branched alkyl group is attached at any available point to produce a stable compound. In many embodiments, a lower alkyl is a straight or branched alkyl group containing from 1-6, 1-4, or 1-2, carbon atoms, such as methyl, ethyl, propyl, isopropyl, butyl, t-butyl, and the like. A "substituted lower alkyl" denotes lower alkyl that is independently substituted, unless indicated otherwise, with one or more, preferably 1, 2, 3, 4 or 5, also 1, 2, or 3 substituents, attached at any available atom to produce a stable compound, wherein the substituents are selected from the group consisting of —F, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR°, —SR°, —OC(O)R°, —OC(S)R°, —C(O)R°, —C(S)R°, —C(O)OR°, —C(S)OR°, —S(O)R°, —S(O)$_2$R°, —C(O)NHR°, —C(S)NHR°, —C(O)NR°R°, —C(S)NR°R°, —S(O)$_2$NHR°, —S(O)$_2$NR°R°, —C(NH)NHR°, —C(NH)NR$^p$R°, —NHC(O)R°, —NHC(S)R°, —NR°C(O)R°, —NR°C(S)R°, —NHS(O)$_2$R°, —NR°S(O)$_2$R°, —NHC(O)NHR°, —NHC(S)NHR°, —NR°C(O)NH$_2$, —NR°C(S)NH$_2$, —NR°C(O)NHR°, —NR°C(S)NHR°, —NHC(O)NR°R°, —NHC(S)NR°R°, —NR°C(O)NR°R°, —NR°C(S)NR°R°, —NHS(O)$_2$NHR°, —NR°S(O)$_2$NH$_2$, —NR°S(O)$_2$NHR°, —NHS(O)$_2$NR°R°, —NR°S(O)$_2$NR°R°, —NHR°, —NR°R°, —R°, —R$^f$, and —R$^g$. Furthermore, possible substitutions include subsets of these substitutions, such as are indicated herein, for example, in the description of compounds of Formula III, attached at any available atom to produce a stable compound. For example "fluoro substituted lower alkyl" denotes a lower alkyl group substituted with one or more fluoro atoms, such as perfluoroalkyl, where preferably the lower alkyl is substituted with 1, 2, 3, 4 or 5 fluoro atoms, also 1, 2, or 3 fluoro atoms. While it is understood that substitutions are attached at any available atom to produce a stable compound, when optionally substituted alkyl is an R group of a moiety such as —OR (e.g. alkoxy), —SR (e.g. thioalkyl), —NHR (e.g. alkylamino), —C(O)NHR, and the like, substitution of the alkyl R group is such that substitution of the alkyl carbon bound to any O, S, or N of the moiety (except where N is a heteroaryl ring atom) excludes substituents that would result in any O, S, or N of the substituent (except where N is a heteroaryl ring atom) being bound to the alkyl carbon bound to any O, S, or N of the moiety. "C$_{2-6}$ alkyl" denotes lower alkyl containing 2-6 carbon atoms. A "substituted C$_{2-6}$ alkyl" denotes optionally substituted lower alkyl containing 2-6 carbon atoms. A "substituted methyl" denotes methyl that is independently substituted, unless indicated otherwise, with 1, 2, or 3 substituents, wherein the substituents are selected as per optionally substituted lower alkyl.

"C$_{1-3}$ alkylene" refers to a divalent alkane-derived radical containing 1-3 carbon atoms, straight chain or branched, from which two hydrogen atoms are taken from the same carbon atom or from different carbon atoms. C$_{1-3}$ alkylene includes methylene —CH$_2$—, ethylene —CH$_2$CH$_2$—, propylene —CH$_2$CH$_2$CH$_2$—, and isopropylene —CH(CH$_3$)CH$_2$— or —CH$_2$CH(CH$_3$)—. C$_{1-3}$ alkylene substituted with one or more substituents indicates C$_{1-3}$ alkylene that is independently substituted, with one or more, preferably 1, 2, 3, 4 or 5, also 1, 2, or 3 substituents as indicated, attached at any available atom to produce a stable compound.

"Lower alkenyl" alone or in combination means a straight or branched hydrocarbon containing 2-6 carbon atoms (unless specifically defined) and at least one, preferably 1-3, more preferably 1-2, most preferably one, carbon to carbon double bond. Carbon to carbon double bonds may be either contained within a straight chain or branched portion. Examples of lower alkenyl groups include ethenyl, propenyl, isopropenyl, butenyl, and the like. A "substituted lower alkenyl" denotes lower alkenyl that is independently substituted, unless indicated otherwise, with one or more, preferably 1, 2, 3, 4 or 5, also 1, 2, or 3 substituents, attached at any available atom to produce a stable compound, wherein the substituents are selected from the group consisting of —F, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR°, —SR°, —OC(O)R°, —OC(S)R°, —C(O)R°, —C(S)R°, —C(O)OR°, —C(S)OR°, —S(O)R°, —S(O)$_2$R°, —C(O)NHR°, —C(S)NHR°, —C(O)NR°R°, —C(S)NR°R°, —S(O)$_2$NHR°, —S(O)$_2$NR°R°, —C(NH)NHR°, —C(NH)NR$^p$R°, —NHC(O)R°, —NHC(S)R°, —NR°C(O)R°, —NR°(S)R°, —NHS(O)$_2$R°, —NR°S(O)$_2$R°, —NHC(O)NHR°, —NHC(S)NHR°, —NR°C(O)NH$_2$, —NR°C(S)NH$_2$, —NR°C(O)NHR°, —NR°C(S)NHR°, —NHC(O)NR°R°, —NHC(S)NR°R°, —NR°C(O)NR°R°, —NR°C(S)NR°R°, —NHS(O)$_2$NHR°, —NR°S(O)$_2$NH$_2$, —NR°S(O)$_2$NHR°, —NHS(O)$_2$NR°R°, —NR°S(O)$_2$NR°R°, —NHR°, —NR°R°, —R$^d$, —R$^f$, and —R$^g$. Further, possible substitutions include subsets of these substitutions, such as are indicated herein, for example, in the description of compounds of Formula III, attached at any available atom to produce a stable compound. For example "fluoro substituted lower alkenyl" denotes a lower alkenyl group substituted with one or more fluoro atoms, where preferably the lower alkenyl is substituted with 1, 2, 3, 4 or 5 fluoro atoms, also 1, 2, or 3 fluoro atoms. While it is understood that substitutions are attached at any available atom to produce a stable compound, substitution of alkenyl groups are such that —F, —C(O)—, —C(S)—, —C(NH)—, —S(O)—, —S(O)$_2$—, —O—, —S—, or N (except where N is a heteroaryl ring atom), are not bound to an alkene carbon thereof. Further, where alkenyl is a substituent of another moiety or an R group of a moiety such as —OR, —NHR, —C(O)R, and the like, substitution of the moiety is such that any —C(O)—, —C(S)—, —S(O)—, —S(O)$_2$—, —O—, —S—, or N thereof (except where N is a heteroaryl ring atom) are not bound to an alkene carbon of the alkenyl substituent or R group. Further, where alkenyl is a substituent of another moiety or an R group of a moiety such as —OR, —NHR, —C(O)NHR, and the like, substitution of the alkenyl R croup is such that substitution of the alkenyl carbon bound to any O, S, or N of the moiety (except where N is a heteroaryl ring atom) excludes substituents that would result in any O, S, or N of the substituent (except where N is a heteroaryl ring atom) being bound to the alkenyl carbon bound to any O, S, or N of the moiety. An "alkenyl carbon" refers to any carbon within an alkenyl group, whether saturated or part of the carbon to carbon double bond. An "alkene carbon" refers to a carbon within an alkenyl group that is part of a carbon to carbon double bond.

"Lower alkynyl" alone or in combination means a straight or branched hydrocarbon containing 2-6 carbon atoms (unless specifically defined) containing at least one, preferably one, carbon to carbon triple bond. Examples of alkynyl groups include ethynyl, propynyl, butyryl, and the like, A "substituted lower alkynyl" denotes lower alkynyl that is independently substituted, unless indicated otherwise, with one or more, preferably 1, 2, 3, 4 or 5, also 1, 2, or 3 substituents, attached at any available atom to produce a stable compound, wherein the substituents are selected from the group consisting of —F, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR°, —SR°, —OC(O)R°, —OC(S)R°, —C(O)R°, —C(S)R°, —C(O)OR°, —C(S)OR°, —S(O)R°, —S(O)$_2$R°, —C(O)NHR°, —C(S)NHR°, —C(O)NR°R°, —C(S)NR°R°, —S(O)$_2$NHR°, —S(O)$_2$NR°R°, —C(NH)NHR°, —C(NH)NR°R°, —NHC(O)R°, —NHC(S)R°, —NR°C(O)R°, —NR°C(S)R°, —NHS(O)$_2$R°, —NR°S(O)$_2$R°, —NHC(O)NHR°, —NHC(S)NHR°, —NR°C(O)NHR°, —NR°C(S)NHR°, —NHC(O)NR°R°, —NHC(S)NR°R°, —NR°C(O)NR°R°, —NR°C(S)NR°R°, —NHS(O)$_2$NHR°, —NR°S(O)$_2$NH$_2$, —NR°S(O)$_2$NHR°, —NHS(O)$_2$NR°R°, —NR°S(O)$_2$NR°R°, —NHR°, —NR°R°, —R$^d$, —R$^e$, and —R$^g$. Further, possible substitutions include subsets of these substitutions, such as are indicated herein, for example, in the description of compounds of Formula III, attached at any available atom to produce a stable compound. For example "fluoro substituted lower alkynyl" denotes a lower alkynyl group substituted with one or more fluoro atoms, where preferably the lower alkynyl is substituted with 1, 2, 3, 4 or 5 fluoro atoms, also 1, 2, or 3 fluoro atoms. While it is understood that substitutions are attached at any available atom to produce a stable compound, substitution of alkynyl groups are such that —F, —C(O)—, —C(S)—, —C(NH)—, —S(O)—, —S(O)$_2$—, —O—, —S—, or N (except where N is a heteroaryl ring atom) are not bound to an alkyne carbon thereof. Further, where alkynyl is a substituent of another moiety or an R group of a moiety such as —OR, —NHR, —C(O)R, and the like, substitution of the moiety is such that any —C(O)—, —C(S)—, —S(O)—, —S(O)$_2$—, —O—, —S—, or N thereof (except where N is a heteroaryl ring atom) are not bound to an alkyne carbon of the alkynyl substituent or R group. Further, where alkynyl is a substituent of another moiety or an R group of a moiety such as —OR, —NHR, —C(O)NHR, and the like, substitution of the alkynyl R group is such that substitution of the alkynyl carbon bound to any O, S, or N of the moiety (except where N is a heteroaryl ring atom) excludes substituents that would result in any O, S, or N of the substituent (except where N is a heteroaryl ring atom) being bound to the alkynyl carbon bound to any O, S, or N of the moiety. An "alkynyl carbon" refers to any carbon within an alkynyl group, whether saturated or part of the carbon to carbon triple bond. An "alkyne carbon" refers to a carbon within an alkynyl group that is part of a carbon to carbon triple bond.

"Cycloalkyl" refers to saturated or unsaturated, non-aromatic monocyclic, bicyclic or tricyclic carbon ring systems of 3-10, also 3-8, more preferably 3-6, ring members per ring, such as cyclopropyl, cyclopentyl, cyclohexyl, adamantyl, and the like. A "substituted cycloalkyl" is a cycloalkyl that is independently substituted, unless indicated otherwise, with one or more, preferably 1, 2, 3, 4 or 5, also 1, 2, or 3 substituents, attached at any available atom to produce a stable compound, wherein the substituents are selected from the group consisting of halogen, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR$^o$, —SR$^o$, —OC(O)R$^o$, —OC(S)R$^o$, —C(O)R$^o$, —C(S)R$^o$, —C(O)OR$^o$, —C(S)OR$^o$, —S(O)R$^o$, —S(O)$_2$R$^o$, —C(O)NHR$^o$, —C(S)NHR$^o$, —C(O)NR$^o$R$^o$, —C(S)NR$^o$R$^o$, —S(O)$_2$NHR$^o$, —S(O)$_2$NR$^o$R$^o$, —C(NH)NHR$^o$, —C(NH)NR$^p$R$^c$, —NHC(O)R$^o$, —NHC(S)R$^o$, —NR$^o$C(O)R$^o$, —NR$^o$C(S)R$^o$, —NHS(O)$_2$R$^o$, —NR$^o$S(O)$_2$R$^o$, —NHC(O)NHR$^o$, —NHC(S)NHR$^o$, —NR$^o$C(O)NH$_2$, —NR$^o$C(S)NH$_2$, —NR$^o$C(O)NHR$^o$, —NR$^o$C(S)NHR$^o$, —NHC(O)NR$^o$R$^o$, —NHC(S)NR$^o$R$^o$, —NR$^o$C(O)NR$^o$R$^o$, —NR$^o$C(S)NR$^o$R$^o$, —NHS(O)$_2$NHR$^o$, —NR$^o$S(O)$_2$NH$_2$, —NR$^o$S(O)$_2$NHR$^o$, —NHS(O)$_2$NR$^o$R$^o$, —NR$^o$S(O)$_2$NR$^o$R$^o$, —NHR$^o$, —NR$^o$R$^o$, —R$^d$, —R$^e$, —R$^f$, and —R$^g$.

"Heterocycloalkyl" refers to a saturated or unsaturated non-aromatic cycloalkyl group having from 5 to 10 atoms in which from 1 to 3 carbon atoms in the ring are replaced by heteroatoms of O, S or N, and are optionally fused with benzo or heteroaryl of 5-6 ring members. Heterocycloalkyl is also intended to include oxidized S or N, such as sulfinyl, sulfonyl and N-oxide of a tertiary ring nitrogen. Heterocycloalkyl is also intended to include compounds in which a ring carbon may be oxo substituted, i.e. the ring carbon is a carbonyl group, such as lactones and lactams. The point of attachment of the heterocycloalkyl ring is at a carbon or nitrogen atom such that a stable ring is retained. Examples of heterocycloalkyl groups include, but are not limited to, murpholino, tetrahydrofuranyl, dihydropyridinyl, piperidinyl, pyrrolidinyl, pyrrolidonyl, piperazinyl, dihydrobenzofuryl, and dihydroindolyl. A "substituted heterocycloalkyl" is a heterocycloalkyl that is independently substituted, unless indicated otherwise, with one or more, preferably 1, 2, 3, 4 or 5, also 1, 2, or 3 substituents, attached at any available atom to produce a stable compound, wherein the substituents are selected from the group consisting of halogen, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR$^o$, —SR$^o$, —OC(O)R$^o$, —OC(S)R$^o$, —C(O)R$^o$, —C(S)R$^o$, —C(O)OR$^o$, —C(S)OR$^o$, —S(O)R$^o$, —S(O)$_2$R$^o$, —C(O)NHR$^o$, —C(S)NHR$^o$, —C(O)NR$^o$R$^o$, —C(S)NR$^o$R$^o$, —S(O)$_2$NHR$^o$, —S(O)$_2$NR$^o$R$^o$, —C(NH)NHR$^o$, —C(NH)NR$^p$R$^c$, —NHC(O)R$^o$, —NHC(S)R$^o$, —NR$^o$C(O)R$^o$, —NR$^o$C(S)R$^o$, —NHS(O)$_2$R$^o$, —NR$^o$S(O)$_2$R$^o$, —NHC(O)NHR$^o$, —NHC(S)NHR$^o$, —NR$^o$C(O)NH$_2$, —NR$^o$C(S)NH$_2$, —NR$^o$C(O)NHR$^o$, —NR$^o$C(S)NHR$^o$, —NHC(O)NR$^o$R$^o$, —NHC(S)NR$^o$R$^o$, —NR$^o$C(O)NR$^o$R$^o$, —NR$^o$C(S)NR$^o$R$^o$, —NHS(O)$_2$NHR$^o$, —NR$^o$S(O)$_2$NH$_2$, —NR$^o$S(O)$_2$NHR$^o$, —NHS(O)$_2$NR$^o$R$^o$, —NR$^o$S(O)$_2$NR$^o$R$^o$, —NHR$^o$, —NR$^o$R$^o$, —R$^d$, —R$^e$, —R$^f$, and —R$^g$.

"Aryl" alone or in combination refers to a monocyclic or bicyclic ring system containing aromatic hydrocarbons such as phenyl or naphthyl, which may be optionally fused with a cycloalkyl of preferably 5-7, more preferably 5-6, ring members. "Arylene" is a divalent aryl. A "substituted aryl" is an aryl that is independently substituted, unless indicated otherwise, with one or more, preferably 1, 2, 3, 4 or 5, also 1, 2, or 3 substituents, attached at any available atom to produce a stable compound, wherein the substituents are selected from the group consisting of halogen, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR$^o$, —OC(O)R$^o$, —OC(S)R$^o$, —C(O)R$^o$, —C(S)R$^o$, —C(O)OR$^o$, —C(S)OR$^o$, —S(O)R$^o$, —S(O)$_2$R$^o$, —C(O)NHR$^o$, —C(S)NHR$^o$, —C(O)NR$^o$R$^o$, —C(S)NR$^o$R$^o$, —S(O)$_2$NHR$^o$, —S(O)$_2$NR$^o$R$^o$, —C(NH)NHR$^o$, —C(NH)NR$^p$R$^c$, —NHC(O)R$^o$, —NHC(S)R$^o$, —NR$^o$C(O)R$^o$, —NR$^o$C(S)R$^o$, —NHS(O)$_2$R$^o$, —NR$^o$S(O)$_2$R$^o$, —NHC(O)NHR$^o$, —NHC(S)NHR$^o$, —NR$^o$C(O)NH$_2$, —NR$^o$C(S)NH$_2$, —NR$^o$C(O)NHR$^o$, —NR$^o$C(S)NHR$^o$, —NHC(O)NR$^o$R$^o$, —NHC(S)NR$^o$R$^o$, —NR$^o$C(O)NR$^o$R$^o$, —NR$^o$C(S)NR$^o$R$^o$, —NHS(O)$_2$NHR$^o$, —NR$^o$S(O)$_2$NH$_2$, —NR$^o$S(O)$_2$NHR$^o$, —NHS(O)$_2$NR$^o$R$^o$, —NR$^o$S(O)$_2$NR$^o$R$^o$, —NHR$^o$, —NR$^o$R$^o$, —R$^d$, —R$^e$, —R$^f$, and —R$^g$. A "substituted arylene" is a divalent substituted aryl.

"Heteroaryl" alone or in combination refers to a monocyclic aromatic ring structure containing 5 or 6 ring atoms, or a bicyclic aromatic group having 8 to 10 atoms, containing one or more, preferably 1-4, more preferably 1-3, even more preferably 1-2, heteroatoms independently selected from the group consisting of O, S, and N. Heteroaryl is also intended to include oxidized S or N, such as sulfinyl, sulfonyl and N-oxide of a tertiary ring nitrogen. A carbon or nitrogen atom is the point of attachment of the heteroaryl ring structure such that a stable compound is produced. Examples of heteroaryl groups include, but are not limited to, pyridinyl, pyridazinyl, pyrazinyl, quinaoxalyl, indolizinyl, benzo[b]thienyl, quinazolinyl, purinyl, indolyl, quinolinyl, pyrimidinyl, pyrrolyl, pyrazolyl, oxazolyl, thiazolyl, thienyl, isoxazolyl, oxathiadiazolyl, isothiazolyl, tetrazolyl, imidazolyl, triazolyl, furanyl, benzofuryl, and indolyl. "Nitrogen containing heteroaryl" refers to hetcroaryl wherein any heteroatoms are N. "Heteroarylene" is a divalent heteroaryl. A "substituted heteroaryl" is a heteroaryl that is independently substituted, unless indicated otherwise, with one or more, preferably 1, 2, 3, 4 or 5, also 1, 2, or 3 substituents, attached at any available atom to produce a stable compound, wherein the substituents are selected from the group consisting of halogen, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR$^o$, —SR$^o$, —OC (O)R$^o$, —OC(S)R$^o$, —C(O)R$^o$, —C(S)R$^o$, —C(O)OR$^o$, —C(S)OR$^o$, —S(O)R$^o$, —S(O)$_2$R$^o$, —C(O)NHR$^o$, —C(S)NHR$^o$, —C(O)NR$^o$R$^o$, —C(S)NR$^o$R$^o$, —S(O)$_2$NHR$^o$, —S(O)$_2$NR$^o$R$^o$, —C(NH)NHR$^o$, —C(NH)NR$^p$R$^c$, —NHC(O)R$^o$, —NHC(S)R$^o$, —NR$^o$C(O)R$^o$, —NR$^o$C(S)R$^o$, —NHS(O)$_2$R$^o$, —NR$^o$S(O)$_2$R$^o$, —NHC(O)NHR$^o$, —NHC(S)NHR$^o$, —NR$^o$C(O)NH$_2$, —NR$^o$C(S)NH$_2$, —NR$^o$C(O)NHR$^o$, —NR$^o$C(S)NHR$^o$, —NHC(O)NR$^o$R$^o$, —NHC(S)NR$^o$R$^o$, —NR$^o$C(O)NR$^o$R$^o$, —NR$^o$C(S)NR$^o$R$^o$, —NHS(O)$_2$NHR$^o$, —NR$^o$S(O)$_2$NH$_2$, —NR$^o$S(O)$_2$NHR$^o$, —NHS(O)$_2$NR$^o$R$^o$, —NR$^o$S(O)$_2$NR$^o$R$^o$, —NHR$^o$, —NR$^o$R$^o$, —R$^d$, —R$^e$, —R$^f$, and —R$^g$. "Substituted heteroarylene" is a divalent substituted heteroaryl.

The variables R$^o$, R$^p$, R$^c$, R$^d$, R$^e$, R$^f$ and R$^g$ as used in the description of optional substituents for alkyl, alkenyl, alkynyl, cycloalkyl, heterocycloalkyl, aryl and heteroaryl are defined as follows: each R$^o$, R$^p$, and R$^c$ are independently selected from the group consisting of R$^d$, R$^e$, R$^f$, and R$^g$, or R$^p$ and R$^c$ combine with the nitrogen to which they are attached to form a 5-7 membered heterocycloalkyl or a 5 or 7 membered nitrogen containing heteroaryl, wherein the 5-7 membered heterocycloalkyl or 5 or 7 membered nitrogen containing heteroaryl are optionally substituted with one or more, preferably 1, 2, 3, 4 or 5, also 1, 2, or 3 substituents selected from the group consisting of halogen, —NO$_2$, —CN, —OH, —NH$_2$, —OR$^u$, —SR$^u$, —NHR$^u$, —NR$^u$R$^u$, —R$^x$, and —R$^y$;
each R$^d$ is independently lower alkyl, wherein lower alkyl is optionally substituted with one or more, preferably 1, 2, 3, 4 or 5, also 1, 2 or 3 substituents selected from the group consisting of fluoro, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR$^k$, —SR$^k$, —OC(O)R$^k$, —OC(S)R$^k$, —C(O)R$^k$, —C(S)R$^k$, —C(O)OR$^k$, —C(S)OR$^k$, —S(O)R$^k$, —S(O)$_2$R$^k$, —C(O)NHR$^k$, —C(S)NHR$^k$, —C(O)NR$^k$R$^k$, —C(S)NR$^k$R$^k$, —S(O)$_2$NHR$^k$, —S(O)$_2$NR$^k$R$^k$, —C(NH)NHR$^k$, —C(NH)NR$^m$R$^n$, —NHC(O)R$^k$, —NHC(S)R$^k$, —NR$^k$C(O)R$^k$, —NR$^k$C(S)R$^k$, —NHS(O)$_2$R$^k$, —NR$^k$S(O)$_2$R$^k$, —NHC(O)NHR$^k$, —NHC(S)NHR$^k$, —NR$^k$C(O)NH$_2$, —NR$^k$C(S)NH$_2$, —NR$^k$C(O)NHR$^k$, —NR$^k$C(S)NHR$^k$, —NHC(O)NR$^k$R$^k$, —NHC(S)NR$^k$R$^k$, —NR$^k$C(O)NR$^k$R$^k$, —NR$^k$C(S)NR$^k$R$^k$, —NHS(O)$_2$NHR$^k$, —NR$^k$S(O)$_2$NH$_2$, —NR$^k$S(O)$_2$NHR$^k$, —NHS(O)$_2$NR$^k$R$^k$, —NR$^k$S(O)$_2$NR$^k$R$^k$, —NHR$^k$, —NR$^k$R$^k$, —R$^i$, and —R$^j$;
each R$^e$ is independently lower alkenyl, wherein lower alkenyl is optionally substituted with one or more, preferably 1, 2, 3, 4 or 5, also 1, 2 or 3 substituents selected from the group consisting of fluoro, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR$^k$, —SR$^k$, —OC(O)R$^k$, —OC(S)R$^k$, —C(O)R$^k$, —C(S)R$^k$, —C(O)OR$^k$, —C(S)OR$^k$, —S(O)R$^k$, —S(O)$_2$R$^k$, —C(O)NHR$^k$, —C(S)NHR$^k$, —C(O)NR$^k$R$^k$, —C(S)NR$^k$R$^k$, —S(O)$_2$NHR$^k$, —S(O)$_2$NR$^k$R$^k$, —C(NH)NHR$^k$, —C(NH)NR$^m$R$^n$, —NHC(O)R$^k$, —NHC(S)R$^k$, —NR$^k$C(O)R$^k$, —NR$^k$C(S)R$^k$, —NHS(O)$_2$R$^k$, —NR$^k$S(O)$_2$R$^k$, —NHC(O)NHR$^k$, —NHC(S)NHR$^k$, —NR$^k$C(O)NH$_2$, —NR$^k$C(S)NH$_2$, —NR$^k$C(O)NHR$^k$, —NR$^k$C(S)NHR$^k$, —NHC(O)NR$^k$R$^k$, —NHC(S)NR$^k$R$^k$, —NR$^k$C(O)NR$^k$R$^k$, —NR$^k$C(S)NR$^k$R$^k$, —NHS(O)$_2$NHR$^k$, —NR$^k$S(O)$_2$NH$_2$, —NR$^k$S(O)$_2$NHR$^k$, —NHS(O)$_2$NR$^k$R$^k$, —NR$^k$S(O)$_2$NR$^k$R$^k$, —NHR$^k$, —NR$^k$R$^k$, —R$^h$, and —R$^j$;
each R$^f$ is independently lower alkynyl, wherein lower alkynyl is optionally substituted with one or more, preferably 1, 2, 3, 4 or 5, also 1, 2 or 3 substituents selected from the group consisting of fluoro, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR$^k$, —SR$^k$, —OC(O)R$^k$, —OC(S)R$^k$, —C(O)R$^k$, —C(S)R$^k$, —C(O)OR$^k$, —C(S)OR$^k$, —S(O)R$^k$, —S(O)$_2$R$^k$, —C(O)NHR$^k$, —C(S)NHR$^k$, —C(O)NR$^k$R$^k$, —C(S)NR$^k$R$^k$, —S(O)$_2$NHR$^k$, —S(O)$_2$NR$^k$R$^k$, —C(NH)NHR$^k$, —C(NH)NR$^m$R$^n$, —NHC(O)R$^k$, —NHC(S)R$^k$, —NR$^k$C(O)R$^k$, —NR$^k$C(S)R$^k$, —NHS(O)$_2$R$^k$, —NR$^k$S(O)$_2$R$^k$, —NHC(O)NHR$^k$, —NHC(S)NHR$^k$, —NR$^k$C(O)NH$_2$, —NR$^k$C(S)NH$_2$, —NR$^k$C(O)NHR$^k$, —NR$^k$C(S)NHR$^k$, —NHC(O)NR$^k$R$^k$, —NHC(S)NR$^k$R$^k$, —NR$^k$C(O)NR$^k$R$^k$, —NR$^k$C(S)NR$^k$R$^k$, —NHS(O)$_2$NHR$^k$, —NR$^k$S(O)$_2$NH$_2$, —NR$^k$S(O)$_2$NHR$^k$, —NHS(O)$_2$NR$^k$R$^k$, —NR$^k$S(O)$_2$NR$^k$R$^k$, —NHR$^k$, —NR$^k$R$^k$, —R$^h$, and —R$^j$;
each R$^g$ is independently selected from the group consisting of cycloalkyl, heterocycloalkyl, aryl, and heteroaryl, wherein cycloalkyl, heterocycloalkyl, aryl, and heteroaryl are optionally substituted with one or more, preferably 1, 2, 3, 4 or 5, also 1, 2 or 3 substituents selected from the group consisting of halogen, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR$^k$, —SR$^k$, —OC(O)R$^k$, —OC(S)R$^k$, —C(O)R$^k$, —C(S)R$^k$, —C(O)OR$^k$, —C(S)OR$^k$, —S(O)R$^k$, —S(O)$_2$R$^k$, —C(O)NHR$^k$, —C(S)NHR$^k$, —C(O)NR$^k$R$^k$, —C(S)NR$^k$R$^k$, —S(O)$_2$NHR$^k$, —S(O)$_2$NR$^k$R$^k$, —C(NH)NHR$^k$, —C(NH)NR$^m$R$^n$, —NHC(O)R$^k$, —NHC(S)R$^k$, —NR$^k$C(O)R$^k$, —NR$^k$C(S)R$^k$, —NHS(O)$_2$R$^k$, —NR$^k$S(O)$_2$R$^k$, —NHC(O)NHR$^k$, —NHC(S)NHR$^k$, —NR$^k$C(O)NH$_2$, —NR$^k$C(S)NH$_2$, —NR$^k$C(O)NHR$^k$, —NR$^k$C(S)NHR$^k$, —NHC(O)NR$^k$R$^k$, —NHC(S)NR$^k$R$^k$, —NR$^k$C(O)NR$^k$R$^k$, —NR$^k$C(S)NR$^k$R$^k$, —NHS(O)$_2$NHR$^k$, —NR$^k$S(O)$_2$NH$_2$, —NR$^k$S(O)$_2$NHR$^k$, —NHS(O)$_2$NR$^k$R$^k$, —NR$^k$S(O)$_2$NR$^k$R$^k$, —NHR$^k$, —NR$^k$R$^k$, —R$^h$, —R$^i$, and —R$^j$;

wherein R$^k$, R$^m$, and R$^n$ at each occurrence are independently selected from the group consisting of R$^h$, R$^i$, and R$^j$, or R$^m$ and R$^n$ combine with the nitrogen to which they are attached form a 5-7 membered heterocycloalkyl or a 5 or 7 membered nitrogen containing heteroaryl, wherein the 5-7 membered heterocycloalkyl or 5 or 7 membered nitrogen containing heteroaryl are optionally substituted with one or more, preferably 1, 2, 3, 4 or 5, also 1, 2, or 3 substituents selected from the group consisting of halogen, —NO$_2$, —CN, —OH, —NH$_2$, OR$^u$, —SR$^u$, —NHR$^u$, —NR$^u$R$^u$, —R$^x$, and —R$^y$;

wherein each R$^h$ is independently lower alkyl optionally substituted with one or more, preferably 1, 2, 3, 4 or 5, also 1, 2 or 3 substituents selected from the group consisting of fluoro, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR$^r$, —SR$^r$, —OC(O)R$^r$, —OC(S)R$^r$, —C(O)R$^r$, —C(S)R$^r$, —C(O)OR$^r$, —C(S)OR$^r$, —S(O)R$^r$, —S(O)$_2$R$^r$, —C(O)NHR$^r$, —C(S)NHR$^r$, —C(O)NR$^r$R$^r$, —C(S)NR$^r$R$^r$, —S(O)$_2$NHR$^r$, —S(O)$_2$NR$^r$R$^r$, —C(NH)NHR$^r$, —C(NH)NR$^s$R$^t$, —NHC(O)R$^r$, —NHC(S)R$^r$, —NR$^r$C(O)R$^r$, —NR$^r$C(S)R$^r$, —NHS(O)$_2$R$^r$, —NR$^r$S(O)$_2$R$^r$, —NHC(O)NHR$^r$, —NHC(S)NHR$^r$, —NR$^r$C(O)NH$_2$, —NR$^r$C(S)NH$_2$, —NR$^r$C(O)NHR$^r$, —NR$^r$C(S)NHR$^r$, —NHC(O)NR$^r$R$^r$, —NHC(S)NR$^r$R$^r$, —NR$^r$C(O)NR$^r$R$^r$, —NR$^r$C(S)NR$^r$R$^r$, —NHS(O)$_2$NHR$^r$, —NR$^r$S(O)$_2$NH$_2$, —NR$^r$S(O)$_2$NHR$^r$, —NHS(O)$_2$NR$^r$R$^r$, —NR$^r$S(O)$_2$NR$^r$R$^r$, —NHR$^r$, —NR$^r$R$^r$, —R$^i$, and —R$^j$;

wherein each W is independently selected from the group consisting of lower alkenyl and lower alkenyl, wherein lower alkenyl or lower alkynyl are optionally substituted with one or more, preferably 1, 2, 3, 4 or 5, also 1, 2 or 3 substituents selected from the group consisting of fluoro, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR$^r$, —SR$^r$, —OC(O)R$^r$, —OC(S)R$^r$, —C(O)R$^r$, —C(S)R$^r$, —C(O)OR$^r$, —C(S)OR$^r$, —S(O)R$^r$, —S(O)$_2$R$^r$, —C(O)NHR$^r$, —C(S)NHR$^r$, —C(O)NR$^r$R$^r$, —C(S)NR$^r$R$^r$, —S(O)$_2$NHR$^r$, —S(O)$_2$NR$^r$R$^r$, —C(NH)NHR$^r$, —C(NH)NR$^s$R$^t$, —NHC(O)R$^r$, —NHC(S)R$^r$, —NR$^r$C(O)R$^r$, —NR$^r$C(S)R$^r$, —NHS(O)$_2$R$^r$, —NR$^r$S(O)$_2$R$^r$, —NHC(O)NHR$^r$, —NHC(S)NHR$^r$, —NR$^r$C(O)NH$_2$, —NR$^r$C(S)NH$_2$, —NR$^r$C(O)NHR$^r$, —NR$^r$C(S)NHR$^r$, —NHC(O)NR$^r$R$^r$, —NHC(S)NR$^r$R$^r$, —NR$^r$C(O)NR$^r$R$^r$, —NR$^r$C(S)NR$^r$R$^r$, —NHS(O)$_2$NHR$^r$, —NR$^r$S(O)$_2$NH$_2$, —NR$^r$S(O)$_2$NHR$^r$, —NHS(O)$_2$NR$^r$R$^r$, —NR$^r$S(O)$_2$NR$^r$R$^r$, —NHR$^r$, —NR$^r$R$^r$, and —R$^j$;

wherein each R$^j$ is independently selected from the group consisting of cycloalkyl, heterocycloalkyl, aryl, and heteroaryl, wherein cycloalkyl, heterocycloalkyl, aryl, and heteroaryl are optionally substituted with one or more, preferably 1, 2, 3, 4 or 5, also 1, 2 or 3 substituents selected from the group consisting of halogen, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR$^r$, —SR$^r$, —OC(O)R$^r$, —OC(S)R$^r$, —C(O)R$^r$, —C(S)R$^r$, —C(O)OR$^r$, —C(S)OR$^r$, —S(O)R$^r$, —S(O)$_2$R$^r$, —C(O)NHR$^r$, —C(S)NHR$^r$, —C(O)NR$^r$R$^r$, —C(S)NR$^r$R$^r$, —S(O)$_2$NHR$^r$, —S(O)$_2$NR$^r$R$^r$, —C(NH)NHR$^r$, —C(NH)NR$^s$R$^t$, —NHC(O)R$^r$, —NHC(S)R$^r$, —NR$^r$C(O)R$^r$, —NR$^r$C(S)R$^r$, —NHS(O)$_2$R$^r$, —NR$^r$S(O)$_2$R$^r$, —NHC(O)NHR$^r$, —NHC(S)NHR$^r$, —NR$^r$C(O)NH$_2$, —NR$^r$C(S)NH$_2$, —NR$^r$C(O)NHR$^r$, —NR$^r$C(S)NHR$^r$, —NHC(O)NR$^r$R$^r$, —NHC(S)NR$^r$R$^r$, —NR$^r$C(O)NR$^r$R$^r$, —NR$^r$C(S)NR$^r$R$^r$, —NHS(O)$_2$NHR$^r$, —NR$^r$S(O)$_2$NH$_2$, —NR$^r$S(O)$_2$NHR$^r$, —NHS(O)$_2$NR$^r$R$^r$, —NR$^r$S(O)$_2$NR$^r$R$^r$, —NHR$^r$, —NR$^r$R$^r$, cycloalkylamino, and —R$^x$;

wherein each R$^r$, R$^s$, and R$^t$ at each occurrence are independently selected from the group consisting of lower alkyl, C$_{3-6}$ alkenyl, C$_{3-6}$ alkynyl, cycloalkyl, heterocycloalkyl, aryl and heteroaryl, wherein lower alkyl is optionally substituted with one or more, preferably 1, 2, 3, 4 or 5, also 1, 2, or 3 substituents selected from the group consisting of —R$^y$, fluoro, —OH, —NH$_2$, lower alkoxy, fluoro substituted lower alkoxy, lower alkylthio, fluoro substituted lower alkylthio, mono-alkylamino, di-alkylamino, and cycloalkylamino, provided, however, that any substitution of the lower alkyl carbon bound to any O, S, or N, of —OR$^r$, —SR$^r$, —C(O)OR$^r$, —C(S)OR$^r$, —C(O)NHR$^r$, —C(S)NHR$^r$, —C(O)NR$^r$R$^r$, —C(S)NR$^r$R$^r$, —S(O)$_2$NHR$^r$, —S(O)$_2$NR$^r$R$^r$, —C(NH)NHR$^r$, —NR$^r$C(O)R$^r$, —NR$^r$C(S)R$^r$, —NR$^r$S(O)$_2$R$^r$, —NHC(O)NHR$^r$, —NHC(S)NHR$^r$, —NR$^r$C(O)NH$_2$, —NR$^r$C(S)NH$_2$, —NR$^r$C(O)NHR$^r$, —NR$^r$C(S)NHR$^r$, —NHC(O)NR$^r$R$^r$, —NHC(S)NR$^r$R$^r$, —NR$^r$C(O)NR$^r$R$^r$, —NR$^r$C(S)NR$^r$R$^r$, —NHS(O)$_2$NHR$^r$, —NR$^r$S(O)$_2$NH$_2$, —NR$^r$S(O)$_2$NHR$^r$, —NHS(O)$_2$NR$^r$R$^r$, —NR$^r$S(O)$_2$NR$^r$R$^r$, —NHR$^r$, or —NR$^r$R$^r$ is selected from the group consisting of fluoro and —R$^y$, and wherein C$_{3-6}$ alkenyl or C$_{3-6}$ alkenyl are optionally substituted with one or more, preferably 1, 2, 3, 4 or 5, also 1, 2, or 3 substituents selected from the group consisting of —R$^y$, fluoro, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino, provided, however, that any substitution of the C$_{3-6}$ alkenyl or C$_{3-6}$ alkynyl carbon bound to any O, S, or N, of —OR$^r$, —SR$^r$, —C(O)OR$^r$, —C(S)OR$^r$, —C(O)NHR$^r$, —C(S)NHR$^r$, —C(O)NR$^r$R$^r$, —C(S)NR$^r$R$^r$, —S(O)$_2$NHR$^r$, —S(O)$_2$NR$^r$R$^r$, —C(NH)NHR$^r$, —NR$^r$C(O)R$^r$, —NR$^r$C(S)R$^r$, —NR$^r$S(O)$_2$R$^r$, —NHC(O)NHR$^r$, —NHC(S)NHR$^r$, —NR$^r$C(O)NH$_2$, —NR$^r$C(S)NH$_2$, —NR$^r$C(O)NHR$^r$, —NR$^r$C(S)NHR$^r$, —NHC(O)NR$^r$R$^r$, —NHC(S)NR$^r$R$^r$, —NR$^r$C(O)NR$^r$R$^r$, —NR$^r$C(S)NR$^r$R$^r$, —NHS(O)$_2$NHR$^r$, —NR$^r$S(O)$_2$NH$_2$, —NR$^r$S(O)$_2$NHR$^r$, —NHS(O)$_2$NR$^r$R$^r$, —NR$^r$S(O)$_2$NR$^r$R$^r$, —NHR$^r$, or —NR$^r$R$^r$ is selected from the group consisting of fluoro, lower alkyl, fluoro substituted lower alkyl, and —R$^y$, and wherein cycloalkyl, heterocycloalkyl, aryl, and heteroaryl are optionally substituted with one or more, preferably 1, 2, 3, 4 or 5, also 1, 2, or 3 substituents selected from the group consisting of halogen, —OH, —NH$_2$, —NO$_2$, —CN, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino, or R$^s$ and R$^t$ combine with the nitrogen to which they are attached form a 5-7 membered heterocycloalkyl or a 5 or 7 membered nitrogen containing heteroaryl, wherein the 5-7 membered heterocycloalkyl or 5 or 7 membered nitrogen containing heteroaryl are optionally substituted with one or more, preferably 1, 2, 3, 4 or 5, also 1, 2, or 3 substituents selected from the group consisting of halogen, —NO$_2$, —CN, —OH, —NH$_2$, OR$^u$, —SR$^u$, —NHR$^u$, —NR$^u$R$^u$, —R$^x$, and —R$^y$;

wherein each R$^u$ is independently selected from the group consisting of lower alkyl, C$_{3-6}$ alkenyl, C$_{3-6}$ alkynyl, cycloalkyl, heterocycloalkyl, aryl, and heteroaryl, wherein lower alkyl is optionally substituted with one or more, preferably 1, 2, 3, 4 or 5, also 1, 2, or 3 substituents selected from the group consisting of —R$^y$, fluoro, —OH, —NH$_2$, lower alkoxy, fluoro substituted lower alkoxy, lower alkylthio, fluoro substituted lower alkylthio, mono-alkylamino, di-alkylamino, and cycloalkylamino, provided, however, that any substitution of the lower alkyl carbon bound to the O of —OR$^u$, S of —SR$^u$, or N of —NHR$^u$ is fluoro or —R$^y$, and wherein C$_{3-6}$ alkenyl or C$_{3-6}$ alkynyl are optionally substituted with one or more, preferably 1, 2, 3, 4 or 5, also 1, 2, or 3 substituents selected from the group consisting of —R$^y$, fluoro, —OH, —NH$_2$, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino, provided, however, that any substitution of the C$_{3-6}$ alkenyl or C$_{3-6}$ alkynyl carbon bound to the O of —OR$^u$, S of —SR$^u$, or N of —NHR$^u$ is fluoro, lower alkyl, fluoro substituted lower alkyl, or —R$^y$, and wherein cycloalkyl, heterocycloalkyl, aryl, and heteroaryl are optionally substituted with one or more, preferably 1, 2, 3, 4 or 5, also 1, 2, or 3 substituents selected from the group consisting of halogen, —OH, —NH$_2$, —NO$_2$, —CN, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino;

wherein each $R^x$ is selected from the group consisting of lower alkyl, lower alkenyl and lower alkynyl, wherein lower alkyl is optionally substituted with one or more, preferably 1, 2, 3, 4 or 5, also 1, 2, or 3 substituents selected from the group consisting of —$R^y$, fluoro, —OH, —NH$_2$, lower alkoxy, fluoro substituted lower alkoxy, lower alkylthio, fluoro substituted lower alkylthio, mono-alkylamino, di-alkylamino, and cycloalkylamino, and wherein lower alkenyl or lower alkynyl are optionally substituted with one or more, preferably 1, 2, 3, 4 or 5, also 1, 2, or 3 substituents selected from the group consisting of —$R^y$, fluoro, —OH, —NH$_2$, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino;

wherein each $R^y$ is selected from the group consisting of cycloalkyl, heterocycloalkyl, aryl, and heteroaryl, wherein cycloalkyl, heterocycloalkyl, aryl, and heteroaryl are optionally substituted with one or more, preferably 1, 2, 3, 4 or 5, also 1, 2, or 3 substituents selected from the group consisting of halogen, —OH, —NH$_2$, —NO$_2$, —CN, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino.

In some embodiments, all occurrences of optionally substituted lower alkyl, optionally substituted $C_{2-6}$ alkyl, optionally substituted lower alkenyl, or optionally substituted lower alkynyl are optionally substituted with one or more, also 1, 2 or 3 groups or substituents selected from the group consisting of fluoro, —NO$_2$, —CN, —OR$^{1a}$, —SR$^{1a}$, —NR$^{1a}$R$^{1a}$, —OC(O)R$^{1a}$, —OC(S)R$^{1a}$, —C(O)R$^{1a}$, —C(S)R$^{1a}$, —C(O)OR$^{1a}$, —C(S)OR$^{1a}$, —C(O)NR$^{1a}$R$^{1a}$, —C(S)NR$^{1a}$R$^{1a}$, —S(O)$_2$NR$^{1a}$R$^{1a}$, —C(NH)NR$^{1a}$R$^{1a}$, —NR$^{1a}$C(O)R$^{1a}$, —NR$^{1a}$C(S)R$^{1a}$, —NR$^{1a}$S(O)$_2$R$^{1a}$, —NR$^{1a}$C(O)NR$^{1a}$R$^{1a}$, —NR$^{1a}$C(S)NR$^{1a}$R$^{1a}$, —NR$^{1a}$S(O)$_2$NR$^{1a}$R$^{1a}$, —S(O)R$^{1a}$, —S(O)$_2$R$^{1a}$, cycloalkyl, heterocycloalkyl, aryl and heteroaryl, wherein cycloalkyl, heterocycloalkyl, aryl and heteroaryl are optionally substituted with one or more, also 1, 2 or 3 groups or substituents selected from the group consisting of halogen, —NO$_2$, —CN, —OR$^{1a}$, —SR$^{1a}$, —NR$^{1a}$R$^{1a}$, —OC(O)R$^{1a}$, —OC(S)R$^{1a}$, —C(O)R$^{1a}$, —C(S)R$^{1a}$, —C(O)OR$^{1a}$, —C(S)OR$^{1a}$, —C(O)NR$^{1a}$R$^{1a}$, —C(S)NR$^{1a}$R$^{1a}$, —S(O)$_2$NR$^{1a}$R$^{1a}$, —C(NH)NR$^{1a}$R$^{1a}$, —NR$^{1a}$C(O)R$^{1a}$, —NR$^{1a}$C(S)R$^{1a}$, —NR$^{1a}$S(O)$_2$R$^{1a}$, —NR$^{1a}$C(O)NR$^{1a}$R$^{1a}$, —NR$^{1a}$C(S)NR$^{1a}$R$^{1a}$, —NR$^{1a}$S(O)$_2$NR$^{1a}$R$^{1a}$, —S(O)R$^{1a}$, —S(O)$_2$R$^{1a}$, —R$^{1b}$, and lower alkyl optionally substituted with one or more, also 1, 2 or 3 groups or substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino, and —R$^{1b}$, and all occurrences of optionally substituted cycloalkyl, optionally substituted heterocycloalkyl, optionally substituted 5-7 membered heterocycloalkyl, optionally substituted aryl, optionally substituted arylene, optionally substituted heteroaryl, optionally substituted heteroarylene, or optionally substituted 5 or 7 membered nitrogen containing heteroaryl are optionally substituted with one or more, also 1, 2, or 3 groups or substituents selected from the group consisting of halogen, —NO$_2$, —CN, —OR$^{1a}$, —SR$^{1a}$, —NR$^{1a}$R$^{1a}$, —OC(O)R$^{1a}$, —OC(S)R$^{1a}$, —C(O)R$^{1a}$, —C(S)R$^{1a}$, —C(O)OR$^{1a}$, —C(S)OR$^{1a}$, —C(O)NR$^{1a}$R$^{1a}$, —C(S)NR$^{1a}$R$^{1a}$, —S(O)$_2$NR$^{1a}$R$^{1a}$, —C(NH)NR$^{1a}$R$^{1a}$, —NR$^{1a}$C(O)R$^{1a}$, —NR$^{1a}$C(S)R$^{1a}$, —NR$^{1a}$S(O)$_2$R$^{1a}$, —NR$^{1a}$C(O)NR$^{1a}$R$^{1a}$, —NR$^{1a}$C(S)NR$^{1a}$R$^{1a}$, —NR$^{1a}$S(O)$_2$NR$^{1a}$R$^{1a}$, —S(O)R$^{1a}$, —S(O)$_2$R$^{1a}$, —R$^{1b}$, and lower alkyl optionally substituted with one or more, also 1, 2 or 3 groups or substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino, and —R$^{1b}$, wherein R$^{1a}$ is selected from the group consisting of hydrogen, provided, however, that hydrogen is not bound to any of C(S), C(O), S(O), or S(O)$_2$ of —OC(O)R$^{1a}$, —OC(S)R$^{1a}$, —C(O)R$^{1a}$, —C(S)R$^{1a}$, —NR$^{1a}$C(O)R$^{1a}$, —NR$^{1a}$C(S)R$^{1a}$, —NR$^{1a}$S(O)$_2$R$^{1a}$, —S(O)R$^{1a}$, or —S(O)$_2$R$^{1a}$, —R$^{1b}$, and lower alkyl optionally substituted with one or more, also 1, 2 or 3 groups or substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino, and —R$^{1b}$, provided, however, that any substitution of the alkyl carbon bound to O, S, or N of —OR$^{1a}$, —SR$^{1a}$, —NR$^{1a}$R$^{1a}$, —C(O)OR$^{1a}$, —C(S)OR$^{1a}$, —C(O)NR$^{1a}$R$^{1a}$, —C(S)NR$^{1a}$R$^{1a}$, —S(O)$_2$NR$^{1a}$R$^{1a}$, —C(NH)NR$^{1a}$R$^{1a}$, —NR$^{1a}$C(O)R$^{1a}$, —NR$^{1a}$C(S)R$^{1a}$, —NR$^{1a}$S(O)$_2$R$^{1a}$, —NR$^{1a}$C(O)NR$^{1a}$R$^{1a}$, —NR$^{1a}$C(S)NR$^{1a}$R$^{1a}$, or —NR$^{1a}$S(O)$_2$NR$^{1a}$R$^{1a}$, is fluoro or —R$^{1b}$, and wherein —R$^{1b}$ is selected from the group consisting of cycloalkyl, heterocycloalkyl, aryl and heteroaryl, wherein cycloalkyl, heterocycloalkyl, aryl and heteroaryl are optionally substituted with one or more, also 1, 2 or 3 groups or substituents selected from the group consisting of halogen, —CN, —OH, —NH$_2$, lower alkoxy, fluoro substituted lower alkoxy, lower alkylthio, fluoro substituted lower alkylthio, mono-alkylamino, di-alkylamino, and cycloalkylamino.

In some embodiments, all occurrences of optionally substituted lower alkyl, optionally substituted $C_{2-6}$ alkyl, optionally substituted lower alkenyl, or optionally substituted lower alkynyl are optionally substituted with one or more, also 1, 2 or 3 groups or substituents selected from the group consisting of fluoro, —CN, —OR$^{1a}$, —SR$^{1a}$, —NR$^{1a}$R$^{1a}$, —C(O)R$^{1a}$, —C(S)R$^{1a}$, —C(O)OR$^{1a}$, —C(O)NR$^{1a}$R$^{1a}$, —C(S)NR$^{1a}$R$^{1a}$, —S(O)$_2$NR$^{1a}$R$^{1a}$, —NR$^{1a}$C(O)R$^{1a}$, —NR$^{1a}$C(S)R$^{1a}$, —NR$^{1a}$S(O)$_2$R$^{1a}$, —S(O)R$^{1a}$, —S(O)$_2$R$^{1a}$, cycloalkyl, heterocycloalkyl, aryl and heteroaryl, wherein cycloalkyl, heterocycloalkyl, aryl and heteroaryl are optionally substituted with one or more, also 1, 2 or 3 groups or substituents selected from the group consisting of halogen, —CN, —OR$^{1a}$, —SR$^{1a}$, —NR$^{1a}$R$^{1a}$, —C(O)R$^{1a}$, —C(S)R$^{1a}$, —C(O)OR$^{1a}$, —C(O)NR$^{1a}$R$^{1a}$, —C(S)NR$^{1a}$R$^{1a}$, —S(O)$_2$NR$^{1a}$R$^{1a}$, —NR$^{1a}$C(O)R$^{1a}$, —NR$^{1a}$C(S)R$^{1a}$, —NR$^{1a}$S(O)$_2$R$^{1a}$, —S(O)R$^{1a}$, —S(O)$_2$R$^{1a}$, —R$^{1b}$, and lower alkyl optionally substituted with one or more, also 1, 2 or 3 groups or substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino, and —R$^{1b}$, and all occurrences of optionally substituted cycloalkyl, optionally substituted heterocycloalkyl, optionally substituted 5-7 membered heterocycloalkyl, optionally substituted aryl, optionally substituted arylene, optionally substituted heteroaryl, optionally substituted heteroarylene, or optionally substituted 5 or 7 membered nitrogen containing heteroaryl are optionally substituted with one or more, also 1, 2, or 3 groups or substituents selected from the group consisting of halogen, —CN, —OR$^{1a}$, —SR$^{1a}$, —NR$^{1a}$R$^{1a}$, —C(O)R$^{1a}$, —C(S)R$^{1a}$, —C(O)OR$^{1a}$, —C(O)NR$^{1a}$R$^{1a}$, —C(S)NR$^{1a}$R$^{1a}$, —S(O)$_2$NR$^{1a}$R$^{1a}$, —NR$^{1a}$C(O)R$^{1a}$, —NR$^{1a}$C(S)R$^{1a}$, —NR$^{1a}$S(O)$_2$ $R^{1a}$, —S(O)$R^{1a}$, —S(O)$R^{1a}$, —S(O)$_2R^{1a}$, —$R^{1b}$, and lower alkyl optionally substituted with one or more, also 1, 2 or 3 groups or substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino, and —$R^{1b}$, wherein $R^{1a}$ is selected from the group consisting of hydrogen, provided, however, that hydrogen is not bound to any of C(S), C(O), S(O), or S(O)$_2$ of —C(O)$R^{1a}$, —C(S)$R^{1a}$, —$NR^{1a}$C(O)$R^{1a}$, —$NR^{1a}$C(S)$R^{1a}$, —$NR^{1a}$S(O)$_2R^{1a}$, —S(O)$R^{1a}$, or —S(O)$_2R^{1a}$, —$R^{1b}$, and lower alkyl optionally substituted with one or more, also 1, 2 or 3 groups or substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino, and —$R^{1b}$, provided, however, that any substitution of the alkyl carbon bound to O, S, or N of —O$R^{1a}$, —S$R^{1a}$, —$NR^{1a}R^{1a}$, —C(O)O$R^{1a}$, —C(O)$NR^{1a}R^{1a}$, —C(S)$NR^{1a}R^{1a}$, —S(O)$_2NR^{1a}R^{1a}$, —$NR^{1a}$C(O)$R^{1a}$, —$NR^{1a}$C(S)$R^{1a}$, or —$NR^{1a}$S(O)$_2R^{1a}$, is fluoro or —$R^{1b}$, and wherein —$R^{1b}$ is selected from the group consisting of cycloalkyl, heterocycloalkyl, aryl and heteroaryl, wherein cycloalkyl, heterocycloalkyl, aryl and heteroaryl are optionally substituted with one or more, also 1, 2 or 3 groups or substituents selected from the group consisting of halogen, —CN, —OH, —NH$_2$, lower alkoxy, fluoro substituted lower alkoxy, lower alkylthio, fluoro substituted lower alkylthio, mono-alkylamino, di-alkylamino, and cycloalkylamino.

"Lower alkoxy" denotes the group —O$R^z$, where $R^z$ is lower alkyl. "Substituted lower alkoxy" denotes lower alkoxy in which $R^z$ is lower alkyl substituted with one or more substituents as indicated herein, for example, in the description of compounds of Formula III, including descriptions of substituted cycloalkyl, cycloheteroalkyl, aryl and heteroaryl, attached at any available atom to produce a stable compound. Preferably, substitution of lower alkoxy is with 1, 2, 3, 4, or 5 substituents, also 1, 2, or 3 substituents. For example "fluoro substituted lower alkoxy" denotes lower alkoxy in which the lower alkyl is substituted with one or more fluoro atoms, where preferably the lower alkoxy is substituted with 1, 2, 3, 4 or 5 fluoro atoms, also 1, 2, or 3 fluoro atoms. While it is understood that substitutions on alkoxy are attached at any available atom to produce a stable compound, substitution of alkoxy is such that O, S, or N (except where N is a heteroaryl ring atom), are not bound to the alkyl carbon bound to the alkoxy O. Further, where alkoxy is described as a substituent of another moiety, the alkoxy oxygen is not bound to a carbon atom that is bound to an O, S, or N of the other moiety (except where N is a heteroaryl ring atom), or to an alkene or alkyne carbon of the other moiety.

"Lower alkylthio" denotes the group —S$R^{aa}$, where $R^{aa}$ is lower alkyl. "Substituted lower alkylthio" denotes lower alkylthio in which $R^{aa}$ is lower alkyl substituted with one or more substituents as indicated herein, for example, in the description of compounds of Formula III, including descriptions of substituted cycloalkyl, cycloheteroalkyl, aryl and heteroaryl, attached at any available atom to produce a stable compound. Preferably, substitution of lower alkylthio is with 1, 2, 3, 4, or 5 substituents, also 1, 2, or 3 substituents. For example "fluoro substituted lower alkylthio" denotes lower alkylthio in which the lower alkyl is substituted with one or more fluoro atoms, where preferably the lower alkylthio is substituted with 1, 2, 3, 4 or 5 fluoro atoms, also 1, 2, or 3 fluoro atoms. While it is understood that substitutions on alkylthio are attached at any available atom to produce a stable compound, substitution of alkylthio is such that O, S, or N (except where N is a heteroaryl ring atom), are not bound to the alkyl carbon bound to the alkylthio S. Further, where alkylthio is described as a substituent of another moiety, the alkylthio sulfur is not bound to a carbon atom that is bound to an O, S, or N of the other moiety (except where N is a heteroaryl ring atom), or to an alkene or alkyne carbon of the other moiety.

"Amino" or "amine" denotes the group —NH$_2$. "Mono-alkylamino" denotes the group —NH$R^{bb}$ where $R^{bb}$ is lower alkyl. "Di-alkylamino" denotes the group —N$R^{bb}R^{cc}$, where $R^{bb}$ and $R^{cc}$ are independently lower alkyl. "Cycloalkylamino" denotes the group —N$R^{dd}R^{ee}$, where $R^{dd}$ and $R^{ee}$ combine with the nitrogen to form a 5-7 membered heterocycloalkyl, where the heterocycloalkyl may contain an additional heteroatom within the ring, such as O, N, or S, and may also be further substituted with lower alkyl. Examples of 5-7 membered heterocycloalkyl include, but are not limited to, piperidine, piperazine, 4-methylpiperazine, morpholine, and thiomorpholine. While it is understood that when mono-alkylamino, di-alkylamino, or cycloalkylamino are substituents on other moieties that are attached at any available atom to produce a stable compound, the nitrogen of mono-alkylamino, di-alkylamino, or cycloalkylamino as substituents is not bound to a carbon atom that is bound to an O, S, or N of the other moiety.

A "nitrogen protecting group" is a chemical group covalently bound to a nitrogen atom of a compound that is used to protect the nitrogen from reaction during a synthetic step. The nitrogen protecting group may be added to a compound and removed in a subsequent step by methods known to those of skill in the art. Nitrogen protecting groups include, without limitation, carbamates, amides, N-sulfonyl derivatives, groups of formula —C(O)OR, wherein R is, for example, methyl, ethyl, t-butyl, benzyl, phenylethyl, CH$_2$=CHCH$_2$—, and the like, groups of the formula —C(O)R', wherein R' is, for example, methyl, phenyl, trifluoromethyl, and the like, groups of the formula —SO$_2$R", wherein R" is, for example, tolyl, phenyl, trifluoromethyl, 2,2,5,7,8-pentamethylchroman-6-yl, 2,3,6-trimethyl-4-methoxyphenyl, and the like, and silanyl containing groups, such as 2-trimethylsilylethoxymethyl, t-butyldimethylsilyl, triisopropylsilyl, and the like. Other suitable nitrogen protecting groups may be found in texts such as T. W. Greene R. P. G. M. Wuts, *Protective Groups in Organic Synthesis*, John Wiley & Sons, 1991.

As used herein, the term "composition" refers to a formulation suitable for administration to an intended animal subject for therapeutic purposes that contains at least one pharmaceutically active compound and at least one pharmaceutically acceptable carrier or excipient.

The term "pharmaceutically acceptable" indicates that the indicated material does not have properties that would cause a reasonably prudent medical practitioner to avoid administration of the material to a patient, taking into consideration the disease or conditions to be treated and the respective route of administration. For example, it is commonly required that such a material be essentially sterile, e.g., for injectibles.

In the present context, the term "therapeutically effective" or "effective amount" indicates that the materials or amount of material is effective to prevent, alleviate, or ameliorate one or more symptoms of a disease or medical condition, and/or to prolong the survival of the subject being treated.

In the present context, the terms "synergistically effective" or "synergistic effect" indicate that two or more compounds that are therapeutically effective, when used in combination, provide improved therapeutic effects greater than the additive effect that would be expected based on the effect of each compound used by itself.

As used herein, the terms "ligand" and "modulator" are used equivalently to refer to a compound that changes (i.e., increases or decreases) the activity of a target biomolecule, e.g., an enzyme such as a kinase. Generally a ligand or modulator will be a small molecule, where "small molecule refers to a compound with a molecular weight of 1500 daltons or less, or preferably 1000 daltons or less, 800 daltons or less, or 600 daltons or less. Thus, an "improved ligand" is one that possesses better pharmacological and/or pharmacokinetic properties than a reference compound, where "better" can be defined by one skilled in the relevant art for a particular biological system or therapeutic use.

In the context of binding compounds and ligands, the term "derivative" or "derivative compound" refers to a compound having a chemical structure that contains a common core chemical structure as a parent or reference compound, but differs by having at least one structural difference, e.g., by having one or more substituents added and/or removed and/or replaced, and/or by having one or more atoms replaced with different atoms. Unless clearly indicated to the contrary, the term "derivative" does not mean that the derivative is synthesized using the parent compound as a starting material or as an intermediate, although in some cases, the derivative may be synthesized from the parent.

Thus, the term "parent compound" refers to a reference compound having structural features also found in the derivative compound. Often but not always, a parent compound has a simpler chemical structure than the derivative.

By "chemical structure" or "chemical substructure" is meant any definable atom or group of atoms that constitute an individually identifiable portion of a molecule, such as a substituent moiety, a core which is optionally substituted, and the like. Normally, chemical substructures of a ligand can have a role in binding of the ligand to a target molecule, or can influence the three-dimensional shape, electrostatic charge, and/or conformational properties of the ligand.

The term "binds" in connection with the interaction between a target and a potential binding compound indicates that the potential binding compound associates with the target to a statistically significant degree as compared to association with proteins generally (i.e., non-specific binding). Thus, the term "binding compound" refers to a compound that has a statistically significant association with a target molecule. Preferably a binding compound interacts with a specified target with a dissociation constant ($K_D$) of 1 mM or less, 1 µM or less, 100 nM or less, 10 nM or less, or 1 nM or less.

In the context of compounds binding to a target, the terms "greater affinity" and "selective" indicates that the compound binds more tightly than a reference compound, or than the same compound in a reference condition, i.e., with a lower dissociation constant. In some embodiments, the greater affinity is at least 2, 3, 4, 5, 8, 10, 50, 100, 200, 400, 500, 1000, or 10,000-fold greater affinity.

As used herein in connection with compounds of the invention, the term "synthesizing" and like terms means chemical synthesis from one or more precursor materials. Further, by "assaying" is meant the creation of experimental conditions and the gathering of data regarding a particular result of the experimental conditions. For example, enzymes can be assayed based on their ability to act upon a detectable substrate. A compound or ligand can be assayed based on its ability to bind to a particular target molecule or molecules.

As used herein, the term "modulating" or "modulate" refers to an effect of altering a biological activity, especially a biological activity associated with a particular biomolecule such as a protein kinase. For example, an agonist or antagonist of a particular biomolecule modulates the activity of that biomolecule, e.g., an enzyme, by either increasing (e.g. agonist, activator), or decreasing (e.g. antagonist, inhibitor) the activity of the biomolecule, such as an enzyme. Such activity is typically indicated in terms of an inhibitory concentration ($IC_{50}$) or excitation concentration ($EC_{50}$) of the compound for an inhibitor or activator, respectively, with respect to, for example, an enzyme.

In the context of the use, testing, or screening of compounds that are or may be modulators, the term "contacting" means that the compound(s) are caused to be in sufficient proximity to a particular molecule, complex, cell, tissue, organism, or other specified material that potential binding interactions and/or chemical reaction between the compound and other specified material can occur.

As used herein in connection with amino acid or nucleic acid sequence, the term "isolate" indicates that the sequence is separated from at least a portion of the amino acid and/or nucleic acid sequences with which it would normally be associated.

In connection with amino acid or nucleic sequences, the term "purified" indicates that the subject molecule constitutes a significantly greater proportion of the biomolecules in a composition than the proportion observed in a prior composition, e.g., in a cell culture. The greater proportion can be 2-fold, 5-fold, 10-fold, or more than 10-fold, with respect to the proportion found in the prior composition.

I. General

The present invention concerns compounds of Formula I and all sub-generic formulae, compounds of Formula II and all sub-generic formulae, and compounds of Formula III and all sub-generic formulae that are modulators of protein kinases, for example without limitation, the compounds are modulators of at least one of the kinases selected from the group consisting of Abl, Akt1, Akt2, Akt3, ALK, Alk5, B-Raf, Brk, Btk, Cdk2, CDK4, CDK5, CDK6, CHK1, c-Raf-1, Csk, EGFR, EphA1, EphA2, EphB2, EphB4, Erk2, Fak, FGFR1, FGFR2, FGFR3, FGFR4, Flt1, Flt3, Flt4, Fms, Frk, Fyn, Gsk3α, Gsk3β, HCK, Her2/Erbb2, Her4/Erbb4, IGF1R, IKK beta, Irak4, Itk, Jak1, Jak2, Jak3, Jnk1, Jnk2, Jnk3, Kdr, Kit, LCK, MAP2K1, MAP2K2, MAP4K4, MAPKAPK2, Met, Mnk1, MLK1, p38, PDGFRA, PDGFRB, PDPK1, Pim1, Pim2, Pim3, PKC alpha, PKC beta, PKC theta, Plk1, Pyk2, Ret, ROCK1, ROCK2, Ron, Src, Stk6, Syk, TEC, Tie2, TrkA, Yes, and Zap70, and the use of such compounds in the treatment of diseases or conditions.

II. Kinase Targets and Indications of the Invention

Protein kinases play key roles in propagating biochemical signals in diverse biological pathways. More than 500 kinases have been described, and specific kinases have been implicated in a wide range of diseases or conditions (i.e., indications), including for example without limitation, cancer, cardiovascular disease, inflammatory disease, neurological disease, and other diseases. As such, kinases represent important control points for small molecule therapeutic intervention. Description of specific target protein kinases contemplated by the present invention follow:

Abl: Target Abl (i.e., Abelson Murine Leukemia Viral Oncogene Homolog 1) is a 122.9 kDa tyrosine kinase encoded by chromosome 9q34.1 (symbol: ABL1.) The mature protein comprises SH3 (i.e., Src homology region 3) and SH2 (i.e., Src homology region 2) domains and the TK (i.e., tyrosine kinase) domain.

OMIM indicates Abl is expressed ubiquitously and can be localized to the nucleus where it hinds DNA. Accordingly, Abl has been implicated in processes of cell differentiation, cell division, cell adhesion, and stress response. Alterations of the gene ABL1 by a t(9;22)(q34;q11) chromosomal rearrangement or viral transduction lead to malignant transformation, as in chronic myeloid leukemia (CML). The kinase activity of Abl is negatively regulated by the constituent SH3 domain, and deletion of the SH3 domain turns ABL1 into an oncogene. The t(9;22) translocation occurs in greater than 90% of chronic myelogeneous leukemia, 25 to 30% of adult and 2 to 10% of childhood acute lymphoblastic leukemia (ALL), and rare cases of acute myelogenous leukemia. The translocation results in the head-to-tail fusion of the BCR and ABL genes (Chissoe et al., Genomics 1995, 27: 67-82). The DNA-binding activity of Abl is regulated by CDC2-mediated phosphorylation suggesting a cell cycle function for ABL. Welch & Wang (Cell 1993, 75: 779-790) showed that the tyrosine kinase activity of nuclear Abl is regulated in the cell cycle through a specific interaction with the retinoblastoma protein RB1. A domain in the C-terminus of RB1 binds to the ATP-binding lobe of Abl, resulting in kinase inhibition. The RB-ABL interaction is not affected by the viral oncoproteins that bind to RB. Hyperphosphorylation of RB correlates with release of Abl and activation of Abl in S phase cells. In the nucleus Abl can enhance transcription, and this activity is inhibited by RB. Thus, nuclear Abl is an S phase-activated tyrosine kinase that might participate directly in the regulation of transcription. (Online Mendelian Inheritance in Man, OMIM™. Johns Hopkins University, Baltimore, Md. MIM Number: 189980: Dec. 20, 2005. World Wide Web URL: http://www3.ncbi.nlm.nih.gov/omim/). Abl inhibitors may be useful in treating leukemia, including chronic myelogeneous leukemia, acute lymphoblastic leukemia, and acute myelogenous leukemia.

Akt1: Target kinase Akt1 (i.e., v-akt murine thymoma viral oncogene homolog 1) is a 55.7 kDa STK encoded by chromosome 14q32.32 (symbol: AKT1), Akt1 is also known as protein kinase B-alpha, or PKB-alpha. OMIM indicates phosphoinositide 3-kinases (i.e., PI3Ks) generate specific inositol lipids implicated in the regulation of cell growth, proliferation, survival, differentiation, and cytoskeletal changes. One of the best characterized targets of PI3K lipid products is the protein kinase AKT, or protein kinase B (PKB). In quiescent cells, PKB resides in the cytosol in a low-activity conformation. Upon cellular stimulation, PKB is activated through recruitment to cellular membranes by PI3K lipid products and by phosphorylation by 3-prime phosphoinositide-dependent kinase-1. Most proliferating cells are programmed to undergo apoptosis unless specific survival signals are provided. PDGF promotes cellular proliferation, inhibits apoptosis, and activates the RAS/PIK3/AKT1/IKBKA/NFKB1 pathway (Romashkova and Makarov, Nature 1999, 401: 86-90). In this pathway, NFKB1 does not induce c-myc and apoptosis, but instead induces putative antiapoptotic genes. In response to PDGF, Akt1 transiently associates with IKBK and induces IKBK activation (OMIM MINI Number: 164730: Oct. 26, 2005) Aberrant Akt1 activity is correlated with) including gastric and prostate tumors, colorectal, ovarian, pancreatic, and breast cancer, glioblastoma and leukemia. Sun et al., Am J Pathol 2001, 159(2):431-7, report that significantly increased AKT1 kinase activity was detected in primary carcinomas of prostate (16 of 30), breast (19 of 50), and ovary (11 of 28), Tanno et al., Cancer Res 2001, 61(2): 589-93, provide evidence for a link between AKT signaling and the regulation of IGF-IR expression and demonstrate that active AKT promotes the invasiveness of pancreatic cancer cells through the up-regulation of IGF-IR expression. Neri et al., Mol Cancer Res 2003, 1(3):234-46, suggest that an up-regulation of the PI3K/AKT1 pathway might be one of the survival mechanisms responsible for the onset of resistance to chemotherapeutic and differentiating therapy in patients with acute leukemia. Akt1 activity is also important in schizophrenia and bipolar disorders. Emamian et al., Nat Genet 2004, 36(2):115-6, present convergent evidence for a decrease in AKT1 protein levels and levels of phosphorylation of GSK3beta at Ser9 in the peripheral lymphocytes and brains of individuals with schizophrenia; a significant association between schizophrenia and an AKT1 haplotype associated with lower AKT1 protein levels; and a greater sensitivity to the sensorimotor gating-disruptive effect of amphetamine, conferred by AKT1 deficiency. Akt1 inhibitors may be useful in treating cancer, including gastric, prostate, colorectal, ovarian, pancreatic and breast cancer, glioblastoma and leukemia, and also for use in combination with other chemotherapeutic drugs.

Akt2: Target kinase Akt2 (i.e., v-akt murine thymoma viral oncogene homolog 2) is a 55.8 kDa STK encoded by chromosome 19q13.1-13.2 (symbol: AKT2). Akt2 is also known as protein kinase B beta, PKB-beta, OMIM indicates that the Akt2 isoform of Akt (see e.g., Akt1 and Akt3) is enriched in insulin-responsive tissues and has been implicated in the metabolic actions of insulin. Glucose homeostasis depends on insulin responsiveness in target tissues, most importantly, muscle and liver. The critical initial steps in insulin action include phosphorylation of scaffolding proteins and activation of phosphatidylinositol 3-kinase. These early events lead to activation of the serine-threonine protein kinase Akt, also known as protein kinase B. Cho et al., Science 2001, 292: 1728-1731, showed that mice deficient in Akt2 are impaired in the ability of insulin to lower blood glucose because of defects in the action of the hormone on liver and skeletal muscle. Ablation of Akt2 in mice results in a mild but statistically significant fasting hyperglycemia due to peripheral insulin resistance and nonsuppressible hepatic glucose production accompanied by inadequate compensatory hyperinsulinemia (OMIM MIM Number: 164731: Oct. 26, 2005). Arboleda et al., Cancer Res 2003, 63(1):196-206 showed that AKT2 transfected breast and ovarian cancer cells demonstrated increased adhesion and invasion through collagen IV because of up-regulation of beta1 integrins and that AKT2 cells were more metastatic than control cells in vivo. Yamamoto et al., Clin Cancer Res 2004, 10(8):2846-50 studied the prognostic significance of Akt2 and activated Akt expression in pancreatic ductal adenocarcinoma (PDAC), concluding that p-Akt expression is a significant prognostic indicator for PDAC and inhibition of Akt is a possible molecular approach for treatment of PDAC. Yuan et al., Oncogene 2000, 19(19): 2324-30, demonstrate that activation of AKT2 is a common occurrence in human ovarian cancer and that the PI 3-kinase/ Akt pathway may be an important target for ovarian cancer intervention. Yuan et al., J Biol Chem 2003, 278(26):23432-40, demonstrate that constitutively active AKT2 renders cisplatin-sensitive A2780S ovarian cancer cells resistant to cisplatin, whereas phosphatidylinositol 3-kinase inhibitor or dominant negative AKT2 sensitizes A2780S and cisplatin-resistant A2780CP cells to cisplatin-induced apoptosis through regulation of the ASK1/JNK/p38 pathway. Akt2 inhibitors may be useful in treating cancer, including ovarian and pancreatic cancers, pancreatic ductal adenocarcinoma, and metastases of breast and ovarian cancer, and also for use in combination with other chemotherapeutic drugs, where such use sensitizes the tumor cells to the effects of the other chemotherapeutics.

Akt3: Target kinase Akt3 (i.e., v-akt murine thymoma viral oncogene homolog 3) is a 55.8 kDa STK encoded by chromosome 1q43-q44 (symbol:AKT3); Akt3 is also known as PKB gamma. Akt3 was identified as a protein kinase with high homology with the protein kinases A and C, hence, the name PKB. Akt3 comprises a PH domain that preferentially binds PtdIns(3,4,5)P$_3$ and PtdIns(3,4)P$_2$ over other phosphatidyl inositols (PIs). In quiescent cells, PKB resides in the cytosol in a low-activity conformation.

Upon cellular stimulation, PKB is activated through recruitment to cellular membranes by PI3K lipid products and phosphorylation by 3'-phosphoinositide-dependent kinase-1 (PDK1). Active PKB then appears to detach from the plasma membrane and to translocate through the cytosol to the nucleus.

Stahl et al. have found that selective activation of the Akt3 protein promotes cell survival and tumor development in 43 to 60% of nonfamilial melanomas. The predominant Akt isoform active in melanomas was identified by showing that small interfering RNA (siRNA) against only Akt3, and not Akt1 or Akt2, lowered the amount of phosphorylated (active) Akt in melanoma cells. The amount of active Akt3 increased progressively during melanoma tumor progression with highest levels present in advanced-stage metastatic melanomas. Mechanisms of Akt3 deregulation occurred through a combination of overexpression of Akt3 accompanying copy number increases of the gene and decreased PTEN protein function occurring through loss or haploinsufficiency of the PTEN gene. Targeted reduction of Akt3 activity with siRNA or by expressing active PTEN protein stimulated apoptotic signaling, which reduced cell survival by increasing apoptosis rates thereby inhibiting melanoma tumor development. Therefore, Akt3 is a selective target in melanoma cells which provides therapeutic opportunities for subjects in advanced stages of the disease (Stahl et al., Cancer Res. 2004, 64:7002-10). Nakatani et al., J Biol Chem 1999, 274(31):21528-32 showed that in estrogen receptor-deficient breast cancer cells and androgen-insensitive prostate cells, the amount of Akt3 enzymatic activity was approximately 20-60-fold higher than in cells that were estrogen- or androgen-responsive. These and other results indicate that Akt3 may contribute to the more aggressive clinical phenotype of the estrogen receptor-negative breast cancers and androgen-insensitive prostate carcinomas and inhibitors may provide therapeutic benefits in treating these cancers. Akt3 inhibitors may be useful in treating cancer, including estrogen receptor-negative breast cancers, androgen-insensitive prostate carcinomas, and melanomas.

ALK: Target kinase ALK (i.e., anaplastic lymphoma kinase) is a 176.4 kDa receptor tyrosine kinase encoded by chromosome 2p23 (symbol: ALK). ALK appears to play a role in the development of the central nervous system. Perkins, et al., show that systemic ALCL is highly associated with anaplastic lymphoma kinase (ALK) gene translocations with over-expression of ALK protein. Anaplastic large cell lymphoma (ALCL) comprises 10-15% of childhood non-Hodgkin lymphomas (NHL) (Perkins et al., Br J Haematol 2005, 131(5):624-7). Marzec et al., states aberrant expression of the ALK tyrosine kinase as a chimeric protein with nucleophosmin (NPM) and other partners plays a key role in malignant cell transformation of T-lymphocytes and other cells. Further, studies with inhibitors of NPM/ALK enzyme activity suggest ALK as an attractive therapeutic target in T-cell lymphomas and other malignancies that express the kinase in an active form (Marzec et al., Lab Invest 2005, 85(12):1544-54). ALK inhibitors may be useful in treating cancer, including anaplastic large cell lymphoma and other T cell lymphomas.

Alk5: Target kinase Alk5 (i.e., Activin receptor-like kinase 5) is a 56.0 kDa STK encoded by chromosome 9q22 (symbol: TGFBR1). Alk5, the gene for which was isolated by Franzen et al (Cell 1993, 75: 681-692), is also known as transforming growth factor-beta receptor, type I, from which term the gene symbol derives. Among other activities, Alk5 mediates the induction of multiple genes involved in cell-matrix interactions. Alk5 inhibitors may be useful in treating pancreatic and biliary cancers and cutaneous T-cell lymphoma.

B-Raf: Target kinase B-Raf (i.e., v-raf murine sarcoma viral oncogene homolog B1) is a 84.4 kDa serine/threonine kinase encoded by chromosome 7q34 (symbol: BRAF). The mature protein comprises RBD (i.e., Ras binding domain), C1 (i.e., protein kinase C conserved region 1) and STK (i.e., serine/threonine kinase) domains.

Target kinase B-Raf is involved in the transduction of mitogenic signals from the cell membrane to the nucleus and may play a role in the postsynaptic responses of hippocampal neurons, As such, genes of the RAF family encode kinases that are regulated by Ras and mediate cellular responses to growth signals. Indeed, B-Raf kinase is a key component of the RAS→Raf→MEK→ERK/MAP kinase signaling pathway, which plays a fundamental role in the regulation of cell growth, division and proliferation, and, when constitutively activated, causes tumorigenesis. Among several isoforms of Raf kinase, the B-type, or B-Raf, is the strongest activator of the downstream MAP kinase signaling.

The BRAF gene is frequently mutated in a variety of human tumors, especially in malignant melanoma and colon carcinoma. The most common reported mutation was a missense thymine (T) to adenine (A) transversion at nucleotide 1796 (T1796A; amino acid change in the B-Raf protein is Val<600> to Glu<600>) observed in 80% of malignant melanoma tumors. Functional analysis reveals that this transversion is the only detected mutation that causes constitutive activation of B-Raf kinase activity, independent of RAS activation, by converting B-Raf into a dominant transforming protein.

Niihori et al., report that in 43 individuals with cardiofacio-cutaneous (CFC) syndrome, they identified two heterozygous KRAS mutations in three individuals and eight BRAF mutations in 16 individuals, suggesting that dysregulation of the RAS-RAF-ERK pathway is a common molecular basis for the three related disorders (Niihori et al., Nat Genet. 2006, 38(3):294-6).

B-Raf inhibitors may be useful in treating neurologic diseases such as ischemic stroke, multi-infarct dementia, head injury, spinal cord injury, Alzheimer's disease (AD), Parkinson's disease; neoplastic diseases including, but not limited to, melanoma, glioma, sarcoma, carcinoma (e.g. lung, breast, pancreatic, renal), lymphoma (e.g. histiocytic lymphoma) and cancer of the thyroid, lung (e.g. small cell lung cancer), liver, breast, ovary and colon, neurofibromatosis, myelodysplastic syndrome, leukemia, tumor angiogenesis; pain of neuropathic or inflammatory origin, including acute pain, chronic pain, and migraine; cardiovascular diseases including heart failure, cardiac hypertrophy, thrombosis (e.g. thrombotic microangiopathy syndromes), atherosclerosis, reperfusion injury; inflammation including, but not limited to, psoriasis, polycystic kidney disease (PKD), arthritis and autoimmune diseases and conditions, osteoarthritis, endometriosis, scarring, vascular restenosis, fibrotic disorders, rheumatoid arthritis, inflammatory bowel disease (IBD); immunodeficiency diseases, organ transplant rejection, graft versus host disease; renal or prostatic diseases including diabetic nephropathy, nephrosclerosis, glomerulonephritis, prostate hyperplasia; metabolic disorders, obesity; infection, including, but not limited to *Helicobacter pylori* and *Influenza* virus, fever, sepsis; pulmonary diseases including chronic obstructive pulmonary disease (COPD) and acute respiratory distress syndrome (ARDS); genetic developmental diseases such as Noonan's syndrome, Costello syndrome, (faciocutaneoskeletal syndrome), leopard syndrome, cardiofaciocutaneous syndrome (CFC), and neural crest syndrome abnormalities causing cardiovascular, skeletal, intestinal, skin, hair and endocrine diseases.

c-Raf-1: Target kinase c-Raf-1 (i.e., v-raf murine sarcoma viral oncogene homolog 1) is a 73.0 kDa STK encoded by chromosome 3p25 (symbol: RAF1). c-Raf-1 can be targeted to to the mitochondria by BCL2 (i.e., oncogene B-cell leukemia 2) which is a regulator of apoptotic cell death. Active c-Raf-1 improves BCL2-mediated resistance to apoptosis, and c-Raf-1 phosphorylates BAD (i.e., BCL2-binding protein). c-Raf-1 is implicated in carcinomas, including colorectal, ovarian, lung and renal cell carcinoma. C-Raf-1 is also implicated as an important mediator of tumor angiogenesis (Hood, J. D. et al., 2002, Science 296, 2404). C-Raf-1 inhibitors may also be useful for the treatment of acute myeloid leukemia and myelodysplastic syndromes (Crump, Curr Pharm Des 2002, 8(25):2243-8). Raf-1 activators may be useful as treatment for neuroendocrine tumors, such as medullary thyroid cancer, carcinoid, small cell lung cancer and pheochromocytoma (Kunnimalaiyaan et al., Anticancer Drugs 2006, 17(2):139-42). C-Raf-1 inhibitors may be useful in treating colorectal, ovarian, lung and renal cell carcinoma, acute myeloid leukemia, myelodysplastic syndromes, tumor angiogenesis, and neuroendocrine tumors such as medullary thyroid cancer, carcinoid, small cell lung cancer and pheochromocytoma.

Brk: Target kinase Brk (i.e. breast tumor kinase, also known as PTK6) is a 51.8 kDa non-receptor tyrosine kinase encoded by human chromosome 20q13.3 (symbol: BRK). The kinase has an SH3 domain, an SH2 domain, and a catalytic domain. In normal tissues, the expression of Brk (breast tumor kinase) is restricted to differentiating epithelial cells of the skin and gastrointestinal tract. According to Harvey and Crompton, Brk is expressed in over 60% of breast carcinoma tissue samples and breast tumour cell lines, but not normal mammary tissue or benign lesions. They used RNA interference to efficiently and specifically downregulate Brk protein levels in breast carcinoma cells, and determined that this results in a significant suppression of their proliferation (Harvey and Crompton, Oncogene, 2003, 22(32): 5006-5010). Lin et al. identified protein-tyrosine kinases that may be involved in the development and progression of head and neck squamous cell carcinoma (HNSCC), and their findings suggest that the signaling pathways mediated through EphA1, Brk, and Ron may be involved in the development and progression of HNSCC (Lin et al., Arch Otolaryngol Head Neck Surg, 2004, 130(3):311-6). Llor et al. examined BRK expression in the normal gastrointestinal tract, colon tumor cell lines, and primary colon tumor samples and showed BRK is expressed in normal epithelial cells of the gastrointestinal tract that are undergoing terminal differentiation. BRK expression also increased during differentiation of the Caco-2 colon adenocarcinoma cell line. Modest increases in BRK expression were detected in primary colon tumors by RNase protection, in situ hybridization, and immunohistochemical assays (Llor et al., Clin Cancer Res. 1999, 5(7): 1767-77). Brk inhibitors may be useful in treating cancer, such as breast and colon cancer, and head and neck squamous cell carcinoma.

Btk: Target kinase Btk (i.e., Bruton's tyrosine kinase) is a 76.3 kDa tyrosine kinase encoded by chromosome Xq21.33-q22 (symbol: BTK). The mature kinase comprises a PH (i.e., Pleckstrin homology) domain, a BTK (i.e., Bruton's tyrosine kinase motif) motif, two SH3 domains, and a TK domain. Mao et al. determined the X-ray crystal structure of the Btk kinase domain in its unphosphorylated state to 2.1-angstrom resolution (Mao et al., J. Biol. Chem., 2001, 276:41435).

As a member of the BTK/Tec family of protein tyrosine kinases (i.e., PTKs), cytoplasmic Btk is involved in signal transduction pathways regulating growth and differentiation of B-lineage lymphoid cells (Rawlings, D. J., and Witte, O. N., 1994. Immunol. Rev. 138:105-119; Kurosaki, T., 1997, Curr Opin. Immunol 9:309-318; Uckun, F. M., 1998, Biochemical Pharmacology 56:683-691). As such, Btk participates in signal transduction pathways initiated by the binding of a variety of extracellular ligands to their cell surface receptors. For example, following ligation of B cell antigen receptors (BCR), Btk activation by the concerted actions of the PTKs Lyn and Syk (Kurosaki, T. (1997) Curr Opin. Immunol. 9, 309-318) is required for induction of phospholipase C-[gamma]2 mediated calcium mobilization (Kurosaki, T., 1997, Curr Opin. Immunol. 9:309-318). Furthermore, Btk regulates B cell antigen receptor-mediated JNK1 response through Rac1 and phospholipase C-gamma2 activation.

Mutations in the human BTK gene are the cause of X-linked agammaglobulinemia (XLA), a male immune deficiency disorder characterized by a lack of mature, immunoglobulin producing, peripheral B cells (Tsukada, S., et al. (1993) Cell 72, 279-290; and Vetrie, D., et al. (1993) Nature 361, 226-233) and associated with a failure of Ig heavy chain rearrangement. Patients are unusually prone to bacterial infection but not to viral infection. A clinical picture resembling rheumatoid arthritis develops in many. Before antibiotics, death occurred in the first decade. In the more usual X-linked form of the disease, plasma cells are lacking. A rarer form of agammaglobulinemia (Hitzig, W. H et al. 1961, Med. Wschr., 91:1625), which is inherited as an autosomal recessive, shows marked depression of the circulating lymphocytes, and lymphocytes are absent from the lymphoid tissue, Mensink et al. (Clin. Genet., 1987, 31:91) mapped XLA to Xq21.3-q22. Schwaber (Clin. Invest., 1992, 89:2053) presented direct evidence that of a failure of V(D)J recombination which causes arrest in the transition from pre-B cell to B lymphocyte. XLA patients have been classified in 2 general groups: those presenting at an early age with particularly severe infections and those with less severe disease in which production of immunoglobulin is sustained at low-to-normal levels well into the first decade of life. In the latter cases, an ontogenetic change may occur in which the defective tyrosine kinase no longer can sustain the B-cell population, and a progressive reduction in immunoglobulin production occurs (Ohta, Y et al., Proc. Nat. Acad. Sci., 1994, 91:9062)

Btk is an inhibitor of the Fas/APO-1 death inducing signaling complex (DISC) in B-lineage lymphoid cells (Vassilev, A., et al., 1998, J. Biol. Chem., 274:1646-1656). Additionally, Btk prevents ceramide- and vincristine-induced apoptosis. The fate of leukemia/lymphoma cells may reside in the balance between the opposing proapoptotic effects of caspases activated by DISC and an upstream anti-apoptotic regulatory mechanism involving Btk and/or its substrates (Vassilev, A., et al, 1998, J. Biol. Chem. 274:1646-1656).

Accordingly, inhibitors of Btk are likely to enhance the drug sensitivity of B-lineage (e.g. leukemia/lymphoma such as acute lymphocytic leukemia) cells. Thus, pharmacological agents with Btk-modulatory activity can be used as chemosensitizing agents for treating Btk-expressing malignancies or diseases caused by proliferation and antibody production of BTK-expressing B-cells, and as B-cell reconstituting agents in humoral immunodeficiencies with decreased numbers or absence of B-cells. Furthermore, Btk modulating agents are useful as immunosuppressive agents for prevention of hyperacute rejection of organs in transplantation, which is directed by B-cells, autoimmune diseases, and conversion of immunity to drugs (e.g. antibodies or biologicals) or blood products (e.g. coagulation factors such as Factor VIII) in patients who develop antibodies to such agents.

Significant additional research has defined the role of Btk in the cell. For example, Cheng et al. (Proc. Nat. Acad. Sci., 1994, 91:8152) showed that Btk interacts with the SH3 domains of Fyn, Lyn, and Hck, all of which are activated upon stimulation of B- and T-cell receptors. These findings extended the range of interactions mediated by SH3 domains and provide indication of a link between Btk and previously established signaling pathways in B lymphocytes. Further, linkage studies involving 1,114 progeny backcross revealed colocalization of X-linked immunodeficiency (xid) mutation in mice with the BTK gene for (Thomas, J. D. et al., Science 1993, 261:355). And further, Uckun et al. (Uckun, F. M et al. 1996, Science 273: 1096) reported that DT-40 lymphoma B cells rendered Btk deficient through targeted disruption of the BTK gene did not undergo radiation-induced apoptosis. Finally, Btk plays a key role in endotoxin-induced TNFα release from monocytes (Horwood, N. J. et al., J. Exp. Med. 2003, 197:1603).

Btk inhibitors may be useful in treating multiple sclerosis, systemic lupus erythematosis, rheumatoid arthritis, and Graves' disease, in addition to the diseases discussed above.

Cyclin dependent kinases: The cyclin dependent kinases (Cdk) play a major role in the signaling of cell cycles. The Cdk binds cyclin protein to form complex involved in the various stages of the cell cycle. Aberrant cell cycle progression occurs in cancers, often involving the activity of Cdk, such that inhibitors of Cdk are potential anti-cancer therapeutics.

Cdk2: Target kinase Cdk2 (i.e., Cyclin dependent kinase 2) is a 33.9 kDa serine/threonine kinase (STK) encoded by chromosome 12q13 (symbol: CDK2). Cdk2 is also known as p33 protein kinase, and cell division protein kinase 2. De Bondt et al. reported the X-ray crystallographic structure of Cdk2 (De Bondt et al., Nature 1993, 363: 595-602). Cdk2 is involved in control of the human cell cycle. Cdk2 activation requires association with cyclins and leads to cell proliferation. Further, inhibition of cellular proliferation occurs upon association of inhibitors (e.g., cyclin-dependent kinase inhibitor 1B) with the cyclin-Cdk2 complex. Cyclin E/Cdk2 complexes play a role in carcinogenesis, for example, Cdk2 amplication is associated with concurrent Cyclin E amplification in several cancers, including colorectal and ovarian cancer (Kitahara et al., Int. J. Cancer, 1995, 53: 1986-1989; Marone et al., Int. J. Cancer, 1998, 75: 31-39). Teixeira et al. show that retinoic acid inhibits cell cycle progression of MCF-7 human breast cancer cells by inhibiting cdk2 mRNA and protein production and by decreasing cdk2 activity (Teixeira et al., Mol Endocrinol 1997, 11(9):1191-202). Cipriano and Chen studied the TGF-beta1 effect on normal human prostate and carcinoma cells, and showed that normal cells were sensitive to growth inhibition, whereas tumor cells were not or only minimally inhibited regardless of the concentration of TGF-beta1, and correlated these results to Cdk2 activity. Their results indicate that a lack of inhibition of the Cdk2 activity correlates with insensitivity to TGF-beta1 in prostate tumor cells (Cipriano and Chen, Oncogene 1998, 17(12): 1549-56). Cdk2 inhibitors may be useful in treating cancer, including prostate, breast, colorectal and ovarian cancer.

Cdk4: Target kinase Cdk4 (i.e., Cyclin dependent kinase 4) is a 33 kDa STK encoded by chromosome 12q14 (symbol: CDK4). Lam et al. reported expression of CDK4 and CDK6 was elevated relative to matched normal brain tissue in eight of 18 glioblastoma multiforme (GBM) tumours (44%), Their data attests to the functional importance of both CDK4 and CDK6 in astrocytic tumourigenesis, particularly during the later stages of tumour progression (Lam et al., Br J Neurosurg 2000, 14(1):28-32). Backlund et at found that loss of both wild-type copies of any of the three tumour suppressor genes CDKN2A, CDKN2B and RB1 or gene amplification of CDK4, disrupting the Rb1 pathway, were associated with shorter survival in anaplastic astrocytoma patients (Backlund et al., Br J Cancer 2005, 93(1):124-30). Yu et al. report that the ability of cyclin D1 to activate cyclin-dependent kinase CDK4 underlies the critical role for cyclin D1 in breast cancer formation. They also found that the continued presence of CDK4-associated kinase activity is required to maintain breast tumorigenesis (Yu et al., Cancer Cell 2006, 9(1):23-32). Cdk4 inhibitors may be useful in treating cancer, including glioblastoma (e.g. glioblastoma multiforme), anaplastic astrocytoma, and breast cancer.

Cdk5: Target kinase Cdk5 (i.e., Cyclin dependent kinase 5) is a 33.3 kDa STK encoded by chromosome 7q36 (symbol: CDK5). Cruz et al. state that proteolytic cleavage of p35 generates p25, leading to aberrant Cdk5 activation. The accumulation of p25 is implicated in several neurodegenerative diseases. Their findings provide compelling evidence that in vivo deregulation of Cdk5 by p25 plays a causative role in neurodegeneration and the development of neurofibrillary pathology (Cruz et al., Neuron 2003, 40(3):471-83). Takahashi et al. investigated the Cdk5 distribution pattern in diffuse Lewy body disease brains using immunohistochemistry. Their data suggest that Cdk5 may be associated with Lewy body formation (Takahashi et al., Brain Res 2000, 862(1-2): 253-6). Cdk5 inhibitors may be useful in treating neurodegenerative disorders, including Alzheimer's disease, amyotrophic lateral sclerosis and Lewy body disease.

Cdk6: Target kinase Cdk6 (i.e., Cyclin dependent kinase 6) is a 36.9 kDa STK encoded by chromosome 7q21-q22 (symbol: CDK6). Lam et al. reported expression of CDK4 and CDK6 was elevated relative to matched normal brain tissue in eight of 18 glioblastoma multiforme (GBM) tumours (44%). Their data attests to the functional importance of both CDK4 and CDK6 in astrocytic tumourigenesis, particularly during the later stages of tumour progression (Lam et al., Br J Neurosurg 2000, 14(1):28-32). Costello et al., applied restriction landmark genomic scanning to matched samples of glioma and normal brain DNA and found tumor-specific amplification of the gene encoding cyclin-dependent kinase 6 (CDK6). They also corroborated this finding by identifying both amplification-associated and amplification-independent increases in CDK6 protein levels in gliomas relative to matched normal brain samples (Costello et al., Cancer Res 1997, 57(7):1250-4). Corcoran et al. found in two samples from patients with splenic lymphoma with villous lymphocytes (SLVL), the CDK6 protein was markedly overexpressed. They suggest that dysregulation of CDK6 gene expression contributes to the pathogenesis of SLVL and splenic marginal zone lymphoma (SMZL) (Oncogene 1999, 18(46):6271-7). Chilosi et al. provide evidence that CDK6 is abnormally expressed in T-cell lymphoblastic lymphoma/leukemia (T-LBL/ALL) and may be involved in the pathogenesis of this malignancy (Chilosi et al., Am J Pathol 1998, 152(1):209-17). Cram et al. show that Indole-3-carbinol (I3C) can induce a G(1) cell cycle arrest of human MCF-7 breast cancer cells that is accompanied by the selective inhibition of cyclin-dependent kinase 6 (CDK6) expression (Cram et al., J Biol Chem 2001, 276(25):22332-40). Cdk6 inhibitors may be useful in treating cancer, including glioblastoma multiforme, non-Hodgkin's lymphoma, splenic marginal zone lymphoma, T-cell lymphoblastic lymphoma (T-LBL) and T-cell acute lymphoblastic leukemia (T-ALL).

CHK1: Target kinase Chk1 (i.e., Checkpoint kinase) is a 54.4 kDa STK encoded by chromosome 11q24 (symbol: CHEK1, CHK1). CHK1 is involved in DNA damage checkpoint. Carassa et al., to understand the role of Chk1 and Chk2 in the cellular response to different anticancer agents, knocked down the expression of each protein or simultaneously of both proteins by using the small interfering RNA technique in a HCT-116 colon carcinoma cell line and in its isogenic systems in which p53 and p21 had been inactivated by targeted homologous recombination. They show that inhibition of Chk1 but not of Chk2 in p21(−/−) and p53(−/−) cells caused a greater abrogation of G(2) block induced by ionizing radiation and cis-diamine-dichloroplatinum treatments and a greater sensitization to the same treatments than in the parental cell line with p53 and p21 wild type proteins. Their data further emphasise the role of Chk1 as a molecular target to inhibit in tumors with a defect in the G(1) checkpoint with the aim of increasing the selectivity and specificity of anticancer drug treatments (Carrassa et al., Cell Cycle 2004, 3(9):1177-81). Similarly, studies by Hirose et al. focused on the mechanism by which Temozolomide (TMZ) induces G(2)-M arrest and on whether inhibition of such G(2)-M arrest might sensitize glioma cells to TMZ-induced toxicity. U87MG glioma cells treated with TMZ underwent G(2)-M arrest associated with Chk1 activation and phosphorylation of both cdc25C and cdc2. These TMZ-induced effects were inhibited by the Chk1 kinase inhibitor UCN-01. Although not in itself toxic, UCN-01 increased the cytotoxicity of TMZ 5-fold, primarily by inhibiting cellular senescence and increasing the percentage of cells bypassing G(2)-M arrest and undergoing mitotic catastrophe. In addition to enhancing TMZ-induced cytotoxicity in p53-proficient cells, UCN-01 also blocked TMZ-induced Chk1 activation and transient G(2)-M arrest in p53-deficient U87MG-E6 cells and similarly enhanced TMZ-induced mitotic catastrophe and cell death, Taken together, their results indicate that Chk1 links TMZ-induced DNA mismatch repair to G(2)-M arrest. Furthermore, inhibition of the cytoprotective G(2) arrest pathway sensitizes cells to TMZ-induced cytotoxicity and may represent a novel, mechanism-based means of increasing TMZ efficacy in both p53 wild-type and p53 mutant glioma cells, (Hirose et al., Cancer Res 2001, 61(15):5843-9). As such, CHK1 inhibitors may be used in combination therapy to improve the therapeutic efficacy of chemotherapeutic drugs. CHK1 inhibitors may be useful in combination with chemotherapeutic drugs in treating cancer.

Csk: Target kinase Csk (i.e., c Src kinase) is a 50.7 kDa tyrosine kinase encoded by chromosome 15q23-q25 (symbol: CSK). Csk, cloned by Partanen et al. (Oncogene 1991, 6: 2013-2018), is a cytoplasmic tyrosine kinase that downregulates the tyrosine kinase activity of the Src oncoprotein through tyrosine phosphorylation of the Src carboxy terminus. Activation of Csk may be therapeutic for cancers in which Src is activated, such as in colon and pancreatic carcinomas (Lutz et al., Biochem Biophys Res Commun 1998, 243(2):503-8; Cam et al., Cancer 2001, 92(1):61-70). Zheng and She state that the lymphoid-specific phosphatase (LAT) encoded by PTPN22 is involved in preventing spontaneous T-cell activation by dephosphorylating and inactivating T-cell receptor-associated Csk kinase. They genotyped 396 type 1 diabetic patients and 1,178 control subjects of Caucasian descent from north central Florida and report a strong association between type 1 diabetes and a polymorphism (R620W) in the PTPN22 gene. In vitro experiments have shown that the mutant 620W LYP protein (1858T) does not bind Csk. Together with previous reports of the association between PTPN22 and type 1 diabetes, as well as rheumatoid arthritis and systemic lupus erythematosus, these results provide compelling evidence that LYP is a critical player in multiple autoimmune disorders (Zheng and She, Diabetes 2005, 54(3):906-8). Csk modulators, including inhibitors, may be useful in treating autoimmune diseases, including type 1 diabetes, rheumatoid arthritis and systemic lupus erythematosus.

EGFR: Target kinase EGFR (i.e., Epidermal Growth Factor Receptor) is a 134.3 kDa transmembrane tyrosine kinase coded by chromosome 7p12.3-p12.1 (symbol: EGFR). OMIM indicates that EGF enhances phosphorylation of several endogenous membrane proteins, including EGFR. EGFR has 2 components of different molecular weight; both contain phosphotyrosine and phosphothreonine but only the higher molecular weight form contains phosphoserine (Carlin and Knowles, Proc. Nat. Acad. Sci. 1982, 79: 5026-5030.). Carlin et al. (Cytogenet. Cell Genet. 1982, 32: 256) showed that the specific cell surface antigen previously called SA7 (Aden and Knowles, Immunogenetics 1976, 3: 209-211) is identical to EGFR. EGFR signaling involves small GTPases of the Rho family, and EGFR trafficking involves small GTPases of the Rab family. Lanzetti et al. (Nature 2000, 408: 374-377) reported that the EPS8 protein connects these signaling pathways. EPS8 is a substrate of EGFR that is held in a complex with SOS1 by the adaptor protein E3B1, thereby mediating activation of RAC. Through its SH3 domain, EPS8 interacts with. Further, Lanzetti et al. (ibid) showed that RNTRE is a RAB5 GTPase-activating protein whose activity is regulated by EGFR. By entering in a complex with EPS8, RNTRE acts on RAB5 and inhibits internalization of EGFR. Furthermore, RNTRE diverts EPS8 from its RAC-activating function, resulting in the attenuation of RAC signaling. Thus, depending on its state of association with E3B1 or RNTRE, EPS8 participates in both EGFR signaling through RAC and EGFR trafficking through RAB5 (OMIM MIM Number: 131550: Dec. 16, 2005).

EGFR is implicated in breast cancer, colorectal, and bladder cancer, and modulation of EGFR activity is a therapeutic route to amelioration of these pathologic states (Xu et al., Mol Cancer Ther 2005, 4(3):435-42). An important unmet need has emerged in non small cell lung cancer patients who initially respond to treatment with EGFR inhibitors but then develop resistance to the initial drug (Koboyashi, S. et al. N Engl J Med. 2005, 352:786-92). EGFR is also a possible target for treating glioblastoma multiforme (Raizer, J Neurooncol 2005, 74(1):77-86), and squamous cell carcinomas, for example in the esophagus (Hanawa et al., Int J Cancer 2006, 118(5):1173-80), head and neck (Hambek et al., Anticancer Res 2004, 24(6):3881-6), and oral cavity and tongue (Ekberg et al., Int J Oncol 2005, 26(5):1177-85). Unlu and Leake studied the effect of epidermal growth factor (EGF) and a specific inhibitor of EGFR, on the growth and invasiveness of the prostate cancer cell lines PC3 and DU145. Their results indicate that EGF is a potent stimulative agent for both growth and invasion in prostate cancer cells, and that targeting the EGFR function inhibits not only tumor growth but also invasiveness (Unlu and Leake, Int J Biol Markers 2003, 18(2):139-46). EGFR inhibitors may be useful in treating cancer, including breast, colon, bladder, prostate and non small cell lung cancer, squamous cell carcinomas of the head and neck, oral cavity, and esophagus, and glioblastoma multiforme.

EphA1: Target kinase EphA1 (i.e., Ephrin Receptor A1) is a 108.1 kDa tyrosine kinase encoded by chromosome 7q32-q34 (symbol: EPHA1). OMIM indicates that the EPH and EPH-related receptors comprise the largest subfamily of receptor protein-tyrosine kinases. They have been implicated in mediating developmental events, particularly in the nervous system. Receptors in the Eph subfamily typically have a single kinase domain and an extracellular region containing a Cys-rich domain and 2 fibronectin type III repeats. The ligands for Eph receptors have been named "ephrins" by the Eph Nomenclature Committee (Cell 1997, 90: 403-404). Based on their structures and sequence relationships, ephrins are divided into the ephrin-A (EFNA) class, which are anchored to the membrane by a glycosylphosphatidylinositol linkage, and the ephrin-B (EFNB) class, which are transmembrane proteins. The Eph family of receptors are divided into 2 groups based on the similarity of their extracellular domain sequences and their affinities for binding ephrin-A and ephrin-B ligands. The Eph Nomenclature Committee (ibid.) proposed that Eph receptors interacting preferentially with ephrin-A proteins be called EphA and Eph receptors interacting preferentially with ephrin-B proteins be called EphB. Maru et al. (1988) reported characterization of the novel receptor tyrosine kinase gene, EPH. The splicing points of kinase domain-encoding exons were completely distinct from those of other protein tyrosine kinase genes, suggesting that this is the earliest evolutionary split within this family. In Northern blot analysis, EPH gene mRNA was detected in liver, lung, kidney, and testes of rat; screening of 25 human cancers of various cell types showed preferential expression in cells of epithelial origin. Overexpression of EPH mRNA was found in a hepatoma and a lung cancer without gene amplification. Southern blot analysis of DNAs from human-mouse hybrid clones with an EPH probe showed that this gene is present on human chromosome 7. Two other receptor tyrosine kinase genes, MET and EGFR, are on the same chromosome. By in situ hybridization, Yoshida et al. (1989) assigned the EPH locus to 7q32-q36. Although ephrins form a high-affinity multivalent complex with their receptors present on axons, axons can be rapidly repelled rather than being bound (OMIM MIM Number: 179610: Sep. 5, 2000). Lin et al. identified 5 PTKs that were overexpressed in head and neck squamous cell carcinoma (HNSCC) using a reverse transcriptase-PCR technique and confirmed the overexpression of 3 known PTKs in some of the 8 archival HNSCC specimens studied. Their finding suggests that the signaling pathways mediated through EphA1, Brk, and Ron may be involved in the development and progression of HNSCC (Lin et al., Arch Otolaryngol Head Neck Surg 2004, 130(3):311-6). EphA1 inhibitors may be useful in treating cancer, including liver and lung cancer, and head and neck squamous cell carcinoma.

EphA2: Target kinase EphA2 (i.e., Ephrin Receptor A2) is a 108.3 kDa tyrosine kinase encoded by chromosome 1p36.1 (symbol: EPHA2). EphA2, similar to other ephrin receptors, is found in epithelial, lymphoid, and especially neuron tissue where EphA2 is critically involved in short-range contact-mediated axonal guidance. Further, EphA2 is highly expressed in metastatic melanoma cells. Ephrin A1, a ligand for EphA2, was shown to be up regulated during melanoma progression (Easty et al., Int J Cancer 1999, 84(5):494-501). Hattori et al. showed that ephrin-A2 forms a stable complex with the metalloproteinase Kuzbanian, involving interactions outside the cleavage region and the protease domain. Eph receptor binding triggered ephrin-A2 cleavage in a localized reaction specific to the cognate ligand. The cleavage-inhibiting mutation in ephrin-A2 delayed axon withdrawal. Hattori et al. (ibid) concluded that their studies reveal mechanisms for protease recognition and control of cell surface proteins, and, for ephrin-A2, they may provide a means for efficient axon detachment and termination of signaling (Hattori et al., Science 2000, 289: 1360-1365). Ireton and Chen review EphA2 as a promising target for cancer therapeutics, indicating EphA2 is overexpressed in breast, prostate, lung, and colon cancers (Ireton and Chen, Curr Cancer Drug Targets 2005, 5(3):149-57). Landen et al. state that EphA2 is involved in many processes crucial to malignant progression, such as migration, invasion, metastasis, proliferation, survival and angiogenesis. Inducing EphA2 downregulation by any one of several mechanisms (antibody-mediated inhibition of signalling, antibody-mediated downregulation of total EphA2 expression and siRNA-mediated inhibition of expression) has been shown to decrease tumour growth, prolong survival and inhibit angiogenesis in multiple preclinical models of ovarian, breast and pancreatic cancer. Targeting EphA2 is especially attractive in ovarian cancer, in which overexpression is present in >75% of cases (Landen et al., Expert Opin Ther Targets 2005, 9(6):1179-87). Abraham et al. state that the clinical significance of the expression of EphA2 was observed in breast, prostate, colon, skin, cervical, ovarian, and lung cancers. They studied EphA2 to determine the expression of EphA2 and its ligand, Ephrin A-1, and E-cadherin in carcinoma of the urinary bladder, and determine EphA2 as a new target for therapy in bladder cancer. They conclude EphA2 may serve as a novel target for bladder cancer therapy, (Abraham et al., Clin Cancer Res 2006, 12(2): 353-60). EphA2 inhibitors may be useful in treating cancer, including bladder, breast, prostate, colon, skin, cervical, ovarian, pancreatic, and lung cancer and melanoma.

EphB2: Target kinase EphB2 (i.e., Ephrin Receptor B2) is a 117.5 kDa transmembrane tyrosine kinase encoded by chromosome 1p36.1-p35 (symbol: EPHB2). Mann et al. state that forward and reverse signaling mediated by EphB tyrosine kinase receptors and their transmembrane ephrin-B ligands play important roles in axon pathfinding. In their investigations of growth cones from the ventral (EphB receptor-bearing) and dorsal (ephrin-B-bearing) embryonic Xenopus retina designed to investigate the signaling mechanisms in both forward and reverse directions, it is reported that unclustered, but not clustered, EphB2 ectodomains trigger fast (5-10 min) transient collapse responses in growth cones. This collapse response is mediated by low levels of intracellular cyclic GMP and requires proteasome function. In contrast, clustered, but not unclustered, ephrin-B1 ectodomains cause slow (30-60 min) growth cone collapse that depends on high cGMP levels and is insensitive to inhibition of the proteasomal pathway. Upon receptor-ligand binding, endocytosis occurs in the reverse direction (EphB2-Fc into dorsal retinal growth cones), but not the forward direction, and is also sensitive to proteasomal inhibition. Endocytosis is functionally important because blocking of EphB2 internalization inhibits growth cone collapse. They state their data reveals that distinct signaling mechanisms exist for B-type Eph/cphrin-mediated growth cone guidance and suggest that endocytosis provides a fast mechanism for switching off signaling in the reverse direction (Mann et al., J Neurobiol 2003, 57(3): 323-36). Nakada et al. demonstrate that migrating glioblastoma cells overexpress EphB2 in vitro and in vivo; glioma migration and invasion are promoted by activation of EphB2 or inhibited by blocking EphB2. Dysregulation of EphB2 expression or function may underlie glioma invasion (Nakada et al, Cancer Res 2004, 64(9):3179-85). Wu et al., investigated the expression of EphB2 and EphB4 in breast carcinomas. Clinicopathological and survival correlations were statistically analyzed in a series of 94 breast carcinomas, 9 normal specimens and 4 breast carcinoma cell lines. Both EphB2 and EphB4 RTPCR products could be detected in all specimens. Increased EphB2 protein expression was negatively associated with overall survival (Wu et al., Pathol Oncol Res 2004, 10(1):26-33). Ilafner et al. studied expression profiles of 12 different Eph receptors and 8 ephrins inhuman lung, colorectal, kidney, liver, and brain cancers. They report EphB2 was up-regulated 9-fold in hepatocellular carcinoma (Bather et al., Clinical Chemistry 2004, 50:490-99). Umeda et al. studied the expression of ephrinB2 and EphB receptors within fibroproliferative membranes in patients with ocular angiogenic diseases collected during vitrectomy. EphB2 and EphB3 expression was observed on fibroproliferative membranes that were harvested from patients with proliferative diabetic retinopathy (EphB2, 90.0%; EphB3, 70.0%) and retinopathy of prematurity (EphB2, 35.0%; EphB3, 45.0%). Their data suggest that the ephrinB2-EphB2/B3 system may play an important role in ocular angiogenesis (Umeda et al., Am J Ophthalmol 2004, 138(2):270-9). EphB2 inhibitors may be useful in treating cancer, including breast cancer, hepatocellular carcinoma and glioblastoma, and for use in treating ocular angiogenesis diseases, including retinopathy (e.g. retinopathy of prematurity and proliferative diabetic retinopathy).

EphB4: Target kinase EphB4 (i.e., Ephrin Receptor B4) is a 108.3 kDa transmembrane tyrosine kinase encoded by chromosome 7q22 (symbol: EPHB4). EphB4 belongs to the Eph family of receptor tyrosine kinases. Developmental studies have shown that the Eph receptors, by regulating cell adhesion and cell movement in the embryo, are important for the proper organization and integrity of tissues. Because tissue disorganization and abnormal cell adhesion, movement, and survival characterize the more advanced stages of cancer, the inappropriate functioning of an Eph receptor in breast tumor cells enhances malignancy. Xia et al. studied the biological function of the receptor tyrosine kinase EphB4 in bladder cancer. All of nine bladder cancer cell lines examined expressed EphB4. Further, they showed EphB4 knockdown using specific siRNA and antisense oligodeoxynucleotides molecules led to a profound inhibition in cell viability associated with apoptosis via activation of caspase-8 pathway and downregulation of antiapoptotic factor, bcl-xl. Furthermore, EphB4 knockdown significantly inhibited tumor cell migration and invasion. EphB4 knockdown in an in vivo murine tumor xenograft model led to a nearly 80% reduction in tumor volume associated with reduced tumor proliferation, increased apoptosis and reduced tumor microvasculature (Xia et al., Oncogene 2006, 25(5):769-80). Xia et al. also studied the expression and biological role of EphB4 in prostate cancer. They found EphB4 mRNA is expressed in 64 of 72 (89%) prostate tumor tissues assessed and EphB4 protein expression is found in the majority (41 of 62, 66%) of tumors, and 3 of 20 (15%) normal prostate tissues. They also showed knockdown of the EphB4 protein using EphB4 short interfering RNA or antisense oligodeoxynucleotide significantly inhibits cell growth/viability, migration, and invasion, and induces apoptosis in prostate cancer cell lines (Xia et al., Cancer Res 2005, 65(11):4623-32). Lee et al. used RT-PCR, western blotting and immunohistochemical techniques to examine EphB4 expression and protein levels in human prostate cancer cell lines LNCaP, DU145 and PC3. Immunohistochemistry was also used to examine localisation of EphB4 in tissue samples from 15 patients with prostate carcinomas. All three prostate cancer cell lines expressed the EphB4 gene and protein. EphB4 immunoreactivity in vivo was significantly greater in human prostate cancers as compared with matched normal prostate epithelium and there appeared to be a trend towards increased expression with higher grade disease (Lee et al., BMC Cancer 2005, 5:119). Stephenson et al. used commercially available cDNA arrays to identify EphB4 as a gene that is up-regulated in colon cancer tissue when compared with matched normal tissue from the same patient (Stephenson et al., BMC Mol Biol 2001, 2:15). Takai et al. used fluorescent immunohistochemistry to analyze serial frozen sections of 20 endometrial carcinomas and 20 normal endometria for EphB4 and ephrin-B2 protein expression. Further, they analyzed the relationship between the patient's characteristics and the percentages of EphB4- and ephrin-B2-stained cells. They indicate the results demonstrate that increased EphB4 and ephrin-B2 expression may reflect or induce in endometrial carcinomas increased potential for growth and tumorigenicity (Takai et al., Oncol Rep 2001, 8(3):567-73). Sinha et al., studied expression of EphB4 in six men with primary squamous cell carcinoma of the head and neck (HNSCC) that had metastasized to the cervical lymph nodes. They obtained specimens of the primary tumor, the nodal metastasis, and the adjacent normal mucosa, and performed immunocytochemistry on each. They observed EphB4 expression in all primary and metastatic tumors and no expression in the normal tissue. In each of the six patients, expression was greater in the metastatic tumor than in the primary tumor (Sinha et al., Ear Nose Throat J 2003, 82(11): 866, 869-70, 887). EphB4 inhibitors may be useful in treating cancer, including breast, bladder, prostate, colon, and endometrial cancers and head and neck squamous cell carcinoma.

Erk2: Target kinasc Erk2 (i.e., extracellular signal-regulated kinase 2) is a 41.4 kDa dual function serine/threonine-tyrosine kinase encoded by chromosome 22q11.2 (symbol: MAPK1). Erk2 is a member of the mitogen-activated protein (MAP) kinase family and is alternatively known as mitogen-activated protein kinase 1 (i.e., MAPK1). MAP kinases act as an integration point for multiple biochemical signals, and are involved in a wide variety of cellular processes such as proliferation, differentiation, transcription regulation and development.

The activation of Erk2 requires phosphorylation by upstream kinases. Upon activation, Erk2 translocates to the nucleus of the stimulated cells, where it phosphorylates nuclear targets, in addition to other targets including microtubule associated protein 2, myelin basic protein and ELK1. MacKenzie et al. state that the cAMP-specific phosphodiesterase family 4, subfamily D, isofonn 3 (i.e., PDE4D3) is shown to have FQF (i.e., Phe-Gln-Phe) and KIM (i.e., Kinase Interaction Motif) docking sites for Erk2. These sites straddle the Ser(579) target residue for Erk2 phosphorylation of PDE4D3. Mutation of either or both of these docking sites prevent Erk2 from being co-immunoprecipitated with PDE4D3, ablate the ability of epidermal growth factor (EGF) to inhibit PDE4D3 through Erk2 action in transfected COS cells, and attenuate the ability of Erk2 to phosphorylate PDE4D3 in vitro. The two conserved NH(2)-terminal blocks of sequence, called upstream conserved regions 1 and 2 (i.e., UCR1 and UCR2), that characterize PDE4 long isoforms, are proposed to amplify the small, inherent inhibitory effect that Erk2 phosphorylation exerts on the PDE4D catalytic unit. In contrast to this, the lone intact UCR2 region found in PDE4D1 directs COOH-terminal Erk2 phosphorylation to cause the activation of this short isoform. From the analysis of PDE4D3 truncates, it is suggested that UCR1 and UCR2 provide a regulatory signal integration module that serves to orchestrate the functional consequences of Erk2 phosphorylation. The PDE4D gene thus encodes a series of isoenzymes that are either inhibited or activated by Erk2 phosphorylation and thereby offers the potential for ERK2 activation either to increase or decrease cAMP levels in cellular compartments (MacKenzie et al., J Biol Chem 2000, 275(22):16609-17).

According to OMIM, Pleschka et al. (Nature Cell Biol., 2001, 3: 301-305) proposed that Erk2 regulates a cellular factor involved in the viral nuclear export protein function, They suggested that local application of MEK inhibitors may have only minor toxic effects on the host while inhibiting viral replication without giving rise to drug-resistant virus variants (OMIM MIM Number: 176948: Oct. 27, 2005). Erk2 is involved in cytokine signaling and is a target for treating inflammation, Ramesh and Philipp state that lipoproteins are the key inflammatory molecule type of *Borrelia burgdorferi*, the spirochete that causes Lyme disease. They investigated whether specific inhibition of p38 and Erk1/2 MAPK would inhibit TNF-alpha and IL-6 production and thus astrocyte apoptosis, and proliferation, respectively. Lipoprotein-stimulated IL-6 production was unaffected by the MAPK inhibitors. In contrast, inhibition of both p38 and Erk1/2 significantly diminished TNF-alpha production, and totally abrogated production of this cytokine when both MAPK pathways were inhibited simultaneously. MAPK inhibition thus may be considered as a strategy to control inflammation and apoptosis in Lyme neuroborreliosis (Ramesh and Philipp, Neurosci Lett 2005, 384(1-2):112-6). The role of Erk2 in signaling of cell differentiation, proliferation and survival suggests that inhibition of Erk2 may be therapeutic for several types of cancer. Husain et al. studied the effect of NSAIDs on MAPK activity and phosphorylation in gastric cancer. They conclude that NS-398 (a selective COX-2 inhibitor) and indomethacin (a non-selective NSAID) significantly inhibit proliferation and growth of human gastric cancer cell line MKN28. This effect is mediated by NSAID-induced inhibition of MAPK (ERK2) kinase signaling pathway, essential for cell proliferation (Husain et al., Life Sci 2001, 69(25-6): 3045-54). Erk2 inhibitors may be useful in treating cancer, including gastric cancer, and in treating inflammation, including control of inflammation and apoptosis in Lyme neuroborreliosis.

Fak: Target kinase Fak (i,e., Focal adhesion kinase 1, aka protein tyrosine kinase 2, PTK2) is a 119.2 kDa tyrosine kinase encoded by chromosome 8q24.3 (symbol: PTK2). The structure of Fak comprises a B41 (i.e., Band 4.1 homology) domain in addition to the TK domain. Fak and a related protein Pyk2/CAK-beta are cytoplasmic non-receptor protein tyrosine kinases. Localization of Fak via its C-terminal Focal Adhesion Targeting domain to focal complexes/adhesions (sites of integrin receptor clustering) is a prerequisite for Fak activation. Auto- or trans-phosphorylation of Fak on Tyr397 allows for docking of the Src family kinases, among other molecules. Src kinases phosphorylate Fak not only on the Tyr residues in the activation loop of the FAK kinase, but also create binding sites for downstream signaling components. Moreover, FAK can be activated by other receptors, linking them to the integrin signaling pathway. Activation of FAK can promote cell spreading, locomotion, survival and anchorage-dependent growth.

FAK-related non-kinase (FRNK), the C-terminal portion of FAK is expressed in some cell types by activating transcription from an alternative promoter. FRNK is proposed to function as an endogenous inhibitor of Fak signaling.

The role of Fak in signaling of cell proliferation, migration, adhesion and survival may be targeted in therapeutics for several types of cancer. Lightfoot et al. used immunohistochemical techniques to assess FAK expression in patients with fibrocystic disease (FCD), atypical ductal hyperplasia (ADH), ductal carcinoma in situ (DCIS) and infiltrating ductal carcinoma (DC). The pattern of FAK expression in DCIS was significantly higher than ADH (p<0.0001) and IDC (p=0.02). They conclude that FAK overexpression in preinvasive, DCIS tumors precedes tumor cell invasion or metastasis, suggesting that FAK may function as a survival signal and be an early event in breast tumorigcnesis (Lightfoot et al., Breast Cancer Res Treat 2004, 88(2):109-16). Miyazaki et al. performed an inununohistochemical analysis of FAK protein expression to determine the relationship between FAK overexpression and clinicopathological factors in oesophageal squamous cell carcinoma (ESCC). They concluded that FAK overexpression of ESCC was related to cell differentiation, tumour invasiveness, and lymph node metastasis. Consequently, patients with ESCC who had FAK overexpression had a poor prognosis (Miyazaki et al., Br J Cancer 2003, 89(11:140-5). Smith et al. tested antisense oligonucleotide inhibitors of FAK, in combination with 5-fluorouracil (5-FU), to increase its sensitivity in human melanoma cell lines. They conclude their data show that the downregulation of FAK by antisense oligonucleotide combined with 5-FU chemotherapy results in a greater loss of adhesion and greater apoptosis in melanoma cells than treatment with either agent alone, suggesting that the combination may be a potential therapeutic agent for human melanoma in vivo (Smith et al., Melanoma Res 2005, 15(5):357-62). In a review, Natarajan et al. summarize data that has demonstrated 1) elevated FAK expression in anaplastic astrocytoma and glioblastoma tumor biopsy samples, 2) a role for FAK in the promotion of glioblastoma cell proliferation, survival and migration in vitro, and 3) a role for FAK in the promotion of glioblastoma cell proliferation in vivo in an animal model (Natarajan et al., Cancer J 2003, 9(2):126-33). Rovin et al. investigated FAK expression in human prostate specimens by using immunohistochemistry. In their conclusion, they suggest that the sustained elevated levels of FAK expression during prostate tumor cell progression is consistent with a role for FAK in the development and maintenance of prostate carcinoma (Rovin at al., Prostate 2002, 53(2):124-32). Itoh et al. investigated whether focal adhesion kinase (FAK) is involved in the progression of human hepatocellular carcinoma (BCC). They conclude their data suggests that FAK plays an important role in promoting tumor progression, especially vascular invasion, in HCC (Itoh et al., Clin Cancer Res 2004, 10(8):2812-7). von Sengbusch et al. state that organ-specific tumor cell adhesion to extracellular matrix (ECM) components and cell migration into host organs often involve integrin-mediated cellular processes that can be modified by environmental conditions acting on metastasizing tumor cells, such as shear forces within the blood circulation. Since the focal adhesion kinase (FAK) appears to be essential for the regulation of the integrin-mediated adhesive and migratory properties of tumor cells, they investigated its role in early steps of the metastatic cascade using in vitro and in vivo approaches. They summarize that FAK appears to be involved in early events of integrin-mediated adhesion of circulating carcinoma cells under fluid flow in vitro and in vivo. This kinase may take part in the establishment of definitive adhesive interactions that enable adherent tumor cells to resist fluid shear forces, resulting in an organ-specific formation of distant metastases (von Sengbusch et al., Am J Pathol 2005, 166(2):585-96).

Westhoff et al., note that elevated expression of the nonreceptor tyrosine kinases Src and Fak correlates with maliimancy potential and poor clinical prognosis in colon and breast tumors. They also state that recent studies monitoring focal adhesion dynamics in cells deficient for Fak and Src implicate Src and Fak as critical mediators of intcgrin adhesion turnover that promote cell migration. Cells devoid of FAK exhibit impaired migration and have large peripheral focal adhesion structures, while cells lacking the three ubiquitous Src family members Src, Fyn, and Yes also demonstrate altered distribution of focal adhesions and impaired cell migration. Src kinase activity is clearly necessary for focal adhesion turnover and cell motility, presumably by tyrosine phosphorylation of key focal adhesion substrates, such as FAK. The extracellular regulated kinase (ERK)/mitogen-activated protein kinase (MAPK) pathway is also important in regulating focal adhesion dynamics during cell motility and it is likely that ERK/MAPK contributes to Src-induced focal adhesion turnover. Further, Westhoff et al. have recently reported that ERK/MAPK, which is recruited to focal adhesions following v-Src activation, is required for maximal activity of the protease calpain 2 promoting focal adhesion turnover and migration of v-Src-transformed cells. ERK/MAPK-induced activation of calpain 2 is also required for epidermal growth factor-induced substrate deadhesion and cell motility. Six major tyrosine phospho-acceptor sites have been identified on Fak, at positions 397, 407, 576, 577, 861, and 925. Tyr 397 becomes phosphorylated (presumed by auto-phosphorylation) upon integrin engagement. This leads to the formation of a consensus binding site for the Src SH2 domain, promoting association between Src and FAK. Phosphorylation of the remaining tyrosine residues on Fak is considered to be Src-dependent. Westhoff et al., generated a FAK mutant (4-9F-Fak) in which each of the putative Src-induced tyrosine phosphorylation sites (Tyr 407, 576, 577, 861, and 925) has been mutated to a phenylalanine (Phe). They found that v-Src-induced phosphorylation of FAK on tyrosine residues is necessary to enhance the adaptor function of Fak with regard to assembly of the calpain 2/FAK/p42ERK complex. Src-induced phosphorylation of Fak is also required for Fak to undergo proteolytic cleavage by calpain in v-Src-transformed cells and is necessary for calpain-mediated focal adhesion turnover during transformation and cell migration. In addition, they show that Src-induced phosphorylation of Fak also regulates F-actin assembly and cell spreading. We further demonstrate a role for Src-induced tyrosine phosphorylation of Fak in survival and anchorage-independent growth of transformed cells (Westhoff et al., Molecular and Cellular Biology, 2004, 24: 8113-8133).

Fak inhibitors may be useful in treating cancer, including colon and breast cancers, melanoma, ductal carcinoma in situ, oesophageal squamous cell carcinoma, anaplastic astrocytoma and glioblastoma, and human hepatocellular and prostate carcinomas, as well as in reducing tumor metastasis. They may also be used in combination with other chemotherapeutic dries to provide synergistic effects in treating cancers such as melanoma.

FGFR kinase family: The FGFRs (i.e., Fibroblast Growth Factor Receptors) comprise a family of related but individually distinct tyrosine kinase receptors. They have a similar protein structure, with 3 imrnunoglobulin-like domains in the extracellular region, a single membrane spanning segment, and a cytoplasmic tyrosine kinase domain. The fibroblast growth factor receptors that have been identified are FGFR1, FGFR2, FGFR3, which is mutant in achondroplasia: and FGFR4. Sequence analysis of the 4.5-kb human FGFR2 gene shows an open reading frame encoding the typical membrane-spanning, tyrosine kinase receptor structure of the FGFR gene family. A discussion of FGFR1, FGFR2, FGFR3, and FGFR4 follows.

FGFR

FGFR1: Target FGFR1 (i.e., Fibroblast Growth Factor Receptor 1) is a 91.9 kDa transmembrane tyrosine kinase encoded by chromosome 8p11.2p11.1 (symbol: FGFRI). FGFR1 is also known as FMS-like tyrosine kinase 2 (i.e., Flt2). FGFR1 is implicated in a variety of cancers (e.g. 8p11 syndrome, Braun & Shannon, Cancer Cell 2004, 5:203). Additionally, FGFR1 is an important mediator of tumor angiogenesis (Compagni et al., Cancer Res. 2000, 60:7163). The X-ray crystallographic structure of FGFR1 bound to fibroblast growth factor 2 has been reported by Plotnikov et al (Cell 1999, 98: 641-650). Rossi et al report an FGFR1 P252R mutation in families affected by Pfeiffer syndrome (Rossi et al., Clin Dysmorphol. 2003, 12(4):269-74). FGFR1 inhibitors may be useful in treating 8p11 myeloproliferative syndrome.

FGFR2: Target FGFR2 (i.e., Fibroblast Growth Factor Receptor 2) is a 92 kDa transmembrane tyrosine kinase encoded by chromosome 10q26 (symbol: FGFR2). According to OMIM, from a human tumor cDNA library, Houssaint et al. (Proc. Nat. Acad. Sci.1990, 87: 8180-8184) isolated a gene encoding a putative receptor-like protein-tyrosine kinase that they called TK14. The amino acid sequence was closely related to that of the mouse protein bek (bacterially expressed kinase), and more distantly related to the sequences of a chicken basic fibroblast growth factor receptor (73% sequence homology) and its presumed human equivalent, the FLG protein. Overexpression of the TK14 protein by transfection of COS-1 cells led to the appearance of new cell-surface binding sites for both acidic and basic fibroblast growth factors (OMIM MIM Number: 176943: Apr. 6, 2006).

Sequence analysis of the 4.5-kbp human FGFR2 gene shows an open reading frame encoding the typical membrane-spanning, tyrosine kinase receptor structure of the FGFR gene family. Two alternative gene products have been characterized: KGFR and BEK. These two isoforms are identical except for a 49-amino acid sequence spanning the second half of the third Ig loop in the extracellular region. This local diversity is due to the presence of alternative exons within FGFR2, exon B being expressed in the BEK product and exon K26 in KGFR. Control of these alternative splice sites is thought to involve transacting factors (Gilbert et al., Molec, Cell. Biol. 1993, 13: 5461-5468). The variation in expressed gene product is highly significant because the ligand-binding characteristics of KGFR and BEK are quite distinct. Furthermore, they have different patterns of expression in murine embryogenesis. Whereas KGFR appears to have a role in skin development, BEK is preferentially expressed in osteogenesis. BEK transcripts are concentrated in the frontal bones, maxilla, mandibula, and ossicles of the middle ear.

To elucidate the structural determinants governing specificity in FGF signaling, Plotnikov et al. (Cell 2000, 101: 413-424) determined the crystal structures of FGF1 and FGF2 complexed with the immunoglobulin-like ligand-binding domains 2 and 3 (D2 and D3) of FGFR1 and FGFR2, respectively. They found that highly conserved FGF-D2 and FGF-linker (between D2 and D3) interfaces define a general binding site for all FGF-FGFR complexes. Specificity is achieved through interactions between the N-terminal and central regions of FGFs and 2 loop regions in D3 that are subject to alternative splicing. These structures provide a molecular basis for FGF1 as a universal FGFR ligand and for modulation of FGF-FGFR specificity through primary sequence variations and alternative splicing (OMIM MIM Number: 176943: Apr. 6, 2006).

Defects in FGFR2 are a cause of Crouzon Syndrome (CS); also called craniofacial dysostosis type I (CFD1). CS is an autosomal dominant syndrome characterized by craniosynostosis (premature fusion of the skull sutures), hypertelorism, exophthalmos and external strabismus, parrot-beaked nose, short upper lip, hypoplastic maxilla, and a relative mandibular prognathism (OMIM MIM Number: #123500: May 4, 2000).

Further, defects in FGFR2 are a cause of Jackson-Weiss syndrome (JWS). JWS is an autosomal dominant craniosynostosis syndrome characterized by craniofacial abnormalities and abnormality of the feet including broad great toes with medial deviation and tarsal-metatarsal coalescence (OMIM MIM Number: 176943: Apr. 6, 2006).

Further, defects in FGFR2 are a cause of Apert Syndrome, also known as acrocephalo-syndactyly type I (ACS1), which is characterized by craniosynostosis (premature fusion of the skull sutures) and severe syndactyly (cutaneous and bony fusion of the digits), and is autosomal dominant.

Further, defects in FGFR2 are a cause of Pfeiffer Syndrome (PS), also known as acrocephalosyndactyly type V (ACS), which is characterized by craniosynostosis with deviation and enlargement of the thumbs and great toes, brachymesophalangy, with phalangeal ankylosis and a varying degree of soft tissue syndactyly. Three subtypes of PS have been described: mild autosomal dominant form (type 1); cloverleaf skull, elbow ankylosis, early death, sporadic (type 2); craniosynostosis, early demise, sporadic (type 3).

Further, defects in FGFR2 are the cause of beare-stevenson cutis gyrata syndrome (BSCGS) which is an autosomal dominant condition characterized by the furrowed skin disorder of cutis gyrata, acanthosis nigricans, craniosynostosis, craniofacial dysmorphism, digital anomalies, umbilical and anogenital abnormalities and early death (OMIM MIM Number: 176943: Apr. 6, 2006).

Further, defects in FGFR2 are the cause of Antley-Bixler syndrome which is characterized by trapezoidocephaly, midface hypoplasia, humeroradial synostosis, bowing of femora, fractures and other abnormalities (OMIM MIM Number: #207410: Nov. 29, 2005). FGFR2 inhibitors may be useful in treating Crouzon Syndrome, Jackson-Weiss Syndrome, Apert Syndrome, craniosynostosis, Pfeiffer Syndrome, acrocephalo syndactyly type V, and Beare-Stevenson Cutis Gyrata Syndrome.

FGFR3: Target kinase FGFR3 (i.e., Fibroblast Growth Factor Receptor 3) is a 87.7 kDa transmembrane tyrosine kinase encoded by chromosome 4p16.3 (symbol: FGFR3). As a member of the fibroblast growth factor family, FGFR3 is involved in a variety of activities, including mitogenesis, angiogenesis, and wound healing. Furthermore, FGFR3 plays a role in the development and maintenance of bone and brain tissue. FGFR3 regulates bone growth by limiting the formation of bone from cartilage, particularly in the long bones. In addition, FGFR3 is activated by translocation in approximately 15% of multiple myeloma (Trudel, S., Blood 2004, 103:3521). FGFR3 inhibitors may be useful in treating angiogenesis disorders, wounds, achondroplasia, Muenke craniosynostosis, Crouzon syndrome, acanthosis nigricans, thanatophoric dysplasia, bladder carcinomas, and multiple myeloma.

FGFR4: Target kinase FGFR4 (i.e., Fibroblast Growth Factor Receptor 4) is a 88.0 kDa transmembrane tyrosine kinase encoded by chromosome 5q35.3 (symbol: FGFR4). According to OMIM, Partanen et al. (EMBO J. 1991, 10: 1347-1354) reported the cDNA cloning and analysis of a novel member of the fibroblast growth factor receptor (FGFR) gene family expressed in K562 erythroleukemia cells. Its deduced amino acid sequence was 55% identical with the previously characterized FGFRs, FLG (FGFR1) and BEK, and had the structural characteristics of an FGFR family member including 3 immunoglobulin-like domains in its extracellular part. The expression pattern of FGFR4 was found to be distinct from that of FLG and BEK and also distinct from that of FGFR3, which had also cloned from K562 erythroleukemia cells. To elucidate further the physiologic relevance of protein-tyrosine kinases and to search for additional members of the gene family as possible factors in carcinogenesis, Holtrich et al. (Proc. Nat. Acad. Sci, 1991, 88: 10411-10415) amplified mRNA from lung tissue by the polymerase chain reaction (PCR) using PTK-specific primers followed by sequencing of the clones. They identified a novel protein-tyrosine kinase, which they called TKF (tyrosine kinase related to fibroblast growth factor receptor). Among a wide variety of cells and tissues tested, including human lymphocytes and macrophages, TKF was found to be expressed only in lung and in some tumors of lung origin as well as in malignancies not derived from lung tissues. Sequence comparison has demonstrated that TKF is identical to FGFR4 (OMIM MIM Number: 134935: May 3, 2002).

The FGFR4 protein interacts with specific growth factors to conduct signals from the environment outside the cell to the nucleus. Animal studies indicate that the FGFR4 gene is involved in muscle development and the maturation of bone cells in the skull. FGFR4 may also play a role in the development and maintenance of specialized cells (called foveal cones) in the light-sensitive layer (retina) at the back of the eye. Aberrant expression of FGFR4 is correlated with cancer of the breast, ovary, endometrium, and fallopian tube, and with leiomyosarcoma. FGFR4 inhibitors may be useful in treating cancer of the breast, lung, colon, medullary thyroid, pancreas, ovary, prostate, endometrium, and fallopian tube, head and neck squamous cell carcinomas and leiomyosarcoma.

Flt1: Target kinase Flt1 (i.e., Fms like tyrosine kinase 1) is a 150.7 kDa transmembrane tyrosine kinase encoded by chromosome 13q12 (symbol: FLT1), also known as VEGFR1 (i.e., Vascular Endothelial Growth Factor Receptor 1). According to OMIM, oncogene FLT belongs to the SRC gcnc family and is related to oncogene ROS. Like other members of this family, it shows tyrosine protein kinase activity that is important for the control of cell proliferation and differentiation via interaction with PLC-gammas, PTPN11, GRB2, CRK, NCK I and other proteins. The name is due to the resemblance of the sequence structure of the FLT gene to that of the FMS gene. VEGF and its high-affinity binding receptors, the tyrosine kinases Flk1 and Flt1, are thought to be important for the development of embryonic vasculature. Studying transgenic mice in whom the Flk1 gene was disrupted, Shalaby et al. (Nature 1995, 376: 62-65) demonstrated a total failure of embryonic mice to develop blood vessels and failure of blood island formation in the yolk sac. Fong et al. (Nature 1995, 376: 65-69) reported that in mice Fltl is essential for the organization of embryonic vasculature, but is not essential for endothelial cell differentiation. Transgenic mouse embryos homozygous for a targeted mutation in the Flt1 locus formed endothelial cells in both embryonic and extraembryonic regions, but assembled these cells into abnormal vascular channels and died in utero at mid-somite stages. At earlier stages, the blood islands of homozygous mice were abnormal, with angioblasts in the interior as well as on the periphery. Fong et al. (ibid.) suggested that the Flt1 signaling pathway may regulate normal endothelial cell-cell or cell-matrix interactions during vascular development (OMIM MIM Number: 165070: Mar. 27, 2006). Flt 1 inhibitors may be useful in treating non-small cell lung carcinoma, prostate carcinoma, and colorectal cancer.

Flt3: Target kinase Flt3 Fms-like tyrosine kinase 3) is a transmembrane tyrosine kinase of 117.8 kDa encoded by chromosome 13q12 (symbol: FLT3). According to OMIM, Rosnet et al. (Genomics 1991, 9: 380-385) isolated a novel member of the class 3 receptors discussed above. They demonstrated that this gene of the tyrosine kinase family, called FLT3, has strong sequence similarities with other members of the group. Lymphohematopoietic stem cells serve as a reservoir for virtually all blood cells but make up only approximately 0.01% of human or murine marrow cells. The ability to isolate and expand this population has clinical applications in bone marrow transplantations for cancer and genetic diseases. Small et al. (Proc. Nat. Acad. Sci. 1994, 91: 459-463) cloned the cDNA for stem cell tyrosine kinase 1, the human homolog of murine Flk2/Flt3, from a CD34+ hematopoietic stem cell-enriched library. The cDNA encoded a protein of 993 amino acids with 85% identity and 92% similarity to the murine homolog. STK1, which is identical to FLT3, is a member of the type III receptor tyrosine kinase family that includes KIT, FMS, and platelet-derived growth factor receptor. STK1 expression in human blood and marrow is restricted to CD34+ cells, a population greatly enriched by stem/progenitor cells. Antisense oligonucleotides directed against STK1 sequences inhibited hematopoietic colony formation, most strongly in long-term bone marrow cultures. The data suggested that STK1 may function as a erowth factor receptor on hematopoietic stem and/or progenitor cells (OMIM MIM Number: 136351; Mar. 3, 2005).

Levis et al., state that Internal tandem duplication (ITD) mutations of the receptor tyrosine kinase FLT3 have been found in 20% to 30% of patients with acute myeloid leukemia (AML). These mutations constitutively activate the receptor and appear to be associated with a poor prognosis. In their study, dose-response cytotoxic assays were performed with AG1295, a tyrosine kinase inhibitor active against FLT3, on primary blasts from patients with AML, and they found that AG1295 was specifically cytotoxic to AML blasts harboring FLT3/ITD mutations. They suggest that these mutations contribute to the leukemic process and that the FLT3 receptor represents a therapeutic target in AML (Levis et al., Blood 2001, 98:885-887). Flt3 inhibitors may be useful in treating acute myeloid leukemia, myelodysplastic syndrome, acute lymphoblastic leukemia.

Flt4: Target kinase Flt4 (i.e., Fms-like tyrosine kinase 4) is a transmembrane tyrosine kinase of 145.6 kDa encoded by chromosome 5q35.3 (symbol: FLT4). Flt4 is also known as VEGFR3 (i.e., Vascular Endothelial Growth Factor Receptor 3). According to OMIM, by screening a placenta cDNA library with a mouse Flt3 probe, Galland et al. (Genomics 1992, 13; 475-478) isolated a human gene encoding a putative receptor-type tyrosine kinase, FLT4. The deduced amino acid sequence of the intracellular portion of the molecule showed that it was strongly related to FLT1 and KDR and to a lesser degree to members of the class 3 receptor-type tyrosine kinases: FMS, PDGFR, KIT, and FLT3. Primary lymphoedema, a rare, autosomal dominant disorder that leads to a disabling and disfiguring swelling of the extremities and, when untreated, tends to worsen with time, has been linked to the FLT4 locus (Karkkaincn et al., Nat. Genet. 2000, 25: 153-9), All disease-associated alleles analyzed had missense mutations and encoded proteins with an inactive tyrosine kinase, preventing downstream gene activation (OMIM MIM Number: 136352; Nov. 19, 2003). Flt4 inhibitors may be useful in treating primary lymphoedema.

Fms: Target kinase Fms (i.e., feline McDonough sarcoma) is a member of the family of genes originally isolated from the Susan McDonough strain of feline sarcoma viruses. Fms is a transmembrane tyrosine kinase of 108.0 kDa coded by chromosome 5q33.2-q33.3 (symbol; CSF1R). The structure of the transmembrane receptor Fms comprises two Ig-like domains, a IgG2-like domain, two additional Ig-like domains, a TM domain, and the TK domain.

Fms is the receptor for the macrophage colony-stimulating factor (M-CSF), and is crucial for the growth and differentiation of the monocyte-macrophage lineage. Upon binding of M-CSF to the extracellular domain of Fms, the receptor dimerizes and trans-autophosphorylates cytoplasmic tyrosine residues.

M-CSF, first described by Robinson and co-workers (Blood. 1969, 33:396-9), is a cytokine that controls the production, differentiation, and function of macrophages. M-CSF stimulates differentiation of progenitor cells to mature monocytes, and prolongs the survival of monocytes. Furthermore, M-CSF enhances cytotoxicity, superoxide production, phagocytosis, chemotaxis, and secondary cytokine production of additional factors in monocytes and macrophages. Examples of such additional factors include granulocyte colony stimulating factor (G-CSF), interleukin-6 (IL-6), and interleukin-8 (IL-8). M-CSF stimulates hematopoiesis, promotes differentiation and proliferation of osteoclast progenitor cells, and has profound effects on lipid metabolism. Furthermore, M-CSF is important in pregnancy. Physiologically, large amounts of M-CSF are produced in the placenta, and M-CSF is believed to play an essential role in trophoblast differentiation (Motoyoshi, Int J Hematol. 1998, 67:109-22). The elevated serum M-CSF levels of early pregnancy may participate in the immunologic mechanisms responsible for the maintenance of the pregnancy (Flanagan & Lader, Curr Opin Hematol. 1998, 5:181-5).

Aberrant expression and/or activation of Fms has been implicated in acute myeloid leukemia, AML (Ridge ct al, Proc. Nat. Acad. Sci., 1990, 87:1377-1380). Mutations at codon 301 are believed to lead to neoplastic transformation by ligand independence and constitutive tyrosine kinase activity of the receptor. The tyrosine residue at codon 969 has been shown to be involved in a negative regulatory activity, which is disrupted by amino acid substitutions. Accordingly, Fms mutations are most prevalent (20%) in chronic myelomonocytic leukemia and AML type M4 (23%), both of which are characterized by monocytic differentiation.

A condition related to AML is chronic myeloid leukemia (CML). During the myeloid blast crisis (BC) of CML, non-random additional chromosome abnormalities occur in over 80% of patients, However, these cytogenetic changes have been reported to precede the clinical signs of CML-BC by several months to years suggesting that other biological events may participate in the multistep process of acute transformation of CML. The autocrine production of growth factors has been shown to occur in several hematological malignancies and particularly in AML. Specchia et al [Br J Haematol. 1992 March; 80(3):310-6] have demonstrated that IL-1 beta gene is expressed in almost all cases of CML in myeloid blast crisis, and that a high proportion of cases showed constitutive expression of the M-CSF gene. Many of the same patients in the Specehia et al study demonstrated simultaneous co-expression of Fms. After exposure of leukemic cells to phorbol myristate acetate (PMA), release of M-CSF protein was documented in three of five patients studied; however, no significant interleukin-3 (IL-3), granulocyte-macrophage colony-stimulating factor (GM-CSF) or granulocyte colony-stimulating factor (G-CSF), was detected in these patients. This demonstrates that different patterns of growth factors secretion exist in AML and CML, and that distinct molecular events are likely involved in the control of leukemic proliferation.

The observation that production of M-CSF, the major macrophage growth factor, is increased in tissues during inflammation (Le Meur et al, J. Leukocyte Biology. 2002; 72:530-537) provides a role for Fms in certain diseases. For example, COPD is characterized by airflow limitation that is not fully reversible. The airflow limitation is usually progressive and associated with an abnormal inflammatory response of the lungs to noxious particles or gases. The chronic inflammation of COPD is observed through the airways, parenchyma, and pulmonary vasculature. The inflammatory cell population consists of neutrophils, macrophages, and T lymphocytes, along with eosinophils in some patients. Macrophages are postulated to play an orchestrating role in COPD inflammation by releasing mediators such as TNF-a, 1L-8 and LTB4, which are capable of damaging lung structures and/or sustaining neutrophilic inflammation.

Further, M-CSF/fms signaling is critical to osteoclast formation and survival of osteoclast precursors. For example, estrogen loss in menopause results in increased M-CSF and thus increased osteoclast number and bone resorption which leads to increased risk of fracture and osteoporosis. Accordingly, blockage of this signal is a target for the inhibition of bone resorption (Teitelbaum, Science. 2000; 289:1504; Rohan, Science. 2000; 289:1508).

Atherosclerosis, an inflammatory disease of the vessel walls, is associated with significant morbidity and mortality. A effect for Fms inhibition in the treatment and prevention of atherosclerosis depends on several observations (Libby, Nature. 2002; 420:868-874). First, monocytes resident in the arterial intima increase expression of scavenger receptors and internalize modified lipoproteins. The resulting lipid-laden macrophages develop into foam cells characteristic of the atherosclerotic lesion. Macrophages in atheroma secrete cytokines and growth factors involved in lesion progression. Additionally, macrophages replicate within the intima. Through Fms, M-CSF activates the transition from monocyte to lipid-laden macrophage and augments expression of scavenger receptor A. Indeed, atherosclerotic plaques over-express M-CSF which is critical for atherosclerotic progression. Mice deficient in M-CSF have been found to experience less severe atherosclerosis than mice with normal M-CSF (Rajavashisth, et. al., J. Clin. Invest. 1998; 101:2702-2710; Qiao, et, al., Am. J. Path. 1997; 150:1687-1699). Accordingly, inhibitors of Fms disrupt M-CSF signaling, compromising monocyte to macrophage foam cell progression, macrophage survival and replication, and cytokine signaling that participates in lesion progression.

Wegener's granulomatosis, also known as vasculitis, is characterized by granulomatous inflammation of the blood vessels with necrosis. This inflammation limits blood flow to organs with consequent damage. Although the disease can involve any organ system, Wegener's granulomatosis mainly affects the respiratory tract (i.e., sinuses, nose, trachea, and lungs) and the kidneys. The endothelium plays a central role in the immunopathology of several vascular disorders in many intlanumatory conditions such as Wegener's granulomatosis in which use of intravenous immunoglobulin (IV Ig) has been shown to be beneficial (sec e.g., Basta et al, J Clin Invest 1994, 94:1729-1735). It has been reported (Xu et al, Am. J. Path., 1998:153:1257-1266) that IV Ig inhibits endothelial cell proliferation in a dose- and time-dependent manner and down-regulates the expression of adhesion molecule mRNA (ICAM-1 and VCAM-1), chemokine mRNA (MCP-1, M-CSF, and GM-CSF), and proinflammatory cytokine mRNA (TNF-α, IL-1β, and IL-6) induced by TNF-α or IL-1β. These results may explain, at least in part, the therapeutic effect of IV Ig in vascular and inflammatory disorders.

Additionally, these results suggest that inhibition of M-CSF activity at the level of interaction with Fms is an efficacious treatment strategy.

The role of M-CSF and Fms in emphysema appears to involve the regulation of elastin metabolism through control of matrix metalloproteins. M-CSF has a role in the modulation of the accumulation and function of alveolar macrophages (AMs) in vivo (Shibata et al, Blood 2001, 98: pp. 2845-2852). Osteopetrotic (Op/Op) mice have no detectable M-CSF and show variable tissue-specific reductions in macrophage numbers. Accordingly, it was hypothesized that AMs would be decreased in number and have altered function in Op/Op mice because of the absence of M-CSF. Shibata et al found that lung macrophages identified in lung sections were decreased in number in 20-day-old Op/Op mice but not Op/Op mice older than 4 months compared with findings in age-matched littermate controls. The numbers of AMs recovered by bronchoalveolar lavage (BAL) were also reduced in young but not adult Op/Op mice compared with controls. Importantly, AMs of Op/Op mice spontaneously release higher levels of matrix metalloproteinases (MMPs) than AMs of controls. Consistent with an increased release of MMP, Op/Op mice have abnormal elastin deposition and spontaneously develop emphysema in the absence of molecular or cellular evidence of lung inflammation. Accordingly, the modulation of metalloelastase activity in macrophages by M-CSF may control the degradation of elastin fibers in lungs or blood vessels.

Metastatic cancer cells cause hone destruction, with associated fracture, pain, deformation, and hypercalcaemia, due to production of osteoclasticogenic factors including M-CSF by tumor cells (Clohisy et al, Clin. Orthop. 2000, 373: 104-14). Binding of M-CSF to the Fms product stimulates formation of osteoclasts and osteolytic activity (Kodama et al, J. Exp. Med. 1991, 173: 269-72: Feng et al, Endocrinology 2002, 143: 4868-74). Accordingly, inhibition of osteoclast activity at the level of Fms offers a compelling target for amelioration of bone metastasis.

Nephritis is inflammation of the kidneys. It may be caused for example by a bacterial infection of the kidneys or exposure to a toxin. However, nephritis more commonly develops from an abnormal immune reaction, which can occur, for example, when an antibody attacks either the kidney itself or an antigen attached to kidney cells, or when an antigen-antibody complex formed elsewhere in the body attachs to cells in the kidney. Some types of nephritis involve infiltration of kidney tissues by white blood cells and deposits of antibodies. In other types of nephritis, inflammation may consist of tissue swelling or scarring without white blood cells or antibodies. Furthermore, nephritis can occur anywhere in the kidneys. With respect to the glomeruli, progressive damage to glomeruli causes urine production to fall and metabolic waste products to build up in the blood. When damage to glomeruli is severe, inflammatory cells and injured glomerular cells accumulate, compressing the capillaries within the glomerulus and interfering with filtration. Scarring may develop, impairing kidney function and reducing urine production. In some cases, microthrombi may fonn in the small blood vessels, further decreasing kidney function. Less commonly, nephritis involves the tubulointerstitial tissues; such inflammation is called tubulointerstitial nephritis. When inflammation damages the tubules and the tubulointerstitial tissues, the kidneys may become unable to concentrate urine, eliminate (excrete) metabolic waste products from the body, or balance the excretion of sodium and other electrolytes, such as potassium. When the tubules and tubulointerstitial tissues are damaged, kidney failure often develops. Accordingly, inhibition of Fms offers a target for therapeutic intervention in nephritis due to the modulation of the inflammatory response comprising the etiology of the disease.

Lupus nephritis, i.e., renal involvement in systemic lupus erythematosus (SEE), is a common disease manifestation with a poor prognosis. At least three potentially overlapping, immuno-pathogenic mechanisms for lupus nephritis are supported by experimental data. First, circulating immune complexes consisting chiefly of DNA and anti-DNA are deposited in the kidney. Resulting complement activation and chemotaxis of neutrophils leads to a local inflammatory process. Second, in situ formation of antigen and antibody complexes may similarly lead to complement activation and leucocyte mediated injury. Third, antibodies against specific cellular targets may produce renal injury. An additional mechanism is observed in SLE patients with the antiphospholipid antibody syndrome. Glomerular thrombosis can result from the hypercoagulability that accompanies antibodies directed against negatively charged phospholipid-protein complexes (e.g. biologic false positive VDRL, anticardiolipin antibodies, and lupus anticoagulant). Mesangial lupus nephritis is accompanied by normal diagnostic findings or with a mild degree of proteinuria but typically absence of hypertension or abnormal urinary sediment. Focal and diffuse proliferative lupus glomerulonephritis are often associated with the worst prognosis for renal survival and can be accompanied by nephrotic syndrome, significant hypertension and abnormal urine sediment. Membranous lupus nephritis often presents with proteinuria, moderate to high grade, but usually normal urinary sediment in the absence of hypertension. Mesangial lupus nephropathy is generally associated with an excellent prognosis, whereas proliferative lupus nephropathy, especially diffuse variant, is often characterized by hypertension, red cell casts and significant deterioration of renal function. Nephrotic syndrome in the absence of hypertension, active urinary sediment or significant hypocomplementemia suggest the membranous variant of lupus nephropathy. Membranous nephropathy generally is associated with a good prognosis and relative preservation of renal function. However, in the presence of persistent nephrotic range proteinuria, membranous lupus nephropathy can, in fact, lead to loss of renal function and end stage renal disease (ESRD). Accordingly, inhibition of Fms offers a target for therapeutic intervention in lupus due to the modulation of the inflammatory response comprising the etiology of the disease.

Macrophage accumulation is a prominent feature in many forms of glomerulonephritis. Local proliferation of macrophages within the kidney has been described in human and experimental glomerulonephritis and may have an important role in augmenting the inflammatory response. Isbel et al (Nephrol Dial Transplant 2001, 16: 1638-1647) examined the relationship between local macrophage proliferation and renal expression of M-CSF. Glomerular and tubulointerstitial M-CSF expression was found to be up-regulated in human glomerulonephritis, being most prominent in proliferative forms of disease. Because this correlates with local macrophage proliferation, it suggests that increased renal M-CSF production plays an important role in regulating local macrophage proliferation in human glomerulonephritis. In a model of renal inflammation (UUO—unilateral ureteric obstruction) anti-Fms antibody treatment reduced macrophage accumulation (Le Meur et.al., J Leukocyte Biology, 2002, 72: 530-537). Accordingly, inhibition of Fms offers a target for therapeutic intervention in glomerulonephritis.

Insulin resistance and obesity are hallmark of type II diabetes and there is a strong correlation exists between insulin resistance and abdominal visceral fact accumulation (Bjorntrop, Diabetes Metab, Res. Rev., 1999, 15: 427-441). Current evidence indicates that macrophages accumulating in adipose tissue release TNF-a and other factors that cause adipocyte changes (hypertrophy, lipolysis, reduced insulin sensitivity) and also promote insulin resistance in surrounding tissues. Therefore, macrophage accumulation in type 2 diabetes is important for disease progression. Accordingly, inhibition of Fms has potential in preventing the development of insulin resistance and hyperglycemia.

Similarly, the observation that production of M-CSF, the major macrophage growth factor, is increased in tissues during inflammation points out a role for Fms in diseases, such as for example inflammatory diseases. More particularly, because elevated levels of M-CSF are found in the disease state, modulation of the activity of Fms can ameliorate disease associated with increased levels of M-CSF.

Fms inhibitors may be useful in treating to immune disorders, including rheumatoid arthritis, systemic lupus erythematosis (SLE), Wegener's granulomatosis, and transplant rejection, inflammatory diseases including Chronic Obstructive Pulmonary Disease (COPD), emphysema, and atherosclerosis, metabolic disorders, including insulin resistance, hyperglycemia, and lipolysis, disorders of bone structure or mineralization, including osteoporosis, increased risk of fracture, hypercalcemia, and bone metastases, kidney diseases, including nephritis (e.g. glomerulonephritis, interstitial nephritis, Lupus nephritis), tubular necrosis, diabetes-associated renal complications, and hypertrophy and cancers, including multiple myeloma, acute myeloid leukemia, chronic myeloid leukemia (CML), breast cancer, and ovarian cancer.

Frk: Target kinase Frk (Fyn-related kinase) is a 58.5 kDa tyrosine kinase encoded by chromosome 6q21-q22.3 (symbol: FRK). The structure comprises an SH2, an SH3 and a tyrosine kinase domain. Hosoya et al., report the the identification of a SRC-like tyrosine kinase gene, FRK (Fyn-related kinase), fused with ETV6 in a patient with acute myelogenous leukemia carrying t(6;12)(q21;p13). The ETV6/FRK protein was shown to be constitutively autophosphorylated on its tyrosine residues. ETV6/FRK phosphorylated histones H2B and H4 in vitro to a greater extent than did FRK, suggesting it had elevated kinase activity. ETV6/FRK could transform both Ba/F3 cells and NIH3T3 cells, which depended on its kinase activity (Hosoya et al., Genes Chromosomes Cancer 2005, 42(3):269-79). Welsh et al. concluded that FRKIRAK contributes to cytokine-induced beta-cell death, and inhibition of this kinase could provide means to suppress beta-cell destruction in Type I diabetes (Welsh et al., Biochem J 2004, 382(1):261-8). Frk inhibitors may be useful in treating acute myeloid leukemia and type I diabetes.

Fyn: Target kinase Fyn (i.e., Fyn oncogene related to Src, Fgr, Yes) is a 60.6 kDa non-receptor tyrosine kinase encoded by chromosome 6q21 (symbol: FYN). Fyn is involved in regulation of mast cell degranulation in a synergistic confluence of Fyn and Lyn (i.e., v-Yes-1 Yamaguchi sarcoma viral related oncogene homolog) pathways at the level of protein kinase C and calcium regulation. Fyn inhibitors may be useful in treating Alzheimer's disease, schizophrenia and in prevention of metastases, e.g. in melanoma and squamous cell carcinoma.

Gsk3α, Gsk3β: Target kinase Gsk3β (i.e., Glycogen synthase kinase 3 beta) is a 46.8 kDa STK encoded by chromosome 3q13.3 (symbol: GSK3B), Target kinase Gsk3α (i.e., Glycogen synthase kinase 3 alpha) is a 51.0 kDa STK encoded by chromosome 19q13.2 (symbol: GSK3A).Gsk3 is a proline-directed serine-threonine kinase that was initially identified as a phosphorylating and inactivating glycogen synthase. Two isoforms, alpha and beta, show a high degree of amino acid homology (Stambolie & Woodgett, *Biochem. J.* 1994, 303: 701-704). GSK3B is involved in energy metabolism, neuronal cell development, and body pattern formation (Plyte et al., *Biochim. Biophys. Acta* 1992, 1114: 147-162). The X-ray crystallographic structure of Gsk3 has been reported by Dajani et al. (*Cell* 2001, 105: 721-732). Klein & Melton (*Proc. Nat. Acad. Sci.* 1996, 93: 8455-8459) proposed that Gsk3 is the endogenous target of lithium in diverse systems, For example, lithium potently and specifically inhibits Gsk3 activity in vitro. This suggests a mechanism whereby lithium can mimic insulin action, and lithium inhibition of the Gsk3 pathway in the brain could explain the actions of lithium action in manic-depressive illness in addition to its effects on development and its insulinlike activity.

Phiel et al., show that therapeutic concentrations of lithium, a GSK-3 inhibitor, block the production of Abeta peptides by interfering with APP cleavage at the gamma-secretase step, but do not inhibit Notch processing. Importantly, lithium also blocks the accumulation of Abeta peptides in the brains of mice that overproduce APP. The target of lithium in this setting is GSK-3alpha, which is required for maximal processing of APP. Since GSK-3 also phosphorylates tau protein, the principal component of neurofibrillary tangles, inhibition of GSK-3alpha offers a new approach to reduce the formation of both amyloid plaques and neurofibrillary tangles, two pathological hallmarks of Alzheimer's disease (Phiel et al., Nature 2003, 423:435-439). Eldar-Finkelman states that GSK-3 inhibitors might prove useful as therapeutic compounds in the treatment of conditions associated with elevated levels of enzyme activity, such as type 2 diabetes and Alzheimer's disease. The pro-apoptotic feature of GSK-3 activity suggests a potential role for its inhibitors in protection against neuronal cell death, and in the treatment of traumatic head injury and stroke. Finally, selective inhibitors of GSK-3 could mimic the action of mood stabilizers such as lithium and valproic acid and be used in the treatment of bipolar mood disorders (Eldar-Finkelman, Trends Mol Med 2002, 8:126-132). Martinez ct al. state that glycogen synthase kinase 3 (GSK-3) was initially described as a key enzyme involved in glycogen metabolism, but is now known to regulate a diverse array of cell functions. Two forms of the enzyme, GSK-3alpha and GSK-3beta, have been previously identified. Small molecules inhibitors of GSK-3 may, therefore, have several therapeutic uses, including the treatment of neurodegenerative diseases, diabetes type II, bipolar disorders, stroke, cancer, and chronic inflammatory disease (Martinez et al., Med Res Rev 2002, 22(4):373-84). GSK inhibitors may be useful in treating CNS disorders such as Alzheimer's disease, Parkinson's disease, amyotrophic lateral sclerosis, diabetes type II, bipolar disorders, stroke, cancer, chronic inflammatory disease, leucopenia, schizophrenia, chronic pain, neuropathic pain, and traumatic head injury.

HCK: Target kinase LICK (hemopoietic cell kinase) is a 59.5 kDa tyrosine kinase encoded by chromosome 20q11.21 (symbol: HCK). The protein structure comprises an SH3, and SH2 and a bipartite kinase domain. TICK inhibitors may be useful in treating chronic myelogenous leukemia and acute lymphocytic leukemia.

Her2/Erbb2: Target kinase Her2/Erbb2 (i.e., Human EGF receptor 2) is a 137.9 kDa transmembrane tyrosine kinase encoded by chromosome 17q11.2-q12/17q21.2 (symbol: ERBB2). According to OMIM, the ERBB2 locus 17q21 is the chromosome 17 breakpoint in acute promyelocytic leukemia (APL). Amplification of ERBB2 is observed in human salivary gland adenocarcinoma (Semba et al., Proc. Nat. Acad. Sci. 1985, 82:6497-6501) and in a gastric cancer cell line (Fukushige et al., Molec. Cell. Biol. 1986, 6:955-958). Overexpression of ERBB2 has been implicated in the neoplastic transformation of prostate cancer. Interleukin-6 (IL6) is a cytokine that was initially recognized as a regulator of immune and inflammatory responses, but also regulates the growth of many tumor cells, including prostate cancer. Qui et al. showed that treatment of a prostate cancer cell line with IL6 induces tyrosine phosphorylation of ERBB2 and ERBB3, but not ERBB1/EGFR. ERBB2 also forms a complex with the gp130 subunit of the IL6 receptor (IL6R) in an IL6-dependent manner. This association is important because the inhibition of ERBB2 activity results in abrogation of IL6-induced MAPK activation (Qui et al., Nature 1998, 393: 83-85). Thus, ERBB2 is a critical component of IL6 signaling through the MAP kinase pathway. Additionally, overexpression of ERBB2 confers Taxol resistance in breast cancers by inhibiting p34 (CDC2) activation (Yu et al., Molec. Cell 1998, 2:581-91) (OMIM MIM Number: 164870: Jan. 30, 2006). Her2/Erbb2 inhibitors may be useful in treating prostate and breast cancer.

Her4/Erbb4: Target kinase Her4/Erbb4 (i.e., Human EGF receptor 4) is a 146.8 kDa transmembrane tyrosine kinase encoded by chromosome 2q33.3-q34 (symbol: ERBB4). According to OMIM, the HER4/ERBB4 gene is a member of the type I receptor tyrosine kinase subfamily that includes EGFR, ERBB2, and ERBB3. The gene product of ERBB4 is a receptor for NDF/heregulin, which are essential for neuronal development. Her4/Erbb4−/− mouse embryos exhibit axonal misprojections which correlate with aberrant migration of a subpopulation of hindbrain-derived cranial neural crest cells. Accordingly, Her4/Erbb4 signaling provides patterning information essential for the proper migration of neural crest cells (OMIM MIM Number: 600543: Jul. 27, 2005). Her4/Erbb4 inhibitors may be useful in treating childhood medulloblastoma.

IGF1R: Target kinase IGF1R (insulin-like growth factor 1 receptor) is a 154.8 kDa receptor tyrosine kinase encoded by chromosome 15q26.1 (symbol: IGF1R). Overexpressed in breast and prostate cancer, acting to enhance tumor cell survival. IGF1R inhibitors may be useful in treating prostate cancer and hepatocellular carcinoma.

IKK beta: Target kinase IKK beta (i.e., inhibitor of nuclear factor kappa B kinase beta) is a 86.6 kDa STK encoded by chromosome 8p11.2 (symbol: IKI3KB). According to OMIM, IKK beta phosphorylates serine residues of I-kappa-B proteins which marks them for destruction via the ubiquitination pathway, thereby allowing activation of the NF-kappa-B complex. Activated NF-κB complex translocates into the nucleus and binds DNA at kappa-B-binding motifs, Yin et al (Nature 396: 77-80, 1998) have shown that the antiinflammatory properties of aspirin and salicylate are mediated in part by their specific inhibition of IKK-beta, thereby preventing activation by NF-kappa-B of genes involved in the pathogenesis of the inflammatory response. Rossi et al (403: 103-108, 2000) demonstrated a novel mechanism of antiinflammatory activity that was based on the direct inhibition and modification of the IKK-beta subunit of IKK. Since IKK-beta is responsible for the activation of NF-kappa-B by proinflammatory stimuli, Rossi et al. (ibid.) suggested that their findings explained how cyclopentenone prostaglandins function and can be used to improve the utility of COX2 inhibitors (OMIM MIM Number: 603258: Nov. 16, 2005).

IKKbeta inhibitors may be useful in treating leukemia of T-cells, necrosis, neoplasms, insulin resistance, and malignant neoplasms.

Irak4: Target kinase Irak4 (i.e., Interleukin 1 receptor associated kinase 4) is a 51.5 kDa serine/threonine kinase encoded by chromosome 12q12 (symbol: IRAK4). Interleukin-1 receptor associated kinases (e.g., IRAK1) are important mediators in the signal transduction of Toll-like receptor (TER, e.g., TLR4) and RJR family members are collectively referred to as TIRs. Irak4 functions in this signal transduction pathway. The structure of Irak4 comprises a DEATH domain adjacent a STK domain. The DEATH domain is a protein-protein interaction motif found in certain proteins of the apoptotic pathway.

Irak4 was originally identified as NY-REN-64, one of 65 human tumor antigens recognized by autologous antibodies from patients with renal cell carcinoma using serological analysis of recombinant cDNA expression libraries (SEREX). Sequence analysis of the NY-REN-64 cDNA clone identified in the SEREX screen revealed a novel gene encoding a transcript of 2.8 kilobases and a predicted protein of 460 amino acids (Genbank Accession AF 155118) noted to bear a protein kinase motif (Scanlan et al., Int. J. Cancer, 1999, 83, 456-464). Based on its homology to the other IL-1 receptor-associated kinases, this gene has more recently been placed in the IRAK family and given the name IL-1 receptor-associated kinase-4.

Irak4 is required for the efficient recruitment of IRAK1 to the IL-1 receptor complex following IL-1 engagement, triggering intracellular signaling cascades leading to transcriptional up-regulation and mRNA stabilization. Irak4 Phosphorylates Irak1. Effective Irak4 functioning is crucial for protective immunity against specific bacteria, including pyogenic bacterial, but is redundant against other microorganism.

Irak4 inhibitors may be useful in treating immunodeficiency syndrome, Crohn's disease, ulcerative colitis, asthma, chronic bronchitis, cardio hypertrophy, and kidney hypertension.

Itk: Target kinase Itk (i.e., IL-2 inducible T-cell kinase) is a tyrosine kinase of 71.8 kDa encoded by chromosome 5q31-q32 (symbol: ITK). Itk is a T-cell specific homology of kinase Btk, The EMT Tec family kinases are non-receptor type protein-tyrosine kinase that are highly expressed in many hematopoietic cell lines. The TEC-family protein tyrosine kinases ITK, RLK(TXK) and TEC have been identified as key components of T-cell-receptor signalling that contribute to the regulation of phospholipase C-gamma, the mobilization of Ca2+ and the activation of mitogen-activated protein kinases. Recent data also show that TEC kinases contribute to T-cell-receptor-driven actin reorganization and cell polarization, which are required for productive T-cell activation. Functional studies have implicated TEC kinases as important mediators of pathways that control the differentiation of CD4+ T helper cells (Schwartzberg et al., 2005, Nature immunology, 5:284).

T cells express three TEC kinases, ITK, RLK and TEC, all of which are activated downstream of the T-cell receptor (TCR) (Berg, L. J et al., Annu. Rev. Immunol., 2005, 23:549) and have been shown to be involved in signaling through the TCR (Schaeffer, E. M. et al., 1999, Science, 284:638). Although ITK, RLK and TEC are all found in T cells, they are expressed at different levels and by different subpopulations. (Lucas, J. A et al., 2003, Immunol. Rev., 191; 119. Colgan, J. et al. 2004, Immunity, 21:189). High expression of TEC was seen in each of 3 patients examined with myelodysplastic syndrome(Sato K et al., 1994, Leukemia, 8:1663). Although no human disease has been associated with mutations of the TEC kinases that are expressed by T cells, ITK-deficient mice have specific defects in T Helper 2 (TH2)-cell responses and reduced pathology in models of allergic asthma (Fowell et al. 1999, Immunity, 11:399). Specific ITK inhibitors reduce disease in a mouse model of allergic asthma19, TEC kinases are activated through phosphorylation by SRC-family kinases, such as LCK, and recruitment to the plasma membrane through binding of PtdIns(3A5)P3, where they are brought into TCRsignalling complexes through interactions with SLP76, LAT and other molecules (Bunnell, S. C. et al. 2000, J. Biol. Chem., 275:2219).

Consistent with a role for ITK in allergic responses, increased ITK expression has been seen in peripheralblood T cells from humans with atopic dermatitis(Matsumoto, Y. et al., 2002, Int. Arch. Allergy Immunol. 129:327). Importantly, Itk mice cannot mount effective TH2-cell responses to infection with many pathogens that are used to evaluate TH2-cell differentiation, including *Nippostrongylus brasiliensis, Schistosoma mansoni* and *Leishmania* major (Fowell, D. J. et al. 1999, Immunity, 11:399. Schaeffer, E. et al. 2001, Nature Immunol., 2:1183).

TH2-cell responses have been implicated in the pathology of allergic asthma, which is characterized by an increased number of TH2 cells in the lungs, increased TH2-cytokine production, increased mucus production in the lungs and inflammation of the airways (Cohn, L et al. 2004, Arum. Rev. Immunol., 22:789), For several reasons, ITK, however, might be an ideal therapeutic target for TH2-cell-mediated diseases, provided that the inhibitor has a high degree of specificity. Itk inhibitors may be useful in treating allergic asthma.

Jak1: Target kinase Jak1 (i.e., Janus kinase 1) is a 132 kDa tyrosine kinase encoded by chromosome 1p31.3 (symbol: JAK1). Jak1 inhibitors may be useful in treating Hepatitis C virus infection.

Jak2: Target kinase Jak2 (i.e., Janus kinase 2) is a 130.7 kDa tyrosine kinase encoded by chromosome 9p24 (symbol: JAK2). Jak2 inhibitors may be useful in treating myeloproliferative disorders such as polvcythaemia vera, myelofibrosis, essential thrombocythemia, myeloid metaplasia and leukemias, including acute lymphoblastic leukemia, chronic neutrophilic leukemia, juvenile myelomonocytic leukemia, CMML, Philadelphia chromosome-negative CML, megakaryocytic leukemia, and acute erythroid leukemia Jak3: Target kinase Jak3 (i.e., Janus kinase 3) is a 125.1 kDa tyrosine kinase encoded by chromosome 19p13.1 (symbol: JAK3). According to OMIM, JAK3 is a member of the Janus kinase (JAK) family of tyrosine kinases involved in cytokine receptor-mediated intracellular signal transduction, Interleukin-2 (IL2) signaling requires the dimerization of IL2 receptor-beta (IL2RB) with the common gamma chain (gamma-c; IL2RG). Mutations in the IL2RG gene cause X-linked severe combined immunodeficiency. Interleukins IL2, IL4, IL7, IL9, and IL15, whose receptors are known to contain the common gamma chain, induce the tyrosine phosphorylation and activation of Jak3. Truncations of gamma-c and a point mutation of gamma-c, causing moderate X-linked combined immunodeficiency, decrease the association between the common gamma chain and Jak3. Since mutations in the IL2RG gene in at least some XSCID and XCID patients prevent normal Jak3 activation, mutations in Jak3 may result in an XSCID-like phenotype (OMIM MIM Number: 600173: Apr. 4, 2006). A related kinase, Jak2, is activated through mutation in patients with a variety of myeloproliferative disorders (Kralovics R. et al. N Engl J Med. 2005 352:1779-90). The role of Jak3 in B and T lymphocyte maturation and T cell function makes Jak3 a target for treating transplant rejection and autoimmune diseases. Jak3 inhibitors may be useful in treating X-linked severe combined immunodeficiency, myeloproliferative disorders, transplant rejection and autoimmune diseases such as rheumatoid arthritis, inflammatory bowel syndrome, Crohn's disease, systemic lupus erythematosis, ulcerative colitis, psoriasis and multiple sclerosis.

Jnk1: Target Jnk1 (i.e., c-Jun kinase 1) is a 48.3 kDa serine/threonine kinase encoded by chromosome 10q11.22 (symbol: MAPKS), also known as mitogen-activated protein kinase S. Jnk1 is a mitogen-activated protein kinase (i.e., MAPK) which form a family of serine-threonine protein kinases that participate in a major signaling system by which cells transduce extracellular stimuli into intracellular responses. MAPKs comprise the extracellular regulated kinases, or ERKs, for example Erk2, and the stress-activated protein kinases (SAPKs). MAPKs respond to activation by environmental stress and pro-inflammatory cytokines by phosphorylating a number of transcription factors, primarily components of AP-1 such as c-Jun and ATF2 and thus regulates AP-1 transcriptional activity. In T-cells, Jnk1 and Jnk2 are required for polarized differentiation of T-helper cells into Th1 cells. Jnk1 is activated by threonine and tyrosine phosphorylation by either of two dual specificity kinases, MAP2K4 and MAP2K7 and inhibited by dual specificity phosphatases, such as DUSP1. Jnk1 inhibitors may be useful in treating type 1 diabetes, type 2 diabetes, metabolic syndrome, obesity and hepatic steatosis.

Jnk2: Target kinase Jnk2 (i.e., c-Jun kinase 2) is 48.1 kDa serine/threonine kinase encoded by chromosome 5q35 (symbol: MAPK9). According to OMIM, the transcriptional activity of the c-Jun protooncoprotein is augmented through phosphorylation at two sites by c-Jun kinases (JNKs). Using in-gel kinase assays, Hibi et al. (1993) identified 2 JNKs, 46 and 55 kD in size. The 46-kD protein Jnk1 was shown to be a member of the mitogen-activated protein kinase (MAPK) family. Using a JNK1 cDNA as a probe, Kallunki et al. (1994) and Sluss et al. (1994) isolated cDNAs encoding the 55-kD protein, which both designated Jnk2. Kallunki et al. (1994) reported that the sequence of the predicted 424-amino acid JNK2 protein is 83% identical to that of JNK 1. Both JNKs contain a thr-pro-tyr phosphorylation motif. Northern blot analysis revealed that JNK2 is expressed as multiple transcripts in many cell types (OMIM MIM Number: 602896: Jul. 7, 2005).

Jnk2 responds to activation by environmental stress and pro-inflammatory cytokines by phosphorylating a number of transcription factors, primarily components of AP-1 such as c-Jun and ATF2 and thus regulates AP-1 transcriptional activity. In T-cells, JNK1 and JNK2 are required for polarized differentiation of T-helper cells into Th1 cells. Jnk2 isoforms display different binding patterns: alpha-1 and alpha-2 preferentially bind to c-Jun, whereas beta-1 and beta-2 bind to ATF2. However, there is no correlation between binding and phosphorylation, which is achieved at about the same efficiency by all isoforms. Jnk2 is activated by threonine and tyrosine phosphorylation by either of two dual specificity kinases, MAP2K4 and MAP2K7. Further, Jnk2 is inhibited by dual specificity phosphatascs, such as DUSP1. Jnk2 inhibitors may be useful in treating atherosclerosis.

Jnk3: Target kinase Jnk3 (i.e., c-Jun kinase 3) is 52.6 kDa serine/threonine kinase encoded by chromosome 4q21-q22 (symbol: MAPK10). According to OMIM, the c-Jun kinases (JNKs) are members of the mitogen-activated protein kinase (MAPK) family that activate the Jun transcription factor. Gupta et al. (EMBO J. 1996, 15: 2760-2770) isolated brain cDNAs encoding 10 different JNK isoforms, 8 of which were derived from either JNK1 or JNK2. The other 2 cDNAs were from a gene that the authors designated JNK3. JNK3 contains an extended N-terminal region not found in JNK1 or JNK2. The 2 JNK3 isoforms, called JNK3-alpha-1 and JNK3-alpha-2, have different C termini. By SDS-PAGE of in vitro transcription/translation products, Gupta et al. (ibid.) determined that JNK3-alpha-1 migrates as a 45-to-48-kD doublet and JNK3-alpha-2 migrates as a 54-to-57-kD doublet. They stated that the lower band probably represents translation from a second in-frame start codon that corresponds to the first codon in JNK1 and JNK2. All the JNKs were activated by treatment of cells with the inflammatory cytokine IL1. Multiple JNK isoforms were shown to be inactivated by MKPL Comparison of the binding activity of the JNK isoforms demonstrated that they differ in their interactions with the ATE2 (CREB2), ELK1, and Jun transcription factors. Gupta et al. (ibid.) suggested that individual JNKs selectively target specific transcription factors in vivo, providing a mechanism for the generation of tissue-specific responses to the activation of the INK signal transduction pathway. Mohit et al. (Neuron 1995, 14: 67-78) identified JNK3, or p49-3F12 kinase, as the gene encoding a 49-kD antigen found in the hippocampus and neocortex. The distribution of JNK3-expressing neurons closely matches that of Alzheimer disease targeted neurons in those areas of the brain. Northern blot analysis revealed that INTO is expressed as a 2.7-kb mRNA exclusively in the nervous system. Mice defective for Jnk3 are resistant to excitotoxicity induced apoptosis (Yang D. D. et al., Nature 1997, 389:865) (OMIM MIM Number: 602897: Mar. 13, 2006).

Jnk3 responds to activation by environmental stress and pro-inflammatory cytokines by phosphorylating a number of transcription factors, primarily components of AP-1 such as c-Jun and ATE2 and thus regulates AP-1 transcriptional activity. Jnk3 is required for stress-induced neuronal apoptosis and the pathogenesis of glutamate excitotoxicity. Jnk3 is activated by threonine and tyrosine phosphorylation by two dual specificity kinases, MAP2K4 and MAP2K7. MAP2K7 phosphorylates MAPK10 on Thr-221 causing a conformational change and a large increase in Vmax. MAP2K4 then phosphorylates Tyr-223 resulting in a further increase in Vmax. Jnk3 is inhibited by dual specificity phosphatases, such as DUSP1.

Jnk3 inhibitors may be useful in treating inflammatory diseases including autoimmune diseases such as rheumatoid arthritis, inflammatory bowel syndrome, Crohn's disease, systemic lupus erythematosis, Sjogren's Syndrome, psoriasis and multiple sclerosis, airway inflammatory diseases such as asthma, allergy, pulmonary fibrosis, and chronic obstructive pulmonary disease, and inflammation in other organs, such as CNS inflanunation, pancreatitis, nephritis, and hepatitis; neurologic diseases such as stroke, cerebrovaseular ischemia, and neurodegenerative diseases such as Parkinson's disease. Alzheimer's disease, and Huntington's disease; and neoplastic diseases such as prostate tumors and myeloid leukemia.

Kdr: Target kinase Kdr (i.e., Kinase Insert Domain Receptor) is a transmembrane tyrosine kmase of 151.5 kDa encoded by chromosome 4q12 (symbol: KDR). Kdr has a complex secondary structure comprising three Ig-like (i.e., immunoglobulin-like) domains, one IGC2 (i.e., immunoglobulin-like C2-type) domain, two additional Ig-like domains, one additional IGC2 domain, one TM (i.e., transmembrane) domain, and a split TK domain. Kdr, also known as VEGFR2 Vascular Endothelial Growth Factor Receptor 2), Flt7, and Flk1 (i.e., fetal liver kinase 1), is the receptor for Vegf and VegfC (i.e., Vascular endothelial growth factor C) and plays a key role in vascular development and regulation of vascular permeability. Walter et al. (Genes Chromosomes Cancer, 2002, 33:295-303) has proposed based on an observed mutation in the kinase domain of KDR that a potential mechanism involved in hemangioma fol illation is the alteration of the VEGF signaling pathway in endothelial and/or pericytic cells.

Due to the role of angiogenesis, and aberrant control thereof in pathologic states, Kdr is a target for therapeutic intervention. Angiogenesis is the process by which new blood vessel growth occurs from pre-existing vasculature and is mediated through multiple pro-angiogenic factors, including for example Kdr. Under normal adult physiological conditions, angiogenesis occurs during wound healing, organ regeneration, and in some aspects of female reproductive function. Angiogenesis is also important for the progression of many pathological disorders such as solid tumor growth (ovarian, lung, breast, prancreatic, prostate, colon, gastrointestinal stromal tumor, non small cell lung cancer, and epidermoid cancer), metastasis, psoriasis, rheumatoid arthritis, diabetic retinopathy and age related macular degeneration. (Hoeben et al., 2004, Pharmacol. Rev. 56:549-580).

When the dimeric cytokine VEGF binds to the receptor tyrosine kinases Flt-1 and/or KDR, receptor dimerization occurs, followed by autophosphorylation which leads to kinase activation and phosphorylation of intracellular substrates. This receptor tyrosine kinase activity initiates a cellular signaling pathway which leads to endothelial cell proliferation and migration that is necessary for the process of angiogencsis.

Tumors that grow beyond 1-2 mm in size require the process of angiogenesis in order to receive the appropriate nutrients and oxygen that is required for tumor progression. Accordingly, inhibition of this process by small molecules that bind to the surface of receptor tyrosine kinases such as, for example, Kdr, inhibits tumor growth in both animal and human models. Direct evidence of the role of VEGF as a tumor angiogenesis factor in vivo is shown in studies in which VEGF expression or VEGF activity was inhibited. This has been achieved with anti-VEGF antibodies, with dominant-negative VEGFR-2 mutants which inhibited sitmal transduction, and with anti-sense VEGF RNA techniques. All approaches led to the reduction in tumor cell lines in vivo as a result of inhibited tumor angiogencsis. (Scappaticci., 2002, J. Clin. Oncology 20(18):3906-3927 and references within).

Kdr inhibitors may be useful in treating solid tumor growth (e.g. ovarian, lung, breast, prancreatic, prostate, colon, gastrointestinal stromal tumor, non small cell lung cancer, and epidermoid cancer), metastasis, psoriasis, rheumatoid arthritis, diabetic retinopathy and age related macular degeneration.

Kit: Target kinase Kit (i.e., feline Hardy-Zuckerman 4 sarcoma viral oncogene) is a 109.9 kDa transmembrane tyrosine kinase encoded by chromosome 4q12 (symbol: KIT). Receptor protein tyrosine kinases (RPTKs) regulate key signal transduction cascades that control cellular growth and proliferation. The Stem Cell Factor (SCF) receptor Kit is a type III transmembrane RPTK that includes five extracellular immunoglobulin (IG) domains, a single transmembrane domain, and a split cytoplasmic kinase domain separated by a kinase insert segment. Kit plays an important role in the development of melanocytes, mast, germ, and hematopoietic cells.

Stem Cell Factor (SCF) is a protein encoded by the S1 locus, and has also been called kit ligand (KL) and mast cell growth factor (MGF), based on the biological properties used to identify it (reviewed in Tsujimura, Pathol Int 1996, 46:933-938; Loveland, et al., J. Endocrinol 1997, 153:337-344; Vliagoftis, et al., Clin Immunol 1997, 100:435-440; Broudy, Blood 1997, 90:1345-1364; Pignon, Hermatol Cell Ther 1997, 39:114-116; and Lyman, et al., Blood 1998, 91:1101-1134). Herein the abbreviation SCF refers to the ligand for Kit.

SCF is synthesized as a transmembrane protein with a molecular weight of 220 or 248 Dalton, depending on alternative splicing of the mRNA to encode exon 6. The larger protein can be proteolytically cleaved to form a soluble, glycosylated protein which noncovalently dimerizes. Both the soluble and membrane-bound forms of SCF can bind to and activate Kit. For example, in the skin, SCF is predominantly expressed by fibroblasts, keratinocytes, and endothelial cells, which modulate the activity of melanocytes and mast cells expressing Kit. In bone, marrow stromal cells express SCF and regulate hematopoiesis of Kit expressing stem cells. In the gastrointestinal tract, intestinal epithelial cells express SCF and affect the interstitial cells of Cajal and intraepithelial lymphocytes. In the testis, sertoli cells and granulosa cells express SCF which regulates spermatogenesis by interaction with Kit on germ cells.

According to OMIM, Signaling from Kit is essential for primordial germ cell growth both in vivo and in vitro. Many downstream effectors of the KIT signaling pathway have been identified in other cell types, but how these molecules control primordial germ cell survival and proliferation are unknown. Determination of the KIT effectors acting in primordial germ cells has been hampered by the lack of effective methods to manipulate easily gene expression in these cells. De Miguel et al. (2002) overcame this problem by testing the efficacy of retroviral-mediated gene transfer for manipulating gene expression in mammalian germ cells. They found that primordial germ cells can successfully be infected with a variety of types of retroviruses. They used this method to demonstrate an important role of the AKT1 in regulating primordial germ cell growth (OMIM MIM Number: 164920: Apr. 17, 2006).

Aberrant expression andior activation of Kit has been implicated in a variety of pathologic stztes. For example, evidence for a contribution of Kit to neoplastic pathology includes its association with leukemias and mast cell tumors, small cell lung cancer, testicular cancer, and some cancers of the gastrointestinal tract and central nervous system. In addition, Kit has been implicated in playing a role in carcinogenesis of the female genital tract sarcomas of neuroectodermal origin, and Schwann cell neoplasia associated with neurofibromatosis. It was found that mast cells are involved in modifying the tumor microenvironment and enhancing tumor growth (Yang et al., J Clin Invest. 2003, 112:1851-1861; Viskochil, J Clin Invest, 2003, 112:1791-1793).

Kit inhibitors may be useful in treating malignancies, including mast cell tumors, small cell lung cancer, testicular cancer, gastrointestinal stromal tumors (GISTs), glioblastoma, astrocytoma, neuroblastoma, carcinomas of the female genital tract, sarcomas of neuroectodermal origin, colorectal carcinoma, carcinoma in situ, Schwann cell neoplasia associated with neurofIbromatosis, acute myelocytic leukemia, acute lymphocytic leukemia, chronic myelogenous leukemia, mastocytosis, melanoma, and canine mast cell tumors, and inflammatory diseases, including asthma, rheumatoid arthritis, allergic rhinitis, multiple sclerosis, inflammatory bowel syndrome, transplant rejection, and hypereosinophilia.

LCK: Target kinase MCK (i.e., lymphocyte-specific protein tyrosine kinase) is a 57.9 kDa membrane associated non receptor tyrosine kinase encoded by chromosome 1p34.3 (symbol: LCK). The protein structure comprises an SH3 and SH2 domain. LCK inhibitors may be useful in treating acute lymphoblastic leukemia. T-cell lymphoma, lymphopenia, renal carcinoma, colon carcinoma, severe combined immunodeficiency, multiple sclerosis, inflammatory bowel and type I diabetes.

MAP2K1: Target kinase MAP2K1 (i.e., Mitogen-activated protein kinase kinase 1) is a threoninetyrosine kinase of 43.3 kDa encoded by chromosome 15q22.1-q22.33 (symbol:

MAP2K1). According to OMIM, MAP2K1 is also known as MEK1 (i.e., MAPK/ERK Kinase 1). Mitogen-activated protein (MAP) kinases, also known as extracellular signal-regulated kinases (ERKs) are thought to act as an integation point for multiple biochemical signals because they are activated by a wide variety of extracellular signals, are rapidly phosphorylated on threonine and tyrosine residues, and are highly conserved in evolution (Crews et al., Science 1992 258: 478-480), MAP2K1 is a critical protein kinase lying upstream of MAP kinase which stimulates the enzymatic activity of MAP kinase Crews et al. (ibid.) found that Mek1 (i.e., MAP2K1) expressed in bacteria phosphorylates the Erk gene product in vitro. They showed that the Mek1 gene is highly expressed in murine brain. Seger et al. (J. Biol. Chem., 1992, 267: 25628-25631) cloned a eDNA encoding the human homolog of Mek1, symbolized MKK1 by them, from a human T-cell cDNA library. When overexpressed in COS cells, the predicted 43,439-Da protein led to increased phorbol ester-stimulated MAP kinase kinase activity. They also isolated a related cDNA, called MKK1b, that appears to be an alternatively spliced form of MKK1. Seger et al. (ibid.) detected a 2.6-kb MKK1 transcript by Northern blot analysis in all tissues examined. Zheng and Guan (J. Biol. Chem., 1993, 268: 11435-11439) also cloned a human cDNA corresponding to MEK1. They noted that the 393-amino acid protein shares 99% amino acid identity with murine Mek1 and 80% homology with human MEK2. The authors characterized biochemically the human MEK1 and MEK2 gene products. The gene is also symbolized MAP2K1, or PRKMK1. MAP2K1 catalyzes the concomitant phosphorylation of a threonine and a tyrosine residue in a Thr-Glu-Tyr sequence located in MAP kinases and activates ERK1 and ERK2 MAP kinases. Certain inhibitors of MEKI are potent anti-cancer agents (Sebolt-Leopold, J. S., et al., Nat. Med. 1999, 5:810) (OMIM MIM Number: 176872: Jun. 6, 2005). MAP2K1 inhibitors may be useful in treating acute myeloid leukemia, breast, ovarian and liver cancer.

MAP2K2: Target kinase MAP2K2 (i.e., Mitogen-activated protein kinase kinase 2) is a threonine/tyrosinc kinase of 44.4 kDa encoded by chromosome 7q32 (symbol: MAP2K2); MAP2K2 is also known as Mek2; see MAP2K1 above. According to OMIM, Zheng and Guan (ibid.) isolated and sequenced 2 human cDNAs encoding members of the MAP kinase kinase (MAP2K) family, designated MEK1 and MEK2 by them. The MEK2 cDNA encodes a predicted 400-amino acid protein that shares 80% sequence identity with human MEK1. Zheng and Guan (ibid.) showed that recombinant MEK2 and MEK1 both could activate human Erkl in vitro. They further characterized biochemically both MAP2Ks (OMIM MIM Number: 601263: Oct. 23, 2003).

The mitogen-activated protein kinase (MAPK) pathway is a major pathway in the cellular signal transduction cascade from growth factors to the cell nucleus. The pathway involves kinases at two levels: MAP kinase kinases (MAPKK), and their substrates MAP (mitogen activated protein) kinases (MAPK). There are different isoforms in the MAP kinase family. [For review, see Seger, R.; Krebs, E. G. FASEB, 9, 726, (1995)]. The compounds of this invention can inhibit the action of one or both of these kinases: MEK, a MAP kinase kinase, and its substrate ERK, a MAP kinase. ERK (extracellular regulated kinases), a p42 MAPK, is found to be essential for cell proliferation and differentiation. Overexpression and/or over activation of MEK or ERK has been found to be associated with various human cancers [For example, Sivaraman, V. S. et al., C. C. J. Chit, Invest., 99, 1478 (1997)]. It has been demonstrated that inhibition of MEK prevents activation of ERK and subsequent activation of ERK substrates in cells, resulting in inhibition of cell growth stimulation and reversal of the phenotype of ras-transformed cells [Dudley, D. T. et al., Proc. Nat. Acad. Sci., 92, 7686 (1995)]. MAP2K2 inhibitors may be useful in treating cancer and inflammation.

MAP4K4: Target kinase MAP4K4 Mitogen-activated protein kinase kinase 4) is a serine threonine kinase of 152.1 kDa encoded by chromosome 2q11.2 (symbol: MAP4K4) and is also known as HGK. MAP4K4 inhibitors may be useful in treating cancer, tumor metastasis, diabetes and metabolic syndrome.

MAPKAPK2: Target kinase MAPKAPK2 (i.e., Mitogen activated protein kinase activated protein kinase 2) is 45.6 kDa serine/threonine kinase encoded by chromosome 1q32 (symbol: MAPKAPK2). According to OMIM, Stokoe et al. (Biochem. J. 1993, 296:843-849) described a protein kinase, which they designated MAPKAP kinase-2, that was active only after phosphorylation by mitogen-activated protein kinase (MAP kinase). They identified several features that distinguish MAPKAP kinase-2 from the MAPKAP kinase-1 family. Stokoe et al. (ibid.) stated that MAPKAP kinase-2 was identified based on its in vitro phosphorylation of glycogen synthase; however, its phosphorylation of glycogen synthase had not been shown in vivo. Stokoe et al. (ibid.) cloned a partial human MAPKAP kinase-2 cDNA from a teratocarcinoma cell line cDNA library. The cDNA sequence revealed the following features (in 5-prime to 3-prime order): a proline-rich region containing 2 putative SH3-binding sites, a kinase catalytic domain, a threonine residue phosphorylated by MAP kinase, and a nuclear localization signal. By Northern analysis, Stokoe et al. (ibid.) demonstrated that the gene is expressed as a 3.3-kb transcript in all of the 6 human tissues tested. The physiological substrate of MAPKAP kinase 2 appears to be the small heat shock protein (HSP27/HSP25) (OMIM MIM Number: 602006: Mar. 3, 2005).

In vitro, MAPKAP kinase 2 can phosphorylate glycogen synthase at Ser-7 and tyrosine hydroxylase (on Ser-19 and Ser-40). This kinase phosphorylates Ser in the peptide sequence, Hyd-X-R-X(2)-S, where Hyd is a large hydrophobic residue. MAPKAP kinase 2 is activated by two distinct pathways: the first involves the stimulation of p42/p44 MAPK by growth factors, and the second, triggered by stress and heat shock, depends on the activation of MPK2 and upstream MAPKK/MAPKKK. MAPKAPK2 inhibitors may be useful in treating cancer (e.g. prostate, breast), stroke, menengitis, and inflammatory disorders.

Met: Target kinase Met (i.e., Hepatocyte growth factor receptor) is 155.5 kDa transmembrane tyrosine kinase encoded by chromosome 7q31 (symbol: MET). According to OMIM, Cooper et al. (Nature 1984, 311: 29-33) cloned a transfoiming gene from a chemically transformed human osteosarcoma-derived cell line and mapped it to 7p11.4-qter Identity to all previously known oncogenes except ERBB was ruled out by the fact that they are encoded by other chromosomes; identity to ERBB is probably excluded by failure of direct hybridizations of the 2 probes. MET was the designation suggested by Cooper et al. (ibid.). Dean et al. (Nature 1985, 318: 385-388) showed that MET is in the tyrosine kinase family of oncogenes. It appeared to be most closely related in sequence to the human insulin receptor and ABL oncogene. From the sequence of MET cDNA, Park et al. (Proc. Nat. Acad. Sci. 1987, 84: 6379-6383) concluded that this oncogene is a cell-surface receptor for a then unknown ligand. The cellular MET protooncogene product is a receptor-like tyrosine kinase comprised of disulfide-linked subunits of 50 kD (alpha) and 145 kD (beta). In the fully processed Met product, the alpha subunit is extracellular, and the beta subunit has extracellular, transmembrane, and tyrosine kinase domains as well as sites of tyrosine phosphorylation (OMIM MIM Number: 164860: Oct. 18, 2005). Met inhibitors may be useful in treating a variety of neoplasms including kidney, breast, bladder, non-small-cell lung, colorectal, and bladder cancers, and in hepatocellular carcinoma.

MLK1: Target kinase MLK1 (i.e., mixed-lineage kinase 1, aka mitogen-activated protein kinase kinase kinase 9) is a 121.9 kDa serine/threonine kinase encoded by chromosome 14q24.3-q31 (symbol: MAP3K9). MLK1 is expressed in epithelial tumor cell lines of colon, breast and esophageal origin. Silva et al. review the mixed lineage kinase (MLK)-c-jun N-terminal kinase (JNK) signaling cascade, which leads to the phosphorylation and activation of the transcription factor c-jun. There is much evidence, from in vitro and in vivo studies, that this cascade can mediate cell death. In addition, there is evidence that it is operative upstream in the death process. It is possible that abrogation of this pathway may forestall death before irreversible cellular injury. They review the evidence that inhibition of the MLKs can prevent dopamine neuron cell death and the degeneration of their axons (Silva et al., Mov Disord 2005, 20(6):653-64). Lund et al. state that MLK inhibitor CEP-1347 blocks the activation of the c-Jun/JNK apoptotic pathway in neurons exposed to various stressors and attenuates neurodegeneration in animal models of Parkinson's disease (PD). Microglial activation may involve kinase pathways controlled by MLKs and might contribute to the pathology of neurodegenerative diseases. They explored the possibility that CEP-1347 modulates the microglial inflammatory response [tumour necrosis factor-alpha (TNF-alpha), interleukin-6 (IL-6), and monocyte chemotactic protein-1 (MCP-1)] and report that the MLK inhibitor CEP-1347 reduced cytokine production in primary cultures of human and murine microglia, and in monocyte/macrophage-derived cell lines, stimulated with various endotoxins or the plaque forming peptide Abetal-40. Moreover, CEP-1347 inhibited brain TNF production induced by intracerebroventricular injection of lipopolysaccharide in mice. As expected from a MLK inhibitor, CEP-1347 acted upstream of p38 and c-Jun activation in microglia by dampening the activity of both pathways. These data imply MLKs as important, yet unrecognized, modulators of microglial inflammation, and demonstrate a novel anti-inflammatory potential of CEP-1347 (Lund et al., J Neurochem 2005, 92(6): 1439-51). MLK1 inhibitors may be useful in treating neurodegenerative disorders such as Alzheimer's and Parkinson's disease and inflammatory disorders.

Mnk1: Target kinase Mnk1 (i.e., MAP kinase interacting serine/threonine kinase 1) is a 51.3 kDa STK encoded by chromosome 1p34.1 (symbol: MKNK1). According to OMIM, Fukunaga and Hunter (EMBO J. 1997, 16:1921-1933) observed that the C-terminal region of Mnk1 was phosphorylated and activated in vivo and in vitro by Erk1 and p38 MAP kinases, but not by JNK/SAPK. Waskiewicz et al., (EMBO J. 1997, 16:1909-1920) reported that in vitro, Mnk1 rapidly phosphorylates eIF4E at the physiologically relevant site, ser209. In cells, they observed that Mnk1 is posttranslationally modified and enzymatically activated in response to mitogenic and stress stimuli. This activation could be blocked by inhibitors of MAP kinase kinase-1 and p38, and Waskiewicz et al. (ibid.) concluded that Mnk1 is downstream of multiple MAP kinases (OMIM MIM Number: 606724: Feb. 27, 2002).

Accordingly, dephosphorylation of eIF4E strongly correlates with inhibition or impairment of cap-dependent mRNA translation under certain stress conditions such as heat shock, nutrient deprivation, oxidative or osmotic stress, and infection of mammalian cells with certain viruses such as adenovirus (Ad) or influenza virus, among others. Mnk1 inhibitors may be useful in treating conditions associated with heat shock, nutrient deprivation, oxidative or osmotic stress, infection of mammalian cells (e.g. with viruses such as adenovirus (Ad) or influenza virus), and autoimmune diseases.

p38: Target kinase p38 (i.e., Mitogen-activated Protein Kinase 14) is a 41.5 kDa STK encoded by chromosome 6p21.3-p21.2 (symbol: MAPK14). According to OMIM, production of interleukin-1 and tumor necrosis factor (TNF) from stimulated human monocytes is inhibited by a series of pyridinyl-imidazole compounds called CSAIDs (cytokine-suppressive antiinflammatory drugs). These agents have shown activity in a variety of animal models of acute and chronic inflammation. Using radiolabeled chemical probes for radioligand binding assays and photoaffinity labeling experiments, Lee et al. (Nature 1994, 372:739-746) identified, purified, cDNA-cloned, and biochemically characterized 2 CSBPs (CSAID-binding proteins) as molecular targets of pyridinyl-imidazole cytokine inhibitors. They designated the 2 closely related mitogen-activated protein kinases (MAPKs) CSBP1 and CSBP2. Binding of pyridinyl-imidazole compounds inhibited CSBP kinase activity and was directly correlated with their ability to inhibit cytokine production, suggesting that the CSBPs are critical for cytokine production. Lee et al. (ibid.) considered the 2 to be products of alternative splicing. The 4.2-kb CSBP mRNA encodes a predicted 360-amino acid protein and was expressed in all tissues tested. CSBP1 and CSBP2 are identical except for a 75-nucleotide stretch within the coding region. Han et al. (Science 1994, 265: 808-811) cloned the mouse homolog as a protein that is tyrosine phosphorylated as part of the protein kinase cascades induced by endotoxic lipopolysaccharide. They named this 38-kD protein p38. As p38 is a member of the stress-activated protein kinase (SAPK) class of MAPKs, Goedert et al. (Genomics 1997, 41:501-502) referred to this protein as SAPK2A. Zervos et al. (Proc. Nat. Acad. Sci. 1995, 92:10531-10534) identified p38 as a human protein that interacts with MAX protein and designated it MXI2. The MXI2 gene encodes a 297-residue protein whose sequence indicates that it is related to the extracellular signal-regulated kinases (ERK protein kinases). MXI2 in yeast interacts with Max and with the C terminus of c-Myc. MXI2 phosphorylates MAX both in vitro and in vivo. The authors speculated that phosphorylation by MXI2 may effect the ability of MAX to oligomerize with itself and its partners, bind DNA, or regulate gene expression (OMIM MIM Number: 600289: Feb. 13, 2006).

There are four known isoforms of p38, i.e., p38-α, p38β, p38γ, and p38δ. The α and β isoforms are expressed in inflammatory cells and are key mediators of TNF-α production. Inhibiting the p38α and β enzymes in cells results in reduced levels of TNF-α expression. Also, administering p38α and β inhibitors in animal models of inflammatory disease has proven that such inhibitors are effective in treating those diseases. Accordingly, the p38 enzymes serve an important role in inflammatory processes mediated by IL-1 and TNF-α. Compounds that reportedly inhibit p38 kinase and cytokines such as IL-1 and TNF-α for use in treating inflammatory diseases are disclosed in the following published international patent applications: WO 00/12497 (quinazoline derivatives as p38 kinase inhibitors); WO 00/56738 (pyridine and pyrimidine derivatives for the same purpose); WO 00/12497 (discusses the relationship between p38 kinase inhibitors); and WO 00/12074 (piperazine and piperidine compounds useful as p38 inhibitors).

p38 responds to activation by environmental stress, pro-inflammatory cytokines and lipopolysaccharide (LPS) by phosphorylating a number of transcription factors, such as ELK1 and ATF2 and several downstream kinases, such as MAPKAPK2 and MAPKAPK5. Additionally, p38 plays a critical role in the production of some cytokines, for example IL-6. p38 phosphorylates ELK1 and ATF2.

p38 is activated by threonine and tyrosine phosphorylation by either of two dual specificity kinases, MAP2K3 or MAP2K6, and potentially also MAP2K4 and it is inhibited by dual specificity phosphatases, such as DUSP1. p38 is specifically inhibited by the binding of pyridinyl-imidazole compounds, which are cytokine-suppressive anti-inflammatory drugs (CSAID).

p38 inhibitors have the potential to treat a number of diseases, including, but not limited to acute coronary syndrome, stroke, atherosclerosis, and inflammatory diseases such as rheumatoid arthritis, inflammatory bowel disease, and Crohn's disease.

PDGFR kinase family: Related to Fms and Kit are two platelet-derived growth factor receptors, alpha (i.e., PDGFRA) and beta (PDGFRB). The gene coding for PDGFRA is located on chromosome 4q12 in the same region of chromosome 4 as the oncogene coding for Kit. Most gastrointestinal stromal tumors (GIST) have activating mutations in Kit, and most patients with GISTs respond well to Gleevec, which inhibits Kit. Heinrich et al. (Science 2003, 299:708-10.) have shown that approximately 35% of GISTs lacking Kit mutations have intragenic activation mutations in the gene encoding pdgfra, and that tumors expressing Kit or PDGFRA were indistinguishable with respect to activation of downstream signaling intermediates and cytogenetic changes associated with tumor progression, Thus, Kit and PDGFRA mutations appear to be alternative and mutually exclusive oncogenic mechanisms in GISTs. PDGF is a potent growth factor and chemoattractant for smooth muscle cells (SMCs), and the renarrowing of coronary arteries following angioplasty is due in part to the enhanced proliferation of SMCs in response to increased levels of PDGF. Therefore, compounds that inhibit the kinase activity of PDGFr may be useful in the treatment of restenosis. In addition, since PDGF and PDGFr are overexpressed in several types of human gliomas, small molecules capable of suppressing PDGFr activity have potential utility as anticancer therapeutics [Nister, M., J. Biol. Chem., 266, 16755 (1991); Strawn. L. M., J. Biol. Chem, 269, 21215 (1994)].

PDGFRα: Target PDGFRα (i.e., Plate Derived Growth Factor Receptor, alpha) is a 122.7 kDa transmembrane tyrosine kinate encoded by chromosome 4q12 (symbol: PDGFRA). According to OMIM, The KIT oncogene, another member of the PDGF growth factor receptor subfamily, is located in the same region of chromosome 4 (Stenman et al., Genes Chromosomes Cancer 1989, 1:155-158). PDGFR1 (i.e. PDGFRB) and CSF1R (i.e. FMS) are also membrane-spanning growth factor receptors with tyrosine kinase activity, The PDGFR1 and CSF1R genes appear to have evolved from a common ancestral gene by gene duplication, inasmuch as these 2 genes are tandemly linked on chromosome 5 (Roberts et al., Cell 1988, 55: 655-661). They are oriented head-to-tail with the 5-prime exon of FMS located only 500 by from the last 3-prime exon of PDGFRB. An analogous situation may exist for the PDGFR2 (i.e. PDGFRA) and KIT genes on chromosome 4. From an evolutionary point of view, it is possible that the distribution of these 4 loci, PDGFR2, KIT, PDGFR1, and FMS, on chromosomes 4 and 5 is a result of gene duplication and chromosome doubling (tetraploidization) (OMIM MIM Number: 173490: Mar. 21, 2005). PDGFRA inhibitors may be useful in treating idiopathic hypereosinophilic syndrome, chronic eosinophilic leukemia, glioma, gastrointestinal stromal tumors (GISTs), juvenile myelomonocytic leukemia, metastatic medulloblastoma, atherogenesis, and restenosis.

PDGFRβ: Target PDGFRβ (i.e., Plate Derived Growth Factor Receptor, beta) is a 124.0 kDa transmembrane tyrosine kinate encoded by chromosome 5q31-q32 (symbol: PDGFRB). According to OMIM, stimulation of cell proliferation of the receptor for PDGF has been implicated in atherogenesis and in cell transformation by the SIS oncogene. Escobedo et al. (1986) sequenced the receptor and cloned its gene. Gronwald et al. (Proc. Nat. Acad. Sci. 1988, 85:3435-3439) cloned a cDNA coding for human PDGFR and studied its expression. The cDNA contained an open reading frame that coded for a protein of 1,106 amino acids. In transfectants, Gronwald et al. (ibid.) found that the PDGFR clone expressed a high affinity receptor specific for the BB isofonn of PDGF, i.e., PDGF dimers composed of 2 B chains. There may be a separate class of PDGF receptor that binds both the homodimers and the heterodimer. Claesson-Welsh et al. (Molec, Cell. Biol, 1988, 8:3476-3486) determined the structure of the human PDGF receptor as deduced from a full-length cDNA clone. The receptor expressed in Chinese hamster ovary cells was found to bind specifically to B-chain-containing PDGF molecules. With the description of a second PDGF receptor, it is necessary to use the symbol PDGFR1. Matsui et al. (1989) designated the second type of PDGFR as type alpha because PDGF binding was blocked by AA as well as BB isoforms of the ligand; the product of the earlier cloned PDGF receptor was termed type beta (OMIM MIM Number: 173410: Nov. 19, 2003).

PDGFRβ has been implicated in hematological cancers, such as chronic myelomonocytic leukemia (CMML), in which a significant number of patients have a t(5;12)(q33; p13) translocation resulting in TEL-PDGFRβ fusion protein. Golub et al. report that the consequence of the t(5;12) translocation is expression of a fusion transcript in which the tyrosine kinase domain of the platelet-derived growth factor receptor beta (PDGFRβ) on chromosome 5 is coupled to a novel ets-like gene, tel, on chromosome 12. The tel-PDGFR beta fusion demonstrates the oncogenic potential of PDGFRβ and may provide a paradigm for early events in the pathogenesis of AML (Golub et al., Cell 1994, 77:307-316). PDGFRB inhibitors may be useful in treating idiopathic hypereosinophilic syndrome, chronic eosinophilic leukemia, juvenile myelomonocytic leukemia, and metastatic medulloblastoma.

PDPK1: Target PDPK1 (3-phosphoinositide dependent protein kinase-1) is a 63.2 kDa serine/threonine kinase encoded by chromosome 16p13.3 (symbol: PDPK1). PDPK1 inhibitors may be useful in treating cancers and diabetes.

Pim1: Target Pim1 (i.e., Proviral Integration Site 1) is a 35.7 kDa serine/threonine kinase encoded by chromosome 6p21.2 (symbol: PIM1) found in the cytoplasm and nucleus. The structure of Pim1 comprises a STK (i.e., serine/threonine kinase) domain. X-ray crystal structures of Pim1 bound to various small molecules have recently been solved (Jacobs, et al., J Biol Chem 2005 280: 13728-34; Qian, et al., J Biol Chem 2005 280: 6130-7; Kumar, et al., J Mol Biol 2005 348: 183-93).

Pim1 is the first described member of a unique family of serinelthreonine kinases, which includes at least two other kinases (PIM2 and PIM3) with significant sequence homology to Pim1 (van der Lugt, et al., Embo J 1995 14: 2536-44; Feldman, et al., J Biol Chem 1998 273: 16535-43). The PIM1 protooncogene was originally identified as a genetic locus frequently activated by the proviral insertion of Moloney murine leukemia virus into mouse T cell lymphomas (Cuypers et al., Cell 1984, 37:141-150). Several substrates of Pim1 phosphorylation have been identified, including c-Myb (Winn, et al., Cell Cycle 2003 2: 258-62), BAD (Yan, et al., J Biol Chem 2003 278: 45358-67; Aho, et al., FEBS Lett 2004 571: 43-9), SOCS-1 (Chen, et al., Proc Natl Acad Sci U S A 2002 99: 2175-80), Cdc25A (Mochizuki, et al., J Biol Chem 1999 274: 18659-66), IIP1 (Koike, et al., FEBS Lett 2000 467: 17-21), PAP-1 (Maita, et al., Eur J Biochem 2000 267: 5168-78), $p21^{eip1/waf1}$ (Wang, et al., Biochim Biophys Acta 2002 1593: 45-55), PTP-U2S (Wang, et al, Arch Biochem Biophys 2001 390: 9-18), and NFATc1 (Rainio, et al., J Immunol 2002 168: 1524-7). Pim1 has been shown to have diverse biological roles in cell survival, proliferation, differentiation, and immune response (Wang, et al., J Vet Sci 2001 2: 167-79; Bachmann, et al., Int J Biochem Cell Biol 2005 37: 726-30). However, mice lacking all three Pim genes have recently been shown to be viable and demonstrate that the PIM kinases are important for growth factor signaling, but are not essential for development (Mikkers, et al., Mol Cell Biol 2004 24: 6104-15). During embryonal development PIM genes are expressed in partially overlapping fashion in cells in both immune and central nervous system as well as in epithelia (Eichmann A, Yuan L, Breant C, Alitalo K, and Koskinen PJ. (2000) Developmental expression of PIM kinases suggests functions also outside of the hematopoietic system. Oncogene 19: 1215-1224). PIM-1, the prototypical member of the PIM family is located both in the cytoplasm and nucleus, but its precise role in these two locations has not been fully elucidated.

Dysfunction of Pim1 has been implicated in the progression of multiple cancers, including several hematopoietic and prostate cancers. Although the exact mechanisms by which Pim1 participates in cell transformation have not been completely elucidated, several reports point to the ability of Pim1 to prolong cell survival (Lilly, et al., Cancer Res 1997 57: 5348-55; Lilly, et al., Oncogene 1999 18: 4022-31; Moroy, et al., Proc Natl Acad Sci U S A 1993 90: 10734-8). Overexpression of Pim1 has been observed in myeloid and lymphoid acute leukemia and Pim1 is constitutively expressed in some myeloid leukemia cell lines (Lilly, et al., Oncogene 1992 7: 727-32; Amson, et al., Proc Natl Acad Sci U S A 1989 86: 8857-61). Increased Pim1 expression has also been identified in neoplastic prostate cancer specimens from patients by cDNA microarray analysis and by anti-Pim1 antibody staining (Dhanasekaran, et al., Nature 2001 412: 822-6). In a transgenic murine model of prostate cancer in which human c-myc is expressed, the gene expression profile is consistent with that seen in human prostate cancer, including upregulation of Pim1 (Ellwood-Yen, et al., Cancer Cell 2003 4: 223-38). In addition, Pim1 may participate in deregulated cell growth in prostate cancer through the hormone independent activation of the androgen receptor, a typical characteristic of advanced prostate cancer that offers poor patient prognosis (Kim, et al., Oncogene 2004 23: 1838-44). The PIM-1 proto-oncogene has also been implicated in human hematopoietic malignancies with its overexpression frequently detected in human hematopoietic cell lines as well as in fresh tumor cells from patients with leukemia (Nagarajan et al. Proc. Natl. Acad. Sci, USA, 1986, 83:2556-2560; Meeker et al., Oncogene Res. 1987, 1: 87-101; Amson et al., Proc. Natl. Acad. Sci. USA, 1989, 86: 8857-8861).

In diffuse large cell lymphoma (DLCL), the most common form of non-Hodgkin's lymphoma, Pim1 has been shown to undergo chromosomal translocations, resulting in its overexpression (Akasaka, et al., Cancer Res 2000 60: 2335-41). A recent study showed that Pim1 was also the target of an aberrant somatic hypermutation in DLCL (Pasqualucci, et al., Nature 2001 412: 341-6). Hypermutation sites are distributed in both 5' UTR and coding sequence, and independent of the chromosomal translocations. Notably, there are seven missense mutations introduced into the coding exons of the gene. These missense mutations may affect the three-dimensional structure and, in some cases, the kinase activity of the Pim1 protein. Hypermutations are also detected in Pim1 found in primary central nervous system lymphomas (Montesinos-Rongen, et al., Blood 2004 103: 1869-75) and multiple subtypes of AIDS-induced non-Hodgkin's lymphomas (Gaidano, et al., Blood 2003 102: 1833-41). Inhibition of Pim1 kinase activity by small molecules has the potential to offer a therapeutic benefit in these diseases.

Transgenic mice with PIM-1 driven by Emu enhancer sequences demonstrated that PIM-1 function as a weak oncogene because by itself it does not lead to tumor formation but does so after a second oncogenic gene become overexpressed. In 75% of the tumors over-expressing PIM-1, the second gene found to be over-expressed is c-myc (van der Houven van Oordt C W, Schouten T G, van Krieken J H, van Dierendonck J H, van der Eb A J, Breuer M L. (1998) X-ray-induced lymphomagenesis in E mu-PIM-1 transgenic mice: an investigation of the co-operating molecular events. Carcinogenesis 19:847-853). In fact when crosses were made between Emu-PIM transgenic mice and Emu-myc transgenic mice, the combination of genes is so oncogenic that the off-springs die in utero due to pre B cell lymphomas (Verbeek S, van Lohuizen M, van der Valk M, Domen J, Kraal G, and Berns A. (1991) Mice bearing the Emu-myc and Emu-PIM-1 transgenes develop pre-B-cell leukemia prenatally. Mol. Cell. Biol., 11: 1176-1179).

Mice deficient for PIM-1 show normal synaptic transmission and short-term plasticity but failed to consolidate enduring LTP (i.e., long term potentiation) even though PIM-2 and PIM-3 are expressed in the hippocampus (Konietzko U, Kauselmann G, Scafidi J, Staubli U, Mikkers 1-1, Berns A, Schweizer M, Waltereit R, and Kuhl D. (1999) PIM kinase expression is induced by LTP stimulation and required for the consolidation of enduring ETP. EMBO J. 18: 3359-3369).

Various factors are known to enhance the transcription of PIM-1 kinase in mouse and human. PIM-1 closely cooperates with another oncoprotein, c-myc, in triggering intracellular signals leading to both transformation and apoptosis and the selective inhibition of apoptotic signaling pathways leading to Bcl-2 (van Lohuizen M, Verbeek S, Krimpenfort P, Domen J, Saris C, Radaszkiewicz T, and Berns A. (1989) Predisposition to lymphomagenesis in PIM-1 transgenic mice: cooperation with c-myc and N-myc in murine leukemia virus-induced tumors. Cell 56:673-682; Breuer M L, Cuypers H T, Berns A. (1989). Evidence for the involvement of PIM-2, a new common proviral insertion site, in progression of lymphomas. EMBO J. 8:743-748; Verbcck S, van Lohuizen M, van der Valk M, Domen J, Kraal G, and Berns A. (1991) Mice bearing the E mu-myc and E mu-PIM-1 transgenes develop pre-B-cell leukemia prenatally. Mol. Cell. Biol. 11: 1176-1179; Shirogane T, Fukada T, Muller J M, Shima D T, Hibi M, and Hirano T. (1999) Synergistic roles for PIM-1 and c-Myc in STAT3-mediated cell cycle progression and antiapoptosis. Immunity, 11: 709-719). PIM-1 kinase is induced by T cell antigen receptor cross linking by cytokines and growth factors and by mitogens including IL2, IL3, IL6, IL9, IL12, IL15, GM-CSF, G-CSF, IFNa, INFg, prolactin, ConA, PMA and anti-CD3 antibodies (Zhu N, Ramirez L M, Lee R L, Magnuson N S, Bishop G A, and Gold M R. (2002) CD40 signaling in B cells regulates the expression of the PIM-1 kinase via the NF-kappa B pathway. J Immunol. 168: 744-754). PIM-1 expression is rapidly induced after cytokine stimulation and the proliferative response to cytokines is impaired in cells from PIM-1 deficient mice (Domen J, van der Lugt N M, Acton D, Laird P W, Linders K, Berns A. (1993) PIM-1 levels determine the size of early B lymphoid compartments in bone marrow. J. Exp. Med. 178: 1665-1673).

Members of the PIM family of kinases interact with Socs-1 protein, a potent inhibitor of JAK activation thereby playing a major role in signaling down stream of cytokine receptors. The phosphorylation of Socs-1 by PIM family of kinases prolongs the half-life of Socs-1 protein, thus potentiating the inhibitory effect of Socs-1 on JAK-STAT activation (Chen X P, Losman J A, Cowan S, Donahue E, Fay S, Vuong B Q, Nawijn M C, Capece D, Cohan V L, Rothman P. (2002) PIM serine/threonine kinases regulate the stability of Socs-1 protein. Proc. Natl. Acad. Sci. USA 99:2175-2180). PIM-1 is expressed during G1/S phase of the cell cycle suggesting that it is involved in cell cycle regulation (Liang H, Mittelman W, Nagarajan L., Ubiquitous expression and cell cycle regulation of the protein kinase PIM-1. (1996) Arch Biochem Biophys. 330:259-265).). PIM-1 kinase activity and the protein level is increased in CD 40 mediated B cell signaling and this increase in PIM-1 level is mediated through the activation of NF-kB (Zhu et al. 2002. supra). PIM-1 can physically interact with NFATc transcription factors enhancing NFATc dependant transactivation and IL2 production in Jurkat cells (Rainio E M, Sandholm J, Koskinen P J. (2002) Cutting edge: Transcriptional activity of NFATc1 is enhanced by the PIM-1 kinase. J. Immunol. 168:1524-1527). This indicates a novel phosphorylation dependant regulatory mechanism targeting NFATc1 through which PIM-1 acts as down stream effector of ras to facilitate IL2 dependant proliferation and survival of lymphoid cells (ibid.).

Pim1 is shown to interact with many other targets. Phosphorylation of Cdc25A phosphatase, a direct transcriptional target of c-myc, increase its phosphatase activity both in-vivo and in-vitro indicating that Cdc25A link PIM-1 and c-myc in cell transformation and apoptosis (Mochizuki T, Kitanaka C, Noguchi K, Muramatsu T, Asai A, and Kuchino Y. (1999) Physical and functional interactions between PIM-1 kinase and Cdc25A phosphatase. Implications for the PIM-1-mediated activation of the c-Myc signaling pathway; J. Biol. Chem. 274:18659-18666). PIM-1 also phosphorylate PTP-U2S, a tyrosine phosphatase associated with differentiation and apoptosis in myeloid cells, decreasing its phosphatase activity and hence preventing premature onset of apoptosis following PMA-induced differentiation (Wang et al. (2001) Pim-1 negatively regulates the activity of PTP-U2S phosphatase and influences terminal differentiation and apoptosis of monoblastoid leukemia cells, Arch. Biochem. Biophys. 390:9-18). The phosphorylation of another PIM-1 target, heterochromatin protein 1(HP1) has been shown to be involved in transcription repression (Koike et al., FEBS Lett. 2000, 467: 17-21).

Pim1 inhibitors may be useful in treating cancers such as hematopoietic (e.g. acute myeloid and acute lymphoid leukemias) and prostate cancers, and non-Hodgkin's lymphomas.

Pim2: Target kinase Pim2 (i.e., Serine/threonine-protein kinase Proviral Integration Site 2) is a 34.2 kDa STK encoded by chromosome Xp11.23 (symbol: PIM2). Pim2 has also been shown to play a role in cell survival and the control of apoptosis and its value as an inhibitor target has been considered (Yan, et al., J Biol Chem 2003 278: 45358-67; Giles, Blood 2005 105: 4158-4159; Fox, et al., Genes Dev 2003 17: 1841-54). Pim2 has been found to be overexpressed in some lymphomas (Cohen, et al., Leuk Lymphoma 2004 45: 951-5). Additionally, Pim2 is required for the rapamycin resistant T-cell survival and the rapamycin-resistant growth of non-transformed hematopoietic cells (Hammerman, et al., Blood 2005 105: 4477-83; Fox, et al., J Exp Med 2005 201: 259-66). Pim2 inhibitors may be useful in treating lymphomas.

Pim3: Target kinase Pim3 (i.e., Serine/threonine-protein kinase Proviral Integration Site 3) is a 35.8 kDa STK encoded by chromosome 22q13 (symbol: PIM3). Pim3 has recently been shown to be overexpressed in human hepatocellular carcinoma cells and its ablation resulted in attenuated cell proliferation and enhanced apoptosis, suggesting that Pim3 can also participate in abnormal cell growth and inhibition of apoptosis (Fujii, et al., Int J Cancer 2005 114: 209-18). Pim3 inhibitors may be useful in treating hepatocellular carcinoma.

PKC alpha: Target kinase PKC alpha (i.e., Protein kinase C alpha) is a 76.8 kDa STK encoded by chromosome 17q22-q23.2 (symbol: PRKCA). Protein kinase C (PKC) is the major phorbol ester receptor. Nine mammalian members of the PKC family have been identified and designated alpha, beta, gamma, delta, epsilon, zeta, eta, theta, and lambda. According to OMIM, Parker et al. (Science 1986, 233:853-859) purified PKC from bovine brain and through the use of oligonucleotide probes based on partial amino acid sequence, derived cDNA clones from bovine cDNA libraries. Activation of PKC by calcium ions and the second messenger diacylglycerol is thought to play a central role in the induction of cellular responses to a variety of ligand-receptor systems and in the regulation of cellular responsiveness to external stimuli. Birnbaum et al. (Science 2004, 306:882-884) showed that high levels of PKC activity in prefrontal cortex, as seen for example during stress exposure, markedly impaired behavioral and electrophysiologic measures of working memory. Birnbaum (ibid.) concluded that excessive PKC activation can disrupt prefrontal cortical regulation of behavior and thought, possibly contributing to signs of prefrontal cortical dysfunction such as distractibility, impaired judgment, impulsivity, and thought disorder (OMIM MIM Number: 176960: Apr. 17, 2006), A mutation in PKC-alpha (D294G) correlates with pituitary tumor. PKC alpha inhibitors may be useful in treating pituitary tumors and prefrontal cortical dysfunction such as distractibility, impaired judgment, impulsivity, and thought disorder, also may be used to sensitize chemotherapy in breast, colon, and non small cell lung cancers.

PKC beta: Target kinase PKC beta (i.e., Protein kinase C, beta 1) is a 76.7 kDa STK encoded by chromosome 16p11.2 (symbol: PRKCB1). According to OMIM, Leitges et al. (Science 1996, 273:788-791) found that mice homozygous for a targeted disruption of the PRKCB1 gene develop an immunodeficiency characterized by impaired humoral immune responses and reduced cellular responses of B cells similar to X-linked immunodeficiency (Xid) in mice. Thus, they concluded that the 2 isoforms, PKC-beta-I (PRKCB1) and PKC-beta-II (PRKCB2), play an important role in B-cell activation and may be functionally linked to Bruton tyrosine kinase in antigen receptor-mediated signal transduction (OMIM MIM Number: 176970: Mar. 3, 2006). In general, inhibitors PKC beta and PKC isoforms may be effective in treating disorders characterized by dysregulated NFKB survival signaling. PKC beta inhibitors may be useful in treating diabetic retinopathy.

PKC theta: Target kinase PKC-theta (i.e., Protein kinase, theta) is a 81.9 kDa STK encoded by chromosome 10p15 (symbol: PRKCQ). According to OMIM, in an attempt to find PKC isoforms that are involved in growth control and/or activation of T lymphocytes, Baier et al., (J. Biol. Chem. 1993, 268:4997-5004) used a human peripheral blood lymphocyte-derived cDNA library was employed to identify a novel PKC isoform, termed PKC-theta. The gene encodes a protein of approximately 80 kD, expressed predominantly in lymphoid tissues and hematopoietic cell lines, particularly T cells. The alpha form (PRKCA) has been mapped to chromosome 17, the beta form (PRKCB1) to chromosome 16, the gamma form (PRKCG) to chromosome 19, and the delta form (PRKCD) to chromosome 3. By fluorescence in situ hybridization, Erdel et al. (Genomics 1995, 25:595-597) assigned the PRKCQ gene to 10p15. Blanco and Brown (Mammalian Genome 1997, 8:70-71) mapped the homolog Pkcq to mouse chromosome 2 by analysis of an interspecific backcross, Sun et al. (Nature 2000, 404:402-407) demonstrated that PKC-theta is essential for T-cell antigen receptor (TCR)-mediated T-cell activation but dispensable during TCR-dependent thymocyte development. They generated mice deficient in Pkc-theta by homologous recombination. Mutant mice were normal and fertile. TCR-initiated NF-kappa-B activation was absent from PKC-theta −/− mature T lymphocytes, but was intact in thymocytes. Activation of NE-kappa-B by tumor necrosis factor-alpha and interleukin-1 was unaffected in the mutant mice. Induction of JNK was normal in T cells from mutant mice. Sun et al. (ibid.) concluded that PKC-theta functions in a unique pathway that links the TCR signaling complex to the activation of NF-kappa-B in mature T lymphocytes. Using hyperinsulinemic-euglycemic clamps, Kim et al. (J. Clin. Invest, 2004, 114:823-827) demonstrated that skeletal muscle and hepatic insulin action did not differ between wildtype and Pkc-theta null mice, A 5-hour lipid infusion decreased insulin-stimulated skeletal muscle glucose uptake in the wildtype mice that was associated with 40 to 50% decreases in insulin-stimulated tyrosine phosphorylation of insulin receptor substrate-1 (IRS 1) and IRS 1-associated PI3K activity. In contrast, Pkc-theta inactivation prevented fat-induced defects in insulin signaling and glucose transport in skeletal muscle. Kim et al. (ibid.) concluded that PKC-theta is a crucial component mediating fat-induced insulin resistance in skeletal muscle (OMIM MIM Number: 600448: Oct. 15, 2004).

Li et al, report that PKC plays a critical role in competitive activity-dependent synapse modification at the neuromuscular synapse in vitro and in vivo. This action involves a reduction of the strength of inactive inputs to muscle cells that are activated by other inputs. A decrease of postsynaptic responsiveness and a loss of postsynaptic acetyl choline receptors account for the heterosynaptic loss in vitro. The loss is not seen in preparations in which PKC has been blocked pharmacologically. Here, they show that the loss does not occur in in vitro preparations made from animals genetically modified to lack the theta isoform of PKC. Synapse elimination in the newborn period in vivo is delayed but is eventually expressed in knock-out animals. PKC-dependent synapse reduction is suppressed in heterologous cultures combining normal nerve and PKC-theta-deficient muscle, as might be expected from the postsynaptic locus of the changes that underlie the activity-dependent plasticity. Preparations in which PKC-theta-deficient neurons innervated normal muscle also exhibited a marked deficit in PKC-deficient synapse reduction. The presynaptic action of PKC-theta implied by this observation is blocked by TTX, and the authors propose that the activity-related synapse strengthening is decreased by presynaptic PKC-theta. Thus, PKC-theta in both presynaptic and postsynaptic elements plays a critical role in activity-dependent synapse modulation and loss (Li et al., Journal of Neuroscience 2004, 24(15):3762-3769). PKC theta inhibitors may be useful in treating insulin resistance, T-cell lymphoma.

Plk1: Target kinase Plk1 (i.e., Polo like kinase 1) is a 68.3 kDa STK encoded by chromosome 16p12.3 (symbol: PLK1). Plk1 is a regulator required for multiple mitotic processes, including bipolar mitotic spindle formation, actin ring formation, and chromosomal segregation. According to OMIM, Holtrich et al. (Proc. Nat. Acad. Sci. 1994, 91:1736-1740) observed that PLK1 transcripts are present at high level in tumors of various origins. In vertebrate cells, the nuclear entry of mitosis-promoting factor (MPF) during prophase is thought to be essential for the induction and coordination of M-phase events, Phosphorylation of cyclin B1 is central to its nuclear translocation. Toyoshima-Morimoto et al. (*Nature* 2001, 410:215-2201 purified a protein kinase from *Xenopus* M-phase extracts that phosphorylates a crucial serine residue (S147) in the middle of the nuclear export signal sequence of cyclin B1. They identified this kinase as Plx1, a *Xenopus* homolog of PLK1. During cell cycle progression in HeLa cells, a change in the kinase activity of endogenous Pls1 toward S147 and/or S133 correlates with a kinase activity in the cell extracts. An anti-PLK1 antibody depleted the M-phase extracts of the kinase activity toward S147 and/or S133. An anti-phospho-S147 antibody reacted specifically with cyclin B1 only during G2/M phase. A mutant cyclin B1 in which S133 and S147 were replaced by alanines remained in the cytoplasm, whereas wildtype cyclin B1 accumulated in the nucleus during prophase. Further, coexpression of constitutively active Plk1 stimulates nuclear entry of cyclin B1. Toyoshima-Morimoto et al. (ibid.) concluded that Plk1 may be involved in targeting MPF to the nucleus during prophase (OMIM MIM Number: 602098: Aug. 5, 2005). Plk1 inhibitors may be useful in treating cancers (e.g. lymphoma of the thyroid, non-Hodgkin's lymphomas, colorectal cancers, leukemias and melanoma), also useful as sensitizer in chemotherapy.

Pyk2: Target kinase Pyk2 (i.e., Protein-Tyrosine Kinase 2) is a 115.9 kDa tyrosine kinase of the FAK family (see e.g., target Fak) encoded by chromosome 8p21.1 (symbol: PTK2B). As with target kinase Fak, Pyk2 comprises B41 and TK domains, and Pyk2 is also known as Fak2 (i.e., Focal Adhesion Kinase 2). Because Pyk2 is calcium dependent, it is also known as CADAK (i.e., calcium-dependent tyrosine kinase).

As mentioned, another member of the FAK subfamily is kinase Fak. Pyk2 and Fak shares 65% sequence identity in the kinase domain and have similar domain structure: an N-terminus domain for integrin binding, and a C-terminus domain for Paxillin binding. Fak is ubiquitously expressed while Pyk2 exhibits a more restricted tissue expression pattern primarily in neuronal and hematopoetic tissues.

According to OMIM, Focal adhesion kinases (i.e., FAKs) are cytoplasmic protein-tyrosine kinases associated with focal adhesions and whose activity is induced by ligand binding to various receptors including those of, for example, integrin and growth factors. FAKs are known to target paxillin and are substrates for Src family kinases (Calalb et al., Molec. Cell. Biol. 1995, 15:954-963). Herzog et al. (Genomics 1996, 32:484-486) identified a gene for another focal adhesion kinase by low-stringency screening of a hippocampus cDNA library. They symbolized the gene FAK2. The FAK2 cDNA encodes a predicted 1,009-amino acid protein with 42% identity to FAK1. Northern blot analysis detected a 4.5-kb mRNA in brain, kidney, spleen, and lymphocytes. Protein-tyrosine kinases in the central nervous system are activated in response to a variety of neurotrophic factors that control neuronal differentiation and survival via cell surface receptors. Also, protein phosphorylation is involved in membrane excitability and the function of ion channels. Lev et al. (Nature 1995, 376:737-745) discovered a nonreceptor type protein kinase that is highly expressed in adult rat brain. The kinase, which they symbolized PYK2 (proline-rich tyrosine kinase-2), was cloned from a rat spinal cord cDNA library using degenerate PCR primers corresponding to conserved tyrosine kinase motifs of PYK1 (see Manser et al., Nature 1993, 363:364-367). Lev et al. (ibid.) cloned the human homolog from a human fetal brain cDNA library using the rat sequence as a probe. The predicted protein of 1,009 amino acids has 61% sequence identity to the FAK1 protein (Ptk2) (OMIM MIM Number: 601212: Jan. 19, 2005). PKC-theta may represent an important signaling intermediate between neuropeptide activated receptors or neurotransmitters that increase calcium flux and the downstream signals that regulate neuronal activity. PKC-theta interacts with the SH2 domain of Grb2, and may phosphorylate the voltage-gated potassium channel protein Kv1.2. Its activation is highly correlated with the stimulation of c-Jun N-terminal kinase activity.

Pyk2 regulates multiple signaling events crucial for macrophage morphology and migration. It mediates the Jak-dependent activation of MAPK and Stat1. By rapidly translocating to the vicinity of the immune synapse after T cell receptor stimulation, Pyk2 plays an essential role in T cell activation and polarized secretion of cytokines. The morphology and behavior of macrophages in Pyk2–/– mice were impaired. Macrophages isolated from mutant mice failed to become polarized, to undergo membrane ruffling, and to migrate in response to chemokine stimulation. Moreover, the contractile activity in the lamellipodia of Pyk2–/– macrophages was impaired, as revealed by measuring the rearward movement toward the nucleus of fibronectin-coated beads on the lamellipodia in opposition to an immobilizing force generated by optical tweezers.

Pyk2 is implicated in several therapeutic areas including inflammation (e.g. osteoporosis, Polycystic Kidney Disease, rheumatoid arthritis and some bowel diseases) and CNS disease like Parkinson's disease and Alzheimer's disease). Pyk2 in osteoclasts is an adhesion kinase, localized in the sealing zone, activated by ligation of v3 integrin, and phosphorylated by Src kinase. Methods for preventing cell death in a subject and their application in the treatment of neurodegenerative diseases and conditions, such as Alzheimer's disease, stroke, Parkinson's disease have been pattened by Griswold-Premier Irene and Powell Kyle.

Pyk2 is also a potential therapeutic target for tumors. Pyk2 is a novel effector of fibroblast growth factor receptor 3 activation. Pyk2 facilitates EGFR- and c-Src-mediated Stat3 activation and has a role in triggering Stat3-induced oncogenesis. HER3, but not HER2, mediates the phosphorylation of the C-terminal region of PYK2 to promote a mitogenic response through activation of the MAPK pathway. Furthermore, PYK2 phosphorylation by HER3 induces tumor invasion. A central role of PYK2 in signaling downstream of HER3 is substantiated by the demonstration that expression of a dominant-negative PYK2-KM construct abrogates the Heregulin-induced MAPK activity and inhibits the invasive potential of glioma cells.

Overexpression of wild-type RAFTK significantly enhanced breast cancer cell invasion, while overexpression of the mutants Tyr402 or Tyr881 of RAFTK inhibited this migration. Therefore, Pyk2 may serve as a mediator and an integration point between focal adhesion molecules in HRG-mediated signaling in T47D breast cancer cells.

A murine pancreatic cancer cell line overexpressing Pyk2, mPanc02, was treated with a Pyk2-dominant negative adenovirus (Ad-Pyk2DN), or GFP (ad-GFP) adenovirus. The dominant negative Pyk2 adenovirus is able to decrease tumor growth and increase survival in several in vivo tumor models.

Although no point mutation of Pyk2 has been reported to be significant in any disease, human umbilical vein endothelial cells express mRNA transcripts for both the full length isoform Pyk2 and the truncated isoform Pyk2-H containing the C-terminal deletion.

Pyk 2 inhibitors may be useful in treating inflammation (e.g. osteoporosis, polycystic kidney disease, rheumatoid arthiritis and inflammatory bowel disease), CNS disease (e.g. Parkinson's disease and Alzheimer's disease), stroke and cancers (e.g. gliomas, breast cancer, and pancreatic cancer).

Ret: Target Ret (i.e., Rearranged during Transfection) is a 124.3 kDa tyrosine kinase encoded by chromosome 10q11.2 (symbol: RET). Ret is also known as c-ret (i.e., cellular ret). The domain structure of Ret comprises cadherin, transmembrane, and TK domains. Cadherins are glycoproteins involved in Ca2+-mediated cell-cell adhesion; see e.g., Yap et al., Annu Rev Cell Dev Biol. 1997; 13:119-46).

According to OMIM, the RET protooncogene is one of the receptor tyrosine kinases, cell-surface molecules that transduce signals for cell growth and differentiation. The RET gene was defined as an oncogene by a classical transfection assay. RET can undergo oncogenic activation in vivo and in vitro by cytogenetic rearrangement (Grieco ct al., Cell 1990, 60:557-563). Mutations in the RET gene are associated with multiple endocrine neoplasia, type IIA (MEN2A), multiple endocrine neoplasia, type IIB (MEN2B), Hirschsprung disease (HSCR; aganglionic megacolon), and medullary thyroid carcinoma (MTC) (OMIM MIM Number: 164761: Jan. 27, 2006).

Ret (Rearranged during Transformation) was identified as a rearranged human oncogene in the classic NIH3T3 transformation assay (Takahashi et al., 1985, Cell 42(2):581-8) and subsequently characterized as a Receptor Tyrosine kinase (Takahashi et al., 1988, Oncogene 3(5):571-8).

Ret and NTRK1 (i.e., Neutrotrophic tyrosine receptor kinase 1) are receptor tyrosine kinase (RTK) proteins which play a role in the development and maturation of specific components of the nervous system. Their alterations have been associated to several human diseases, including some forms of cancer and developmental abnormalities. These features have contributed to the concept that one gene can be responsible for more than one disease. Moreover, both genes encoding for the two RTKs show genetic alterations that belong to either "gain of function" or "loss of function" class of mutations. In fact, receptor rearrangements or point mutations convert Ret and NTRK 1 into dominantly acting transforming genes leading to thyroid tumors, whereas inactivating mutations, associated with Hirschsprung's disease (HSCR) and congenital insensitivity to pain with anhidrosis (CIPA), impair Ret and NTRK1 functions, respectively.

Implication of Ret in human tumorigenesis was indicated by the frequent identification of rearranged Ret sequences that transformed NIH3T3 cells in the DNA isolated from Papillary Thyroid Carcinoma DNAs. In these cases, the Ret gene was fused to as yet unknown PTC DNA sequences in the tumor DNA but not the normal patient DNA (Grieco et al., 1990, Cell 60(4):557-63). In addition, the chromosomal mapping of Ret to chromosome 10q11.2 co-localized with genetic mapping data that implicated a gene involved in patients with MEN2A (Multiple Endocrine Neoplasia 2A) (Ishizaka et al, 1989 Oncogene 4(12):1519-21). Expression analysis of the RET oncogene in a number of human tumors consistently detected expression of normal-sized transcripts of the RET proto-oncogene in human pheochromocytomas and in human medullary thyroid carcinomas, both of familial and sporadic type (Santoro et al., 1990, Oncogene 5:1595-8).

Further analysis of the tumor DNA of patients with Multiple endocrine neoplasia type 2A (MEN 2A) and familial medullary thyroid carcinoma (FMTC) identified mutations in the RET sequence resulting in amino acid changes in the encoded Ret protein (Donis-Keller 1993, Hum Mol Genet. 2(7):851-6). Likewise, mutations in the RET gene were correlated with Hirschprung disease, a developmental disorder with genetic deletions and mutations in the chromosomal location of the RET gene (Luo et al., 1993, Hum Mol Genet. 2(11):1803-8).

By early 1994, multiple papers describe the inactivation of the RET gene in patients with Hirschsprung disease and similar phenotype in knock out mice. In addition, activating mutations in Ret are now identified in patients with MEN2A, MEN2B, and FMTC (reviewed by van Heyningen V., 1994, Nature 367(6460:319-20).

It was determined that Ret regulates cell survival. Signal transduction molecules that form a complex with Ret as a result of these phosphoryl moieties, such as GRB2, SOS, ras, and raf, propagate a signal in the cell that promotes neural survival. Thus, compounds that promote the interactions of the se stimulatory molecules of Ret would enhance the activity of c-Ret. Alternatively, protein phosphatases can remove the phosphoryl moieties placed on the intracellular region of Ret in response to GDNF, and thus inhibit the signaling capability c-Ret. Thus, compounds that inhibit phosphatases of Ret will probably enhance the signaling capacity of c-Ret.

Ret is implicated in the development and survival of enteric, synaptic, and sensory neurons and neurons of the renal system upon stimulation by GDNF (Jing, et al., 1996, Cell 85:1113-1124; Trupp, et al., 1996, Nature 381:785-789; Durbec, et al., 1996, Nature 381:789-793). Lack of function mutations in Ret can lead to Hirschsprung's disease, for example, which manifests itself as a decrease in intestinal tract innervation in mammals. Thus, compounds that activate Ret are potential therapeutic agents for the treatment of neurodegenerative disorders, including, but not limited to, Hirschsprung's disease, Parkinson's disease, Alzheimer's disease, and amyotrophic lateral sclerosis. Compounds that inhibit Ret function can also be anti-cancer agents as overexpression of Ret in cells is implicated in cancers, such as cancer of the thyroid.

Modulation of Ret activity may also be useful in treating cancers of the nerve tissue, such as neuroblastoma, even if an abnormality is not found the signaling pathway.

As stated above, RET gene is responsible for MEN2 syndromes, which are inherited in an autosomal dominant fashion with high penetrance and diverse clinical manifestations. The predominant RET mutation is missense mutation which is restricted to 9 codons (codons 609, 611, 618, 620, 630, 634, 768, 804 and 918). The MEN2 syndromes have 3 subtypes: multiple endocrine neoplasia type 2A (MEN2A), MEN2B, and familial medullary thyroid carcinoma (FMTC). Missense mutations at exon 10 (codons 609, 611, 618, and 620) and exon 11 (codons 630 and 634) have been identified in 98% of MEN2A families and in 85% of FMTC families. Missense mutations at codons 768 and 804 have been known to be responsible for 5.about.10% of FMTC cases. In addition, missense mutations at exon 16 (codon 918) have been found in 95% of MEN2B cases.

Ret inhibitors may be useful in treating cancer of the thyroid, neuroblastoma, familial medullary thyroid carcinoma (FMTC), multiple endocrine neoplasia type IIA and IIB (MEN2A, MEN2B), and neurodegenerative disorders (e.g. Hirschsprung's disease, Parkinson's disease, Alzheimer's disease, and amyotrophic lateral sclerosis)

Ron: Target kinase Ron (i.e., Ron protein tyrosine kinase) is a 152.2 kDa transmembrane tyrosine kinase encoded by chromosome 3p21.3 (symbol: MST1R), also known as macrophage stimulating protein receptor (i.e., MSP receptor). Ron, a member of the Met hepatocyte growth factor receptor family, was originally cloned from a human foreskin keratinocyte cDNA library by Ronsin et al (*Oncogene* 1993, 8: 1195-1202). RON is expressed in various cell types including macrophages, epithelial and hematopoietic cells. Ron activation results in a variety of cellular responses in vitro, such as activation of macrophages, proliferation, migation, and invasion, which suggest abroad biologic role in vivo. Hemizygous mice (Ron +/−) grow to adulthood; however, these mice are highly susceptible to endotoxic shock and appeared to be compromised in their ability to downregulate nitric oxide production. Accordingly, Ron plays a role in early mouse development and may play a limited role in the inflammatory response. Further, Ron may be involved in cancer development and progression (OMIM MIM Number: 600168: Jan. 20, 2006). Ron inhibitors may be useful in treating cancer and inflammation.

ROCK (ROCK1 and ROCK2): Target kinase ROCK1 (i.e., Rho-associated, coiled-coil containing protein kinase 1) is a 158.2 kDa serine/threonine kinase encoded by chromosome 18q11.1 (symbol: ROCK1). Target kinase ROCK2 (i.e., Rho-associated, coiled-coil containing protein kinase 2) is a 160.9 kDa serine/threonine kinase encoded by chromosome 2p24 (symbol: ROCK2.). ROCK inhibitors may be useful in treating related to cancers (e.g. ovarian cancer, hepatocellular carcinoma, pancreatic cancer), ocular disease (e.g. glaucoma), cardiac hypertrophy, improved renal perfusion, transplant rejection, and acute respiratory distress syndrome.

Src: Target kinase Src (i.e., v-Src Avian Sarcoma Schmidt-Ruppin A-2 viral oncogene) is a 59.8 kDa non-receptor tyrosine kinase encoded by chromosome 20q12-q13 (symbol: SRC). The structure of Src comprises SH3 and SH2 domains adjacent to the TK domain. According to OMIM, Azarnia et al. (Science 1988, 239:398-401) found that overexpression of the SRC gene in 3T3 cells caused reduction of cell-to-cell transmission of molecules in the 400- to 700-dalton range. Downregulation was enhanced by point mutation of tyrosine-527, whereas mutation of tyrosine-416 suppressed both the downregulation of communication by the tyr-527 mutation and that by gene overexpression. The regulation of communication by SRC may be important in the control of embryonic development and cellular growth. Luttrell et al. (Science 1999, 283:655-661) demonstrated that c-src binds to the amino terminus of beta-arrestin-1 in a complex resulting from the stimulation of beta-2 adrencrgic receptors. Activated beta-2-adrenergic receptor bound beta-arrestin-1, which then bound c-src. This interaction targeted the complex to clathrin-coated pits and allowed for beta-2-adrenergic activation of the MAP kinases Erk1 and Erk2. TRANCE, a TNF family member, and its receptor, RANK, are critical regulators of dendritic cell and osteoclast function. Wong et al. (Molec. Cell 1999, 4:1041-1049) demonstrated that TRANCE activates the antiapoptotic serineithreonine kinase PKB (AKT1) through a sigialing complex involving SRC and TRAF6, A deficiency in SRC or addition of SRC family kinase inhibitors blocked TRANCE-mediated PKB activation in osteoclasts. SRC and TRAF6 interacted with each other and with upon receptor engagement. TRAF6, in turn, enhanced the kinase activity of SRC, leading to tyrosine phosphorylation of downstream signaling molecules such as CBL. These results defined a mechanism by which TRANCE activates SRC family kinases and PKB, and provided evidence of cross-talk between TRAF proteins and SRC family kinases. Using a colon cancer cell line, Avizienyte et al. (Nature Cell Biol. 2002, 4:632-638) studied the role of SRC in cell adhesion and metastasis. Transfection and overexpression of a constitutively active SRC mutant reduced cell-cell contacts and caused redistribution of adherens junction components to discrete adhesion-like structures at the tips of membrane protrusions, Expression of active SRC also impaired the movement of E-cadherin from the cell interior to the plasma membrane following exposure to high calcium. Avizienyte et al. (ibid.) provided evidence that the alpha-V and beta-1 integrins and FAK were required for the adhesion changes induced by SRC. Sandilands et al. (Dev, Cell 2004, 7:855-869) found that RhoB colocalized with active Src in the cytoplasm of mouse embryonic fibroblasts, and they presented evidence that RhoB is a component of 'outside-in' signaling pathways that coordinate Src activation with translocation to transmembrane receptors (OMIM MIM Number: 190090: Jan. 7, 2005).

The Src family of cytoplasmic protein tyrosine kinases consists of at least eight members (Src, Fyn, Lyn, Yes, Lck, Fgr, Hck and Blk) that participate in a variety of signaling pathways [Schwartzberg, P, L., Oncogene, 17, 1463 (1998)]. The prototypical member of this tyrosine kinase family is p60src (Src). Src is involved in proliferation and migration responses in many cell types. In limited studies, Src activity has been shown to be elevated in breast, colon (~90%), pancreatic (>90%) and liver (>90%) tumors. Greatly increased Src activity is also associated with metastasis (>90%) and poor prognosis. Antisense Src message impedes growth of colon tumor cells in nude mice [Staley et al., Cell Growth & Differentiation, 8, 269 (1997)], suggesting that Src inhibitors should slow tumor growth. In addition to its role in cell proliferation, Src also acts in stress response pathways, including the hypoxia response. Previous studies have shown that colonic tumor cells genetically engineered to express antisense Sre message form tumors demonstrating reduced vascularization in nude mouse models [Ellis, et al., J. Biol. Chem., 273, 1052 (1998)], suggesting that Src inhibitors would be anti-angiogenic as well as anti-proliferative.

Apart from its role in cancer, Src also appears to play a role in osteoporosis. Mice genetically engineered to be deficient in src production were found to exhibit osteopetrosis, the failure to resorb bone [Soriano, P., Cell, 64, 693 (1991); Boyce, 13. F., J. Clin. Invest., 90, 1622 (1992)]. This defect was characterized by a lack of osteoclast activity. Since osteoclasts normally express high levels of Src, inhibition of Src kinase activity may be useful in the treatment of osteoporosis [Missbach, M., Bone, 24, 437 (1999)]. Src inhibitors may be useful in treating cancer and osteoporosis.

Stk6: Target Stk6 (i.e., Serine/Threonine protein kinase 6) is a 45.8 kDa serine/threonine kinase encoded by chromosome 20q13.2-q13.3 (symbol: STK6). According to OMIM, Kimura et al. (J. Biol. Chem. 1997, 272:13766-13771) cloned a cDNA encoding a novel human serine/threonine kinase, STK6, that has high homology with the Aurora and Ipll kinases, Mutations in these yeast kinases are known to cause abnormal spindle formation and missegregation of chromosomes. Northern and Western blot analyses revealed a high level of STK6 expression product in testis and proliferating culture cells such as HeLa cells. The endogenous levels of STK6 protein and protein kinase activity were tightly regulated during cell cycle progression in HeLa cells. The protein was upregulated during G2/M and rapidly reduced after mitosis. Immunofluorescence studies revealed specific localization of STK6 protein to the spindle pole region during mitosis. The results suggested that STK6, like Aurora and Ip11, is involved in cell growth and/or chromosome segregation (OMIM MIM Number: 602687: Apr. 1, 2003).

Aurora A belongs to the family of STKs that are involved in mitotic events such as centrosome separation and chromosome segregation and are therefore essential for cell proliferation (Bischoff & Plowman, Trends Cell Biol. 1999, 9:454-459); Giet & Prigent. 1999, Cell Science 112: 3591-3601). Inhibitors of the Aurora kinase family therefore have the potential to block growth of all tumors.

The three identified Aurora kinases of this family are known under various names: Aurora-A (Aurora 1), Aurora B (Aurora 2) and Aurora C (Aurora 3). Alternate names for Aurora A, described here further are serine/threonine protein kinase 15 (STK 15), BTAK Aurora-related kinase 1 (ARK1). The mouse homolog of Aurora A, STK6 also referred to as AIK, is highly homologous to STK15. All Aurora kinase family members are highly homologous proteins responsible for mitotic events such as centrosome maturation and seggregation, chromosome segregation, mitotic spindle function and cytokinesis. Peak expression of Aurora occurs during the G2 and mitotic phase in cycling cells and then decreases and remains low or undetectable in resting cells (Shindo et al., 1998, Biochem. Biophys. Res. Commun. 244: 285-292). In mammalian cells proposed substrates for Aurora include histone H3, a protein involved in chromosome condensation, and CENP-A, myosin II regulatory light chain, protein phosphatase 1, TPX2, all of which are required for cell devision.

Zhou et al., (Zhou et al., 1998, *Nature Genet.* 20: 189-193) found that Aurora is involved in the induction of centrosome duplication-distribution abnormalities and aneuploidy in mammalian cells. Centrosomes appear to maintain genomic stability through the establishment of bipolar spindles during cell division, ensuring equal segregation of replicated chromosomes to 2 daughter cells. Deregulated duplication and distribution of centrosomes are implicated in chromosome segregation abnormalities, leading to aneuploidy seen in many cancer cell types. Zhou et al., (Zhou et al., 1998, *Nature Genet.* 20: 189-193) found amplification of Aurora A in approximately 12% of primary breast tumors, as well as in breast, ovarian, colon, prostate, neuroblastoma, and cervical cancer cell lines. Additionally, high expression of Aurora A mRNA was detected in tumor cell lines without evidence of gene amplification. Ectopic expression of Aurora A in mouse NIH 3T3 cells led to the appearance of abnormal centrosome number (amplification) and transformation in vitro. Finally, over-expression of Aurora A in near-diploid human breast epithelial cells revealed similar centrosome abnormality, as well as induction of aneuploidy. These findings suggested that Aurora A is a critical kinase-encoding gene, whose over-expression leads to centrosome amplification, chromosomal instability, and transformation in mammalian cells.

The AURKA gene is over expressed in many human cancers. Ectopic over-expression of aurora kinase A in mammalian cells induces centrosome amplification, chromosome instability, and oncogenic transformation, a phenotype characteristic of loss-of-function mutations of p53. Katayama et al. (Katayama et al., 2004, *Nature Genet.* 36: 55-62) showed that Aurora A kinase phosphorylates p53 at ser315, leading to its ubiquitination by MDM2 and proteolysis. P53 is not degraded in the presence of inactive Aurora A or ubiquitination-defective MDM2. Silencing of Aurora kinase A results in less phosphorylation of p53 at ser315, greater stability of p53, and cell-cycle arrest at G2-M. Cells depleted of Aurora kinase A are more sensitive to cisplatin-induced apoptosis, and elevated expression of aurora kinase A abolishes this response. In a sample of bladder tumors with wildtype p53, (Katayama et al., 2004, *Nature Genet.* 36: 55-62) found a correlation between elevated expression of aurora kinase A and low p53 concentration. They concluded that Aurora A kinase is a key regulatory component of the p53 pathway and that over-expression of Aurora A leads to increased degradation of p53, causing down-regulation of checkpoint-response pathways and facilitating oncogenic transformation of cells.

By immunoprecipitation of epitope-tagged proteins from transfected HEK293 cells. Kunitoku et al. (Kunitoku et al., 2003, Dev. Cell 5: 853-854) demonstrated direct interaction between the genes CENPA and AURKA. In vitro, AURKA phosphorylated CENPA on ser7, a residue that is also phosphorylated by AURKB. Examination of the role of both kinases in the phosphorylation of CENPA revealed that the reaction is mediated sequentially by AURKA and AURKB in early mitosis. Mitotic cells in which phosphorylation of CENPA on ser7 was prevented exhibited a substantial proportion of misaligned chromosomes resulting from a defect in the ability of kinetochores to attach to microtubules.

By yeast 2-hybrid analysis of HeLa cells, Hirota et al. (Hirota et al., 2003, Cell 114: 585-598) determined that AURKA interacts with Ajuba (JUB). The two proteins interacted in mitotic cells and became phosphorylated as they did so. In vitro analysis revealed that Ajuba induced the autophosphorylation and consequent activation of AURKA, Depletion of Ajuba prevented activation of AURKA at centrosomes in late G2 phase and inhibited mitotic entry. Hirota et al. (Hirota ct al., 2003, Cell 114: 585-598) concluded that Ajuba is an essential activator of AURKA in mitotic commitment.

The mammalian Aurora kinase family has been implicated in tumorigenesis of a variety of different cancers. The main role of Aurora A in tumor development is in controlling chromosome segregation during mitosis (Bischoff & Plowman, Trends Cell Biol, 1999, 9:454-459). Over-expression of Aurora A transforms rodent fibroblasts (Bischoff et al., 1998, EMBO J. 17:3052-3065). The elevated levels of Aurora A induce misregulation of chromosome segregation that results in cells containing multiple centrosomes and multipolar spindles leading to aneuploidy, a distinctive feature of most cancers. (Zhou et al., 1998, Nature Genet. 20: 189-193). Ewart-Toland et al. (Ewart-Toland et al., 2003, Nature Genet, 34: 403-412) found that tumors from individuals carrying the 91A allele showed more evidence of aneuploidy than those from individuals who were homozygous for the common 91T allele. They concluded that individuals with even one copy of the Aurora A 91A allele develop tumors that have on average a higher degree of aneuploidy than those from individuals homozygous for 91T. The oncogenic activity of Aurora kinases is likely to be linked to the generation of such genetic instability. Miyoshi et al. (Miyoshi et al., 2001, Int. J. Cancer 92: 370-373) and Sakakura et al. (Sakakura, et al., 2001, Br. J. Cancer 84: 824-831) report a correlation between amplification of the Aurora A locus and chromosomal instability in mammary and gastric tumors.

Over-expression of Aurora kinases have been reported in a wide range of human tumors. Aurora A expression is elevated in tumor cell lines derived from colon, breast, lung, melanoma, kidney, ovary, pancreas, CNS, gastric tract and leukemia cells (Tatsuka et al., 1998, Cancer Res. 58(21): 4811-6.) Elevated expression of Aurora A has been detected in over 50% of colorectal, ovarian and gastric tumors and in 94% of invasive duct adenocarcinomas of the breast (Colorectal tumors: Bischoff et al., 1998, E MBO J. 17:3052-3065, Takahashi et al., 2000, Jpn. J. Cancer Res. 91:1007-1014, Ovarian tumors: Gritsko et al., 2003, Clin. Cancer Res. 9:1420-1426; gastric tumors: Sakakura, et al., 2001, Br, J. Cancer 84: 824-831; breast tumors: Tanaka et al., 1999, Cancer Res. 59:2041-2044). High levels of Aurora A have also been reported in renal, cervical, neuroblastoma, melanoma, lymphoma, pancreatic and prostate tumor cell lines (Bischofict al., 1998, EMBO J. 17:3052-3065; Zhou et al., 1998, Nature Genetics 20:189-193; Li et al., 2003, Clin. Cancer Res. 9 (3): 991-997). Amplification and over-expression of Aurora A is further observed in human bladder cancers and where it is associated with aneuploidy and aggressive clinical behavior (Sen et al., 2002, J. Natl. Cancer Inst. 94(17): 1320-1329). Isola et al. (Isola et al., 1995, Am. J. Pathology 147: 905-911) further found that amplification of the Aurora A locus correlates with poor prognosis for patients with node-negative breast cancer.

Based on the known function of the Aurora kinases, inhibition of their activity should disrupt mitosis leading to cell cycle arrest. In vivo, an Aurora inhibitor therefore slows tumor growth and induces regression. Stk6 inhibitors may be useful in treating gastric, bladder, breast, lung, CNS, ovarian, kidney, colon, prostate, pancreas, and cervical cancers, melanoma, leukemia, and neuroblastoma.

Syk: Target kinase Syk (i.e., spleen tyrosine kinase) is a 72.1 kDa tyrosine kinase encoded by chromosome 9q22.2 (symbol: SYK). Syk inhibitors may be useful in treating lymphomas, such as mantle cell lymphoma.

TEC: Target kinase TEC (i.e., tec protein tyrosine kinase) is a 73.6 kna non receptor tyrosine kinase encoded by chromosome 4p12 (symbol: TEC). TEC inhibitors may be useful in treating sepsis, septic shock, inflammation, rheumatoid arthritis, Crohn's disease, irritable bowel disease (IBD), and ulcerative colitis.

Tie2: Target kinase Tie2 (i.e., tyrosine kinase, endothelial) is a 125.8 kDa receptor tyrosine kinase encoded by chromosome 9p21 (symbol: TEK). Tie2 inhibitors may be useful in treating cancer, arthritis (e.g. rheumatoid arthritis), and atherosclerosis.

TrkA: Target kinase TrkA (i.e., neurotrophic tyrosine kinase, receptor, type 1) is a 87.5 kDa tyrosine kinase encoded by chromosome 1q21-q22 (symbol: NTRK1). TrkA inhibitors may be useful in treating pain (e.g. chronic pain, neuropathic pain), cancer, arthritis, diabetic retinopathy, macular degeneration and psoriasis.

Yes: Target kinase Yes (i.e., Yamaguchi Sarcoma Oncogene homolog 1) is a 60.8 kDa tyrosine kinase encoded by chromosome 18p11.31-p11.21 (symbol: YES1). The structure of Yes comprises SH3 and SH2 domains followed by a TK domain. The YES oncogene is homologous to the Yamaguchi sarcoma virus gene, and the amino acid sequence of Yes shows a high degree of homology with that of the SRC gene product of Rous sarcoma virus. The Yes kinase is highly expressed in multiple mammalian cell types, including neurons, spermatozoa, platelets, and epithelial cells. The target kinase Yes is amplified and overexpressed in various cancers including esophageal squamous cell carcinoma. Yes inhibitors may be useful in treating cancers including esophageal squamous cell carcinoma.

Zap70: Target kinase Zap70 (i.e., Zeta-chain associated protein kinase, 70 kDa) is a 69.9 kDa tyrosine kinase encoded by chromosome 2q11-13 (symbol: ZAP70). Zap70 was first reported by Chan et al. (Cell 1992, 71: 649-662). The mature protein comprises two SH2 domains and a TK domain.

Zap70 is crucial to the transduction of the T-cell receptor (TCR) signalling pathway, which leads ultimately to cellular differentiation and proliferation. (Weiss & Imboden 1987, Adv. Immunol. 41: 1-38). On stimulation of the T-cell antigen receptor tyrosine phosphorylation takes place in a number of intracellular substrates, mediated by sequential activation of two distinct families of cytoplasmic PTKs, One substrate is the TCR-zeta chain, which can mediate the transduction of extracellular stimuli into cellular effector functions. The Src kinases Lck and Fyn phosphorylate tyrosine residues on the TCR zeta-chain, contained within conserved sequences known as immunoreceptor tyrosine-based activation motifs (ITAMs). The Zap70 protein associates with the phosphorylated ITAMs in the zeta chain of the activated TCR complex (Chan et al., 1991, PNAS 88: 9166-9170. Recruitment of Zap70 to the TCR and its subsequent phosphorylation and activation triggers all downstream signaling events (Irving & Weiss, 1991, Cell 64: 891-902). This interaction is believed to be critical for TCR signaling, since zeta-phosphopeptides that block the interaction of Zap70 with the zeta-chain also inhibit TCR signaling events (Wange et al., 1995, J. Biol. Chem. 270:944-948).

The essential role of Zap70 in T-cell function has been demonstrated in human patients, human T-cell lines and mice. Elder et al. (Elder et al., 1997, J. of Pedriatic Hematology/Oncology 19(6): 546-550) reported studies of human patient suffering from a rare form of severe combined immune deficiency syndrome (SCID). The patient was found to be homozygous for a 13-bp deletion involving nucleotides 1719-1731 of the ZAP70 gene, resulting in premature termination 35 codons downstream and yielding a mutant protein 82 residues shorter than wildtype Zap70. This kind of patients have profound immunodeficiency, lack CD8+ T-cells and have CD4+ T-Cells that are unresponsive to T-cell receptor (TCR)-mediated stimulation. Following TCR activation the CD4+ cells show severe defects in Ca2+ mobilization, tyrosine phosphorylation of down-stream substrates, proliferation and IL-2 production (Elder et al., Pedriatric Research 39: 743-748).

ZAP70 deficient human Jurkat cells also demonstrate the important function of ZAP70 in T-cell receptor signaling. A Jurkat clone (p116) lacking the Zap70 protein was shown to have defects in TCR signaling which was correctable by re-introduction of wild type ZAP70 (Williams et al., 1998, Molecular and Cellular Biology 18 (3): 1388-1399.)

Studies of ZAP70 deficient mice also underline the crucial role of the PTK in T-cell signal transduction. ZAP70 deficient mice had neither CD4 nor CD8 single-positive T cells, but human Zap70 reconstitutes both CD4 and CD8 single-positive populations. Besides the defects in T-cell development the TCR signalling in thymocytes was found to be profoundly impaired, suggesting that Zap70 is a central signalling molecule during thymic selection for CD4 and CD8 lineage, (Negishi et al.,1995, Nature 376: 435-438, Sakaguchi et al. (Sakaguchi et al, 2003, Nature 426: 454-460) reported that the mouse strain SKG, which is derived from a closed breeding colony of BALB/c mice, spontaneously develops chronic arthritis. This autosomal recessive trait was found to be caused by a mutation (W163C) in the second SH2 domain of Zap70. The phenotype showed altered signal transduction from TCRs and a change in the threshold of T-cells to thymic selection, leading to the positive selection of otherwise negatively selected autoimmune T-cells.

The importance of the Zap70 kinase domain function has been demonstrated by Elder et al. (Elder et al., 2001, J. Immunology 166(1): 656-661). In studies of humans patients and mice showed that missense mutations within the highly conserved DLAARN motif within the kinase domain of Zap70 result in SOD. This mutation caused the loss of catalytic function of Zap70, resulting in defective T-cell receptor signaling. The requirement of the catalytic function of Zap70 was further illustrated by Williams et al., who found an inactive Zap70 mutant (Lys369Arg) was unable to restore TCR signaling in a ZAP70 deficient Jurkat cell clone (p116) (Williams et al., 1998, Mol. Cell Biology 18 (3): 1388-1399).

Zap70 further participates in early B-cell differentiation and is a prognostic factor in chronic lymphocytic leukaemia (CLL). The course of CLL is variable. Crespo and coworkers (Crespo et al., 2003, New Eng. J. Med. 348: 1764-1775) found that Zap70 expression by cells in CLL is a simple and reliable surrogate for the identification of immunoglobulin heavy chain variable region mutations. In the aggressive progression of the disease, Zap70 is associated with CLL cells expressing an unmutated configuration of the immunoglobulin heavy chain variable region gene (IgVH) (Carreras et al., 2005, Journal of Pathology 205 (4): 507-513). Whereas in indolent disease, the CLL cells usually express a mutated immunoglobulin heavy chain variable region gene but lack expression of ZAP70. Rassenti et al. (Rassenti et al., 2004, New Eng. J. Med. 351: 893-901) found thet although the presence of an unmutated immunoglobulin heavy chain variable region gene in CLL patients was strongly associated with expression of Zap70, Zap70 was a stronger predictor of the need for treatment in B-cell CLL. T-cell Zap70 overexpression in CLL patients was found to not only correlate with Zap70 levels in CLL cells, but also with clinical stage and disease progression. (Herishanu et al., 2005, Leukemia advance online publication).

The protein tyrosine kinase Zap70 functions in the signaling pathway that plays an essential role in T-cell activation and development. After TCR stimulation, Zap70 is associated with the receptor complex through the interaction of its two SH2 domains with the doubly phosphorylated ITAMs. The association of Zap70 with the TCR ITAMs facilitates its autophosphorylation and the tyrosine phosphorylation of Zap70 mediated by Src family PTKs, e.g. Lck and Fyn. (Iwashima et al., 1994, Science 263:1136-1139). The recruitment of adaptor molecules like Lat and S1p76 to Zap70 in turn couple to more distal signaling pathways including Ras and PLC-gamma (Chu et al., 2003, Journal of Biology, 2 (3): 2-21).

Mutations in the ZAP70 gene are associated with the selective T-cell defect (STD) and severe combined inamunodeficiency (SCID) in human patients. The variety of point mutations, missense mutations, deletions and chromosomal rearrangements are identified in Zap70 all result in the same phenotype (OMIM database with genetic mutations).

Zap70 inhibitors may be useful in treating autoimmune, inflammatory, proliferative and hyperproliferative diseases, immunologically mediated diseases, AIDS, systemic lupus erythematosus, myasthenia gravis, atherosclerosis, rejection of transplanted organs or tissues, allograft rejection including acute and chronic allograft rejection, graft versus host disease, rheumathoid arthritis, psoriasis, systemic sclerosis, atopic dermatitis, eczematous dermatitis, alopecia, and inflammation of the nasal mucus membrane, including all forms of rhinitis.

III. Binding Assays

The methods of the present invention can involve assays that are able to detect the binding of compounds to a target molecule. Such binding is at a statistically significant level, preferably with a confidence level of at least 90%, more preferably at least 95, 97, 98, 99%/u or greater confidence level that the assay signal represents binding to the target molecule, i.e., is distinguished from background. Preferably controls are used to distinguish target binding from non-specific binding. A large variety of binding assays are known for different target types and can be used for this invention.

Binding compounds can also be characterized by their effect on the activity of the target molecule. Compounds of the present invention (i.e., compounds of Formula I, including Formulae Ia-Iz, and all sub-embodiments disclosed herein, or Formula II, including Formulae IIa-IIo, and all sub-embodiments disclosed herein) may be assayed with respect to a particular kinase to assess inhibitory concentration ($IC_{50}$) or excitation concentration ($EC_{50}$) of the compound with respect to that kinase. The $IC_{50}$ (or $EC_{50}$) is defined as the concentration of compound at which 50% of the activity of the target kinase activity being measured is lost (or gained) relative to activity when no compound is present. Activity can be measured using methods known to those of ordinary skill in the art, e.g., by measuring any detectable product or signal produced by occurrence of an enzymatic reaction, or other activity by a protein being measured. Compounds will have an $IC_{50}$ or $EC_{50}$ of less than 10 µM, also less than 1 µM, also less than 100 nM, also less than 10 nM or less than 1 nM.

By "background signal" in reference to a binding assay is meant the signal that is recorded under standard conditions for the particular assay in the absence of a test compound, molecular scaffold, or ligand that binds to the target molecule. Persons of ordinary skill in the art will realize that accepted methods exist and are widely available for determining background signal.

By "standard deviation" is meant the square root of the variance. The variance is a measure of how spread out a distribution is. It is computed as the average squared deviation of each number from its mean. For example, for the numbers 1, 2, and 3, the mean is 2 and the variance is:

$$\sigma^2 = \frac{(1-2)^2 + (2-2)^2 + (3-2)^2}{3} = 0.667.$$

Surface Plasmon Resonance

Binding parameters can be measured using surface plasmon resonance, for example, with a BIAcore® chip (Biacore, Japan) coated with immobilized binding components. Surface plasmon resonance is used to characterize the microscopic association and dissociation constants of reaction between an sFv or other ligand directed against target molecules. Such methods are generally described in the following references which are incorporated herein by reference. Vely F. et al., (2000) BIAcore® analysis to test phosphopeptide-SH2 domain interactions, *Methods in Molecular Biology*. 121:313-21; Liparoto et al., (1999) Biosensor analysis of the interleukin-2 receptor complex, *Journal of Molecular Recognition*. 12:316-21; Lipschultz et al., (2000) Experimental design for analysis of complex kinetics using surface plasmon resonance, *Methods*. 20(3):310-8; Malmqvist, (1999) BIACORE: an affinity biosensor system for characterization of biomolecular interactions, Biochemical Society Transactions 27:335-40; Alfthan, (1998) Surface plasmon resonance biosensors as a tool in antibody engineering, *Biosensors & Bioelectronics*. 13:653-63; Fivash et al., (1998) BIAcore for macromolecular interaction, Current Opinion in Biotechnology. 9:97-101; Price et al.; (1998) Summary report on the ISOBM TD-4 Workshop: analysis of 56 monoclonal antibodies against the MUC1 mucin. *Tumour Biology* 19 Suppl 1:1-20; Malmqvist et al, (1997) Biomolecular interaction analysis: affinity biosensor technologies for functional analysis of proteins, *Current Opinion in Chemical Biology*. 1:378-83; O'Shannessy et al., (1996) Interpretation of deviations from pseudo-first-order kinetic behavior in the characterization of ligand binding by biosensor technology, *Analytical Biochemistry*. 236:275-83; Malmborg et al., (1995) BIAcore as a tool in antibody engineering, *Journal of Immunological Methods*. 183:7-13; Van Regenmortel, (1994) Use of biosensors to characterize recombinant proteins, *Developments in Biological Standardization*. 83:143-51; and O'Shannessy, (1994) Determination of kinetic rate and equilibrium binding constants for macromolecular interactions: a critique of the surface plasmon resonance literature, *Current Opinions in Biotechnology*. 5:65-71.

BIAcore® uses the optical properties of surface plasmon resonance (SPR) to detect alterations in protein concentration bound to a dextran matrix lying on the surface of a gold/glass sensor chip interface, a dextran biosensor matrix. In brief, proteins are covalently bound to the dextran matrix at a known concentration and a ligand for the protein is injected through the dextran matrix. Near infrared light, directed onto the opposite side of the sensor chip surface is reflected and also induces an evanescent wave in the gold film, which in turn, causes an intensity dip in the reflected light at a particular angle known as the resonance angle. If the refractive index of the sensor chip surface is altered (e.g., by ligand binding to the bound protein) a shift occurs in the resonance angle. This angle shift can be measured and is expressed as resonance units (RUs) such that 1000 RUs is equivalent to a change in surface protein concentration of 1 ng/mm$^2$. These changes are displayed with respect to time along the y-axis of a sensorgram, which depicts the association and dissociation of any biological reaction.

High Throughput Screening (HTS) Assays

HTS typically uses automated assays to search through large numbers of compounds for a desired activity. Typically HTS assays are used to find new drugs by screening for chemicals that act on a particular enzyme or molecule. For example, if a chemical inactivates an enzyme it might prove to be effective in preventing a process in a cell which causes a disease. High throughput methods enable researchers to assay thousands of different chemicals against each target molecule very quickly using robotic handling systems and automated analysis of results.

As used herein, "high throughput screening" or "HTS" refers to the rapid in vitro screening of large numbers of compounds (libraries); generally tens to hundreds of thousands of compounds, using robotic screening assays. Ultra high-throughput Screening (uHTS) generally refers to the high-throughput screening accelerated to greater than 100,000 tests per day.

To achieve high-throughput screening, it is advantageous to house samples on a multicontainer carrier or platform. A multicontainer carrier facilitates measuring reactions of a plurality of candidate compounds simultaneously. Multi-well microplates may be used as the carrier. Such multi-well microplates, and methods for their use in numerous assays, are both known in the art and commercially available.

Screening assays may include controls for purposes of calibration and confirmation of proper manipulation of the components of the assay. Blank wells that contain all of the reactants but no member of the chemical library are usually included. As another example, a known inhibitor (or activator) of an enzyme for which modulators are sought, can be incubated with one sample of the assay, and the resulting decrease (or increase) in the enzyme activity used as a comparator or control. It will be appreciated that modulators can also be combined with the enzyme activators or inhibitors to find modulators which inhibit the enzyme activation or repression that is otherwise caused by the presence of the known the enzyme modulator. Similarly, when ligands to a sphingolipid target are sought, known ligands of the target can be present in control/calibration assay wells.

Measuring Enzymatic and Binding Reactions During Screening Assays

Techniques for measuring the progression of enzymatic and binding reactions, e.g., in multicontainer carriers, are known in the art and include, but are not limited to, the following.

Spectrophotometric and spectrofluorometric assays are well known in the art. Examples of such assays include the use of colorimetric assays for the detection of peroxides, as described in Gordon, A. J. and Ford, R, A., (1972) *The Chemist's Companion: A Handbook Of Practical Data, Techniques, And References*, John Wiley and Sons, N.Y., Page 437.

Fluorescence spectrometry may be used to monitor the generation of reaction products. Fluorescence methodology is generally more sensitive than the absorption methodology. The use of fluorescent probes is well known to those skilled in the art. For reviews, see Bashford et al., (1987) *Spectrophotometry and Spectrofluorometry: A Practical Approach*, pp. 91-114, IRL Press Ltd.; and Bell, (1981) *Spectroscopy In Biochemistry, Vol. I, pp.* 155-194, CRC Press.

In spectrofluorometric methods, enzymes are exposed to substrates that change their intrinsic fluorescence when processed by the target enzyme. Typically, the substrate is non-fluorescent and is converted to a fluorophore through one or more reactions. As a non-limiting example, SMase activity can be detected using the Amplex® Red reagent (Molecular Probes, Eugene, Oreg.). In order to measure sphingomyelinase activity using Amplex® Red, the following reactions occur. First, SMase hydrolyzes sphingomyelin to yield ceramide and phosphorylcholine. Second, alkaline phosphatase hydrolyzes phosphorylcholine to yield choline. Third, choline is oxidized by choline oxidase to betaine. Finally, $H_2O_2$, in the presence of horseradish peroxidase, reacts with Amplex® Red to produce the fluorescent product, Resorufin, and the signal therefrom is detected using spectrofluorometry.

Fluorescence polarization (FP) is based on a decrease in the speed of molecular rotation of a fluorophore that occurs upon binding to a larger molecule, such as a receptor protein, allowing for polarized fluorescent emission by the bound ligand. FP is empirically determined by measuring the vertical and horizontal components of fluorophore emission following excitation with plane polarized light. Polarized emission is increased when the molecular rotation of a fluorophore is reduced. A fluorophore produces a larger polarized signal when it is bound to a larger molecule (i.e. a receptor), slowing molecular rotation of the fluorophore. The magnitude of the polarized signal relates quantitatively to the extent of fluorescent ligand binding. Accordingly, polarization of the "bound" signal depends on maintenance of high affinity binding.

FP is a homogeneous technology and reactions are very rapid, taking seconds to minutes to reach equilibrium. The reagents are stable, and large batches may be prepared, resulting in high reproducibility. Because of these properties, FP has proven to be highly automatable, often performed with a single incubation with a single, premixed, tracer-receptor reagent. For a review, see Owiekiet al., (1997). Application of Fluorescence Polarization Assays in High-Throughput Screening, *Genetic Engineering News*, 17:27.

FP is particularly desirable since its readout is independent of the emission intensity (Checovich, W. J., et al., (1995) *Nature* 375:254-256; Dandliker, W. B., et al., (1981) *Methods in Enzymology* 74:3-28) and is thus insensitive to the presence of colored compounds that quench fluorescence emission. FP and FRET (see below) are well-suited for identifying compounds that block interactions between sphingolipid receptors and their ligands. See, for example, Parker et al, (2000) Development of high throughput screening assays using fluorescence polarization: nuclear receptor-ligand-binding and kinaseiphosphatase assays, J Biomol Screen 5:77-88.

Fluorophores derived from sphingolipids that may be used in FP assays are commercially available. For example, Molecular Probes (Eugene, Oreg.) currently sells sphingomyelin and one ceramide flurophores. These are, respectively, N-(4,4-difluoro-5,7-dimethyl-4-bora-3a,4a-diaza-s-indacene-3-pentanoyl)sphingosyl phosphocholine (BODIPY® FL C5-sphingomyelin); N-(4,4-difluoro-5,7-dimethyl-4-bora-3a,4a-diaza-s-indacene-3-dodecanoyl)sphingosyl phosphocholine (BODIPY® FL C12-sphingomyelin): and N-(4,4-difluoro-5,7-dimethyl-4-bora-3a,4a-diaza-s-indacene-3-pentanoyl)sphingosine (BODIPY® FL C5-ceramide). U.S. Pat. No. 4,150,949, (Immunoassay for gentamicin), discloses fluorescein-labelled gentamicins, including fluoresceinthiocarbanyl gentamicin. Additional fluorophores may be prepared using methods well known to the skilled artisan.

Exemplary normal-and-polarized fluorescence readers include the POLARION® fluorescence polarization system (Tecan A G, Hombrechtikon, Switzerland). General multiwell plate readers for other assays are available, such as the VERSAMAX® reader and the SPECTRAMAX® multiwell plate spectrophotometer (both from Molecular Devices).

Fluorescence resonance energy transfer (FRET) is another useful assay for detecting interaction and has been described. See, e.g., Heim et al., (1996) *Curr. Biol.* 6:178-182; Mitra et al., (1996) *Gene* 173:13-17; and Selvin et al., (1995) *Meth. Enzymol.* 246:300-345. FRET detects the transfer of energy between two fluorescent substances in close proximity, having known excitation and emission wavelengths. As an example, a protein can be expressed as a fusion protein with green fluorescent protein (GFP). When two fluorescent proteins are in proximity, such as when a protein specifically interacts with a target molecule, the resonance energy can be transferred from one excited molecule to the other. As a result, the emission spectrum of the sample shifts, which can be measured by a fluorometer, such as a fMAX multiwell fluorometer (Molecular Devices, Sunnyvale Calif.).

Scintillation proximity assay (SPA) is a particularly useful assay for detecting an interaction with the target molecule. SPA is widely used in the pharmaceutical industry and has been described (Hanselman et al., (1997) *J. Lipid Res.* 38:2365-2373; Kahl et al., (1996) *Anal. Biochem*, 243:282-283; Undenfriend et al., (1987) *Anal. Biochem,* 161:494-500). See also U.S. Pat. Nos. 4,626,513 and 4,568.649, and European Patent No. 0,154,734. One commercially available system uses FLASHPLATE® scintillant-coated plates (NEN Life Science Products, Boston, Mass.).

The target molecule can be bound to the scintillator plates by a variety of well known means. Scintillant plates are available that are derivatized to bind to fusion proteins such as GST, His6 or Flag fusion proteins. Where the target molecule is a protein complex or a multimer, one protein or subunit can be attached to the plate first, then the other components of the complex added later under binding conditions, resulting in a bound complex.

In a typical SPA assay, the gene products in the expression pool will have been radiolabeled and added to the wells, and allowed to interact with the solid phase, which is the immobilized target molecule and scintillant coating in the wells. The assay can be measured immediately or allowed to reach equilibrium. Either way, when a radiolabel becomes sufficiently close to the scintillant coating, it produces a signal detectable by a device such as a TOPCOUNT NXT® microplate scintillation counter (Packard BioScience Co., Meriden Conn.). If a radiolabeled expression product binds to the target molecule, the radiolabel remains in proximity to the scintillant long enough to produce a detectable signal.

In contrast, the labeled proteins that do not bind to the target molecule, or bind only briefly, will not remain near the scintillant long enough to produce a signal above background. Any time spent near the scintillant caused by random Brownian motion will also not result in a significant amount of signal. Likewise, residual unincorporated radiolabel used during the expression step may be present, but will not generate significant signal because it will be in solution rather than interacting with the target molecule. These non-binding interactions will therefore cause a certain level of background signal that can be mathematically removed. If too many signals are obtained, salt or other modifiers can be added directly to the assay plates until the desired specificity is obtained (Nichols et al., (1998) *Anal. Biochem.* 257:112-119).

IV. Kinase Activity Assays

A number of different assays for kinase activity can be utilized for assaying for active modulators and/or determining specificity of a modulator for a particular kinase or group or kinases. In addition to the assay mentioned in the Examples below, one of ordinary skill in the art will know of other assays that can be utilized and can modify an assay for a particular application. For example, numerous papers concerning kinases describe assays that can be used.

Additional alternative assays can employ binding determinations. For example, this sort of assay can be formatted either in a fluorescence resonance energy transfer (FRET) format, or using an AlphaScreen (amplified luminescent proximity homogeneous assay) format by varying the donor and acceptor reagents that are attached to streptavidin or the phosphor-specific antibody.

V. Organic Synthetic Techniques

The versatility of computer-based modulator design and identification lies in the diversity of structures screened by the computer programs. The computer programs can search databases that contain very large numbers of molecules and can modify modulators already complexed with the enzyme with a wide variety of chemical functional groups. A consequence of this chemical diversity is that a potential modulator of kinase function may take a chemical form that is not predictable. A wide array of organic synthetic techniques exist in the art to meet the challenge of constructing these potential modulators. Many of these organic synthetic methods are described in detail in standard reference sources utilized by those skilled in the art. One example of suh a reference is March, 1994, *Advanced Organic Chemistry; Reactions, Mechanisms and Structure*, New York, McGraw Hill. Thus, the techniques useful to synthesize a potential modulator of kinase function identified by computer-based methods are readily available to those skilled in the art of organic chemical synthesis.

Regarding the synthetic examples described herein, solvents include polar and non-polar solvents known to those of skill in the art, including polar aprotic and polar protic solvents. Polar solvents include, without limitation, protic solvents such as methanol, ethanol, isopropyl alcohol, t-butanol, n-butanol, acetic acid, formic acid or water, or aprotic solvents such as tetrahydrofuran (THF), acetonitrile, dioxane, methylene chloride, dimethylsulfoxide (DMSO), acetone, N,N-dimethylformamide (DMF), N,N-dimethylacetamide (DMA), ethyl acetate, 1,2-dimethoxyethane, 1,2-dichloroethane, chloroform, 1,2-dichloroethane, or pyridine. Polar solvents include a mixture of water with any of the above, or a mixture of any two or more of the above. A polar solvents include, without limitation, toluene, benzene, chlorobenzene, xylenes and hexanes.

Regarding the synthetic examples described herein, reducing agent includes, without limitation, a reducing agent such as catalytic reducing agents using hydrogen and transition metal catalysts such as palladium, platinum, rhodium, etc. (e.g. Pt/acetic acid/$H_2$); a mixture of trifluoroacetic acid and triethylsilane, borane tetrahydrofuran complex, diborane, borane dimethylsulfide complex, and a combination of sodium borohydride and boron trifluoride; metals such as reduced iron, zinc powder, magnesium etc.; metal hydrogen complex compounds such as alkali metal borohydrides (for example, potassium borohydride, sodium borohydride, lithium borohydride, zinc borohydride, sodium triacetoxyborohydride, etc.), aluminum lithium hydride, etc.; metal hydrides such as sodium hydride, etc.; organic tin compounds (triphenyltin hydride, etc.); and metal salts such as nickel compounds, zinc compounds, tin compounds (for example tin(II) chloride), and samarium iodide/pivalic acid/hexamethylphorphoric triamide.

Regarding the synthetic examples described herein, oxidizing agent includes, without limitation, an oxidizing agent such as Dess-Martin reagent, TEMPO (2,2,6,6-tetramethylpiperidine-N-oxide), DDQ (2,3-Dichloro-5,6-dicyano-1,4-benzoquinone), PDC (pyridinium dichromate), PCC (pyridinium chlorochromate), Pyridine.SO3, Chromium trioxide, p-nitroperbenzoic acid, magnesium monoperoxyphthalate, sodium periodate, potassium periodate, hydrogen peroxide, urea peroxide, alkali metal bromates, cumene hydroperoxide, tert-butyl peroxide, peracids such as performic acid, peracetic acid, pertrifluoroacetic acid, perbenzoic acid, m-chloroperbenzoic acid, o-carboxyperbenzoic acid and the like; sodium metaperiodate, bichromic acid; bichromates such as sodium bichromate, potassium bichromate; permanganic acid; permanganates such as potassium permanganate, sodium permanganate; and lead salts such as lead tetraacetate.

VI. Alternative Compound Forms or Derivatives

Compounds contemplated herein are described with reference to both generic formulae and specific compounds. In addition, invention compounds may exist in a number of different forms or derivatives, all within the scope of the present invention. These include, for example, tautomers, stereoisomers, racemic mixtures, regioisomers, salts, prodrugs (e.g., carboxylic acid esters), solvated forms, different crystal forms or polymorphs, and active metabolites.

(a) Tautomers, Stereoisomers, Regioisomers, and Solvated Forms

It is understood that some compounds may exhibit tautomerism. In such cases, the formulae provided herein expressly depict only one of the possible tautomeric forms. It is therefore to be understood that the formulae provided herein are intended to represent any tautomeric form of the depicted compounds and are not to be limited merely to the specific tautomeric form depicted by the drawings of the formulae.

Likewise, some of the compounds according to the present invention may exist as stereoisomers, i.e. having the same atomic connectivity of covalently bonded atoms yet differing in the spatial orientation of the atoms. For example, compounds may be optical stereoisomers, which contain one or more chiral centers, and therefore, may exist in two or more stereoisomeric forms (e.g. enantiomers or diastereomers). Thus, such compounds may be present as single stereoisomers (i.e., essentially free of other stereoisomers), racemates, and/or mixtures of enantiomers and/or diastereomers. As another example, stereoisomers include geometric isomers, such as cis- or trans-orientation of substituents on adjacent carbons of a double bond. All such single stereoisomers, racemates and mixtures thereof are intended to be within the scope of the present invention. Unless specified to the contrary, all such steroisomeric forms are included within the formulae provided herein.

In some embodiments, a chiral compound of the present invention is in a form that contains at least 80% of a single isomer (60% enantiomeric excess ("e.e.") or diastereomeric excess ("d.c.")), or at least 85% (70% e.e. or d.e.), 90% (80% e.e. or d.e.), 95% (90% e.e. or d.e.), 97.5% (95% e.e. or d.e.), or 99% (98% e.e. or d.e.). As generally understood by those skilled in the art, an optically pure compound having one chiral center is one that consists essentially of one of the two possible enantiomers (i.e., is enantiomerically pure), and an optically pure compound having more than one chiral center is one that is both diastereomerically pure and enantiomerically pure. In some embodiments, the compound is present in optically pure form.

For compounds in which synthesis involves addition of a single group at a double bond, particularly a carbon-carbon double bond, the addition may occur at either of the double bond-linked atoms. For such compounds, the present invention includes both such regioisomers.

Additionally, the formulae are intended to cover solvated as well as unsolvated forms of the identified structures. For example, the indicated structures include both hydrated and non-hydrated forms. Other examples of solvates include the structures in combination with a suitable solvent such as isopropanol, ethanol, methanol, DMSO, ethyl acetate, acetic acid, or ethanolamine.

(b) Prodrugs and Metabolites

In addition to the present formulae and compounds described herein, the invention also includes prodrugs (generally pharmaceutically acceptable prodrugs), active metabolic derivatives (active metabolites), and their pharmaceutically acceptable salts.

Prodrugs are compounds or pharmaceutically acceptable salts thereof which, when metabolized under physiological conditions or when converted by solvolysis, yield the desired active compound. Prodrugs include, without limitation, esters, amides, carbamates, carbonates, ureides, solvates, or hydrates of the active compound. Typically, the prodrug is inactive, or less active than the active compound, but may provide one or more advantageous handling, administration, and/or metabolic properties. For example, some prodrugs are esters of the active compound; during metabolysis, the ester group is cleaved to yield the active drug. Also, some prodrugs are activated enzymatically to yield the active compound, or a compound which, upon further chemical reaction, yields the active compound.

In this context, a common example or a prodrug is an alkyl ester of a carboxylic acid. Relative to compounds of Formula I, further examples include, without limitation, an amide or carbamate derivative at the 1-position nitrogen of the azaindole core.

As described in *The Practice of Medicinal Chemistry*, Ch. 31-32 (Ed. Wermuth, Academic Press, San Diego, Calif., 2001), prodrugs can be conceptually divided into two non-exclusive categories, bioprecursor prodrugs and carrier prodrugs. Generally, bioprecursor prodrugs are compounds that are inactive or have low activity compared to the corresponding active drug compound, that contain one or more protective groups and are converted to an active form by metabolism or solvolysis. Both the active drug form and any released metabolic products should have acceptably low toxicity. Typically, the formation of active drug compound involves a metabolic process or reaction that is one of the follow types:

Oxidative reactions: Oxidative reactions are exemplified without limitation to reactions such as oxidation of alcohol, carbonyl, and acid functionalities, hydroxylation of aliphatic carbons, hydroxylation of alicyclic carbon atoms, oxidation of aromatic carbon atoms, oxidation of carbon-carbon double bonds, oxidation of nitrogen-containing functional groups, oxidation of silicon, phosphorus, arsenic, and sulfur, oxidative N-dealkylation, oxidative O- and S-dealkylation, oxidative deamination, as well as other oxidative reactions.

Reductive reactions: Reductive reactions are exemplified without limitation to reactions such as reduction of carbonyl functionalities, reduction of alcholo functionalities and carbon-carbon double bonds, reduction of nitrogen-containing function groups, and other reduction reactions.

Reactions without change in the oxidation state: Reactions without change in the state of oxidation are exemplified without limitation to reactions such as hydrolysis of esters and ethers, hydrolytic cleavage of carbon-nitrogen single bonds, hydrolytic cleavage of non-aromatic heterocycles, hydration and dehydration at multiple bonds, new atomic linkages resulting from dehydration reactions, hydrolytic dehalogenation, removal of hydrogen halide molecule, and other such reactions.

Carrier prodrugs are drug compounds that contain a transport moiety, e.g., that improves uptake and/or localized delivery to a site(s) of action. Desirably for such a carrier prodrug, the linkage between the drug moiety and the transport moiety is a covalent bond, the prodrug is inactive or less active than the drug compound, the prodrug and any release transport moiety are acceptably non-toxic. For prodrugs where the transport moiety is intended to enhance uptake, typically the release of the transport moiety should be rapid. In other cases, it is desirable to utilize a moiety that provides slow release, e.g., certain polymers or other moieties, such as cyclodextrins. (See, e.g., Cheng et al., U.S. Patent Publ. No. 20040077595, application Ser. No. 10/656,838, incorporated herein by reference). Such carrier prodrugs are often advantageous for orally administered drugs. Carrier prodrugs can, for example, be used to improve one or more of the following properties: increased lipophilicity, increased duration of pharmacological effects, increased site-specificity, decreased toxicity and adverse reactions, and/or improvement in drug formulation (e.g., stability, water solubility, suppression of an undesirable organoleptic or physiochemical property). For example, lipophilicity can be increased by esterification of hydroxyl groups with lipophilic carboxylic acids, or of carboxylic acid groups with alcohols, e.g., aliphatic alcohols. Wermuth, supra.

Prodrugs may proceed from prodrug form to active form in a single step or may have one or more intermediate forms which may themselves have activity or may be inactive.

Metabolites, e.g., active metabolites overlap with prodrugs as described above, e.g., bioprecursor prodrugs. Thus, such metabolites are pharmacologically active compounds or compounds that further metabolize to pharmacologically active compounds that are derivatives resulting from metabolic process in the body of a subject. Of these, active metabolites are such pharmacologically active derivative compounds. For prodrugs, the prodrug compound is generally inactive or of lower activity than the metabolic product. For active metabolites, the parent compound may be either an active compound or may be an inactive prodrug.

Prodrugs and active metabolites may be identified using routine techniques know in the art. See, e.g., Bertolini et al, 1997, *J Med Chem* 40:2011-2016; Shan et al., *J Pharm Sci* 86:756-757; Bagshawe, 1995, *Drug Dev Res* 34:220-230; Wermuth, supra.

(c) Pharmaceutically Acceptable Salts

Compounds can be formulated as or be in the form of pharmaceutically acceptable salts. Contemplated pharmaceutically acceptable salt forms include, without limitation, mono, bis, tris, tetrakis, and so on. Pharmaceutically acceptable salts are non-toxic in the amounts and concentrations at which they are administered. The preparation of such salts can facilitate the pharmacological use by altering the physical characteristics of a compound without preventing it from exerting its physiological effect. Useful alterations in physical properties include lowering the melting point to facilitate transmucosal administration and increasing the solubility to facilitate administering higher concentrations of the drug.

Pharmaceutically acceptable salts include acid addition salts such as those containing sulfate, chloride, hydrochloride, fumarate, maleate, phosphate, sulfamate, acetate, citrate, lactate, tartrate, methanesulfonate, ethanesulfonate, benzenesulfonate, p-toluenesulfonate, cyclohexylsulfamate and quinate. Pharmaceutically acceptable salts can be obtained from acids such as hydrochloric acid, maleic acid, sulfuric acid, phosphoric acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfamic acid, fumaric acid, and quinic acid.

Pharmaceutically acceptable salts also include basic addition salts such as those containing benzathine, chloroprocaine, choline, diethanolamine, ethanolamine, t-butylamine, ethylenediamine, meglumine, procaine, aluminum, calcium, lithium, magnesium, potassium, sodium, ammonium, alkylamine, and zinc, when acidic functional groups, such as carboxylic acid or phenol are present. For example, see *Remington's Pharmaceutical Sciences*, 19$^{th}$ ed., Mack Publishing Co., Easton, Pa., Vol. 2, p. 1457, 1995. Such salts can be prepared using the appropriate corresponding bases.

Pharmaceutically acceptable salts can be prepared by standard techniques. For example, the free-base form of a compound can be dissolved in a suitable solvent, such as an aqueous or aqueous-alcohol solution containing the appropriate acid and then isolated by evaporating the solution. In another example, a salt can be prepared by reacting the free base and acid in an organic solvent.

Thus, for example, if the particular compound is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

Similarly, if the particular compound is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as L-glycine, L-lysine, and L-arginine, ammonia, primary, secondary, and tertiary amines, and cyclic amines, such as hydroxyethylpyrrolidine, piperidine, morpholine or piperazine, and inorganic salts derived from sodium, calcium, potassium, magnesium, manganese, iron, copper, zinc, aluminum and lithium. Further examples of pharmaceutically acceptable salts of compounds of Formulae I-III include, without limitation, the mono-sodium and bis-potassium salts thereof.

The pharmaceutically acceptable salt of the different compounds may be present as a complex. Examples of complexes include 8-chlorotheophylline complex (analogous to, e.g., dimenhydrinate: diphenhydramine 8-chlorotheophylline (1:1) complex; Dramamine) and various cyclodextrin inclusion complexes.

Unless specified to the contrary, specification of a compound herein includes pharmaceutically acceptable salts of such compound.

(d) Polymorphic Forms

In the case of agents that are solids, it is understood by those skilled in the art that the compounds and salts may exist in different crystal or polymorphic forms, all of which are intended to be within the scope of the present invention and specified formulae.

VII. Administration

The methods and compounds will typically be used in therapy for human subjects. However, they may also be used to treat similar or identical indications in other animal subjects. In this context, the terms "subject," "animal subject," and the like refer to human and non-human vertebrates, e.g. mammals, such as non-human primates, sports and commercial animals, e.g., equines, bovines, porcines, ovines, rodents, and pets, e.g., canines and felines.

Suitable dosage forms, in part, depend upon the use or the route of administration, for example, oral, transdermal, transmucosal, inhalant or by injection (parenteral). Such dosage forms should allow the compound to reach target cells. Other factors are well known in the art, and include considerations such as toxicity and dosage forms that retard the compound or composition from exerting its effects. Techniques and formulations generally may be found in The Science and Practice of Pharmacy, 21$^{st}$ edition, Lippincott, Williams and Wilkins, Philadelphia, Pa., 2005 (hereby incorporated by reference herein).

Compounds of the present invention, i.e. Formula I, can be formulated as pharmaceutically acceptable salts.

Carriers or excipients can be used to produce compositions. The carriers or excipients can be chosen to facilitate administration of the compound. Examples of carriers include calcium carbonate, calcium phosphate, various sugars such as lactose, glucose, or sucrose, or types of starch, cellulose derivatives, gelatin, vegetable oils, polyethylene glycols and physiologically compatible solvents. Examples of physiologically compatible solvents include sterile solutions of water for injection (WFI), saline solution, and dextrose.

The compounds can be administered by different routes including intravenous, intraperitoneal, subcutaneous, intramuscular, oral, transmucosal, rectal, transdermal, or inhalant. Oral administration is preferred. For oral administration, for example, the compounds can be formulated into conventional oral dosage forms such as capsules, tablets, and liquid preparations such as syrups, elixirs, and concentrated drops.

For inhalants, compounds of the invention may be formulated as dry powder or a suitable solution, suspension, or aerosol. Powders and solutions may be formulated with suitable additives known in the art. For example, powders may include a suitable powder base such as lactose or starch, and solutions may comprise propylene glycol, sterile water, ethanol, sodium chloride and other additives, such as acid, alkali and buffer salts. Such solutions or suspensions may be administered by inhaling via spray, pump, atomizer, or nebulizer, and the like. The compounds of the invention may also be used in combination with other inhaled therapies, for example corticosteroids such as fluticasone proprionate, beclomethasone dipropionate, triamcinolone acetonide, budesonide, and mometasone furoate; beta agonists such as albuterol, salmeterol, and formoterol; anticholinergic agents such as ipratroprium bromide or tiotropium; vasodilators such as treprostinal and iloprost; enzymes such as DNAase; therapeutic proteins; immunoglobulin antibodies; an oligonucleotide, such as single or double stranded DNA or RNA, siRNA; antibiotics such as tobramycin; muscarinic receptor antagonists; leukotriene antagonists; cytokine antagonists; protease inhibitors; cromolyn sodium; nedocril sodium; and sodium cromoglycate.

Pharmaceutical preparations for oral use can be obtained, for example, by combining the active compounds with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethylcellulose (CMC), and/or polyvinylpyrrolidone (PVP: povidone). If desired, disintegrating agents may be added, such as the cross linked polyvinylpyrrolidone, agar, or alginic acid, or a salt thereof such as sodium alginate.

Dragee cores are provided with suitable coatings. For this purpose, concentrated sugar solutions may be used, which may optionally contain, for example, gum arabic, talc, polyvinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active compound doses.

Pharmaceutical preparations that can be used orally include push-fit capsules made of gelatin ("gelcaps"), as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols (PEGs). In addition, stabilizers may be added.

Alternatively, injection (parenteral administration) may be used, e.g., intramuscular, intravenous, intraperitoneal, and/or subcutaneous. For injection, the compounds of the invention are formulated in sterile liquid solutions, preferably in physiologically compatible buffers or solutions, such as saline solution, Hank's solution, or Ringer's solution. In addition, the compounds may be formulated in solid form and redissolved or suspended immediately prior to use. Lyophilized forms can also be produced.

Administration can also be by transmucosal, topical, or transdermal means. For transmucosal, topical or transdermal administration, penetrants appropriate to the barrier to be permeated are used in the formulation. Such penetrants are generally known in the art, and include, for example, for transmucosal administration, bile salts and fusidic acid derivatives. In addition, detergents may be used to facilitate permeation. Transmucosal administration, for example, may be through nasal sprays or suppositories (rectal or vaginal). The topical compositions of this invention are formulated preferably as oils, creams, lotions, ointments and the like by choice of appropriate carriers known in the art. Suitable carriers include vegetable or mineral oils, white petrolatum (white soft paraffin), branched chain fats or oils, animal fats and high molecular weight alcohol (greater than $C_{12}$). The preferred carriers are those in which the active ingredient is soluble. Emulsifiers, stabilizers, humectants and antioxidants may also be included as well as agents imparting color or fragrance, if desired. Creams for topical application are preferably formulated from a mixture of mineral oil, self-emulsifying beeswax and water in which mixture the active ingredient, dissolved in a small amount solvent (e.g., an oil), is admixed. Additionally, administration by transdermal means may comprise a transdermal patch or dressing such as a bandage impregnated with an active ingredient and optionally one or more carriers or diluents known in the art. To be administered in the form of a transdermal delivery system, the dosage administration will, of course, be continuous rather than intermittent throughout the dosage regimen.

The amounts of various compounds to be administered can be determined by standard procedures taking into account factors such as the compound $IC_{50}$, the biological half-life of the compound, the age, size, and weight of the subject, and the disorder associated with the subject. The importance of these and other factors are well known to those of ordinary skill in the art. Generally, a dose will be between about 0.01 and 50 mg/kg, preferably 0.1 and 20 mg/kg of the subject being treated. Multiple doses may be used.

The compounds of the invention may also be used in combination with other therapies for treating the same disease. Such combination use includes administration of the compounds and one or more other therapeutics at different times, or co-administration of the compound and one or more other therapies. In some embodiments, dosage may be modified for one or more of the compounds of the invention or other therapeutics used in combination, e.g., reduction in the amount dosed relative to a compound or therapy used alone, by methods well known to those of ordinary skill in the art.

It is understood that use in combination includes use with other therapies, drugs, medical procedures etc., where the other therapy or procedure may be administered at different times (e.g. within a short time, such as within hours (e.g. 1, 2, 3, 4-24 hours), or within a longer time (e.g. 1-2 days, 2-4 days, 4-7 days, 1-4 weeks)) than a compound of the present invention, or at the same time as a compound of the invention. Use in combination also includes use with a therapy or medical procedure that is administered once or infrequently, such as surgery, along with a compound of the invention administered within a short time or longer time before or after the other therapy or procedure. In some embodiments, the present invention provides for delivery of compounds of the invention and one or more other drug therapeutics delivered by a different route of administration or by the same route of administration. The use in combination for any route of administration includes delivery of compounds of the invention and one or more other drug therapeutics delivered by the same route of administration together in any formulation, including formulations where the two compounds are chemically linked in such a way that they maintain their therapeutic activity when administered. In one aspect, the other drug therapy may be co-administered with one or more compounds of the invention. Use in combination by co-administration includes administration of co-formulations or formulations of chemically joined compounds, or administration of two or more compounds in separate formulations within a short time of each other (e.g. within an hour, 2 hours, 3 hours, up to 24 hours), administered by the same or different routes. Co-administration of separate formulations includes co-administration by delivery via one device, for example the same inhalant device, the same syringe, etc., or administration from separate devices within a short time of each other, Co-formulations of compounds of the invention and one or more additional drug therapies delivered by the same route includes preparation of the materials together such that they can be administered by one device, including the separate compounds combined in one formulation, or compounds that are modified such that they are chemically joined, yet still maintain their biological activity. Such chemically joined compounds may have a linkage that is substantially maintained in vivo, or the linkage may break down in vivo, separating the two active components.

EXAMPLES

Examples related to the present invention are described below. In most cases, alternative techniques can be used. The examples are intended to be illustrative and are not limiting or restrictive to the scope of the invention. In some examples, the mass spectrometry result indicated for a compound may have more than one value due to the isotope distribution of an atom in the molecule, such as a compound having a bromo or chloro substituent.

Example 1

Synthesis of propane-1-sulfonic acid [3-(5-bromo-1H-pyrrolo[2,3-b]pyridine-3-carbonyl)-2,4-difluoro-phenyl]-amide P-0773 and related compounds Compound P-0773 was synthesized in five steps from 2,4-difluoro-phenylamine 42 as shown in Scheme 13.

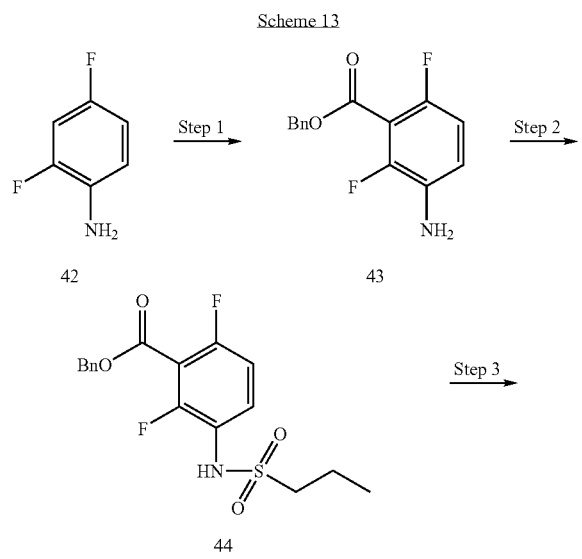

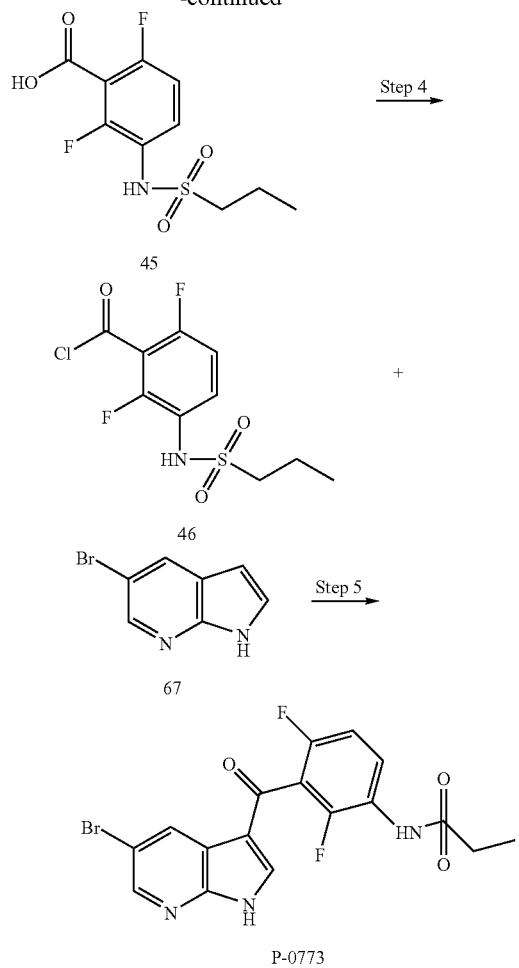

Step 1—Preparation of 3-amino-2,6-difluoro-benzoic acid benzyl ester (43)

To 2,4-difluoro-phenylamine (42, 5.11 ml. 50.7 mmol) in tetrahydrofuran (250 mL), cooled with dry ice/acetone bath under an atmosphere of nitrogen, was added n-butyllithium (1.60 M in hexane, 34.0 mL, 54.4 mmol) slowly. After 30 minutes, 1,2-Bis-(chloro-dimethyl-silanyl)-ethane (11.5 g, 53.4 mmol) dissolved in tetrahydrofuran (40.0 mL) was added to the reaction slowly. After 1 hour, n-butyllithium (1.60 M in hexane, 31.9 mL, 51.0 mmol) was added slowly to the reaction. The reaction was stirred at -78 QC for 30 minutes and then allowed to warm to room temperature over 40 minutes. The reaction was cooled to −78° C., followed by addition of n-butyllithium (1.60 M in hexane, 35.1 mL, 56.2 mmol) slowly. After 70 minutes, benzyl chloroformate (7.97 mL, 55.8 mmol) was added to the reaction. The reaction mixture was stirred at −78° C. overnight followed by addition of 2 N HCl (120 mL). The reaction was allowed to warm to room temperature for 2 hours. The organic layer was separated. The aqueous layer was basified with potassium carbonate and extracted with ethyl acetate. The organic layers were combined and washed with brine, dried over anhydrous sodium sulfate, filtrated and concentrated. The desired compound was isolated by silica gel column chromatography (ethyl acetate/hexane 20%) to give a colorless oil (43, 10.6 g, 79.7%). MS(ESI) [M+H$^+$]$^+$=264.1.

Step 2—Preparation of 2,6-difluoro-3-(propane-1-sulfonylamino)-benzoic acid benzyl ester (44)

To 3-amino-2,6-difluoro-benzoic acid benzyl ester (43, 6.00 g, 22.8 mmol) in methylene chloride (150 mL) was added pyridine (2.76 mL, 34.2 mmol) and propane-1-sulfonyl chloride (3.80 mL, 33.8 mmol). The reaction was stirred at room temperature overnight. Then the reaction was poured into water, and extracted with ethyl acetate. The organic layer was washed with brine, dried over anhydrous sodium sulfate, filtrated and concentrated. The desired compound was isolated with silica gel column chromatography to give a colorless oil (44, 7.0 g, 83.1%). MS(ESI) [M+H$^+$]$^+$=370.1.

Step 3 Preparation of 2,6-difluoro-3-(propane-1-sulfonylamino)-benzoic acid (45)

To 2,6-difluoro-3-(propane-1-sulfonylamino)-benzoic acid benzyl ester (44, 2.0 g, mmol) in methanol (30 mL) was added 20% palladium hydroxide on carbon (100 mg). The reaction was stirred under hydrogen at 1 atm for 15 minutes. The reaction was filtrated and concentrated to give white solid 45 that was used in the next step.

Step 4—Preparation of 2,6-difluoro-3-(propane-T-sulfonylamino)-benzoyl chloride (46)

To 2,6-difluoro-3-(propane-1-sulfonylamino)-benzoic acid (45, 1.50 g, 5.4 mmol) was added toluene (7.0 mL) and thionyl chloride (15.0 mL, 0.21 mmol). The reaction was heated to reflux for 3 hours. The reaction was concentrated to give crude compound that was used in the next step.

Step 5—Preparation of propane-1-sulfonic acid [3-(5-bromo-1H-pyrrolo[2,3-b]pyridin-3-carbonyl)-2,4-difluoro-phenyl]-amide (P-0773)

To aluminum trichloride (8.89 g, 66.7 mmol) was added methylene chloride (150 mL) under an atmosphere of nitrogen below 5° C. Into this, 5-bromo-7-azaindole (67, 1.64 g, 8.34 mmol) in methylene chloride (20 mL) was added. The reaction was stirred for 60.0 minutes and 2,6-difluoro-3-(propane-1-sulfonylamino)-benzoyl chloride (46, 3.50 g. 11.8 mmol) in methylene chloride (20 mL) was added. The reaction was stirred for 6 hours and warmed to room temperature overnight. The reaction mixture was poured into water and extracted with ethyl acetate. The organic layer was dried over anhydrous sodium sulfate, filtrated and concentrated. The desired compound was isolated by silica gel column chromatography (methylene chloride/methanol 5%) to give a white solid (P-0773, 1.2 g, 31.4%). MS(ESI) [M+H$^+$]$^+$=460.0, 462.0.

N-[3-(5-Bromo-1H-pyrrolo[2,3-b]pyridine-3-carbonyl)-4-chloro-2-fluoro-phenyl]-methanesulfonamide P-0868

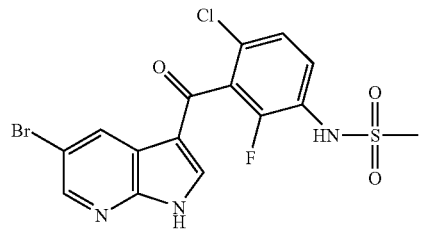 [SMILES: CS(=O)(=O)Nc1ccc(F)c(C(=O)c2c[nH]c3ncc(Br)cc23)c1F]

was prepared following the protocol of Scheme 13, substituting propane-1-sulfonyl chloride with methanesulfonyl chloride in Step 2 and 2,4-difluoro-phenylamine with 4-chloro-2-fluoro-phenylamine in Step 1. MS (ESI) [M−H$^+$]$^+$=443.9 445.9.

N-[3-(5-Bromo-1H-pyrrolo[2,3-b]pyridine-3-carbonyl)-2,4-difluoro-phenyl]-methanesulfonamide P-0162

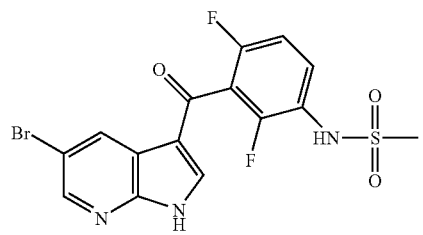

was prepared following the protocol of Scheme 13, substituting propane-1-sulfonyl chloride with methanesulfonyl chloride in Step 2. This was isolated and reacted further (50 mg, 0.10 mmol) in methanol (20 mL) by adding 20% palladium hydroxide on carbon (53 mg). The reaction was stirred under hydrogen at 40 psi for 12 hours. The reaction mixture was filtered and concentrated to give product methanesulfonic acid [2,4-difluoro-3-1H-pyrrolo-[2,3-b]pyridine-3-carbonyl)-phenyl]-amide P-0811 (40 mg, 95%).

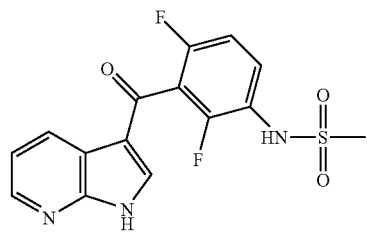 [SMILES: CS(=O)(=O)Nc1ccc(F)c(C(=O)c2c[nH]c3ncccc23)c1F]

MS(ESI) [M+H$^+$]$^+$=352.3.

N-[3-(5-Bromo-1H-pyrrolo[2,3-b]pyridine-3-carbonyl)-2,4-difluoro-phenyl]-benzenesulfonamide P-0798 and N-[3-(5-bromo-1H-pyrrolo[2,3-b]pyridine-3-carbonyl)-2,4-difluoro-phenyl]-3-fluoro-benzenesulfonamide

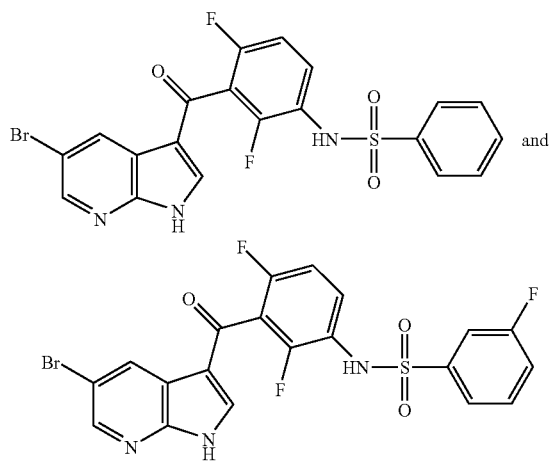

P-0798 and were prepared following the protocol of Scheme 13, substituting propane-1-sulfonyl chloride with benzenesulfonyl chloride and 3-fluoro-benzenesulfonyl chloride, respectively, in Step 2. P-0798 MS(ESI) [M−H$^+$]$^−$=491.9.

Propane-1-sulfonic acid [3-(5-bromo-1H-pyrrolo[2,3-b]pyridine-3-carbonyl)-4-chloro-2-fluoro-phenyl]-amide P-0805

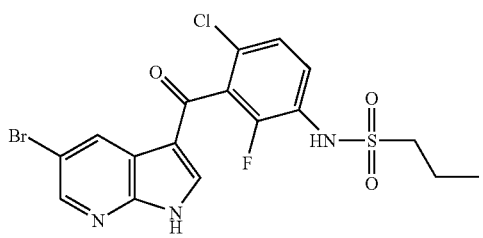 [SMILES: CCCS(=O)(=O)Nc1ccc(Cl)c(C(=O)c2c[nH]c3ncc(Br)cc23)c1F]

was prepared following the protocol of Scheme 13, substituting 2,4-difluoro-phenylamine with 4-chloro-2-fluoro-phenylamine in Step 1. MS(ESI) [M−H$^+$]$^−$=471.9, 473.9.

Propane-1-sulfonic acid [2,4-difluoro-3-(1H-pyrrolo[2,3-b]pyridine-3-carbonyl)-phenyl]-amide P-0007

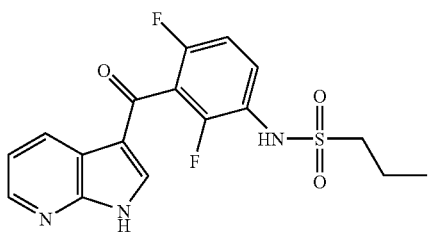 [SMILES: CCCS(=O)(=O)Nc1ccc(F)c(C(=O)c2c[nH]c3ncccc23)c1F]

was prepared following the protocol of Scheme 13, substituting 5-bromo-7-azaindole with 7-azaindole in Step 5. MS(ESI) [M+H$^+$]$^+$=380.1.

Propane-1-sulfonic acid [2,4-difluoro-3-(5-methoxy-1H-pyrrolo[2,3-b]pyridine-3-carbonyl)-phenyl]-amide P-0806

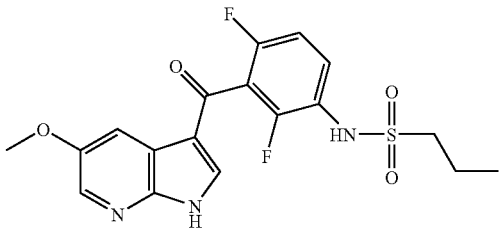 [SMILES: CCCS(=O)(=O)Nc1ccc(F)c(C(=O)c2c[nH]c3ncc(OC)cc23)c1F]

was prepared following the protocol of Scheme 13, substituting 5-bromo-7-azaindole with 5-methoxy-7-azaindole 104 (prepared as described in Example 16) in Step 5. MS(ESI) [M−H$^+$]$^−$=410.1.

(5-Bromo-1H-pyrrolo[2,3-b]pyridin-3-yl)-(2-fluoro-3-methoxy-phenyl)-methanone P-0265

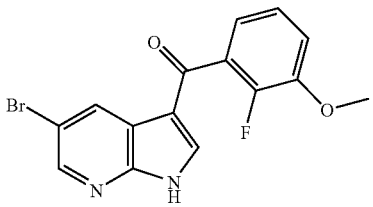 [SMILES: COc1cccc(C(=O)c2c[nH]c3ncc(Br)cc23)c1F]

was prepared using the protocol of steps 4 and 5 of Scheme 13, substituting 2,6-difluoro-3-(propane-1-sulfonylamino)-benzoic acid with 2-fluoro-3-methoxy-benzoic acid in Step 4. MS (ESI) [M−H$^+$]$^−$=347, 349.

N-[3-(5-Bromo-1H-pyrrolo[2,3-b]pyridine-3-carbonyl)-4-fluoro-phenyl]-methanesulfonamide P-0170

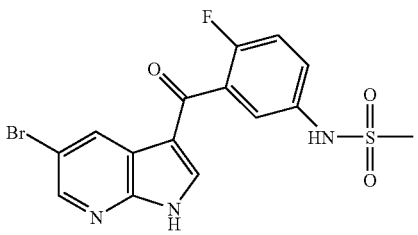 [SMILES: CS(=O)(=O)Nc1ccc(F)c(C(=O)c2c[nH]c3ncc(Br)cc23)c1]

was prepared using the protocol of steps 2, 4, and 5 of Scheme 13, substituting 3-amino-2,6-difluoro-benzoic acid benzyl ester with 5-amino-2-fluoro-benzoic acid and propane-1-sulfonyl chloride with methanesulfonyl chloride in Step 2, to provide the acid that is carried through in Step 4. MS (ESI) [M−H$^+$]$^−$=410.0, 412.0.

N-[3-(5-Bromo-1H-pyrrolo[2,3-b]pyridine-3-carbonyl)-2-methyl-phenyl]-methanesulfonamide P-0180

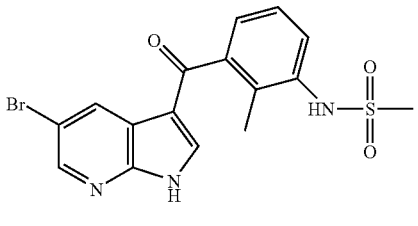 [SMILES: Cc1c(NS(C)(=O)=O)cccc1C(=O)c1c[nH]c2ncc(Br)cc12]

was prepared using the protocol of steps 2, 4, and 5 of Scheme 13, substituting 3-amino-2,6-difluoro-benzoic acid benzyl ester with 3-amino-2-methyl-benzoic acid and propane-1-sulfonyl chloride with methanesulfonyl chloride in Step 2, to provide the acid that is carried through in Step 4. MS (ESI) [M−H+]−=405.9, 407.9.

(5-Bromo-1H-pyrrolo[2,3-b]pyridin-3-yl)-(3-chloro-2-fluoro-phenyl)-methanone P-0299

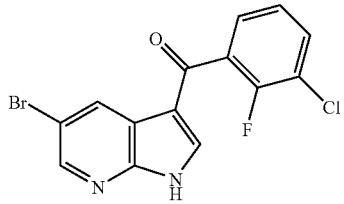 [SMILES: O=C(c1cccc(Cl)c1F)c1c[nH]c2ncc(Br)cc12]

was prepared using the protocol of Step 5 of Scheme 13, substituting 2,6-difluoro-3-(propane-1-sulfonylamino)-benzoyl chloride with 3-chloro-2-fluoro-benzoyl chloride. MS (ESI) [M−H+]−=350.9, 352.9.

Example 2

Synthesis of Propane-1-sulfonic acid [3-(5-bromo-1H-pyrrolo[2,3-b]pyridine-3-carbonyl)-2-fluoro-phenyl]-amide P-0955 and related compounds Compound P-0955 was synthesized in six steps from 4-chloro-2-fluoro-phenylamine 47 as shown in Scheme 14.

Scheme 14

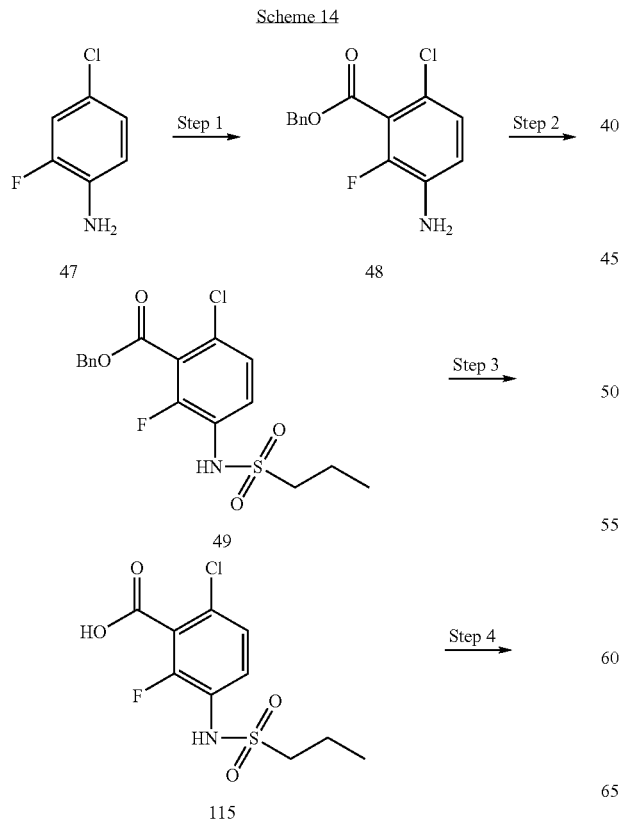

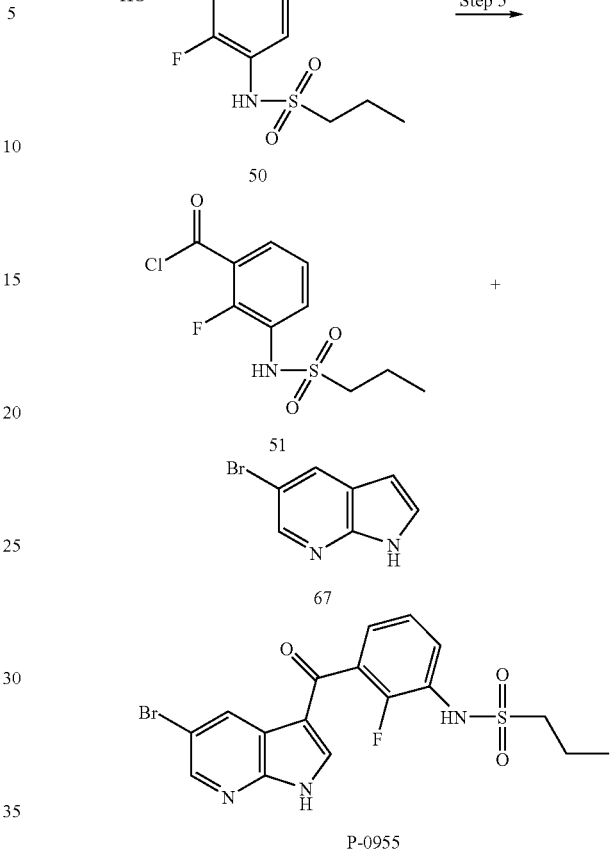

Step 1—Preparation of 3-Amino-6-chloro-2-fluoro-benzoic acid benzyl ester (48)

To 4-chloro-2-fluoro-phenylamine (47, 6.30 mL, 57 0 mmol) in tetrahydrofuran (300 mL), cooled with dry ice/acetone bath under an atmosphere of nitrogen, was added n-butyllithium (2.500 M in hexane, 24.4 mL) slowly. After 20 minutes, 1,2-Bis-(chloro-dimethyl-silanyl)-ethane (12.9 g, 60.0 mmol) dissolved in tetrahydrofuran (40.0 mL) was added to the reaction slowly. After 1 hour, n-butyllithium (2.50 M in hexane, 25.0 mL) was added slowly to the reaction. The reaction was stirred at −78° C. for 20 minutes and allowed to warm to room temperature over 60 minutes. The reaction was cooled to −78° C., followed by addition of n-butyllithium (2.50 M in hexane, 26.0 mL) slowly. After 80 minutes, benzyl chloroformate (10.0 mL, 70.0 mmol) was added to the reaction. The reaction mixture was stirred at −78° C. overnight followed by addition of water (80 mL) and concentrated hydrochloric acid (25 mL). The reaction was allowed to warm to room temperature for 2 hours. The organic layer was separated and the aqueous layer was basified with potassium carbonate and extracted with ethyl acetate. The organic layers were combined and washed with brine, dried over anhydrous sodium sulfate, filtrated and concentrated. The desired compound was isolated by silica gel column chromatography (ethyl acetate/hexane 20%) to give a colorless oil (48, 12.5 g, 78.3%), MS(ESI) [M+H+]+=280.0.

Step 2—Preparation of 6-chloro-2-fluoro-3-(propane-1-sulfonylamino)-benzoic acid benzyl ester (49)

To 3-amino-6-chloro-2-fluoro-benzoic acid benzyl ester (48, 1.20 g, 4.3 mmol) in methylene chloride (28 mL) was added pyridine (0.52 ml., 6.4 mmol) and propane-1-sulfonyl chloride (0.685 g, 4.8 mmol). The reaction was stirred at room temperature overnight. The reaction was poured into water and extracted with ethyl acetate. The organic layer was washed with brine, dried over anhydrous sodium sulfate, filtrated and concentrated. The desired compound was isolated with silica gel column chromatography to give a colorless oil (49, 960 mg, 58.0%). MS(ESI) $[M-H^+]^-=384.1$.

Step 3—Preparation of 6-chloro-2-fluoro-3-(propane-1-sulfonylamino)-benzoic acid (115)

To 6-chloro-2-fluoro-3-(propane-1-sulfonylamino)-benzoic acid benzyl ester (49, 6.00 g, 15.6 mmol) in tetrahydrofuran (100 mL) was added 1.0 M aqueous potassium hydroxide (100 mL). The reaction was heated to reflux overnight. The reaction was poured into water, acidified to pH 2 with 1 N hydrochloric acid and extracted with ethyl acetate. The organic portion was dried over anhydrous sodium sulfate, filtrated and concentrated to give a white solid 115 (3.95 g, 85.8%).

Step 4—Preparation of 2-fluoro-3-(propane-1-sulfonylamino)-benzoic acid (50)

To 6-chloro-2-fluoro-3-(propane-1-sulfonylamino)-benzoic acid (115, 0.69 g, 2.3 mmol) in methanol (10 mL) was added 20% palladium hydroxide on carbon (200 mg). The reaction was stirred under hydrogen at 50 psi for 2 hours. The reaction was filtrated and concentrated to give white solid 50 that was used in the next step. MS(ESI) $[M-H^+]^-=260.1$.

Step 5—Preparation of 2-fluoro-3-(propane-1-sulfonylamino)-benzoyl chloride (51)

To 2-fluoro -3-(propane-1-sulfonylamino)-benzoic acid (50, 1.17 g, 4.5 mmol) was added thionyl chloride (10.0 mL). The reaction was heated to reflux for 3 hours. The reaction was concentrated to give crude compound 51 that was used in the next step.

Step 6—Preparation of Propane-1-sulfonic acid [3-(5-bromo-1H-pyrrolo[2,3-b]pyridine-3-carbonyl)-2-fluoro-phenyl]-amide (P-0955)

Aluminum trichloride (2.52 g, 18.9 mmol) and methylene chloride (60.0 mL) were combined under an atmosphere of nitrogen. Into the reaction mixture, was added 5-bromo-7-azaindole (67, 630.0 mg, 3.2 mmol) in methylene dichloride (20.0 mL). The reaction was stirred at room temperature for 70 minutes, then 2-fluoro-3-(propane-1-sulfonylamino)-benzoyl chloride (51, 0.749 g, 2.68 mmol) in methylene chloride (20 mL) was added. The reaction was stirred at room temperature for 2 hours. The reaction was poured into water and extracted with ethyl acetate. The organic layer was dried over anhydrous sodium sulfate and filtered. The filtrate was concentrated and purified by silica gel column chromatography eluting with 30% ethyl acetate in hexane to give compound P-0955 (65 mg, 5.5%). MS(ESI) $[M+H^+]^+=440.2, 442.2$.

Using the protocol of Scheme 14, substituting 5-bromo-azaindole with either 5-chloro-7-azaindole (80, prepared as described in Example 9), 5-fluoro-7-azaindole (81, prepared as described in Example 9) or 7-azaindole in Step 6, propane-1-sulfonic acid [3-(5-chloro-1H-pyrrolo[2,3-b]pyridine-3-carbonyl)-2-fluoro-phenyl]-amide P-1013 (MS(ESI) $[M-H^+]^-=394.1$), propane-1-sulfonic acid [2-fluoro-3-(5-fluoro-1H-pyrrolo[2,3-b]pyridine-3-carbonyl)-phenyl]-amide P-1028 (MS(ESI) $[M-H^+]^-=378.1$), and propane-1-sulfonic acid [2-fluoro-3-(1H-1-pyrrolo[2,3-b]pyridine-3-carbonyl)-phenyl]-amide P-1056 (MS(ESI) $[M+H^+]^+=362.2$) were prepared, respectively:

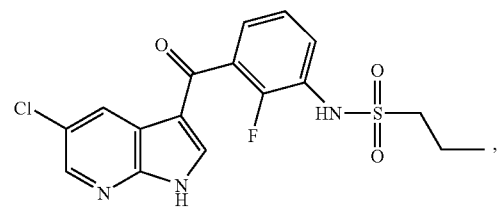

P-1013

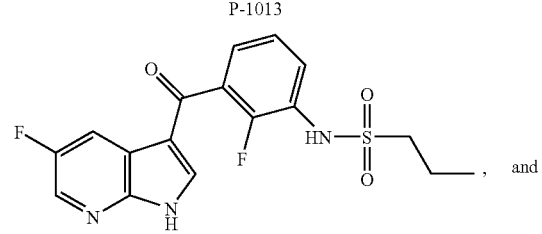

P-1028

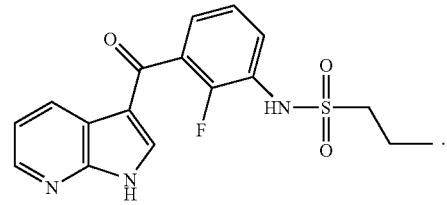

P-1056

Example 3

Propane-1-sulfonic acid [2,4-difluoro-3-(5-pyridin-3-yl-1H-pyrrolo[2,3-b]pyridine-3-carbonyl)-phenyl]-amide P-0088 and related compounds Compound P-0088 was synthesized in one step from propane-1-sulfonic acid [3-(5-bromo-1H-pyrrolo[2,3-b]pyridine-3-carbonyl)-2,4-difluoro-phenyl]-amide P-0773 by Suzuki coupling ((Muyaura and Suzuki, *Chem. Rev.* 1995, 95:2457) as shown in Scheme 15.

Scheme 15

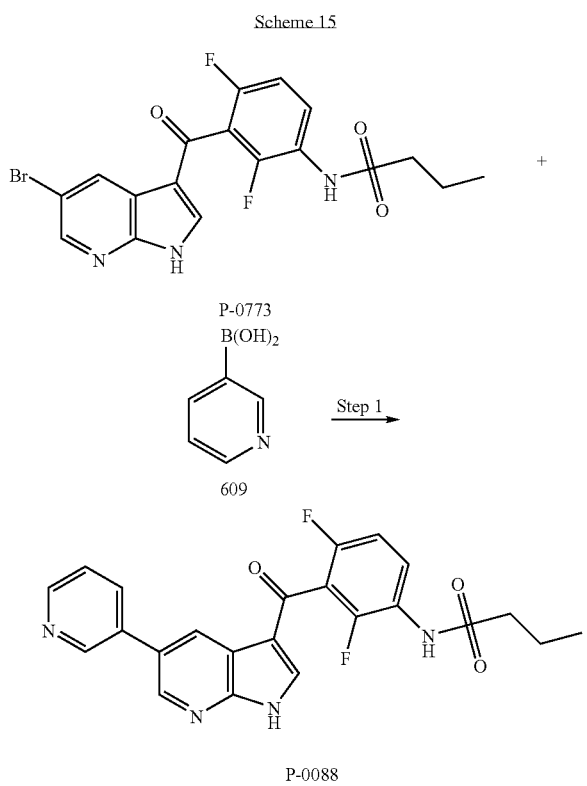

Step 1—Preparation of propane-1-sulfonic acid [2,4-difluoro-3-(5-pyridin-3-yl-1H-pyrrolo[2,3-b]pyridine-3-carbonyl)-phenyl]-amide (P-0088)

To propane-1-sulfonic acid [3-(5-bromo-1H-pyrrolo[2,3-b]pyridine-3-carbonyl)-2,4-difluoro-phenyl]-amide (P-0773, prepared as described in Example 1, 65.0 mg, 0.14 mmol) in acetonitrile (4.0 mL) was added pyridine-3-boronic acid (609, 25.0 mg, 0.20 mmol), tetrakis (triphenylphosphine) palladium(0) (11 mg, 1.0 mmol) and aqueous potassium carbonate (1.0 M, 2.0 mL). The reaction was heated to 160° C. for 10 minutes in a CEM Discover microwave instrument. The reaction was poured into water, and extracted with ethyl acetate. The organic layer was washed with brine, dried over anhydrous sodium sulfate, filtrated and concentrated. The desired compound was isolated by silica gel column chromatography (methylene chloride/methanol 5%) to give a white solid (P-0088, 30 mg, 46.9%). MS(ESI) [M+H$^+$]$^+$=457.2.

Additional compounds were prepared following the protocol of Scheme 15, optionally replacing propane-1-sulfonic acid [3-(5-bromo-1H-pyrrolo[2,3-b]pyridine-3-carbonyl)-2,4-difluoro-phenyl]-amide P-0773 with an appropriate 5-bromo azaindole and/or pyridine-3-boronic acid 609 with an appropriate boronic acid or boronic acid ester. The 5-bromo azaindole used was synthesized as described in either Example 1, 2, 5, 10, or 73. The following compounds were made following this procedure:

N-[2-Methyl-3-(5-phenyl-1H-pyrrolo[2,3-b]pyridine-3-carbonyl)-phenyl]-methanesulfonamide (P-0082), N-[2-Methyl-3-(5-pyridin-3-yl-1H-pyrrolo[2,3-b]pyridine-3-carbonyl)-phenyl]-methanesulfonamide (P-0121), N-[4-Fluoro-3-(5-pyridin-3-yl-1H-pyrrolo[2,3-b]pyridine-3-carbonyl)-phenyl]-methanesulfonamide (P-0079), N-[4-Fluoro-3-(5-phenyl-1H-pyrrolo[2,3-b]pyridine-3-carbonyl)-phenyl]-methanesulfonamide (P-0308), N-{4-Fluoro-3-[5-(3-methanesulfonylamino-phenyl)-1H-pyrrolo[2,3-b]pyridine-3-carbonyl]-phenyl}-methanesulfonamide (P-0156), N-{4-Fluoro-3-[5-(3-methanesulfonyl-phenyl)-1H-pyrrolo[2,3-b]pyridine-3-carbonyl]-phenyl}-methanesulfonamide (P-0297), 3-[3-(2-Fluoro-5-methanesulfonylamino-benzoyl)-1H-pyrrolo[2,3-b]pyridin-5-yl]-benzamide (P-0228), 3-[3-(2-Fluoro-5-hydroxy-benzoyl)-1H-pyrrolo[2,3-b]pyridin-5-yl]-benzamide (P-0037), (2-Fluoro-5-hydroxy-phenyl)-[5-(3-methanesulfonyl-phenyl)-1H-pyrrolo[2,3-b]pyridin-3-yl]-methanone (P-0008), N-{3-[3-(2-Fluoro-5-hydroxy-benzoyl)-1H-pyrrolo[2,3-b]pyridin-5-yl]-phenyl}-methanesulfonamide (P-0716), N-[2,4-Difluoro-3-(5-pyridin-3-yl-1H-pyrrolo[2,3-b]pyridine-3-carbonyl)-phenyl]-methanesulfonamide (P-0700), N-{4-Chloro-2-fluoro-3-[5-(3-methanesulfonyl-phenyl)-1H-pyrrolo[2,3-b]pyridine-3-carbonyl]-phenyl}-methanesulfonamide (P-0841), N-[4-Chloro-2-fluoro-3-(5-pyridin-3-yl-1H-pyrrolo[2,3-b]pyridine-3-carbonyl)-phenyl]-methanesulfonamide (P-0734), N-{4-Chloro-2-fluoro-3-[5-(3-methanesulfonylamino-phenyl)-1H-pyrrolo[2,3-b]pyridine-3-carbonyl]-phenyl}-methanesulfonamide (P-0745), N-{2,4-Difluoro-3-[5-(3-methanesulfonylamino-phenyl)-1H-pyrrolo[2,3-b]pyridine-3-carbonyl]-phenyl}-methanesulfonamide (P-0746), 3-[3-(2,6-Difluoro-3-methanesulfonylamino-benzoyl)-1H-pyrrolo[2,3-b]pyridin-5-yl]-benzamide (P-0721), N-[2,4-Difluoro-3-(5-phenyl-1H-pyrrolo[2,3-b]pyridine-3-carbonyl)-phenyl]-methanesulfonamide (P-0184), N-[2,4-Difluoro-3-(5-pyridin-3-yl-1H-pyrrolo[2,3-b]pyridine-3-carbonyl)-phenyl]-benzenesulfonamide (P-0685), Propane-1-sulfonic acid [4-chloro-2-fluoro-3-(5-pyridin-3-yl-1H-pyrrolo[2,3-b]pyridine-3-carbonyl)-phenyl]-amide (P-0753), Propane-1-sulfonic acid [2,4-difluoro-3-(5-phenyl-1H-pyrrolo[2,3-b]pyridine-3-carbonyl)-phenyl]-amide (P-0636), Propane-1-sulfonic acid [4-chloro-2-fluoro-3-(5-phenyl-1H-pyrrolo[2,3-b]pyridine-3-carbonyl)-phenyl]-amide (P-0776)

Propane-1-sulfonic acid {3-[5-(4-chloro-phenyl)-1H-pyrrolo[2,3-b]pyridine-3-carbonyl]-2,4-difluoro-phenyl}-amide (P-0956), Propane-1-sulfonic acid {3-[5-(4-dimethylamino-phenyl)-1H-pyrrolo[2,3-b]pyridine-3-carbonyl]-2,4-difluoro-phenyl}-amide (P-0889), Propane-1-sulfonic acid {2,4-difluoro-3-[5-(4-methoxy-phenyl)-1H-pyrrolo[2,3-b]pyridine-3-carbonyl]-phenyl}-amide (P-0877), Propane-1-sulfonic acid {2,4-difluoro-3-[5-(4-trifluoromethyl-phenyl)-1H-pyrrolo[2,3-b]pyridine-3-carbonyl]-phenyl}-amide (P-0912), Propane-1-sulfonic acid {2,4-difluoro-3-[5-(3-methoxy-phenyl)-1H-pyrrolo[2,3-b]pyridine-3-carbonyl]-phenyl}-amide (P-0874), Propane-1-sulfonic acid {3-[5-(3-dimethylamino-phenyl)-1H-pyrrolo[2,3-b]pyridine-3-carbonyl]-2,4-difluoro-phenyl}-amide (P-0876), Propane-1-sulfonic acid [2-fluoro-3-(5-phenyl-1H-pyrrolo[2,3-b]pyridine-3-carbonyl)-phenyl]-amide (P-0897), Propane-1-sulfonic acid {3-[5-(4-chloro-phenyl)-1H-pyrrolo[2,3-b]pyridine-3-carbonyl]-2-fluoro-phenyl}-amide (P-1009), (2-Fluoro-3-hydroxy-phenyl)-(5-pyridin-3-yl-1H-pyrrolo[2,3-b]pyridin-3-yl)-methanone (P-0027), (3-Chloro-2-fluoro-phenyl)-(5-pyridin-3-yl-1H-pyrrolo[2,3-b]pyridin-3-yl)-methanone (P-0165), 5-phenyl-1H-pyrrolo[2,3-b]pyridine, Propane-1-sulfonic acid [2-fluoro-3-(5-pyridin-3-yl-1H-pyrrolo[2,3-b]pyridine-3-carbonyl)-phenyl]-amide (P-1251), Propane-1-sulfonic acid {2,4-difluoro-3-[5-(3-fluoro-phenyl)-1H-pyrrolo[2,3-b]pyridine-3-carbonyl]-phenyl}-amide (P-1259), Propane-1-sulfonic acid {2,4-difluoro-3-[5-(4-fluoro-phenyl)-1H-pyrrolo[2.3 b]pyridine-3-carbonyl]-phenyl}-amide (P-1260), Propane-1-sulfonic acid [2-fluoro-3-(5-pyridin-3-yl-1H-pyrrolo[2,3-b]pyridine-3-carbonyl)-phenyl]-amide (P-1261), Propane-1-sulfonic acid [2,4-difluoro-3-(5-pyridin-4-yl-1H-pyrrolo[2,3-b]pyridine-3-carbonyl)-phenyl]-amide (P-1262), 3-{3-[2,6-Difluoro-3-(propane-1-sulfonylamino)-benzoyl]-1H-pyrrolo[2,3-b]pyridin-5-yl}-benzoic acid (P-1266), Propane-1-sulfonic acid {2,4-difluoro-3-[5-(3-morpholin-4-yl-phenyl)-1H-pyrrolo[2,3-b]pyridine-3-carbonyl]-phenyl}-amide (P-1873), Propane-1-sulfonic acid {2,4-difluoro-3-[5-(3-morpholin-4-ylmethyl-phenyl)-1H-pyrrolo[2,3-b]pyridine-3-carbonyl]-phenyl}-amide (P-1878), Propane-1-sulfonic acid {2,4-difluoro-3-[5-(6-methoxy-pyridin-3-yl)-1H-pyrrolo[2,3-b]pyridine-3-carbonyl]-phenyl}-amide (P-1879), Propane-1-sulfonic acid {2,4-difluoro-3-[5-(6-morpholin-4-yl-pyridin-3-yl)-1H-pyrrolo[2,3-b]pyridine-3-carbonyl]-phenyl}-amide (P-1881), Propane-1-sulfonic acid (2,4-difluoro-3-{5-[6-(4-methyl-piperazine-1-yl)-pyridin-3-yl]-1H-pyrrolo[2,3-b]pyridine-3-carbonyl}-phenyl)-amide (P-1882), Propane-1-sulfonic acid {3-[5-(4-cyano-3,5-dimethyl-phenyl)-1H-pyrrolo[2,3-b]pyridine-3-carbonyl]-2,4-difluoro-phenyl}-amide (P-1980), N-{2,4-Difluoro-3-[5-(1-methyl-1H-pyrazol-4-yl)-1H-pyrrolo[2,3-b]pyridine-3-carbonyl]-phenyl}-4-trifluoromethyl-benzenesulfonamide (P-1996), N-{2,4-Difluoro-3-[5-(1-methyl-1H-pyrazol-4-yl)-1H-pyrrolo[2,3-b]pyridine-3-carbonyl]-phenyl}-3-fluoro-benzenesulfonamide (P-1997), Propane-1-sulfonic acid {2,4-difluoro-3-[5-(1-methyl-1H-pyrazol-4-yl)-1H-pyrrolo[2,3-b]pyridine-3-carbonyl]-phenyl}-amide (P-1864), Propane-1-sulfonic acid {3-[5-(4-chloro-phenyl)-1H-pyrrolo[2,3-b]pyridine-3-carbonyl]-4-fluoro-phenyl}-amide (P-1432), 4-{3-[2,6-Difluoro-3-(propane-1-sulfonylamino)-benzoyl]-1H-pyrrolo[2,3-b]pyridin-5-yl}-benzamide (P-1546), 4-{3-[2,6-Difluoro-3-(propane-1-sulfonylamino)-benzoyl]-1H-pyrrolo[2,3-b]pyridin-5-yl}-N,N-dimethyl-benzamide (P-1547), Propane-1-sulfonic acid (2,4-difluoro-3-{5-[4-(morpholine-4-carbonyl)-phenyl]-1H-pyrrolo[2,3]-pyridine-3-carbonyl}-phenyl)-amide (P-1548), 3-{3-[2,6-Difluoro-3-(propane-1-sulfonylamino)-benzoyl]-1H-pyrrolo[2,3-b]pyridin-5-yl}-benzamide (P-1549), Propane-1-sulfonic acid {2,4-difluoro-3-[5-(4-methyl-1H-imidazol-2-yl)-1H-pyrrolo[2,3-b]pyridine-3-carbonyl]-phenyl}-amide (P-2006), N-{2,4-Difluoro-3-[5-(6-methoxy-pyridin-3-yl)-1H-pyrrolo[2,3-b]pyridine-3-carbonyl]-phenyl}-3-fluoro-benzenesulfonamide (P-2012), (3-Difluoromethoxy-2,6-difluoro-phenyl)-(5-pyridin-3-yl-1H-pyrrolo[2,3-b]pyridin-3-yl)-methanone (P-1528), N-{3-[3-(3-Difluoromethoxy-2,6-difluoro-benzoyl)-1H-pyrrolo[2,3-b]pyridin-5-yl]-phenyl}-methanesulfonamide (P-1527), (2,2-Difluoro-benzo[1,3]dioxol-5-yl)-(5-pyridin-3-yl-1H-pyrrolo[2,3-b]pyridin-3-yl)-methanone (P-1558), N-{3-[3-(2,2-Difluoro-benzo[1,3]dioxole-5-carbonyl)-1H-pyrrolo[2,3-b]pyridin-5-yl]-phenyl}-methanesulfonamide (P-1564), 3-(2,3-Dihydro-benzo[1,4]dioxin-6-ylmethyl)-5-pyridin-3-yl-1H-pyrrolo[2,3-b]pyridine (P-1529), N-{3-[3-(2,3-Dihydro-benzo[1,4]dioxin-6-ylmethyl)-1H-pyrrolo[2,3-b]pyridin-5-yl]-phenyl}-methanesulfonamide (P-1530), (3,5-Bis-difluoromethoxy-phenyl)-(5-pyridin-3-yl-1H-pyrrolo[2,3-b]pyridin-3-yl)-methanone (P-1520), N-{3-[3-(3,5-Bis-difluoromethoxy-benzoyl)-1H-pyrrolo[2,3-b]pyridin-5-yl]-phenyl}-methanesulfonamide (P-1522), (2,2-Difluoro-benzo[1,3]dioxol-4-yl)-(5-pyridin-3-yl-1H-pyrrolo[2,3-b]pyridin-3-yl)-methanone (P-1515), N-{3-[3-(2,2-Difluoro-benzo[1,3]dioxole-4-carbonyl)-1H-pyrrolo[2,3-b]pyridin-5-yl]-phenyl}-methanesulfonamide (P-1516), (2,6-Difluoro-3-methoxy-phenyl)-(5-phenyl-1H-pyrrolo[2,3-b]pyridin-3-yl)-methanone (P-1387), (2,6-Difluoro-3-methoxy-phenyl)-(5-pyridin-3-yl-1H-pyrrolo[2,3-b]pyridin-3-yl)-methanone (P-1388), (2,6-Difluoro-3-methoxy-phenyl)-(5-pyridin-4-yl-1H-pyrrolo[2,3-b]pyridin-3-yl)-methanone (P-1389), N-{3-[3-(2,6-Difluoro-3-methoxy-benzoyl)-1H-pyrrolo[2,3-b]pyridin-5-yl]-phenyl}-acetamide (P-1390), N-{3-[3-(2,6-Difluoro-3-methoxy-benzoyl)-1H-pyrrolo[2,3-b]pyridin-5-yl]-phenyl}-methanesulfonamide (P-1391), 3-(2-Fluoro-3-methoxy-benzyl)-5-phenyl-1H-pyrrolo[2,3-b]pyridine (P-1323), 3-(2-Fluoro-3-methoxy-benzyl)-5-(4-trifluoromethyl-phenyl)-1H-pyrrolo[2,3-b]pyridine (P-1324), 3-(2-Fluoro-3-methoxy-benzyl)-5-(3-trifluoromethyl-phenyl)-1H-pyrrolo[2,3-b]pyridine (P-1325), 5-(3-Chloro-phenyl)-3-(2-fluoro-3-methoxy-benzyl)-1H-pyrrolo[2,3-b]pyridine (P-1326).

3-(2-Fluoro-3-methoxy-benzyl)-5-(3-fluoro-phenyl)-1H-pyrrolo[2,3-b]pyridine (P-1327), 3-(2-Fluoro-3-methoxy-benzyl)-5-(3-trifluoromethoxy-phenyl)-1H-pyrrolo[2,3-b]pyridine (P-1328), N-{3-[3-(2-Fluoro-3-methoxy-benzyl)-1H-pyrrolo[2,3-b]pyridin-5-yl]-phenyl}-methanesulfonamide (P-1329), (2-Fluoro-3-methoxy-phenyl)-[4-(4-trifluoromethyl-phenyl)-1H-pyrrolo[2,3-b]pyridin-3-yl]-methanone (P-1330), (2-Fluoro-3-methoxy-phenyl)-[4-(3-trifluoromethyl-phenyl)-1H-pyrrolo[2,3-b]pyridin-3-yl]-methanone (P-1331),
[5-(3-Chloro-phenyl)-1H-pyrrolo[2,3-b]pyridin-3-yl]-(2-fluoro-3-methoxy-phenyl)-methanone (P-1332),
[5-(4-Chloro-phenyl)-1H-pyrrolo[2,3-b]pyridin-3-yl]-(2-fluoro-3-methoxy-phenyl)-methanone (P4333),
[5-(3,5-Difluoro-phenyl)-1H-pyrrolo[2,3-b]pyridin-3-yl]-(2-fluoro-3-methoxy-phenyl)-methanone (P-1334),
4-[3-(2-Fluoro-3-methoxy-benzoyl)-1H-pyrrolo[2,3-b]pyridin-5-yl]-benzonitrile (P-1335),
N-{3-[3-(2-Fluoro-3-methoxy-benzoyl)-1H-pyrrolo[2,3-b]pyridin-5-yl]-phenyl}-acetamide (P-1336),
(2-Fluoro-3-methoxy-phenyl)-(5-phenyl-1H-pyrrolo[2,3-b]pyridin-3-yl)-methanone (P-1338),
(2-Fluoro-3-methoxy-phenyl)-[5-(4-trifluoroethoxy-phenyl)-1H-pyrrolo[2,3-b]pyridin-3-yl]-methanone (P4339),
(2-Fluoro-3-methoxy-phenyl)-(5-pyridin-3-yl-1H-pyrrolo[2,3-b]pyridin-3-yl)-methanone (P4343),
(2-Fluoro-3-methoxy-phenyl)-[5-(3-trifluoromethoxy-phenyl)-1H-pyrrolo[2,3-b]pyridin-3-yl]-methanone (P-1344),
(5-Phenyl-1H-pyrrolo[2,3-b]pyridin-3-yl)-(3-trifluoromethoxy-phenyl)-methanone (P-1408),
(5-Pyridin-3-yl-1H-pyrrolo[2,3-b]pyridin-3-yl)-(3-trifluoromethoxy-phenyl)-methanone (P-1413),
N-{3-[3-(3-Trifluoromethoxy-benzoyl)-1H-pyrrolo[2,3-b]pyridin-5-yl]-phenyl}-methanesulfonamide (P-1428),
N-{3-[3-(3-Trifluoromethoxy-benzoyl)-1H -pyrrolo[2,3-b]pyridin-5-yl]-phenyl}-acetamide (P-1422),
(E)-3-{3-[3-(3-Trifluoromethoxy-benzoyl)-1H-pyrrolo[2,3-b]pyridin-5-yl]-phenyl}-acrylic acid (P-1417),
(3-Difluoromethoxy-phenyl)-(5-phenyl-1H-pyrrolo[2,3-b]pyridin-3-yl)-methanone (P-1409),
(3-Difluoromethoxy-phenyl)-(5-pyridin-3-yl-1H-pyrrolo[2,3-b]pyridin-3-yl)-methanone (P-1415),
N-{3-[3-(3-Difluoromethoxy-benzoyl)-1H-pyrrolo[2,3-b]pyridin-5-yl]-phenyl}-methanesulfonamide (P-1430).
N-{3-[3-(3-Difluoromethoxy-benzoyl)-1H-pyrrolo[2,3-b]pyridin-5-yl]-phenyl}-acetamide (P-1424),
(E)-3-{3-[3-(3-Difluoromethoxy-benzoyl)-1H-pyrrolo[2,3-b]pyridin-5-yl]-phenyl}-acrylic acid (P-1418),
(3,5-Dimethoxy-phenyl)-(5-phenyl-1H-pyrrolo[2.3 b]pyridin-3-yl)-methanone (P-1406),
(3,5-Dimethoxy-phenyl)-(5-pyridin-3-yl-1H-pyrrolo[2,3-b]pyridin-3-yl)-methanone (P-1411),
N-{3-[3-(3,5-Dimethoxy-benzoyl)-1H-pyrrolo[2,3-b]pyridin-5-yl]-phenyl}-methanesulfonamide (P-1426),
N-{3-[3-(3,5-Dimethoxy-benzoyl)-1H-pyrrolo[2,3-b]pyridin-5-yl]-phenyl}-acetamide (P-1420),
(3-Fluoro-5-trifluoromethyl-phenyl)-(5-phenyl-1H-pyrrolo[2,3-b]pyridin-3-yl)-methanone (P-1407),
(3-Fluoro-5-trifluoromethyl-phenyl)-(5-pyridin-3-yl-1H-pyrrolo[2,3-b]pyridin-3-yl)-methanone (P-1412),
N-{3-[3-(3-Fluoro-5-trifluoromethyl-benzoyl)-1H-pyrrolo[2,3-b]pyridin-5-yl]-phenyl}-methanesulfonamide (P-1427),
N-{3-[3-(3-Fluoro-5-trifluoromethyl-benzoyl)-1H-pyrrolo[2,3-b]pyridin-5-yl]-phenyl}-acetamide (P4421).
(3,5-Dichloro-phenyl)-(5-pyridin-3-yl-1H-pyrrolo[2,3-b]pyridin-3-yl)-methanone (P-1414),
N-{3-[3-(3,5-Dichloro-benzoyl)-1H-pyrrolo[2,3-b]pyridin-5-yl]-phenyl}-methanesulfonamide (P-1429),
N-{3-[3-(3,5-Dichloro-benzoyl)-1H-pyrrolo[2,3-b]pyridin-5-yl]-phenyl}-acetamide (P-1423),
(5-Phenyl-1H-pyrrolo[2,3-b]pyridin-3-yl)-(3-trifluoromethyl-phenyl)-methanone (P-1405),
(5-Pyridin-3-yl-1H-pyrrolo[2,3-b]pyridin-3-yl)-(3-trifluoromethyl-phenyl)-methanone (P-1410),
N-{3-[3-(3-Trifluoromethyl-benzoyl)-1H-pyrrolo[2,3-b]pyridin-5-yl]-phenyl}-methanesulfonamide (P4425),
N-{3-[3-(3-Trifluoromethyl-benzoyl)-1H-pyrrolo[2,3-b]pyridin-5-yl]-phenyl}-acetamide (P-1419), and
(E)-3-{3-[3-(3-Trifluoromethyl-benzoyl)-1H-pyrrolo[2,3-b]pyridin-5-yl]-phenyl}-acrylic acid (P-1416).

The following table indicates the 5-bromo azaindole (column 2) and boronic acid (column 3) used to afford the compound (column 4). Column 1 provides the compound number and column 5 the observed mass.

| P-0082 | | B(OH)₂ (phenyl) | | 406.2 |
| P-0121 | | B(OH)₂ (3-pyridyl) | | 407.2 |
| P-0079 | | B(OH)₂ (3-pyridyl) | | 411.1 |
| P-0308 | | B(OH)₂ (3-pyridyl) | | 410.2 |

-continued

| | 5-Brazaindole | Boronic acid | Compound | MS(ESI) [M + H]+ observed |
|---|---|---|---|---|
| P-0156 | | | | 503.2 |
| P-0297 | | | | 526.1 |
| P-0228 | | | | 453.1 |

| | 5-Brazaindole | Boronic acid | Compound | MS(ESI) [M + H]+ observed |
|---|---|---|---|---|
| P-0037 | | | | 376.1 |
| P-0008 | | | | 411.1 |
| P-0716 | | | | 424.0 [M − H+]− |
| P-0700 | | | | 429.1 |

| | 5-Brazaindole | Boronic acid | Compound | MS(ESI) [M+H]+ observed |
|---|---|---|---|---|
| P-0841 | | | | 522.1 |
| P-0734 | | | | 445.0 |
| P-0745 | | | | 535.0 [M−H+]− |
| P-0746 | | | | 519.2 [M−H+]− |

-continued

| | 5-Brazaindole | Boronic acid | Compound | MS(ESI) [M + H]+ observed |
|---|---|---|---|---|
| P-0210 | | | | 504.2 [M − H+]− |
| P-0721 | | | | 469.0 |
| P-0184 | | | | 428.1 |
| P-0685 | | | | 491.1 |

| 5-Br azaindole | Boronic acid | Compound | MS(ESI) [M + H]+ observed |
|---|---|---|---|
| P-0753 | | | 473.1 |
| P-0636 | | | 456.1 |
| P-0776 | | | 472.1 |
| P-0956 | | | 490.1 |

| | | | MS(ESI) [M + H]+ observed |
|---|---|---|---|
| | 5-Brazaindole | Boronic acid | Compound |
| P-0889 | | | 499.2 |
| P-0877 | | | 486.3 |
| P-0912 | | | 524.1 |

| | 5-Brazaindole | Boronic acid | Compound | MS(ESI) [M + H]+ observed |
|---|---|---|---|---|
| P-0874 | 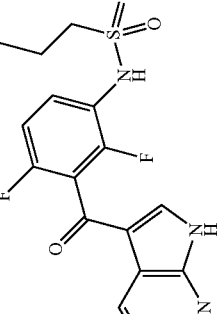 | 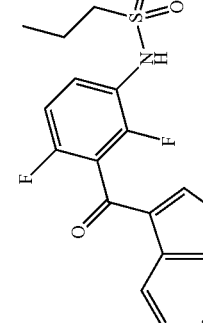 | 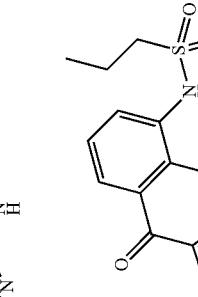 | 484.3 [M − H+]− |
| P-0876 | | | | 499.3 |
| P-0897 | | | | 438.3 |
| P-1009 | | | | 472.2 |

-continued

| | 5-Br azaindole | Boronic acid | Compound | MS(ESI) [M + H]+ observed |
|---|---|---|---|---|
| P-0027 | | | | 334.1 |
| P-0165 | | | | 352.1 |
| P-0857 | | | | 455.1 [M − H+]− |

| 5-Brazaindole | Boronic acid | Compound | MS(ESI) [M + H]+ observed |
|---|---|---|---|
| P-1251 | 3-pyridyl B(OH)₂ | | 439.3 |
| P-1259 | 3-fluorophenyl B(OH)₂ | | 474.2 |
| P-1260 | 4-fluorophenyl B(OH)₂ | | 474.2 |
| P-1261 | 3-chlorophenyl B(OH)₂ | | 490.2 |

| | 5-Brazaindole | Boronic acid | Compound | MS(ESI) [M + H]+ observed |
|---|---|---|---|---|
| P-1262 | | | | 457.2 |
| P-1266 | | | | 500.1 |
| P-1873 | | | | 541.2 |

| | 5-Brazaindole | Boronic acid | Compound | MS(ESI) [M+H]+ observed |
|---|---|---|---|---|
| P-1878 | 5-bromo-7-azaindole ketone structure | morpholinomethyl phenyl boronate | compound structure | 555.3 |
| P-1879 | 5-bromo-7-azaindole ketone structure | 6-methoxypyridine boronate | compound structure | 487.3 |
| P-1881 | 5-bromo-7-azaindole ketone structure | 6-morpholinopyridine boronate | compound structure | 542.3 |

| | 5-Brazaindole | Boronic acid | Compound | MS(ESI) [M + H]+ observed |
|---|---|---|---|---|
| P-1882 | 5-bromo-7-azaindole with propylsulfonamido-fluorophenyl ketone | 6-(4-methylpiperazin-1-yl)pyridin-3-yl pinacol boronate | propylsulfonamide-fluorophenyl ketone-7-azaindole-pyridyl-piperazine | 555.3 |
| P-1980 | 5-bromo-7-azaindole with propylsulfonamido-fluorophenyl ketone | 4-cyano-3,5-dimethylphenylboronic acid | propylsulfonamide-fluorophenyl ketone-7-azaindole-cyanodimethylphenyl | 509.2 |
| P-1996 | 5-bromo-7-azaindole with (4-trifluoromethylphenyl)sulfonamido-fluorophenyl ketone | 1-methylpyrazol-4-yl pinacol boronate | (4-trifluoromethylphenyl)sulfonamide-fluorophenyl ketone-7-azaindole-methylpyrazole | 562.2 |

| | 5-Brazaindole | Boronic acid | Compound | MS(ESI) [M + H]+ observed |
|---|---|---|---|---|
| P-1997 | | | | 512.2 |
| P-1864 | | | | 460.2 |
| P-1432 | | | | 472.2 |
| P-1546 | | | | 497.2 |

| | 5-Brazaindole | Boronic acid | Compound | MS(ESI) [M + H]+ observed |
|---|---|---|---|---|
| P-1547 | | | | 527.3 |
| P-1548 | | | | 569.3 |
| P-1549 | | | | 499.3 |

| | 5-Brazaindole | Boronic acid | Compound | MS(ESI) [M + H]+ observed |
|---|---|---|---|---|
| P-2006 | | | | 560.2 |
| P-2012 | | | | 632.1 |
| P-1528 | | | | |
| P-1527 | | | | |

| 5-Brazaindole | Boronic acid | Compound | MS(ESI) [M + H]+ observed |
|---|---|---|---|
| P-1558 | | | |
| P-1564 | | | |
| P-1529 | | | |
| P-1530 | | | |

| 5-Brazaindole | Boronic acid | Compound | MS(ESI) [M + H]+ observed |
|---|---|---|---|
| P-1520 | | | |
| P-1522 | | | |
| P-1515 | | | |
| P-1516 | | | |

-continued

| 5-Brazaindole | Boronic acid | Compound | MS(ESI) [M + H]+ observed |
|---|---|---|---|
| P-1387 | | | |
| P-1388 | | | |
| P-1389 | | | |
| P-1390 | | | |

| | 5-Br azaindole | Boronic acid | Compound | MS(ESI) [M + H]+ observed |
|---|---|---|---|---|
| P-1391 | | | | |
| P-1323 | | | | |
| P-1324 | | | | |
| P-1325 | | | | |

| | 5-Brazaindole | Boronic acid | Compound | MS(ESI) [M+H]+ observed |
|---|---|---|---|---|
| P-1326 | 5-bromo-3-(2-fluoro-3-methoxybenzyl)-1H-pyrrolo[2,3-b]pyridine | 3-chlorophenylboronic acid | 5-(3-chlorophenyl)-3-(2-fluoro-3-methoxybenzyl)-1H-pyrrolo[2,3-b]pyridine | |
| P-1327 | 5-bromo-3-(2-fluoro-3-methoxybenzyl)-1H-pyrrolo[2,3-b]pyridine | 3-fluorophenylboronic acid | 3-(2-fluoro-3-methoxybenzyl)-5-(3-fluorophenyl)-1H-pyrrolo[2,3-b]pyridine | |
| P-1328 | 5-bromo-3-(2-fluoro-3-methoxybenzyl)-1H-pyrrolo[2,3-b]pyridine | 3-(trifluoromethoxy)phenylboronic acid | 3-(2-fluoro-3-methoxybenzyl)-5-(3-(trifluoromethoxy)phenyl)-1H-pyrrolo[2,3-b]pyridine | |
| P-1329 | 5-bromo-3-(2-fluoro-3-methoxybenzyl)-1H-pyrrolo[2,3-b]pyridine | 3-(methylsulfonamido)phenylboronic acid | N-(3-(3-(2-fluoro-3-methoxybenzyl)-1H-pyrrolo[2,3-b]pyridin-5-yl)phenyl)methanesulfonamide | |

| | 5-Brazaindole | Boronic acid | Compound | MS(ESI) [M + H]+ observed |
|---|---|---|---|---|
| P-1330 | | | | |
| P-1331 | | | | |
| P-1332 | | | | |
| P-1333 | | | | |

-continued

| | 5-Brazaindole | Boronic acid | Compound | MS(ESI) [M + H]+ observed |
|---|---|---|---|---|
| P-1334 | | | | |
| P-1335 | | | | |
| P-1336 | | | | |
| P-1338 | | | | |

-continued

| 5-Brazaindole | Boronic acid | Compound | MS(ESI) [M + H]+ observed |
|---|---|---|---|
| P-1339 | | | |
| P-1343 | | | |
| P-1344 | | | |
| P-1408 | | | |

| 5-Brazaindole | Boronic acid | Compound | MS(ESI) [M+H]+ observed |
|---|---|---|---|
| P-1413 | | | |
| P-1428 | | | |
| P-1422 | | | |
| P-1417 | | | |

| 5-Brazaindole | Boronic acid | Compound | MS(ESI) [M+H]+ observed |
|---|---|---|---|
| P-1409 | | | |
| P-1415 | | | |
| P-1430 | | | |
| P-1424 | | | |

| | 5-Brazaindole | Boronic acid | Compound | MS(ESI) [M + H]+ observed |
|---|---|---|---|---|
| P-1418 | 5-bromo-3-(3-(difluoromethoxy)benzoyl)-7-azaindole | 3-(2-carboxyvinyl)phenylboronic acid | 3-(3-(difluoromethoxy)benzoyl)-5-(3-(2-carboxyvinyl)phenyl)-7-azaindole | |
| P-1406 | 5-bromo-3-(3,5-dimethoxybenzoyl)-7-azaindole | phenylboronic acid | 3-(3,5-dimethoxybenzoyl)-5-phenyl-7-azaindole | |
| P-1411 | 5-bromo-3-(3,5-dimethoxybenzoyl)-7-azaindole | pyridin-3-ylboronic acid | 3-(3,5-dimethoxybenzoyl)-5-(pyridin-3-yl)-7-azaindole | |
| P-1426 | 5-bromo-3-(3,5-dimethoxybenzoyl)-7-azaindole | 3-(methylsulfonamido)phenylboronic acid | 3-(3,5-dimethoxybenzoyl)-5-(3-(methylsulfonamido)phenyl)-7-azaindole | |

| 5-Br azaindole | Boronic acid | Compound | MS(ESI) [M + H]+ observed |
|---|---|---|---|
| P-1420 | | | |
| P-1407 | | | |
| P-1412 | | | |

-continued

| | 5-Brazaindole | Boronic acid | Compound | MS(ESI) [M + H]+ observed |
|---|---|---|---|---|
| P-1427 | (5-bromo-7-azaindol-3-yl)(3-fluoro-5-trifluoromethylphenyl)methanone | 3-(methanesulfonamido)phenylboronic acid | (3-fluoro-5-trifluoromethylphenyl)(5-(3-methanesulfonamidophenyl)-7-azaindol-3-yl)methanone | |
| P-1421 | (5-bromo-7-azaindol-3-yl)(3-fluoro-5-trifluoromethylphenyl)methanone | 3-acetamidophenylboronic acid | (3-fluoro-5-trifluoromethylphenyl)(5-(3-acetamidophenyl)-7-azaindol-3-yl)methanone | |
| P-1414 | (5-bromo-7-azaindol-3-yl)(3,5-dichlorophenyl)methanone | pyridin-3-ylboronic acid | (3,5-dichlorophenyl)(5-(pyridin-3-yl)-7-azaindol-3-yl)methanone | |

-continued

| | 5-Brazaindole | Boronic acid | Compound | MS(ESI) [M+H]+ observed |
|---|---|---|---|---|
| P-1429 | | | | |
| P-1423 | | | | |
| P-1405 | | | | |
| P-1410 | | | | |

-continued

| | 5-Brazaindole | Boronic acid | Compound | MS(ESI) [M + H]+ observed |
|---|---|---|---|---|
| P-1425 | 5-bromo-3-(3-trifluoromethylbenzoyl)-7-azaindole | 3-(methanesulfonylamino)phenylboronic acid | 3-(3-trifluoromethylbenzoyl)-5-[3-(methanesulfonylamino)phenyl]-7-azaindole | |
| P-1419 | 5-bromo-3-(3-trifluoromethylbenzoyl)-7-azaindole | 3-acetamidophenylboronic acid | 3-(3-trifluoromethylbenzoyl)-5-(3-acetamidophenyl)-7-azaindole | |
| P-1416 | 5-bromo-3-(3-trifluoromethylbenzoyl)-7-azaindole | 3-(2-carboxyvinyl)phenylboronic acid | 3-(3-trifluoromethylbenzoyl)-5-[3-(2-carboxyvinyl)phenyl]-7-azaindole | |

Example 4

Synthesis of N-[2,4-difluoro-3-(5-pyridin-3-yl-1H-pyrrolo[2,3-b]pyridine-3-carbonyl)-phenyl]-ethane-sulfonamide P-0728

Compound P-0728 was synthesized in eight steps from 2,4-difluorophenylamine 42 as shown in Scheme 16.

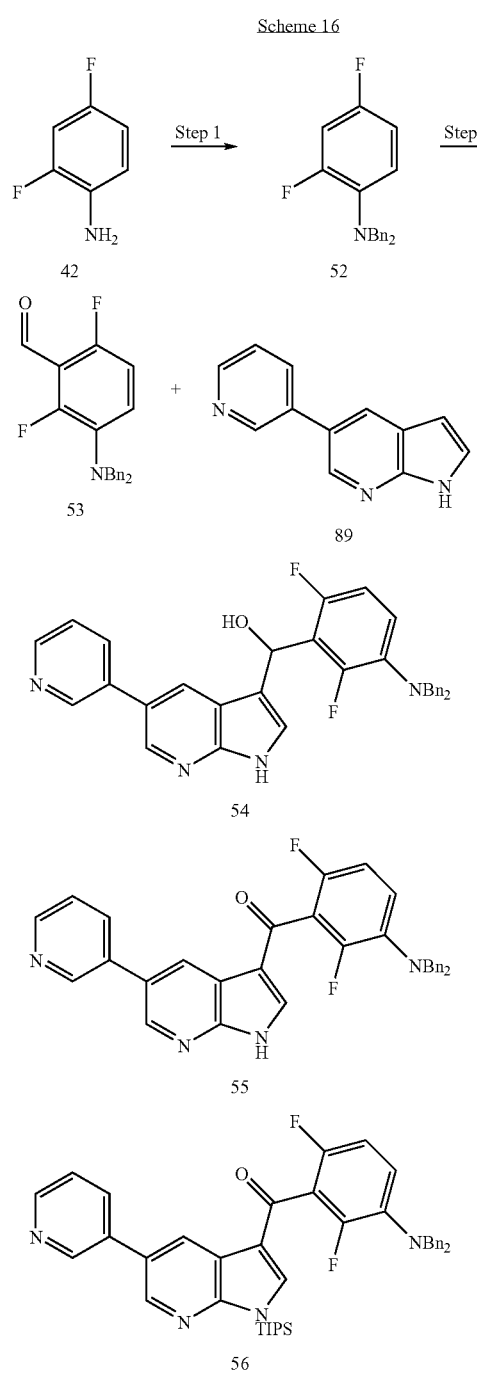

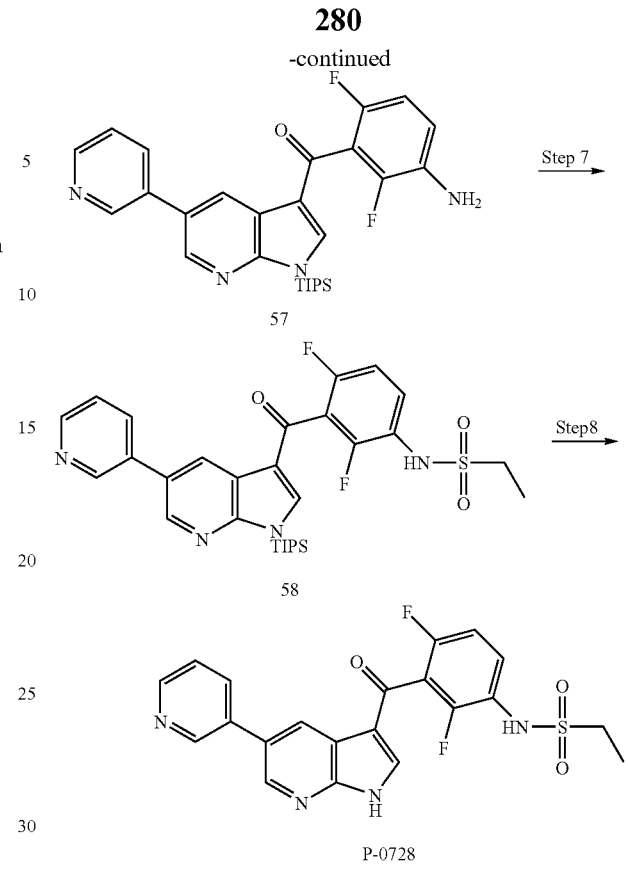

Step 1—Preparation of dibenzyl-(2,4-difluoro-phenyl)-amine (52)

To 2,4-difluoro-phenylamine (42, 10.0 g, 77.4 mmol) in N,N-dimethylformamide (130 mL) were added potassium carbonate (32.1 g, 0.23 mol) and benzyl bromide (21.2 mL, 0.18 mol). The reaction was stirred at room temperature overnight. The reaction was poured into water and extracted with ethyl acetate. The organic layer was washed with brine, dried over anhydrous sodium sulfate and filtrated. The filtrate was concentrated and purified by silica gel column chromatography eluting with 10% ethyl acetate in hexane. The appropriate fractions were combined and concentrated to provide the compound (52, 12.0 g, 50%). MS(ESI) [M+H$^+$]$^+$=310.2.

Step 2—Preparation of 3-dibenzylamino-2,6-difluoro-benzaldehyde (53)

To dibenzyl-(2,4-difluoro-phenyl)-amine (52, 4.30 g, 13.9 mmol) in tetrahydrofuran (60 mL), under an atmosphere of nitrogen, cooled in a −78° C. acetone/dry ice bath, was added n-butyllithium (2.50 M in hexane, 6.1 mL, 15.3 mmol) slowly. The reaction was stirred for 1 hour, N,N-dimethylformamide (1.2 mL, 15.3 mmol) was added and the reaction was allowed to warm to room temperature for 1 hour. The reaction was poured into water and extracted with ethyl acetate. The organic layer was washed with brine, dried over anhydrous sodium sulfate and filtered. The filtrate was concentrated and purified by silica gel column chromatography eluting with 10% ethyl acetate in hexane to provide the compound (53, 4.0 g, 85%). MS(ESI) [M+H$^+$]$^+$=337.2.

Step 3—Preparation of (3-dibenzylamino-2,6-difluoro-phenyl)-(5-pyridin-3-yl-1H-pyrrolo[2,3-b]pyridin-3-yl)-methanol (54)

To 3-dibenzylamino-2,6-difluoro-benzaldehyde (53, 0.76 g, 2.3 mmol) in methanol (50 mL) were added 5-pyridin-3-yl-1H-pyrrolo[2,3-b]pyridine (89, 0.40 g, 2.1 mmol, prepared as described in Example 17) and potassium hydroxide (0.50 g, 8.9 mmol) under an atmosphere of nitrogen. The reaction was stirred at room temperature overnight. The reaction was poured into water and extracted with ethyl acetate. The organic layer was washed with brine, dried over anhydrous sodium sulfate and filtered. The filtrate was concentrated and purified by silica gel column chromatography eluting with 5% methanol in methylene chloride to provide the compound (54, 0.60 g, 50%). MS(ESI) [M+H$^+$]$^+$=533.2.

Step 4—Preparation of (3-dibenzylamino-2,6-difluoro-phenyl)-(5-pyridin-3-yl-1H-pyrrolo[2,3]-pyridin-3-yl)-methanone (55)

To (3-dibenzylamino-2,6-difluoro-phenyl)-(5-pyridin-3-yl-1H-pyrrolo[2,3-b]pyridin-3-yl)-methanol (54, 0.90 g, 1.7 mmol) in methylene chloride (20 mL) under an atmosphere of nitrogen was added Dess-Martin periodane (0.97 g, 2.3 mmol). The reaction was stirred at room temperature for 15 minutes. The reaction was poured into a solution of sodium bicarbonate and sodium thiosulfate and extracted with ethyl acetate. The organic layer was washed with brine, dried over anhydrous sodium sulfate and filtered. The filtrate was concentrated and purified by silica gel column chromatography eluting with 5% methanol in methylene chloride to provide the compound (55, 0.70 g, 78%). MS(ESI) [M+H$^+$]$^+$=531.2.

Step 5—Preparation of (3-dibenzylamino-2,6-difluoro-phenyl)-(5-pyridin-3-yl-1-triisopropylsilanyl-1H-pyrrolo[2,3-b]pyridin-3-yl)-methanone (56)

To (3-dibenzylamino-2,6-difluoro-phenyl)-(5-pyridin-3-yl-1H-pyrrolo[2,3-b]pyridin-3-yl)-methanone (55, 0.84 g, 1.6 mmol) in tetrahydrofuran (150 mL) was added sodium hydride (210.0 mg, 60% in mineral oil, 5.3 mmol) under an atmosphere of nitrogen. The reaction was stirred for 5 minutes. Triisopropylsilyl chloride (0.80 mL, 3.8 mmol) was added and the reaction was stirred at room temperature for 3 hours. The reaction mixture was poured into water and extracted with ethyl acetate. The organic layer was washed with brine, dried over anhydrous sodium sulfate and filtered. The filtrate was concentrated and purified by silica gel column chromatography eluting with 10% ethyl acetate in hexane to provide the compound (56, 420 mg, 39%). MS(ESI) [M+H$^+$]$^+$=687.4.

Step 6—Preparation of (3-amino-2,6-difluoro-phenyl)-(5-pyridin-3-yl-1-triisopropylsilanyl-1H-pyrrolo[2,3-b]pyridin-3-A-methanone (57)

To (3-dibenzylamino-2,6-difluoro-phenyl)-(5-pyridin-3-yl-1-triisopropylsilanyl-1H-pyrrolo[2,3-b]pyridin-3-yl)-methanone (56, 55.0 mg, 0.080 mmol) in methanol (15 ml) was added 20% palladium hydroxide on carbon (20 mg). The reaction was stirred under an atmosphere of hydrogen overnight. The reaction was filtered to remove the catalyst, and then concentrated to give the crude compound that was used in the next step.

Step 7—Preparation of N-[2,4-difluoro-3-(5-pyridin-3-yl-1-triisopropylsilanyl-1H-pyrrolo[2,3-b]pyridin-3-carbonyl)-phenyl]-ethanesulfonamide (58)

To (3-amino-2,6-difluoro-phenyl)-(5-pyridin-3-yl-1-triisopropylsilanyl-1H-pyrrolo[2,3-b]pyridin-3-yl)-methanone (57, 35.0 mg. 0.069 mmol) in methylene chloride (6 mL) was added methanesulfonyl chloride (0.30 mL, 3.9 mmol) and triethylamine (0.40 mL, 2.9 mmol). The reaction was stirred at room temperature overnight. The reaction was poured into water and extracted with ethyl acetate. The organic layer was dried over anhydrous sodium sulfate and concentrated to give the crude compound that was used in the next step.

Step 8—Preparation of N-[2,4-difluoro-3-(5-pyridin-3-yl-1H-pyrrolo[2,3-b]pyridine-3-carbonyl)-phenyl]ethanesulfonamide (P-0728)

To N-[2,4-difluoro-3-(5-pyridin-3-yl-1-triisopropylsilanyl-1H-pyrrolo[2,3-b]pyridine-3-carbonyl)-phenyl]-ethanesulfonamide (58, 35.0 mg, 0.060 mmol) in tetrahydrofuran (10 mL) was added tetra-n-butylammonium fluoride (19 mg, 0.072 mmol). The reaction was stirred at room temperature for 5 minutes. The reaction was poured into water and extracted with ethyl acetate. The organic layer was washed with brine, dried over anhydrous sodium sulfate and filtered. The filtrate was concentrated and purified by silica gel column chromatography eluting with 5% methanol in methylene chloride to provide the compound (P-0728, 5.6 mg, 22%), MS(ESI) [M+H$^+$]$^+$=443.1.\

Also, (3-Benzylamino-2,6-difluoro-phenyl)-(5-pyridin-3-yl-1H-pyrrolo[2,3-b]pyridin-3-yl)-methanone P-0807 and (3-amino-2,6-difluoro-phenyl)-(5-pyridin-3-yl-1H-pyrrolo[2,3-b]pyridin-3-yl)-methanone P-0763

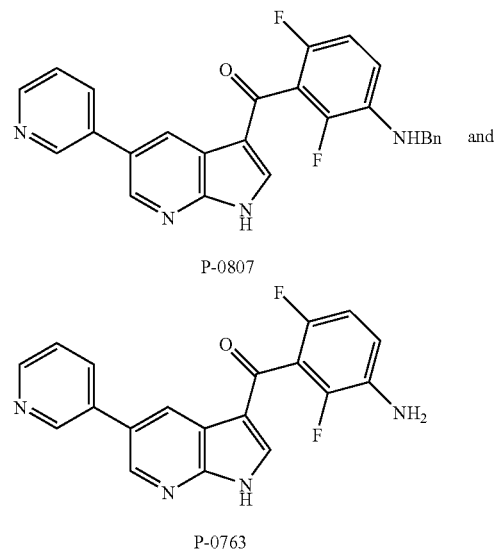

were synthesized by reacting (3-dibenzylamino-2,6-difluoro-phenyl)-(5-pyridin-3-yl-1-triisopropylsilanyl-1H-pyrrolo[2,3-b]pyridin-3-yl)-methanone (56, 20.0 mg, 0.033 mmol) and (3-Amino-2,6-difluoro-phenyl)-(5-pyridin-3-yl-1-triisopropylsilanyl-1H-pyrrolo[2,3-b]pyridin-3-yl)-methanone (57, 20.0 mg, 0.039 mmol), respectively, in tetrahydrofuran (5.0 mL) with tetra-n-butylammonium fluoride (13 mg, 0.050 mmol). The reaction mixtures were stirred at room temperature for 10 minutes, poured into water and extracted with ethyl acetate. The organic layer was washed with brine, dried over anhydrous sodium sulfate and concentrated. The products were isolated by silica gel column chromatography eluting with 10% ethyl acetate in hexane to give P-0807 (2.0 mg, MS(ESI) [M+H$^+$]$^+$=441.1) and P-0763 (1.7 mg, MS(ESI) [M–H$^+$]$^+$=351.1) as white solids.

Example 5

Preparation of propane-2-sulfonic acid [2,4-difluoro-3-(5-pyridin-3-yl-1H-pyrrolo[2,3-b]pyridin-3-carbonyl)-phenyl]-amide P-0850

Compound P-0850 was synthesized in four steps from 2,4-difluorophenylamine 42 as shown in Scheme 17.

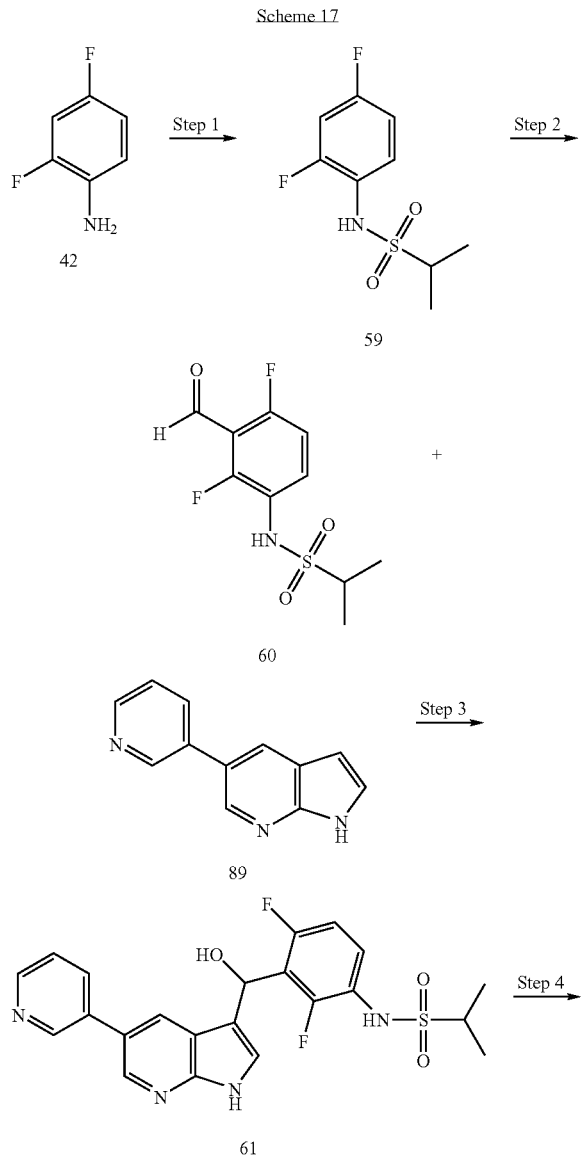

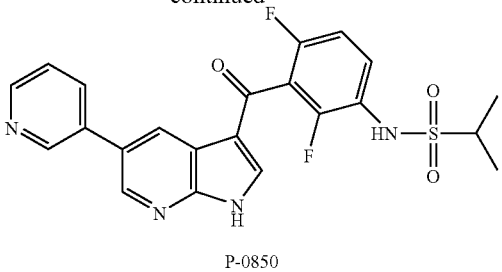

P-0850

Step 1—Preparation of propane-2-sulfonic acid (2,4-difluoro-phenyl)-amide (59)

To 2,4-difluoro-phenylamine (42, 4.0 mL, 40.0 mmol) in methylene chloride (50 mL) were added pyridine (3.37 mL, 42.3 mmol), propane-2-sulfonyl chloride (6.00 g, 42.3 mmol) and dimethylaminopyridine (0.20 g, 1.64 mmol) under an atmosphere of nitrogen. The reaction was stirred at 45° C. overnight. The reaction was poured into water and extracted with ethyl acetate. The organic layer was washed with brine, dried over anhydrous sodium sulfate and filtered. The filtrate was concentrated and purified by silica gel column chromatography 3% methanol in methylene chloride to give a white solid (59, 8.0 g, 85%). MS(ESI) [M–H$^+$]$^+$=234.0.

Step 2—Preparation of propane-2-sulfonic acid (2,4-difluoro-3-formyl-phenyl)-amide (60)

To propane-2-sulfonic acid (2,4-difluoro-phenyl)-amide (59, 2.35 g, 9.95 mmol) in tetrahydrofuran (70 mL) under an atmosphere of nitrogen cooled with a dry ice/acetone bath was added 1.60 M of n-butyllithium (1.60 M in hexane, 6.53 mL, 10.45 mmol). The reaction was stirred for 40 minutes, and then another portion of n-butyllithium (1.60 M in hexane, 6.84 mL, 10.94 mmol). The reaction was stirred for 1 hour and N,N-dimethylformamide (0.92 mL, 11.9 mmol) was added. The reaction was allowed to warm to room temperature overnight. The reaction was poured into water extracted with ethyl acetate. The organic layer was washed with brine, dried over anhydrous sodium sulfate and filtrated. The filtrate was concentrated and purified by silica gel column chromatography (dichloromethane/methanol 5%) to give the compound (60, 1.4 g, 53.4%). MS(ESI) [M–H$^+$]$^-$=263.4.

Step 3—Preparation of propane-2-sulfonic acid {2,4-difluoro-3-[hydroxy-(5-pyridin-3-yl-1H-pyrrolo[2,3-b]pyridin-3-yl)-methyl]-phenyl}-amide (61)

To propane-2-sulfonic acid (2,4-difluoro-3-formyl-phenyl)-amide (60, 220.0 mg, 0.83 mmol) in methanol (15 mL) was added 5-pyridin-3-yl-1H-pyrrolo[2,3-b]pyridine (89, 150.0 mg, 0.77 mmol, prepared as described in Example 17) and potassium hydroxide (537.0 mg, 9.6 mmol) under an atmosphere of nitrogen. The reaction was stirred at room temperature overnight. The reaction was poured into water and extracted with ethyl acetate. The organic layer was washed with brine, dried over sodium sulfate and filtrated. The filtrate was concentrated and purified by silica gel column chromatography eluting with 5% methanol in dichloromethane to give the compound (61, 160 mg, 45.3%). In this step, minor compound Propane-2-sulfonic acid {2,4-difluoro-3-[methoxy-(5-pyridin-3-yl-1H-pyrrolo[2,3-b]pyridin-3-yl)-methyl]-phenyl}-amide was also formed and isolated. MS(ESI) [M+H$^+$]$^+$=460.1.

Step 4—Preparation of propane-2-sulfonic acid [2,4-difluoro-3(5-pyridin-3-yl-1H-pyrrolo[2,3-b]pyridin-3-carbonyl)-phenyl]-amide (P-0850)

To propane-2-sulfonic acid {2,4-difluoro-3-[hydroxy-(5-pyridin-3-yl-1H-pyrrolo[2,3-b]pyridin-3-yl)-methyl]-phenyl}-amide (61, 40.0 mg, 0.087 mmol) in tetrahydrofuran (10 mL) was added Dess-Martin periodane (48.0 mg. 0.11 mmol). The reaction was stirred at room temperature for 5 minutes. The reaction was poured into sodium thiosulfate and potassium carbonate solution and extracted with ethyl acetate. The organic layer was washed with brine, dried over anhydrous sodium sulfate and filtrated. The filtrate was concentrated and purified by silica gel column chromatography eluting with 5% methanol in methylene chloride to give the compound (P-0850, 114 mg, 33.5%). MS(ESI) [M+H$^+$]$^+$=458.1.

N-(2,4-Difluoro-3-formyl-phenyl)-3-trifluoromethyl-benzenesulfonamide 579, N-(2,4-difluoro-3-formyl-phenyl)-4-trifluoromethyl-benzenesulfonamide 580, and N-(2,4-difluoro-3-formyl-phenyl)-4-fluoro-benzenesulfonamide 581, and (2,4-difluoro-3-formyl-phenyl)-carbamic acid benzyl ester

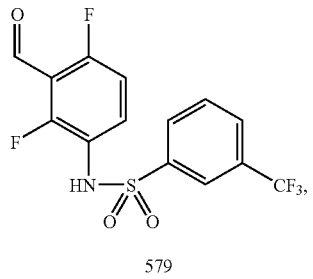

579

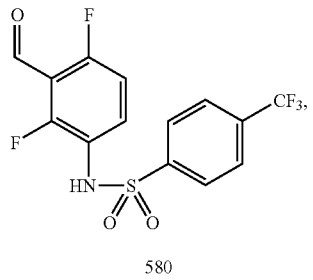

580

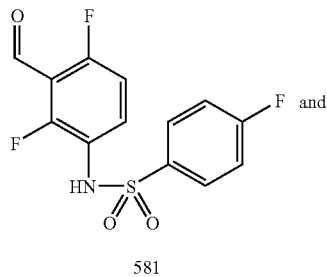

581

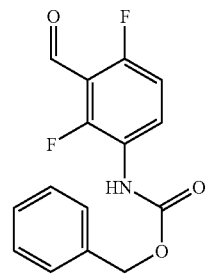

were prepared following Steps 1 and 2 of Scheme 17, substituting propane-2-sulfonyl chloride with 3-trifluoromethyl-benzenesulfonyl chloride, 4-trifluoromethyl-benzenesulfonyl chloride, 4-fluoro-benzenesulfonyl chloride, and benzyl chloroformate, respectively, in Step 1.

Propane-1-sulfonic acid [4-chloro-3-(5-chloro-1H-pyrrolo[2,3-b]pyridine-3-carbonyl)-2-fluoro-phenyl]-amide P-1004

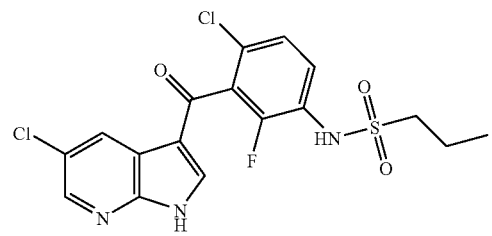 [SMILES: CCCS(=O)(=O)Nc1ccc(Cl)c(C(=O)c2c[nH]c3ncc(Cl)cc23)c1F]

was prepared using the protocol of Scheme 17, substituting 2,4-difluoro-phenylamine with 4-chloro-2-fluoro-phenylamine and propane-2-sulfonyl chloride with propane-1-sulfonyl chloride in Step 1, and 5-pyridin-3-yl-1H-pyrrolo[2,3-b]pyridine 89 with 5-chloro-7-azaindole 80 (see Example 9) in Step 3. MS(ESI) [M+H$^+$]$^+$=430.1.

Propane-1-sulfonic acid [4-chloro-2-fluoro-3-(1H-pyrrolo[2,3-b]pyridine-3-carbonyl)-phenyl]-amide P-0904

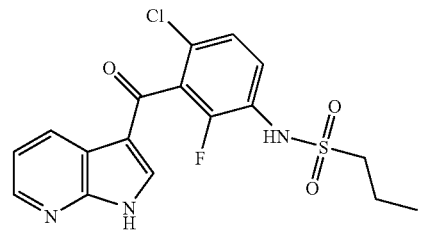 [SMILES: CCCS(=O)(=O)Nc1ccc(Cl)c(C(=O)c2c[nH]c3ncccc23)c1F]

was prepared using the protocol of Scheme 17, substituting 2,4-difluoro-phenylamine with 4-chloro-2-fluoro-phenylamine and propane-2-sulfonyl chloride with propane-1-sulfonyl chloride in Step 1, and 5-pyridin-3-yl-1H-pyrrolo[2,3-b]pyridine 89 with 7-azaindole 94 in Step 3. MS(ESI) [M+H$^+$]$^+$=396.2.

[2,4-Difluoro-3-(1H-pyrrolo[2,3-b]pyridine-3-carbonyl)-phenyl]-carbamic acid methyl ester P-0974 and [2,4-Difluoro-3-(1H-pyrrolo[2,3-b]pyridine-3-carbonyl)-phenyl]-carbamic acid benzyl ester P-0894

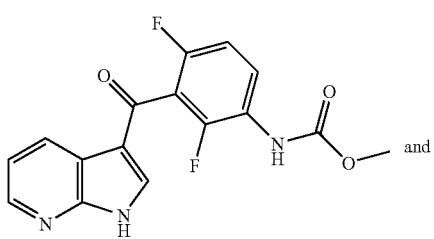

P-0974

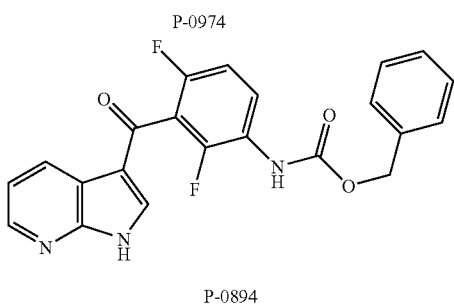

P-0894 were prepared using the protocol of Scheme 17, substituting propane-2-sulfonyl chloride with benzyl chloroformate in Step 1 and 5-pyridin-3-yl-1H-pyrrolo[2,3-b]pyridine 89 with 7-azaindole in Step 3. The products of Step 3 were a mixture of {2,4-Difluoro-3-[hydroxy-(1H-pyrrolo[2,3-b]pyridin-3-yl)-methyl]-phenyl}-carbamic acid methyl ester and {2,4-Difluoro-3-[hydroxy-(1H-pyrrolo[2,3-b]pyridin-3-yl)-methyl]-phenyl}-carbamic acid benzyl ester that were separated by silica gel column chromatography and carried through Step 4 separately to provide P-0974 and P-0894, respectively. P-0974 MS (ESI) [M–H+]+=330.1. P-0894 MS (ESI) [M–H+]+=406.1.

[2,4-Difluoro-3-(5-pyridin-3-yl-1H-pyrrolo[2,3-b]pyridine-3-carbonyl)-phenyl]-carbamic acid methyl ester P-0486 and [2,4-Difluoro-3-(5-pyridin-3-yl-1H-pyrrolo[2,3-b]pyridine-3-carbonyl)-phenyl]-carbamic acid benzyl ester P-0302

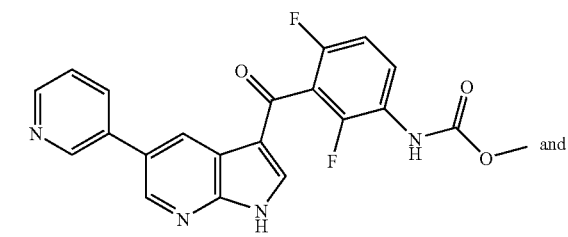

P-0486

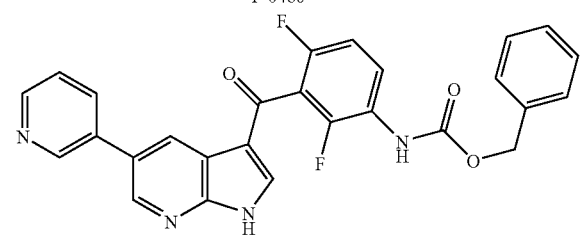

P-0302 were prepared using the protocol of Scheme 17, substituting propane-2-sulfonyl chloride with benzyl chloroformate in Step 1. The products of Step 3 were a mixture of {2,4-Difluoro-3-[hydroxy-(5-pyridin-3-yl-1H-pyrrolo[2,3-b]pyridin-3-yl)-methyl]-phenyl}-carbamic acid methyl ester and {2,4-Difluoro-3-[hydroxy-(5-pyridin-3-yl-1H-pyrrolo[2,3-b]pyridin-3-yl)-methyl]-phenyl}-carbamic acid benzyl ester that were separated by silica gel column chromatography and carried through Step 4 separately to provide P-0486 and P-0302, respectively. P-0486 MS (ESI) [M+H+]+=409.1. P-0302 MS (ESI) [M+H+]+=485.1,

[5-(3-Methanesulfonyl-phenyl)-1H-pyrrolo[2,3-b]pyridin-3-yl]-(2,3,6-trifluoro-phenyl)-methanone P-0102

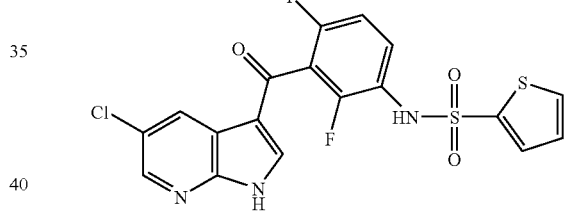

was prepared using the protocol of Steps 3 and 4 of Scheme 17, substituting propane-2-sulfonic acid (2,4-difluoro-3-formyl-phenyl)-amide with 2,3,6-Trifluoro-benzaldehyde and 5-pyridin-3-yl-1H-pyrrolo[2,3-b]pyridine 89 with 5-(3-methanesulfonyl-phenyl)-1H-pyrrolo[2,3-b]pyridine in Step 3. MS(ESI) [M–H+]–=429.0.

Thiophene-2-sulfonic acid [3-(5-chloro-1H-pyrrolo[2,3-b]pyridine-3-carbonyl)-2,4-difluoro-phenyl]-amide P-1267

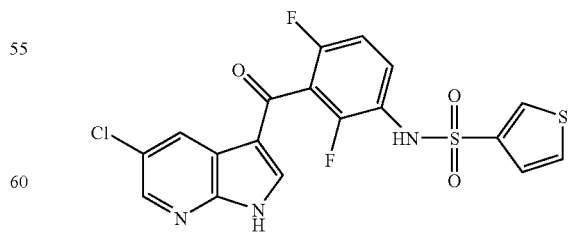

was prepared using the protocol of Steps 3 and 4 of Scheme 17, substituting 5-pyridin-3-yl-1H-pyrrolo[2,3-b]pyridin 89 with 5-chloro-7-azaindole 80 (see Example 9) and propane-2-sulfonic acid (2,4-difluoro-3-formyl-phenyl)-amide 60 with thiophene-2-sulfonic acid (2,4-difluoro-3-formyl-phenyl)-amide 512 (see Example 21) in Step 3. MS(ESI) [M+H+]–=451.9.

Thiophene-3-sulfonic acid [3-(5-chloro-1H-pyrrolo[2,3-b]pyridine-3-carbonyl)-2,4-difluoro-phenyl]-amide P-1268 was prepared using the protocol of Steps 3 and 4 of Scheme 17, substituting 5-pyridin-3-yl-1H-pyrrolo[2,3-b]pyridine 89 with 5-chloro-7-azaindole 80 (see Example 9) and propane-2-sulfonic acid (2,4-difluoro-3-formyl-phenyl)-amide 60 with thiophene-3-sulfonic acid (2,4-difluoro-3-formyl-phenyl)-amide 513 (see Example 21) in Step 3. MS(ESI) [M+H⁺]⁺=454.1.

Additional compounds were prepared following the protocol of Scheme 17, optionally replacing propane-2-sulfonyl chloride with an appropriate acid chloride in Step 1 and/or 5-pyridin-3-yl-1H-pyrrolo[2,3-b]pyridine with an appropriate azaindole in Step 3. Azaindoles were purchased or synthesized as described in Examples 6, 13, 14, 16 and 17. Some compounds were isolated after Step 3, as either hydroxy or methoxy derivatives. The following compounds were made following this procedure:

Dimethylamine-1-sulfonic acid {3-[5-(4-chloro-phenyl)-1H-pyrrolo[2,3-b]pyridin-3-carbonyl]-2,4-difluoro-phenyl}-amide (P-1257),
N-[3-(5-Bromo-1H-pyrrolo[2,3-b]pyridine-3-carbonyl)-2,4-difluoro-phenyl]-benzenesulfonamide (P-0798),
Propane-1-sulfonic acid [3-(5-bromo-1H-pyrrolo[2.3 b]pyridine-3-carbonyl)-2,4-difluoro-phenyl]-amide (P-0773),
Dimethylamine-1-sulfonic acid [3-(5-bromo-1H-pyrrolo[2,3-b]pyridine-3-carbonyl)-2,4-difluoro-phenyl]-amide (P-0898),
N-[3-(5-Chloro-1H-pyrrolo[2,3-b]pyridine-3-carbonyl)-2,4-difluoro-phenyl]-benzenesulfonamide (P-0885),
N-[2,4-Difluoro-3-(5-fluoro-1H-pyrrolo[2,3-b]pyridine-3-carbonyl)-phenyl]-benzenesulfonamide (P-0902),
Propane-1-sulfonic acid {2,4-difluoro-3-[hydroxy-(5-isopropenyl-1H-pyrrolo[2,3-b]pyridin-3-yl)-methyl]-phenyl}-amide (P-1239),
Propane-1-sulfonic acid [2,4-difluoro-3-(5-isopropenyl-1H-pyrrolo[2,3-b]pyridine-3-carbonyl)-phenyl]-amide (P-0991),
Propane-1-sulfonic acid {2,4-difluoro-3-[hydroxy-(5-methyl-1H-pyrrolo[2,3-b]pyridin-3-yl)-methyl]-phenyl}-amide (P-1240),
Propane-1-sulfonic acid {2,4-difluoro-3-[methoxy-(5-methyl-1H-pyrrolo[2,3-b]pyridin-3-yl)-methyl]-phenyl}-amide (P-1241),
Propane-1-sulfonic acid {2,4-difluoro-3-[hydroxy-(5-isopropyl-1H-pyrrolo[2,3-b]pyridin-3-yl)-methyl]-phenyl}-amide (P-1242),
Propane-1-sulfonic acid [2,4-difluoro-3-(5-isopropyl-1H-pyrrolo[2,3-b]pyridine-3-carbonyl-phenyl]-amide (P-0997),
Propane-1-sulfonic acid {2,4-difluoro-3-[hydroxy-(5-methoxy-1H-pyrrolo[2,3-b]pyridin-3-yl)-methyl]-phenyl}-amide (P-1243),
Propane-1-sulfonic acid {2,4-difluoro-3-[methoxy-(5-methoxy-1H-pyrrolo[2,3-b]pyridin-3-yl)-methyl]-phenyl}-amide (P-1244).
Propane-1-sulfonic acid (2,4-difluoro-3-{hydroxy-[5-(4-methyl-piperazine-1-yl)-1H-pyrrolo[2,3-b]pyridin-3-yl]-methyl}-phenyl)-amide (P-1245),
Propane-1-sulfonic acid [3-(5-chloro-1H-pyrrolo[2,3-b]pyridine-3-carbonyl)-2,4-difluoro-phenyl]-amide (P-0933),
Propane-1-sulfonic acid [2,4-difluoro-3-(5-fluoro-1H-pyrrolo[2,3-b]pyridine-3-carbonyl)-phenyl]-amide (P-0907),
Piperidine-1-sulfonic acid [3-(5-chloro-1H-pyrrolo[2,3-b]pyridine-3-carbonyl)-2,4-difluoro-phenyl]-amide (P-1020),
N-[3-(5-Chloro-1H-pyrrolo[2,3-b]pyridine-3-carbonyl)-2,4-difluoro-phenyl]-4-methoxy-benzenesulfonamide (P-0983),
N-[3-(4-Chloro-1H-pyrrolo[2,3-b]pyridine-3-carbonyl)-2,4-difluoro-phenyl]-benzenesulfonamide (P-0954),
N-[2,4-Difluoro-3-(5-pyridin-3-yl-1H-pyrrolo[2,3-b]pyridine-3-carbonyl)-phenyl]-acetamide (P-1002),
Dimethylamine-1-sulfonic acid [3-(1H-pyrrolo[2,3-b]pyridine-3-carbonyl)-2,4-difluoro-phenyl]-amide (P-0950),
Dimethylamine-1-sulfonic acid [3-(5-pyridin-3-yl-1H-pyrrolo[2,3-b]pyridine-3-carbonyl)-2,4-difluoro-phenyl]-amide (P-0837),
Dimethylamine-1-sulfonic acid [3-(5-chloro-1H-pyrrolo[2,3-b]pyridine-3-carbonyl)-2,4-difluorophenyl]-amide (P-1258),
Butane-1-sulfonic acid [3-(5-bromo-1H-pyrrolo[2,3-b]pyridine-3-carbonyl)-2,4-difluoro-phenyl]-amide (P-1263),
Butane-1-sulfonic acid [2,4-difluoro-3-(5-methoxy-1H-pyrrolo[2,3-b]pyridine-3-carbonyl)-phenyl]-amide (P-1264),
Butane-1-sulfonic acid [3-(5-chloro-1H-pyrrolo[2,3-b]pyridine-3-carbonyl)-2,4-difluoro-phenyl]-amide (P-1265),
Propane-1-sulfonic acid [3-(5-ethoxy-1H-pyrrolo[2,3-b]pyridine-3-carbonyl)-2,4-difluoro-phenyl]-amide (P-1252),
Propane-1-sulfonic acid {2,4-difluoro-3-[5-(2-methoxy-ethoxy)-1H-pyrrolo[2,3-b]pyridine-3-carbonyl]-phenyl}-amide (P-1253),
Propane-1-sulfonic acid {3-[5-(2-diethylamino-ethoxy)-1H-pyrrolo[2,3-b]pyridine-3-carbonyl]-2,4-difluoro-phenyl}-amide (P-1254),
N-[3-(5-Chloro-1H-pyrrolo[2,3-b]pyridine-3-carbonyl)-2,4-difluoro-phenyl]-4-ethyl-benzenesulfonamide (P-1700),
N-[3-(5-Ethyl-1H-pyrrolo[2,3-b]pyridine-3-carbonyl)-2,4-difluoro-phenyl]-4-trifluoromethyl-benzenesulfonamide (P-1783),
Thiophene-3-sulfonic acid [3-(5-bromo-1H-pyrrolo[2,3-b]pyridine-3-carbonyl)-2,4-difluoro-phenyl]-amide (P-1798),
Benzo[b]thiophene-2-sulfonic acid [3-(5-chloro-1H-pyrrolo[2,3-b]pyridine-3-carbonyl)-2,4-difluoro-phenyl]-amide (P-1799),
5-Pyridin-2-yl-thiophene-2-sulfonic acid [3-(5-chloro-1H-pyrrolo[2,3-b]pyridine-3-carbonyl)-2,4-difluoro-phenyl]-amide (P-1800),
N-[3-(5-Chloro-1H-pyrrolo[2,3-b]pyridine-3-carbonyl)-2,4-difluoro-phenyl]-4-cyano-benzenesulfonamide (P1822),
N-[3-(5-Chloro-1H-pyrrolo[2,3-b]pyridine-3-carbonyl)-2,4-difluoro-phenyl]-3-fluoro-4-methyl-benzenesulfonamide (P-1823),
N-[3-(5-Chloro-1H-pyrrolo[2,3-b]pyridine-3-carbonyl)-2,4-difluoro-phenyl]-4-isopropyl-benzenesulfonamide (P-1839),
N-[3-(5-Chloro-1H-pyrrolo[2,3-b]pyridine-3-carbonyl)-2,4-difluoro-phenyl]-4-fluoro-benzenesulfonamide (P-1840),
N-[3-(5-Chloro-1H-pyrrolo[2,3-b]pyridine-3-carbonyl)-2,4-difluoro-phenyl]-3,5-difluoro-benzenesulfonamide (P-1841),
N-[3-(5-Chloro-1H-pyrrolo[2,3-b]pyridine-3-carbonyl)-2,4-difluoro-phenyl]-4-methyl-benzenesulfonamide (P-1842),
N-[3-(5-Chloro-1H-pyrrolo[2,3-b]pyridine-3-carbonyl)-2,4-difluoro-phenyl]-4-oxazol-5-yl-benzenesulfonamide (P-1843), N-[2,4-Difluoro-3-(1H-pyrrolo[2,3-b]pyridine-3-carbonyl)-phenyl]-4-fluoro-benzenesulfonamide (P-1865),
N-{2,4-Difluoro-3-[5-(2-methoxy-ethoxy)-1H-pyrrolo[2,3-b]pyridine-3-carbonyl]-phenyl}-3-fluoro-benzenesulfonamide (P-1871),
N-{2,4-Difluoro-3-[5-(2-methoxy-ethoxy)-1H-1-pyrrolo[2,3-b]pyridine-3-carbonyl]-phenyl}-4-fluoro-benzenesulfonamide (P-1872),
Propane-1-sulfonic acid (2,4-difluoro-3-{5-[4-(2-methoxy-ethoxy)-phenyl]-1H-pyrrolo[2,3-b]pyridine-3-carbonyl}-phenyl)-amide (P-1998),
N-{2,4-Difluoro-3-[5-(2-methoxy-ethoxy)-1H-pyrrolo[2,3-b]pyridine-3-carbonyl]-phenyl}-4-trifluoromethyl-benzenesulfonamide (P-2005), and
N-(2,4-Difluoro-3-{5-[4-(2-methoxy-ethoxy)-phenyl]-1H-pyrrolo[2,3-b]pyridine-3-carbonyl}-phenyl)-4-trifluoromethyl-benzenesulfonamide (P-2013).

The following table indicates the acid chloride (column 2) and the azaindole (column 3) used to afford the target compounds (column 4). Column 1 provides the compound number and column 5 the observed mass. Compounds isolated after Step 3 of Scheme 17 are so noted in column 1

| | Sulfonyl chloride | Azaindole | Compound | MS(ESI) [M + H$^+$]$^+$ observed |
|---|---|---|---|---|
| P-1257 | | | | 415.1 |
| P-0798 | | | | 489.9 491.1 [M − H$^+$]$^-$ |
| P-0773 | | | | 455.9 457.9 [M − H$^+$]$^-$ |
| P-0898 | | | | 497.0 499.1 |
| P-0885 | | | | 446.1 448.1 [M − H$^+$]$^-$ |

-continued

| | Sulfonyl chloride | Azaindole | Compound | MS(ESI) [M + H⁺]⁺ observed |
|---|---|---|---|---|
| P-0902 | phenyl-SO₂Cl | 5-fluoro-7-azaindole | | 430.1 [M − H⁺]⁻ |
| P-1239 Step 3 | propyl-SO₂Cl | 5-isopropenyl-7-azaindole | | 422.2 [M − H⁺]⁻ |
| P-0991 | propyl-SO₂Cl | 5-isopropenyl-7-azaindole | | 420.2 |
| P-1240 Step 3 | propyl-SO₂Cl | 5-methyl-7-azaindole | | 396.4 [M − H⁺]⁻ |
| P-1241 Step 3 | propyl-SO₂Cl | 5-methyl-7-azaindole | | 410.3 [M − H⁺]⁻ |
| P-1242 Step 3 | propyl-SO₂Cl | 5-isopropyl-7-azaindole | | 424.3 [M − H⁺]⁻ |

-continued

| | Sulfonyl chloride | Azaindole | Compound | MS(ESI) [M + H⁺]⁺ observed |
|---|---|---|---|---|
| P-0997 | propyl-SO₂Cl | 5-isopropyl-7-azaindole | | 422.3 |
| P-1243 Step 3 | propyl-SO₂Cl | 5-methoxy-7-azaindole | (hydroxymethyl linker) | 412.3 [M − H⁺]⁻ |
| P-1244 Step 3 | propyl-SO₂Cl | 5-methoxy-7-azaindole | (methoxymethyl linker) | 426.4 [M − H⁺]⁻ |
| P-1245 Step 3 | propyl-SO₂Cl | 5-(4-methylpiperazin-1-yl)-7-azaindole | (hydroxymethyl linker) | 480.3 [M − H⁺]⁻ |
| P-0933 | propyl-SO₂Cl | 5-chloro-7-azaindole | | 414.2 |
| P-0907 | propyl-SO₂Cl | 5-fluoro-7-azaindole | | 396.1 [M − H⁺]⁻ |

-continued
| | Sulfonyl chloride | Azaindole | Compound | MS(ESI) [M + H+]+ observed |
|---|---|---|---|---|
| P-1020 | 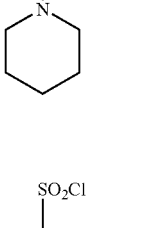 | 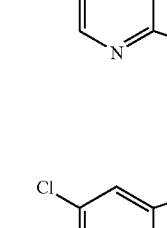 | 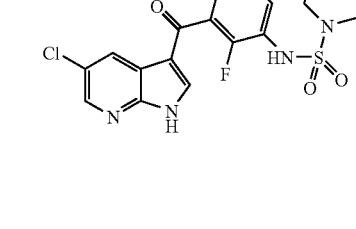 | 455.2 |
| P-0983 | 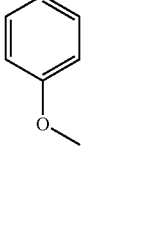 | 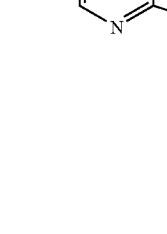 | 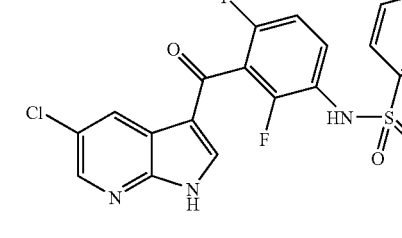 | 476.1 [M − H+]− |
| P-0954 | 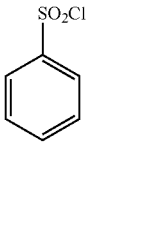 | 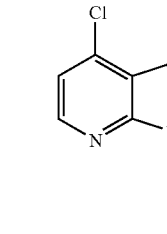 | 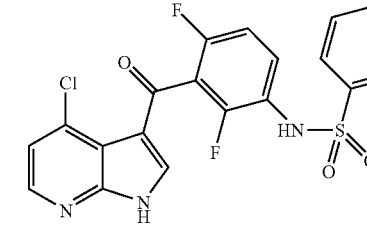 | 448.2 |
| P-1002 | 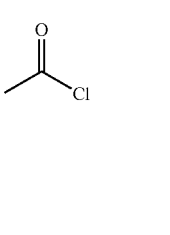 | 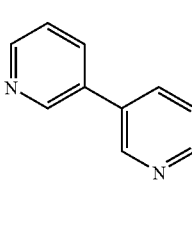 | 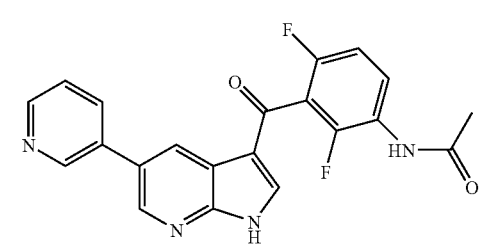 [SMILES: CC(=O)Nc1ccc(F)c(C(=O)c2c[nH]c3ncc(-c4cccnc4)cc23)c1F] | 393.2 |
| P-0950 | 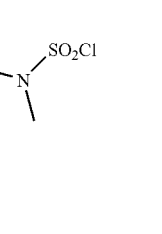 | 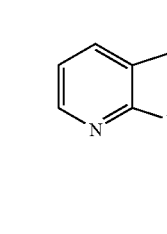 | 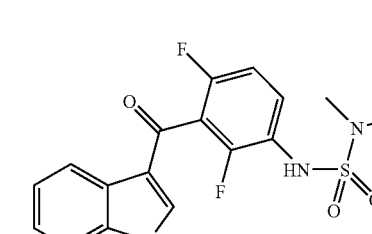 | 381.2 |
| P-0837 | 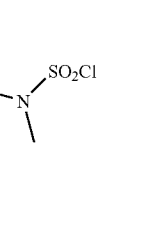 | 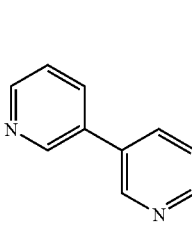 | 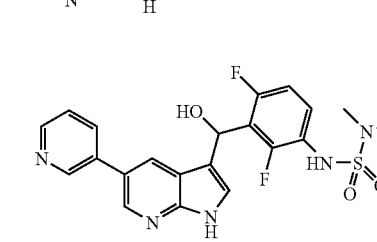 | 458.1 |

-continued
| | Sulfonyl chloride | Azaindole | Compound | MS(ESI) [M + H+]+ observed |
|---|---|---|---|---|
| P-1258 | 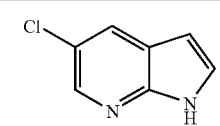 | 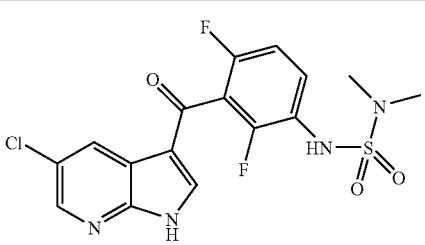 [SMILES: CN(C)S(=O)(=O)Nc1ccc(F)c(C(=O)c2c[nH]c3ncc(Cl)cc23)c1F] | 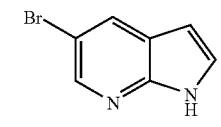 | 415.1 |
| P-1263 | 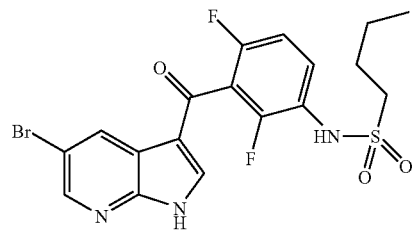 [SMILES: CCCCS(=O)(=O)Nc1ccc(F)c(C(=O)c2c[nH]c3ncc(Br)cc23)c1F] | 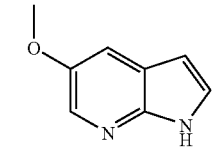 | 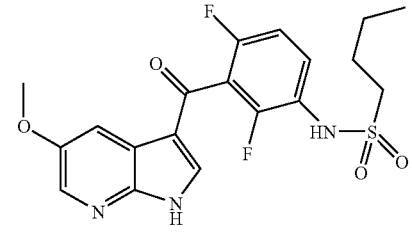 [SMILES: CCCCS(=O)(=O)Nc1ccc(F)c(C(=O)c2c[nH]c3ncc(OC)cc23)c1F] | 472.1 474.1 |
| P-1264 | 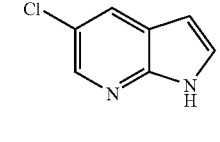 | 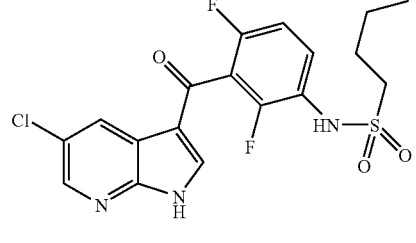 | 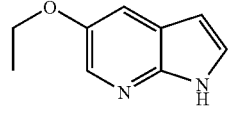 | 424.2 |
| P-1265 | 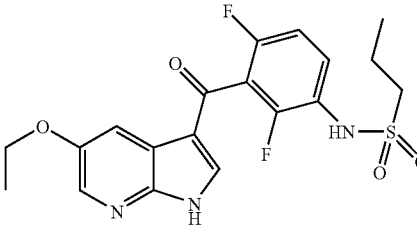 | 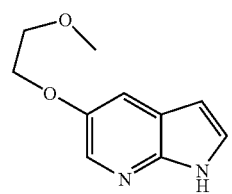 | 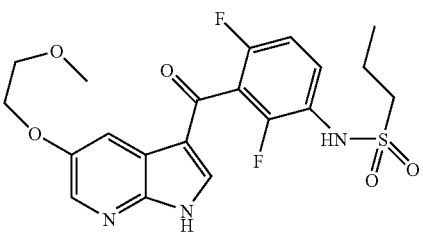 [SMILES: CCCS(=O)(=O)Nc1ccc(F)c(C(=O)c2c[nH]c3ncc(OCCOC)cc23)c1F] | 426.0 [M − H+]− |
| P-1252 | | | | 424.2 |
| P-1253 | | | | 454.2 |

-continued

| | Sulfonyl chloride | Azaindole | Compound | MS(ESI) [M + H+]+ observed |
|---|---|---|---|---|
| P-1254 | propyl-SO₂Cl | 5-(2-diethylaminoethoxy)-7-azaindole | | 495.3 |
| P-1700 | 4-ethylphenyl-SO₂Cl | 5-chloro-7-azaindole | | 476.2 |
| P-1783 | 4-trifluoromethylphenyl-SO₂Cl | 5-ethyl-7-azaindole | | 510 |
| P-1798 | thiophene-3-SO₂Cl | 5-bromo-7-azaindole | | 495.9 497.6 [M − H+]− |
| P-1799 | benzothiophene-2-SO₂Cl | 5-chloro-7-azaindole | | 502.0 (−) |

-continued
| | Sulfonyl chloride | Azaindole | Compound | MS(ESI) [M + H+]+ observed |
|---|---|---|---|---|
| P-1800 | 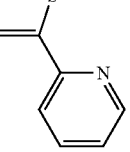 | 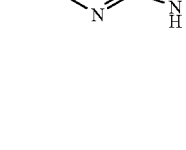 | 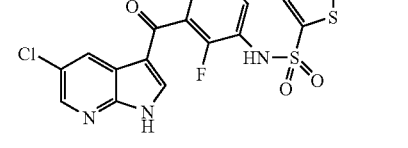 | 531.1 |
| P-1822 | 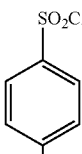 | 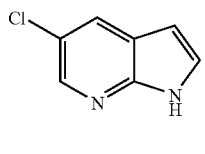 | 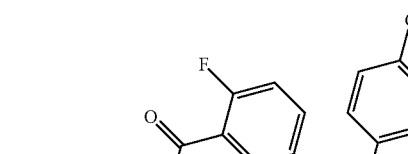 | 473.1 |
| P-1823 |  |  | 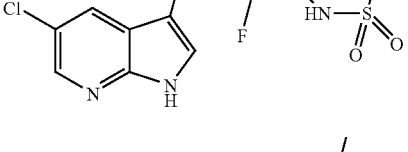 | 480.1 |
| P-1839 | 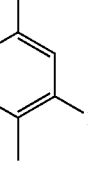 | 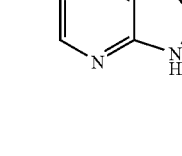 | 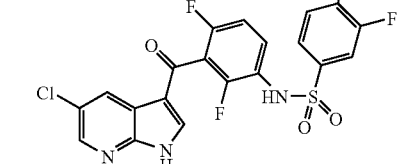 | 488 |
| P-1840 | 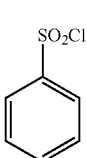 | 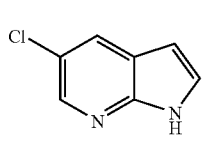 | 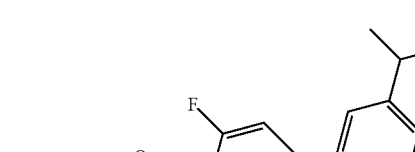 | 464 |
| P-1841 | 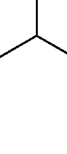 |  | 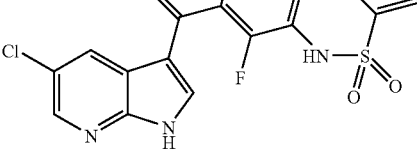 | 482 |

| | Sulfonyl chloride | Azaindole | Compound | MS(ESI) [M + H+]+ observed |
|---|---|---|---|---|
| P-1842 | 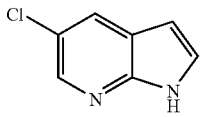 | 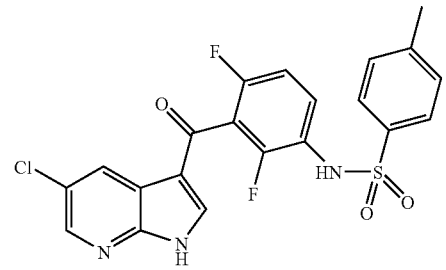 [SMILES: Cc1ccc(S(=O)(=O)Nc2ccc(F)c(C(=O)c3c[nH]c4ncc(Cl)cc34)c2F)cc1] | 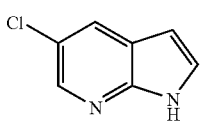 | 460.0 [M − H+]− |
| P-1843 | 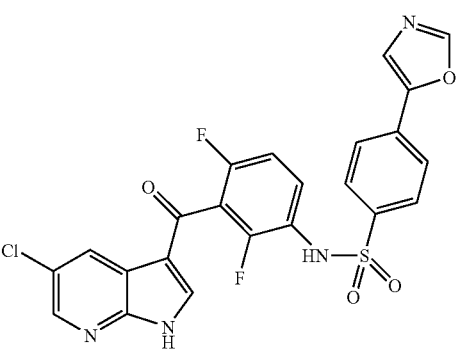 [SMILES: O=C(c1c(F)ccc(NS(=O)(=O)c2ccc(-c3cnco3)cc2)c1F)c1c[nH]c2ncc(Cl)cc12] | 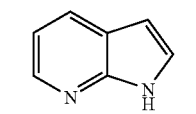 | 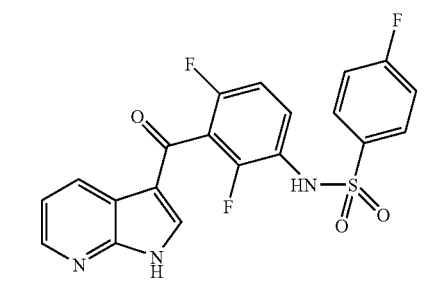 [SMILES: O=C(c1c(F)ccc(NS(=O)(=O)c2ccc(F)cc2)c1F)c1c[nH]c2ncccc12] | 513.0 [M − H+]− |
| P-1865 | 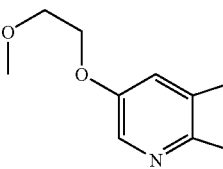 | 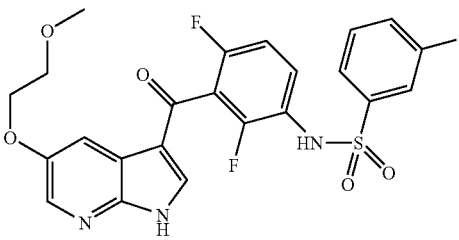 | 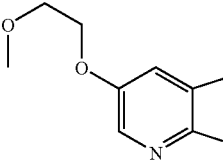 | 432.1 |
| P-1871 | 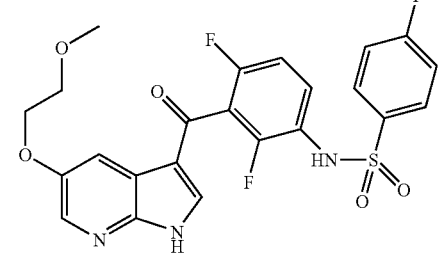 | | | 506.2 |
| P-1872 | | | | 506.2 |

| | Sulfonyl chloride | Azaindole | Compound | MS(ESI) [M + H⁺]⁺ observed |
|---|---|---|---|---|
| | 4-CF₃-C₆H₄-SO₂Cl | 5-bromo-7-azaindole | (structure) | |
| P-1998 | propyl-SO₂Cl | 5-(4-(2-methoxyethoxy)phenyl)-7-azaindole | (structure) | 530.3 |
| P-2005 | 4-CF₃-C₆H₄-SO₂Cl | 5-(2-methoxyethoxy)-7-azaindole | (structure) | 556.0 |
| P-2013 | 4-CF₃-C₆H₄-SO₂Cl | 5-(4-(2-methoxyethoxy)phenyl)-7-azaindole | (structure) | 539.2 |

Example 6

Synthesis of propane-1-sulfonic acid [2,4-difluoro-3-(5-phenylamino-1H-pyrrolo[2,3-b]pyridine-3-carbonyl)-phenyl]-amide P-0848 and related compounds Propane-1-sulfonic acid [2,4-difluoro-3-(5-phenylamino-1H-pyrrolo[2,3-b]pyridine-3-carbonyl)-phenyl]-amide P-0848 was synthesized in five steps from 5-bromo-7-azaindole 67 as shown in Scheme 18.

Scheme 18

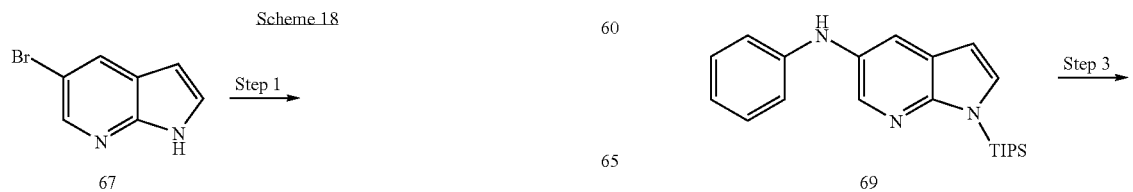

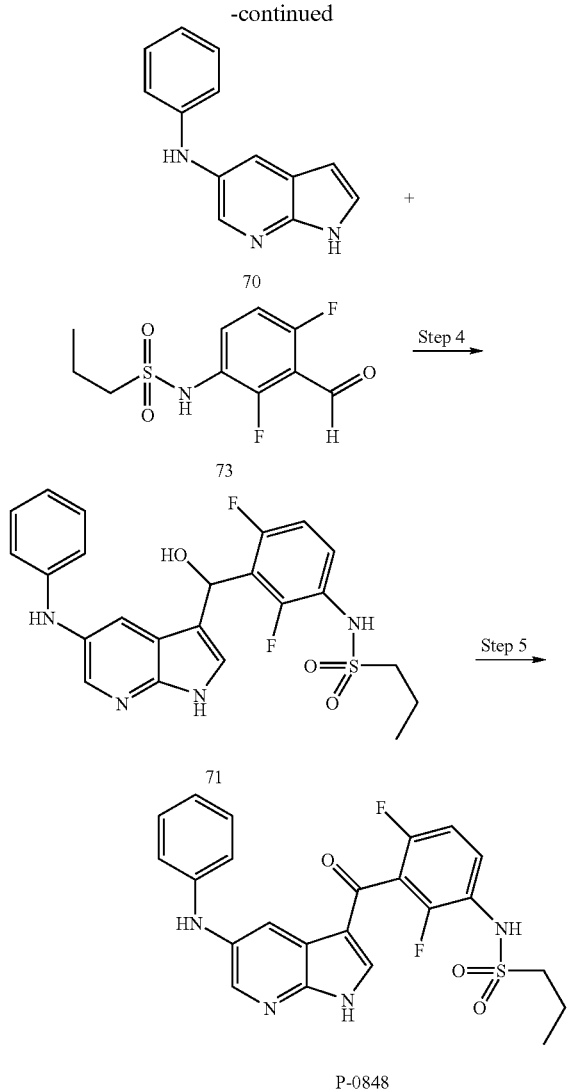

Step 1—Preparation of 5-bromo-1-triisopropylsilanyl-1H-pyrrolo[2,3-b]pyridin (68)

To 5-bromo-7-azaindole (67, 1.5 g, 7.6 mmol) in N,N-dimethylformamide (20 mL) were added sodium hydride (60% in mineral oil, 0.27 g, 11.0 mmol) and triisopropylsilyl chloride (2.6 mL, 12.0 mmol), under an atmosphere of nitrogen. The reaction was stirred for 2 hours at room temperature. The reaction was poured into water and extracted with ethyl acetate. The organic layer was washed with brine, dried over anhydrous sodium sulfate and filtered. The filtrate was concentrated and purified by silica gel column chromatography eluting with 10% ethyl acetate in hexane to give the compound (68, 1.6 g, 59%). MS(ESI) [M+H$^+$]$^+$=352.3.

Step 2—Preparation of 5-phenyl-(1-triisopropylsilanyl-1H-pyrrolo[2,3-b]pyridin-5-yl)-amine (69)

To 5-bromo-1-triisopropylsilanyl-1H-pyrrolo[2,3-b]pyridine (68, 0.10 g, 0.3 mmol) in toluene (5 mL) were added aniline (0.04 mL, 0.42 mmol), sodium tert-butoxide (0.15 g, 1.56 mmol), tris(dibenzyllideneacetone)dipalladium(0) (9.2 mg, 0.01 mmol) and (S)-(−)-2,2'-bis(diphenylphosphino)-1,1'-binaphthyl (6.3 mg, 0.01 mmol). The reaction was heated to 160° C. for 10 minutes in a CEM Discover microwave instrument. The reaction was concentrated and purified by silica gel column chromatography eluting with 3% ethyl acetate in hexane to give the compound (69, 40 mg, 40%). MS(ESI) [M+H$^+$]$^+$=366.6.

Step 3—Preparation of phenyl-(-1H-pyrrolo[2,3-b]pyridin-5-yl)-amine (70)

To 5-phenyl-(1-triisopropylsilanyl-1H-pyrrolo[2,3-b]pyridine-5-yl)-amine (69, 0.14 g, mmol) in tetrahydrofuran (3.0 mL) was added tetra-n-butylammonium fluoride (0.197 g, 0.76 mmol). The reaction was stirred for 1 hour at room temperature. The reaction was concentrated and purified by silica gel column chromatography eluting with 3% ethyl acetate in hexane to give the compound (70, 60 mg, 76%). MS(ESI) [M+H$^+$]$^+$=210.3.

Step 4—Preparation of propane-1-sulfonic acid {2,4-difluoro-3-[hydroxy-(5-phenylamino-1H-pyrrolo[2,3-b]pyridin-3-yl)-methyl]-phenyl}-amide (71)

To phenyl-(-1H-pyrrolo[2,3-b]pyridine-5-yl)-amine (70, 17.0 mg, 0.09 mmol) in methanol (5.0 mL) were added potassium hydroxide (92.0 mg, 1.6 mmol) and propane-1-sulfonic acid (2,4-difluoro-3-formyl-phenyl)-amide (73, 19.0 mg, 0.072 mmol, prepared as described in Example 7) under an atmosphere of nitrogen. The reaction was stirred for 12 hours at room temperature. The reaction was concentrated and purified by silica gel column chromatography eluting with 1% methanol in dichloromethane to give the compound (71, 17 mg, 50%). MS(ESI) [M+H$^+$]$^+$=473.5.

Step 5—Preparation of propane-1-sulfonic acid [2,4-difluoro-3-(5-phenylamino-1H-pyrrolo[2,3-b]pyridin-3-carbonyl)-phenyl]-amide (P-0848)

To propane-1-sulfonic acid {2,4-difluoro-3-[hydroxy-(5-phenylamino-1H-pyrrolo[2,3-b]pyridin-3-yl)-methyl]-phenyl}-amide (71, 7.5 mg, 0.016 mmol) in tetrahydrofuran (3 mL) was added Dess-Martin periodane (6.70 mg, 0.0158 mmol) under an atmosphere of nitrogen. The reaction was stirred for 20 minutes. The reaction was concentrated and purified by silica gel column chromatography eluting with 1% methanol in dichloromethane to give the compound (P-0848, 6.2 mg, 84%). MS(ESI) [M+H$^+$]$^+$=471.2.

Propane-1-sulfonic acid [2,4-difluoro-3-(5-morpholin-4-yl-1H-pyrrolo[2,3-b]pyridine-3-carbonyl)-phenyl]-amide P-0853, propane-1-sulfonic acid {2,4-difluoro-3-[5-(4-methyl-piperidin-1-yl)-1H-pyrrolo[2,3-b]pyridine-3-carbonyl]-phenyl}-amide P-0860, and propane-1-sulfonic acid {2,4-difluoro-3-[5-(4-methyl-piperazin-1-yl)-1H-pyrrolo[2,3-b]pyridine-3-carbonyl]-phenyl}-amide P-1246,

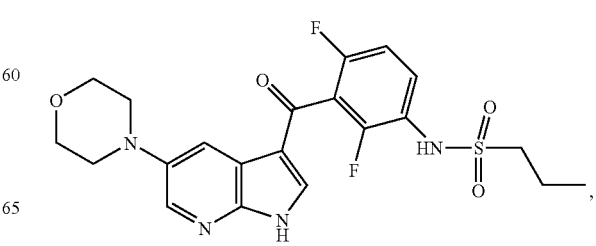

-continued

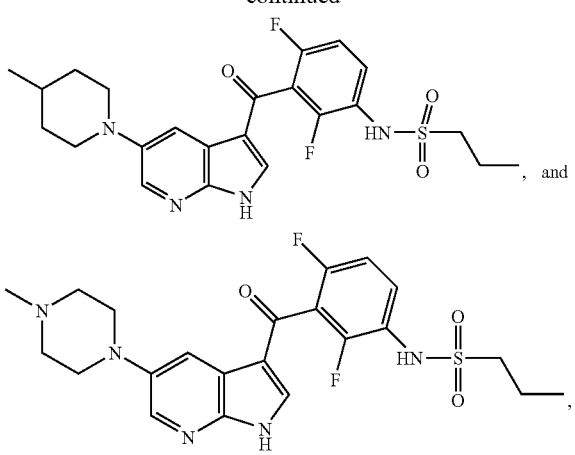

respectively, were prepared using the protocol of Scheme 18, substituting aniline with morpholine, 4-methyl-piperidine, and 4-methyl-piperazine, respectively, in Step 2. P-0853 MS(ESI) [M+H$^+$]$^+$=465.2. P-0860 MS(ESI) [M+H$^+$]$^+$=477.3. P-1246 MS(ESI) [M−H$^+$]$^−$=478.4.

4-[5-(3-Chloro-4-methoxy-phenylamino)-1H-pyrrolo[2,3-b]pyridine-3-carbonyl]-indole-1-carboxylic acid butylamide P-1859

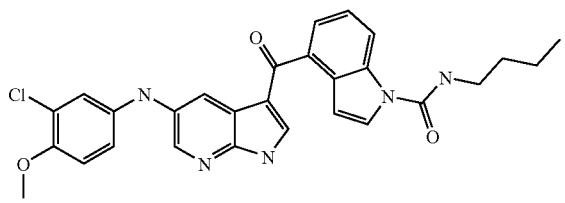 [SMILES: CCCCNC(=O)n1ccc2c(C(=O)c3c[nH]c4ncc(Nc5ccc(OC)c(Cl)c5)cc34)cccc21]

was prepared using the protocol of Scheme 18, substituting aniline with 3-chloro-4-methoxy-phenylamine in Step 2 and propane-1-sulfonic acid (2,4-difluoro-3-formyl-phenyl)-amide 73 with 4-Formyl-indole-1-carboxylic acid butylamide 519 (see Example 22) in Step 4. MS(ESI) [M+H$^+$]$^+$=516.2.

(1H-Indol-4-yl)-[5-(4-morpholin-4-yl-phenylamino)-1H-pyrrolo[2,3-b]pyridin-3-yl]-methanone P-1792, [5-(4-Chloro-phenylamino)-1H-pyrrolo[2,3-b]pyridin-3-yl]-(1H-indol-4-yl)-methanone P-1793, (1H-Indol-4-yl)-[5-(4-piperidin-1-yl-phenylamino)-1H-pyrrolo[2,3-b]pyridin-3-yl]-methanone P-1794, and [5-(3-Chloro-4-methoxy-phenylamino)-1H-pyrrolo[2,3-b]pyridin-3-yl]-(1H-indol-4-yl)-methanone P-1795,

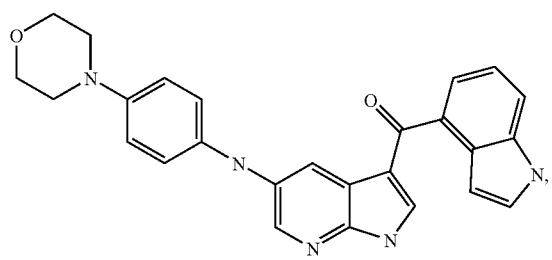

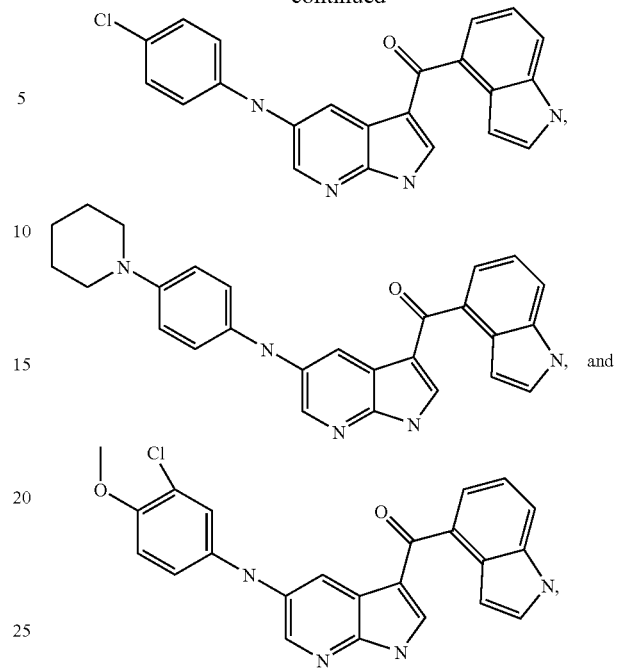

respectively, were prepared using the protocol of Steps 1-3 of Scheme 18 substituting 5-bromo-7-azaindole with 4-(5-Bromo-1H-pyrrolo[2,3-b]pyridine-3-carbonyl)-indole-1-carboxylic acid butylamide (P-1687, prepared as described in Example 22, Scheme 41) in Step 1 and replacing aniline with 4-morpholin-4-yl-phenylamine, 4-chloro-phenylamine, 4-piperidin-1-yl-phenylamine, and 3-chloro-4-methoxy-phenylamine, respectively, in Step 2. P-1792 MS (ESI) [M+H$^+$]$^+$=438.3. P-1793 MS (ESI) [M+H$^+$]$^+$=3871 P-1794 MS (ESI) [M+H$^+$]$^+$=436.3. P-1795 MS (EST) [M+H$^+$]$^+$=417.1.

Example 7

Synthesis of propane-1-sulfonic acid (2,4-difluoro-3-formyl-phenyl)-amide 73

Compound 73 was synthesized in two steps from 2,4-difluorophenylamine 42 as shown in Scheme 19.

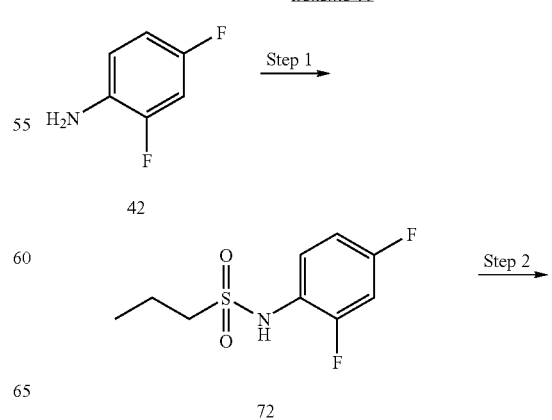

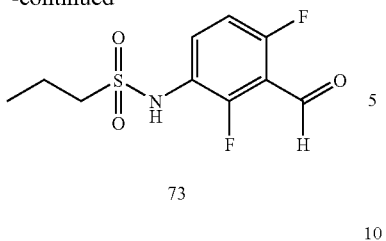

73

Step 1—Preparation of Propane-1-sulfonic acid (2,4-difluoro-phenyl)-amide (72)

To 2,4-difluoro-phenylamine (42, 3.0 mL, 29.8 mmol) in tetrahydrofuran (50 mL) were added triethylamine (9.13 mL, 65.5 mmol) and propane-1-sulfonyl chloride (2.90 mL, 25.8 mmol) under an atmosphere of nitrogen. The reaction was stirred at room temperature overnight. The reaction was poured into 1 M HCl and extracted with ethyl acetate. The organic layer was washed with brine, dried over anhydrous sodium sulfate and filtered. The filtrate was concentrated to give the compound (72, 2.0 g, 28%) that was used in the next step.

Step 2—Preparation of propane-1-sulfonic acid (2,4-difluoro-3-formyl-phenyl)-amide (73)

To propane-1-sulfonic acid (2,4-difluoro-phenyl)-amide (72, 1.5 g, 6.38 mmol) in tetrahydrofuran (10 mL) under an atmosphere of nitrogen, cooled in a −78° C. acetone/dry ice bath was added lithium diisopropylamide (0.80 M in tetrahydrofuran, 24 mL, freshly prepared from n-butyllithium and diisopropylamine). After 30 minutes, N,N-dimethyl-formamide (542 µL, 7.018 mmol) was added dropwise to the reaction. The reaction was stirred for 30 minutes at −78° C. and then allowed to warm to room temperature for 40 minutes. The reaction was poured into water and extracted with ethyl acetate. The organic layer was washed with brine, dried over anhydrous sodium sulfate and filtered. The filtrate was concentrated and purified by silica gel column chromatography eluting with 5% ethyl acetate in hexane to give a light yellow solid (73, 300 mg, 18%). MS(ESI) [M−H+]−=262.3.

Example 8

Synthesis of propane-1-sulfonic acid [3-(5-bromo-1H-pyrrolo[2,3-b]pyridin-3-carbonyl)-phenyl]-amide P-1116

Compound P-1116 was synthesized in four steps from 3-amino-benzoic acid ethyl ester 74 as shown in Scheme 20.

Scheme 20

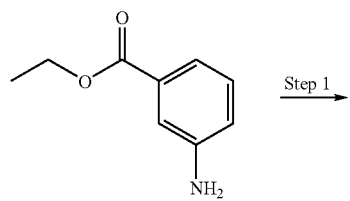

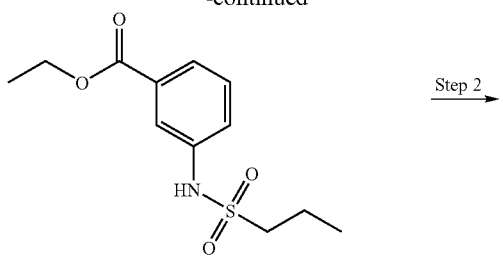

Step 1—Preparation of 3-(propane-1-sulfonylamino)-benzoic acid ethyl ester (75)

To 3-amino-benzoic acid ethyl ester (74, 5.0 g, 0.030 mol) in methylene chloride (30.0 mL) were added pyridine (3.67 mL, 0.045 mol) and propane-1-sulfonyl chloride (3.75 mL, 33.0 mmol). The reaction was stirred at room temperature for 2 hours. The reaction mixture was poured into water and extracted with ethyl acetate. The organic layer was washed with brine, dried over anhydrous sodium sulfate and concentrated. The desired compound was isolated by silica gel column chromatography eluting with 20% ethyl acetate in hexane to give a white solid (75, 6.0 g, 74.1%).

Step 2—Preparation of 3-(propane-1-sulfonylamino)-benzoic acid (76)

To 3-(propane-1-sulfonylamino)-benzoic acid ethyl ester (75, 1.60 g, 5.90 mmol) in water was added lithium hydroxide (1.0 g, 4.2 mmol) and tetrahydrofuran (20 mL). The reaction was stirred at room temperature overnight. The reaction mixture was acidified with 1 N HCl, and extracted with ethyl acetate. The organic layer was dried over anhydrous sodium sulfate and filtered. The filtrate was concentrated and washed with ethyl acetate to give the compound (76, 1.2 g, 84.5%) as white solid. MS(ESI) $[M-H^+]^+=242.1$.

Step 3—Preparation of 3-(propane-1-sulfonylamino)-benzoyl chloride (77)

A solution of 3-(propane-1-sulfonylamino)-benzoic acid (76, 1.20 g, 4.93 mmol) in thionyl chloride was heated to reflux for 3.0 hours. Evaporation of the solvent gave compound 77 as white solid that was used for the next step.

Step 4—Preparation of propane-1-sulfonic acid [3-(5-bromo-1H-pyrrolo[2,3-b]pyridin-3-carbonyl)-phenyl]-amide (P-1116)

To aluminum trichloride (4.8 g, 36.0 mmol) in methylene chloride (70.0 mL), under an atmosphere of nitrogen, was added 5-bromo-1H-pyrrolo[2,3-b]pyridine (67, 797 mg, 4.04 mmol) dissolved in methylene chloride (5.0 mL). The reaction was stirred at room temperature for 30 minutes, followed by addition of 3-(propane-1-sulfonylamino)-benzoyl chloride (77, 1.10 g, 4.20 mmol) dissolved in methylene dichloride (4.0 mL). The reaction was stirred at room temperature for 2 hours. The reaction was poured into water and extracted with ethyl acetate. The organic layer was dried over anhydrous sodium sulfate and filtered. The filtrate was concentrated and purified by silica gel column chromatography eluting with 30% ethyl acetate in hexane to give a white solid (P-1116, 300.0 mg). MS(ESI) $[M-H^+]^-=420.1, 422.1$.

Example 9

Synthesis of 5-chloro-1H-pyrrolo[2,3-b]pyridine 80

Compound 80 was synthesized in two steps from 5-bromo-1-triisopropylsilyl-7-azaindole 68 as shown in Scheme 21.

Scheme 21

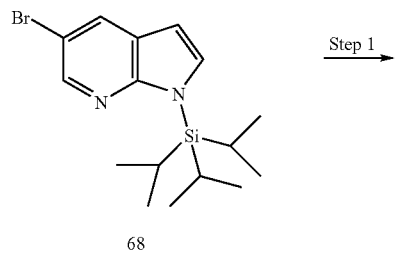

68

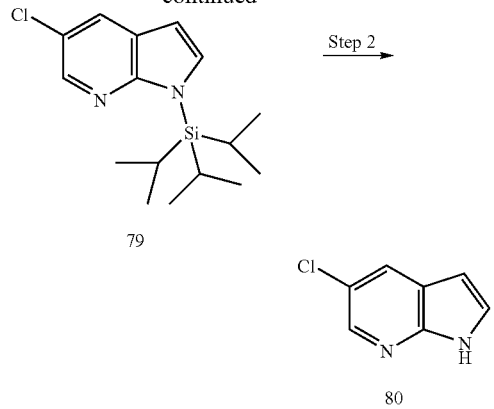

Step 1—Preparation 5-chloro-1-triisopropylsilanyl-1H-pyrrolo[2,3-b]pyridin (79)

To 5-bromo-1-triisopropylsilyl-7-azaindole (68, 1.60 g, 4.53 mmol, prepared as described in Example 6) in tetrahydrofuran (50.0 mL), under an atmosphere of nitrogen at −78° C., was added tert-butyllithium (1.70 M in hexane, 6.12 mL). The reaction was stirred for 1 hour, followed by addition of hexachloroethane (1.29 g, 5.43 mmol). The reaction was stirred for 3 hours, poured into water, and extracted with ethyl acetate. The organic layer was dried over anhydrous sodium sulfate and filtered. The filtrate was concentrated to give the crude compound (79, 1.60 g). MS(ESI) $[M+H^+]^+=309.3$.

Step 2—Preparation 5-chloro-1H-pyrrolo[2,3-b]pyridin (80)

To 5-chloro-1-triisopropylsilanyl-1H-pyrrolo[2,3-b]pyridin (79, 1.40 g, 4.53 mmol) in tetrahydrofuran (15 mL) was added tetra-n-butylammonium fluoride (1.42 g, 5.43 mmol). The reaction mixture was stirred at room temperature for 10 minutes. The reaction mixture was concentrated and isolated by silica gel column chromatography eluting with 30% ethyl acetate in hexane to give the compound (80, 0.40 g. 58% over 2 steps). MS(ESI) $[M-H^+]^+=153.1$.

5-Fluoro-1H-pyrrolo[2,3-b]pyridine 81 was prepared using the protocol of Scheme 21, substituting hexachloroethane with N-fluoro-N-(phenylsulfonyl)benzenesulfonamide in Step 1. MS(ESI) $[M+H^+]^+=137.1$.

Example 10

Synthesis of 2,4-difluoro-3-(5-pyridin-3-yl-1H-pyrrolo[2,3-b]pyridin-3-ylmethyl)-phenol P-0078 and related compounds Compound P-0078 was synthesized in two steps from 5-pyridin-3-yl-1H-pyrrolo[2,3-b]pyridine 89 as shown in Scheme 24.

Scheme 24

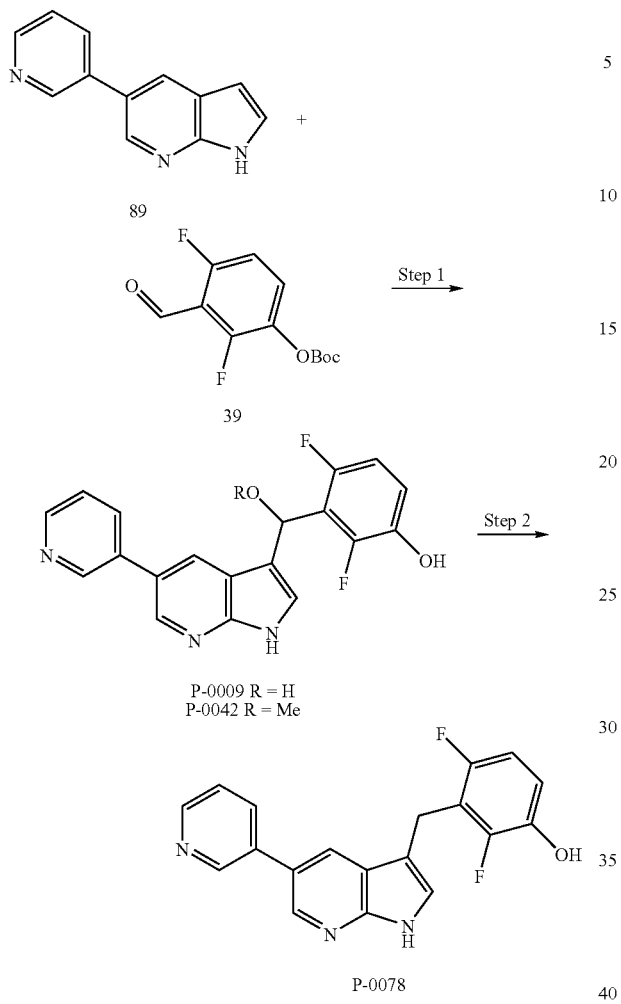

Step 1—Preparation of 2,4-difluoro-3-[hydroxy-(5-pyridin-3-yl-1H-pyrrolo[2,3-b]pyridin-3-yl)-methyl]-phenol (P-0009)

To carbonic acid tert-butyl ester 2,4-difluoro-3-formyl-phenyl ester (39, 0.405 g, 15.7 mmol) in methanol (36 mL), under an atmosphere of nitrogen, was added 5-pyridin-3-yl-1H-pyrrolo[2,3-b]pyridine (89, 288.0 mg, 14.8 mmol, prepared as described in Example 17) and potassium hydroxide (145.0 mg, 25.9 mmol). The reaction was stirred at room temperature overnight. Then, the reaction was poured into water, and extracted with ethyl acetate. The organic layer was washed with brine dried over anhydrous sodium sulfate and concentrated. The mixture was purified by silica gel column chromatography eluting with 4% methanol in methylene chloride to provide two separate compounds, a colorless oil (P-0009, 0.23 g, 44.1%, MS(ESI) [M+H$^+$]$^+$=354.1), and a colorless oil (P-0042, 0.050 g, 9.2%, MS(ESI) [M+H$^+$]$^+$=367.1).

Step 2—Preparation of 4-difluoro-3-(5-pyridin-3-yl-1H-pyrrolo[2,3-b]pyridin-3-ylmethyl)-phenol (P-0078)

To 2,4-difluoro-3-[hydroxy-(5-pyridin-3-yl-1H-pyrrolo[2,3-b]pyridin-3-yl)-methyl]-phenol (P-0009, 34.0 mg, 0.096 mmol) in acetonitrile (15 mL), were added trifluoroacetic acid (1.0 mL, 13.0 mmol) and triethylsilane (2.0 mL, 12.0 mmol). The reaction was stirred at room temperature for 48 hours. The reaction mixture was poured sodium bicarbonate solution, and extracted with ethyl acetate. The organic layer was washed with brine, dried over anhydrous sodium sulfate and filtered. The filtrate was concentrated and purified by silica gel column chromatography eluting with 30% ethyl acetate in hexane to give the compound (P-0078, 6.0 mg, 19%). MS(ESI) [M+H$^+$]$^+$=338.1.

Additional compounds were prepared following the protocol of Scheme 24, replacing either or both of carbonic acid tort-butyl ester 2,4-difluoro-3-formyl-phenyl ester 39 with an appropriate aldehyde and/or 5-pyridin-3-yl-1H-pyrrolo[2,3-b]pyridine 89 with an appropriate azaindole in Step 1. Azaindoles were purchased or synthesized as described in Examples 6 and 17. Aldehydes were prepared as described in Example 5 (through Step 2). Some compounds were isolated after Step 1, as either hydroxy or methoxy derivatives. The following compounds were made following this procedure:

3-[(5-Bromo-1H-pyrrolo[2,3-b]pyridin-3-yl)-methoxy-methyl]-2,4-difluoro-phenol (P-0126),
3-[(5-Bromo-1H-pyrrolo[2,3-b]pyridin-3-yl)-hydroxy-methyl]-2,4-difluoro-phenol (P-1180),
3-(5-Bromo-1H-pyrrolo[2,3-b]pyridin-3-ylmethyl)-2,4-difluoro-phenol (P-0122),
{2,4-Difluoro-3-[hydroxy-(5-pyridin-3-yl-1H-pyrrolo[2,3b]pyridin-3-yl)-methyl]-phenyl}-carbamic acid benzyl ester (P-0095),
[2,4-Difluoro-3-(5-pyridin-3-yl-1H-pyrrolo[2,3-b]pyridin-3-ylmethyl)-phenyl]-carbamic acid benzyl ester (P-0396),
{2,4-Difluoro-3-[hydroxy-(5-pyridin-3-yl-1H-pyrrolo[2,3-b]pyridin-3-yl)-methyl]-phenyl}-carbamic acid methyl ester (P-0065),
[2,4-Difluoro-3-(5-pyridin-3-yl-1H-pyrrolo[2,3-b]pyridin-3-ylmethyl)-phenyl]-carbamic acid methyl ester (P-0257),
Propane-2-sulfonic acid {3-[(5-bromo-1H-pyrrolo[2,3-b]pyridin-3-yl)-methoxy-methyl]-2,4-difluoro-phenyl}-amide (P-0356),
Propane-2-sulfonic acid [3-(5-bromo-1H-pyrrolo[2,3-b]pyridin-3-ylmethyl)-2,4-difluoro-phenyl]-amide (P-0867),
Propane-2-sulfonic acid {2,4-difluoro-3-[methoxy-(5-pyridin-3-yl-1H-pyrrolo[2,3-b]pyridin-3-yl)-methyl]-phenyl}-amide (P-0947),
Propane-1-sulfonic acid {3-[(5-bromo-1H-pyrrolo[2,3-b]pyridin-3-yl)-hydroxy-methyl]-2,4-difluoro-phenyl}-amide (P-0188),
Propane-1-sulfonic acid [3-(5-bromo-1H-pyrrolo[2,3-b]pyridin-3-ylmethyl)-2,4-difluoro-phenyl]-amide (P-0910),
Dimethylamino-1-sulfonic acid {2,4-difluoro-3-[hydroxy-(5-pyridin-3-yl-1H-pyrrolo[2,3-b]pyridin-3-yl)-methyl]-phenyl}-amide (P-0944),
3-(2-Fluoro-3-methoxy-benzyl)-5-pyridin-3-yl-1H-pyrrolo[2,3-b]pyridine (P-0269),
Propane-1-sulfonic acid [2,4-difluoro-3-(5-phenylamino-1H-pyrrolo[2,3-b]pyridin-3-ylmethyl)-phenyl]-amide (P-0818),
Propane-1-sulfonic acid [2,4-difluoro-3-(5-phenyl-1H-pyrrolo[2,3-b]pyridin-3-ylmethyl)-phenyl]-amide (P-0911),
Propane-1-sulfonic acid [2,4-difluoro-3-(5-morpholin-4-yl-1H-pyrrolo[2,3-b]pyridin-3-ylmethyl)-phenyl]-amide (P-0964), Propane-1-sulfonic acid {2,4-difluoro-3-[5-(4-methyl-piperidin-1-yl)-1H-pyrrolo[2,3-b]pyridin-3-ylmethyl]-phenyl}-amide (P-0984),
{3-[(5-Bromo-1H-pyrrolo[2,3-b]pyridin-3-yl)-hydroxy-methyl]-2,4-difluoro-phenyl}-carbamic acid tert-butyl ester (P-0318),
{3-[(5-Chloro-1H-pyrrolo[2,3-b]pyridin-3-yl)-hydroxy-methyl]-2,4-difluoro-phenyl}-carbamic acid methyl ester,
{2,4-Difluoro-3-[hydroxy-(5-methoxy-1H-pyrrolo[2,3-b]pyridin-3-yl)-methyl]-phenyl}-carbamic acid methyl ester, and
{2,4-Difluoro-3-[hydroxy-(1H-pyrrolo[2,3-b]pyridin-3-yl)-methyl]-phenyl}-carbamic acid methyl ester,
5-Bromo-3-(2,3-dihydro-benzo[1,4]dioxin-6-ylmethyl)-1H-pyrrolo[2,3-b]pyridine (P-1474), and
5-Bromo-3-(2-fluoro-3-methoxy-benzyl)-1H-pyrrolo[2,3-b]pyridine (P-0535).

The following table indicates the aldehyde (column 2) and azaindole (column 3) used to afford the target compound (column 4). Column 1 provides the compound number and column 5 the observed mass. Compounds isolated after Step 1 of Scheme 24 are so noted in column 1.

| | Aldehyde | Azaindole | Compound | MS(ESI) [M + H⁺]⁺ observed |
|---|---|---|---|---|
| P-0126 Step 1 | | | | 369.1 371.1 |
| P-1180 Step 1 | | | | 353.0 355.0 |
| P-0122 | | | | 339.0 341.0 |
| P-0095 P-0065 Step 1* | | | | |

-continued

| | Aldehyde | Azaindole | Compound | MS(ESI) [M + H⁺]⁺ observed |
|---|---|---|---|---|
| P-0396 | | | | 471.2 |
| P-0257 | | | | 395.1 |
| P-0356 Step 1 | | | | 474.1 476.1 |
| P-0867 | | | | 460.2 |
| P-0947 Step 1 | | | | 459.2 |

-continued
| | Aldehyde | Azaindole | Compound | MS(ESI) [M + H⁺]⁺ observed |
|---|---|---|---|---|
| P-0188 Step 1 | 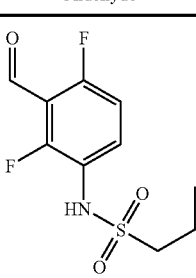 | 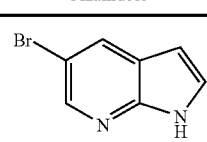 | 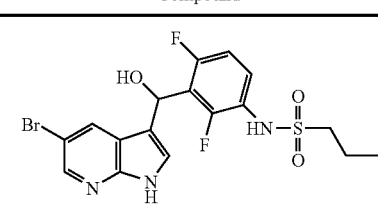 | 460 462 |
| P-0910 | 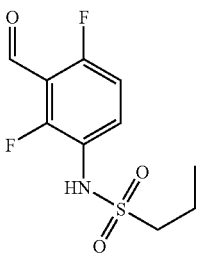 [SMILES: CCCS(=O)(=O)Nc1ccc(F)c(C=O)c1F] | 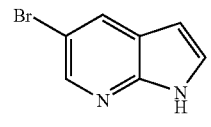 | 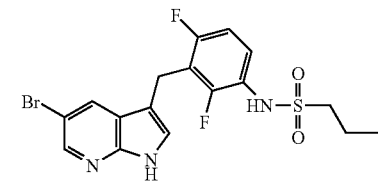 [SMILES: CCCS(=O)(=O)Nc1ccc(F)c(Cc2c[nH]c3ncc(Br)cc23)c1F] | 444.1 446.1 |
| P-0944 Step 1 | 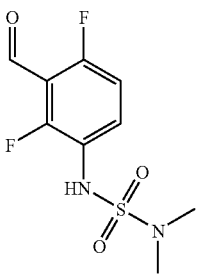 [SMILES: CN(C)S(=O)(=O)Nc1ccc(F)c(C=O)c1F] | 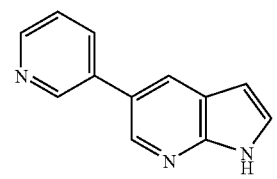 [SMILES: c1cncc(-c2cnc3[nH]ccc3c2)c1] | 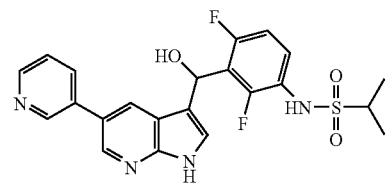 [SMILES: CC(C)S(=O)(=O)Nc1ccc(F)c(C(O)c2c[nH]c3ncc(-c4cccnc4)cc23)c1F] | 460.2 |
| P-0269 | 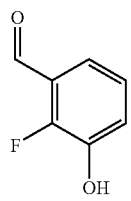 | 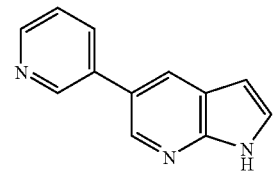 [SMILES: c1cncc(-c2cnc3[nH]ccc3c2)c1] | 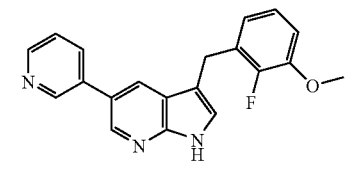 [SMILES: COc1cccc(Cc2c[nH]c3ncc(-c4cccnc4)cc23)c1F] | 334.2 |
| P-0818 | 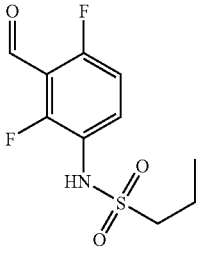 [SMILES: CCCS(=O)(=O)Nc1ccc(F)c(C=O)c1F] | 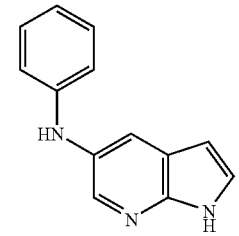 [SMILES: c1ccc(Nc2cnc3[nH]ccc3c2)cc1] | 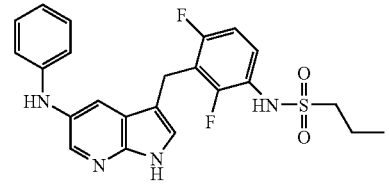 [SMILES: CCCS(=O)(=O)Nc1ccc(F)c(Cc2c[nH]c3ncc(Nc4ccccc4)cc23)c1F] | 457.1 |
| P-0911 | 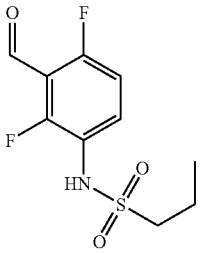 [SMILES: CCCS(=O)(=O)Nc1ccc(F)c(C=O)c1F] | 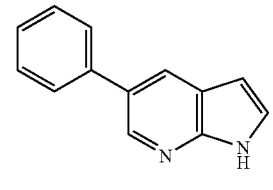 [SMILES: c1ccc(-c2cnc3[nH]ccc3c2)cc1] | 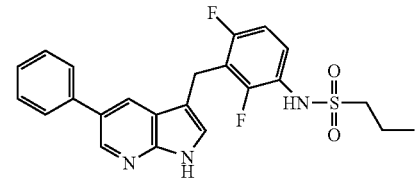 [SMILES: CCCS(=O)(=O)Nc1ccc(F)c(Cc2c[nH]c3ncc(-c4ccccc4)cc23)c1F] | 442.2 |

-continued

| | Aldehyde | Azaindole | Compound | MS(ESI) [M + H⁺]⁺ observed |
|---|---|---|---|---|
| P-0964 | | | | 449.3 [M − H⁺]⁻ |
| P-0984 | | | | 463.3 |
| P-0318 Step 1 | | | | 454.1 456.1 |
| Isolated Step1 | | | | |
| Isolated Step1 | | | | |
| Isolated Step1 | | | | |

| | Aldehyde | Azaindole | Compound | MS(ESI) [M + H+]+ observed |
|---|---|---|---|---|
| Isolated Step1 | (2,4-difluoro-3-(Cbz-amino)benzaldehyde) | 5-(3-methylsulfonylphenyl)-7-azaindole | (alcohol intermediate, methyl carbamate variant) | |
| P-1474 | 2,3-dihydrobenzo[1,4]dioxine-6-carbaldehyde | 5-bromo-7-azaindole | 5-bromo-3-(2,3-dihydrobenzo[1,4]dioxin-6-ylmethyl)-7-azaindole | 345.1 347.1 |
| P-0535 | 2-fluoro-3-methoxybenzaldehyde | 5-bromo-7-azaindole | 5-bromo-3-(2-fluoro-3-methoxybenzyl)-7-azaindole | 335.1 337.1 |

*P-0095 and P-0065 were both produced in Step 1 and isolated from the mixture. These were carried through to step 2 to provide P-0396 and P-0257, respectively.

Example 11

Synthesis of N-[2,4-difluoro-3-(1H-pyrrolo[2,3-b]pyridine-3-carbonyl) phenyl]-3-methoxy-benzene-sulfonamide P-0971

Compound P-0971 was synthesized in four steps from 2,4-difluorophenylamine 42 as shown in Scheme 26.

Scheme 26

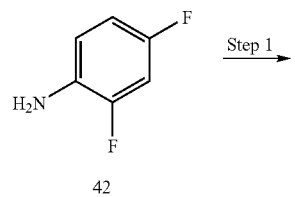

42

Step 1 →

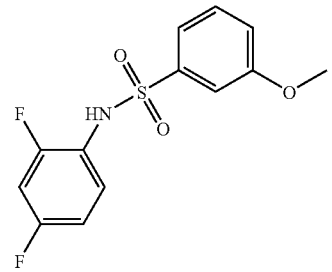

91

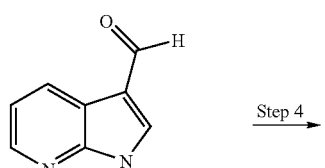

96

Step 4 →

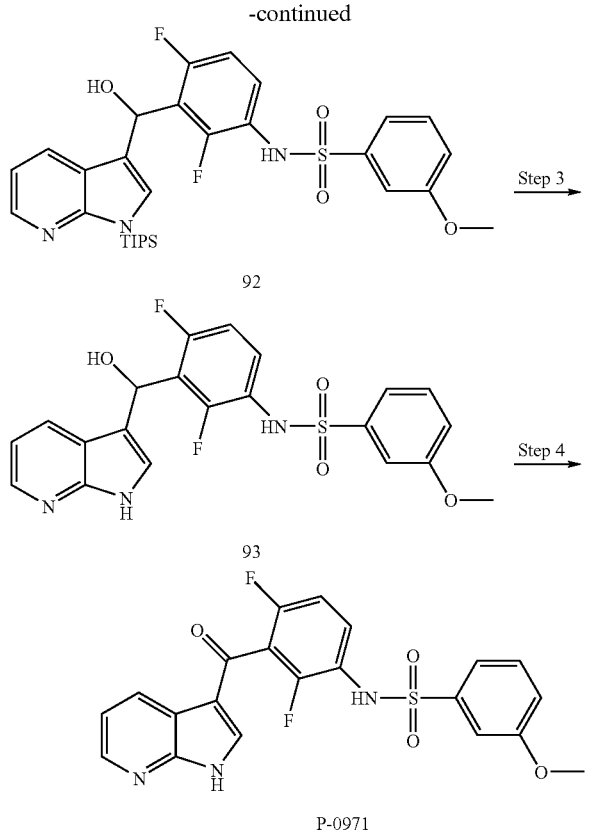

Step 1—Preparation of N-(2,4-difluoro-phenyl)-3-methoxy-benzenesulfonamide (91)

To 2,4-difluoro-phenylamine(42, 0.44 mL, 4.4 mmol) in methylene chloride (10.0 mL), under an atmosphere of nitrogen, were added pyridine (1.00 mL, 12.4 mmol) and 3-methoxy-benzenesulfonyl chloride (1.00 g, 4.84 mmol). After 12 hours, the reaction was poured into cold 1 M HCl and extracted with ethyl acetate. The organic layer was washed with brine, dried over anhydrous sodium sulfate and filtered. The filtrate was concentrated and purified by silica gel column chromatography eluting with 20% ethyl acetate in hexane to give light yellow solid (91, 0.90 g, 69%). MS(ESI) [M+H$^+$]$^+$=300.

Step 2—Preparation of N-{2,4-difluoro-3-[hydroxy-(1-triisopropylsilanyl-1H-pyrrolo[2,3-b]pyridin-3-yl)-methyl]-phenyl}-3-methoxy-benzenesulfonamide (92)

To N-(2,4-difluoro-phenyl)-3-methoxy-benzenesulfonamide (91, 0.148 g, 0.494 mmol) in tetrahydrofuran (10.0 mL) cooled in a −78° C. acetone/dry ice bath, under an atmosphere of nitrogen, was added lithium diisopropylamide (0.85 M in tetrahydrofuran, 1.45 mL, 1.23 mmol) dropwise. After 30 minutes, 1-triisopropylsilanyl-1H-pyrrolo[2,3-b]pyridine-3-carbaldehyde (96, 0.15 g, 0.500 mmol, prepared as described in Example 12) was added in tetrahydrofuran (2.0 mL) into the reaction dropwise. Then the reaction was stirred for 1 hour at −78° C. and allowed to reach room temperature. The reaction was poured into water and extracted with ethyl acetate. The organic layer was washed with brine, dried over anhydrous sodium sulfate and filtered. The filtrate was concentrated and purified by silica gel column chromatography eluting with 40% ethyl acetate in hexane to give light yellow solid (92, 0.080 g, 26.8%). MS(ESI) [M+H$^+$]$^+$=602.

Step 3—Preparation of N-{2,4-difluoro-3-[hydroxy-(1H-pyrrolo[2,3-b]pyridin-3-yl)methyl]-phenyl}-3-methoxy-benzenesulfonamide (93)

To N-{2,4-difluoro-3-[hydroxy-(1-triisopropylsilanyl-1H-pyrrolo[2,3-b]pyridin-3-yl)-methyl]-phenyl}-3-methoxy-benzenesulfonamide (92, 0.075 g, 0.12 mmol) in tetrahydrofuran (3.0 mL), was added tetra-n-butylammonium fluoride (0.039 g, 0.15 mmol). The reaction was stirred at room temperature for 20 minutes. The reaction was poured into water and extracted with ethyl acetate. The organic layer was washed with brine, dried over anhydrous sodium sulfate and filtered. The filtrate was concentrated and purified by silica gel column chromatography eluting with 3% methanol in dichloromethane to give light yellow solid (93, 0.030 g, 55%). MS(ESI)[M+H$^+$]$^+$=446.

Step 4—Preparation of N-[2,4-difluoro-3-(1H-pyrrolo[2,3-b]pyridine-3-carbonyl)phenyl]-3-methoxy-benzenesulfonamide (P-0971)

To N-{2,4-difluoro-3-[hydroxy-(1H-pyrrolo[2,3-b]pyridin-3-yl)methyl]-phenyl}-3-methoxy-benzenesulfonamide (93, 0.02 g, 0.05 mmol) in tetrahydrofuran (3.0 mL) was added Dess-Martin periodane (0.02 g, 0.015 mmol) under an atmosphere of nitrogen. The reaction was stirred for 10 minutes at room temperature. The reaction was poured into water and extracted with ethyl acetate. The organic layer was washed with brine, dried over anhydrous sodium sulfate and filtered. The filtrate was concentrated and purified by silica gel column chromatography eluting with 3% methanol in dichloromethane to give light yellow solid (P-0971, 0.010 g, 50%). MS(ESI)[M+H$^+$]$^+$=444.

Additional compounds were prepared following the protocol of Scheme 26, replacing 3-methoxy-benzene sulfonyl chloride with the appropriate sulfonyl chloride in Step 1. The following compounds were made following this procedure:

N-[2,4-Difluoro-3-(1H-pyrrolo[2,3-b]pyridine-3-carbonyl)-phenyl]-2,5-dimethoxy-benzenesulfonamide (P-1131),
N-[2,4-Difluoro-3-(1H-pyrrolo[2,3-b]pyridine-3-carbonyl)-phenyl]-4-methoxy-benzenesulfonamide (P-0958),
Piperidine-1-sulfonic acid [2,4-difluoro-3-(1H-pyrrolo[2,3-b]pyridine-3-carbonyl)-phenyl]-amide (P-0952),
N-[2,4-Difluoro-3-(1H-pyrrolo[2,3-b]pyridine-3-carbonyl)-phenyl]-4-trifluoromethyl-benzenesulfonamide (P-0931),
4-Butoxy-N-[2,4-difluoro-3-(1H-pyrrolo[2,3-b]pyridine-3-carbonyl)-phenyl]-benzenesulfonamide (P1006),
4-Chloro-N-[2,4-difluoro-3-(1H-pyrrolo[2,3-b]pyridine-3-carbonyl)-phenyl]-benzenesulfonamide (P-0937),
N-[2,4-Difluoro-3-(1H-pyrrolo[2,3-b]pyridine-3-carbonyl)-phenyl]-3,4-dimethoxy-benzenesulfonamide, (P-1090), and
3,4-Dichloro-N-[2,4-difluoro-3-(1H-pyrrolo[2,3-b]pyridine-3-carbonyl)-phenyl]-benzenesulfonamide (P-1015).

The following table indicates the sulfonyl chloride (column 2) used to afford the target compound (column 3). Column 1 provides the compound number and column 4 gives the observed mass.

| | Sulfonyl chloride | Compound | MS(ESI) [M + H+]+ observed |
|---|---|---|---|
| P-1131 | 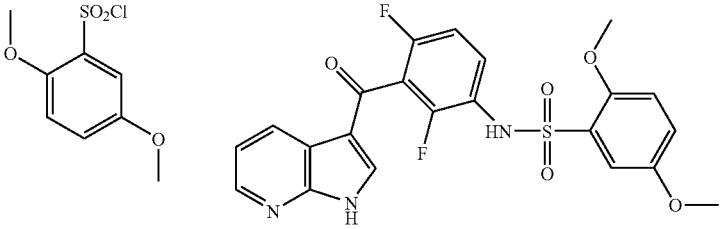 | 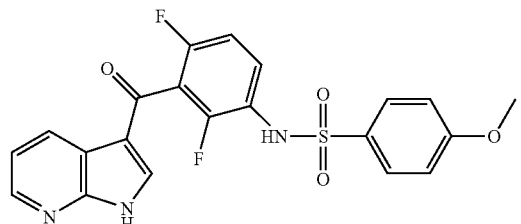 | 474.2 |
| P-0958 | 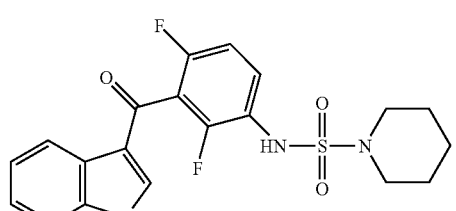 | 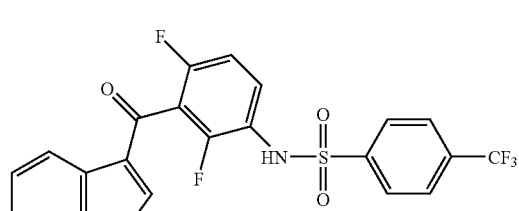 | 444.2 |
| P-0952 | 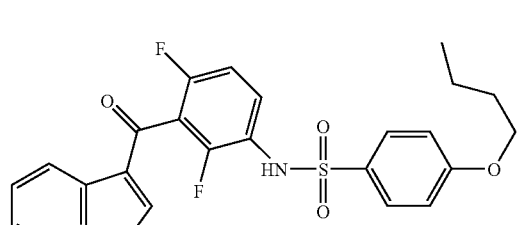 | 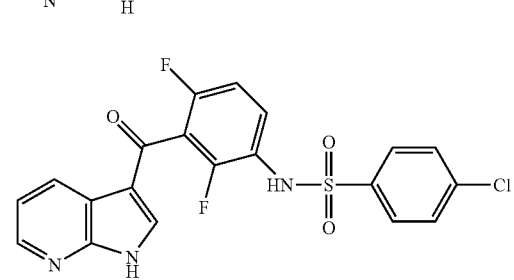 | 421.2 |
| P-0931 | | | 482.2 |
| P-1006 | | | 486.2 |
| P-0937 | | | 446.1 [M − H+]− |

| Sulfonyl chloride | Compound | MS(ESI) [M + H⁺]⁺ observed |
|---|---|---|
| P-1090 | | 474.2 |
| P-1015 | | 480.0 482.1 [M − H⁺]⁻ |

* Piperidine-1-sulfonyl chloride prepared from sulfuryl chloride and piperidine in acetonitrile, refluxed for 8 hours, concentrated, and used without further purification.

Example 12

Synthesis of 1-triisopropylsilanyl-1H-pyrrolo[2,3-b]pyridine-3-carbaldehyde 96

Compound 96 was synthesized in two steps from 7-azaindole 94 as described in Scheme 27.

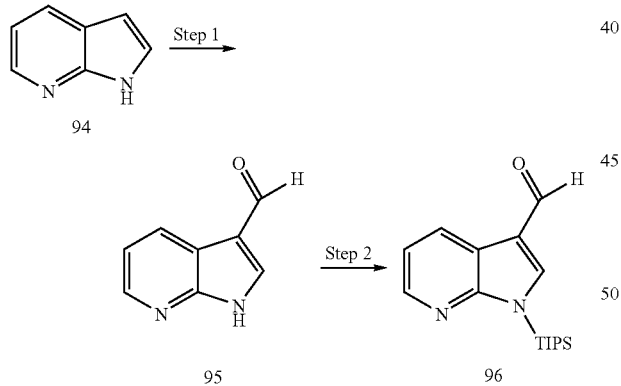

Step 1—Preparation of 1H-pyrrolo[2,3-b]pyridine-3-carbaldehyde (95)

To 1H-Pyrrolo[2,3-b]pyridine (94, 16.0 g, 135 mmol) in water (110 mL), were added hexamethylenetetramine (26.0 g, 185 mmol), and acetic acid (55.0 mL, 967 mmol). The reaction was refluxed for 12 hours. Water (329 mL) was added and the reaction was cooled to room temperature. The reaction was filtrated and washed with water to give the compound (95, 15.0 g, 76%). MS(ESI)[M+H⁺]⁺=147.

Step 2—Preparation of 1-triisopropylsilanyl-1H-pyrrolo[2,3-b]pyridine-3-carbaldehyde (96)

To 1H-Pyrrolo[2,3-b]pyridine-3-carbaldehyde (95, 4.05 g, 27.71 mmol) in tetrahydrofuran (30.0 mL) were added sodium hydride (60% in mineral oil, 1.5 g, 38 mmol) and trriisopropylsilyl chloride (8.0 mL, 38 mmol) under an atmosphere of nitrogen. The reaction was stirred for 2 hours at room temperature. The reaction was poured into water and extracted with ethyl acetate. The organic layer was washed with brine, dried over anhydrous sodium sulfate and filtered. The filtrate was concentrated and purified by silica gel column chromatography eluting with 10% ethyl acetate in hexane to give the compound (96, 3.0 g, 36%). MS(ESI)[M+H⁺]⁺=303.

Example 13

Synthesis of 5-isopropyl-1H-pyrrolo[2,3-b]pyridine 99

Compound 98 was synthesized in three steps from 5-bromo-1-triisopropylsilanyl-1H-pyrrolo[2,3-b]pyridine 68 described in Scheme 28.

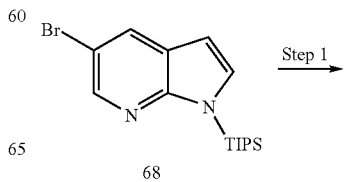

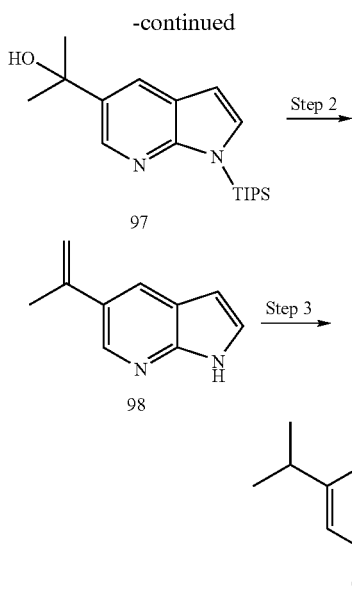

Step 1—Preparation of 2-(1-triisopropylsilanyl-1H-pyrrolo[2,3-b]pyridin-5-yl)-propan-2-ol (97)

To 5-bromo-1-triisopropylsilanyl-1H-pyrrolo[2,3-b]pyridine (68, 2.0 g, 5.66 mmol, prepared as described in Example 6) in tetrahydrofuran (20.0 mL), cooled in a −78° C. acetone/dry ice bath, under an atmosphere of nitrogen, was added tert-butyllithium (1.7 M in tetrahydrofuran, 7.3 mL, 12 mmol) dropwise. After 20 minutes, acetone (0.830 mL, 11 mmol) was added dropwise to the reaction. The reaction was stirred for 30 minutes at −78° C. and then allowed to reach room temperature. The reaction was poured into water and extracted with ethyl acetate. The organic layer was washed with brine, dried over anhydrous sodium sulfate and filtered. The filtrate was concentrated and purified by silica gel column chromatography eluting with 10% ethyl acetate in hexane to give the compound (97, 1.30 g, 69%). MS(ESI)[M+H$^+$]$^+$=333.

Step 2—Preparation of 5-isopropenyl-1H-pyrrolo[2,3-b]pyridine (98)

To 2-(1-triisopropylsilanyl-1H-pyrrolo[2,3-b]pyridin-5-yl)-propan-2-ol (97, 0.500 g, 1.5 mmol) in acetonitrile (10.0 mL) were added triethylsilane (1.00 mL, 6.3 mmol) and trifluoroacetic acid (0.50 mL, 6.5 mmol) under an atmosphere of nitrogen. The reaction was refluxed for 3 hours, then cooled down to room temperature. The reaction was poured into water and extracted with ethyl acetate. The organic layer was washed with brine, dried over anhydrous sodium sulfate and filtered. The filtrate was concentrated and purified by silica gel column chromatography eluting with 50% ethyl acetate in hexane to give the compound (98, 0.200 g, 84%). MS(ESI)[M+H$^+$]$^+$=159.

Step 3—Preparation of 5-isopropyl-1H-pyrrolo[2,3-b]pyridine (99)

To 5-isopropenyl-1H-pyrrolo[2,3-b]pyridine (98, 0.080 g, 0.501 mmol) in tetrahydrofuran (5.0 mL) was added 20% palladium hydroxide on carbon (5.0 mg). The reaction was stirred under hydrogen at 40 psi for 30 minutes. The reaction mixture was filtered and concentrated to give the compound (99, 0.078 g, 96%). MS(ESI)[M+H$^+$]$^+$=161.

Example 14

Synthesis of 5-Methyl-1H-pyrrolo[2,3-b]pyridine 101

Compound 101 was synthesized in two steps from 5-bromo-1-triisopropylsilanyl-1H-pyrrolo[2,3-b]pyridine 68 described in Scheme 29.

Scheme 29

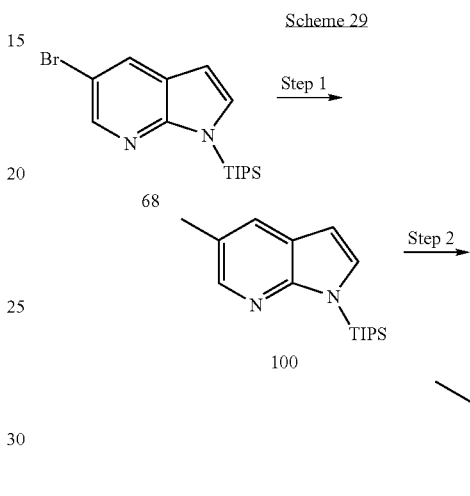

Step 1—Preparation of 5-Methyl-1-triisopropylsilanyl-1H-pyrrolo[2,3-b]pyridine (100)

To PdCl$_2$(dppf) (0.04 g, 0.05 mmol) in toluene (10.0 mL) under an atmosphere of nitrogen were added 5-bromo-1-triisopropylsilanyl-1H-pyrrolo[2,3-b]pyridine (68, 0.3 g, 0.8 mmol, prepared as described in Example 6, 1.0 mL in toluene) and methylmagnesium bromide (1.0 M in tetrahydrofuran, 3.0 mL, 3.0 mmol). The reaction was stirred 90° C. for 2 hours and then allowed to reach to room temperature. The reaction was poured into citric acid (0.1 M in water) and extracted with ethyl acetate. The organic layer was washed with brine, dried over anhydrous sodium sulfate and filtered. The filtrate was concentrated and purified by silica gel column chromatography eluting with 50% ethyl acetate in hexane to give the compound (100, 0.16 g, 60.0%), MS(ESI)[M+H$^+$]$^+$=289.4.

Step 2—Preparation of 5-Methyl-1H-pyrrolo[2,3-b]pyridine (101)

To 5-Methyl-1-triisopropylsilanyl-1H-pyrrolo[2,3-b]pyridine (100, 0.160 g, 0.55 mmol) in tetrahydrofuran (3.0 mL) was added tetra-n-butylammonium fluoride (0.145 g, 0.55 mmol). The reaction was stirred for 1 hour at room temperature. The reaction was poured into water and extracted with ethyl acetate. The organic layer was washed with brine, dried over anhydrous sodium sulfate and filtered. The filtrate was concentrated and purified by silica gel column chromatography eluting with 3% methanol in dichloromethane to provide light yellow solid (101, 0.07 g, 95%). MS(ESI)[M+H$^+$]$^+$=133.2.

5-Methyl-1H-pyrrolo[2,3-b]pyridine

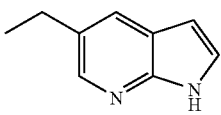

was prepared following the protocol of Scheme 29, substituting methylmagnesium bromide with ethylmagnesium bromide in Step 1.

Example 15

Synthesis of 1-[2,4-difluoro-3-(5-pyridin-3-yl-1H-pyrrolo[2,3-b]pyridine-3-carbonyl)-phenyl]-3-propyl-urea P-0774 and Related Compounds Compound P-0774 was synthesized in two steps from {2,4-difluoro-3-[hydroxy-(5-pyridin-3-yl-1H-pyrrolo[2,3b]pyridin-3-yl)-methyl]-phenyl}-carbamic acid methyl ester P-0065 described in Scheme 30.

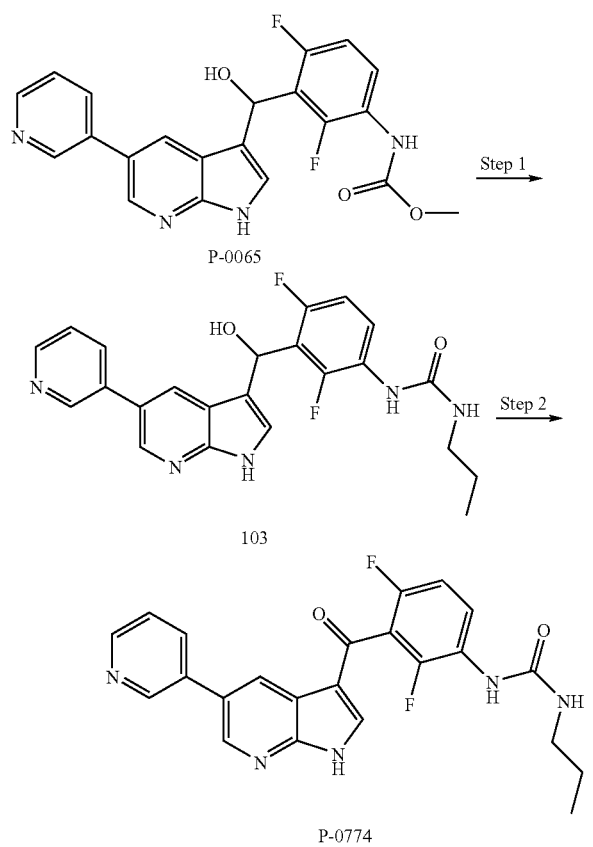

Step 1—Preparation of 1-{2,4-difluoro-3-[hydroxy-(5-pyridin-3-yl-1H-pyrrolo[2,3 b]pyridin-3-yl)-methyl]-phenyl}-3-propyl-urea (103)

To {2,4-difluoro-3-[hydroxy-(5-pyridin-3-yl-1H-pyrrolo[2,3b]pyridin-3-yl)-methyl]-phenyl}-carbamic acid methyl ester (P-0065, 30.0 mg, 0.07 mmol, prepared as described in Example 10) was added 1-propanamine (2.0 mL, 20 mmol) and the reaction was heated to 120° C. for 20 minutes in a CEM Discover microwave instrument. The reaction was poured into water and extracted with ethyl acetate. The organic layer was washed with brine, dried over anhydrous sodium sulfate and filtered. The filtrate was concentrated and purified by silica gel column chromatography eluting with 5% methanol in methylene chloride to give the compound (103, 20.0 mg, 60%). MS(ESI)[M+H$^+$]$^+$=438.51.

Step 2—Preparation of 1-[2,4-difluoro-3-(5-pyridin-3-yl-1H-pyrrolo[2,3-b]pyridine-3-carbonyl)-phenyl]-3-propyl-urea (P-0774)

To 1-{2,4-difluoro-3-[hydroxy-(5-pyridin-3-yl-1H-pyrrolo[2,3b]pyridin-3-yl)-methyl]-phenyl}-3-propyl-urea (103, 20.0 mg, 0.04 mmol) in tetrahydrofuran (3 mL) was added Dess-Martin periodane (23.0 mg, 0.055 mmol) under an atmosphere of nitrogen. The reaction was stirred for 10 minutes. The reaction was concentrated and purified by silica gel column chromatography eluting with 1% methanol in dichloromethane to give the compound (P-0774, 6.0 mg, 30%). MS(ESI)[M+H$^+$]$^+$=436.5.

Additional compounds were prepared following the protocol of Scheme 30, replacing 1-propanamine with an appropriate amine and optionally replacing {2,4-difluoro-3-[hydroxy-(5-pyridin-3-yl-1H-pyrrolo[2,3b]pyridin-3-yl)-methyl]-phenyl}-carbamic acid methyl ester P-0065 with an appropriate carbamic acid methyl ester (see Example 10) in Step 1. The following compounds were made following this procedure:

1-sec-Butyl-3-[2,4-difluoro-3-(5-pyridin-3-yl-1H-pyrrolo[2,3-b]pyridine-3-carbonyl)-phenyl]-urea (P-1289),
1-Cyclopentyl-3-[2,4-difluoro-3-(5-pyridin-3-yl-1H-pyrrolo[2,3-b]pyridine-3-carbonyl)-phenyl]-urea (P-1317),
1-Butyl-3-[2,4-difluoro-3-(5-pyridin-3-yl-1H-pyrrolo[2,3-b]pyridine-3-carbonyl)-phenyl]-urea (P-1318),
1-Butyl-3-[2,4-difluoro-3-(5-methoxy-1H-pyrrolo[2,3-b]pyridine-3-carbonyl)-phenyl]-urea (P-1567),
1-[3-(5-Chloro-1H-pyrrolo[2,3-b]pyridine-3-carbonyl)-2,4-difluoro-phenyl]-3-(2-morpholin-4-yl-ethyl)-urea (P-1580),
1-Butyl-3-[3-(5-chloro-1H-pyrrolo[2,3-b]pyridine-3-carbonyl)-2,4-difluoro-phenyl]-urea (P-1586),
Morpholine-4-carboxylic acid [3-(5-chloro-1H-pyrrolo[2,3-b]pyridine-3-carbonyl)-2,4-difluoro-phenyl]-amide (P-1606),
1-Butyl-3-[3-(5-chloro-1H-pyrrolo[2,3-b]pyridine-3-carbonyl)-2,4-difluoro-phenyl]-1-methyl-urea (P-1612),
1-Butyl-3-[2,4-difluoro-3-(5-methoxy-1H-pyrrolo[2,3-b]pyridine-3-carbonyl)-phenyl]-1-methyl-urea (P-1884),
Morpholine-4-carboxylic acid [2,4-difluoro-3-(5-methoxy-1H-pyrrolo[2,3-b]pyridine-3-carbonyl)-phenyl]-amide (P-1894),
1-Butyl-3-[2,4-difluoro-3-(1H-pyrrolo[2,3-b]pyridine-3-carbonyl)-phenyl]-1-ethyl-urea (P-1983),
1-Butyl-3-[2,4-difluoro-3-(5-methoxy-1H-pyrrolo[2,3-b]pyridine-3-carbonyl)-phenyl]-1-ethyl-urea (P-1994), and
3-Diethylamino-pyrrolidine-1-carboxylic acid [2,4-difluoro-3-(5-methoxy-1H-pyrrolo[2,3-b]pyridine-3-carbonyl)-phenyl]-amide (P-2015).

The following table indicates the amine (column 2) and the carbamic acid methyl ester (column 3) used to afford the target compounds (column 4). Column 1 provides the compound number and column 5 the observed mass.

| | Amine | Carbamic acid methyl ester | Compound | MS(ESI) [M + H+]+ observed |
|---|---|---|---|---|
| P-1289 |  | 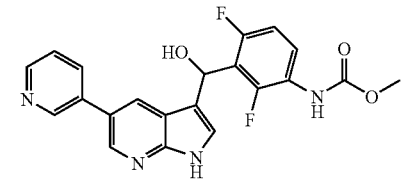 [SMILES: COC(=O)Nc1ccc(F)c(C(O)c2c[nH]c3ncc(-c4cccnc4)cc23)c1F] | 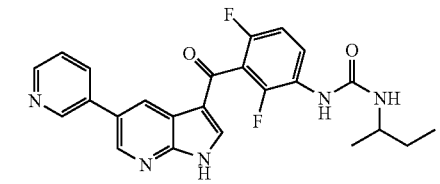 [SMILES: CCC(C)NC(=O)Nc1ccc(F)c(C(=O)c2c[nH]c3ncc(-c4cccnc4)cc23)c1F] | 450.4 |
| P-1317 | 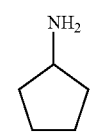 | 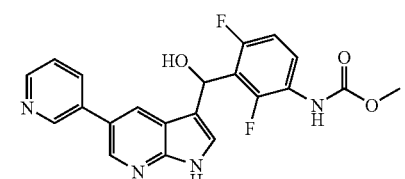 | 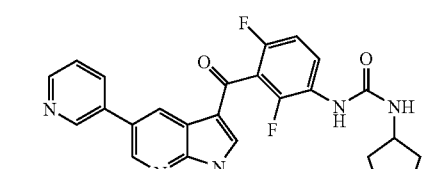 | 462.4 |
| P-1318 | 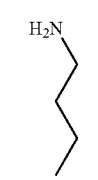 | 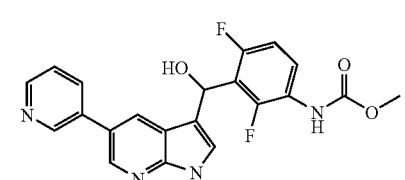 | 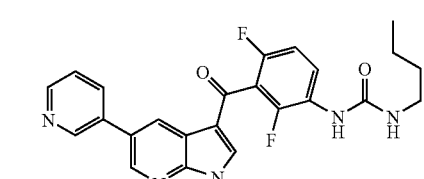 | 450.5 |
| P-1567 | 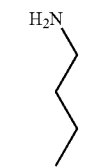 | 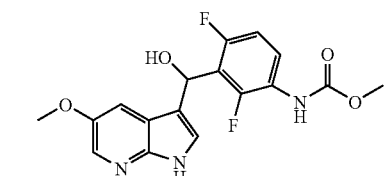 | 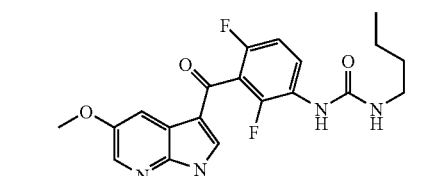 | 403.2 |
| P-1580 | 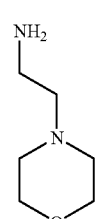 | 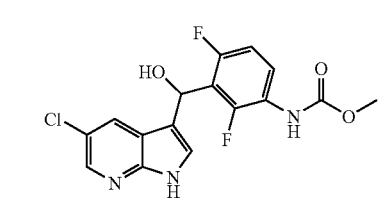 [SMILES: COC(=O)Nc1ccc(F)c(C(O)c2c[nH]c3ncc(Cl)cc23)c1F] | 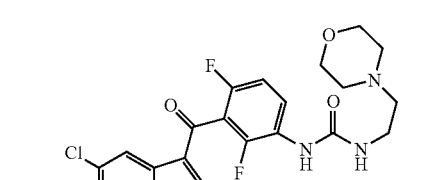 | 464.3 |
| P-1586 | 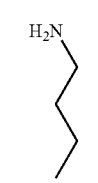 |  | 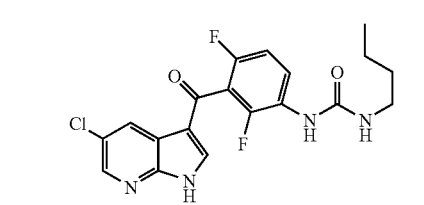 [SMILES: CCCCNC(=O)Nc1ccc(F)c(C(=O)c2c[nH]c3ncc(Cl)cc23)c1F] | 407.3 |
| P-1606 | 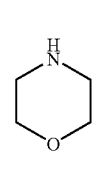 | 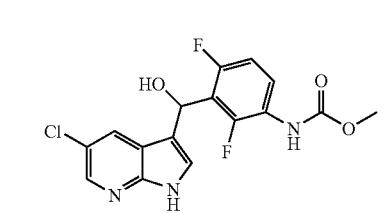 [SMILES: COC(=O)Nc1ccc(F)c(C(O)c2c[nH]c3ncc(Cl)cc23)c1F] |  | 421.1 |

-continued

| Amine | Carbamic acid methyl ester | Compound | MS(ESI) [M + H⁺]⁺ observed |
|---|---|---|---|
| P-1612 | | | 421.3 |
| P-1884 | | | 417.4 |
| P-1894 | | | 417.4 |
| P-1983 | | | 401.4 |
| P-1994 | | | 431.4 |
| P-2015 | | | 472.4 |

The intermediate product of Step 1 of Scheme 30 can alternatively be reacted under reducing conditions to provide analogous compounds in which the carbonyl linker of the 3-position of azaindole to the phenyl ring is methylene. The product of Step 1 is a mixture of the hydroxyl and methoxy methyl linker of the 3-position, which may be carried through the reduction Step as the mixture or may be isolated as either the hydroxyl or methoxy for use in this reaction. This reduction is exemplified as follows using the product of Step 1 in the preparation of P-1567 to prepare 1-Butyl-3-[2,4-difluoro-3-(5-methoxy-1H-pyrrolo[2,3-b]pyridin-3-ylmethyl)-phenyl]-urea P-1571.

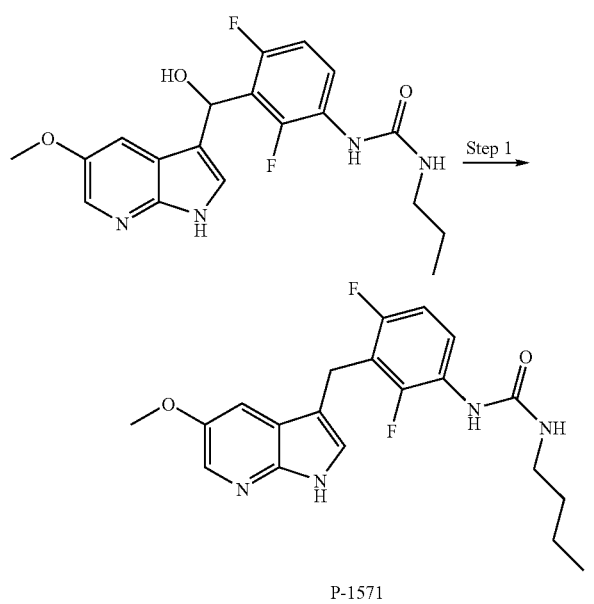

P-1571

Step 1—Preparation of 1-Butyl-3-[2,4-difluoro-3-(5-methoxy-1H-pyrrolo[2,3-b]pyridin-3-ylmethyl)-phenyl]-urea (P-1571)

A mixture of 1-Butyl-3-2,4-difluoro-3-[hydroxy-(5-methoxy-1H-pyrrolo[2,3-b]pyridin-3-yl)-methyl]-phenyl-urea (41 mg, 0.000081 mol, isolated from Step 1 of Scheme 30), triethylsilane (2 mL, 0.01 mol), and trifluoroacetic acid (1 mL, 0.01 mol) in 20 ml of acetonitrile was refluxed for 3 hrs. The mixture was concentrated and the residue was redissolved in ethyl acetate and sodium bicarbonate solution. The organic layer was collected and dried over MgSO$_4$. An off-white solid compound was obtained after chromatography (P-1571, 18 mg, 57%). MS(ESI) [M–H$^+$]$^-$=389.2.

Additional compounds were prepared following the protocol of Step 1 of Scheme 30 followed by the reduction step above as Step 2, where the product of Scheme 30 Step 1 may be isolated as either the hydroxyl or methoxy derivative, or used as the mixture, replacing 1-propanamine with an appropriate amine and {2,4-difluoro-3-[hydroxy-(5-pyridin-3-yl-1H-pyrrolo[2,3b]pyridin-3-yl)-methyl]-phenyl}-carbamic acid methyl ester P-0065 with an appropriate carbamic acid methyl ester (see Example 10) in Step 1. The following compounds were made following this procedure:

1-Cyclopentyl-3-[2,4-difluoro-3-(5-methoxy-1H-pyrrolo[2,3-b]pyridin-3-ylmethyl)-phenyl]-urea (P-1572), 1-[3-(5-Chloro-1H-pyrrolo[2,3-b]pyridin-3-ylmethyl)-2,4-difluoro-phenyl]-3-cyclopentyl-urea (P-1575), 1-Butyl-3-[3-(5-chloro-1H-pyrrolo[2,3-b]pyridin-3-ylmethyl)-2,4-difluoro-phenyl]-urea (P-1587), 1-[3-(5-Chloro-1H-pyrrolo[2,3-b]pyridin-3-ylmethyl)-2,4-difluoro-phenyl]-3-(2-morpholin-4-yl-ethyl)-urea (P4594), Morpholine-4-carboxylic acid [3-(5-chloro-1H-pyrrolo[2,3-b]pyridin-3-ylmethyl)-2,4-difluoro-phenyl]-amide (P-1595), 1-[3-(5-Chloro-1H-pyrrolo[2,3-b]pyridin-3-ylmethyl)-2,4-difluoro-phenyl]-3-(2,2,2-trifluoro-ethyl)-urea (P-1601), 1-Cyclopentyl-3-{2,4-difluoro-3-[5-(3-methanesulfonyl-phenyl)-1H-pyrrolo[2,3-b]pyridin-3-ylmethyl]-phenyl}-urea (P-1615), 1-Butyl-3-[3-(5-chloro-1H-pyrrolo[2,3-b]pyridin-3-ylmethyl)-2,4-difluoro-phenyl]-1-methyl-urea (P-1625), 1-[3-(5-Chloro-1H-pyrrolo[2,3-b]pyridin-3-ylmethyl)-2,4-difluoro-phenyl]-3-cyclopropylmethyl-urea (P-1652), 1-[3-(5-Chloro-1H-pyrrolo[2,3-b]pyridin-3-ylmethyl)-2,4-difluoro-phenyl]-3-(4-fluoro-phenyl)-urea (P-1657), 1-[3-(5-Chloro-1H-pyrrolo[2,3-b]pyridin-3-ylmethyl)-2,4-difluoro-phenyl]-3-(4-fluoro-benzyl)-urea (P-1654), and 3-Diethylamino-pyrrolidine-1-carboxylic acid [2,4-difluoro-3-(5-methoxy-1H-pyrrolo[2,3-b]pyridin-3-ylmethyl)-phenyl]-amide (P-2014).

The following table indicates the amine (column 2) and the carbamic acid methyl ester (column 3) used to afford the target compound (column 4). For the carbamic acid methyl ester, R can be H or CH$_3$, where the compound was either a mixture of the two, or either of the isolated compounds wherein R is H or R is CH$_3$. Column 1 provides the compound number and column 5 the observed mass.

| | Amine | Carbamic acid methyl ester | Compound | MS(ESI) [M + H$^+$]$^+$ observed |
|---|---|---|---|---|
| P-1572 | NH$_2$-cyclopentyl | | | 401.2 |

-continued

| Amine | Carbamic acid methyl ester | Compound | MS(ESI) [M + H+]+ observed |
|---|---|---|---|
| P-1575 | | | 405.2 |
| P-1587 | | | 393.3 |
| P-1594 | | | 450.3 |
| P-1595 | | | 407.2 |
| P-1601 | | | 419.2 |

| | Amine | Carbamic acid methyl ester | Compound | MS(ESI) [M + H+]+ observed |
|---|---|---|---|---|
| P-1615 | 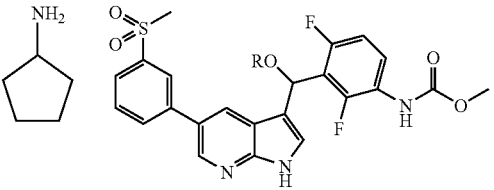 | 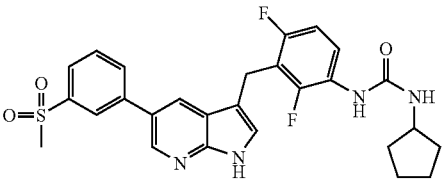 [SMILES: CS(=O)(=O)c1cccc(-c2cnc3[nH]cc(Cc4c(F)ccc(NC(=O)NC5CCCC5)c4F)c3c2)c1] | 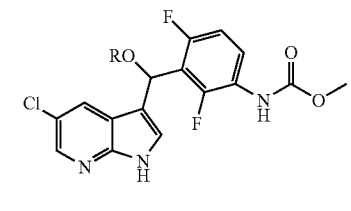 | 525.2 |
| P-1625 | 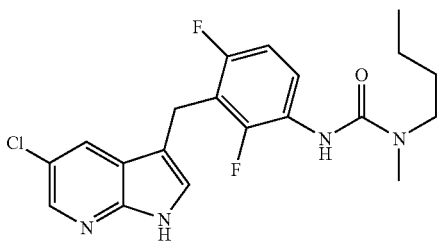 [SMILES: CCCCN(C)C(=O)Nc1ccc(F)c(Cc2c[nH]c3ncc(Cl)cc23)c1F] | 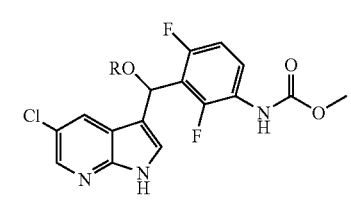 | 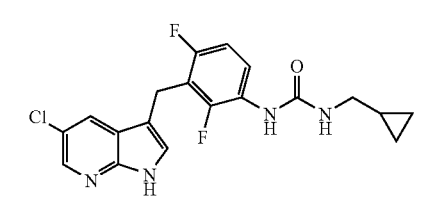 [SMILES: O=C(NCC1CC1)Nc1ccc(F)c(Cc2c[nH]c3ncc(Cl)cc23)c1F] | 407.3 |
| P-1652 | 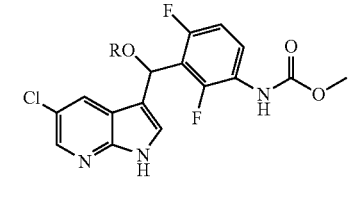 | 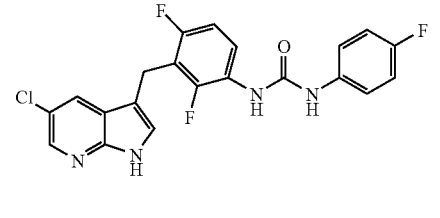 [SMILES: O=C(Nc1ccc(F)cc1)Nc1ccc(F)c(Cc2c[nH]c3ncc(Cl)cc23)c1F] | 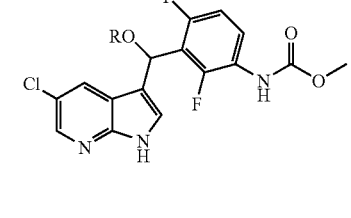 | 391.2 |
| P-1657 | 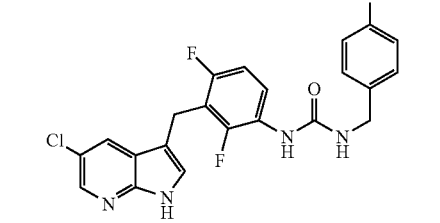 | 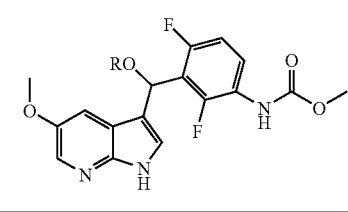 | 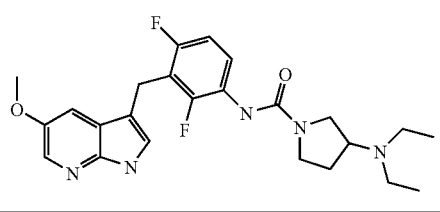 | 461.2 |
| P-1654 | | | | 445.2 |
| P-2014 | | | | 458.4 |

Example 16

Synthesis of 5-Methoxy-1H-pyrrolo[2,3-b]pyridine 104 and Related Compounds

Compound 104 was synthesized in one step from 5-bromo-1H-pyrrolo[2,3-b]pyridine 67 as described in Scheme 31.

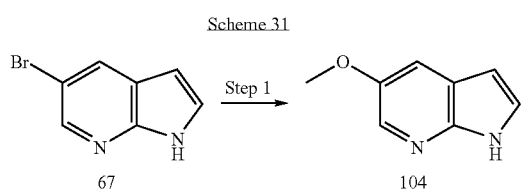

Step 1—Preparation of 5-Methoxy-1H-pyrrolo[2,3-b]pyridine (104)

To 5-bromo-7-azaindole (67, 500.0 mg, 2.53 mmol) in N,N-dimethylformamide (8 mL) were added copper(I) iodide (966 mg, 5.08 mmol) and sodium methoxide in methanol (3 M, 5 mL). The reaction was stirred overnight at 120° C. under an atmosphere of Argon. The reaction was poured into water, and extracted with ethyl acetate. The organic layer was dried over anhydrous sodium sulfate, filtered. The filtrate was concentrated and purified with silica gel column chromatograph eluting with 20% ethyl acetate in hexane to give white solid (104, 140 mg, 28%). MS(ESI)[M+H$^+$]$^+$=149.1. In an alternative method, 2.3 g (11.7 mmol) 5-bromo-7-azaindole (67, 2.3 g, 11.7 mmol) was dissolved in 75 mL N,N-dimethylformamide and 50 mL methanol (50 mL), adding sodium methoxide (32 g, 0.6 mol) and copper-(I) bromide (3.2 g, 22.4 mmol) at room temperature. The reaction was stirred for three hours at 100° C. under an atmosphere of argon. The mixture was diluted with ethyl acetate and poured into a solution of ammonium chloride:ammonium hydroxide (4:1). The organic layer was extracted with ammonium chloride:ammonium hydroxide (4:1), washed with brine, dried over anhydrous sodium sulfate, filtered and concentrated. The desired compound was isolated by silica gel column chromatography eluting with 30% to 70% ethyl acetate in hexanes to give a yellow solid (104, 0.27 g, 15.6%). MS(EST) [M+H$^+$]$^+$=149.2.

5-Ethoxy-1H-pyrrolo[2,3-b]pyridine 506

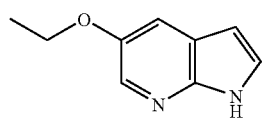

was prepared using the protocol of Scheme 31, substituting methanol with ethanol and sodium methoxide with sodium ethoxide.

5-(2-Methoxy-ethoxy)-1H-pyrrolo[2,3-b]pyridine 507

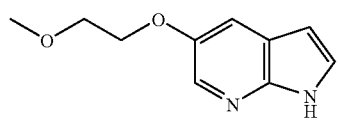

was prepared using the protocol of Scheme 31, substituting methanol with 2-Methoxy-ethanol and sodium methoxide with sodium 2-Methoxy-ethoxide (prepared from 2-Methoxy-ethanol and sodium hydride). MS(ESI) [M+H$^+$]$^+$=193.3.

Diethyl-[2-(1H-pyrrolo[2,3-b]pyridin-5-yloxy)-ethyl]-amine 508

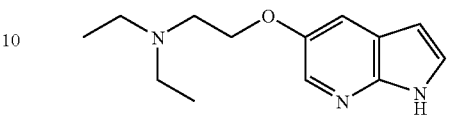

was prepared using the protocol of Scheme 31, substituting methanol with 2-diethylamino-ethanol and sodium methoxide with sodium 2-diethylamino-ethoxide (prepared from 2 2-diethylamino-ethanol and sodium hydride). MS(ESI) [M+H$^+$]$^+$=234.5.

Example 17

Synthesis of 5-Pyridin-3-yl-1H-pyrrolo[2,3-b]pyridine 89

5-Pyridin-3-yl-1H-pyrrolo[2,3-b]pyridine 89 was synthesized in one step from 5-bromo-1H-pyrrolo[2,3-b]pyridine 67 as described in Scheme 32.

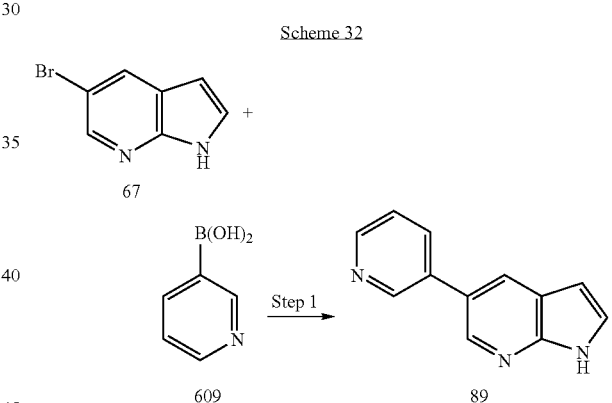

Step 1—Preparation of 5-Pyridin-3-yl-1H-pyrrolo[2,3-b]pyridine (89)

To 5-bromo-7-azaindole (67, 1.00 g, 5.08 mmol) in water (13.0 mL) and acetonitrile (36 mL) were added pyridine-3-boronic acid (609, 1.0 g, 8.1 mmol), potassium carbonate (1.79 g, 0.0130 mol) and Tetrakis(triphenylphosphine)palladium(0) (50.0 mg, 0.043 mmol) under an atmosphere of nitrogen. The reaction mixture was heated to 170° C. overnight. The reaction mixture was poured into water and extracted with ethyl acetate. The organic layer was washed with brine, dried over sodium sulfate, and concentrated. The residue was purified with silica gel column chromatography eluting with 25% ethyl acetate in hexane to provide a light yellow solid (89, 820 mg, 82%). MS(ESI)[M+H$^+$]$^+$=196.1.

Additional compounds were prepared following the protocol of Scheme 32, either by substituting pyridine-3-boronic acid with an appropriate boronic acid or by substituting the 5-bromo-7-azaindole with 5-(4,4,5,5-Tetramethyl-[1,3,2]dioxaborolan-2-yl)-1H-pyrrolo[2,3-b]pyridine and reacting with a suitable aryl or heteroaryl halide (i.e. coupling with the boronic acid ester on the azaindole, and the halide on the group to be coupled to the 5-position of the azaindole). The following compounds were prepared by this procedure:

5-(4-Chloro-phenyl)-1H-pyrrolo[2,3-b]pyridine (514),
5-(4-Fluoro-phenyl)-1H-pyrrolo[2,3-b]pyridine (605),
5-Phenyl-1H-pyrrolo[2,3-b]pyridine,
5-(6-Methoxy-pyridin-3-yl)-1H-pyrrolo[2,3-b]pyridine,
5-(2-Methoxy-pyrimidin-5-yl)-1H-pyrrolo[2,3-b]pyridine,
5-Pyridin-4-yl-1H-pyrrolo[2,3-b]pyridine,
4-(1H-Pyrrolo[2,3-b]pyridin-5-yl)-benzenesulfonamide,
3-(1H-Pyrrolo[2,3-b]pyridin-5-yl)-benzenesulfonamide,
5-Pyrimidin-5-yl-1H-pyrrolo[2,3-b]pyridine,
5-(3-Methanesulfonyl-phenyl)-1H-pyrrolo[2,3-b]pyridine (P-0173), and
3-(1H-Pyrrolo[2,3-b]pyridin-5-yl)-benzamide (P-1622), The following table indicates either 5-bromo-7-azaindole or 5-(4,4,5,5-Tetramethyl-[1,3,2]dioxaborolan-2-yl)-1H-pyrrolo[2,3-b]pyridine starting material (column 1) and the appropriate reagent to be coupled to the 5 position of the azaindole (column 2) to afford the resulting compound (column 3), with the observed mass given in column 4.

| Starting azaindole | Reagent coupled to 5 position | Compound | MS(ESI) $[M + H^+]^+$ observed |
|---|---|---|---|
| 5-bromo-7-azaindole | 4-chlorophenylboronic acid | 5-(4-chlorophenyl)-7-azaindole | 229.1 |
| 5-bromo-7-azaindole | 4-fluorophenylboronic acid | 5-(4-fluorophenyl)-7-azaindole | 213.1 |
| 5-bromo-7-azaindole | phenylboronic acid | 5-phenyl-7-azaindole | 195.2 |
| 5-bromo-7-azaindole | 6-methoxypyridin-3-yl boronic acid | 5-(6-methoxypyridin-3-yl)-7-azaindole | 226.2 |
| 5-bromo-7-azaindole | 2-methoxypyrimidin-5-yl boronic acid | 5-(2-methoxypyrimidin-5-yl)-7-azaindole | 227.2 |
| 5-(pinacolboronate)-7-azaindole | 4-iodopyridine | 5-(pyridin-4-yl)-7-azaindole | 196.2 |

| Starting azaindole | Reagent coupled to 5 position | Compound | MS(ESI) [M + H⁺]⁺ observed |
|---|---|---|---|
| | | | 274.1 |
| | | | 274.1 |
| | | | 197.2 |
| | | | 273.1 |
| | | | 238.2 |

Example 18

Synthesis of 3-(4-(4-chlorobenzyloxy)-3-methoxy-benzyl)-1H-pyrrolo[2,3-b]pyridine P-1247

Compound P-1247 was synthesized in three steps from 4-hydroxy-3-methoxybenzaldehyde 105 as shown in Scheme 33.

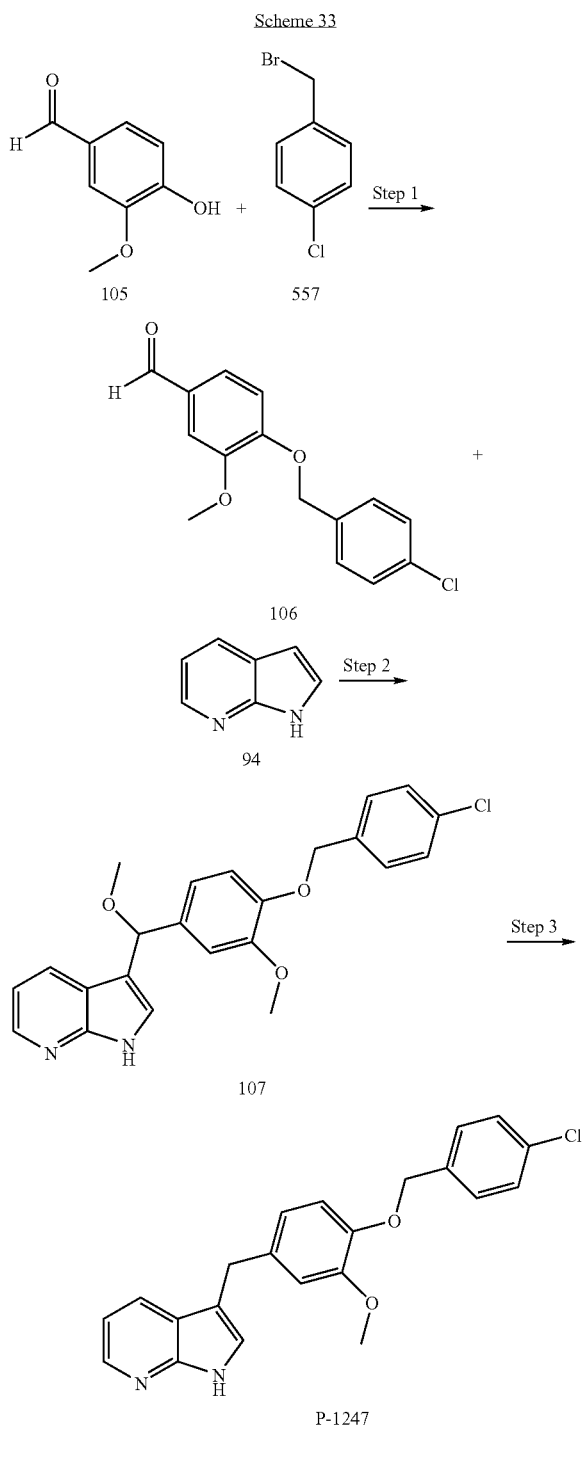

Step 1—Preparation of 4-(4-chlorobenzyloxy)-3-methoxybenzaldehyde (106)

To 4-hydroxy-3-methoxybenzaldehyde (105, 600.0 mg, 3.94 mmol) and 4-chlorobenzyl bromide (557, 1.20 g, 5.84 mmol) in acetonitrile (6 mL) was added potassium carbonate (0.390 g, 2.82 mmol). The reaction was microwaved on 300 watts, 120° C. for 10 minutes. The reaction was extracted with ethyl acetate and water. The organic layer was washed with brine, dried over magnesium sulfate, filtered and the volatiles removed by evaporation. The desired compound was purified by recrystallization from hexanes to provide 106 (1.01 g, 93%). MS(ESI) $[M-H^+]^-=275.1$.

Step 2—Preparation of 3-((4-(4-chlorobenzyloxy)-3-methoxyphenyl)(methoxy)methyl)-1H-pyrrolo[2,3-b]pyridine (107)

To 1H-Pyrrolo[2,3-b]pyridine (94, 0.235 g, 1.99 mmol) and 4-(4-chlorobenzyloxy)-3-methoxybenzaldehyde (106, 0.500 g, 1.81 mmol) was added 5 mL of methanol followed by the addition of solid potassium hydroxide (0.203 g, 3.61 mmol). The reaction was allowed to stir at ambient temperature for 18 days. The reaction mixture was poured into water and extracted with ethyl acetate. The organic layer was separated and volatiles removed to give a solid which was suspended in hot ethyl acetate. The suspension was allowed to cool and the solid collected by vacuum filtration to provide 107 (548 mg, 74%). MS(ESI) $[M+H^+]^+=409.4$.

Step 3—Preparation of 3-(4-(4-chlorobenzyloxy)-3-methoxybenzyl)-1H-pyrrolo[2,3-b]pyridine (P-1247)

To 3-((4-(4-chlorobenzyloxy)-3-methoxyphenyl)(methoxy)methyl)-1H-pyrrolo[2,3-b]pyridine (107, 0.548 g, 1.34 mmol) in acetonitrile (20 mL) was added trifluoroacetic acid (1.7 mL, 2.21 mmol) and triethylsilane (3.47 mL, 2.17 mmol). The reaction was stirred at 60° C. for 15 hours. The volatiles were removed and the desired compound was purified by silica gel chromatography, eluting with a gradient from 0% to 60% ethyl acetate in hexanes to provide a white solid (P-1247, 505 mg, 99%). MS(ESI) $[M+H^+]^+=379.4$.

Additional compounds were prepared using the protocol of Scheme 33, Steps 2 and 3, replacing 4-(4-chlorobenzyloxy)-3-methoxybenzaldehyde 106 with a suitable aldehyde (prepared as described in Example 34), and optionally replacing 1H-Pyrrolo[2,3-b]pyridine 94 with an appropriate substituted 7-azaindole (see Example 9 or Example 16) in Step 2. The following compounds were made following this procedure:

3-[3-Methoxy-4-(4-trifluoromethyl-benzyloxy)-benzyl]-1H-pyrrolo[2,3-b]pyridine (P-1721),
3-[3-Trifluoromethyl-4-(4-trifluoromethyl-benzyloxy)-benzyl]-1H-pyrrolo[2,3-b]pyridine (P-1797),
3-{3-Methoxy-4-[4-(4-methyl-piperazin-1-ylmethyl)-benzyloxy]-benzyl}-1H-pyrrolo[2,3-b]pyridine (P-1821),
3-[4-(4-Chloro-benzyloxy)-2-fluoro-5-methoxy-benzyl]-1H-pyrrolo[2,3-b]pyridine (P-1844),
3-[4-(3-Fluoro-4-trifluoromethyl-benzyloxy)-3-methoxy-benzyl]-1H-pyrrolo[2,3-b]pyridine (P-1849),
3-[4-(4-Chloro-3-trifluoromethyl-benzyloxy)-3-methoxy-benzyl]-1H-pyrrolo[2,3-b]pyridine (P-1851),
2-[2-Methoxy-4-(1H-pyrrolo[2,3-b]pyridin-3-ylmethyl)-phenoxymethyl]-1H-benzoimidazole (P1870), 3-[4-(4-Chloro-2-fluoro-benzyloxy)-2-fluoro-5-methoxy-benzyl]-5-methoxy-1H-pyrrolo[2,3-b]pyridine (P-1885),
3-[4-(3,4-Dichloro-benzyloxy)-3-methoxy-benzyl]-1H-pyrrolo[2,3-b]pyridine (P-1886),
3-[4-(4-Chloro-benzyloxy)-3-fluoro-benzyl]-1H-pyrrolo[2,3-b]pyridine (P-1896),
2-[2-Fluoro-4-(1H-pyrrolo[2,3-b]pyridin-3-ylmethyl)-phenoxymethyl]-1H-benzoimidazole (P-1899),
3-(4-Benzyloxy-2,5-difluoro-benzyl)-1H-pyrrolo[2,3-b]pyridine (P-1901),
5-Chloro-3-[4-(4-chloro-benzyloxy)-2-fluoro-5-methoxy-benzyl]-1H-pyrrolo[2,3-b]pyridine (P-1970),
5-Chloro-3-[4-(4-chloro-2-fluoro-benzyloxy)-2-fluoro-5-methoxy-benzyl]-1H-pyrrolo[2,3-b]pyridine (P-1972),
3-[4-(4-Chloro-2-fluoro-benzyloxy)-2-fluoro-5-methoxy-benzyl]-1H-pyrrolo[2,3-b]pyridine (P-1973),
2-[4-(5-Chloro-1H-pyrrolo[2,3-b]pyridin-3-ylmethyl)-5-fluoro-2-methoxy-phenoxymethyl]-1H-benzoimidazole (P-1976),
2-[5-Fluoro-2-methoxy-4-(5-methoxy-1H-pyrrolo[2,3-b]pyridin-3-ylmethyl)-phenoxymethyl]-1H-benzoimidazole (P-1977),
2-[5-Fluoro-2-methoxy-4-(1H-pyrrolo[2,3-b]pyridin-3-ylmethyl)-phenoxymethyl]-1H-benzoimidazole (P-1978),
3-{4-[2-(2-Bromo-ethoxy)-ethoxy]-2-fluoro-5-methoxy-benzyl}-5-chloro-1H-pyrrolo[2,3-b]pyridine (P-1984),
5-Chloro-3-[2,5-difluoro-4-(2-methoxy-ethoxy)-benzyl]-1H-pyrrolo[2,3-b]pyridine (P-1986),
5-Chloro-3-[2-fluoro-5-methoxy-4-(2-methoxy-ethoxy)-benzyl]-1H-pyrrolo[2,3-b]pyridine (P-1990),
{3-[4-(5-Chloro-1H-pyrrolo[2,3-b]pyridin-3-ylmethyl)-5-fluoro-2-methoxy-phenoxy]-propyl}-diethyl-amine (P-2004),
5-Chloro-3-{2-fluoro-5-methoxy-4-[2-(2-methoxy-ethoxy)-ethoxy]-benzyl}-1H-pyrrolo[2,3-b]pyridine (P-2002),
3-(4-Benzyloxy-2,6-difluoro-benzyl)-1H-pyrrolo[2,3-b]pyridine (P-2022),
3-{2-Fluoro-5-methoxy-4-[2-(2-methoxy-ethoxy)-ethoxy]-benzyl}-5-methoxy-1H-pyrrolo[2,3-b]pyridine (P-2025), and
3-{2-Fluoro-5-methoxy-4-[2-(2-methoxy-ethoxy)-ethoxy]-benzyl}-1H-pyrrolo[2,3-b]pyridine (P-2026).

The following table indicates the aldehyde (column 2) and the azaindole (column 3) used to afford the target compound (column 4). Column 1 indicates the compound number and column 5 the observed mass.

| | Aldehyde | Azaindole | Compound | MS(ESI) [M + H⁺]⁺ observed |
|---|---|---|---|---|
| P-1721 | | | | 413.2 |
| P-1797 | | | | 451.3 |
| P-1821 | | | | 457.4 |

-continued

| | Aldehyde | Azaindole | Compound | MS(ESI) [M + H+]+ observed |
|---|---|---|---|---|
| P-1844 | | | | 397.2 |
| P-1849 | | | | 432.4 |
| P-1851 | | | | |
| P-1870 | | | | 385.4 |
| P-1885 | | | | 445.3 |

-continued

| | Aldehyde | Azaindole | Compound | MS(ESI) [M + H+]+ observed |
|---|---|---|---|---|
| P-1886 | | | | 413.3 |
| P-1896 | | | | 367.3 |
| P-1899 | | | | 373.4 |
| P-1901 | | | | 351.4 |
| P-1970 | | | | 431.2 |

-continued

| | Aldehyde | Azaindole | Compound | MS(ESI) [M + H⁺]⁺ observed |
|---|---|---|---|---|
| P-1972 | | | | 449.2 |
| P-1973 | | | | 415.3 |
| P-1976 | | | | 437.3 |
| P-1977 | | | | 433.4 |
| P-1978 | | | | 403.4 |

| | Aldehyde | Azaindole | Compound | MS(ESI) [M + H+]+ observed |
|---|---|---|---|---|
| P-1984 | 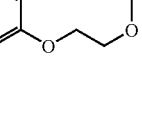 | 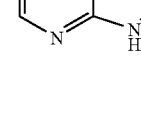 | 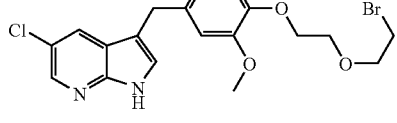 | 457.4 459.4 |
| P-1986 | 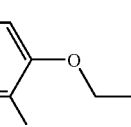 | 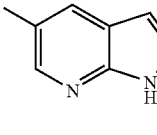 | 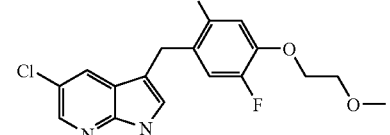 | 353.4 |
| P-1990 |  | 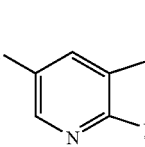 | 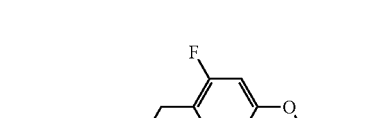 | 365.3 |
| P-2004 | 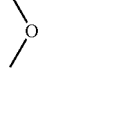 |  | 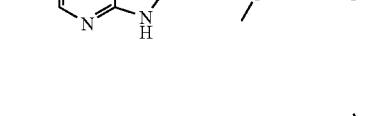 | 420.4 |
| P-2002 | 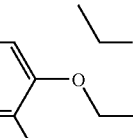 | 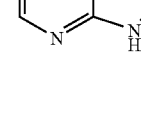 | 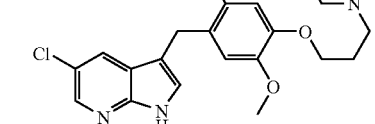 | 409.3 |
| P-2022 | 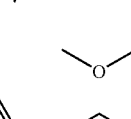 | 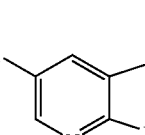 | 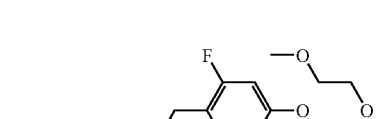 | 438.1 |
| P-2025 | 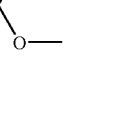 | 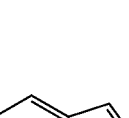 | 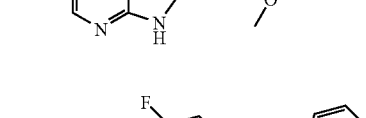 | 405.2 |

| | Aldehyde | Azaindole | Compound | MS(ESI) [M + H⁺]⁺ observed |
|---|---|---|---|---|
| P-2026 | 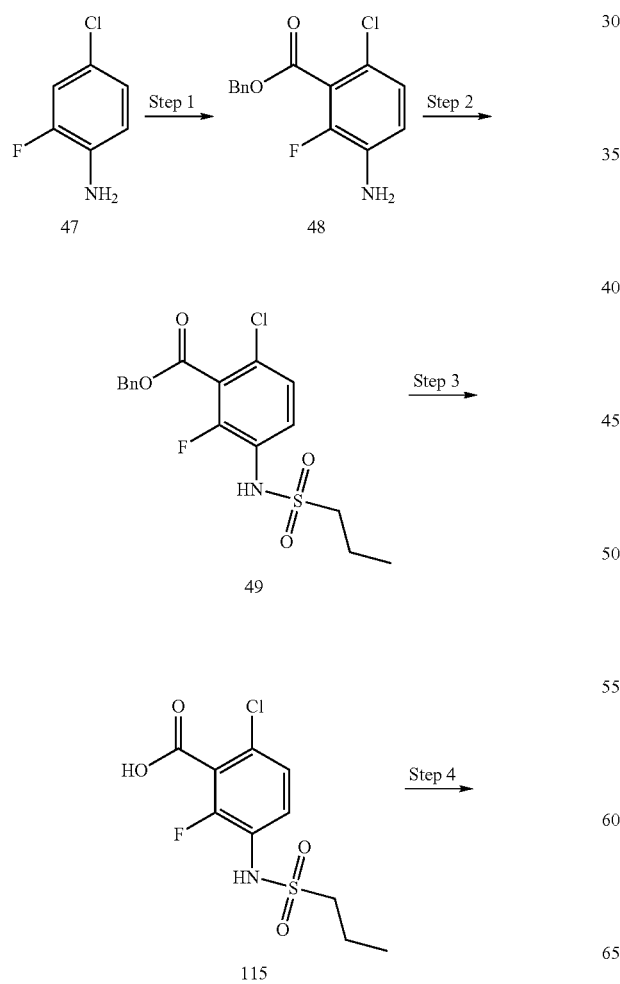 | | | 373.2 |
Example 19
Synthesis of Propane-1-sulfonic acid [3-(5-bromo-1H-pyrrolo[2,3-b]pyridine-3-carbonyl)-2-fluoro-phenyl]-amide P-0955 and Related Compounds
As an alternative method to that of Example 2, compound P-0955 was synthesized in nine steps from 4-chloro-2-fluoro-phenylamine 47 as shown in Scheme 37.
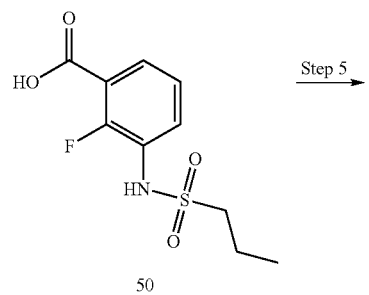
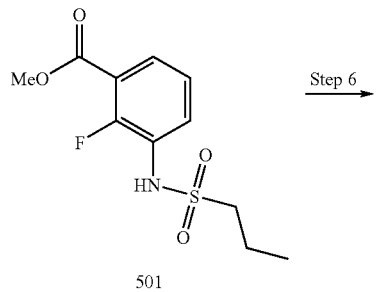
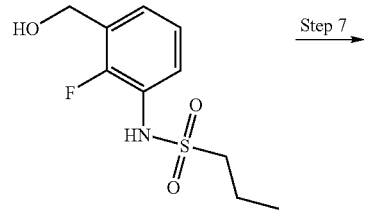
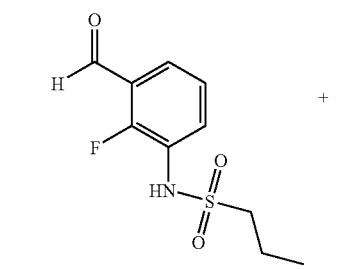
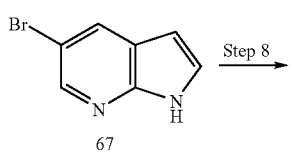

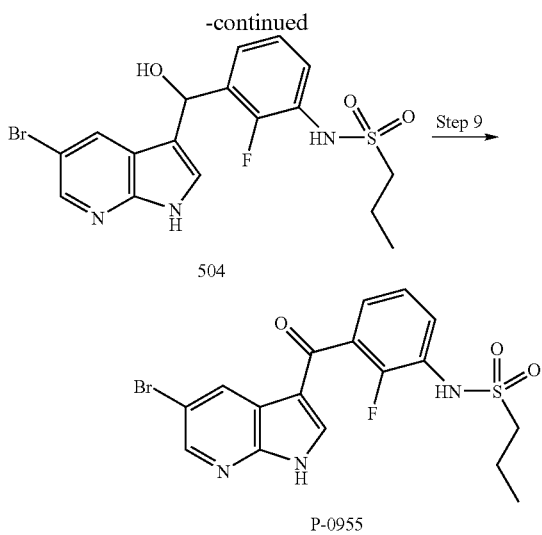

Step 1—Preparation of 3-Amino-6-chloro-2-fluoro-benzoic acid benzyl ester (48)

To 4-chloro-2-fluoro-phenylamine (47, 6.30 mL, 57.0 mmol) in tetrahydrofuran (300 mL), cooled with dry ice/acetone bath under an atmosphere of nitrogen, n-butyllithium (2.50 M in hexane, 24.4 mL) was added slowly. After 20 minutes, 1,2-Bis-(chloro-dimethyl-silanyl)-ethane (12.9 g, 60.0 mmol) dissolved in tetrahydrofuran (40.0 mL) was added slowly to the reaction. After 1 hour, n-butyllithium (2.50 M in hexane, 25.0 mL) was added slowly to the reaction. The reaction was stirred at −78° C. for 20 minutes and then allowed to warm to room temperature over 60 minutes. The reaction was cooled to −78° C., followed by addition of n-butyllithium (2.50 M in hexane, 26.0 mL) slowly. After 80 minutes, benzyl chloroformate (10.0 mL 70.0 mmol) was added to the reaction. The reaction mixture was stirred at −78° C. overnight followed by addition of water (80 mL) and concentrated hydrochloric acid (25 mL). The reaction was allowed to warm to room temperature for 2 hours. The organic layer was separated. The aqueous layer was basified with potassium carbonate and extracted with ethyl acetate. The organic layers were combined and washed with brine, dried over anhydrous sodium sulfate, filtered and concentrated. The desired compound was isolated by silica gel column chromatography (ethyl acetate hexane 20%) to give a colorless oil (48, 12.5 g, 78.3%). MS(ESI) [M+H$^+$]$^+$=280.0.

Step 2—Preparation of 6-chloro-2-fluoro-(propane-1-sulfonylamino)-benzoic acid benzyl ester (49)

To 3-amino-6-chloro-2-fluoro-benzoic acid benzyl ester (48, 1.20 g, 4.3 mmol) in methylene chloride (28 mL) was added pyridine (0.52 mL, 6.4 mmol) and propanesulfonyl chloride (0.685 g, 4.8 mmol). The reaction was stirred at room temperature overnight, then poured into water, and extracted with ethyl acetate. The organic layer was washed with brine, dried over anhydrous sodium sulfate, filtered and concentrated. The desired compound was isolated with silica gel column chromatography to give a colorless oil (49, 960 mg, 58.0%). MS(ESI) [M−H$^+$]$^−$=384.1.

Step 3—Preparation of 6-chloro-2-fluoro-3-(propane-1-sulfonylamino)-benzoic acid (115)

To 6-chloro-2-fluoro-3-(propane-1-sulfonylamino)-benzoic acid benzyl ester (49, 6.00 g, 15.6 mmol) in tetrahydrofuran (100 mL) was added 1.0 M aqueous potassium hydroxide (100 mL). The reaction was heated to reflux overnight. The reaction was poured into water, acidified to pH 2 with 1 N hydrochloric acid and extracted with ethyl acetate. The organic portion was dried over anhydrous sodium sulfate, filtered and concentrated to give a white solid 115 (3.95 g, 85.8%).

Step 4—Preparation of 2-fluoro-3-(propane-1-sulfonylamino)-benzoic acid (50)

To 6-chloro-2-fluoro-3-(propane-1-sulfonylamino)-benzoic acid (115, 0.69 g, 2.3 mmol) in methanol (10 mL) was added 20% palladium hydroxide on carbon (200 mg). The reaction was stirred under hydrogen at 50 psi for 2 hours. The reaction was filtered and concentrated to give white solid 50 that was used in the next step. MS(ESI) [M−H$^+$]$^+$=260.1.

Step 5—Preparation of 2-fluoro-3-(propane-1-sulfonylamino)-benzoic acid methyl ester (501)

To a 2-fluoro-3-(propane-1-sulfonylamino)-benzoic acid (50, 5.05 g, 0.0193 mol) in methylene chloride (100 mL) was added N,N-dimethylformamide (0.075 mL, 0.97 mmol) under an atmosphere of nitrogen. The reaction was cooled with ice/water, followed by slow addition of Oxalyl chloride (2.00 M of in methylene chloride, 10.8 mL, 21.6 mmol). The reaction mixture was stirred at room temperature for 3.0 hours. The reaction was cooled with ice/water, followed by addition of methanol (36.0 mL, 0.89 mol) slowly. The reaction was stirred at room temperature overnight. The reaction was concentrate and purified with silica gel column chromatography eluting with 30% ethyl acetate in hexane to give a crude white solid 4.0 g.

Step 6—Preparation of Propane-1-sulfonic acid (2-fluoro-3-hydroxymethyl-phenyl)-amide (502)

To 2-fluoro-3-(propane-1-sulfonylamino)-benzoic acid methyl ester (501, 3.80 g, 13.8 mmol) in tetrahydrofuran (133 mL) was added lithium tetrahydroaluminate (1.00 M in tetrahydrofuran, 20.0 mL, 20.0 mmol) under an atmosphere of nitrogen at room temperature. The reaction was stirred at room temperature for 8 hours, followed by addition of 10 g of NaSO$_4$.10H$_2$O. After 12 hours, the reaction was filtered, concentrated and purified with silica gel column chromatography eluting with 5% methanol in methylene chloride to give a white solid (502, 3.0 g. 87.9%).

Step 7—Preparation of propane-1-sulfonic acid (2-fluoro-3-formyl-phenyl-amide (503)

To propane-1-sulfonic acid (2-fluoro-3-hydroxymethyl-phenyl)-amide (502, 0.20 g, 0.81 mmol) in tetrahydrofuran (5.0 mL) was added Dess-Martin periodinane (0.377 g, 0.89 mmol). The reaction was stirred at room temperature for 10 minutes, then poured into water and extracted with ethyl acetate. The organic layer was dried over anhydrous sodium sulfate, and filtered. The filtrate was concentrated and purified by silica gel column chromatography eluting with 20% ethyl acetate in hexane to give a white solid (503, 100 mg, 50.0%). MS(ESI) [M−H$^+$]$^+$=244.1.

Step 8—Preparation of Propane-1-sulfonic acid {3-[(5-bromo-1H-pyrrolo[2,3-b]pyridin-3-yl)-hydroxy-methyl]-2-fluoro-phenyl}-amide (504)

To 5-bromo-7-azaindole 67 (312 mg, 1.58 mmol) in methanol (28 mL) were added propane-1-sulfonic acid (2-fluoro-3-formyl-phenyl)-amide (503, 370 mg, 1.5 mmol) and potassium hydroxide (422.8 mg, 7.5 mmol) under an atmosphere of nitrogen. The reaction was stirred at room temperature overnight, then poured into water and extracted with ethyl acetate. The organic layer was dried over anhydrous sodium sulfate, and filtered. The filtrate was concentrated and purified by silica gel column chromatography eluting with 20% ethyl acetate in hexane to give the desired compound as white solid (504, 300 mg, 45.0%).

Step 9—Preparation of propane-1-sulfonic acid [3-(5-bromo-1H-pyrrolo[2,3-b]pyridine-3-carbonyl)-2,4-difluoro-phenyl]-amide (P-0955)

To Propane-1-sulfonic acid {3-[(5-bromo-1H-pyrrolo[2,3-b]pyridin-3-yl)-hydroxy-methyl]-2-fluoro-phenyl}-amide (504, 0.650 g, 1.47 mmol) in tetrahydrofuran (25.0 mL) cooled with ice/water was added Dess-Martin periodinane (0.748 g, 1.76 mmol). The reaction was stirred at room temperature for 15 minutes. The reaction was poured into water containing sodium thiosulfate and potassium carbonate and extracted with ethyl acetate. The organic layer was dried over anhydrous sodium sulfate, and filtered. The filtrate was concentrated and purified by silica gel column chromatography eluting with 20% ethyl acetate in hexane and washed with ethyl acetate to give white solid. (P-0955, 0.35 g, 54.1%). MS(ESI) [M+H$^+$]$^+$=460.0, 462.0.

Butane-1-sulfonic acid [3-(5-chloro-1H-pyrrolo[2,3-b]pyridine-3-carbonyl)-2-fluoro-phenyl]-amide P-1250

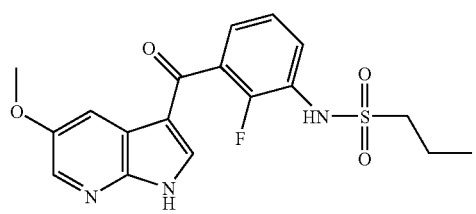 [SMILES: CCCS(=O)(=O)Nc1cccc(C(=O)c2c[nH]c3ncc(OC)cc23)c1F]

was prepared following the protocol of Scheme 37, substituting propane-2-sulfonyl chloride with butane-1-sulfonyl chloride in Step 1 and 5-bromo-1H-pyrrolo[2,3-b]pyridine 67 with 5-chloro-1H-pyrrolo[2,3-b]pyridine 80 (see Example 9) in step 8. MS(ESI) [M–H$^+$]$^-$=408.1.

Propane-1-sulfonic acid [2-fluoro-3-(5-methoxy-1H-pyrrolo[2,3-b]pyridine-3-carbonyl)-phenyl]-amide P-1256 was prepared following the protocol of Scheme 37, substituting 5-bromo-1H-pyrrolo[2,3-b]pyridine 67 with 5-methoxy-1H-pyrrolo[2,3-b]pyridine 104 (see Example 16) in step 8. MS(ESI) [M–H$^+$]$^-$=390.1

N-[3-(5-chloro-1H-pyrrolo[2,3-b]pyridine-3-carbonyl)-2-fluoro-phenyl]benzenesulfonamide P-1255

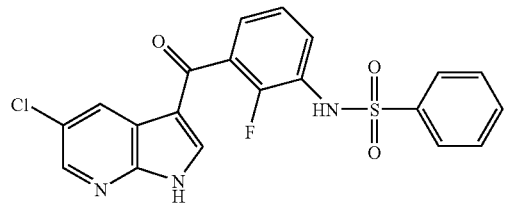 [SMILES: O=C(c1cccc(NS(=O)(=O)c2ccccc2)c1F)c1c[nH]c2ncc(Cl)cc12]

was prepared following the protocol of Scheme 37, substituting propane-2-sulfonyl chloride with benzenesulfonyl chloride in Step 1 and 5-bromo-1H-pyrrolo[2,3-b]pyridine 67 with 5-chloro-1H-pyrrolo[2,3-b]pyridine 80 (see Example 9) in step 8. MS(ESI) [M–H$^+$]$^-$=428.0.

Example 20

Synthesis of 3-3-[2,6-difluoro-3-(propane-1-sulfonylamino)-benzoyl]-1H-pyrrolo[2,3-b]pyridin-5-yl-propionic acid P-1270

Compound P-1270 was synthesized in three steps from propane-1-sulfonic acid [3-(5-bromo-1H-pyrrolo[2,3-b]pyridine-3-carbonyl)-2,4-difluoro-phenyl]-amide P-0773 as shown in Scheme 38.

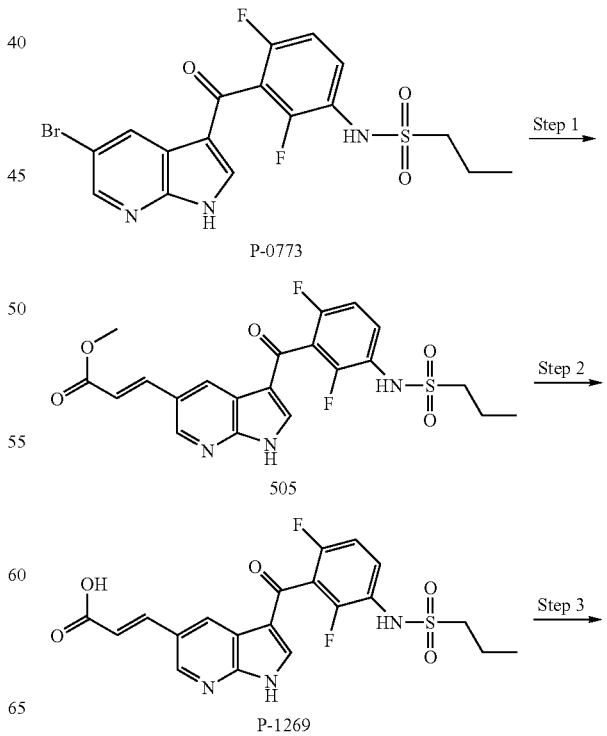

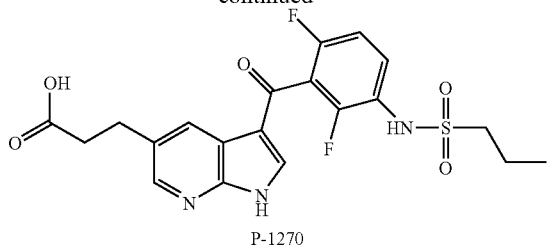

P-1270

Step 1—Preparation of (E)-3-3-[2,6-difluoro-3-(propane-1-sulfonylamino)-benzoyl]-1H-pyrrolo[2,3-b]pyridin-5-yl-acrylic acid methyl ester (505)

To propane-1-sulfonic acid [3-(5-bromo-1H-pyrrolo[2,3-b]pyridine-3-carbonyl)-2,4-difluoro-phenyl]-amide (P-0773, 125.0 mg, 0.27 mmol, prepared as described in Example 4) in N,N-dimethylformamide (4.0 mL) were added palladium acetate (15 mg, 0.068 mmol), triphenylphosphine (36 mg, 0.14 mmol), methyl acrylate (0.098 mL, 1.1 mmol) and triethylamine (0.114 mL, 0.82 mmol) under an atmosphere of nitrogen. The reaction was stirred at 140° C. overnight, then poured into water, acidified with water and extracted with ethyl acetate. To the filtrate in methylene chloride (5.0 mL) was added 1,8-diazabicyclo[5.4.0]undec-7-ene (0.50 mL, 3.3 mmol). The reaction was stirred at room temperature for 3 hours. The reaction was concentrated and purified with silica gel column chromatography eluting with 30% ethyl acetate in hexane to give a light yellow oil that was used directly in the next step.

Step 2—Preparation of 3-3-[2,6-difluoro-3-(propane-1-sulfonylamino)-benzoyl]-1H-pyrrolo[2,3-b]pyridin-5-yl-acrylic acid (P-1269)

To (E)-3-3-[2,6-difluoro-3-(propane-1-sulfonylamino)-benzoyl]-1H-pyrrolo[2,3-b]pyridin-5-yl-acrylic acid methyl ester (100.0 mg, 0.22 mmol) in tetrahydrofuran (5.0 mL) and water (1.50 mL) was added lithium hydroxide (21 mg, 0.86 mmol). The reaction was stirred at room temperature overnight. The reaction was poured into water, acidified with 1N HCl to pH around 1, and then extracted with ethyl acetate. The organic layer was dried over anhydrous sodium sulfate, and filtered. The filtrate was concentrated and purified by silica gel column chromatography eluting with 20% ethyl acetate in hexane to give a white solid (P-1269, 30 mg). MS(ESI) [M−H$^+$]$^-$=448.0.

Step 3—3-3-[2,6-difluoro-3-(propane-1-sulfonylamino)-1H-pyrrolo[2,3-b]pyridin-5-yl-propionic acid (P-1270)

To 3-3-[2,6-difluoro-3-(propane-1-sulfonylamino)-benzoyl]-1H-pyrrolo[2,3-b]pyridin-5-yl-acrylic acid (P-1269, 20.0 mg, 0.045 mmol) in methanol (5.0 mL) was added 20% Pd(OH)2/C (10 mg) under an atmosphere of hydrogen. The reaction was stirred at room temperature for 2 hours. The reaction mixture was filtered, concentrated and purified with silica gel column chromatography eluting with 10% methanol in methylene chloride to give a white solid (P-1270, 8.8 mg). MS(ESI) [M−H$^+$]$^-$=450.1.

Example 21

Synthesis of thiophene-2-sulfonic acid (2,4-difluoro-3-formyl-phenyl)-amide 508

Compound 512 was synthesized in four steps from 2,4-difluorophenylamine 42 as shown in Scheme 39.

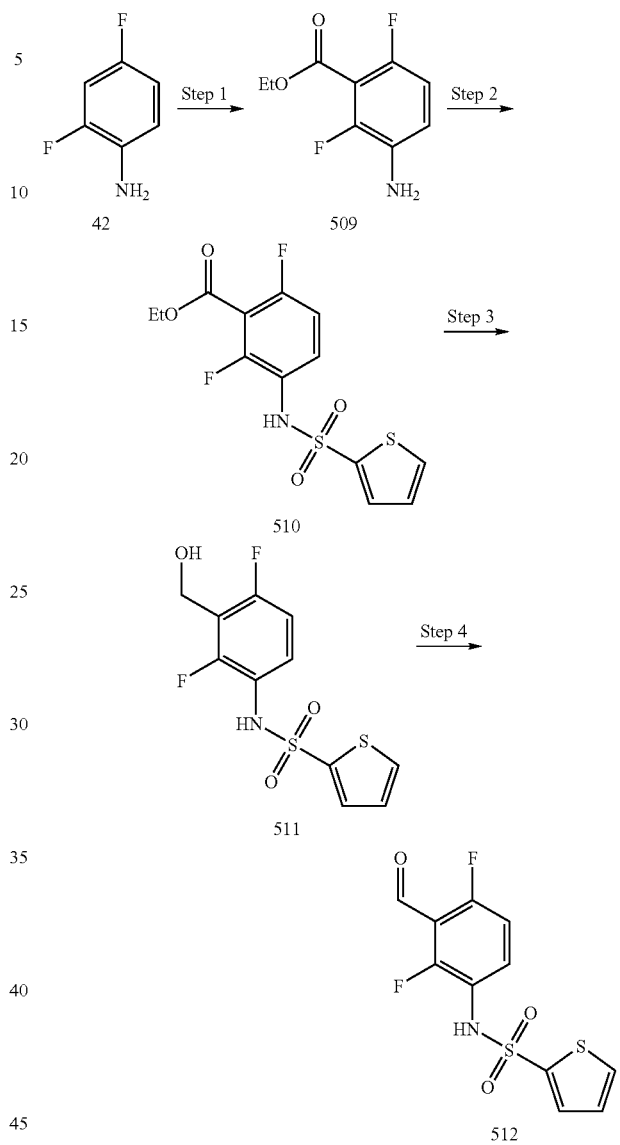

Step 1—Preparation of 3-amino-4,2-difluoro-benzoic acid ethyl ester (509)

To 4,2-difluoro-phenylamine (42, 6.30 mL, 57.0 mmol) in tetrahydrofuran (300 mL), cooled with dry ice/acetone bath under an atmosphere of nitrogen, n-butyllithium (2.50 M in hexane, 24.4 mL) was added slowly. After 20 minutes, 1,2-Bis-(chloro-dimethyl-silanyl)-ethane (12.9 g, 60.0 mmol) dissolved in tetrahydrofuran (40.0 mL) was slowly added to the reaction. After 1 hour, n-butyllithium (2.50 M in hexane, 25.0 mL) was slowly added to the reaction. The reaction was stirred at −78° C. for 20 minutes and then allowed to warm to room temperature over 60 minutes. The reaction was cooled to −78° C., followed by addition of n-butyllithium (2.50 M in hexane, 26.0 mL) slowly. After 80 minutes, ethyl chloroformate (6.69 mL, 70.0 mmol) was added to the reaction. The reaction mixture was stirred at −78° C. overnight followed by addition of water (80 mL) and concentrated hydrochloric acid (25 mL). The reaction was allowed to warm to room temperature for 2 hours. The organic layer was separated. The aqueous layer was basified with potassium carbonate and extracted with ethyl acetate. The organic layers were combined and washed with brine, dried over anhydrous sodium sulfate, filtered and concentrated. The desired compound was isolated by silica gel column chromatography (ethyl acetate/hexane 20%) to give a colorless oil (509, 4.6 g, 39%). MS(ESI) [M+H$^+$]$^+$=218.1.

Step 2—Preparation of 2,6-difluoro-3-(thiophene-2-sulfonylamino)-benzoic acid ethyl ester (510)

To 3-amino-2,4-difluoro-benzoic acid ethyl ester (509, 1.20 g, 5.93 mmol) in methylene chloride (28 mL) was added pyridine (0.52 mL, 6.4 mmol) and thiophene-2-sulfonyl chloride (0.97 g, 5.38 mmol). The reaction was stirred at room temperature overnight, then poured into water and extracted with ethyl acetate. The organic layer was washed with brine, dried over anhydrous sodium sulfate, filtered and concentrated. The desired compound was isolated with silica gel column chromatography (ethyl acetate/hexane 20%) to give a colorless oil (510, 1.2 g, 65.0%). MS(ESI) [M+H$^+$]$^+$=348.2.

Step 3—Preparation of thiophene-2-sulfonic acid (2,4-difluoro-3-hydroxymethyl-phenyl)-amide (511)

To 2,6-difluoro-3-(thiophene-2-sulfonylamino)-benzoic acid ethyl ester (510, 1.6 g, 3.5 mmol) in tetrahydrofuran (25.0 mL) was added lithium tetrahydroaluminate (1.00 M in tetrahydrofuran, 8.08 mL, 8.08 mmol) under an atmosphere of nitrogen at room temperature. The reaction was stirred at room temperature for 8 hours, followed by addition of 10 g of NaSO$_4$.10H$_2$O. After 12 hours, the reaction was filtered, concentrated and purified with silica gel column chromatography eluting with 5% methanol in methylene chloride to give a white solid (511, 300.0 mg, 21.0%).

Step 4—Preparation of thiophene-2-sulfonic acid (2,4-difluoro-3-formyl-phenyl)-amide (512)

To thiophene-2-sulfonic acid (2,4-difluoro-3-hydroxymethyl-phenyl)-amide (511, 0.46 g, 1.52 mmol) in tetrahydrofuran (5.0 mL) was added Dess-Martin periodinane (0.71 g, 1.67 mmol). The reaction was stirred at room temperature for 10 minutes, then poured into water and extracted with ethyl acetate. The organic layer was dried over anhydrous sodium sulfate, and filtered. The filtrate was concentrated and purified by silica gel column chromatography eluting with 20% ethyl acetate in hexane to give a white solid (512, 100 mg, 21%). MS(ESI) [M+H$^+$]$^+$=304.2.

Thiophene-3-sulfonic acid (2,4-difluoro-3-formyl-phenyl)-amide 513

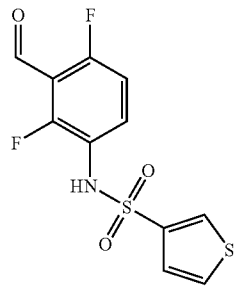 [SMILES: O=Cc1c(F)ccc(NS(=O)(=O)c2ccsc2)c1F]

was prepared following the protocol of Scheme 39, substituting thiophene-2-sulfonyl chloride with thiophene-3-sulfonyl chloride in Step 2. MS(ESI) [M+H$^+$]$^+$=304.2.

N-(2,4-Difluoro-3-formyl-phenyl)-methanesulfonamide 577

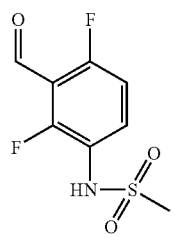

was prepared following the protocol of Scheme 39, substituting thiophene-2-sulfonyl chloride with methanesulfonyl chloride in Step 2.

N-(2,4-Difluoro-3-formyl-phenyl)-3-fluoro-benzenesulfonamide 578

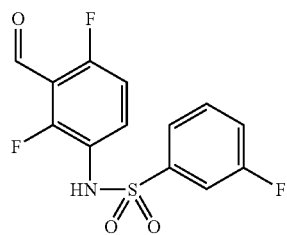 [SMILES: O=Cc1c(F)ccc(NS(=O)(=O)c2cccc(F)c2)c1F]

was prepared following the protocol of Scheme 39, substituting thiophene-2-sulfonyl chloride with 3-fluoro-benzenesulfonyl chloride in Step 2.

Example 22

Synthesis of 4-(5-Pyridin-3-yl-1H-pyrrolo[2,3-b]pyridine-3-carbonyl)-indole-1-carboxylic acid butylamide P-1486 and related compounds Compound P-1486 was synthesized in three steps from 1H-indole-4-carbaldehyde 518 as shown in Scheme 41.

Scheme 41

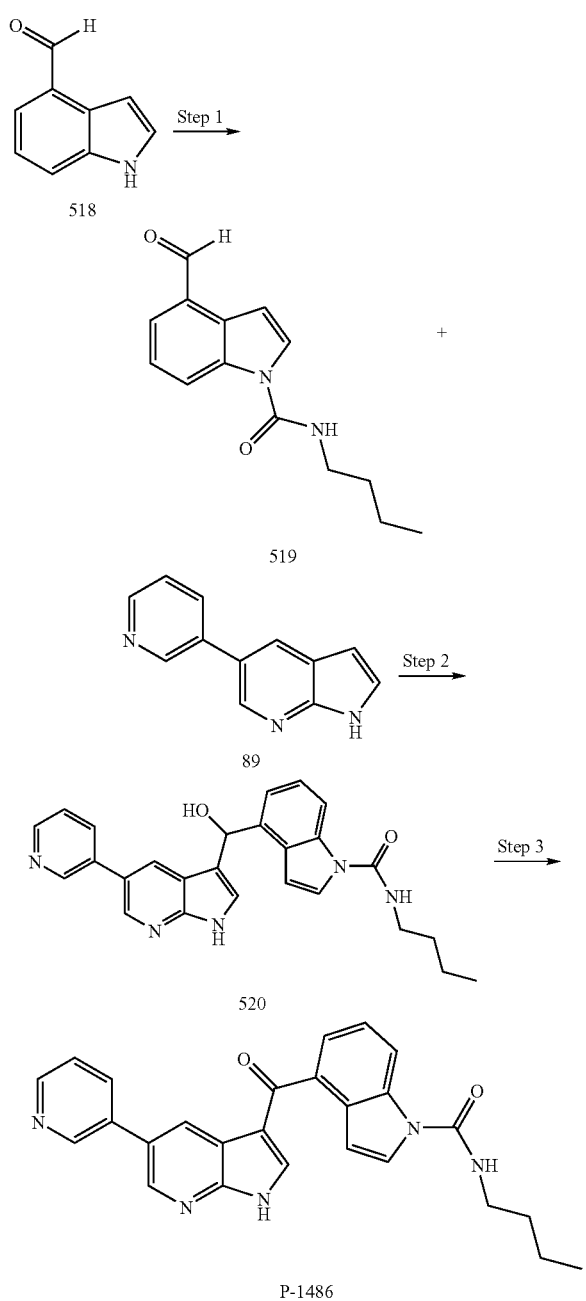

Step 1—Preparation 4-Formyl-indole-1-carboxylic acid butylamide (519)

To 1H-Indole-4-carbaldehyde (518, 1.57 g, 10.8 mmol) in acetonitrile (20 mL) was added 1-isocyanatobutane (1.81 mL, 16.2 mmol), followed by 4-dimethylaminopyridine (130 mg, 1.1 mmol). The reaction was refluxed for 48 hours. The reaction solution was quenched with 1M HCl (aq.) and extracted with ethyl acetate. The organic layer was washed with sodium bicarbonate and brine, dried over anhydrous magnesium sulfate, filtrated and concentrated to give a light yellow solid (519, 2.62 g, 45%). MS(ESI) [M+H$^+$]$^+$=245.2.

Step 2—Preparation of 4-[Hydroxy-(5-pyridin-3-yl-1H-pyrrolo[2,3-b]pyridin-3-yl)-methyl]-indole-1-carboxylic acid butylamide (520)

To 5-Pyridin-3-yl-1H-pyrrolo[2,3-b]pyridine (89, 51 mg, 0.26 mmol, prepared as in Example 17) in methanol (2 mL), was added 4-Formyl-indole-1-carboxylic acid butylamide (519, 84 mg, 0.34 mmol) and potassium hydroxide (44 mg, 0.78 mmol). The reaction was stirred at room temperature overnight. The reaction was poured into water and extracted with ethyl acetate. The organic layer was washed with water and brine, dried over anhydrous magnesium sulfate, filtrated and concentrated. The desired compound was isolated with silica gel column chromatography to give an off-white solid (520, 7 mg, 6%). MS(ESI) [M+H$^+$]$^+$=440.3.

Step 3—Preparation of 4-(5-Pyridin-3-yl-1H-pyrrolo[2,3-b]pyridine-3-carbonyl)-indole-1-carboxylic acid butylamide (P-1486)

To 4-[Hydroxy-(5-pyridin-3-yl-1H-pyrrolo[2,3-b]pyridin-3-yl)-methyl]-indole-1-carboxylic acid butylamide (520, 7 mg, 0.016 mmol) in tetrahydrofuran (1 mL) was added Dess-Martin periodinane (7.4 mg, 0.017 mmol). The reaction was stirred at room temperature for 30 minutes, then poured into water and extracted with ethyl acetate. The organic layer was washed with saturated sodium bicarbonate and brine, dried over anhydrous magnesium sulfate, filtrated and concentrated. The desired compound was purified by Prep HPLC using a gradient of buffer A (5% acetonitrile, 95% water, 0.1% formic acid) and buffer B (95% acetonitrile, 5% water, 0.1% formic acid). P-1486 was isolated as a fluffy white solid (2.8 mg, 40%). MS(ESI) [M+H$^+$]$^+$=438.3.

Additional compounds were prepared following the protocol of Scheme 41, optionally substituting 1-isocyanatobutane with an appropriate isocyanate in Step 1 under suitable base/solvent conditions (dimethylaminopyridine and acetonitrile per Scheme 41 Step 1 or appropriate conditions) and optionally substituting 5-pyridin-3-yl-1H-pyrrolo[2,3-b]midine 89 with a suitable 7-azaindole in Step 2. The azaindole was purchased or synthesized as described in Examples 16 and 17. The following compounds were made following this procedure:

(1-Benzyloxymethyl-1H-indol-4-yl)-(5-pyridin-3-yl-1H-pyrrolo[2,3-b]pyridin-3-yl)-methanone (P-1523),
(1-Benzenesulfonyl-1H-indol-4-yl)(5-bromo-1H-pyrrolo[2,3-b]pyridin-3-yl)-methanone (P-1524),
4-(5-Phenyl-1H-pyrrolo[2,3-b]pyridine-3-carbonyl)-indole-1-carboxylic acid butylamide (P-1576),
4-[5-(4-Chloro-phenyl)-1H-pyrrolo[2,3-b]pyridine-3-carbonyl]-indole-1-carboxylic acid butylamide (P4602),
4-(5-Phenyl-1H-pyrrolo[2,3-b]pyridine-3-carbonyl)-indole-1-carboxylic acid benzylamide (P-1611),
4-[5-(4-Chloro-phenyl)-1H-pyrrolo[2,3-b]pyridine-3-carbonyl]-indole-1-carboxylic acid benzylamide (P-1618),
4-(5-Bromo-1H-pyrrolo[2,3-b]pyridine-3-carbonyl)-indole-1-carboxylic acid butylamide (P-1687),
4-(5-Pyridin-3-yl-1H-pyrrolo[2,3-b]pyridine-3-carbonyl)-indole-1-sulfonic acid dimethylamide (P4744),
(1-But-2-ynyl-1H-indol-4-yl)-(5-pyridin-3-yl-1H-pyrrolo[2,3-b]pyridin-3-yl)-methanone (P-1820),
4-(5-Pyridin-3-yl-1H-pyrrolo[2,3-b]pyridine-3-carbonyl)-indole-1-sulfonic acid butyl-methyl-amide (P1830),
4-[5-(4-Sulfamoyl-phenyl)-1H-pyrrolo[2,3-b]pyridine-3-carbonyl]-indole-1-carboxylic acid butylamide (P1854), 4-[5-(3-Sulfamoyl-phenyl)-1H-pyrrolo[2,3-b]pyridine-3-carbonyl]-indole-1-carboxylic acid butylamide (P-1858),
4-[5-(2-Methoxy-pyrimidin-5-yl)-1H-pyrrolo[2,3-b]pyridine-3-carbonyl]-indole-1-carboxylic acid butylamide (P-1860),
4-(5-Pyrimidin-5-yl-1H-pyrrolo[2,3-b]pyridine-3-carbonyl)-indole-1-carboxylic acid butylamide (P-1862),
4-(5-Methoxy-1H-pyrrolo[2,3-b]pyridine-3-carbonyl)-indole-1-carboxylic acid butylamide (P1875), and
4-[5-(6-Methoxy-pyridin-3-yl)-1H-pyrrolo[2,3-b]pyridine-3-carbonyl]-indole-1-carboxylic acid (pyridin-3-ylmethyl)-amide (P-1887).

The following table indicates the base/solvent (column 2) and isocyanate used in Step 1 (column 3), and the 7-azaindole used in Step 2 (column 4) to afford the target compound (column 5). Column 1 provides the compound number and column 6 the observed mass.

| | Step 1 Base/Solvent | Step 1 reagent | Azaindole | Compound | MS(ESI) [M + H⁺]⁺ observed |
|---|---|---|---|---|---|
| P-1523 | NaH/THF | | | | 459.4 |
| P-1524 | KOH/CH₂Cl₂ water | | | | 480.1 482.1 |
| P-1576 | * | | | | 437.3 |
| P-1602 | * | | | | 471.2 |
| P-1611 | * | | | | 471.3 |
| P-1618 | * | | | | 505.2 |

-continued

| Step 1 Base/ Solvent | Step 1 reagent | Azaindole | Compound | MS(ESI) [M + H⁺]⁺ observed |
|---|---|---|---|---|
| P-1687 | * | | | 439.2 441.2 |
| P-1744 | NaH/ THF | | | 446.2 |
| P-1820 | NaH/ THF | | | 391.2 |
| P-1830 | KOH/ CH₂Cl₂ water | | | |
| P-1854 | * | | | 514.2 [M − H⁺]⁻ |
| P-1858 | * | | | 516.2 |
| P-1860 | * | | | 469.3 |
| P-1862 | * | | | 439.3 |

| | Step 1 Base/ Solvent | Step 1 reagent | Azaindole | Compound | MS(ESI) [M + H⁺]⁺ observed |
|---|---|---|---|---|---|
| P-1875 | * | (butyl isocyanate) | 5-methoxy-7-azaindole | (structure) | 391.4 |
| P-1887 | * | (pyridin-3-ylmethyl isocyanate) | 5-(6-methoxypyridin-3-yl)-7-azaindole | (structure) | 503.4 |

The product of Step 2 of Scheme 41 can alternatively be reacted to form the corresponding compounds with methylene linker at the 3 position of the azaindole. For example, 4-(5-pyridin-3-yl-1H-pyrrolo[2,3-b]pyridin-3-ylmethyl)-indole-1-carboxylic acid butylamide P-1656 was prepared from 4-[Hydroxy-(5-pyridin-3-yl-1H-pyrrolo[2,3-b]pyridin-3-yl)-methyl]-indole-1-carboxylic acid butylamide 520 as shown in Scheme 41a.

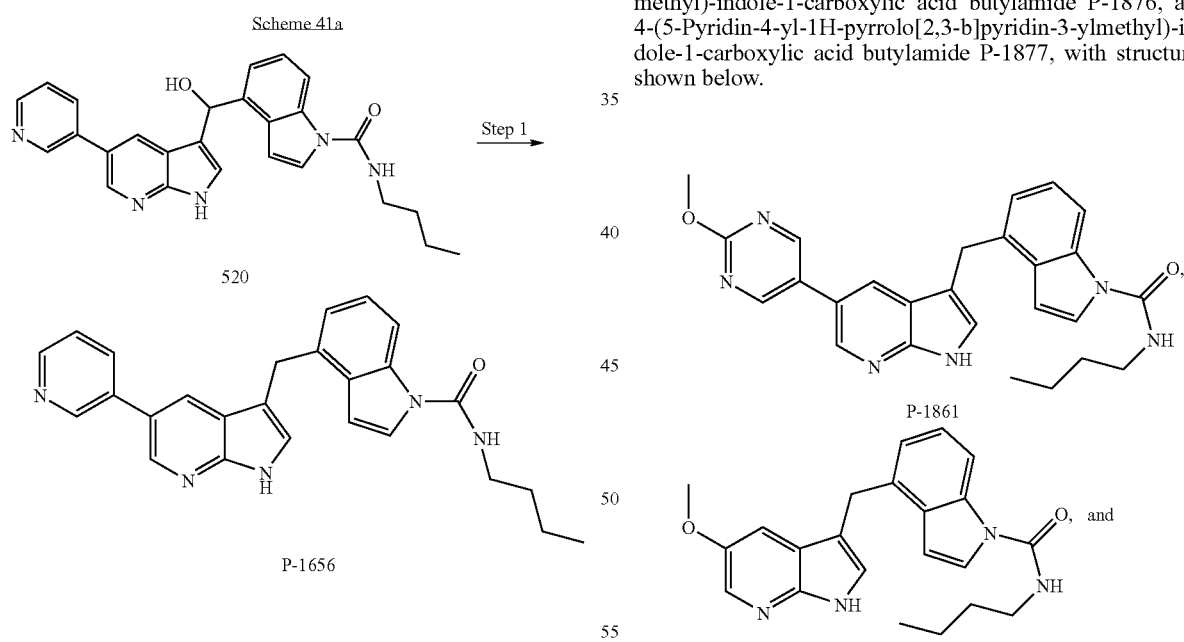

Step 1—Preparation of 4-(5-pyridin-3-yl-1H-pyrrolo[2,3-b]pyridin-3-ylmethyl)-indole-1-carboxylic acid butylamide (P-1656)

A mixture of 4-[hydroxy-(5-1H-pyrrolo[2,3-b]pyridin-3-yl)-methyl]-indole-1-carboxylic acid butylamide (520, 18 mg, 0.041 mmol), trifluoroacetic acid (0.5 mL), triethylsilane (1 mL), and acetonitrile (8 mL) was refluxed for 4 hours. The reaction was poured into water and extracted with ethyl acetate. The organic layer was washed with saturated sodium bicarbonate and brine, dried over anhydrous magnesium sulfate, filtrated and concentrated. The desired compound was purified by Prep HPLC using a gradient of buffer A (5% acetonitrile, 95% water, 0,1% formic acid) and buffer B (95% acetonitrile, 5% water, 0.1% formic acid). P-1656 was isolated as an off-white solid (4.8 mg, 28%). MS(ESI) [M+H⁺]⁺=424.2.

The corresponding hydroxy-methyl derivative of Scheme 41 Step 2 was reacted following the protocol of Scheme 41a to prepare 4-[5-(2-methoxy-pyrimidin-5-yl)-1H-pyrrolo[2,3-b]pyridin-3-ylmethyl]-indole-1-carboxylic acid butylamide P-1861, 4-(5-methoxy-1H-pyrrolo[2,3-b]pyridin-3-ylmethyl)-indole-1-carboxylic acid butylamide P-1876, and 4-(5-Pyridin-4-yl-1H-pyrrolo[2,3-b]pyridin-3-ylmethyl)-indole-1-carboxylic acid butylamide P-1877, with structures shown below.

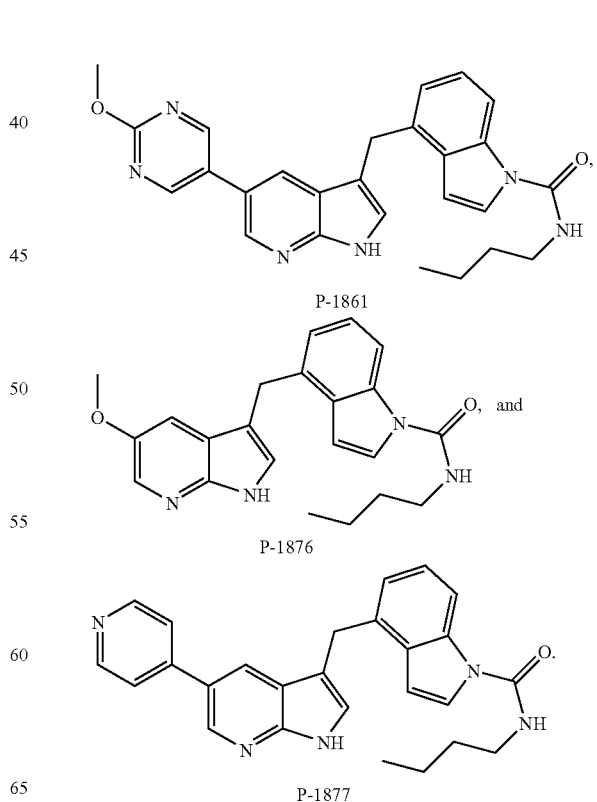

Example 23

Synthesis of (3-Benzyloxy-2,6-difluoro-phenyl)-(5-pyridin-3-yl-1H-pyrrolo[2,3-b]pyridin-3-yl)-methanone P-1467 and Related Compounds Compound P-1467 was synthesized in four steps from 2,4-difluorophenol 35 as shown in Scheme 43.

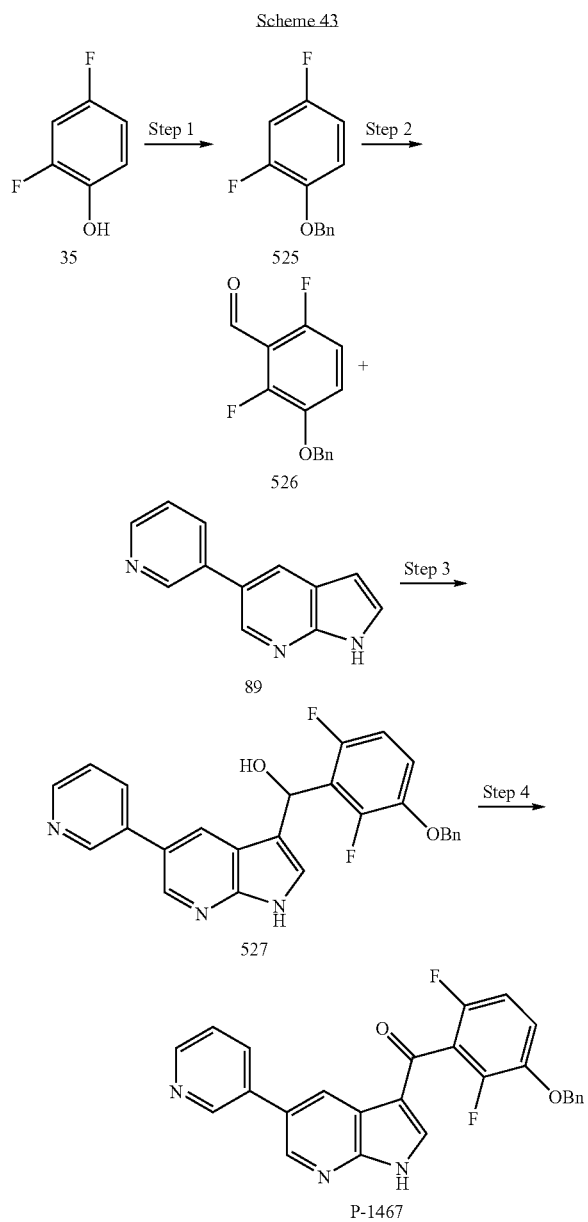

Step 1—Preparation of 1-Benzyloxy-2,4-difluoro-benzene (525)

To 2,4-difluoro-phenol (35, 7.60 g, 0.0584 mol) in N,N-dimethylformamide (50.0 mL) were added benzyl bromide (8.0 mL, 0.067 mol) and potassium carbonate (9.00 g, 0.0651 mol) under an atmosphere of nitrogen. The reaction was stirred at room temperature overnight. The reaction was poured into water and extracted with ethyl acetate. The organic layer was dried over anhydrous sodium sulfate and filtered. The filtrate was concentrated and purified by silica gel column chromatography eluting with 20% ethyl acetate in hexane to give the compound as white solid (525, 3.20 g, 25%).

Step 2—Preparation of 3-Benzyloxy-2,6-difluoro-benzaldehyde (526)

To 1-Benzyloxy-2,4-difluoro-benzene (525, 3.00 g, 13.6 mmol) in Tetrahydrofuran (48 mL) under an atmosphere of nitrogen and cooled with dry ice/acetone was added n-Butyllithium (1.60 M in hexane, 8.94 mL). After 20 minutes, N,N-dimethylformamide (1.46 mL, 0.0189 mol) was added to the reaction. After another 20 minutes, the flask was stirred at room temperature for 30 minutes. The reaction mixture was poured into water, acidified to pH=1, and extracted with ethyl acetate. The organic layer was washed with brine, dried over sodium sulfate, concentrated and purified with silica gel column chromatography eluting with 30% ethyl acetate in hexane to give the compound as a yellow solid (526, 2.5 g, 74%).

Step 3—Preparation of (3-Benzyloxy-2,6-difluoro-phenyl)-(5-pyridin-3-yl-1H-pyrrolo[2,3-b]pyridin-3-yl)-methanol (527)

To 5-Pyridin-3-yl-1H-pyrrolo[2,3-b]pyridine (89, 750.0 mg, 0.003842 mol, prepared as in Example 17) in methanol (20.0 mL) were added 3-Benzyloxy-2,6-difluoro-benzaldehyde (526, 1.12 g, 4.5 mmol) and potassium hydroxide (1.50 g, 0.0267 mol) under an atmosphere of nitrogen. The reaction was stirred at room temperature overnight and then poured into water, acidified with 1N HCl to pH around 2 and extracted with ethyl acetate. The organic layer was dried over anhydrous sodium sulfate and filtered. The filtrate was concentrated and purified by silica gel column chromatography eluting with 20% ethyl acetate in hexane to give the compound (527, 700 mg, 35%).

Step 4—Preparation of (3-Benzyloxy-2,6-difluoro-phenyl)-(5-pyridin-3-yl-1H-pyrrolo[2,3-d]pyridin-3-yl)-methanone (P-1467)

To (3-Benzyloxy-2,6-difluoro-phenyl)-(5-pyridin-3-yl-1H-pyrrolo[2,3-b]pyridin-3-yl)-methanol (527, 300.0 mg, 0.68 mmol) in tetrahydrofuran (10.0 mL) was added Dess-Martin periodinane (344 mg, 0.81 mmol). The reaction was stirred at room temperature for 10 minutes. The reaction mixture was concentrated with silica and purified with silica gel column chromatography eluting with 10% methanol in dichloromethane to give the compound (P-1467, 240 mg, 80%). MS(ESI) [M–H+]+=442.2.

(5-Bromo-1H-pyrrolo[2,3-b]pyridin-3-yl)-[2,6-difluoro-3-(2-methoxy-ethoxy)-phenyl]-methanone P-1453

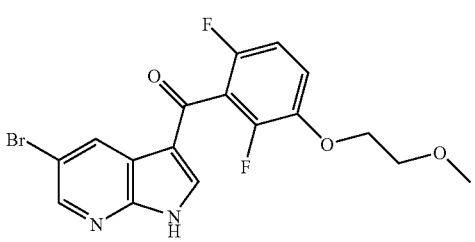 [SMILES: COCCOc1ccc(F)c(C(=O)c2c[nH]c3ncc(Br)cc23)c1F]

was prepared following the protocol of Scheme 43, substituting benzyl bromide with 1-Bromo-2-methoxy-ethane in Step 1 and 5-Pyridin-3-yl-1H-pyrrolo[2,3-b]pyridine with 5-Bromo-1H-pyrrolo[2,3-b]pyridine (67) in Step 3. MS (ESI) [M−H$^+$]$^+$=410.1, 412.1.

[2,6-Difluoro-3-(2-methoxy-ethoxy)-phenyl]-(5-methoxy-1H-pyrrolo[2,3-b]pyridin-3-yl)-methanone P-1584

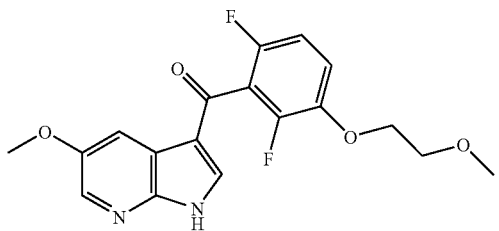

was prepared following the protocol of Scheme 43, substituting benzyl bromide with 1-Bromo-2-methoxy-ethane in Step 1 and 5-Pyridin-3-yl-1H-pyrrolo[2,3-b]pyridine with 5-methoxy-1H-pyrrolo[2,3-b]pyridine (104, prepared as in Example 22) in Step 3. MS (ESI) [M+H$^+$]$^+$=363.2.

(3-Benzyloxy-2,6-difluoro-phenyl)-(5-methoxy-1H-pyrrolo[2,3-b]pyridin-3-yl)-methanone P-1597

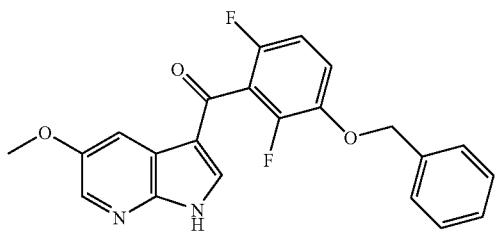 [SMILES: COc1cnc2[nH]cc(C(=O)c3c(F)ccc(OCc4ccccc4)c3F)c2c1]

was prepared following the protocol of Scheme 43, substituting 5-Pyridin-3-yl-1H-pyrrolo[2,3-b]pyridine with 5-methoxy-1H-pyrrolo[2,3-b]pyridine (104, prepared as in Example 16) in Step 3. MS(ESI) [M+H$^+$]$^+$=395.2.

(5-Bromo-1H-pyrrolo[2,3-b]pyridin-3-yl)-(2,6-difluoro-3-methoxy-phenyl)-methanone P-1386

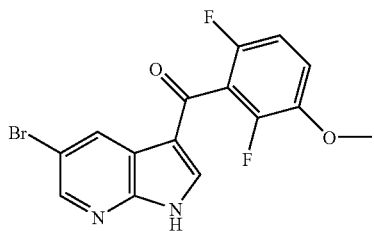 [SMILES: COc1ccc(F)c(C(=O)c2c[nH]c3ncc(Br)cc23)c1F]

was prepared following the protocol of Steps 2, 3 and 4 of Scheme 43, substituting 1-Benzyloxy-2,4-difluoro-benzene 525 with 2,4-Difluoro-1-methoxy-benzene in Step 2 and 5-Pyridin-3-yl-1H-pyrrolo[2,3-b]pyridine with 5-bromo-1H-pyrrolo[2,3-b]pyridine (67) in Step 3. MS (ESI) [M+H$^+$]$^+$=367.0, 369.0.

(3-Benzyloxy-2,6-difluoro-phenyl)-(1H-pyrrolo[2,3-b]pyridin-3-yl)-methanone P-1802

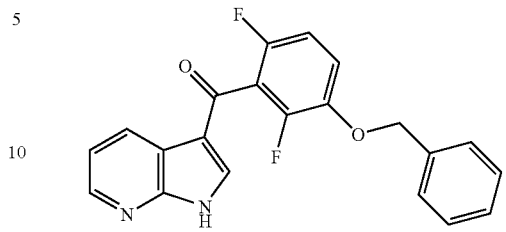

was prepared following the protocol of Scheme 43, substituting 5-pyridin-3-yl-1H-pyrrolo[2,3-b]pyridine with 7-azaindole. To a solution of (3-benzyloxy-2,6-difluoro-phenyl)-(1H-pyrrolo[2,3-b]pyridin-3-yl)-methanone (P-1802, 0.5 g, 1.37 mol) in methanol (70 mL) and tetrahydrofuran (30 mL) was added palladium on carbon (120 mg. 10% wt., 0.58 mol). The mixture was stirred under hydrogenation (60 psi) for six hours. After removal of solvent, the residue was dried under vacuum, which provided (2,6-Difluoro-3-hydroxy-phenyl)-(1H-pyrrolo[2,3-b]pyridine-3-yl)-methanone 651

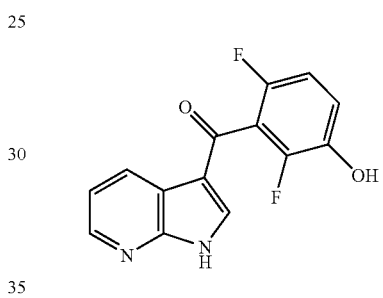

as a white solid (363 mg, 96%). MS (ESI) [M+H$^+$]$^+$=275.36.

Additional compounds were prepared following steps 3 and 4 of Scheme 43, replacing 3-benzyloxy-2,6-difluoro-benzaldehyde 526 with an appropriate aldehyde and/or pyridin-3-yl-1H-pyrrolo[2,3-b]pyridine 89 with an appropriate azaindole in Step 3. The azaindoles used were synthesized as described in Examples 9 or 16. The aldehydes used were synthesized as described in Example 5 or 21. The following compounds were made following this procedure:
(5-Bromo-1H-pyrrolo[2,3-b]pyridin-3-yl)-(3,5-dimethoxy-phenyl)-methanone (P-1463),
(5-Bromo-1H-pyrrolo[2,3-b]pyridin-3-yl)-(3-fluoro-5-trifluoromethyl-phenyl)-methanone,
(5-Bromo-1H-pyrrolo[2,3-b]pyridin-3-yl)-(3-trifluoromethoxy-phenyl)-methanone,
(5-Bromo-1H-pyrrolo[2,3-b]pyridin-3-yl)-(3-trifluoromethyl-phenyl)-methanone,
(5-Bromo-1H-pyrrolo[2,3-b]pyridin-3-yl)-(3,5-dichloro-phenyl)-methanone,
(2,6-Dichloro -phenyl)-(1H-pyrrolo[2,3-b]pyridin-3-yl)-methanone,
(2,6-Difluoro-phenyl)-(1H-pyrrolo[2,3-b]pyridin-3-yl)-methanone,
(2,6-Dimethyl-phenyl)-(1H-pyrrolo[2,3-b]pyridin-3-yl)-methanone,
(2,6-Dichloro-phenyl)-(5-pyridin-3-yl-1H-pyrrolo[2,3-b]pyridin-3-yl)-methanone,
(2,6-Difluoro-phenyl)-(5-pyridin-3-yl-1H -pyrrolo[2,3-b]pyridin-3-yl)-methanone,
(2,6-Dimethyl-phenyl)-(5-pyridin-3-yl-1H-pyrrolo[2,3-b]pyridin-3-yl)-methanone,
(5-Bromo-1H-pyrrolo[2,3-b]pyridin-3-yl)-(2,2-difluoro-benzo[1,3]dioxol-4-yl)-methanone (P-1513), (5-Bromo-1H-pyrrolo[2,3-b]pyridin-3-yl)-(3-difluoromethoxy-phenyl)-methanone (P-1514),
(5-Bromo-1H-pyrrolo[2,3-b]pyridin-3-yl)-(2,2-difluorobenzo[1,3]dioxol-5-yl)-methanone (P-1551),
N-[3-(5-Chloro-1H-pyrrolo[2,3-b]pyridine-3-carbonyl)-2,4-difluoro-phenyl]-4-trifluoromethyl-benzenesulfonamide (P-1541),
N-[2,4-Difluoro-3-(5-methoxy-1H-pyrrolo[2,3-b]pyridine-3-carbonyl)-phenyl]-4-trifluoromethyl-benzenesulfonamide (P-1542),
N-[2,4-Difluoro-3-(5-methoxy-1H-pyrrolo[2,3-b]pyridine-3-carbonyl)-phenyl]-3-fluoro-benzenesulfonamide (P-1581),
N-[2,4-Difluoro-3-(5-methoxy-1H-pyrrolo[2,3-b]pyridine-3-carbonyl)-phenyl]-4-fluoro-benzenesulfonamide (P-1582),
N-[3-(5-Chloro-1H-pyrrolo[2,3-b]pyridine-3-carbonyl)-2,4-difluoro-phenyl]-3-fluoro-benzenesulfonamide (P-1583),
N-[2,4-Difluoro-3-(5-methoxy-1H-pyrrolo[2,3-b]pyridine-3-carbonyl)-phenyl]-3-trifluoromethyl-benzenesulfonamide (P-1598),
N-[3-(5-Chloro-1H-pyrrolo[2,3-b]pyridine-3-carbonyl)-2,4-difluoro-phenyl]-3-trifluoromethyl-benzenesulfonamide (P-1599),
(5-Chloro-1H-pyrrolo[2,3-b]pyridin-3-yl)-{2-fluoro-5-methoxy-4-[2-(2-methoxy-ethoxy)-ethoxy]-phenyl}-methanone (P-2003),
(4-Benzyloxy-2,6-difluoro-phenyl)-(1H-pyrrolo[2,3-b]pyridin-3-yl)-methanone (P-2020), and
[4-(4-Chloro-benzyloxy)-3-methoxy-phenyl]-(1H-pyrrolo[2,3-b]pyridin-3-yl)-methanone (P-1698).

The following table indicates the aldehyde (column 2) and the azaindole (column 3) used to afford the target compound (column 4). Column 1 provides the compound number and column 5 the observed mass.

| | Aldehyde | Azaindole | Compound | MS(ESI) [M + H]+ observed |
|---|---|---|---|---|
| P-1463 | | | | 347.1 349.1 |
| 567 | | | | |
| 568 | | | | |
| 569 | | | | |

-continued

| | Aldehyde | Azaindole | Compound | MS(ESI) [M + H+]+ observed |
|---|---|---|---|---|
| 570 | 3,5-dichlorobenzaldehyde | 5-bromo-7-azaindole | (5-bromo-1H-pyrrolo[2,3-b]pyridin-3-yl)(3,5-dichlorophenyl)methanone | |
| 571 | 2,6-dichlorobenzaldehyde | 7-azaindole | (2,6-dichlorophenyl)(1H-pyrrolo[2,3-b]pyridin-3-yl)methanone | |
| 572 | 2,6-difluorobenzaldehyde | 7-azaindole | (2,6-difluorophenyl)(1H-pyrrolo[2,3-b]pyridin-3-yl)methanone | |
| 573 | 2,6-dimethylbenzaldehyde | 7-azaindole | (2,6-dimethylphenyl)(1H-pyrrolo[2,3-b]pyridin-3-yl)methanone | |
| 574 | 2,6-dichlorobenzaldehyde | 5-(pyridin-3-yl)-7-azaindole | (2,6-dichlorophenyl)(5-(pyridin-3-yl)-1H-pyrrolo[2,3-b]pyridin-3-yl)methanone | |
| 575 | 2,6-difluorobenzaldehyde | 5-(pyridin-3-yl)-7-azaindole | (2,6-difluorophenyl)(5-(pyridin-3-yl)-1H-pyrrolo[2,3-b]pyridin-3-yl)methanone | |

-continued

| | Aldehyde | Azaindole | Compound | MS(ESI) [M + H]+ observed |
|---|---|---|---|---|
| 576 | | | | |
| P-1513 | | | | 381.0 383.0 |
| P-1514 | | | | 367.1 369.1 |
| P-1551 | | | | 381.1 383.1 |
| P-1541 | | | | 516.2 |
| P-1542 | | | | 512.2 |
| P-1581 | | | | 462.2 |

US 8,415,469 B2

-continued

| | Aldehyde | Azaindole | Compound | MS(ESI) [M + H⁺]⁺ observed |
|---|---|---|---|---|
| P-1582 | | | | 462.2 |
| P-1583 | | | | 466.1 |
| P-1598 | | | | 510.1 |
| P-1599 | | | | 514.0 |
| P-2003 | | | | 423.3 |
| P-2020 | | | | 363.1 |
| P-1698 | | | | 393.2 |

Example 24

Synthesis of 3-(3-Benzyloxy-2,6-difluoro-benzyl)-5-pyridin-3-yl-1H-pyrrolo[2,3-b]pyridine P-1455

Compound P-1455 was synthesized in four steps from 2,4-difluorophenol 35 as shown in Scheme 43a.

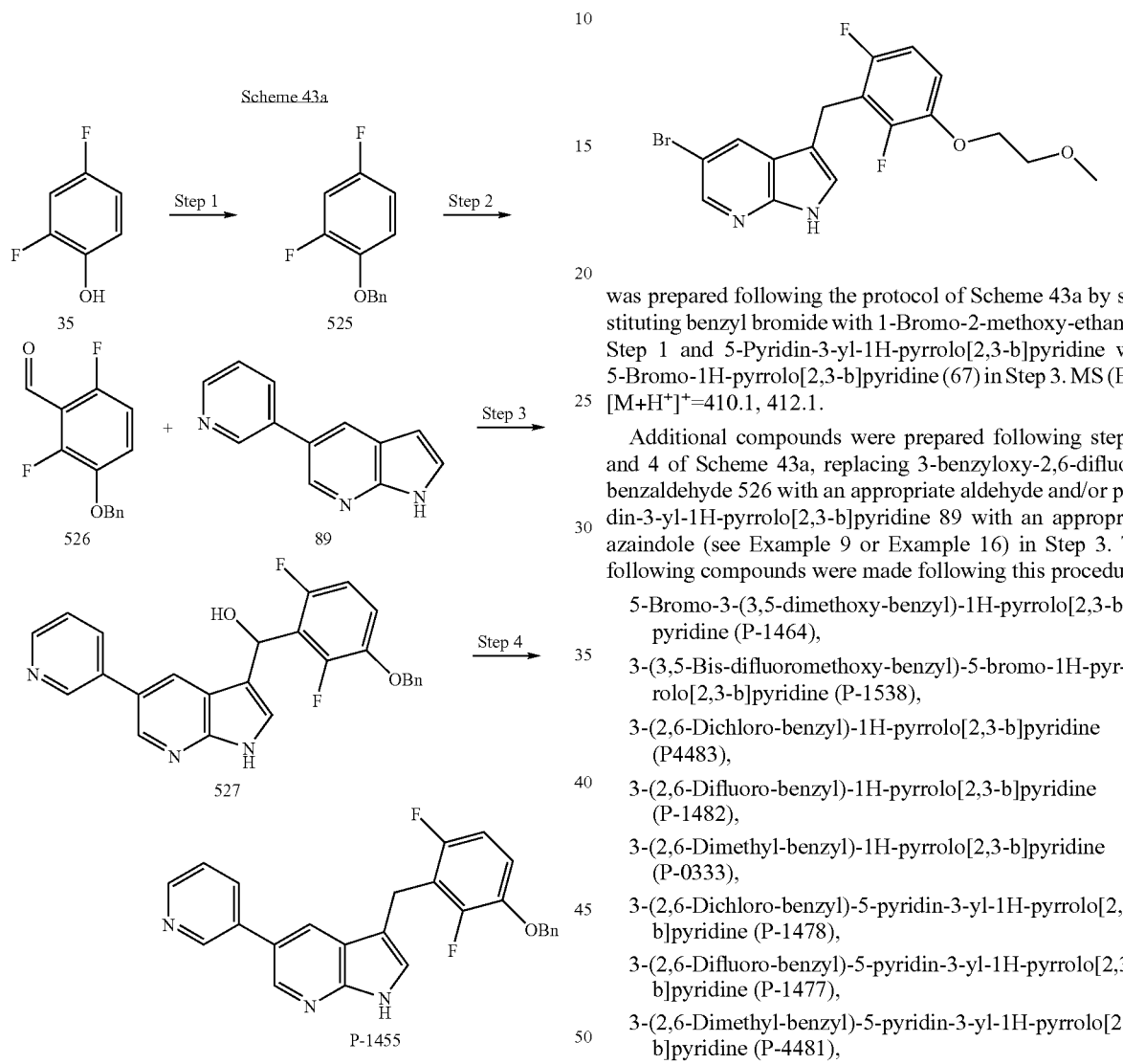

Steps 1-3 are identical to Steps 1-3 of Scheme 43.

Step 4—Preparation of 3-(3-Benzyloxy-2,6-difluoro-benzyl)-5-pyridin-3-yl-1H-pyrrolo[2,3-b]pyridine (P-1455)

To (3-Benzyloxy-2,6-difluoro-phenyl)-(5-pyridin-3-yl-1H-pyrrolo[2,3-b]pyridin-3-yl)-methanol (527, 580.0 mg, 1.3 mmol) in acetonitrile (29.0 mL) were added trifluoroacetic acid (1.9 mL, 0.025 mol) and triethylsilane (3.9 mL, 0.024 mol). The reaction was stirred at 80° C. for 1 hour. The reaction was poured into water, basified with 1 M potassium carbonate to pH=4, and extracted with ethyl acetate. The organic layer was dried over anhydrous sodium sulfate and filtered. The filtrate was concentrated and purified by silica gel column chromatography eluting with 50% ethyl acetate in hexane to give as a yellow solid (P-1455, 530 mg). MS(ESI) [M+H$^+$]$^+$=428.3.

5-Bromo-3-[2,6-difluoro-3-(2-methoxy-ethoxy)-benzyl]-1H-pyrrolo[2,3-b]pyridine P-1454

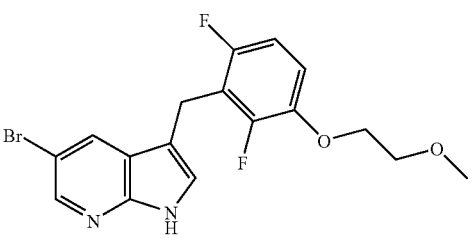 [SMILES: COCCOc1ccc(F)c(Cc2c[nH]c3ncc(Br)cc23)c1F]

was prepared following the protocol of Scheme 43a by substituting benzyl bromide with 1-Bromo-2-methoxy-ethane in Step 1 and 5-Pyridin-3-yl-1H-pyrrolo[2,3-b]pyridine with 5-Bromo-1H-pyrrolo[2,3-b]pyridine (67) in Step 3. MS (ESI) [M+H$^+$]$^+$=410.1, 412.1.

Additional compounds were prepared following steps 3 and 4 of Scheme 43a, replacing 3-benzyloxy-2,6-difluorobenzaldehyde 526 with an appropriate aldehyde and/or pyridin-3-yl-1H-pyrrolo[2,3-b]pyridine 89 with an appropriate azaindole (see Example 9 or Example 16) in Step 3. The following compounds were made following this procedure:

5-Bromo-3-(3,5-dimethoxy-benzyl)-1H-pyrrolo[2,3-b]pyridine (P-1464), 3-(3,5-Bis-difluoromethoxy-benzyl)-5-bromo-1H-pyrrolo[2,3-b]pyridine (P-1538), 3-(2,6-Dichloro-benzyl)-1H-pyrrolo[2,3-b]pyridine (P4483), 3-(2,6-Difluoro-benzyl)-1H-pyrrolo[2,3-b]pyridine (P-1482), 3-(2,6-Dimethyl-benzyl)-1H-pyrrolo[2,3-b]pyridine (P-0333), 3-(2,6-Dichloro-benzyl)-5-pyridin-3-yl-1H-pyrrolo[2,3-b]pyridine (P-1478), 3-(2,6-Difluoro-benzyl)-5-pyridin-3-yl-1H-pyrrolo[2,3-b]pyridine (P-1477), 3-(2,6-Dimethyl-benzyl)-5-pyridin-3-yl-1H-pyrrolo[2,3-b]pyridine (P-4481), N-[2,4-Difluoro-3-(5-methoxy-1H-pyrrolo[2,3-b]pyridin-3-ylmethyl)-phenyl]-3-trifluoromethyl-benzenesulfonamide (P-1590), N-[2,4-Difluoro-3-(5-chloro-1H-pyrrolo[2,3-b]pyridin-3-ylmethyl)-phenyl]-3-trifluoromethyl-benzenesulfonamide (P-1600), N-[2,4-Difluoro-3-(1H-pyrrolo[2,3-b]pyridin-3-ylmethyl)-phenyl]-methanesulfonamide (P-1603), and N-[2,4-Difluoro-3-(5-pyridin-3-yl-1H-pyrrolo[2,3-b]pyridin-3-ylmethyl)-phenyl]-methanesulfonamide (P-1605).

The following table indicates the aldehyde (column 2) and the azaindole (column 3) used to afford the target compound (column 4). Column 1 indicates the compound number and column 5 the observed mass.

| | Aldehyde | Azaindole | Product | MS(ESI) [M + H⁺]⁺ observed |
|---|---|---|---|---|
| P-1464 | | | | 347.1 349.1 |
| P-1538 | | | | 419.1 421.1 |
| P-1483 | | | | |
| P-1482 | | | | |
| P-0333 | | | | |
| P-1478 | | | | |

-continued

|  | Aldehyde | Azaindole | Product | MS(ESI) [M + H⁺]⁺ observed |
|---|---|---|---|---|
| P-1477 | | | | |
| P-1481 | | | | |
| P-1590 | | | | |
| P-1600 | | | | |
| P-1603 | | | | |
| P-1605 | | | | |

Example 25

Synthesis of 3-[2,6-difluoro-3-(propane-1-sulfonylamino)-benzoyl]-1H-pyrrolo[2,3-b]pyridine-5-carboxylic acid ethylamide P-1630

Compound P-1630 was synthesized in six steps from 5-bromo-1-triisopropylsilyl-7-azaindole 68 as shown in Scheme 45.

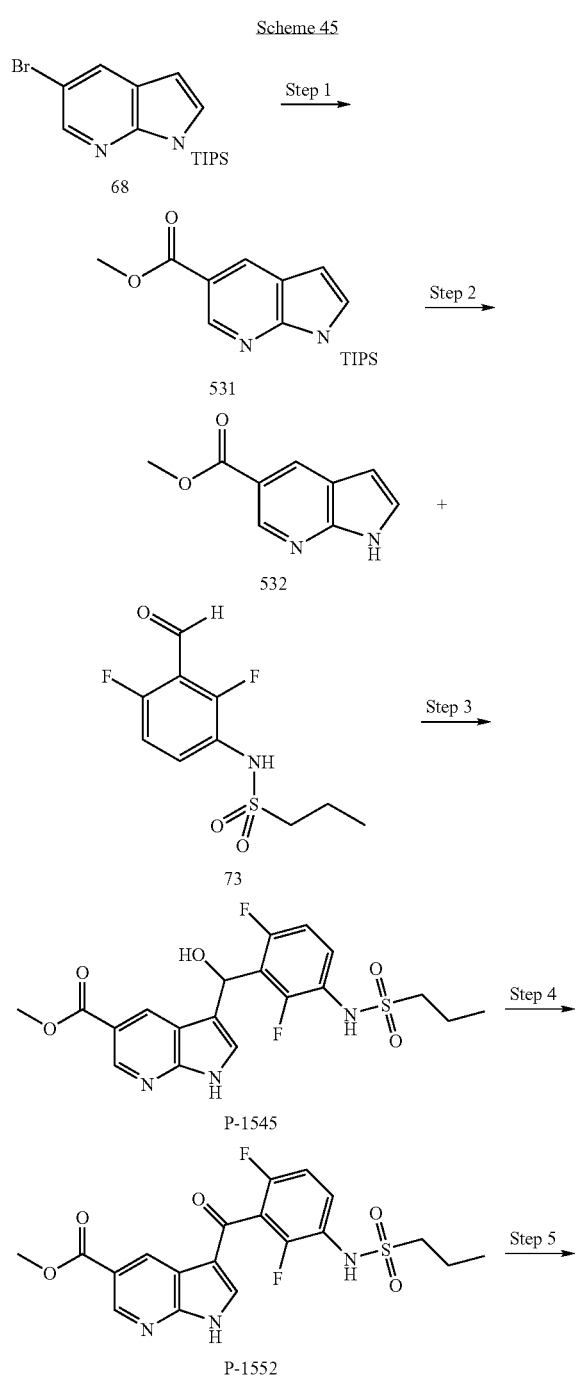

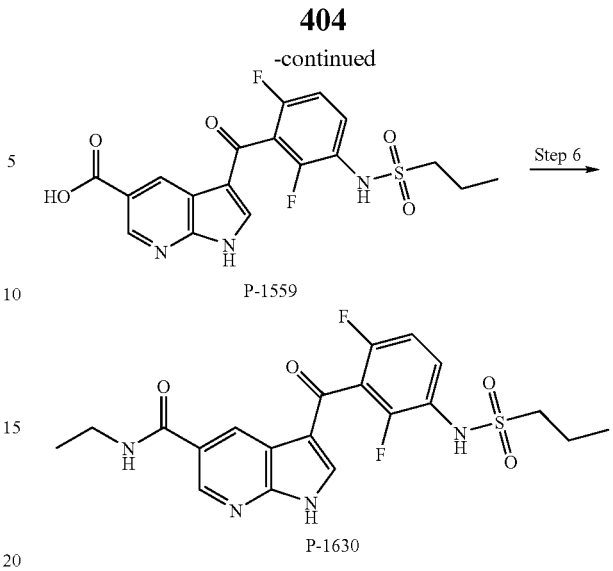

Step 1—Preparation of 1-Triisopropylsilanyl-1H-pyrrolo[2,3-b]pyridine-5-carboxylic acid methyl ester (531)

To 5-bromo-1-triisopropylsilyl-7-azaindole (68, 1.50 g, 4.2 mmol, prepared as described in Example 6) in tetrahydrofuran (20.0 mL) under an atmosphere of nitrogen, cooled with dry ice/acetone, was slowly added n-Butyllithium (10.0 M in hexane, 0.467 mL). After 60 minutes, methyl chloroformate (0.394 mL, 5.1 mmol) was added to the reaction. After another hour, the reaction was poured into water and extracted with ethyl acetate. The organic layer was dried over anhydrous sodium sulfate and filtered. The filtrate was concentrated to give the crude compound as a light yellow solid that was used directly in the next step.

Step 2—Preparation of 1H-Pyrrolo[2,3-b]pyridine-5-carboxylic acid methyl ester (532)

To 1-Triisopropylsilanyl-1H-pyrrolo[2,3-b]pyridine-5-carboxylic acid methyl ester (531, 0.950 g, 2.9 mmol) in tetrahydrofuran (20.0 mL) was added tetrabutyl-ammonium fluoride, trihydrate (1.20 g, 3.8 mmol). The reaction was stirred at room temperature for 10 minutes. The reaction was concentrated and purified with silica gel column chromatography eluting with 4% methanol in methylene chloride to give the compound as a white solid (532, 300 mg, 60%). MS(ESI) [M+H$^+$]$^+$=177.2.

Step 3—Preparation of 3-[2,6-difluoro-3-(propane-1-sulfonylamino)-phenyl]-hydroxy-methyl-1H-pyrrolo[2,3-b]pyridine-5-carboxylic acid methyl ester (P-1545)

To 1H-Pyrrolo[2,3-b]pyridine-5-carboxylic acid methyl ester (532, 155.0 mg, 0.88 mmol) in methanol (15.0 mL) were added propane-1-sulfonic acid (2,4-difluoro-3-formyl-phenyl)-amide (73, 260.0 mg, 0.99 mmol, prepared as described in Example 7) and potassium hydroxide (859 mg, 15.3 mmol) under an atmosphere of nitrogen. The reaction was stirred at room temperature overnight. The reaction was poured into water and extracted with ethyl acetate. The organic layer was dried over anhydrous sodium sulfate and filtered. The filtrate was concentrated and purified by silica gel column chromatography eluting with 20% ethyl acetate in hexane to give the compound as white solid (P-1545, 110 mg, 28%). MS(ESI) [M+H⁺]⁺=440.2.

Step 4—Preparation of 3-[2,6-difluoro-3-(propane-1-sulfonylamino)-benzoyl]-1H-pyrrolo[2,3-b]pyridine-5-carboxylic acid methyl ester (P-1552)

To 3-[2,6-difluoro-3-(propane-1-sulfonylamino)-phenyl]-hydroxy-methyl-1H-pyrrolo[2,3-b]pyridine-5-carboxylic acid methyl ester (P-1545, 100.0 mg, 0.23 mmol) in tetrahydrofuran (10 mL) was added Dess-Martin periodinane (107 mg, 2.5 mmol). The reaction was stirred at room temperature for 10 minutes. The reaction mixture was concentrated with silica gel and then purified with silica gel column chromatography eluting with 30% ethyl acetate in hexane to give the compound as white solid (P-1552, 80 mg, 80%), MS(ESI) [M+H⁺]⁺=438.2.

Step 5—Preparation of 3-[2,6-difluoro-3-(propane-1-sulfonylamino)-benzoyl]-1H-pyrrolo[2,3-b]pyridine-5-carboxylic acid (P-1559)

To 3-[2,6-difluoro-3-(propane-1-sulfonylamino)-benzoyl]-1H-pyrrolo[2,3-b]pyridine-5-carboxylic acid methyl ester (P-1552, 80.0 mg, 0.18 mmol) in tetrahydrofuran (10.0 mL) were added water (3.0 mL) and lithium hydroxide (82 mg, 3.4 mmol). The reaction was stirred at room temperature overnight. The reaction was poured into water, acidified with 1 N HCl to pH around 1, and extracted with ethyl acetate. The organic layer was dried over anhydrous sodium sulfate, filtered, concentrated, and washed with ethyl acetate to give an off-white solid (P-1559, 60 mg, 77%) MS(ESI) [M+H⁺]⁺=424.2.

Step 6: Preparation of 3-[2,6-difluoro-3-(propane-1-sulfonylamino)-benzoyl]-1H-pyrrolo[2,3-b]pyridine-5-carboxylic acid ethylamide (P-1630)

To 3-[2,6-difluoro-3-(propane-1-sulfonylamino)-benzoyl]-1H-pyrrolo[2,3-b]pyridine-5-carboxylic acid (P-1559, 38.0 mg, 0.090 mmol) in tetrahydrofuran (2.3 mL) was added a solution of ethylamine (2.0 M in tetrahydrofuran, 0.20 mL), bromo-tris-pyrrolidino-phosphonium hexafluorophosphate (80.0 mg, 0.17 mmol) and triethylamine (0.30 mL, 2.2 mmol) under an atmosphere of nitrogen. The reaction mixture was stirred overnight at room temperature. The reaction was poured into water and extracted with ethyl acetate. The organic layer was dried over anhydrous sodium sulfate and filtered. The filtrate was concentrated and purified by silica gel column chromatography eluting with 40% ethyl acetate in hexane to give the compound as a white solid (P-1630, 13.2 mg, 33%). MS(ESI) [M−H⁺]⁻=449.0.

Example 26

Synthesis of 1-butyl-3-[3-(5-pyridin-3-yl-1H-pyrrolo[2,3-b]pyridin-3-ylmethyl)-phenyl]-urea P-1445

Compound P-1445 was synthesized in six steps from 5-pyridin-3-yl-1H-pyrrolo[2,3-b]pyridine 89 as shown in Scheme 49.

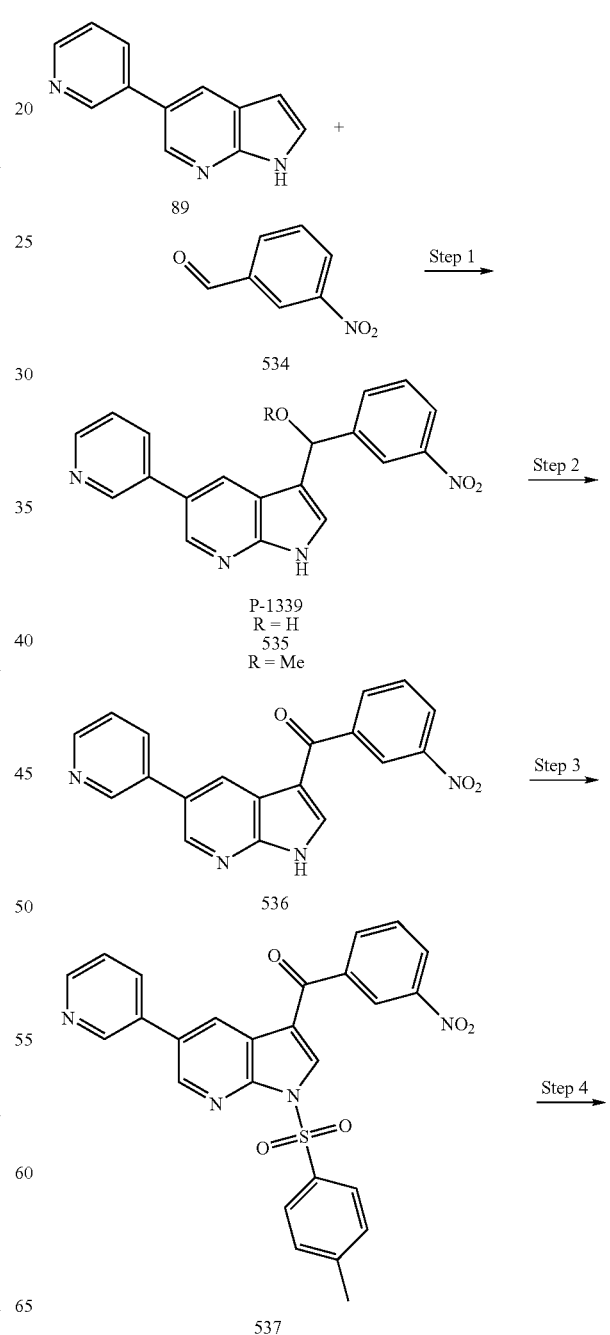

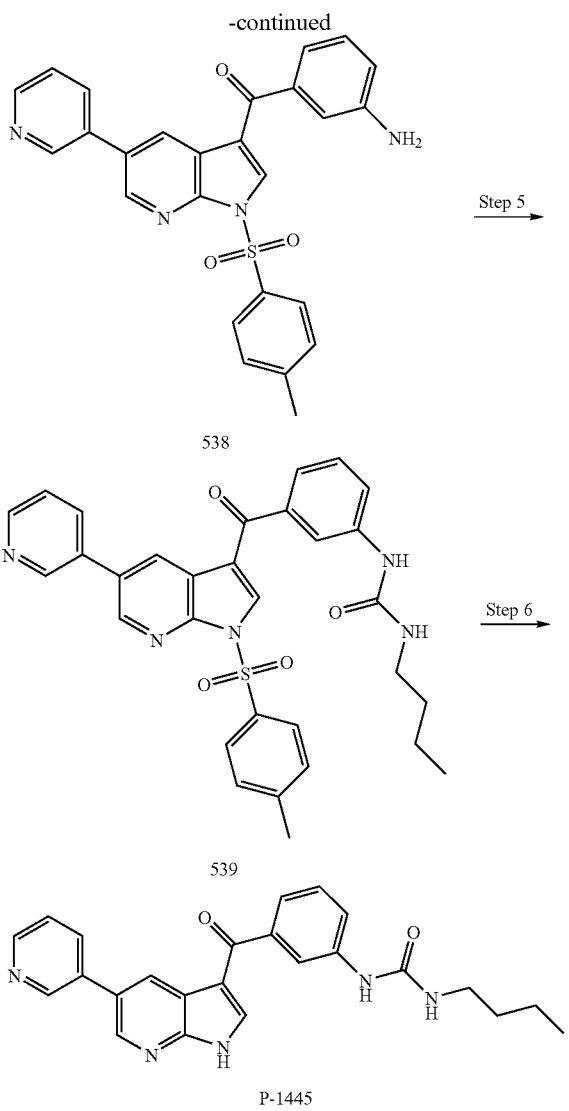

Step 1—Preparation of (3-nitro-phenyl)-(5-pyridin-3-yl-1H-pyrrolo[2,3-b]pyridin-3-yl)-methanol (P-1399)

To 3-nitrobenzaldehyde (534, 1.08 g, 7.17 mmol) in methanol (34 mL) was added 5-pyridin-3-yl-1H-pyrrolo[2,3-b]pyridine (89, 1.08 g, 5.52 mmol, prepared as described in Example 17) and potassium hydroxide (1.55 g, 27.6 mmol). The reaction was stirred at room temperature for four hours. The reaction was poured into water and extracted with ethyl acetate. The organic layer was washed with brine, dried over anhydrous sodium sulfate and concentrated. The mixture was purified by silica gel column chromatography eluting with 4% methanol in dichloromethane to provide two different compounds, a white solid (P-1399, R=H, 1.20 g, 63%) MS(ESI) [M+H$^+$]$^+$=347.2, and a light yellow solid (535, R=Me, 0.434 g, 22%).

Step 2—Preparation of (3-nitro-phenyl)-(5-pyridin-3-yl-1H-pyrrolo[2,3-b]pyridin-3-yl)-methanone (536)

To (3-nitro-phenyl)-(5-pyridin-3-yl-1H-pyrrolo[2,3-b]pyridin-3-yl)-methanol (P-1399, R=H, 500 mg, 1.44 mmol) in dimethylformamide (26 mL) was added Dess-Martin periodane (674 mg, 1.59 mmol). The reaction was stirred for one hour and the reaction was poured into water. All solids were filtered and purified by silica gel column chromatography eluting with 3% methanol in dichloromethane to give the compound (536, 295 mg, 59%). MS(ESI)[M+H$^+$]$^+$=345.2.

Step 3—Preparation of (3-nitro-phenyl)-[5-pyridin-3-yl-1-(toluene-4-sulfonyl-1H-pyrrolo[2,3-b]pyridin-3-yl)-methanone (537)

To (3-nitro-phenyl)-(5-pyridin-3-yl-1H-pyrrolo[2,3-b]pyridin-3-yl)-methanone (536, 291 mg, 0.85 mmol) in tetrahydrofuran (7 mL) was added 1.5 M of lithium diisopropylamide in cyclohexane (676 µl, 1.59 mmol) at −78° C. under an atmosphere of nitrogen. After 30 minutes, p-toluenesulfonyl chloride (209 mg, 1.10 mmol) was added in tetrahydrofuran and the reaction was stirred for three hours. The reaction was poured into water and extracted with ethyl acetate. The organic layer was washed with brine, dried over anhydrous sodium sulfate and concentrated. All solids were filtered and purified by silica gel column chromatography eluting with 60% ethyl acetate in hexane to give the compound (537, 182 mg, 43%). MS(ESI)[M+H$^+$]$^+$=499.2.

Step 4—Preparation of (3-Amino-phenyl-[5-pyridin-3-yl-1-(toluene-4-sulfonyl)-1H-pyrrolo[2,3-b]pyridin-3-yl]-methanone (538)

To (3-nitro-phenyl)-5-pyridin-3-yl-1-(toluene-4-sulfonyl)-1H-pyrrolo[2,3-b]pyridin-3-yl)-methanone (537, 180 mg, 0.361 mmol) in methanol (4 mL) was added 10% palladium on carbon (20 mg) and few drops of concentrated aqueous hydrochloric acid. The resulting mixture was stirred under an atmosphere of hydrogen overnight and the catalyst was filtered out through a bed of celite. The filtrate was concentrated and purified by silica gel column chromatography eluting with 90% ethyl acetate in hexane to give the compound (538, 58 mg, 34%). MS(ESI)[M+H$^+$]$^+$=469.3.

Step 5—Preparation of 1-Butyl-3-3-[5-pyridin-3-yl-1-(toluene-4-sulfonyl)-1H-pyrrolo[2,3-b]pyridine-3-carbonyl]-phenyl-urea (539)

To (3-Amino-phenyl)-[5-pyridin-3-yl-1-(toluene-4-sulfonyl)-1H-pyrrolo[2,3-b]pyridin-3-yl]-methanone (538, 53 mg, 0.11 mmol) in tetrahydrofuran (1.6 mL) was added 1-isocyanatobutane (12 mg, 0.12 mmol). The reaction was heated at 90° C. overnight and it was concentrated and purified by silica gel column chromatography eluting with 2% methanol in dichloromethane to give the compound (539, 39 mg, 61%). MS(ESI)[M+H$^+$]$^+$=568.4.

Step 6—Preparation of 1-Butyl-3-[3-(5-pyridin-3-yl-1H-pyrrolo[2,3-b]pyridine-3-carbonyl)-phenyl]-urea (P-1445)

To 1-Butyl-3-3-[5-pyridin-3-yl-1-(toluene-4-sulfonyl)-1H-pyrrolo[2,3-b]pyridine-3-carbonyl]-phenyl-urea (539, 33 mg, 0.058 mmol) in tetrahydrofuran (2 mL) was added 1.0 M tetra-n-butylammonium fluoride in tetrahydrofuran (192 µl) under an atmosphere of nitrogen and the reaction was stirred for three hours. The reaction was poured into water and extracted with ethyl acetate. The organic layer was washed with brine, dried over anhydrous sodium sulfate and concentrated. All solids were filtered and purified by silica gel column chromatography eluting with 4% methanol in dichloromethane to give the compound (P-1445, 8 mg, 30%). MS(ESI)[M+H$^+$]$^+$=414.3.

Example 27

Synthesis of 1-butyl-3-[3-(5-pyridin-3-yl-1H-pyrrolo[2,3-b]pyridin-3-ylmethyl)-phenyl]-urea P-1447

Compound P-1447 was synthesized in five steps from 3-[(3-nitro-phenyl)-methoxy-methyl]-5-pyridin-3-yl-1H-pyrrolo[2,3-b]pyridine 535 as shown in Scheme 50.

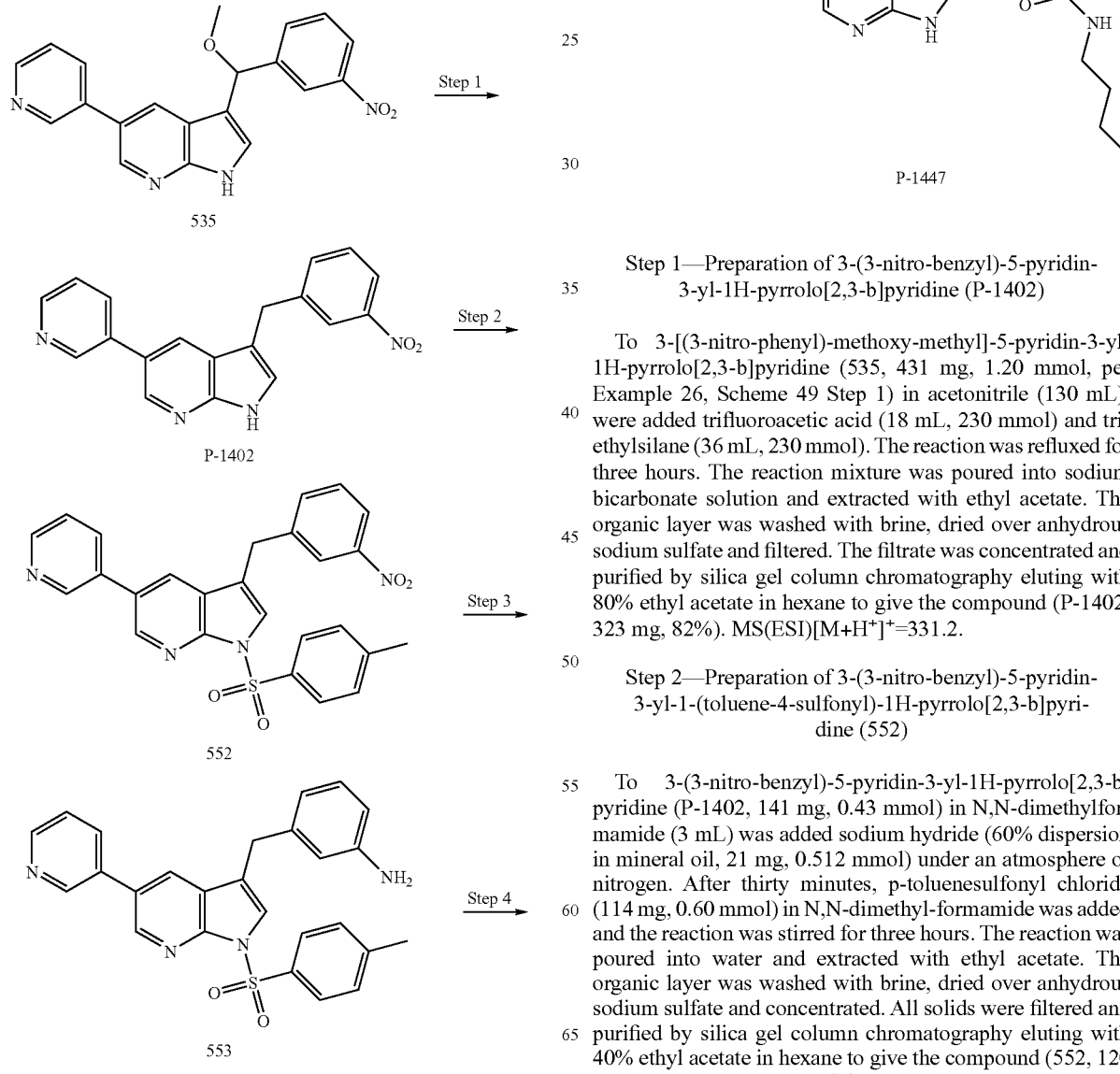

Step 1—Preparation of 3-(3-nitro-benzyl)-5-pyridin-3-yl-1H-pyrrolo[2,3-b]pyridine (P-1402)

To 3-[(3-nitro-phenyl)-methoxy-methyl]-5-pyridin-3-yl-1H-pyrrolo[2,3-b]pyridine (535, 431 mg, 1.20 mmol, per Example 26, Scheme 49 Step 1) in acetonitrile (130 mL), were added trifluoroacetic acid (18 mL, 230 mmol) and triethylsilane (36 mL, 230 mmol). The reaction was refluxed for three hours. The reaction mixture was poured into sodium bicarbonate solution and extracted with ethyl acetate. The organic layer was washed with brine, dried over anhydrous sodium sulfate and filtered. The filtrate was concentrated and purified by silica gel column chromatography eluting with 80% ethyl acetate in hexane to give the compound (P-1402, 323 mg, 82%). MS(ESI)[M+H$^+$]$^+$=331.2.

Step 2—Preparation of 3-(3-nitro-benzyl)-5-pyridin-3-yl-1-(toluene-4-sulfonyl)-1H-pyrrolo[2,3-b]pyridine (552)

To 3-(3-nitro-benzyl)-5-pyridin-3-yl-1H-pyrrolo[2,3-b]pyridine (P-1402, 141 mg, 0.43 mmol) in N,N-dimethylformamide (3 mL) was added sodium hydride (60% dispersion in mineral oil, 21 mg, 0.512 mmol) under an atmosphere of nitrogen. After thirty minutes, p-toluenesulfonyl chloride (114 mg, 0.60 mmol) in N,N-dimethyl-formamide was added and the reaction was stirred for three hours. The reaction was poured into water and extracted with ethyl acetate. The organic layer was washed with brine, dried over anhydrous sodium sulfate and concentrated. All solids were filtered and purified by silica gel column chromatography eluting with 40% ethyl acetate in hexane to give the compound (552, 120 mg, 58%). MS(ESI)[M+H$^+$]$^+$=485.25.

Step 3—Preparation of 3-[5-Pyridin-3-yl-1-(toluene-4-sulfonyl)-1H-pyrrolo[2,3-b]pyridin-3-ylmethyl]-phenylamine (553)

To 3-(3-nitro-benzyl)-5-pyridin-3-yl-1-(toluene-4-sulfonyl)-1H-pyrrolo[2,3-b]pyridine (552, 230 mg, 0.14 mmol) in methanol (5 mL) was added 10% palladium on carbon (10 mg) and few drops of concentrated aqueous hydrochloric acid. The resulting mixture was stirred under an atmosphere of hydrogen overnight, and the catalyst was filtered out through a bed of celite. The filtrate was concentrated and purified by silica gel column chromatography eluting with 90% ethyl acetate in hexane to give the compound (553, 88 mg, 41%). MS(ESI)[M+H$^+$]$^+$=455.3.

Step 4—Preparation of 1-butyl-3-3-[5-pyridin-3-yl-1-(toluene-4-sulfonyl)-1H-pyrrolo[2,3-b]pyridin-3-ylmethyl]-phenyl-urea (554)

To 3-[5-pyridin-3-yl-1-(toluene-4-sulfonyl)-1H-pyrrolo[2,3-b]pyridin-3-ylmethyl]-phenylamine (553, 14 mg, 0.031 mmol) in tetrahydrofuran (0.5 mL) was added 1-isocyanatobutane (3.4 mg, 0.03 mmol). The reaction was heated at 90° C. overnight and was concentrated and purified by silica gel column chromatography eluting with 2% methanol in dichloromethane to give the compound (554, 7.2 mg, 42%). MS(ESI)[M+H$^+$]$^+$=554.4.

Step 5—Preparation of 1-Butyl-3-[3-(5-pyridin-3-yl-1H-pyrrolo[2,3-b]pyridin-3-ylmethyl)-phenyl]-urea (P-1447)

To 1-butyl-3-3-[5-pyridin-3-yl-1-(toluene-4-sulfonyl)-1H-pyrrolo[2,3b]pyridin-3-ylmethyl]-phenyl-urea (554, 11 mg, 0.02 mmol) in tetrahydrofuran (0.7 mL) was added 1.0 M tetra-n-butylammonium fluoride in tetrahydrofuran (66 μl) under an atmosphere of nitrogen and the reaction was stirred for three hours. The reaction was poured into water and extracted with ethyl acetate. The organic layer was washed with brine, dried over anhydrous sodium sulfate and concentrated. All solids were filtered and purified by silica gel column chromatography eluting with 4% methanol in dichloromethane to give the compound (P-1447, 2.5 mg, 31%). MS(ESI)[M+H$^+$]$^+$=400.3.

1-Cyclopentyl-3-[3-(5-pyridin-3-yl-1H-pyrrolo[2,3-b]pyridin-3-ylmethyl)-phenyl]-urea P-1446

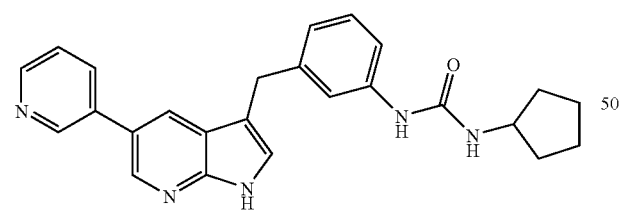

was prepared following the protocol of Scheme 50, substituting 1-isocyanatobutane with isocyanato-cyclopentane in Step 4. MS(ESI) [M+H$^+$]$^+$=412.4.

Example 28

Synthesis of 3-[3-chloro-4-(4-chloro-benzyloxy)-benzyl]-1H-pyrrolo[2,3-b]pyridine P-1449

Compound P-1449 was synthesized in three steps from 3-chloro-4-hydroxy-benzaldehyde 556 as shown in Scheme 51.

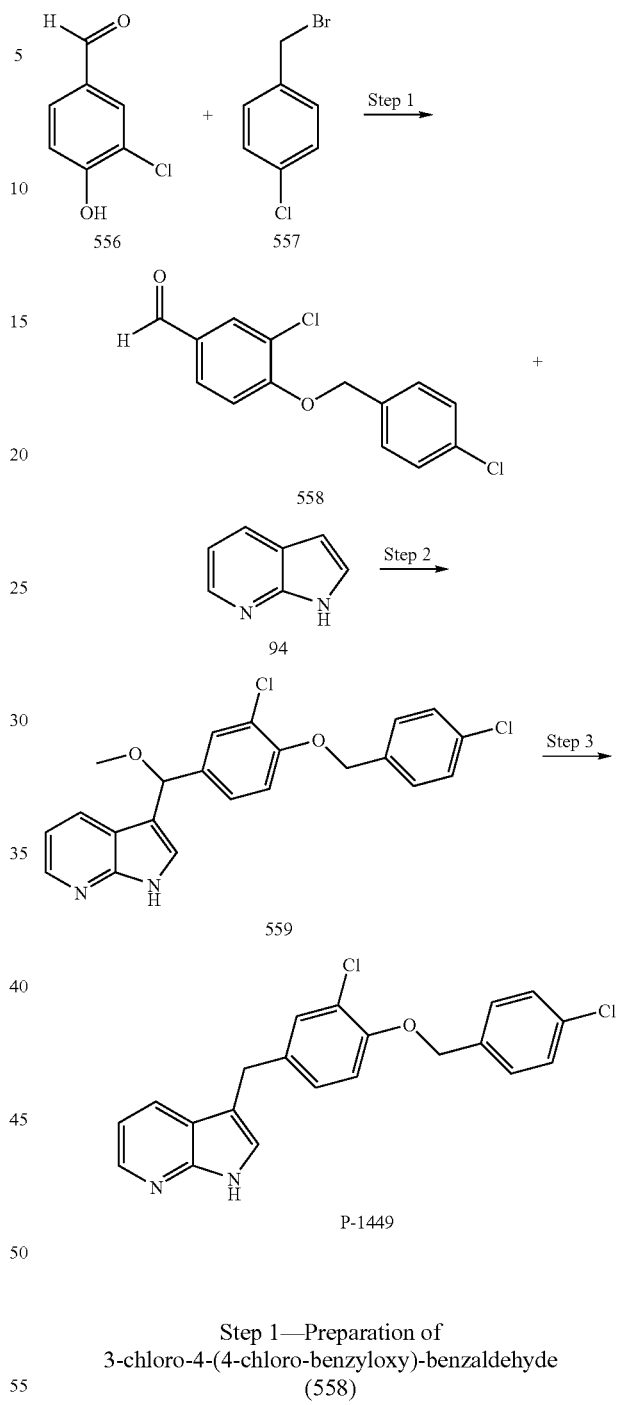

Step 1—Preparation of 3-chloro-4-(4-chloro-benzyloxy)-benzaldehyde (558)

To acetonitrile (15.0 mL) were added 3-chloro-4-hydroxy-benzaldehyde (556, 0.6 g, 4 mmol), 4-chlorobenzyl bromide (557, 1.2 g, 6 mmol), and potassium carbonate (0.9 g, 7 mmol). The reaction was heated to 150° C. for 10 minutes in a CEM Discover microwave instrument. The reaction was poured into water, extracted with ethyl acetate, and washed with brine. The organic layer was dried over anhydrous sodium sulfate, filtered and concentrated. The desired compound was isolated by silica gel column chromatography (ethyl acetate: hexanes) (558, 0.85 g, 76%).

Step 2—Preparation of 3-[3-chloro-4-(4-chloro-benzyloxy)-phenyl]methoxy-methyl-1H-pyrrolo[2,3-b]pyridine (559)

1H-Pyrrolo[2,3-b]pyridine (94, 0.3 g, 2.8 mmol) was mixed with 3-chloro-4-(4-chloro-benzyloxy)-benzaldehyde (558, 0.8 g, 3 mmol), potassium hydroxide (0.9 g, 17 mmol) and methanol (90.0 mL). The reaction was heated to 50° C. under an atmosphere of nitrogen for six days. After neutralization with 6N hydrochloric acid the reaction was poured into water, extracted with ethyl acetate, and washed with brine. The organic layer was dried over anhydrous sodium sulfate, filtered and concentrated. The desired compound was isolated by silica gel column chromatography (ethyl acetate: hexanes) to give a yellow solid (559, 0.6 g, 41%). MS(ESI) [M+H$^+$]$^+$=413.2, 415.2 [M–H$^+$]$^-$=411.1, 413.1.

Step 3—Preparation of 3-[3-chloro-4-(4-chloro-benzyloxy)-benzyl]-1H-pyrrolo[2,3-b]pyridine (P-1449)

3-[3-Chloro-4-(4-chloro-benzyloxy)-phenyl]-methoxy-methyl-1H-pyrrolo[2,3-b]pyridine (559, 0.2 g, 0.6 mmol) was mixed with trifluoroacetic acid (0.226 mL, 3 mmol), triethylsilane (0.4 mL, 3 mmol) and acetonitrile (5 mL). The reaction was heated at 50° C. and stirred for two days. The reaction was concentrated. The residue was diluted with ethyl acetate and neutralized with 2M aqueous sodium hydroxide. The reaction was poured into water, extracted with ethyl acetate, and washed with brine. The organic layer was dried over anhydrous sodium sulfate, filtered and concentrated. The desired compound was isolated by silica gel column chromatography (ethyl acetate: hexanes) to give a yellow solid (P-1449, 0.0744 g, 33%). MS(ESI) [M+H$^+$]$^+$=383.2, 385.2.

Additional compounds were prepared following the protocol of Scheme 51, replacing 3-chloro-4-hydroxy-benzaldehyde 556 with an appropriate aldehyde and optionally replacing 4-chlorobenzyl bromide 557 with an appropriate benzyl halide in Step 1, and optionally replacing 1H-pyrrolo[2,3-b]pyridine 94 with an appropriate azaindole in Step 2. The following compounds were made following this procedure:

- 3-[4-(4-chloro-benzyloxy)-2-methoxy-benzyl]-1H-pyrrolo[2,3-b]pyridine (P-1450),
- 3-[4-(4-Chloro-benzyloxy)-benzyl]-1H-pyrrolo[2,3-b]pyridine (P-1462),
- 3-[4-(4-Chloro-benzyloxy)-3-fluoro-5-methoxy-benzyl]-1H-pyrrolo[2,3-b]pyridine (P-1466),
- 3-[4-(4-Chloro-benzyloxy)-3-ethoxy-benzyl]-1H-pyrrolo[2,3-b]pyridine (P-1470),
- 3-[2-Chloro-4-(4-chloro-benzyloxy)-benzyl]-1H-pyrrolo[2,3-b]pyridine (P-1471),
- 3-[4-(4-Chloro-benzyloxy)-3-trifluoromethoxy-benzyl]-1H-pyrrolo[2,3-b]pyridine (P-1487),
- 3-[4-(4-Chloro-benzyloxy)-3-methoxy-benzyl]-5-methoxy-1H-pyrrolo[2,3-b]pyridine (P-1531),
- 5-Chloro-3-[4-(4-chloro-benzyloxy)-3-methoxy-benzyl]-1H-pyrrolo[2,3-b]pyridine (P-1532),
- 3-[4-(4-Chloro-2-fluoro-benzyloxy)-3-methoxy-benzyl]-1H-pyrrolo[2,3-b]pyridine (P-1544),
- 3-[4-(2,4-Dichloro-benzyloxy)-3-methoxy-benzyl]-1H-pyrrolo[2,3-b]pyridine (P-1568),
- 3-[3-Methoxy-4-(4-methoxy-benzyloxy)-benzyl]-1H-pyrrolo[2,3-b]pyridine (P-1569),
- 3-[3-Methoxy-4-(2,4,6-trifluoro-benzyloxy)-benzyl]-1H-pyrrolo[2,3-b]pyridine (P-1578),
- 3-[4-(2,6-Dichloro-benzyloxy)-3-methoxy-benzyl]-1H-pyrrolo[2,3-b]pyridine (P-1579), and 3-[3-Chloro-4-(4-chloro-benzyloxy)-5-methoxy-benzyl]-1H-pyrrolo[2,3-b]pyridine (P-1616), The following table indicates the aldehyde (Column 2), the benzyl halide (Column 3), and the azaindole (Column 4) used to afford the target compound (Column 5). Column 1 indicates the compound number and column 6 the observed mass.

| | Aldehyde | Benzyl halide | Azaindole | Compound | MS(ESI) [M + H$^+$]$^+$ observed |
|---|---|---|---|---|---|
| P-1450 | | | | | 379.2 381.2 |
| P-1462 | | | | | 349.1 351.2 |

-continued

| | Aldehyde | Benzyl halide | Azaindole | Compound | MS(ESI) [M + H+]+ observed |
|---|---|---|---|---|---|
| P-1466 | 3-fluoro-4-hydroxy-5-methoxybenzaldehyde | 4-chlorobenzyl bromide | 7-azaindole | | 397.2 399.2 |
| P-1470 | 3-ethoxy-4-hydroxybenzaldehyde | 4-chlorobenzyl bromide | 7-azaindole | | 393.2 395.2 |
| P-1471 | 2-chloro-4-hydroxybenzaldehyde | 4-chlorobenzyl bromide | 7-azaindole | | 383.1 385.1 |
| P-1487 | 4-hydroxy-3-(trifluoromethoxy)benzaldehyde | 4-chlorobenzyl bromide | 7-azaindole | | 433.2 435.2 |
| P-1531 | 4-hydroxy-3-methoxybenzaldehyde | 4-chlorobenzyl bromide | 5-methoxy-7-azaindole | | 409.2 |
| P-1532 | 4-hydroxy-3-methoxybenzaldehyde | 4-chlorobenzyl bromide | 5-chloro-7-azaindole | | 413.1 |

US 8,415,469 B2
417                                418
-continued
| | Aldehyde | Benzyl halide | Azaindole | Compound | MS(ESI) [M + H+]+ observed |
|---|---|---|---|---|---|
| P-1544 |  |  | 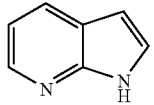 | 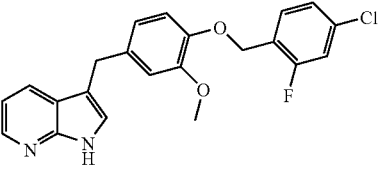 | 397.2 |
| P-1568 |  | 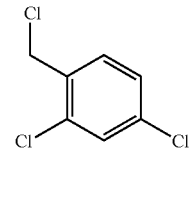 | 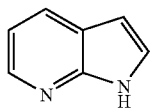 | 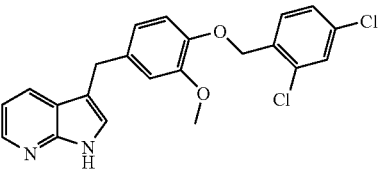 [SMILES: COc1cc(Cc2c[nH]c3ncccc23)ccc1OCc1ccc(Cl)cc1Cl] | 413.1<br>415.1<br>416.2 |
| P-1569 |  | 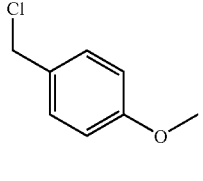 | 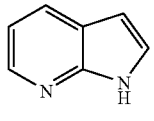 | 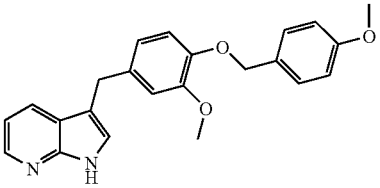 [SMILES: COc1ccc(COc2ccc(Cc3c[nH]c4ncccc34)cc2OC)cc1] | 375.2 |
| P-1578 |  | 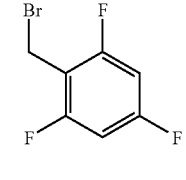 | 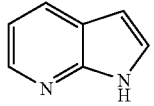 | 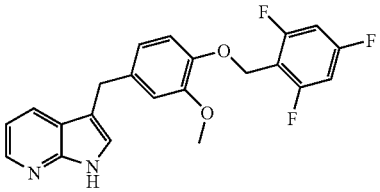 [SMILES: COc1cc(Cc2c[nH]c3ncccc23)ccc1OCc1c(F)cc(F)cc1F] | 399.2<br>397.1<br>([M − H+]−) |
| P-1579 |  | 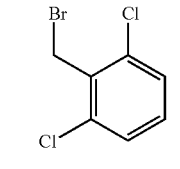 | 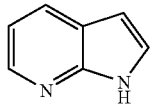 | 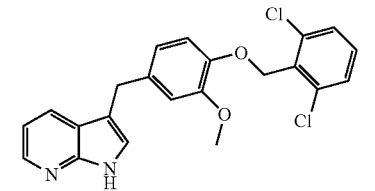 [SMILES: COc1cc(Cc2c[nH]c3ncccc23)ccc1OCc1c(Cl)cccc1Cl] | 413.2<br>415.2<br>416.2<br>([M − H+]−) |
| P-1616 |  | 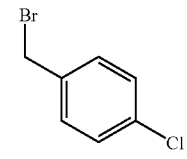 | 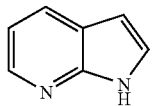 | 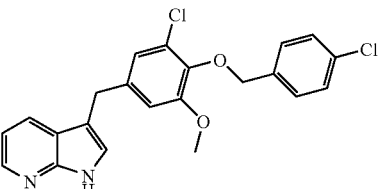 | 413.1 |

Example 29

Synthesis of 3-(4-benzyloxy-3-methoxy-benzyl)-1H-pyrrolo[2,3-b]pyridine P-1613

Compound P-1613 was synthesized in two steps from 4-benzyloxy-3-methoxy-benzaldehyde 564 as shown in Scheme 53.

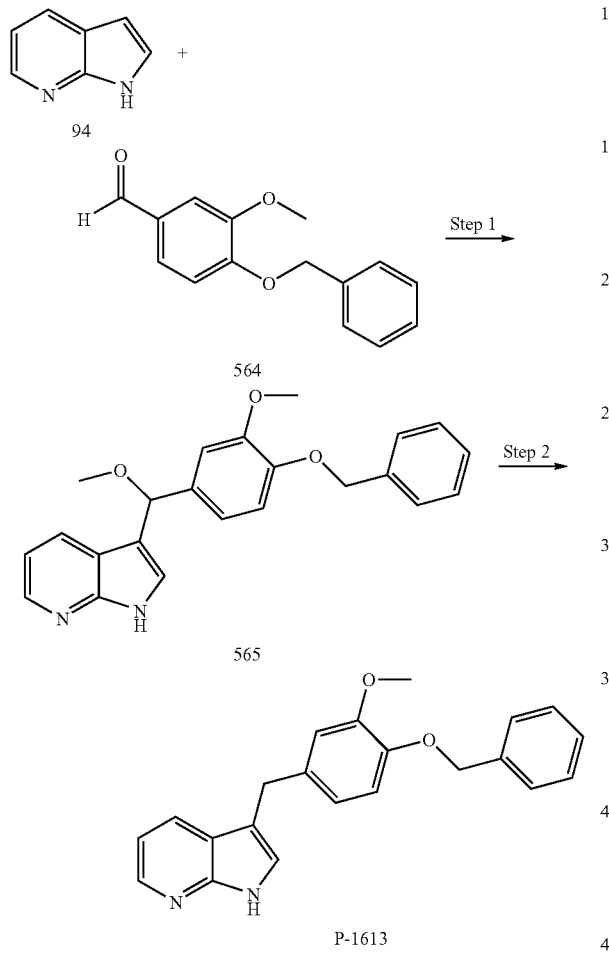

Step 1—Preparation of 3-[(4-benzyloxy-3-methoxy-phenyl)-methoxy-methyl]-1H-pyrrolo[2,3-b]pyridine (565)

Methanol (125 mL) and potassium hydroxide (4.4 g, 79 mmol) were mixed with 1H-pyrrolo[2,3-b]pyridine (94, 3.1 g, 26.6 mmol) and 4-benzyloxy-3-methoxy-benzaldehyde (564, 12.9 g, 53.2 mmol). The reaction was stirred at room temperature for 2 days. The resulting white solid was filtered and washed with water. Crude material was carried forward without further purification.

Step 2—Preparation of 3-(4-benzyloxy-3-methoxy-benzyl)-1H-pyrrolo[2,3-b]pyridine (P-1613)

3-[(4-Benzyloxy-3-methoxy-phenyl)-methoxy-methyl]-1H-pyrrolo[2,3-b]pyridine (565, 0.9 g, 2.4 mmol) and acetonitrile (50 mL) were mixed with trifluoroacetic acid (0.360 mL, 4.7 mmol) and triethylsilane (0.746 mL, 4.7 mmol). The reaction was heated at 80° C. and stirred overnight. The reaction was concentrated. The mixture was extracted with ethyl acetate and saturated sodium bicarbonate. The organic layer was dried over anhydrous sodium sulfate, filtered and concentrated. The desired compound was isolated by silica gel column chromatography to give the compound (P-1613, 0.454 g 54.8%). MS(ESI) [M+H$^+$]$^+$=345.3.

Example 30

Synthesis of 1-[3-(5-bromo-1H-pyrrolo[2,3-b]pyridine-3-carbonyl)-phenyl]-3-butyl-urea P-1596

Compound P-1596 was synthesized in one step from 5-bromo-1H-pyrrolo[2,3-b]pyridine 67 as shown in Scheme 55.

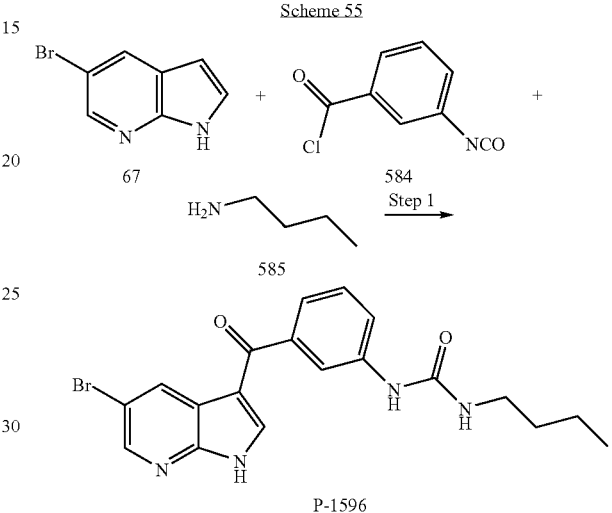

Step 1—Preparation of 1-[3-(5-bromo-1H-pyrrolo[2,3-b]pyridine-3-carbonyl)-phenyl]-3-butyl-urea (P-1596)

To aluminum trichloride (3.67 g, 0.0275 mol) in dichloromethane (100 mL, 2 mol) under an atmosphere of nitrogen was added 5-bromo-7-azaindole (67, 1.08 g, 0.00548 mol) at room temperature. After one hour, 3-isocyanato-benzoyl chloride (584, 5.00 g, 0.0275 mol) was added under an atmosphere of nitrogen at room temperature. The resulting mixture was stirred over night at room temperature. 1-Butanamine (585, 54 mL, 0.54 mol) was added carefully. All solvents were removed. The residue was purified by silica gel column chromatography to give the compound (P-1596, 172 mg, 8%). MS(ESI) [M−H+]−=413.1, 415.0.

Additional compounds were prepared following the protocol of Scheme 55, replacing 1-butanamine 585 with an appropriate amine and optionally replacing 5-bromo-7-azaindole 67 with 5-pyridin-3-yl-1H-pyrrolo[2,3-b]pyridine 89 (prepared as described in Example 17). The following compounds were made following this procedure:
- 1-Benzyl-3-[3-(5-bromo-1H-pyrrolo[2,3-b]pyridine-3-carbonyl)-phenyl]-urea (P-1553)
- 1-Benzyl-3-[3-(5-pyridin-3-yl-1H-pyrrolo[2,3-b]pyridine-3-carbonyl)-phenyl]-urea (P-1554),
- 1-(2-Methoxy-ethyl)-3-[3-(5-pyridin-3-yl-1H-pyrrolo[2,3-b]pyridine-3-carbonyl)-phenyl]-urea (P-1566), and
- 1-Phenyl-3-[3-(5-pyridin-3-yl-1H-pyrrolo[2,3-b]pyridine-3-carbonyl)-phenyl]-urea (P-1591).

The following table indicates the amine (column 2) and the azaindole (column 3) used to afford the target compound (column 4). The compound number is provided in column 1 and the observed mass in column 5.

| Amine | Azaindole | Compound | MS(ESI) [M + H+]+ observed |
|---|---|---|---|
| P-1553 | | | 447.0 449.1 |
| P-1554 | | | 448.3 |
| P-1566 | | | 416.3 |
| P-1591 | | | 434.3 |

Example 31

Synthesis of 1-Butyl-3-3-[5-(1-methyl-1H-pyrazol-4-yl)-1H-pyrrolo[2,3-b]pyridine-3-carbonyl]-phenyl-urea P-1880

Compound P-1880 was synthesized in one step from 1-[3-(5-bromo-1H-pyrrolo[2,3-b]pyridine-3-carbonyl)-phenyl]-3-butyl-urea P-1596 as shown in Scheme 56.

Scheme 56

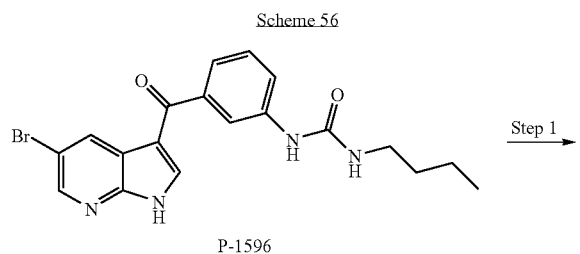

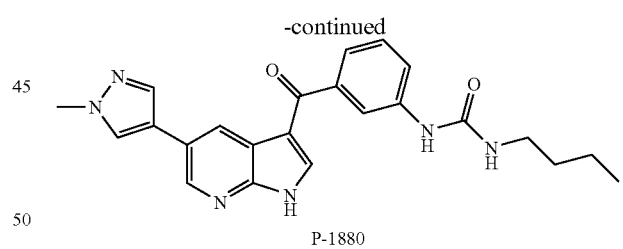

Step 1—Preparation of 1-Butyl-3-3-[5-(1-methyl-1H-pyrazol-4-yl)-1H-pyrrolo[2,3-b]pyridine-3-carbonyl]-phenyl-urea (P-1880)

In a microwave tube, 1-[3-(5-bromo-1H-pyrrolo[2,3-b]pyridine-3-carbonyl)-phenyl]-3-butyl-urea (P-1596, 0.077 g, 0.00018 mol, prepared as described in Example 30, Scheme 55), 1-Methyl-4-(4,4,5,5-tetramethyl-[1,3,2]dioxaborolan-2-yl)-1H-pyrazole (0.0964 g, 0.000464 mol), and Tetrakis(triphenylphosphine)palladium(0) (0.011 g, 0.0000093 mol) were mixed in 1.00 M of potassium carbonate in water (1.2 mL), acetonitrile (2.0 mL, 0.037 mol), and tetrahydrofuran (1.0 mL, 0.012 mol). The resulting mixture was heated at 100° C. in the microwave for 20 minutes, then at 120° C. for 10 minutes. The reaction was poured into water and extracted with ethyl acetate. The organic layer was washed with brine, dried over anhydrous sodium sulfate and filtered. The filtrate was concentrated and purified by silica gel column chromatography to give the compound (P-1880, 52 mg, 67%). MS(ESI)[M+H$^+$]$^+$=417.4.

Example 32

Synthesis of 1-Butyl-3-[2-chloro-3-(5-pyridin-3-yl-1H-pyrrolo[2,3-b]pyridine-3-carbonyl)-phenyl]-urea P-1828

Compound P-1828 was synthesized in two steps from 3-amino-2-chlorobenzoic acid 586 as shown in Scheme 57.

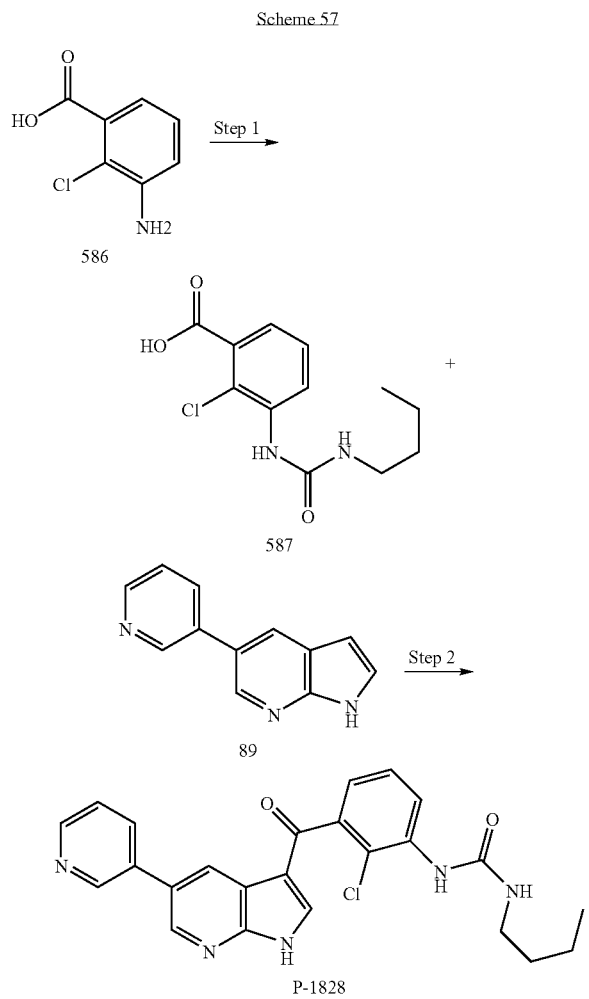

Step 1—Preparation of -(3-Butyl-ureido)-2-chloro-benzoic acid (587)

To N,N-diisopropylamine (1.72 mL, 0.0122 mol) in tetrahydrofuran (12 mL, 0.14 mol), was added 1.6 M n-butyllithium in hexane (7.6 mL) at −78° C. under an atmosphere of nitrogen. After 30 minutes, 3-amino-2-chlorobenzoic acid (586, 1.00 g, 0.00583 mol) was added. After another 30 minutes, 1-isocyanatobutane (2.60 mL, 0.0233 mol) was added at −78° C. under an atmosphere of nitrogen and allowed to stir for two hours. The reaction mixture was warmed up to room temperature and stirred at room temperature for 30 minutes. The reaction was quenched with 1M HCl (aqueous) solution and extracted with ethyl acetate twice. The combined organic layers were washed with brine, dried over anhydrous magnesium sulfate and filtered. The filtrate was concentrated and purified by silica gel column chromatography eluting with dichloromethane:methanol:acetic acid 40:2:1 to give the compound as an off-white solid (587, 147 mg, 9%).

Step 2—Preparation of 1-Butyl-3-[2-chloro-3-(5-pyridin-3-yl-1H-pyrrolo[2,3-b]pyridine-3-carbonyl)-phenyl]-urea (P-1828)

To 3-(3-Butyl-ureido)-2-chloro-benzoic acid (587, 103 mg, 0.000380 mol) was added dichloromethane (10 mL, 0.2 mol) followed by thionyl chloride (110 μL, 0.0015 mol) and 1 drop of dimethylformamide to give a suspension. The reaction was stirred at room temperature for 2 hours. Solid material was still present in the reaction mixture, so tetrahydrofuran (0.5 mL, 0.006 mol) was added and continued stirring at room temperature. The reaction became a clear solution after 2 hours, then stirred for another hour. All volatiles were removed under vacuum and the residue stripped from toluene, twice. The solid was then dried under high vacuum for 60 minutes and dissolved in dichloromethane (5 mL). This was added to 5-(pyridin-3-yl)-1H-pyrrolo[2,3-b]pyridine (89, 0.074 g 0.00038 mol, prepared as described in Example 17) which had been treated with aluminum trichloride (0.25 g, 0.0019 mol) in dichloromethane (10 mL) for 1 hour. The reaction was stirred at room temperature overnight, then quenched with methanol (5 mL). The resulting solution was extracted with ethyl acetate and water with added saturated sodium bicarbonate to adjust pH~8. The organic layer was washed with sodium bicarbonate and brine and dried over magnesium sulfate and filtered. The organic layer was concentrated and purified by silica gel column chromatography eluting with 2% methanol in dichloromethane followed by 5% methanol in dichloromethane to give the compound as a white solid (P-1828, 45 mg, 26%).
MS(ESI) [M+H$^+$]$^+$=448.3.

Additional compounds were prepared following the protocol of Scheme 57, replacing 3-amino-2-chlorobenzoic acid 586 with an appropriate carboxylic acid and optionally replacing 1-isocyanatobutane with an appropriate isocyanate in Step 1 and optionally replacing 5-(pyridin-3-yl)-1H-pyrrolo[2,3-b]pyridine 89 with an appropriate substituted 7-azaindole (see Example 17) in Step 2, The following compounds were made following this procedure:
  1-Butyl-3-[2-methyl-3-(5-pyridin-3-yl-1H-pyrrolo[2,3-b]pyridine-3-carbonyl)-phenyl]-urea (P-1742),
  3-Butyl-1-methyl-1-[2-methyl-3-(5-pyridin-3-yl-1H-pyrrolo[2,3-b]pyridine-carbonyl)-phenyl]-urea (P-1855),
  [3-(5-Bromo-1H-pyrrolo[2,3-b]pyridine-3-carbonyl)-4-fluoro-phenyl]-urea (P-1570),
  [4-Fluoro-3-(5-phenyl-1H-pyrrolo[2,3-b]pyridine-3-carbonyl)-phenyl]-urea (P-1589),
  3-{3-[5-(3-Butyl-ureido)-2-fluoro-benzoyl]-1H-pyrrolo[2,3-b]pyridin-5-yl}-benzamide (P-1621),
  1-Butyl-3-{4-fluoro-3-[5-(3-methane sulfonyl-phenyl)-1H-pyrrolo[2,3-b]pyridine-3-carbonyl]-phenyl}-urea (P-1627), and
  1-[3-(5-Bromo-1H-pyrrolo[2,3-b]pyridine-3-carbonyl)-4-fluoro-phenyl]-3-butyl-urea (P-1637).

The following table indicates the carboxylic acid (column 2), the isocyanate (column 3), and the azaindole (column 4) used to afford the target compound (column 5). Column 1 indicates the compound number and column 6 the observed mass.

| Compound | Acid | Iso-cyanate | Azaindole | Compound | MS(ESI) [M + H⁺]⁺ observed |
|---|---|---|---|---|---|
| P-1742 | | | | | 428.3 |
| P-1855 | | | | | 442.3 |
| P-1570 | | | | | 377.1 / 379.1 |
| P-1589 | | | | | 375.2 |
| P-1621 | | | | | 474.3 |
| P-1627 | | | | | 509.2 |

| Acid | Iso-cyanate | Azaindole | Compound | MS(ESI) [M + H⁺]⁺ observed |
|---|---|---|---|---|
| P-1637 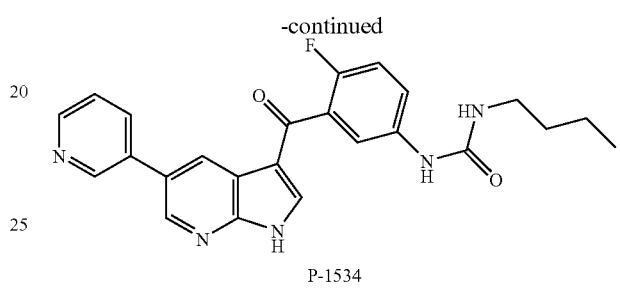 | | | | 433.1 435.1 |

Example 33

Synthesis of 1-Butyl-3-[4-fluoro-3-(5-pyridin-3-yl-1H-pyrrolo[2,3-b]pyridine-3-carbonyl)-phenyl]-urea (P-1534)

Compound P-1534 was synthesized in two steps from 5-(3-butylureido)-2-fluorobenzoic acid 588 (prepared from 3-fluoro-5-aminobenzoic acid and 1-isocyanatobutane following the protocol described in Step 1 of Scheme 57, Example 32) and 5-bromo-7-azaindole 67 as shown in Scheme 58.

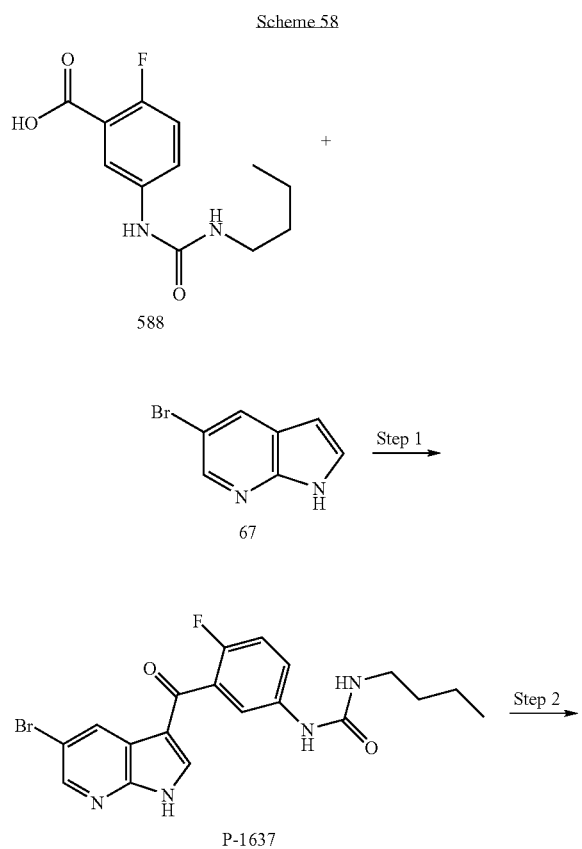

Scheme 58

Step 1—Preparation of 1-[3-(5-bromo-1H-pyrrolo[2,3-b]pyridine-3-carbonyl)-4-fluoro-phenyl]-3-butyl-urea (P-1637)

To aluminum trichloride (0.524 g, 0.00393 mol) and dichloromethane (20 mL, 0.3 mol) under an atmosphere of nitrogen was added 5-bromo-7-azaindole (67, 0.155 g, 0.000787 mol) in dichloromethane. To 5-(3-butylureido)-2-fluorobenzoic acid (588, 0.200 g, 0.000787 mol) was added 4 mL of dichloromethane (4 mL) followed by thionyl chloride (69 µL, 0.00094 mol) and a drop of N,N-dimethylformamide. After 1 hour, the reaction remained a suspension so additional thionyl chloride was added along with tetrahydrofuran. The reaction remained a suspension, so was placed in a 50° C. oil bath. After another hour, the reaction was still a suspension, and so was left to react at 50° C. overnight. The reaction had become a clear solution. All volatiles were removed under vacuum, then the residue dissolved in dichloromethane and added to the 5-bromo-7-azaindole and aluminum trichloride suspension. The reaction was allowed to stir at room temperature for 4.5 hours, followed by the addition of water and extraction with ethyl acetate. The organic layer was dried over magnesium sulfate and filtered. The filtrate was concentrated and purified by silica gel column chromatography eluting with a gradient of methanol (0 to 10%) in dichloromethane to give the compound (P-1637, 14 mg, 4%).

Step 2—Preparation of 1-Butyl-3-[4-fluoro-3-(5-pyridin-3-yl-1H-pyrrolo[2,3-b]pyridine-3-carbonyl)-phenyl]-urea (P-1534)

To 1-[3-(5-bromo-1H-pyrrolo[2,3-b]pyridine-3-carbonyl)-4-fluoro-phenyl]-3-butyl-urea (P-1637, 14.0 mg, 0.0000323 mol), 3-pyridylboronic acid (5.96 mg, 0.0000485 mol), and Tetrakis(triphenylphosphine)palladium(0) (0.820 mg, 7.09E-7 mol) were mixed in 1.00 M potassium carbonate in water (1.00 mL) and acetonitrile (2.00 mL, 0.0353 mol).

The resulting mixture was heated at 120° C. in the microwave for 40 minutes. The reaction was extracted with ethyl acetate and water twice, and the combined organic layers were washed with 1M sodium bicarbonate followed by brine and the organic layer was dried over magnesium sulfate and filtered. The organic layer was concentrated and purified by reverse phase HPLC (acetonitrile and water with 0.1% formic acid) to give the compound as a white solid (P-1637, 8.5 mg, 61%). MS(ESI) [M+H⁺]⁺=432.3.

1-Butyl-3-{4-fluoro-3-[5-(3-trifluoromethoxy-phenyl)-1H-pyrrolo[2,3-b]pyridine-3-carbonyl]-phenyl}-urea P-1660

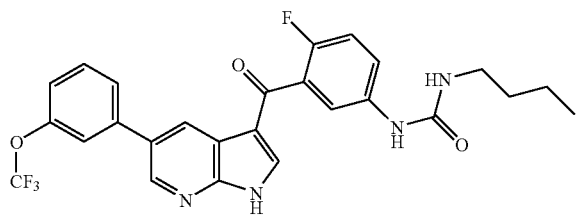 [SMILES: CCCCNC(=O)Nc1ccc(F)c(C(=O)c2c[nH]c3ncc(-c4cccc(OC(F)(F)F)c4)cc23)c1]

was prepared following the protocol of Scheme 58, replacing 3-Pyridylboronic acid with 3-trifluoromethoxy-phenylboronic acid in Step 2. MS(ESI) [M+H⁺]⁺=515.2.

Example 34

Synthesis of aldehyde reagents for coupling to 7-azaindoles

Aldehyde compounds for coupling to the 3-position of a 7-azaindole are shown in the following Schemes. 3-Methoxy-4-[4-(4-methyl-piperazin-1-ylmethyl)-benzyloxy]-benzaldehyde 591 was prepared in one Step as shown in Scheme 59.

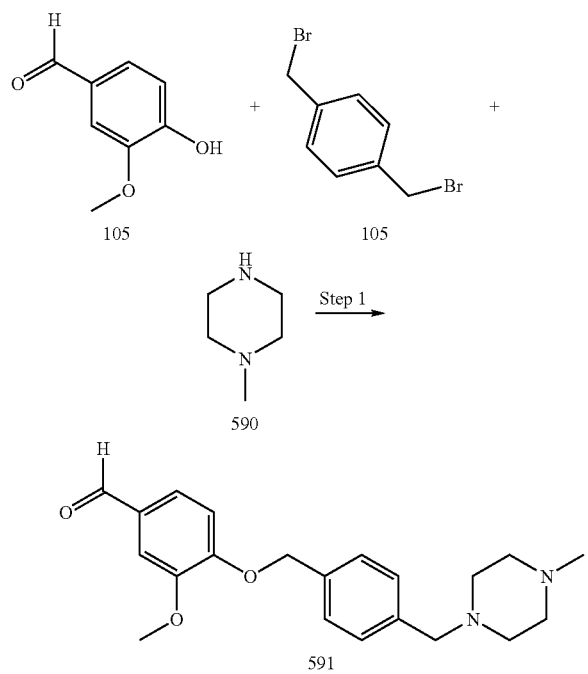

Step 1—Synthesis of 3-Methoxy-4-[4-(4-methyl-piperazin-1-ylmethyl)-benzyloxy]-benzaldehyde (591)

To 4-Hydroxy-3-methoxybenzaldehyde (105, 2.1 g, 0.014 mol) in N,N-dimethylformamide (40.0 mL) were added 1,4-bis(bromomethyl)-benzene (589, 4.00 g, 0.0152 mol) and potassium carbonate (5.0 g, 0.036 mol) under an atmosphere of nitrogen. After 12 hours 1-methyl-piperazine (590, 3.8 mL, 0.034 mol) was added to the reaction. After 2 hours, the reaction was poured into water and extracted with ethyl acetate. The organic layer was dried over anhydrous sodium sulfate and filtered. The filtrate was concentrated and purified by silica gel column chromatography eluting with 20% methanol in dichloromethane to give the compound (589, 1.2 g, 25.0%). MS(ESI) [M+H⁺]⁺=355.3.

2-Fluoro-4-hydroxy-5-methoxy-benzaldehyde 593 was synthesized in one step from 2-fluoro-4,5-dimethoxy-benzaldehyde 592 as shown in Scheme 60.

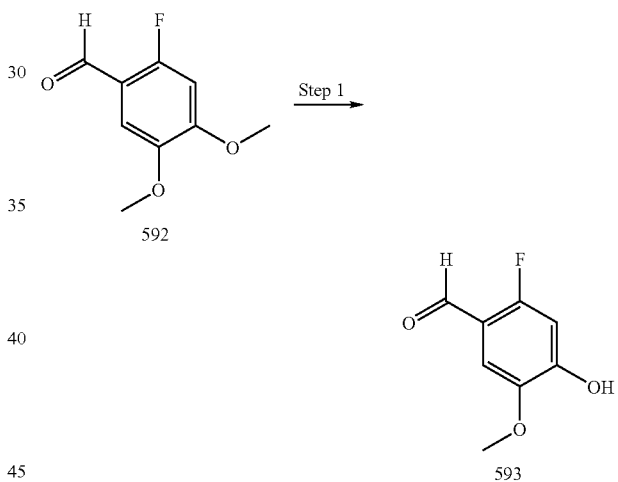

Step 1—Synthesis of 2-fluoro-4-hydroxy-5-methoxy-benzaldehyde (593)

To 2-fluoro-4,5-dimethoxy-benzaldehyde (592, 1.00 g, 5.43 mol) in dichloromethane (50.0 mL) was added aluminum trichloride (4.34 g, 32.6 mmol) under an atmosphere of nitrogen. The reaction was stirred at room temperature overnight. The reaction was poured into water and extracted with ethyl acetate. The organic layer was dried over anhydrous sodium sulfate and filtered. The filtrate was concentrated and washed with ethyl acetate and hexane to give a white solid (593, 0.70 g, 76.0%).

2,5-Difluoro-4-hydroxy-benzaldehyde 597 was synthesized in three steps from 2,5-difluorophenol 594 as shown in Scheme 61.

Scheme 61

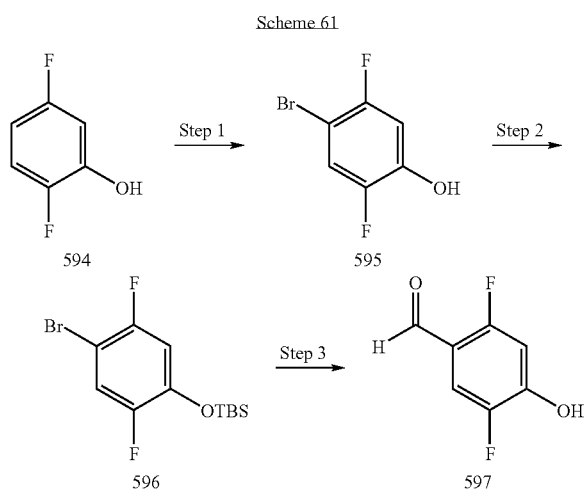

Step 1—Synthesis of 4-bromo-2,5-difluoro-phenol (595)

To 2,5-difluorophenol (594, 5.50 g, 0.0423 mol) in chloroform (110.0 mL), bromine (2.18 mL, 0.0423 mol) was added slowly. After 3 hours, the reaction was poured into a solution of sodium thiosulfate and extracted with ethyl acetate. The organic layer was dried over sodium sulfate, concentrated and purified with silica gel column chromatography eluting with 20% ethyl acetate in hexane to give a colorless oil (595, 6.20 g, 70.2%).

Step 2—(4-Bromo-2,5-difluoro-phenoxy)-tert-butyl-dimethyl-silane (596)

To 4-bromo-2,5-difluoro-phenol (595, 3.50 g, 0.0167 mol) in N,N-dimethylformamide (50.0 mL) were added tert-butyldimethylsilyl chloride (3.83 g, 0.0254 mol) and 1H-imidazole (6.00 g, 0.0529 mol). The reaction was stirred at room temperature overnight, then poured into water and extracted with ethyl acetate. The organic layer was dried over anhydrous sodium sulfate and filtered. The filtrate was concentrated and purified by silica gel column chromatography eluting with 20% ethyl acetate in hexane to give the compound (596, 3.0 g, 55.4%).

Step 3—2,5-Difluoro-4-hydroxy-benzaldehyde (597)

To (4-bromo-2,5-difluoro-phenoxy)-tert-butyl-dimethyl-silane (596, 3.00 g, 9.28 mmol) in tetrahydrofuran (37.5 mL), under an atmosphere of nitrogen at −78° C., n-butyllithium (3.90 mL, 2.50 M in hexane) was added slowly. After 30 minutes, N,N-dimethylformamide (0.825 mL, 0.0106 mol) was added to the reaction. One hour later, the reaction was allowed to come to room temperature. The reaction was poured into water and 1 N HCl, then extracted with ethyl acetate. The organic layer was dried over anhydrous sodium sulfate and filtered. The filtrate was concentrated and purified by silica gel column chromatography eluting with 20% ethyl acetate in hexane to give the compound as an off-white solid (597, 0.86 g, 59.0%).

4-(4-Chloro-benzyloxy)-3-fluoro-benzaldehyde 599 was synthesized in one step from 3-fluoro-4-hydroxy-benzaldehyde 598 as shown in Scheme 62.

Scheme 62

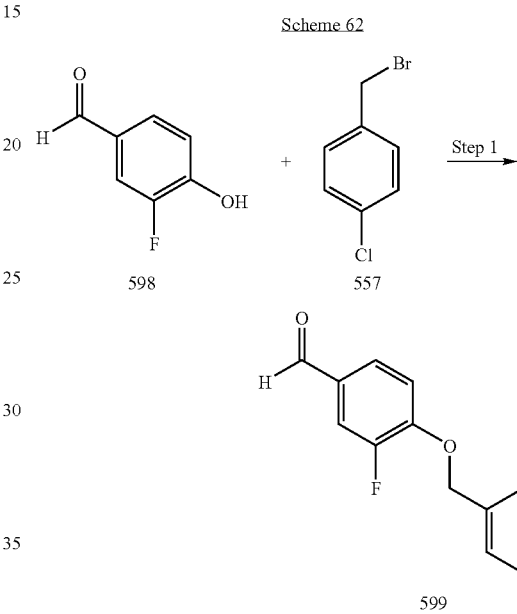

Step 1—Synthesis of 4-(4-chloro-benzyloxy)-3-fluoro-benzaldehyde (599)

To 3-fluoro-4-hydroxy-benzaldehyde (598, 0.800 g, 5.71 mmol) in N,N-dimethylformamide (50.0 mL) was added sodium hydride (260.0 mg, 60% in mineral oil, 6.50 itunol). After 15 minutes, 4-chlorobenzyl bromide (557, 1.29 g, 6.28 mmol) was added to the reaction mixture. The reaction was stirred at 80° C. for 5 hours. The reaction was poured into water and extracted with ethyl acetate. The organic layer was dried over anhydrous sodium sulfate and filtered. The filtrate was concentrated and purified by silica gel column chromatography eluting with 30% ethyl acetate in hexane to give the compound (599, 1.3 g, 86.0%).

Additional aldehydes were prepared using the protocol of Scheme 62, replacing either 4-chlorobenzyl bromide 557 with a suitable alkylating agent, and/or 3-fluoro-4-hydroxy-benzaldehyde 598 with a suitable aldehyde. The following table indicates the alkylating agent (column 1) and the starting aldehyde (column 2) used to afford the aldehyde (column 3) synthesized following this protocol.

| Alkylating agent | Aldehyde | Compound |
|---|---|---|

| Alkylating agent | Aldehyde | Compound |
|---|---|---|

Example 35

Synthesis of [4-(4-chloro-benzyloxy)-3-fluoro-phenyl]-(1H-pyrrolo[2,3-b]pyridin-3-yl)-methanone P-1897 and Related Compounds Compound P-1897 was synthesized in two steps from 4-(4-chloro-benzyloxy)-3-fluoro-benzaldehyde 599 as shown in Scheme 63.

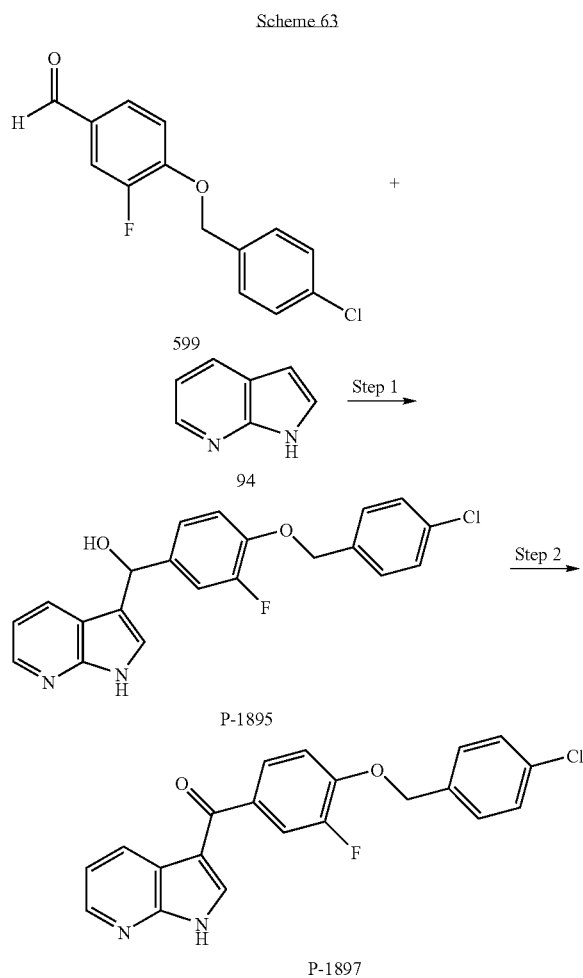

Scheme 63

Step 1—Synthesis of [4-(4-chloro-benzyloxy)-3-fluoro-phenyl]-1H-pyrrolo[2,3-b]pyridin-3-yl)-methanol (P-1895)

To 1H-Pyrrolo[2,3-b]pyridine (94, 100.0 mg, 0.85 mmol) in methanol (50.0 mL) were added 4-(4-chloro-benzyloxy)-3-fluoro-benzaldehyde (599, 250.0 mg, 0.94 mmol, prepared as described in Example 34) and potassium hydroxide (1.00 g, 17.82 mmol) under an atmosphere of nitrogen. The reaction was stirred at room temperature overnight. The reaction was poured into water and extracted with ethyl acetate. The organic layer was dried over anhydrous sodium sulfate and filtered. The filtrate was concentrated and purified by silica gel column chromatography eluting with 30% ethyl acetate in hexane to give the compound (P-1895, 55 mg, 17.0%). MS(ESI) [M+H$^+$]$^+$=383.3.

Step 2—Synthesis of [4-(4-chloro-benzyloxy)-3-fluoro-phenyl]-(1H-pyrrolo[2,3-b]pyridin-3-yl)-methanone (P-1897)

To [4-(4-chloro-benzyloxy)-3-fluoro-phenyl]-(1H-pyrrolo[2,3-b]pyridin-3-yl)-methanol (P-1895, 17.7 mg, 0.046 mmol) in tetrahydrofuran (10.0 mL) was added Dess-Martin periodinane (23.5 mg, 0.056 mmol). The reaction was stirred at room temperature for 15 minutes. The reaction was concentrated, then purified with silica gel column chromatography eluting with 50% ethyl acetate in hexane to give a white solid (P-1897, 6.4 mg, 36.3%). MS(ESI) [M+H$^+$]$^+$=381.3.

Additional compounds were prepared using the protocol of Scheme 63, replacing 4-4-(4-chloro-benzyloxy)-3-fluoro-benzaldehyde 599 with a suitable aldehyde (prepared as described in Example 34), and optionally replacing 1H-Pyrrolo[2,3-b]pyridine 94 with an appropriate substituted 7-azaindole (see Example 9 or Example 16) in Step 1. The following compounds were made following this procedure:

[4-(4-Chloro-benzyloxy)-2-fluoro-5-methoxy-phenyl]-(1H-pyrrolo[2,3-b]pyridin-3-yl)-methanone (P-1845),

[4-(4-Chloro-3-trifluoromethyl-benzyloxy)-3-methoxy-phenyl]-(1H-pyrrolo[2,3-b]pyridin-3-yl)-methanone (P-1850).

[4-(1H-Benzoimidazol-2-ylmethoxy)-3-fluoro-phenyl]-(1H-pyrrolo[2,3-b]pyridin-3-yl)-methanone (P-1900), (4-Benzyloxy-2,5-difluoro-phenyl)-(1H-pyrrolo[2,3-b]pyridin-3-yl)-methanone (P-1903),

[4-(1H-Benzoimidazol-2-ylmethoxy)-2-fluoro-5-methoxy-phenyl]-(5-methoxy-1H-pyrrolo[2,3-b]pyridin-3-yl)-methanone (P-1979),

[4-(1H-Benzoimidazol-2-ylmethoxy)-2-fluoro-5-methoxy-phenyl]-(1H-pyrrolo[2,3-b]pyridin-3-yl)-methanone (P-1982),

[4-(1H-Benzoimidazol-2-ylmethoxy)-2,5-difluoro-phenyl]-(1H-pyrrolo[2,3-b]pyridin-3-yl)-methanone (P-1987), {4-[2-(2-Bromo-ethoxy)-ethoxy]-2-fluoro-5-methoxy-phenyl}-(5-chloro-1H-pyrrolo[2,3-b]pyridin-3-yl)-methanone (P-1988), (5-Chloro-1H-pyrrolo[2,3-b]pyridin-3-yl)-[2,5-difluoro-4-(2-methoxy-ethoxy)-phenyl]-methanone (P-1989), and (5-Chloro-1H-pyrrolo[2,3-b]pyridin-3-yl)-[2-fluoro-5-methoxy-4-(2-methoxy-ethoxy)-phenyl]-methanone (P-1991).

The following table indicates the aldehyde (column 2) and the azaindole (column 3) used to afford the target compound (column 4). Column 1 indicates the compound number and column 5 the observed mass.

| | Aldehyde | Azaindole | Compound | MS(ESI) [M + H⁺]⁺ observed |
|---|---|---|---|---|
| P-1845 | | | | 409.6 [M − H⁺]⁻ |
| P-1850 | | | | |
| P-1900 | | | | 387.4 |
| P-1903 | | | | 363.3 [M − H⁺]⁻ |
| P-1979 | | | | 447.4 |

-continued

| | Aldehyde | Azaindole | Compound | MS(ESI) [M + H+]+ observed |
|---|---|---|---|---|
| P-1982 | | | | 417.3 |
| P-1987 | | | | 405.3 |
| P-1988 | | | | 471.2 473.2 |
| P-1989 | | | | 365.2 [M − H+]− |
| P-1991 | | | | 377.2 [M − H+]− |

Example 36

Synthesis of 3-(4-Benzyloxy-2,5-difluoro-benzyl)-1H-pyrrolo[2,3-b]pyridine P-1901

Compound P-1901 was synthesized in four steps from 4-bromo-2,5-difluoro-phenol 595 as shown in Scheme 64.

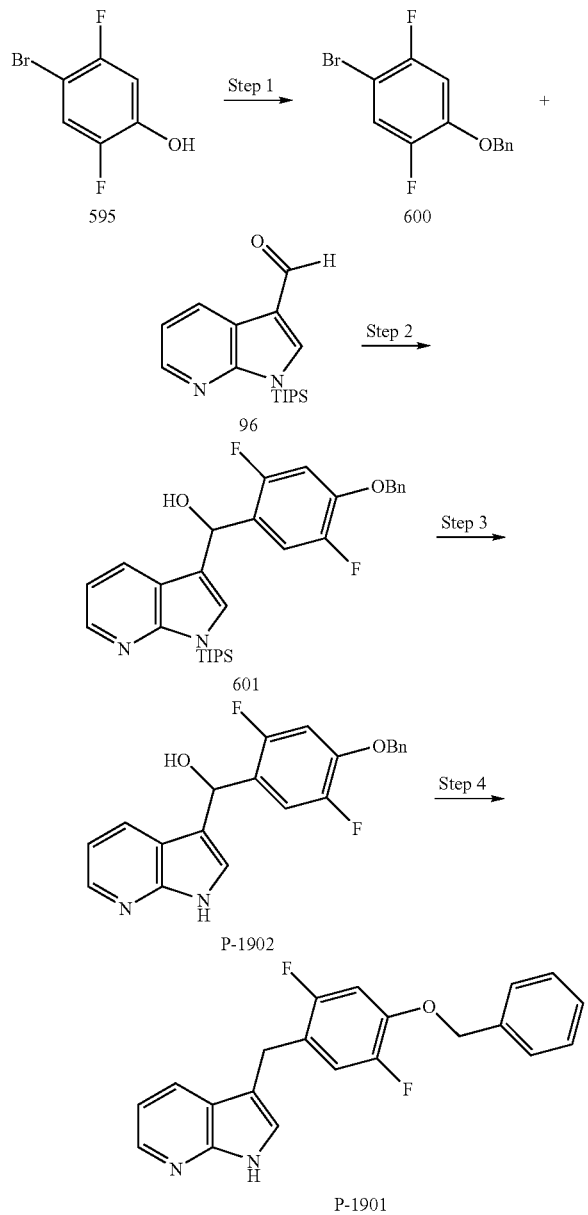

Step 1—Synthesis of 1-Benzyloxy-4-bromo-2,5-trifluoro-benzene (600)

To 4-bromo-2,5-difluoro-phenol (595, 0.90 g, 0.0043 mol, prepared as described in Example 34, Scheme 61) in N,N-dimethylformamide (30.0 mL) were added sodium hydride (0.21 g, 60% in mineral oil, 0.0052 mol) and benzyl bromide (0.563 int, 0.00474 mol). The reaction was stirred at room temperature overnight. The reaction was poured into water and extracted with ethyl acetate. The organic layer was dried over anhydrous sodium sulfate and filtered. The filtrate was concentrated and purified by silica gel column chromatography eluting with 5% ethyl acetate in hexane to give a white solid (600, 0.84 g, 65.0%).

Step 2—(4-Benzyloxy-2,5-difluoro-phenyl-(1-triisopropylsilanyl-1H-pyrrolo[2,3-b]pyridin-3-yl)-methanol (601)

To 1-Benzyloxy-4-bromo-2,5-difluoro-benzene (600, 0.84 g, 2.80 mmol) in tetrahydrofuran (15.0 mL) and ether (15.0 mL), under an atmosphere of nitrogen at −78° C., n-butyl-lithium (1.20 mL, 2.50 M in hexane) was added slowly. After 20 minutes, 1-Triisopropylsilanyl-1H-pyrrolo[2,3-b]pyridine-3-carbaldehyde (96, 0.82 g, 0.0027 mol, prepared as described in Example 18) was added to the reaction. After 20 minutes, the reaction was allowed to warm to room temperature for 10 minutes, then poured into water and extracted with ethyl acetate. The organic layer was dried over anhydrous sodium sulfate and filtered. The filtrate was concentrated and purified with silica gel column chromatography eluting with 20% ethyl acetate in hexane to a white solid (601, 1.0 g, 70.0%). MS(ESI) [M+H$^+$]$^+$=523.4.

Step 3—Synthesis of (4-Benzyloxy-2,5-difluoro-phenyl)-(1H-pyrrolo[2,3-b]pyridin-3-yl)-methanol (P-1902)

To (4-Benzyloxy-2,5-difluoro-phenyl)-(1-triisopropylsilanyl-1H-pyrrolo[2,3-b]pyridin-3-yl)-methanol (601, 1.00 g. 1.91 mmol) in tetrahydrofuran (15.0 mL) was added tetrabutylammonium fluoride, trihydrate (0.63 g, 2.04 mmol). The reaction was stirred at room temperature for 10 minutes. The reaction was roto-evaporated and purified with silica gel column chromatography eluting with 50% ethyl acetate in hexane to give the compound as a white solid (P-1902, 0.59 g, 84.0%). MS(ESI) [M+H$^+$]$^+$=367.4.

Step 4—Synthesis of 3-(4-Benzyloxy-2,5-difluoro-benzyl)-1H-pyrrolo[2,3-b]pyridine (P-1901)

To (4-Benzyloxy-2,5-difluoro-phenyl)-(1H-pyrrolo[2,3-b]pyridin-3-yl)-methanol (P-1902, 500.0 mg, 1.37 mmol) in acetonitrile (25.0 mL) were added triethylsilane (2.00 mL, 0.0125 mol) and trifluoroacetic acid (1.00 mL, 0.0130 mol). The reaction was heated to reflux for 2 hours. The reaction was concentrated and purified with silica gel column chromatography eluting with 50% ethyl acetate in hexane to give a white solid (P-1901, 60.0 mg, 94.1%). MS(ESI) [M+H$^+$]$^+$=351.4.

3-[3-Trifluoromethyl-4-(4-trifluoromethyl-benzyloxy)-benzyl]-1H-pyrrolo[2,3-b]pyridine P-1797

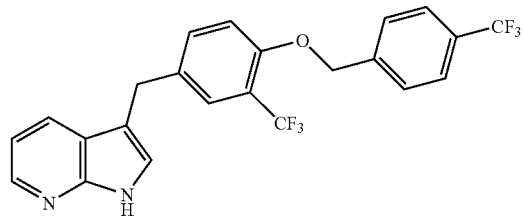 [SMILES: FC(F)(F)c1ccc(COc2ccc(Cc3c[nH]c4ncccc34)cc2C(F)(F)F)cc1]

445 was prepared using the protocol of Scheme 64, substituting 4-bromo-2,5-difluoro-phenol 595 with 4-bromo-2-trifluoromethyl-phenol (prepared as described in Example 34, Scheme 61, Step 1, substituting 2,5-difluoro-phenol 594 with 2-trifluoromethyl-phenol) and benzyl bromide with 1-bromomethyl-4-trifluoromethyl-benzene in Step 1. MS(ESI) [M+H⁺]⁺=451.

Example 37

Synthesis of 3-[4-(4-chloro-benzyloxy)-2,5-difluoro-benzyl]-1H-pyrrolo[2,3-b]pyridine P-1974

Compound P-1974 was synthesized in four steps from 3-(4-benzyloxy-2,5-difluoro-benzyl)-1H-pyrrolo[2,3-b]pyridine P-1901 as shown in Scheme 65.

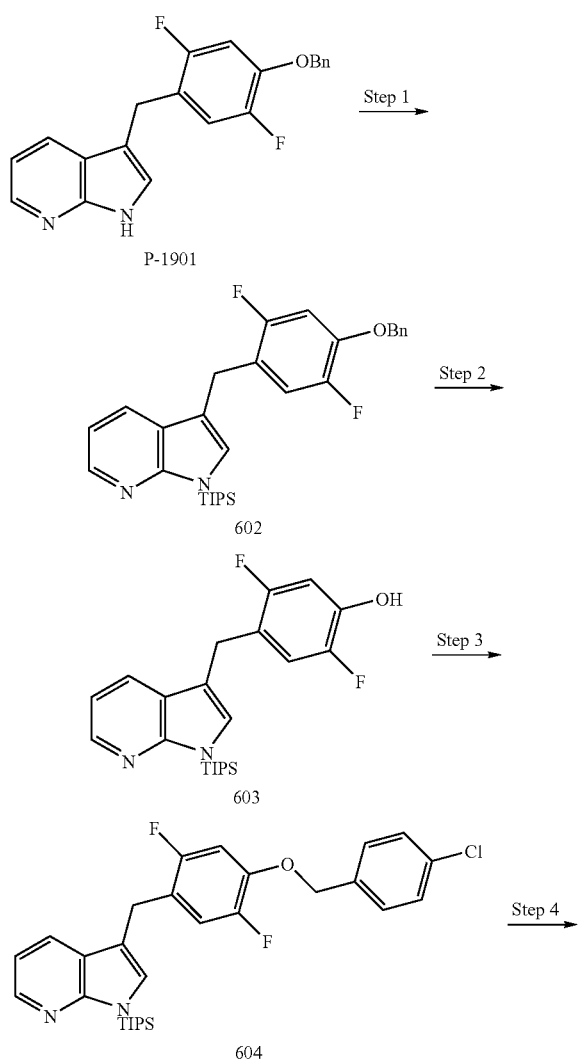

446

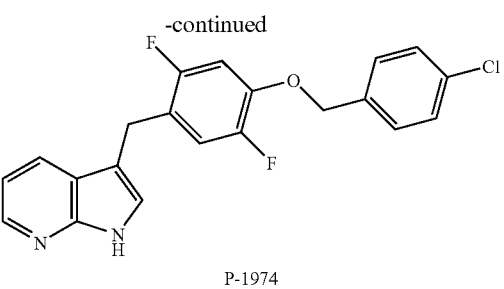

P-1974

Step 1—Synthesis of 3-(4-Benzyloxy-2,5-difluoro-benzyl)-1-triisopropylsilanyl-1H-pyrrolo[2,3-b]pyridine (602)

To 3-(4-Benzyloxy-2,5-difluoro-benzyl)-1H-pyrrolo[2,3-b]pyridine (P-1901, 560.0 mg, 1.60 mmol, prepared as described in Example 18, Scheme 33) in tetrahydrofuran (28.0 mL) was added sodium hydride (100.0 mg, 60% in mineral oil, 2.50 mmol). After 10 minutes, triisopropylsilyl chloride (0.500 mL, 2.36 mmol) was added to the reaction. After 4 hours, the reaction was poured into water and extracted with ethyl acetate. The organic layer was dried over anhydrous sodium sulfate and filtered. The filtrate was concentrated and purified by silica gel column chromatography eluting with 30% ethyl acetate in hexane to give the compound (602, 0.70 g, 86.1%).

Step 2—Synthesis of 2,5-difluoro-4-(1-triisopropylsilanyl-1H-pyrrolo[2,3-b]pyridin-3-ylmethyl)-phenol (603)

To 3-(4-Benzyloxy-2,5-difluoro-benzyl)-1-triisopropylsilanyl-1H-pyrrolo[2,3-b]pyridine (602, 0.70 g, 0.0014 mol) in methanol (30.0 mL) was added 50%© palladium hydroxide on carbon (0.1 g) under an atmosphere of hydrogen. The reaction was stirred at room temperature overnight. The reaction was filtered and concentrated to give a colorless oil (603, 0.47 g. 82.0%).

Step 3—3-[4-(4-Chloro-benzyloxy)-2,5-difluoro-benzyl]-1-triisopropylsilanyl-1H-pyrrolo[2,3-b]pyridine (604)

To 2,5-difluoro-4-(1-triisopropylsilanyl-1H-pyrrolo[2,3-b]pyridin-3-ylmethyl)-phenol (603, 120.0 mg, 0.29 mmol) in N,N-dimethylformamide (15.0 mL) was added sodium hydride (18.0 mg, 60% in mineral oil, 0.45 mol) under an atmosphere of nitrogen. After 10 minutes, 4-chlorobenzyl bromide (65.1 mg, 0.32 mol) was added to the reaction. The reaction was stirred at 40° C. overnight. The reaction was poured into water and extracted with ethyl acetate. The organic layer was dried over anhydrous sodium sulfate, and filtered. The filtrate was concentrated to give the crude compound (604, 0.15 g) that was used directly in the next step.

Step 4—Synthesis of 3-[4-(4-chloro-benzyloxy)-2,5-difluoro-benzyl]-1H-pyrrolo[2,3-b]pyridine (P-1974)

To 3-[4-(4-chloro-benzyloxy)-2,5-difluoro-benzyl]-1-triisopropylsilanyl-1H-pyrrolo[2,3-b]pyridine (604, 0.150 g, 0.28 mmol) in tetrahydrofuran (10.0 mL) was added tetra-n-butylammonium fluoride (80.0 mg, 0.31 mmol). After 10 minutes, the reaction was concentrated and purified by silica gel column chromatography eluting with 50% ethyl acetate in hexane to give the compound as a white solid (P-1974, 30.8 mg, 28.9%). MS(ESI) [M+H⁺]⁺=385.3.

2-[2,5-Difluoro-4-(1H-pyrrolo[2,3-b]pyridin-3-ylmethyl)-phenoxymethyl]-1H-benzoimidazole P-1975

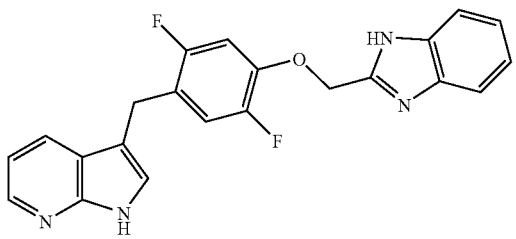 [SMILES: Fc1cc(OCc2nc3ccccc3[nH]2)c(F)cc1Cc1c[nH]c2ncccc12]

was prepared using the protocol of Scheme 65, substituting 4-chlorobenzyl bromide with 2-chloromethyl-1H-benzoimidazole in step 3. MS(ESI) [M+H⁺]⁺=391.3.

Example 38

Synthesis of 1-(4-Butoxy-phenyl)-3-{3-[5-(4-fluoro-phenyl)-1H-pyrrolo[2,3-b]pyridine-3-carbonyl]-phenyl}-urea P-1754

Compound P-1754 was synthesized in three steps from 5-(4-fluorophenyl)-1H-pyrrolo[2,3-b]pyridine 605 as shown in Scheme 66.

Scheme 66

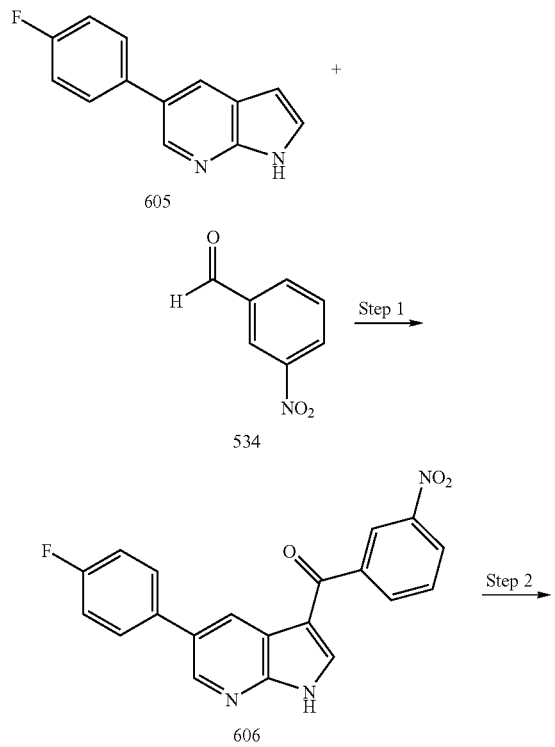

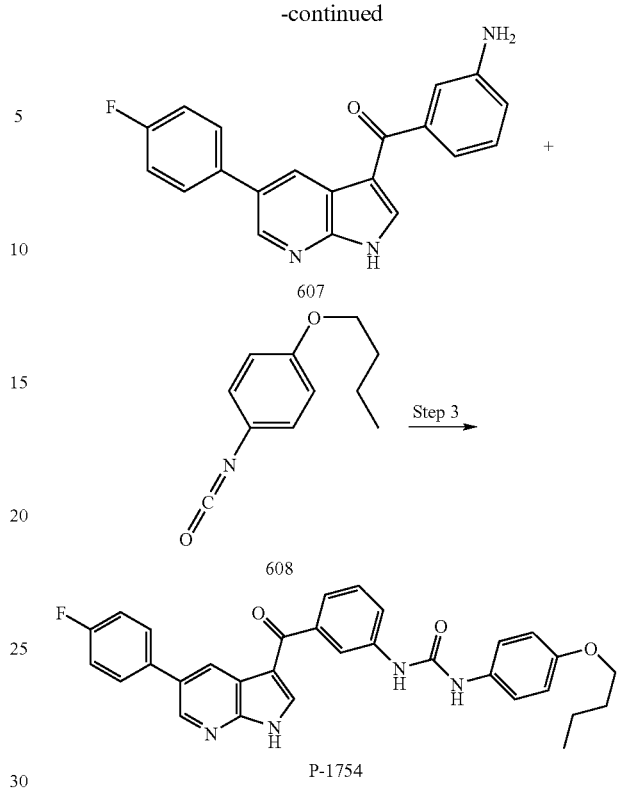

Step 1—Preparation of (3-chloro-phenyl)-[5-(4-fluoro-phenyl)-1H-pyrrolo[2,3-b]pyridin-3-yl]-methanone (606)

To 5-(4-fluoro-phenyl)-1H-pyrrolo[2,3-b]pyridine (605, 530 mg, 2.5 mmol, prepared as described in Example 23) dissolved in 20 mL of dioxane was added 3-nitrobenzaldehyde (534, 758 mg, 5 mmol) and potassium hydroxide (4 mL of 2.5M aqueous). The vial was shaken on an orbital shaker for 16 hrs and the dioxane was removed under reduced pressure. The residue was partitioned between ethyl acetate and water. The aqueous layer was neutralized with the addition of 1M HCl. The organic layer was washed with brine, dried over magnesium sulfate and concentrated under reduced pressure to give yellow-orange oil (1.5 g). The crude material was dissolved in dichloromethane (150 mL) and chilled to 0° C. With vigorous stirring, pyridinium chlorochromate (3.0 g, 14 mmol) was added slowly, maintaining the solution temperature at 0° C. After complete addition the solution was allowed to stir at ambient temperature for 1 hour. The resulting dark brown/black solution was diluted with chloroform and passed through a plug of silica. Elution with methanol gave 1.5 g of crude 606 that was carried on to the next step without further purification.

Step 2—Preparation of (3-Amino-phenyl)-[5-(4-fluoro-phenyl)-1H-pyrrolo[2,3-b]pyridin-3-yl]-methanone (607)

Crude (3-chloro-phenyl)-[5-(4-fluoro-phenyl)-1H-pyrrolo[2,3-b]pyridin-3-yl]-methanone (606, 1.5 g) was dissolved in a minimal amount of methanol (~5 mL) and Pd/C (5%, ~10 mg) was added. The reaction mixture was shaken on a Parr shaker under 70 psi H₂ overnight. The reaction mixture was filtered through Celite® and concentrated under reduced pressure to give 1.4 g of crude 607 that was carried on to the next step without further purification.

Step 3—Preparation of 1-(4-Butoxy-phenyl)-3-{3-[5-(4-fluoro-phenyl)-1H-pyrrolo[2,3-b]pyridine-3-carbonyl]-phenyl}-urea (P-1754)

To a solution of (3-Amino-phenyl)-[5-(4-fluoro-phenyl)-1H-pyrrolo[2,3-b]pyridin-3-yl]-methanone (607, 7.5 mg) in anhydrous pyridine (200 µL) was added neat 1-butoxy-4-isocyanato-benzene (608, 1.6 mg) and the reaction mixture was stirred at ambient temperature for 2 hours. The reaction mixture was concentrated under reduced pressure and the residue was dissolved in DMSO (200 µL) and purified using reverse phase HPLC with an acetonitrile/water gradient. MS(ESI) [M+H$^+$]$^+$=523.5.

Additional compounds were prepared following the protocol of Scheme 66, optionally substituting 5-(4-fluoro-phenyl)-1H-pyrrolo[2,3-b]pyridine 605 with a suitable azaindole in Step 1 and/or optionally substituting 1-butoxy-4-isocyanato-benzene 608 with a suitable isocyanate in Step 3. Azaindoles were purchased or prepared as described in Examples 9 or 17, The following compounds were prepared by this procedure:

- 1-(2-Methoxy-ethyl)-3-[3-(5-pyridin-3-yl-1H-pyrrolo[2,3-b]pyridine-3-carbonyl)-phenyl]-urea (P1566),
- 1-Phenyl-3-[3-(5-pyridin-3-yl-1H-pyrrolo[2,3-b]pyridine-3-carbonyl)-phenyl]-urea (P-1591),
- 1-Phenyl-3-[3-(1H-pyrrolo[2,3-b]pyridine-3-carbonyl)-phenyl]-urea (P-1703),
- 1-(4-Fluoro-phenyl)-3-[3-(1H-pyrrolo[2,3-b]pyridine-3-carbonyl)-phenyl]-urea (P-1704),
- 1-(4-Methoxy-phenyl)-3-[3-(1H-pyrrolo[2,3-b]pyridine-3-carbonyl)-phenyl]-urea (P-1705),
- 1-(3,4-Difluoro-phenyl)-3-[3-(1H-pyrrolo[2,3-b]pyridine-3-carbonyl)-phenyl]-urea (P-1706),
- 1-(3-Methoxy-phenyl)-3-[3-(1H-pyrrolo[2,3-b]pyridine-3-carbonyl)-phenyl]-urea (P-1707),
- 1-(3,4-Dimethoxy-phenyl)-3-[3-(1H-pyrrolo[2,3-b]pyridine-3-carbonyl)-phenyl]-urea (P-1708),
- 1-(4-Chloro-phenyl)-3-[3-(1H-pyrrolo[2,3-b]pyridine-3-carbonyl)-phenyl]-urea (P-1709),
- 1-(3-Chloro-phenyl)-3-[3-(1H-pyrrolo[2,3-b]pyridine-3-carbonyl)-phenyl]-urea (P-1710),
- 1-(4-Chloro-3-trifluoromethyl-phenyl)-3-[3-(1H-pyrrolo[2,3-b]pyridine-3-carbonyl)-phenyl]-urea (P-1711),
- 1-(2-Chloro-5-trifluoromethyl-phenyl)-3-[3-(1H-pyrrolo[2,3-b]pyridine-3-carbonyl)-phenyl]-urea (P-1712),
- 1-(2-Chloro-4-trifluoromethyl-phenyl)-3-[3-(1H-pyrrolo[2,3-b]pyridine-3-carbonyl)-phenyl]-urea (P-1713),
- 1-(2-Fluoro-3-trifluoromethyl-phenyl)-3-[3-(1H-pyrrolo[2,3-b]pyridine-3-carbonyl)-phenyl]-urea (P-1714),
- 1-(4-Butoxy-phenyl)-3-[3-(1H -pyrrolo[2,3-b]pyridine-3-carbonyl)-phenyl]-urea (P-1715),
- 1-(3-Fluoro-phenyl)-3-[3-(1H-pyrrolo[2,3-b]pyridine-3-carbonyl)-phenyl]-urea (P-1716),
- 1-[3-(1H-Pyrrolo[2,3-b]pyridine-3-carbonyl)-phenyl]-3-(4-trifluoromethyl-phenyl)-urea (P-1717),
- 1-[3-(1H-Pyrrolo[2,3-b]pyridine-3-carbonyl)-phenyl]-3-p-tolyl-urea (P-1718),
- 1-[3-(1H-Pyrrolo[2,3-b]pyridine-3-carbonyl)-phenyl]-3-m-tolyl-urea (P-1719),
- 1-[3-(1H-Pyrrolo[2,3-b]pyridine-3-carbonyl)-phenyl]-3-o-tolyl-urea (P-1720),
- 1-(4-Methoxy-phenyl)-3-[3-(5-pyridin-3-yl 1H-pyrrolo[2,3-b]pyridine-3-carbonyl)-phenyl]-urea (P-1723),
- 1-(3,4-Difluoro-phenyl)-3-[3-(5-pyridin-3-yl-1H-pyrrolo[2,3-b]pyridine-3-carbonyl)-phenyl]-urea (P-1724),
- 1-(3,4-Dimethoxy-phenyl)-3-[3-(5-pyridin-3-yl-1H-pyrrolo[2,3-b]pyridine-3-carbonyl)-phenyl]-urea (P-1725),
- 1-(3-Chloro-phenyl)-3-[3-(5-pyridin-3-yl-1H-pyrrolo[2,3-b]pyridine-3-carbonyl)-phenyl]-urea (P-1726),
- 1-(2-Chloro-4-trifluoromethyl-phenyl)-3-[3-(5-pyridin-3-yl-1H-pyrrolo[2,3-b]pyridine-3-carbonyl)-phenyl]-urea (P-1727),
- 1-(2-Fluoro-3-trifluoromethyl-phenyl)-3-[3-(5-pyridin-3-yl-1H-pyrrolo[2,3-b]pyridine-3-carbonyl)-phenyl]-urea (P-1728),
- 1-(4-Butoxy-phenyl)-3-[3-(5-pyridin-3-yl-1H-pyrrolo[2,3-b]pyridine-3-carbonyl)-phenyl]-urea (P-1729),
- 1-(3-Fluoro-phenyl)-3-[3-(5-pyridin-3-yl-1H-pyrrolo[2,3-b]pyridine-3-carbonyl)-phenyl]-urea (P-1730),
- 1-[3-(5-Pyridin-3-yl-1H-pyrrolo[2,3-b]pyridine-3-carbonyl)-phenyl]-3-(4-trifluoromethyl-phenyl)-urea (P-1731),
- 1-(2-Chloro-5-trifluoromethyl-phenyl)-3-[3-(5-pyridin-3-yl-1H-pyrrolo[2,3-b]pyridine-3-carbonyl)-phenyl]-urea (P-1732),
- 1-[3-(5-Chloro-1H-pyrrolo[2,3-b]pyridine-3-carbonyl)-phenyl]-3-phenyl-urea (P-1733),
- 1-[3-(5-Chloro-1H-pyrrolo[2,3-b]pyridine-3-carbonyl)-phenyl]-3-(4-methoxy-phenyl)-urea (P-1734),
- 1-[3-(5-Chloro-1H-pyrrolo[2,3-b]pyridine-3-carbonyl)-phenyl]-3-(3,4-difluoro-phenyl)-urea (P-1735),
- 1-(3-Chloro-phenyl)-3-[3-(5-chloro-1H-pyrrolo[2,3-b]pyridine-3-carbonyl)-phenyl]-urea (P-1736),
- 1-[3-(5-Chloro-1H-pyrrolo[2,3-b]pyridine-3-carbonyl)-phenyl]-3-(4-chloro-3-trifluoromethyl-phenyl)-urea (P-1737),
- 1-[3-(5-Chloro-1H-pyrrolo[2,3-b]pyridine-3-carbonyl)-phenyl]-3-(2-chloro-5-trifluoromethyl-phenyl)-urea (P-1738),
- 1-[3-(5-Chloro-1H-pyrrolo[2,3-b]pyridine-3-carbonyl)-phenyl]-3-(2-chloro-4-trifluoromethyl-phenyl)-urea (P-1739),
- 1-[3-(5-Chloro-1H-pyrrolo[2 3-b]pyridine-3-carbonyl)-phenyl]-3-(2-fluoro-3-trifluoromethyl-phenyl)-urea (P-1740),
- 1-(4-Butoxy-phenyl)-3-[3-(5-chloro-1H-pyrrolo[2,3-b]pyridine-3-carbonyl)-phenyl]-urea (P-1741),
- 1-[3-(1H-Pyrrolo[2,3-b]pyridine-3-carbonyl)-phenyl]-3-(3-trifluoromethyl-phenyl)-urea (P-1746),
- 1-[3-(5-Chloro-1H-pyrrolo[2,3-b]pyridine-3-carbonyl)-phenyl]-3-(3-trifluoromethyl-phenyl)-urea (P-1747),
- 1-(4-Fluoro-phenyl)-3-[3-(5-pyridin-3-yl-1H-pyrrolo[2,3-b]pyridine-3-carbonyl)-phenyl]-urea (P-1748),
- 1-(3-Methoxy-phenyl)-3-[3-(5-pyridin-3-yl-1H-pyrrolo[2,3-b]pyridine-3-carbonyl)-phenyl]-urea (P-1749),
- 1-(4-Chloro-phenyl)-3-[3-(5-pyridin-3-yl-1H-pyrrolo[2,3-b]pyridine-3-carbonyl)-phenyl]-urea (P-1750).
- 1-(4-Chloro-3-trifluoromethyl-phenyl)-3-[3-(5-pyridin-3-yl-1H-pyrrolo[2,3-b]pyridine-3-carbonyl)-phenyl]-urea (P-1751),
- 1-(2-Chloro-5-trifluoromethyl-phenyl)-3-{3-[5-(4-fluoro-phenyl)-1H-pyrrolo[2,3-b]pyridine-3-carbonyl]-phenyl}-urea (P-1752),
- 1-(2-Chloro-4-trifluoromethyl-phenyl)-3-{3-[5-(4-fluoro-phenyl)-1H-pyrrolo[2,3-b]pyridine-3-carbonyl]-phenyl}-urea (P-1753),
- 1-(4-Butoxy-phenyl)-3-{3-[5-(4-fluoro-phenyl)-1H-pyrrolo[2,3-b]pyridine-3-carbonyl]-phenyl}-urea (P-1754), 1-[3-(5-Pyridin-3-yl-1H-pyrrolo[2,3-b]pyridine-3-carbonyl)-phenyl]-3-(3-trifluoromethyl-phenyl)-urea (P-1755),
1-[3-(5-Pyridin-3-yl-1H-pyrrolo[2,3-b]pyridine-3-carbonyl)-phenyl]-3-p-tolyl-urea (P-1756),
1-[3-(5-Pyridin-3-yl-1H-pyrrolo[2,3-b]pyridine-3-carbonyl)-phenyl]-3-m-tolyl-urea (P-1757),
1-{3-[5-(4-Fluoro-phenyl)-1H-pyrrolo[2,3-b]pyridine-3-carbonyl]-phenyl}-3-m-tolyl-urea (P-1758),
1-[3-(5-Pyridin-3-yl-1H-pyrrolo[2,3-b]pyridine-3-carbonyl)-phenyl]-3-o-tolyl-urea (P-1759),
1-Pyridin-4-yl-3-[3-(1H-pyrrolo[2,3-b]pyridine-3-carbonyl)-phenyl]-urea (P-1760),
1-(2-Methoxy-ethyl)-3-[3-(1H-pyrrolo[2,3-b]pyridine-3-carbonyl)-phenyl]urea (P-1761),
1-(3-Methoxy-5-trifluoromethyl-phenyl)-3-[3-(1H-pyrrolo[2,3-b]pyridine-3-carbonyl)-phenyl]-urea (P-1762),
1-(6-Methoxy-pyridin-3-yl)-3-[3-(1H-pyrrolo[2,3-b]pyridine-3-carbonyl)-phenyl]-urea (P-1763),
1-Isoxazol-3-yl-3-[3-(1H-pyrrolo[2,3-b]pyridine-3-carbonyl)-phenyl]-urea (P-1764),
1-(3-Methyl-isoxazol-5-yl)-3-[3-(1H-pyrrolo[2,3-b]pyridine-3-carbonyl)-phenyl]-urea (P-1765),
1-(3-Chloro-4-trifluoromethyl-phenyl)-3-[3-(1H-pyrrolo[2,3-b]pyridine-3-carbonyl)-phenyl]-urea (P-1766),
1-(3,4-Dimethyl-isoxazol-5-yl)-3-[3-pyrrolo[2,3-b]pyridine-3-carbonyl)-phenyl]-urea (P-1767),
1-[3-(5-Chloro-1H-pyrrolo[2,3-b]pyridine-3-carbonyl)-phenyl]-3-pyridin-4-yl-urea (P-1770),
1-[3-(5-Chloro-1H-pyrrolo[2,3-b]pyridine-3-carbonyl)-phenyl]-3-pyridin-3-yl-urea (P-1771),
1-[3-(5-Chloro-1H-pyrrolo[2 3-b]pyridine-3-carbonyl)-phenyl]-3-(2-methoxy-ethyl)-urea (P-1772),
1-[3-(5-Chloro-1H-pyrrolo[2,3-b]pyridine-3-carbonyl)-phenyl]-3-(3-methoxy-5-trifluoromethyl-phenyl)-urea (P-1773),
1-[3-(5-Chloro-1H-pyrrolo[2,3-b]pyridine-3-carbonyl)-phenyl]-3-(6-methoxy-pyridin-3-yl)-urea (P-1774),
1-[3-(5-Chloro-1H-pyrrolo[2,3-b]pyridine-3-carbonyl)-phenyl]-3-isoxazol-3-yl-urea (P-1775),
1-[3-(5-Chloro-1H-pyrrolo[2,3-b]pyridine-3-carbonyl)-phenyl]-3-(3,4-dimethyl-isoxazol-5-yl)-urea (P-1776),
1-Pyridin-4-yl-3-[3-(5-pyridin-3-yl-1H-pyrrolo[2,3-b]pyridine-3-carbonyl)-phenyl]-urea (P-1777),
1-(3-Methoxy-5-trifluoromethyl-phenyl)-3-[3-(5-pyridin-3-yl-1H-pyrrolo[2,3-b]pyridine-3-carbonyl)-phenyl]-urea (P-1778),
1-(6-Methoxy-pyridin-3-yl)-3-[3-(5-pyridin-3-yl-1H-pyrrolo[2,3-b]pyridine-3-carbonyl)-phenyl]-urea (P-1779),
1-(4-Dimethylamino-phenyl)-3-[3-(1H-pyrrolo[2,3-b]pyridine-3-carbonyl)-phenyl]-urea (P-1780),
1-Pyridin-3-yl-3-[3-(1H-pyrrolo[2,3-b]pyridine-3-carbonyl)-phenyl]-urea (P-1781),
1-[3-(5-Chloro-1H-pyrrolo[2,3-b]pyridine-3-carbonyl)-phenyl]-3-(4-dimethylamino-phenyl)-urea (P-1782),
1-(4-Fluoro-phenyl)-3-{3-[5-(4-fluoro-phenyl)-1H-pyrrolo[2,3-b]pyridine-3-carbonyl]-phenyl}-urea (P-1816),
1-(3,4-Difluoro-phenyl)-3-{3-[5-(4-fluoro-phenyl)-1H-pyrrolo[2,3-b]pyridine-3-carbonyl]-phenyl}-urea (P-1817),
1-(3,4-Dimethoxy-phenyl)-3-{3-[5-(4-fluoro-phenyl)-1H-pyrrolo[2,3-b]pyridine-3-carbonyl]-phenyl}-urea (P-1818), and
1-(3-Fluoro-phenyl)-3-{3-[5-(4-fluoro-phenyl)-1H-pyrrolo[2,3-b]pyridine-3-carbonyl]-phenyl}-urea (P-1819).

The following table indicates the azaindole (column 2) and isocyanate (column 3) used to afford the target compound (column 4). Column 1 provides the compound number and the observed mass is given in column 5.

| | Azaindole | Isocyanate | Compound | MS(ESI) [M + H⁺]⁺ observed |
|---|---|---|---|---|
| P-1566 | | | | 416.3 |
| P-1591 | | | | 434.3 |
| P-1703 | | | | 357.1 |

-continued

| | Azaindole | Isocyanate | Compound | MS(ESI) [M + H⁺]⁺ observed |
|---|---|---|---|---|
| P-1704 | | | | 375.1 |
| P-1705 | | | | 387.1 |
| P-1706 | | | | 393.1 |
| P-1707 | | | | 387.1 |
| P-1708 | | | | 417.5 |
| P-1709 | | | | 391.1 |
| P-1710 | | | | 391.1 |
| P-1711 | | | | 459.1 |

-continued
| | Azaindole | Isocyanate | Compound | MS(ESI) [M + H+]+ observed |
|---|---|---|---|---|
| P-1712 | 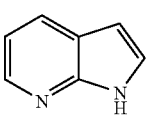 | 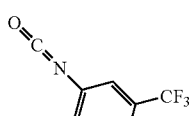 | 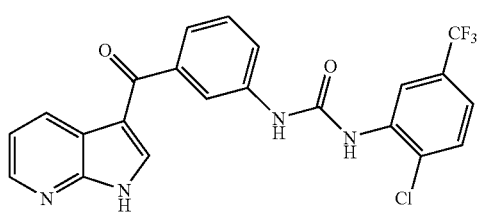 [SMILES: O=C(Nc1cccc(C(=O)c2c[nH]c3ncccc23)c1)Nc1cc(C(F)(F)F)ccc1Cl] | 459.1 |
| P-1713 | 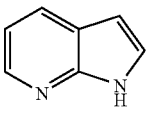 | 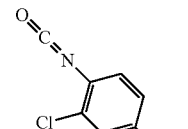 | 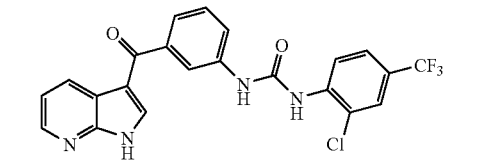 [SMILES: O=C(Nc1cccc(C(=O)c2c[nH]c3ncccc23)c1)Nc1ccc(C(F)(F)F)cc1Cl] | 459.1 |
| P-1714 | 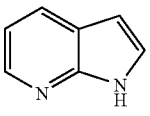 | 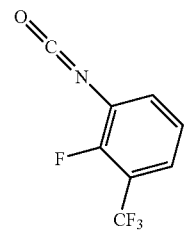 [SMILES: O=C=Nc1cccc(C(F)(F)F)c1F] | 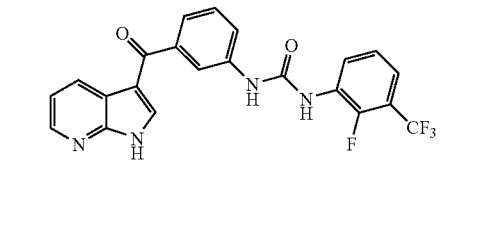 [SMILES: O=C(Nc1cccc(C(=O)c2c[nH]c3ncccc23)c1)Nc1cccc(C(F)(F)F)c1F] | 443.1 |
| P-1715 | 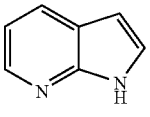 | 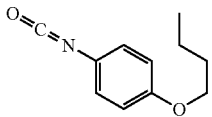 | 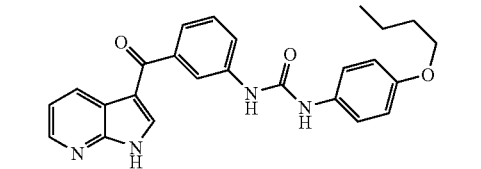 [SMILES: CCCCOc1ccc(NC(=O)Nc2cccc(C(=O)c3c[nH]c4ncccc34)c2)cc1] | 429.1 |
| P-1716 | 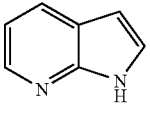 | 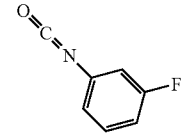 | 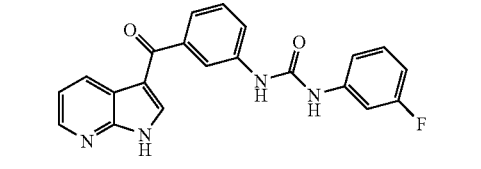 [SMILES: O=C(Nc1cccc(F)c1)Nc1cccc(C(=O)c2c[nH]c3ncccc23)c1] | 375.1 |
| P-1717 | 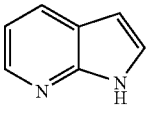 | 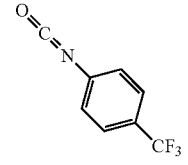 [SMILES: O=C=Nc1ccc(C(F)(F)F)cc1] | 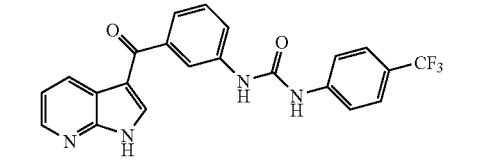 [SMILES: O=C(Nc1ccc(C(F)(F)F)cc1)Nc1cccc(C(=O)c2c[nH]c3ncccc23)c1] | 425.1 |
| P-1718 | 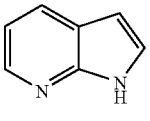 | 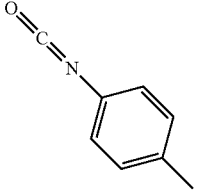 | 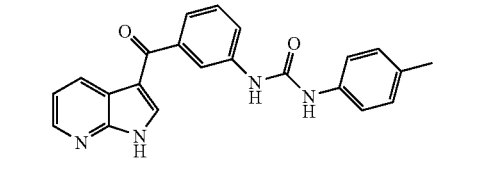 [SMILES: Cc1ccc(NC(=O)Nc2cccc(C(=O)c3c[nH]c4ncccc34)c2)cc1] | 371.1 |

-continued

| | Azaindole | Isocyanate | Compound | MS(ESI) [M + H+]+ observed |
|---|---|---|---|---|
| P-1719 | | | | 371.1 |
| P-1720 | | | | 371.1 |
| P-1723 | | | | 463.9 |
| P-1724 | | | | 470.3 |
| P-1725 | | | | 494.3 |
| P-1726 | | | | 468.3 |
| P-1727 | | | | 535.9 |
| P-1728 | | | | 520.3 |

-continued

| | Azaindole | Isocyanate | Compound | MS(ESI) [M + H⁺]⁺ observed |
|---|---|---|---|---|
| P-1729 | | | | 505.9 |
| P-1730 | | | | 451.9 |
| P-1731 | | | | 502.3 |
| P-1732 | | | | 535.9 |
| P-1733 | | | | 391.1 |
| P-1734 | | | | 421.1 |
| P-1735 | | | | 427.1 |
| P-1736 | | | | 425.1 |

-continued

| | Azaindole | Isocyanate | Compound | MS(ESI) [M + H⁺]⁺ observed |
|---|---|---|---|---|
| P-1737 | | | | 493.1 |
| P-1738 | | | | 493.1 |
| P-1739 | | | | 493.1 |
| P-1740 | | | | 477.1 |
| P-1741 | | | | 463.1 |
| P-1746 | | | | 425.1 |
| P-1747 | | | | 459.1 |
| P-1748 | | | | 451.9 |

| | Azaindole | Isocyanate | Compound | MS(ESI) [M + H+]+ observed |
|---|---|---|---|---|
| P-1749 | | | | 463.9 |
| P-1750 | | | | 467.9 |
| P-1751 | | | | 535.9 |
| P-1752 | | | | 553.2 |
| P-1753 | | | | 553.2 |
| P-1754 | | | | 523.5 |
| P-1755 | | | | 502.3 |
| P-1756 | | | | 447.9 |

-continued

| | Azaindole | Isocyanate | Compound | MS(ESI) [M + H+]+ observed |
|---|---|---|---|---|
| P-1757 | | | | 447.9 |
| P-1758 | | | | 465.1 |
| P-1759 | | | | 447.9 |
| P-1760 | | | | 358.3 |
| P-1761 | | | | 339.1 |
| P-1762 | | | | 455.1 |
| P-1763 | | | | 388.3 |
| P-1764 | | | | 348.3 |

-continued

| | Azaindole | Isocyanate | Compound | MS(ESI) [M + H⁺]⁺ observed |
|---|---|---|---|---|
| P-1765 | | | | 362.3 |
| P-1766 | | | | 459.1 |
| P-1767 | | | | 376.3 |
| P-1770 | | | | 392.3 |
| P-1771 | | | | 392.3 |
| P-1772 | | | | 373.1 |
| P-1773 | | | | 489.1 |

-continued
| | Azaindole | Isocyanate | Compound | MS(ESI) [M + H⁺]⁺ observed |
|---|---|---|---|---|
| P-1774 | 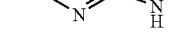 | 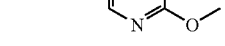 |  | 421.9 |
| P-1775 | 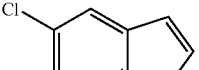 | 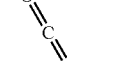 | 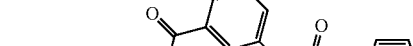 | 382.3 |
| P-1776 |  |  |  | 410.3 |
| P-1777 |  |  |  | 435.1 |
| P-1778 |  |  |  | 531.9 |
| P-1779 |  |  |  | 465.1 |
| P-1780 | 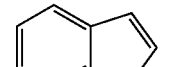 |  | 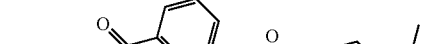 | 400.3 |
| P-1781 | 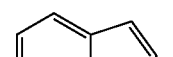 |  | 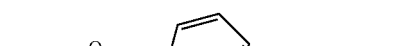 | 358.3 |

-continued
| | Azaindole | Isocyanate | Compound | MS(ESI) [M + H⁺]⁺ observed |
|---|---|---|---|---|
| P-1782 | | | | 434.3 |
| P-1816 | | | | 468.1 |
| P-1817 | | | | 486.1 |
| P-1818 | | | | 510.2 |
| P-1819 | | | | 468.1 |
Example 39
Synthesis of N-[3-(5-chloro-1H-pyrrolo[2,3-b]pyridine-3-carbonyl)-2,4-difluoro-phenyl]-3,5-difluorobenzenesulfonamide P-1841
Compound P-1841 was synthesized in six steps from 2,4-difluoroaniline 42 as shown in Scheme 67.
Scheme 67
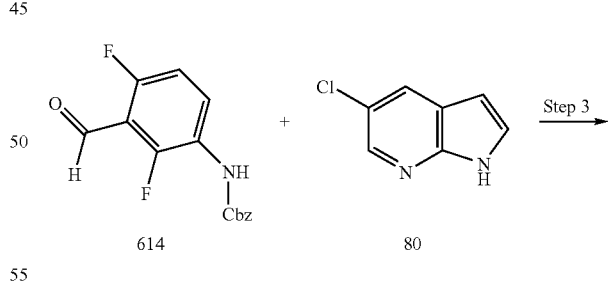
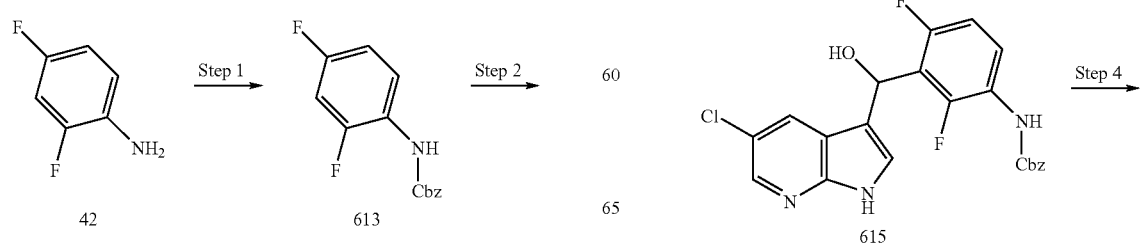

-continued

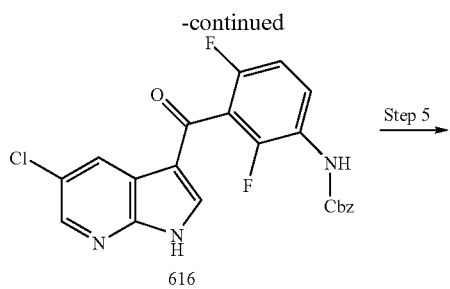

616

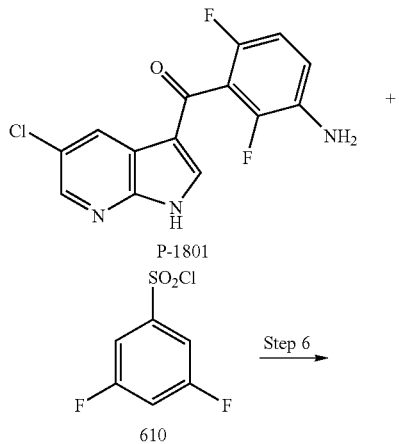

P-1801

610

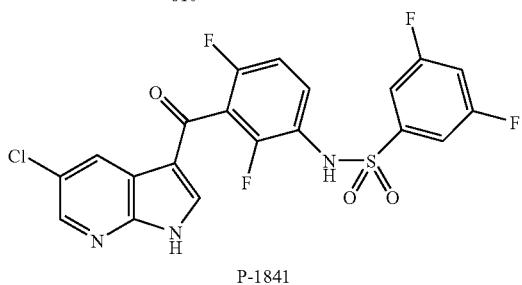

P-1841

Step 1—Preparation of (2,4-difluoro-phenyl)-carbamic acid benzyl ester (613)

To 2,4-difluoroaniline (42, 7.0 mL, 0.070 mol) in 100 mL of dichloromethane was added pyridine (11 mL, 0.14 mol) and benzyl chloroformate (11.9 mL, 0.0834 mol). The reaction mixture was stirred at ambient temperature for 1.5 hours. The reaction mixture was concentrated under reduced pressure and the residue was partitioned between ethyl acetate and KHSO$_4$ solution. The organic layer was dried (MgSO$_4$), concentrated and crystallized from hexanes to give compound 613 (15.6 g, 85%).

Step 2—Preparation of (2,4-difluoro-3-formyl-phenyl)-carbamic acid benzyl ester (614)

Into a round bottom flask was added (2,4-difluoro-phenyl)-carbamic acid benzyl ester (613, 3.83 g, 14.5 mmol) in tetrahydrofuran (148 mL, 1.82 mol). The solution was chilled to −78° C. and n-butyllithium (1.60 M in hexane, 19.1 mL, 30.0 mmol) was added over 30 minutes followed by the addition of, N,N-dimethylformamide (1.12 mL, 14.5 mol). The reaction mixture was allowed to warm to ambient temperature and was stirred overnight. The reaction mixture was poured into water and extracted with ethyl acetate. The organic layer was washed with brine, dried over sodium sulfate, concentrated and crystallized from ether to give compound 614 (3.0 g, 71%).

Step 3—Preparation of {2,4-difluoro-3-[hydroxy-(1H-pyrrolo[2,3-b]pyridin-3-yl)-methyl]-phenyl}-carbamic acid benzyl ester (615)

Into a round bottom flask was added 5-chloro-1H-pyrrolo[2,3-b]pyridine (80, 0.524 g, 3.43 mmol, prepared as described in Example 9) in methanol (5.00 mL, 0.123 mol). Potassium hydroxide (0.800 g. 14.2 mmol) and (2,4-difluoro-3-formyl-phenyl)-carbamic acid benzyl ester (614, 1.02 g, 3.5 mmol) were added and the reaction mixture was stirred overnight. The reaction mixture was poured into 1N HCl and extracted with ethyl acetate. The organic layer was washed with brine, dried over sodium sulfate, concentrated and crystallized from ethyl acetate to give compound 615 (710 mg, 46%). MS(ESI)[M+H$^+$]$^+$=444.

Step 4—Preparation of [2,4-difluoro-3-(1H-pyrrolo[2,3-b]pyridine-3-carbonyl)-phenyl]-carbamic acid benzyl ester (616)

Into a round bottom flask was added {2,4-difluoro-3-[hydroxy-(1H-pyrrolo[2,3-b]pyridin-3-yl)-methyl]-phenyl}-carbamic acid benzyl ester (615, 1.01 g, 2.28 mmol) in tetrahydrofuran (5.00 mL, 0.0616 mol). Dess-Martin periodinane (1.20 g, 2.89 mmol) was added in portions. The reaction mixture was stirred at ambient temperature for 10 minutes, then poured into water and extracted with ethyl acetate. The organic layer was washed with brine, dried over sodium sulfate, concentrated and purified by silica gel chromatography to give compound 616 (914 mg, 91%). MS(ESI)[M+H$^+$]$^+$=442.

Step 5—Preparation of (3-Amino-2,6-difluoro-phenyl)-(5-chloro-1H-pyrrolo[2,3-b]pyridin-3-yl)-methanone (P-1801)

[2,4-difluoro-3-(1H-pyrrolo[2,3-b]pyridine-3-carbonyl)-phenyl]-carbamic acid benzyl ester (616, 800 mg, 1.81 mmol) was added to 10 M NaOH (15.00 mL) and warmed to reflux overnight. The reaction mixture was diluted with 30 mL of water and was extracted with ethyl acetate to give compound P-1801 (450 mg, 81%).

Step 6—Preparation of N-[3-(5-chloro-1H-pyrrolo[2,3-b]pyridine-3-carbonyl)-2,4-difluoro-phenyl]-3,5-difluorobenzenesulfonamide (P-1841)

Into a microwave reaction vessel were combined (3-amino-2,6-difluoro-phenyl)-(5-chloro-1H-pyrrolo[2,3-b]pyridin-3-yl)-methanone (P-1801, 50 mg, 0.16 mmol), 3,5-difluorobenzenesulfonyl chloride (610, 103 mg, 0.49 mmol), pyridine (0.5 mL, 6.1820 mol) and tetrahydrofuran (3.0 mL). The reaction was warmed in the CEM microwave at 300 watts, 130° C. for 10 minutes. The reaction mixture was partitioned between ethyl acetate and brine. The organic layer was collected, dried over Na$_2$SO$_4$, filtered and concentrated. The compound (P-1841) was isolated using column chromatography (silica, hexane:ethyl acetate 70:30) to obtain 36 mg (46%) compound. MS=482.0.

Additional compounds were prepared following the protocol of Scheme 67 Step 6, optionally substituting (3-Amino-2,6-difluoro-phenyl)-(5-chloro-1H-pyrrolo[2,3-b]pyridin-3- yl)-methanone P-1801 with (3-Amino-2,6-difluoro-phenyl)-(1H-pyrrolo[2,3-b]pyridin-3-yl)-methanone P-2021 (prepared per Scheme 67 Steps 1-5, substituting 5-chloro-1H-pyrrolo[2,3-b]pyridine 80 with 1H-pyrrolo[2,3-b]pyridine 94 in Step 3) and/or 3,5-difluorobenzenesulfonyl chloride 610 with an appropriate sulfonyl chloride. The following compounds were prepared by this procedure:

- N-[3-(5-chloro-1H-pyrrolo[2,3-b]pyridine-3-carbonyl)-2,4-difluoro-phenyl]-4-isopropyl-benzenesulfonamide (P-1839),
- N-[2,4-Difluoro-3-(1H-pyrrolo[2,3-b]pyridine-3-carbonyl)-phenyl]-benzenesulfonamide (P-0913),
- N-[2,4-Difluoro-3-(1H-pyrrolo[2,3-b]pyridine-3-carbonyl)-phenyl]-3-nitro-benzenesulfonamide (P-1937),
- N-{4-[2,4-Difluoro-3-(1H-pyrrolo[2,3-b]pyridine-3-carbonyl)-phenylsulfamoyl]-phenyl}-acetamide (P-1938),
- N-[2,4-Difluoro-3-(1H-pyrrolo[2,3-b]pyridine-3-carbonyl)-phenyl]-4-methoxy-benzenesulfonamide (P-0958),
- 5-[2,4-Difluoro-3-(1H-pyrrolo[2,3-b]pyridine-3-carbonyl)-phenylsulfamoyl]furan-2-carboxylic acid methyl ester (P-1941),
- 5-[2,4-Difluoro-3-(1H-pyrrolo[2,3-b]pyridine-3-carbonyl)-phenylsulfamoyl]-2-methyl-furan-3-carboxylic acid methyl ester (P-1942),
- 5-Oxazol-5-yl-thiophene-2-sulfonic acid [2,4-difluoro-3-(1H-pyrrolo[2,3-b]pyridine-3-carbonyl)-phenyl]amide (P-1943),
- 5-Isoxazol-5-yl-thiophene-2-sulfonic acid [2,4-difluoro-3-(1H-pyrrolo[2,3-b]pyridine-3-carbonyl)-phenyl]-amide (P-1948),
- N-[2,4-Difluoro-3-(1H-pyrrolo[2,3-b]pyridine-3-carbonyl)-phenyl]-2,4-dimethoxy-benzenesulfonamide (P-1951),
- 2,5-Dimethyl-thiophene-3-sulfonic acid [2,4-difluoro-3-(1H-pyrrolo[2,3-b]pyridine-3-carbonyl)-phenyl]-amide (P-1952),
- 2,5-Dimethyl-furan-3-sulfonic acid [2,4-difluoro-3-(1H-pyrrolo[2,3-b]pyridine-3-carbonyl)-phenyl]-amide (P-1953),
- N-[2,4-Difluoro-3-(1H-pyrrolo[2,3-b]pyridine-3-carbonyl)-phenyl]-2-methyl-benzenesulfonamide (P-1954),
- 2,3-Dihydro-benzo[1,4]dioxine-6-sulfonic acid [2,4-difluoro-3-(1H-pyrrolo[2,3-b]pyridin-3-carbonyl)-phenyl]-amide (P-1955),
- 2,4-Dimethyl-thiazole-5-sulfonic acid [2,4-difluoro-3-(1H-pyrrolo[2,3-b]pyridine-3-carbonyl)-phenyl]-amide (P-1956),
- N-[2,4-Difluoro-3-(1H-pyrrolo[2,3-b]pyridine-3-carbonyl)-phenyl]-4-trifluoromethyl-benzenesulfonamide (P-0931),
- N-[2,4-Difluoro-3-(1H-pyrrolo[2,3-b]pyridine-3-carbonyl)-phenyl]-5-fluoro-2-methyl-benzenesulfonamide (P-1961),
- N-[2,4-Difluoro-3-(1H-pyrrolo[2,3-b]pyridine-3-carbonyl)-phenyl]-3-methyl-benzenesulfonamide (P-1962),
- N-[2,4-Difluoro-3-(1H-pyrrolo[2,3-b]pyridine-3-carbonyl)-phenyl]-4-oxazol-5-yl-benzenesulfonamide (P-1963),
- N-[2,4-Difluoro-3-(1H-pyrrolo[2,3-b]pyridine-3-carbonyl)-phenyl]-2,5-dimethoxy-benzenesulfonamide (P-1131),
- 2-Cyano-N-[2,4-difluoro-3-(1H-pyrrolo[2,3-b]pyridine-3-carbonyl)-phenyl]-benzenesulfonamide (P-1965),
- 3-Cyano-N-[2,4-difluoro-3-(1H-pyrrolo[2,3-b]pyridine-3-carbonyl)-phenyl]-benzenesulfonamide (P-1966),
- N-[2,4-Difluoro-3-(1H-pyrrolo[2,3-b]pyridine-3-carbonyl)-phenyl]-4-isopropyl-benzenesulfonamide (P-1968),
- Benzothiazole-6-sulfonic acid [2,4-difluoro-3-(1H-pyrrolo[2,3-b]pyridine-3-carbonyl)-phenyl]-amide (P-1969),
- N-[3-(5-Chloro-1H-pyrrolo[2,3-b]pyridine-3-carbonyl)-2,4-difluoro-phenyl]-3-methoxy-benzenesulfonamide (P-2011),
- N-[3-(5-Chloro-1H-pyrrolo[2,3-b]pyridine-3-carbonyl)-2,4-difluorophenyl]-benzenesulfonamide (P-0885),
- Thiophene-2-sulfonic acid [3-(5-chloro-1H-pyrrolo[2,3-b]pyridine-3-carbonyl)-2,4-difluoro-phenyl]-amide (P-1267),
- N-[3-(5-Chloro-1H-pyrrolo[2,3-b]pyridine-3-carbonyl)-2,4-difluoro-phenyl]-4-methyl-benzenesulfonamide (P-1842),
- N-{4-[3-(5-Chloro-1H-pyrrolo[2,3-b]pyridine-3-carbonyl)-2,4-difluoro-phenylsulfamoyl]-phenyl}-acetamide (P-1905),
- N-[3-(5-Chloro-1H-pyrrolo[2,3-b]pyridine-3-carbonyl)-2,4-difluoro-phenyl]-4-methoxy-benzenesulfonamide (P-0983),
- N-[3-(5-Chloro-1H-pyrrolo[2,3-b]pyridine-3-carbonyl)-2,4-difluoro-phenyl]-3-trifluoromethyl-benzenesulfonamide (P-1599),
- 5-[3-(5-Chloro-1H-pyrrolo[2,3-b]pyridine-3-carbonyl)-2,4-difluoro-phenylsulfamoyl]-furan-2-carboxylic acid methyl ester (P-1907),
- 5-[3-(5-Chloro-1H-pyrrolo[2,3-b]pyridine-3-carbonyl)-2,4-difluoro-phenylsulfamoyl]-2-methyl-furan-3-carboxylic acid methyl ester (P-1908),
- 1,2-Dimethyl-1H-imidazole-4-sulfonic acid [3-(5-chloro-1H-pyrrolo[2,3-b]pyridine-3-carbonyl)-2,4-difluoro-phenyl]-amide (P-1911),
- N-[3-(5-Chloro-1H-pyrrolo[2,3-b]pyridine-3-carbonyl)-2,4-difluoro-phenyl]-2-fluoro-benzenesulfonamide (P-1912),
- N-[3-(5-Chloro-1H-pyrrolo[2,3-b]pyridine-3-carbonyl)-2,4-difluoro-phenyl]-4-difluoromethoxy-benzenesulfonamide (P-1916),
- N-[3-(5-Chloro-1H-pyrrolo[2,3-b]pyridine-3-carbonyl)-2,4-difluoro-phenyl]-2,4-dimethoxy-benzenesulfonamide (P-1918),
- 2,5-Dimethyl-thiophene-3-sulfonic acid [3-(5-chloro-1H-pyrrolo[2,3-b]pyridine-3-carbonyl)-2,4-difluoro-phenyl]-amide (P-1919),
- 2,5-Dimethyl-furan-3-sulfonic acid [3-(5-chloro-1H-pyrrolo[2,3-b]pyridine-3-carbonyl)-2,4-difluoro-phenyl]-amide (P-1920),
- N-[3-(5-Chloro-1H-pyrrolo[2,3-b]pyridine-3-carbonyl)-2,4-difluoro-phenyl]-2-methyl-benzenesulfonamide (P-1921),
- 2,3-Dihydro-benzo[1,4]dioxine-6-sulfonic acid [3-(5-chloro-1H-pyrrolo[2,3-b]pyridine-3-carbonyl)-2,4-difluoro-phenyl]-amide (P-1922).
- 2,4-Dimethyl-thiazole-5-sulfonic acid [3-(5-chloro-1H-pyrrolo[2,3-b]pyridine-3-carbonyl)-2,4-difluoro-phenyl]-amide (P-1923),
- N-[3-(5-Chloro-1H-pyrrolo[2,3-b]pyridine-3-carbonyl)-2,4-difluoro-phenyl]-2,4-difluoro-benzenesulfonamide (P-1926),
- N-[3-(5-Chloro-1H-pyrrolo[2,3-b]pyridine-3-carbonyl)-2,4-difluoro-phenyl]-5-fluoro-2-methyl-benzenesulfonamide (P-1927), N-[3-(5-Chloro-1H-pyrrolo[2,3-b]pyridine-3-carbonyl)-2,4-difluoro-phenyl]-3-methyl-benzenesulfonamide (P-1928),
N-[3-(5-Chloro-1H-pyrrolo[2,3-b]pyridine-3-carbonyl)-2,4-difluoro-phenyl]-2,5-dimethoxy-benzenesulfonamide (P-1929),
N-[3-(5-Chloro-1H-pyrrolo[2,3-b]pyridine-3-carbonyl)-2,4-difluoro-phenyl]-2-cyano-benzenesulfonamide (P-1931), and N-[3-(5-Chloro-1H-pyrrolo[2,3-b]pyridine-3-carbonyl)-2,4-difluoro-phenyl]-3-cyano-benzenesulfonamide (P-1932).

The following table indicates the azaindole (column 2) and the sulfonyl chloride (column 3) used to afford the target compound (column 4). The compound number is provided in column 1, with the observed mass given in column 5.

| | Azaindole | Sulfonyl chloride | Compound | MS(ESI) [M + H$^+$]$^+$ observed |
|---|---|---|---|---|
| P-1839 | | | | 489.9 |
| P-0913 | | | | 413.9 |
| P-1937 | | | | 459.1 |
| P-1938 | | | | 471.1 |
| P-0958 | | | | 444.3 |

-continued

| | Azaindole | Sulfonyl chloride | Compound | MS(ESI) [M + H⁺]⁺ observed |
|---|---|---|---|---|
| P-1941 | | | | 462.3 |
| P-1942 | | | | 475.9 |
| P-1943 | | | | 487.1 |
| P-1948 | | | | 487.1 |
| P-1951 | | | | 473.9 |
| P-1952 | | | | 447.9 |

-continued

| | Azaindole | Sulfonyl chloride | Compound | MS(ESI) [M + H⁺]⁺ observed |
|---|---|---|---|---|
| P-1953 | | | | 432.3 |
| P-1954 | | | | 427.9 |
| P-1955 | | | | 472.3 |
| P-1956 | | | | 448.7 |
| P-0931 | | | | 481.9 |
| P-1961 | | | | 445.9 |

-continued

| | Azaindole | Sulfonyl chloride | Compound | MS(ESI) [M + H⁺]⁺ observed |
|---|---|---|---|---|
| P-1962 | | | | 427.9 |
| P-1963 | | | | 481.1 |
| P-1131 | | | | 473.9 |
| P1965 | | | | 439.1 |
| P-1966 | | | | 439.1 |
| P-1968 | | | | 456.3 |

-continued

| | Azaindole | Sulfonyl chloride | Compound | MS(ESI) [M + H⁺]⁺ observed |
|---|---|---|---|---|
| P-1969 | | | | 471.1 |
| P-2011 | | | | 477.9 |
| P-0885 | | | | 447.9 |
| P-1267 | | | | 453.9 |
| P-1842 | | | | 462.3 |
| P-1905 | | | | 505.1 |

-continued

| | Azaindole | Sulfonyl chloride | Compound | MS(ESI) [M + H⁺]⁺ observed |
|---|---|---|---|---|
| P-0983 | | | | 477.9 |
| P-1599 | | | | 515.9 |
| P-1907 | | | | 496.3 |
| P-1908 | | | | 509.9 |
| P-1911 | | | | 466.3 |
| P-1912 | | | | 465.9 |

-continued

| | Azaindole | Sulfonyl chloride | Compound | MS(ESI) [M + H⁺]⁺ observed |
|---|---|---|---|---|
| P-1916 | | | | 513.9 |
| P-1918 | | | | |
| P-1919 | | | | 481.9 |
| P-1920 | | | | 465.9 |
| P-1921 | | | | 461.9 |
| P-1922 | | | | 505.9 |

-continued

| | Azaindole | Sulfonyl chloride | Compound | MS(ESI) [M + H⁺]⁺ observed |
|---|---|---|---|---|
| P-1923 | | | | 483.1 |
| P-1926 | | | | 483.9 |
| P-1927 | | | | 479.9 |
| P-1928 | | | | 461.9 |
| P-1929 | | | | 507.9 |
| P-1931 | | | | 473.1 |

| Azaindole | Sulfonyl chloride | Compound | MS(ESI) [M + H⁺]⁺ observed |
|---|---|---|---|
| P-1932 | | | 473.1 |

Example 40

Synthesis of 4-(5-pyridin-3-yl-1H-pyrrolo[2,3-b]pyridine-3-carbonyl)-indole-1-carboxylic acid dibutylamide P-1636

Compound P-1636 was synthesized in two steps from 1H-indole-4-carboxylic acid 611 as shown in Scheme 68.

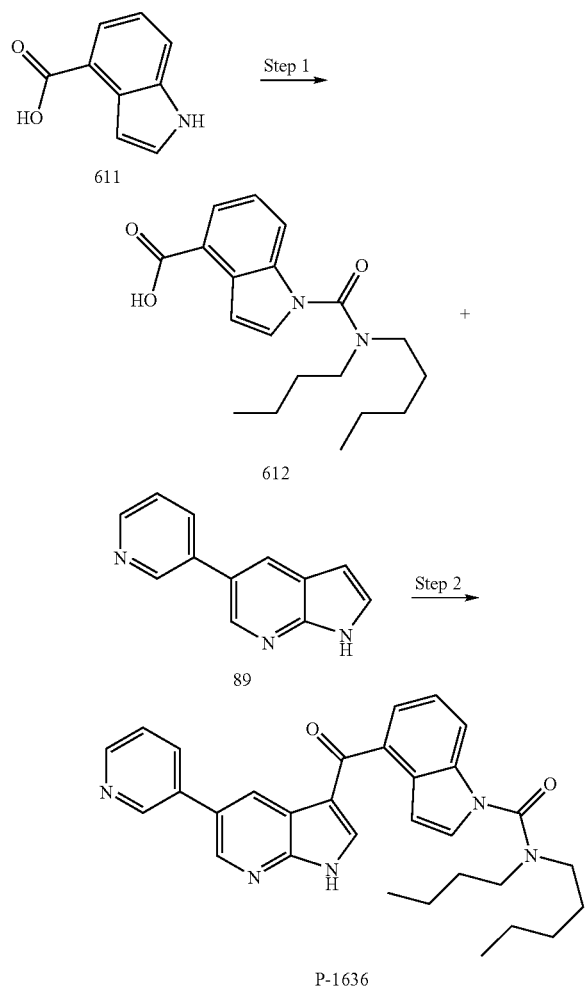

Scheme 68

Step 1—Preparation of 1-dibutylcarbamoyl-1H-indole-4-carboxylic acid (612)

To 1H-Indole-4-carboxylic acid (611, 251 mg, 1.56 mmol) in tetrahydrofuran (3 mL), was added 2.5M n-butyllithium in hexane (1.28 mL, 3.19 mmol) at −78° C. After 30 minutes, dibutyl carbamyl chloride (657 mg, 3.43 mmol) was added and stirred for two hours. The reaction solution was quenched with 1M HCl (aq.) and extracted with ethyl acetate. The organic layer was washed with brine, dried over anhydrous magnesium sulfate, filtrated and concentrated. The desired compound was isolated with silica gel column chromatography using 10% ethyl acetate in hexane to give a white solid (612, 88 mg, 18%). MS(ESI) [M−H⁺]⁻=315.1.

Step 2—Preparation of 4-(5-pyridin-3-yl-1H-pyrrolo[2,3-b]pyridine-3-carbonyl)-indole-1-carboxylic acid dibutylamide (P-1636)

To 1-dibutylcarbamoyl-1H-indole-4-carboxylic acid (612, 78 mg, 0.25 mmol) in dichloromethane (2 mL), thionyl chloride (25 μL, 0.34 mmol) was added and stirred for one hour, followed by rotary evaporation to remove solvents to provide the dried acid chloride, which was dissolved in dichloromethane for later use. Meanwhile, 5-pyridin-3-yl-1H-pyrrolo[2,3-b]pyridine (89, 55 mg, 0.28 mmol, prepared as described in Example 17) in dichloromethane (8 mL), was mixed with aluminum trichloride (215 mg, 1.6 mmol) and stirred for one hour, followed by addition of the dried acid chloride in dichloromethane (3 mL). The reaction was stirred at room temperature overnight, then quenched with methanol and all volatiles were removed. The desired compound was isolated with silica gel column chromatography using 10% methanol in dichloromethane to give a solid (P-1636, 11 mg, 9%). MS(ESI) [M+H⁺]⁺=494.3.

Additional compounds were prepared following the protocol of Scheme 68, substituting dibutyl carbamyl chloride with a suitable reagent in Step 1 and optionally substituting 5-pyridin-3-yl-1H-pyrrolo[2,3-b]pyridine 89 with 5-(6-Methoxy-pyridin-3-yl)-1H-pyrrolo[2,3-b]pyridine (see Example 17) in Step 2. The following compounds were prepared following this procedure:

[1-(Butane-1-sulfonyl)-1H-indol-4-yl]-(5-pyridin-3-yl-1H-pyrrolo[2,3-b]pyridin-3-yl)-methanone (P-1661),
4-(5-Pyridin-3-yl-1H-pyrrolo[2,3-b]pyridine-3-carbonyl)-indole-1-carboxylic acid pentylamide (P-1702),
4-(5-Pyridin-3-yl-1H-pyrrolo[2,3-b]pyridine-3-carbonyl)-indole-1-carboxylic acid dipropylamide (P-1722), and
4-[5-(6-Methoxy-pyridin-3-yl)-1H-pyrrolo[2,3-b]pyridine-3-carbonyl]-indole-1-carboxylic acid butylamide (P-1827).

The following table indicates the reagent used in place of dibutyl carbamyl chloride (column 2) and the azaindole (column 3) used to afford the target compound (column 3). The compound number is provided in column 1, and the observed mass is given in column 5.

| Step 1 reagent | Azaindole | Compound | MS(ESI) [M + H+]+ observed |
|---|---|---|---|
| P-1661 | | | 459.2 |
| P-1702 | | | 452.3 |
| P-1722 | | | 466.3 |
| P-1827 | | | 468.3 |
Example 41
Synthesis of 3-(3-Benzyloxy-2-chloro-6-fluoro-benzyl)-1H-pyrrolo[2,3-b]pyridine P-1852, (3-Benzyloxy-2-chloro-6-fluoro-phenyl)-(1H-pyrrolo[2,3-b]pyridin-3-yl)-methanone P-1853 and related compounds
Compounds P-1852 and P-1853 were synthesized in four steps from 2-chloro-4-fluorophenol 617 and 1H-pyrrolo[2,3-b]pyridine 94 as shown in Scheme 69.
Scheme 69
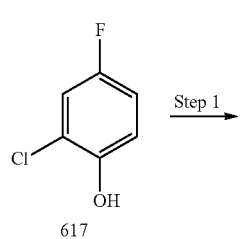
617
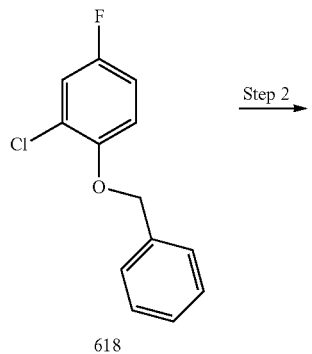
618
-continued -continued

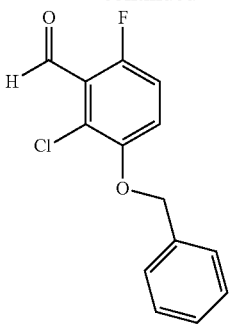

619

+

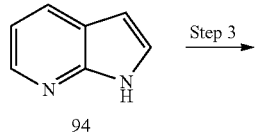

94

Step 3 →

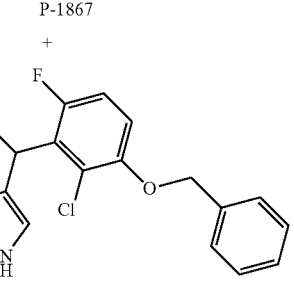

P-1867

+

P-1868

Step 4a →

Step 4b →

-continued

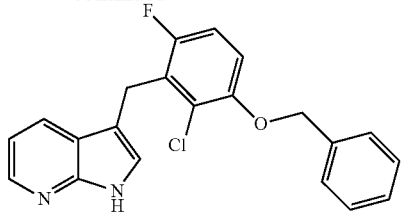

P-1852

+

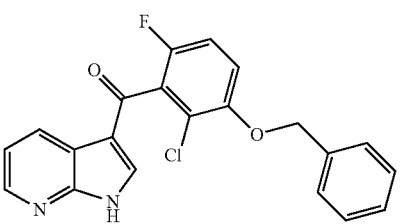

P-1853

Step 1—Preparation of 1-Benzyloxy-2-chloro-4-fluoro-benzene (618)

To a solution of 2-chloro-4-fluorophenol (617, 7 g, 0.05 mol) in tetrahydrofuran (100 mL) was added sodium hydride (1.8 g, 95% dry powder, 0.071 mol) at room temperature over 15 minutes under an atmosphere of nitrogen. The reaction mixture was stirred at room temperature for 30 minutes. Benzyl bromide (10 g, 0.060 mol) was added slowly to the reaction mixture, then stirred at room temperature overnight. The reaction mixture was poured into ice water, extracted with ethyl acetate, washed with hydrochloric acid (10%), water, brine, and dried over magnesium sulfate. After removal of solvent, the residue was purified by silica gel column chromatography eluting with ethyl acetate in hexane to provide compound as a white solid (618, 7.6 g, 60%).

Step 2—Preparation of 3-Benzyloxy-2-chloro-6-fluoro-benzaldehyde (619)

To a solution of 1-benzyloxy-2-chloro-4-fluoro-benzene (618, 5.8 g, 0.024 mol) in tetrahydrofuran (100 mL) was added 2.50 M of n-butyllithium (2.7 mL, 2.50 M in hexane, 0.029 mol) slowly at −78° C. over 15 minutes under nitrogen. The reaction mixture was stirred at −78° C. for 30 minutes. To the reaction mixture was then added N,N-dimethylformamide (4.2 mL, 0.054 mol). The reaction was allowed to warm to room temperature and was continued at room temperature overnight. The reaction mixture was poured into ice water, extracted with ethyl acetate, washed with hydrochloric acid (10%), water, brine, and dried over magnesium sulfate. After removal of solvent, the residue was purified by silica gel column chromatography eluting with ethyl acetate in hexane to provide the compound as a white solid (619, 2.1 g, 32%). MS(ESI) [M+H$^+$]$^+$=265.08.

Step 3—Preparation of 3-[(3-Benzyloxy-2-chloro-6-fluoro-phenyl)-methoxy-methyl]-1H-pyrrolo[2,3-b]pyridine (P-1867) and (3-Benzyloxy-2-chloro-6-fluoro-phenyl)-(1H-pyrrolo[2,3-b]pyridin-3-yl)-methanol (P-1868)

A mixture of 1H-pyrrolo[2,3-b]pyridine (94, 0.5 g, 4 mmol), 3-benzyloxy-2-chloro-6-fluoro-benzaldehyde (619, 1.3 g, 4.9 mmol), and potassium hydroxide (0.99 g, 18 mmol) in methanol (30 mL) was stirred at room temperature overnight. The reaction mixture was concentrated and the residue was dissolved in ethyl acetate and water. The organic layer was collected and washed with brine. After removal of solvent, the residue was purified by silica gel column chromatography eluting with ethyl acetate in hexane to provide compound P-1867 as a white solid (1.3 g, 70%, MS(ESI) [M+H$^+$]$^+$=397.16), and compound P-1868 as an off-white solid (0.2 g, 10, MS(ESI) [M+H$^+$]$^+$=383.14).

Step 4a—Preparation of 3-(3-Benzyloxy-2-chloro-6-fluoro-benzyl)-1H-pyrrolo[2,3-b]pyridine (P-1852)

A mixture of 3-[(3-Benzyloxy-2-chloro-6-fluoro-phenyl)-methoxy-methyl]-1H-pyrrolo[2,3-b]pyridine (P-1867, 0.1 g, 0.2 mmol), trifluoroacetic acid (0.6 mL, 8 mmol), and triethylsilane (0.3 mL, 2 mmol) in acetonitrile (10 mL) was refluxed for 2 hours. The mixture was concentrated and the residue was dissolved in ethyl acetate. The solution was washed with saturated sodium bicarbonate, brine, and dried over sodium sulfate. After removal of solvent, the residue was purified by silica gel column chromatography eluting with methanol in dichloromethane to provide compound as an off-white solid (P-1852, 62 mg, 70%). MS(ESI) [M+H$^+$]$^+$=367.16.

Step 4b—Preparation of (3-Benzyloxy-2-chloro-6-fluoro-phenyl)-(1H-pyrrolo[2,3-b]pyridin-3-yl)-methanone (P-1853)

To a solution of (3-Benzyloxy-2-chloro-6-fluoro-phenyl)-(1H-pyrrolo[2,3-b]pyridin-3-yl)-methanol (P-1868, 65 mg, 0.17 mmol) in tetrahydrofuran (10 mL) was added Dess-Martin periodinane (79 mg, 0.19 mmol) at 0° C. The reaction mixture was stirred at room temperature for 2 hours. The reaction was quenched with a saturated solution of sodium thiosulfate, extracted with ethyl acetate, washed with sodium bicarbonate, brine, and dried over magnesium sulfate. After removal of solvent, the residue was purified by silica gel column chromatography eluting with methanol in dichloromethane to provide the compound as a light yellow solid (P-1853, 32 mg, 50%). MS(ESI) [M+H$^+$]$^+$=381.13.

Additional compounds were prepared following the protocol of Scheme 69, optionally replacing 2-chloro-4-fluorophenol 617 with 2,6-difluorophenol or 2,6-dichlorophenol, optionally replacing benzyl bromide with an appropriate substituted benzyl bromide, and optionally replacing 1H-pyrrolo[2,3-b]pyridine 94 with an appropriate substituted 1H-pyrrolo[2,3-b]pyridine. Azaindoles were purchased or prepared as described in Examples 9 or 16. The following compounds were made following this procedure:
 3-[2,6-Dichloro-3-(4-chloro-benzyloxy)-benzyl]-1H-pyrrolo[2,3-b]pyridine (P-1768),
 [2,6-Dichloro-3-(4-chloro-benzyloxy)-phenyl]-(1H-pyrrolo[2,3-b]pyridin-3-yl)methanone (P-1769),
 (3-Benzyloxy-2,6-difluoro-phenyl)-(1H-pyrrolo[2,3-b]pyridin-3-yl)-methanone (P-1802),
 3-(3-Benzyloxy-2,6-difluoro-benzyl)-1H-pyrrolo[2,3-b]pyridine (P-1803),
 3-(3-Benzyloxy-2,6-difluoro-benzyl)-5-methoxy-1H-pyrrolo[2,3-b]pyridine (P-1804),
 3-(3-Benzyloxy-2,6-difluoro-benzyl)-5-chloro-1H-pyrrolo[2,3-b]pyridine (P-1824),
 (3-Benzyloxy-2,6-difluoro-phenyl)-(5-chloro-1H-pyrrolo[2,3-b]pyridin-3-yl)-methanone (P-1825),
 3-[(3-Benzyloxy-2-chloro-6-fluoro-phenyl)-methoxy-methyl]-1H-pyrrolo[2,3-b]pyridine (P-1867),
 (3-Benzyloxy-2-chloro-6-fluoro-phenyl)-(1H-pyrrolo[2,3-b]pyridin-3-yl)-methanol (P-1868),
 [2-Chloro-3-(3-chloro-benzyloxy)-6-fluoro-phenyl]-(1H-pyrrolo[2,3-b]pyridin-3-yl)-methanone (P-1869),
 [2-Chloro-3-(4-chloro-benzyloxy)-6-fluoro-phenyl]-(1H-pyrrolo[2,3-b]pyridin-3-yl)-methanone (P-1874),
 3-[2,6-Difluoro-3-(pyridin-4-ylmethoxy)-benzyl]-1H-pyrrolo[2,3-b]pyridine (P-1993), and
 3-[3-(4-Chloro-2-fluoro-benzyloxy)-2,6-difluoro-benzyl]-1H-pyrrolo[2,3-b]pyridine (P-1992).

The phenol, benzyl bromide and azaindole used in Steps 1, 2, and 3, respectively, are indicated in columns 2, 3, and 4 of the following table, respectively, to afford the target compound (column 5). The compound number is provided in column 1, and the observed mass is given in column 6.

| | Phenol | Benzyl bromide | Azaindole | Compound | MS (ESI) [M + H$^+$]$^+$ observed |
|---|---|---|---|---|---|
| P-1768 | 2,4-dichlorophenol | 4-chlorobenzyl bromide | 7-azaindole | [structure shown] | 417.14 |

-continued

| | Phenol | Benzyl bromide | Azaindole | Compound | MS (ESI) [M + H⁺]⁺ observed |
|---|---|---|---|---|---|
| P-1769 | 2,4-dichlorophenol | 4-chlorobenzyl bromide | 7-azaindole | | 431.09 |
| P-1802 | 2,4-difluorophenol | benzyl bromide | 7-azaindole | | 365.23 |
| P-1803 | 2,4-difluorophenol | benzyl bromide | 7-azaindole | | 351.23 |
| P-1804 | 2,4-difluorophenol | benzyl bromide | 5-methoxy-7-azaindole | | 381.26 |
| P-1824 | 2,4-difluorophenol | benzyl bromide | 5-chloro-7-azaindole | | 385.22 |
| P-1825 | 2,4-difluorophenol | benzyl bromide | 5-chloro-7-azaindole | | 399.21 |

-continued
| | Phenol | Benzyl bromide | Azaindole | Compound | MS (ESI) [M + H⁺]⁺ observed |
|---|---|---|---|---|---|
| P-1869 | | | | | 415.24 |
| P-1874 | | | | | 415.23 |
| P-1993 | | | | | 352.39 |
| P-1992 | | | | | |
Example 42
Synthesis of (3-Benzyloxy-2-methyl-phenyl)-(1H-pyrrolo[2,3-b]pyridin-3-yl)-methanone P-1848 and 3-(3-Benzyloxy-2-methyl-benzyl)-1H-pyrrolo[2,3-b]pyridine P-1857
Compounds P-1848 and P-1857 were synthesized in five steps from compounds 620 and 1H-pyrrolo[2,3-b]pyridine 94 as shown in Scheme 70.
Scheme 70
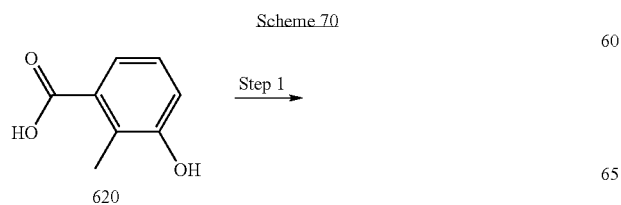
-continued
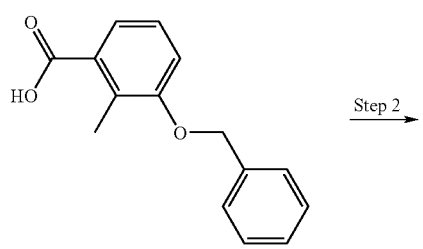

-continued

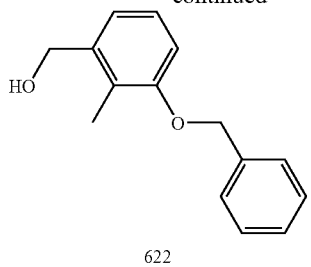
622

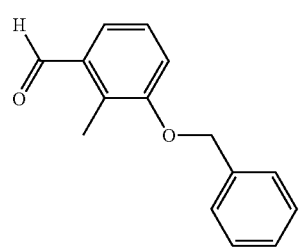
623

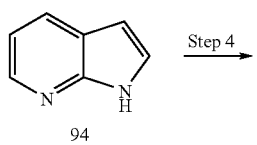
94

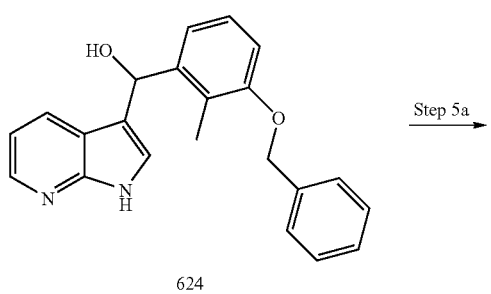
624

+

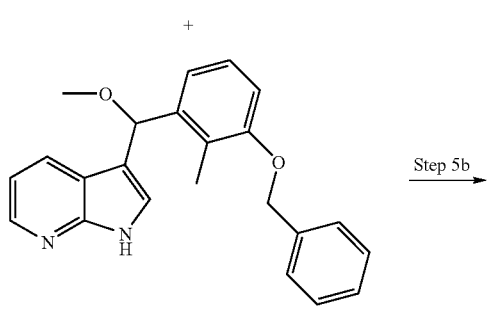
625

Step 3 →

Step 4 →

Step 5a →

Step 5b →

-continued

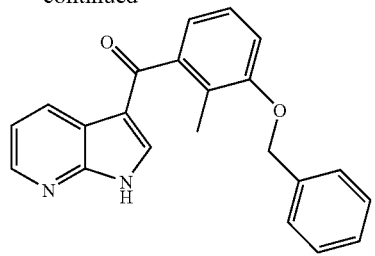
P-1848

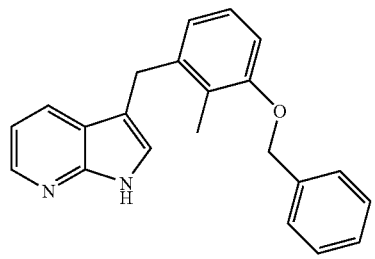
P-1857

Step 1—Preparation of
3-Benzyloxy-2-methyl-benzoic acid (621)

To a solution of 3-hydroxy-2-methyl-benzoic acid (620, 5.0 g, 0.033 mol) in tetrahydrofuran (100 mL) and N,N-dimethylformamide (50 mL), sodium hydride (4.4 g as 60% dispersion in mineral oil, 0.11 mol) was added slowly over 30 minutes and the reaction was stirred at 0° C. under an atmosphere of nitrogen. The reaction mixture was allowed to warm to room temperature, then stirred at room temperature for 1 hour. Benzyl bromide (9.0 mL, 0.076 mol) was added slowly into the reaction mixture, and the reaction mixture was stirred at room temperature overnight. The reaction mixture was poured into water, extracted with ethyl acetate, washed with a solution of ammonium chloride and ammonium hydroxide (4:1), brine, and dried over magnesium sulfate. After removal of solvent, the residue was purified by silica gel column chromatography eluting with ethyl acetate in hexane to provide the compound as a white solid (621, 5.8 g, 73%).

Step 2—Preparation of
(3-Benzyloxy-2-methyl-phenyl)-methanol (622)

To a solution of 3-benzyloxy-2-methyl-benzoic acid (621, 3.0 g, 0.012 mol) in tetrahydrofuran (100 mL), lithium aluminum hydride (25 mL, 1M solution in tetrahydrofuran, 0.025 mol) was added dropwise at 0° C. for 5 minutes. The reaction mixture was then stirred at room temperature overnight under an atmosphere of nitrogen. After sodium sulfate decahydrate (20.0 g, 0.062 mol) was added, the reaction mixture was stirred at room temperature for 10 minutes. A white solid was collected by filtration. The solid compound was further washed with a mixture of hexane and dichloromethane (9:1) and dried under high-vacuum (622, 2.8 g, 91%).

Step 3—Preparation of
3-Benzyloxy-2-methyl-benzaldehyde (623)

To a solution of (3-benzyloxy-2-methyl-phenyl)-methanol (622, 627 mg, 2.75 mmol) in tetrahydrofuran (60 mL) was added Dess-Martin periodinane (2.9 g, 6.87 mmol) at 0° C. The resulting mixture was stirred at 0° C. for 50 minutes. The reaction mixture was quenched with a solution of saturated sodium thiosulfate, extracted with ethyl acetate, washed with sodium bicarbonate, brine, and dried over magnesium sulfate. After removal of solvent, the residue was purified by silica gel column chromatography eluting with ethyl acetate in hexane to provide the compound as a white solid (623, 0.55 g, 84%).

Step 4—Preparation of (3-Benzyloxy-2-methyl-phenyl)-(1H-pyrrolo[2,3-b]pyridin-3-yl)-methanol (624) and 3-[(3-Benzyloxy-2-methyl-phenyl)-methoxy-methyl]-1H-pyrrolo[2,3-b]pyridine (625)

A mixture of 1H-pyrrolo[2,3-b]pyridine (94, 0.33 g, 2.8 mmol), 3-benzyloxy-2-methyl-benzaldehyde (623, 0.55 g, 2.4 mmol), and potassium hydroxide (0.39 g, 6.1 mmol) in methanol (40 mL) was stirred at room temperature for 17 hours. The reaction mixture was poured into water and then extracted with ethyl acetate. The organic layer was collected, washed with brine, and dried over sodium sulfate. After removal of solvent, the residue was purified by silica gel column chromatography eluting with ethyl acetate in hexane to provide compound 624 as an off-white solid (330 mg, 39%, MS(ESI) [M+H$^+$]$^+$=345.29, and compound 625 as a white solid (24 mg, 3%, MS(ESI) [M+H$^+$]$^+$=359.30).

Step 5a—Preparation of (3-Benzyloxy-2-methyl-phenyl)-(1H-pyrrolo[2,3-b]pyridin-3-yl)-methanone (P-1848)

To a solution of (3-Benzyloxy-2-methyl-phenyl)-(1H-pyrrolo[2,3-b]pyridin-3-yl)-methanol (624, 0.12 g, 0.35 mmol) in tetrahydrofuran (15 mL) was added Dess-Martin periodinane (0.37 g, 0.89 mmol) at 0° C. The reaction mixture was stirred at 0° C. for 50 minutes, then quenched with a saturated solution of sodium thiosulfate, extracted with ethyl acetate, washed with sodium bicarbonate, brine, and dried over magnesium sulfate. After removal of solvent, the residue was washed with a mixture of ethyl ether and hexanes (1:1) to provide the compound as a yellow solid (P-1848, 108 mg, 90%). MS(ESI) [M+H$^+$]$^+$=343.22.

Step 5b—Preparation of 3-(3-Benzyloxy-2-methyl-benzyl)-1H-pyrrolo[2,3-b]pyridine (P-1857)

A mixture of 3-[(3-benzyloxy-2-methyl-phenyl)-methoxy-methyl]-1H-pyrrolo[2,3-b]pyridine (625, 24 mg, 0.067 mmol), trifluoroacetic acid (1 mL, 13 mmol), and triethylsilane (2 mL, 12.5 mmol) in acetonitrile (10 mL) was refluxed for 4 hours. The mixture was concentrated and the residue was dissolved in ethyl acetate. The solution was washed with saturated sodium bicarbonate, brine, and dried over sodium sulfate. After removal of solvent, the residue was washed with a mixture of ethyl ether and hexanes (1:1) to provide the compound as a yellow solid (P-1857, 17 mg, 75%). MS(ESI) [M+H$^+$]$^+$=329.24.

Example 43

Synthesis of [3-(4-chloro-benzyloxy)-2-ethoxy-phenyl]-(1H-pyrrolo[2,3-b]pyridin-3-yl)-methanone P-1892 and 3-[3-(4-chloro-benzyloxy)-2-ethoxy-benzyl]-1H-pyrrolo[2,3-b]pyridine P-1893

Compounds P-1892 and P-1893 were synthesized in five steps from compounds 626, 557 and 1H-pyrrolo[2,3-b]pyridine 94 as shown in Scheme 71.

Scheme 71

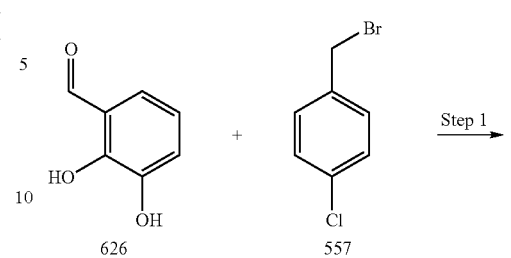

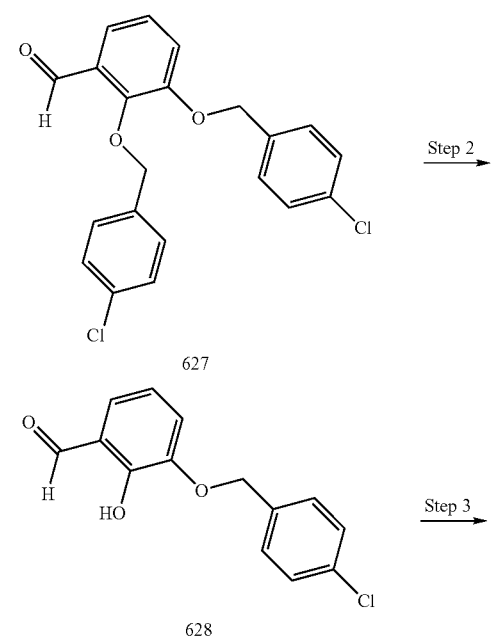

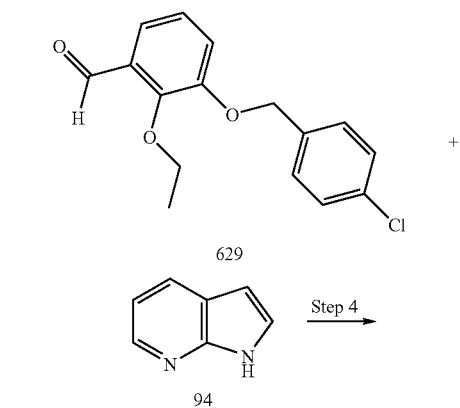

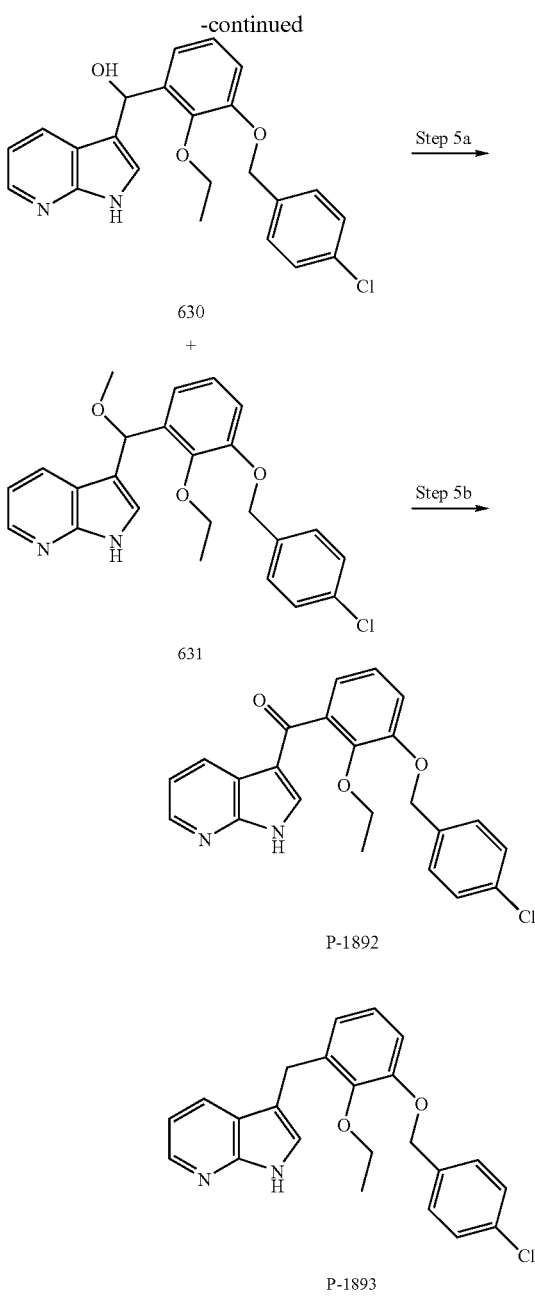

P-1892

P-1893

Step 1—Preparation of 2,3-Bis-(4-chloro-benzyloxy)-benzaldehyde (627)

To a solution of 2,3-dihydroxybenzaldehyde (626, 2.0 g, 14.5 mmol) in tetrahydrofuran (100 mL) was added sodium hydride (0.52 g, 13.0 mmol) at 0° C. under an atmosphere of nitrogen. The reaction mixture was allowed to warm to room temperature and was stirred at room temperature for 30 minutes. To the reaction mixture was then added 4-chlorobenzyl bromide (557, 2.7 g, 13.0 mmol). The reaction mixture was stirred at room temperature under an atmosphere of nitrogen overnight. N,N-dimethylformamide (50 mL) was added into the reaction mixture and it was stirred at room temperature for 24 hours. The reaction mixture was poured into ice water and extracted with ethyl acetate. The organic layer was collected, washed with brine, and dried over magnesium sulfate. After removal of solvent, the residue was purified by silica gel column chromatography eluting with ethyl acetate in hexane to provide the compound as an off-white solid (627, 2.3 μm, 46%).

Step 2—Preparation of 3-(4-chloro-benzyloxy)-2-hydroxy-benzaldehyde (628)

To magnesium (0.098 g, turnings, 4.0 mmol) in a mixture of anhydrous ether (20 mL) and benzene (20 mL) at 0° C., bromine (0.10 mL, 2.0 mmol) was added dropwise. When the reaction had started, stirring was commenced and the addition of bromine continued until complete. The ice bath was removed and the reaction mixture was heated until the solution was almost colorless. After cooling down, the reaction mixture was slowly added to a solution of 2,3-bis-(4-chloro-benzyloxy)-benzaldehyde (627, 0.78 g, 2.0 mmol) in benzene (60 mL) at room temperature while stirring vigorously. Upon completion of the addition, the reaction mixture was stirred at room temperature overnight, then refluxed for 36 hours. After the reaction mixture was cooled down to room temperature, a solid was collected by filtration and washed with benzene, then boiled in hydrochloric acid (100 mL, 1.0 M) for 30 minutes. After cool down, the solution was extracted with dichloromethane. The organic layer was washed with brine and dried over magnesium sulfate. An off-white solid was obtained after removal of the solvent (628, 0.32 mg, 60%). MS(ESI) [M−H−]=261.25.

Step 3—Preparation of 3-(4-chloro-benzyloxy)-2-ethoxy-benzaldehyde (629)

To a mixture of 3-(4-chloro-benzyloxy)-2-hydroxy-benzaldehyde (110 mg, 0.42 mmol), potassium carbonate (150 mg, 1.1 mmol) in acetonitrile (8 mL) was added iodoethane (0.2 mL, 2.5 mmol) at room temperature. The mixture was stirred at 98° C. for 18 hours. The reaction mixture was poured into a solution of saturated ammonium chloride and was extracted with ethyl acetate. The organic layer was collected, washed with brine, and dried over magnesium sulfate. After removal of solvent, a light yellow solid was obtained (629, 116 mg, 95%).

Step 4—Preparation of [3-(4-chloro-benzyloxy)-2-ethoxy-phenyl]-(1H-pyrrolo[2,3-b]pyridin-3-yl)-methanol (630) and 3-{[3-(4-chloro-benzyloxy)-2-ethoxy-phenyl]-methoxymethyl}-1H-pyrrolo[2,3-b]pyridine (631)

A mixture of 1H-Pyrrolo[2,3-b]pyridine (94, 26 mg, 0.22 mmol), 3-(4-chloro-benzyloxy)-2-ethoxy-benzaldehyde (629, 54 mg, 0.19 mmol), and potassium hydroxide (30 mg, 0.4.6 mmol) in methanol (5 mL) was stirred at room temperature for 4 days. The reaction mixture was poured into water and extracted with ethyl acetate. The organic layer was collected, washed with brine, and dried over sodium sulfate. After removal of solvent, the residue was purified by silica gel column chromatography eluting with ethyl acetate in hexane to provide compound 630 as an off-white solid (20 mg, 26%, MS(ESI) [M+H+]+=409.32) and compound 631 as an off-white solid (44 mg, 56%, MS(ESI) [M+H+]+=423.31.

Step 5a—Preparation of [3-(4-chloro-benzyloxy)-2-ethoxy-phenyl]-(1H-pyrrolo[2,3-b]pyridin-3-yl)-methanone (P-1892)

To a solution of [3-(4-chloro-benzyloxy)-2-ethoxy-phenyl]-(1H-pyrrolo[2,3-b]pyridin-3-yl)-methanol (630, 20 mg, 0.05 mmol) in tetrahydrofuran (8 mL) was added Dess-Martin periodinane (52 mg, 0.12 mmol) at 0° C. The reaction mixture was stirred at 0° C. for 50 minutes. The reaction was quenched with a saturated solution of sodium thiosulfate, extracted with ethyl acetate, washed with sodium bicarbonate, brine, and dried over magnesium sulfate. After removal of solvent, the residue was washed with a mixture of ethyl ether and hexanes (1:1) to provide the compound as a yellow solid (P-1892, 15 mg, 75%). MS(ESI) [M+H$^+$]$^+$=407.38.

Step 5b—Preparation of 3-[3-(4-chloro-benzyloxy)-2-ethoxy-benzyl]-1H-pyrrolo[2,3-b]pyridine (P-1893)

A mixture of 3-{[3-(4-chloro-benzyloxy)-2-ethoxy-phenyl]-methoxy-methyl}-1H-pyrrolo[2,3-b]pyridine (631, 44 mg, 0.1 mmol), trifluoroacetic acid (1 mL, 13 mmol), and triethylsilane (2 mL, 12.5 mmol) in acetonitrile (10 mL) was refluxed for 4 hours. The mixture was concentrated and the residue was dissolved in ethyl acetate. The solution was washed with saturated sodium bicarbonate, brine, and dried over sodium sulfate. After removal of solvent, the residue was washed with a mixture of ethyl ether and hexanes (1:1) to provide the compound as a yellow solid (P-1893, 40 mg, 98%). MS(ESI) [M+H$^+$]$^+$=393.39.

[3-(4-Chloro-benzyloxy)-2-methoxy-phenyl]-(1H-pyrrolo[2,3-b]pyridin-3-yl)-methanone (P-1891), [3-(4-Chloro-benzyloxy)-2-(2,2,2-trifluoroethoxy)-phenyl]-(1H-pyrrolo[2,3-b]pyridin-3-yl)-methanone (P-2076), and [3-(4-chloro-2-fluoro-benzyloxy)-2-ethoxy-phenyl]-(5-methoxy-1H-pyrrolo[2,3-b]pyridin-3-yl)-methanone (P-2016)

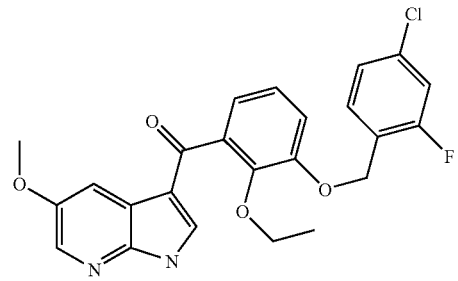

were prepared following the protocol of Scheme 71, substituting iodoethane with iodomethane in Step 3 to provide P-1891, or substituting iodoethane with 2-iodo-1,1,1-trifluoroethane in Step 3 to provide P-2076, or substituting 4-chlorobenzyl bromide 557 with 4-chloro-2-fluoro-benzyl bromide in Step 1 and 7-azaindole 94 with 5-methoxy-7-azaindole in Step 4 to provide P-2016. MS(ESI) [M+H$^+$]$^+$=393.4 (P-1891), 461.08 (P-2076), and 455.2 (P-2016).

Example 44

Synthesis of Propane-1-sulfonic acid {3-[5-(4-chloro-phenyl)-1H-pyrrolo[2,3-b]pyridine-3-carbonyl]-2,4-difluoro-phenyl}-amide P-0956

Compound P-0956 was synthesized in three steps from 5-(4-chlorophenyl)-1H-pyrrolo[2,3-b]pyridine 514 and propane-1-sulfonic acid (2,4-difluoro-3-formyl-phenyl)-amide 73 as shown in Scheme 72.

Scheme 72

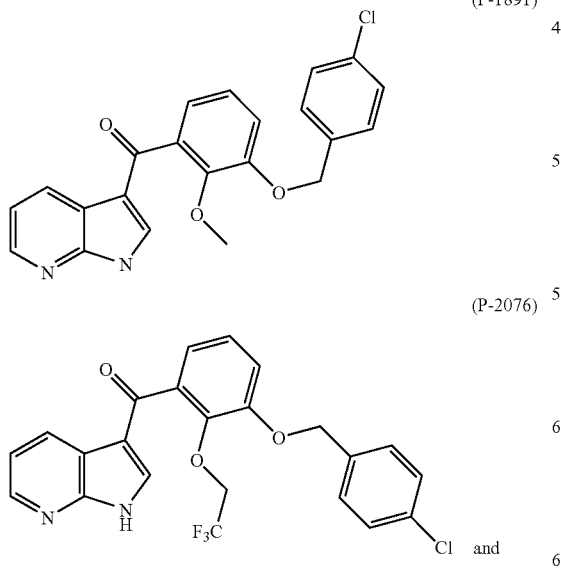

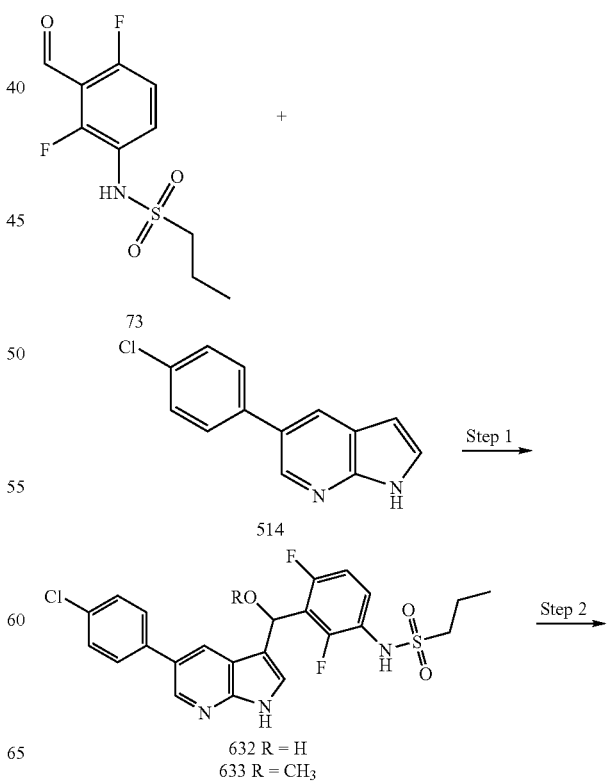

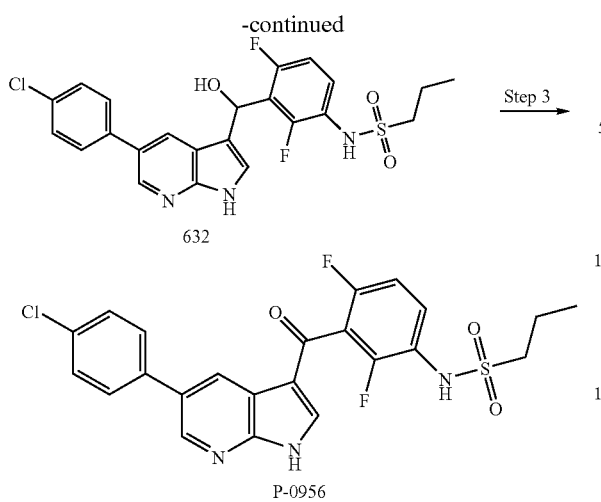

Step 1-Preparation of Propane-1-sulfonic acid (3-{[5-(4-chloro-phenyl)-1H-pyrrolo[2,3-b]pyridin-3-yl]-hydroxy-methyl}-2,4-difluoro-phenyl)-amide (632) and Propane-1-sulfonic acid (3-{[5-(4-chloro-phenyl)-1H-pyrrolo[2,3-b]pyridin-3-yl]-methoxy-methyl}-2,4-difluoro-phenyl)-amide (633)

To a suspension of 5-(4-chloro-phenyl)-1H-pyrrolo[2,3-b]pyridine (514, 64.9 g, 158 nM, prepared as described in Example 17) and propane-1-sulfonic acid (2,4-difluoro-3-formyl-phenyl)-amide (73, 90.4 g, 191 mM, prepared as described in Example 7) in methanol in a water bath was added potassium hydroxide (128.8 g, 1.28 M). The reaction was stirred 72 hours at room temperature and then adjusted to pH 7 with 4N hydrochloric acid. The resulting mixture was evaporated in vacua to remove methanol and extracted 3× with ethyl acetate. The combined organic layers were dried over sodium sulfate and evaporated in vacua to give a crude oil. The crude oil was triturated with 3:1 MTBE/heptane to give a 1:3 solid mixture of 632 and 633 that was used directly for the next step.

Step 2—Preparation of Propane-1-sulfuric acid (3-{[5-(4-chloro-phenyl)-1H-pyrrolo[2,3-b]pyridin-3-yl]-hydroxy-methyl}-2,4-difluoro-phenyl)-amide (632)

To a solution of 632 and 633 (ca. 315 mM) in acetic acid was added 48% hydrobromic acid (final 8%). The resulting mixture was stirred overnight at room temperature and then evaporated in vacuo. The crude residue was taken up with equal volumes of ethyl acetate and water, and adjusted to pH 7 with solid potassium carbonate. The layers were split and the aqueous layer was extracted 2× with ethyl acetate. The combined organic layers were dried over sodium sulfate and evaporated in vacuo to give 632 as a viscous oil that was used directly for the next step.

Step 3—Preparation of Propane-1-sulfonic acid {3-[5-(4-chloro-phenyl)-1H-pyrrolo[2,3-b]pyridine-3-carbonyl]-2,4-difluoro-phenyl}-amide (P-0956)

To a solution of 632 (ca. 386 mM) in 1,4-dioxane was added 2,3-dichloro-5,6-dicyanobenzoquinone (83.8 g, 502 mM) followed by water (final 4.8%). The resulting mixture was stirred 2 hours at room temperature and then quenched with one volume of saturated sodium bicarbonate. The mixture was evaporated in vacuo to remove 1,4-dioxane and extracted 3× with ethyl acetate. The combined organic layers were dried over sodium sulfate and evaporated in vacuo to give a crude solid that was purified on a silica-gel column with 94:5:1 dichloromethane/methanol/ammonium hydroxide as eluent to give P-0956 (approximately 50% yield for 3 steps) as a white solid.

Example 45

Synthesis of 3-Iodo-1-triisopropylsilanyl-1H-pyrrolo[2,3-b]pyridine 635

3-Iodo-1-triisopropylsilanyl-1H-pyrrolo[2,3-b]pyridine 635 was synthesized in one step from 3-Iodo-1H-pyrrolo[2,3-b]pyridine 634 as shown in Scheme 73.

Scheme 73

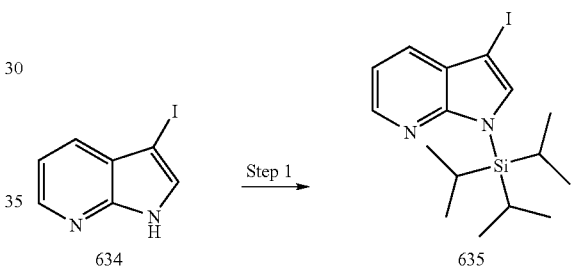

Step 1—Preparation of 3-Iodo-1-triisopropylsilanyl-1H-pyrrolo[2,3-b]pyridine (635)

3-Iodo-1H-pyrrolo[2,3-b]pyridine 634 (2.00 g, 8.20 mmol) was dissolved in N,N-dimethylformamide (50 mL). Sodium hydride (60% dispersion in mineral oil, 390 mg, 9.8 mmol) was added. After 20 minutes, triisopropylsilyl chloride (1.74 mL, 8.20 mmol) was added dropwise. After 1.5 hours, the reaction was poured into water and extracted with ethyl acetate, washed with saturated sodium bicarbonate and brine. The organic portions were dried over anhydrous sodium sulfate and concentrated. Purification by silica gel chromatography, 0-25% gradient ethyl acetate; hexane gave compound 635 as a white solid (3.224 g, 98.2%). $^1$H-NMR was consistent with the desired compound.

Example 46

Synthesis of 1-(tert-Butyl-dimethyl-silanyl)-3-iodo-1H-pyrrolo[2,3-b]pyridine 636

1-(tert-Butyl-dimethyl-silanyl)-3-iodo-1H-pyrrolo[2,3-b]pyridine 636 was synthesized in one step from 3-Iodo-1H-pyrrolo[2,3-b]pyridine 634 as shown in Scheme 74.

Scheme 74

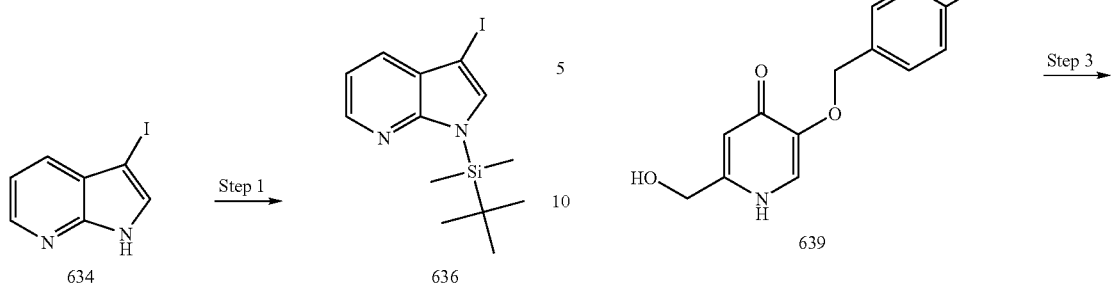

Step 1—Preparation of 1-(tert-Butyl-dimethyl-silanyl)-3-iodo-1H-pyrrolo[2,3-b]pyridine (636)

3-Iodo-1H-pyrrolo[2,3-b]pyridine 634 (1.11 g, 4.6 mmol) was dissolved in tetrahydrofuran (120 mL). Sodium hydride (60% dispersion in mineral oil, 0.13 g, 5.5 mmol) was added, followed by tert-butyldimethylsilyl chloride (0.85 g, 5.5 mmol). The reaction was stirred at room temperature overnight. The reaction was poured into water and extracted with ethyl acetate. The organic portion was washed with brine, dried over anhydrous sodium sulfate and filtered. The filtrate was concentrated and purified with silica gel column chromatography eluting with 30% ethyl acetate in hexane to give the compound as a white solid (636, 100 mg, 15%).

Example 47

Synthesis of [5-(4-chloro-benzyloxy)-4-methoxy-pyridin-2-yl]-(1H-pyrrolo[2,3-b]pyridin-3-yl)-methanone P-2024

[5-(4-Chloro-benzyloxy)-4-methoxy-pyridin-2-yl]-(1H-pyrrolo[2,3-b]pyridin-3-yl)-methanone P-2024 was synthesized in six steps from Kojic acid, 3, and 3-iodo-1-triisopropylsilanyl-1H-pyrrolo[2,3-b]pyridine, 2, as shown in Scheme 75.

Scheme 75

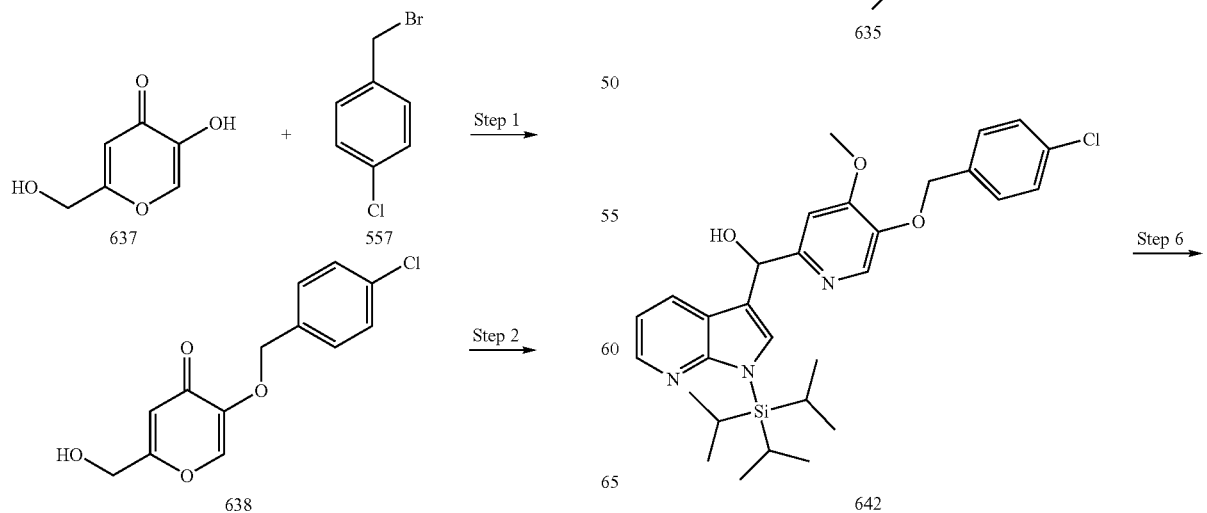

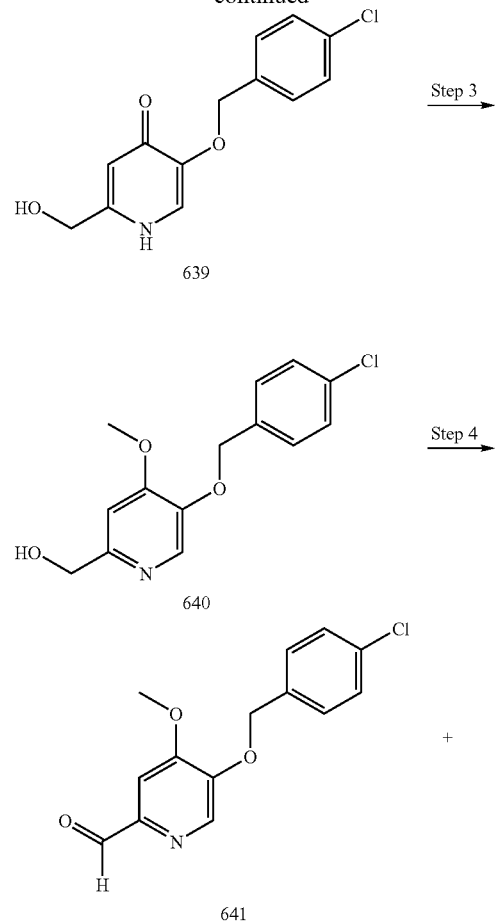

-continued

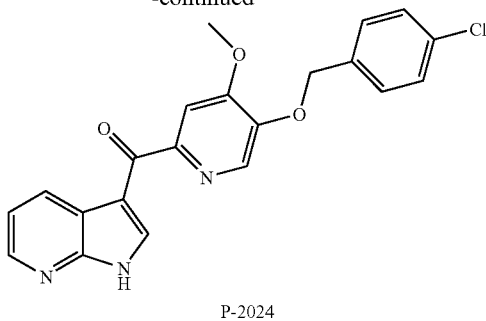

P-2024

Step 1—Preparation of 5-(4-chloro-benzyloxy)-2-hydroxymethyl-pyran-4-one (638)

Kojic acid (637, 5.00 g, 35.2 mmol) and 4-chlorobenzyl bromide (557, 7.95 g, 38.7 mmol) were suspended in methanol (40 mL) in an 80 mL sealed tube. Sodium hydroxide in water (12 M, 2.93 mL) was added. The reaction was heated at 80° C. overnight. The resulting suspension was concentrated. Water was added and the mixture was filtered and washed with water to provide a brown solid. Washing with minimal methanol on the filter removed the brown color. A white solid (638, 7.58 g, 80%) was isolated. $^1$H-NMR was consistent with the desired compound.

Step 2—Preparation of 5-(4-chloro-benzyloxy)-2-hydroxymethyl-1H-pyridin-4-one (639)

5-(4-Chloro-benzyloxy)-2-hydroxymethyl-pyran-4-one (638, 8.00 g, 3.00 mmol) was suspended in ammonium hydroxide (200 mL) in an 80 mL sealed tube. The reaction was heated at 90° C. overnight. Upon cooling, the reaction was lowered to pH 10 with 6N HCl to provide a beige solid that was collected by filtration (639, 7.8 g, 98%).

Step 3—Preparation of [5-(4-chloro-benzyloxy)-4-methoxy-pyridin-2-yl]-methanol (640)

5-(4-Chloro-benzyloxy)-2-hydroxymethyl-1H-pyridin-4-one (639, 1.06 g, 3.99 mmol) was dissolved in methanol (8.5 mL) and N,N-dimethylformamide (46 mL). Trimethylsilyldiazomethane in hexane (2.00 M, 3.99 mL) was added. The reaction was stirred at room temperature overnight, then additional trimethylsilyldiazomethane in hexane (2.00 M, 3.99 mL) was added. The reaction was stirred at room temperature for 2 days. The mixture was adsorbed onto silica and purified by silica gel chromatography, methanol:dichloromethane to provide the compound (640, 798 mg, 72%). MS(ESI) [M+H$^+$]$^+$=280.4, 282.4.

Step 4—Preparation of 5-(4-chloro-benzyloxy)-4-methoxy-pyridine-2-carbaldehyde (641)

[5-(4-Chloro-benzyloxy)-4-methoxy-pyridin-2-yl]-methanol (640, 480 mg, 1.7 mmol) was dissolved in dimethyl sulfoxide (26 mL) and Dess-Martin periodinane (909 mg, 2.1 mmol) was added. The reaction was allowed to stir at room temperature for 2 hours. The reaction was concentrated under high vacuum and then poured into a solution of NaHCO$_3$ and Na$_2$S$_2$O$_3$. The mixture was extracted with ethyl acetate. The organic portions were dried with anhydrous sodium sulfate and filtered. The filtrate was adsorbed onto silica and purified by silica gel chromatography, ethyl acetate:hexanes, to provide the desired compound as a white powder (641, 343 mg, 72%).

Step 5—Preparation of [5-(4-chloro-benzyloxy)-4-methoxy-pyridin-2-yl]-(1-triisopropylsilanyl-1H-pyrrolo[2,3-b]pyridin-3-yl)-methanol (642)

3-Iodo-1-triisopropylsilanyl-1H-pyrrolo[2,3-b]pyridine (635, 180 mg, 0.450 mmol) was dissolved in tetrahydrofuran (2.5 mL) and the reaction was cooled to −20° C. under an atmosphere of nitrogen. Isopropylmagnesium chloride in tetrahydrofuran (2.00 M, 0.243 mL) was added. The reaction was stirred for 1 hour, during which the temperature rose to 0° C. The reaction was cooled to −20° C. and 5-(4-chloro-benzyloxy)-4-methoxy-pyridine-2-carbaldehyde (641, 80.0 mg, 0.288 mmol) in tetrahydrofuran (0.75 mL) was added. The reaction was allowed to warm to room temperature and stirred overnight. The reaction was quenched with methanol and adsorbed onto silica, then purified by silica gel chromatography, methanol: dichloromethane, to provide the desired product, (642, 94 mg, 59%). $^1$H-NMR was consistent with the desired compound. MS(ESI) [M+H$^+$]$^+$=552.4, 554.4, 555.4.

Step 6—Preparation of [5-(4-chloro-benzyloxy)-4-methoxy-pyridin-2-yl]-(1H-pyrrolo[2,3-b]pyridin-3-yl)-methanone (P-2024)

[5-(4-Chloro-benzyloxy)-4-methoxy-pyridin-2-yl]-(1-triisopropylsilanyl-1H-pyrrolo[2,3-b]pyridin-3-yl)-methanol (642, 60.0 mg, 0.11 mmol) was dissolved in tetrahydrofuran (2.00 mL). Dess-Martin periodinane (55.3 mg, 0.13 mmol) was added to the reaction and it was stirred at room temperature overnight. The mixture was extracted with ethyl acetate and saturated sodium bicarbonate. The organic portions were dried with anhydrous sodium sulfate, filtered and the filtrate was adsorbed onto silica and purified by silica gel chromatography, methano:dichloromethane, to provide the desired compound (P-2024, 10.7 mg, 25%). $^1$H-NMR was consistent with the desired compound. MS(ESI) [M+H$^+$]$^+$=394.1, 396.1.

Example 48

Synthesis of 3-4-[1-(4-chloro-phenyl)-ethoxy]-3-methoxy-benzyl-1H-pyrrolo[2,3-b]pyridine P-2000

3-4-[1-(4-Chloro-phenyl)-ethoxy]-3-methoxy-benzyl-1H-pyrrolo[2,3-b]pyridine P-2000 was synthesized in three steps from vanillin 105, 4-chlorophenylmethylcarbinol 643, and 1-(tert-butyl-dimethyl-silanyl)-3-iodo-1H-pyrrolo[2,3-b]pyridine 636, as shown in Scheme 76.

Scheme 76

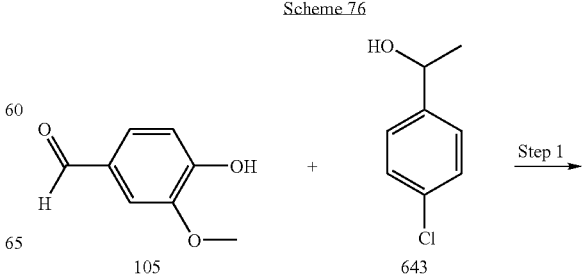

105      643

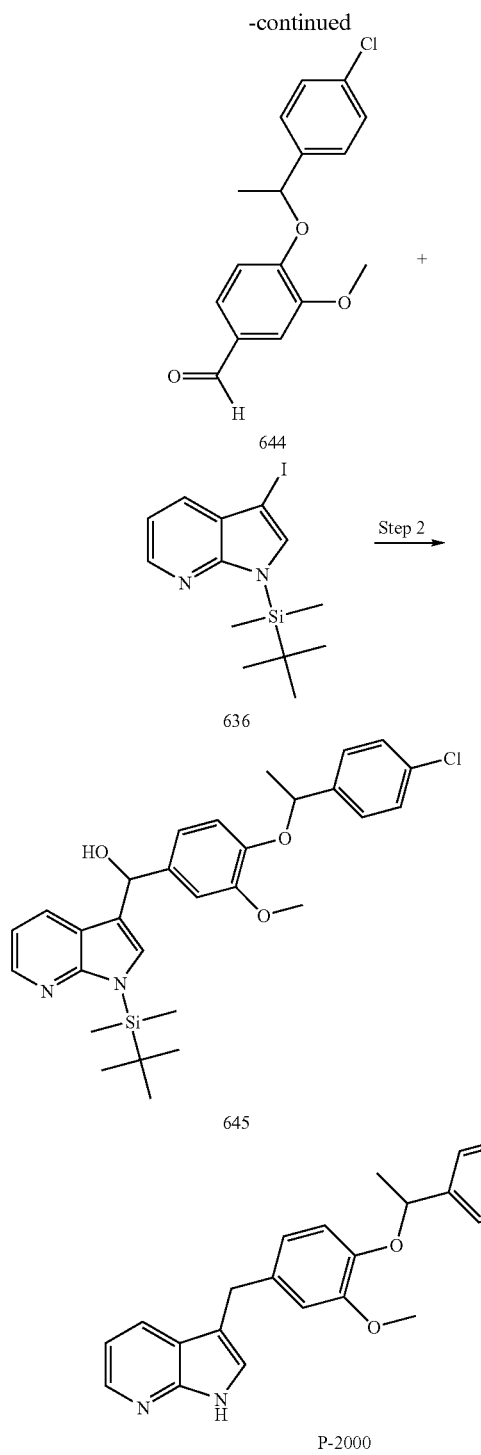

was adsorbed onto silica and purified by silica gel chromatography, ethyl acetate:hexanes, to provide the desired compound, (644, 1.14 g, 60%). ¹H-NMR was consistent with the desired compound.

Step 2—Preparation of [1-(tert-Butyl-dimethyl-silanyl)-1H-pyrrolo[2,3-b]pyridin-3-yl]-4-[1-(4-chloro-phenyl)-ethoxy]-3-methoxy-phenyl-methanol (645)

1-(tert-Butyl-dimethyl-silanyl)-3-iodo-1H-pyrrolo[2,3-b]pyridine (636, 647.0 mg, 1.81 mmol) was dissolved in tetrahydrofuran (10.0 mL) at −20° C. under an atmosphere of nitrogen. Isopropylmagnesium chloride in tetrahydrofuran (2.0 M, 0.98 mL) was added to the reaction. The reaction was stirred for 1 hour, during which the temperature rose to 0° C. The reaction was cooled to −20° C. and 4-[1-(4-chloro-phenyl)-ethoxy]-3-methoxy-benzaldehyde (644, 420 mg, 1.4 mmol) in tetrahydrofuran (3.00 mL) was added. The reaction was stirred for 2 hours during which time the temperature rose to 10° C. The reaction was quenched with methanol and adsorbed onto silica, then purified by silica gel chromatography, ethyl acetate:hexanes, to provide the desired compound, (645, 463 mg, 61%). ¹H-NMR was consistent with the desired compound.

Step 2—Preparation of 3-4-[1-(4-chloro-phenyl)-ethoxy]-3-methoxy-benzyl-1H-pyrrolo[2,3-b]pyridine (P-2000)

[1-(tert-Butyl-dimethyl-silanyl)-1H -pyrrolo[2,3-b]pyridin-3-yl]-4-[1-(4-chloro-phenyl)-ethoxy]-3-methoxy-phenyl-methanol (645, 0.200 g, 0.382 mmol) was dissolved in acetonitrile (5.00 mL). Trifluoroacetic acid (0.138 mL) was added and the reaction was stirred for five minutes. Triethylsilane (0.285 mL) was added and the reaction was heated at 80° C. for 2 hours. The reaction was concentrated, then redissolved in ethyl acetate and adsorbed onto silica and purified by silica gel chromatography, ethyl acetate:hexanes, to provide the desired compound (P-2000, 57 mg, 38%). ¹H-NMR was consistent with the desired compound. MS(ESI): [M+H⁺]⁺=393.3, 395.3.

Example 49

Synthesis of 5-[4-(2-methoxyethoxy)-phenyl]-1H-pyrrolo[2,3-b]pyridine 648

5-[4-(2-Methoxyethoxy)-phenyl]-1H-pyrrolo[2,3-b]pyridine 648 was synthesized in two steps from 4-bromophenol 646 as shown in Scheme 77.

Scheme 77

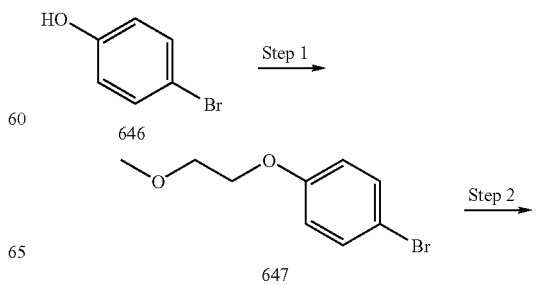

Step 1—Preparation of 4-[1-(4-chloro-phenyl)-ethoxy]-3-methoxy-benzaldehyde (644)

4-Chlorophenylmethylcarbinol (643, 0.668 mL, 6.57 mmol) was dissolved in tetrahydrofuran (60.0 mL) at 0° C. under an atmosphere of nitrogen. 4-Hydroxy-3-methoxybenzaldehyde (105, 1.00 g, 6.57 mmol) and triphenylphosphine (2.07 g, 7.89 mmol) were added to the reaction, followed by diisopropyl azodicarboxylate (1.55 mL, 7.89 mmol) over 10 minutes. The reaction was stirred for 2 hours. The mixture

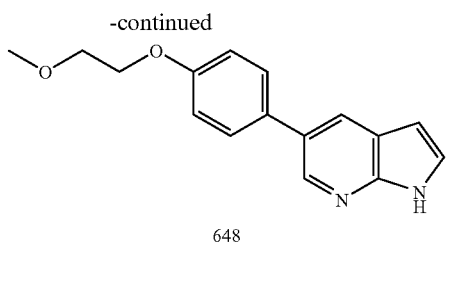

648

Step 1—Preparation 1-Bromo-4-(2-methoxy-ethoxy)-benzene (647)

To a solution of 4-bromophenol (646, 5.0 g, 28.9 mmol) in dimethylformamide (15 mL) were added potassium carbonate (4.40 g, 31.8 mmol) and 1-bromo-2-methoxyethane (5.00 g, 36.0 mmol) under an atmosphere of nitrogen. The reaction mixture was stirred at ambient temperature overnight and concentrated under reduced pressure. The residue was slurried in ethyl acetate (50 mL) and filtered. The filtrate was washed with saturated sodium bicarbonate solution, dried over magnesium sulfate and filtered. Silica gel column chromatography (0-10% ethyl acetate in hexanes) gave the desired compound as a colorless oil (647, 3.2 g, 48%).

Step 2—Preparation of 5-[4-(2-Methoxy-ethoxy)-phenyl]-1H-pyrrolo[2,3-b]pyridine (648)

To a solution of 5-(4,4,5,5-tetramethyl-[1,3,2]dioxaborolan-2-yl)-1H-pyrrolo[2,3-b]pyridine (1.1 g, 4.3 mmol) in tetrahydrofuran (40 mL) was added 1-bromo-4-(2-methoxyethoxy)-benzene (647, 1.50 g, 6.49 mmol) and tetrakis(triphenylphosphine)palladium (0) (0.25 g, 0.21 mmol). The reaction mixture was stirred with potassium carbonate solution (10 mL, 1.0 M) and warmed to reflux overnight. The biphasic reaction mixture was diluted with ethyl acetate (50 mL) and saturated sodium carbonate solution (20 mL). The organic layer was separated, washed with brine, dried over magnesium sulfate and purified by silica gel column chromatography (50-100% ethyl acetate in hexanes) to give the desired compound as a colorless solid (648, 782 mg, 67%). MS (ESI) [M+H$^+$]$^+$=267.4.

Example 50

Synthesis of 3-[2-fluoro-5-methoxy-4-(pyridin-4-ylmethoxy)-benzyl]-1H-pyrrolo[2,3-b]pyridine P-2040 and related compounds Compound P-2040 was synthesized in one step from 5-fluoro-2-methoxy-4-(1-triisopropylsilanyl-1H-pyrrolo[2,3-b]pyridin-3-ylmethyl)-phenol 649 and pyridin-4-yl-methanol 650 as shown in Scheme 78.

Scheme 78

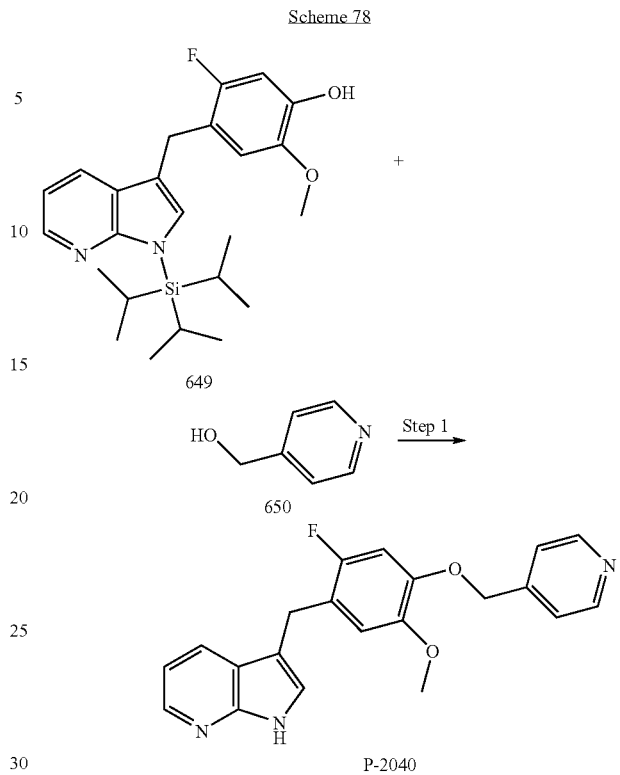

Step 1—Preparation of 3-[2-fluoro-5-methoxy-4-(pyridin-4-ylmethoxy)-benzyl]-1H-pyrrolo[2,3-b]pyridine (P-2040)

5-Fluoro-2-methoxy-4-(1-triisopropylsilanyl-1H-pyrrolo[2,3-b]pyridine-3-ylmethyl)-phenol (649, 10 mg, 0.024 mmol, prepared as described in Example 52) was combined with pyridin-4-yl-methanol (650, 3.2 mg, 0.029 mmol) in a 4 mL vial and dissolved in dry tetrahydrofuran (200 μl). Triphenylphosphine (7.7 mg) was added and the solution was shaken until homogenous. The mixture was cooled to below 0° C. in a liquid nitrogen bath and diisopropyl azodicarboxylate solution (50 μl of 20 mg/50 μl in THF) was added. The reaction mixture was allowed to warm to room temperature. After 2 hours, the solvent was removed under reduced atmosphere. The crude material was dissolved in dimethyl sulfoxide (300 μl) and potassium fluoride (10 mg, 0.18 mmol) was added. The mixture was heated gently and allowed to react overnight at room temperature. The vial was centrifuged and the DMSO solution was purified by reverse phase HPLC using a YMC-Pack ODS-A C-18 column (50 mm×10 mm ID), and eluting with water with 0.1% TFA and a gradient of 15%-80% acetonitrile with 0.1% TFA over 8 minutes and a flow rate of 6 mL/minute to provide the compound (P-2040, 4.4 mg, 50%). MS (ESI) [M+H$^+$]$^+$=364.3.

Additional compounds were prepared following the protocol of Scheme 78, replacing pyridin-4-yl-methanol 650 with an appropriate alcohol. The following compounds were made following this procedure:

3-[2-Fluoro-5-methoxy-4-(2-morpholin-4-yl-ethoxy)-benzyl]-1H-pyrrolo[2,3-b]pyridine (P-2037),
3-[2-Fluoro-5-methoxy-4-(pyridin-3-ylmethoxy)-benzyl]-1H-pyrrolo[2,3-b]pyridine (P-2038), 3-[2-Fluoro-5-methoxy-4-(6-methyl-pyridin-2-yl-methoxy)-benzyl]-1H-pyrrolo[2,3-b]pyridine (P-2039), 3-[2-Fluoro-5-methoxy-4-(pyridin-2-ylmethoxy)-benzyl]-1H-pyrrolo[2,3-b]pyridine (P-2041), 3-[2-Fluoro-4-(2-fluoro-4-trifluoromethyl-benzyloxy)-5-methoxy-benzyl]-1H-pyrrolo[2,3-b]pyridine (P-2042), 3-[4-(4-Chloro-2-fluoro-benzyloxy)-2-fluoro-5-methoxy-benzyl]-1H-pyrrolo[2,3-b]pyridine (P-1973), 3-[4-(2,4-Dimethyl-thiazol-5-ylmethoxy)-2-fluoro-5-methoxy-benzyl]-1H-pyrrolo[2,3-b]pyridine (P-2043), 3-[4-(2,5-Dimethyl-2H-pyrazol-3-ylmethoxy)-2-fluoro-5-methoxy-benzyl]-1H-pyrrolo[2,3-b]pyridine (P-2044), 3-[2-Fluoro-5-methoxy-4-(3-morpholin-4-yl-propoxy)-benzyl]-1H-pyrrolo[2,3-b]pyridine (P-2045), 1-{2-[5-Fluoro-2-methoxy-4-(1H-pyrrolo[2,3-b]pyridin-3-ylmethyl)-phenoxy]-ethyl}-pyrrolidin-2-one (P-2046), 3-[2-Fluoro-4-(2-fluoro-benzyloxy)-5-methoxy-benzyl]-1H-pyrrolo[2,3-b]pyridine (P-2047), 3-[2-Fluoro-5-methoxy-4-(3-methyl-pyridin-4-yl-methoxy)-benzyl]-1H-pyrrolo[2,3-b]pyridine (P-2048), 3-[2-Fluoro-5-methoxy-4-(6-trifluoromethyl-pyridin-3-ylmethoxy)-benzyl]-1H-pyrrolo[2,3-b]pyridine (P-2049), 3-[4-(2,4-Dichloro-benzyloxy)-2-fluoro-5-methoxy-benzyl]-1H-pyrrolo[2,3-b]pyridine (P-2050), 3-[2-Fluoro-4-(4-imidazol-1-yl-benzyloxy)-5-methoxy-benzyl]-1H-pyrrolo[2,3-b]pyridine (P-2051), 3-[4-(2,4-Difluoro-benzyloxy)-2-fluoro-5-methoxy-benzyl]-1H-pyrrolo[2,3-b]pyridine (P-2052), 3-{2-Fluoro-4-[1-(2-fluoro-phenyl)-ethoxy]-5-methoxy-benzyl}-1H-pyrrolo[2,3-b]pyridine (P-2053), 3-[4-(3-Cyclopentyl-propoxy)-2-fluoro-5-methoxy-benzyl]-1H-pyrrolo[2,3-b]pyridine (P-2054), 3-[4-(1,5-Dimethyl-1H-pyrazol-3-ylmethoxy)-2-fluoro-5-methoxy-benzyl]-1H-pyrrolo[2,3-b]pyridine (P-2055), and 3-[4-(2-Cyclopentyl-ethoxy)-2-fluoro-5-methoxy-benzyl]-1H-pyrrolo[2,3-b]pyridine (P-2056)

The following table indicates the alcohol (column 2) used in Scheme 78 to provide the compounds (column 4) Column 1 provides the compound number and column 4 the observed mass.

| Alcohol | Compound | MS(ESI) [M + H$^+$]$^+$ observed |
|---|---|---|
| P-2037 | | 386.3 |
| P-2038 | | 364.3 |
| P-2039 | | 378.3 |

-continued

| | Alcohol | Compound | MS(ESI) [M + H+]+ observed |
|---|---|---|---|
| P-2041 | | | 364.3 |
| P-2042 | | | 448.7 |
| P-1973 | | | 415.1 |
| P-2043 | | | 397.9 |
| P-2044 | | | 381.1 |
| P-2045 | | | 400.3 |

| | Alcohol | Compound | MS(ESI) [M + H+]+ observed |
|---|---|---|---|
| P-2046 |  | 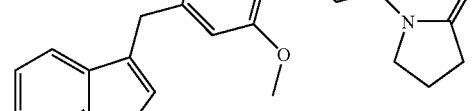 | 384.3 |
| P-2047 | 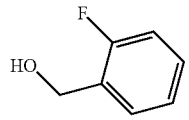 | 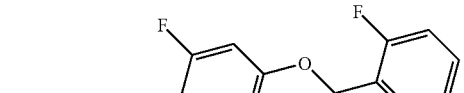 | 381.1 |
| P-2048 | 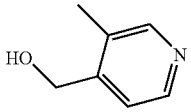 | 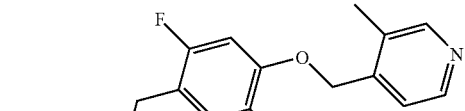 | 378.3 |
| P-2049 | 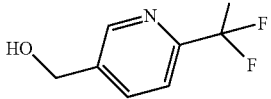 | 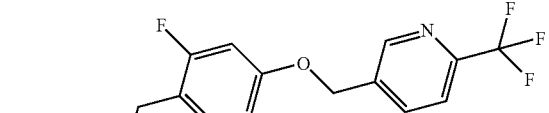 | 432.3 |
| P-2050 | 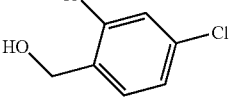 | 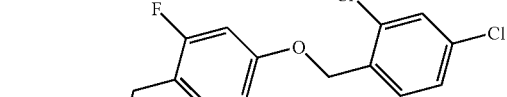 | 431.1 |
| P-2051 | 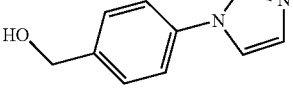 | 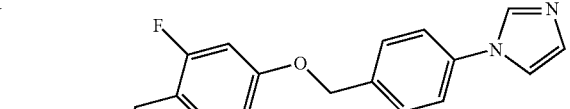 | 429.1 |

-continued

| | Alcohol | Compound | MS(ESI) [M + H⁺]⁺ observed |
|---|---|---|---|
| P-2052 | 2,4-difluorobenzyl alcohol | | 399.1 |
| P-2053 | 1-(2-fluorophenyl)ethanol | | 395.1 |
| P-2054 | 3-cyclopentylpropan-1-ol | | 383.1 |
| P-2055 | (1,5-dimethyl-1H-pyrazol-3-yl)methanol | | 381.1 |
| P-2056 | 2-cyclopentylethanol | | 369.1 |

Example 51

Synthesis of [2,6-difluoro-3-(pyridin-3-ylmethoxy)-phenyl]-(1H-pyrrolo[2,3-b]pyridin-3-yl)-methanone P-2058 and related compounds Compound P-2058 was synthesized in 1 step from (2,6-Difluoro-3-hydroxy-phenyl)-(1H-pyrrolo[2,3-b]pyridin-3-yl)-methanone 651 and Pyridin-3-yl-methanol 652 as shown in Scheme 79.

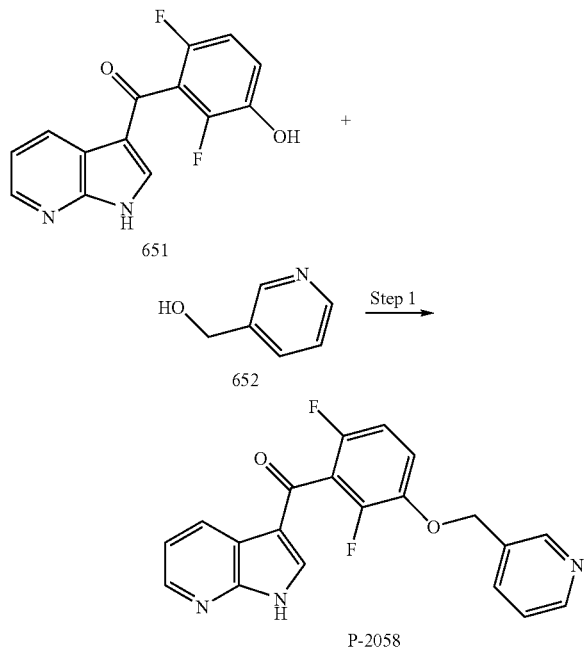

Scheme 79

Step 1—Preparation of [2,6-Difluoro-3-(pyridin-3-ylmethoxy)-phenyl]-(1H-pyrrolo[2,3-b]pyridin-3-yl)-methanone (P-2058)

In a 4 mL vial, (2,6-Difluoro-3-hydroxy-phenyl)-(1H-pyrrolo[2,3-b]pyridine-3-yl)-methanone (651, 10 mg, 0.037 mmol, prepared as described in Example 23) was combined with pyridin-3-yl-methanol (652, 4.9 mg 0.044 mmol). The solids were dissolved in dry tetrahydrofuran (200 µl) and triphenylphosphine (11.5 mg, 0.044 mmol) was added. Once the solution was homogenous, the mixture was cooled to below 0° C. in liquid nitrogen bath and diisopropyl azodicarboxylate solution (50 µl of 20 mg/50 µl THF) was added. The reaction mixture was allowed to warm to room temperature and the reaction was continued for 2 hours. The solvents were removed under reduced atmosphere. The resultant residue was diluted with 200 µl DMSO and the mixture purified by reverse phase HPLC using a YMC-Pack ODS-A C-18 column (50 mm×10 mm ID), and eluting with water with 0.1% TFA and a gradient of 15%-80% acetonitrile with 0.1% TFA over 8 minutes and a flow rate of 6 mL/minute to provide P-2058 (5.9 mg, 44%). MS (ESI) [M+H$^+$]$^+$=365.9.

Additional compounds were prepared following the protocol of Scheme 79, replacing pyridin-3-yl-methanol 652 with an appropriate alcohol. The following compounds were made following this procedure:

[2,6-Difluoro-3-(1-methyl-1H-imidazol-2-ylmethoxy)-phenyl]-(1H-pyrrolo[2,3-b]pyridin-3-yl)-methanone (P-2033),

[2,6-Difluoro-3-(6-morpholin-4-yl-pyridin-3-ylmethoxy)-phenyl]-(1H-pyrrolo[2,3-b]pyridin-3-yl)-methanone (P-2034), {2,6-Difluoro-3-[4-(5-methyl-[1,2,4]oxadiazol-3-yl)-benzyloxy]-phenyl}-(1H-pyrrolo[2,3-b]pyridin-3-yl)-methanone (P-2035),

[3-(6-Diethylamino-pyridin-3-ylmethoxy)-2,6-difluoro-phenyl]-(1H-pyrrolo[2,3-b]pyridin-3-yl)-methanone (P-2036),

[3-(2-Chloro-4-fluoro-benzyloxy)-2,6-difluoro-phenyl]-(1H-pyrrolo[2,3-b]pyridin-3-yl)-methanone (P-2057),

[2,6-Difluoro-3-(6-methyl-pyridin-2-ylmethoxy)-phenyl]-(1H-pyrrolo[2,3-b]pyridin-3-yl)-methanone (P-2059),

[2,6-Difluoro-3-(pyridin-4-ylmethoxy)-phenyl]-(1H-pyrrolo[2,3-b]pyridin-3-yl)-methanone (P-2060),

[3-(4-Chloro-2-fluoro-benzyloxy)-2,6-difluoro-phenyl]-(1H-pyrrolo[2,3-b]pyridin-3-yl)-methanone (P-2061),

[3-(2,4-Dimethyl-thiazol-5-ylmethoxy)-2,6-difluoro-phenyl]-(1H-pyrrolo[2,3-b]pyridin-3-yl)-methanone (P-2062),

[3-(2,5-Dimethyl-2H-pyrazol-3-ylmethoxy)-2,6-difluoro-phenyl]-(1H-pyrrolo[2,3-b]pyridin-3-yl)-methanone (P-2063), and

[2,6-Difluoro-3-(3-morpholin-4-yl-propoxy)-phenyl]-(1H-pyrrolo[2,3-b]pyridin-3-yl)-methanone (P-2064).

The following table indicates the alcohol (column 2) used to afford the compound (column 3). Column 1 provides the compound number and column 4 the observed mass.

| Alcohol | Compound | MS(ESI) [M + H+]+ observed |
|---|---|---|
| P-2034 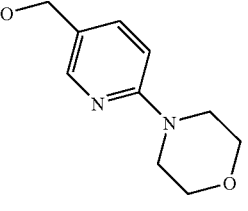 | 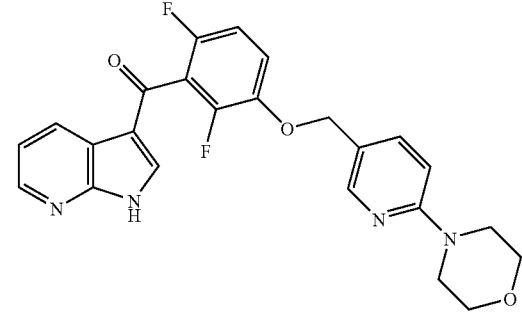 [SMILES: O=C(c1c(F)ccc(OCc2ccc(N3CCOCC3)nc2)c1F)c1c[nH]c2ncccc12] | 451.1 |
| P-2035 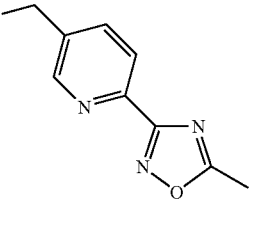 | 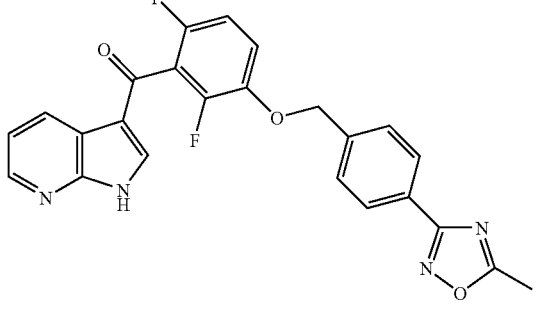 | 447.1 |
| P-2036 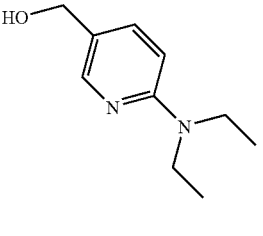 | 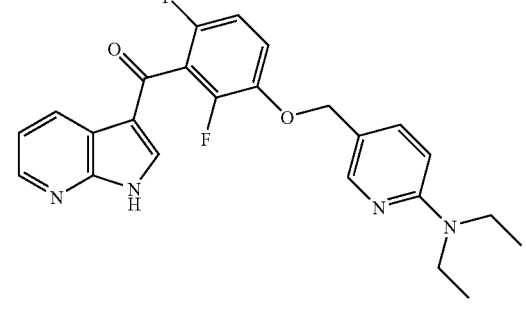 | 437.1 |
| P-2057 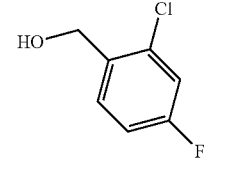 | 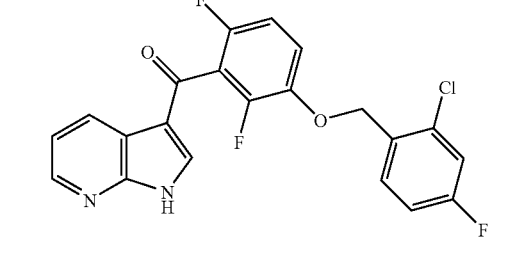 | 417.1 |
| P-2059 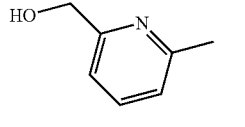 | 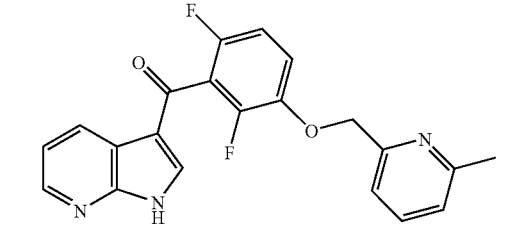 [SMILES: Cc1cccc(COc2ccc(F)c(C(=O)c3c[nH]c4ncccc34)c2F)n1] | 380.3 |

-continued
| | Alcohol | Compound | MS(ESI) [M + H⁺]⁺ observed |
|---|---|---|---|
| P2060 | 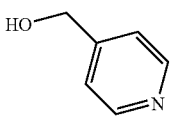 | 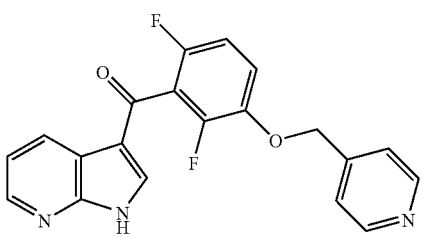 [SMILES: O=C(c1c(F)ccc(OCc2ccncc2)c1F)c1c[nH]c2ncccc12] | 365.9 |
| P-2061 | 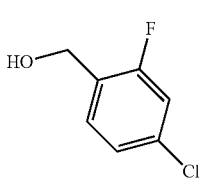 | 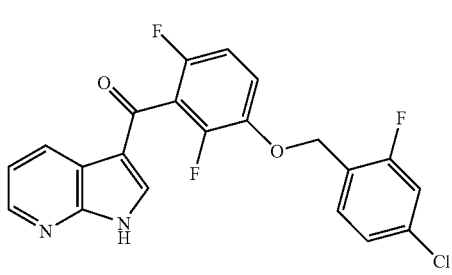 [SMILES: O=C(c1c(F)ccc(OCc2ccc(Cl)cc2F)c1F)c1c[nH]c2ncccc12] | 417.1 |
| P-2062 | 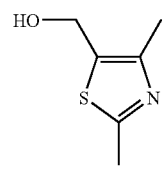 | 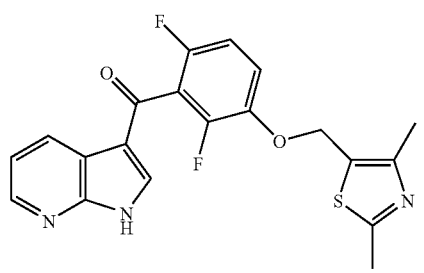 [SMILES: Cc1nc(C)c(COc2ccc(F)c(C(=O)c3c[nH]c4ncccc34)c2F)s1] | 399.9 |
| P-2063 | 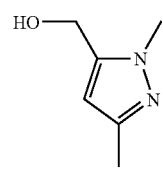 | 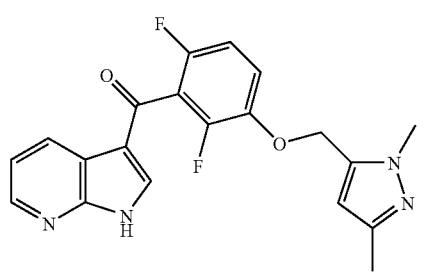 [SMILES: Cc1cc(COc2ccc(F)c(C(=O)c3c[nH]c4ncccc34)c2F)n(C)n1] | 383.1 |
| P-2064 | 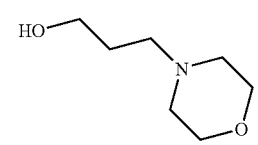 | 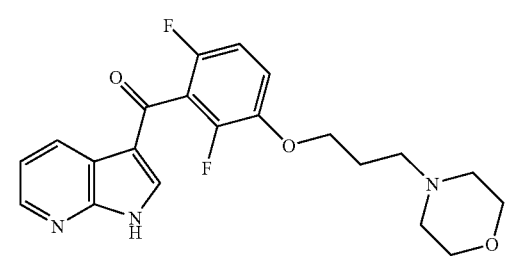 [SMILES: O=C(c1c(F)ccc(OCCCN2CCOCC2)c1F)c1c[nH]c2ncccc12] | 402.3 |

Example 52

Synthesis of 5-fluoro-2-methoxy-4-(1-triisopropylsilanyl-1H-pyrrolo[2,3-b]pyridin-3-ylmethyl)-phenol 649

5-Fluoro-2-methoxy-4-(1-triisopropylsilanyl-1H-pyrrolo[2,3-b]pyridin-3-ylmethyl)-phenol 649 was synthesized in five steps from 2-fluoro-4-hydroxy-5-methoxy-benzaldehyde 653 and benzyl bromide as shown in Scheme 80.

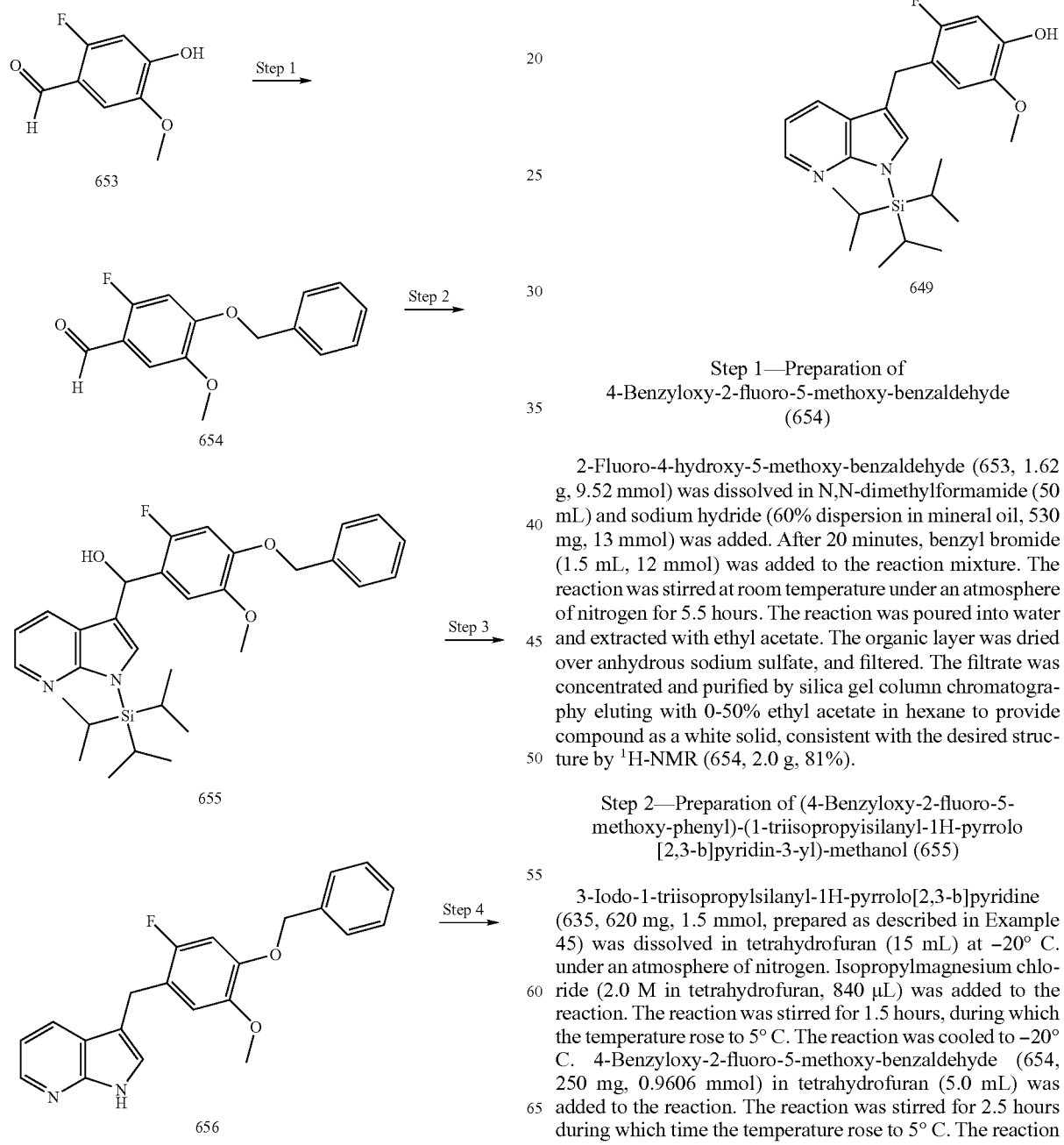

Step 1—Preparation of 4-Benzyloxy-2-fluoro-5-methoxy-benzaldehyde (654)

2-Fluoro-4-hydroxy-5-methoxy-benzaldehyde (653, 1.62 g, 9.52 mmol) was dissolved in N,N-dimethylformamide (50 mL) and sodium hydride (60% dispersion in mineral oil, 530 mg, 13 mmol) was added. After 20 minutes, benzyl bromide (1.5 mL, 12 mmol) was added to the reaction mixture. The reaction was stirred at room temperature under an atmosphere of nitrogen for 5.5 hours. The reaction was poured into water and extracted with ethyl acetate. The organic layer was dried over anhydrous sodium sulfate, and filtered. The filtrate was concentrated and purified by silica gel column chromatography eluting with 0-50% ethyl acetate in hexane to provide compound as a white solid, consistent with the desired structure by $^1$H-NMR (654, 2.0 g, 81%).

Step 2—Preparation of (4-Benzyloxy-2-fluoro-5-methoxy-phenyl)-(1-triisopropylsilanyl-1H-pyrrolo[2,3-b]pyridin-3-yl)-methanol (655)

3-Iodo-1-triisopropylsilanyl-1H-pyrrolo[2,3-b]pyridine (635, 620 mg, 1.5 mmol, prepared as described in Example 45) was dissolved in tetrahydrofuran (15 mL) at −20° C. under an atmosphere of nitrogen. Isopropylmagnesium chloride (2.0 M in tetrahydrofuran, 840 µL) was added to the reaction. The reaction was stirred for 1.5 hours, during which the temperature rose to 5° C. The reaction was cooled to −20° C. 4-Benzyloxy-2-fluoro-5-methoxy-benzaldehyde (654, 250 mg, 0.9606 mmol) in tetrahydrofuran (5.0 mL) was added to the reaction. The reaction was stirred for 2.5 hours during which time the temperature rose to 5° C. The reaction was poured into water. The mixture was extracted with ethyl acetate. The organic layer was dried over anhydrous sodium sulfate, and filtered. The filtrate was concentrated and purified by silica gel column chromatography eluting with 2-25% ethyl acetate in hexane to provide compound as a white solid (655, 501 mg, 63%). MS (ESI) [M+H⁺]⁺=535.4.

Step 3—Preparation of 3-(4-Benzyloxy-2-fluoro-5-methoxy-benzyl)-1H-pyrrolo[2,3-b]pyridine (656)

(4-Benzyloxy-2-fluoro-5-methoxy-phenyl)-(1-triisopropylsilanyl-1H-pyrrolo[2,3-b]pyridin-3-yl)-methanol (655, 1.49 g, 2.79 mmol) was dissolved in acetonitrile (50 mL) and trifluoroacetic Acid (1.1 mL) was added. The reaction was stirred for 5 minutes. Triethylsilane (2.2 mL) was added to the reaction. The reaction was heated at 80° C. for 6 hours. The reaction was concentrated and the crude material was dissolved into ethyl acetate and washed with 1 N HCl, saturated sodium bicarbonate, and brine. The organic portion was dried over anhydrous sodium sulfate and concentrated. The solid obtained was used in the next reaction without further purification (656, 833 mg, 83%). MS (ESI) [M+H⁺]⁺=363.4.

Step 4—Preparation of 3-(4-Benzyloxy-2-fluoro-5-methoxy-benzyl)-1-triisopropylsilanyl-1H-pyrrolo[2,3-b]pyridine (657)

3-(4-Benzyloxy-2-fluoro-5-methoxy-benzyl)-1H-pyrrolo[2,3-b]pyridine (656, 0.877 g, 2.42 mmol) was dissolved in N,N-dimethylformamide (30 mL). Sodium hydride (60% dispersion in mineral oil, 140 mg, 3.6 mmol) was added at room temperature. After 20 minutes, triisopropylsilyl chloride (513 μL, 2.42 mmol) was added dropwise. The reaction was stirred for four hours. The reaction was poured into water and extracted with ethyl acetate. The organic portion was washed with saturated sodium bicarbonate and brine. The organic portion was dried over anhydrous sodium sulfate and filtered. The filtrate was adsorbed onto silica gel and purified by silica gel chromatography using 20-80% ethyl acetate/hexane. The resulting material was purified a second time with 5-30% gradient ethyl acetate/hexane to provide the desired compound (657, 831 mg, 66%). MS (ESI) [M+H⁺]⁺=519.4.

Step 5—Preparation of 5-Fluoro-2-methoxy-4-(1-triisopropylsilanyl-1H-pyrrolo[2,3-b]pyridin-3-ylmethyl)-phenol (649)

3-(4-Benzyloxy-2-fluoro-5-methoxy-benzyl)-1-triisopropylsilanyl-1H-pyrrolo[2,3-b]pyridine (657, 0.831 g, 1.60 mmol) was dissolved in methanol (40 mL) and tetrahydrofuran (40 mL). 10% Palladium on carbon (3.41 g) was added. The reaction was shaken at 50 psi for 1 hour. The reaction was filtered through Celite and washed with methanol. The organic portion was passed through celite several times until a clear solution was obtained. The organic portion was concentrated under reduced pressure to provide the desired compound as an off-white solid (649, 587 mg, 86%). MS (ESI) [M+H⁺]⁺=429.5.

Example 53

Synthesis of (5-bromo-1H-pyrrolo[2,3-b]pyridin-3-yl)-(2-fluoro-3-hydroxy-phenyl)-methanone P-0067 and related compounds Compound P-0067 was synthesized in two steps from 5-bromo-1H-pyrrolo[2,3-b]pyridine 67 as shown in Scheme 10.

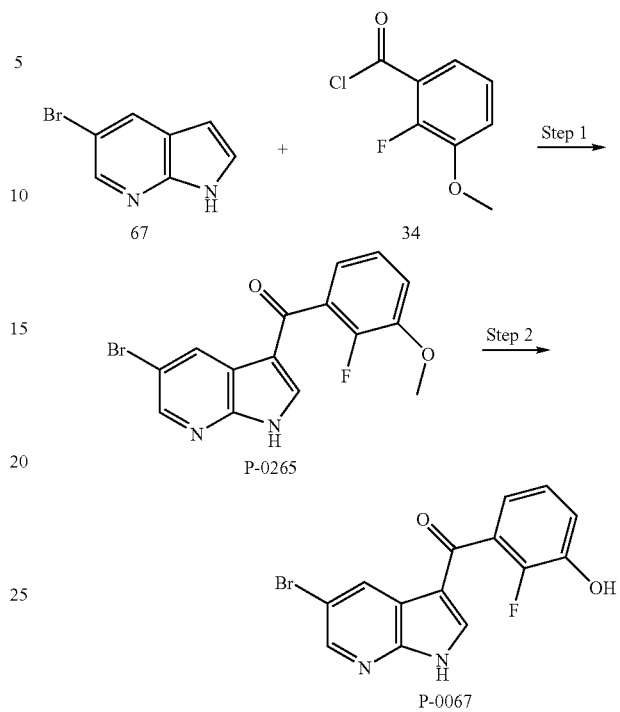

Scheme 10

Step 1—Preparation of (5-bromo-1H-pyrrolo[2,3-b]pyridin-3-yl)-(2-fluoro-3-methoxy-phenyl)-methanone (P-0265)

To 5-bromo-1H-pyrrolo[2,3-b]pyridine (67, 2.00 g, 0.0102 mol) in methylene chloride (120 mL), under an atmosphere of nitrogen, was added aluminum trichloride (8.20 g, 0.0615 mol). The reaction was stirred at room temperature for 60 minutes, then 2-fluoro-3-methoxy-benzoyl chloride (34, 2.12 g, 0.0112 mol, prepared from the corresponding carboxylic acid using the protocol of Example 1, Scheme 13, Step 4), dissolved in methylene chloride (20.0 mL), was added. After 2 hours, the reaction mixture was poured into water and extracted with ethyl acetate. The organic layer was washed with brine, dried over sodium sulfate, concentrated and purified by silica gel chromatography, eluting with 25% ethyl acetate in hexane to provide P-0265 (approx 2.6 g, 73%). MS (ESI) [M–H⁺]⁺=347, 349.

Step 2—Preparation of (5-bromo-1H-pyrrolo[2,3-b]pyridin-3-yl)-(2-fluoro-3-hydroxy-phenyl)-methanone (P-0067)

To (5-bromo-1H-pyrrolo[2,3-b]pyridin-3-yl)-(2-fluoro-3-methoxy-phenyl)-methanone (P-0265, 430.0 mg, 1.23 mmol) in methylene chloride (60 nit) was added boron tribromide (1.0 M in methylene chloride, 10 mL). The reaction mixture was stirred at room temperature overnight. The reaction was quenched with methanol (3.0 mL), poured into water and extracted with ethyl acetate. The organic layer was dried, concentrated and purified by silica eel chromatography eluting with 25% ethyl acetate in hexane to provide the compound (P-0067, 180 mg, 44%). MS (ESI) [M–H⁺]⁻=333.0, 335.0.

2-Fluoro-3-(5-pyridin-3-yl-1H-pyrrolo[2,3-b]pyridin-3-ylmethyl)-phenol P-0778

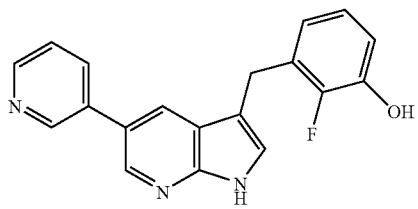 [SMILES: Oc1cccc(Cc2c[nH]c3ncc(-c4cccnc4)cc23)c1F]

was prepared using the protocol of Scheme 10, Step 2, replacing (5-Bromo-1H-pyrrolo[2,3-b]pyridin-3-yl)-(2-fluoro-3-methoxy-phenyl)-methanone P-0265 with 3-(2-Fluoro-3-methoxy-benzyl)-5-pyridin-3-yl-1H-pyrrolo[2,3-b]pyridine (P-0269, prepared as described in Example 10, Scheme 24). MS(ESI) [M+H$^+$]$^+$=320.2.

(5-Bromo-1H-pyrrolo[2,3-b]pyridin-3-yl)-(2-fluoro-5-hydroxy-phenyl)-methanone P-0068

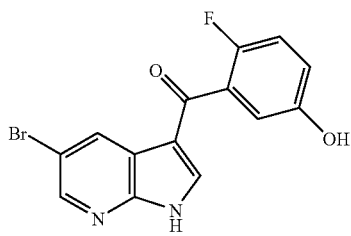 [SMILES: O=C(c1cc(O)ccc1F)c1c[nH]c2ncc(Br)cc12]

was prepared using the protocol of Scheme 10, replacing 2-Fluoro-3-methoxy-benzoyl chloride 34 with 2-Fluoro-5-methoxy-benzoyl chloride (prepared from the corresponding carboxylic acid using the protocol of Example 1, Scheme 13, Step 4) in Step 1. MS(ESI) [M−H$^+$]$^+$=347, 349.

Example 54

Synthesis of (2-fluoro-3-hydroxy-phenyl)-(5-phenyl-1H-pyrrolo[2,3-b]pyridin-3-yl)-methanone P-0036

Compound P-0036 was synthesized in three steps from (5-Bromo-1H-pyrrolo[2,3-b]pyridin-3-yl)-(2-fluoro-3-hydroxy-phenyl)-methanone P-0067 as shown in Scheme 11.

Scheme 11

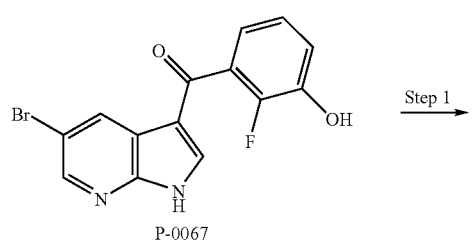

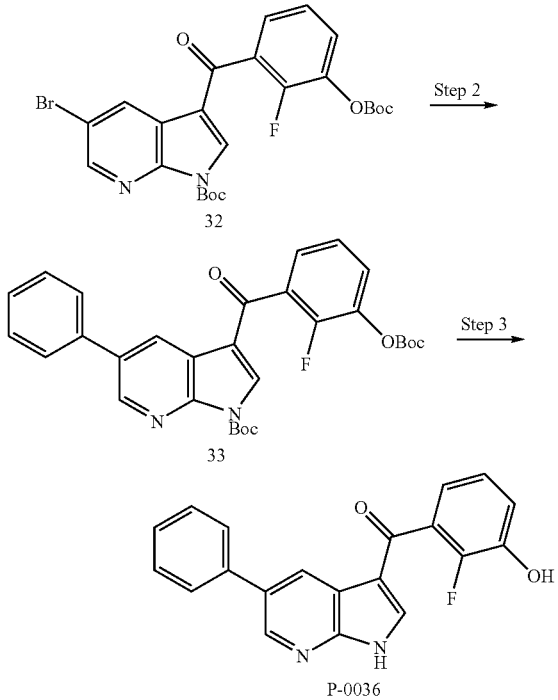

Step 1—Preparation of 5-bromo-3-(3-tert-butoxycarbonyloxy-2-fluoro-benzoyl)-pyrrolo[2,3-b]pyridine-1-carboxylic acid tert-butyl ester (32)

To (5-bromo-1H-pyrrolo[2,3-b]pyridin-3-yl)-(2-fluoro-3-hydroxy-phenyl)-methanone (P-0067, 310.0 mg, 0.93 mmol, prepared as described in Example 53, Scheme 10) in tetrahydrofuran (40 mL) were added sodium hydride (60% dispersion, 81.4 mg, 2.04 mmol) and di-tert-butyldicarbonate (0.50 g, 2.3 mmol). The reaction was stirred at room temperature for 1 hour. The reaction mixture was poured into water and extracted with ethyl acetate. The organic layer was washed with brine, dried over sodium sulfate, concentrated and purified by silica gel chromatography, eluting with 20% ethyl acetate in hexane to provide the compound (32, 0.45 g, 91%).

Step 2—Preparation of 3-(3-tert-butoxycarbonyloxy-2-fluoro-benzoyl)-5-phenyl-pyrrolo[2,3-b]pyridine-1-carboxylic acid tert-butyl ester (33)

To 5-bromo-3-(3-tert-butoxycarbonyloxy-2-fluoro-benzoyl)-pyrrolo[2,3-b]pyridine-1-carboxylic acid tert-butyl ester (32, 55.0 mg, 0.10 mmol) in tetrahydrofuran (10 mL) were added 1.0 M potassium carbonate in water (3.5 mL), phenylboronic acid (18.8 mg, 0.15 mmol) and tetrakis(triphenylphosphine)palladium(0) (3.9 mg, 0.0034 mmol) under an atmosphere of nitrogen. The reaction was stirred at 65° C. for 3 hours, and then poured into water and extracted with ethyl acetate. The organic layer was washed with brine, dried over sodium sulfate, and concentrated to give crude compound 33 that was used in the next step.

Step 3—Preparation of (2-fluoro-3-hydroxy-phenyl)-(5-phenyl-1H-pyrrolo[2,3-b]pyridin-3-yl)-methanone (P-0036)

To 3-(3-tert-butoxycarbonyloxy-2-fluoro-benzoyl)-5-phenyl-pyrrolo[2,3-b]pyridine-1-carboxylic acid tert-butyl ester (33, 30.0 mg, 0.056 mmol) in methylene chloride (6.0 mL) was added 4 N HCl in dioxane (2.0 mL). The reaction was stirred at room temperature for 36 hours. Solvents were removed by evaporation. The residue was poured into water and extracted with ethyl acetate. The organic layer was washed with brine, dried over sodium sulfate, concentrated and purified by silica gel chromatography, eluting with 25% ethyl acetate in hexane to give a white solid (P-0036, 4.8 mg, 24%). MS(ESI) [M+H$^+$]$^+$=333.2.

Additional compounds were prepared following the protocol of Scheme 11, optionally replacing (5-bromo-1H-pyrrolo[2,3-b]pyridin-3-yl)-(2-fluoro-3-hydroxy-phenyl)-methanone P-0067 with (5-Bromo-1H-pyrrolo[2,3-b]pyridin-3-yl)-(3-hydroxy-2-methyl-phenyl)-methanone P-0055 (prepared as described in Example 56, Scheme 22) in Step 1 and optionally replacing phenylboronic acid with an appropriate boronic acid in Step 2, The following compounds were made following this procedure:

N-{3-[3-(2-Fluoro-3-hydroxy-benzoyl)-1H-pyrrolo[2,3-b]pyridin-5-yl]-phenyl}-acetamide (P-0035),
N-{3-[3-(2-Fluoro-3-hydroxy-benzoyl)-1H-pyrrolo[2,3-b]pyridin-5-yl]-phenyl}-methanesulfonamide (P-0038),
3-[3-(2-Fluoro-3-hydroxy-benzoyl)-1H-pyrrolo[2,3-b]pyridin-5-yl]benzamide (P-0034),
(3-Hydroxy-2-methyl-phenyl)-(5-pyridin-3-yl-1H-pyrrolo[2,3b]pyridin-3-yl)-methanone (P-0006),
(3-Hydroxy-2-methyl-phenyl)-(5-thiophen-2-yl-1H-pyrrolo[2,3b]pyridin-3-yl)-methanone (P-0114),
(3-Hydroxy-2-methyl-phenyl)-(5-phenyl-1H-pyrrolo[2,3b]pyridin-3-yl)-methanone (P-0016),
(2-Fluoro-3-hydroxy-phenyl)-[5-(3-methanesulfonylphenyl)1H-pyrrolo[2,3-b]pyridin-3-yl]-methanone (P-0026),
(2-fluoro-3-hydroxy-phenyl)-(5-pyrimidin-5-yl-1H-pyrrolo[2,3-b]pyridin-3-yl)-methanone (P-0744), and
[5-(3-amino-phenyl)-1H-pyrrolo[2,3-b]pyridin-3-yl]-(2-fluoro-3-hydroxy-phenyl)methanone (P-0004).

The following table indicates the boronic acid (column 2) and the 5-Br azaindole (column 3) used to afford the compound (column 4), Column 1 provides the compound number and column 5 the observed mass.

-continued

| | Boronic acid | 5-Br azaindole | Compound | MS(ESI) [M + H⁺]⁺ observed |
|---|---|---|---|---|
| P-0114 | | | | 335.1 |
| P-0016 | | | | 329.2 |
| P-0026 | | | | 411.0 |
| P-0744 | | | | 335.1 |
| P-0004 | | | | 348.1 |

Example 55

Synthesis of (2,6-Difluoro-3-hydroxy-phenyl)-(5-pyridin-3-yl-1H-pyrrolo[2,3-b]pyridin-3-yl)-methanone P-8066

Compound P-0066 was synthesized in six steps from 2,4-difluoro-phenol 35 as shown in Scheme 12.

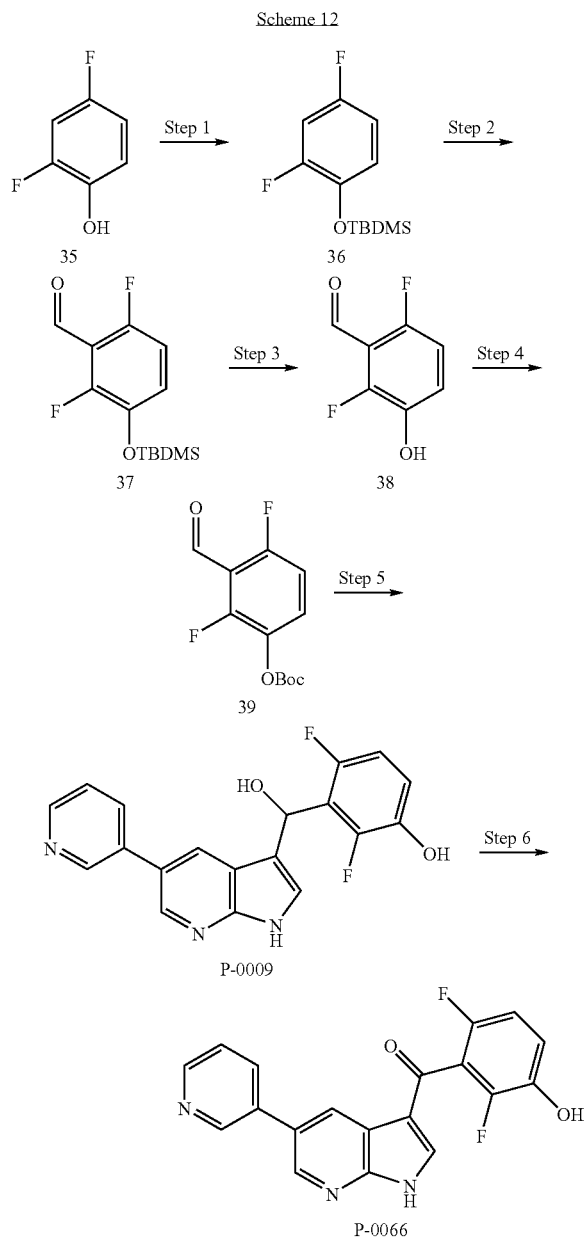

Scheme 12

Step 1—Preparation of tert-butyl-(2,4-difluoro-phenoxy)-dimethyl-silane (36)

To 2,4-difluoro-phenol (35, 5.00 g, 38.4 mmol) in N,N-dimethylformamide (100 mL) were added tert-butyldimethylsilyl chloride (7.00 g, 46.4 mmol) and imidazole (6.28 g, 92.2 mmol). The reaction was stirred at room temperature overnight. The reaction was poured into water and extracted with ethyl acetate. The organic layer was washed with brine, dried over anhydrous sodium sulfate and filtrated. The filtrate was concentrated and purified by silica gel column chromatography eluting with 10% ethyl acetate in hexane. The appropriate fractions were combined and concentrated to provide the compound (36, 7.50 g, 80.0%). MS(ESI) [M+H$^+$]$^+$=245.1.

Step 2—Preparation of 3-(tert-butyl-dimethyl-silanyloxy)-2,6-difluoro-benzaldehyde (37)

To tert-butyl-(2,4-difluoro-phenoxy)-dimethyl-silane (36, 5.90 g, 24.1 mmol) in tetrahydrofuran (100 mL), under an atmosphere of nitrogen, cooled in a −78° C. acetone/dry ice bath, was added n-butyllithium (2.50 M in hexane, 10.6 mL, 26.5 mmol) slowly. The reaction was allowed to stir for 1 hour, then N,N-dimethylformamide (2.24 mL, 29.0 mmol) was added and the reaction was allowed to warm to room temperature overnight. The reaction mixture was poured into water and extracted with ethyl acetate. The organic layer was washed with brine, dried over anhydrous sodium sulfate and concentrated The compound was isolated by silica gel column chromatography eluting with 10% ethyl acetate in hexane to give a colorless oil (37, 5.0 g, 76.0%). MS(ESI) [M+H$^+$]$^+$=272.2.

Step 3—Preparation of 2,6-difluoro-3-hydroxy-benzaldehyde (38)

To 3-(tert-butyl-dimethyl-silanyloxy)-2,6-difluoro-benzaldehyde (37, 3.50 g, 12.9 mmol) in N,N-dimethylformamide (50 mL) was added tetrabutylammonium fluoride trihydrate (4.40 g, 14.0 mmol). The reaction was stirred at room temperature for 1 hour. The reaction mixture was poured into water and extracted with ethyl acetate. The organic layer was washed with brine, dried over anhydrous sodium sulfate and concentrated to give crude compound 38 that was used in the next step.

Step 4—Preparation of carbonic acid tert-butyl ester 2,4-difluoro-3-formyl-phenyl ester (39)

To 2,6-difluoro-3-hydroxy-benzaldehyde (38, 1.90 g, 12.0 mmol) in tetrahydrofuran (60 mL) was added sodium hydride (60% in mineral oil, 0.58 g, 14.5 mmol) and di-tert-butyldicarbonate (3.90 g, 17.9 mmol). The reaction was stirred at room temperature overnight. The reaction mixture was poured into water and extracted with ethyl acetate. The organic layer was washed with brine, dried over anhydrous sodium sulfate and concentrated. The desired compound was isolated by silica gel column chromatography eluting with 10% ethyl acetate in hexane to give a colorless oil (39, 2.50 g, 80.8%). MS(ESI) [M+H$^+$]$^+$=258.1.

Step 5—Preparation of 2,4-difluoro-3-[hydroxy-(5-pyridin-3-yl-1H-pyrrolo[2,3-b]pyridin-3-yl)-methyl]-phenol (P-0009)

To carbonic acid tort-butyl ester 2,4-difluoro-3-formyl-phenyl ester (39, 0.405 g, 15.7 mmol) in methanol (36 mL), under an atmosphere of nitrogen, was added 5-pyridin-3-yl-1H-pyrrolo[2,3-b]pyridine (89, 288.0 mg, 14.8 mmol, prepared as in Example 17, Scheme 32) and potassium hydroxide (145.0 mg, 25.9 mol). The reaction was stirred at room temperature overnight. The reaction was poured into water and extracted with ethyl acetate. The organic layer was washed with brine, dried over anhydrous sodium sulfate and concentrated. The desired compound was isolated by silica gel column chromatography eluting with 4% methanol in methylene chloride to give a colorless oil (P-0009, 0.23 g, 44.1%). MS(ESI) [M+H⁺]⁺=354.1.

Step 6—Preparation of (2,6-difluoro-3-hydroxy-phenyl)-(5-pyridin-3-yl-1H-pyrrolo[2,3]pyridin-3-yl)-methanone (P-0066)

To 2,4-difluoro-3-[hydroxy-(5-pyridin-3-yl-1H-pyrrolo[2,3-b]pyridin-3-yl)-methyl]-phenol (P-0009, 45.0 mg, 1.27 mmol) in tetrahydrofuran (15 mL) and N,N-dimethylformamide (5 mL) was added dichlorodicyanoquinone (87 mg, 3.8 mmol). The reaction was stirred at room temperature for 50 hours. The reaction was poured into water and extracted with ethyl acetate. The organic layer was washed with brine, dried over anhydrous sodium sulfate and concentrated. The desired compound was isolated by silica eel column chromatography eluting with 5% methanol in methylene chloride to give a white solid (P-0066, 7 mg, 15.6%). MS(ESI) [M+H⁺]⁺=352.1.

(5-bromo-1H-pyrrolo[2,3-b]pyridin-3-yl)-(2,6-difluoro-3-hydroxy-phenyl)-methanone P-1271

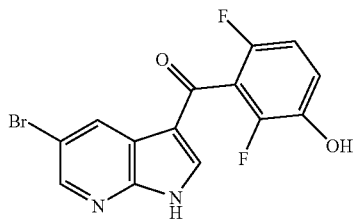 [SMILES: O=C(c1c(F)ccc(O)c1F)c1c[nH]c2ncc(Br)cc12]

was prepared following the protocol of Scheme 12, substituting 5-pyridin-3-yl-1H-pyrrolo[2,3-b]pyridine 89 with 5-bromo-1H-pyrrolo[2,3-b]pyridine 67 in Step 5. This was reacted further (70.0 mg, 0.20 mmol) in methylene chloride (15 mL) by adding pyridine (0.50 mL, 6.2 mmol), propane-1-sulfonyl chloride (0.50 g, 3.5 mmol) and 4-dimethylaminopyridine (0.10 g, 0.82 mmol). The reaction was stirred at room temperature overnight. The reaction mixture was poured into water and extracted with ethyl acetate. The organic layer was washed with brine, dried over anhydrous sodium sulfate and concentrated. The compound, propane-1-sulfonic acid 3-(5-bromo-1H-pyrrolo[2,3-b]pyridine-3-carbonyl)-2,4-difluoro-phenyl ester P-0919

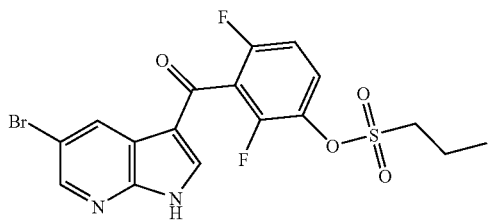 [SMILES: CCCS(=O)(=O)Oc1ccc(F)c(C(=O)c2c[nH]c3ncc(Br)cc23)c1F]

was isolated by silica gel column chromatography eluting with 10% ethyl acetate in hexane to give a white solid (15 mg, 16%). MS(ESI) [M−H⁺]⁻=456.9, 458.9.

Example 56

Synthesis of (5-Bromo-1H-pyrrolo[2,3-b]pyridin-3-yl)-(3-hydroxy-2-methyl-phenyl)-methanone P-0055

Compound P-0055 was synthesized in two steps from 5-Bromo-7-azaindole 67 as shown in Scheme 22.

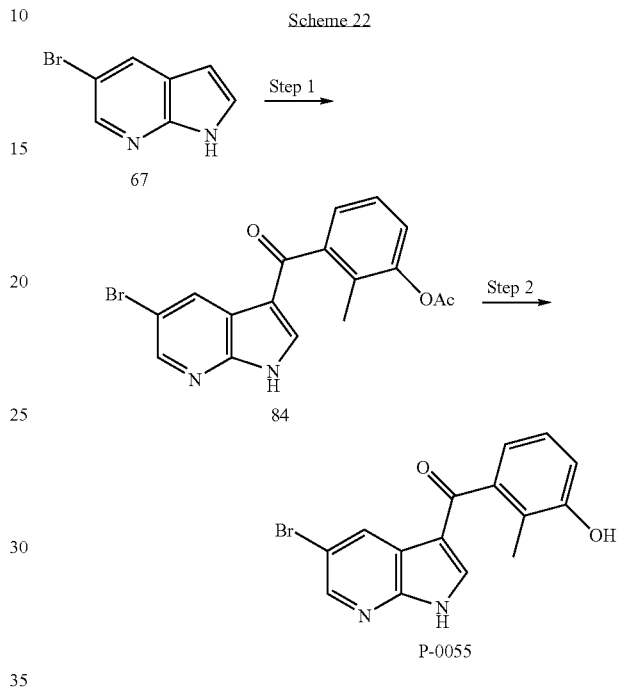

Scheme 22

Step 1—Preparation of acetic acid 3-(5-bromo-1H-pyrrolo[2,3-b]pyridine-3-carbonyl)-2-methyl-phenyl ester (84)

To aluminum trichloride (6.14 g, 0.046 mol) in methylene chloride (26 mL) under an atmosphere of nitrogen was added 5-Bromo-7-azaindole (67, 1.05 g, 5.31 mmol) dissolved in methylene dichloride (20.0 mL). The reaction was stirred at room temperature for 65.0 minutes, then acetic acid 3-chlorocarbonyl-2-methyl-phenyl ester (1.25 g, 5.88 mmol) in methylene dichloride (7.0 mL) was added. The reaction was stirred for 2 hours at room temperature, poured into water and extracted with ethyl acetate. The organic layer was washed with brine, dried over anhydrous sodium sulfate and concentrated to give crude compound 84 that was used directly in the next step.

Step 2—Preparation of (5-Bromo-1H-pyrrolo[2,3-b]pyridin-3-yl)-(3-hydroxy-2-methyl-phenyl)-methanone (P-0055)

A solution of acetic acid 3-(5-bromo-1H-pyrrolo[2,3-b]pyridine-3-carbonyl)-2-methyl-phenyl ester (84, 25.0 mg, 0.067 mmol) in 6 N HCl (4.0 mL) was heated with a CEM Discover microwave instrument at 110° C. for 10 min. The reaction mixture was poured into water, neutralized with 1 M aqueous potassium carbonate, and extracted with ethyl acetate. The organic layer was washed with brine, dried over anhydrous sodium sulfate and concentrated. The desired compound was isolated by silica gel column chromatography eluting with 10% ethyl acetate in hexane to give a colorless oil (P-0055, 4.7 mg, 21%). MS(ESI) [M−H+]−=329.0, 331.0.

Example 57

Synthesis of 2-Fluoro-3-(5-thiophen-2-yl-1H-pyrrolo[2,3-b]pyridin-3-ylmethyl)-phenol P-0052

Compound P-0052 was synthesized in five steps from (5-Bromo-1H-pyrrolo[2,3-b]pyridin-3-yl)-(2-fluoro-3-methoxy-phenyl)-methanone P-0265 as shown in Scheme 23.

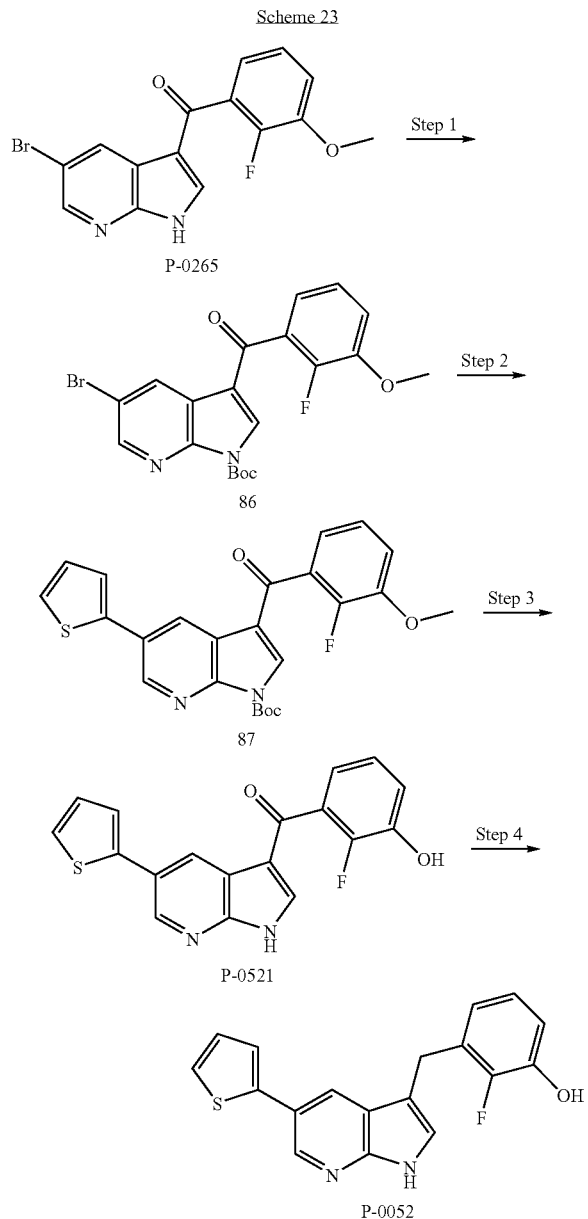

Step 1—Preparation of 5-bromo-3-(2-fluoro-3-methoxy-benzoyl)-pyrrolo[2,3-b]pyridine-1-carboxylic acid tert-butyl ester (86)

To (5-Bromo-1H-pyrrolo[2,3-b]pyridin-3-yl)-(2-fluoro-3-methoxy-phenyl)-methanone (P-0265, 600.0 mg, 1.72 mmol, prepared as described in Example 1 or 53) in tetrahydrofuran (20 mL) was added sodium hydride (60% dispersion, 103 mg, 2.58 mmol) under an atmosphere of nitrogen. After 15 minutes, di-tert-butyldicarbonate (648 mg, 2.97 mmol) was added. The reaction mixture was stirred at room temperature for 1 hour, poured into water and extracted with ethyl acetate. The organic layer was washed with brine, dried over anhydrous sodium sulfate and concentrated. The desired compound was isolated by silica gel column chromatography eluting with 10% ethyl acetate in hexane to give a colorless oil (86, 0.64 g, 82.3%).

Step 2—Preparation of 3-(2-fluoro-3-methoxy-benzoyl)-5-thiophen-2-yl-pyrrolo[2,3-b]pyridine-1-carboxylic acid tert-butyl ester (87)

To 5-bromo-3-(2-fluoro-3-methoxy-benzoyl)-pyrrolo[2,3-b]pyridine-1-carboxylic acid tert-butyl ester (86, 350.0 mg, 0.78 mmol) in tetrahydrofuran (30 mL) and water (10 mL) were added 2-thiophene boronic acid (190 mg, 1.49 mmol), tetrakis(triphenyl-phosphine)palladium(0) (40.0 mg, 0.0346 mmol) and potassium carbonate (780 mg, 5.64 mmol) under an atmosphere of nitrogen. The reaction mixture was refluxed for 2 hours. The reaction mixture was poured into water and extracted with ethyl acetate. The organic layer was washed with brine, dried over anhydrous sodium sulfate and concentrated to give crude compound (87, 0.30 g, 85%).

Step 3—Preparation of (2-fluoro-3-hydroxy-phenyl)-(5-thiophen-2-yl-1H-pyrrolo[2,3-b]pyridin-3-yl)-methanone (P-0521)

To 3-(2-fluoro-3-methoxy-benzoyl)-5-thiophen-2-yl-pyrrolo[2,3-b]pyridine-1-carboxylic acid tert-butyl ester (87, 200 mg, 0.44 mmol) in methylene chloride (10 mL), under an atmosphere of nitrogen, cooled in a −78° C. acetone/dry ice bath, was added boron tribromide (1.0 M in hexane, 2.0 mL). The reaction mixture was allowed to warm to room temperature and stirred overnight. The reaction was quenched with methanol (3.0 mL), poured into water and extracted with ethyl acetate. The organic layer was washed with brine, dried over anhydrous sodium sulfate and concentrated. The desired compound was isolated by silica gel column chromatography eluting with 5% methanol in methylene chloride to give a white solid (P-0521, 119 mg, 82.6%). MS(ESI)[M−H+]−=337.

Step 4—Preparation of 2-Fluoro-3-(5-thiophen-2-yl-1H-pyrrolo[2,3-b]pyridin-3-ylmethyl)-phenol (P-0052)

To (2-fluoro-3-hydroxy-phenyl)-(5-thiophen-2-yl-1H-pyrrolo[2,3-b]pyridin-3-yl)-methanone (P-0521, 50.0 mg, 0.15 mmol) in diethylene glycol (5.0 mL) were added hydrazine hydrate (1.0 mL, 0.020 mol) and potassium hydroxide (200.0 mg, 3.56 mmol). The reaction mixture was heated in a CEM Discovery microwave instrument at 180° C. for 20 minutes, poured into water and extracted with ethyl acetate. The organic layer was washed with brine, dried over anhydrous sodium sulfate and concentrated. The desired compound was isolated by silica gel column chromatography eluting with 5% methanol in methylene chloride to give a white solid (P-0052, 10 mg, 20%). MS(ESI) [M+H+]−=325.2.

Example 58

Synthesis of
(2,4-Difluoro-3-formyl-phenyl)-carbamic acid
tert-butyl ester 124

(2,4-Difluoro-3-formyl-phenyl)-carbamic acid tert-butyl ester 124 was synthesized in two steps from 2,4-Difluorophenylamine 42 as shown in Scheme 25.

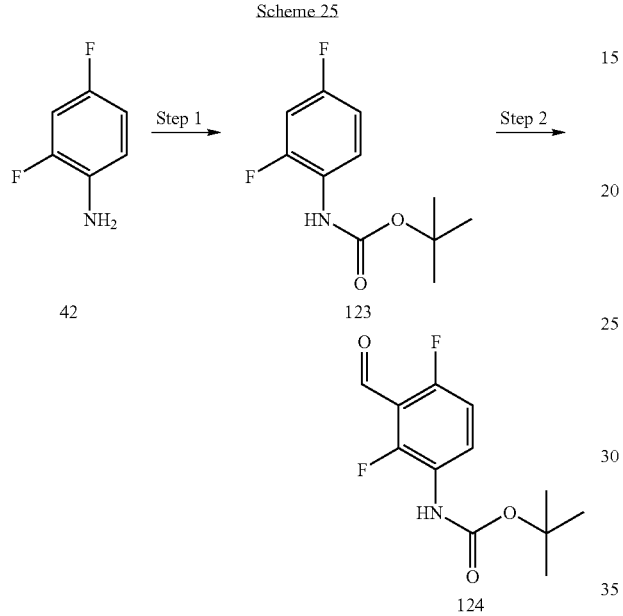

Step 1—Preparation of
(2,4-Difluoro-phenyl)-carbamic acid tert-butyl ester
(123)

To 2,4-difluoro-phenylamine (42, 5.0 g, 0.039 mol) in methylene chloride (100 mL) were added di-tert-butyldicarbonate (21.1 g, 0.0968 mol), triethylamine (16 mL, 0.12 mol) and 4-dimethylaminopyridine (0.2 g, 0.002 mol). The reaction was stirred at room temperature overnight, poured into water and extracted with ethyl acetate. The organic layer was washed with brine, dried over sodium sulfate, concentrated and purified by silica gel chromatography, eluting with 20% ethyl acetate in hexane to provide compound 123.

Step 2—Preparation of
(2,4-Difluoro-3-formyl-phenyl)-carbamic acid
tert-butyl ester (124)

To 2,4-difluoro-phenyl)-carbamic acid tert-butyl ester (123, 1.41 g, 6.17 mmol) in tetrahydrofuran (60.0 mL) under an atmosphere of nitrogen at 78° C. were added n-butyllithium (2.50 M in hexane, 2.59 mL) for 30 min. Lithium diisopropylamide (2.0 M in hexane, 3.4 mL) was added to the reaction. After 35 min, N,N-dimethylformamide (1.05 mL, 0.0136 mol) was added to the reaction mixture. The reaction was allowed to cool to room temperature overnight. The organic layer was washed with brine, dried over sodium sulfate, concentrated and purified by silica gel chromatography, eluting with 20% ethyl acetate in hexane to provide compound 124.

Example 59

Synthesis of 1-[4-(1H-Pyrrolo[2,3-b]pyridin-3-ylmethyl)-phenyl]-3-(3-trifluoromethyl-phenyl)-urea
P-0262

Compound P-0262 was synthesized in seven steps from 1H-Pyrrolo[2,3-b]pyridine 94 as shown in Scheme 34.

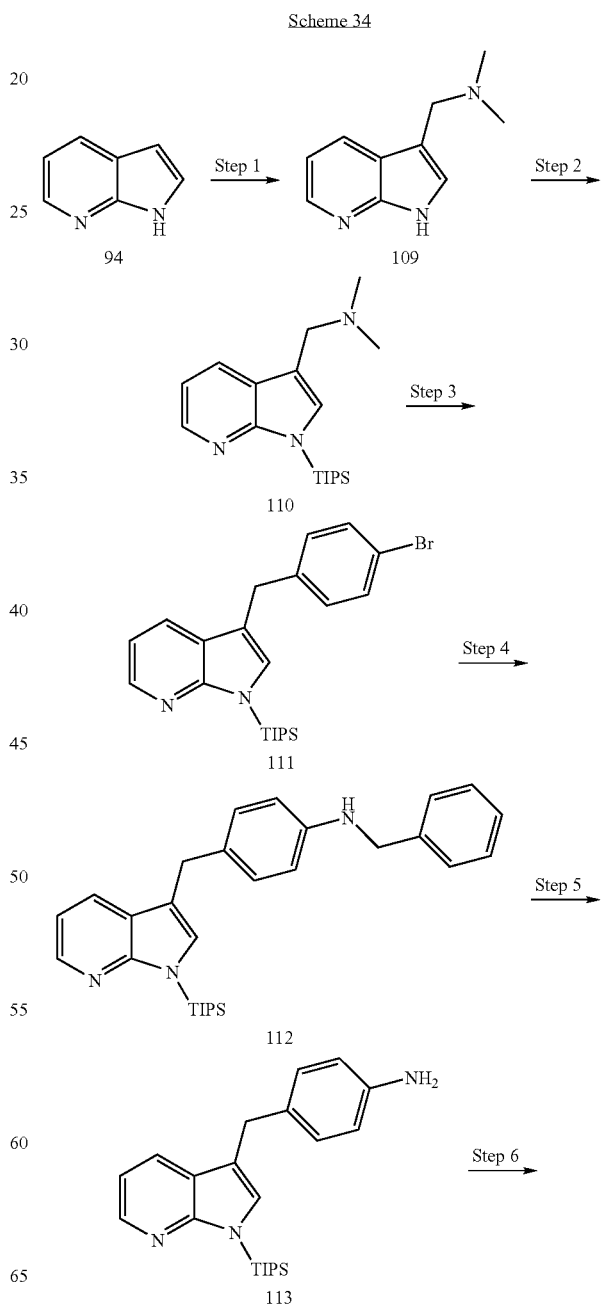

-continued

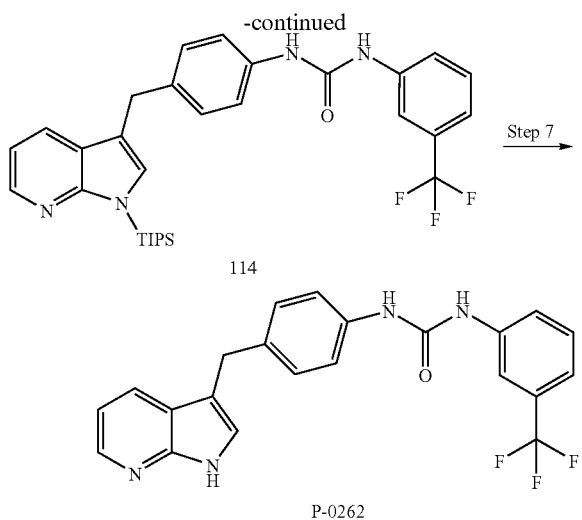

Step 1—Preparation of Dimethyl-(1H-pyrrolo[2,3-b]pyridin-3-ylmethyl)-amine (109)

1H-Pyrrolo[2,3-b]pyridine (94, 5.0 g, 42 mmol), dimethylamine hydrochloride (3.8 g, 46 mmol), formaldehyde (1.4 g, 46 mmol) and isopropyl alcohol (220.0 mL) were combined in a pressure tube. The reaction mixture was stirred at 20° C. for 12 hours and then refluxed for 2 hours. The clear solution was evaporated to dryness in vacuo. Water (40 mL) and concentrated hydrochloric acid (4 mL) were added to the residue. The mixture was extracted with ether and then made strongly basic with potassium carbonate. The basified aqueous layer was extracted with ethyl acetate. The organic layer was washed with brine, dried over sodium sulfate, concentrated and purified by silica gel chromatography to give the compound (109, 5.0 g, 68%).

Step 2—Preparation of Dimethyl-(1-triisopropylsilanyl-1H-pyrrolo[2,3-b]pyridin-3-yl)methyl)-amine (110)

Dimethyl-(1H-pyrrolo[2,3-b]pyridin-3-ylmethyl)-amine 109 (5.0 g, 28 mmol), was dissolved in N,N-dimethylformamide (80.0 mL) and sodium hydride (60% dispersion in mineral oil, 1.25 g, 31.4 mmol) was added, followed by triisopropylsilyl chloride (6.3 mL, 30.0 mmol). The reaction was stirred at room temperature for 12 hours, then poured into water and extracted with ethyl acetate. The organic portion was washed with brine, dried over sodium sulfate, concentrated and purified with silica gel chromatography to give the compound (110, 6.5 g, 70%).

Step 3—Preparation of 3-(4-Bromo-benzyl)-1-triisopropylsilanyl-1H-pyrrolo[2,3-b]pyrimidine (111)

1-bromo-4-iodobenzene (2.1 g, 7.4 mmol) was dissolved in tetrahydrofuran (15.0 mL) under an atmosphere of nitrogen at −30° C. Isopropylmagnesium chloride in tetrahydrofuran (2.0 M, 4.0 mL) was added. The reaction mixture was stirred below −20° C. for 1 hour to provide a solution of 1-bromo-4-benzene magnesium chloride.
Dimethyl-(1-triisopropylsilanyl-1H-pyrrolo[2,3-b]pyridin-3-ylmethyl)-amine 110 (1.25 g, 3.77 mmol) was added to toluene (20.0 mL) under an atmosphere of nitrogen at room temperature. Isopropyl chloroformate in toluene (1.0 M, 4.0 mL) was added. The reaction mixture was stirred at room temperature for 3 hours to provide a solution of 3-chloromethyl-1-triisopropylsilanyl-1H-pyrrolo[2,3-b]pyridine.
CuCN.2LiCl in tetrahydrofuran (0.7 M, 10 mL) was added to the solution of 1-bromo-4-benzene magnesium chloride at −20° C. The reaction mixture was allowed to warm to room temperature for 10 minutes. Trimethyl phosphite (1.8 mL, 0.015 mol) was added to the reaction. After 5 minutes, the solution of 3-chloromethyl-1-triisopropylsilanyl-1H-pyrrolo[2,3-b]pyridine was added to the reaction at room temperature. The reaction was stirred for 12 hours at room temperature. The reaction mixture was poured into water and extracted with ethyl acetate. The organic layer was washed with brine, dried over sodium sulfate, concentrated and purified with silica gel chromatography to give the compound (111, 850 mg, 51%).

Step 4—Preparation of Benzyl-[4-(1-triisopropylsilanyl-1H-pyrrolo[2,3-b]pyridin-3-ylmethyl)-phenyl]-amine (112)

3-(4-Bromo-benzyl)-1-triisopropylsilanyl-1H-pyrrolo[2,3-b]pyridine (111, 330.0 mg, 0.74 mmol), benzylamine (160 mg, 1.5 mmol), 2-[di(tert-butyl)phosphino]-1,1'-biphenyl (15.0 mg, 0.05 mmol), tris(dibenzylideneacetone)dipalladium(0) (15.0 mg, 0.016 mmol), potassium tert-butoxide (100 mg, 0.89 mmol) and toluene (10.0 mL) were combined under an atmosphere of nitrogen. The reaction mixture was refluxed overnight, then poured into water and extracted with ethyl acetate. The organic layer was washed with brine, dried over sodium sulfate, concentrated and purified with silica eel chromatography to give the compound (112, 260 mg, 75%).

Step 5—Preparation of 4-(1-Triisopropylsilanyl-1H-pyrrolo[2,3-b]pyridin-3-ylmethyl)-phenylamine (113)

Benzyl-[4-(1-triisopropylsilanyl-1H-pyrrolo[2,3-b]pyridin-3-ylmethyl)-phenyl]-amine (112, 210.0 mg, 0.447 mmol), methanol (15.0 mL) and palladium hydroxide (30.0 mg, 0.214 mmol) were combined. The reaction mixture was hydrogenated under under an atmosphere of hydrogen (1 atm) at room temperature for 2 hours. Filtration and concentration gave the compound (113, 154 mg, 91%).

Step 6—Preparation of 1-(3-Trifluoromethyl-phenyl)-3-[4-(1-triisopropylsilanyl-1H-pyrrolo[2,3-b]pyridin-3-ylmethyl)-phenyl]-urea (114)

4-(1-Triisopropylsilanyl-1H-pyrrolo[2,3-b]pyridin-3-ylmethyl)-phenylamine (113, 70.0 mg, 0.184 mmol) was dissolved in tetrahydrofuran (12 mL) and 3-trifluoromethylphenyl isocyanate (41 rag, 0.22 mmol) and triethylamine (28 mg, 0.28 mmol) were added under an atmosphere of nitrogen. The reaction mixture was stirred at room temperature overnight, then poured into water and extracted with ethyl acetate. The organic layer was washed with brine, dried over sodium sulfate, concentrated to give crude compound 114 used in the next step.

Step 7—Preparation of 1-[4-(1H-Pyrrolo[2,3-b]pyridin-3-ylmethyl)-phenyl]-3-(3-trifluoromethyl-phenyl)-urea (P-0262)

1-(3-Trifluoromethyl-phenyl)-3-[4-(1-triisopropylsilanyl-1H-pyrrolo[2,3-b]pyridin-3-ylmethyl)-phenyl]-urea (114, 85.0 mg, 0.150 mmol) was dissolved in tetrahydrofuran (10.0 mL) and tetra-n-butylammonium fluoride (52.2 mg, 0.200 mmol) was added. After 10 minutes, the reaction mixture was poured into water and extracted with ethyl acetate. The organic layer was washed with brine, dried over sodium sulfate, concentrated and purified with by silica gel chromatography to give the compound (P-0262, 23 mg, 38% over steps 6 & 7). MS(ESI)[M+H$^+$]$^+$=411.2

Example 60

Synthesis of (4-Hydroxy-phenyl)-(5-thiophen-2-yl-1H-pyrrolo[2,3-b]pyridin-3-yl)-methanone P-0024

Compound P-0024 was synthesized in four steps from 5-bromo-7-azaindole 67 as shown in Scheme 35.

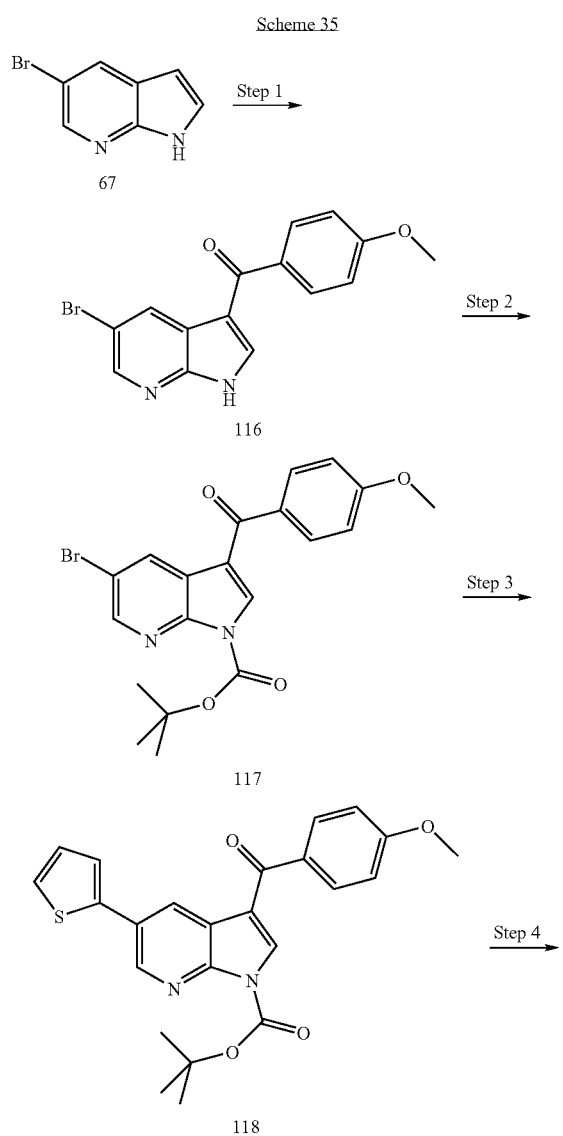

-continued

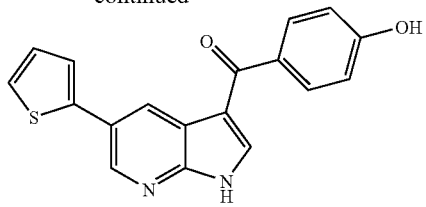

P-0024

Step 1—Preparation of (5-Bromo-1H-pyrrolo[2,3-b]pyridin-3-yl)-(4-methoxy-phenyl)-methanone (116)

Aluminum trichloride (2.7 g, 20.0 mmol) and methylene chloride (30 mL) were combined under an atmosphere of nitrogen and 5-bromo-7-azaindole (67, 400.0 mg, 2.30 mmol) in methylene dichloride (20 mL) was added. The reaction was stirred at room temperature for 70 minutes. 4-Methoxybenzoic acid chloride (0.38 g, 2.2 mmol) (prepared from the corresponding carboxylic acid using the protocol described in Example 1, Scheme 13, Step 4) in methylene dichloride (7.0 mL) was added. The reaction was stirred at room temperature for 2 hours, then poured into water and extracted with ethyl acetate. The organic layer was washed with brine, dried over sodium sulfate, and concentrated to give the compound (116, 250 mg, 34%).

Step 2—Preparation of 5-Bromo-3-(4-methoxy-benzoyl)-pyrrolo[2,3-b]pyridine-1-carboxylic acid tert-butyl ester (117)

(5-Bromo-1H-pyrrolo[2,3-b]pyridin-3-yl)-(4-methoxy-phenyl)-methanone (116, 220.0 mg, 0.66 mmol) was dissolved in tetrahydrofuran (15.0 mL) and sodium hydride (60% dispersion, 29 mg, 0.73 mmol) was added under an atmosphere of nitrogen. The reaction was stirred for 15 minutes. Di-tert-butyldicarbonate (220 mg, 1.0 mmol) was added. The reaction was stirred for one hour, then poured into water and extracted with ethyl acetate. The organic portion was washed with brine, dried over sodium sulfate and concentrated to give compound 117.

Step 3—Preparation of 3-(4-Methoxy-benzoyl)-5-thiophen-2-yl-pyrrolo[2,3-b]pyridine-1-carboxylic acid tert-butyl ester (118)

5-Bromo-3-(4-methoxy-benzoyl)-pyrrolo[2,3-b]pyridine-1-carboxylic acid tert-butyl ester (117, 100.0 mg, 0.23 mmol), thiophene-2-boronic acid (59 mg. 0.46 mmol), tetrakis(triphenylphosphine)palladium(0) (20.0 mg, 0.017 mmol), potassium carbonate (80 mg, 0.58 mmol), tetrahydrofuran (15.0 mL) and water (5.0 mL) were combined under an atmosphere of nitrogen. The reaction mixture was refluxed overnight, then poured into water and extracted with ethyl acetate. The organic layer was washed with brine, dried over sodium sulfate, concentrated and purified with silica gel chromatography to give compound 118 (100 mg).

Step 4—Preparation of (4-Hydroxy-phenyl)-(5-thiophen-2-yl-1H-pyrrolo[2,3-b]pyridin-3-yl)-methanone (P-0024)

3-(4-Methoxy-benzoyl)-5-thiophen-2-yl-pyrrolo[2,3-b]pyridine-1-carboxylic acid tert-butyl ester (118, 100.0 mg, 0.23 mmol) and methylene chloride (15.0 mL) were combined under an atmosphere of nitrogen. Boron tribromide (1.0 M in methylene chloride, 3.0 mL) was added. The reaction was stirred at room temperature overnight. Methanol (2.0 mL) was added into the the reaction mixture. The reaction was concentrated to remove solvents. The residue was extracted with water and ethyl acetate. The organic layer was washed with brine, dried over sodium sulfate, concentrated and purified with silica gel chromatography. The product was washed with methanol to provide compound (P-0024, 25.0 mg, 34%). MS(ESI) [M+H⁺]⁺=321.

Example 61

Synthesis of 4-Benzofuran-2-yl-1H-pyrrolo[2,3-b]pyridine-2-carboxylic acid ethyl ester P-1248

Compound P-1248 was synthesized in four steps from 4-chloro-7-azaindole 119 as shown in Scheme 36.

Scheme 36

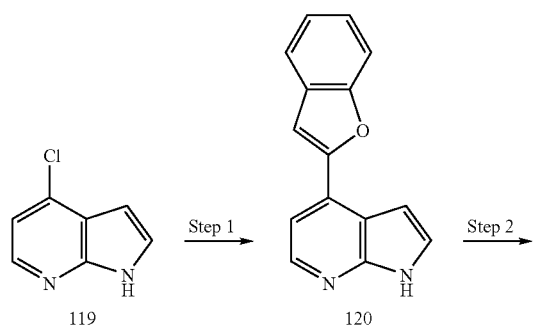

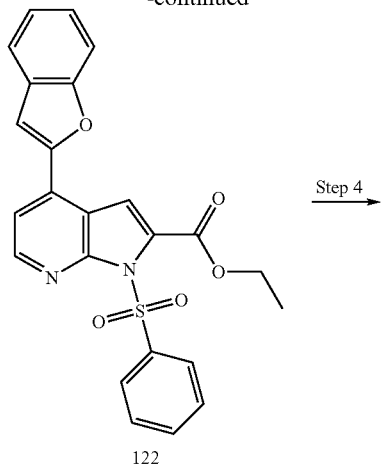

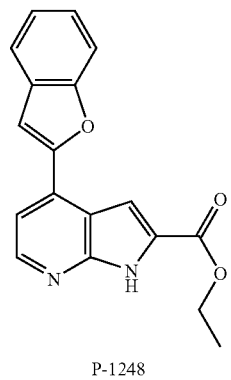

P-1248

Step 1—Preparation of 4-Benzofuran-2-yl-1H-pyrrolo[2,3-b]pyridine (120)

4-Chloro-7-azaindole (119, 100 mg, 0.66 mmol, prepared as described in Example 70, Scheme 81), 2-Benzofuranboronic acid (212 mg, 1.31 mmol) and Potassium fluoride (127 mg, 2.18 mmol) were stirred in 3 mL of anhydrous dioxane. Tris(dibenzylideneacetone)dipalladium(0) chloroform adduct (10.2 mg, 9.83E-3 mmol) and tri t-butylphosphine (6.6 mg, 0.033 mol) were added and the suspension was stirred at 100° C. for 4 hours in a pressure tube under inert atmosphere. The reaction mixture was cooled to room temperature and was adsorbed onto silica gel and purified by chromatography to provide the compound (120, 56 mg, 36%). MS(ESI) [M+H⁺]⁺=235.20.

Step 2—Preparation of 1-Benzenesulfonyl-4-benzofuran-2-yl-1H-pyrrolo[2,3-b]pyridine (121)

Into a Round bottom flask 4-benzofuran-2-yl-1H-pyrrolo[2,3-b]pyridine (120, 100 mg, 0.43 mmol) was suspended in methylene chloride (10 mL) and 50% KOH solution (5 mL) was added. Tetrabutylammonium hydrogen sulfate (10 mg, 0.03 mmol) and benzenesulfonyl chloride (81.4 mg, 0.46 mmol) were added. The resulting yellow solution was stirred at ambient temperature for 2 hours. The reaction mixture was partitioned between ethyl acetate and water and the organic layer was separated and washed with water and brine then dried over MgSO₄, filtered and concentrated under reduced pressure to provide compound 121. MS(ESI) [M+H⁺]⁺=375.29.

Step 3—1-Benzenesulfonyl-4-benzofuran-2-yl-1H-pyrrolo[2,3-b]pyridine-2-carboxylic acid ethyl ester (122)

To a chilled (−78° C. acetone/dry ice bath) solution of 1-benzenesulfonyl-4-benzofuran-2-yl-1H-pyrrolo[2,3-b]pyridine (121, 66.0 mg, 0.18 mmol) in tetrahydrofuran (5.0 mL) under an atmosphere of nitrogen, n-butyllithium (1.6 M in tetrahydrofuran, 0.14 mL, 0.23 mmol) was added dropwise. The reaction mixture was stirred for 30 minutes and ethyl chloroformate (0.02 mL, 0.19 mmol) was added. The reaction mixture was stirred for 1 hour while allowing it to reach room temperature, poured into water and extracted with ethyl acetate. The organic layer was washed with brine, dried over anhydrous sodium sulfate and filtered. The filtrate was concentrated under reduced pressure and purified by silica gel column chromatography, eluting with 20% ethyl acetate in hexane, to give light yellow solid (122, 0.015 g, 19%). MS(ESI)[M+H$^+$]$^+$=447.3.

Step 4—4-Benzofuran-2-yl-1H-pyrrolo[2,3-b]pyridine-2-carboxylic acid ethyl ester (P-1248)

To a solution of 1-benzenesulfonyl-4-benzofuran-2-yl-1H-pyrrolo[2,3-b]pyridine-2-carboxylic acid ethyl ester (122, 14.0 mg, 0.03 mmol) in tetrahydrofuran (3.0 mL), was added tetra N-butylammonium fluoride (26.0 mg, 0.10 mmol). The reaction was stirred for 48 hours at room temperature, then poured into water and extracted with ethyl acetate. The organic layer was washed with brine, dried over anhydrous sodium sulfate and filtered. The filtrate was concentrated under reduced pressure and purified by silica gel column chromatography, eluting with 50% Ethyl acetate in hexane, to give light yellow solid (P-1248, 3.0 mg, 36%). MS(ESI) [M+H$^+$]$^+$=307.2.

Example 62

Synthesis of N-phenyl-1H-pyrrolo[2,3-b]pyridin-6-amine P-1350 and related compounds Compound P-1350 was synthesized in five steps from 1H-pyrrolo[2,3-b]pyridine 94 as shown in Scheme 40.

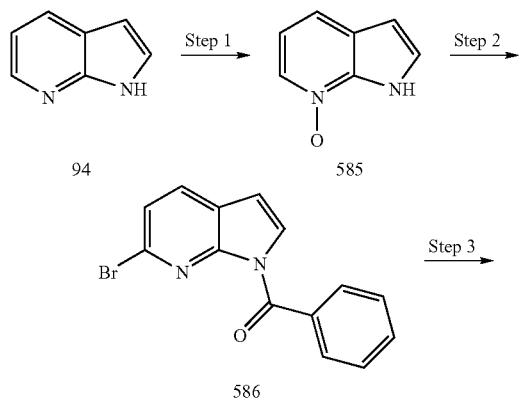

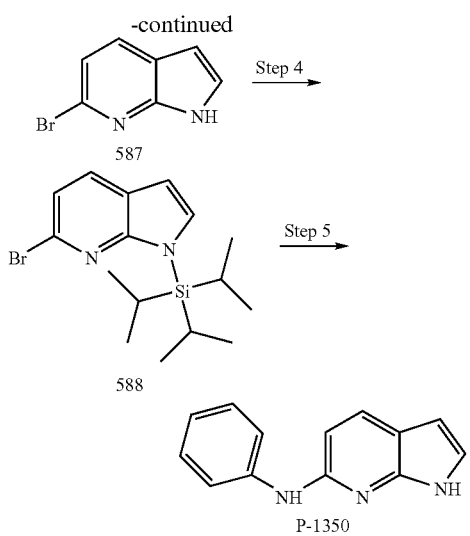

Step 1—Preparation of 1H-pyrrolo[2,3-b]pyridine-N-oxide (585)

To 1H-pyrrolo[2,3-b]pyridine (94, 3.0 g, 25.3 mmol) dissolved in 175 ml, of diethyl ether was added m-CPBA (1.5 equiv) in portions over 30 minutes with vigorous stirring. The solution turned yellow, and precipitates formed. After two hours the solid was collected, washed with 2×50 mL of ether, and recrystallized from acetone:ether. Yield was approximately 125% due to contaminating acid. This crude material was carried through to the next step.

Step 2—(6-bromo-1H-pyrrolo[2,3-b]pyridin-1-yl) (phenyl)methanone (586)

1H-pyrrolo[2,3-b]pyridine-N-oxide (585, 500 mg, 3.72 mmol) was dissolved in 40 mL of dry benzene. In a separate dry flask, benzoyl bromide (2.5 equiv) and 1,1,1,3,3,3-hexamethyldisilazane (1.0 equiv) were combined in 20 mL, of dry benzene. The bromide solution was added in 5 mL aliquots over 30 minutes to the reaction flask. The reaction was stirred at ambient temperature for two hours. It was then washed with 3×30 mL NaHCO$_3$ (aq., satd.) and 1×30 mL brine. The organic layer was dried over sodium sulfate and evaporated. The crude material was taken directly to the next step without further purification.

Step 3—Preparation of 6-bromo-1H-pyrrolo[2,3-b]pyridine (587)

(6-bromo-1H-pyrrolo[2,3-b]pyridin-1-yl)(phenyl)methanone, 586 was dissolved in 20 mL of dioxane and 20 mL of 2M KOH (aq). This was stirred at ambient temperature until analysis indicated all of the starting material had been consumed (2 to 4 hours). The reaction was diluted with 50 mL of ethyl acetate and washed with 2×25 mL of NaHCO$_3$ (aq. satd.) and 25 mL of brine. The organic layer was dried with sodium sulfate, evaporated and purified by column chromatography. Combined steps 2 and 3 gave approximately 65% overall yield.

Step 4—Preparation of 6-bromo-1-(triisopropylsilyl)-1H-pyrrolo[2,3-b]pyridine (588)

6-bromo-1H-pyrrolo[2,3-b]pyridine (587, 275 mg, 1.39 mmol) was dissolved in 4 mL of dry dioxane. DIEA (3 equiv)

and TIPS-OTf (2.5 equiv) were added and the reaction was stirred at 50° C. overnight. The reaction was then diluted with 20 mL of ethyl acetate and washed 2 times with 10 mL NaHCO$_3$ (aq., 5%) and once with 10 mL brine. The organic fraction was dried over MgSO$_4$, evaporated and diluted with 5.5 mL of dry toluene (~10 mg bromide per 0.2 mL of solution) to use directly in the next reaction step.

Step 5—Preparation of
N-phenyl-1H-pyrrolo[2,3-b]pyridin-6-amine
(P-1350)

A 1 dram vial was charged with aniline (2-3 equiv), and 0.200 mL of the 588 stock solution of bromide in toluene was added. A catalyst stock solution containing 3 mmol Pd(OAc)$_2$, 3 mmol biphenyl-2-yl-di-tert-butyl-phosphane and 15 mL of toluene was prepared and 0.050 mL of the catalyst solution was added to the reaction. An excess of NaOtBu was added as a solid to the reaction. The vial was placed in an 80° C. oven for 60 minutes (shaken several times over the hour). After cooling, the reaction was neutralized with 0.100 mL of TPA. After 30 minutes the sample was evaporated and resolvated in 0.300 mL of DMSO. The desired compound was isolated by preparative HPLC/MS. MS(ESI) [M+H$^+$]$^+$=210.4.

The following compounds were prepared following the protocol of scheme 40, substituting aniline with a suitable amine is Step 5:

Cyclohexyl-(1H-pyrrolo[2,3-b]pyridin-6-yl)-amine (P-1290),
Benzyl-(1H-pyrrolo[2,3-b]pyridin-6-yl)-amine (P-1291),
Cyclopropylmethyl-(1H-pyrrolo[2,3-b]pyridin-6-yl)-amine (P-1292),
(3-Methoxy-benzyl)-(1H-pyrrolo[2,3-b]pyridin-6-yl)-amine (P-1293),
(1H-Pyrrolo[2,3-b]pyridin-6-yl)-(3-trifluoromethyl-benzyl)-amine (P4294),
(1H-Pyrrolo[2,3-b]pyridin-6-yl)-(2-trifluoromethyl-benzyl)-amine (P-1295),
Cyclohexylmethyl-(1H-pyrrolo[2,3-b]pyridin-6-yl)-amine (P-1296),
(1H-Pyrrolo[2,3-b]pyridin-6-yl)-(4-trifluoromethoxy-benzyl)-amine (P-1297),
(1H-Pyrrolo[2,3-b]pyridin-6-yl)-(3-trifluoromethoxy-benzyl)-amine (P-1298),
(1H-Pyrrolo[2,3-b]pyridin-6-yl)-(2-trifluoromethoxy-benzyl)-amine (P-1299),
Pyridin-2-ylmethyl-(1H-pyrrolo[2,3-b]pyridin-6-yl)-amine (P-1300),
(4-Methanesulfonyl-benzyl)-(1H-pyrrolo[2,3-b]pyridin-6-yl)-amine (P-1301),
(4-Methoxy-benzyl)-(1H-pyrrolo[2,3-b]pyridin-6-yl)-amine (P-1302),
Ethyl-(1H-pyrrolo[2,3-b]pyridin-6-yl)-amine (P-1303),
(3-Chloro-benzyl)-(1H-pyrrolo[2,3-b]pyridin-6-yl)-amine (P-1304),
(4-Methyl-benzyl)-(1H-pyrrolo[2,3-b]pyridin-6-yl)-amine (P-1305),
(1-Methyl-piperidin-4-yl)-(1H-pyrrolo[2,3-b]pyridin-6-yl)-amine (P-1306),
Pyridin-3-ylmethyl-(1H-pyrrolo[2,3-b]pyridin-6-yl)-amine (P-1307),
[4-(Morpholine-4-sulfonyl)-phenyl]-(1H-pyrrolo[2,3-b]pyridin-6-yl)-amine (P-1308),
(4-Methanesulfonyl-phenyl)-(1H-pyrrolo[2,3-b]pyridin-6-yl)-amine (P-1309),
(2-Chloro-benzyl)-(1H-pyrrolo[2,3-b]pyridin-6-yl)-amine (P-1310),
(1H-Pyrrolo[2,3-b]pyridin-6-yl)-(tetrahydro-pyran-4-yl)-amine (P-1311),
(4-Chloro-benzyl)-(1H-pyrrolo[2,3-b]pyridin-6-yl)-amine (P-1312),
(3-Methyl-benzyl)-(1H-pyrrolo[2,3-b]pyridin-6-yl)-amine (P-1313),
[3-(Morpholine-4-sulfonyl)-phenyl]-(1H-pyrrolo[2,3-b]pyridin-6-yl)-amine (P-1314),
(3-Methanesulfonyl-phenyl)-(1H-pyrrolo[2,3-b]pyridin-6-yl)-amine (P-1315),
Pyridin-3-yl-(1H-pyrrolo[2,3-b]pyridin-6-yl)-amine (P-1351),
(2-Methoxy-phenyl)-(1H-pyrrolo[2,3-b]pyridin-6-yl)-amine (P-1352),
(1H-Pyrrolo[2,3-b]pyridin-6-yl)-(3-trifluoromethyl-phenyl)-amine (P-1353),
(1H-Pyrrolo[2,3-b]pyridin-6-yl)-(4-trifluoromethoxy-phenyl)-amine (P-1354),
(4-Methoxy-phenyl)-(1H-pyrrolo[2,3-b]pyridin-6-yl)-amine (P-1355),
N,N-Dimethyl-N'-(1H-pyrrolo[2,3-b]pyridin-6-yl)-benzene-1,4-diamine (P-1356),
(3-Methoxy-phenyl)-(1H-pyrrolo[2,3-b]pyridin-6-yl)-amine (P-1357),
(4-Morpholin-4-yl-phenyl)-(1H-pyrrolo[2,3-b]pyridin-6-yl)-amine (P-1358),
(4-Piperidin-1-yl-phenyl)-(1H-pyrrolo[2,3-b]pyridin-6-yl)-amine (P-1359),
(1H-Pyrrolo[2,3-b]pyridin-6-yl)-(3-trifluoromethoxy-phenyl)-amine (P-1360),
(1H-Pyrrolo[2,3-b]pyridin-6-yl)-p-tolyl-amine (P-1361),
(3-tert-Butyl-phenyl)-(1H-pyrrolo[2,3-b]pyridin-6-yl)-amine (P-1362),
(3-Dimethylamino-benzyl)-(1H-pyrrolo[2,3-b]pyridin-6-yl)-amine (P-1363),
(3,5-Dichloro-phenyl)-(1H-pyrrolo[2,3-b]pyridin-6-yl)-amine (P-1364),
(1H-Pyrrolo[2,3-b]pyridin-6-yl)-(4-trifluoromethyl-benzyl)-amine (P-1371),
N,N-Dimethyl-N'-(1H-pyrrolo[2,3-b]pyridin-6-yl)-benzene-1,3-diamine (P-1372),
(3-Chloro-phenyl)-(1H-pyrrolo[2,3-b]pyridin-6-yl)-amine (P-1373),
(4-Chloro-phenyl)-(1H-pyrrolo[2,3-b]pyridin-6-yl)-amine (P-1374),
(2-Chloro-phenyl)-(1H-pyrrolo[2,3-b]pyridin-6-yl)-amine (P-1375),
(5-Methyl-isoxazol-3-yl)-(1H-pyrrolo[2,3-b]pyridin-6-yl)-amine (P-1376),
(2-Morpholin-4-yl-phenyl)-(1H-pyrrolo[2,3-b]pyridin-6-yl)-amine (P-1377), and
(2-Methanesulfonyl-phenyl)-(1H-pyrrolo[2,3-b]pyridin-6-yl)-amine (P-1378).

The following table indicates the amine (Column 2) that is substituted in place of the aniline in Step 5 to afford the compound (Column 3). Column 1 provides the compound number and Column 4 the observed mass.

| Compound number | Amine | Compound structure | MS(ESI) [M + H⁺]⁺ observed |
|---|---|---|---|
| P-1290 | cyclohexylamine | N-cyclohexyl-7-azaindol-6-amine | 216.3 |
| P-1291 | benzylamine | N-benzyl-7-azaindol-6-amine | 224.3 |
| P-1292 | cyclopropylmethylamine | N-(cyclopropylmethyl)-7-azaindol-6-amine | 188.2 |
| P-1293 | 3-methoxybenzylamine | N-(3-methoxybenzyl)-7-azaindol-6-amine | 254.3 |
| P-1294 | 3-(trifluoromethyl)benzylamine | N-(3-(trifluoromethyl)benzyl)-7-azaindol-6-amine | 291.9 |
| P-1295 | 2-(trifluoromethyl)benzylamine | N-(2-(trifluoromethyl)benzyl)-7-azaindol-6-amine | 291.9 |
| P-1296 | cyclohexylmethylamine | N-(cyclohexylmethyl)-7-azaindol-6-amine | 230.3 |
| P-1297 | 4-(trifluoromethoxy)benzylamine | N-(4-(trifluoromethoxy)benzyl)-7-azaindol-6-amine | 308.3 |
| P-1298 | 3-(trifluoromethoxy)benzylamine | N-(3-(trifluoromethoxy)benzyl)-7-azaindol-6-amine | 308.3 |
| P-1299 | 2-(trifluoromethoxy)benzylamine | N-(2-(trifluoromethoxy)benzyl)-7-azaindol-6-amine | 308.3 |

-continued

| Compound number | Amine | Compound structure | MS(ESI) [M + H⁺]⁺ observed |
|---|---|---|---|
| P-1300 | (pyridin-2-yl)methanamine | N-(pyridin-2-ylmethyl)-7H-pyrrolo[2,3-b]pyridin-6-amine | 225.1 |
| P-1301 | (4-(methylsulfonyl)phenyl)methanamine | N-(4-(methylsulfonyl)benzyl)-7H-pyrrolo[2,3-b]pyridin-6-amine | 302.3 |
| P-1302 | (4-methoxyphenyl)methanamine | N-(4-methoxybenzyl)-7H-pyrrolo[2,3-b]pyridin-6-amine | 254.3 |
| P-1303 | ethanamine | N-ethyl-7H-pyrrolo[2,3-b]pyridin-6-amine | 162.2 |
| P-1304 | (3-chlorophenyl)methanamine | N-(3-chlorobenzyl)-7H-pyrrolo[2,3-b]pyridin-6-amine | 258.3 |
| P-1305 | (2-(trifluoromethyl)phenyl)methanamine | N-(4-methylbenzyl)-7H-pyrrolo[2,3-b]pyridin-6-amine | 238.3 |
| P-1306 | 1-methylpiperidin-4-amine | N-(1-methylpiperidin-4-yl)-7H-pyrrolo[2,3-b]pyridin-6-amine | 231.1 |
| P-1307 | (pyridin-3-yl)methanamine | N-benzyl-7H-pyrrolo[2,3-b]pyridin-6-amine | 225.1 |
| P-1308 | 4-(morpholinosulfonyl)aniline | N-(4-(morpholinosulfonyl)phenyl)-7H-pyrrolo[2,3-b]pyridin-6-amine | 359.1 |
| P-1309 | 4-(methylsulfonyl)aniline | N-(4-(methylsulfonyl)phenyl)-7H-pyrrolo[2,3-b]pyridin-6-amine | 287.9 |
| P-1310 | (2-chlorophenyl)methanamine | N-(2-chlorobenzyl)-7H-pyrrolo[2,3-b]pyridin-6-amine | 258.3 |

| Compound number | Amine | Compound structure | MS(ESI) [M + H+]+ observed |
|---|---|---|---|
| P-1311 | 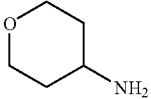 | 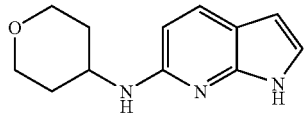 [SMILES: c1cc2ccc(NC3CCOCC3)nc2[nH]1] | 218.3 |
| P-1312 | 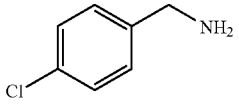 | 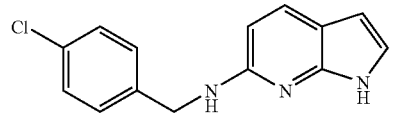 [SMILES: Clc1ccc(CNc2ccc3cc[nH]c3n2)cc1] | 258.3 |
| P-1313 | 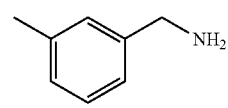 | 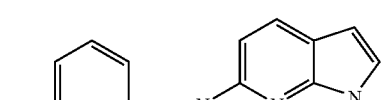 | 238.3 |
| P-1314 | 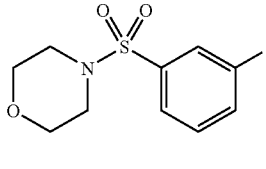 | 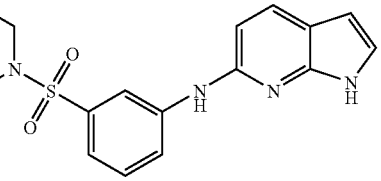 | 359.1 |
| P-1315 | 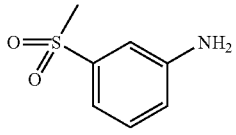 | 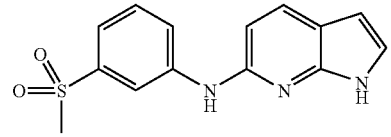 [SMILES: CS(=O)(=O)c1cccc(Nc2ccc3cc[nH]c3n2)c1] | 287.9 |
| P-1351 | 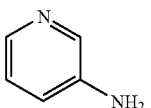 | 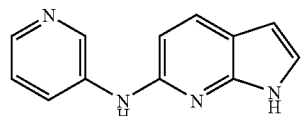 | 211.0 |
| P-1352 | 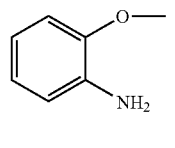 | 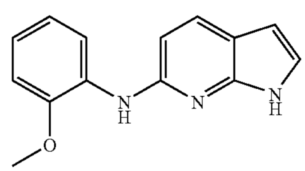 [SMILES: COc1ccccc1Nc1ccc2cc[nH]c2n1] | 240.3 |
| P-1353 | 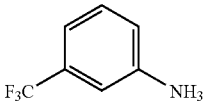 | 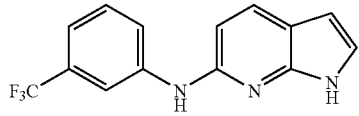 | 278.3 |
| P-1354 | 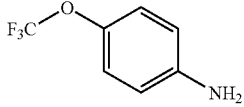 | 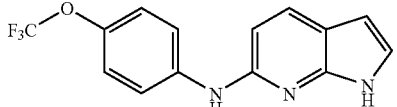 | 293.9 |
| P-1355 | 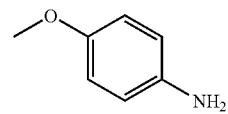 | 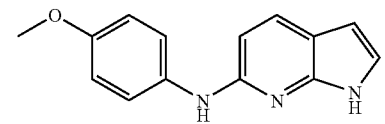 [SMILES: COc1ccc(Nc2ccc3cc[nH]c3n2)cc1] | 240.3 |

-continued
| Compound number | Amine | Compound structure | MS(ESI) [M + H⁺]⁺ observed |
|---|---|---|---|
| P-1356 | 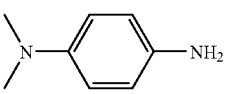 | 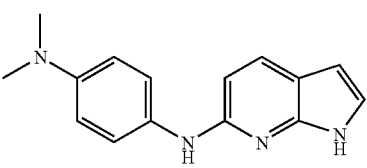 [SMILES: CN(C)c1ccc(Nc2ccc3cc[nH]c3n2)cc1] | 253.1 |
| P-1357 | 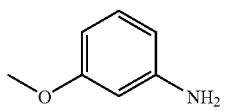 | 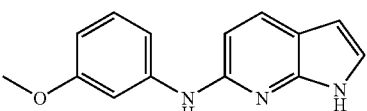 | 240.3 |
| P-1358 | 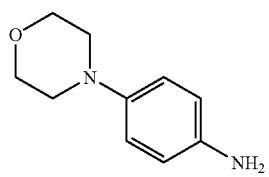 [SMILES: Nc1ccc(N2CCOCC2)cc1] | 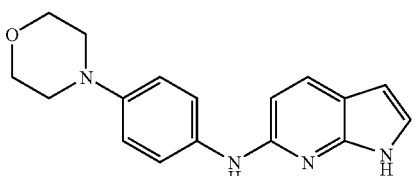 | 295.1 |
| P-1359 | 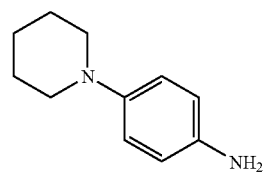 [SMILES: Nc1ccc(N2CCCCC2)cc1] | 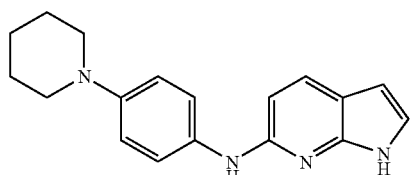 | 293.1 |
| P-1360 | 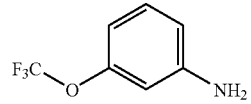 [SMILES: Nc1cccc(OC(F)(F)F)c1] | 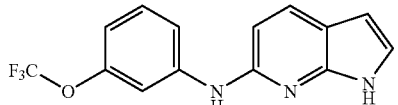 | 293.9 |
| P-1361 | 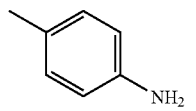 | 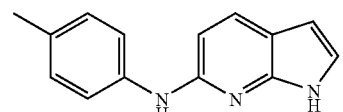 | 224.3 |
| P-1362 | 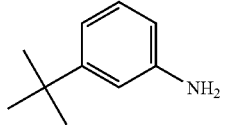 | 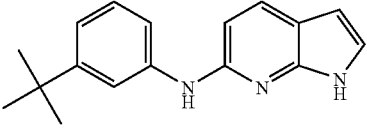 [SMILES: CC(C)(C)c1cccc(Nc2ccc3cc[nH]c3n2)c1] | 266.3 |
| P-1363 | 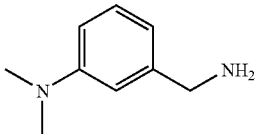 | 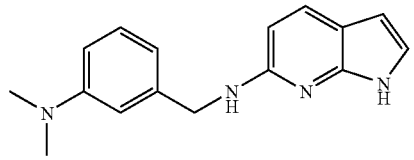 [SMILES: CN(C)c1cccc(CNc2ccc3cc[nH]c3n2)c1] | 267.1 |
| P-1364 | 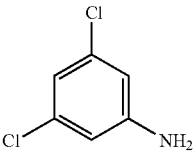 | 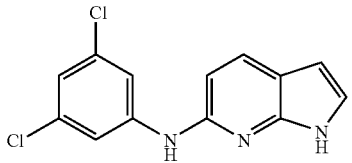 [SMILES: Clc1cc(Cl)cc(Nc2ccc3cc[nH]c3n2)c1] | 278.3 |

-continued
| Compound number | Amine | Compound structure | MS(ESI) [M + H⁺]⁺ observed |
|---|---|---|---|
| P-1371 | 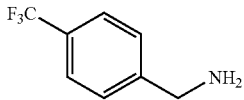 | 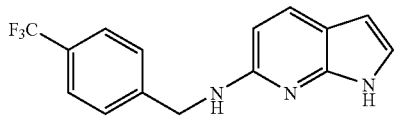 [SMILES: FC(F)(F)c1ccc(CNc2ccc3cc[nH]c3n2)cc1] | 291.9 |
| P-1372 | 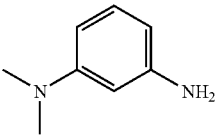 | 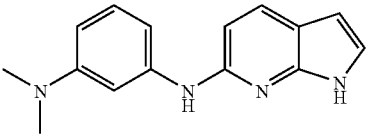 [SMILES: CN(C)c1cccc(Nc2ccc3cc[nH]c3n2)c1] | 253.1 |
| P-1373 | 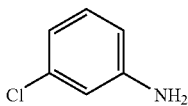 | 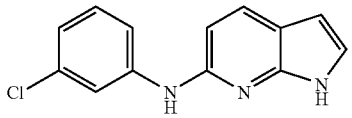 [SMILES: Clc1cccc(Nc2ccc3cc[nH]c3n2)c1] | 244.3 |
| P-1374 | 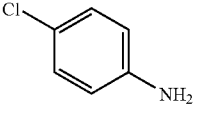 | 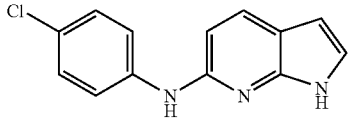 [SMILES: Clc1ccc(Nc2ccc3cc[nH]c3n2)cc1] | 244.3 |
| P-1375 | 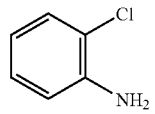 | 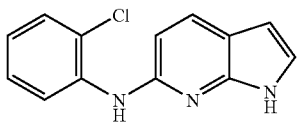 [SMILES: Clc1ccccc1Nc1ccc2cc[nH]c2n1] | 244.3 |
| P-1376 | 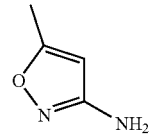 | 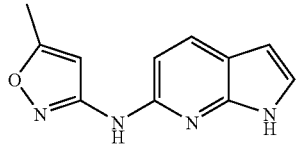 [SMILES: Cc1cc(Nc2ccc3cc[nH]c3n2)no1] | 215.0 |
| P-1377 | 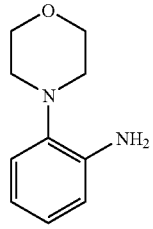 [SMILES: Nc1ccccc1N1CCOCC1] | 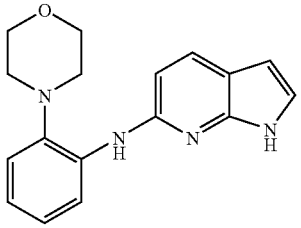 [SMILES: c1ccc(N2CCOCC2)c(Nc2ccc3cc[nH]c3n2)c1] | 295.1 |

| Compound number | Amine | Compound structure | MS(ESI) [M + H⁺]⁺ observed |
|---|---|---|---|
| P-1378 | (2-methylsulfonyl aniline structure) | (2-methylsulfonyl phenyl amino 7-azaindole structure) | 287.9 |

Example 63

Synthesis of 2-[2,4-Difluoro-3-(5-pyridin-3-yl-1H-pyrrolo[2,3-b]pyridin-3-ylmethyl)-phenoxy]-ethanol P-1395 and related compounds Compound P-1395 was synthesized in four steps from 4-Chloro-2-fluoro-phenol 521 as shown in Scheme 42.

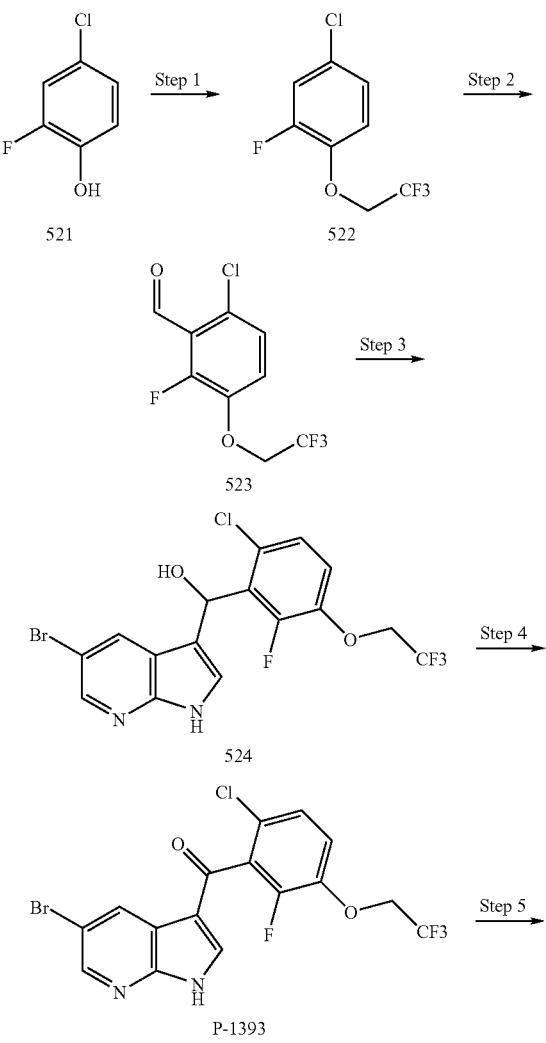

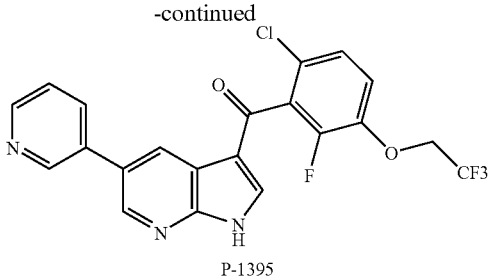

Step 1—Preparation of 4-Chloro-2-fluoro-1-(2,2,2-trifluoro-ethoxy)-benzene (522)

To 4-Chloro-2-fluoro-phenol (521, 5.0 g, 0.034 mol) in methanol (50.0 mL) was added potassium fluoride (2.2 g, 0.038 mol). The solvent was removed. The resulting salt was added to N,N-dimethylformaldehyde (25 mL), followed by adding 1,1,1-trifluoro-2-iodo-ethane (8.60 g, 40.9 mmol). The reaction was stirred at 50° C. overnight. The reaction was poured into water and extracted with ethyl acetate. The organic layer was dried over anhydrous sodium sulfate and filtered. The filtrate was concentrated and purified by silica gel column chromatography eluting with 20% ethyl acetate in hexane to give colorless oil (522, 2.0 g, 26%).

Step 2—Preparation of 6-Chloro-2-fluoro-3-(2,2,2-trifluoro-ethoxy)-benzaldehyde (523)

To 4-Chloro-2-fluoro-1-(2,2,2-trifluoro-ethoxy)-benzene (522, 0.80 g, 3.5 mmol) in THF (20 mL), cooled in dry ice/acetone bath and under an atmosphere of nitrogen, was slowly added n-butyllithium (1.60 M in Hexane, 2.30 mL). After an hour, N,N-dimethylformamide (0.298 mL, 3.85 mmol) was added to the reaction. After 30 minutes, the reaction was allowed to reach room temperature and was stirred for 10 minutes. The reaction was poured into water and extracted with ethyl acetate. The organic layer was dried over anhydrous sodium sulfate and filtered. The filtrate was concentrated and purified by silica gel column chromatography eluting with 20% ethyl acetate in hexane to give the compound (523, 450 mg, 50%).

Step 3—Preparation of (5-Bromo-1H-pyrrolo[2,3-b]pyridin-3-yl)-[6-chloro-2-fluoro-3-(2,2,2-trifluoro-ethoxy)-phenyl]-methanol (524)

To 5-bromo-7-azaindole (67, 291 mg, 1.48 mmol) in methanol mL) were added 6-Chloro-2-fluoro-3-(2,2,2-trifluoro-ethoxy)-benzaldehyde (523, 400.0 mg, 1.6 mmol) and potassium hydroxide (1.49 g, 26.6 mmol) under an atmosphere of nitrogen. The reaction was stirred at room temperature for 48 hours. The reaction was poured into water and extracted with ethyl acetate. The organic layer was dried over anhydrous sodium sulfate and filtered. The filtrate was concentrated and purified by silica gel column chromatography eluting with 25% ethyl acetate in hexane to give the compound (524, 300 mg, 42%). MS (ESI) [M+H$^+$]$^+$=453.1, 455.1.

Step 4—Preparation of (5-Bromo-1H-pyrrolo[2,3-b]pyridin-3-yl)-[6-chloro-2-fluoro-3-(2,2,2-trifluoro-ethoxy)-phenyl]-methanol (P-1393)

To (5-Bromo-1H-pyrrolo[2,3-b]pyridin-3-yl)-[6-chloro-2-fluoro-3-(2,2,2-trifluoro-ethoxy)-phenyl]-methanol (524, 140.0 mg, 0.31 mmol) in trahydrofuran (6.0 mL) was added Dess-Martin periodinane (157 mg, 0.37 mmol). The reaction was stirred at room temperature for 10 minutes. The reaction was poured into water and extracted with ethyl acetate. The organic layer was dried over anhydrous sodium sulfate and filtered. The filtrate was concentrated and purified by silica gel column chromatography eluting with 20% ethyl acetate in hexane to give the compound (P-1393, 100 mg, 72%). MS (ESI) [M−H+]−=448.9, 450.9.

Step 5—Preparation of [6-Chloro-2-fluoro-3-(2,2,2-trifluoro-ethoxy)-phenyl]-(5-pyridin-3-yl-1H-pyrrolo[2,3-b]pyridin-3-yl)-methanone (P-1395)

To (5-Bromo-1H-pyrrolo[2,3-b]pyridin-3-yl)-[6-chloro-2-fluoro-3-(2,2,2-trifluoro-ethoxy)-phenyl]-methanol (P-1393, 53.0 mg, 0.12 mmol) in acetonitrile (4.0 mL) was added Tetrakis(triphenylphosphine)palladium(0) (5.0 mg, 0.0043 mmol), 3-pyridylboronic acid (15.1 mg, 0.12 mmol) and 1 M potassium carbonate solution (1.5 mL). The reaction was microwaved (300 watts) at 160° C. for 7 minutes. The reaction was poured into water and extracted with ethyl acetate. The organic layer was dried over anhydrous sodium sulfate and filtered. The filtrate was concentrated and purified by silica gel column chromatography eluting with 60% ethyl acetate in hexane to give the compound (P-1395, 3.8 mg, 53%) as light yellow solid. MS (ESI) [M+H$^+$]$^+$=450.2.

[2,6-Difluoro-3-(2-methoxy-ethoxy)-phenyl]-(5-pyridin-3-yl-1H-pyrrolo[2,3-b]pyridin-3-yl)-methanone P-1456

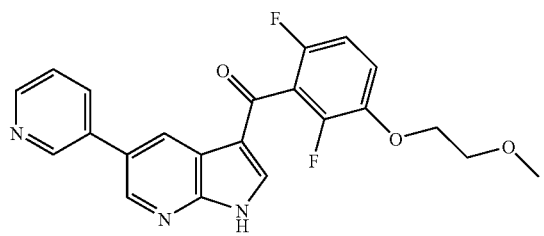 [SMILES: COCCOc1ccc(F)c(C(=O)c2c[nH]c3ncc(-c4cccnc4)cc23)c1F]

was prepared following the protocol of Scheme 42, substituting 4-Chloro-2-fluoro-phenol 521 with 2,4-difluoro-phenol and 1,1,1-Trifluoro-2-iodo-ethane with 1-Bromo-2-methoxy-ethane in Step 1. MS (ESI) [M+H$^+$]$^+$=410.2.

N-(3-{3-[2,6-Difluoro-3-(2-methoxy-ethoxy)-benzoyl]-1H-yrrolo[2,3-b]pyridin-5-yl}-phenyl)-methanesulfonamide P-1472

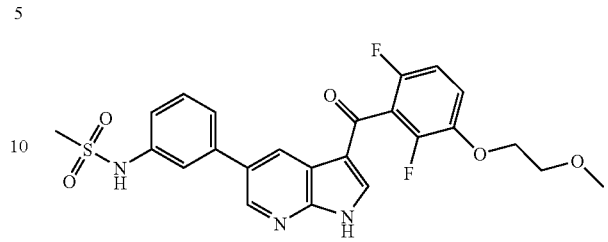

was prepared following the protocol of Scheme 42, substituting 4-Chloro-2-fluoro-phenol 521 with 2,4-difluoro-phenol and 1,1,1-Trifluoro-2-iodo-ethane with 1-Bromo-2-methoxy-ethane in Step 1, and substituting pyridine-3-boronic acid with [(3-methylsulfonyl)aminophenyl]-boronic acid in step 4. MS (ESI) [M+H$^+$]$^+$=502.2.

Example 64

Synthesis of (3,5-Bis-difluoromethoxy-phenyl)-(5-phenyl-1H-pyrrolo[2,3-b]pyridin-3-yl)-methanone P-1521

Compound P-1521 was synthesized in four steps from 3,5-Dihydroxy-benzaldehyde 528 as shown in Scheme 44.

Scheme 44

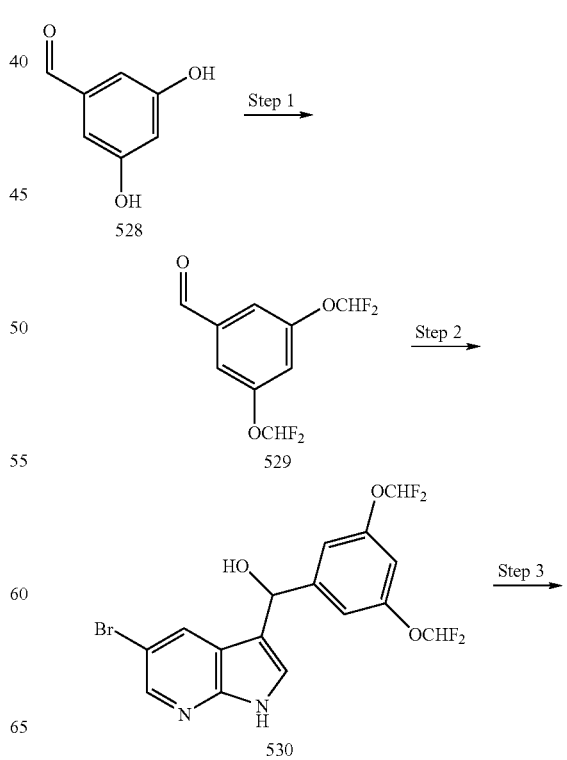

-continued

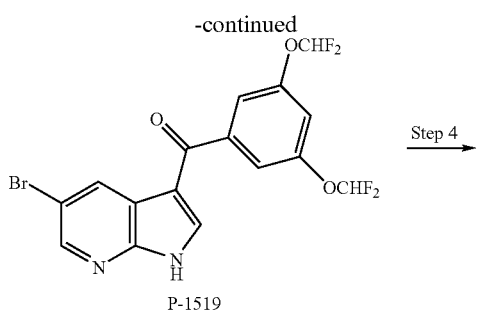

P-1519

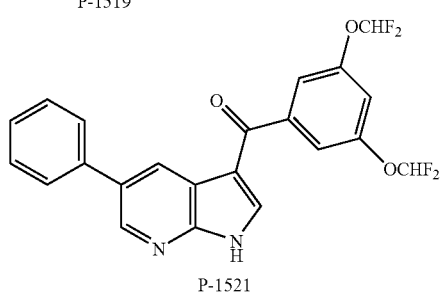

P-1521

Step 1—Preparation of 3,5-Bis-difluoromethoxy-benzaldehyde (529)

To 3,5-Dihydroxy-benzaldehyde (528, 1.50 g, 10.9 mmol) in N,N-Dimethylformamide (100 mL) were added sodium chlorodifluoroacetate (5.90 g, 0.0387 mol), potassium carbonate (6.20 g, 0.0448 mol) and water (10 mL) under an atmosphere of nitrogen. The reaction was stirred at 100° C. overnight. The reaction was poured into water and extracted with ethyl acetate. The organic layer was dried over anhydrous sodium sulfate and filtered. The filtrate was concentrated and purified by silica gel column chromatography eluting with 20% ethyl acetate in hexane to give the compound as colorless oil (529, 50 mg, 2%).

Step 2—Preparation of (3,5-Bis-difluoromethoxy-phenyl)-(5-bromo-1H-pyrrolo[2,3-b]pyridin-3-yl)-methanol (530)

To 5-bromo-7-azaindole (67, 86.4 mg, 0.000438 mol) methanol (10.0 mL) were added 3,5-bis-difluoromethoxy-benzaldehyde (529, 110.0 mg, 0.46 mmol) and potassium hydroxide (200.0 mg, 3.6 mmol) under art atmosphere of nitrogen. The reaction was stirred at room temperature overnight. The reaction was poured into water and extracted with ethyl acetate. The organic layer was dried over anhydrous sodium sulfate and filtered. The filtrate was concentrated and purified by silica gel column chromatography eluting with 20% ethyl acetate in hexane to give the compound as a white solid (530, 70 mg, 35%). MS (ESI) [M+H$^+$]$^+$=435.1, 437.1.

Step 3—Preparation of (3,5-Bis-difluoromethoxy-phenyl)-(5-bromo-1H-pyrrolo[2,3-b]pyridin-3-yl)-methanone (P-1519)

To (3,5-Bis-difluoromethoxy-phenyl)-(5-bromo-1H-pyrrolo[2,3-b]pyridin-3-yl)-methanol (530, 70.0 mg, 0.16 mmol) in tetrahydrofuran (6.0 mL) was added Dess-Martin periodinane (75.0 mg, 0.18 mmol). The reaction was stirred at room temperature for 10 minutes. The reaction mixture was concentrated with silica gel and purified with silica gel column chromatography eluting with 30% ethyl acetate in hexane to give the compound as a white solid (P-1519, 65.0 mg, 93%.). MS (ESI) [M−H$^+$]$^-$=431.0, 433.0.

Step 4—Preparation of (3,5-Bis-difluoromethoxy-phenyl)-(5-phenyl-1H-pyrrolo[2,3-b]pyridin-3-yl)-methanone (P-1521)

To (3,5-Bis-difluoromethoxy-phenyl)-(5-bromo-1H-pyrrolo[2,3-b]pyridin-3-yl)-methanone (P-1519, 29.0 mg, 0.067 mmol) in acetonitrile (4.0 mL) were added phenylboronic acid (12.2 mg, 0.10 mmol), Tetrakis(triphenylphosphine)palladium(0) (10.0 mg, 8.65E-6 mol) and 1.0 M potassium carbonate in water (1.5 mL). The reaction was microwaved (300 watts) at 160° C. for 7 minutes. The reaction mixture was poured into water and extracted with ethyl acetate. The organic layer was washed with brine, dried over sodium sulfate, concentrated, and purified with silica gel column chromatography to give the compound as a white solid (P-1521, 9.4 mg, 33%). MS (ESI) [M+H$^+$]$^+$=431.2.

(5-Bromo-1H-pyrrolo[2,3-b]pyridin-3-yl)-(3-difluoromethoxy-2,6-difluoro-phenyl)-methanone P-1526

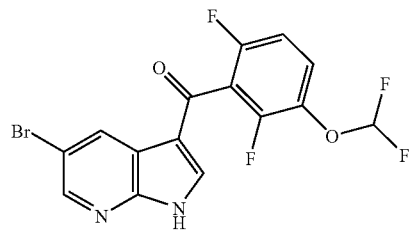 [SMILES: O=C(c1c(F)ccc(OC(F)F)c1F)c1c[nH]c2ncc(Br)cc12]

was prepared using Steps 1-3 of Scheme 44 by substituting 3,5-Dihydroxy-benzaldehyde 528 with N-2,4-Difluoro-phenol in Step 1. MS (ESI) [M+H$^+$]$^+$=401.0, 403.0.

Example 65

Synthesis of N-Benzyl-2-[2,4-difluoro-3-(5-pyridin-3-yl-1H-pyrrolo[2,3-b]pyridin-3-ylmethyl)-phenoxy]-acetamide P-1469

Compound P-1469 was synthesized in four steps from 3-(3-Benzyloxy-2,6-difluoro-benzyl)-5-pyridin-3-yl-1H-pyrrolo[2,3-b]pyridine P-1455 as shown in Scheme 46.

Scheme 46

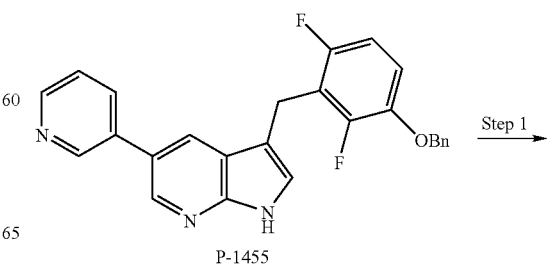

P-1455

Step 1

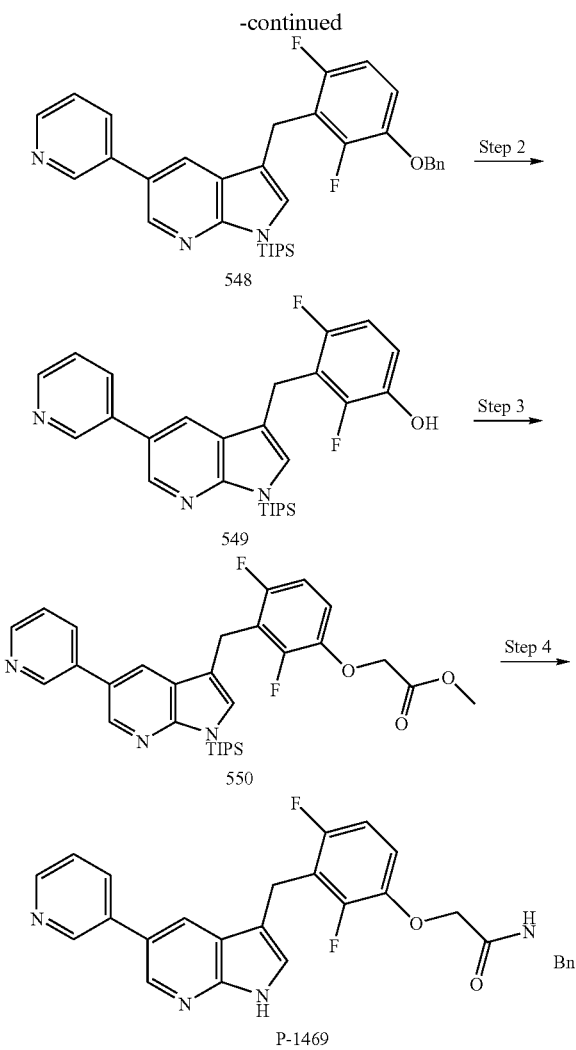

Pd(OH)$_2$/C (50 mg). The reaction was stirred under an atmosphere of hydrogen for 2 hours. Filtration and concentration gave the compound as white solid (549, 427 mg, 99%).

Step 3—Preparation of [2,4-Difluoro-3-(5-pyridin-3-yl-1-triisopropylsilanyl-1H-pyrrolo[2,3-b]pyridin-3-ylmethyl)-phenoxy]-acetic acid methyl ester (550)

To 2,4-Difluoro-3-(5-pyridin-3-yl-1-triisopropylsilanyl-1H-pyrrolo[2,3-b]pyridin-3-ylmethyl)-phenol (549, 427.0 mg, 0.87 mmol) in tetrahydrofuran (20.0 mL) was added sodium hydride (60% in mineral oil, 42.0 mg, 1.1 mmol). 30 minutes later, methyl bromoacetate (146 mg, 0.95 mmol) was added to the reaction. The reaction was stirred at room temperature for 4 hours. The reaction was poured into water and extracted with ethyl acetate. The organic layer was dried over anhydrous sodium sulfate and filtered. The filtrate was concentrated to give the crude compound that was used directly in the next step.

Step 4—Preparation of N-Benzyl-2-[2,4-difluoro-3-(5-pyridin-3-1H-pyrrolo[2,3-b]pyridin-3-ylmethyl)-phenoxy]-acetamide (P-1469)

To [2,4-Difluoro-3-(5-pyridin-3-yl-1-triisopropylsilanyl-1H-pyrrolo[2,3-b]pyridin-3-ylmethyl)-phenoxy]-acetic acid methyl ester (550, 210.0 mg, 0.37 mmol) in methanol (6.0 mL) was added benzylamine (0.45 mL, 4.1 mmol). The reaction was stirred at room temperature for 80 hours. To the reaction was added TBAF (0.31 g. 1.0 mmol). The reaction was concentrated and purified with silical gel column chromatography eluting with 10% methanol in methylene chloride to give the compound as a white solid (P4469, 60 mg, 33%). MS (ESI) [M+H$^+$]$^+$=423.3:

2-[2,4-Difluoro-3-(5-pyridin-3-yl-1H-pyrrolo[2,3-b]pyridin-3-ylmethyl)-phenoxy]-N-ethyl-acetamide P-1475

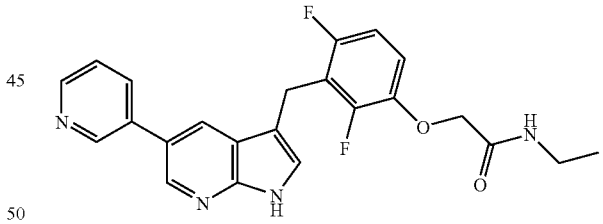

was prepared using the same protocol as Scheme 46 by substituting benzylamine with ethylamine in Step 4. MS (ESI) [M+H$^+$]$^+$=423.3.

Step 1—Preparation of 3-(3-Benzyloxy-2,6-difluoro-benzyl)-5-pyridin-3-yl-1-triisopropylsilanyl-1H-pyrrolo[2,3-b]pyridine (548)

To 3-(3-Benzyloxy-2,6-difluoro-benzyl)-5-pyridin-3-yl-1H-pyrrolo[2,3-b]pyridine (P-1455, 700.0 mg, 1.64 mmol, prepared as described in Example 24, Scheme 43a) in tetrahydrofuran (40.0 mL) was added sodium hydride (60% in mineral oil, 100.0 mg, 2.5 mmol). After 10 minutes, triisopropylsilyl chloride (0.60 mL, 0.0028 mol) was added to the reaction. The reaction was stirred at room temperature for 2 hours. The reaction was poured into water and extracted with ethyl acetate. The organic layer was dried over anhydrous sodium sulfate and filtered. The filtrate was concentrated and purified by silica gel column chromatography eluting with 20% ethyl acetate in hexane to eive the compound as colorless oil (548, 0.85 g, 89%).

Step 2—Preparation of 2,4-Difluoro-3-(5-pyridin-3-yl-1-triisopropylsilanyl-1H-pyrrolo[2,3-b]pyridin-3-ylmethyl)-phenol (549)

To 3-(3-Benzyloxy-2,6-difluoro-benzyl)-5-pyridin-3-yl-1-triisopropylsilanyl-1H-pyrrolo[2,3-b]pyridine (548, 510.0 mg, 0.87 mmol) in methanol (20.0 mL) was added 20%

Example 66

Synthesis of [2,4-difluoro-3-(5-pyridin-3-yl-1H-pyrrolo[2,3-b]pyridin-3-ylmethyl)-phenoxy]-acetic acid P-1468

Compound P-1468 was synthesized in two steps from [2,4-Difluoro-3-(5-pyridin-3-yl-1-triisopropylsilanyl-1H-pyrrolo[2,3-b]pyridin-3-ylmethyl)-phenoxy]-acetic acid methyl ester 550 as shown in Scheme 47.

583

Scheme 47

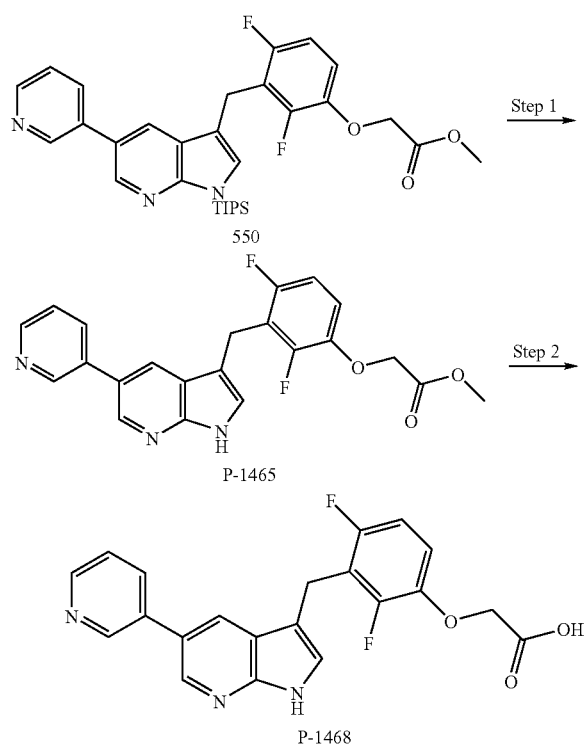

Step 1—Preparation of [2,4-Difluoro-3-(5-pyridin-3-yl-1H-pyrrolo[2,3-b]pyridin-3-ylmethyl)-phenoxy]-acetic acid methyl ester (P4465)

To [2,4-Difluoro-3-(5-pyridin-3-yl-1-triisopropylsilanyl-1H-pyrrolo[2,3-b]pyridin-3-ylmethyl)-phenoxy]-acetic acid methyl ester (550, 40.0 mg, 0.071 mmol, prepared as described in Example 65, Scheme 46) in tetrahydrofuran (5.0 mL) was added tetra-n-butylammonium fluoride (22.2 mg, 0.085 mmol). The reaction was stirred at room temperature for 10 minutes. The crude compound was concentrated with silica gel and purified by silica gel column chromatography eluting with 3% methanol in methylene chloride to give the compound as white solid (P-1465, 20 mg, 69%). MS (ESI) $[M+H^+]^+=410.2$.

Step 2—Preparation of [2,4-Difluoro-3-(5-pyridin-3-yl-1H-pyrrolo[2,3-b]pyridin-3-ylmethyl)-phenoxy]-acetic acid (P-1468)

To [2,4-Difluoro-3-(5-pyridin-3-yl-1H-pyrrolo[2,3-b]pyridin-3-ylmethyl)-phenoxy]-acetic acid methyl ester (P-1465, 20.0 mg, 0.049 mmol) in tetrahydrofuran (8.0 mL) were added potassium hydroxide (100.0 mg, 1.8 mmol) and water (3.0 mL). The reaction was stirred at room temperature overnight and then poured into water, acidified to pH=5 with 1 N HCl, and extracted with ethyl acetate. The organic layer was dried over anhydrous sodium sulfate and filtered. The filtrate was concentrated and purified by silica gel column chromatography eluting with 10% methanol in methylene chloride to give the compound as light yellow solid (P-1468, 9.1 mg, 47%). MS (ESI) $[M+H^+]^+=396.2$.

584

Example 67

Synthesis of 2-[2,4-Difluoro-3-(5-pyridin-3-yl-1H-pyrrolo[2,3-b]pyridin-3-ylmethyl)-phenoxy]-ethanol P-1394

Compound P-1394 was synthesized in four steps from 2,6-Difluoro-3-hydroxy-benzaldehyde 540 as shown in Scheme 48.

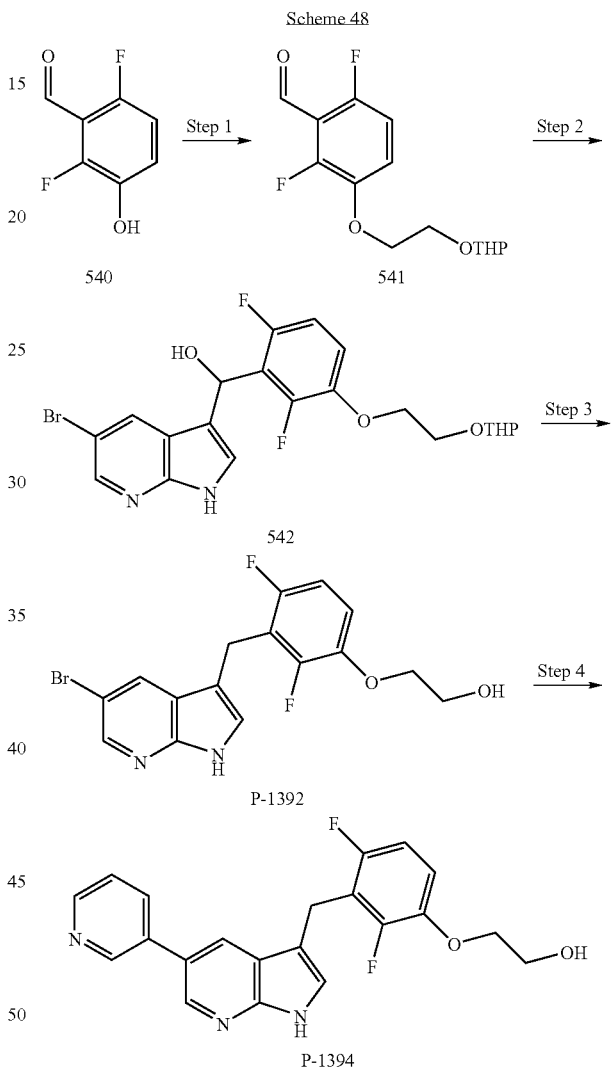

Step 1—Preparation of 2,6-Difluoro-3-[2-(tetrahydro-pyran-2-yloxy)-ethoxy]-benzaldehyde (541)

To 2,6-difluoro-3-hydroxy-benzaldehyde (540, 0.150 g, 0.95 mmol) in N,N-dimethylformamide (8.0 mL) were added 2-(2-bromo-ethoxy)-tetrahydro-pyran (0.218 g, 1.04 mmol) and potassium carbonate (0.52 g, 3.8 mmol) under an atmosphere of nitrogen. The reaction was stirred at room temperature for 72 hours. The reaction was poured into water and extracted with ethyl acetate. The organic layer was dried over anhydrous sodium sulfate and filtered. The filtrate was concentrated and purified by silica gel column chromatography eluting with 20% ethyl acetate in hexane to give the compound as colorless oil (541, 180 mg, 66%).

Step 2—Preparation of (5-Bromo-1H-pyrrolo[2,3-b]pyridin-3-yl)-2,6-difluoro-3-[2-(tetrahydro-pyran-2-yloxy)-ethoxy]-phenyl-methanol (542)

To 5-bromo-7-azaindole (67, 118 mg, 0.000597 mol) in methanol (9.0 mL) were added 2,6-difluoro-3-[2-(tetrahydro-pyran-2-yloxy)-ethoxy]-benzaldehyde (541, 180.0 mg, 0.63 mmol) and potassium hydroxide (601.9 mg, 10.7 mmol) under an atmosphere of nitrogen. The reaction was stirred at room temperature overnight. The reaction was poured into water and extracted with ethyl acetate. The organic layer was dried over anhydrous sodium sulfate and filtered. The filtrate was concentrated to give crude compound that was used directly in the next step.

Step 3—Preparation of 2-[3-(5-Bromo-1H-pyrrolo[2,3-b]pyridin-3-ylmethyl)-2,4-difluoro-phenoxy]-ethanol (P-1392)

To (5-Bromo-1H-pyrrolo[2,3-b]pyridin-3-yl)-2,6-difluoro-3-[2-(tetrahydro-pyran-2-yloxy)-ethoxy]-phenyl-methanol (542, 0.22 g, 0.46 mmol) in acetonitrile (6.0 mL) were added trifluoroacetic acid (0.14 mL, 1.8 mmol) and triethylsilane (0.29 mL, 1.8 mmol). The reaction was stirred at room temperature overnight. The filtrate was concentrated and purified by silica gel column chromatography eluting with 35% ethyl acetate in hexane to give the compound as a white solid (P-1392, 62 mg, 35%). MS (M+H$^+$)$^+$=383.1, 385.1.

Step 4—Preparation of 2-[2,4-Difluoro-3-(5-pyridin-3-yl-1H-pyrrolo[2,3-b]pyridin-3-ylmethyl)-phenoxy]-ethanol (P-1394)

To 2-[3-(5-Bromo-1H-pyrrolo[2,3-b]pyridin-3-ylmethyl)-2,4-difluoro-phenoxy]-ethanol (P-1392, 35.0 mg, 0.091 mmol) in acetonitrile (4.0 mL) were added 3-pyridylboronic acid (14.6 mg, 0.12 mmol), tetrakis(triphenylphosphine)palladium(0) (3.0 mg, 0.0026 mmol) and 1 M potassium carbonate solution (1.5 mL). The reaction was microwaved (300 watts) at 160° C. for 7 minutes. The reaction was poured into water and extracted with ethyl acetate. The organic layer was collected and dried over anhydrous sodium sulfate and filtered. The filtrate was concentrated and purified by silica gel column chromatography eluting 4% methanol in methylene chloride to give the compound as white solid (P-1394, 11.0 mg, 32%). MS (ESI) [M+H$^+$]$^+$=382.2.

Example 68

Synthesis of 3-[4-methoxy-3-(2,2,2-trifluoro-ethoxy)-benzyl]-1H-pyrrolo[2,3-b]pyridine P-1626

Compound P-1626 was synthesized in three steps from 3-hydroxy-4-methoxy-benzaldehyde 560 as shown in Scheme 52.

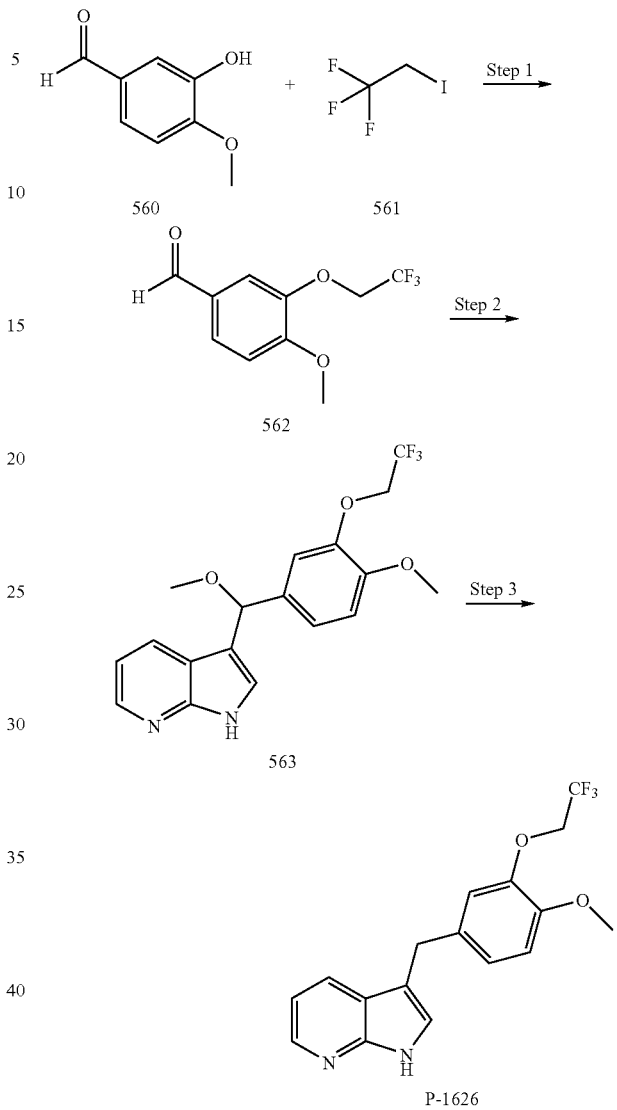

Scheme 52

Step 1—Preparation of 4-Methoxy-3-(2,2,2-trifluoro-ethoxy)-benzaldehyde (562)

3-Hydroxy-4-methoxy-benzaldehyde (560, 2.9 g, 19.5 mmol), 2-iodo-1,1,1-trifluoroethane (561, 2.2 mL, 23 mmol), and potassium carbonate (3.7 g, 27 mmol) were dissolved in N,N-dimethylformamide (100 mL). The solution was stirred at 90° C. overnight under an atmosphere of nitrogen. The reaction was poured into water, extracted with ethyl acetate, and washed with brine. The organic layer was dried over anhydrous sodium sulfate, filtered and concentrated. The compound was isolated by silica gel column chromatography eluting with 25% to 50% ethyl acetate in hexanes to give white powder (562, 1.6 g, 40%).

Step 2—Preparation of 3-Methoxy-[4-methoxy-3-(2,2,2-trifluoro-ethoxy)-phenyl]-methyl-1H-pyrrolo[2,3-b]pyridine (563)

1H-Pyrrolo[2,3-b]pyridine (0.2 g, 1.8 mmol), 4-methoxy-3-(2,2,2-trifluoro-ethoxy)-benzaldehyde (562, 0.4 g, 1.9 mmol) and potassium hydroxide (0.5 g, 9.6 mmol) were combined in methanol (20 mL). The reaction was heated to 50° C. under an atmosphere of nitrogen and stirred for two days. The reaction was poured into water, extracted with ethyl acetate, and washed with brine. The organic layer was dried over anhydrous sodium sulfate, filtered and concentrated. The compound was isolated by silica gel column chromatography eluting with 40% to 75% ethyl acetate in hexanes to give orange oil (563, 0.2 g, 31%). MS (ESI) [M+H$^+$]$^+$=367.2 [M−H$^+$]$^−$=365.1.

Step 3—Preparation of 3-[4-Methoxy-3-(2,2,2-trifluoro-ethoxy)-benzyl]-1H-pyrrolo[2,3-b]pyridine (P-1626)

3-methoxy-[4-methoxy-3-(2,2,2-trifluoro-ethoxy)-phenyl]-methyl-1H-pyrrolo[2,3-b]pyridine (563) was reacted using the same protocol described in Example 28, Scheme 51, Step 3. The compound P-1626 was isolated by silica gel column chromatography eluting with 50% to 75% ethyl acetate in hexanes. MS (ESI) [M+H$^+$]$^+$=337.1.

Example 69

Synthesis of N-phenyl-1H-pyrrolo[2,3-b]pyridin-3-amine P-0221

Compound P-0221 was synthesized in two or three steps from 1H-pyrrolo[2,3-b]pyridine 94 as shown in Scheme 54.

Scheme 54

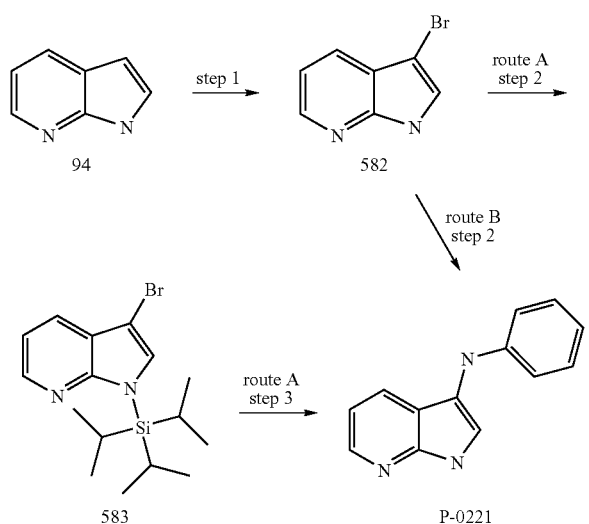

Step 1—Preparation of 3-bromo-1H-pyrrolo[2,3-b]pyridine (582)

To 1H-pyrrolo[2,3-b]pyridine (94, 600 mg) dissolved in 10 mL of 100% acetic acid was added the brominating agent DMAP-Br$_3$ (1.001 equiv.). The reaction was heated at 75° C. until the orange color was gone and a precipitate formed (about 60 min). It was dissolved with 50 mL of water (ppt dissolved) and adjusted to pH 8 with NaHCO$_3$ (aq. sat'd). The compound precipitated from the solution and was collected. The aqueous fraction was extracted with 3×30 mL with ethyl acetate. The combined organics were dried over Na$_2$SO$_4$, evaporated and the solids combined with the previously collected solid (582, 87%).

Route A: Step 2—3-bromo-1-(triisopropylsilyl)-1H-pyrrolo[2,3-b]pyridine (583)

To 3-bromo-1H-pyrrolo[2,3-b]pyridine (582, 0.5 mmol) dissolved in 5 mL of dry dioxane was added HEMP (2.5 equiv): The TIPS-OTf (2.0 equiv) was then added and the reaction was stirred overnight (15 hours). The solution was diluted with 20 mL of ethyl acetate and washed with 5% acetic acid (2×10 mL), water (2×10 mL), and brine (10 mL). The organic layer was dried over Na$_2$SO$_4$, filtered, evaporated and dried under vacuum: This material was used without further purification.

Route A: Step 3—Preparation of N-phenyl-1H-pyrrolo[2,3-b]pyridin-3-amine (P-0221)

A 1 dram vial was charged with aniline (2-3 equiv), and 10 mg of 3-bromo-1-(triisopropylsilyl)-1H-pyrrolo[2,3-b]pyridine 583 in 0.4 mL toluene (dry, degassed). A catalyst stock solution containing 3 mmol Pd(OAc)$_2$, 3 mmol biphenyl-2-yl-di-tert-butyl-phosphane and 15 mL of toluene was prepared. To the reaction mixture, 0.050 mL of the catalyst solution was added. Excess NaOtBu was added as a solid to the reaction. The vial was then placed in a 75° C. oven for 60 minutes (shaken several times over an hour). After cooling, the reaction was neutralized with 0.100 mL of TFA. After 30 minutes the sample was evaporated and re-solvated in 0.300 mL of DMSO. The desired compound was isolated by preparative HPLC/MS.

Rout B. Step 2—Preparation of N-phenyl-1H-pyrrolo[2,3-b]pyridin-3-amine (P-0221)

To 10 mg of 3-bromo-1H-pyrrolo[2,3-b]pyridine 582 was added 0.4 mL of sulfolane and aniline (2-3 equiv). The vial was scaled and heated at 180° C. for 10 minutes. After cooling, the desired compound was isolated by preparative HPLC/MS.

The following compounds were prepared by one of the procedures described in scheme 54, substituting aniline with a suitable amine in Step 5:
  Methyl-phenyl-(1H-pyrrolo[2,3-b]pyridin-3-yl)-amine (P-1434),
  4-[Methyl-(1H-pyrrolo[2,3-b]pyridin-3-yl)-amino]-benzoic acid (P-1435),
  (4-Chloro-phenyl)-methyl-(1H-pyrrolo[2,3-b]pyridin-3-yl)-amine (P-1436),
  Methyl-(1H-pyrrolo[2,3-b]pyridin-3-yl)-m-tolyl-amine (P-1437),
  (4-Methoxy-phenyl)-methyl-(1H-pyrrolo[2,3-b]pyridin-3-yl)-amine (P-1438),
  (3-Chloro-phenyl)-methyl-(1H-pyrrolo[2,3-b]pyridin-3-yl)-amine (P-1439),
  (4-Fluoro-phenyl)-methyl-(1H-pyrrolo[2,3-b]pyridin-3-yl)-amine (P-1440),
  Methyl-(1H-pyrrolo[2,3-b]pyridin-3-yl)-(4-trifluoromethoxy-phenyl)-amine (P-1441),
  (2,4-Difluoro-phenyl)-methyl-(1H-pyrrolo[2,3-b]pyridin-3-yl)-amine (P-1442),
  (3-Fluoro-phenyl)-methyl-(1H-pyrrolo[2,3-b]pyridin-3-yl)-amine (P-1443), (4-Methoxy-phenyl)-(1H-pyrrolo[2,3-b]pyridin-3-yl)-amine (P-1488),
(3-Chloro-phenyl)-(1H-pyrrolo[2,3-b]pyridin-3-yl)-amine (P-1489),
(3-Methoxy-phenyl)-(1H-pyrrolo[2,3-b]pyridin-3-yl)-amine (P-1490),
(4-Chloro-phenyl)-(1H-pyrrolo[2,3-b]pyridin-3-yl)-amine (P-1491),
(1H-Pyrrolo[2,3-b]pyridin-3-yl)-(4-trifluoromethoxy-phenyl)-amine (P-1492),
(1H-Pyrrolo[2,3-b]pyridin-3-yl)-(3-trifluoromethoxy-phenyl)-amine (P-1493),
(3,4-Dichloro-phenyl)-methyl-(1H-pyrrolo[2,3-b]pyridin-3-yl)-amine (P-1494),
(4-Phenoxy-phenyl)-(1H-pyrrolo[2,3-b]pyridin-3-yl)-amine (P-1495),
(3-Phenoxy-phenyl)-(1H-pyrrolo[2,3-b]pyridin-3-yl)-amine (P-1496),
(3-Benzyl-phenyl)-(1H-pyrrolo[2,3-b]pyridin-3-yl)-amine (P-1497),
N-[3-(1H-Pyrrolo[2,3-b]pyridin-3-ylamino)-phenyl]-methanesulfonamide (P-1498),
3-Fluoro-4-(1H-pyrrolo[2,3-b]pyridin-3-ylamino)-phenol (P-1499),
3-(1H-Pyrrolo[2,3-b]pyridin-3-ylamino)-benzene-sulfonamide (P-1500),
(2-Phenoxy-phenyl)-(1H-pyrrolo[2,3-b]pyridin-3-yl)-amine (P-1501),
(3,5-Dichloro-phenyl)-(1H-pyrrolo[2,3-b]pyridin-3-yl)-amine (P-1502),
(3,5-Dimethoxy-phenyl)-(1H-pyrrolo[2,3-b]pyridin-3-yl)-amine (P-1503),
[3-(4-Methyl-4H-[1,2,4]triazol-3-yl)-phenyl]-(1H-pyrrolo[2,3-b]pyridin-3-yl)-amine (P-1504),
(2-Benzyloxy-phenyl)-(1H-pyrrolo[2,3-b]pyridin-3-yl)-amine (P-1505), and
(3-Methoxy-phenyl)-methyl-(1H-pyrrolo[2,3-b]pyridin-3-yl)-amine (P-1506).

The following table indicates the amine (Column 2) that is substituted in place of the aniline in Route B, Step 2, or Route A, Step 3, to afford the compounds (Column 3). Column 1 provides the compound number and Column 4 the observed mass.

| Compound number | Amine | Compound structure | MS(ESI) $[M + H^+]^+$ observed |
|---|---|---|---|
| P-1434 | | 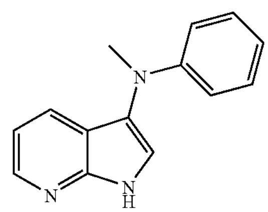 [SMILES: CN(c1ccccc1)c1c[nH]c2ncccc12] | 224.3 |
| P-1435 | | 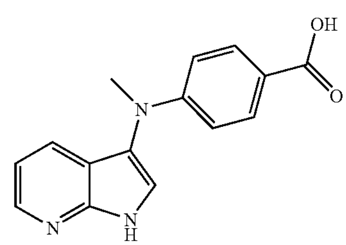 [SMILES: CN(c1ccc(C(=O)O)cc1)c1c[nH]c2ncccc12] | 268.3 |
| P-1436 | | 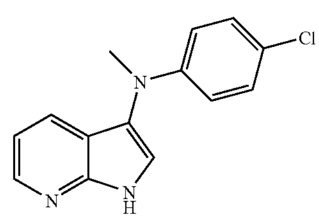 [SMILES: CN(c1ccc(Cl)cc1)c1c[nH]c2ncccc12] | 258.3 |
| P-1437 | | 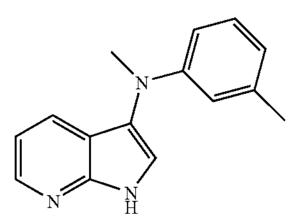 [SMILES: Cc1cccc(N(C)c2c[nH]c3ncccc23)c1] | 237.9 |

-continued

| Compound number | Amine | Compound structure | MS(ESI) [M + H⁺]⁺ observed |
|---|---|---|---|
| P-1438 | | 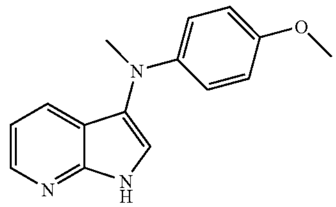 [SMILES: COc1ccc(N(C)c2c[nH]c3ncccc23)cc1] | 254.3 |
| P-1439 | | 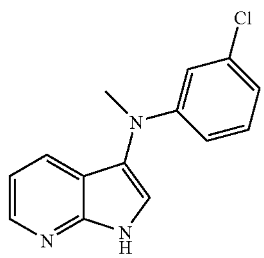 [SMILES: CN(c1cccc(Cl)c1)c1c[nH]c2ncccc12] | 258.3 |
| P-1440 | | 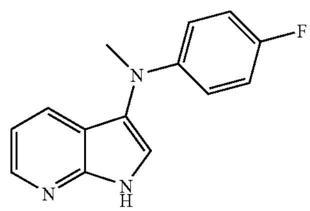 [SMILES: CN(c1ccc(F)cc1)c1c[nH]c2ncccc12] | 242.3 |
| P-1441 | | 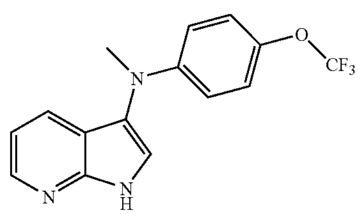 [SMILES: CN(c1ccc(OC(F)(F)F)cc1)c1c[nH]c2ncccc12] | 308.3 |
| P-1442 | | 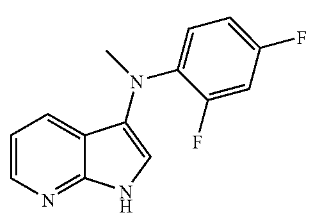 [SMILES: CN(c1ccc(F)cc1F)c1c[nH]c2ncccc12] | 260.3 |
| P-1443 | | 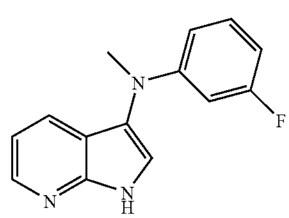 [SMILES: CN(c1cccc(F)c1)c1c[nH]c2ncccc12] | 242.3 |
| P-1488 | | 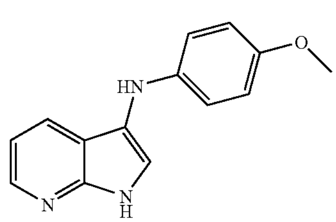 [SMILES: COc1ccc(Nc2c[nH]c3ncccc23)cc1] | 239.9 |

-continued

| Compound number | Amine | Compound structure | MS(ESI) [M + H⁺]⁺ observed |
|---|---|---|---|
| P-1489 | 3-chloroaniline | 3-(3-chlorophenylamino)-7-azaindole | 244.3 |
| P-1490 | 3-methoxyaniline | 3-(3-methoxyphenylamino)-7-azaindole | 240.3 |
| P-1491 | 4-chloroaniline | 3-(4-chlorophenylamino)-7-azaindole | 244.3 |
| P-1492 | 4-trifluoromethoxyaniline | 3-(4-trifluoromethoxyphenylamino)-7-azaindole | 293.9 |
| P-1493 | 3-trifluoromethoxyaniline | 3-(3-trifluoromethoxyphenylamino)-7-azaindole | 293.9 |
| P-1494 | 3,4-dichloro-N-methylaniline | 3-((3,4-dichlorophenyl)(methyl)amino)-7-azaindole | 291.9 |
| P-1495 | 4-phenoxyaniline | 3-(4-phenoxyphenylamino)-7-azaindole | 302.3 |

| Compound number | Amine | Compound structure | MS(ESI) [M + H⁺]⁺ observed |
|---|---|---|---|
| P-1496 | | 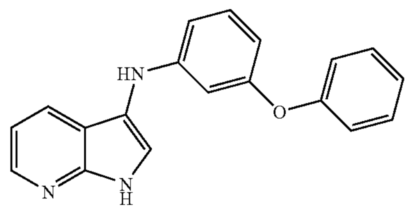 [SMILES: c1ccc(Oc2cccc(Nc3c[nH]c4ncccc34)c2)cc1] | 302.3 |
| P-1497 | | 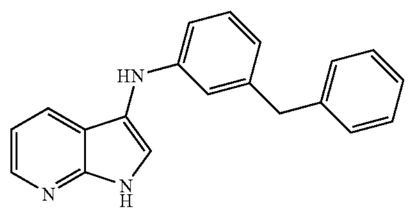 [SMILES: c1ccc(Cc2cccc(Nc3c[nH]c4ncccc34)c2)cc1] | 300.3 |
| P-1498 | | 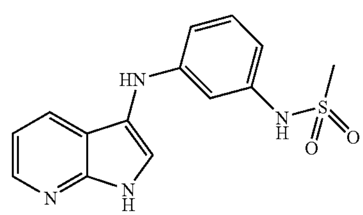 [SMILES: CS(=O)(=O)Nc1cccc(Nc2c[nH]c3ncccc23)c1] | 303.1 |
| P-1499 | | 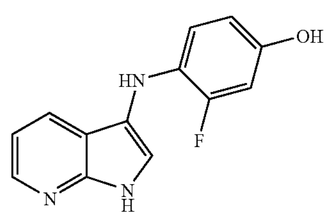 [SMILES: Oc1ccc(Nc2c[nH]c3ncccc23)c(F)c1] | 244.3 |
| P-1500 | | 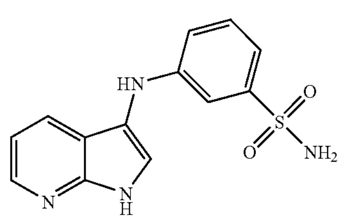 [SMILES: NS(=O)(=O)c1cccc(Nc2c[nH]c3ncccc23)c1] | 289.1 |
| P-1501 | | 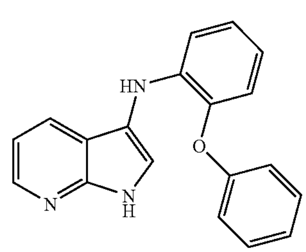 [SMILES: c1ccc(Oc2ccccc2Nc2c[nH]c3ncccc23)cc1] | 302.3 |

-continued
| Compound number | Amine | Compound structure | MS(ESI) [M + H⁺]⁺ observed |
|---|---|---|---|
| P-1502 | 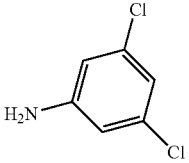 | 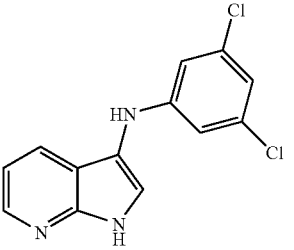 [SMILES: Clc1cc(Cl)cc(Nc2c[nH]c3ncccc23)c1] | 277.9 |
| P-1503 | 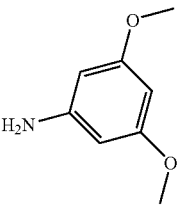 | 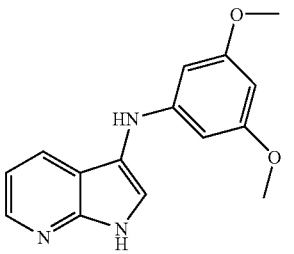 [SMILES: COc1cc(Nc2c[nH]c3ncccc23)cc(OC)c1] | 270.3 |
| P-1504 | 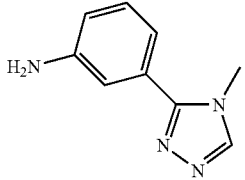 | 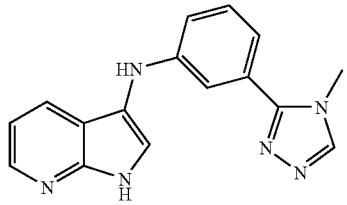 [SMILES: Cn1cnnc1-c1cccc(Nc2c[nH]c3ncccc23)c1] | 291.1 |
| P-1505 | 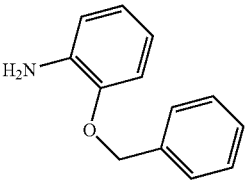 [SMILES: Nc1ccccc1OCc1ccccc1] | 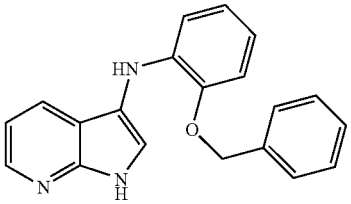 [SMILES: c1ccc(COc2ccccc2Nc2c[nH]c3ncccc23)cc1] | 316.3 |
| P-1506 | 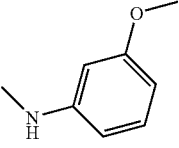 | 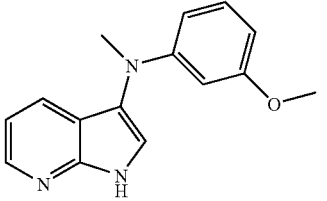 [SMILES: COc1cccc(N(C)c2c[nH]c3ncccc23)c1] | 254.3 |

Example 70

Synthesis of 4-chloro-7-azaindole 119

4-chloro-7-azaindole 119 was synthesized in two steps from 7-azaindole according to the protocol of Scheme 81.

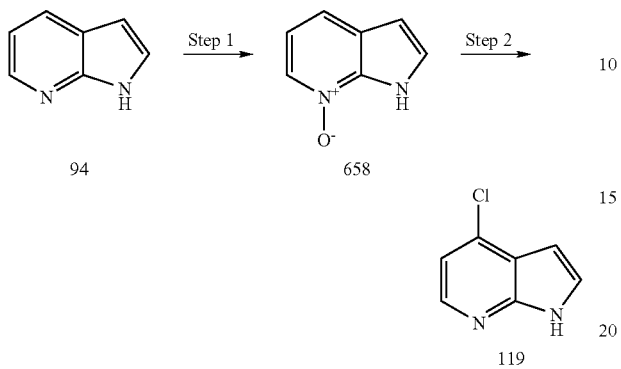

Step-1—Synthesis of 1H-Pyrrolo[2,3-b]pyridine 7-oxide (658)

1H-Pyrrolo[2,3-b]pyridine 7-oxide 658 was synthesized by reacting 7-azaindole 94 with an oxidizing agent (e.g. m-CPBA) in a non-reactive solvent (e.g. dimethoxyethane) as described by Schneller, S. W.; Luo, Jiann-Kuan. J. Org. Chem. 1980, 45:4045-4048. The compound was isolated by filtration of the resulting solid that forms upon standing at 5° C. for typically 1-3 h.

Step-2—Synthesis of 4-chloro-7-azaindole (119)

4-chloro-7-azaindole 119 was synthesized by reacting 1H-Pyrrolo[2,3-b]pyridine 7-oxide 658 with a chlorinating agent (e.g. POCl$_3$) neat as described by Schneller, S. W.; Luo, Jiann-Kuan. J. Org. Chem. 1980, 45:4045-4048, The resulting solution after heating for 3-5 h at elevated temperatures (100-150° C.) was neutralized with a base (e.g. NH$_4$OH) until a solid precipitated. The solid was isolated by filtration.

Example 71

Synthesis of [3-(4-Chloro-2-fluoro-benzyloxy)-2-(2-fluoro-ethoxy)-phenyl]-(1H-pyrrolo[2,3-b]pyridin-3-yl)-methanone P-2086 and 3-[3-(4-Chloro-2-fluoro-benzyloxy)-2-(2-fluoro-ethoxy)-benzyl]-1H-pyrrolo[2,3-b]pyridine P-2085

Compounds P-2086 and P-2085 were synthesized in three steps from compounds 659 and 1H-pyrrolo[2,3-b]pyridine 94 as shown in Scheme 82.

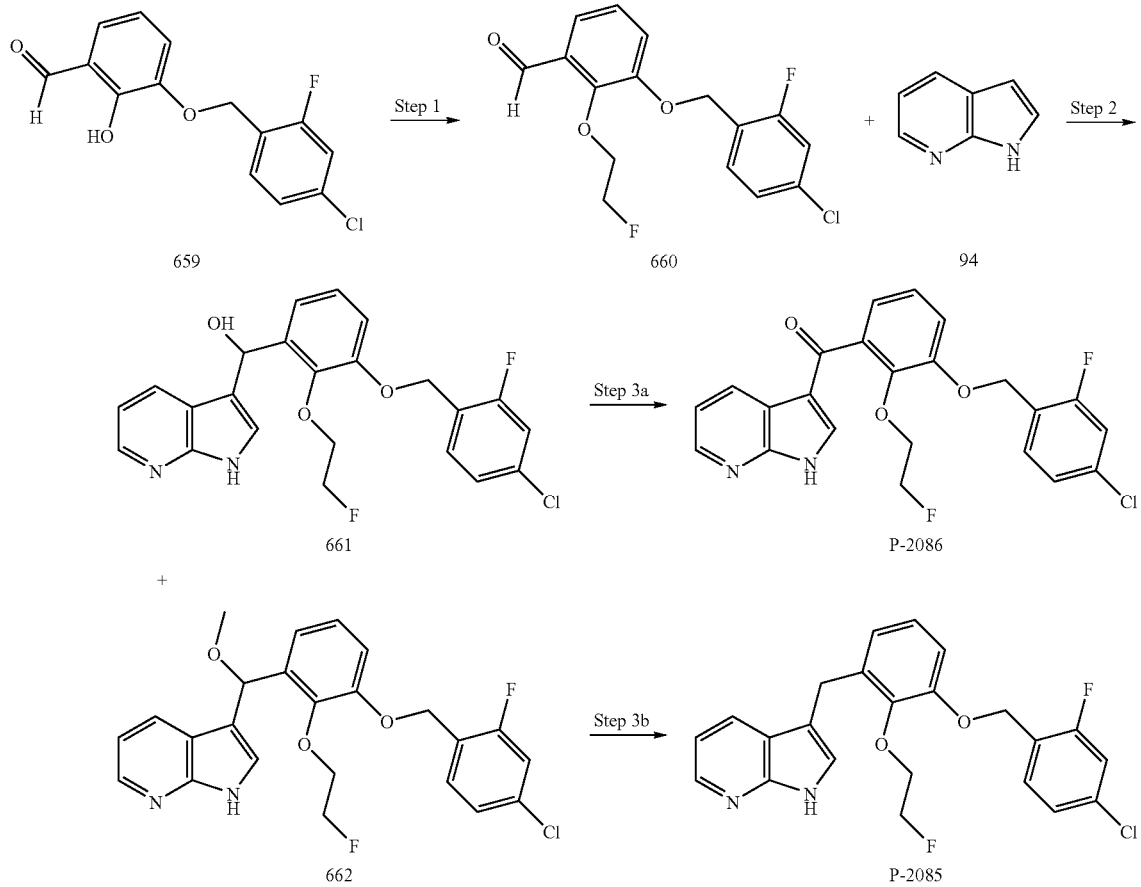

Step 1—Preparation of 3-(4-Chloro-2-fluoro-benzyloxy)-2-(2-fluoro-ethoxy)-benzaldehyde (660)

To a solution of 3-(4-Chloro-2-fluoro-benzyloxy)-2-hydroxy-benzaldehyde (659, 140 mg, 0.5 mmol, prepared by protocol of Example 43, Steps 1 and 2 of Scheme 71, using 4-chloro-2-fluoro-benzyl bromide in place of 4-chloro-benzyl bromide in Step 1) in tetrahydrofuran (8 mL) was added dropwise a mixture of 2-fluoro-ethanol (64 mg, 1.0 mmol), triphenylphosphine (180 mg, 0.7 mmol), and diisopropyl azodicarboxylate (120 mg, 0.6 mol) in tetrahydrofuran (5 ml) at 0° C. The reaction mixture was stirred at 0° C. for 10 minutes and then at 40° C. for 3 days. The reaction mixture was dissolved in water and ethyl acetate. The organic layers were collected, washed with brine, and dried over magnesium sulfate. After removal of solvent, the residue was purified by silica gel column chromatography eluting with ethyl acetate in hexanes to provide the compound as a white solid (660, 88 mg, 54%). MS (ESI) $[M+H^+]^+$=327.12.

Step 2—Preparation of [3-(4-Chloro-2-fluoro-benzyloxy)-2-(2-fluoro-ethoxy)-phenyl]-(1H-pyrrolo[2,3-b]pyridin-3-yl)-methanol (661) and 3-{[3-(4-Chloro-2-fluoro-benzyloxy)-2-(2-fluoro-ethoxy)-phenyl]-methoxy-methyl}-1H-pyrrolo[2,3-b]pyridine (662)

A solution of 3-(4-chloro-2-fluoro-benzyloxy)-2-(2-fluoro-ethoxy)-benzaldehyde (660, 88 mg, 0.27 mmol), 1H-pyrrolo[2,3-b]pyridine (94, 38 mg, 0.32 mmol), and potassium hydroxide (45 mg, 0.81 mol) in methanol (5 mL) was stirred at room temperature for 24 hours. The reaction mixture was poured into water and extracted with ethyl acetate. The organic layer was collected, washed with brine, and dried over sodium sulfate. After removal of solvent, the residue was purified by silica gel column chromatography eluting with ethyl acetate in hexane to provide compound 661 as a white solid (67 mg, 56%), MS(ESI) $[M+H^+]^+$=445.13 and compound 662 as a white solid (36 mg, 29%), MS(ESI) $[M+H^+]^+$=459.15.

Step 3a—Preparation of [3-(4-Chloro-2-fluoro-benzyloxy)-2-(2-fluoro-ethoxy-phenyl]-(1H-pyrrolo[2,3-b]pyridin-3-yl)-methanone (P-2086)

To a solution of [3-(4-chloro-2-fluoro-benzyloxy)-2-(2-fluoro-ethoxy)-phenyl]-(1H-pyrrolo[2,3-b]pyridin-3-yl)-methanol (661, 60 mg, 0.1 mmol) in tetrahydrofuran (10 mL) was added Dess-Martin periodinane (69 mg, 0.16 mmol) at 0° C. The reaction mixture was stirred at room temperature for 3 hours. The reaction was quenched with a saturated solution of sodium thiosulfate, extracted with ethyl acetate, washed with sodium bicarbonate, brine, and dried over magnesium sulfate. After removal of solvent, the residue was purified by silica gel column chromatography eluting with ethyl acetate in hexanes to provide the compound as a white solid (P-2086, 15 mg, 20%). MS(ESI) $[M+H^+]^+$=441.06.

Step 3b—Preparation of 3-[3-(4-Chloro-2-fluoro-benzyloxy)-2-(2-fluoro-ethoxy)-benzyl]-1H-pyrrolo[2,3-b]pyridine (P-2085)

A mixture of 3-{[3-(4-chloro-2-fluoro-benzyloxy)-2-(2-fluoro-ethoxy)-phenyl]-methoxy-methyl}-1H-pyrrolo[2,3-b]pyridine (662, 36 mg, 0.078 mmol), triethylsilane (0.5 mL, 3 mmol), and trifluoroacetic acid (0.2 mL, 2 mmol) in acetonitrile (20 mL) was stirred at 80° C. for 2 hours. The mixture was concentrated and the residue was dissolved in ethyl acetate. The solution was washed with saturated sodium bicarbonate, brine, and dried over sodium sulfate. After removal of solvent, the residue was purified by silica gel column chromatography eluting with ethyl acetate in hexanes to provide the compound as a yellow solid (P-2085, 24 mg, 71%). MS(ESI) $[M+H^+]^+$=429.15.

3-(4-Chloro-benzyloxy)-2-(2,2-difluoro-ethoxy)-phenyl]-(1H-pyrrolo[2,3-b]pyridin-3-yl)-methanone (P-2075)

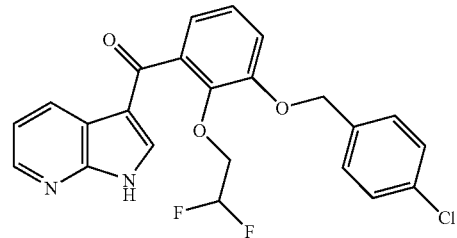

(P-2075)

was prepared following the protocol of Scheme 82, substituting 2-fluoro-ethanol with 2,2-difluoro-ethanol and substituting 3-(4-Chloro-2-fluoro-benzyloxy)-2-hydroxy-benzaldehyde with 3-(4-chloro-benzyloxy)-2-hydroxy-benzaldehyde (628 of Example 43) in Step 1 to provide P-2075. MS(ESI) $[M+H^+]^+$=443.1.

Example 72

Synthesis of [3-(2-Chloro-4-methanesulfonyl-benzyloxy)-2-ethoxy-phenyl]-(1H-pyrrolo[2,3-b]pyridin-3-yl)-methanone P-2094

Compound P-2094 was synthesized in four steps from compounds 635 and 663 as shown in Scheme 83.

Scheme 83

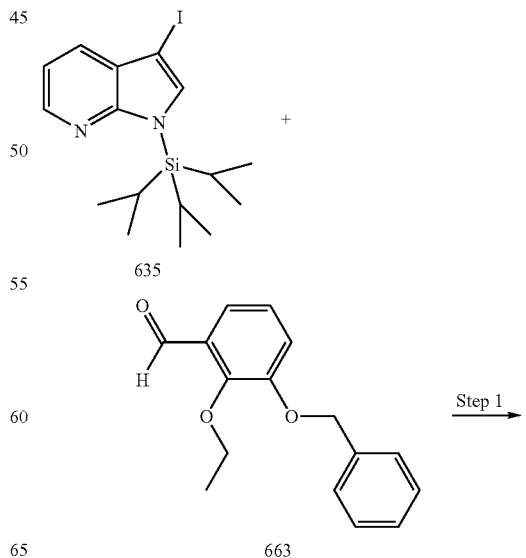

-continued

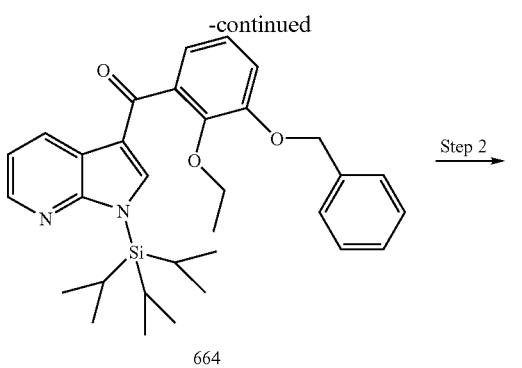
664

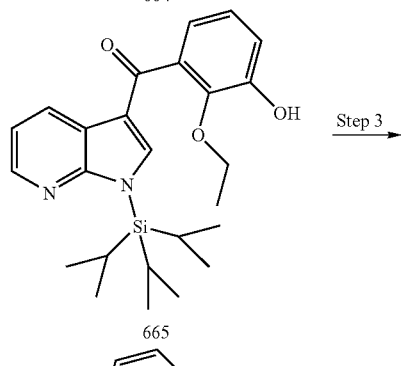
665

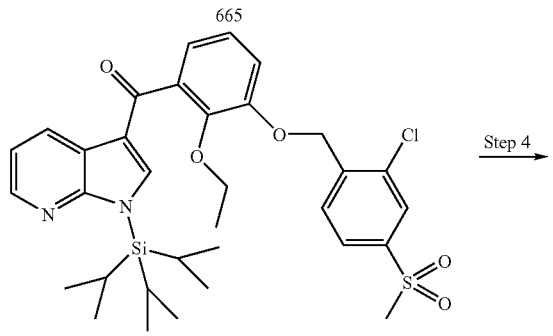
666

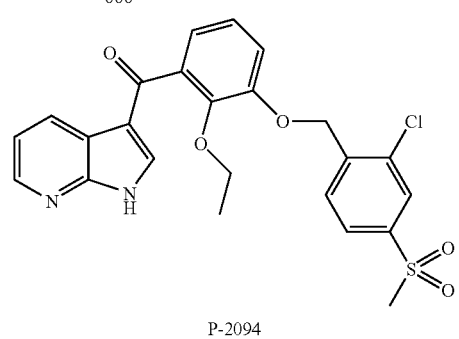
P-2094

Step 1—Preparation of (3-Benzyloxy-2-ethoxyphenyl)-(1-triisopropylsilanyl-1H-pyrrolo[2,3-b]pyridin-3-yl)-methanol (664)

To a solution of 3-iodo-1-triisopropylsilanyl-1H-pyrrolo[2,3-b]pyridine (635, 1.306 g, 3.26 mmol) in tetrahydrofuran (42 mL) at −20° C. under nitrogen was added isopropylmagnesium chloride (1.70 mL, 2.0 M solution in tetrahydrofuran, 3.40 mmol). The reaction mixture was stirred at −20° C. for 1.5 hours. It was allowed to warm to 5° C. and then kept at 5° C. for 1 hour. The reaction mixture was then cooled down to −20° C. To this solution was slowly added a solution of 2-ethoxy-3-benzyloxybenzaldehyde (663, 0.698 g, 2.72 mmol, prepared by protocol of Example 43, Steps 1-3 of Scheme 71, using benzyl bromide in place of 4-chloro-benzyl bromide in Step 1) in tetrahydrofuran (42 mL). The reaction mixture was stirred at −20° C. for 2.5 hrs, and was allowed to warm to 5° C. for 2.5 hours. The reaction mixture was poured into iced water, extracted with ethyl acetate, washed with saturated ammonium chloride and brine, and dried over magnesium sulfate. After removal of solvent, the residue was purified by silica gel column chromatography eluting with ethyl acetate in hexane to provide the compound as light-yellow oil (664, 200 mg, 13.9%).

Step 2—Preparation of (2-ethoxy-3-hydroxy-phenyl)-(1-triisopropylsilanyl-1H-pyrrolo[2,3-b]pyridin-3-yl)-methanone (665)

To a solution of (3-benzyloxy-2-ethoxy-phenyl)-(1-triisopropylsilanyl-1H-pyrrolo[2,3-b]pyridin-3-yl)-methanol (664, 195 mg, 0.37 mmol) in a mixture of methanol (20 mL) and tetrahydrofuran (50 mL) was added palladium on carbon (50 mg, 10% wt., 0.2 mmol). The mixture was stirred under hydrogenation for seventeen hours. After removal of solvent, the residue was washed with a mixture of ethyl ether and hexanes to provide the compound as a white solid (665, 63 mg, 95%). MS(ESI) [M+H$^+$]$^+$=439.37.

Step 3—Preparation of [3-(2-Chloro-4-methanesulfonyl-benzyloxy)-2-ethoxy-phenyl]-(1-triisopropylsilanyl-1H-pyrrolo[2,3-b]pyridin-3-yl)-methanone (666)

To a solution of (2-ethoxy-3-hydroxy-phenyl)-(1-triisopropylsilanyl-1H-pyrrolo[2,3-b]pyridin-3-yl)-methanone (665, 40 mg, 0.064 mmol) in tetrahydrofuran (15 mL) was added sodium hydride (3.32 mg, 0.083 mmol) at room temperature under an atmosphere of nitrogen. The mixture was stirred at room temperature for 40 minutes, then 1-bromomethyl-2-chloro-4-methanesulfonyl-benzene (21.72 mg, 0.077 mmol) was added to the reaction mixture. It was stirred at room temperature overnight. The mixture was then poured into water and was extracted with ethyl acetate. The organic layer was collected and washed with brine, dried over magnesium sulfate. After removal of the solvent, a crude compound as light yellow oil was obtained (666, 84 mg).

Step 4—Preparation of [3-(2-Chloro-4-methanesulfonyl-benzyloxy)-2-ethoxy-phenyl]-(1H-pyrrolo[2,3-b]pyridin-3-yl)-methanone (P-2094)

To a solution of (2-ethoxy-3-hydroxy-phenyl)-(1-triisopropylsilanyl-1H-pyrrolo[2,3-b]pyridin-3-yl)-methanone (666, 84 mg, 0.054 mmol) in methanol (10 mL) was added potassium hydroxide (6 N solution) until pH of the solution turned to over 10. Potassiun fluoride (30 mg, 0.5 mmol) was then added to the reaction mixture and the mixture was stirred at room temperature for 6 hours. The reaction mixture was then poured into saturated sodium carbonate and was extracted with ethyl acetate. The organic layer was collected and washed with brine, dried over magnesium sulfate. After removal of the solvent, the residue was purified by preparative HPLC to provide as a white solid (P-2094, 5 mg, 19%). MS(ESI) [M+H$^-$]$^+$=485.17.

Example 73

Synthesis of Propane-1-sulfonic acid [3-(5-bromo-1H-pyrrolo[2,3-b]pyridine-3-carbonyl)-4-fluoro-phenyl]-amide P-1403

Compound P-1403 was synthesized in seven steps from 3-fluoro-5-nitrobenzoic acid 667 as shown in Scheme 84.

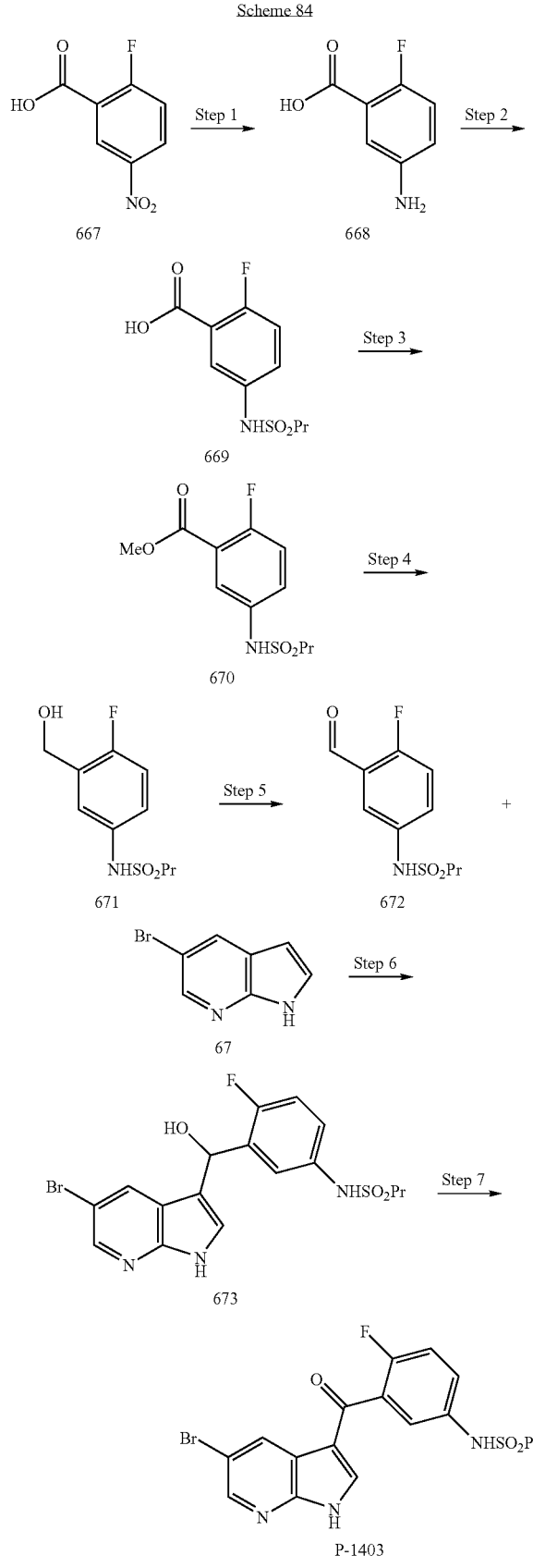

Step 1—Preparation of 3-fluoro-5-aminobenzoic acid (668)

Into a Parr pressure reactor were added 3-fluoro-5-nitrobenzoic acid (667, 5.0 g, 0.027 mol), methanol (50.0 mL), 20% Pd(OH)$_2$ on carbon (300 mg). The reaction was shaken under an atmosphere of hydrogen at 50 psi overnight. The reaction was filtered through celite and was concentrated to dryness to provide a white solid (668, 4.0 g, 95.0%).

Step 2—Preparation of 2-Fluoro-5-(propane-1-sulfonylamino)-benzoic acid (669)

To 3-fluoro-5-aminobenzoic acid (668, 3.00 g, 0.0180 mol) in methylene chloride (204 mL) were added pyridine (41 mL, 0.50 mol) and propane-1-sulfonyl chloride (2.23 mL, 0.0198 mol) under an atmosphere of nitrogen. The reaction was stirred at room temperature for 5 days. The reaction was poured into water, adjusted pH to 1 with 1N HCl, and extracted with ethyl acetate. The organic layer was dried over anhydrous sodium sulfate, and filtered. The filtrate was concentrated and purified by silica gel column chromatography eluting with 5% methanol in methylene chloride to give a white solid (669, 2.0 g, 42%). MS (ESI) [M−H$^+$]$^−$=260.1.

Step 3—Preparation of 2-Fluoro-5-(propane-1-sulfonylamino)-benzoic acid methyl ester (670)

To 2-Fluoro-5-(propane-1-sulfonylamino)-benzoic acid (669, 2.0 g, 0.0076 mol) in methanol (20.0 mL) was added sulfuric acid (0.90 mL, 0.017 mol). The reaction was stirred at room temperature overnight. The reaction was concentrated and purified with silica gel column chromatograph eluting with 20% ethyl acetate in hexane to give a white solid (670, 1.27 g, 62%). MS (ESI) [M−H$^+$]$^−$=274.1.

Step 4—Preparation of Propane-1-sulfonic acid (4-fluoro-3-hydroxymethyl-phenyl)-amide (671)

To 2-Fluoro-5-(propane-1-sulfonylamino)-benzoic acid methyl ester (670, 1.20 g, 0.00436 mol) in tetrahydrofuran (100.0 mL) was added lithium tetrahydroaluminate (1.00 M in tetrahydrofuran, 10.0 mL) under an atmosphere of nitrogen. The reaction was stirred at room temperature overnight. To the reaction was added Na$_2$SO$_4$.10H$_2$O (5 g), and then stirred at room temperature for 1 hour. The reaction was filtered, concentrated and purified with silica gel column chromatography eluting with 50% ethyl acetate in hexane to give the compound (671, 0.90 g, 83%). MS (ESI) [M−H$^+$]$^−$=246.1.

Step 5—Preparation of Propane-1-sulfonic acid (4-fluoro-3-formyl-phenyl)-amide (672)

To propane-1-sulfonic acid (4-fluoro-3-hydroxymethyl-phenyl)-amide (671, 0.483 g, 0.00195 mol) in tetrahydrofuran (10.0 mL), cooled with ice/water, was added Dess-Martin periodinane (1.00 g, 0.00236 mol). The reaction was stirred at room temperature for 10 minutes. The reaction was poured into water and extracted with ethyl acetate. The organic layer was dried over anhydrous sodium sulfate and filtered. The filtrate was concentrated and purified by silica gel column chromatography eluting with 30% ethyl acetate in hexane to give a white solid (672, 360 mg, 75%). MS (ES1)[M−H$^+$]$^−$=244.1.

Step 6—Preparation of Propane-1-sulfonic acid 3-[(5-bromo-1H-pyrrolo[2,3-b]pyridin-3-yl)-hydroxy-methyl]-4-fluoro-phenyl-amide (673)

To 5-bromo-7-azaindole (67, 170.0 mg, 0.86 mmol) in methanol (7.0 mL) were added propane-1-sulfonic acid (4-fluoro-3-formyl-phenyl)-amide (672, 220.0 mg, 0.90 mmol) and potassium hydroxide (0.50 g, 0.0089 mol) under an atmosphere of nitrogen. The reaction was stirred at room temperature overnight. The reaction was poured into water, acidified with 1N HCl to pH=5, and extracted with ethyl acetate. The organic layer was dried over anhydrous sodium sulfate, and filtered. The filtrate was concentrated and purified by silica gel column chromatography eluting with 10% methanol in methylene chloride to give the compound (673, 55.0 mg, 14.0%). MS (ESI) [M+H$^+$]$^+$=442.1, 444.1.

Step 7—Preparation of Propane-1-sulfonic acid [3-(5-bromo-1H-pyrrolo[2,3-b]pyridine-3-carbonyl)-4-fluoro-phenyl]-amide (P-1403)

To propane-1-sulfonic acid 3-[(5-bromo-1H-pyrrolo[2,3-b]pyridin-3-yl)-hydroxy-methyl]-4-fluoro-phenyl-amide (673, 55.0 mg, 0.12 mmol) in tetrahydrofuran (8.0 mL) was added Dess-Martin periodinane (70.0 mg, 0.17 mmol). The reaction was stirred at room temperature for 5 minutes. The reaction was concentrated with silica gel and purified with silica gel column chromatography eluting with 25% ethyl acetate in hexane to give an off-white solid (P-1403, 26.2 mg, 47%). MS (ESI) [M+H$^+$]$^+$=437.9, 439.9.

Example 74

Additional Compounds

Additional compounds of the invention were synthesized following the methods of the Examples above or similar methods, or by methods known to those of skill in the art, and are shown in the following Table 1.

TABLE 1

Additional compounds of the invention

P-0001

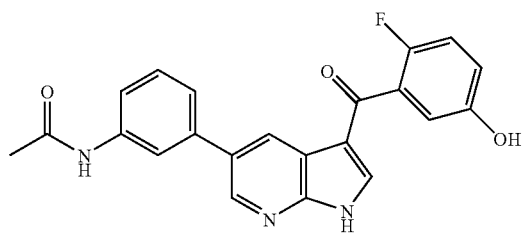 [SMILES: CC(=O)Nc1cccc(-c2cnc3[nH]cc(C(=O)c4cc(O)ccc4F)c3c2)c1]

P-0002

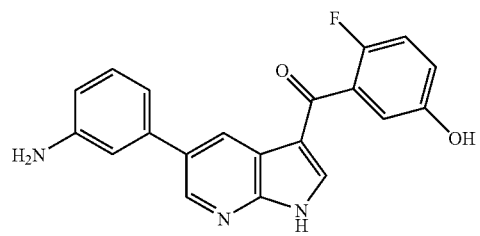 [SMILES: Nc1cccc(-c2cnc3[nH]cc(C(=O)c4cc(O)ccc4F)c3c2)c1]

P-0003

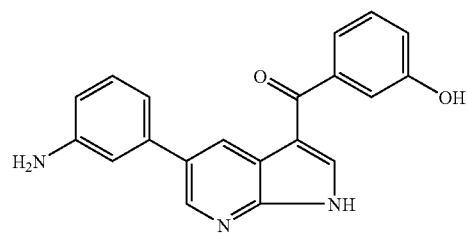 [SMILES: Nc1cccc(-c2cnc3[nH]cc(C(=O)c4cccc(O)c4)c3c2)c1]

P-0005

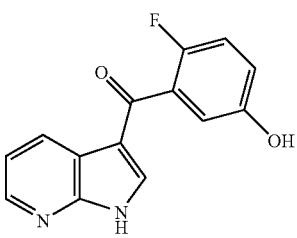 [SMILES: O=C(c1cc(O)ccc1F)c1c[nH]c2ncccc12]

TABLE 1-continued
Additional compounds of the invention
P-0010
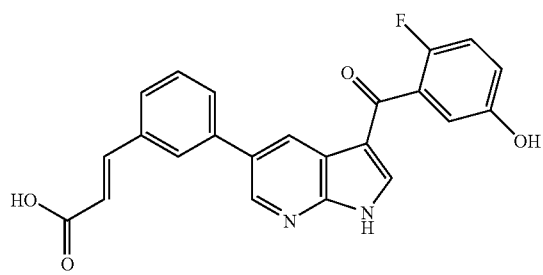 [SMILES: O=C(O)/C=C/c1cccc(-c2cnc3[nH]cc(C(=O)c4cc(O)ccc4F)c3c2)c1]
P-0011
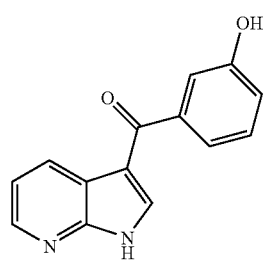 [SMILES: O=C(c1cccc(O)c1)c1c[nH]c2ncccc12]
P-0012
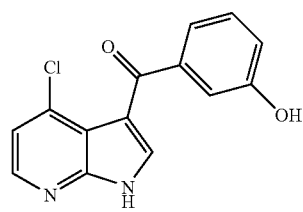 [SMILES: O=C(c1cccc(O)c1)c1c[nH]c2nccc(Cl)c12]
P-0013
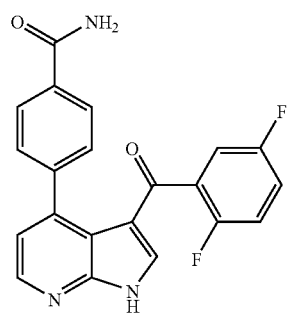 [SMILES: NC(=O)c1ccc(-c2ccnc3[nH]cc(C(=O)c4cc(F)ccc4F)c23)cc1]
P-0014
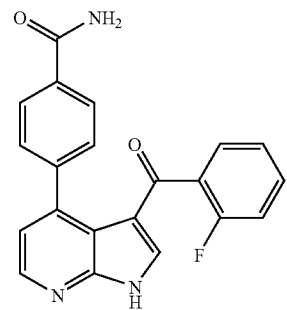

TABLE 1-continued
Additional compounds of the invention
P-0015
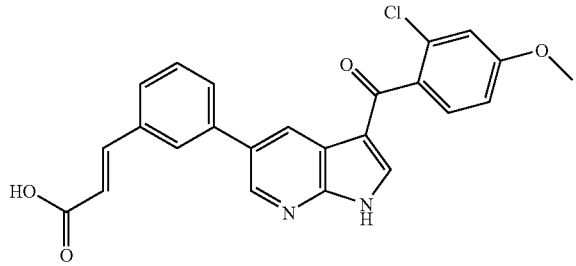 [SMILES: COc1ccc(C(=O)c2c[nH]c3ncc(-c4cccc(/C=C/C(=O)O)c4)cc23)c(Cl)c1]
P-0017
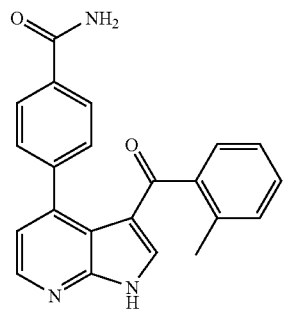 [SMILES: Cc1ccccc1C(=O)c1c[nH]c2nccc(-c3ccc(C(N)=O)cc3)c12]
P-0018
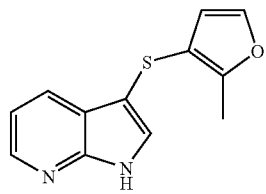 [SMILES: Cc1occc1Sc1c[nH]c2ncccc12]
P-0019
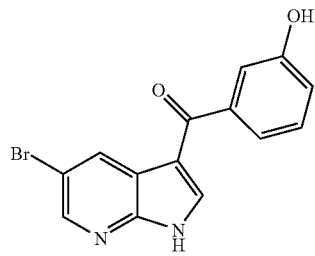 [SMILES: O=C(c1cccc(O)c1)c1c[nH]c2ncc(Br)cc12]
P-0020
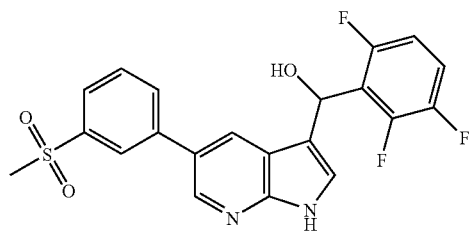 [SMILES: CS(=O)(=O)c1cccc(-c2cnc3[nH]cc(C(O)c4c(F)ccc(F)c4F)c3c2)c1]
P-0021
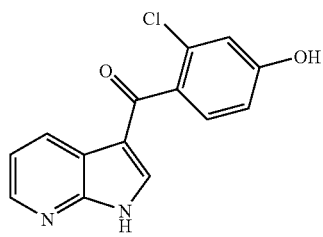 [SMILES: O=C(c1ccc(O)cc1Cl)c1c[nH]c2ncccc12]

TABLE 1-continued
Additional compounds of the invention
P-0022 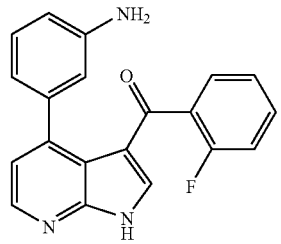 [SMILES: Nc1cccc(-c2ccnc3[nH]cc(C(=O)c4ccccc4F)c23)c1]
P-0023 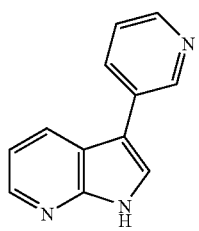 [SMILES: c1cncc(-c2c[nH]c3ncccc23)c1]
P-0025 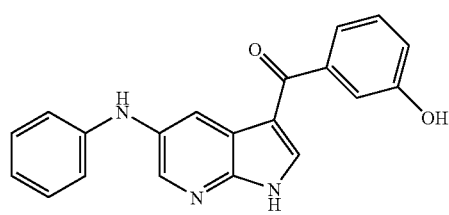 [SMILES: O=C(c1cccc(O)c1)c1c[nH]c2ncc(Nc3ccccc3)cc12]
P-0028 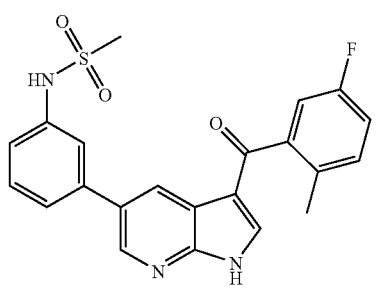 [SMILES: Cc1ccc(F)cc1C(=O)c1c[nH]c2ncc(-c3cccc(NS(C)(=O)=O)c3)cc12]
P-0029 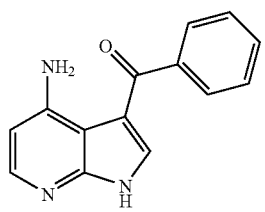 [SMILES: Nc1ccnc2[nH]cc(C(=O)c3ccccc3)c12]
P-0030 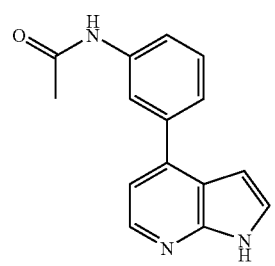 [SMILES: CC(=O)Nc1cccc(-c2ccnc3[nH]ccc23)c1]

TABLE 1-continued
Additional compounds of the invention
P-0031 
P-0032 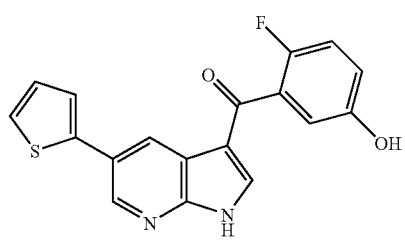 [SMILES: O=C(c1cc(O)ccc1F)c1c[nH]c2ncc(-c3cccs3)cc12]
P-0033 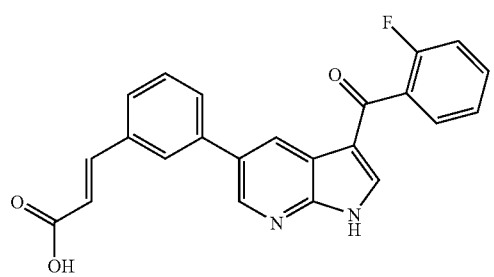 [SMILES: O=C(O)/C=C/c1cccc(-c2cnc3[nH]cc(C(=O)c4ccccc4F)c3c2)c1]
P-0039 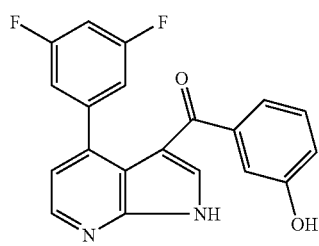
P-0040 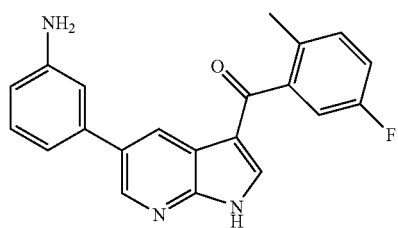 [SMILES: Cc1ccc(F)cc1C(=O)c1c[nH]c2ncc(-c3cccc(N)c3)cc12]
P-0041 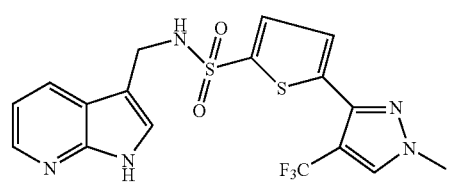 [SMILES: Cn1cc(C(F)(F)F)c(-c2ccc(S(=O)(=O)NCc3c[nH]c4ncccc34)s2)n1]

TABLE 1-continued
Additional compounds of the invention
P-0043 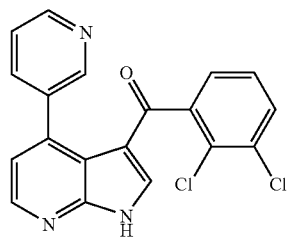 [SMILES: O=C(c1cccc(Cl)c1Cl)c1c[nH]c2nccc(-c3cccnc3)c12]
P-0044 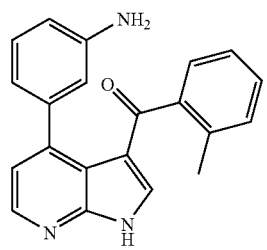 [SMILES: Cc1ccccc1C(=O)c1c[nH]c2nccc(-c3cccc(N)c3)c12]
P-0045 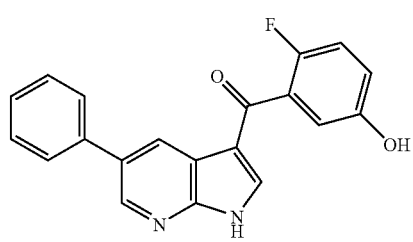 [SMILES: O=C(c1cc(O)ccc1F)c1c[nH]c2ncc(-c3ccccc3)cc12]
P-0046 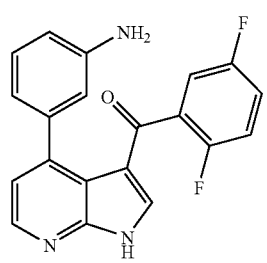 [SMILES: Nc1cccc(-c2ccnc3[nH]cc(C(=O)c4cc(F)ccc4F)c23)c1]
P-0047 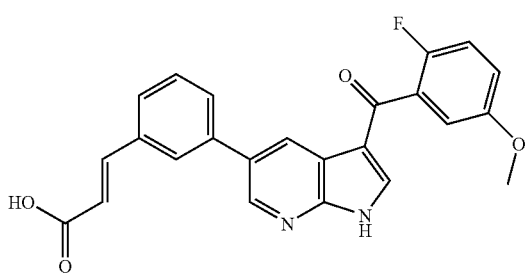 [SMILES: COc1ccc(F)c(C(=O)c2c[nH]c3ncc(-c4cccc(/C=C/C(=O)O)c4)cc23)c1]
P-0048 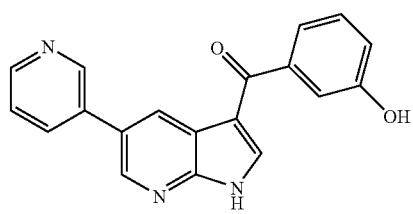 [SMILES: O=C(c1cccc(O)c1)c1c[nH]c2ncc(-c3cccnc3)cc12]

TABLE 1-continued
| Additional compounds of the invention |
P-0049 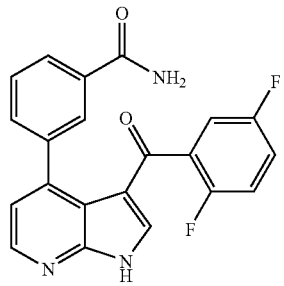 [SMILES: NC(=O)c1cccc(-c2ccnc3[nH]cc(C(=O)c4cc(F)ccc4F)c23)c1]
P-0050 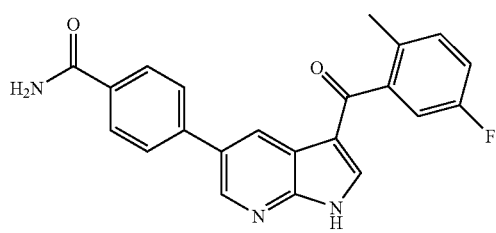 [SMILES: Cc1ccc(F)cc1C(=O)c1c[nH]c2ncc(-c3ccc(C(N)=O)cc3)cc12]
P-0051 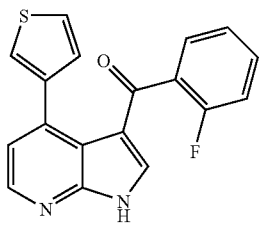 [SMILES: O=C(c1ccccc1F)c1c[nH]c2nccc(-c3ccsc3)c12]
P-0053 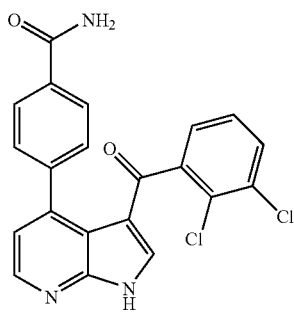 [SMILES: NC(=O)c1ccc(-c2ccnc3[nH]cc(C(=O)c4cccc(Cl)c4Cl)c23)cc1]
P-0054 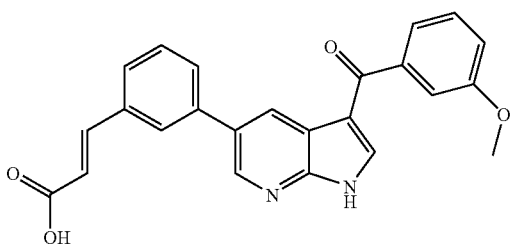 [SMILES: COc1cccc(C(=O)c2c[nH]c3ncc(-c4cccc(/C=C/C(=O)O)c4)cc23)c1]
P-0056 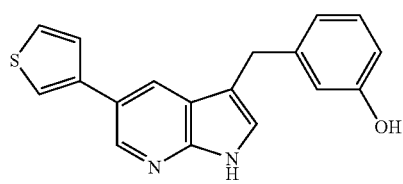 [SMILES: Oc1cccc(Cc2c[nH]c3ncc(-c4ccsc4)cc23)c1]

TABLE 1-continued
Additional compounds of the invention
P-0057 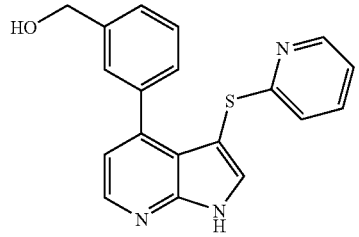 [SMILES: OCc1cccc(-c2ccnc3[nH]cc(Sc4ccccn4)c23)c1]
P-0058 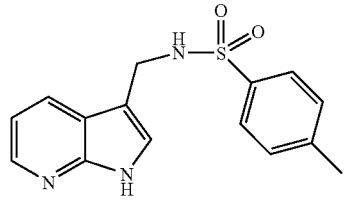 [SMILES: Cc1ccc(S(=O)(=O)NCc2c[nH]c3ncccc23)cc1]
P-0059 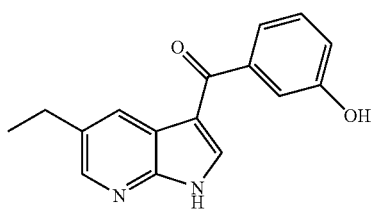 [SMILES: CCc1cnc2[nH]cc(C(=O)c3cccc(O)c3)c2c1]
P-0060 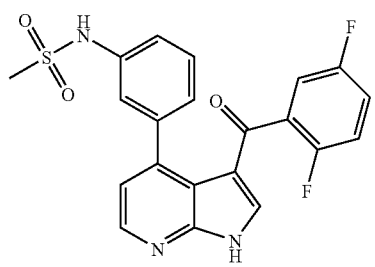 [SMILES: CS(=O)(=O)Nc1cccc(-c2ccnc3[nH]cc(C(=O)c4cc(F)ccc4F)c23)c1]
P-0061 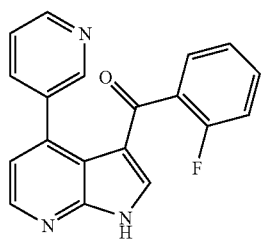 [SMILES: O=C(c1ccccc1F)c1c[nH]c2nccc(-c3cccnc3)c12]
P-0062 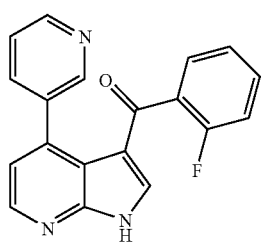 [SMILES: O=C(c1ccccc1F)c1c[nH]c2nccc(-c3cccnc3)c12]

TABLE 1-continued
Additional compounds of the invention
P-0063 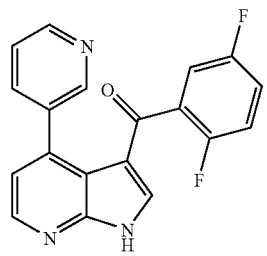 [SMILES: O=C(c1cc(F)ccc1F)c1c[nH]c2nccc(-c3cccnc3)c12]
P-0064 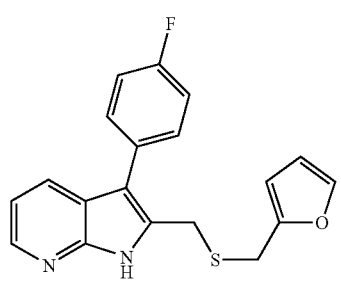 [SMILES: Fc1ccc(-c2c(CSCc3ccco3)[nH]c3ncccc23)cc1]
P-0069 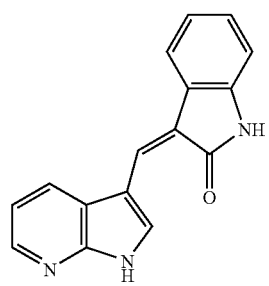 [SMILES: O=C1Nc2ccccc2/C1=C/c1c[nH]c2ncccc12]
P-0070 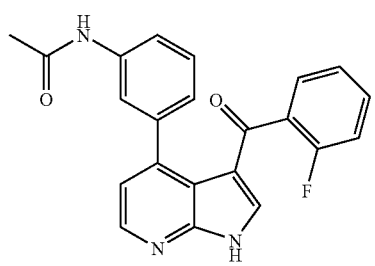 [SMILES: CC(=O)Nc1cccc(-c2ccnc3[nH]cc(C(=O)c4ccccc4F)c23)c1]
P-0071 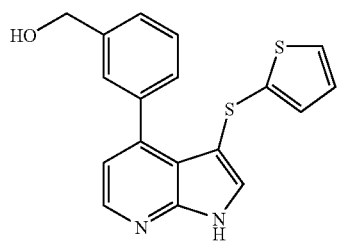 [SMILES: OCc1cccc(-c2ccnc3[nH]cc(Sc4cccs4)c23)c1]
P-0072 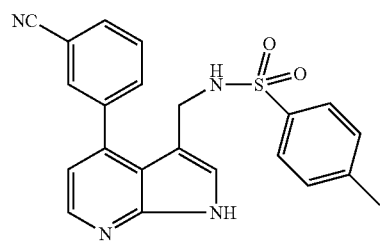

TABLE 1-continued
Additional compounds of the invention
P-0073 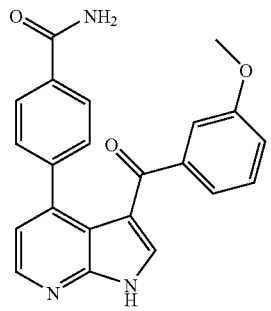 [SMILES: COc1cccc(C(=O)c2c[nH]c3nccc(-c4ccc(C(N)=O)cc4)c23)c1]
P-0074 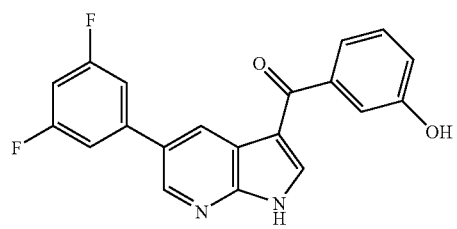 [SMILES: O=C(c1cccc(O)c1)c1c[nH]c2ncc(-c3cc(F)cc(F)c3)cc12]
P-0075 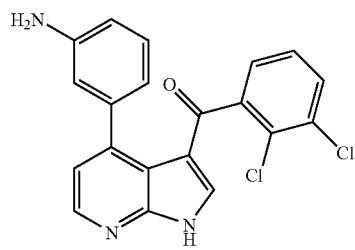 [SMILES: Nc1cccc(-c2ccnc3[nH]cc(C(=O)c4cccc(Cl)c4Cl)c23)c1]
P-0076 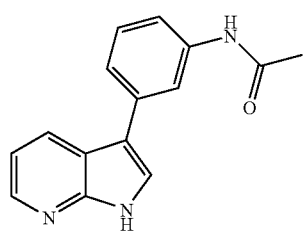 [SMILES: CC(=O)Nc1cccc(-c2c[nH]c3ncccc23)c1]
P-0077 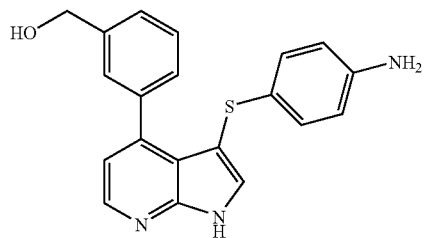 [SMILES: Nc1ccc(Sc2c[nH]c3nccc(-c4cccc(CO)c4)c23)cc1]
P-0080 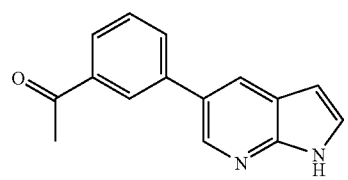 [SMILES: CC(=O)c1cccc(-c2cnc3[nH]ccc3c2)c1]

627 628
TABLE 1-continued
Additional compounds of the invention
P-0081 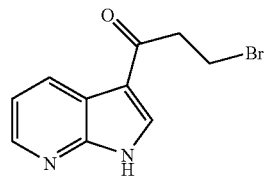 [SMILES: O=C(CCBr)c1c[nH]c2ncccc12]
P-0083 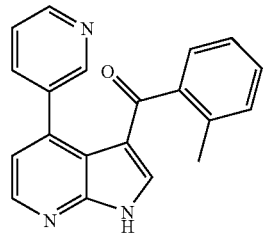 [SMILES: Cc1ccccc1C(=O)c1c[nH]c2nccc(-c3cccnc3)c12]
P-0084 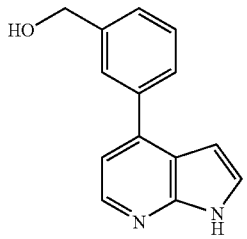 [SMILES: OCc1cccc(-c2ccnc3[nH]ccc23)c1]
P-0085 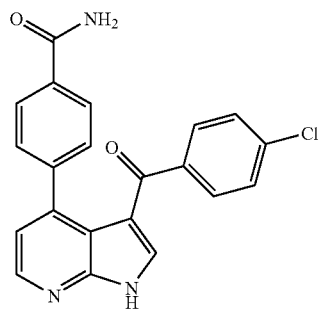 [SMILES: NC(=O)c1ccc(-c2ccnc3[nH]cc(C(=O)c4ccc(Cl)cc4)c23)cc1]
P-0086 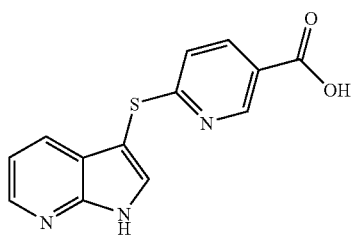 [SMILES: O=C(O)c1ccc(Sc2c[nH]c3ncccc23)nc1]
P-0087 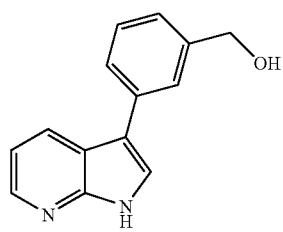 [SMILES: OCc1cccc(-c2c[nH]c3ncccc23)c1]

TABLE 1-continued
Additional compounds of the invention
P-0089
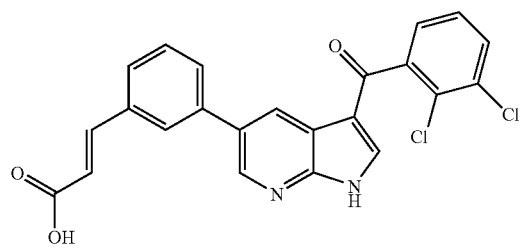 [SMILES: O=C(O)/C=C/c1cccc(-c2cnc3[nH]cc(C(=O)c4cccc(Cl)c4Cl)c3c2)c1]
P-0090
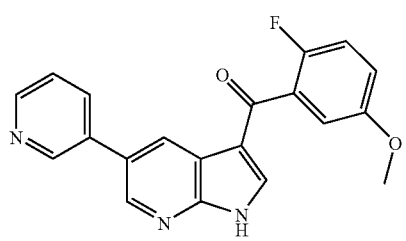 [SMILES: COc1ccc(F)c(C(=O)c2c[nH]c3ncc(-c4cccnc4)cc23)c1]
P-0091
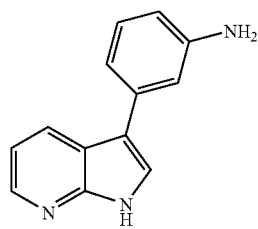 [SMILES: Nc1cccc(-c2c[nH]c3ncccc23)c1]
P-0092
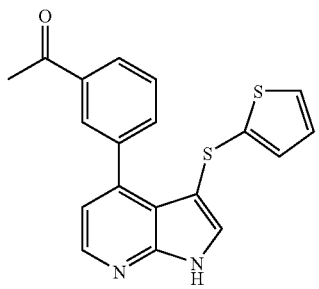 [SMILES: CC(=O)c1cccc(-c2ccnc3[nH]cc(Sc4cccs4)c23)c1]
P-0093
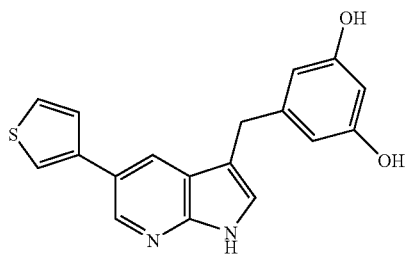 [SMILES: Oc1cc(O)cc(Cc2c[nH]c3ncc(-c4ccsc4)cc23)c1]
P-0094
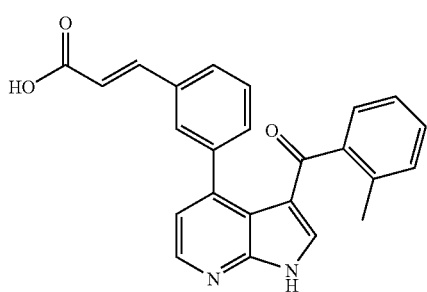 [SMILES: Cc1ccccc1C(=O)c1c[nH]c2nccc(-c3cccc(/C=C/C(=O)O)c3)c12]

TABLE 1-continued
Additional compounds of the invention
P-0096 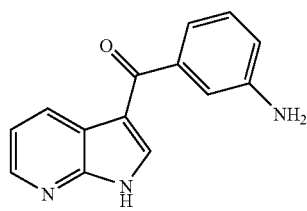 [SMILES: Nc1cccc(C(=O)c2c[nH]c3ncccc23)c1]
P-0097 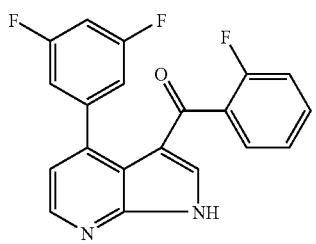 [SMILES: O=C(c1ccccc1F)c1c[nH]c2nccc(-c3cc(F)cc(F)c3)c12]
P-0098 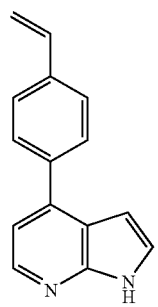 [SMILES: C=Cc1ccc(-c2ccnc3[nH]ccc23)cc1]
P-0099 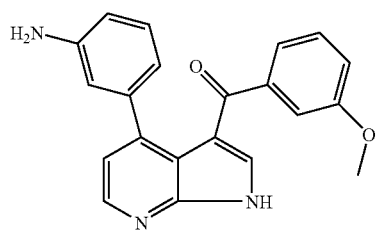 [SMILES: COc1cccc(C(=O)c2c[nH]c3nccc(-c4cccc(N)c4)c23)c1]
P-0100 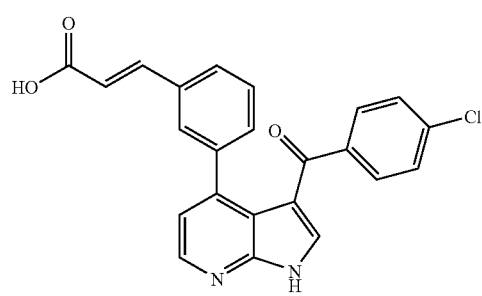 [SMILES: O=C(O)/C=C/c1cccc(-c2ccnc3[nH]cc(C(=O)c4ccc(Cl)cc4)c23)c1]
P-0101 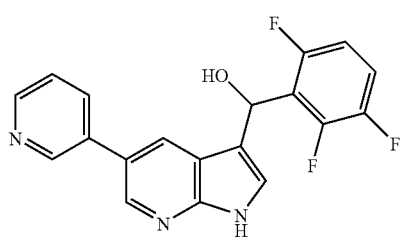 [SMILES: OC(c1c(F)ccc(F)c1F)c1c[nH]c2ncc(-c3cccnc3)cc12]

TABLE 1-continued
Additional compounds of the invention
P-0103
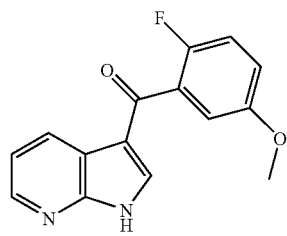 [SMILES: COc1ccc(F)c(C(=O)c2c[nH]c3ncccc23)c1]
P-0104
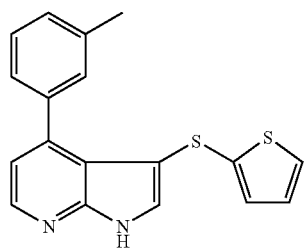 [SMILES: Cc1cccc(-c2ccnc3[nH]cc(Sc4cccs4)c23)c1]
P-0105
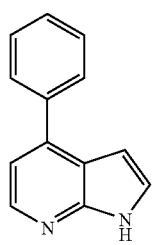 [SMILES: c1ccc(-c2ccnc3[nH]ccc23)cc1]
P-0106
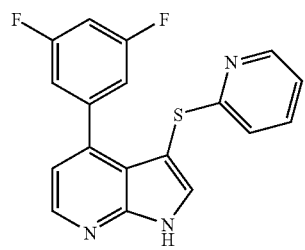 [SMILES: Fc1cc(F)cc(-c2ccnc3[nH]cc(Sc4ccccn4)c23)c1]
P-0107
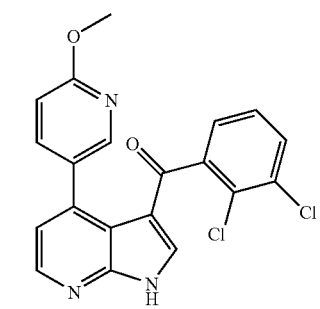 [SMILES: COc1ccc(-c2ccnc3[nH]cc(C(=O)c4cccc(Cl)c4Cl)c23)cn1]
P-0108
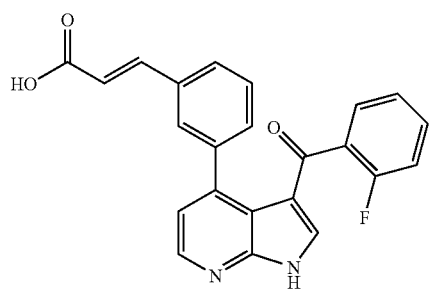

TABLE 1-continued
Additional compounds of the invention
P-0109 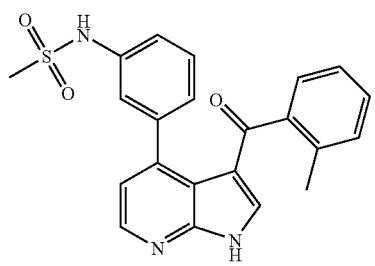
P-0110 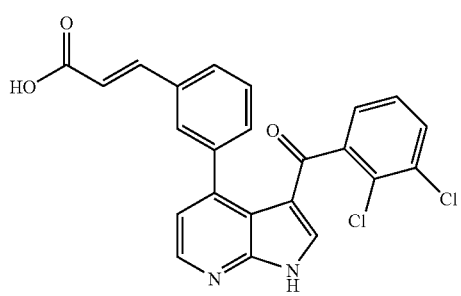 [SMILES: O=C(O)/C=C/c1cccc(-c2ccnc3[nH]cc(C(=O)c4cccc(Cl)c4Cl)c23)c1]
P-0111 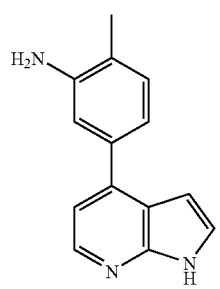 [SMILES: Cc1ccc(-c2ccnc3[nH]ccc23)cc1N]
P-0112 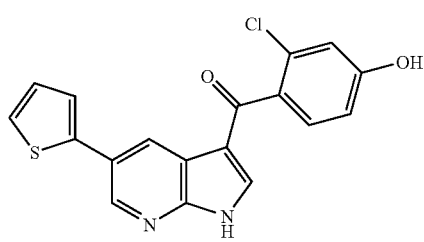 [SMILES: O=C(c1ccc(O)cc1Cl)c1c[nH]c2ncc(-c3cccs3)cc12]
P-0113 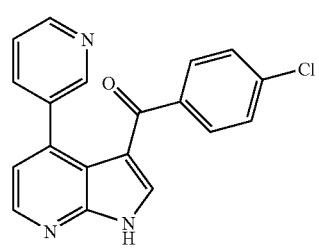 [SMILES: O=C(c1ccc(Cl)cc1)c1c[nH]c2nccc(-c3cccnc3)c12]
P-0115 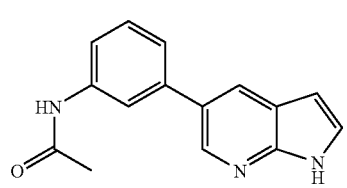 [SMILES: CC(=O)Nc1cccc(-c2cnc3[nH]ccc3c2)c1]

TABLE 1-continued
| Additional compounds of the invention |
|---|
| P-0116 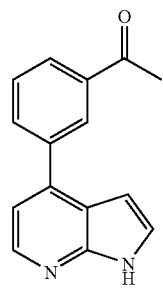 [SMILES: CC(=O)c1cccc(-c2ccnc3[nH]ccc23)c1] |
| P-0117 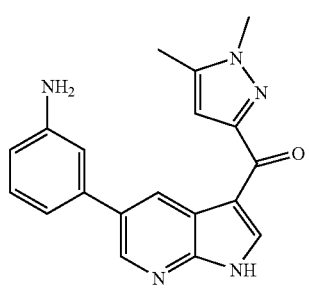 [SMILES: Cc1cc(C(=O)c2c[nH]c3ncc(-c4cccc(N)c4)cc23)nn1C] |
| P-0118 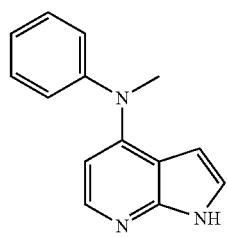 [SMILES: CN(c1ccccc1)c1ccnc2[nH]ccc12] |
| P-0119 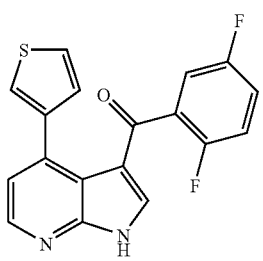 [SMILES: O=C(c1cc(F)ccc1F)c1c[nH]c2nccc(-c3ccsc3)c12] |
| P-0120 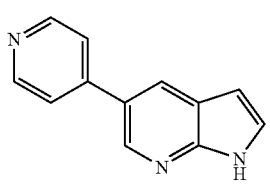 [SMILES: c1cc(-c2cnc3[nH]ccc3c2)ccn1] |
| P-0123 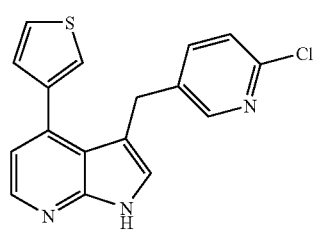 [SMILES: Clc1ccc(Cc2c[nH]c3nccc(-c4ccsc4)c23)cn1] |

TABLE 1-continued
Additional compounds of the invention
P-0124
P-0125
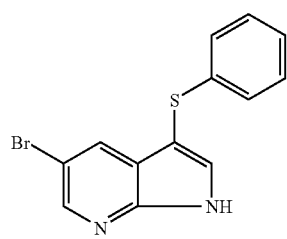 [SMILES: Brc1cnc2[nH]cc(Sc3ccccc3)c2c1]
P-0127
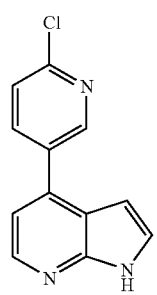 [SMILES: Clc1ccc(-c2ccnc3[nH]ccc23)cn1]
P-0128
P-0129
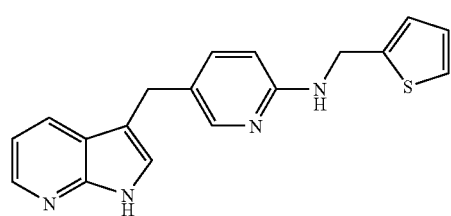 [SMILES: c1csc(CNc2ccc(Cc3c[nH]c4ncccc34)cn2)c1]

TABLE 1-continued
Additional compounds of the invention
P-0130 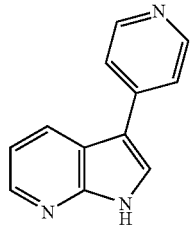 [SMILES: c1cnc2[nH]cc(-c3ccncc3)c2c1]
P-0131 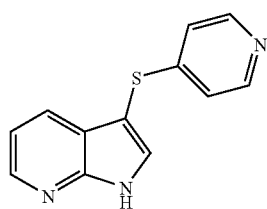 [SMILES: c1cnc2[nH]cc(Sc3ccncc3)c2c1]
P-0132 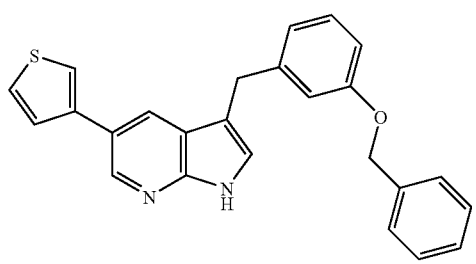 [SMILES: c1ccc(COc2cccc(Cc3c[nH]c4ncc(-c5ccsc5)cc34)c2)cc1]
P-0133 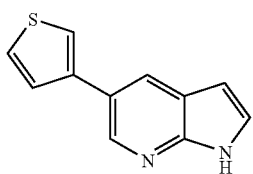 [SMILES: c1cc2cc(-c3ccsc3)cnc2[nH]1]
P-0134 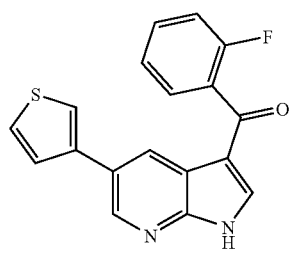 [SMILES: O=C(c1ccccc1F)c1c[nH]c2ncc(-c3ccsc3)cc12]
P-0135 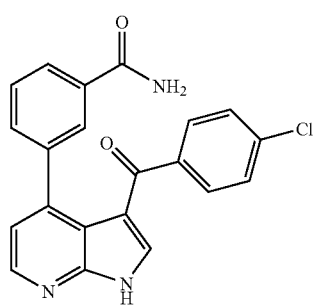 [SMILES: NC(=O)c1cccc(-c2ccnc3[nH]cc(C(=O)c4ccc(Cl)cc4)c23)c1]

TABLE 1-continued
Additional compounds of the invention
P-0136 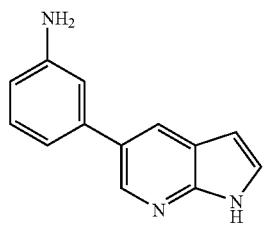 [SMILES: Nc1cccc(-c2cnc3[nH]ccc3c2)c1]
P-0137 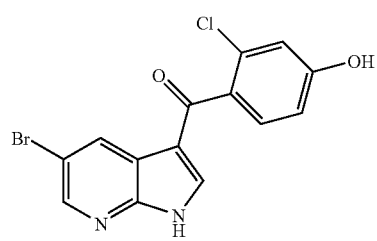 [SMILES: O=C(c1ccc(O)cc1Cl)c1c[nH]c2ncc(Br)cc12]
P-0138 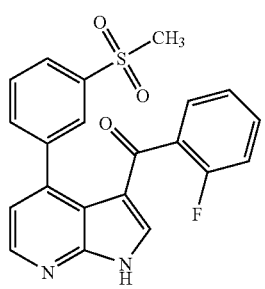 [SMILES: CS(=O)(=O)c1cccc(-c2ccnc3[nH]cc(C(=O)c4ccccc4F)c23)c1]
P-0139 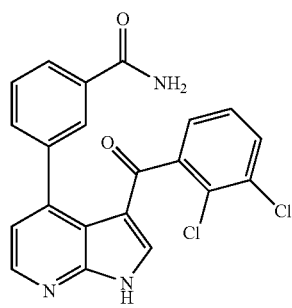 [SMILES: NC(=O)c1cccc(-c2ccnc3[nH]cc(C(=O)c4cccc(Cl)c4Cl)c23)c1]
P-0140 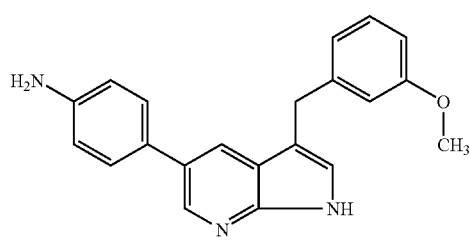 [SMILES: COc1cccc(Cc2c[nH]c3ncc(-c4ccc(N)cc4)cc23)c1]

TABLE 1-continued
Additional compounds of the invention
P-0141
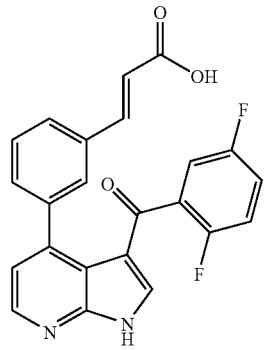 [SMILES: O=C(O)/C=C/c1cccc(-c2ccnc3[nH]cc(C(=O)c4cc(F)ccc4F)c23)c1]
P-0142
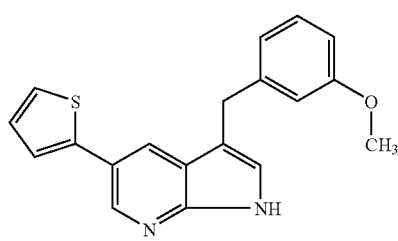 [SMILES: COc1cccc(Cc2c[nH]c3ncc(-c4cccs4)cc23)c1]
P-0143
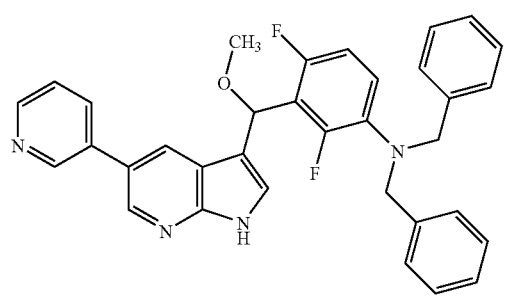 [SMILES: COC(c1c(F)ccc(N(Cc2ccccc2)Cc2ccccc2)c1F)c1c[nH]c2ncc(-c3cccnc3)cc12]
P-0144
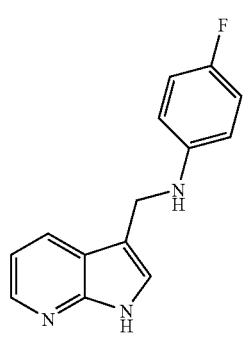 [SMILES: Fc1ccc(NCc2c[nH]c3ncccc23)cc1]
P-0145
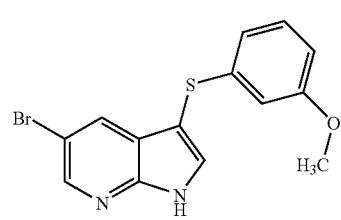 [SMILES: COc1cccc(Sc2c[nH]c3ncc(Br)cc23)c1]

TABLE 1-continued
Additional compounds of the invention
P-0146 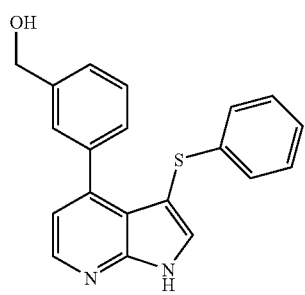 [SMILES: OCc1cccc(-c2ccnc3[nH]cc(Sc4ccccc4)c23)c1]
P-0147 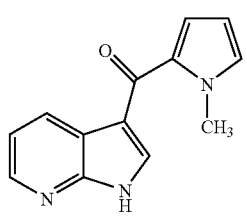 [SMILES: Cn1cccc1C(=O)c1c[nH]c2ncccc12]
P-0148 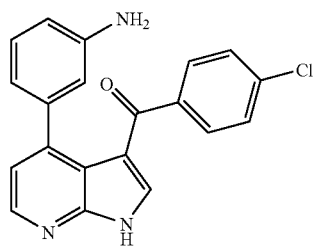 [SMILES: Nc1cccc(-c2ccnc3[nH]cc(C(=O)c4ccc(Cl)cc4)c23)c1]
P-0149 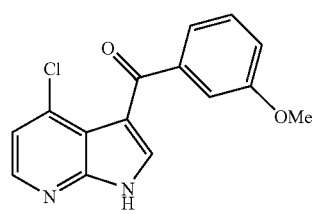 [SMILES: COc1cccc(C(=O)c2c[nH]c3nccc(Cl)c23)c1]
P-0150 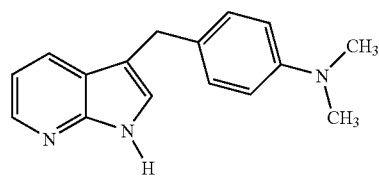 [SMILES: CN(C)c1ccc(Cc2c[nH]c3ncccc23)cc1]
P-0151 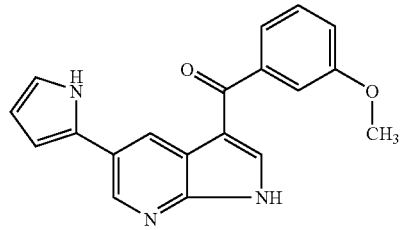 [SMILES: COc1cccc(C(=O)c2c[nH]c3ncc(-c4ccc[nH]4)cc23)c1]

TABLE 1-continued
Additional compounds of the invention
P-0152
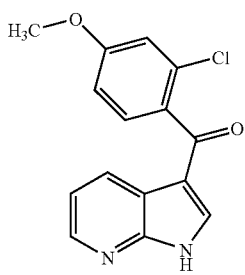 [SMILES: COc1ccc(C(=O)c2c[nH]c3ncccc23)c(Cl)c1]
P-0153
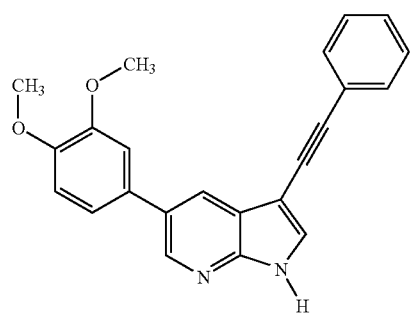 [SMILES: COc1ccc(-c2cnc3[nH]cc(C#Cc4ccccc4)c3c2)cc1OC]
P-0154
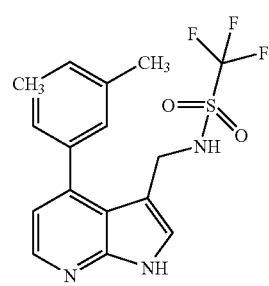 [SMILES: Cc1cccc(-c2ccnc3[nH]cc(CNS(=O)(=O)C(F)(F)F)c23)c1]
P-0155
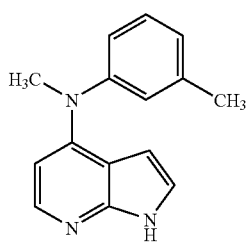 [SMILES: Cc1cccc(N(C)c2ccnc3[nH]ccc23)c1]
P-0157
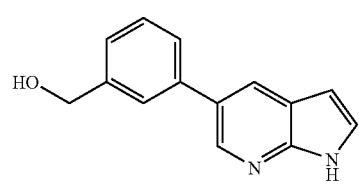 [SMILES: OCc1cccc(-c2cnc3[nH]ccc3c2)c1]
P-0158
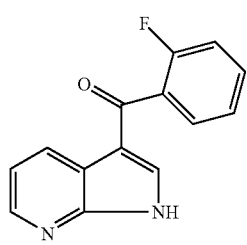 [SMILES: O=C(c1ccccc1F)c1c[nH]c2ncccc12]

651
TABLE 1-continued
Additional compounds of the invention
P-0159 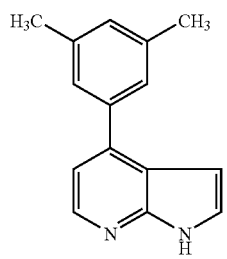
P-0160 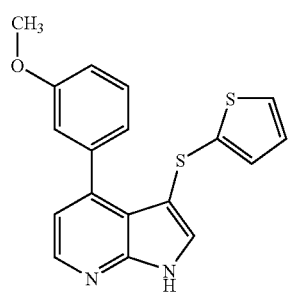 [SMILES: COc1cccc(-c2ccnc3[nH]cc(Sc4cccs4)c23)c1]
P-0161 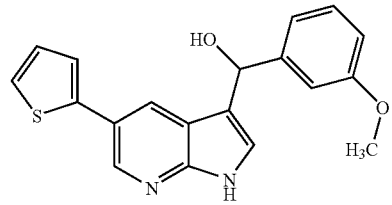 [SMILES: COc1cccc(C(O)c2c[nH]c3ncc(-c4cccs4)cc23)c1]
P-0163 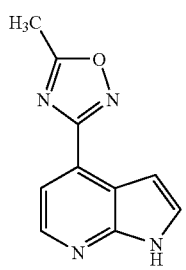
P-0164 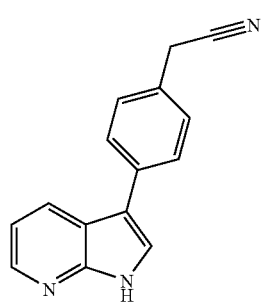 [SMILES: N#CCc1ccc(-c2c[nH]c3ncccc23)cc1]
P-0166 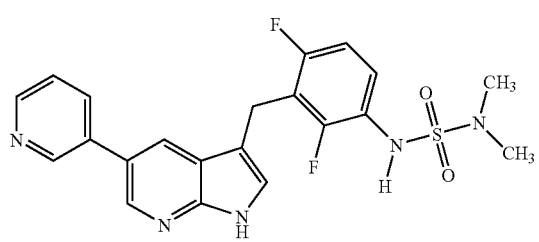 [SMILES: CN(C)S(=O)(=O)Nc1ccc(F)c(Cc2c[nH]c3ncc(-c4cccnc4)cc23)c1F]

TABLE 1-continued
Additional compounds of the invention
P-0167
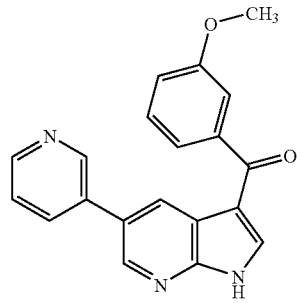 [SMILES: COc1cccc(C(=O)c2c[nH]c3ncc(-c4cccnc4)cc23)c1]
P-0168
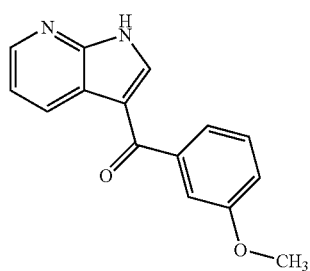 [SMILES: COc1cccc(C(=O)c2c[nH]c3ncccc23)c1]
P-0169
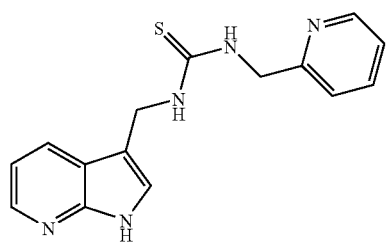
P-0171
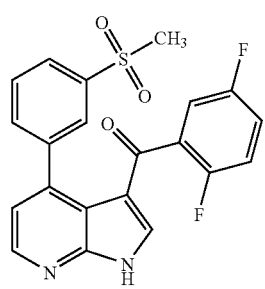 [SMILES: CS(=O)(=O)c1cccc(-c2ccnc3[nH]cc(C(=O)c4cc(F)ccc4F)c23)c1]
P-0172
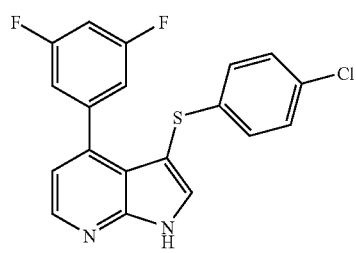 [SMILES: Fc1cc(F)cc(-c2ccnc3[nH]cc(Sc4ccc(Cl)cc4)c23)c1]

TABLE 1-continued
Additional compounds of the invention
P-0174 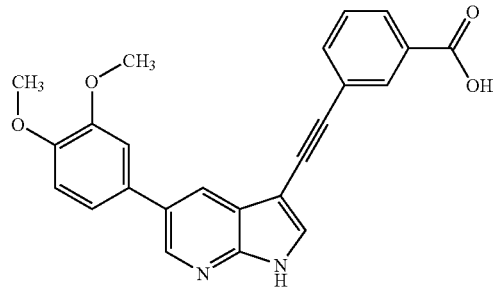 [SMILES: COc1ccc(-c2cnc3[nH]cc(C#Cc4cccc(C(=O)O)c4)c3c2)cc1OC]
P-0175 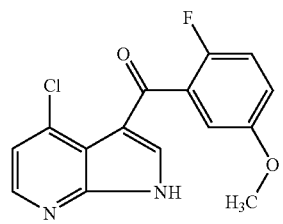 [SMILES: COc1ccc(F)c(C(=O)c2c[nH]c3nccc(Cl)c23)c1]
P-0176 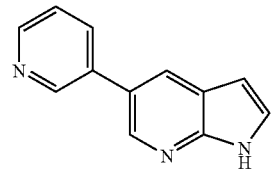 [SMILES: c1cncc(-c2cnc3[nH]ccc3c2)c1]
P-0177 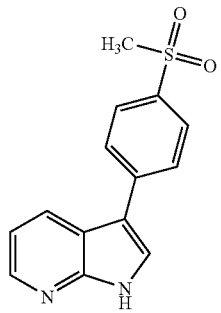 [SMILES: CS(=O)(=O)c1ccc(-c2c[nH]c3ncccc23)cc1]
P-0178 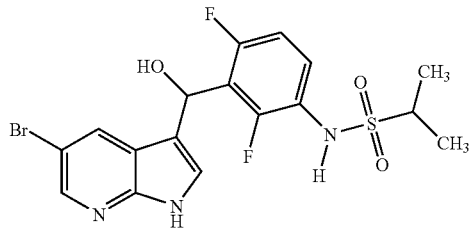 [SMILES: CC(C)S(=O)(=O)Nc1ccc(F)c(C(O)c2c[nH]c3ncc(Br)cc23)c1F]
P-0179 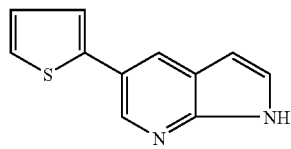 [SMILES: c1csc(-c2cnc3[nH]ccc3c2)c1]

TABLE 1-continued
Additional compounds of the invention
P-0181 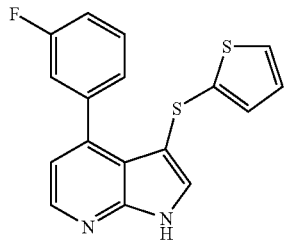 [SMILES: Fc1cccc(-c2ccnc3[nH]cc(Sc4cccs4)c23)c1]
P-0182 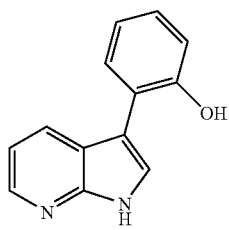 [SMILES: Oc1ccccc1-c1c[nH]c2ncccc12]
P-0183 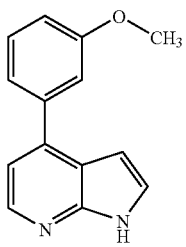 [SMILES: COc1cccc(-c2ccnc3[nH]ccc23)c1]
P-0185 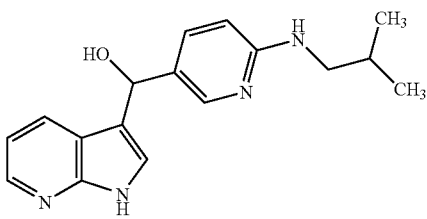 [SMILES: CC(C)CNc1ccc(C(O)c2c[nH]c3ncccc23)cn1]
P-0186 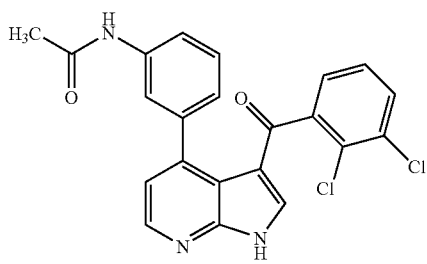 [SMILES: CC(=O)Nc1cccc(-c2ccnc3[nH]cc(C(=O)c4cccc(Cl)c4Cl)c23)c1]
P-0187 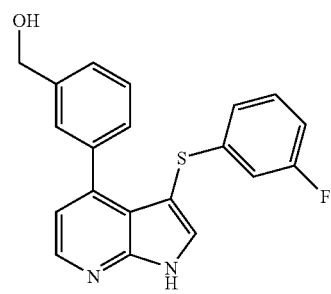

TABLE 1-continued
Additional compounds of the invention
P-0189 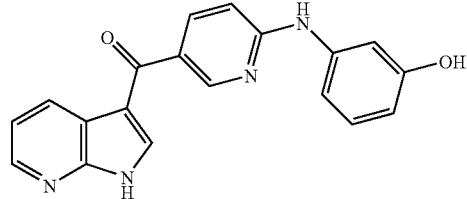 [SMILES: O=C(c1ccc(Nc2cccc(O)c2)nc1)c1c[nH]c2ncccc12]
P-0190 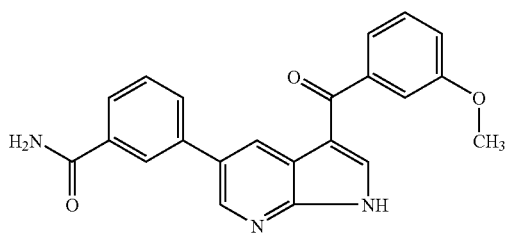 [SMILES: COc1cccc(C(=O)c2c[nH]c3ncc(-c4cccc(C(N)=O)c4)cc23)c1]
P-0191 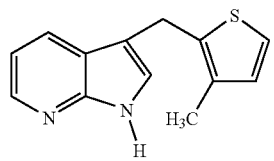 [SMILES: Cc1ccsc1Cc1c[nH]c2ncccc12]
P-0192 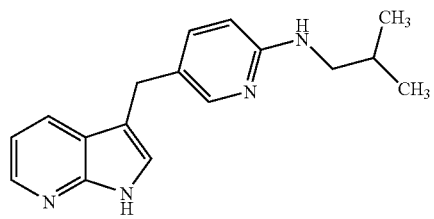 [SMILES: CC(C)CNc1ccc(Cc2c[nH]c3ncccc23)cn1]
P-0193 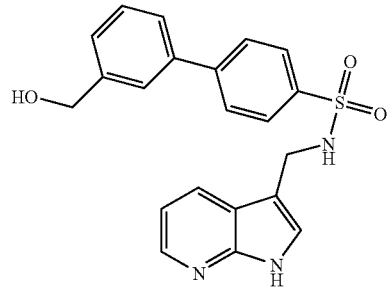 [SMILES: O=S(=O)(NCc1c[nH]c2ncccc12)c1ccc(-c2cccc(CO)c2)cc1]
P-0194 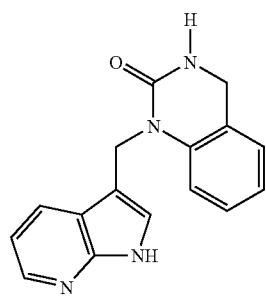 [SMILES: O=C1NCc2ccccc2N1Cc1c[nH]c2ncccc12]

TABLE 1-continued
Additional compounds of the invention
P-0195
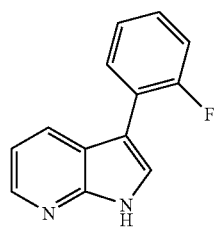 [SMILES: Fc1ccccc1-c1c[nH]c2ncccc12]
P-0196
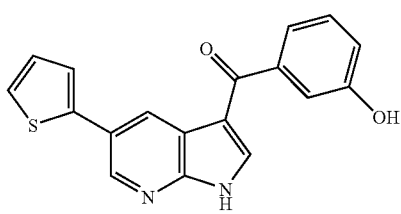 [SMILES: O=C(c1cccc(O)c1)c1c[nH]c2ncc(-c3cccs3)cc12]
P-0197
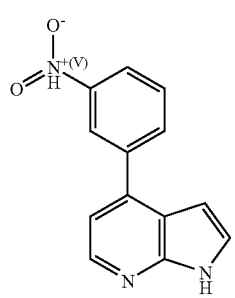
P-0198
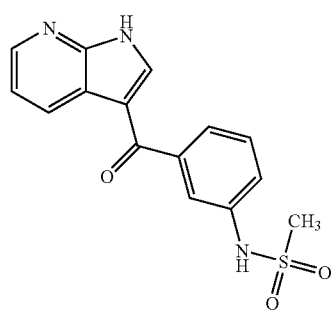 [SMILES: CS(=O)(=O)Nc1cccc(C(=O)c2c[nH]c3ncccc23)c1]
P-0199
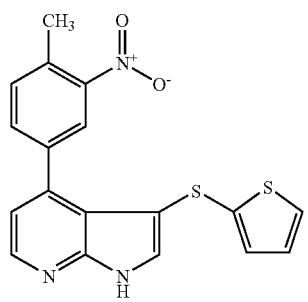 [SMILES: Cc1ccc(-c2ccnc3[nH]cc(Sc4cccs4)c23)cc1[N+](=O)[O-]]
P-0200
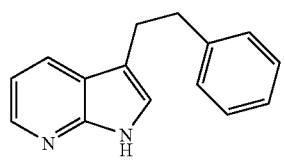 [SMILES: c1ccc(CCc2c[nH]c3ncccc23)cc1]

TABLE 1-continued
Additional compounds of the invention
P-0201
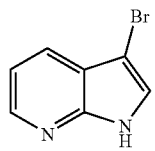
P-0202
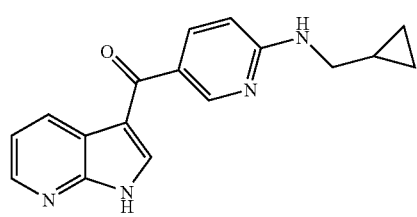 [SMILES: O=C(c1ccc(NCC2CC2)nc1)c1c[nH]c2ncccc12]
P-0203
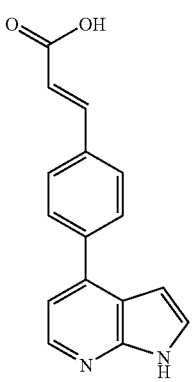 [SMILES: O=C(O)/C=C/c1ccc(-c2ccnc3[nH]ccc23)cc1]
P-0204
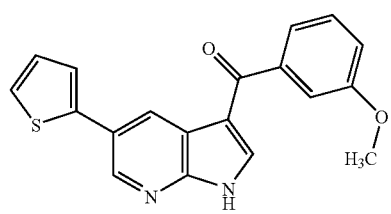 [SMILES: COc1cccc(C(=O)c2c[nH]c3ncc(-c4cccs4)cc23)c1]
P-0205
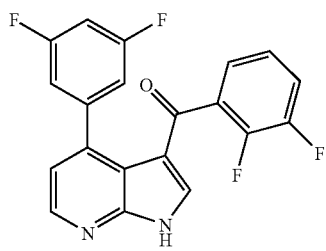 [SMILES: O=C(c1cccc(F)c1F)c1c[nH]c2nccc(-c3cc(F)cc(F)c3)c12]
P-0206
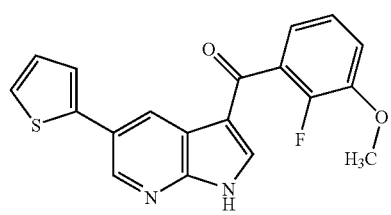 [SMILES: COc1cccc(C(=O)c2c[nH]c3ncc(-c4cccs4)cc23)c1F]

TABLE 1-continued
Additional compounds of the invention
P-0207 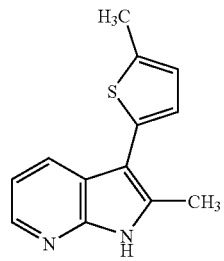 [SMILES: Cc1ccc(-c2c(C)[nH]c3ncccc23)s1]
P-0208 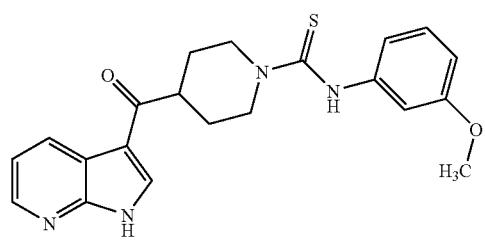 [SMILES: COc1cccc(NC(=S)N2CCC(C(=O)c3c[nH]c4ncccc34)CC2)c1]
P-0209 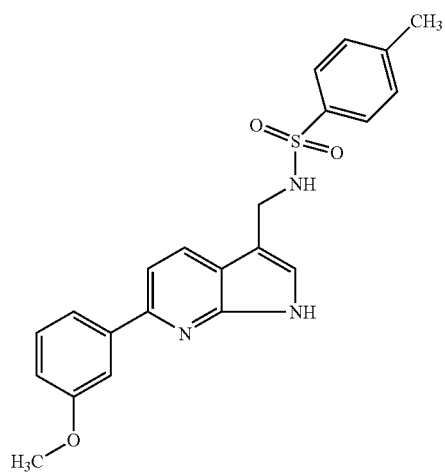 [SMILES: COc1cccc(-c2ccc3c(CNS(=O)(=O)c4ccc(C)cc4)c[nH]c3n2)c1]
P-0210 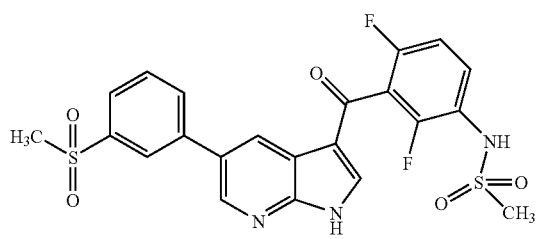 [SMILES: CS(=O)(=O)Nc1ccc(F)c(C(=O)c2c[nH]c3ncc(-c4cccc(S(C)(=O)=O)c4)cc23)c1F]
P-0211 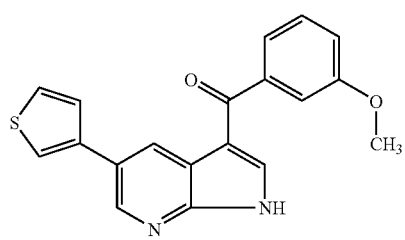 [SMILES: COc1cccc(C(=O)c2c[nH]c3ncc(-c4ccsc4)cc23)c1]

TABLE 1-continued
| Additional compounds of the invention |
P-0212 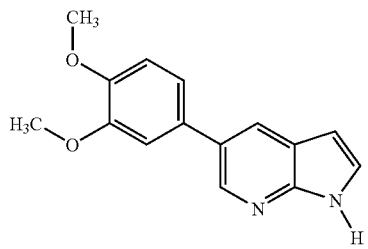 [SMILES: COc1ccc(-c2cnc3[nH]ccc3c2)cc1OC]
P-0213 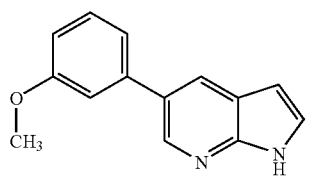 [SMILES: COc1cccc(-c2cnc3[nH]ccc3c2)c1]
P-0214 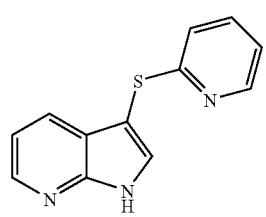 [SMILES: c1ccc(Sc2c[nH]c3ncccc23)nc1]
P-0215 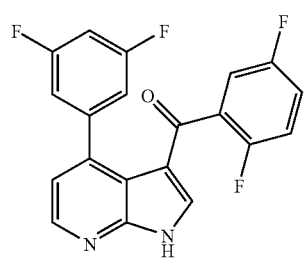 [SMILES: O=C(c1cc(F)ccc1F)c1c[nH]c2nccc(-c3cc(F)cc(F)c3)c12]
P-0216 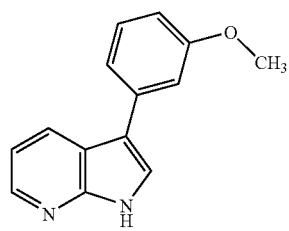 [SMILES: COc1cccc(-c2c[nH]c3ncccc23)c1]
P-0217 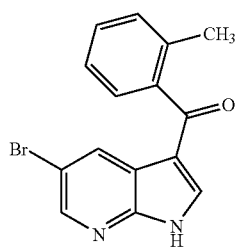 [SMILES: Cc1ccccc1C(=O)c1c[nH]c2ncc(Br)cc12]

TABLE 1-continued
Additional compounds of the invention
P-0218 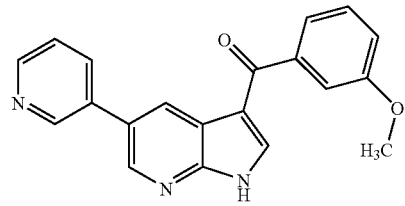 [SMILES: COc1cccc(C(=O)c2c[nH]c3ncc(-c4cccnc4)cc23)c1]
P-0219 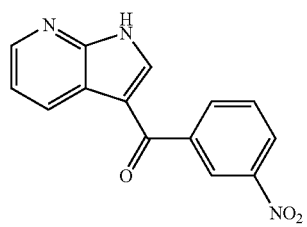 [SMILES: O=C(c1cccc([N+](=O)[O-])c1)c1c[nH]c2ncccc12]
P-0220 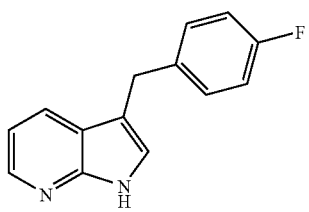 [SMILES: Fc1ccc(Cc2c[nH]c3ncccc23)cc1]
P-0222 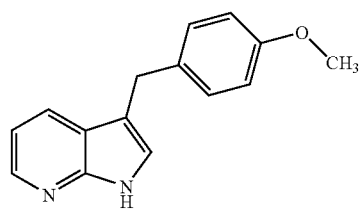 [SMILES: COc1ccc(Cc2c[nH]c3ncccc23)cc1]
P-0223 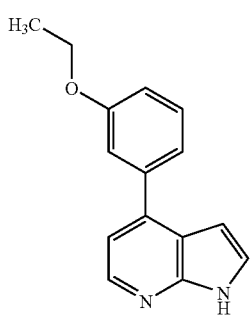 [SMILES: CCOc1cccc(-c2ccnc3[nH]ccc23)c1]
P-0224 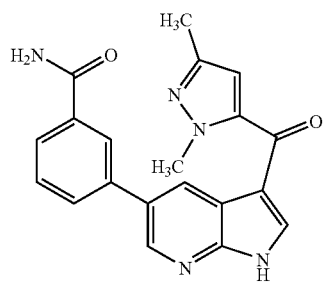 [SMILES: Cc1cc(C(=O)c2c[nH]c3ncc(-c4cccc(C(N)=O)c4)cc23)n(C)n1]

TABLE 1-continued
| Additional compounds of the invention |
P-0225 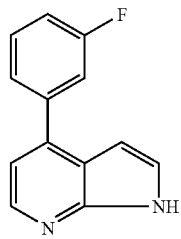 [SMILES: Fc1cccc(-c2ccnc3[nH]ccc23)c1]
P-0226 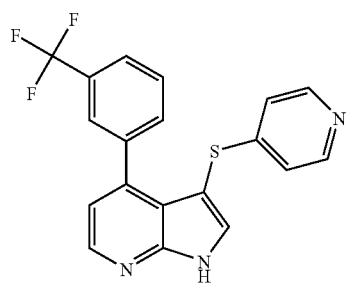 [SMILES: FC(F)(F)c1cccc(-c2ccnc3[nH]cc(Sc4ccncc4)c23)c1]
P-0227 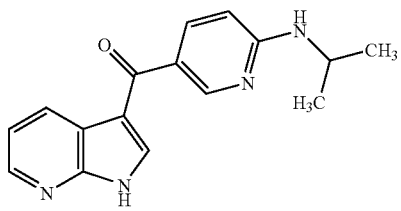 [SMILES: CC(C)Nc1ccc(C(=O)c2c[nH]c3ncccc23)cn1]
P-0229 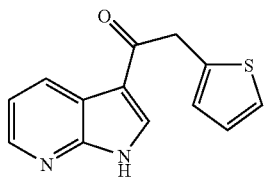 [SMILES: O=C(Cc1cccs1)c1c[nH]c2ncccc12]
P-0230 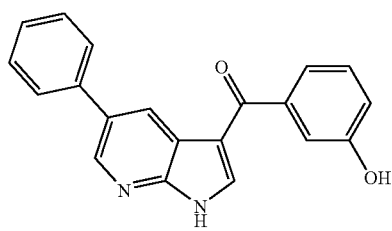 [SMILES: O=C(c1cccc(O)c1)c1c[nH]c2ncc(-c3ccccc3)cc12]
P-0231 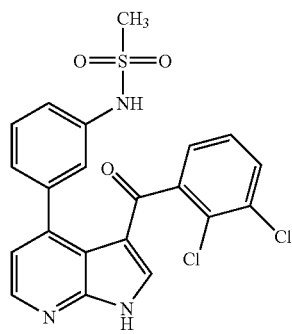 [SMILES: CS(=O)(=O)Nc1cccc(-c2ccnc3[nH]cc(C(=O)c4cccc(Cl)c4Cl)c23)c1]

TABLE 1-continued
Additional compounds of the invention
P-0232
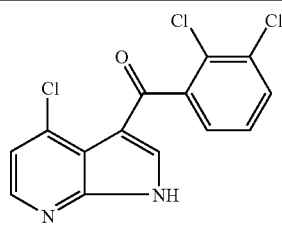
P-0233
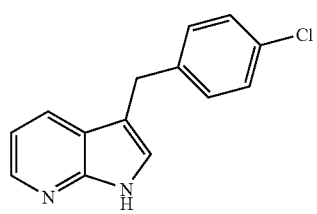 [SMILES: Clc1ccc(Cc2c[nH]c3ncccc23)cc1]
P-0234
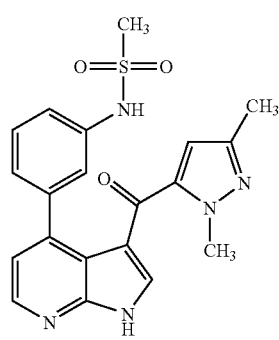 [SMILES: Cc1cc(C(=O)c2c[nH]c3nccc(-c4cccc(NS(C)(=O)=O)c4)c23)n(C)n1]
P-0235
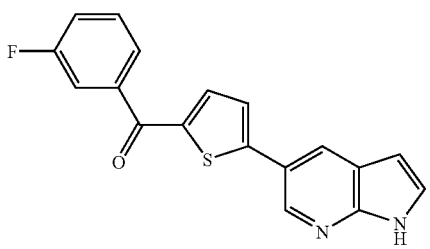 [SMILES: O=C(c1cccc(F)c1)c1ccc(-c2cnc3[nH]ccc3c2)s1]
P-0236
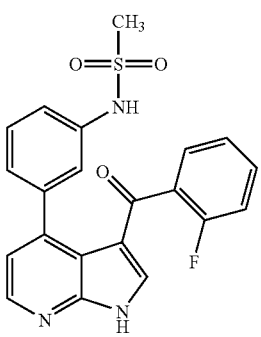 [SMILES: CS(=O)(=O)Nc1cccc(-c2ccnc3[nH]cc(C(=O)c4ccccc4F)c23)c1]
P-0237
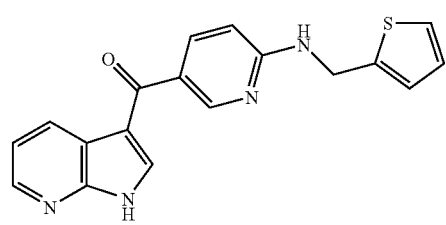 [SMILES: O=C(c1ccc(NCc2cccs2)nc1)c1c[nH]c2ncccc12]

TABLE 1-continued
Additional compounds of the invention
P-0238 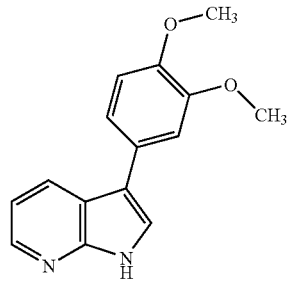 [SMILES: COc1ccc(-c2c[nH]c3ncccc23)cc1OC]
P-0239 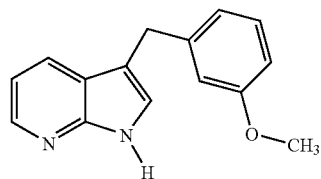 [SMILES: COc1cccc(Cc2c[nH]c3ncccc23)c1]
P-0240 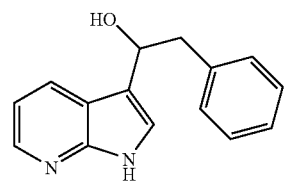 [SMILES: OC(Cc1ccccc1)c1c[nH]c2ncccc12]
P-0241 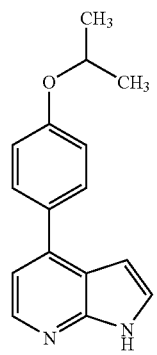 [SMILES: CC(C)Oc1ccc(-c2ccnc3[nH]ccc23)cc1]
P-0242 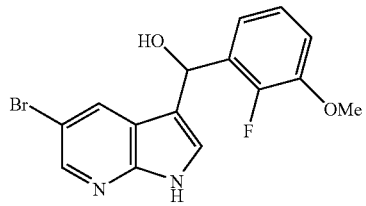 [SMILES: COc1cccc(C(O)c2c[nH]c3ncc(Br)cc23)c1F]
P-0243 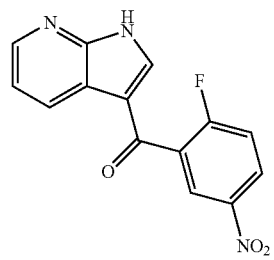 [SMILES: O=C(c1cc([N+](=O)[O-])ccc1F)c1c[nH]c2ncccc12]

TABLE 1-continued
Additional compounds of the invention
P-0244
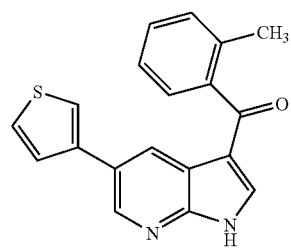 [SMILES: Cc1ccccc1C(=O)c1c[nH]c2ncc(-c3ccsc3)cc12]
P-0245
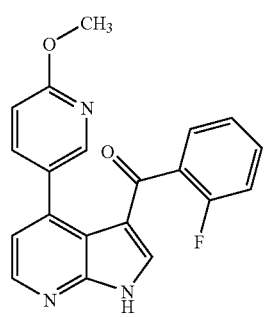 [SMILES: COc1ccc(-c2ccnc3[nH]cc(C(=O)c4ccccc4F)c23)cn1]
P-0246
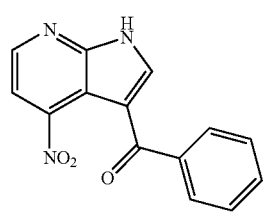 [SMILES: O=C(c1ccccc1)c1c[nH]c2nccc([N+](=O)[O-])c12]
P-0247
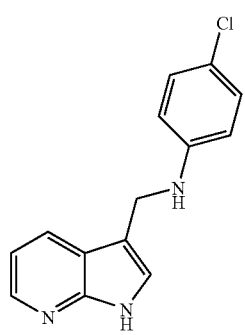 [SMILES: Clc1ccc(NCc2c[nH]c3ncccc23)cc1]
P-0248
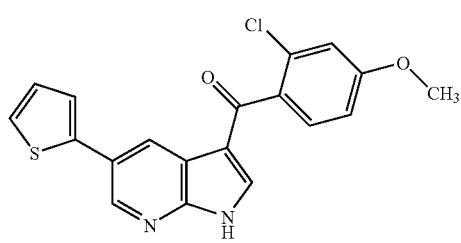 [SMILES: COc1ccc(C(=O)c2c[nH]c3ncc(-c4cccs4)cc23)c(Cl)c1]
P-0249
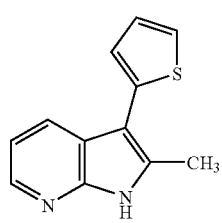

TABLE 1-continued
| Additional compounds of the invention |
P-0250 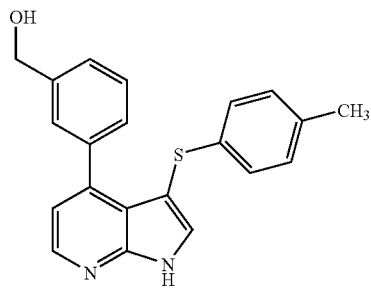 [SMILES: Cc1ccc(Sc2c[nH]c3nccc(-c4cccc(CO)c4)c23)cc1]
P-0251 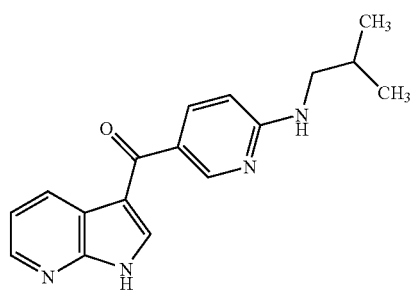 [SMILES: CC(C)CNc1ccc(C(=O)c2c[nH]c3ncccc23)cn1]
P-0252 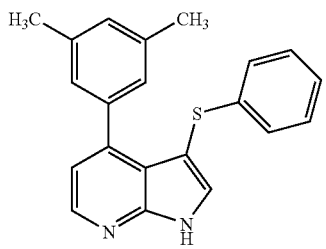
P-0253 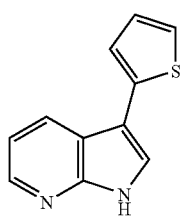 [SMILES: c1csc(-c2c[nH]c3ncccc23)c1]
P-0254 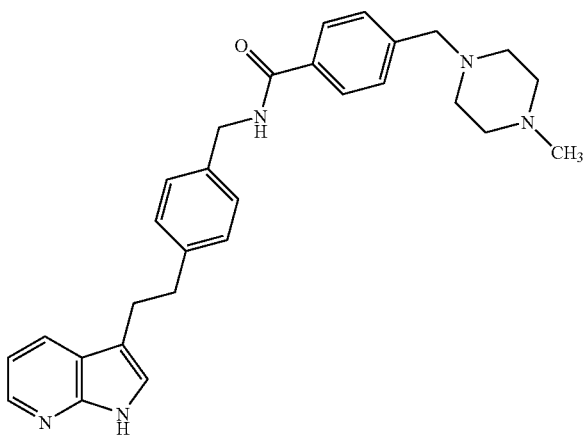 [SMILES: CN1CCN(Cc2ccc(C(=O)NCc3ccc(CCc4c[nH]c5ncccc45)cc3)cc2)CC1]

TABLE 1-continued
Additional compounds of the invention
P-0255 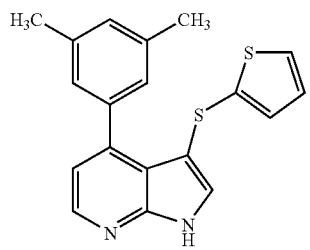 [SMILES: Cc1cc(C)cc(-c2ccnc3[nH]cc(Sc4cccs4)c23)c1]
P-0256 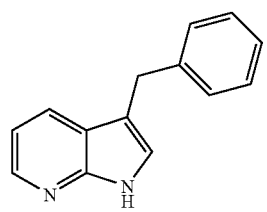 [SMILES: c1ccc(Cc2c[nH]c3ncccc23)cc1]
P-0258 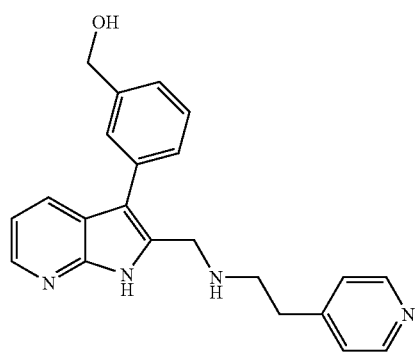 [SMILES: OCc1cccc(-c2c(CNCCc3ccncc3)[nH]c3ncccc23)c1]
P-0259 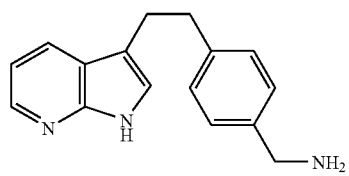 [SMILES: NCc1ccc(CCc2c[nH]c3ncccc23)cc1]
P-0260 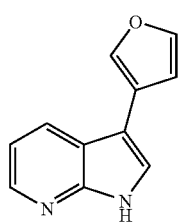 [SMILES: c1cnc2[nH]cc(-c3ccoc3)c2c1]
P-0261 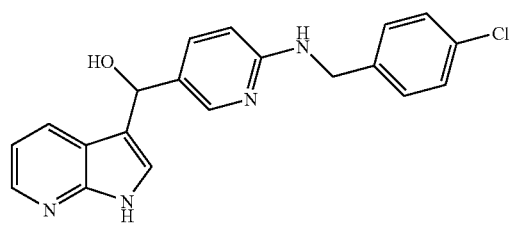 [SMILES: OC(c1ccc(NCc2ccc(Cl)cc2)nc1)c1c[nH]c2ncccc12]

TABLE 1-continued
Additional compounds of the invention
P-0263
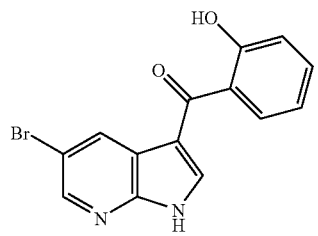 [SMILES: O=C(c1ccccc1O)c1c[nH]c2ncc(Br)cc12]
P-0264
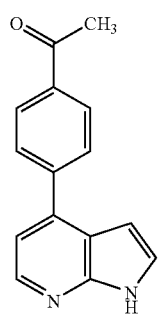 [SMILES: CC(=O)c1ccc(-c2ccnc3[nH]ccc23)cc1]
P-0266
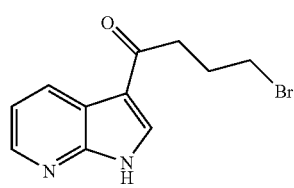 [SMILES: O=C(CCCBr)c1c[nH]c2ncccc12]
P-0267
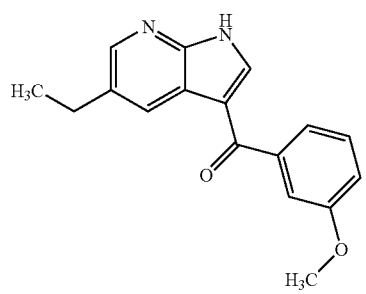 [SMILES: CCc1cnc2[nH]cc(C(=O)c3cccc(OC)c3)c2c1]
P-0268
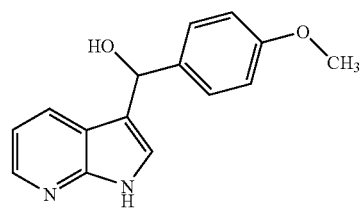 [SMILES: COc1ccc(C(O)c2c[nH]c3ncccc23)cc1]

TABLE 1-continued
Additional compounds of the invention
P-0270
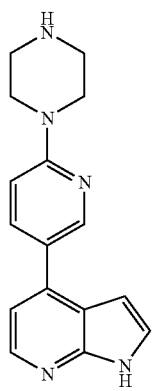 [SMILES: c1cc(-c2ccc(N3CCNCC3)nc2)c2cc[nH]c2n1]
P-0271
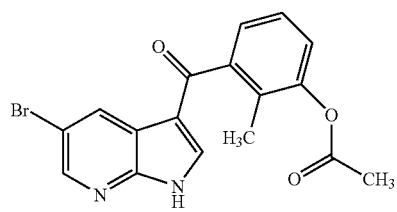 [SMILES: CC(=O)Oc1cccc(C(=O)c2c[nH]c3ncc(Br)cc23)c1C]
P-0272
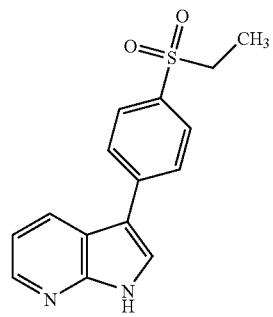 [SMILES: CCS(=O)(=O)c1ccc(-c2c[nH]c3ncccc23)cc1]
P-0273
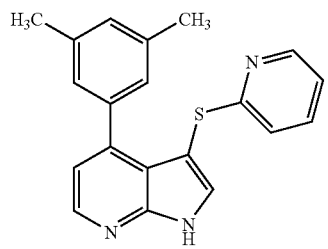 [SMILES: Cc1cc(C)cc(-c2ccnc3[nH]cc(Sc4ccccn4)c23)c1]
P-0274
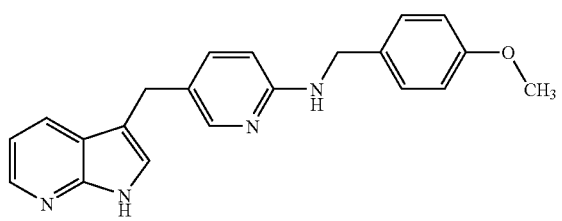 [SMILES: COc1ccc(CNc2ccc(Cc3c[nH]c4ncccc34)cn2)cc1]

TABLE 1-continued
| Additional compounds of the invention |
P-0275 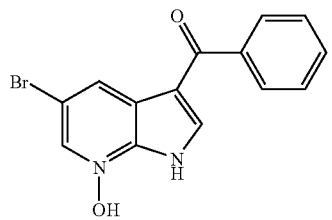
P-0276 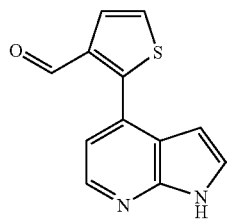 [SMILES: O=Cc1ccsc1-c1ccnc2[nH]ccc12]
P-0277 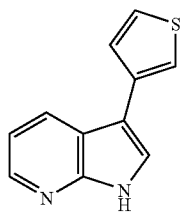 [SMILES: c1cnc2[nH]cc(-c3ccsc3)c2c1]
P-0278 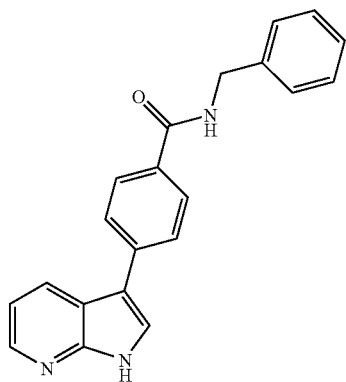 [SMILES: O=C(NCc1ccccc1)c1ccc(-c2c[nH]c3ncccc23)cc1]
P-0279 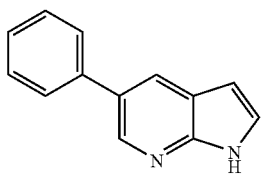 [SMILES: c1ccc(-c2cnc3[nH]ccc3c2)cc1]
P-0280 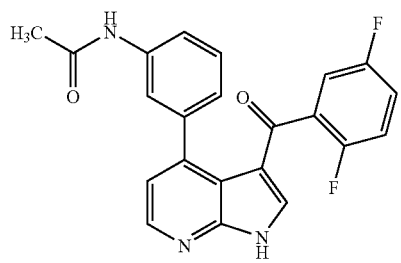 [SMILES: CC(=O)Nc1cccc(-c2ccnc3[nH]cc(C(=O)c4cc(F)ccc4F)c23)c1]

TABLE 1-continued
Additional compounds of the invention
P-0281 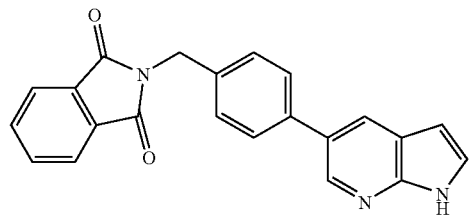 [SMILES: O=C1c2ccccc2C(=O)N1Cc1ccc(-c2cnc3[nH]ccc3c2)cc1]
P-0282 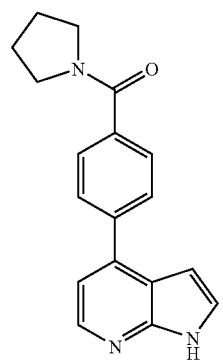 [SMILES: O=C(c1ccc(-c2ccnc3[nH]ccc23)cc1)N1CCCC1]
P-0283 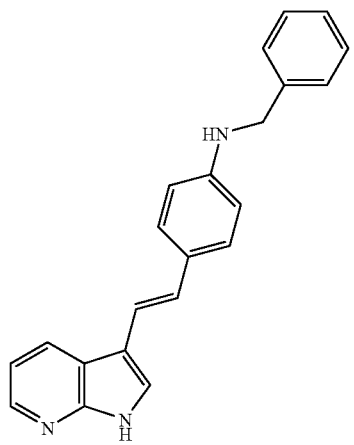 [SMILES: C(=C\c1c[nH]c2ncccc12)/c1ccc(NCc2ccccc2)cc1]
P-0284 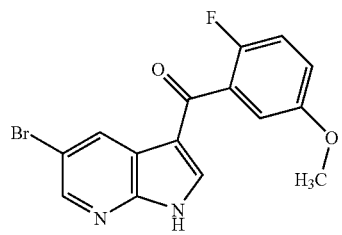 [SMILES: COc1ccc(F)c(C(=O)c2c[nH]c3ncc(Br)cc23)c1]
P-0285 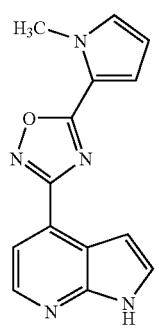 [SMILES: Cn1cccc1-c1nc(-c2ccnc3[nH]ccc23)no1]

TABLE 1-continued
Additional compounds of the invention
P-0286 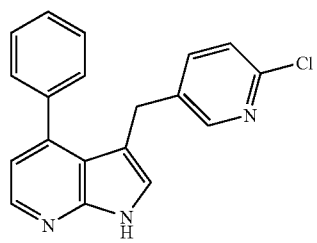 [SMILES: Clc1ccc(Cc2c[nH]c3nccc(-c4ccccc4)c23)cn1]
P-0287 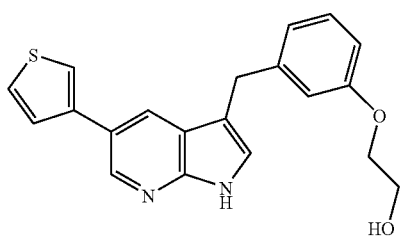 [SMILES: OCCOc1cccc(Cc2c[nH]c3ncc(-c4ccsc4)cc23)c1]
P-0288 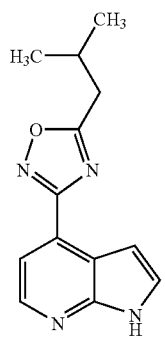
P-0289 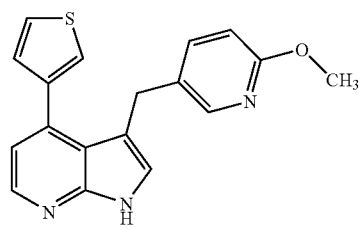 [SMILES: COc1ccc(Cc2c[nH]c3nccc(-c4ccsc4)c23)cn1]
P-0290 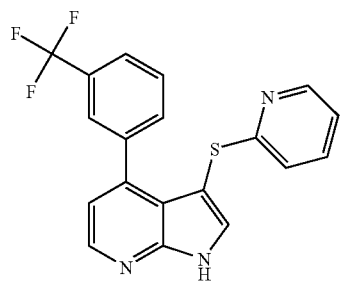 [SMILES: FC(F)(F)c1cccc(-c2ccnc3[nH]cc(Sc4ccccn4)c23)c1]
P-0291 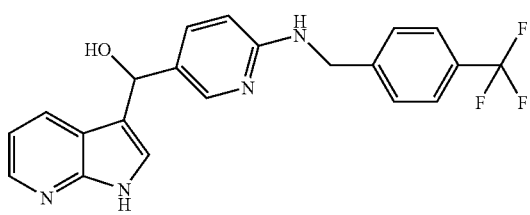 [SMILES: OC(c1ccc(NCc2ccc(C(F)(F)F)cc2)nc1)c1c[nH]c2ncccc12]

TABLE 1-continued
Additional compounds of the invention
P-0292 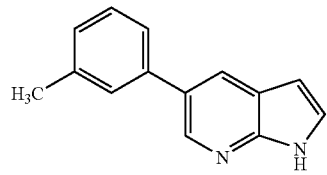 [SMILES: Cc1cccc(-c2cnc3[nH]ccc3c2)c1]
P-0293 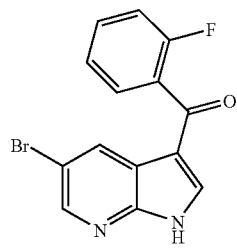
P-0294 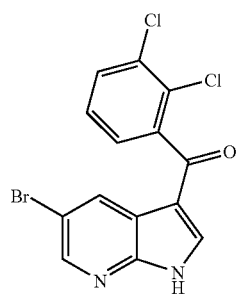
P-0295 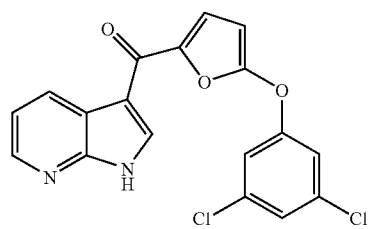 [SMILES: O=C(c1ccc(Oc2cc(Cl)cc(Cl)c2)o1)c1c[nH]c2ncccc12]
P-0296 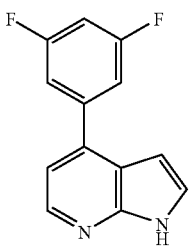 [SMILES: Fc1cc(F)cc(-c2ccnc3[nH]ccc23)c1]
P-0300 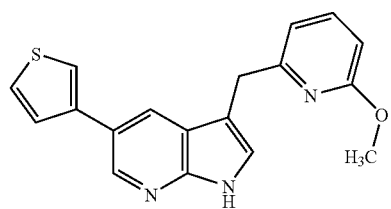 [SMILES: COc1cccc(Cc2c[nH]c3ncc(-c4ccsc4)cc23)n1]

TABLE 1-continued
Additional compounds of the invention
P-0301 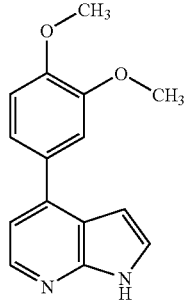 [SMILES: COc1ccc(-c2ccnc3[nH]ccc23)cc1OC]
P-0303 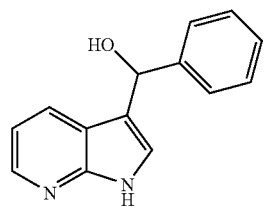 [SMILES: OC(c1ccccc1)c1c[nH]c2ncccc12]
P-0304 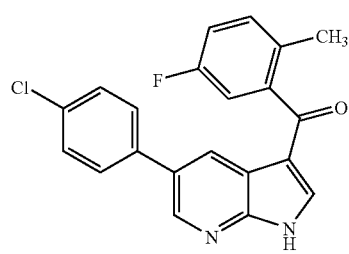 [SMILES: Cc1ccc(F)cc1C(=O)c1c[nH]c2ncc(-c3ccc(Cl)cc3)cc12]
P-0305 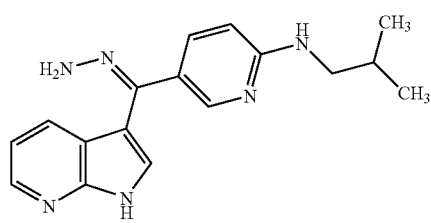 [SMILES: CC(C)CNc1ccc(/C(=N/N)c2c[nH]c3ncccc23)cn1]
P-0306 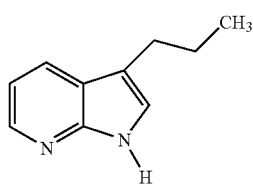
P-0307 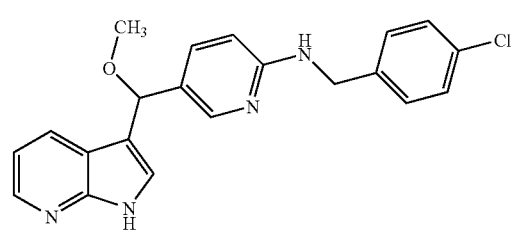 [SMILES: COC(c1ccc(NCc2ccc(Cl)cc2)nc1)c1c[nH]c2ncccc12]

TABLE 1-continued
Additional compounds of the invention
P-0309 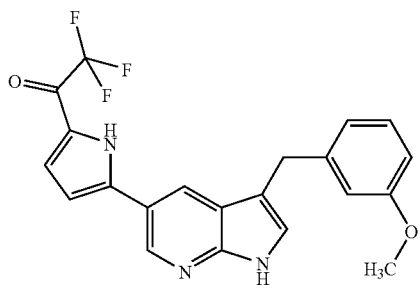 [SMILES: COc1cccc(Cc2c[nH]c3ncc(-c4ccc(C(=O)C(F)(F)F)[nH]4)cc23)c1]
P-0310 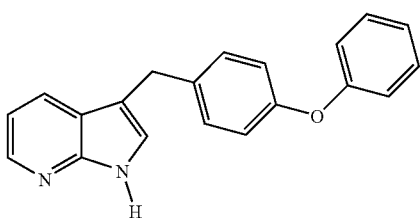 [SMILES: c1ccc(Oc2ccc(Cc3c[nH]c4ncccc34)cc2)cc1]
P-0311 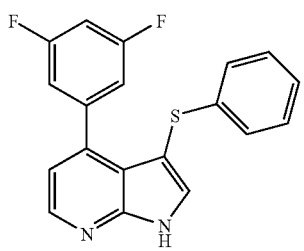 [SMILES: Fc1cc(F)cc(-c2ccnc3[nH]cc(Sc4ccccc4)c23)c1]
P-0312 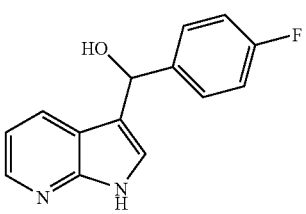 [SMILES: OC(c1ccc(F)cc1)c1c[nH]c2ncccc12]
P-0313 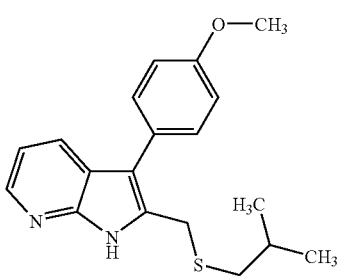 [SMILES: COc1ccc(-c2c(CSCC(C)C)[nH]c3ncccc23)cc1]
P-0314 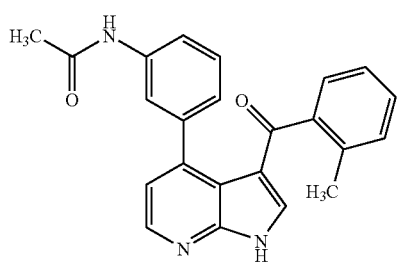 [SMILES: CC(=O)Nc1cccc(-c2ccnc3[nH]cc(C(=O)c4ccccc4C)c23)c1]

TABLE 1-continued
Additional compounds of the invention
P-0315 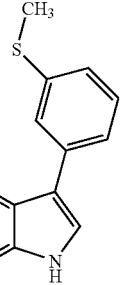
P-0316 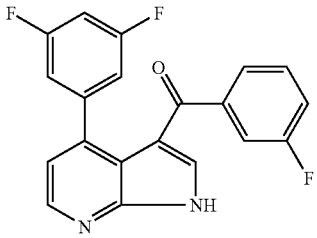 [SMILES: O=C(c1cccc(F)c1)c1c[nH]c2nccc(-c3cc(F)cc(F)c3)c12]
P-0317 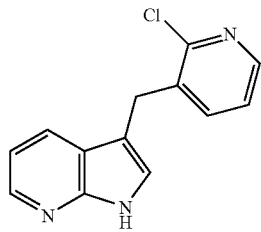 [SMILES: Clc1ncccc1Cc1c[nH]c2ncccc12]
P-0319 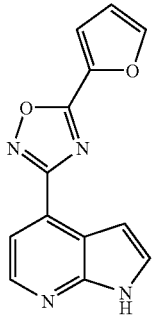 [SMILES: c1coc(-c2nc(-c3ccnc4[nH]ccc34)no2)c1]
P-0320 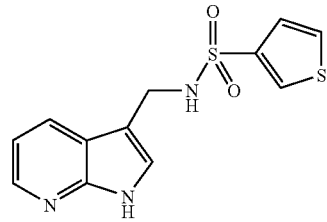 [SMILES: O=S(=O)(NCc1c[nH]c2ncccc12)c1ccsc1]
P-0321 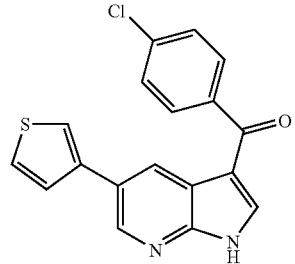 [SMILES: O=C(c1ccc(Cl)cc1)c1c[nH]c2ncc(-c3ccsc3)cc12]

TABLE 1-continued
Additional compounds of the invention
P-0322 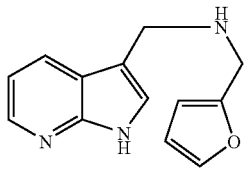
P-0323 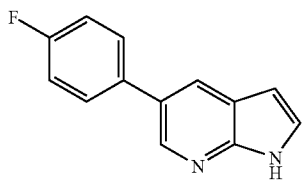 [SMILES: Fc1ccc(-c2cnc3[nH]ccc3c2)cc1]
P-0324 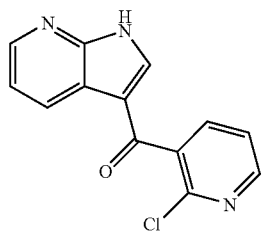 [SMILES: O=C(c1cccnc1Cl)c1c[nH]c2ncccc12]
P-0325 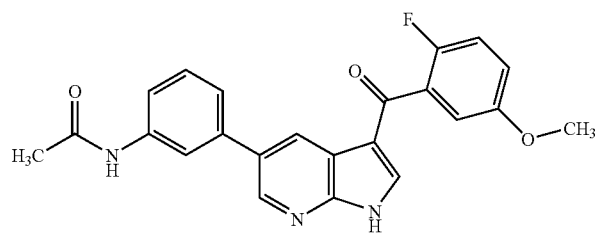 [SMILES: COc1ccc(F)c(C(=O)c2c[nH]c3ncc(-c4cccc(NC(C)=O)c4)cc23)c1]
P-0326 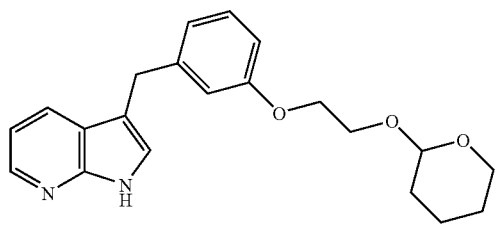 [SMILES: c1cc(Cc2c[nH]c3ncccc23)cc(OCCOC2CCCCO2)c1]
P-0327 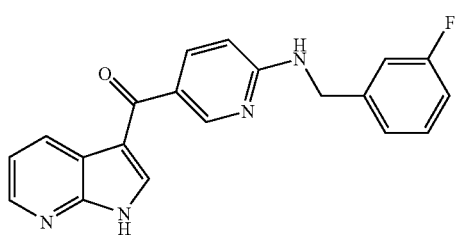 [SMILES: O=C(c1ccc(NCc2cccc(F)c2)nc1)c1c[nH]c2ncccc12]
P-0328 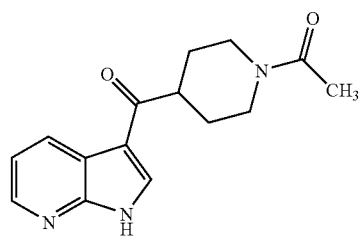 [SMILES: CC(=O)N1CCC(C(=O)c2c[nH]c3ncccc23)CC1]

TABLE 1-continued
Additional compounds of the invention
P-0329 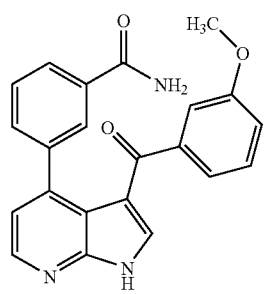 [SMILES: COc1cccc(C(=O)c2c[nH]c3nccc(-c4cccc(C(N)=O)c4)c23)c1]
P-0330 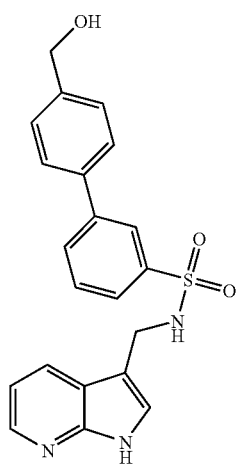 [SMILES: O=S(=O)(NCc1c[nH]c2ncccc12)c1cccc(-c2ccc(CO)cc2)c1]
P-0331 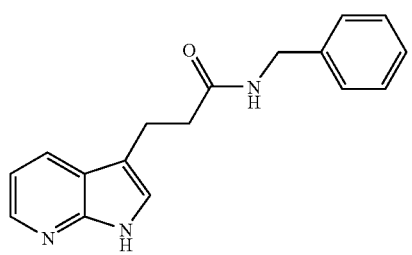 [SMILES: O=C(CCc1c[nH]c2ncccc12)NCc1ccccc1]
P-0332 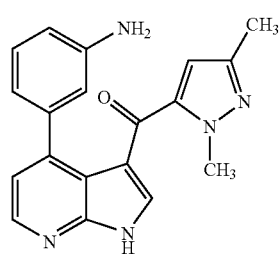 [SMILES: Cc1cc(C(=O)c2c[nH]c3nccc(-c4cccc(N)c4)c23)n(C)n1]
P-0334 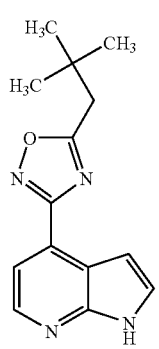

TABLE 1-continued
| Additional compounds of the invention |
P-0335 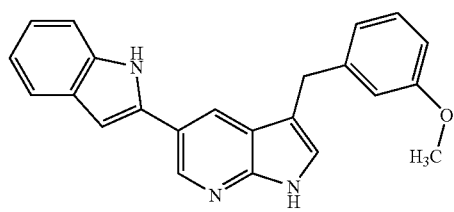 [SMILES: COc1cccc(Cc2c[nH]c3ncc(-c4cc5ccccc5[nH]4)cc23)c1]
P-0336 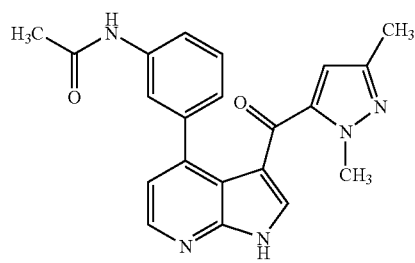 [SMILES: CC(=O)Nc1cccc(-c2ccnc3[nH]cc(C(=O)c4cc(C)nn4C)c23)c1]
P-0337 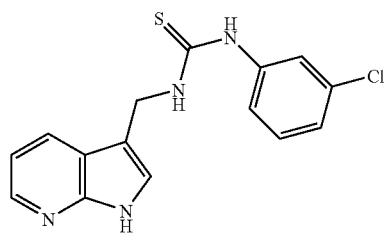 [SMILES: S=C(NCc1c[nH]c2ncccc12)Nc1cccc(Cl)c1]
P-0338 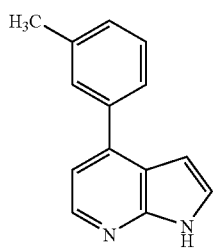 [SMILES: Cc1cccc(-c2ccnc3[nH]ccc23)c1]
P-0339 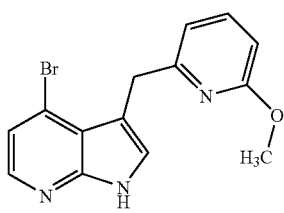 [SMILES: COc1cccc(Cc2c[nH]c3nccc(Br)c23)n1]
P-0340 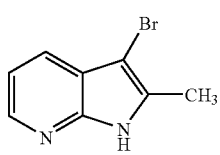
P-0341 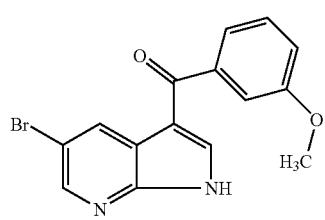 [SMILES: COc1cccc(C(=O)c2c[nH]c3ncc(Br)cc23)c1]

TABLE 1-continued
Additional compounds of the invention
P-0342 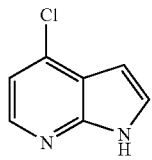
P-0343 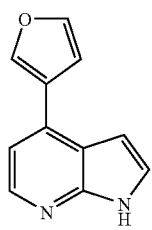 [SMILES: c1cc(-c2ccoc2)c2cc[nH]c2n1]
P-0344 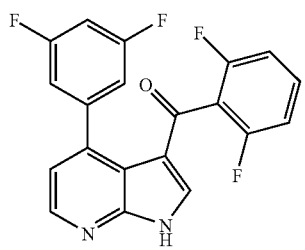 [SMILES: O=C(c1c(F)cccc1F)c1c[nH]c2nccc(-c3cc(F)cc(F)c3)c12]
P-0345 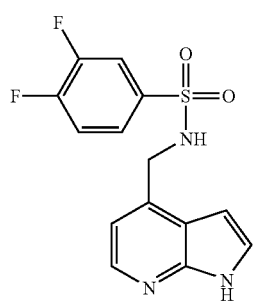 [SMILES: O=S(=O)(NCc1ccnc2[nH]ccc12)c1ccc(F)c(F)c1]
P-0346 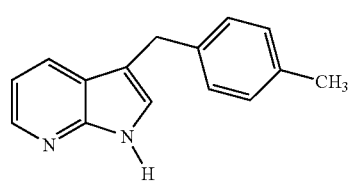 [SMILES: Cc1ccc(Cc2c[nH]c3ncccc23)cc1]
P-0347 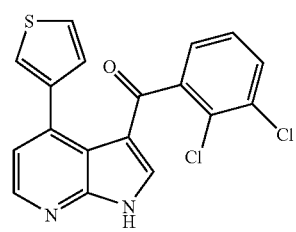 [SMILES: O=C(c1cccc(Cl)c1Cl)c1c[nH]c2nccc(-c3ccsc3)c12]

TABLE 1-continued
Additional compounds of the invention
P-0348 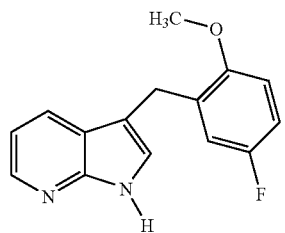 [SMILES: COc1ccc(F)cc1Cc1c[nH]c2ncccc12]
P-0349 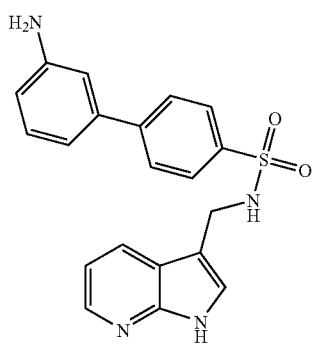 [SMILES: Nc1cccc(-c2ccc(S(=O)(=O)NCc3c[nH]c4ncccc34)cc2)c1]
P-0350 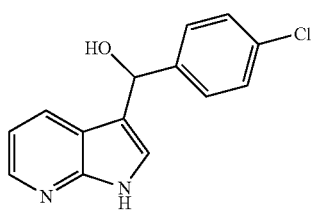 [SMILES: OC(c1ccc(Cl)cc1)c1c[nH]c2ncccc12]
P-0351 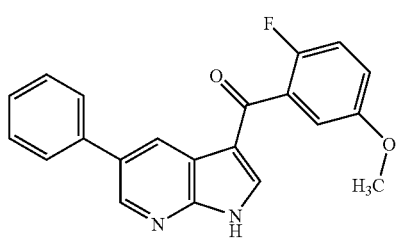 [SMILES: COc1ccc(F)c(C(=O)c2c[nH]c3ncc(-c4ccccc4)cc23)c1]
P-0352 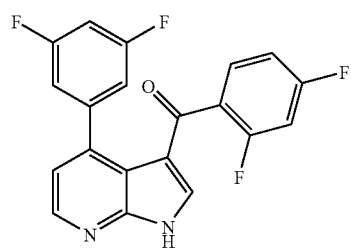 [SMILES: O=C(c1ccc(F)cc1F)c1c[nH]c2nccc(-c3cc(F)cc(F)c3)c12]
P-0353 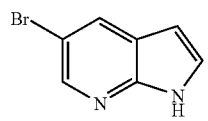

TABLE 1-continued
Additional compounds of the invention
P-0354 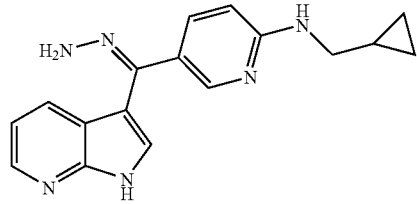 [SMILES: N/N=C(/c1ccc(NCC2CC2)nc1)c1c[nH]c2ncccc12]
P-0355 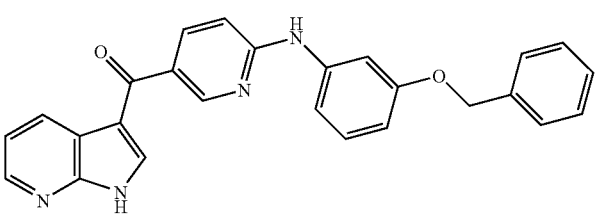 [SMILES: O=C(c1ccc(Nc2cccc(OCc3ccccc3)c2)nc1)c1c[nH]c2ncccc12]
P-0357 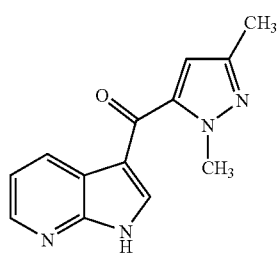 [SMILES: Cc1cc(C(=O)c2c[nH]c3ncccc23)n(C)n1]
P-0358 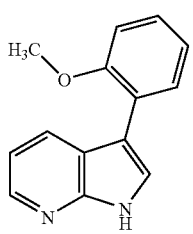
P-0359 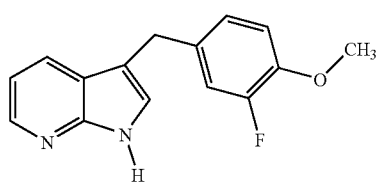 [SMILES: COc1ccc(Cc2c[nH]c3ncccc23)cc1F]
P-0360 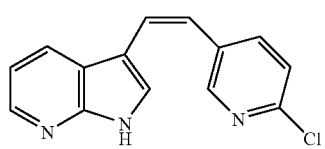 [SMILES: Clc1ccc(/C=C\c2c[nH]c3ncccc23)cn1]
P-0361 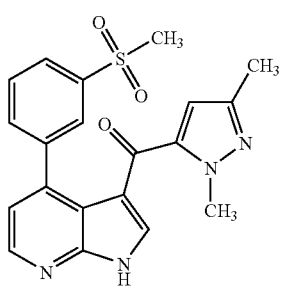 [SMILES: Cc1cc(C(=O)c2c[nH]c3nccc(-c4cccc(S(C)(=O)=O)c4)c23)n(C)n1]

TABLE 1-continued
Additional compounds of the invention
P-0362 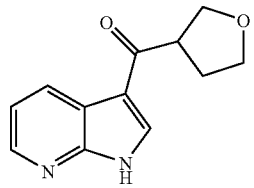 [SMILES: O=C(c1c[nH]c2ncccc12)C1CCOC1]
P-0363 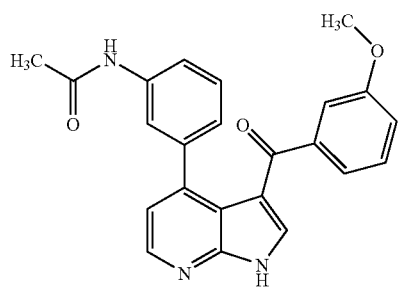 [SMILES: COc1cccc(C(=O)c2c[nH]c3nccc(-c4cccc(NC(C)=O)c4)c23)c1]
P-0364 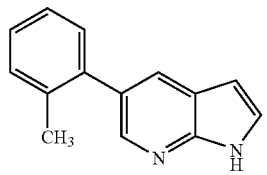 [SMILES: Cc1ccccc1-c1cnc2[nH]ccc2c1]
P-0365 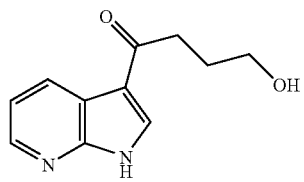 [SMILES: O=C(CCCO)c1c[nH]c2ncccc12]
P-0366 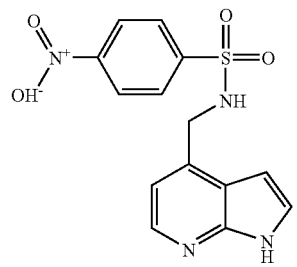 [SMILES: O=[N+]([O-])c1ccc(S(=O)(=O)NCc2ccnc3[nH]ccc23)cc1]
P-0367 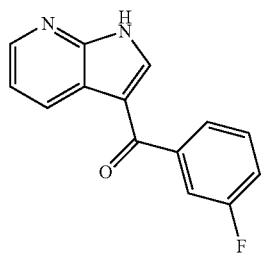 [SMILES: O=C(c1cccc(F)c1)c1c[nH]c2ncccc12]
P-0368 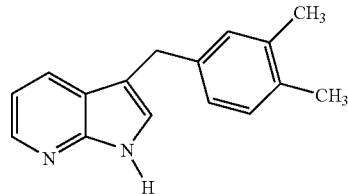 [SMILES: Cc1ccc(Cc2c[nH]c3ncccc23)cc1C]

TABLE 1-continued
Additional compounds of the invention
P-0369
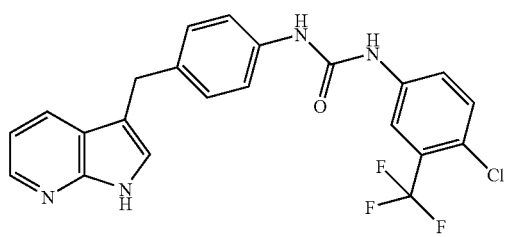 [SMILES: O=C(Nc1ccc(Cc2c[nH]c3ncccc23)cc1)Nc1ccc(Cl)c(C(F)(F)F)c1]
P-0370
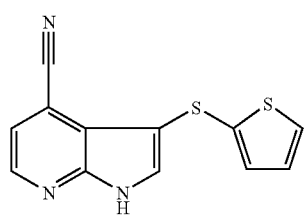 [SMILES: N#Cc1ccnc2[nH]cc(Sc3cccs3)c12]
P-0371
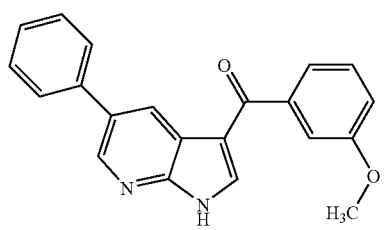 [SMILES: COc1cccc(C(=O)c2c[nH]c3ncc(-c4ccccc4)cc23)c1]
P-0372
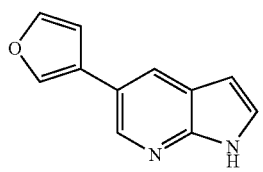 [SMILES: c1cc2cc(-c3ccoc3)cnc2[nH]1]
P-0373
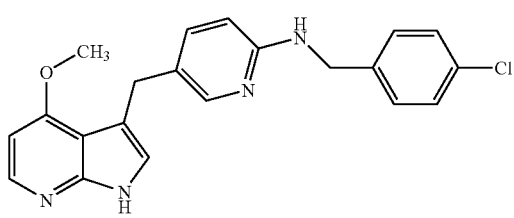 [SMILES: COc1ccnc2[nH]cc(Cc3ccc(NCc4ccc(Cl)cc4)nc3)c12]
P-0374
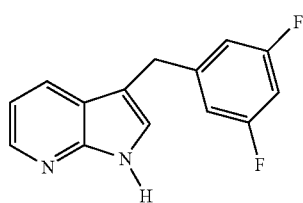 [SMILES: Fc1cc(F)cc(Cc2c[nH]c3ncccc23)c1]

TABLE 1-continued
Additional compounds of the invention
P-0375
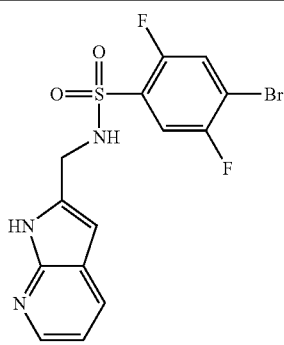
P-0376
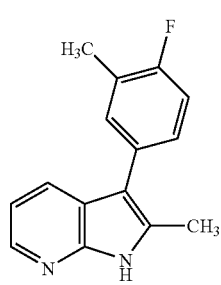 [SMILES: Cc1cc(-c2c(C)[nH]c3ncccc23)ccc1F]
P-0377
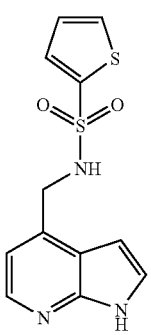 [SMILES: O=S(=O)(NCc1ccnc2[nH]ccc12)c1cccs1]
P-0378
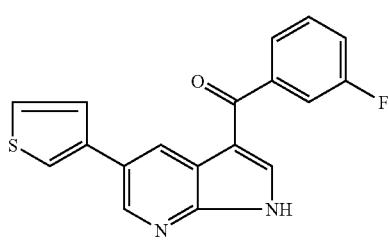 [SMILES: O=C(c1cccc(F)c1)c1c[nH]c2ncc(-c3ccsc3)cc12]
P-0379
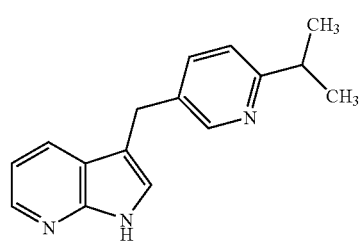 [SMILES: CC(C)c1ccc(Cc2c[nH]c3ncccc23)cn1]
P-0380
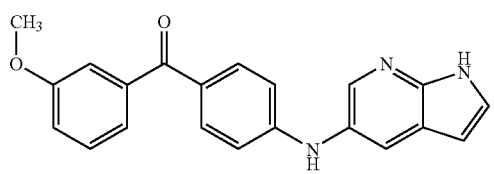 [SMILES: COc1cccc(C(=O)c2ccc(Nc3cnc4[nH]ccc4c3)cc2)c1]

TABLE 1-continued
Additional compounds of the invention
P-0381 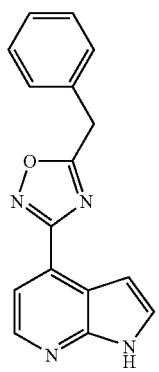 [SMILES: c1ccc(Cc2nc(-c3ccnc4[nH]ccc34)no2)cc1]
P-0382 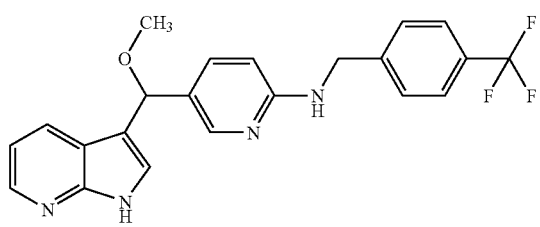 [SMILES: COC(c1ccc(NCc2ccc(C(F)(F)F)cc2)nc1)c1c[nH]c2ncccc12]
P-0384 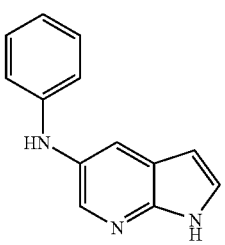 [SMILES: c1ccc(Nc2cnc3[nH]ccc3c2)cc1]
P-0385 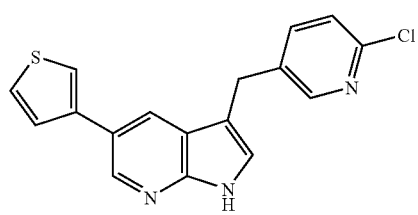 [SMILES: Clc1ccc(Cc2c[nH]c3ncc(-c4ccsc4)cc23)cn1]
P-0386 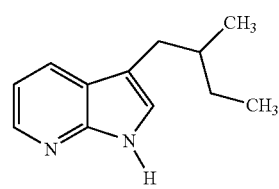
P-0387 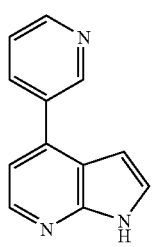 [SMILES: c1cncc(-c2ccnc3[nH]ccc23)c1]

TABLE 1-continued
Additional compounds of the invention
P-0388 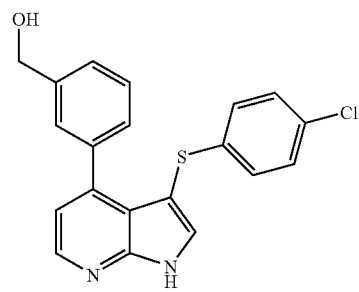 [SMILES: OCc1cccc(-c2ccnc3[nH]cc(Sc4ccc(Cl)cc4)c23)c1]
P-0389 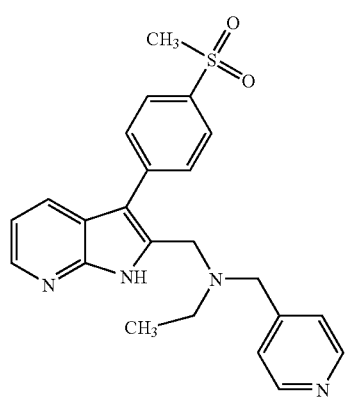 [SMILES: CCN(Cc1ccncc1)Cc1[nH]c2ncccc2c1-c1ccc(S(C)(=O)=O)cc1]
P-0390 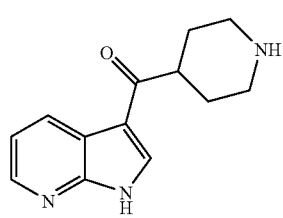 [SMILES: O=C(c1c[nH]c2ncccc12)C1CCNCC1]
P-0391 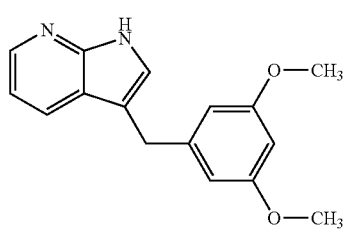 [SMILES: COc1cc(Cc2c[nH]c3ncccc23)cc(OC)c1]
P-0392 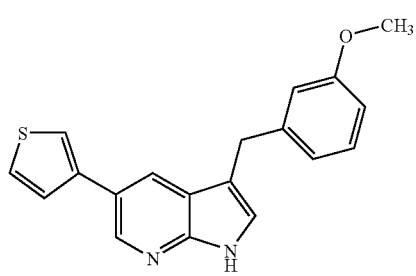 [SMILES: COc1cccc(Cc2c[nH]c3ncc(-c4ccsc4)cc23)c1]

TABLE 1-continued
Additional compounds of the invention
P-0393 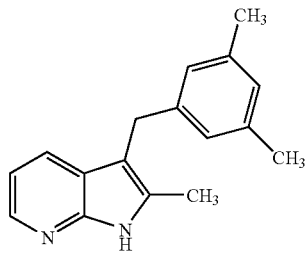 [SMILES: Cc1cc(C)cc(Cc2c(C)[nH]c3ncccc23)c1]
P-0394 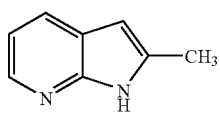
P-0395 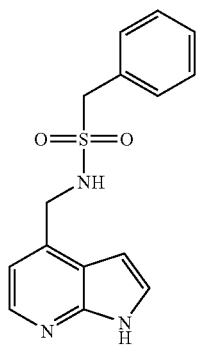 [SMILES: O=S(=O)(Cc1ccccc1)NCc1ccnc2[nH]ccc12]
P-0397 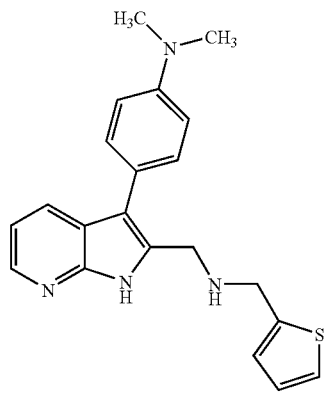 [SMILES: CN(C)c1ccc(-c2c(CNCc3cccs3)[nH]c3ncccc23)cc1]
P-0398 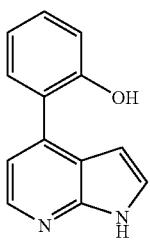 [SMILES: Oc1ccccc1-c1ccnc2[nH]ccc12]

TABLE 1-continued
Additional compounds of the invention
P-0399
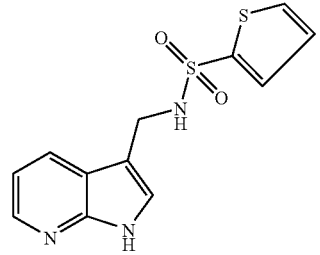 [SMILES: O=S(=O)(NCc1c[nH]c2ncccc12)c1cccs1]
P-0400
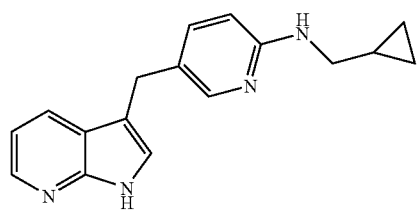 [SMILES: c1cnc2[nH]cc(Cc3ccc(NCC4CC4)nc3)c2c1]
P-0401
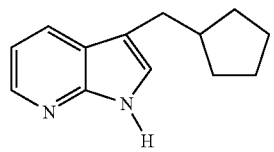
P-0402
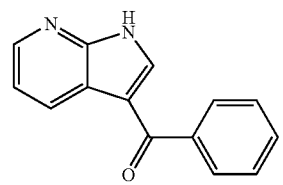 [SMILES: O=C(c1ccccc1)c1c[nH]c2ncccc12]
P-0403
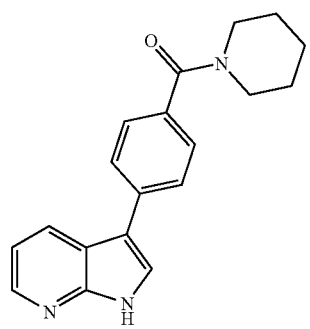 [SMILES: O=C(c1ccc(-c2c[nH]c3ncccc23)cc1)N1CCCCC1]
P-0404
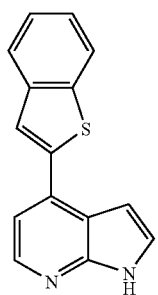 [SMILES: c1ccc2sc(-c3ccnc4[nH]ccc34)cc2c1]

TABLE 1-continued
Additional compounds of the invention
P-0405
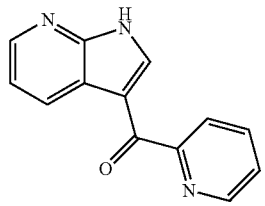 [SMILES: O=C(c1ccccn1)c1c[nH]c2ncccc12]
P-0406
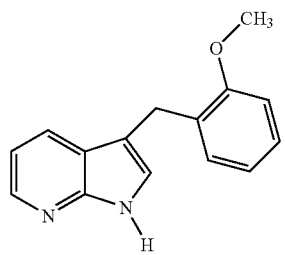 [SMILES: COc1ccccc1Cc1c[nH]c2ncccc12]
P-0407
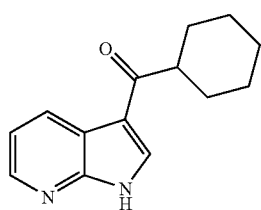 [SMILES: O=C(c1c[nH]c2ncccc12)C1CCCCC1]
P-0408
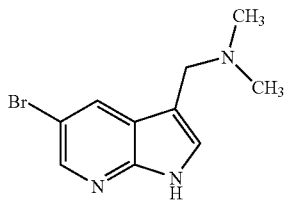
P-0410
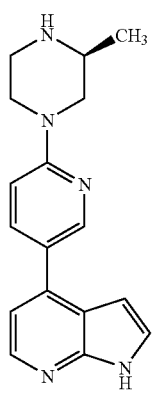 [SMILES: C[C@H]1CN(c2ccc(-c3ccnc4[nH]ccc34)cn2)CCN1]
P-0411
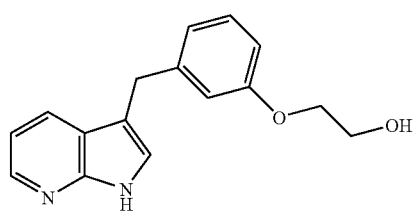 [SMILES: OCCOc1cccc(Cc2c[nH]c3ncccc23)c1]

TABLE 1-continued
Additional compounds of the invention
P-0412
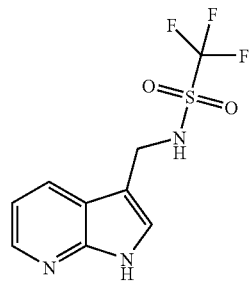 [SMILES: O=S(=O)(NCc1c[nH]c2ncccc12)C(F)(F)F]
P-0413
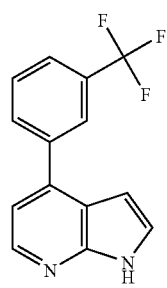
P-0414
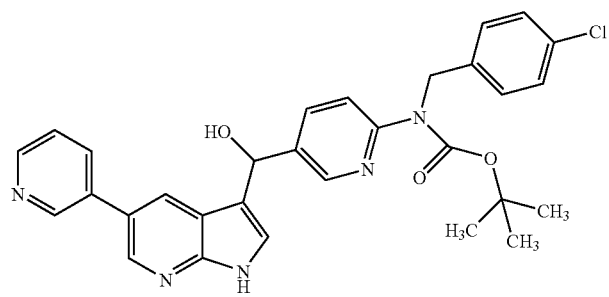 [SMILES: CC(C)(C)OC(=O)N(Cc1ccc(Cl)cc1)c1ccc(C(O)c2c[nH]c3ncc(-c4cccnc4)cc23)cn1]
P-0415
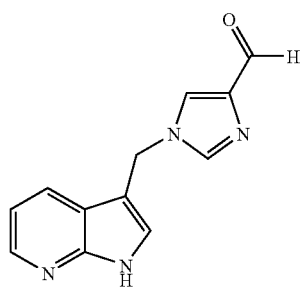 [SMILES: O=Cc1cn(Cc2c[nH]c3ncccc23)cn1]
P-0416
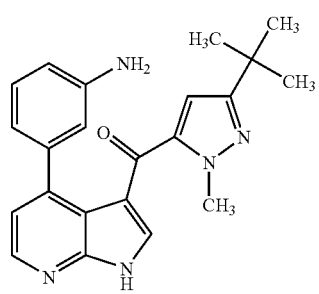 [SMILES: Cn1nc(C(C)(C)C)cc1C(=O)c1c[nH]c2nccc(-c3cccc(N)c3)c12]

TABLE 1-continued
Additional compounds of the invention
P-0417 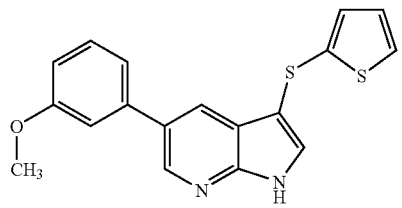 [SMILES: COc1cccc(-c2cnc3[nH]cc(Sc4cccs4)c3c2)c1]
P-0418 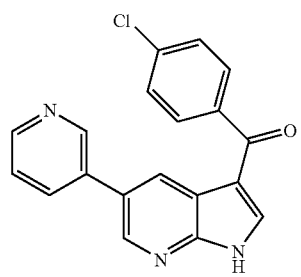 [SMILES: O=C(c1ccc(Cl)cc1)c1c[nH]c2ncc(-c3cccnc3)cc12]
P-0419 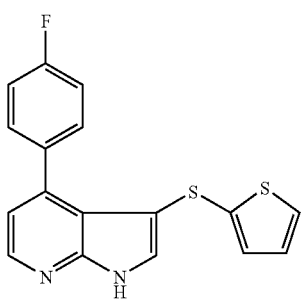 [SMILES: Fc1ccc(-c2ccnc3[nH]cc(Sc4cccs4)c23)cc1]
P-0420 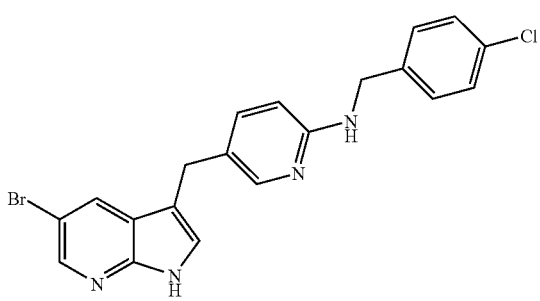 [SMILES: Clc1ccc(CNc2ccc(Cc3c[nH]c4ncc(Br)cc34)cn2)cc1]
P-0422 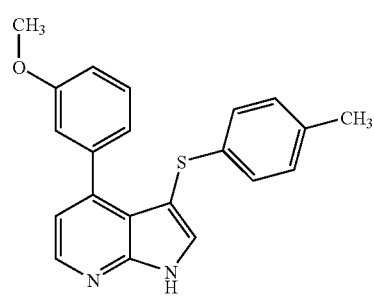

TABLE 1-continued
Additional compounds of the invention
P-0423 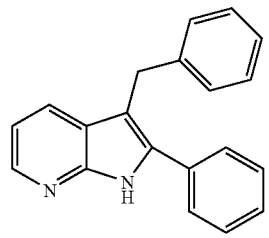 [SMILES: c1ccc(Cc2c(-c3ccccc3)[nH]c3ncccc23)cc1]
P-0424 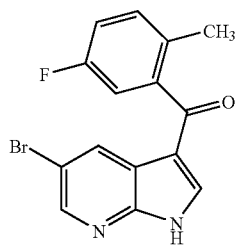
P-0425 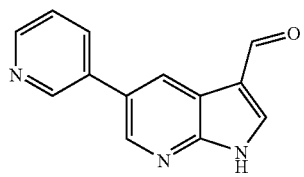 [SMILES: O=Cc1c[nH]c2ncc(-c3cccnc3)cc12]
P-0426 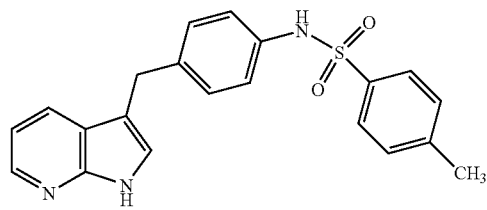 [SMILES: Cc1ccc(S(=O)(=O)Nc2ccc(Cc3c[nH]c4ncccc34)cc2)cc1]
P-0427 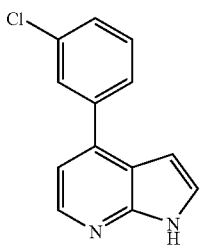 [SMILES: Clc1cccc(-c2ccnc3[nH]ccc23)c1]
P-0428 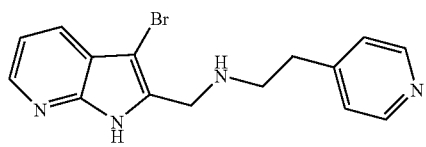 [SMILES: Brc1c(CNCCc2ccncc2)[nH]c2ncccc12]

TABLE 1-continued
Additional compounds of the invention
P-0429
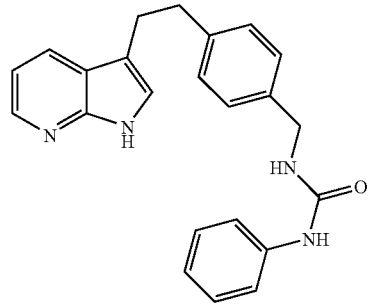 [SMILES: O=C(NCc1ccc(CCc2c[nH]c3ncccc23)cc1)Nc1ccccc1]
P-0430
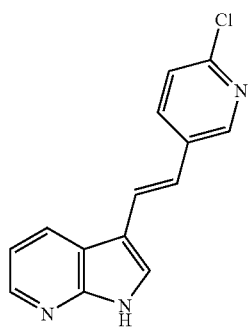 [SMILES: Clc1ccc(/C=C/c2c[nH]c3ncccc23)cn1]
P-0431
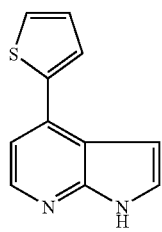 [SMILES: c1csc(-c2ccnc3[nH]ccc23)c1]
P-0432
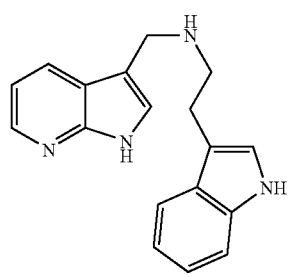 [SMILES: c1ccc2c(CCNCc3c[nH]c4ncccc34)c[nH]c2c1]

TABLE 1-continued
| Additional compounds of the invention |
P-0433 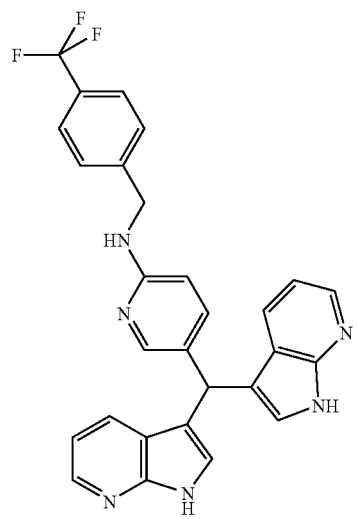 [SMILES: FC(F)(F)c1ccc(CNc2ccc(C(c3c[nH]c4ncccc34)c3c[nH]c4ncccc34)cn2)cc1]
P-0434 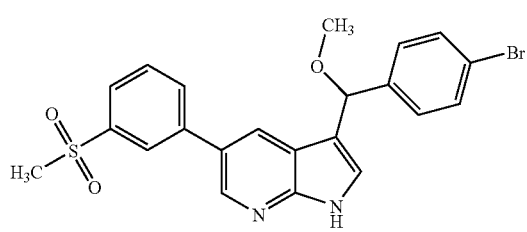 [SMILES: COC(c1ccc(Br)cc1)c1c[nH]c2ncc(-c3cccc(S(C)(=O)=O)c3)cc12]
P-0435 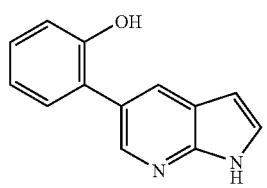 [SMILES: Oc1ccccc1-c1cnc2[nH]ccc2c1]
P-0436 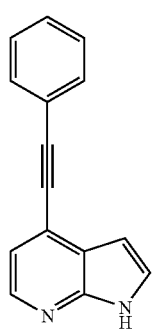 [SMILES: C(#Cc1ccnc2[nH]ccc12)c1ccccc1]
P-0437 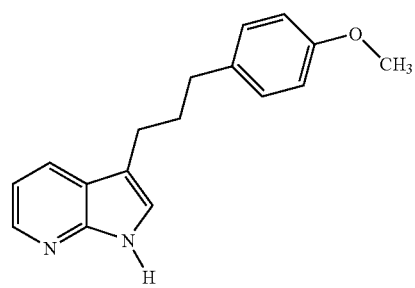 [SMILES: COc1ccc(CCCc2c[nH]c3ncccc23)cc1]

TABLE 1-continued
Additional compounds of the invention
P-0438 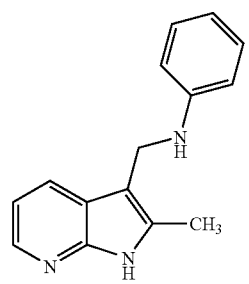 [SMILES: Cc1[nH]c2ncccc2c1CNc1ccccc1]
P-0439 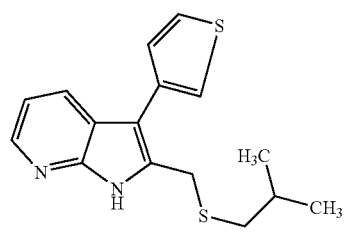 [SMILES: CC(C)CSCc1[nH]c2ncccc2c1-c1ccsc1]
P-0440 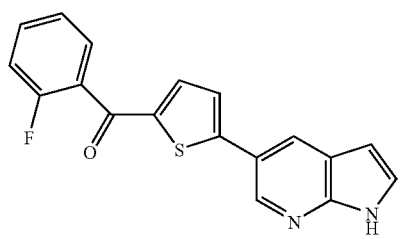 [SMILES: O=C(c1ccc(-c2cnc3[nH]ccc3c2)s1)c1ccccc1F]
P-0441 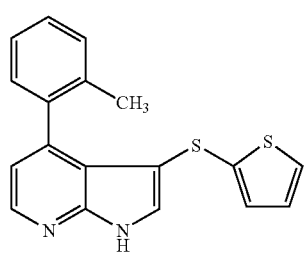 [SMILES: Cc1ccccc1-c1ccnc2[nH]cc(Sc3cccs3)c12]
P-0442 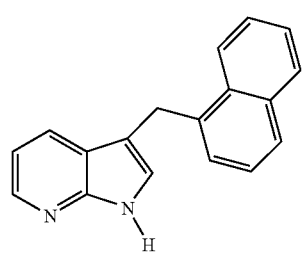 [SMILES: c1ccc2c(Cc3c[nH]c4ncccc34)cccc2c1]
P-0443 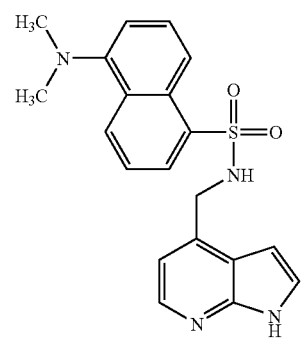 [SMILES: CN(C)c1cccc2c(S(=O)(=O)NCc3ccnc4[nH]ccc34)cccc12]

TABLE 1-continued
Additional compounds of the invention
P-0444 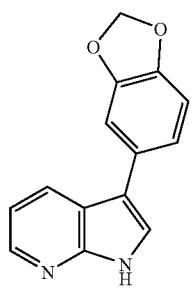 [SMILES: c1cnc2[nH]cc(-c3ccc4c(c3)OCO4)c2c1]
P-0445 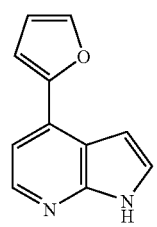 [SMILES: c1coc(-c2ccnc3[nH]ccc23)c1]
P-0446 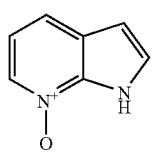
P-0447 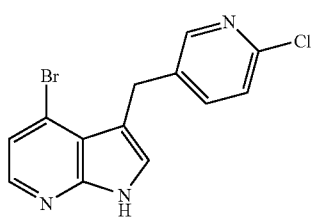 [SMILES: Clc1ccc(Cc2c[nH]c3nccc(Br)c23)cn1]
P-0448 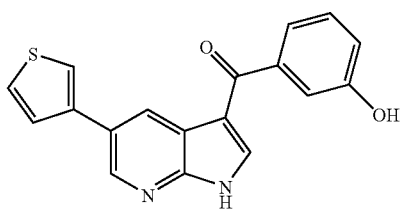 [SMILES: O=C(c1cccc(O)c1)c1c[nH]c2ncc(-c3ccsc3)cc12]
P-0449 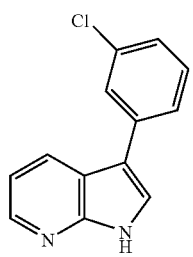 [SMILES: Clc1cccc(-c2c[nH]c3ncccc23)c1]
P-0450 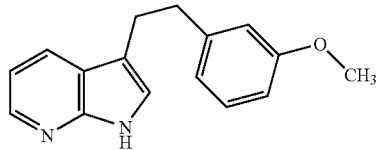 [SMILES: COc1cccc(CCc2c[nH]c3ncccc23)c1]

TABLE 1-continued
| Additional compounds of the invention |
P-0451 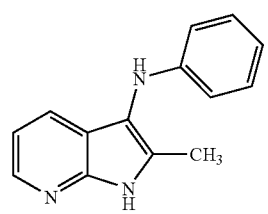 [SMILES: Cc1[nH]c2ncccc2c1Nc1ccccc1]
P-0452 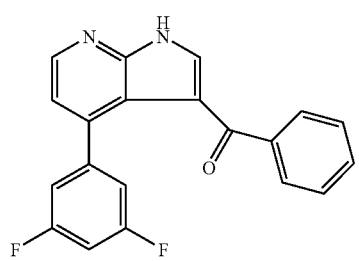 [SMILES: O=C(c1ccccc1)c1c[nH]c2nccc(-c3cc(F)cc(F)c3)c12]
P-0453 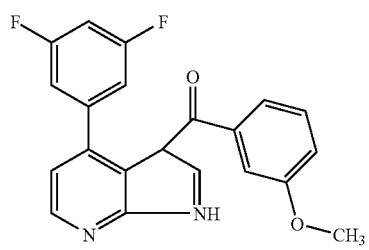 [SMILES: COc1cccc(C(=O)C2C=Nc3nccc(-c4cc(F)cc(F)c4)c32)c1]
P-0454 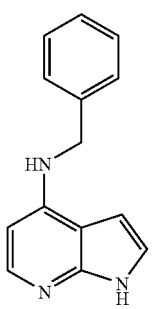 [SMILES: c1ccc(CNc2ccnc3[nH]ccc23)cc1]
P-0455 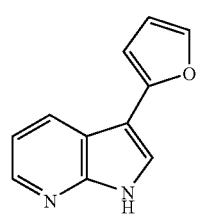 [SMILES: c1coc(-c2c[nH]c3ncccc23)c1]
P-0456 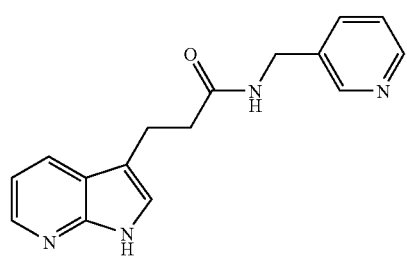 [SMILES: O=C(CCc1c[nH]c2ncccc12)NCc1cccnc1]

TABLE 1-continued
Additional compounds of the invention
P-0457 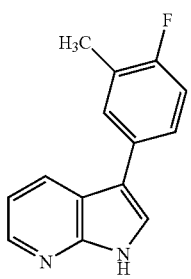 [SMILES: Cc1cc(-c2c[nH]c3ncccc23)ccc1F]
P-0458 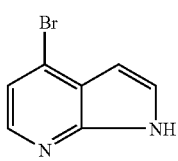
P-0459 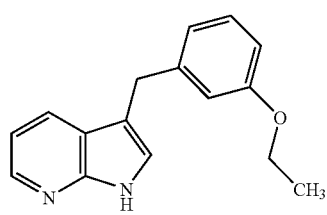 [SMILES: CCOc1cccc(Cc2c[nH]c3ncccc23)c1]
P-0460 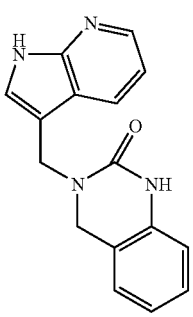 [SMILES: O=C1Nc2ccccc2CN1Cc1c[nH]c2ncccc12]
P-0461 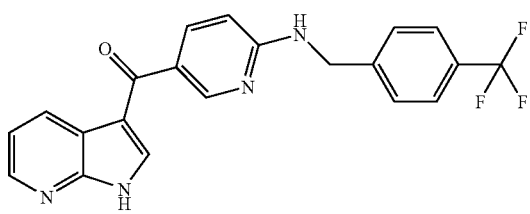 [SMILES: O=C(c1ccc(NCc2ccc(C(F)(F)F)cc2)nc1)c1c[nH]c2ncccc12]
P-0462 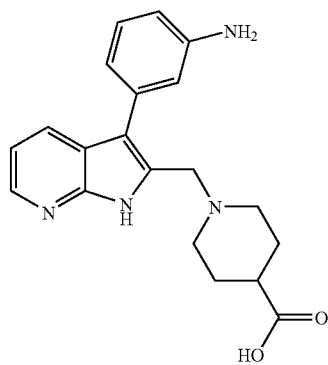 [SMILES: Nc1cccc(-c2c(CN3CCC(C(=O)O)CC3)[nH]c3ncccc23)c1]

TABLE 1-continued
Additional compounds of the invention
P-0463 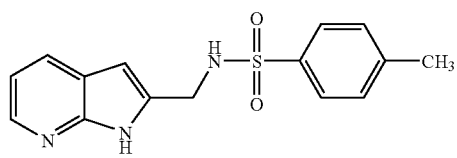
P-0464 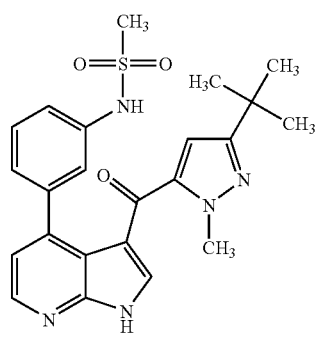 [SMILES: Cn1nc(C(C)(C)C)cc1C(=O)c1c[nH]c2nccc(-c3cccc(NS(C)(=O)=O)c3)c12]
P-0465 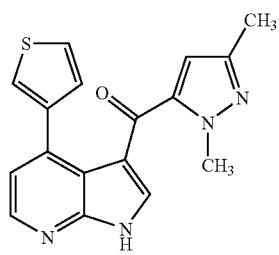 [SMILES: Cc1cc(C(=O)c2c[nH]c3nccc(-c4ccsc4)c23)n(C)n1]
P-0466 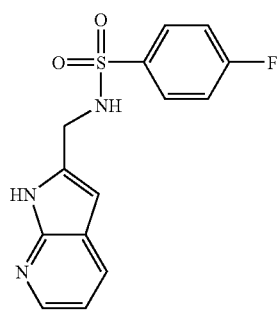 [SMILES: O=S(=O)(NCc1cc2cccnc2[nH]1)c1ccc(F)cc1]
P-0467 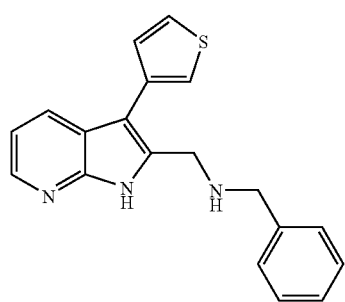 [SMILES: c1ccc(CNCc2[nH]c3ncccc3c2-c2ccsc2)cc1]
P-0468 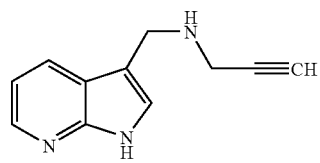

TABLE 1-continued
Additional compounds of the invention
P-0469 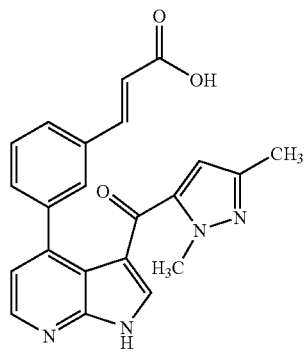 [SMILES: Cc1cc(C(=O)c2c[nH]c3nccc(-c4cccc(/C=C/C(=O)O)c4)c23)n(C)n1]
P-0470 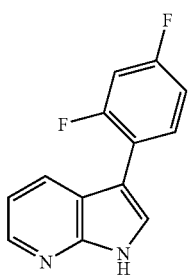 [SMILES: Fc1ccc(-c2c[nH]c3ncccc23)c(F)c1]
P-0471 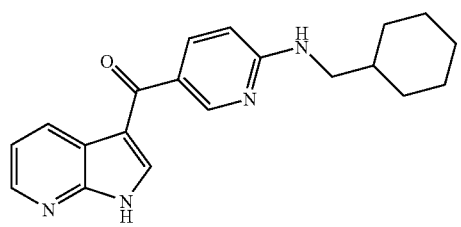 [SMILES: O=C(c1ccc(NCC2CCCCC2)nc1)c1c[nH]c2ncccc12]
P-0472 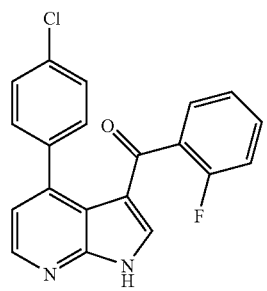 [SMILES: O=C(c1ccccc1F)c1c[nH]c2nccc(-c3ccc(Cl)cc3)c12]
P-0473 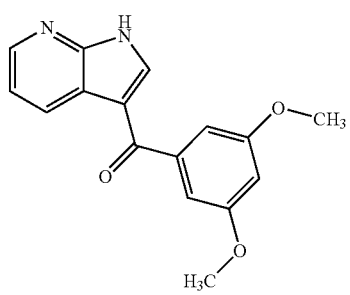 [SMILES: COc1cc(OC)cc(C(=O)c2c[nH]c3ncccc23)c1]

TABLE 1-continued
Additional compounds of the invention
P-0474 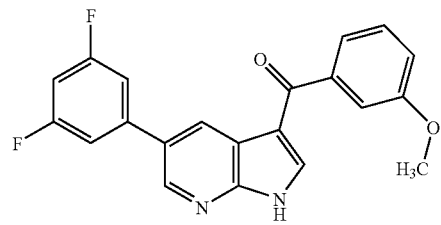 [SMILES: COc1cccc(C(=O)c2c[nH]c3ncc(-c4cc(F)cc(F)c4)cc23)c1]
P-0475 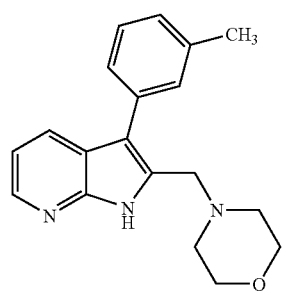 [SMILES: Cc1cccc(-c2c(CN3CCOCC3)[nH]c3ncccc23)c1]
P-0476 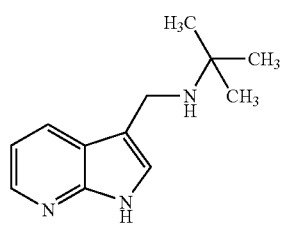
P-0477 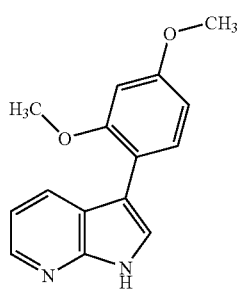
P-0478 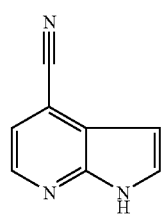 [SMILES: N#Cc1ccnc2[nH]ccc12]
P-0479 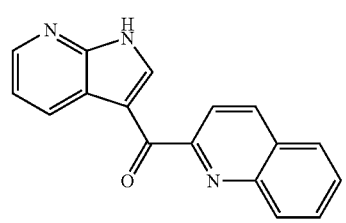 [SMILES: O=C(c1ccc2ccccc2n1)c1c[nH]c2ncccc12]

TABLE 1-continued
Additional compounds of the invention
P-0480 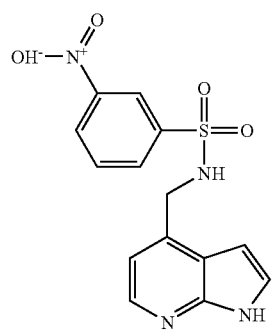 [SMILES: O=[N+]([O-])c1cccc(S(=O)(=O)NCc2ccnc3[nH]ccc23)c1]
P-0481 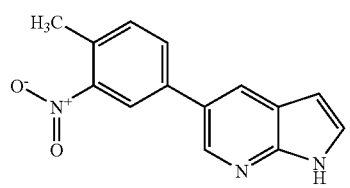 [SMILES: Cc1ccc(-c2cnc3[nH]ccc3c2)cc1[N+](=O)[O-]]
P-0482 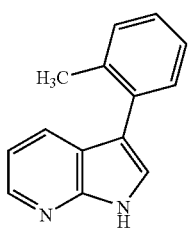 [SMILES: Cc1ccccc1-c1c[nH]c2ncccc12]
P-0483 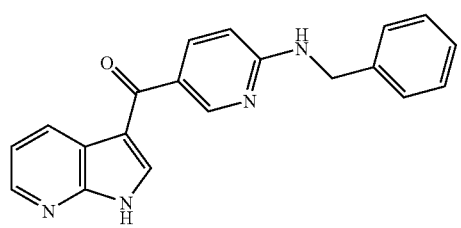 [SMILES: O=C(c1ccc(NCc2ccccc2)nc1)c1c[nH]c2ncccc12]
P-0484 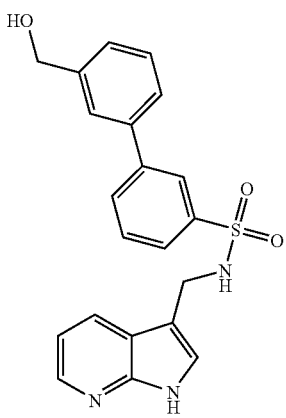 [SMILES: O=S(=O)(NCc1c[nH]c2ncccc12)c1cccc(-c2cccc(CO)c2)c1]
P-0485 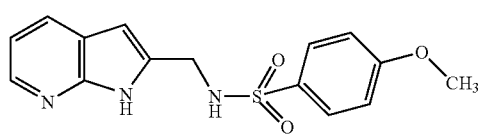 [SMILES: COc1ccc(S(=O)(=O)NCc2cc3cccnc3[nH]2)cc1]

TABLE 1-continued
Additional compounds of the invention
P-0487 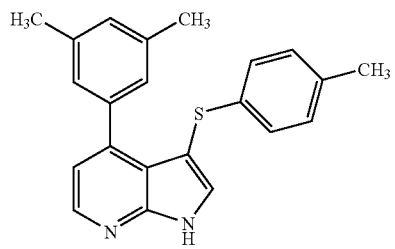
P-0488 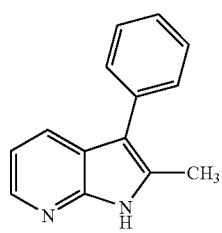 [SMILES: Cc1[nH]c2ncccc2c1-c1ccccc1]
P-0489 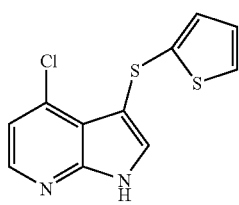 [SMILES: Clc1ccnc2[nH]cc(Sc3cccs3)c12]
P-0490 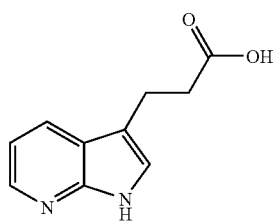 [SMILES: O=C(O)CCc1c[nH]c2ncccc12]
P-0491 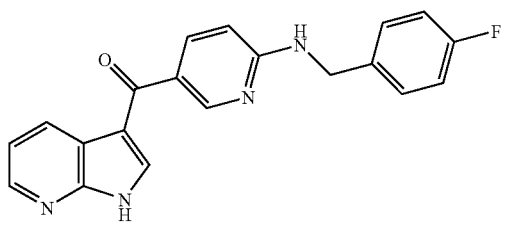 [SMILES: O=C(c1ccc(NCc2ccc(F)cc2)nc1)c1c[nH]c2ncccc12]
P-0492 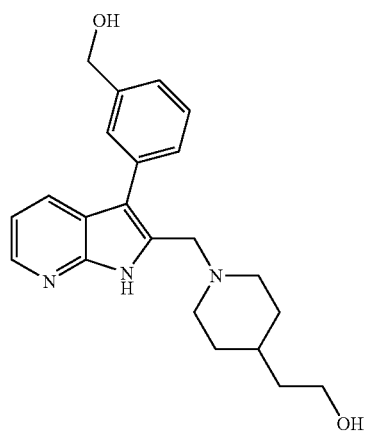 [SMILES: OCCC1CCN(Cc2[nH]c3ncccc3c2-c2cccc(CO)c2)CC1]

TABLE 1-continued
Additional compounds of the invention
P-0493
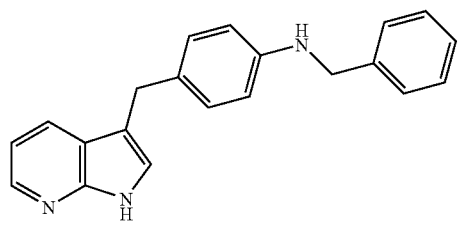 [SMILES: c1ccc(CNc2ccc(Cc3c[nH]c4ncccc34)cc2)cc1]
P-0494
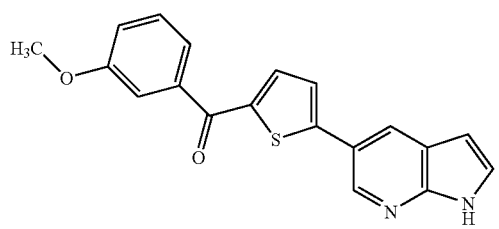 [SMILES: COc1cccc(C(=O)c2ccc(-c3cnc4[nH]ccc4c3)s2)c1]
P-0495
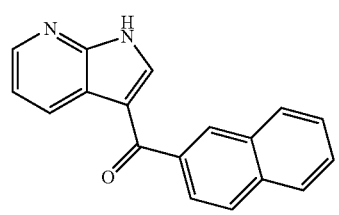 [SMILES: O=C(c1ccc2ccccc2c1)c1c[nH]c2ncccc12]
P-0496
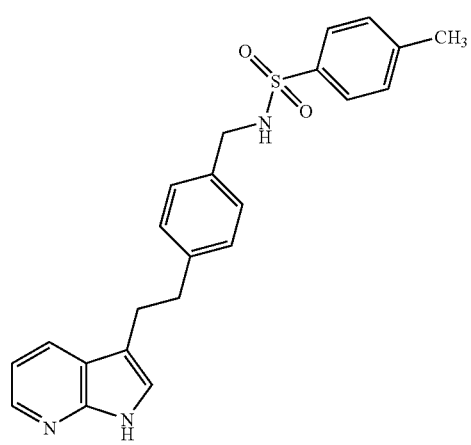 [SMILES: Cc1ccc(S(=O)(=O)NCc2ccc(CCc3c[nH]c4ncccc34)cc2)cc1]
P-0497
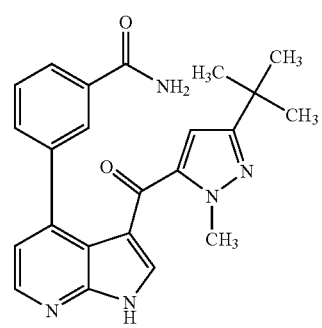 [SMILES: Cn1nc(C(C)(C)C)cc1C(=O)c1c[nH]c2nccc(-c3cccc(C(N)=O)c3)c12]

TABLE 1-continued
Additional compounds of the invention
P-0498 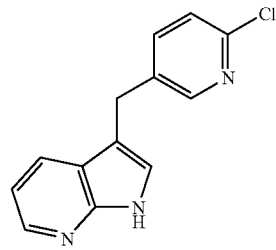 [SMILES: Clc1ccc(Cc2c[nH]c3ncccc23)cn1]
P-0499 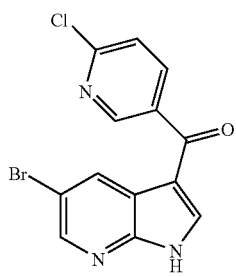 [SMILES: O=C(c1ccc(Cl)nc1)c1c[nH]c2ncc(Br)cc12]
P-0500 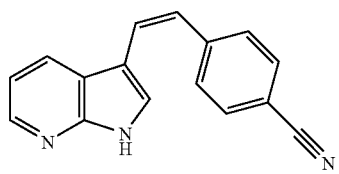 [SMILES: N#Cc1ccc(/C=C\c2c[nH]c3ncccc23)cc1]
P-0501 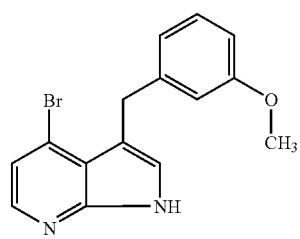 [SMILES: COc1cccc(Cc2c[nH]c3nccc(Br)c23)c1]
P-0502 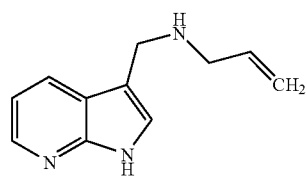
P-0503 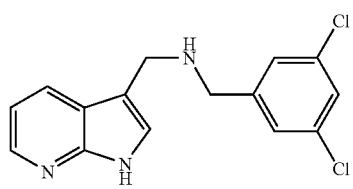 [SMILES: Clc1cc(Cl)cc(CNCc2c[nH]c3ncccc23)c1]

TABLE 1-continued
Additional compounds of the invention
P-0504
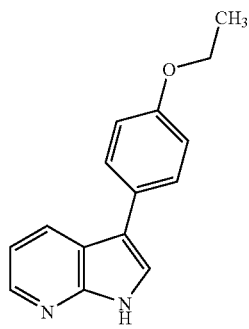 [SMILES: CCOc1ccc(-c2c[nH]c3ncccc23)cc1]
P-0505
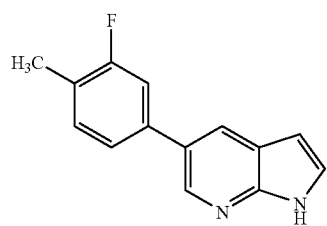 [SMILES: Cc1ccc(-c2cnc3[nH]ccc3c2)cc1F]
P-0506
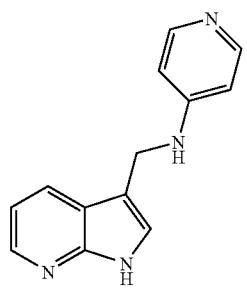 [SMILES: c1cnc2[nH]cc(CNc3ccncc3)c2c1]
P-0507
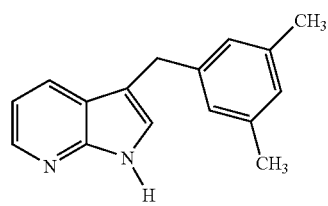 [SMILES: Cc1cc(C)cc(Cc2c[nH]c3ncccc23)c1]
P-0508
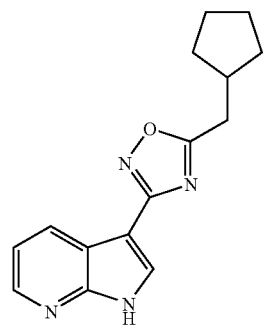 [SMILES: c1cnc2[nH]cc(-c3noc(CC4CCCC4)n3)c2c1]

TABLE 1-continued
Additional compounds of the invention
P-0509 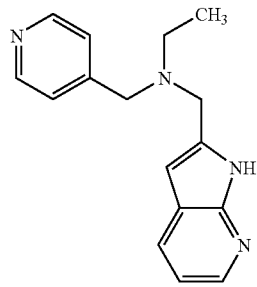 [SMILES: CCN(Cc1ccncc1)Cc1cc2cccnc2[nH]1]
P-0510 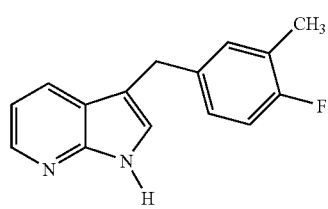 [SMILES: Cc1cc(Cc2c[nH]c3ncccc23)ccc1F]
P-0511 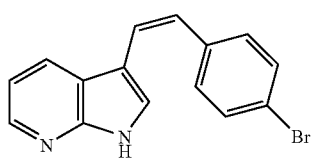 [SMILES: Brc1ccc(/C=C\c2c[nH]c3ncccc23)cc1]
P-0512 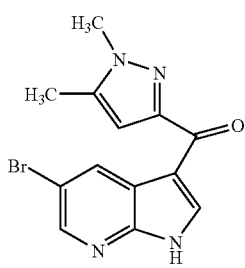 [SMILES: Cc1cc(C(=O)c2c[nH]c3ncc(Br)cc23)nn1C]
P-0513 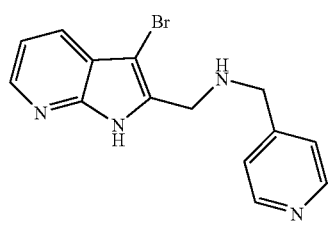 [SMILES: Brc1c(CNCc2ccncc2)[nH]c2ncccc12]
P-0514 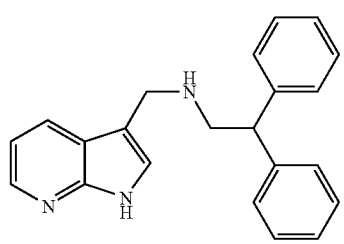 [SMILES: c1ccc(C(CNCc2c[nH]c3ncccc23)c2ccccc2)cc1]

TABLE 1-continued
Additional compounds of the invention
P-0515 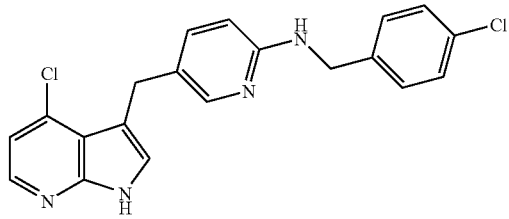 [SMILES: Clc1ccc(CNc2ccc(Cc3c[nH]c4nccc(Cl)c34)cn2)cc1]
P-0516 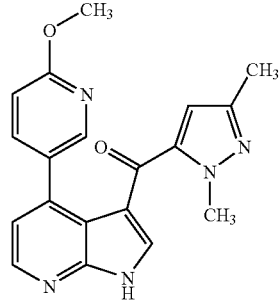 [SMILES: COc1ccc(-c2ccnc3[nH]cc(C(=O)c4cc(C)nn4C)c23)cn1]
P-0517 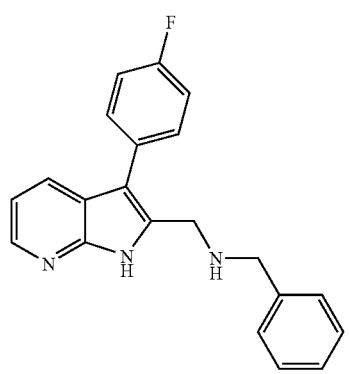 [SMILES: Fc1ccc(-c2c(CNCc3ccccc3)[nH]c3ncccc23)cc1]
P-0518 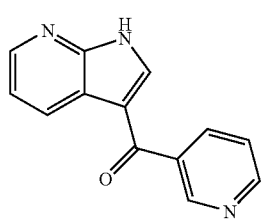 [SMILES: O=C(c1cccnc1)c1c[nH]c2ncccc12]
P-0519 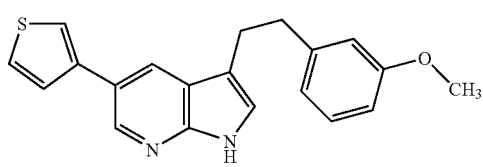 [SMILES: COc1cccc(CCc2c[nH]c3ncc(-c4ccsc4)cc23)c1]
P-0520 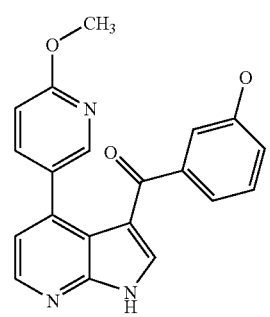 [SMILES: COc1ccc(-c2ccnc3[nH]cc(C(=O)c4cccc(O)c4)c23)cn1]

TABLE 1-continued
Additional compounds of the invention
P-0522
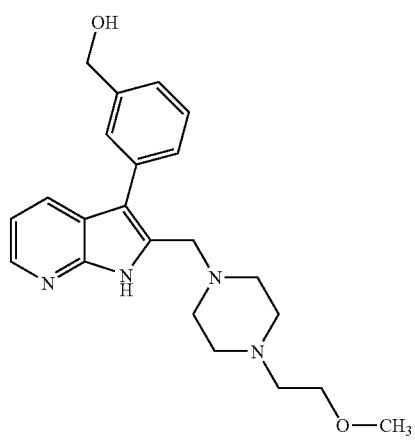 [SMILES: COCCN1CCN(Cc2[nH]c3ncccc3c2-c2cccc(CO)c2)CC1]
P-0523
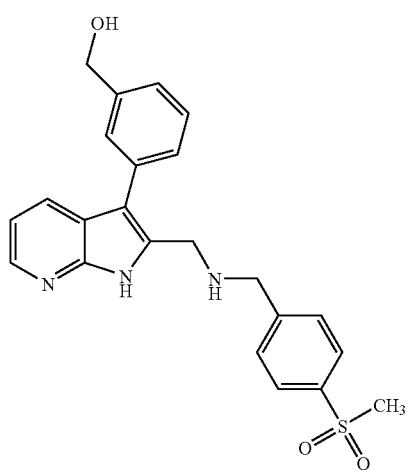 [SMILES: CS(=O)(=O)c1ccc(CNCc2[nH]c3ncccc3c2-c2cccc(CO)c2)cc1]
P-0524
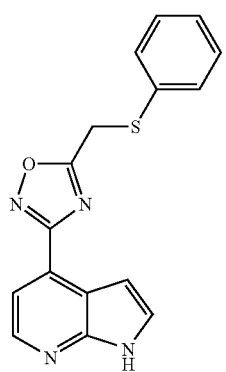 [SMILES: c1ccc(SCc2nc(-c3ccnc4[nH]ccc34)no2)cc1]
P-0525
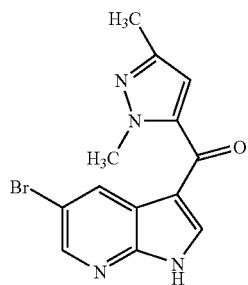 [SMILES: Cc1cc(C(=O)c2c[nH]c3ncc(Br)cc23)n(C)n1]

TABLE 1-continued
| Additional compounds of the invention |
|---|
P-0526 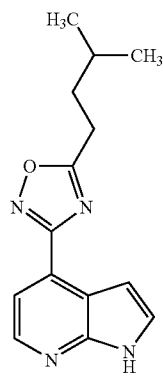 [SMILES: CC(C)CCc1nc(-c2ccnc3[nH]ccc23)no1]
P-0527 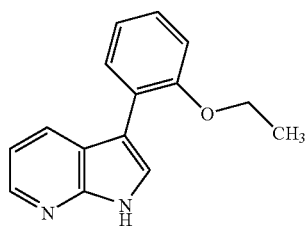 [SMILES: CCOc1ccccc1-c1c[nH]c2ncccc12]
P-0528 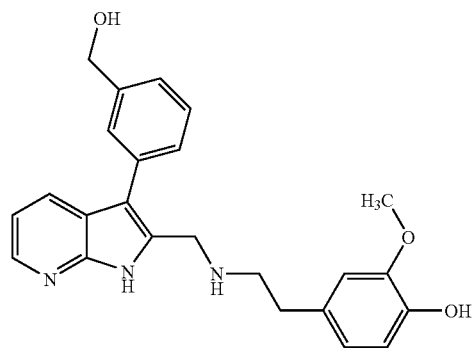 [SMILES: COc1cc(CCNCc2[nH]c3ncccc3c2-c2cccc(CO)c2)ccc1O]
P-0529 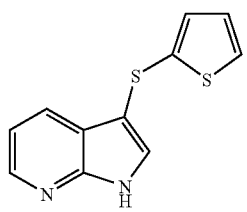 [SMILES: c1csc(Sc2c[nH]c3ncccc23)c1]
P-0530 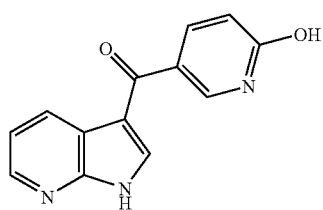 [SMILES: O=C(c1ccc(O)nc1)c1c[nH]c2ncccc12]

TABLE 1-continued
Additional compounds of the invention
P-0531
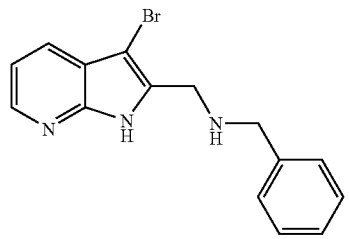 [SMILES: Brc1c(CNCc2ccccc2)[nH]c2ncccc12]
P-0532
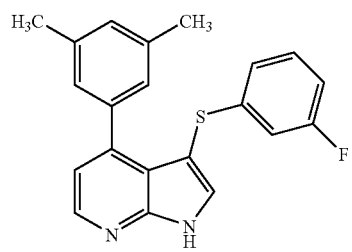 [SMILES: Cc1cc(C)cc(-c2ccnc3[nH]cc(Sc4cccc(F)c4)c23)c1]
P-0533
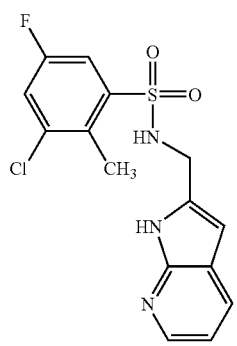 [SMILES: Cc1c(Cl)cc(F)cc1S(=O)(=O)NCc1cc2cccnc2[nH]1]
P-0534
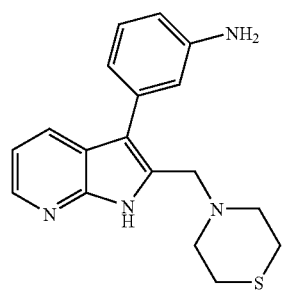 [SMILES: Nc1cccc(-c2c(CN3CCSCC3)[nH]c3ncccc23)c1]
P-0535
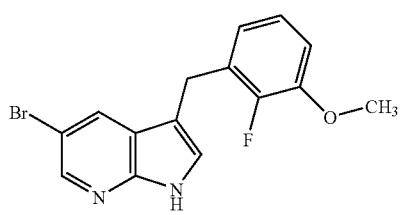 [SMILES: COc1cccc(Cc2c[nH]c3ncc(Br)cc23)c1F]

TABLE 1-continued
Additional compounds of the invention
P-0536 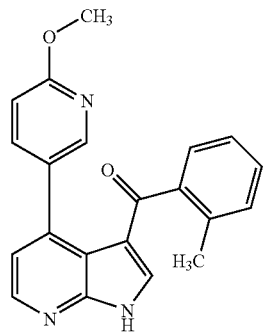 [SMILES: COc1ccc(-c2ccnc3[nH]cc(C(=O)c4ccccc4C)c23)cn1]
P-0537 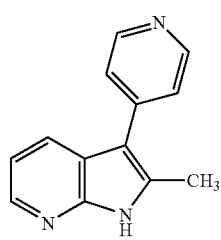 [SMILES: Cc1[nH]c2ncccc2c1-c1ccncc1]
P-0538 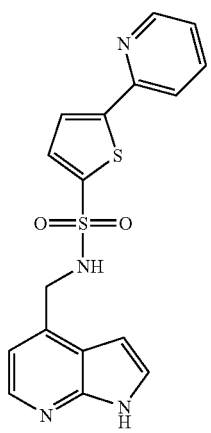 [SMILES: O=S(=O)(NCc1ccnc2[nH]ccc12)c1ccc(-c2ccccn2)s1]
P-0539 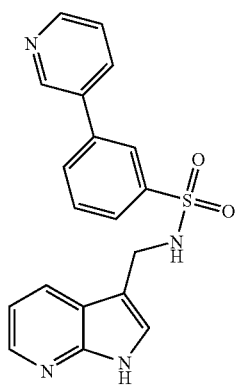 [SMILES: O=S(=O)(NCc1c[nH]c2ncccc12)c1cccc(-c2cccnc2)c1]
P-0540 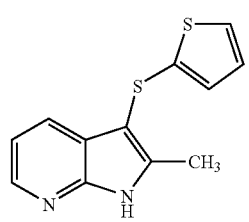 [SMILES: Cc1[nH]c2ncccc2c1Sc1cccs1]

TABLE 1-continued
Additional compounds of the invention
P-0541 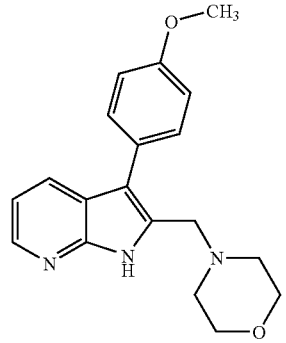 [SMILES: COc1ccc(-c2c(CN3CCOCC3)[nH]c3ncccc23)cc1]
P-0542 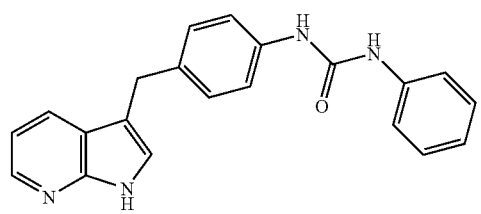 [SMILES: O=C(Nc1ccccc1)Nc1ccc(Cc2c[nH]c3ncccc23)cc1]
P-0543 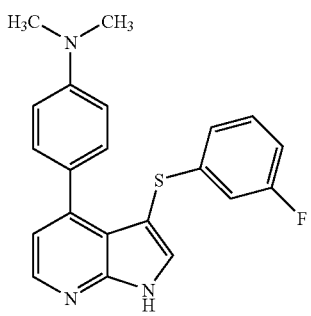 [SMILES: CN(C)c1ccc(-c2ccnc3[nH]cc(Sc4cccc(F)c4)c23)cc1]
P-0544 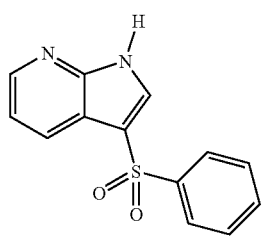 [SMILES: O=S(=O)(c1ccccc1)c1c[nH]c2ncccc12]
P-0545 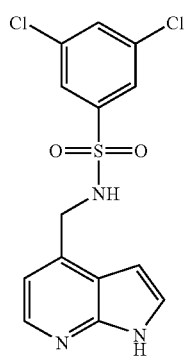 [SMILES: O=S(=O)(NCc1ccnc2[nH]ccc12)c1cc(Cl)cc(Cl)c1]

TABLE 1-continued
Additional compounds of the invention
P-0546
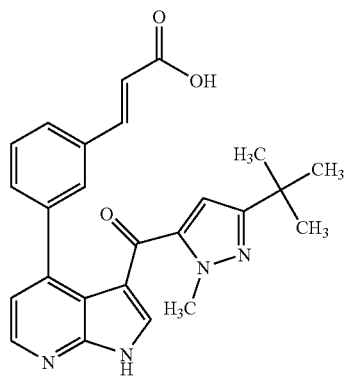 [SMILES: Cn1nc(C(C)(C)C)cc1C(=O)c1c[nH]c2nccc(-c3cccc(/C=C/C(=O)O)c3)c12]
P-0547
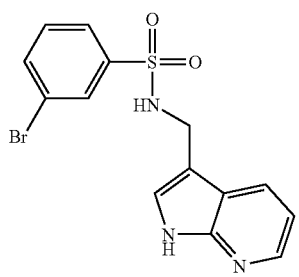 [SMILES: O=S(=O)(NCc1c[nH]c2ncccc12)c1cccc(Br)c1]
P-0548
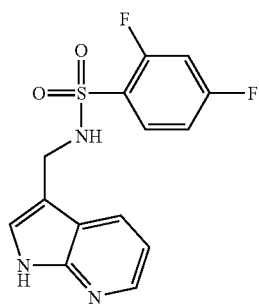 [SMILES: O=S(=O)(NCc1c[nH]c2ncccc12)c1ccc(F)cc1F]
P-0549
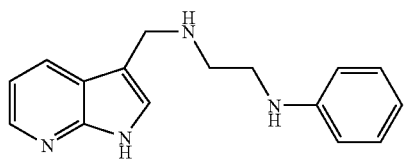 [SMILES: c1ccc(NCCNCc2c[nH]c3ncccc23)cc1]
P-0550
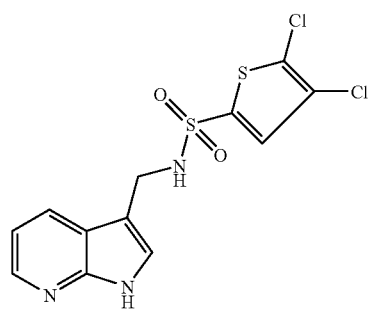 [SMILES: O=S(=O)(NCc1c[nH]c2ncccc12)c1cc(Cl)c(Cl)s1]

TABLE 1-continued
Additional compounds of the invention
P-0551
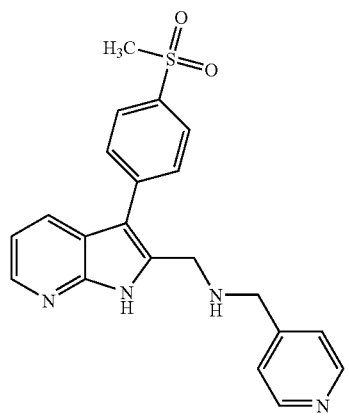 [SMILES: CS(=O)(=O)c1ccc(-c2c(CNCc3ccncc3)[nH]c3ncccc23)cc1]
P-0552
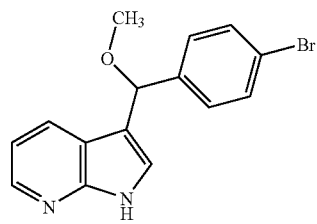 [SMILES: COC(c1ccc(Br)cc1)c1c[nH]c2ncccc12]
P-0553
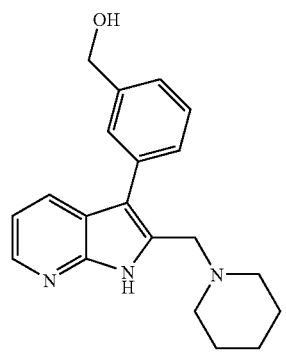 [SMILES: OCc1cccc(-c2c(CN3CCCCC3)[nH]c3ncccc23)c1]
P-0554
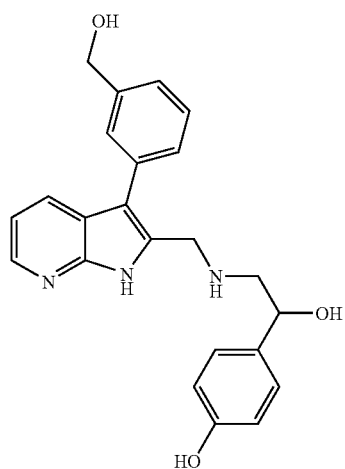 [SMILES: OCc1cccc(-c2c(CNCC(O)c3ccc(O)cc3)[nH]c3ncccc23)c1]

TABLE 1-continued
| Additional compounds of the invention |
P-0555 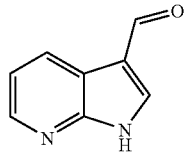 [SMILES: O=Cc1c[nH]c2ncccc12]
P-0556 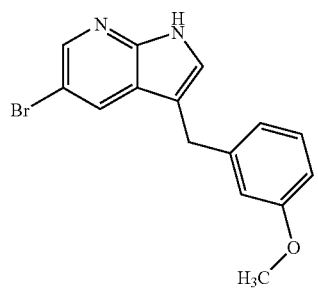 [SMILES: COc1cccc(Cc2c[nH]c3ncc(Br)cc23)c1]
P-0557 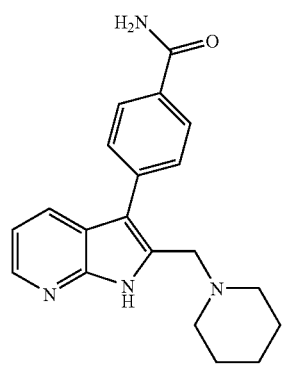 [SMILES: NC(=O)c1ccc(-c2c(CN3CCCCC3)[nH]c3ncccc23)cc1]
P-0558 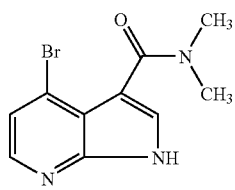
P-0559 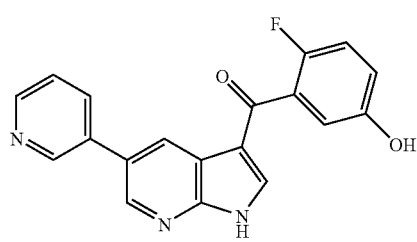 [SMILES: O=C(c1cc(O)ccc1F)c1c[nH]c2ncc(-c3cccnc3)cc12]
P-0560 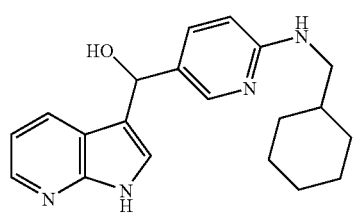 [SMILES: OC(c1ccc(NCC2CCCCC2)nc1)c1c[nH]c2ncccc12]

TABLE 1-continued
| Additional compounds of the invention |
P-0561 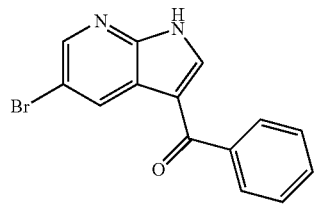 [SMILES: O=C(c1ccccc1)c1c[nH]c2ncc(Br)cc12]
P-0562 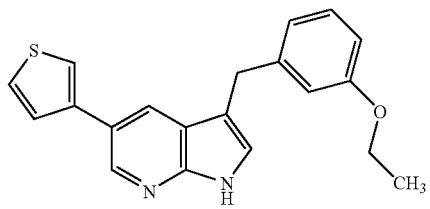 [SMILES: CCOc1cccc(Cc2c[nH]c3ncc(-c4ccsc4)cc23)c1]
P-0563 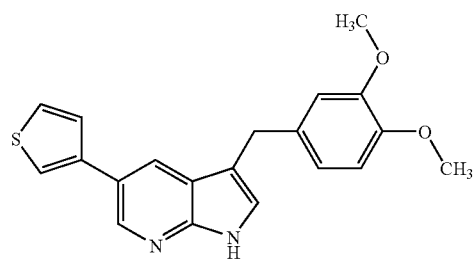 [SMILES: COc1ccc(Cc2c[nH]c3ncc(-c4ccsc4)cc23)cc1OC]
P-0564 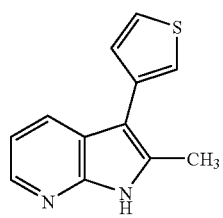
P-0565 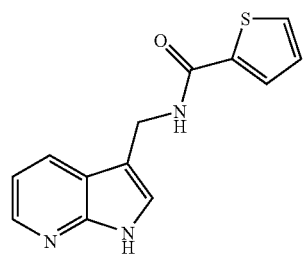 [SMILES: O=C(NCc1c[nH]c2ncccc12)c1cccs1]
P-0566 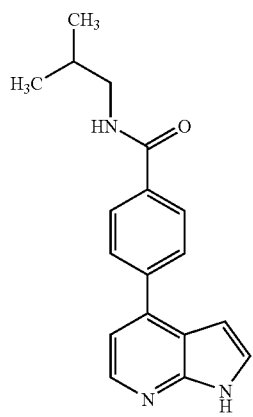 [SMILES: CC(C)CNC(=O)c1ccc(-c2ccnc3[nH]ccc23)cc1]

TABLE 1-continued
Additional compounds of the invention
P-0567
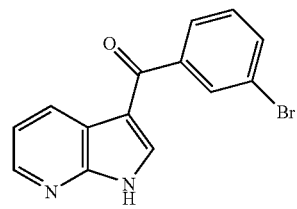 [SMILES: O=C(c1cccc(Br)c1)c1c[nH]c2ncccc12]
P-0568
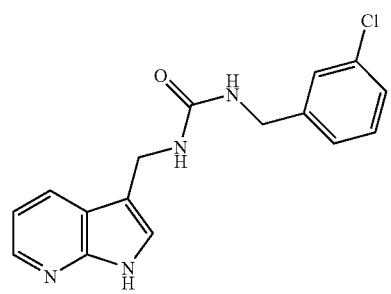 [SMILES: O=C(NCc1cccc(Cl)c1)NCc1c[nH]c2ncccc12]
P-0569
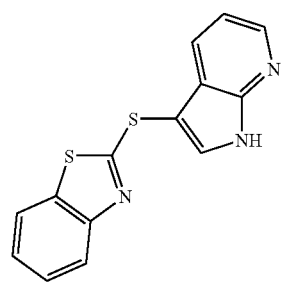 [SMILES: c1ccc2sc(Sc3c[nH]c4ncccc34)nc2c1]
P-0570
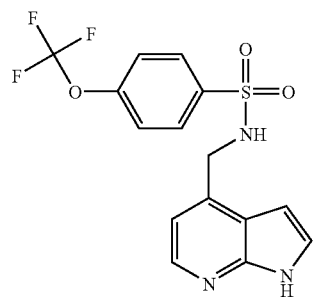 [SMILES: O=S(=O)(NCc1ccnc2[nH]ccc12)c1ccc(OC(F)(F)F)cc1]
P-0571
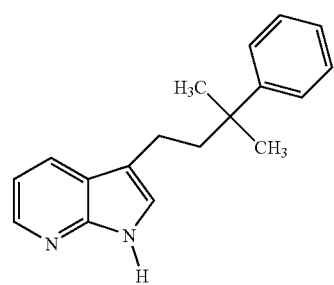 [SMILES: CC(C)(CCc1c[nH]c2ncccc12)c1ccccc1]

TABLE 1-continued
Additional compounds of the invention
P-0572 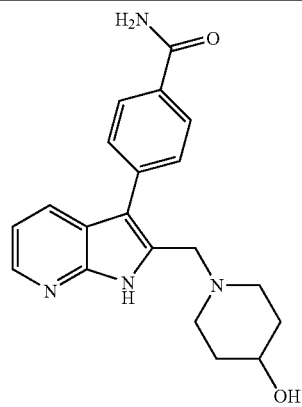
P-0573 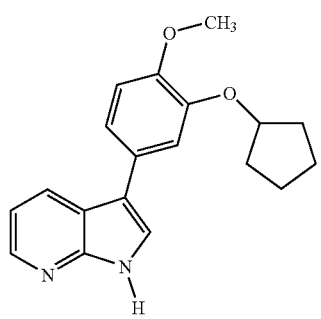 [SMILES: COc1ccc(-c2c[nH]c3ncccc23)cc1OC1CCCC1]
P-0574 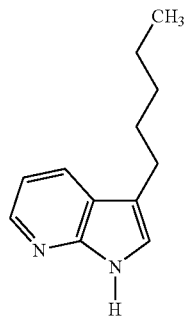
P-0575 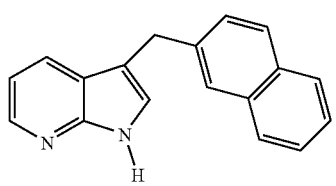 [SMILES: c1ccc2cc(Cc3c[nH]c4ncccc34)ccc2c1]
P-0576 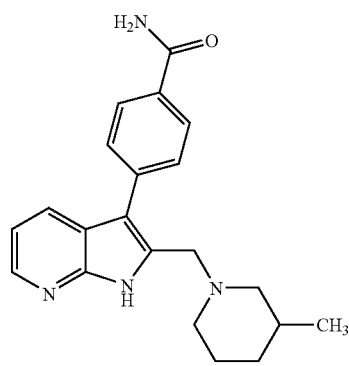 [SMILES: CC1CCCN(Cc2[nH]c3ncccc3c2-c2ccc(C(N)=O)cc2)C1]

TABLE 1-continued
Additional compounds of the invention
P-0577 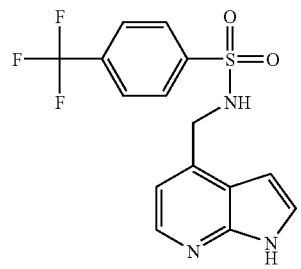 [SMILES: O=S(=O)(NCc1ccnc2[nH]ccc12)c1ccc(C(F)(F)F)cc1]
P-0578 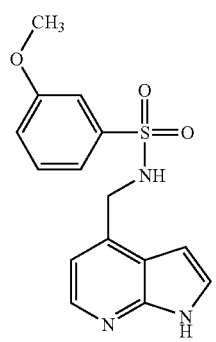 [SMILES: COc1cccc(S(=O)(=O)NCc2ccnc3[nH]ccc23)c1]
P-0579 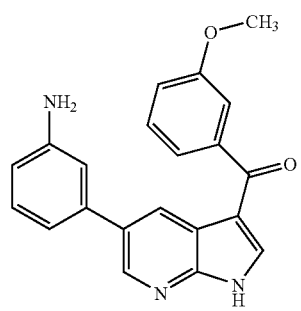 [SMILES: COc1cccc(C(=O)c2c[nH]c3ncc(-c4cccc(N)c4)cc23)c1]
P-0580 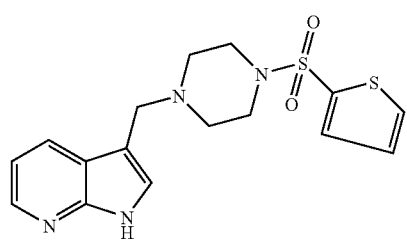 [SMILES: O=S(=O)(c1cccs1)N1CCN(Cc2c[nH]c3ncccc23)CC1]
P-0581 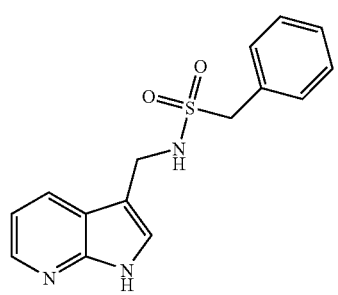 [SMILES: O=S(=O)(Cc1ccccc1)NCc1c[nH]c2ncccc12]

TABLE 1-continued
Additional compounds of the invention
P-0582 
P-0583 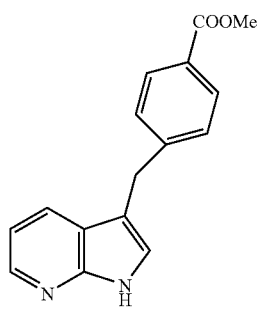 [SMILES: COC(=O)c1ccc(Cc2c[nH]c3ncccc23)cc1]
P-0584 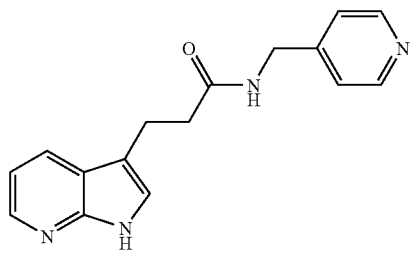 [SMILES: O=C(CCc1c[nH]c2ncccc12)NCc1ccncc1]
P-0585 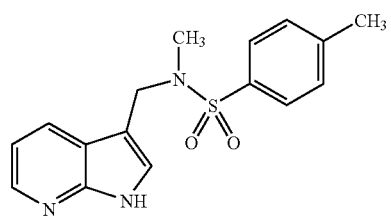 [SMILES: Cc1ccc(S(=O)(=O)N(C)Cc2c[nH]c3ncccc23)cc1]
P-0586 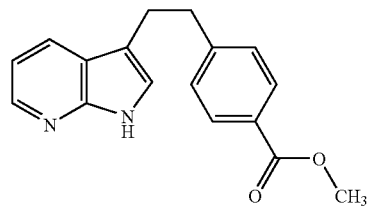 [SMILES: COC(=O)c1ccc(CCc2c[nH]c3ncccc23)cc1]
P-0587 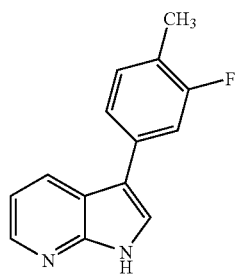 [SMILES: Cc1ccc(-c2c[nH]c3ncccc23)cc1F]

TABLE 1-continued
Additional compounds of the invention
P-0588 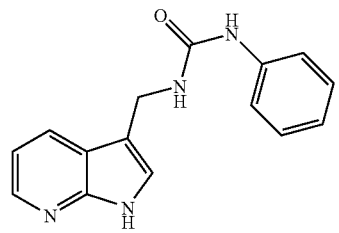 [SMILES: O=C(NCc1c[nH]c2ncccc12)Nc1ccccc1]
P-0589 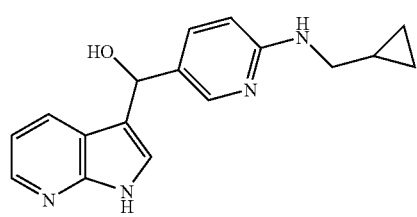 [SMILES: OC(c1ccc(NCC2CC2)nc1)c1c[nH]c2ncccc12]
P-0590 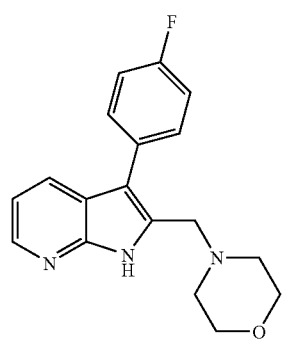 [SMILES: Fc1ccc(-c2c(CN3CCOCC3)[nH]c3ncccc23)cc1]
P-0591 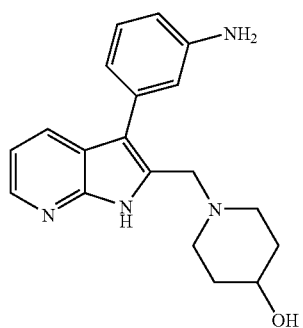 [SMILES: Nc1cccc(-c2c(CN3CCC(O)CC3)[nH]c3ncccc23)c1]
P-0592 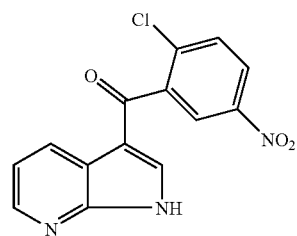 [SMILES: O=C(c1cc([N+](=O)[O-])ccc1Cl)c1c[nH]c2ncccc12]

TABLE 1-continued
| Additional compounds of the invention |
P-0593 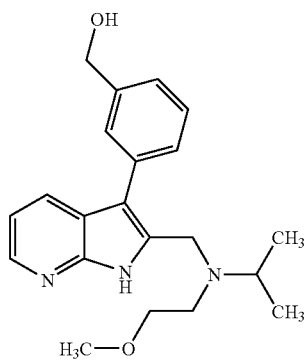 [SMILES: COCCN(Cc1[nH]c2ncccc2c1-c1cccc(CO)c1)C(C)C]
P-0594 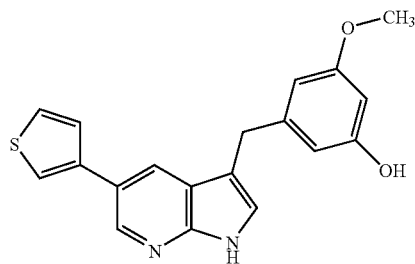 [SMILES: COc1cc(O)cc(Cc2c[nH]c3ncc(-c4ccsc4)cc23)c1]
P-0595 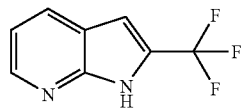
P-0596 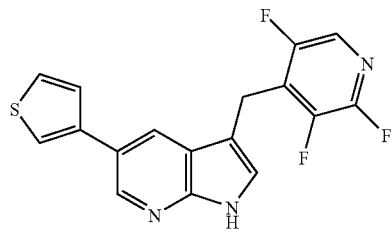 [SMILES: Fc1cnc(F)c(F)c1Cc1c[nH]c2ncc(-c3ccsc3)cc12]
P-0597 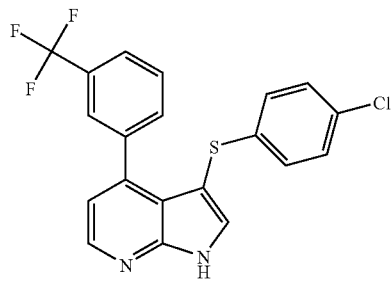 [SMILES: FC(F)(F)c1cccc(-c2ccnc3[nH]cc(Sc4ccc(Cl)cc4)c23)c1]
P-0598 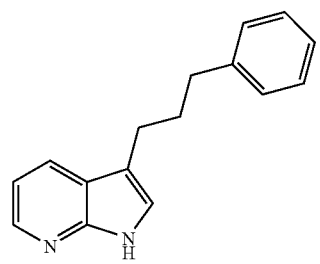 [SMILES: c1ccc(CCCc2c[nH]c3ncccc23)cc1]

TABLE 1-continued
Additional compounds of the invention
P-0599 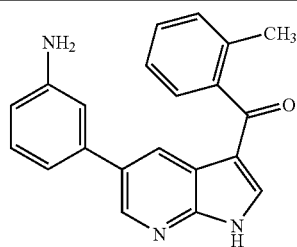
P-0600 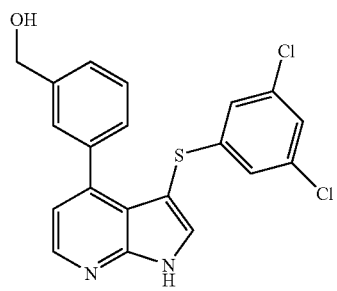 [SMILES: OCc1cccc(-c2ccnc3[nH]cc(Sc4cc(Cl)cc(Cl)c4)c23)c1]
P-0601 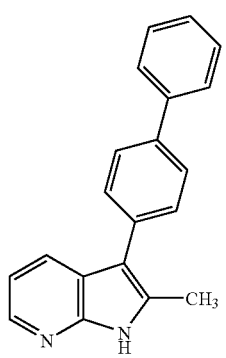
P-0602 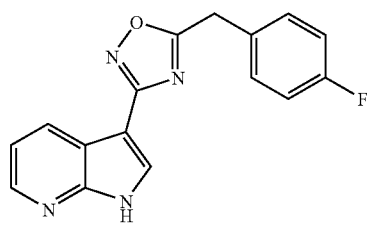 [SMILES: Fc1ccc(Cc2nc(-c3c[nH]c4ncccc34)no2)cc1]
P-0603 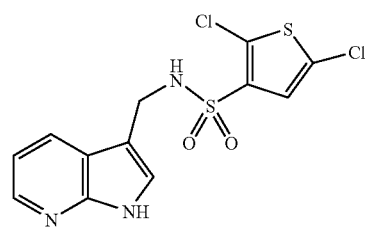 [SMILES: O=S(=O)(NCc1c[nH]c2ncccc12)c1cc(Cl)sc1Cl]
P-0604 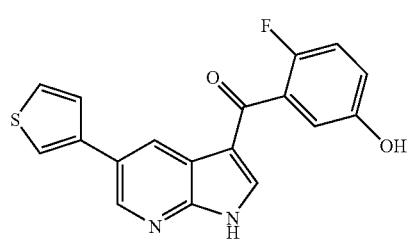 [SMILES: O=C(c1cc(O)ccc1F)c1c[nH]c2ncc(-c3ccsc3)cc12]

TABLE 1-continued
Additional compounds of the invention
P-0605 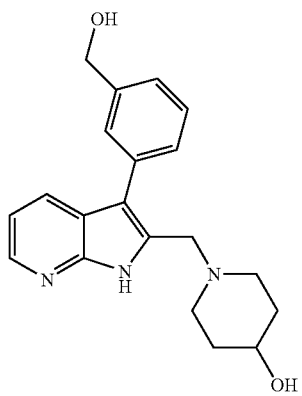 [SMILES: OCc1cccc(-c2c(CN3CCC(O)CC3)[nH]c3ncccc23)c1]
P-0606 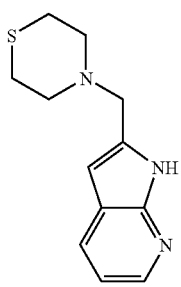 [SMILES: c1cnc2[nH]c(CN3CCSCC3)cc2c1]
P-0607 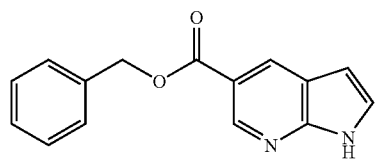 [SMILES: O=C(OCc1ccccc1)c1cnc2[nH]ccc2c1]
P-0608 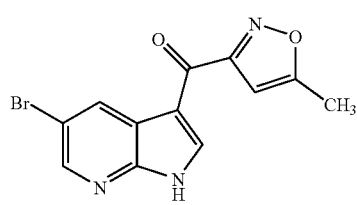 [SMILES: Cc1cc(C(=O)c2c[nH]c3ncc(Br)cc23)no1]
P-0609 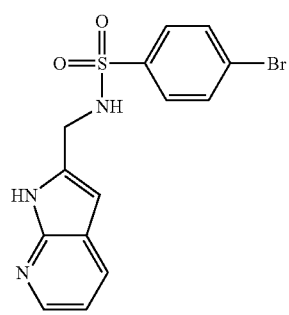 [SMILES: O=S(=O)(NCc1cc2cccnc2[nH]1)c1ccc(Br)cc1]

TABLE 1-continued
Additional compounds of the invention
P-0610
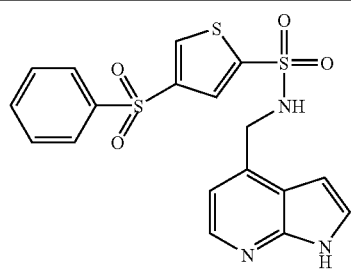
P-0611
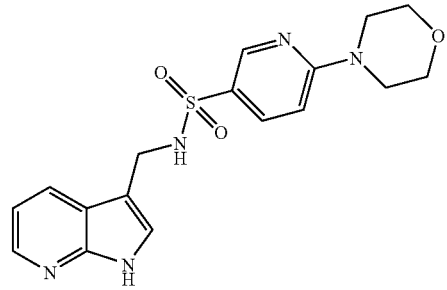 [SMILES: O=S(=O)(NCc1c[nH]c2ncccc12)c1ccc(N2CCOCC2)nc1]
P-0612
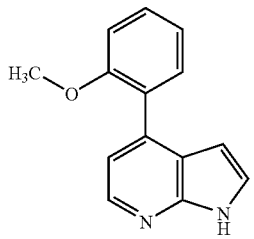 [SMILES: COc1ccccc1-c1ccnc2[nH]ccc12]
P-0613
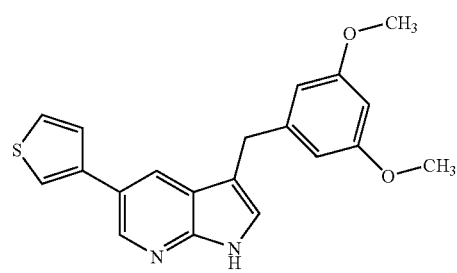 [SMILES: COc1cc(Cc2c[nH]c3ncc(-c4ccsc4)cc23)cc(OC)c1]
P-0614
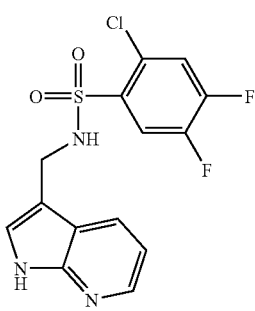
P-0615
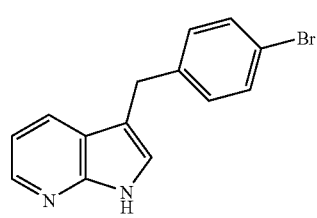 [SMILES: Brc1ccc(Cc2c[nH]c3ncccc23)cc1]

TABLE 1-continued
Additional compounds of the invention
P-0616 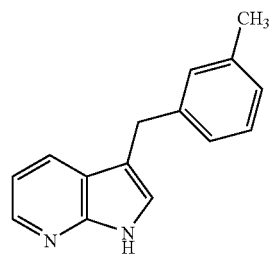 [SMILES: Cc1cccc(Cc2c[nH]c3ncccc23)c1]
P-0617 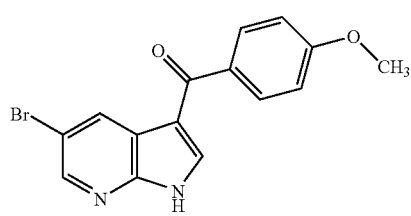 [SMILES: COc1ccc(C(=O)c2c[nH]c3ncc(Br)cc23)cc1]
P-0618 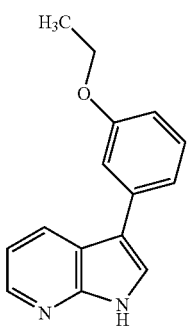 [SMILES: CCOc1cccc(-c2c[nH]c3ncccc23)c1]
P-0619 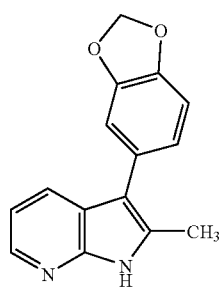 [SMILES: Cc1[nH]c2ncccc2c1-c1ccc2c(c1)OCO2]
P-0620 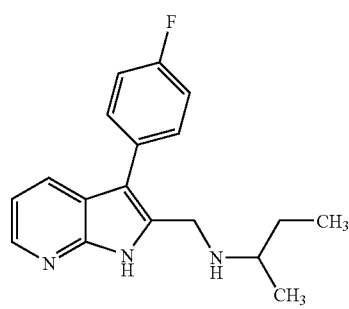 [SMILES: CCC(C)NCc1[nH]c2ncccc2c1-c1ccc(F)cc1]

TABLE 1-continued
Additional compounds of the invention
P-0621
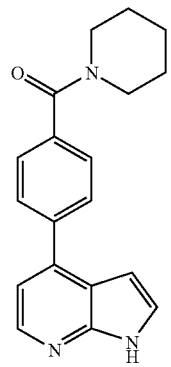 [SMILES: O=C(c1ccc(-c2ccnc3[nH]ccc23)cc1)N1CCCCC1]
P-0622
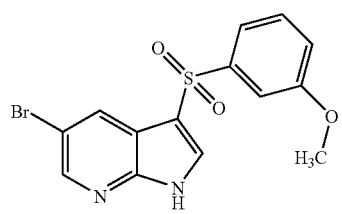 [SMILES: COc1cccc(S(=O)(=O)c2c[nH]c3ncc(Br)cc23)c1]
P-0623
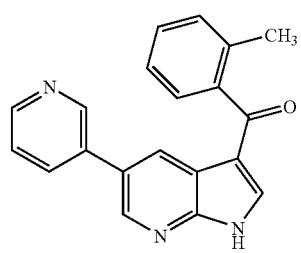 [SMILES: Cc1ccccc1C(=O)c1c[nH]c2ncc(-c3cccnc3)cc12]
P-0624
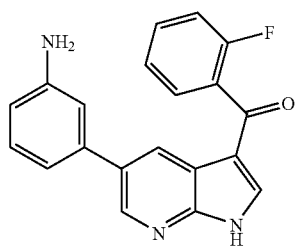 [SMILES: Nc1cccc(-c2cnc3[nH]cc(C(=O)c4ccccc4F)c3c2)c1]
P-0625
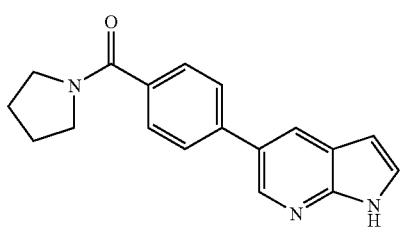 [SMILES: O=C(c1ccc(-c2cnc3[nH]ccc3c2)cc1)N1CCCC1]
P-0626
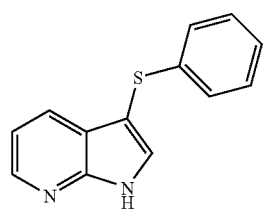 [SMILES: c1ccc(Sc2c[nH]c3ncccc23)cc1]

TABLE 1-continued
Additional compounds of the invention
P-0627 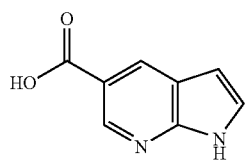 [SMILES: O=C(O)c1cnc2[nH]ccc2c1]
P-0628 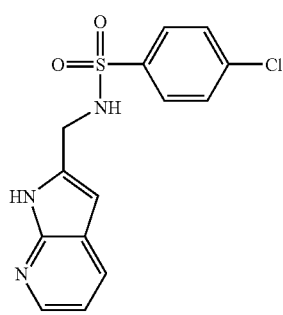
P-0629 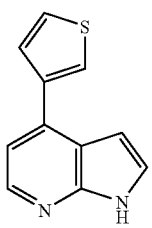 [SMILES: c1cc(-c2ccsc2)c2cc[nH]c2n1]
P-0630 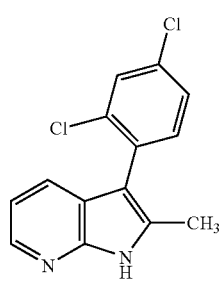 [SMILES: Cc1[nH]c2ncccc2c1-c1ccc(Cl)cc1Cl]
P-0631 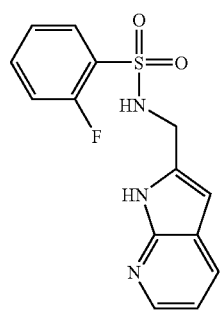 [SMILES: O=S(=O)(NCc1cc2cccnc2[nH]1)c1ccccc1F]
P-0632 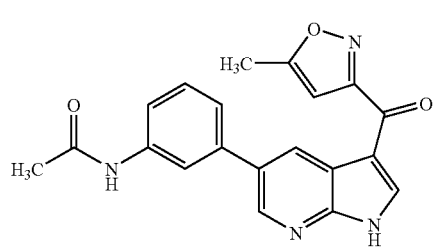 [SMILES: CC(=O)Nc1cccc(-c2cnc3[nH]cc(C(=O)c4cc(C)on4)c3c2)c1]

TABLE 1-continued
Additional compounds of the invention
P-0633
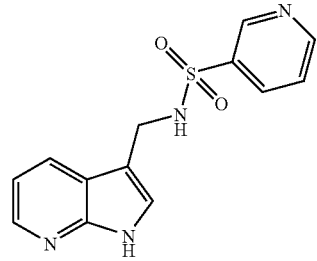 [SMILES: O=S(=O)(NCc1c[nH]c2ncccc12)c1cccnc1]
P-0634
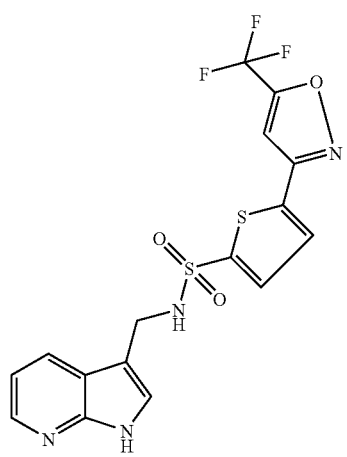 [SMILES: O=S(=O)(NCc1c[nH]c2ncccc12)c1ccc(-c2cc(C(F)(F)F)on2)s1]
P-0635
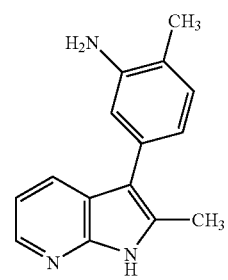 [SMILES: Cc1ccc(-c2c(C)[nH]c3ncccc23)cc1N]
P-0637
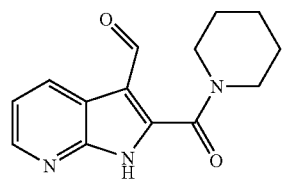 [SMILES: O=Cc1c(C(=O)N2CCCCC2)[nH]c2ncccc12]
P-0638
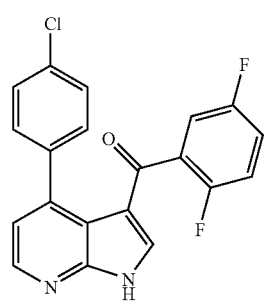 [SMILES: O=C(c1cc(F)ccc1F)c1c[nH]c2nccc(-c3ccc(Cl)cc3)c12]

TABLE 1-continued
Additional compounds of the invention
P-0639
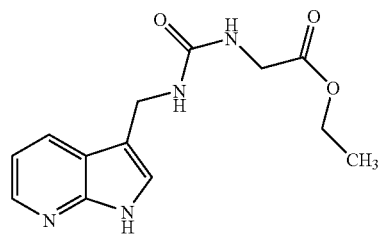 [SMILES: CCOC(=O)CNC(=O)NCc1c[nH]c2ncccc12]
P-0640
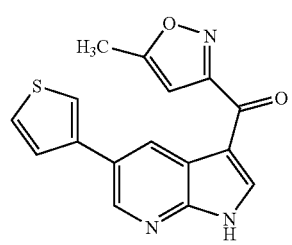 [SMILES: Cc1cc(C(=O)c2c[nH]c3ncc(-c4ccsc4)cc23)no1]
P-0641
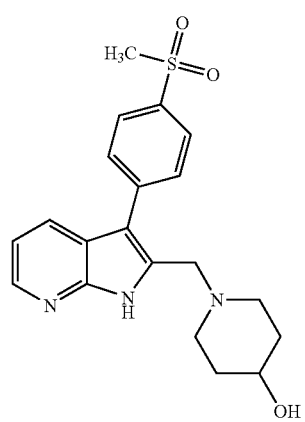 [SMILES: CS(=O)(=O)c1ccc(-c2c(CN3CCC(O)CC3)[nH]c3ncccc23)cc1]
P-0642
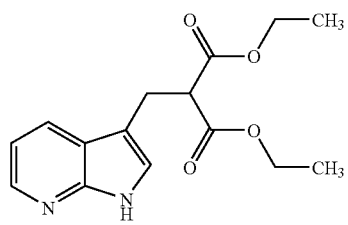 [SMILES: CCOC(=O)C(Cc1c[nH]c2ncccc12)C(=O)OCC]
P-0643
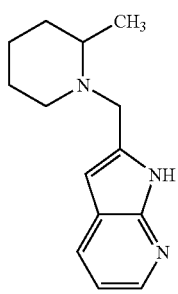 [SMILES: CC1CCCCN1Cc1cc2cccnc2[nH]1]

TABLE 1-continued
Additional compounds of the invention
P-0644
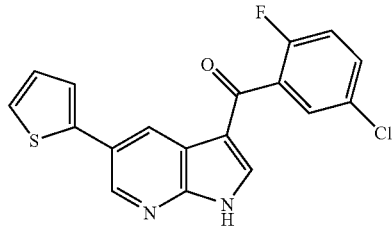 [SMILES: O=C(c1cc(Cl)ccc1F)c1c[nH]c2ncc(-c3cccs3)cc12]
P-0645
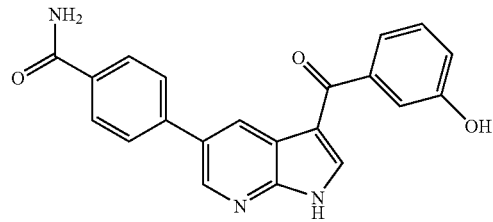 [SMILES: NC(=O)c1ccc(-c2cnc3[nH]cc(C(=O)c4cccc(O)c4)c3c2)cc1]
P-0646
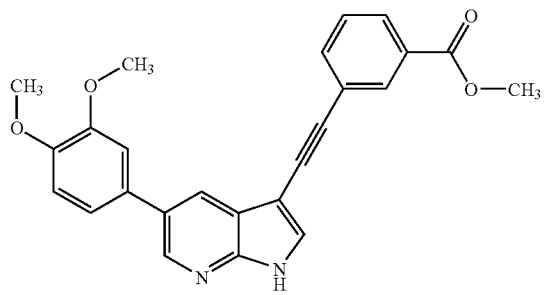 [SMILES: COC(=O)c1cccc(C#Cc2c[nH]c3ncc(-c4ccc(OC)c(OC)c4)cc23)c1]
P-0647
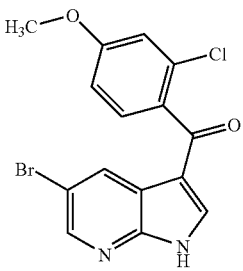 [SMILES: COc1ccc(C(=O)c2c[nH]c3ncc(Br)cc23)c(Cl)c1]
P-0648
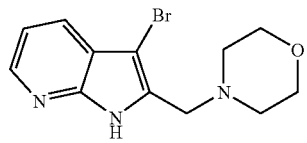 [SMILES: Brc1c(CN2CCOCC2)[nH]c2ncccc12]
P-0649
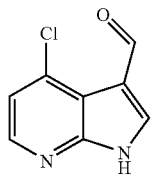 [SMILES: O=Cc1c[nH]c2nccc(Cl)c12]

TABLE 1-continued
Additional compounds of the invention
P-0650
P-0651
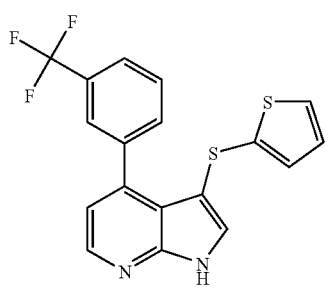 [SMILES: FC(F)(F)c1cccc(-c2ccnc3[nH]cc(Sc4cccs4)c23)c1]
P-0652
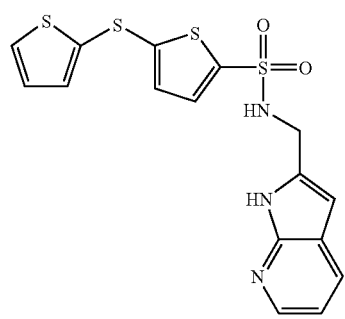 [SMILES: O=S(=O)(NCc1cc2cccnc2[nH]1)c1ccc(Sc2cccs2)s1]
P-0653
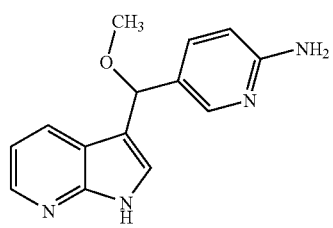 [SMILES: COC(c1ccc(N)nc1)c1c[nH]c2ncccc12]
P-0654
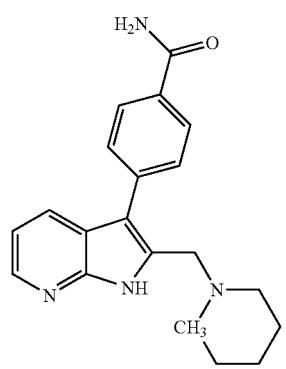 [SMILES: NC(=O)c1ccc(-c2c(CN3CCCCC3)[nH]c3ncccc23)cc1]

TABLE 1-continued
Additional compounds of the invention
P-0655 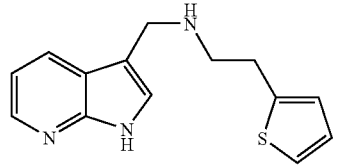 [SMILES: c1csc(CCNCc2c[nH]c3ncccc23)c1]
P-0656 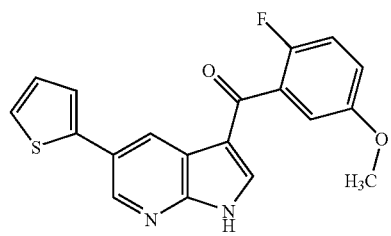 [SMILES: COc1ccc(F)c(C(=O)c2c[nH]c3ncc(-c4cccs4)cc23)c1]
P-0657 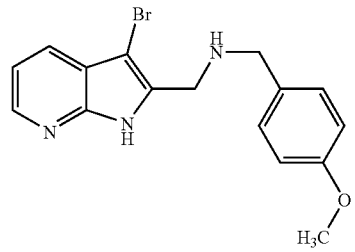 [SMILES: COc1ccc(CNCc2[nH]c3ncccc3c2Br)cc1]
P-0658 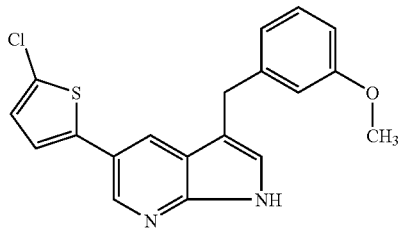 [SMILES: COc1cccc(Cc2c[nH]c3ncc(-c4ccc(Cl)s4)cc23)c1]
P-0659 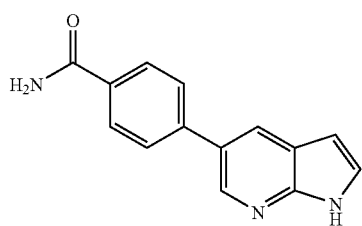 [SMILES: NC(=O)c1ccc(-c2cnc3[nH]ccc3c2)cc1]
P-0660 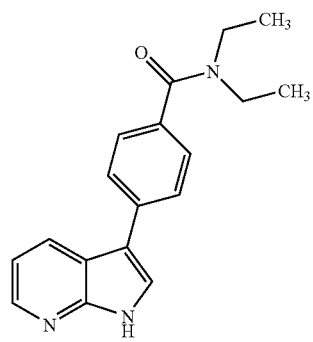 [SMILES: CCN(CC)C(=O)c1ccc(-c2c[nH]c3ncccc23)cc1]

TABLE 1-continued
Additional compounds of the invention
P-0661
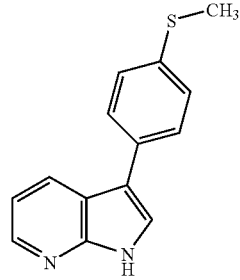 [SMILES: CSc1ccc(-c2c[nH]c3ncccc23)cc1]
P-0662
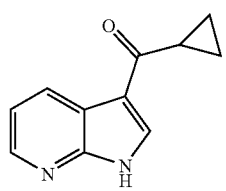 [SMILES: O=C(c1c[nH]c2ncccc12)C1CC1]
P-0663
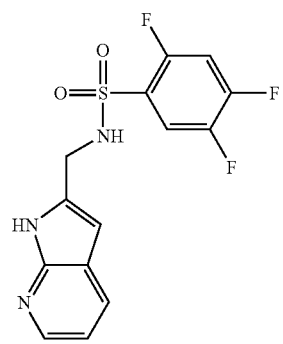 [SMILES: O=S(=O)(NCc1cc2cccnc2[nH]1)c1cc(F)c(F)cc1F]
P-0664
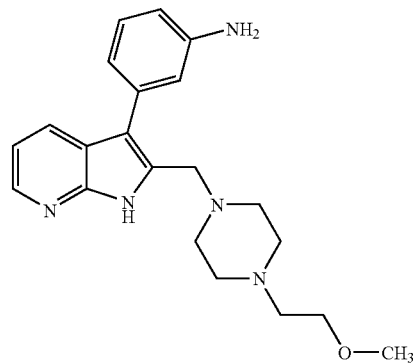 [SMILES: COCCN1CCN(Cc2[nH]c3ncccc3c2-c2cccc(N)c2)CC1]
P-0665
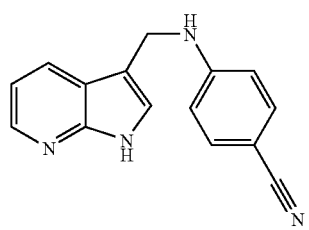 [SMILES: N#Cc1ccc(NCc2c[nH]c3ncccc23)cc1]

TABLE 1-continued
Additional compounds of the invention
P-0666 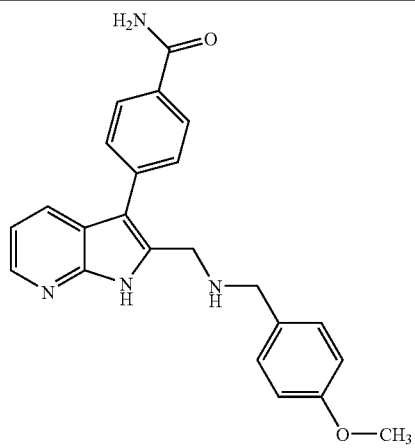
P-0667 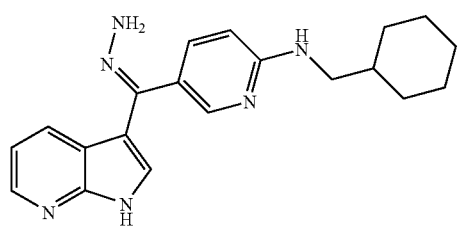 [SMILES: N/N=C(\c1ccc(NCC2CCCCC2)nc1)c1c[nH]c2ncccc12]
P-0668 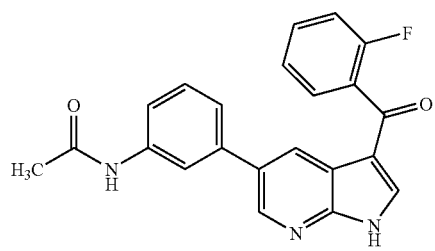 [SMILES: CC(=O)Nc1cccc(-c2cnc3[nH]cc(C(=O)c4ccccc4F)c3c2)c1]
P-0669 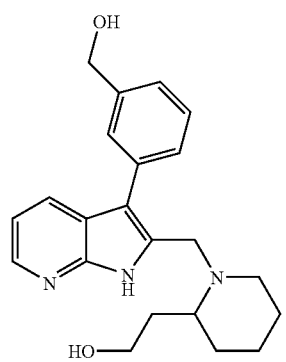 [SMILES: OCCC1CCCCN1Cc1[nH]c2ncccc2c1-c1cccc(CO)c1]
P-0670 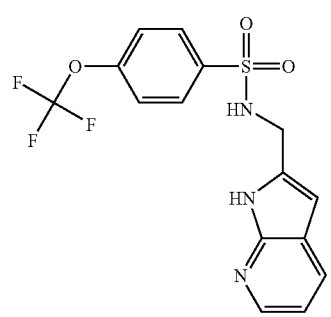 [SMILES: O=S(=O)(NCc1cc2cccnc2[nH]1)c1ccc(OC(F)(F)F)cc1]

TABLE 1-continued
Additional compounds of the invention
P-0671
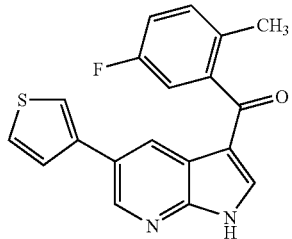 [SMILES: Cc1ccc(F)cc1C(=O)c1c[nH]c2ncc(-c3ccsc3)cc12]
P-0672
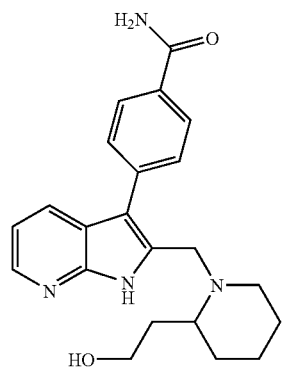 [SMILES: NC(=O)c1ccc(-c2c(CN3CCCCC3CCO)[nH]c3ncccc23)cc1]
P-0673
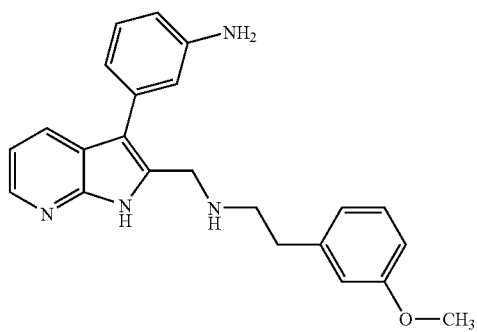 [SMILES: COc1cccc(CCNCc2[nH]c3ncccc3c2-c2cccc(N)c2)c1]
P-0674
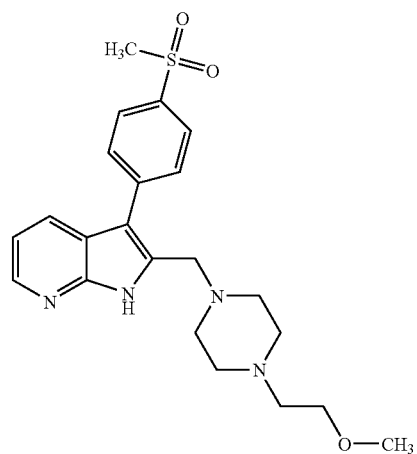 [SMILES: COCCN1CCN(Cc2[nH]c3ncccc3c2-c2ccc(S(C)(=O)=O)cc2)CC1]

TABLE 1-continued
Additional compounds of the invention
P-0675
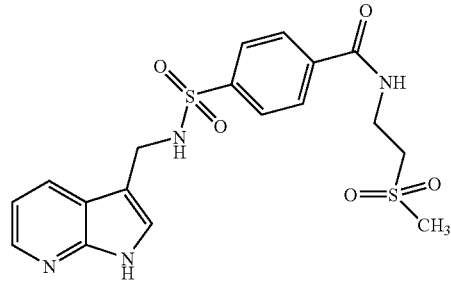 [SMILES: CS(=O)(=O)CCNC(=O)c1ccc(S(=O)(=O)NCc2c[nH]c3ncccc23)cc1]
P-0676
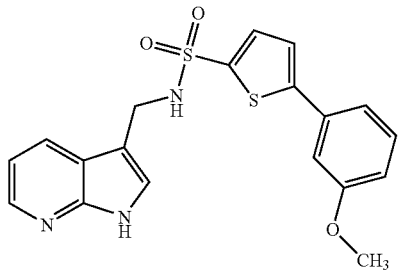 [SMILES: COc1cccc(-c2ccc(S(=O)(=O)NCc3c[nH]c4ncccc34)s2)c1]
P-0677
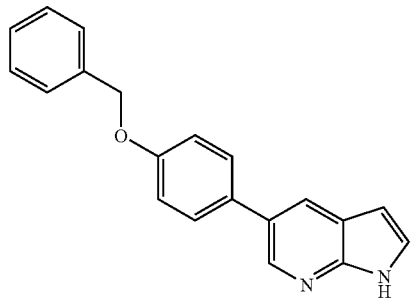 [SMILES: c1ccc(COc2ccc(-c3cnc4[nH]ccc4c3)cc2)cc1]
P-0678
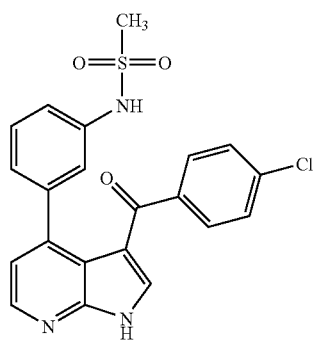 [SMILES: CS(=O)(=O)Nc1cccc(-c2ccnc3[nH]cc(C(=O)c4ccc(Cl)cc4)c23)c1]
P-0679
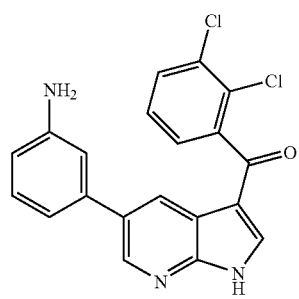 [SMILES: Nc1cccc(-c2cnc3[nH]cc(C(=O)c4cccc(Cl)c4Cl)c3c2)c1]

TABLE 1-continued
Additional compounds of the invention
P-0680 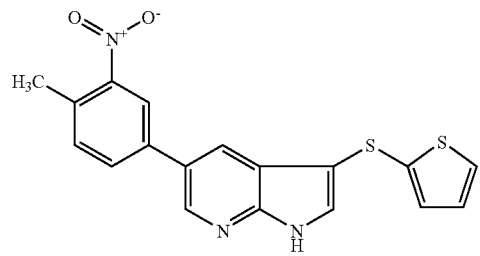 [SMILES: Cc1ccc(-c2cnc3[nH]cc(Sc4cccs4)c3c2)cc1[N+](=O)[O-]]
P-0681 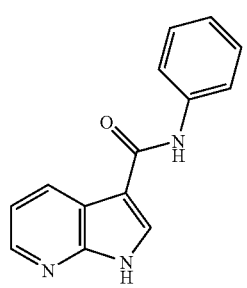 [SMILES: O=C(Nc1ccccc1)c1c[nH]c2ncccc12]
P-0682 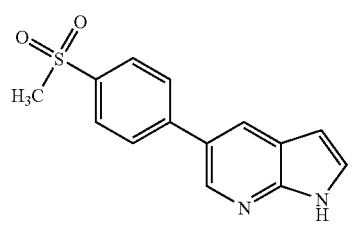 [SMILES: CS(=O)(=O)c1ccc(-c2cnc3[nH]ccc3c2)cc1]
P-0683 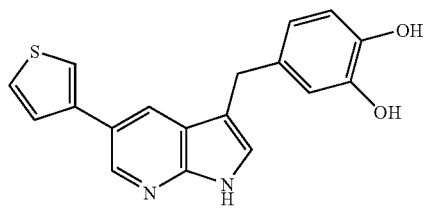 [SMILES: Oc1ccc(Cc2c[nH]c3ncc(-c4ccsc4)cc23)cc1O]
P-0684 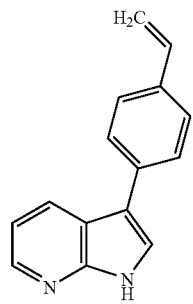 [SMILES: C=Cc1ccc(-c2c[nH]c3ncccc23)cc1]

TABLE 1-continued
Additional compounds of the invention
P-0686 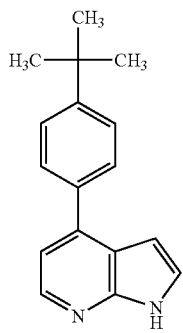 [SMILES: CC(C)(C)c1ccc(-c2ccnc3[nH]ccc23)cc1]
P-0687 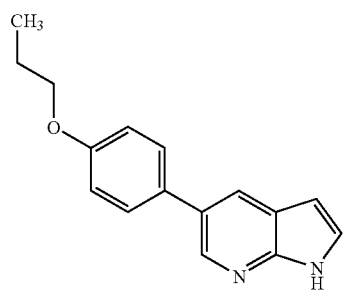 [SMILES: CCCOc1ccc(-c2cnc3[nH]ccc3c2)cc1]
P-0688 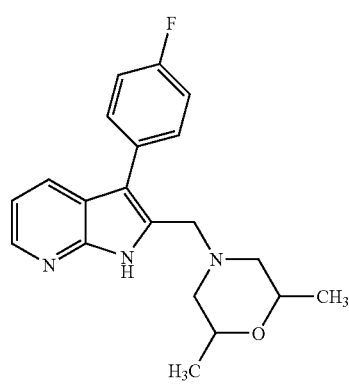 [SMILES: CC1CN(Cc2[nH]c3ncccc3c2-c2ccc(F)cc2)CC(C)O1]
P-0689 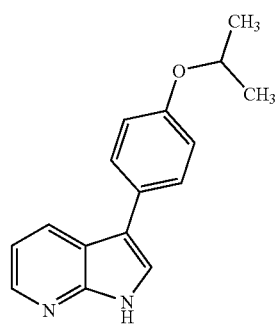 [SMILES: CC(C)Oc1ccc(-c2c[nH]c3ncccc23)cc1]
P-0690 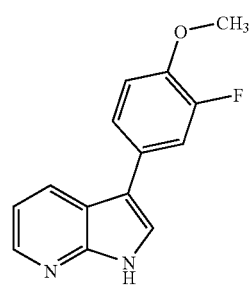 [SMILES: COc1ccc(-c2c[nH]c3ncccc23)cc1F]

TABLE 1-continued
Additional compounds of the invention
P-0691
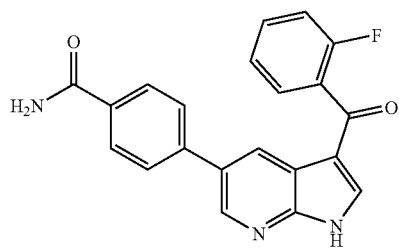 [SMILES: NC(=O)c1ccc(-c2cnc3[nH]cc(C(=O)c4ccccc4F)c3c2)cc1]
P-0692
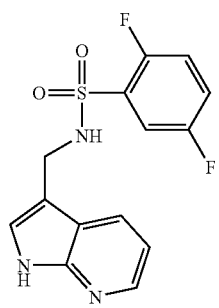 [SMILES: O=S(=O)(NCc1c[nH]c2ncccc12)c1cc(F)ccc1F]
P-0693
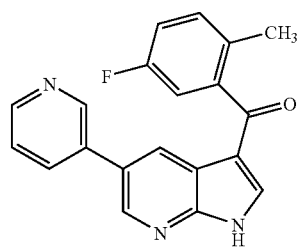 [SMILES: Cc1ccc(F)cc1C(=O)c1c[nH]c2ncc(-c3cccnc3)cc12]
P-0694
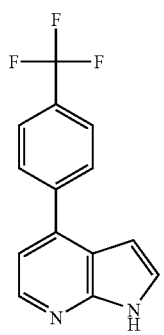
P-0695
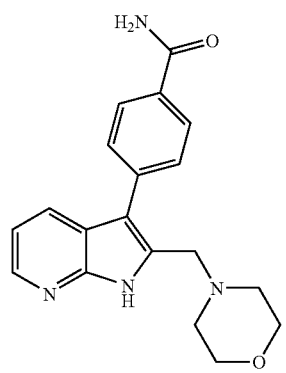 [SMILES: NC(=O)c1ccc(-c2c(CN3CCOCC3)[nH]c3ncccc23)cc1]

TABLE 1-continued
Additional compounds of the invention
P-0696 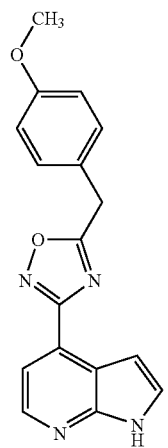 [SMILES: COc1ccc(Cc2nc(-c3ccnc4[nH]ccc34)no2)cc1]
P-0697 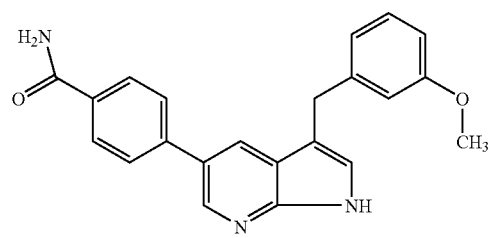 [SMILES: COc1cccc(Cc2c[nH]c3ncc(-c4ccc(C(N)=O)cc4)cc23)c1]
P-0698 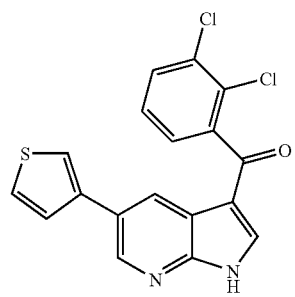 [SMILES: O=C(c1cccc(Cl)c1Cl)c1c[nH]c2ncc(-c3ccsc3)cc12]
P-0699 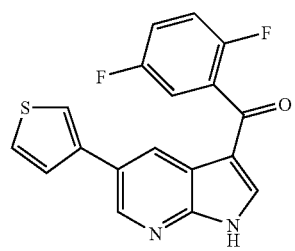 [SMILES: O=C(c1cc(F)ccc1F)c1c[nH]c2ncc(-c3ccsc3)cc12]
P-0701 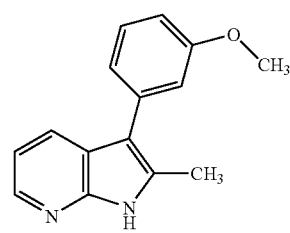 [SMILES: COc1cccc(-c2c(C)[nH]c3ncccc23)c1]

TABLE 1-continued
Additional compounds of the invention
P-0702 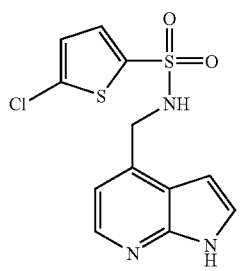 [SMILES: O=S(=O)(NCc1ccnc2[nH]ccc12)c1ccc(Cl)s1]
P-0703 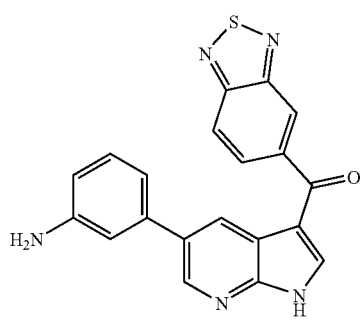 [SMILES: Nc1cccc(-c2cnc3[nH]cc(C(=O)c4ccc5nsnc5c4)c3c2)c1]
P-0704 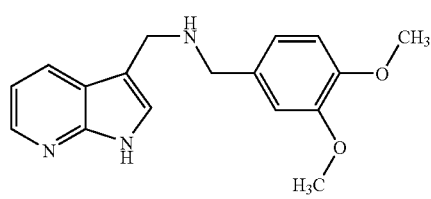 [SMILES: COc1ccc(CNCc2c[nH]c3ncccc23)cc1OC]
P-0705 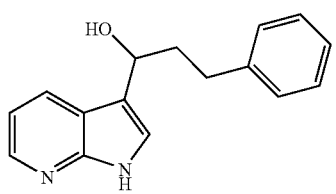 [SMILES: OC(CCc1ccccc1)c1c[nH]c2ncccc12]
P-0706 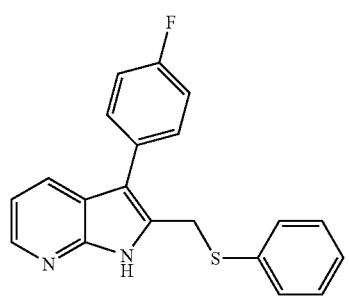 [SMILES: Fc1ccc(-c2c(CSc3ccccc3)[nH]c3ncccc23)cc1]
P-0707 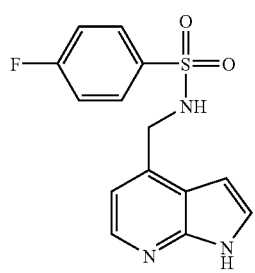 [SMILES: O=S(=O)(NCc1ccnc2[nH]ccc12)c1ccc(F)cc1]

TABLE 1-continued
Additional compounds of the invention
P-0708
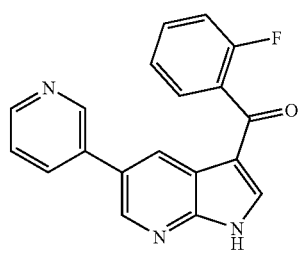 [SMILES: O=C(c1ccccc1F)c1c[nH]c2ncc(-c3cccnc3)cc12]
P-0709
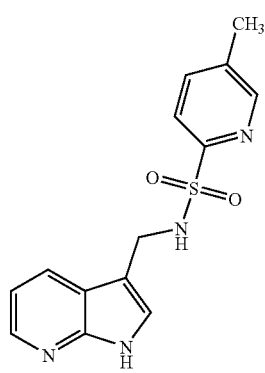 [SMILES: Cc1ccc(S(=O)(=O)NCc2c[nH]c3ncccc23)nc1]
P-0710
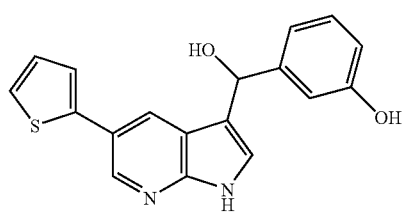 [SMILES: Oc1cccc(C(O)c2c[nH]c3ncc(-c4cccs4)cc23)c1]
P-0711
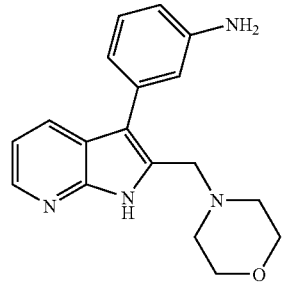
P-0712
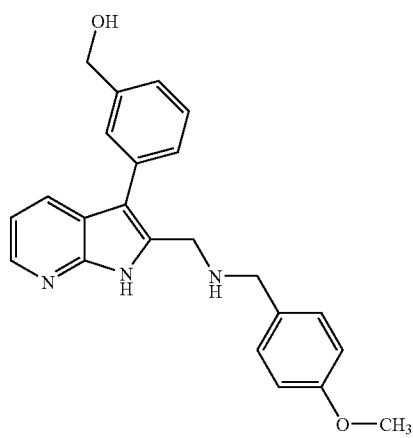 [SMILES: COc1ccc(CNCc2[nH]c3ncccc3c2-c2cccc(CO)c2)cc1]

TABLE 1-continued
Additional compounds of the invention
P-0713 
P-0714 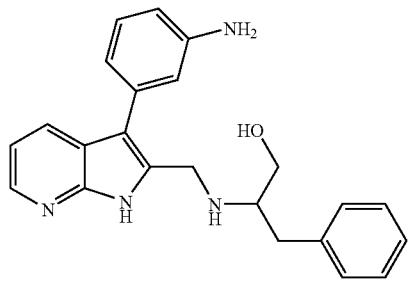 [SMILES: Nc1cccc(-c2c(CNC(CO)Cc3ccccc3)[nH]c3ncccc23)c1]
P-0715 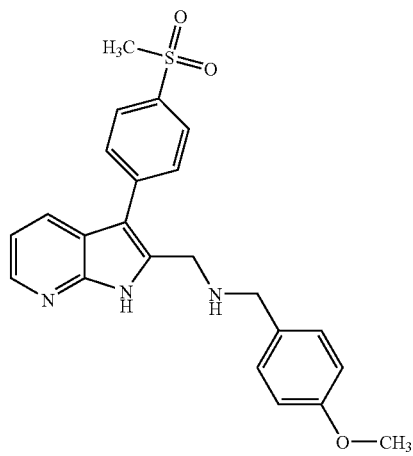 [SMILES: COc1ccc(CNCc2[nH]c3ncccc3c2-c2ccc(S(C)(=O)=O)cc2)cc1]
P-0717 
P-0718 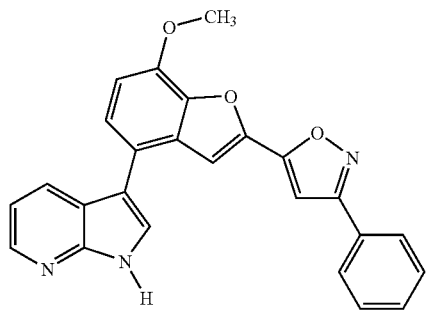 [SMILES: COc1ccc(-c2c[nH]c3ncccc23)c2cc(-c3cc(-c4ccccc4)no3)oc12]

TABLE 1-continued
| Additional compounds of the invention |
P-0719 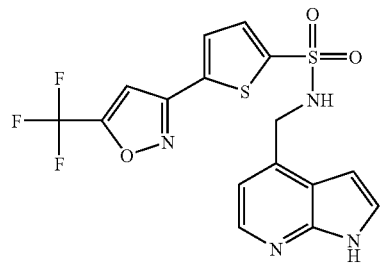 [SMILES: O=S(=O)(NCc1ccnc2[nH]ccc12)c1ccc(-c2cc(C(F)(F)F)on2)s1]
P-0720 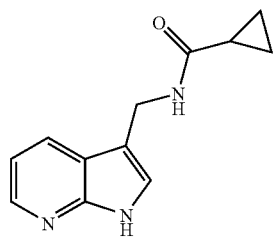 [SMILES: O=C(NCc1c[nH]c2ncccc12)C1CC1]
P-0722 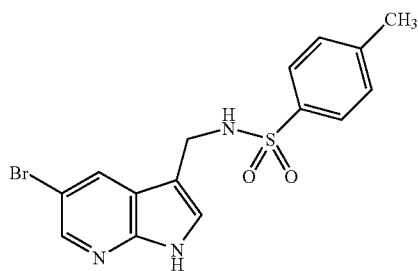 [SMILES: Cc1ccc(S(=O)(=O)NCc2c[nH]c3ncc(Br)cc23)cc1]
P-0723 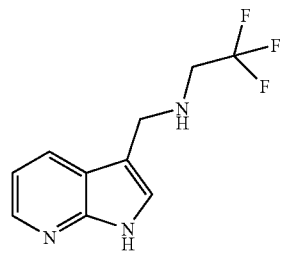 [SMILES: FC(F)(F)CNCc1c[nH]c2ncccc12]
P-0724 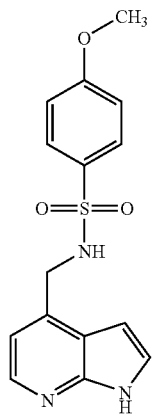 [SMILES: COc1ccc(S(=O)(=O)NCc2ccnc3[nH]ccc23)cc1]

TABLE 1-continued
Additional compounds of the invention
P-0725
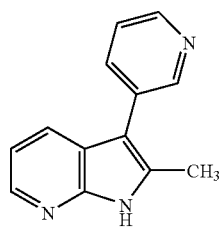 [SMILES: Cc1[nH]c2ncccc2c1-c1cccnc1]
P-0726
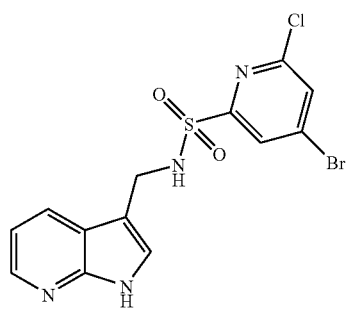 [SMILES: O=S(=O)(NCc1c[nH]c2ncccc12)c1cc(Br)cc(Cl)n1]
P-0727
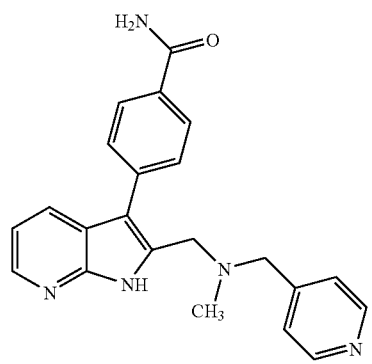 [SMILES: CN(Cc1ccncc1)Cc1[nH]c2ncccc2c1-c1ccc(C(N)=O)cc1]
P-0729
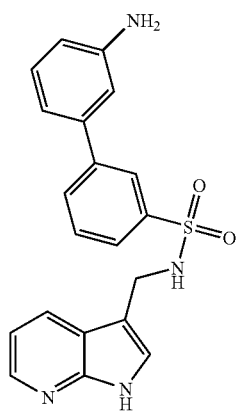 [SMILES: Nc1cccc(-c2cccc(S(=O)(=O)NCc3c[nH]c4ncccc34)c2)c1]
P-0730
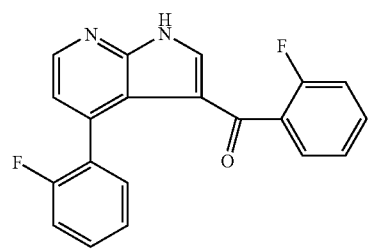 [SMILES: O=C(c1ccccc1F)c1c[nH]c2nccc(-c3ccccc3F)c12]

TABLE 1-continued
Additional compounds of the invention
P-0731 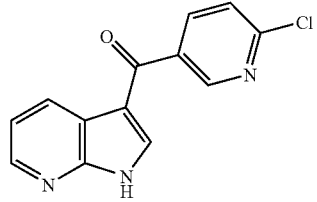 [SMILES: O=C(c1ccc(Cl)nc1)c1c[nH]c2ncccc12]
P-0732 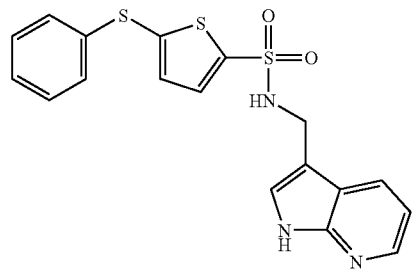 [SMILES: O=S(=O)(NCc1c[nH]c2ncccc12)c1ccc(Sc2ccccc2)s1]
P-0733 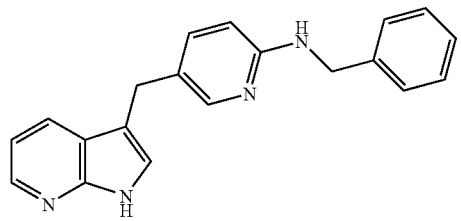
P-0735 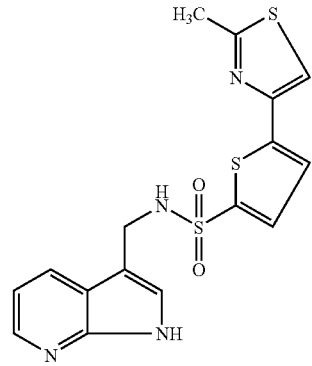 [SMILES: Cc1nc(-c2ccc(S(=O)(=O)NCc3c[nH]c4ncccc34)s2)cs1]
P-0736 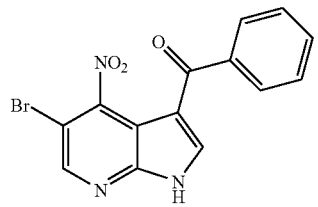 [SMILES: O=C(c1ccccc1)c1c[nH]c2ncc(Br)c([N+](=O)[O-])c12]
P-0737 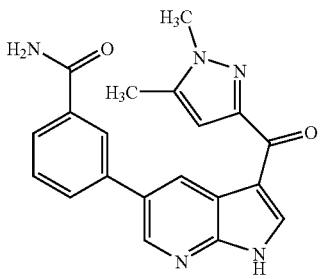 [SMILES: Cc1cc(C(=O)c2c[nH]c3ncc(-c4cccc(C(N)=O)c4)cc23)nn1C]

TABLE 1-continued
Additional compounds of the invention
P-0738 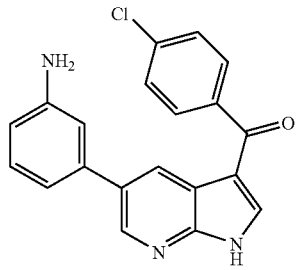 [SMILES: Nc1cccc(-c2cnc3[nH]cc(C(=O)c4ccc(Cl)cc4)c3c2)c1]
P-0739 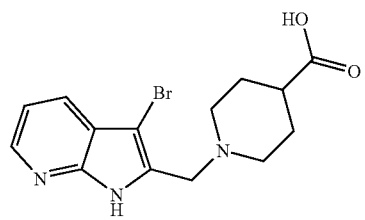 [SMILES: O=C(O)C1CCN(Cc2[nH]c3ncccc3c2Br)CC1]
P-0740 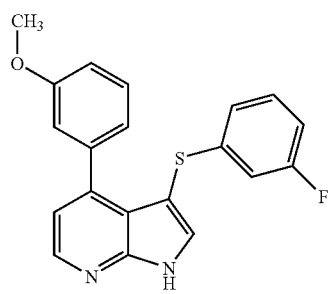 [SMILES: COc1cccc(-c2ccnc3[nH]cc(Sc4cccc(F)c4)c23)c1]
P-0741 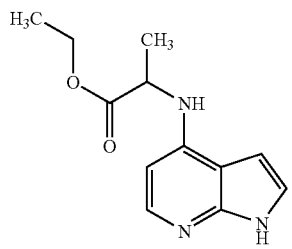 [SMILES: CCOC(=O)C(C)Nc1ccnc2[nH]ccc12]
P-0742 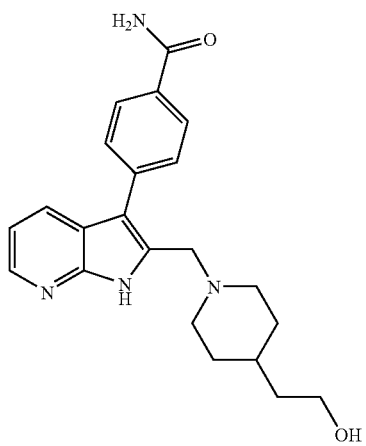 [SMILES: NC(=O)c1ccc(-c2c(CN3CCC(CCO)CC3)[nH]c3ncccc23)cc1]

TABLE 1-continued
Additional compounds of the invention
P-0743
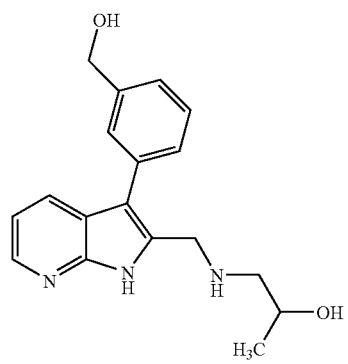 [SMILES: CC(O)CNCc1[nH]c2ncccc2c1-c1cccc(CO)c1]
P-0747
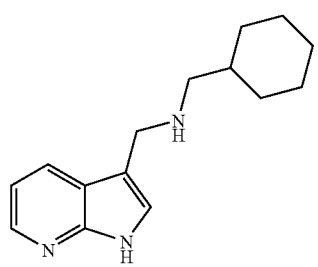 [SMILES: c1cnc2[nH]cc(CNCC3CCCCC3)c2c1]
P-0748
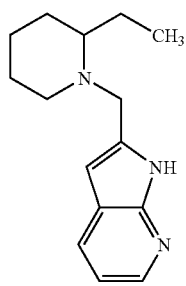 [SMILES: CCC1CCCCN1Cc1cc2cccnc2[nH]1]
P-0749
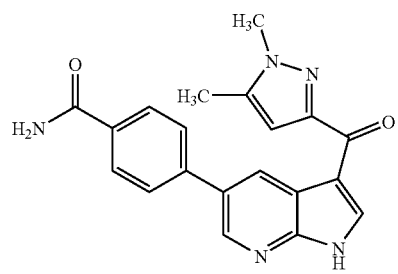 [SMILES: Cc1cc(C(=O)c2c[nH]c3ncc(-c4ccc(C(N)=O)cc4)cc23)nn1C]
P-0750
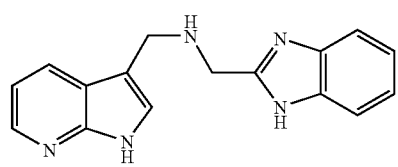 [SMILES: c1ccc2[nH]c(CNCc3c[nH]c4ncccc34)nc2c1]

TABLE 1-continued
Additional compounds of the invention
P-0751 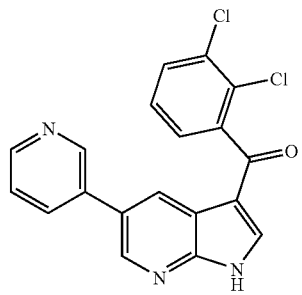 [SMILES: O=C(c1cccc(Cl)c1Cl)c1c[nH]c2ncc(-c3cccnc3)cc12]
P-0752 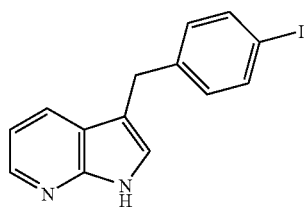 [SMILES: Ic1ccc(Cc2c[nH]c3ncccc23)cc1]
P-0754 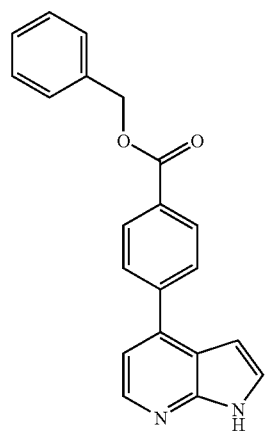 [SMILES: O=C(OCc1ccccc1)c1ccc(-c2ccnc3[nH]ccc23)cc1]
P-0755 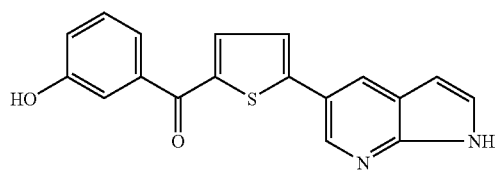 [SMILES: O=C(c1cccc(O)c1)c1ccc(-c2cnc3[nH]ccc3c2)s1]
P-0756 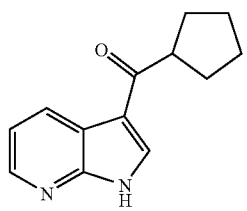 [SMILES: O=C(c1c[nH]c2ncccc12)C1CCCC1]
P-0757 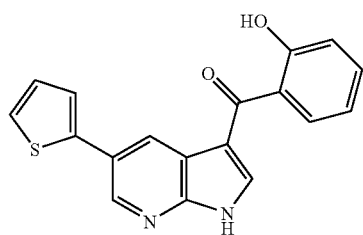 [SMILES: O=C(c1ccccc1O)c1c[nH]c2ncc(-c3cccs3)cc12]

TABLE 1-continued
Additional compounds of the invention
P-0758 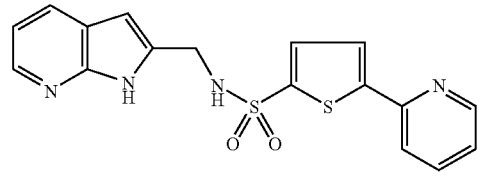 [SMILES: O=S(=O)(NCc1cc2cccnc2[nH]1)c1ccc(-c2ccccn2)s1]
P-0759 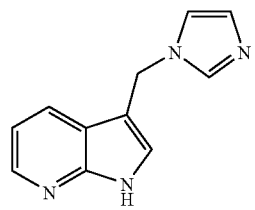 [SMILES: c1cnc2[nH]cc(Cn3ccnc3)c2c1]
P-0760 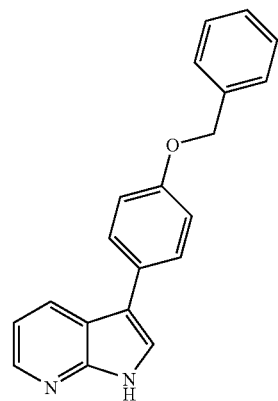 [SMILES: c1ccc(COc2ccc(-c3c[nH]c4ncccc34)cc2)cc1]
P-0761 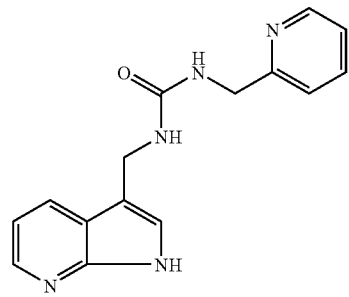 [SMILES: O=C(NCc1ccccn1)NCc1c[nH]c2ncccc12]
P-0762 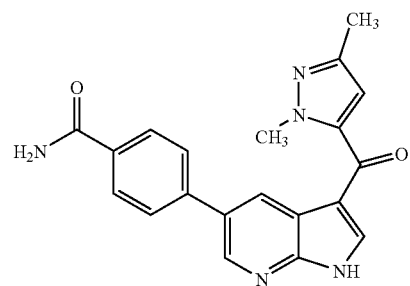 [SMILES: Cc1cc(C(=O)c2c[nH]c3ncc(-c4ccc(C(N)=O)cc4)cc23)n(C)n1]

TABLE 1-continued
Additional compounds of the invention
P-0764
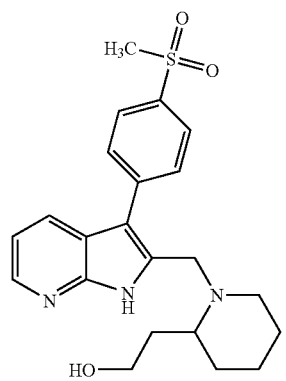 [SMILES: CS(=O)(=O)c1ccc(-c2c(CN3CCCCC3CCO)[nH]c3ncccc23)cc1]
P-0765
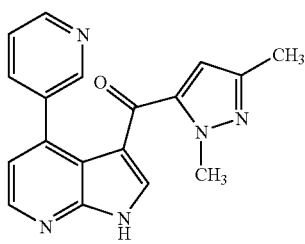 [SMILES: Cc1cc(C(=O)c2c[nH]c3nccc(-c4cccnc4)c23)n(C)n1]
P-0766
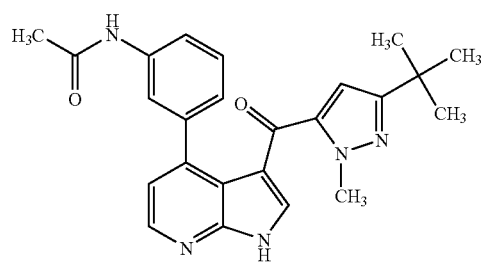 [SMILES: CC(=O)Nc1cccc(-c2ccnc3[nH]cc(C(=O)c4cc(C(C)(C)C)nn4C)c23)c1]
P-0767
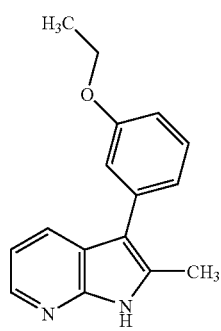 [SMILES: CCOc1cccc(-c2c(C)[nH]c3ncccc23)c1]
P-0768
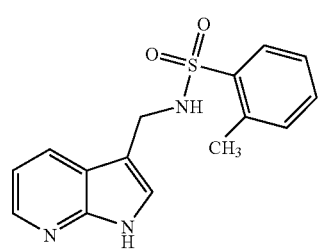 [SMILES: Cc1ccccc1S(=O)(=O)NCc1c[nH]c2ncccc12]

TABLE 1-continued
Additional compounds of the invention
P-0769
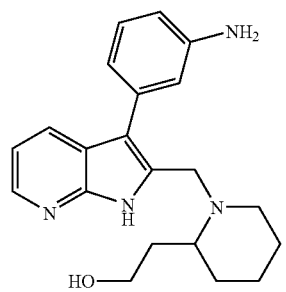 [SMILES: Nc1cccc(-c2c(CN3CCCCC3CCO)[nH]c3ncccc23)c1]
P-0770
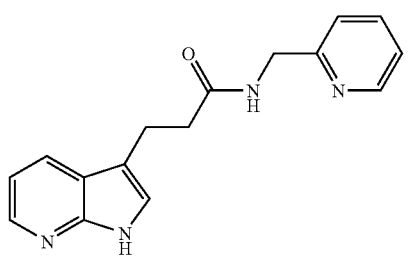 [SMILES: O=C(CCc1c[nH]c2ncccc12)NCc1ccccn1]
P-0771
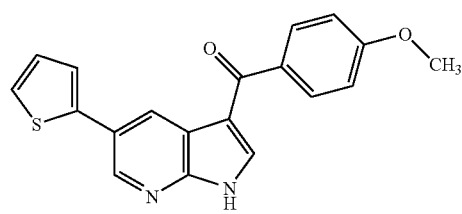 [SMILES: COc1ccc(C(=O)c2c[nH]c3ncc(-c4cccs4)cc23)cc1]
P-0772
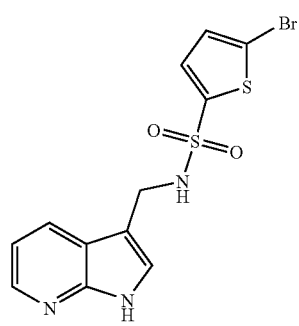 [SMILES: O=S(=O)(NCc1c[nH]c2ncccc12)c1ccc(Br)s1]
P-0775
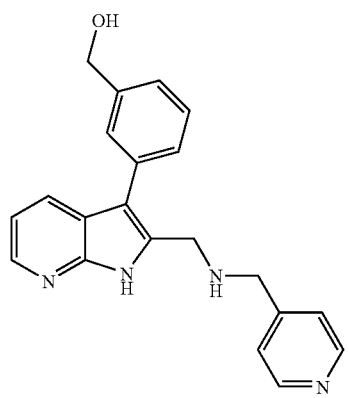 [SMILES: OCc1cccc(-c2c(CNCc3ccncc3)[nH]c3ncccc23)c1]

TABLE 1-continued
Additional compounds of the invention
P-0777
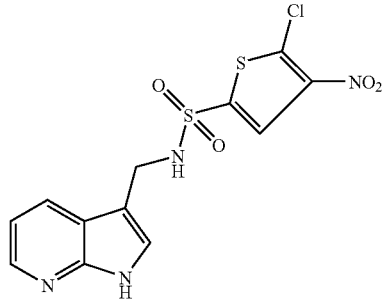 [SMILES: O=[N+]([O-])c1cc(S(=O)(=O)NCc2c[nH]c3ncccc23)sc1Cl]
P-0779
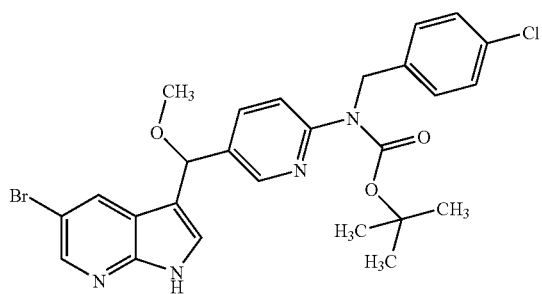 [SMILES: COC(c1ccc(N(Cc2ccc(Cl)cc2)C(=O)OC(C)(C)C)nc1)c1c[nH]c2ncc(Br)cc12]
P-0780
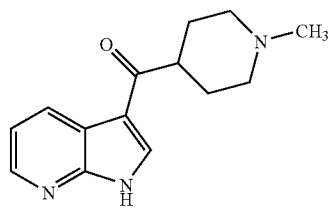 [SMILES: CN1CCC(C(=O)c2c[nH]c3ncccc23)CC1]
P-0781
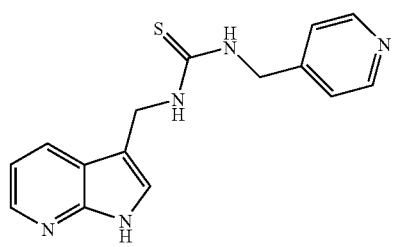 [SMILES: S=C(NCc1ccncc1)NCc1c[nH]c2ncccc12]
P-0782
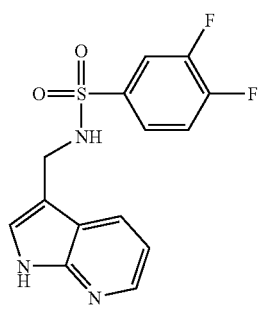 [SMILES: O=S(=O)(NCc1c[nH]c2ncccc12)c1ccc(F)c(F)c1]

TABLE 1-continued
Additional compounds of the invention
P-0783 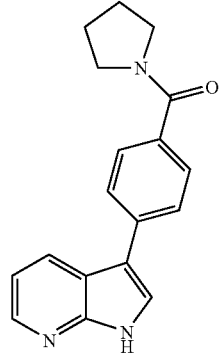 [SMILES: O=C(c1ccc(-c2c[nH]c3ncccc23)cc1)N1CCCC1]
P-0784 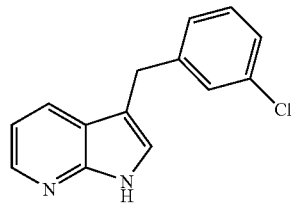 [SMILES: Clc1cccc(Cc2c[nH]c3ncccc23)c1]
P-0785 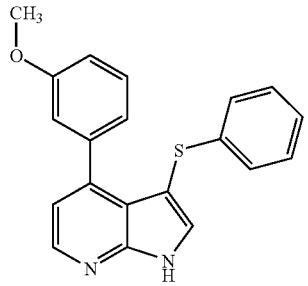 [SMILES: COc1cccc(-c2ccnc3[nH]cc(Sc4ccccc4)c23)c1]
P-0786 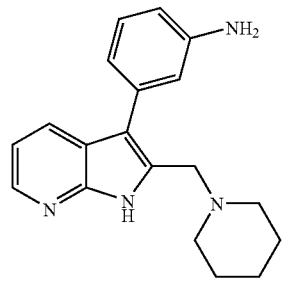 [SMILES: Nc1cccc(-c2c(CN3CCCCC3)[nH]c3ncccc23)c1]
P-0787 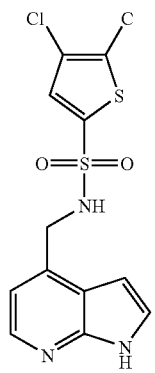 [SMILES: Cc1sc(S(=O)(=O)NCc2ccnc3[nH]ccc23)cc1Cl]

TABLE 1-continued
| Additional compounds of the invention |
|---|
P-0788 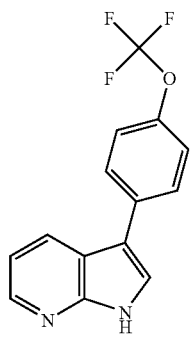 [SMILES: FC(F)(F)Oc1ccc(-c2c[nH]c3ncccc23)cc1]
P-0789 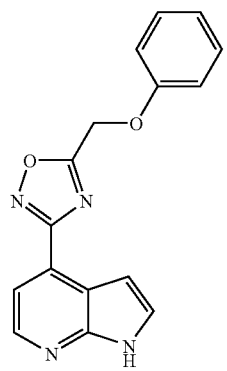 [SMILES: c1ccc(OCc2nc(-c3ccnc4[nH]ccc34)no2)cc1]
P-0790 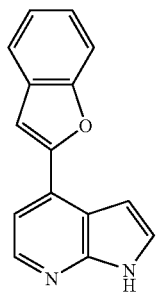 [SMILES: c1ccc2oc(-c3ccnc4[nH]ccc34)cc2c1]
P-0791 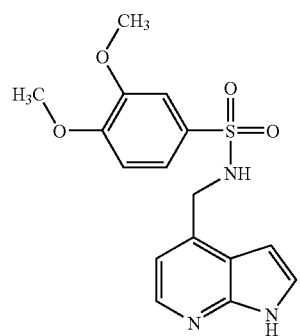 [SMILES: COc1ccc(S(=O)(=O)NCc2ccnc3[nH]ccc23)cc1OC]

TABLE 1-continued
Additional compounds of the invention
P-0792
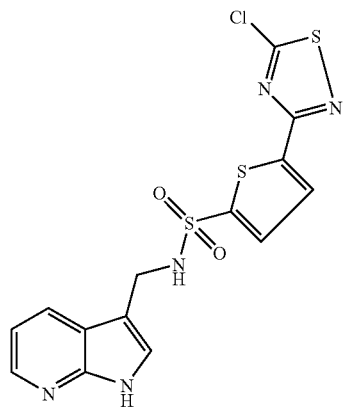 [SMILES: O=S(=O)(NCc1c[nH]c2ncccc12)c1ccc(-c2nsc(Cl)n2)s1]
P-0793
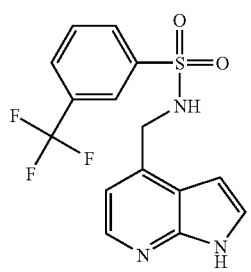 [SMILES: O=S(=O)(NCc1ccnc2[nH]ccc12)c1cccc(C(F)(F)F)c1]
P-0794
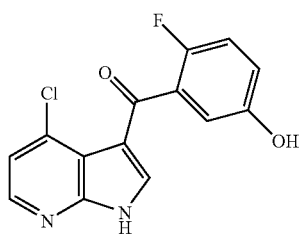 [SMILES: O=C(c1cc(O)ccc1F)c1c[nH]c2nccc(Cl)c12]
P-0795
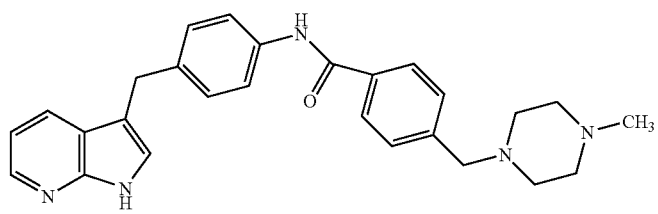 [SMILES: CN1CCN(Cc2ccc(C(=O)Nc3ccc(Cc4c[nH]c5ncccc45)cc3)cc2)CC1]
P-0796
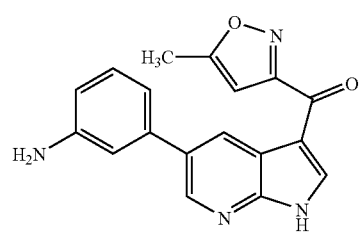 [SMILES: Cc1cc(C(=O)c2c[nH]c3ncc(-c4cccc(N)c4)cc23)no1]

TABLE 1-continued
| Additional compounds of the invention |
P-0797 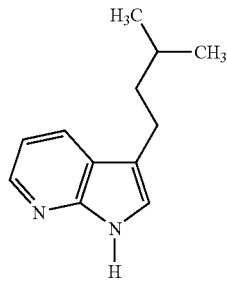
P-0799 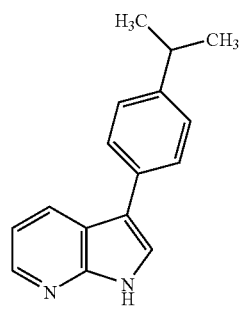 [SMILES: CC(C)c1ccc(-c2c[nH]c3ncccc23)cc1]
P-0800 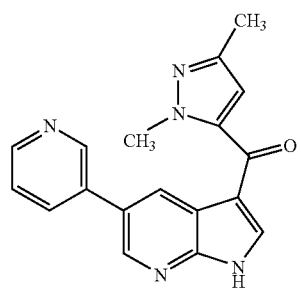 [SMILES: Cc1cc(C(=O)c2c[nH]c3ncc(-c4cccnc4)cc23)n(C)n1]
P-0801 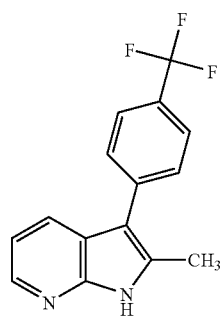 [SMILES: Cc1[nH]c2ncccc2c1-c1ccc(C(F)(F)F)cc1]
P-0802 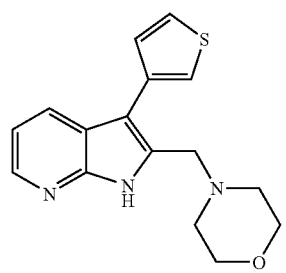 [SMILES: c1cnc2[nH]c(CN3CCOCC3)c(-c3ccsc3)c2c1]

TABLE 1-continued
Additional compounds of the invention
P-0803 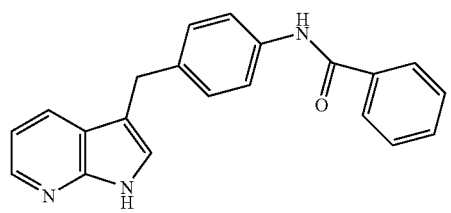 [SMILES: O=C(Nc1ccc(Cc2c[nH]c3ncccc23)cc1)c1ccccc1]
P-0804 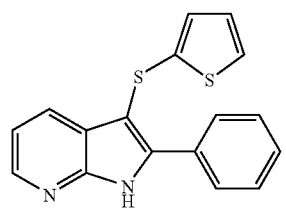 [SMILES: c1ccc(-c2[nH]c3ncccc3c2Sc2cccs2)cc1]
P-0808 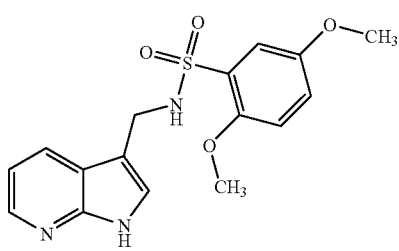 [SMILES: COc1ccc(OC)c(S(=O)(=O)NCc2c[nH]c3ncccc23)c1]
P-0809 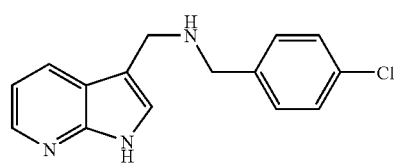 [SMILES: Clc1ccc(CNCc2c[nH]c3ncccc23)cc1]
P-0810 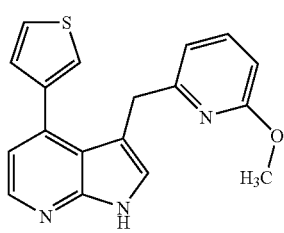 [SMILES: COc1cccc(Cc2c[nH]c3nccc(-c4ccsc4)c23)n1]
P-0812 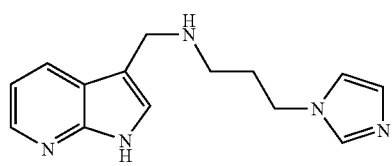 [SMILES: c1cnc2[nH]cc(CNCCCn3ccnc3)c2c1]
P-0813 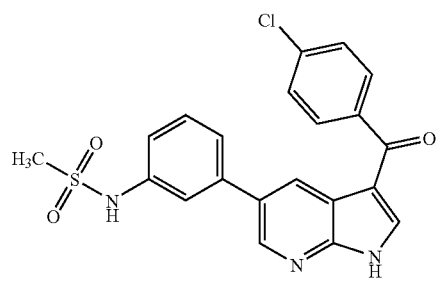 [SMILES: CS(=O)(=O)Nc1cccc(-c2cnc3[nH]cc(C(=O)c4ccc(Cl)cc4)c3c2)c1]

TABLE 1-continued
Additional compounds of the invention
P-0814 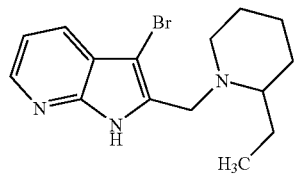 [SMILES: CCC1CCCCN1Cc1[nH]c2ncccc2c1Br]
P-0815 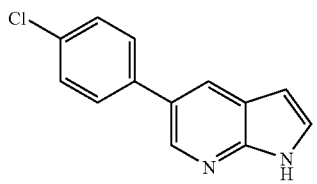 [SMILES: Clc1ccc(-c2cnc3[nH]ccc3c2)cc1]
P-0816 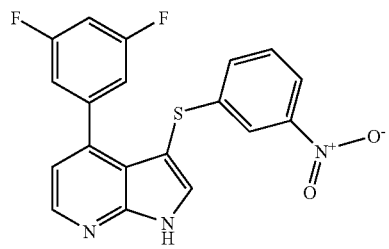 [SMILES: O=[N+]([O-])c1cccc(Sc2c[nH]c3nccc(-c4cc(F)cc(F)c4)c23)c1]
P-0817 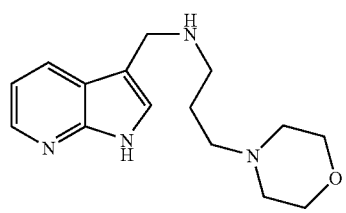 [SMILES: c1cnc2[nH]cc(CNCCCN3CCOCC3)c2c1]
P-0819 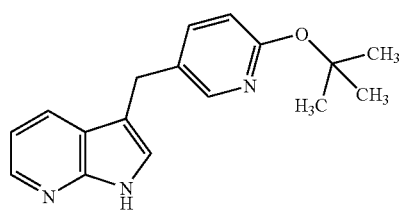 [SMILES: CC(C)(C)Oc1ccc(Cc2c[nH]c3ncccc23)cn1]
P-0820 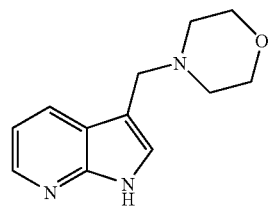 [SMILES: c1cnc2[nH]cc(CN3CCOCC3)c2c1]
P-0821 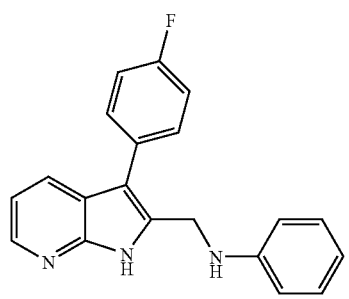

TABLE 1-continued
Additional compounds of the invention
P-0822 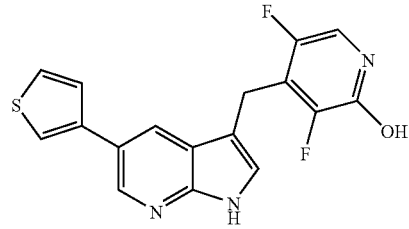 [SMILES: Oc1ncc(F)c(Cc2c[nH]c3ncc(-c4ccsc4)cc23)c1F]
P-0823 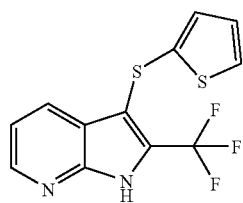 [SMILES: FC(F)(F)c1[nH]c2ncccc2c1Sc1cccs1]
P-0824 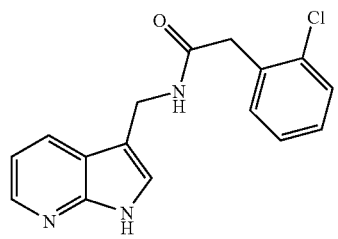 [SMILES: O=C(Cc1ccccc1Cl)NCc1c[nH]c2ncccc12]
P-0825 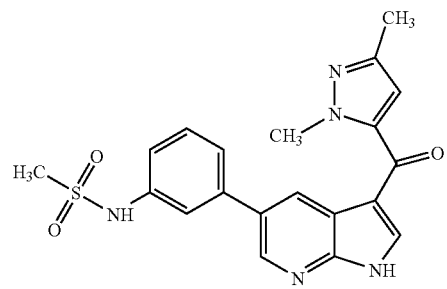 [SMILES: Cc1cc(C(=O)c2c[nH]c3ncc(-c4cccc(NS(C)(=O)=O)c4)cc23)n(C)n1]
P-0826 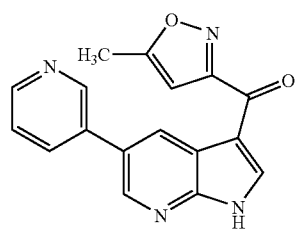 [SMILES: Cc1cc(C(=O)c2c[nH]c3ncc(-c4cccnc4)cc23)no1]
P-0827 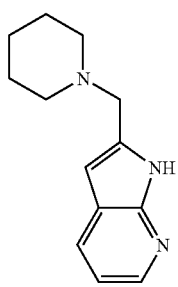 [SMILES: c1cnc2[nH]c(CN3CCCCC3)cc2c1]

TABLE 1-continued
Additional compounds of the invention
P-0828
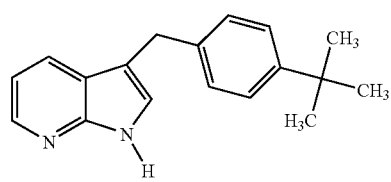 [SMILES: CC(C)(C)c1ccc(Cc2c[nH]c3ncccc23)cc1]
P-0829
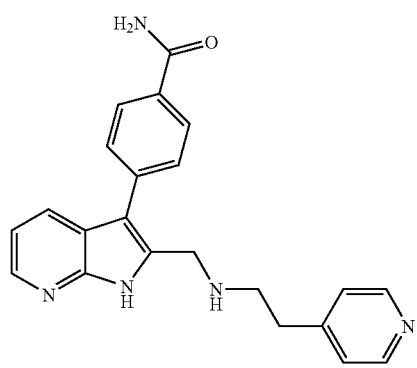 [SMILES: NC(=O)c1ccc(-c2c(CNCCc3ccncc3)[nH]c3ncccc23)cc1]
P-0830
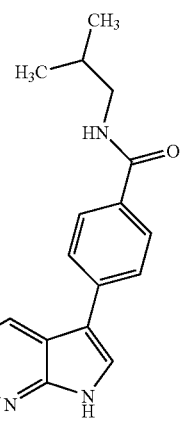
P-0831
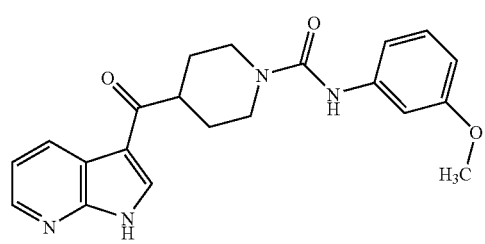 [SMILES: COc1cccc(NC(=O)N2CCC(C(=O)c3c[nH]c4ncccc34)CC2)c1]
P-0832
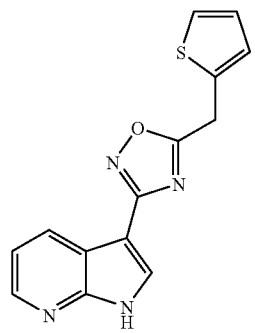 [SMILES: c1csc(Cc2nc(-c3c[nH]c4ncccc34)no2)c1]

TABLE 1-continued
Additional compounds of the invention
P-0833
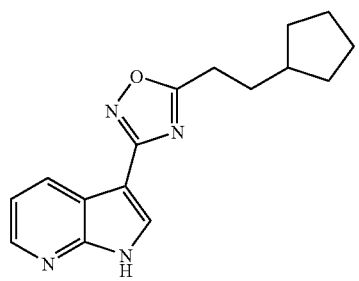 [SMILES: c1cnc2[nH]cc(-c3noc(CCC4CCCC4)n3)c2c1]
P-0834
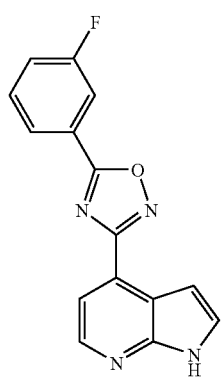 [SMILES: Fc1cccc(-c2nc(-c3ccnc4[nH]ccc34)no2)c1]
P-0835
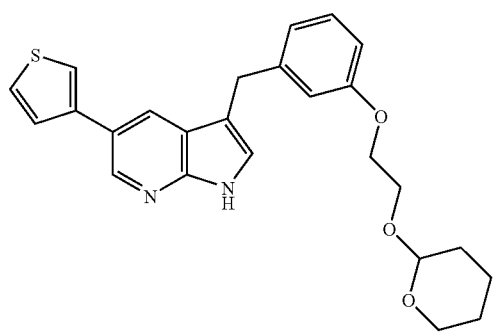 [SMILES: c1cc(Cc2c[nH]c3ncc(-c4ccsc4)cc23)cc(OCCOC2CCCCO2)c1]
P-0836
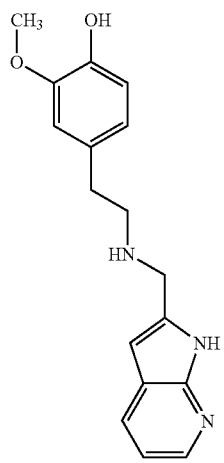 [SMILES: COc1cc(CCNCc2cc3cccnc3[nH]2)ccc1O]

TABLE 1-continued
Additional compounds of the invention
P-0838
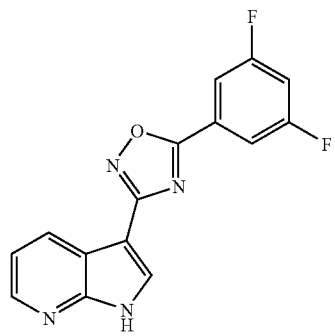 [SMILES: Fc1cc(F)cc(-c2nc(-c3c[nH]c4ncccc34)no2)c1]
P-0839
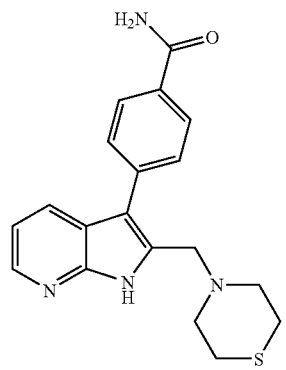 [SMILES: NC(=O)c1ccc(-c2c(CN3CCSCC3)[nH]c3ncccc23)cc1]
P-0840
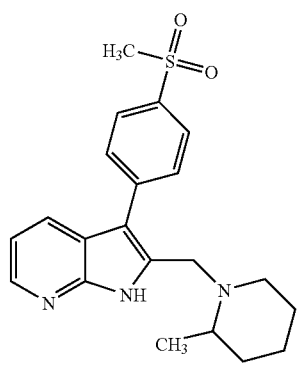 [SMILES: CC1CCCCN1Cc1[nH]c2ncccc2c1-c1ccc(S(C)(=O)=O)cc1]
P-0842
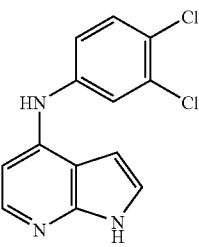 [SMILES: Clc1ccc(Nc2ccnc3[nH]ccc23)cc1Cl]
P-0843
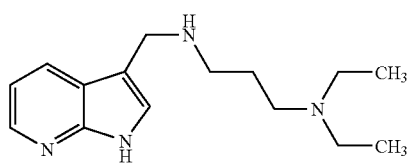

TABLE 1-continued
Additional compounds of the invention
P-0844
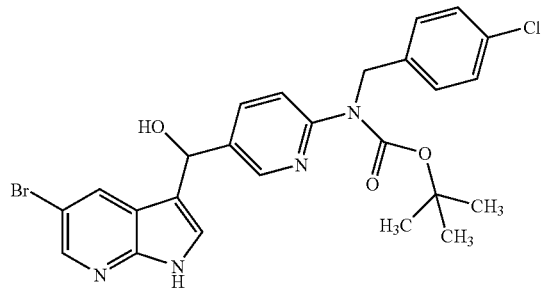 [SMILES: CC(C)(C)OC(=O)N(Cc1ccc(Cl)cc1)c1ccc(C(O)c2c[nH]c3ncc(Br)cc23)cn1]
P-0845
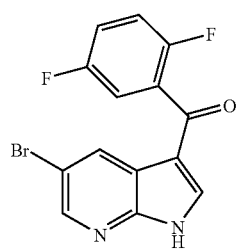
P-0846
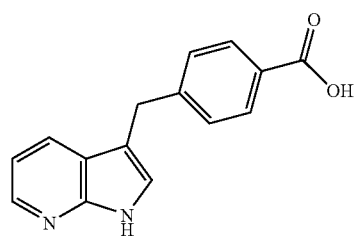 [SMILES: O=C(O)c1ccc(Cc2c[nH]c3ncccc23)cc1]
P-0847
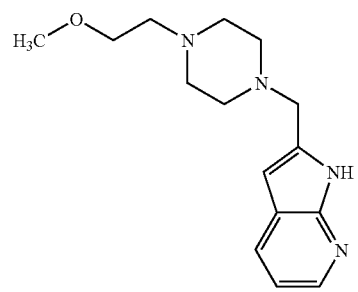 [SMILES: COCCN1CCN(Cc2cc3cccnc3[nH]2)CC1]
P-0849
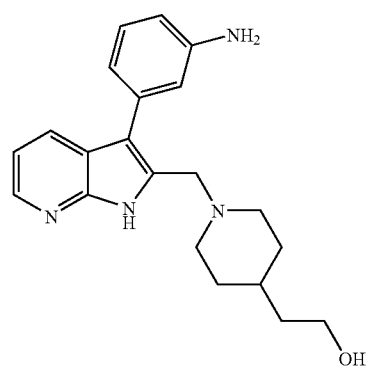 [SMILES: Nc1cccc(-c2c(CN3CCC(CCO)CC3)[nH]c3ncccc23)c1]

TABLE 1-continued
Additional compounds of the invention
P-0851
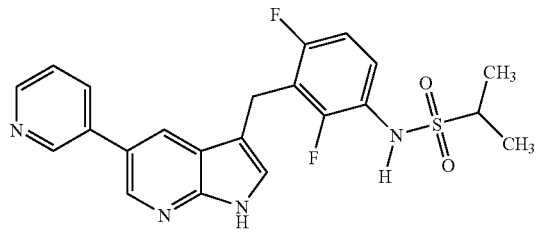
P-0852
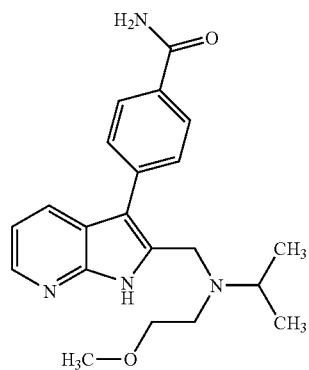 [SMILES: COCCN(Cc1[nH]c2ncccc2c1-c1ccc(C(N)=O)cc1)C(C)C]
P-0854
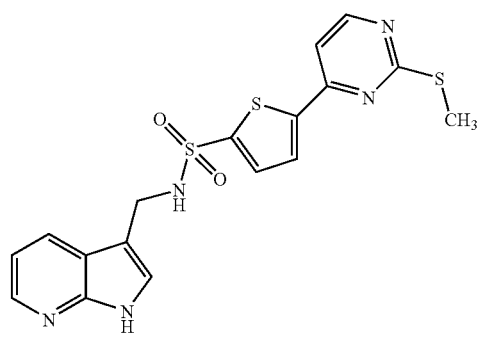 [SMILES: CSc1nccc(-c2ccc(S(=O)(=O)NCc3c[nH]c4ncccc34)s2)n1]
P-0855
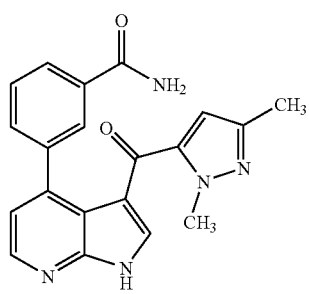 [SMILES: Cc1cc(C(=O)c2c[nH]c3nccc(-c4cccc(C(N)=O)c4)c23)n(C)n1]

TABLE 1-continued
Additional compounds of the invention
P-0856 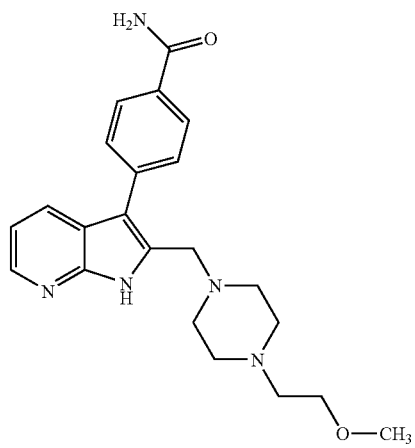 [SMILES: COCCN1CCN(Cc2[nH]c3ncccc3c2-c2ccc(C(N)=O)cc2)CC1]
P-0857 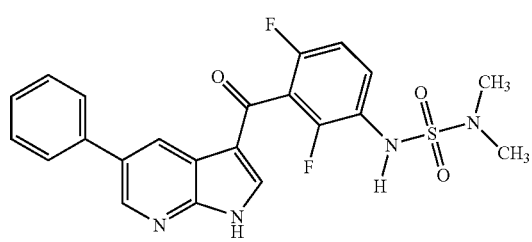 [SMILES: CN(C)S(=O)(=O)Nc1ccc(F)c(C(=O)c2c[nH]c3ncc(-c4ccccc4)cc23)c1F]
P-0858 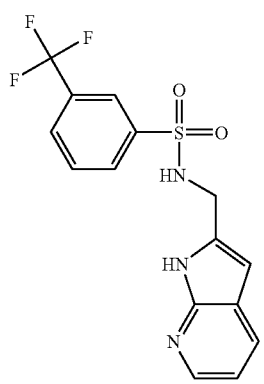 [SMILES: O=S(=O)(NCc1cc2cccnc2[nH]1)c1cccc(C(F)(F)F)c1]
P-0859 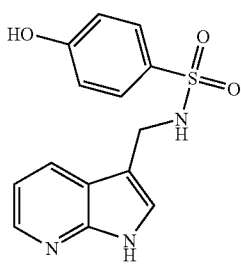 [SMILES: O=S(=O)(NCc1c[nH]c2ncccc12)c1ccc(O)cc1]
P-0861 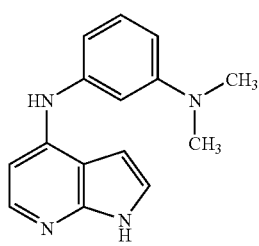 [SMILES: CN(C)c1cccc(Nc2ccnc3[nH]ccc23)c1]

TABLE 1-continued
| Additional compounds of the invention |
|---|
| P-0862 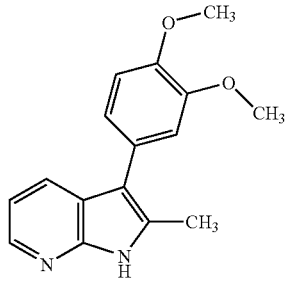 [SMILES: COc1ccc(-c2c(C)[nH]c3ncccc23)cc1OC] |
| P-0863 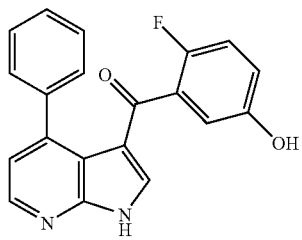 [SMILES: O=C(c1cc(O)ccc1F)c1c[nH]c2nccc(-c3ccccc3)c12] |
| P-0864 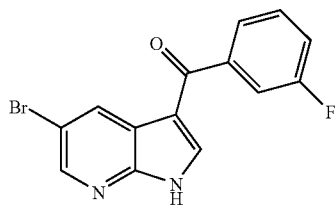 [SMILES: O=C(c1cccc(F)c1)c1c[nH]c2ncc(Br)cc12] |
| P-0865 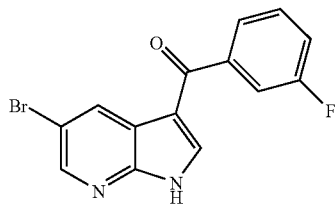 [SMILES: O=C(c1cccc(F)c1)c1c[nH]c2ncc(Br)cc12] |
| P-0866 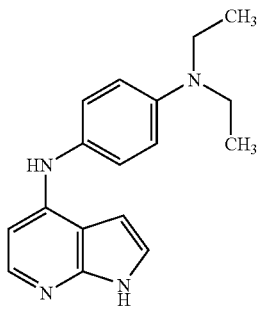 [SMILES: CCN(CC)c1ccc(Nc2ccnc3[nH]ccc23)cc1] |
| P-0869 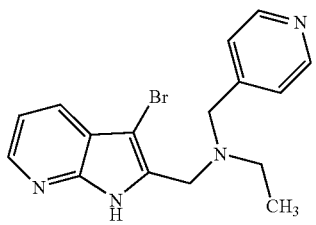 [SMILES: CCN(Cc1ccncc1)Cc1[nH]c2ncccc2c1Br] |

TABLE 1-continued
Additional compounds of the invention
P-0870
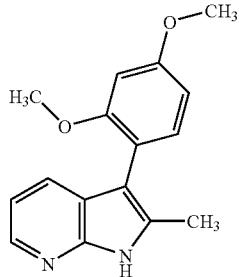
P-0871
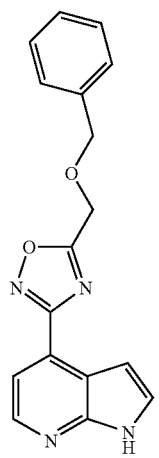
P-0872
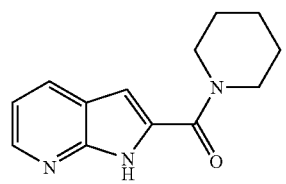 [SMILES: O=C(c1cc2cccnc2[nH]1)N1CCCCC1]
P-0873
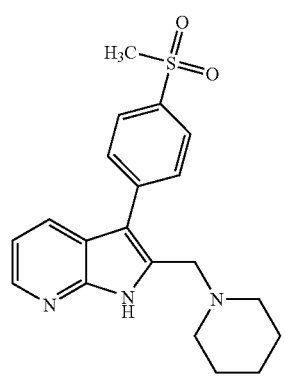 [SMILES: CS(=O)(=O)c1ccc(-c2c(CN3CCCCC3)[nH]c3ncccc23)cc1]
P-0875
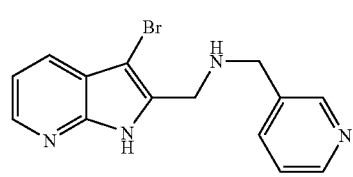 [SMILES: Brc1c(CNCc2cccnc2)[nH]c2ncccc12]

TABLE 1-continued
Additional compounds of the invention
P-0878
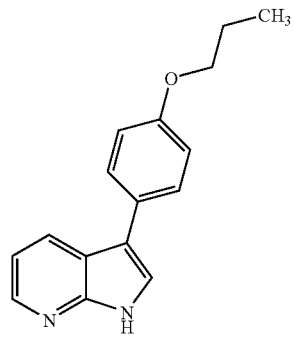 [SMILES: CCCOc1ccc(-c2c[nH]c3ncccc23)cc1]
P-0879
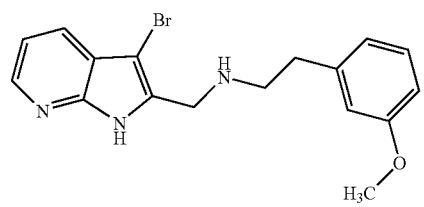 [SMILES: COc1cccc(CCNCc2[nH]c3ncccc3c2Br)c1]
P-0880
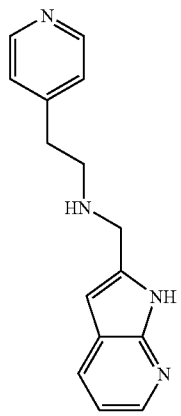 [SMILES: c1cnc2[nH]c(CNCCc3ccncc3)cc2c1]
P-0881
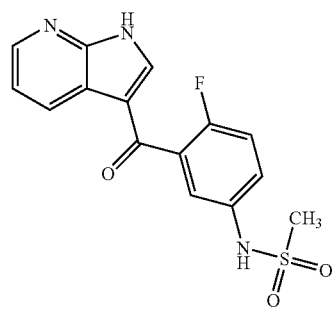 [SMILES: CS(=O)(=O)Nc1ccc(F)c(C(=O)c2c[nH]c3ncccc23)c1]
P-0882
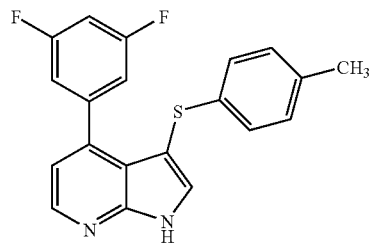 [SMILES: Cc1ccc(Sc2c[nH]c3nccc(-c4cc(F)cc(F)c4)c23)cc1]

TABLE 1-continued
Additional compounds of the invention
P-0883
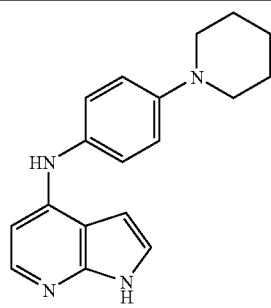
P-0884
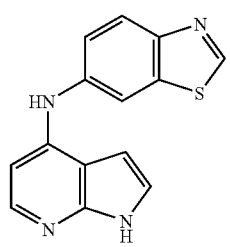 [SMILES: c1cc(Nc2ccc3ncsc3c2)c2cc[nH]c2n1]
P-0886
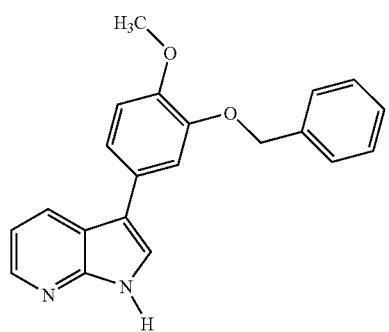 [SMILES: COc1ccc(-c2c[nH]c3ncccc23)cc1OCc1ccccc1]
P-0887
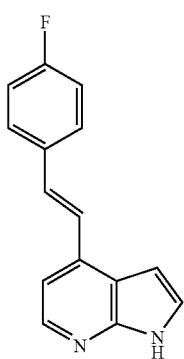 [SMILES: Fc1ccc(/C=C/c2ccnc3[nH]ccc23)cc1]

TABLE 1-continued
Additional compounds of the invention
P-0888
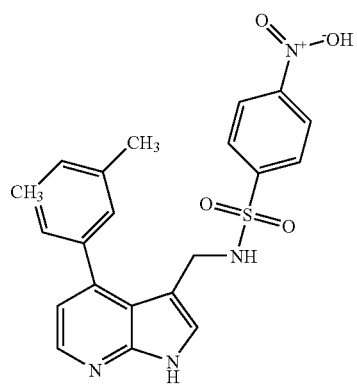 [SMILES: Cc1cccc(-c2ccnc3[nH]cc(CNS(=O)(=O)c4ccc([N+](=O)[O-])cc4)c23)c1]
P-0890
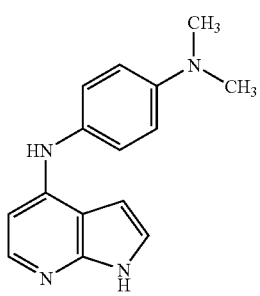 [SMILES: CN(C)c1ccc(Nc2ccnc3[nH]ccc23)cc1]
P-0891
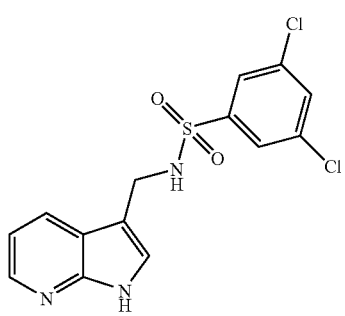 [SMILES: O=S(=O)(NCc1c[nH]c2ncccc12)c1cc(Cl)cc(Cl)c1]
P-0892
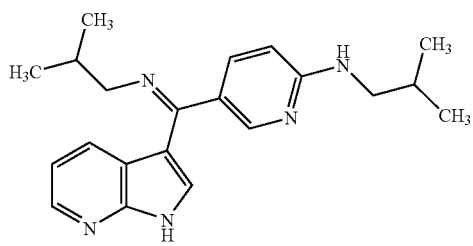 [SMILES: CC(C)C/N=C(/c1ccc(NCC(C)C)nc1)c1c[nH]c2ncccc12]
P-0893
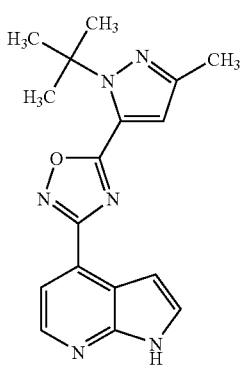 [SMILES: Cc1cc(-c2nc(-c3ccnc4[nH]ccc34)no2)n(C(C)(C)C)n1]

TABLE 1-continued
Additional compounds of the invention
P-0895 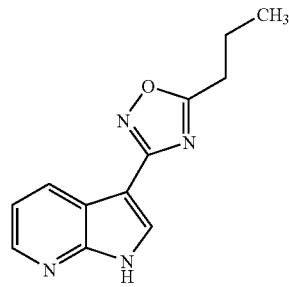 [SMILES: CCCc1nc(-c2c[nH]c3ncccc23)no1]
P-0896 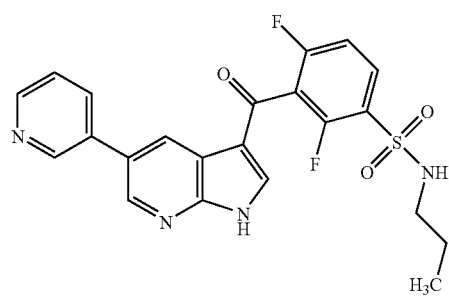 [SMILES: CCCNS(=O)(=O)c1ccc(F)c(C(=O)c2c[nH]c3ncc(-c4cccnc4)cc23)c1F]
P-0899 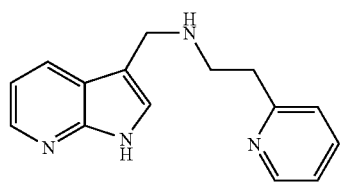 [SMILES: c1ccc(CCNCc2c[nH]c3ncccc23)nc1]
P-0900 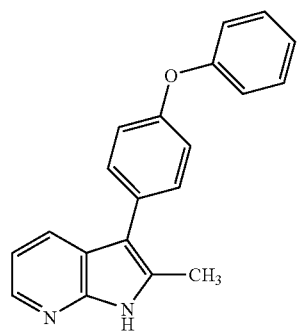 [SMILES: Cc1[nH]c2ncccc2c1-c1ccc(Oc2ccccc2)cc1]
P-0901 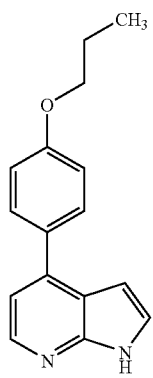 [SMILES: CCCOc1ccc(-c2ccnc3[nH]ccc23)cc1]

TABLE 1-continued
Additional compounds of the invention
P-0903
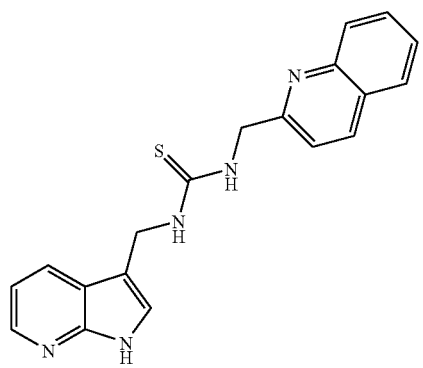 [SMILES: S=C(NCc1ccc2ccccc2n1)NCc1c[nH]c2ncccc12]
P-0905
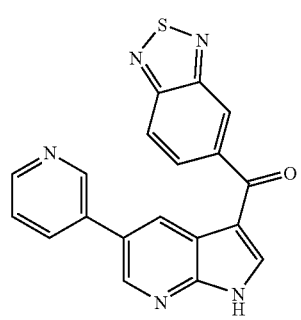 [SMILES: O=C(c1ccc2nsnc2c1)c1c[nH]c2ncc(-c3cccnc3)cc12]
P-0906
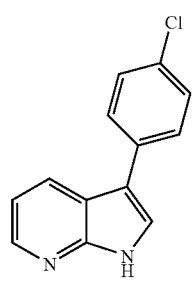 [SMILES: Clc1ccc(-c2c[nH]c3ncccc23)cc1]
P-0908
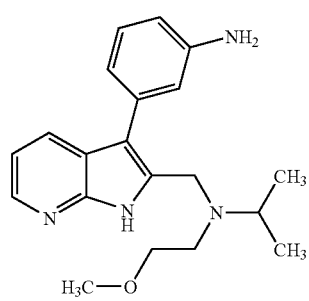 [SMILES: COCCN(Cc1[nH]c2ncccc2c1-c1cccc(N)c1)C(C)C]
P-0909
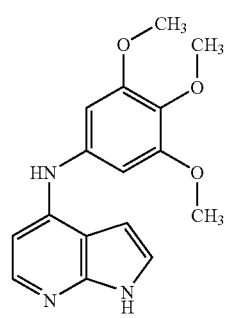 [SMILES: COc1cc(Nc2ccnc3[nH]ccc23)cc(OC)c1OC]

TABLE 1-continued
Additional compounds of the invention
P-0914 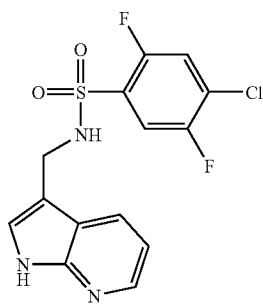 [SMILES: O=S(=O)(NCc1c[nH]c2ncccc12)c1cc(F)c(Cl)cc1F]
P-0915 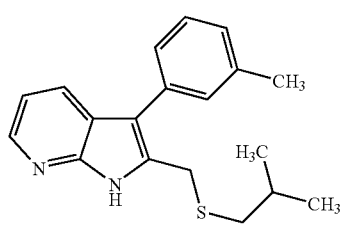 [SMILES: Cc1cccc(-c2c(CSCC(C)C)[nH]c3ncccc23)c1]
P-0916 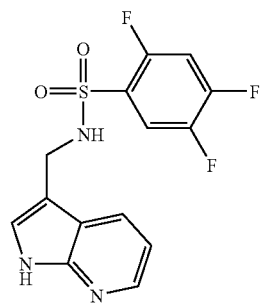 [SMILES: O=S(=O)(NCc1c[nH]c2ncccc12)c1cc(F)c(F)cc1F]
P-0917 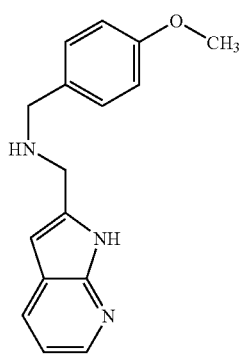 [SMILES: COc1ccc(CNCc2cc3cccnc3[nH]2)cc1]
P-0918 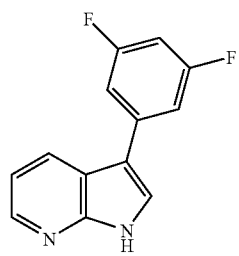 [SMILES: Fc1cc(F)cc(-c2c[nH]c3ncccc23)c1]

TABLE 1-continued
Additional compounds of the invention
P-0920 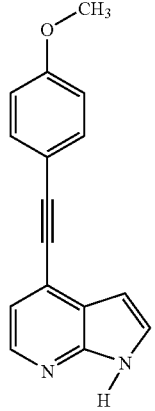 [SMILES: COc1ccc(C#Cc2ccnc3[nH]ccc23)cc1]
P-0921 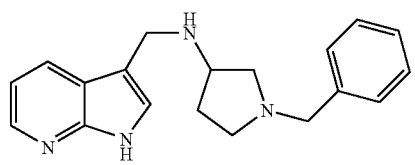 [SMILES: c1ccc(CN2CCC(NCc3c[nH]c4ncccc34)C2)cc1]
P-0922 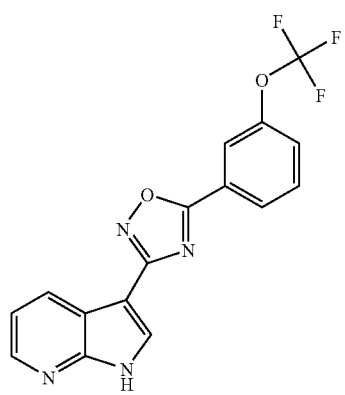 [SMILES: FC(F)(F)Oc1cccc(-c2nc(-c3c[nH]c4ncccc34)no2)c1]
P-0923 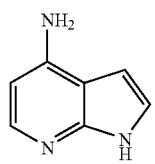
P-0924 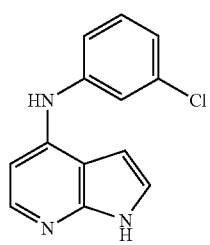 [SMILES: Clc1cccc(Nc2ccnc3[nH]ccc23)c1]

TABLE 1-continued
Additional compounds of the invention
P-0925
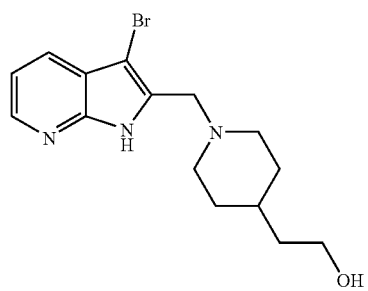 [SMILES: OCCC1CCN(Cc2[nH]c3ncccc3c2Br)CC1]
P-0926
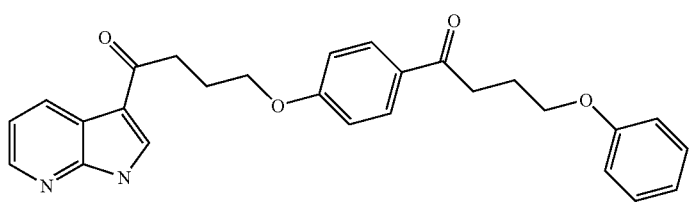 [SMILES: O=C(CCCOc1ccccc1)c1ccc(OCCCC(=O)c2c[nH]c3ncccc23)cc1]
P-0927
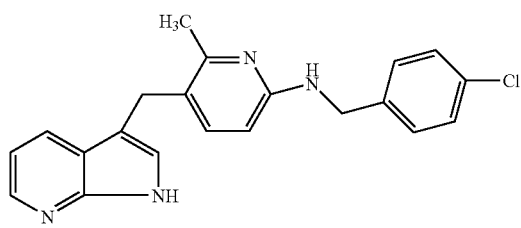 [SMILES: Cc1nc(NCc2ccc(Cl)cc2)ccc1Cc1c[nH]c2ncccc12]
P-0928
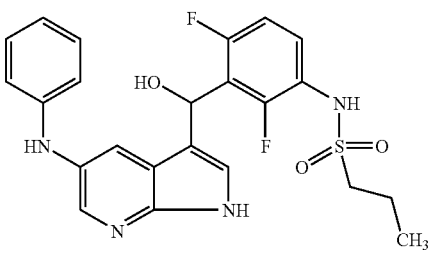 [SMILES: CCCS(=O)(=O)Nc1ccc(F)c(C(O)c2c[nH]c3ncc(Nc4ccccc4)cc23)c1F]
P-0929
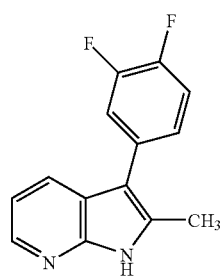 [SMILES: Cc1[nH]c2ncccc2c1-c1ccc(F)c(F)c1]
P-0930
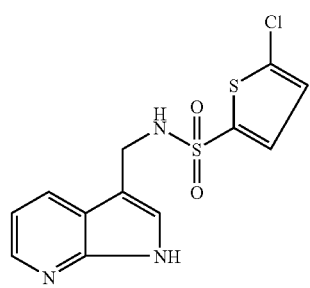 [SMILES: O=S(=O)(NCc1c[nH]c2ncccc12)c1ccc(Cl)s1]

TABLE 1-continued
Additional compounds of the invention
P-0932
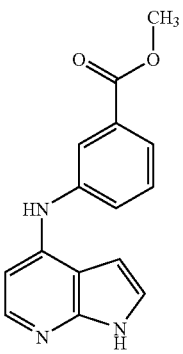 [SMILES: COC(=O)c1cccc(Nc2ccnc3[nH]ccc23)c1]
P-0934
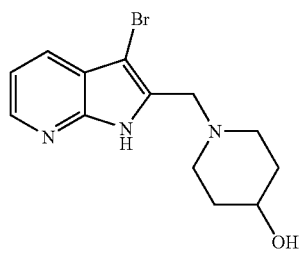 [SMILES: OC1CCN(Cc2[nH]c3ncccc3c2Br)CC1]
P-0935
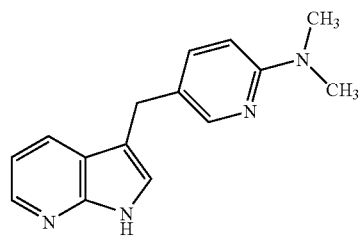
P-0936
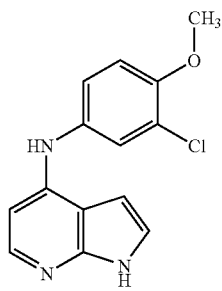 [SMILES: COc1ccc(Nc2ccnc3[nH]ccc23)cc1Cl]
P-0938
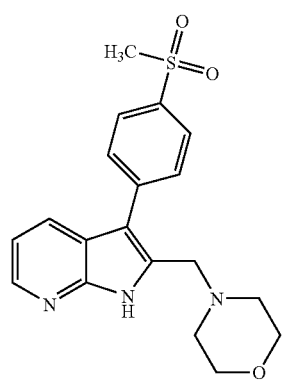 [SMILES: CS(=O)(=O)c1ccc(-c2c(CN3CCOCC3)[nH]c3ncccc23)cc1]

TABLE 1-continued
Additional compounds of the invention
P-0939 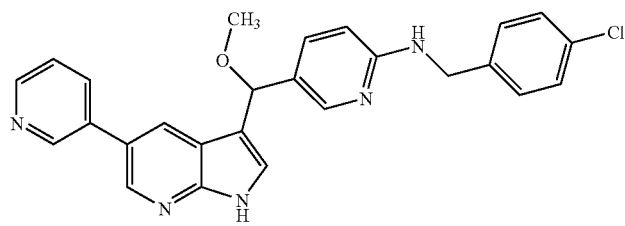 [SMILES: COC(c1ccc(NCc2ccc(Cl)cc2)nc1)c1c[nH]c2ncc(-c3cccnc3)cc12]
P-0940 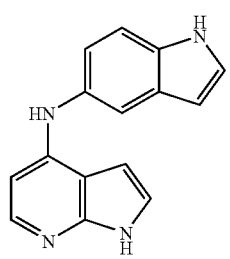 [SMILES: c1cc(Nc2ccc3[nH]ccc3c2)c2cc[nH]c2n1]
P-0941 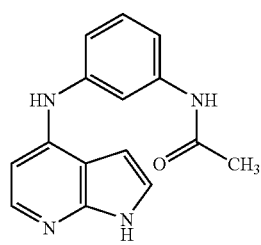 [SMILES: CC(=O)Nc1cccc(Nc2ccnc3[nH]ccc23)c1]
P-0942 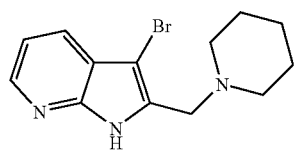 [SMILES: Brc1c(CN2CCCCC2)[nH]c2ncccc12]
P-0943 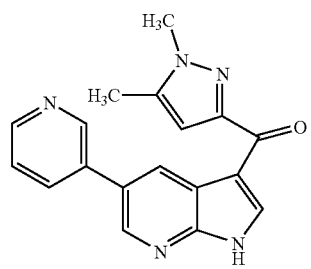 [SMILES: Cc1cc(C(=O)c2c[nH]c3ncc(-c4cccnc4)cc23)nn1C]
P-0945 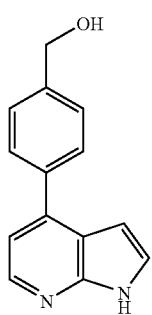 [SMILES: OCc1ccc(-c2ccnc3[nH]ccc23)cc1]

TABLE 1-continued
Additional compounds of the invention
P-0946 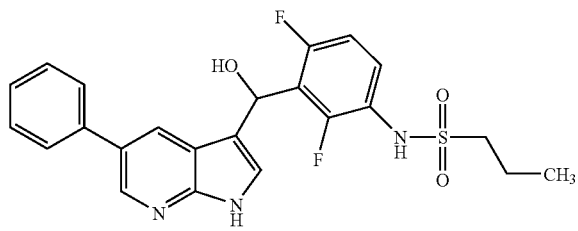 [SMILES: CCCS(=O)(=O)Nc1ccc(F)c(C(O)c2c[nH]c3ncc(-c4ccccc4)cc23)c1F]
P-0948 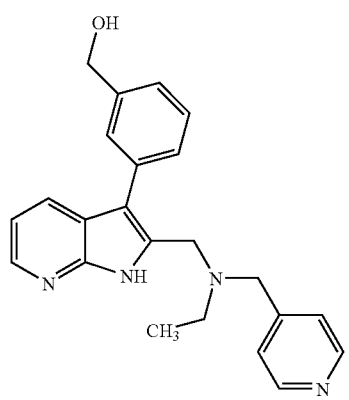 [SMILES: CCN(Cc1ccncc1)Cc1[nH]c2ncccc2c1-c1cccc(CO)c1]
P-0949 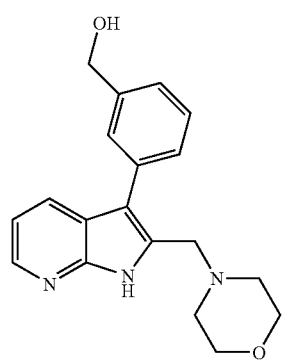 [SMILES: OCc1cccc(-c2c(CN3CCOCC3)[nH]c3ncccc23)c1]
P-0951 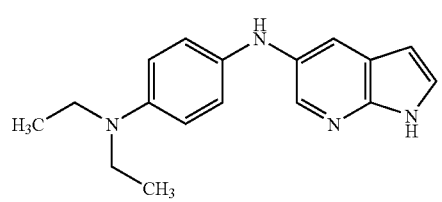 [SMILES: CCN(CC)c1ccc(Nc2cnc3[nH]ccc3c2)cc1]
P-0953 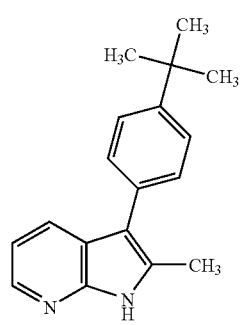 [SMILES: Cc1[nH]c2ncccc2c1-c1ccc(C(C)(C)C)cc1]

TABLE 1-continued
Additional compounds of the invention
P-0957
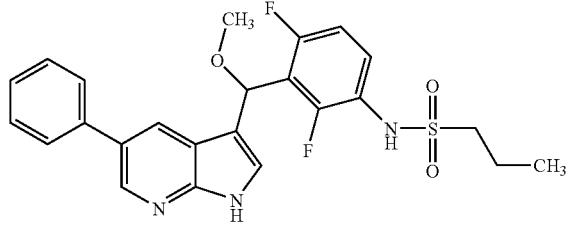 [SMILES: CCCS(=O)(=O)Nc1ccc(F)c(C(OC)c2c[nH]c3ncc(-c4ccccc4)cc23)c1F]
P-0959
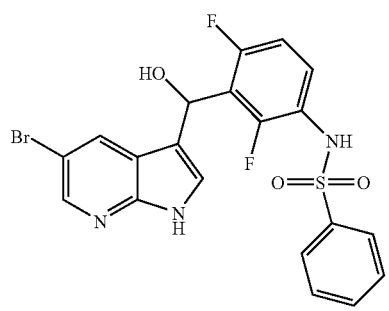 [SMILES: O=S(=O)(Nc1ccc(F)c(C(O)c2c[nH]c3ncc(Br)cc23)c1F)c1ccccc1]
P-0960
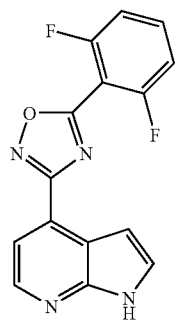 [SMILES: Fc1cccc(F)c1-c1nc(-c2ccnc3[nH]ccc23)no1]
P-0961
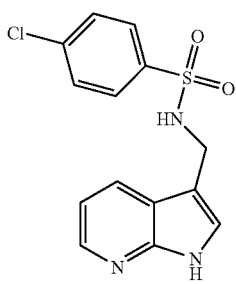
P-0962
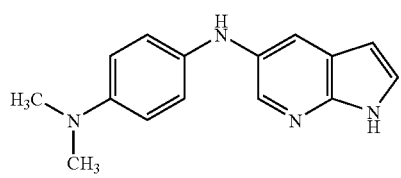 [SMILES: CN(C)c1ccc(Nc2cnc3[nH]ccc3c2)cc1]

TABLE 1-continued
Additional compounds of the invention
P-0963
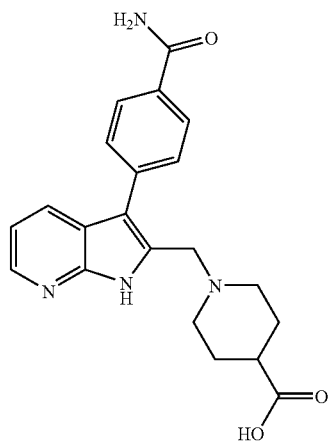 [SMILES: NC(=O)c1ccc(-c2c(CN3CCC(C(=O)O)CC3)[nH]c3ncccc23)cc1]
P-0965
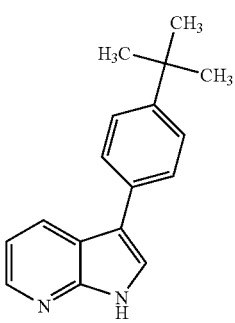 [SMILES: CC(C)(C)c1ccc(-c2c[nH]c3ncccc23)cc1]
P-0966
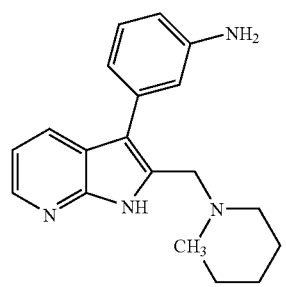 [SMILES: Nc1cccc(-c2c(CN3CCCCC3)[nH]c3ncccc23)c1]
P-0967
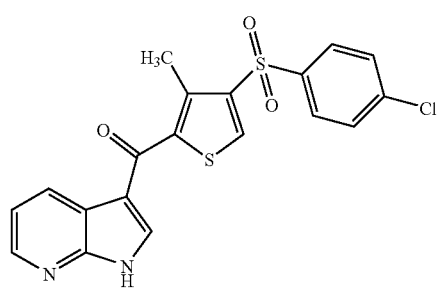 [SMILES: Cc1c(S(=O)(=O)c2ccc(Cl)cc2)csc1C(=O)c1c[nH]c2ncccc12]
P-0968
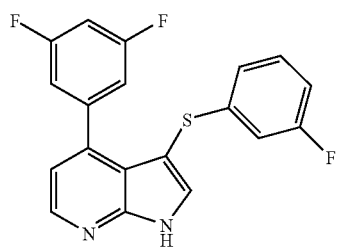 [SMILES: Fc1cccc(Sc2c[nH]c3nccc(-c4cc(F)cc(F)c4)c23)c1]

TABLE 1-continued
Additional compounds of the invention
P-0969 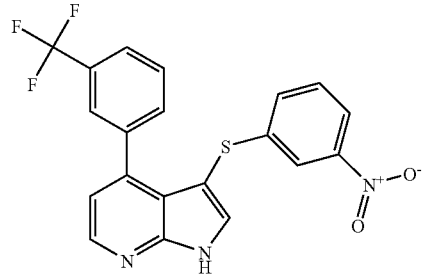 [SMILES: O=[N+]([O-])c1cccc(Sc2c[nH]c3nccc(-c4cccc(C(F)(F)F)c4)c23)c1]
P-0970 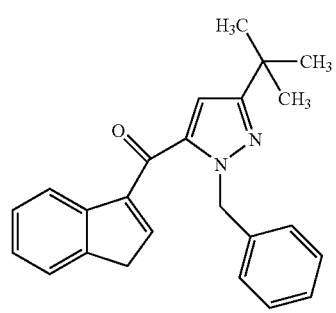 [SMILES: CC(C)(C)c1cc(C(=O)C2=CCc3ccccc32)n(Cc2ccccc2)n1]
P-0972 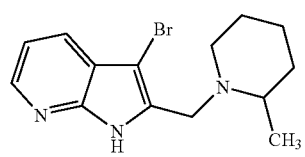 [SMILES: CC1CCCCN1Cc1[nH]c2ncccc2c1Br]
P-0973 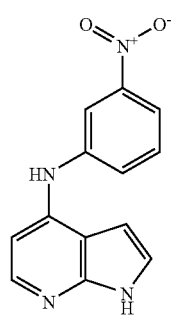 [SMILES: O=[N+]([O-])c1cccc(Nc2ccnc3[nH]ccc23)c1]
P-0975 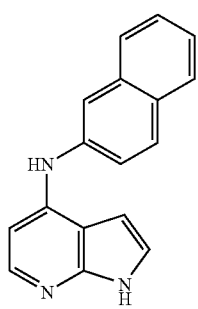 [SMILES: c1ccc2cc(Nc3ccnc4[nH]ccc34)ccc2c1]

TABLE 1-continued
Additional compounds of the invention
P-0976
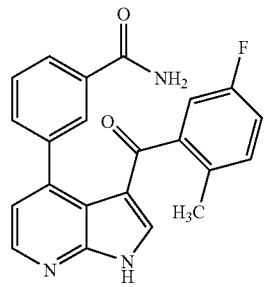 [SMILES: Cc1ccc(F)cc1C(=O)c1c[nH]c2nccc(-c3cccc(C(N)=O)c3)c12]
P-0977
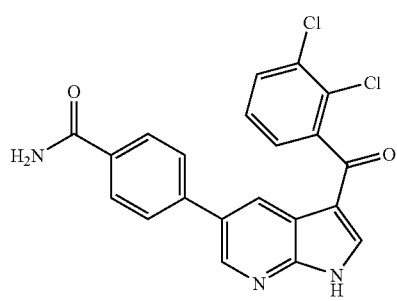 [SMILES: NC(=O)c1ccc(-c2cnc3[nH]cc(C(=O)c4cccc(Cl)c4Cl)c3c2)cc1]
P-0978
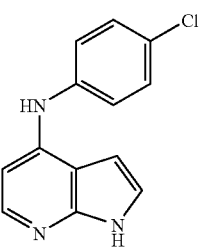 [SMILES: Clc1ccc(Nc2ccnc3[nH]ccc23)cc1]
P-0979
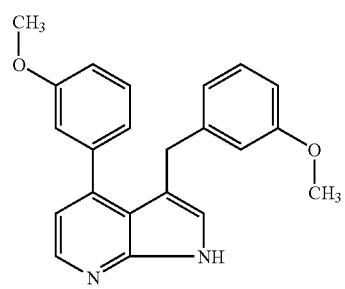 [SMILES: COc1cccc(Cc2c[nH]c3nccc(-c4cccc(OC)c4)c23)c1]
P-0980
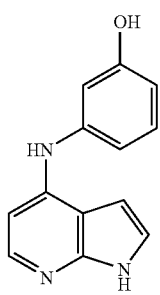

TABLE 1-continued
Additional compounds of the invention
P-0981
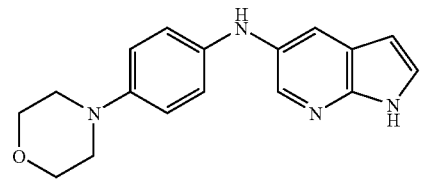 [SMILES: c1cc2cc(Nc3ccc(N4CCOCC4)cc3)cnc2[nH]1]
P-0982
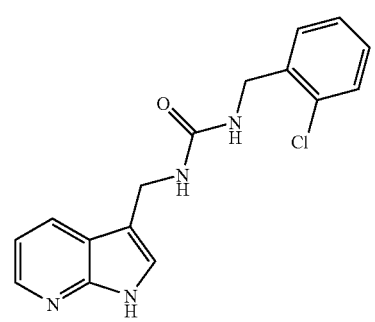 [SMILES: O=C(NCc1ccccc1Cl)NCc1c[nH]c2ncccc12]
P-0985
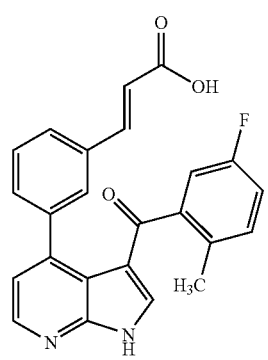 [SMILES: Cc1ccc(F)cc1C(=O)c1c[nH]c2nccc(-c3cccc(/C=C/C(=O)O)c3)c12]
P-0986
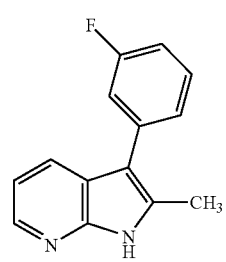 [SMILES: Cc1[nH]c2ncccc2c1-c1cccc(F)c1]
P-0987
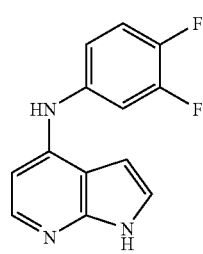 [SMILES: Fc1ccc(Nc2ccnc3[nH]ccc23)cc1F]

TABLE 1-continued
Additional compounds of the invention
P-0988 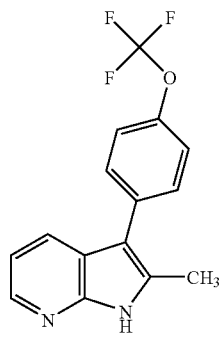 [SMILES: Cc1[nH]c2ncccc2c1-c1ccc(OC(F)(F)F)cc1]
P-0989 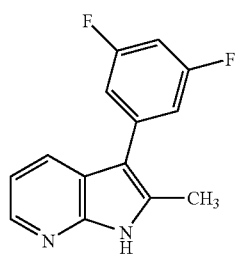 [SMILES: Cc1[nH]c2ncccc2c1-c1cc(F)cc(F)c1]
P-0990 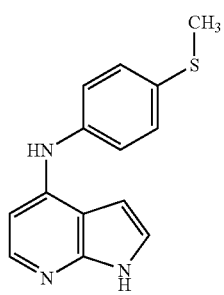 [SMILES: CSc1ccc(Nc2ccnc3[nH]ccc23)cc1]
P-0992 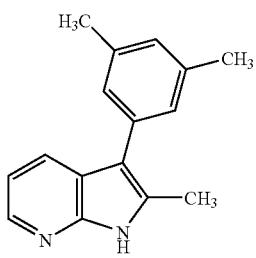 [SMILES: Cc1cc(C)cc(-c2c(C)[nH]c3ncccc23)c1]
P-0993 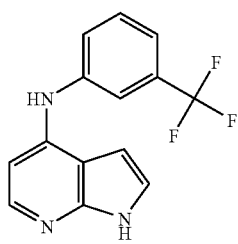 [SMILES: FC(F)(F)c1cccc(Nc2ccnc3[nH]ccc23)c1]

TABLE 1-continued
Additional compounds of the invention
P-0994 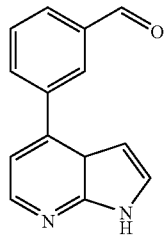
P-0995 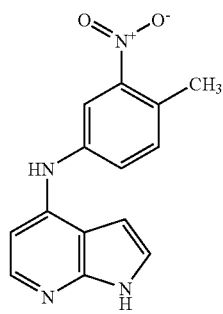 [SMILES: Cc1ccc(Nc2ccnc3[nH]ccc23)cc1[N+](=O)[O-]]
P-0996 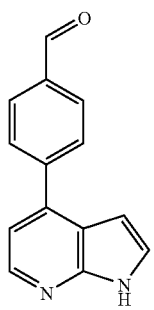 [SMILES: O=Cc1ccc(-c2ccnc3[nH]ccc23)cc1]
P-0998 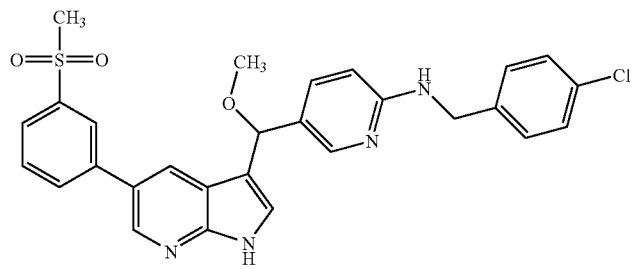 [SMILES: COC(c1ccc(NCc2ccc(Cl)cc2)nc1)c1c[nH]c2ncc(-c3cccc(S(C)(=O)=O)c3)cc12]
P-0999 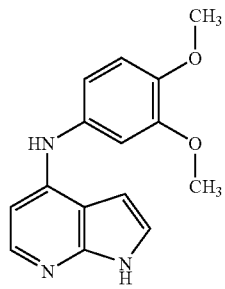 [SMILES: COc1ccc(Nc2ccnc3[nH]ccc23)cc1OC]

TABLE 1-continued
Additional compounds of the invention
P-1000
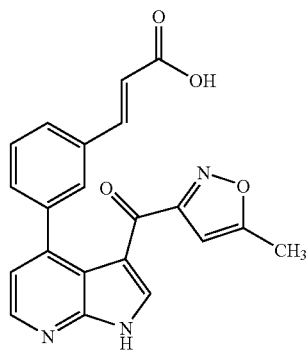 [SMILES: Cc1cc(C(=O)c2c[nH]c3nccc(-c4cccc(/C=C/C(=O)O)c4)c23)no1]
P-1001
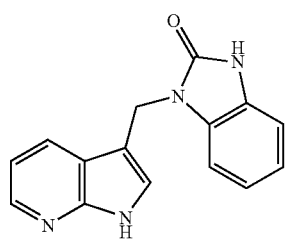 [SMILES: O=c1[nH]c2ccccc2n1Cc1c[nH]c2ncccc12]
P-1003
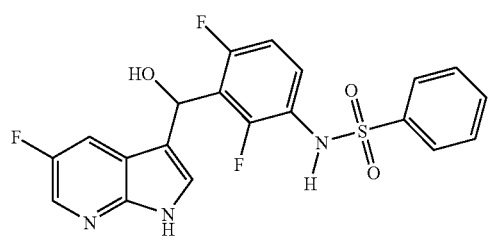 [SMILES: O=S(=O)(Nc1ccc(F)c(C(O)c2c[nH]c3ncc(F)cc23)c1F)c1ccccc1]
P-1005
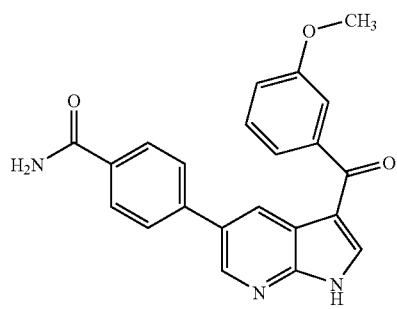 [SMILES: COc1cccc(C(=O)c2c[nH]c3ncc(-c4ccc(C(N)=O)cc4)cc23)c1]
P-1007
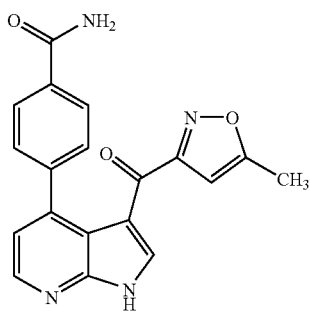 [SMILES: Cc1cc(C(=O)c2c[nH]c3nccc(-c4ccc(C(N)=O)cc4)c23)no1]

TABLE 1-continued
Additional compounds of the invention
P-1008
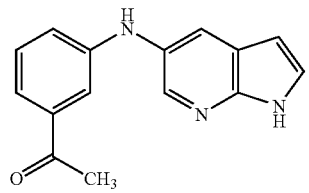 [SMILES: CC(=O)c1cccc(Nc2cnc3[nH]ccc3c2)c1]
P-1010
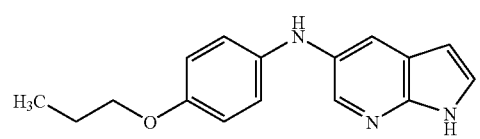 [SMILES: CCCOc1ccc(Nc2cnc3[nH]ccc3c2)cc1]
P-1011
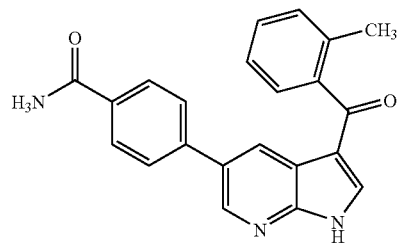 [SMILES: Cc1ccccc1C(=O)c1c[nH]c2ncc(-c3ccc(C(N)=O)cc3)cc12]
P-1012
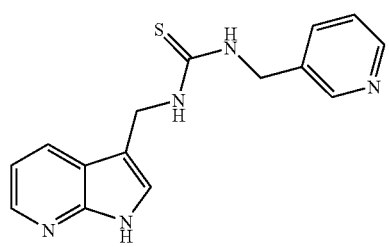
P-1014
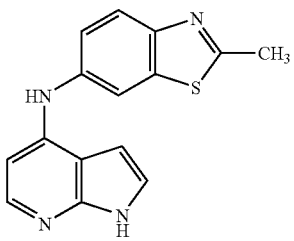 [SMILES: Cc1nc2ccc(Nc3ccnc4[nH]ccc34)cc2s1]
P-1016
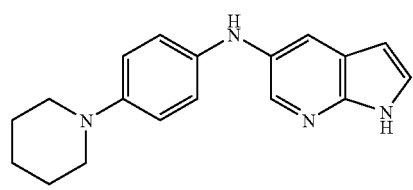 [SMILES: c1cc2cc(Nc3ccc(N4CCCCC4)cc3)cnc2[nH]1]
P-1017
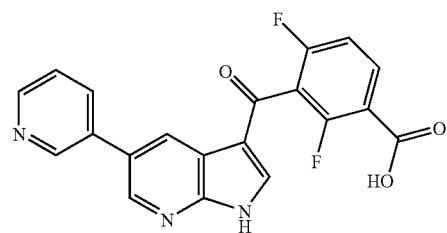 [SMILES: O=C(O)c1ccc(F)c(C(=O)c2c[nH]c3ncc(-c4cccnc4)cc23)c1F]

TABLE 1-continued
Additional compounds of the invention
P-1018 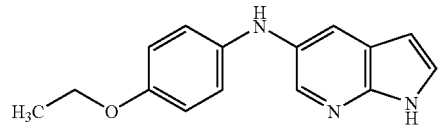 [SMILES: CCOc1ccc(Nc2cnc3[nH]ccc3c2)cc1]
P-1019 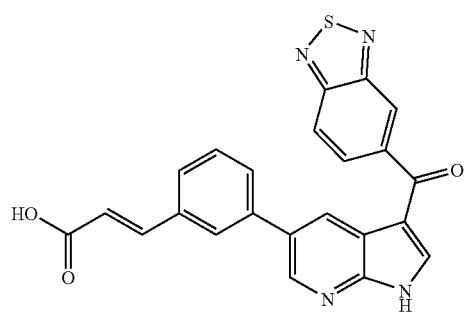 [SMILES: O=C(O)/C=C/c1cccc(-c2cnc3[nH]cc(C(=O)c4ccc5nsnc5c4)c3c2)c1]
P-1021 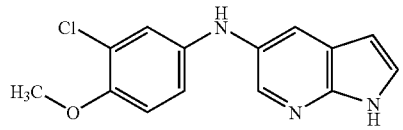 [SMILES: COc1ccc(Nc2cnc3[nH]ccc3c2)cc1Cl]
P-1022 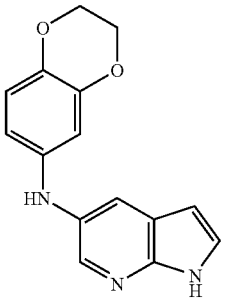 [SMILES: c1cc2cc(Nc3ccc4c(c3)OCCO4)cnc2[nH]1]
P-1023 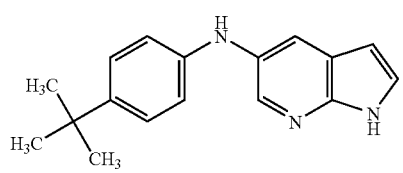 [SMILES: CC(C)(C)c1ccc(Nc2cnc3[nH]ccc3c2)cc1]
P-1024 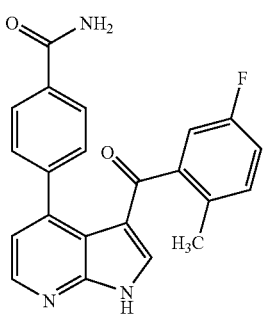 [SMILES: Cc1ccc(F)cc1C(=O)c1c[nH]c2nccc(-c3ccc(C(N)=O)cc3)c12]

TABLE 1-continued
Additional compounds of the invention
P-1025 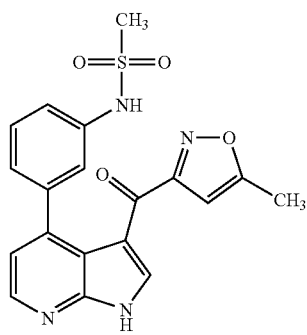 [SMILES: Cc1cc(C(=O)c2c[nH]c3nccc(-c4cccc(NS(C)(=O)=O)c4)c23)no1]
P-1026 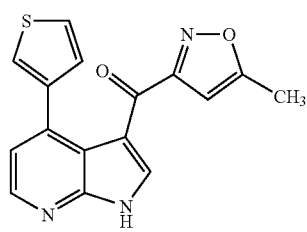 [SMILES: Cc1cc(C(=O)c2c[nH]c3nccc(-c4ccsc4)c23)no1]
P-1027 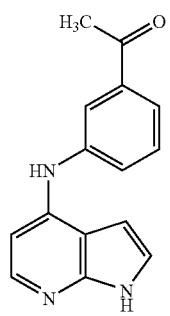 [SMILES: CC(=O)c1cccc(Nc2ccnc3[nH]ccc23)c1]
P-1029 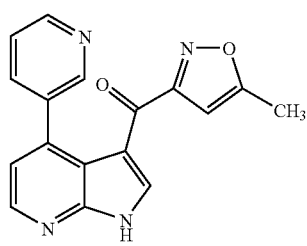 [SMILES: Cc1cc(C(=O)c2c[nH]c3nccc(-c4cccnc4)c23)no1]
P-1030 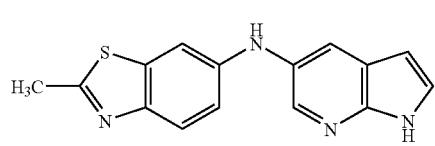 [SMILES: Cc1nc2ccc(Nc3cnc4[nH]ccc4c3)cc2s1]
P-1031 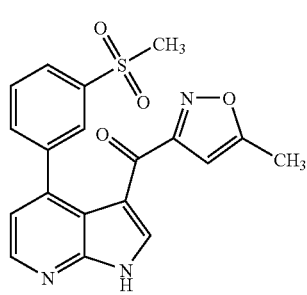 [SMILES: Cc1cc(C(=O)c2c[nH]c3nccc(-c4cccc(S(C)(=O)=O)c4)c23)no1]

TABLE 1-continued
Additional compounds of the invention
P-1032 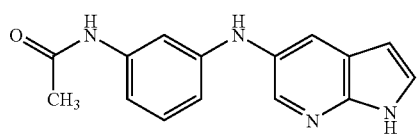 [SMILES: CC(=O)Nc1cccc(Nc2cnc3[nH]ccc3c2)c1]
P-1033 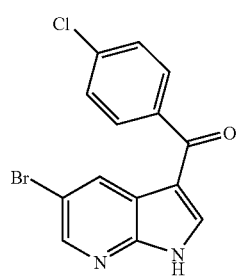 [SMILES: O=C(c1ccc(Cl)cc1)c1c[nH]c2ncc(Br)cc12]
P-1034 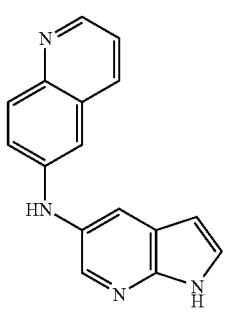 [SMILES: c1cnc2ccc(Nc3cnc4[nH]ccc4c3)cc2c1]
P-1035 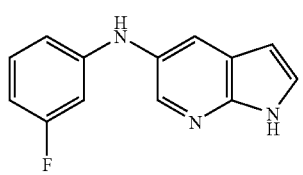 [SMILES: Fc1cccc(Nc2cnc3[nH]ccc3c2)c1]
P-1036 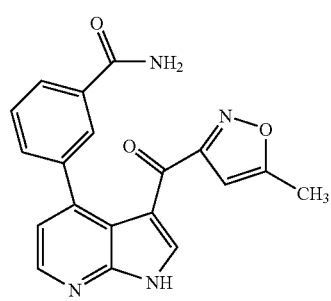 [SMILES: Cc1cc(C(=O)c2c[nH]c3nccc(-c4cccc(C(N)=O)c4)c23)no1]
P-1037 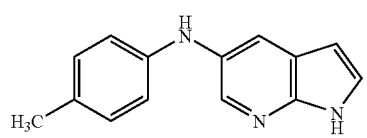 [SMILES: Cc1ccc(Nc2cnc3[nH]ccc3c2)cc1]
P-1038 

TABLE 1-continued
Additional compounds of the invention
P-1039 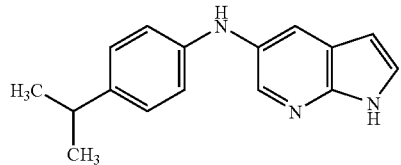 [SMILES: CC(C)c1ccc(Nc2cnc3[nH]ccc3c2)cc1]
P-1040 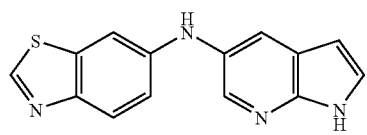 [SMILES: c1cc2cc(Nc3ccc4ncsc4c3)cnc2[nH]1]
P-1041 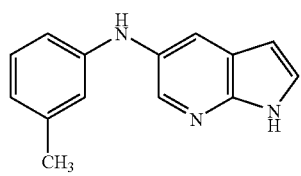 [SMILES: Cc1cccc(Nc2cnc3[nH]ccc3c2)c1]
P-1042 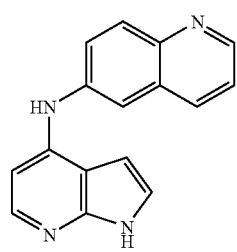 [SMILES: c1cnc2ccc(Nc3ccnc4[nH]ccc34)cc2c1]
P-1043 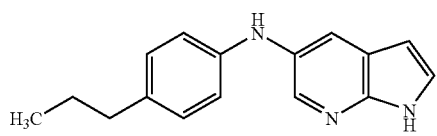 [SMILES: CCCc1ccc(Nc2cnc3[nH]ccc3c2)cc1]
P-1044 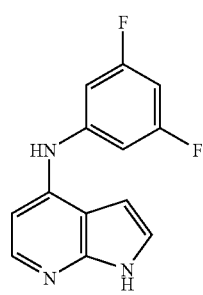 [SMILES: Fc1cc(F)cc(Nc2ccnc3[nH]ccc23)c1]
P-1045 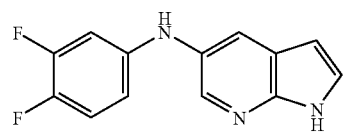 [SMILES: Fc1ccc(Nc2cnc3[nH]ccc3c2)cc1F]
P-1046 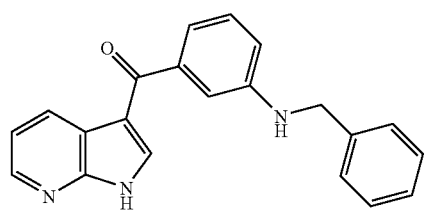 [SMILES: O=C(c1cccc(NCc2ccccc2)c1)c1c[nH]c2ncccc12]

TABLE 1-continued
Additional compounds of the invention
P-1047 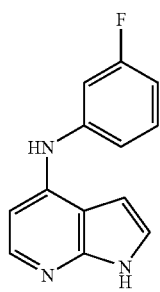 [SMILES: Fc1cccc(Nc2ccnc3[nH]ccc23)c1]
P-1048 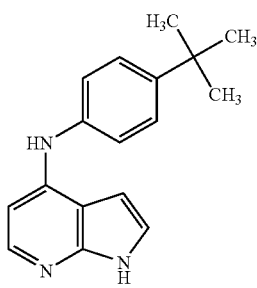 [SMILES: CC(C)(C)c1ccc(Nc2ccnc3[nH]ccc23)cc1]
P-1049 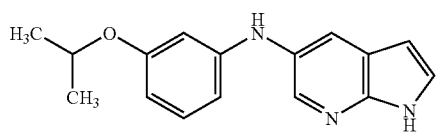 [SMILES: CC(C)Oc1cccc(Nc2cnc3[nH]ccc3c2)c1]
P-1050 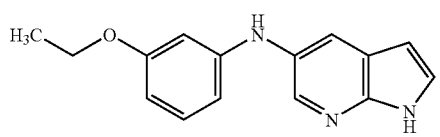 [SMILES: CCOc1cccc(Nc2cnc3[nH]ccc3c2)c1]
P-1051 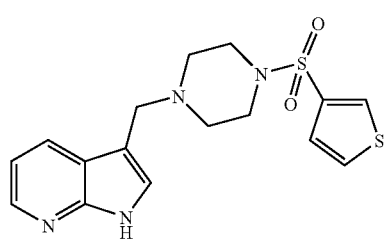 [SMILES: O=S(=O)(c1ccsc1)N1CCN(Cc2c[nH]c3ncccc23)CC1]
P-1052 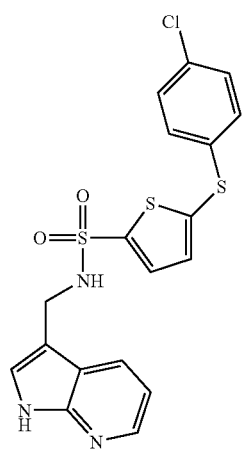 [SMILES: O=S(=O)(NCc1c[nH]c2ncccc12)c1ccc(Sc2ccc(Cl)cc2)s1]

TABLE 1-continued
| Additional compounds of the invention |
|---|
P-1053
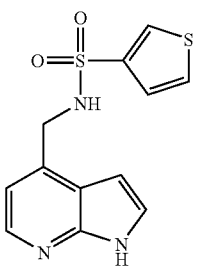 [SMILES: O=S(=O)(NCc1ccnc2[nH]ccc12)c1ccsc1]
P-1054
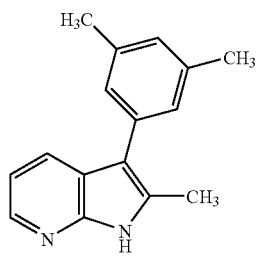 [SMILES: Cc1cc(C)cc(-c2c(C)[nH]c3ncccc23)c1]
P-1055
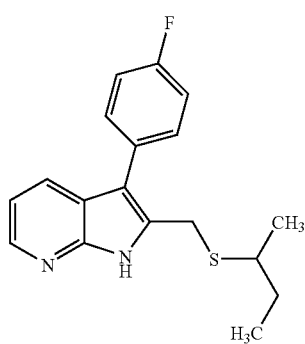 [SMILES: CCC(C)SCc1[nH]c2ncccc2c1-c1ccc(F)cc1]
P-1057
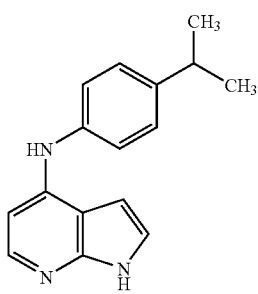 [SMILES: CC(C)c1ccc(Nc2ccnc3[nH]ccc23)cc1]
P-1058
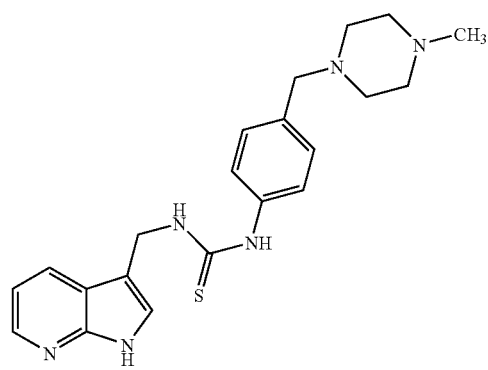 [SMILES: CN1CCN(Cc2ccc(NC(=S)NCc3c[nH]c4ncccc34)cc2)CC1]

TABLE 1-continued
| Additional compounds of the invention |
P-1059 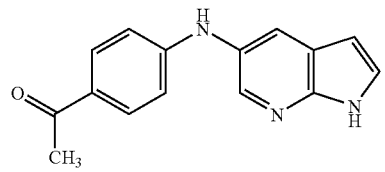 [SMILES: CC(=O)c1ccc(Nc2cnc3[nH]ccc3c2)cc1]
P-1060 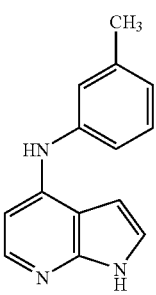 [SMILES: Cc1cccc(Nc2ccnc3[nH]ccc23)c1]
P-1061 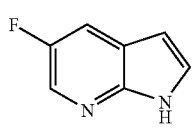
P-1062 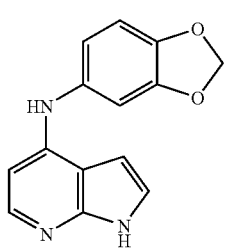 [SMILES: c1cc(Nc2ccc3c(c2)OCO3)c2cc[nH]c2n1]
P-1063 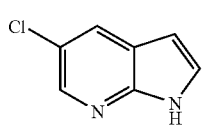
P-1064 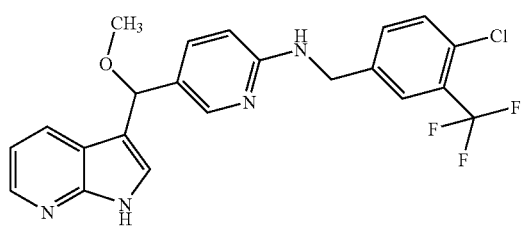 [SMILES: COC(c1ccc(NCc2ccc(Cl)c(C(F)(F)F)c2)nc1)c1c[nH]c2ncccc12]
P-1065 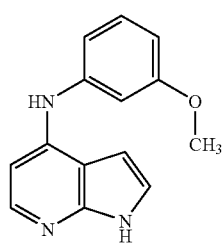 [SMILES: COc1cccc(Nc2ccnc3[nH]ccc23)c1]

TABLE 1-continued
Additional compounds of the invention
P-1066
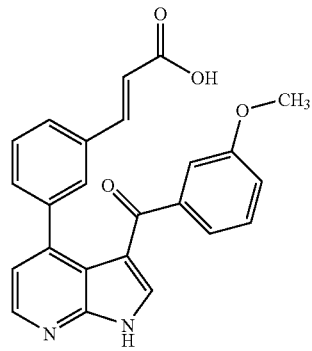 [SMILES: COc1cccc(C(=O)c2c[nH]c3nccc(-c4cccc(/C=C/C(=O)O)c4)c23)c1]
P-1067
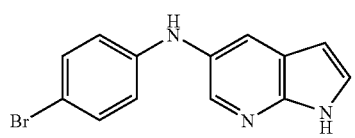
P-1068
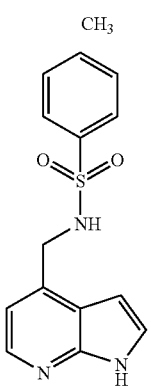
P-1069
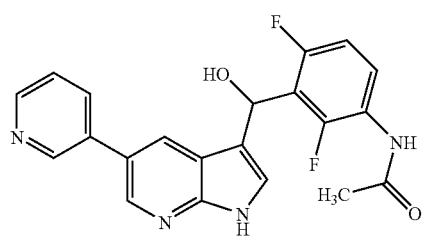 [SMILES: CC(=O)Nc1ccc(F)c(C(O)c2c[nH]c3ncc(-c4cccnc4)cc23)c1F]
P-1070
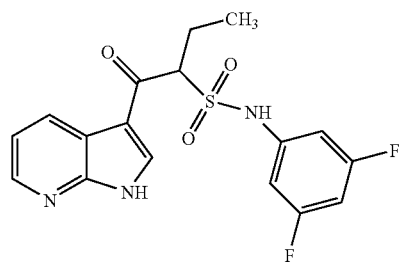 [SMILES: CCC(C(=O)c1c[nH]c2ncccc12)S(=O)(=O)Nc1cc(F)cc(F)c1]

TABLE 1-continued
Additional compounds of the invention
P-1071 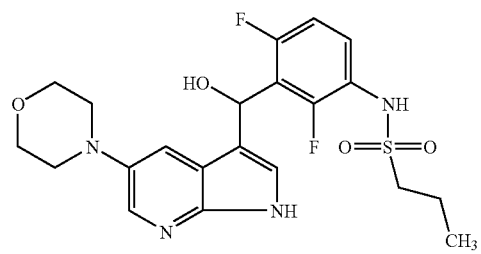 [SMILES: CCCS(=O)(=O)Nc1ccc(F)c(C(O)c2c[nH]c3ncc(N4CCOCC4)cc23)c1F]
P-1072 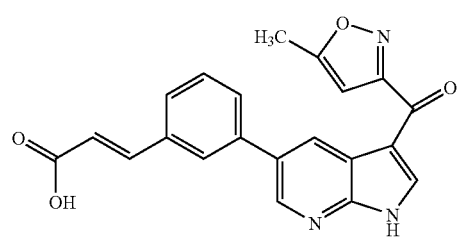 [SMILES: Cc1cc(C(=O)c2c[nH]c3ncc(-c4cccc(/C=C/C(=O)O)c4)cc23)no1]
P-1073 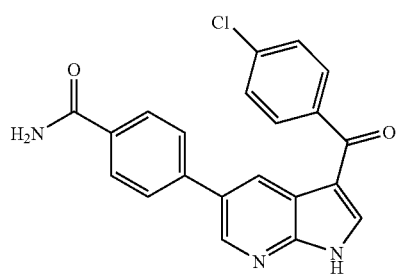 [SMILES: NC(=O)c1ccc(-c2cnc3[nH]cc(C(=O)c4ccc(Cl)cc4)c3c2)cc1]
P-1074 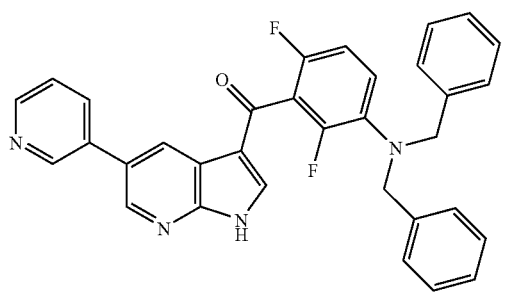 [SMILES: O=C(c1c(F)ccc(N(Cc2ccccc2)Cc2ccccc2)c1F)c1c[nH]c2ncc(-c3cccnc3)cc12]
P-1075 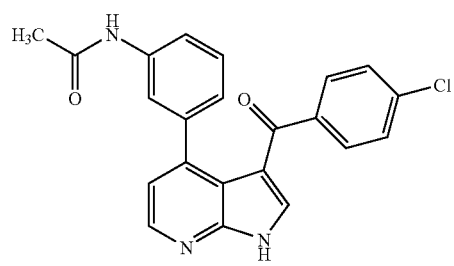 [SMILES: CC(=O)Nc1cccc(-c2ccnc3[nH]cc(C(=O)c4ccc(Cl)cc4)c23)c1]
P-1076 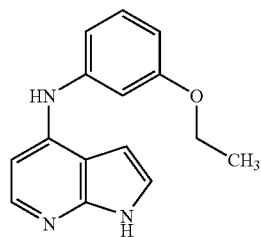 [SMILES: CCOc1cccc(Nc2ccnc3[nH]ccc23)c1]

TABLE 1-continued
Additional compounds of the invention
P-1077
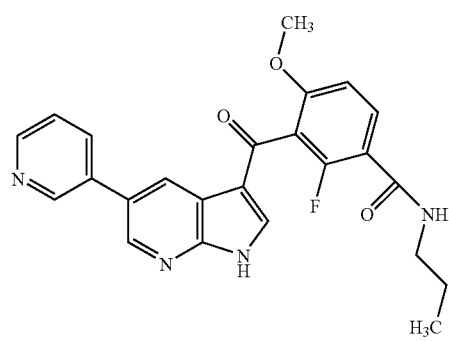 [SMILES: CCCNC(=O)c1ccc(OC)c(C(=O)c2c[nH]c3ncc(-c4cccnc4)cc23)c1F]
P-1078
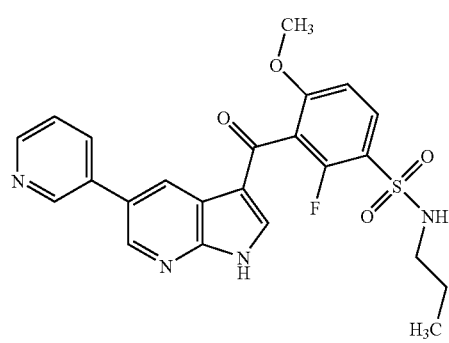 [SMILES: CCCNS(=O)(=O)c1ccc(OC)c(C(=O)c2c[nH]c3ncc(-c4cccnc4)cc23)c1F]
P-1079
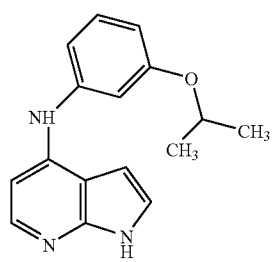 [SMILES: CC(C)Oc1cccc(Nc2ccnc3[nH]ccc23)c1]
P-1080
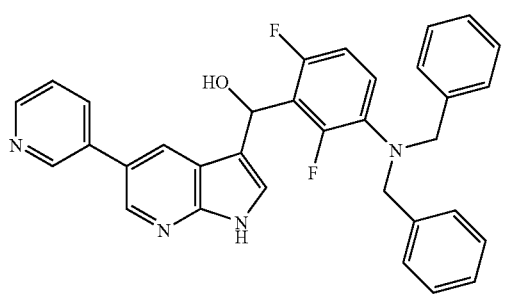 [SMILES: OC(c1c(F)ccc(N(Cc2ccccc2)Cc2ccccc2)c1F)c1c[nH]c2ncc(-c3cccnc3)cc12]
P-1081
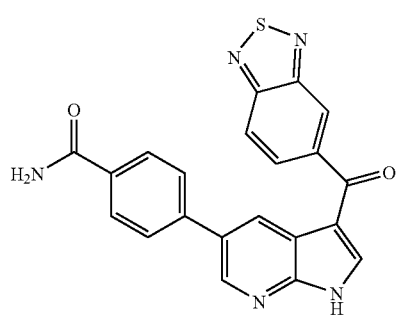 [SMILES: NC(=O)c1ccc(-c2cnc3[nH]cc(C(=O)c4ccc5nsnc5c4)c3c2)cc1]

TABLE 1-continued
Additional compounds of the invention
P-1082 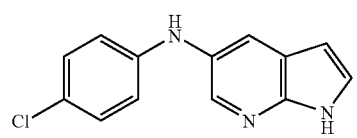 [SMILES: Clc1ccc(Nc2cnc3[nH]ccc3c2)cc1]
P-1083 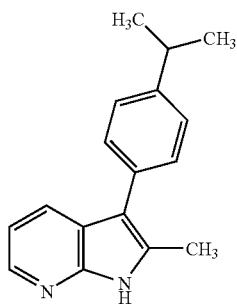 [SMILES: Cc1[nH]c2ncccc2c1-c1ccc(C(C)C)cc1]
P-1084 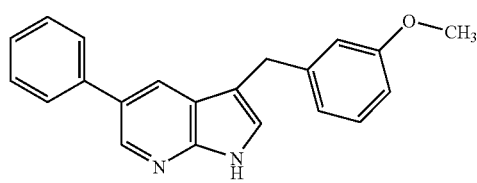 [SMILES: COc1cccc(Cc2c[nH]c3ncc(-c4ccccc4)cc23)c1]
P-1085 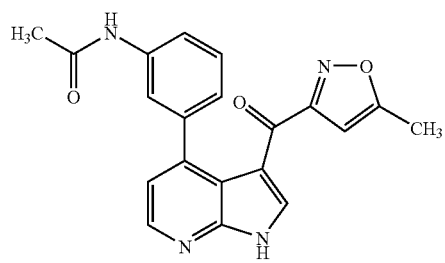 [SMILES: CC(=O)Nc1cccc(-c2ccnc3[nH]cc(C(=O)c4cc(C)on4)c23)c1]
P-1086 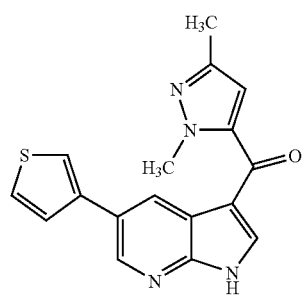 [SMILES: Cc1cc(C(=O)c2c[nH]c3ncc(-c4ccsc4)cc23)n(C)n1]
P-1087 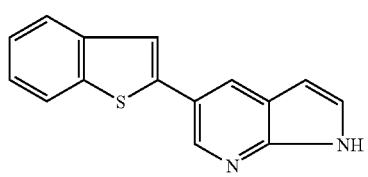 [SMILES: c1ccc2sc(-c3cnc4[nH]ccc4c3)cc2c1]
P-1088 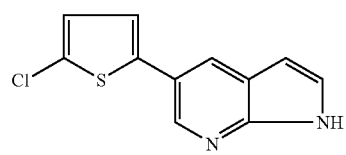 [SMILES: Clc1ccc(-c2cnc3[nH]ccc3c2)s1]

TABLE 1-continued
Additional compounds of the invention
P-1089
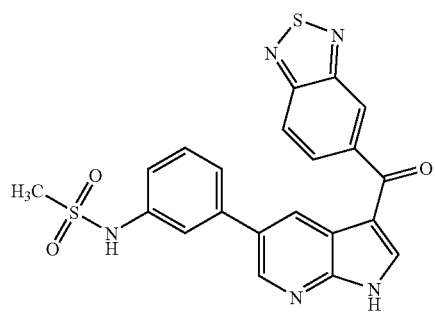 [SMILES: CS(=O)(=O)Nc1cccc(-c2cnc3[nH]cc(C(=O)c4ccc5nsnc5c4)c3c2)c1]
P-1091
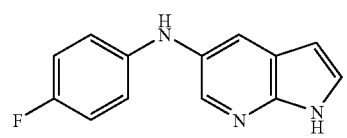 [SMILES: Fc1ccc(Nc2cnc3[nH]ccc3c2)cc1]
P-1092
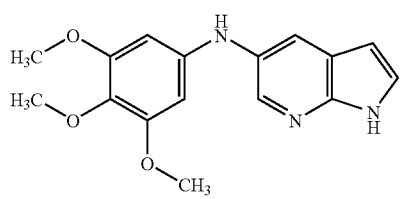 [SMILES: COc1cc(Nc2cnc3[nH]ccc3c2)cc(OC)c1OC]
P-1093
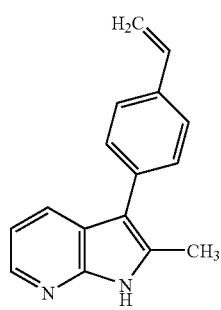 [SMILES: C=Cc1ccc(-c2c(C)[nH]c3ncccc23)cc1]
P-1094
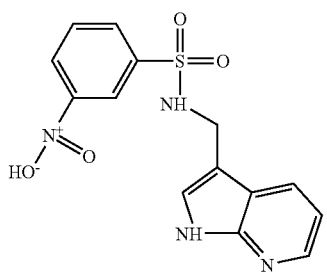 [SMILES: O=[N+]([O-])c1cccc(S(=O)(=O)NCc2c[nH]c3ncccc23)c1]
P-1095
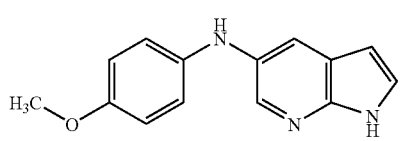 [SMILES: COc1ccc(Nc2cnc3[nH]ccc3c2)cc1]
P-1096
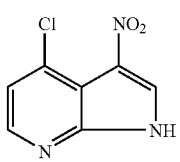 [SMILES: O=[N+]([O-])c1c[nH]c2nccc(Cl)c12]

TABLE 1-continued
Additional compounds of the invention
P-1097 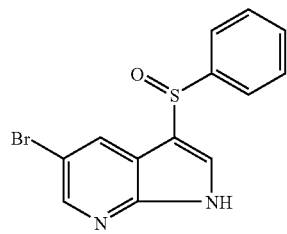 [SMILES: O=S(c1ccccc1)c1c[nH]c2ncc(Br)cc12]
P-1098 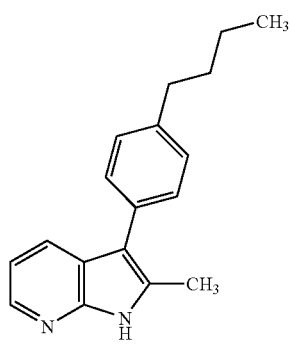 [SMILES: CCCCc1ccc(-c2c(C)[nH]c3ncccc23)cc1]
P-1099 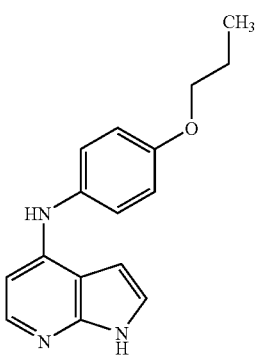 [SMILES: CCCOc1ccc(Nc2ccnc3[nH]ccc23)cc1]
P-1100 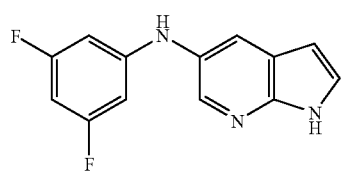 [SMILES: Fc1cc(F)cc(Nc2cnc3[nH]ccc3c2)c1]
P-1101 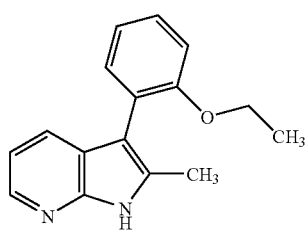 [SMILES: CCOc1ccccc1-c1c(C)[nH]c2ncccc12]

TABLE 1-continued
Additional compounds of the invention
P-1102
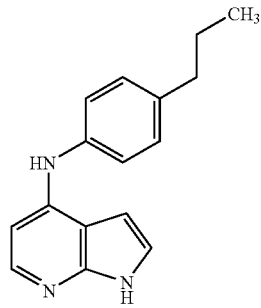 [SMILES: CCCc1ccc(Nc2ccnc3[nH]ccc23)cc1]
P-1103
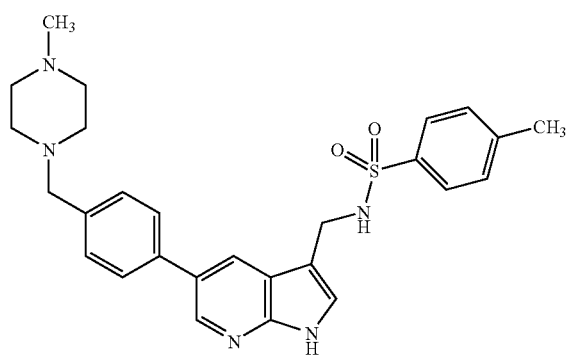 [SMILES: Cc1ccc(S(=O)(=O)NCc2c[nH]c3ncc(-c4ccc(CN5CCN(C)CC5)cc4)cc23)cc1]
P-1104
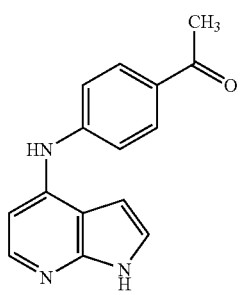 [SMILES: CC(=O)c1ccc(Nc2ccnc3[nH]ccc23)cc1]
P-1105
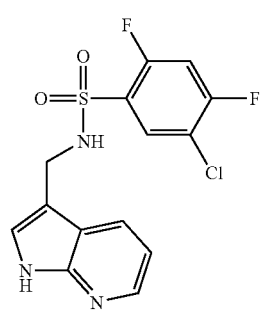
P-1106
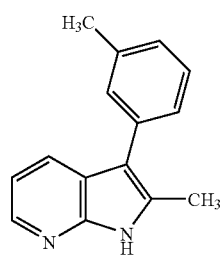 [SMILES: Cc1cccc(-c2c(C)[nH]c3ncccc23)c1]

TABLE 1-continued
| Additional compounds of the invention |
|---|
| P-1107 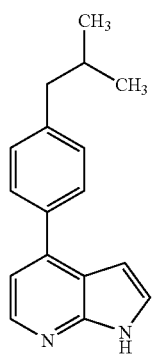 [SMILES: CC(C)Cc1ccc(-c2ccnc3[nH]ccc23)cc1] |
| P-1108 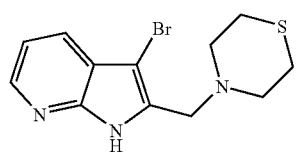 [SMILES: Brc1c(CN2CCSCC2)[nH]c2ncccc12] |
| P-1109 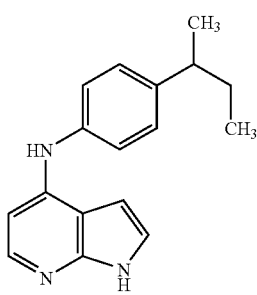 [SMILES: CCC(C)c1ccc(Nc2ccnc3[nH]ccc23)cc1] |
| P-1110 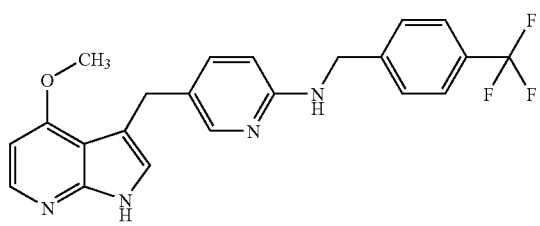 [SMILES: COc1ccnc2[nH]cc(Cc3ccc(NCc4ccc(C(F)(F)F)cc4)nc3)c12] |
| P-1111 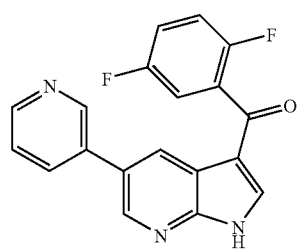 [SMILES: O=C(c1cc(F)ccc1F)c1c[nH]c2ncc(-c3cccnc3)cc12] |
| P-1112 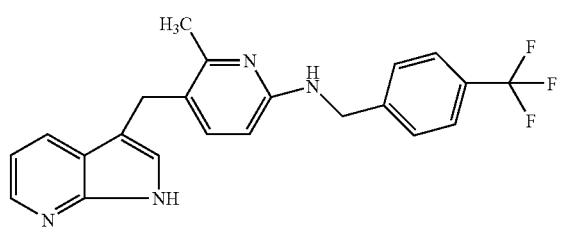 [SMILES: Cc1nc(NCc2ccc(C(F)(F)F)cc2)ccc1Cc1c[nH]c2ncccc12] |

TABLE 1-continued
Additional compounds of the invention
P-1113 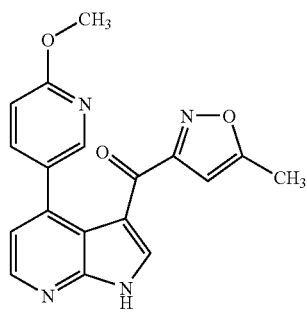 [SMILES: COc1ccc(-c2ccnc3[nH]cc(C(=O)c4cc(C)on4)c23)cn1]
P-1114 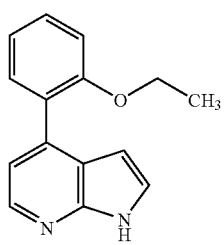 [SMILES: CCOc1ccccc1-c1ccnc2[nH]ccc12]
P-1115 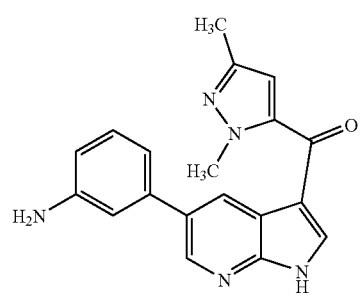 [SMILES: Cc1cc(C(=O)c2c[nH]c3ncc(-c4cccc(N)c4)cc23)n(C)n1]
P-1117 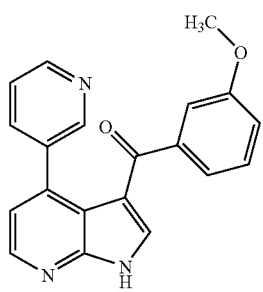 [SMILES: COc1cccc(C(=O)c2c[nH]c3nccc(-c4cccnc4)c23)c1]
P-1118 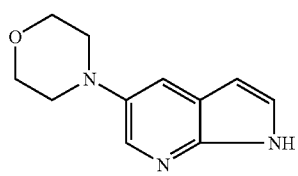 [SMILES: c1cc2cc(N3CCOCC3)cnc2[nH]1]
P-1119 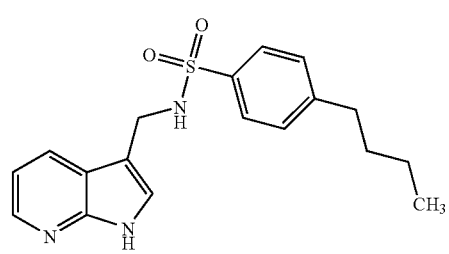 [SMILES: CCCCc1ccc(S(=O)(=O)NCc2c[nH]c3ncccc23)cc1]

TABLE 1-continued
Additional compounds of the invention
P-1120
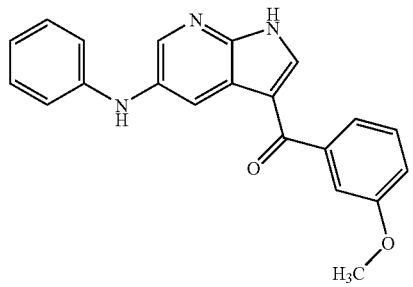 [SMILES: COc1cccc(C(=O)c2c[nH]c3ncc(Nc4ccccc4)cc23)c1]
P-1121
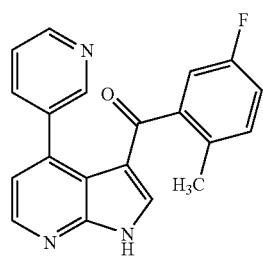 [SMILES: Cc1ccc(F)cc1C(=O)c1c[nH]c2nccc(-c3cccnc3)c12]
P-1122
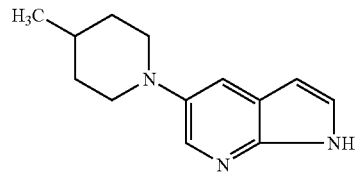 [SMILES: CC1CCN(c2cnc3[nH]ccc3c2)CC1]
P-1123
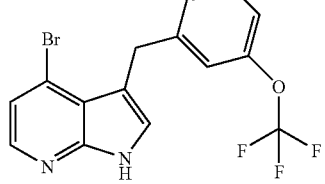
P-1124
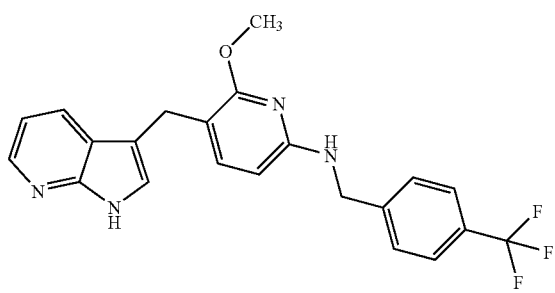 [SMILES: COc1nc(NCc2ccc(C(F)(F)F)cc2)ccc1Cc1c[nH]c2ncccc12]
P-1125
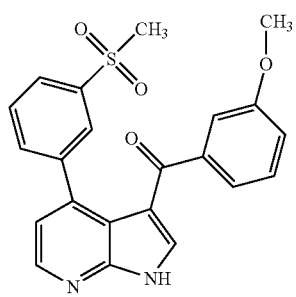 [SMILES: COc1cccc(C(=O)c2c[nH]c3nccc(-c4cccc(S(C)(=O)=O)c4)c23)c1]

TABLE 1-continued
Additional compounds of the invention
P-1126 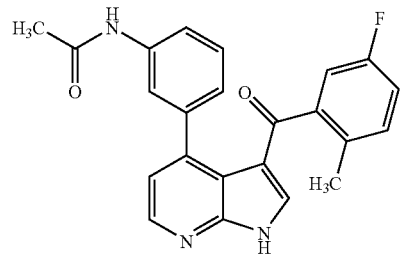 [SMILES: CC(=O)Nc1cccc(-c2ccnc3[nH]cc(C(=O)c4cc(F)ccc4C)c23)c1]
P-1127 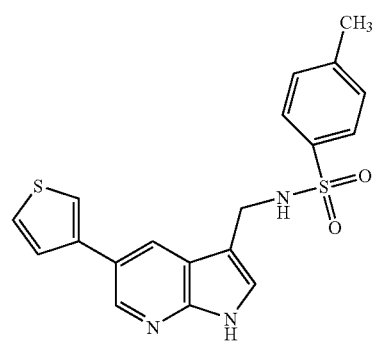 [SMILES: Cc1ccc(S(=O)(=O)NCc2c[nH]c3ncc(-c4ccsc4)cc23)cc1]
P-1128 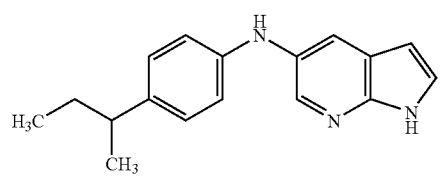 [SMILES: CCC(C)c1ccc(Nc2cnc3[nH]ccc3c2)cc1]
P-1129 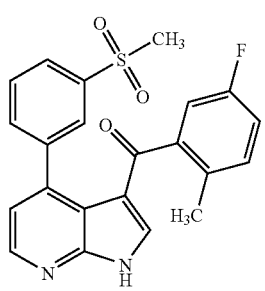 [SMILES: Cc1ccc(F)cc1C(=O)c1c[nH]c2nccc(-c3cccc(S(C)(=O)=O)c3)c12]
P-1130 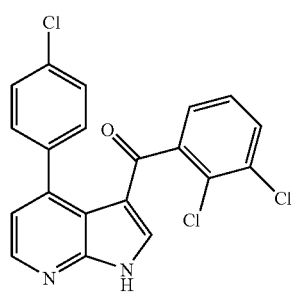 [SMILES: O=C(c1cccc(Cl)c1Cl)c1c[nH]c2nccc(-c3ccc(Cl)cc3)c12]
P-1132 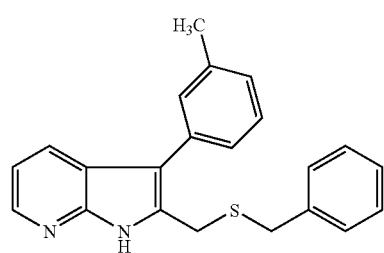 [SMILES: Cc1cccc(-c2c(CSCc3ccccc3)[nH]c3ncccc23)c1]

TABLE 1-continued
Additional compounds of the invention
P-1133 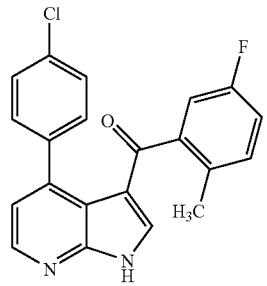 [SMILES: Cc1ccc(F)cc1C(=O)c1c[nH]c2nccc(-c3ccc(Cl)cc3)c12]
P-1134 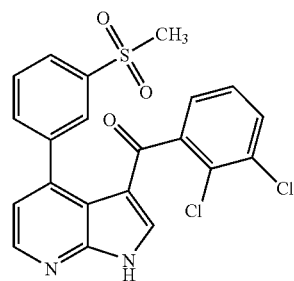 [SMILES: CS(=O)(=O)c1cccc(-c2ccnc3[nH]cc(C(=O)c4cccc(Cl)c4Cl)c23)c1]
P-1135 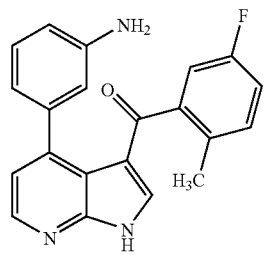 [SMILES: Cc1ccc(F)cc1C(=O)c1c[nH]c2nccc(-c3cccc(N)c3)c12]
P-1136 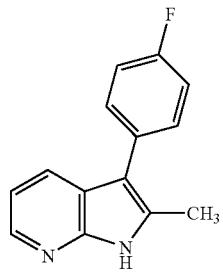 [SMILES: Cc1[nH]c2ncccc2c1-c1ccc(F)cc1]
P-1137 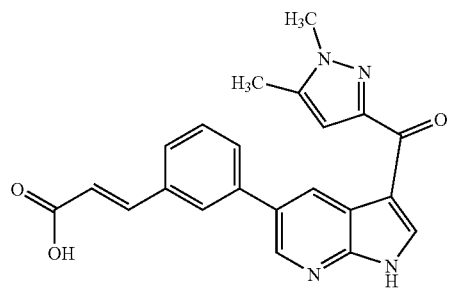 [SMILES: Cc1cc(C(=O)c2c[nH]c3ncc(-c4cccc(/C=C/C(=O)O)c4)cc23)nn1C]

TABLE 1-continued
Additional compounds of the invention
P-1138
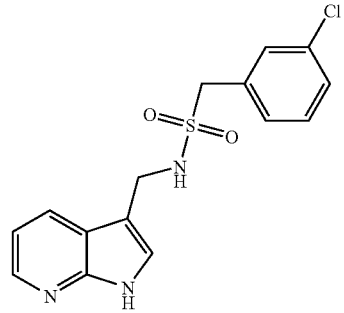 [SMILES: O=S(=O)(Cc1cccc(Cl)c1)NCc1c[nH]c2ncccc12]
P-1139
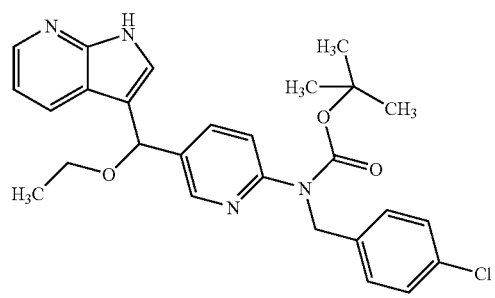 [SMILES: CCOC(c1ccc(N(Cc2ccc(Cl)cc2)C(=O)OC(C)(C)C)nc1)c1c[nH]c2ncccc12]
P-1140
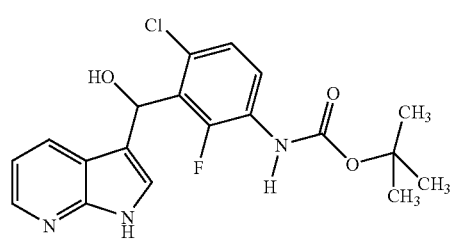 [SMILES: CC(C)(C)OC(=O)Nc1ccc(Cl)c(C(O)c2c[nH]c3ncccc23)c1F]
P-1141
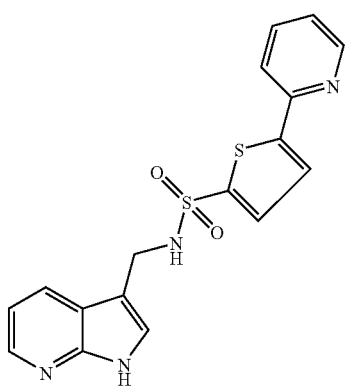 [SMILES: O=S(=O)(NCc1c[nH]c2ncccc12)c1ccc(-c2ccccn2)s1]
P-1142
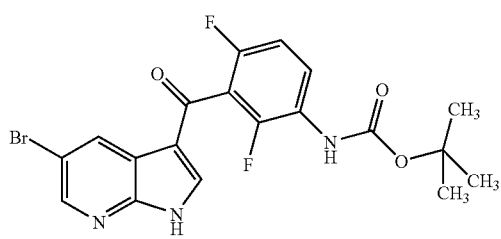 [SMILES: CC(C)(C)OC(=O)Nc1ccc(F)c(C(=O)c2c[nH]c3ncc(Br)cc23)c1F]

TABLE 1-continued
Additional compounds of the invention
P-1143
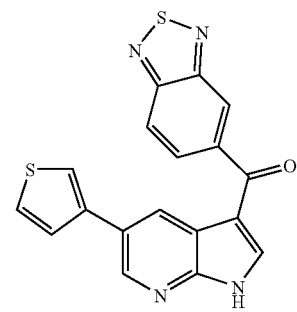 [SMILES: O=C(c1ccc2nsnc2c1)c1c[nH]c2ncc(-c3ccsc3)cc12]
P-1144
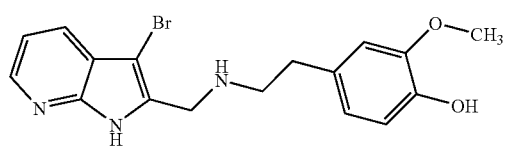 [SMILES: COc1cc(CCNCc2[nH]c3ncccc3c2Br)ccc1O]
P-1145
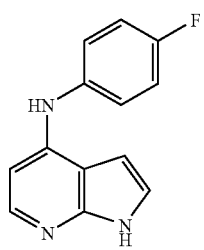 [SMILES: Fc1ccc(Nc2ccnc3[nH]ccc23)cc1]
P-1146
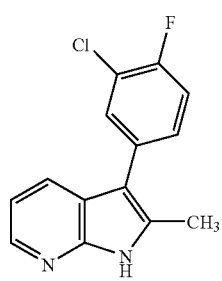 [SMILES: Cc1[nH]c2ncccc2c1-c1ccc(F)c(Cl)c1]
P-1147
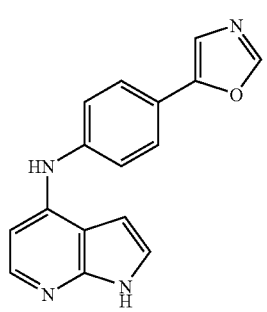 [SMILES: c1cc(Nc2ccc(-c3cnco3)cc2)c2cc[nH]c2n1]
P-1148
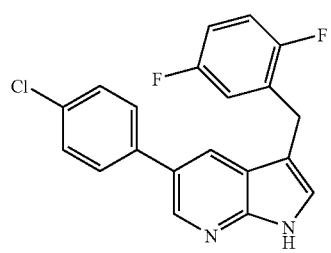 [SMILES: Fc1ccc(F)c(Cc2c[nH]c3ncc(-c4ccc(Cl)cc4)cc23)c1]

TABLE 1-continued
| Additional compounds of the invention |
P-1149 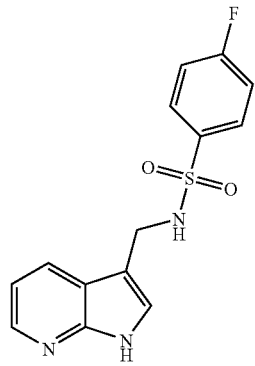 [SMILES: O=S(=O)(NCc1c[nH]c2ncccc12)c1ccc(F)cc1]
P-1150 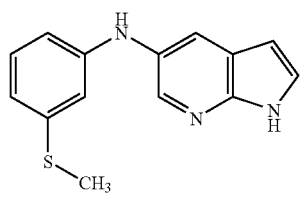 [SMILES: CSc1cccc(Nc2cnc3[nH]ccc3c2)c1]
P-1151 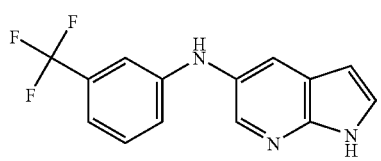 [SMILES: FC(F)(F)c1cccc(Nc2cnc3[nH]ccc3c2)c1]
P-1152 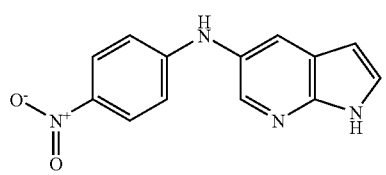 [SMILES: O=[N+]([O-])c1ccc(Nc2cnc3[nH]ccc3c2)cc1]
P-1153 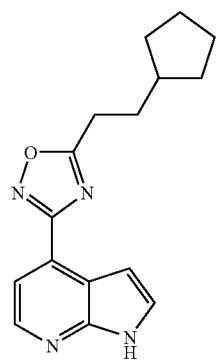 [SMILES: c1cc(-c2noc(CCC3CCCC3)n2)c2cc[nH]c2n1]
P-1154 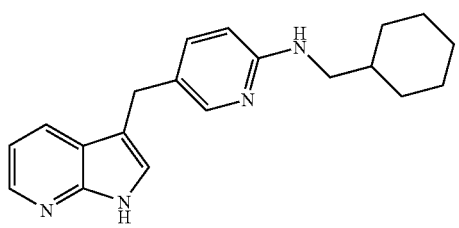 [SMILES: c1cnc2[nH]cc(Cc3ccc(NCC4CCCCC4)nc3)c2c1]

TABLE 1-continued
Additional compounds of the invention
P-1155 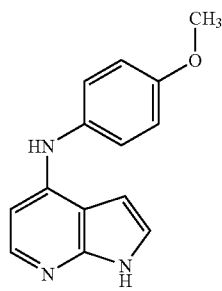
P-1156 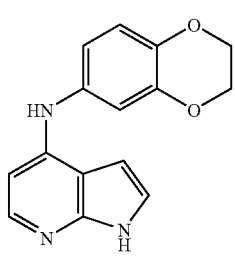 [SMILES: c1cc(Nc2ccc3c(c2)OCCO3)c2cc[nH]c2n1]
P-1157 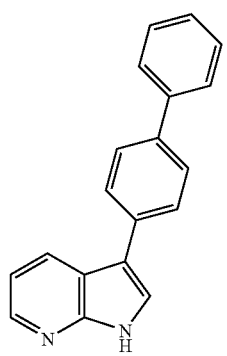 [SMILES: c1ccc(-c2ccc(-c3c[nH]c4ncccc34)cc2)cc1]
P-1158 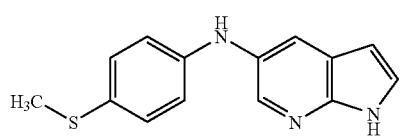
P-1159 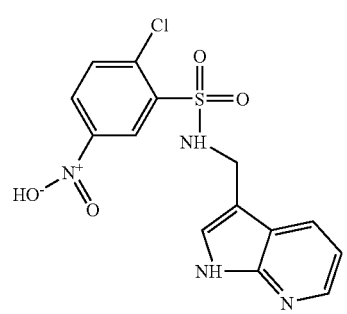 [SMILES: O=[N+]([O-])c1ccc(Cl)c(S(=O)(=O)NCc2c[nH]c3ncccc23)c1]
P-1160 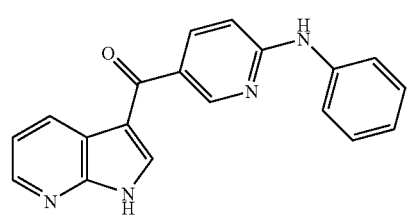 [SMILES: O=C(c1ccc(Nc2ccccc2)nc1)c1c[nH]c2ncccc12]

TABLE 1-continued
Additional compounds of the invention
P-1161
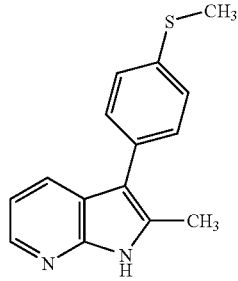 [SMILES: CSc1ccc(-c2c(C)[nH]c3ncccc23)cc1]
P-1162
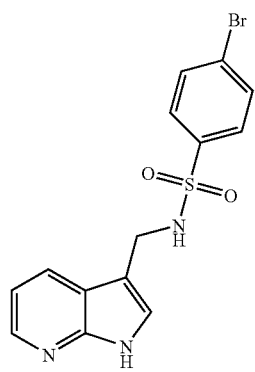 [SMILES: O=S(=O)(NCc1c[nH]c2ncccc12)c1ccc(Br)cc1]
P-1163
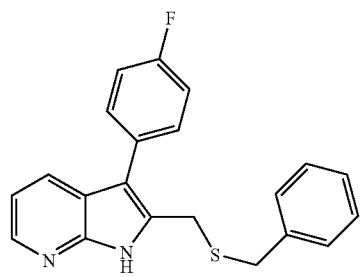 [SMILES: Fc1ccc(-c2c(CSCc3ccccc3)[nH]c3ncccc23)cc1]
P-1164
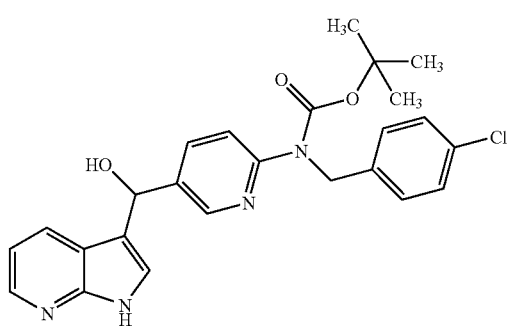 [SMILES: CC(C)(C)OC(=O)N(Cc1ccc(Cl)cc1)c1ccc(C(O)c2c[nH]c3ncccc23)cn1]
P-1165
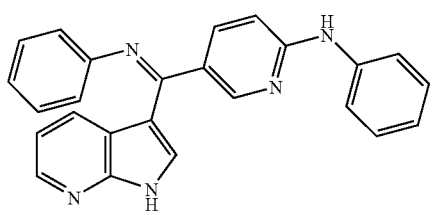 [SMILES: c1ccc(/N=C(/c2ccc(Nc3ccccc3)nc2)c2c[nH]c3ncccc23)cc1]

TABLE 1-continued
Additional compounds of the invention
P-1166
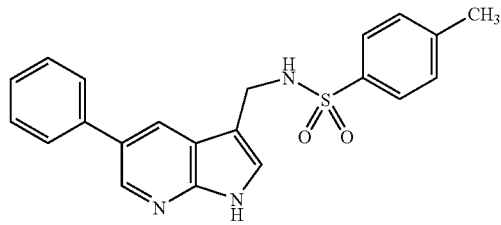 [SMILES: Cc1ccc(S(=O)(=O)NCc2c[nH]c3ncc(-c4ccccc4)cc23)cc1]
P-1167
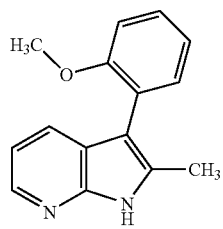 [SMILES: COc1ccccc1-c1c(C)[nH]c2ncccc12]
P-1168
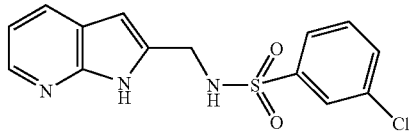 [SMILES: O=S(=O)(NCc1cc2cccnc2[nH]1)c1cccc(Cl)c1]
P-1169
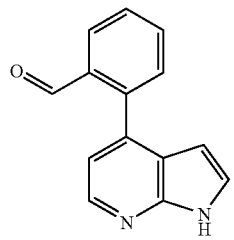 [SMILES: O=Cc1ccccc1-c1ccnc2[nH]ccc12]
P-1170
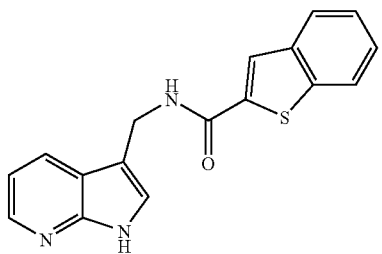 [SMILES: O=C(NCc1c[nH]c2ncccc12)c1cc2ccccc2s1]
P-1171
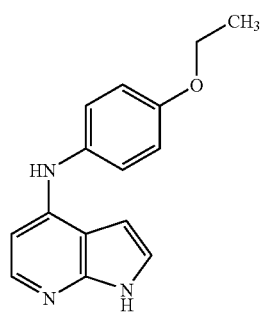 [SMILES: CCOc1ccc(Nc2ccnc3[nH]ccc23)cc1]

TABLE 1-continued
Additional compounds of the invention
P-1172 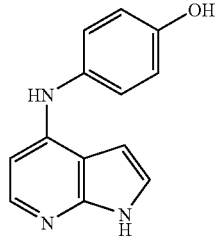 [SMILES: Oc1ccc(Nc2ccnc3[nH]ccc23)cc1]
P-1173 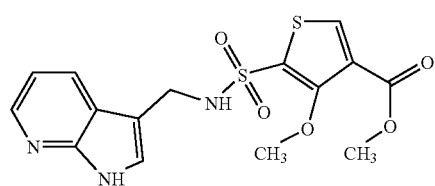 [SMILES: COC(=O)c1csc(S(=O)(=O)NCc2c[nH]c3ncccc23)c1OC]
P-1174 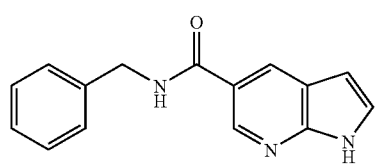 [SMILES: O=C(NCc1ccccc1)c1cnc2[nH]ccc2c1]
P-1175 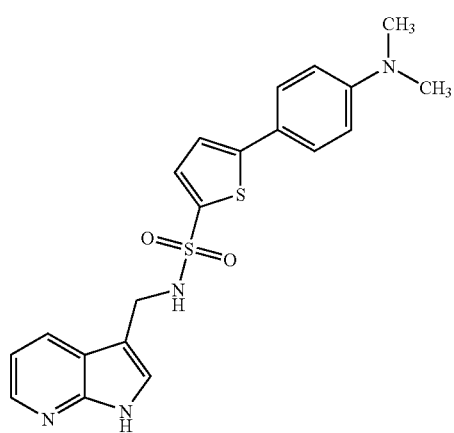 [SMILES: CN(C)c1ccc(-c2ccc(S(=O)(=O)NCc3c[nH]c4ncccc34)s2)cc1]
P-1176 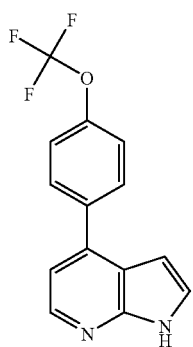

TABLE 1-continued
Additional compounds of the invention
P-1177 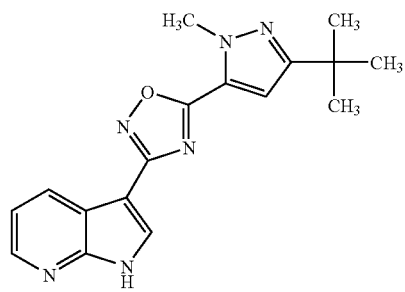 [SMILES: Cn1nc(C(C)(C)C)cc1-c1nc(-c2c[nH]c3ncccc23)no1]
P-1178 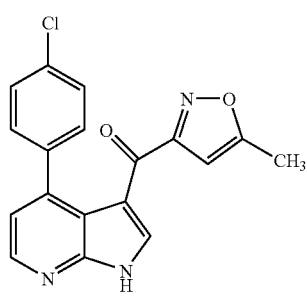 [SMILES: Cc1cc(C(=O)c2c[nH]c3nccc(-c4ccc(Cl)cc4)c23)no1]
P-1179 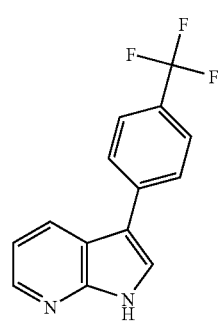 [SMILES: FC(F)(F)c1ccc(-c2c[nH]c3ncccc23)cc1]
P-1181 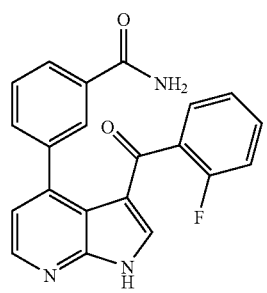 [SMILES: NC(=O)c1cccc(-c2ccnc3[nH]cc(C(=O)c4ccccc4F)c23)c1]
P-1182 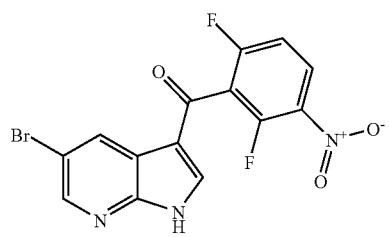 [SMILES: O=C(c1c(F)ccc([N+](=O)[O-])c1F)c1c[nH]c2ncc(Br)cc12]

TABLE 1-continued
Additional compounds of the invention
P-1183
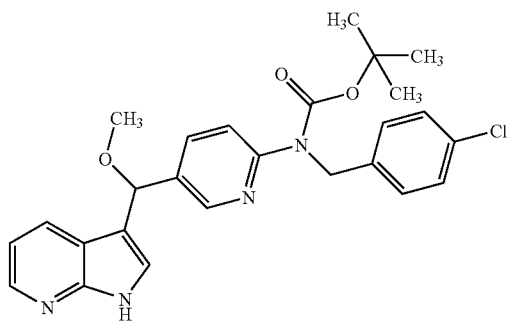 [SMILES: COC(c1ccc(N(Cc2ccc(Cl)cc2)C(=O)OC(C)(C)C)nc1)c1c[nH]c2ncccc12]
P-1184
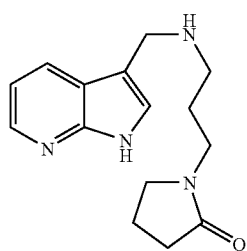 [SMILES: O=C1CCCN1CCCNCc1c[nH]c2ncccc12]
P-1185
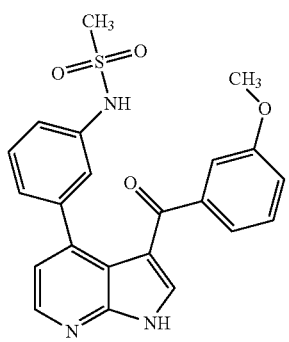 [SMILES: COc1cccc(C(=O)c2c[nH]c3nccc(-c4cccc(NS(C)(=O)=O)c4)c23)c1]
P-1186
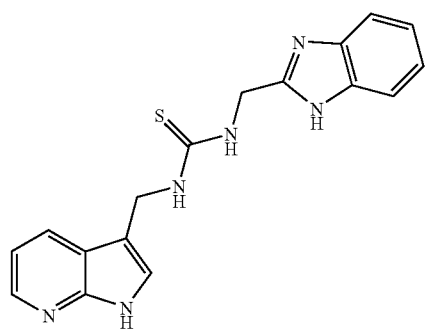 [SMILES: S=C(NCc1nc2ccccc2[nH]1)NCc1c[nH]c2ncccc12]

US 8,415,469 B2
TABLE 1-continued
Additional compounds of the invention
P-1187
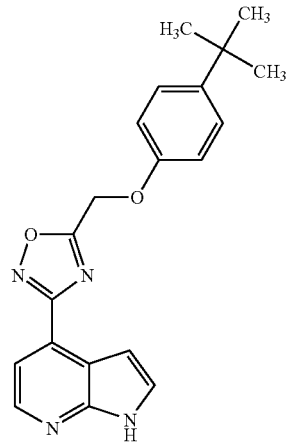 [SMILES: CC(C)(C)c1ccc(OCc2nc(-c3ccnc4[nH]ccc34)no2)cc1]
P-1188
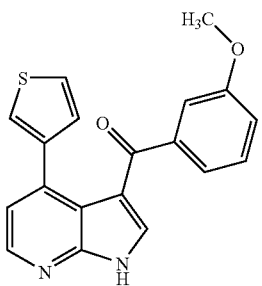 [SMILES: COc1cccc(C(=O)c2c[nH]c3nccc(-c4ccsc4)c23)c1]
P-1189
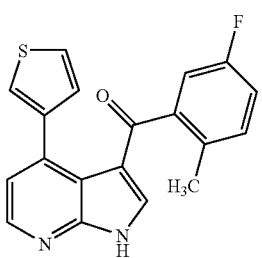 [SMILES: Cc1ccc(F)cc1C(=O)c1c[nH]c2nccc(-c3ccsc3)c12]
P-1190
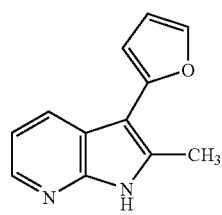
P-1191
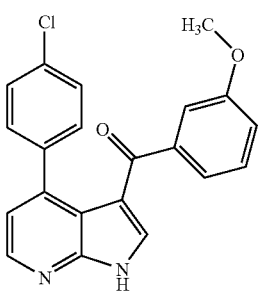 [SMILES: COc1cccc(C(=O)c2c[nH]c3nccc(-c4ccc(Cl)cc4)c23)c1]

TABLE 1-continued
Additional compounds of the invention
P-1192 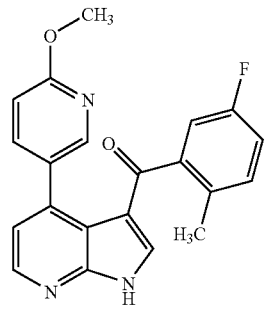 [SMILES: COc1ccc(-c2ccnc3[nH]cc(C(=O)c4cc(F)ccc4C)c23)cn1]
P-1193 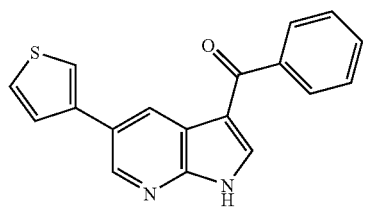 [SMILES: O=C(c1ccccc1)c1c[nH]c2ncc(-c3ccsc3)cc12]
P-1194 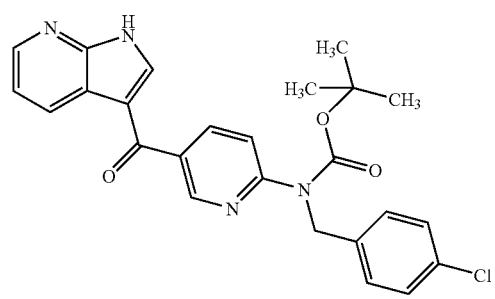 [SMILES: CC(C)(C)OC(=O)N(Cc1ccc(Cl)cc1)c1ccc(C(=O)c2c[nH]c3ncccc23)cn1]
P-1195 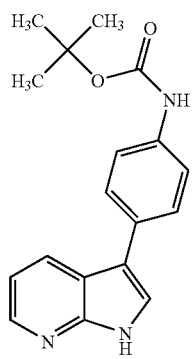 [SMILES: CC(C)(C)OC(=O)Nc1ccc(-c2c[nH]c3ncccc23)cc1]
P-1196 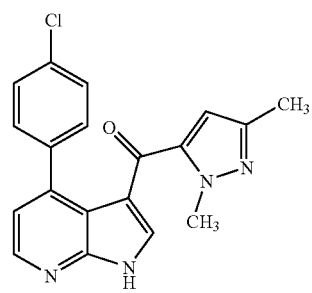 [SMILES: Cc1cc(C(=O)c2c[nH]c3nccc(-c4ccc(Cl)cc4)c23)n(C)n1]

TABLE 1-continued
Additional compounds of the invention
P-1197
P-1198
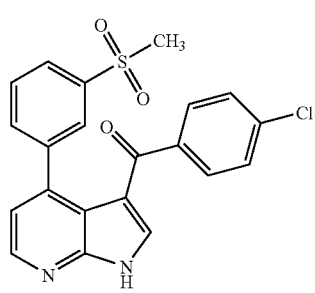 [SMILES: CS(=O)(=O)c1cccc(-c2ccnc3[nH]cc(C(=O)c4ccc(Cl)cc4)c23)c1]
P-1199
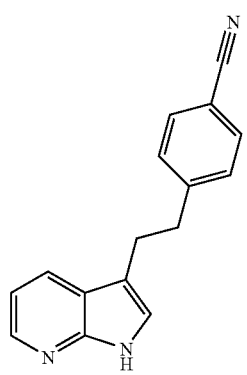 [SMILES: N#Cc1ccc(CCc2c[nH]c3ncccc23)cc1]
P-1200
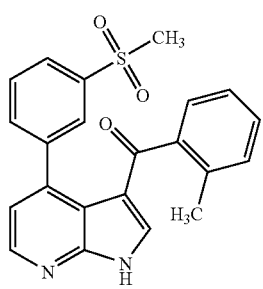 [SMILES: Cc1ccccc1C(=O)c1c[nH]c2nccc(-c3cccc(S(C)(=O)=O)c3)c12]
P-1201
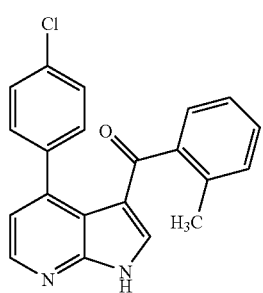 [SMILES: Cc1ccccc1C(=O)c1c[nH]c2nccc(-c3ccc(Cl)cc3)c12]

TABLE 1-continued
Additional compounds of the invention
P-1202
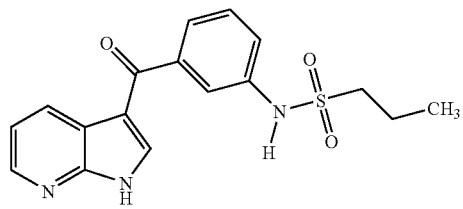 [SMILES: CCCS(=O)(=O)Nc1cccc(C(=O)c2c[nH]c3ncccc23)c1]
P-1203
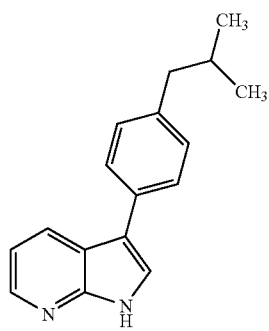 [SMILES: CC(C)Cc1ccc(-c2c[nH]c3ncccc23)cc1]
P-1204
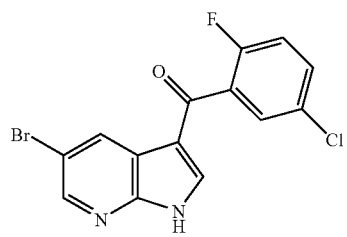 [SMILES: O=C(c1cc(Cl)ccc1F)c1c[nH]c2ncc(Br)cc12]
P-1205
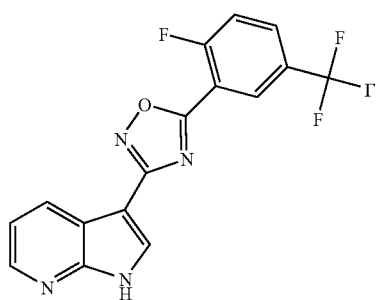
P-1206
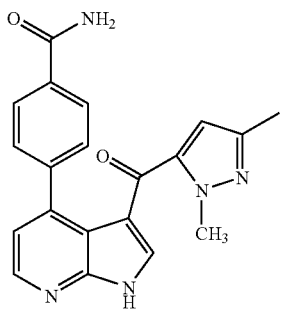 [SMILES: Cc1cc(C(=O)c2c[nH]c3nccc(-c4ccc(C(N)=O)cc4)c23)n(C)n1]

TABLE 1-continued
Additional compounds of the invention
P-1207
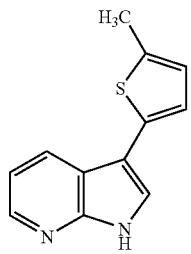
P-1208
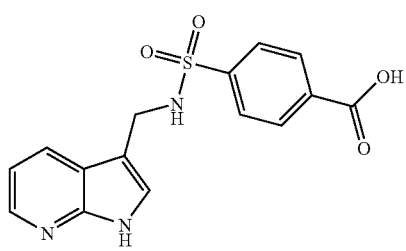 [SMILES: O=C(O)c1ccc(S(=O)(=O)NCc2c[nH]c3ncccc23)cc1]
P-1209
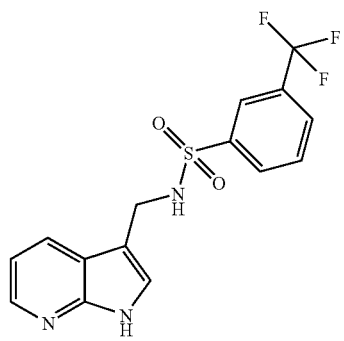 [SMILES: O=S(=O)(NCc1c[nH]c2ncccc12)c1cccc(C(F)(F)F)c1]
P-1210
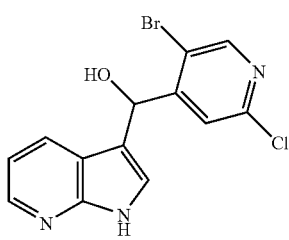 [SMILES: OC(c1cc(Cl)ncc1Br)c1c[nH]c2ncccc12]
P-1211
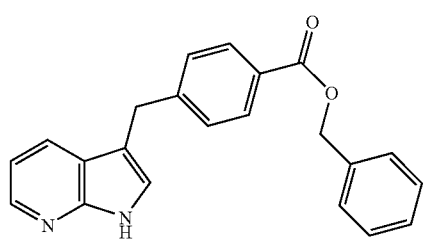 [SMILES: O=C(OCc1ccccc1)c1ccc(Cc2c[nH]c3ncccc23)cc1]

TABLE 1-continued
Additional compounds of the invention
P-1212
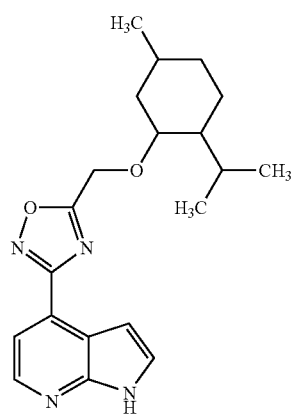 [SMILES: CC1CCC(C(C)C)C(OCc2nc(-c3ccnc4[nH]ccc34)no2)C1]
P-1213
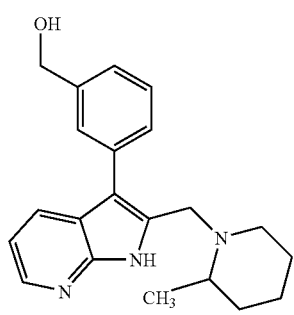 [SMILES: CC1CCCCN1Cc1[nH]c2ncccc2c1-c1cccc(CO)c1]
P-1214
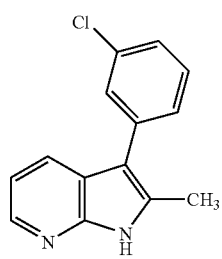 [SMILES: Cc1[nH]c2ncccc2c1-c1cccc(Cl)c1]
P-1215
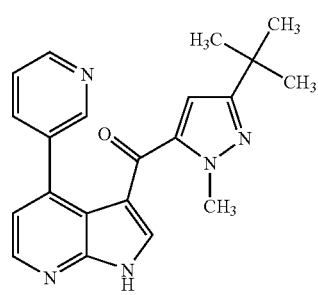 [SMILES: Cn1nc(C(C)(C)C)cc1C(=O)c1c[nH]c2nccc(-c3cccnc3)c12]

TABLE 1-continued
Additional compounds of the invention
P-1216 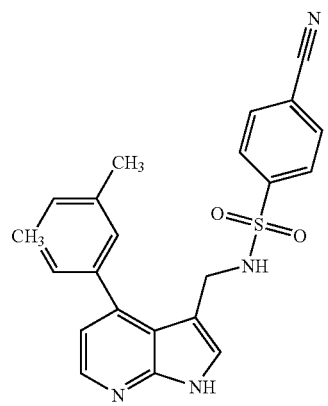 [SMILES: Cc1cccc(-c2ccnc3[nH]cc(CNS(=O)(=O)c4ccc(C#N)cc4)c23)c1]
P-1217 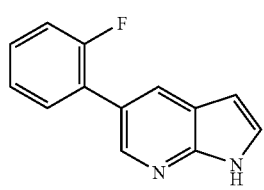 [SMILES: Fc1ccccc1-c1cnc2[nH]ccc2c1]
P-1218 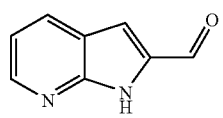 [SMILES: O=Cc1cc2cccnc2[nH]1]
P-1219 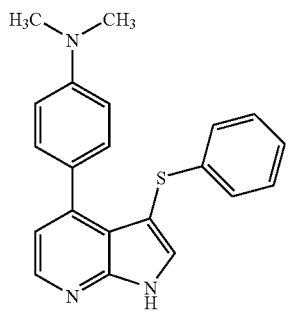 [SMILES: CN(C)c1ccc(-c2ccnc3[nH]cc(Sc4ccccc4)c23)cc1]
P-1220 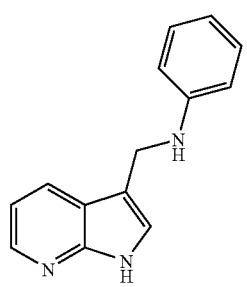 [SMILES: c1ccc(NCc2c[nH]c3ncccc23)cc1]
P-1221 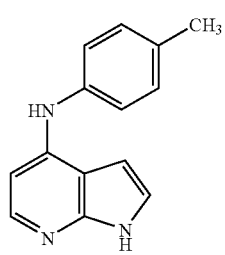 [SMILES: Cc1ccc(Nc2ccnc3[nH]ccc23)cc1]

TABLE 1-continued
Additional compounds of the invention
P-1222
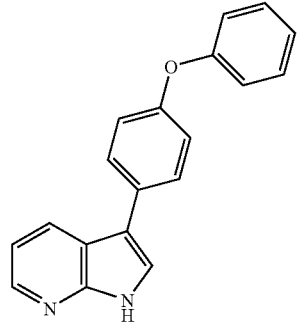 [SMILES: c1ccc(Oc2ccc(-c3c[nH]c4ncccc34)cc2)cc1]
P-1223
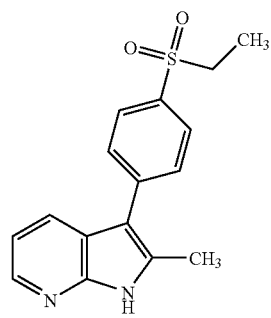 [SMILES: CCS(=O)(=O)c1ccc(-c2c(C)[nH]c3ncccc23)cc1]
P-1224
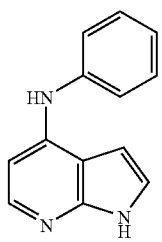 [SMILES: c1ccc(Nc2ccnc3[nH]ccc23)cc1]
P-1225
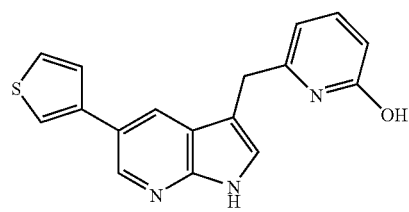 [SMILES: Oc1cccc(Cc2c[nH]c3ncc(-c4ccsc4)cc23)n1]
P-1226
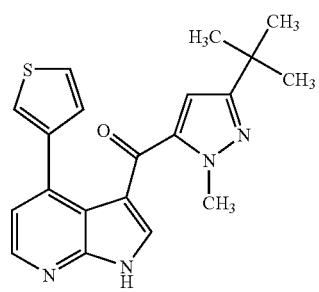 [SMILES: Cn1nc(C(C)(C)C)cc1C(=O)c1c[nH]c2nccc(-c3ccsc3)c12]

TABLE 1-continued
Additional compounds of the invention
P-1227 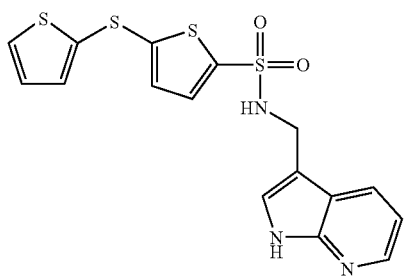 [SMILES: O=S(=O)(NCc1c[nH]c2ncccc12)c1ccc(Sc2cccs2)s1]
P-1228 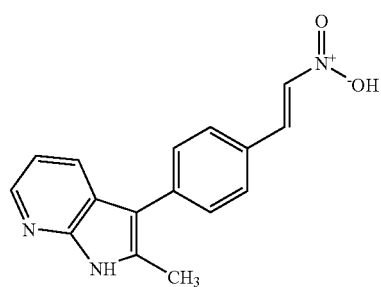 [SMILES: Cc1[nH]c2ncccc2c1-c1ccc(/C=C/[N+](=O)[O-])cc1]
P-1229 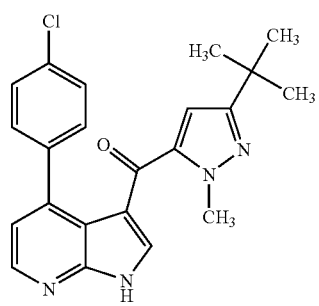 [SMILES: Cn1nc(C(C)(C)C)cc1C(=O)c1c[nH]c2nccc(-c3ccc(Cl)cc3)c12]
P-1230 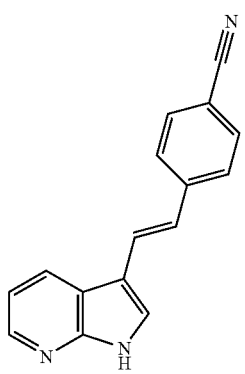 [SMILES: N#Cc1ccc(/C=C/c2c[nH]c3ncccc23)cc1]
P-1231 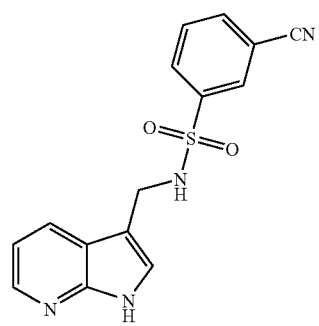 [SMILES: N#Cc1cccc(S(=O)(=O)NCc2c[nH]c3ncccc23)c1]

TABLE 1-continued
Additional compounds of the invention
P-1232 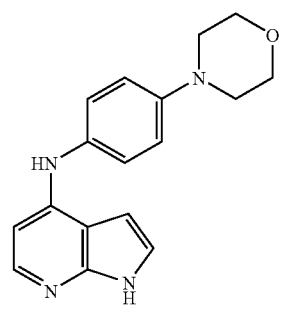 [SMILES: c1cc(Nc2ccc(N3CCOCC3)cc2)c2cc[nH]c2n1]
P-1233 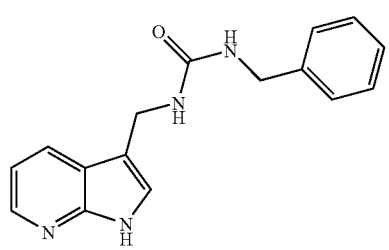 [SMILES: O=C(NCc1ccccc1)NCc1c[nH]c2ncccc12]
P-1234 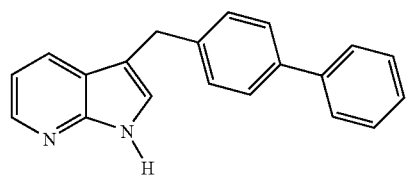 [SMILES: c1ccc(-c2ccc(Cc3c[nH]c4ncccc34)cc2)cc1]
P-1235 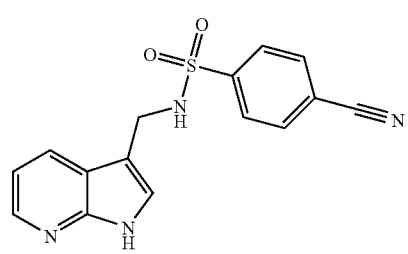 [SMILES: N#Cc1ccc(S(=O)(=O)NCc2c[nH]c3ncccc23)cc1]
P-1236 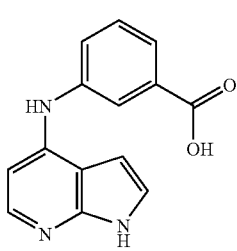 [SMILES: O=C(O)c1cccc(Nc2ccnc3[nH]ccc23)c1]
P-1237 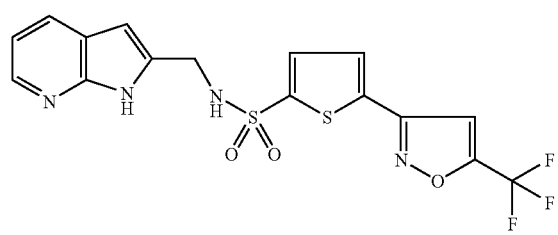 [SMILES: O=S(=O)(NCc1cc2cccnc2[nH]1)c1ccc(-c2cc(C(F)(F)F)on2)s1]

TABLE 1-continued
Additional compounds of the invention
P-1238
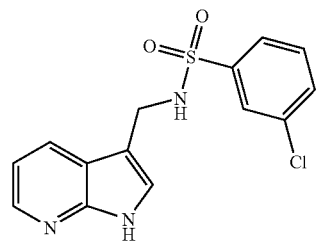 [SMILES: O=S(=O)(NCc1c[nH]c2ncccc12)c1cccc(Cl)c1]
P-1249
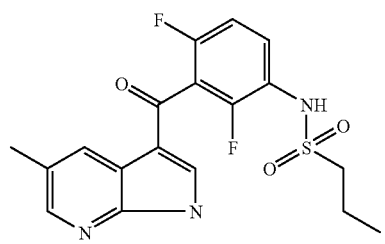 [SMILES: CCCS(=O)(=O)Nc1ccc(F)c(C(=O)c2c[nH]c3ncc(C)cc23)c1F]
P-1272
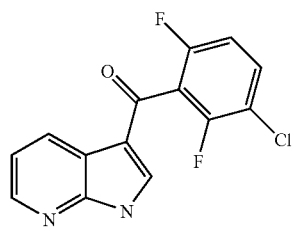 [SMILES: O=C(c1c(F)ccc(Cl)c1F)c1c[nH]c2ncccc12]
P-1273
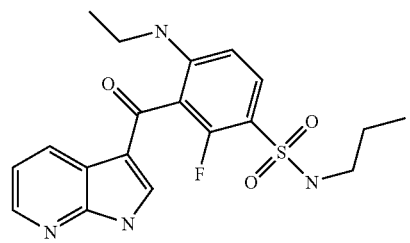 [SMILES: CCCNS(=O)(=O)c1ccc(NCC)c(C(=O)c2c[nH]c3ncccc23)c1F]
P-1274
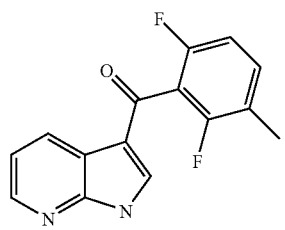 [SMILES: Cc1ccc(F)c(C(=O)c2c[nH]c3ncccc23)c1F]
P-1275
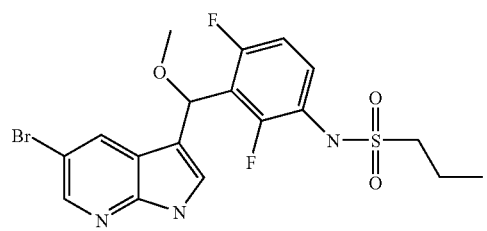 [SMILES: CCCS(=O)(=O)Nc1ccc(F)c(C(OC)c2c[nH]c3ncc(Br)cc23)c1F]

TABLE 1-continued
Additional compounds of the invention
P-1276
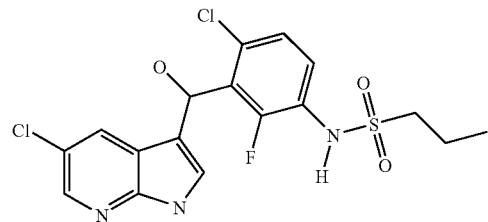 [SMILES: CCCS(=O)(=O)Nc1ccc(Cl)c(C(O)c2c[nH]c3ncc(Cl)cc23)c1F]
P-1277
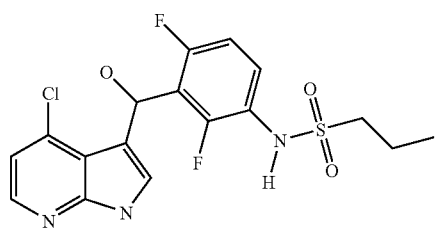 [SMILES: CCCS(=O)(=O)Nc1ccc(F)c(C(O)c2c[nH]c3nccc(Cl)c23)c1F]
P-1278
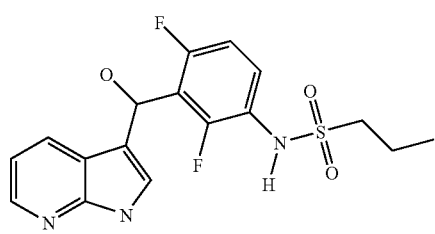 [SMILES: CCCS(=O)(=O)Nc1ccc(F)c(C(O)c2c[nH]c3ncccc23)c1F]
P-1279
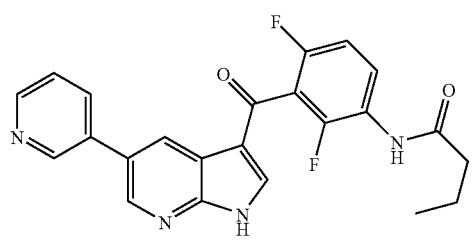 [SMILES: CCCC(=O)Nc1ccc(F)c(C(=O)c2c[nH]c3ncc(-c4cccnc4)cc23)c1F]
P-1280
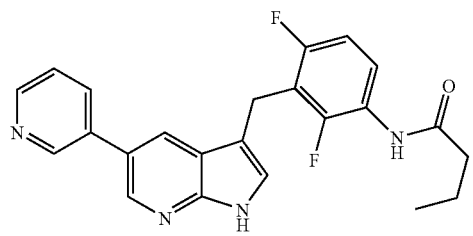 [SMILES: CCCC(=O)Nc1ccc(F)c(Cc2c[nH]c3ncc(-c4cccnc4)cc23)c1F]
P-1281
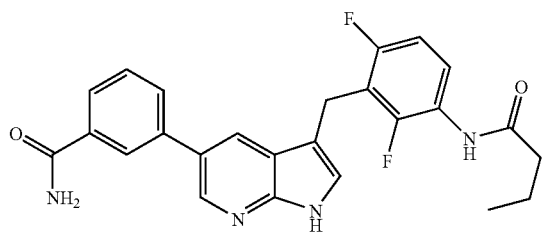 [SMILES: CCCC(=O)Nc1ccc(F)c(Cc2c[nH]c3ncc(-c4cccc(C(N)=O)c4)cc23)c1F]

TABLE 1-continued
Additional compounds of the invention
P-1282
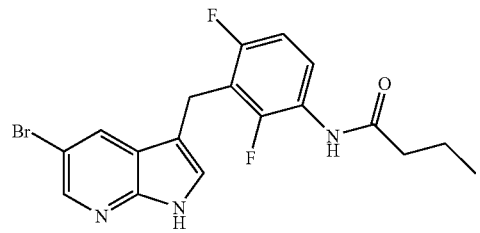 [SMILES: CCCC(=O)Nc1ccc(F)c(Cc2c[nH]c3ncc(Br)cc23)c1F]
P-1283
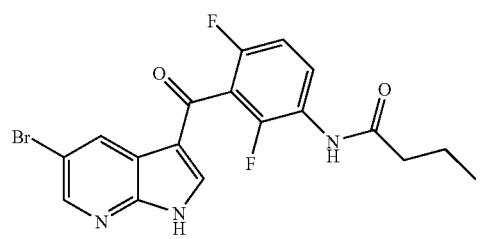 [SMILES: CCCC(=O)Nc1ccc(F)c(C(=O)c2c[nH]c3ncc(Br)cc23)c1F]
P-1284
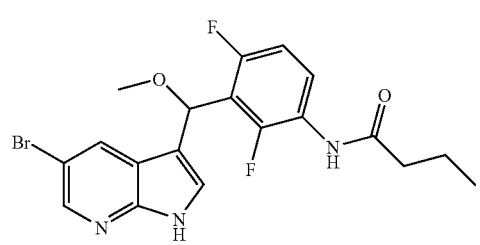 [SMILES: CCCC(=O)Nc1ccc(F)c(C(OC)c2c[nH]c3ncc(Br)cc23)c1F]
P-1285
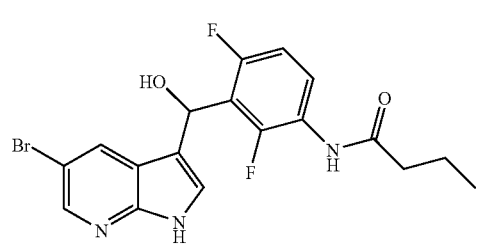
P-1286
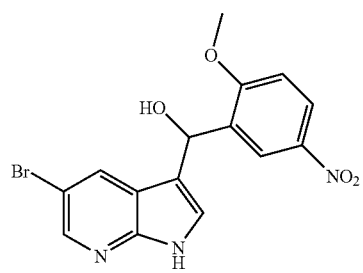 [SMILES: COc1ccc([N+](=O)[O-])cc1C(O)c1c[nH]c2ncc(Br)cc12]
P-1287
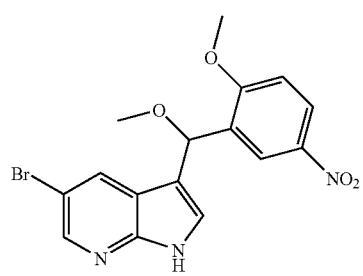 [SMILES: COc1ccc([N+](=O)[O-])cc1C(OC)c1c[nH]c2ncc(Br)cc12]

TABLE 1-continued
Additional compounds of the invention
P-1288
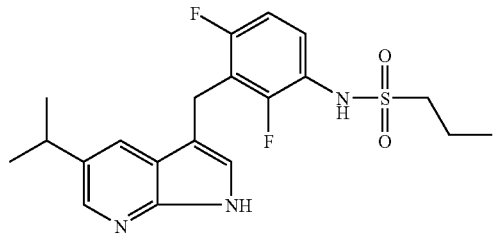 [SMILES: CCCS(=O)(=O)Nc1ccc(F)c(Cc2c[nH]c3ncc(C(C)C)cc23)c1F]
P-1316
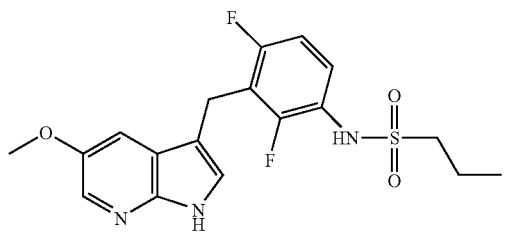 [SMILES: CCCS(=O)(=O)Nc1ccc(F)c(Cc2c[nH]c3ncc(OC)cc23)c1F]
P-1319
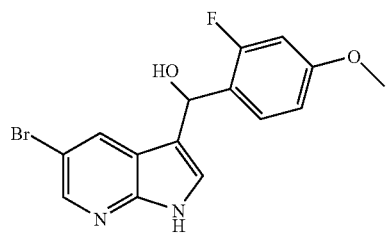 [SMILES: COc1ccc(C(O)c2c[nH]c3ncc(Br)cc23)c(F)c1]
P-1320
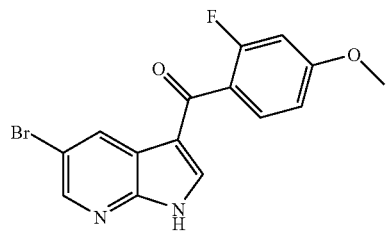 [SMILES: COc1ccc(C(=O)c2c[nH]c3ncc(Br)cc23)c(F)c1]
P-1321
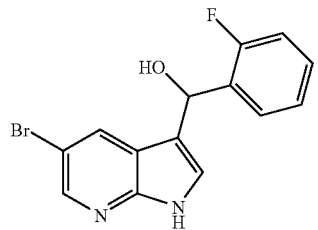 [SMILES: OC(c1ccccc1F)c1c[nH]c2ncc(Br)cc12]
P-1322
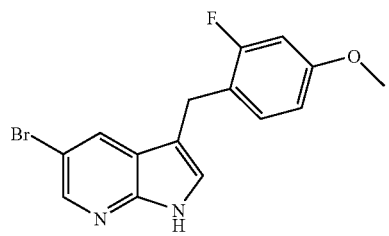 [SMILES: COc1ccc(Cc2c[nH]c3ncc(Br)cc23)c(F)c1]

TABLE 1-continued
Additional compounds of the invention
P-1337
P-1340
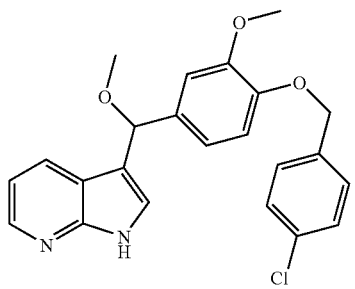 [SMILES: COc1cc(C(OC)c2c[nH]c3ncccc23)ccc1OCc1ccc(Cl)cc1]
P-1341
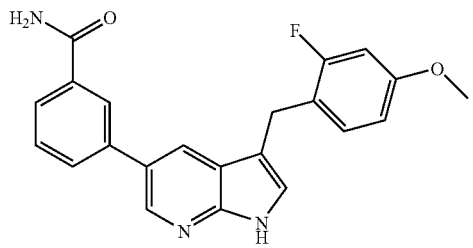 [SMILES: COc1ccc(Cc2c[nH]c3ncc(-c4cccc(C(N)=O)c4)cc23)c(F)c1]
P-1342
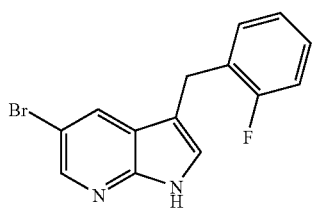 [SMILES: Fc1ccccc1Cc1c[nH]c2ncc(Br)cc12]
P-1345
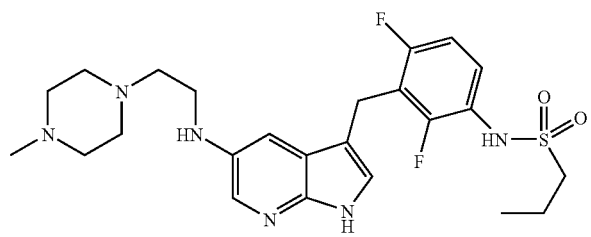 [SMILES: CCCS(=O)(=O)Nc1ccc(F)c(Cc2c[nH]c3ncc(NCCN4CCN(C)CC4)cc23)c1F]
P-1346
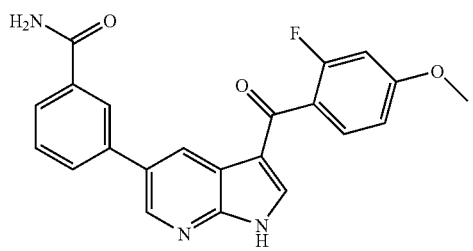 [SMILES: COc1ccc(C(=O)c2c[nH]c3ncc(-c4cccc(C(N)=O)c4)cc23)c(F)c1]

US 8,415,469 B2
1017                                                                                                                          1018
TABLE 1-continued
| Additional compounds of the invention |
P-1347 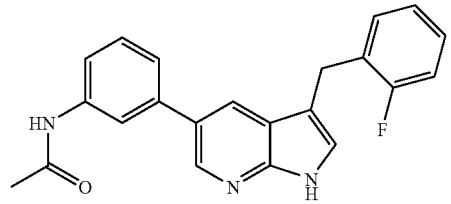 [SMILES: CC(=O)Nc1cccc(-c2cnc3[nH]cc(Cc4ccccc4F)c3c2)c1]
P-1348 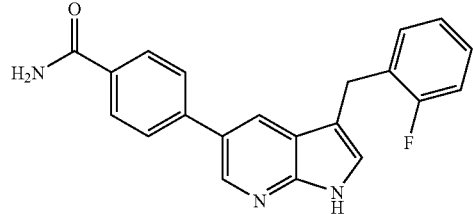 [SMILES: NC(=O)c1ccc(-c2cnc3[nH]cc(Cc4ccccc4F)c3c2)cc1]
P-1349 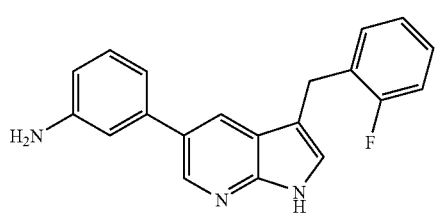 [SMILES: Nc1cccc(-c2cnc3[nH]cc(Cc4ccccc4F)c3c2)c1]
P-1365 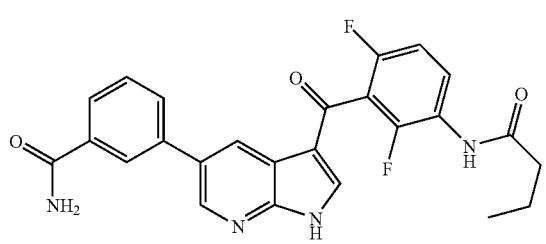 [SMILES: CCCC(=O)Nc1ccc(F)c(C(=O)c2c[nH]c3ncc(-c4cccc(C(N)=O)c4)cc23)c1F]
P-1366 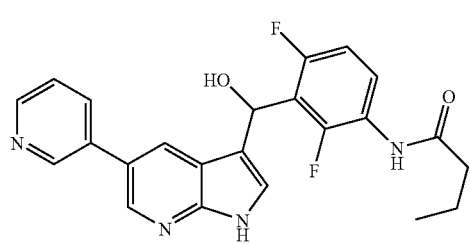 [SMILES: CCCC(=O)Nc1ccc(F)c(C(O)c2c[nH]c3ncc(-c4cccnc4)cc23)c1F]
P-1367 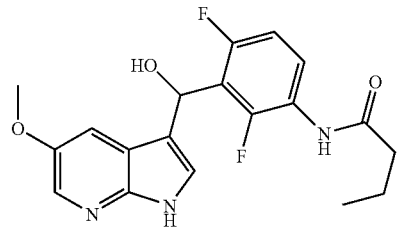 [SMILES: CCCC(=O)Nc1ccc(F)c(C(O)c2c[nH]c3ncc(OC)cc23)c1F]

TABLE 1-continued
Additional compounds of the invention
P-1368 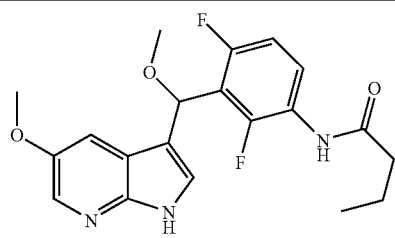
P-1369 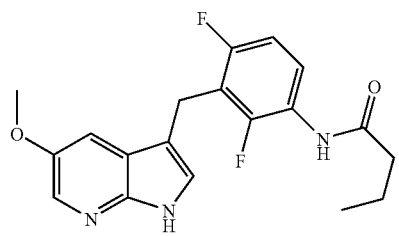 [SMILES: CCCC(=O)Nc1ccc(F)c(Cc2c[nH]c3ncc(OC)cc23)c1F]
P-1370 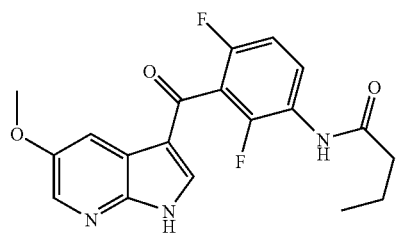 [SMILES: CCCC(=O)Nc1ccc(F)c(C(=O)c2c[nH]c3ncc(OC)cc23)c1F]
P-1379 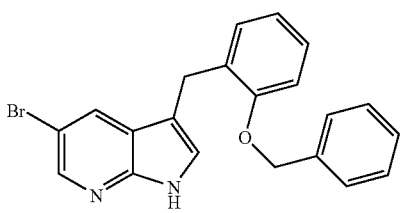 [SMILES: Brc1cnc2[nH]cc(Cc3ccccc3OCc3ccccc3)c2c1]
P-1380 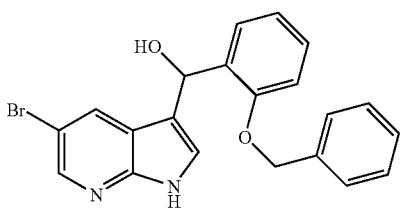 [SMILES: OC(c1ccccc1OCc1ccccc1)c1c[nH]c2ncc(Br)cc12]
P-1381 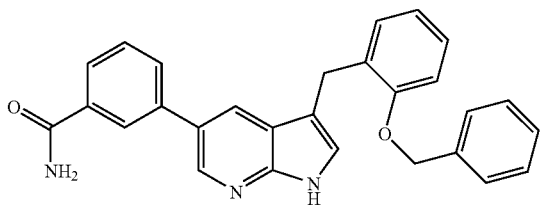 [SMILES: NC(=O)c1cccc(-c2cnc3[nH]cc(Cc4ccccc4OCc4ccccc4)c3c2)c1]
P-1382 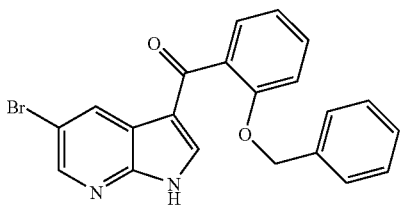 [SMILES: O=C(c1ccccc1OCc1ccccc1)c1c[nH]c2ncc(Br)cc12]

TABLE 1-continued
Additional compounds of the invention
P-1383 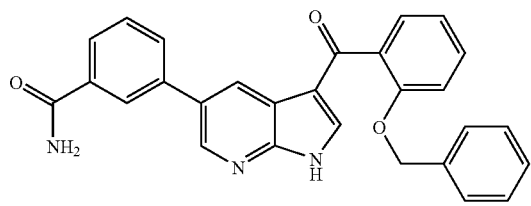 [SMILES: NC(=O)c1cccc(-c2cnc3[nH]cc(C(=O)c4ccccc4OCc4ccccc4)c3c2)c1]
P-1384 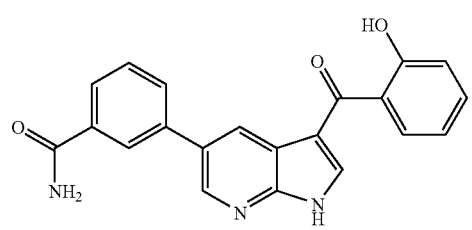 [SMILES: NC(=O)c1cccc(-c2cnc3[nH]cc(C(=O)c4ccccc4O)c3c2)c1]
P-1385 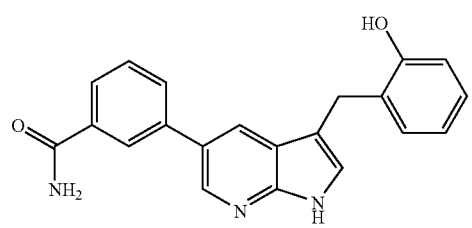 [SMILES: NC(=O)c1cccc(-c2cnc3[nH]cc(Cc4ccccc4O)c3c2)c1]
P-1396 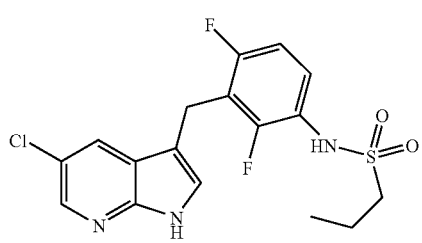 [SMILES: CCCS(=O)(=O)Nc1ccc(F)c(Cc2c[nH]c3ncc(Cl)cc23)c1F]
P-1397 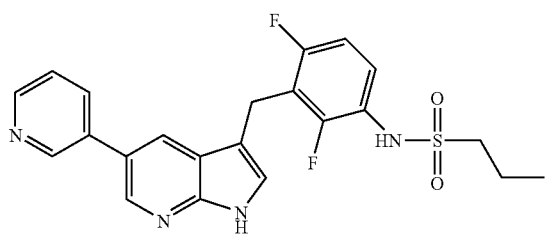 [SMILES: CCCS(=O)(=O)Nc1ccc(F)c(Cc2c[nH]c3ncc(-c4cccnc4)cc23)c1F]
P-1398 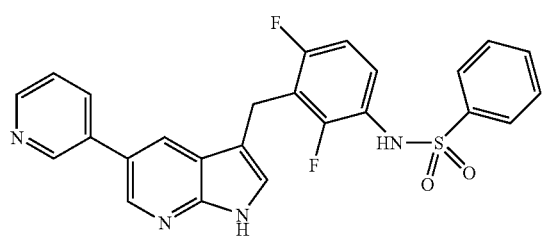 [SMILES: O=S(=O)(Nc1ccc(F)c(Cc2c[nH]c3ncc(-c4cccnc4)cc23)c1F)c1ccccc1]

TABLE 1-continued
Additional compounds of the invention
P-1400
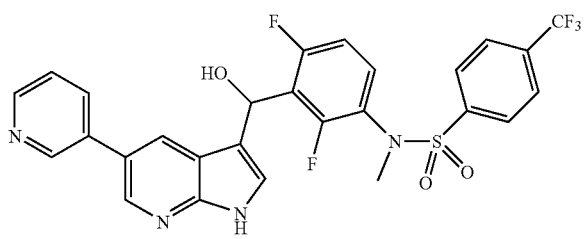 [SMILES: CN(c1ccc(F)c(C(O)c2c[nH]c3ncc(-c4cccnc4)cc23)c1F)S(=O)(=O)c1ccc(C(F)(F)F)cc1]
P-1401
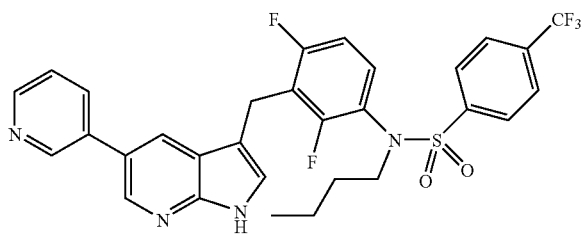 [SMILES: CCCCN(c1ccc(F)c(Cc2c[nH]c3ncc(-c4cccnc4)cc23)c1F)S(=O)(=O)c1ccc(C(F)(F)F)cc1]
P-1404
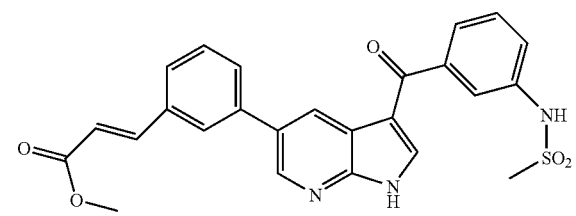 [SMILES: COC(=O)/C=C/c1cccc(-c2cnc3[nH]cc(C(=O)c4cccc(NS(C)(=O)=O)c4)c3c2)c1]
P-1431
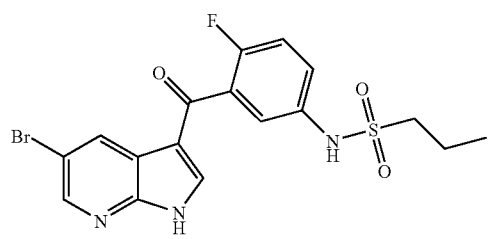 [SMILES: CCCS(=O)(=O)Nc1ccc(F)c(C(=O)c2c[nH]c3ncc(Br)cc23)c1]
P-1433
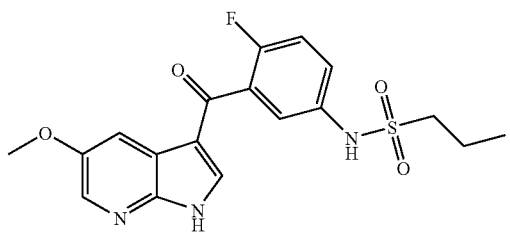 [SMILES: CCCS(=O)(=O)Nc1ccc(F)c(C(=O)c2c[nH]c3ncc(OC)cc23)c1]
P-1444
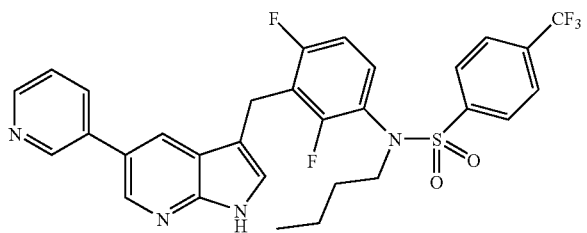 [SMILES: CCCCN(c1ccc(F)c(Cc2c[nH]c3ncc(-c4cccnc4)cc23)c1F)S(=O)(=O)c1ccc(C(F)(F)F)cc1]

TABLE 1-continued
Additional compounds of the invention
P-1448
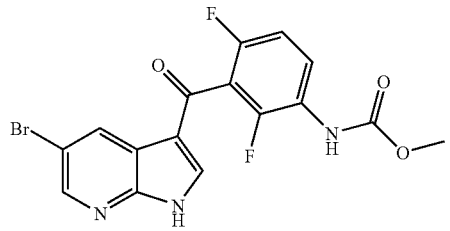 [SMILES: COC(=O)Nc1ccc(F)c(C(=O)c2c[nH]c3ncc(Br)cc23)c1F]
P-1451
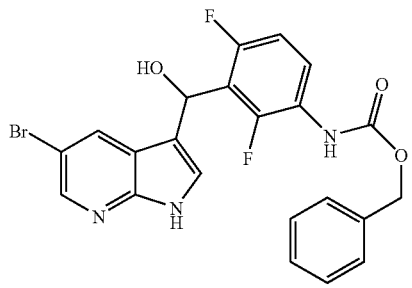 [SMILES: O=C(Nc1ccc(F)c(C(O)c2c[nH]c3ncc(Br)cc23)c1F)OCc1ccccc1]
P-1452
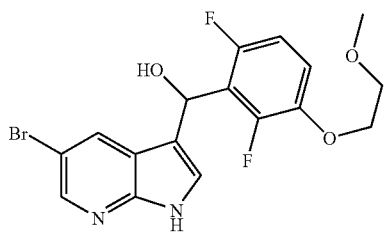 [SMILES: COCCOc1ccc(F)c(C(O)c2c[nH]c3ncc(Br)cc23)c1F]
P-1457
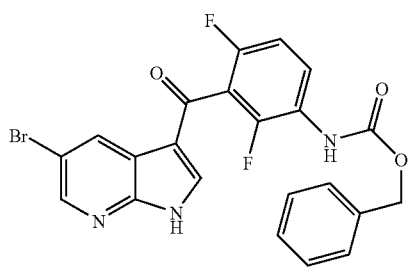 [SMILES: O=C(Nc1ccc(F)c(C(=O)c2c[nH]c3ncc(Br)cc23)c1F)OCc1ccccc1]
P-1458
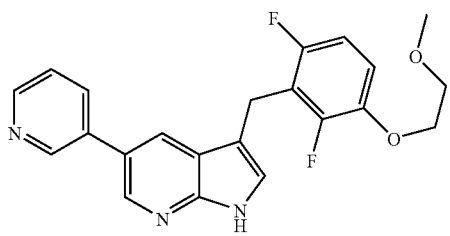 [SMILES: COCCOc1ccc(F)c(Cc2c[nH]c3ncc(-c4cccnc4)cc23)c1F]
P-1459
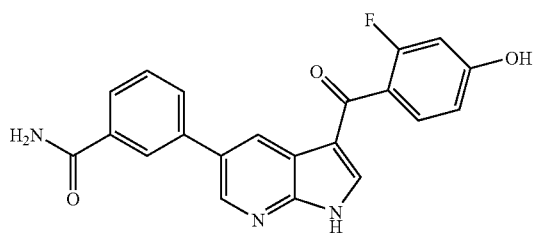 [SMILES: NC(=O)c1cccc(-c2cnc3[nH]cc(C(=O)c4ccc(O)cc4F)c3c2)c1]

TABLE 1-continued
Additional compounds of the invention
P-1460
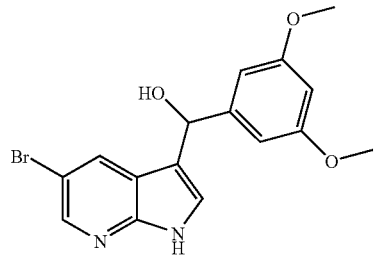 [SMILES: COc1cc(OC)cc(C(O)c2c[nH]c3ncc(Br)cc23)c1]
P-1461
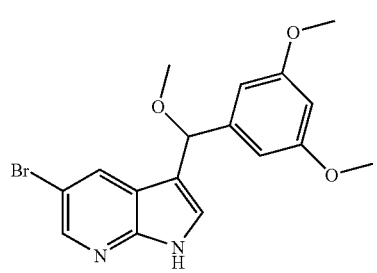 [SMILES: COc1cc(OC)cc(C(OC)c2c[nH]c3ncc(Br)cc23)c1]
P-1473
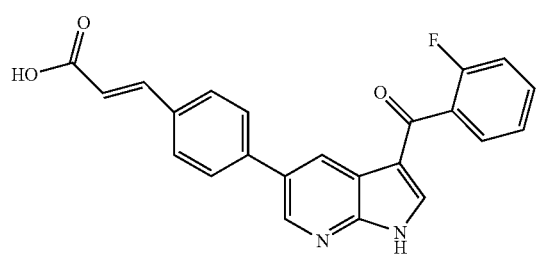 [SMILES: O=C(O)/C=C/c1ccc(-c2cnc3[nH]cc(C(=O)c4ccccc4F)c3c2)cc1]
P-1476
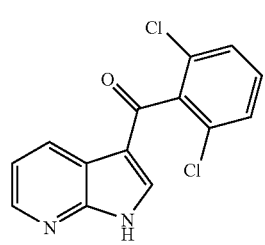
P-1479
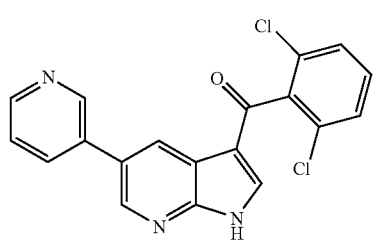 [SMILES: O=C(c1c(Cl)cccc1Cl)c1c[nH]c2ncc(-c3cccnc3)cc12]
P-1480
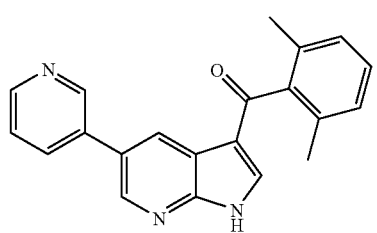 [SMILES: Cc1cccc(C)c1C(=O)c1c[nH]c2ncc(-c3cccnc3)cc12]

1029
TABLE 1-continued
Additional compounds of the invention
P-1484
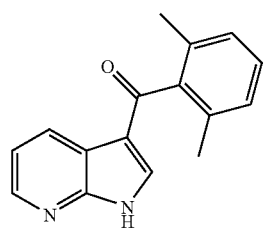 [SMILES: Cc1cccc(C)c1C(=O)c1c[nH]c2ncccc12]
P-1485
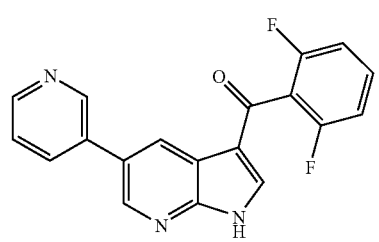 [SMILES: O=C(c1c(F)cccc1F)c1c[nH]c2ncc(-c3cccnc3)cc12]
P-1507
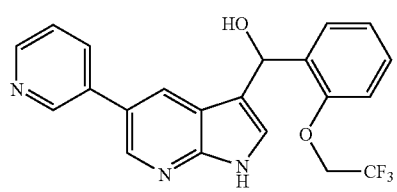 [SMILES: OC(c1ccccc1OCC(F)(F)F)c1c[nH]c2ncc(-c3cccnc3)cc12]
P-1508
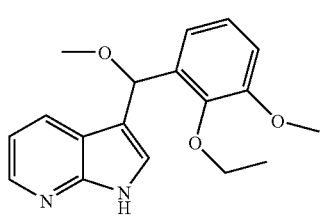 [SMILES: CCOc1c(OC)cccc1C(OC)c1c[nH]c2ncccc12]
P-1509
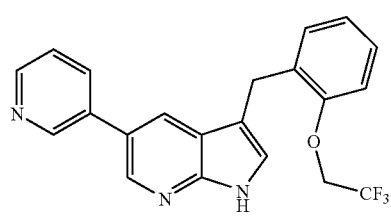 [SMILES: FC(F)(F)COc1ccccc1Cc1c[nH]c2ncc(-c3cccnc3)cc12]
P-1510
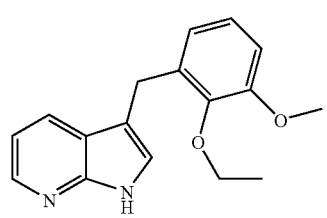 [SMILES: CCOc1c(Cc2c[nH]c3ncccc23)cccc1OC]
P-1511
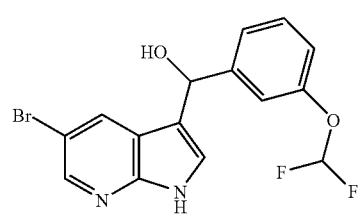 [SMILES: OC(c1cccc(OC(F)F)c1)c1c[nH]c2ncc(Br)cc12]

TABLE 1-continued
Additional compounds of the invention
P-1512
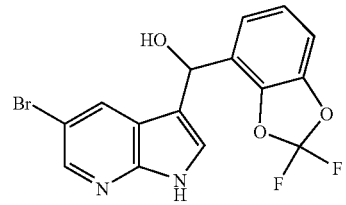 [SMILES: OC(c1cccc2c1OC(F)(F)O2)c1c[nH]c2ncc(Br)cc12]
P-1517
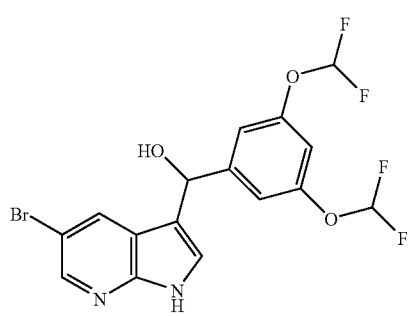 [SMILES: OC(c1cc(OC(F)F)cc(OC(F)F)c1)c1c[nH]c2ncc(Br)cc12]
P-1518
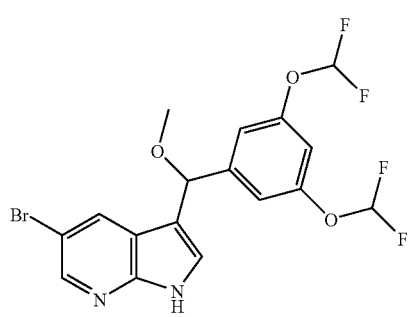 [SMILES: COC(c1cc(OC(F)F)cc(OC(F)F)c1)c1c[nH]c2ncc(Br)cc12]
P-1525
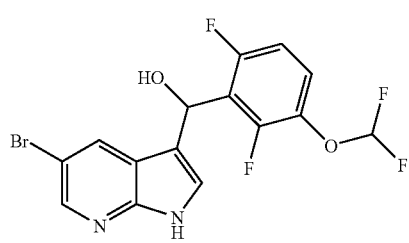 [SMILES: OC(c1c(F)ccc(OC(F)F)c1F)c1c[nH]c2ncc(Br)cc12]
P-1533
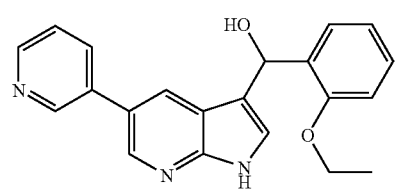 [SMILES: CCOc1ccccc1C(O)c1c[nH]c2ncc(-c3cccnc3)cc12]
P-1535
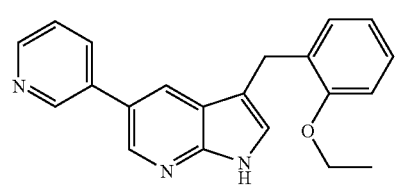 [SMILES: CCOc1ccccc1Cc1c[nH]c2ncc(-c3cccnc3)cc12]

TABLE 1-continued
Additional compounds of the invention
P-1536 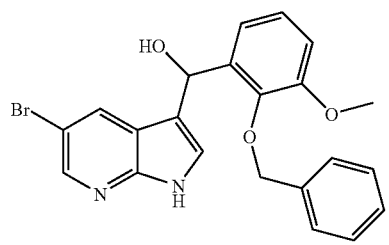
P-1537 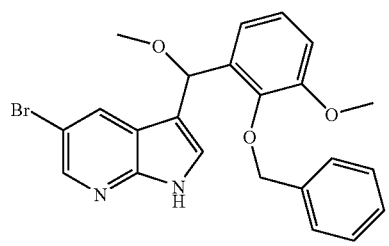 [SMILES: COc1cccc(C(OC)c2c[nH]c3ncc(Br)cc23)c1OCc1ccccc1]
P-1539 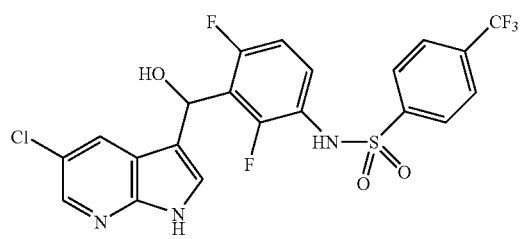 [SMILES: O=S(=O)(Nc1ccc(F)c(C(O)c2c[nH]c3ncc(Cl)cc23)c1F)c1ccc(C(F)(F)F)cc1]
P-1540 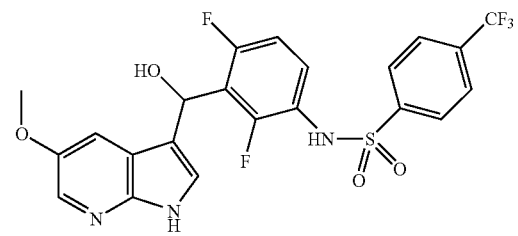 [SMILES: COc1cnc2[nH]cc(C(O)c3c(F)ccc(NS(=O)(=O)c4ccc(C(F)(F)F)cc4)c3F)c2c1]
P-1543 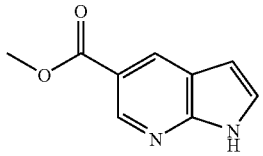
P-1550 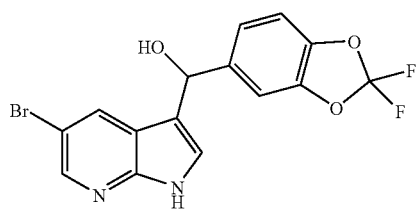 [SMILES: OC(c1ccc2c(c1)OC(F)(F)O2)c1c[nH]c2ncc(Br)cc12]
P-1555 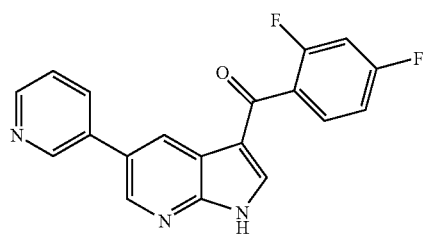 [SMILES: O=C(c1ccc(F)cc1F)c1c[nH]c2ncc(-c3cccnc3)cc12]

TABLE 1-continued
Additional compounds of the invention
P-1556
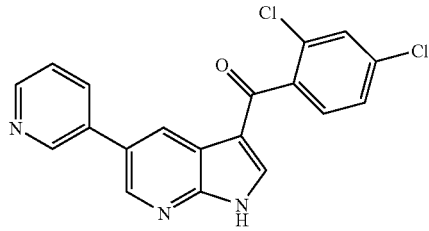 [SMILES: O=C(c1ccc(Cl)cc1Cl)c1c[nH]c2ncc(-c3cccnc3)cc12]
P-1557
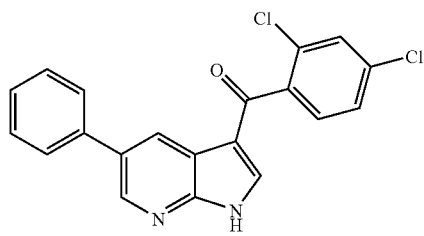 [SMILES: O=C(c1ccc(Cl)cc1Cl)c1c[nH]c2ncc(-c3ccccc3)cc12]
P-1560
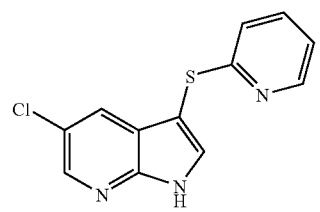 [SMILES: Clc1cnc2[nH]cc(Sc3ccccn3)c2c1]
P-1561
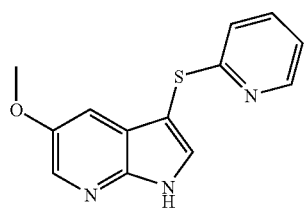 [SMILES: COc1cnc2[nH]cc(Sc3ccccn3)c2c1]
P-1562
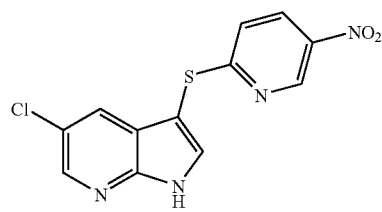 [SMILES: O=[N+]([O-])c1ccc(Sc2c[nH]c3ncc(Cl)cc23)nc1]
P-1563
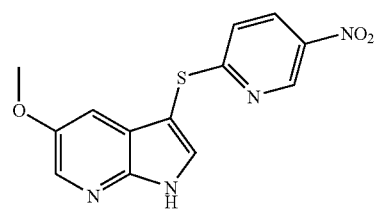 [SMILES: COc1cnc2[nH]cc(Sc3ccc([N+](=O)[O-])cn3)c2c1]
P-1565
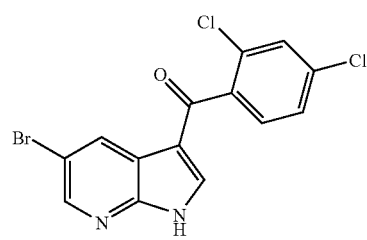 [SMILES: O=C(c1ccc(Cl)cc1Cl)c1c[nH]c2ncc(Br)cc12]

TABLE 1-continued
Additional compounds of the invention
P-1573
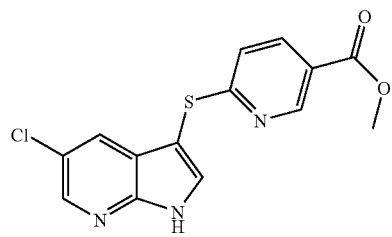 [SMILES: COC(=O)c1ccc(Sc2c[nH]c3ncc(Cl)cc23)nc1]
P-1574
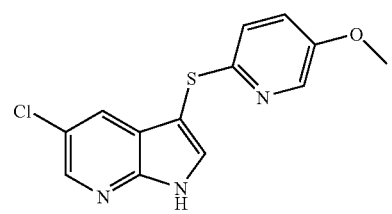 [SMILES: COc1ccc(Sc2c[nH]c3ncc(Cl)cc23)nc1]
P-1577
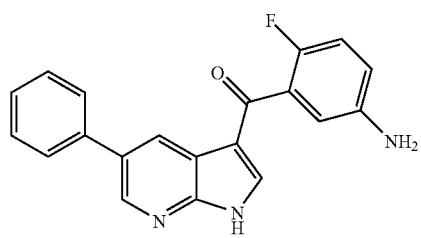 [SMILES: Nc1ccc(F)c(C(=O)c2c[nH]c3ncc(-c4ccccc4)cc23)c1]
P-1585
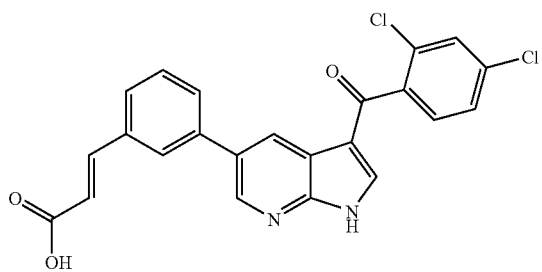 [SMILES: O=C(O)/C=C/c1cccc(-c2cnc3[nH]cc(C(=O)c4ccc(Cl)cc4Cl)c3c2)c1]
P-1588
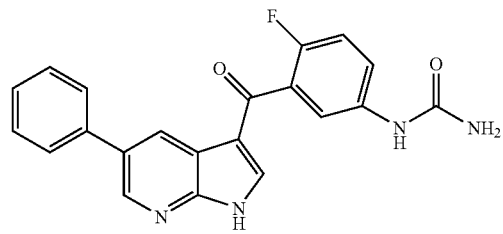 [SMILES: NC(=O)Nc1ccc(F)c(C(=O)c2c[nH]c3ncc(-c4ccccc4)cc23)c1]
P-1592
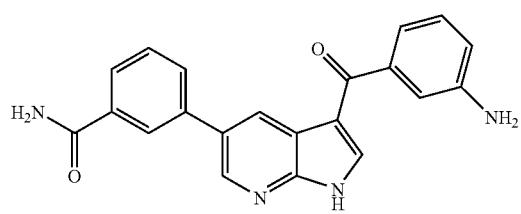 [SMILES: NC(=O)c1cccc(-c2cnc3[nH]cc(C(=O)c4cccc(N)c4)c3c2)c1]

TABLE 1-continued
Additional compounds of the invention
P-1593 
P-1604 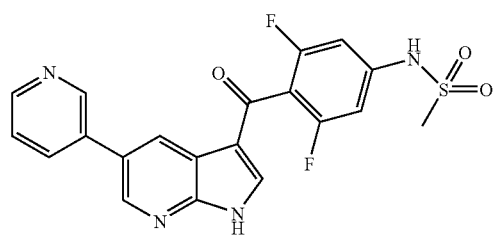 [SMILES: CS(=O)(=O)Nc1cc(F)c(C(=O)c2c[nH]c3ncc(-c4cccnc4)cc23)c(F)c1]
P-1607 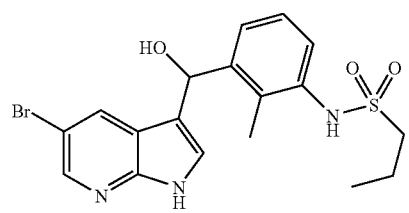 [SMILES: CCCS(=O)(=O)Nc1cccc(C(O)c2c[nH]c3ncc(Br)cc23)c1C]
P-1608 
P-1609 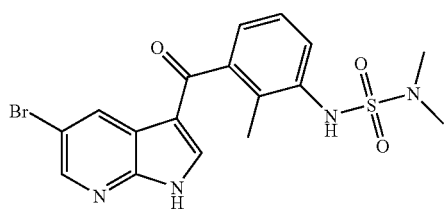 [SMILES: Cc1c(NS(=O)(=O)N(C)C)cccc1C(=O)c1c[nH]c2ncc(Br)cc12]
P-1610 
P-1614 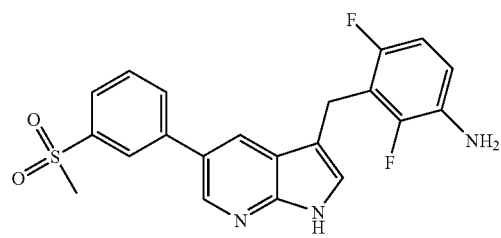 [SMILES: CS(=O)(=O)c1cccc(-c2cnc3[nH]cc(Cc4c(F)ccc(N)c4F)c3c2)c1]

TABLE 1-continued
Additional compounds of the invention
P-1617 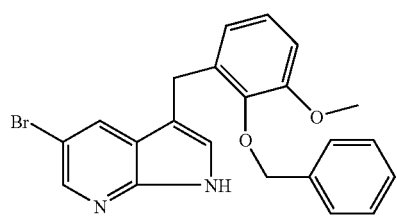 [SMILES: COc1cccc(Cc2c[nH]c3ncc(Br)cc23)c1OCc1ccccc1]
P-1619 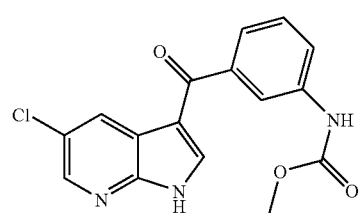 [SMILES: COC(=O)Nc1cccc(C(=O)c2c[nH]c3ncc(Cl)cc23)c1]
P-1620 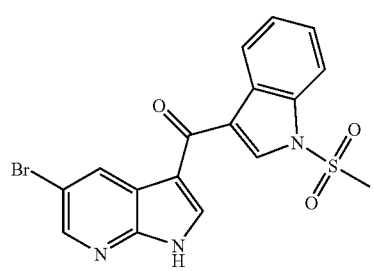 [SMILES: CS(=O)(=O)n1cc(C(=O)c2c[nH]c3ncc(Br)cc23)c2ccccc21]
P-1623 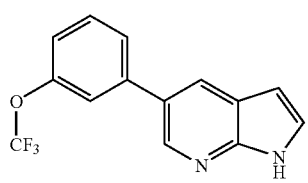 [SMILES: FC(F)(F)Oc1cccc(-c2cnc3[nH]ccc3c2)c1]
P-1624 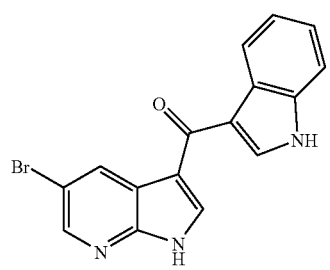 [SMILES: O=C(c1c[nH]c2ccccc12)c1c[nH]c2ncc(Br)cc12]
P-1628 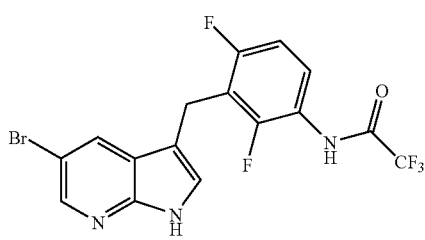 [SMILES: O=C(Nc1ccc(F)c(Cc2c[nH]c3ncc(Br)cc23)c1F)C(F)(F)F]

TABLE 1-continued
Additional compounds of the invention
P-1629 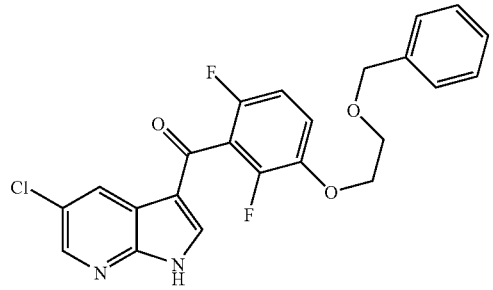 [SMILES: O=C(c1c(F)ccc(OCCOCc2ccccc2)c1F)c1c[nH]c2ncc(Cl)cc12]
P-1631 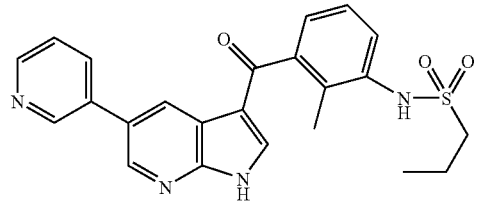 [SMILES: CCCS(=O)(=O)Nc1cccc(C(=O)c2c[nH]c3ncc(-c4cccnc4)cc23)c1C]
P-1632 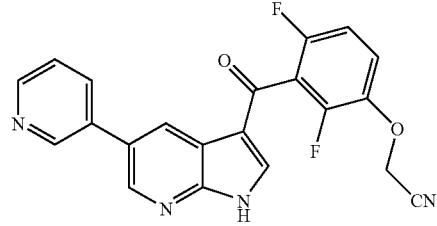 [SMILES: N#CCOc1ccc(F)c(C(=O)c2c[nH]c3ncc(-c4cccnc4)cc23)c1F]
P-1633 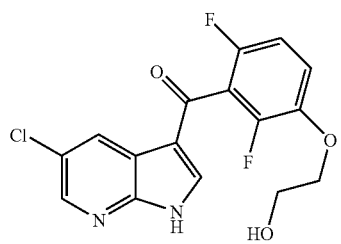 [SMILES: O=C(c1c(F)ccc(OCCO)c1F)c1c[nH]c2ncc(Cl)cc12]
P-1634 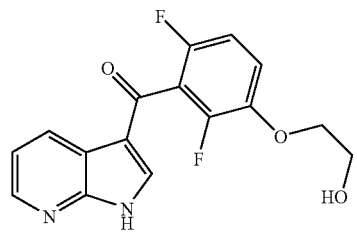 [SMILES: O=C(c1c(F)ccc(OCCO)c1F)c1c[nH]c2ncccc12]
P-1635 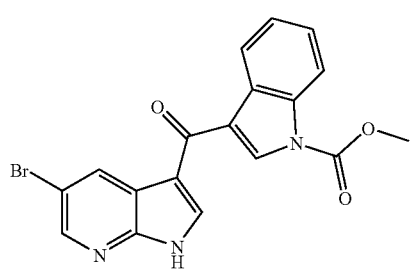 [SMILES: COC(=O)n1cc(C(=O)c2c[nH]c3ncc(Br)cc23)c2ccccc21]

TABLE 1-continued
Additional compounds of the invention
P-1638 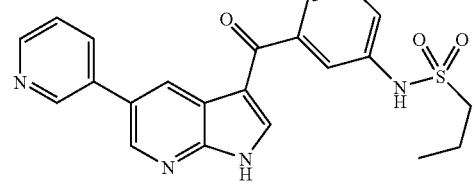
P-1639 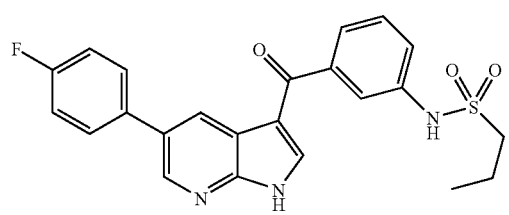 [SMILES: CCCS(=O)(=O)Nc1cccc(C(=O)c2c[nH]c3ncc(-c4ccc(F)cc4)cc23)c1]
P-1640 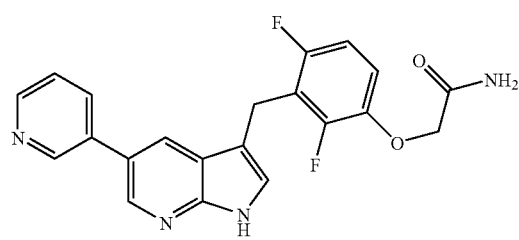 [SMILES: NC(=O)COc1ccc(F)c(Cc2c[nH]c3ncc(-c4cccnc4)cc23)c1F]
P-1641 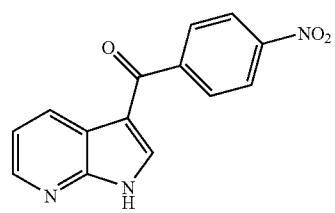 [SMILES: O=C(c1ccc([N+](=O)[O-])cc1)c1c[nH]c2ncccc12]
P-1642 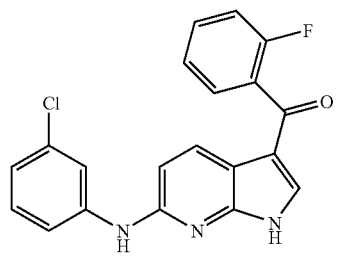 [SMILES: O=C(c1ccccc1F)c1c[nH]c2nc(Nc3cccc(Cl)c3)ccc12]
P-1643 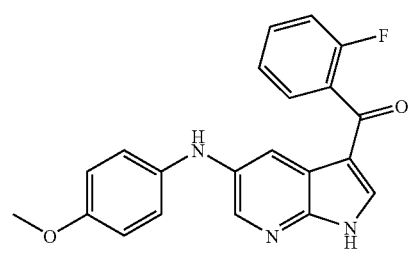 [SMILES: COc1ccc(Nc2cnc3[nH]cc(C(=O)c4ccccc4F)c3c2)cc1]

TABLE 1-continued
Additional compounds of the invention
P-1644 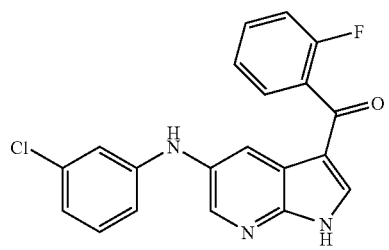 [SMILES: O=C(c1ccccc1F)c1c[nH]c2ncc(Nc3cccc(Cl)c3)cc12]
P-1645 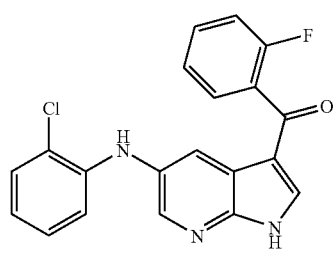 [SMILES: O=C(c1ccccc1F)c1c[nH]c2ncc(Nc3ccccc3Cl)cc12]
P-1646 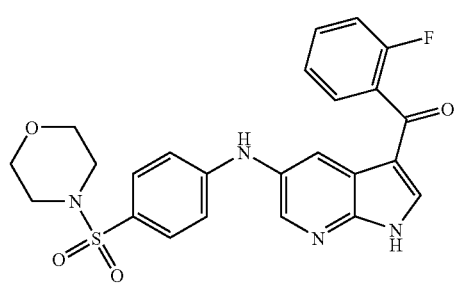 [SMILES: O=C(c1ccccc1F)c1c[nH]c2ncc(Nc3ccc(S(=O)(=O)N4CCOCC4)cc3)cc12]
P-1647 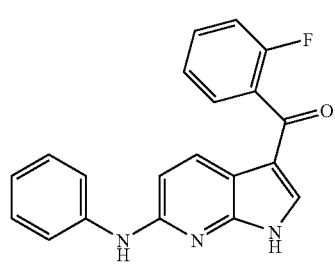 [SMILES: O=C(c1ccccc1F)c1c[nH]c2nc(Nc3ccccc3)ccc12]
P-1648 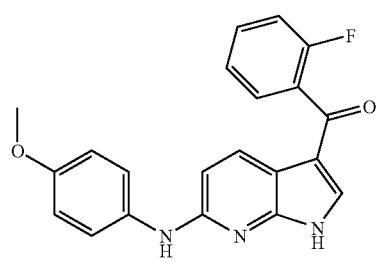 [SMILES: COc1ccc(Nc2ccc3c(C(=O)c4ccccc4F)c[nH]c3n2)cc1]
P-1649 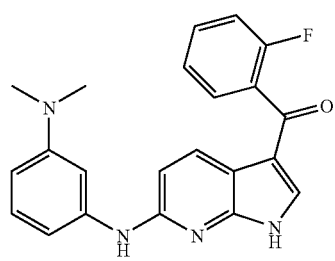 [SMILES: CN(C)c1cccc(Nc2ccc3c(C(=O)c4ccccc4F)c[nH]c3n2)c1]

TABLE 1-continued
Additional compounds of the invention
P-1650
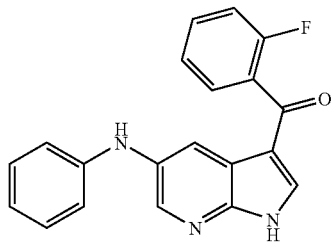 [SMILES: O=C(c1ccccc1F)c1c[nH]c2ncc(Nc3ccccc3)cc12]
P-1651
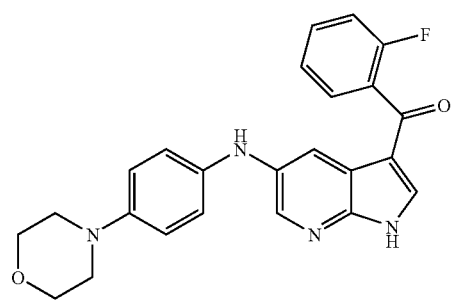 [SMILES: O=C(c1ccccc1F)c1c[nH]c2ncc(Nc3ccc(N4CCOCC4)cc3)cc12]
P-1653
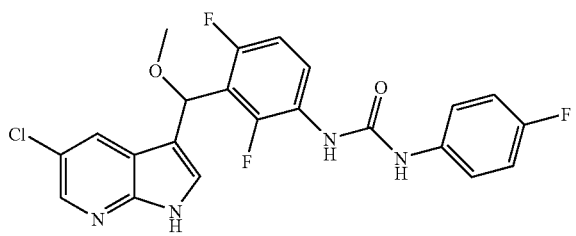 [SMILES: COC(c1c(F)ccc(NC(=O)Nc2ccc(F)cc2)c1F)c1c[nH]c2ncc(Cl)cc12]
P-1655
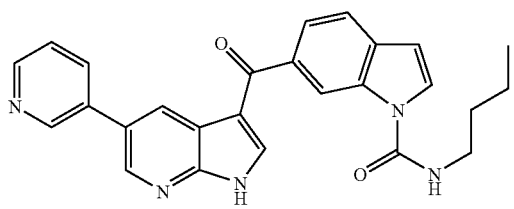 [SMILES: CCCCNC(=O)n1ccc2ccc(C(=O)c3c[nH]c4ncc(-c5cccnc5)cc34)cc21]
P-1658
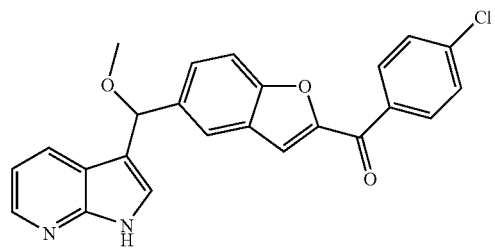 [SMILES: COC(c1ccc2oc(C(=O)c3ccc(Cl)cc3)cc2c1)c1c[nH]c2ncccc12]
P-1659
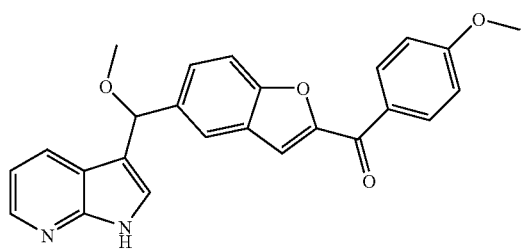 [SMILES: COc1ccc(C(=O)c2cc3cc(C(OC)c4c[nH]c5ncccc45)ccc3o2)cc1]

TABLE 1-continued
Additional compounds of the invention
P-1662
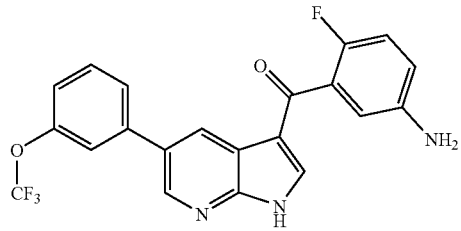 [SMILES: Nc1ccc(F)c(C(=O)c2c[nH]c3ncc(-c4cccc(OC(F)(F)F)c4)cc23)c1]
P-1663
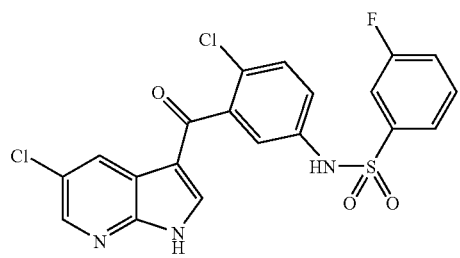 [SMILES: O=C(c1cc(NS(=O)(=O)c2cccc(F)c2)ccc1Cl)c1c[nH]c2ncc(Cl)cc12]
P-1664
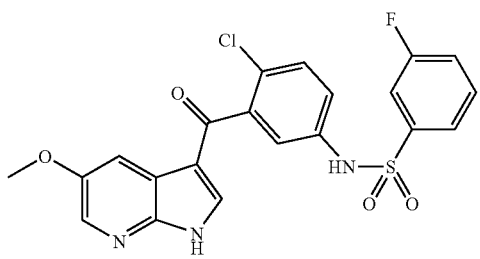 [SMILES: COc1cnc2[nH]cc(C(=O)c3cc(NS(=O)(=O)c4cccc(F)c4)ccc3Cl)c2c1]
P-1665
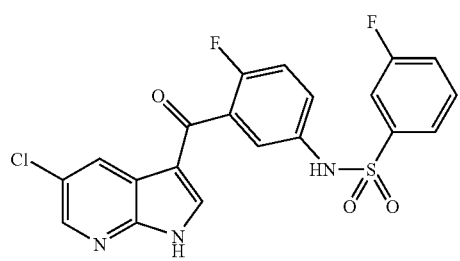 [SMILES: O=C(c1cc(NS(=O)(=O)c2cccc(F)c2)ccc1F)c1c[nH]c2ncc(Cl)cc12]
P-1666
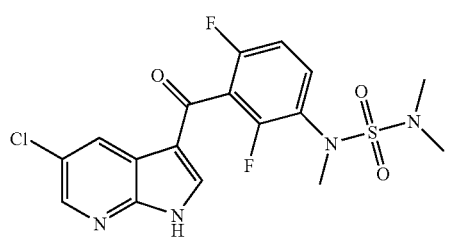 [SMILES: CN(C)S(=O)(=O)N(C)c1ccc(F)c(C(=O)c2c[nH]c3ncc(Cl)cc23)c1F]
P-1667
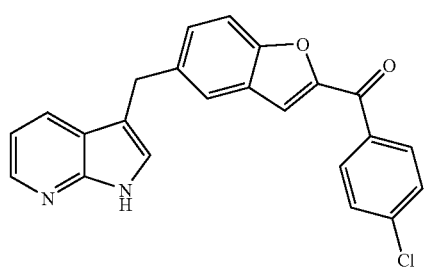 [SMILES: O=C(c1ccc(Cl)cc1)c1cc2cc(Cc3c[nH]c4ncccc34)ccc2o1]

TABLE 1-continued
Additional compounds of the invention
P-1668
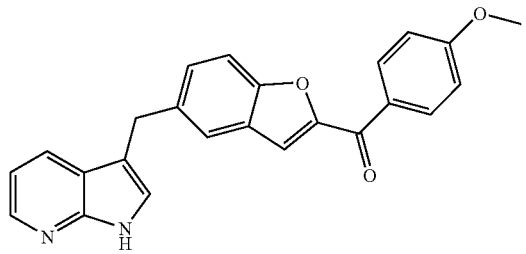 [SMILES: COc1ccc(C(=O)c2cc3cc(Cc4c[nH]c5ncccc45)ccc3o2)cc1]
P-1669
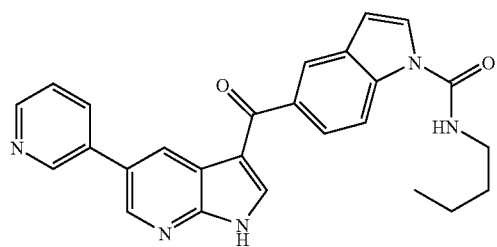 [SMILES: CCCCNC(=O)n1ccc2cc(C(=O)c3c[nH]c4ncc(-c5cccnc5)cc34)ccc21]
P-1670
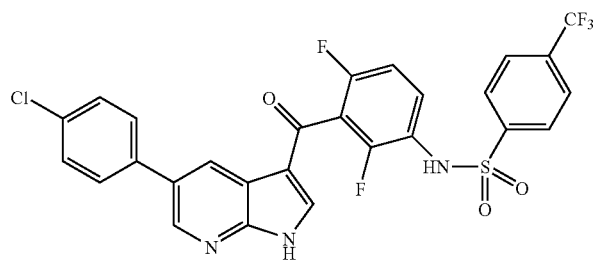 [SMILES: O=C(c1c(F)ccc(NS(=O)(=O)c2ccc(C(F)(F)F)cc2)c1F)c1c[nH]c2ncc(-c3ccc(Cl)cc3)cc12]
P-1671
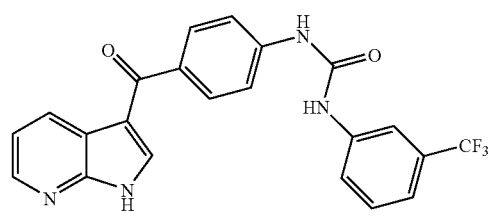 [SMILES: O=C(Nc1ccc(C(=O)c2c[nH]c3ncccc23)cc1)Nc1cccc(C(F)(F)F)c1]
P-1672
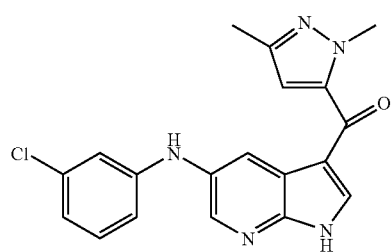 [SMILES: Cc1cc(C(=O)c2c[nH]c3ncc(Nc4cccc(Cl)c4)cc23)n(C)n1]
P-1673
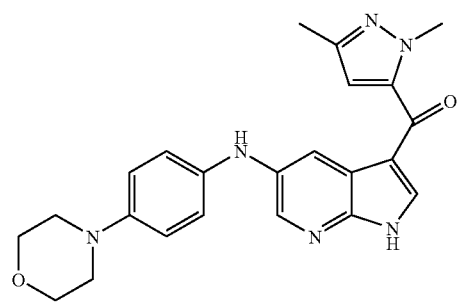 [SMILES: Cc1cc(C(=O)c2c[nH]c3ncc(Nc4ccc(N5CCOCC5)cc4)cc23)n(C)n1]

TABLE 1-continued
Additional compounds of the invention
P-1674
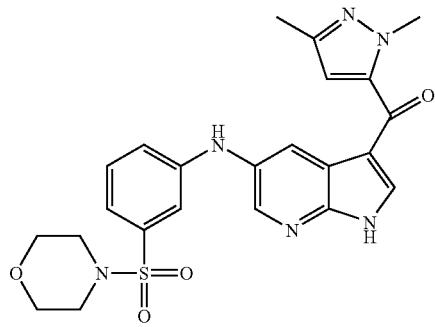 [SMILES: Cc1cc(C(=O)c2c[nH]c3ncc(Nc4cccc(S(=O)(=O)N5CCOCC5)c4)cc23)n(C)n1]
P-1675
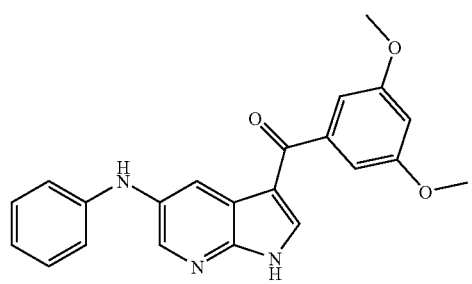 [SMILES: COc1cc(OC)cc(C(=O)c2c[nH]c3ncc(Nc4ccccc4)cc23)c1]
P-1676
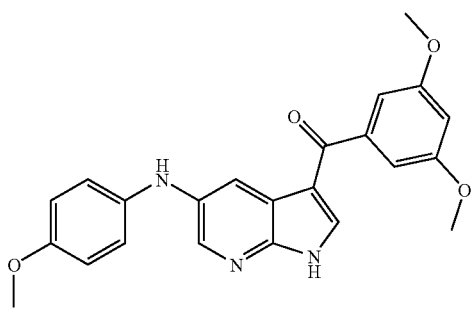 [SMILES: COc1ccc(Nc2cnc3[nH]cc(C(=O)c4cc(OC)cc(OC)c4)c3c2)cc1]
P-1677
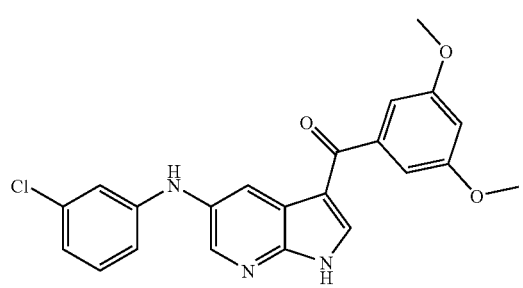 [SMILES: COc1cc(OC)cc(C(=O)c2c[nH]c3ncc(Nc4cccc(Cl)c4)cc23)c1]
P-1678
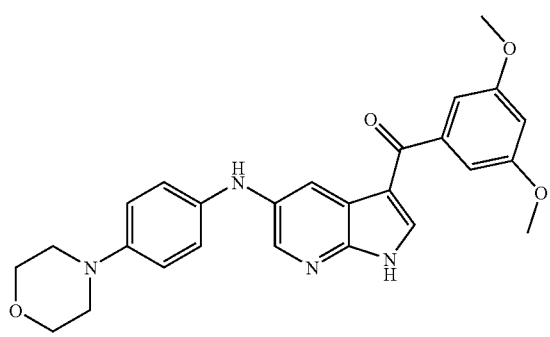 [SMILES: COc1cc(OC)cc(C(=O)c2c[nH]c3ncc(Nc4ccc(N5CCOCC5)cc4)cc23)c1]

TABLE 1-continued
Additional compounds of the invention
P-1679
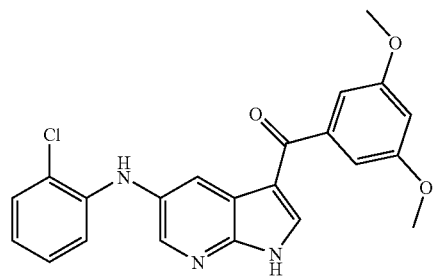 [SMILES: COc1cc(OC)cc(C(=O)c2c[nH]c3ncc(Nc4ccccc4Cl)cc23)c1]
P-1680
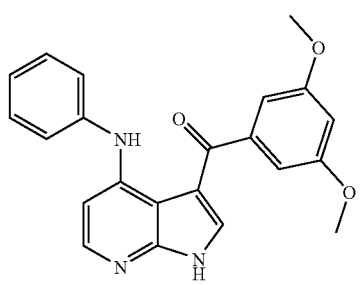 [SMILES: COc1cc(OC)cc(C(=O)c2c[nH]c3nccc(Nc4ccccc4)c23)c1]
P-1681
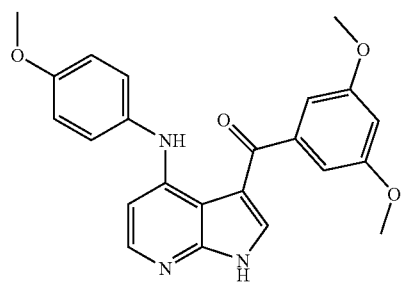 [SMILES: COc1ccc(Nc2ccnc3[nH]cc(C(=O)c4cc(OC)cc(OC)c4)c23)cc1]
P-1682
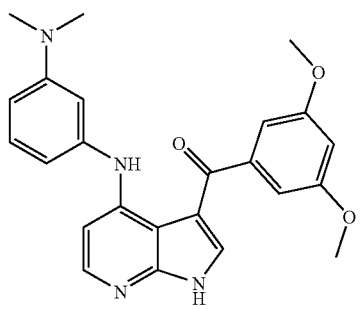 [SMILES: COc1cc(OC)cc(C(=O)c2c[nH]c3nccc(Nc4cccc(N(C)C)c4)c23)c1]
P-1683
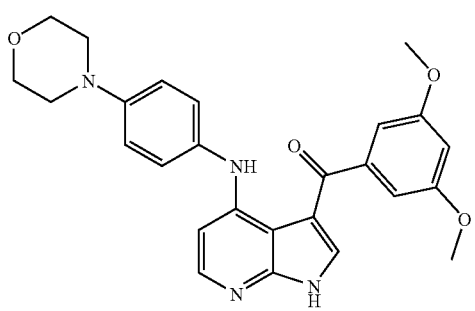 [SMILES: COc1cc(OC)cc(C(=O)c2c[nH]c3nccc(Nc4ccc(N5CCOCC5)cc4)c23)c1]

TABLE 1-continued
Additional compounds of the invention
P-1684
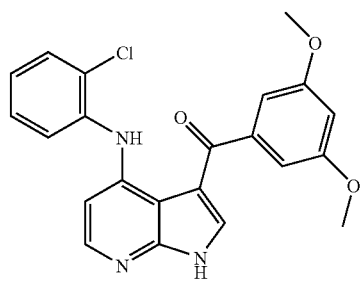 [SMILES: COc1cc(OC)cc(C(=O)c2c[nH]c3nccc(Nc4ccccc4Cl)c23)c1]
P-1685
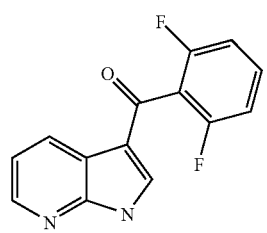 [SMILES: O=C(c1c(F)cccc1F)c1c[nH]c2ncccc12]
P-1686
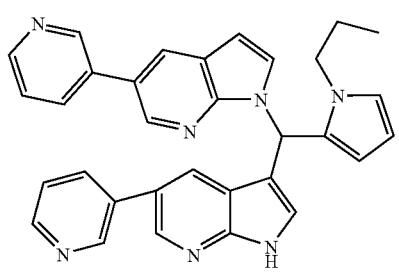 [SMILES: CCCn1cccc1C(c1c[nH]c2ncc(-c3cccnc3)cc12)n1ccc2cc(-c3cccnc3)cnc21]
P-1688
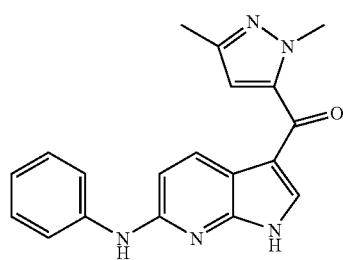 [SMILES: Cc1cc(C(=O)c2c[nH]c3nc(Nc4ccccc4)ccc23)n(C)n1]
P-1689
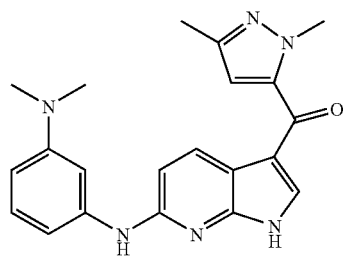 [SMILES: Cc1cc(C(=O)c2c[nH]c3nc(Nc4cccc(N(C)C)c4)ccc23)n(C)n1]
P-1690
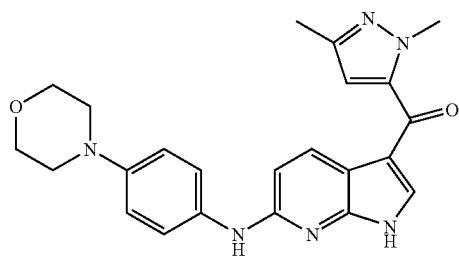 [SMILES: Cc1cc(C(=O)c2c[nH]c3nc(Nc4ccc(N5CCOCC5)cc4)ccc23)n(C)n1]

TABLE 1-continued
Additional compounds of the invention
P-1691
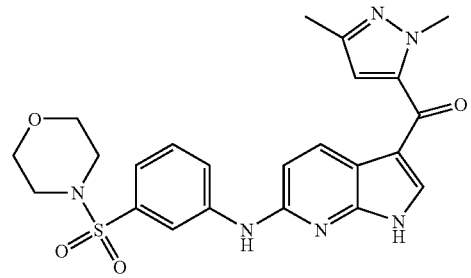 [SMILES: Cc1cc(C(=O)c2c[nH]c3nc(Nc4cccc(S(=O)(=O)N5CCOCC5)c4)ccc23)n(C)n1]
P-1692
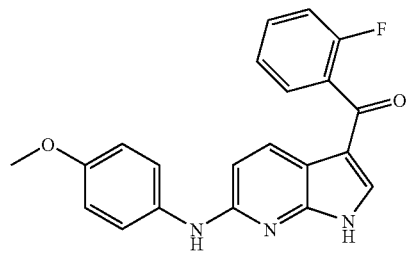 [SMILES: COc1ccc(Nc2ccc3c(C(=O)c4ccccc4F)c[nH]c3n2)cc1]
P-1693
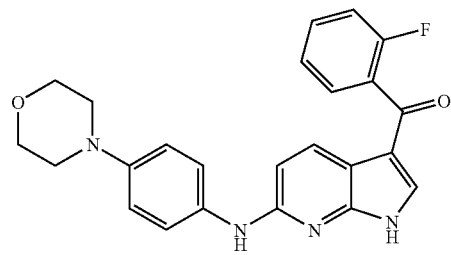 [SMILES: O=C(c1ccccc1F)c1c[nH]c2nc(Nc3ccc(N4CCOCC4)cc3)ccc12]
P-1694
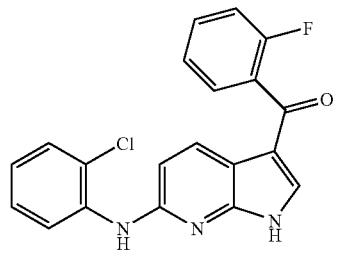
P-1695
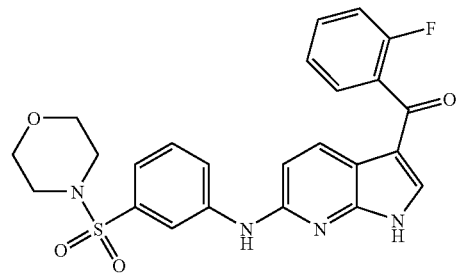 [SMILES: O=C(c1ccccc1F)c1c[nH]c2nc(Nc3cccc(S(=O)(=O)N4CCOCC4)c3)ccc12]
P-1696
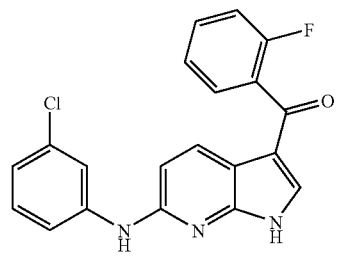 [SMILES: O=C(c1ccccc1F)c1c[nH]c2nc(Nc3cccc(Cl)c3)ccc12]

TABLE 1-continued
Additional compounds of the invention
P-1697
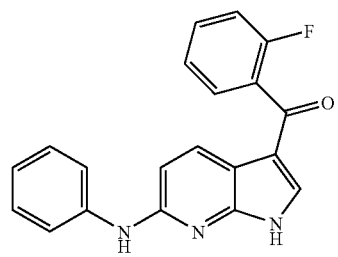 [SMILES: O=C(c1ccccc1F)c1c[nH]c2nc(Nc3ccccc3)ccc12]
P-1699
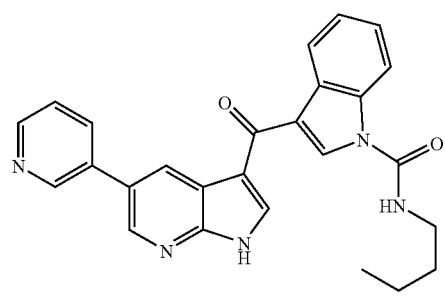 [SMILES: CCCCNC(=O)n1cc(C(=O)c2c[nH]c3ncc(-c4cccnc4)cc23)c2ccccc21]
P-1701
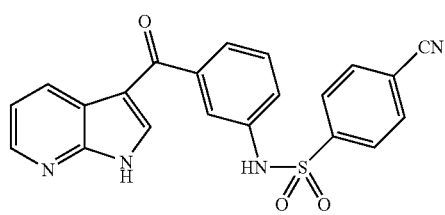 [SMILES: N#Cc1ccc(S(=O)(=O)Nc2cccc(C(=O)c3c[nH]c4ncccc34)c2)cc1]
P-1743
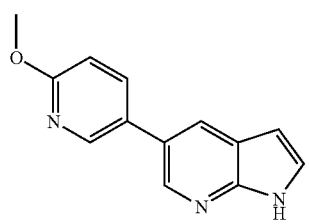 [SMILES: COc1ccc(-c2cnc3[nH]ccc3c2)cn1]
P-1745
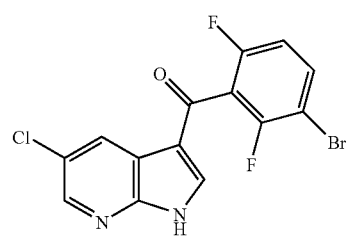 [SMILES: O=C(c1c(F)ccc(Br)c1F)c1c[nH]c2ncc(Cl)cc12]
P-1784
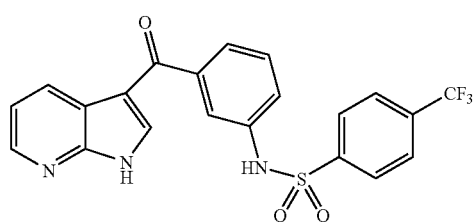 [SMILES: O=C(c1cccc(NS(=O)(=O)c2ccc(C(F)(F)F)cc2)c1)c1c[nH]c2ncccc12]

TABLE 1-continued
Additional compounds of the invention
P-1785
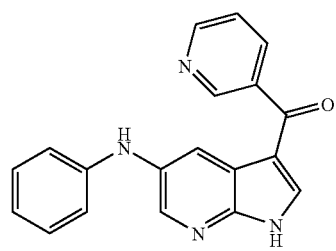 [SMILES: O=C(c1cccnc1)c1c[nH]c2ncc(Nc3ccccc3)cc12]
P-1786
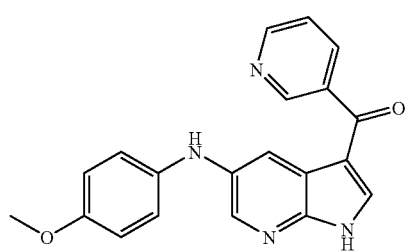 [SMILES: COc1ccc(Nc2cnc3[nH]cc(C(=O)c4cccnc4)c3c2)cc1]
P-1787
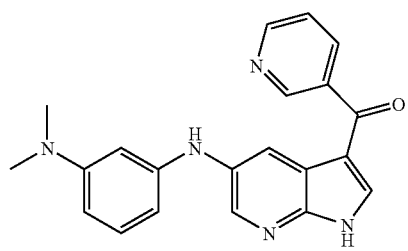 [SMILES: CN(C)c1cccc(Nc2cnc3[nH]cc(C(=O)c4cccnc4)c3c2)c1]
P-1788
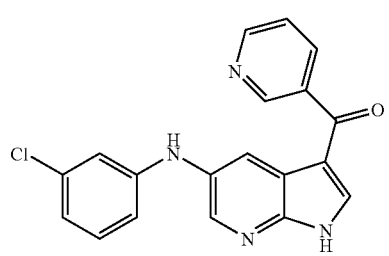 [SMILES: O=C(c1cccnc1)c1c[nH]c2ncc(Nc3cccc(Cl)c3)cc12]
P-1789
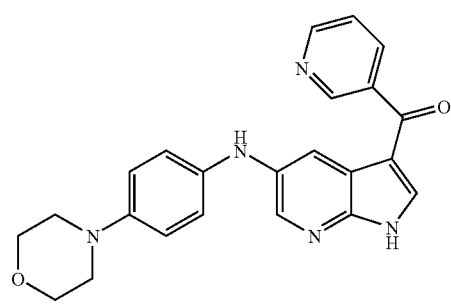 [SMILES: O=C(c1cccnc1)c1c[nH]c2ncc(Nc3ccc(N4CCOCC4)cc3)cc12]
P-1790
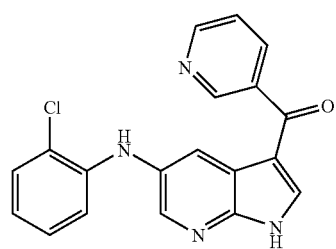 [SMILES: O=C(c1cccnc1)c1c[nH]c2ncc(Nc3ccccc3Cl)cc12]

TABLE 1-continued
Additional compounds of the invention
P-1791
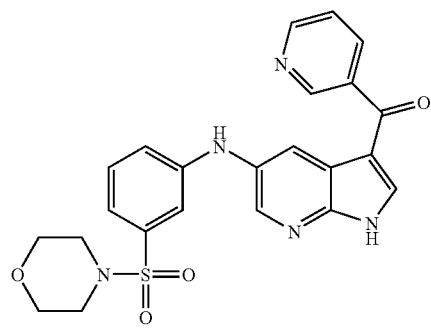 [SMILES: O=C(c1cccnc1)c1c[nH]c2ncc(Nc3cccc(S(=O)(=O)N4CCOCC4)c3)cc12]
P-1805
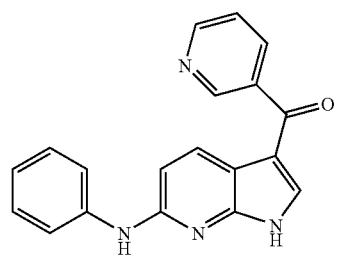 [SMILES: O=C(c1cccnc1)c1c[nH]c2nc(Nc3ccccc3)ccc12]
P-1806
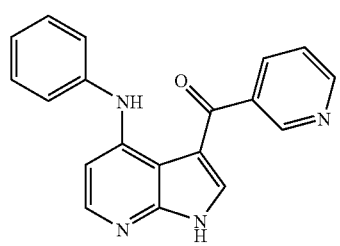 [SMILES: O=C(c1cccnc1)c1c[nH]c2nccc(Nc3ccccc3)c12]
P-1807
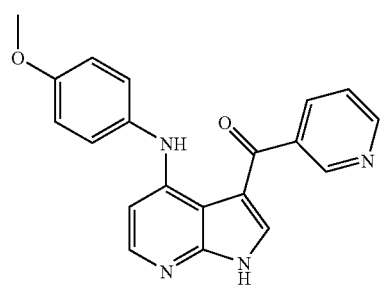 [SMILES: COc1ccc(Nc2ccnc3[nH]cc(C(=O)c4cccnc4)c23)cc1]
P-1808
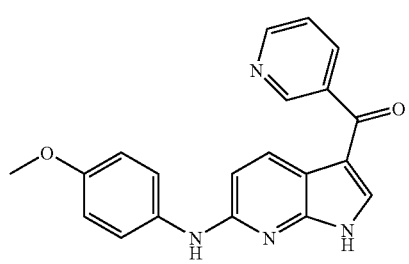 [SMILES: COc1ccc(Nc2ccc3c(C(=O)c4cccnc4)c[nH]c3n2)cc1]

TABLE 1-continued
Additional compounds of the invention
P-1809 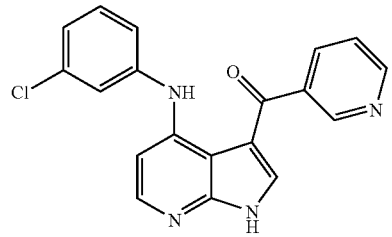 [SMILES: O=C(c1cccnc1)c1c[nH]c2nccc(Nc3cccc(Cl)c3)c12]
P-1810 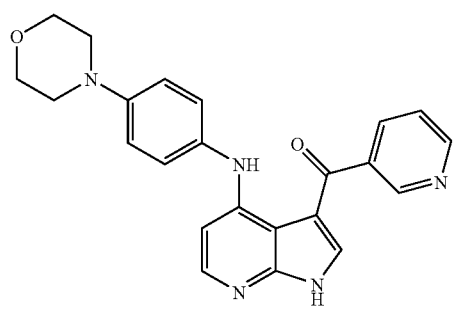 [SMILES: O=C(c1cccnc1)c1c[nH]c2nccc(Nc3ccc(N4CCOCC4)cc3)c12]
P-1811 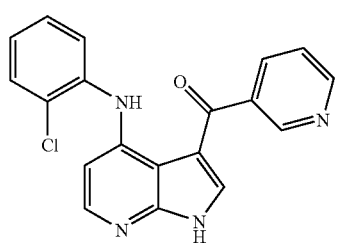 [SMILES: O=C(c1cccnc1)c1c[nH]c2nccc(Nc3ccccc3Cl)c12]
P-1812 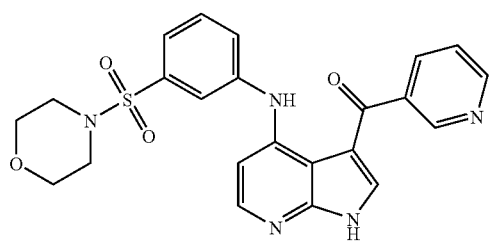 [SMILES: O=C(c1cccnc1)c1c[nH]c2nccc(Nc3cccc(S(=O)(=O)N4CCOCC4)c3)c12]
P-1813 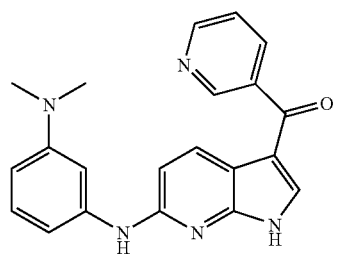 [SMILES: CN(C)c1cccc(Nc2ccc3c(C(=O)c4cccnc4)c[nH]c3n2)c1]
P-1814 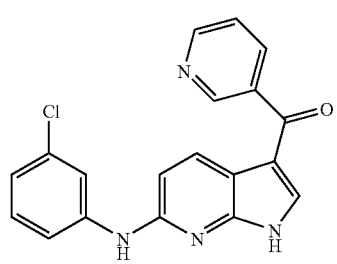 [SMILES: O=C(c1cccnc1)c1c[nH]c2nc(Nc3cccc(Cl)c3)ccc12]

TABLE 1-continued
Additional compounds of the invention
P-1815
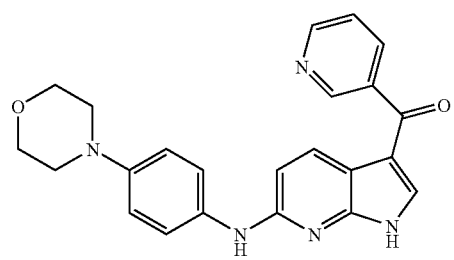 [SMILES: O=C(c1cccnc1)c1c[nH]c2nc(Nc3ccc(N4CCOCC4)cc3)ccc12]
P-1826
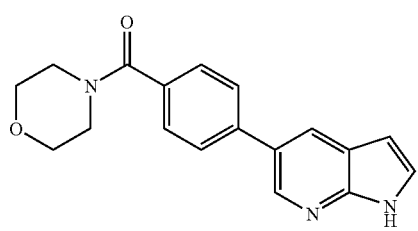 [SMILES: O=C(c1ccc(-c2cnc3[nH]ccc3c2)cc1)N1CCOCC1]
P-1829
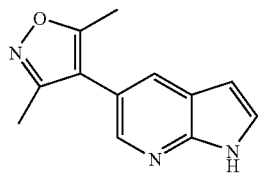 [SMILES: Cc1noc(C)c1-c1cnc2[nH]ccc2c1]
P-1831
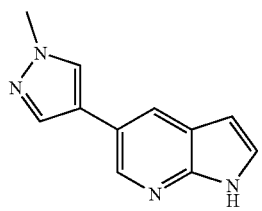
P-1832
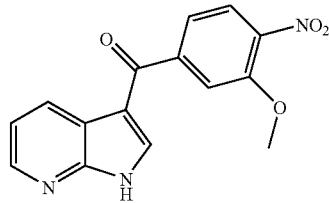 [SMILES: COc1cc(C(=O)c2c[nH]c3ncccc23)ccc1[N+](=O)[O-]]
P-1833
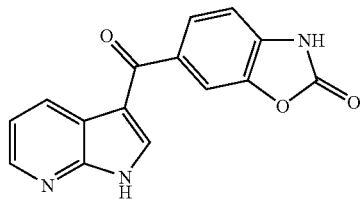 [SMILES: O=C(c1ccc2[nH]c(=O)oc2c1)c1c[nH]c2ncccc12]

TABLE 1-continued
Additional compounds of the invention
P-1834
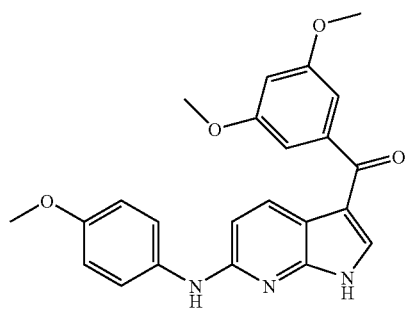 [SMILES: COc1ccc(Nc2ccc3c(C(=O)c4cc(OC)cc(OC)c4)c[nH]c3n2)cc1]
P-1835
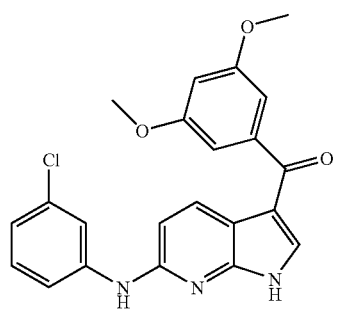 [SMILES: COc1cc(OC)cc(C(=O)c2c[nH]c3nc(Nc4cccc(Cl)c4)ccc23)c1]
P-1836
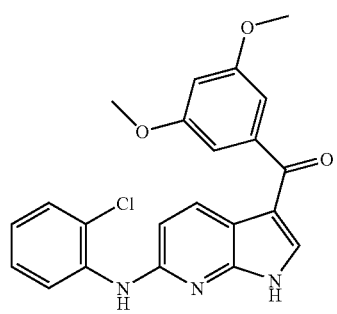 [SMILES: COc1cc(OC)cc(C(=O)c2c[nH]c3nc(Nc4ccccc4Cl)ccc23)c1]
P-1837
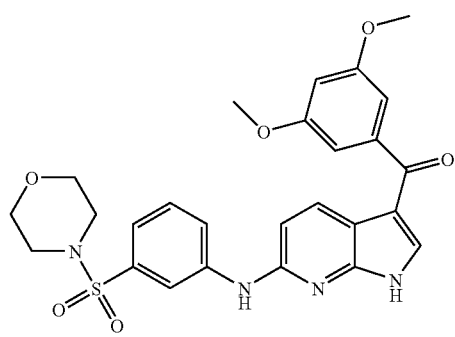 [SMILES: COc1cc(OC)cc(C(=O)c2c[nH]c3nc(Nc4cccc(S(=O)(=O)N5CCOCC5)c4)ccc23)c1]
P-1838
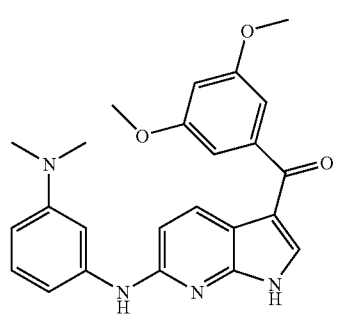 [SMILES: COc1cc(OC)cc(C(=O)c2c[nH]c3nc(Nc4cccc(N(C)C)c4)ccc23)c1]

TABLE 1-continued
Additional compounds of the invention
P-1846 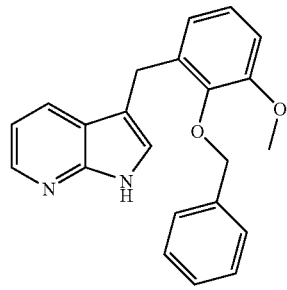 [SMILES: COc1cccc(Cc2c[nH]c3ncccc23)c1OCc1ccccc1]
P-1847 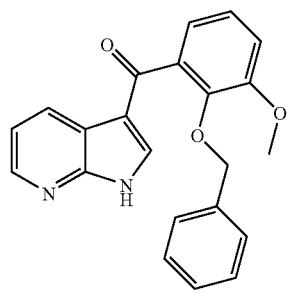 [SMILES: COc1cccc(C(=O)c2c[nH]c3ncccc23)c1OCc1ccccc1]
P-1856 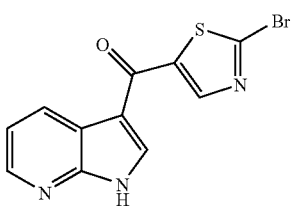 [SMILES: O=C(c1cnc(Br)s1)c1c[nH]c2ncccc12]
P-1863 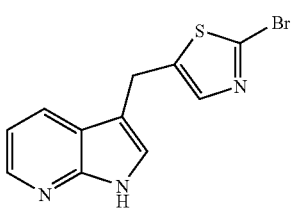 [SMILES: Brc1ncc(Cc2c[nH]c3ncccc23)s1]
P-1866 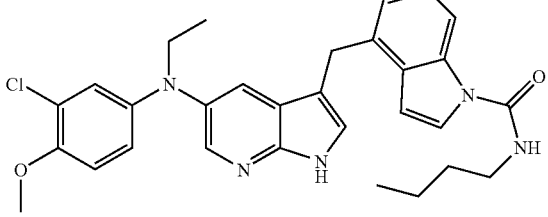
P-1883 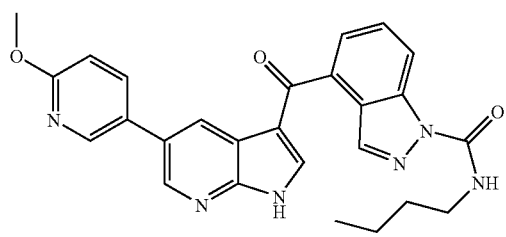

TABLE 1-continued
Additional compounds of the invention
P-1888
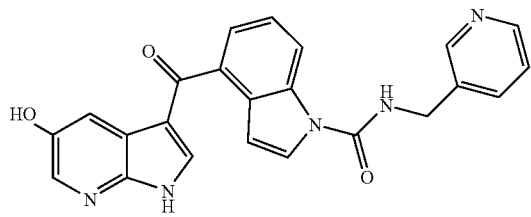 [SMILES: O=C(c1c[nH]c2ncc(O)cc12)c1cccc2c1ccn2C(=O)NCc1cccnc1]
P-1889
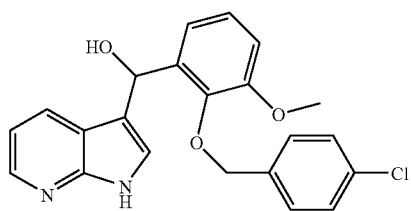 [SMILES: COc1cccc(C(O)c2c[nH]c3ncccc23)c1OCc1ccc(Cl)cc1]
P-1890
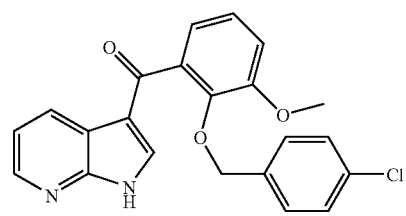 [SMILES: COc1cccc(C(=O)c2c[nH]c3ncccc23)c1OCc1ccc(Cl)cc1]
P-1898
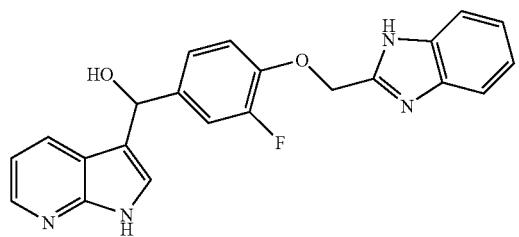 [SMILES: OC(c1ccc(OCc2nc3ccccc3[nH]2)c(F)c1)c1c[nH]c2ncccc12]
P-1936
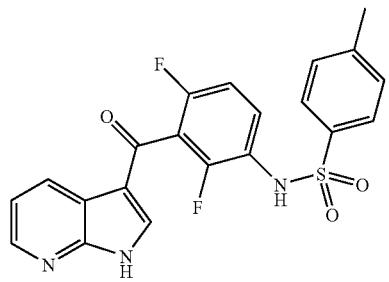 [SMILES: Cc1ccc(S(=O)(=O)Nc2ccc(F)c(C(=O)c3c[nH]c4ncccc34)c2F)cc1]
P-1971
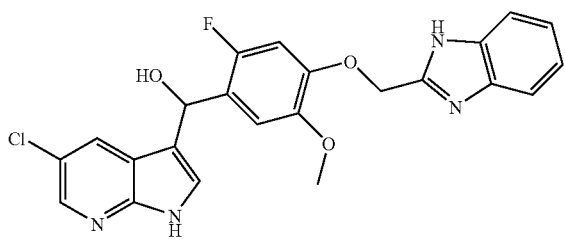 [SMILES: COc1cc(C(O)c2c[nH]c3ncc(Cl)cc23)c(F)cc1OCc1nc2ccccc2[nH]1]

TABLE 1-continued
Additional compounds of the invention
P-1981 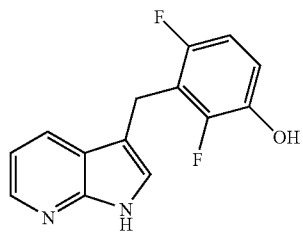 [SMILES: Oc1ccc(F)c(Cc2c[nH]c3ncccc23)c1F]
P-1985 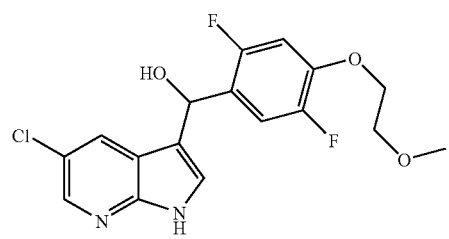 [SMILES: COCCOc1cc(F)c(C(O)c2c[nH]c3ncc(Cl)cc23)cc1F]
P-1995 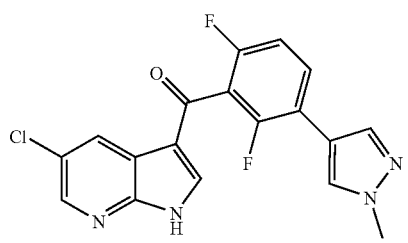 [SMILES: Cn1cc(-c2ccc(F)c(C(=O)c3c[nH]c4ncc(Cl)cc34)c2F)cn1]
P-1999 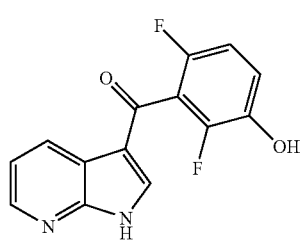 [SMILES: O=C(c1c(F)ccc(O)c1F)c1c[nH]c2ncccc12]
P-2001 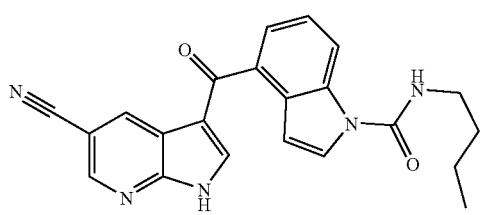 [SMILES: CCCCNC(=O)n1ccc2c(C(=O)c3c[nH]c4ncc(C#N)cc34)cccc21]
P-2007 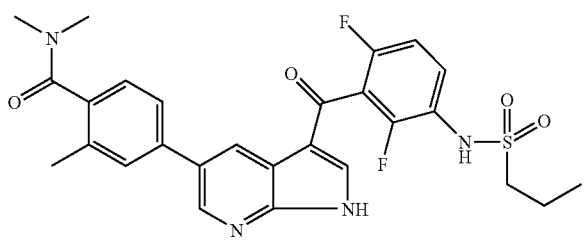 [SMILES: CCCS(=O)(=O)Nc1ccc(F)c(C(=O)c2c[nH]c3ncc(-c4ccc(C(=O)N(C)C)c(C)c4)cc23)c1F]

TABLE 1-continued
Additional compounds of the invention
P-2008
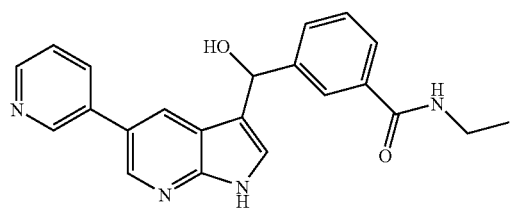 [SMILES: CCNC(=O)c1cccc(C(O)c2c[nH]c3ncc(-c4cccnc4)cc23)c1]
P-2009
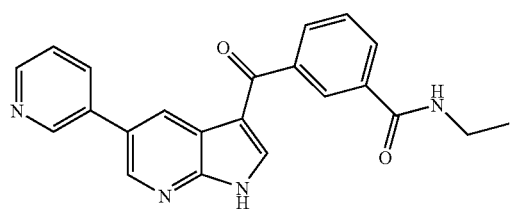
P-2010
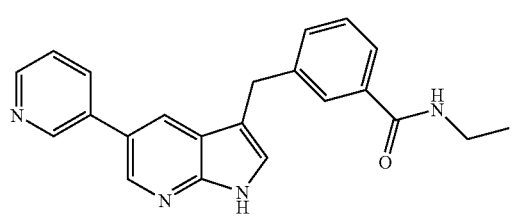 [SMILES: CCNC(=O)c1cccc(Cc2c[nH]c3ncc(-c4cccnc4)cc23)c1]
P-2017
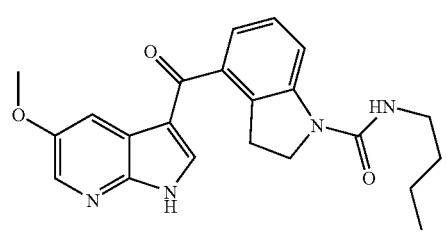 [SMILES: CCCCNC(=O)N1CCc2c(C(=O)c3c[nH]c4ncc(OC)cc34)cccc21]
P-2018
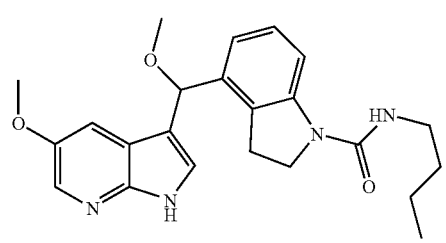 [SMILES: CCCCNC(=O)N1CCc2c(C(OC)c3c[nH]c4ncc(OC)cc34)cccc21]
P-2019
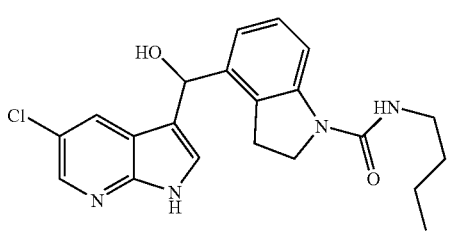 [SMILES: CCCCNC(=O)N1CCc2c(C(O)c3c[nH]c4ncc(Cl)cc34)cccc21]
P-2021
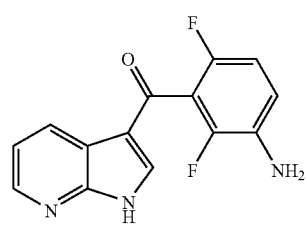 [SMILES: Nc1ccc(F)c(C(=O)c2c[nH]c3ncccc23)c1F]

TABLE 1-continued
Additional compounds of the invention
P-2023
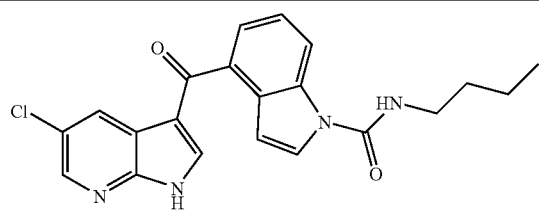
P-2027
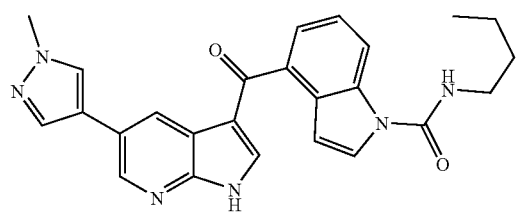 [SMILES: CCCCNC(=O)n1ccc2c(C(=O)c3c[nH]c4ncc(-c5cnn(C)c5)cc34)cccc21]
P-2028
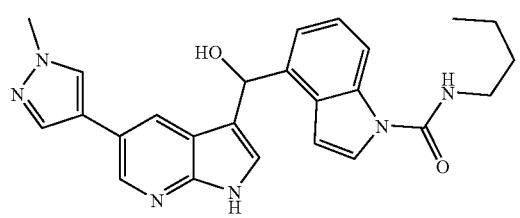 [SMILES: CCCCNC(=O)n1ccc2c(C(O)c3c[nH]c4ncc(-c5cnn(C)c5)cc34)cccc21]
P-2029
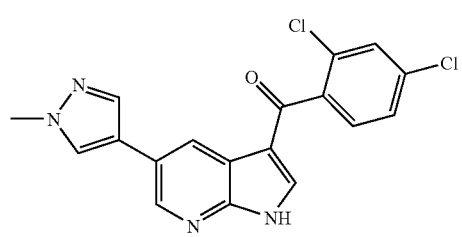 [SMILES: Cn1cc(-c2cnc3[nH]cc(C(=O)c4ccc(Cl)cc4Cl)c3c2)cn1]
P-2030
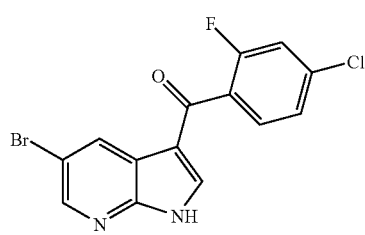 [SMILES: O=C(c1ccc(Cl)cc1F)c1c[nH]c2ncc(Br)cc12]
P-2031
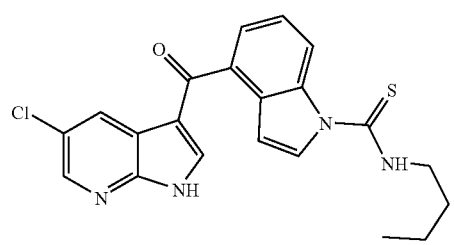 [SMILES: CCCCNC(=S)n1ccc2c(C(=O)c3c[nH]c4ncc(Cl)cc34)cccc21]
P-2032
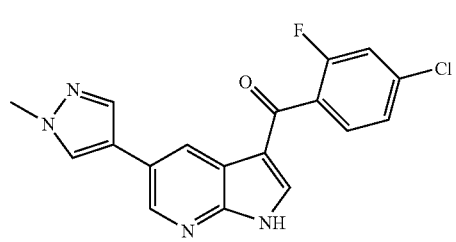 [SMILES: Cn1cc(-c2cnc3[nH]cc(C(=O)c4ccc(Cl)cc4F)c3c2)cn1]

TABLE 1-continued
Additional compounds of the invention
P-2065
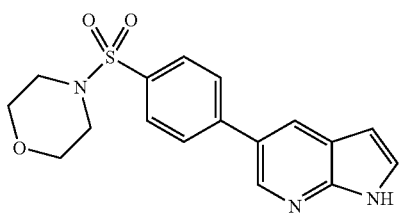 [SMILES: O=S(=O)(c1ccc(-c2cnc3[nH]ccc3c2)cc1)N1CCOCC1]
P-2066
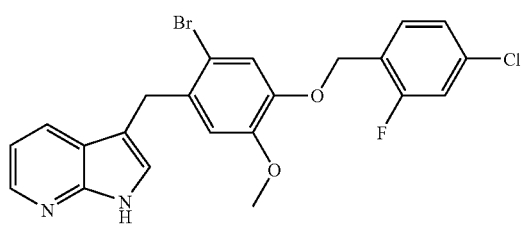 [SMILES: COc1cc(Cc2c[nH]c3ncccc23)c(Br)cc1OCc1ccc(Cl)cc1F]
P-2067
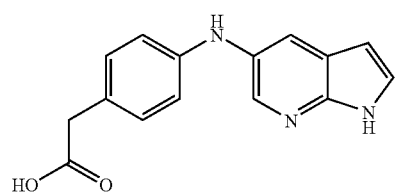 [SMILES: O=C(O)Cc1ccc(Nc2cnc3[nH]ccc3c2)cc1]
P-2068
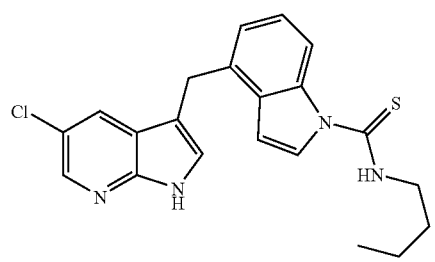 [SMILES: CCCCNC(=S)n1ccc2c(Cc3c[nH]c4ncc(Cl)cc34)cccc21]
P-2069
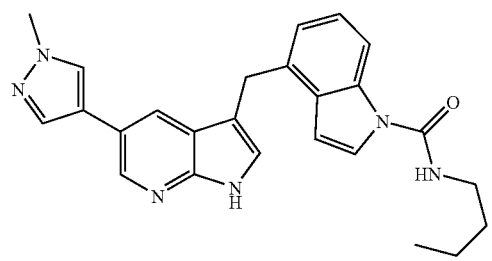 [SMILES: CCCCNC(=O)n1ccc2c(Cc3c[nH]c4ncc(-c5cnn(C)c5)cc34)cccc21]
P-2070
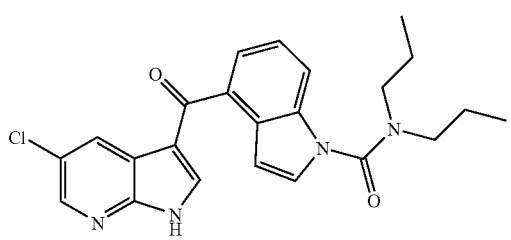 [SMILES: CCCN(CCC)C(=O)n1ccc2c(C(=O)c3c[nH]c4ncc(Cl)cc34)cccc21]

TABLE 1-continued
Additional compounds of the invention
P-2071
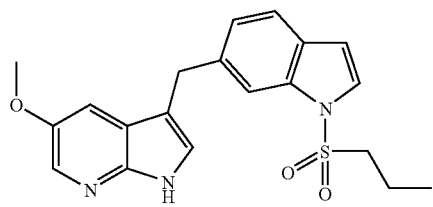 [SMILES: CCCS(=O)(=O)n1ccc2ccc(Cc3c[nH]c4ncc(OC)cc34)cc21]
P-2072
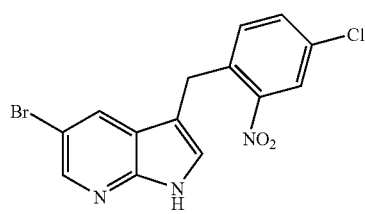 [SMILES: O=[N+]([O-])c1cc(Cl)ccc1Cc1c[nH]c2ncc(Br)cc12]
P-2073
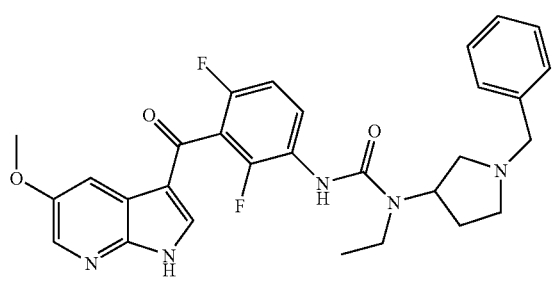 [SMILES: CCN(C(=O)Nc1ccc(F)c(C(=O)c2c[nH]c3ncc(OC)cc23)c1F)C1CCN(Cc2ccccc2)C1]
P-2074
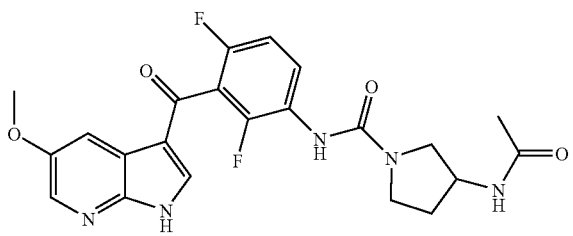 [SMILES: COc1cnc2[nH]cc(C(=O)c3c(F)ccc(NC(=O)N4CCC(NC(C)=O)C4)c3F)c2c1]
P-2077
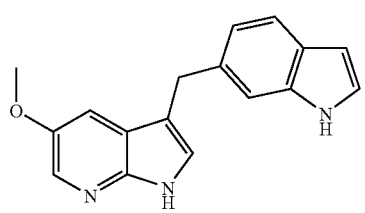 [SMILES: COc1cnc2[nH]cc(Cc3ccc4cc[nH]c4c3)c2c1]
P-2078
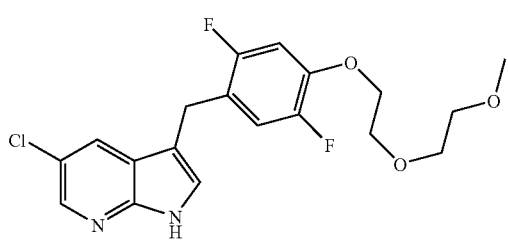 [SMILES: COCCOCCOc1cc(F)c(Cc2c[nH]c3ncc(Cl)cc23)cc1F]

TABLE 1-continued
Additional compounds of the invention
P-2079 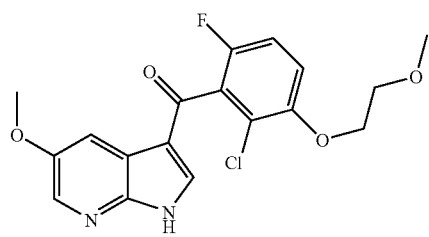 [SMILES: COCCOc1ccc(F)c(C(=O)c2c[nH]c3ncc(OC)cc23)c1Cl]
P-2080 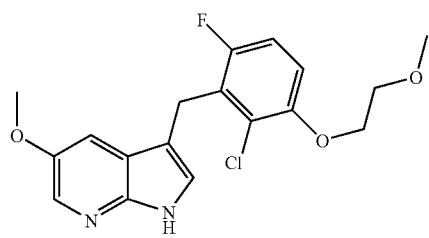 [SMILES: COCCOc1ccc(F)c(Cc2c[nH]c3ncc(OC)cc23)c1Cl]
P-2081 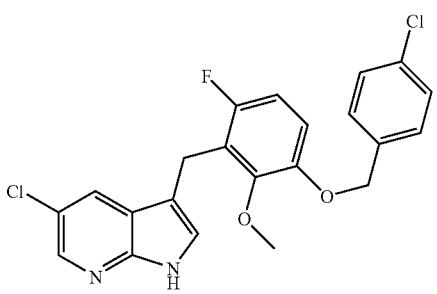 [SMILES: COc1c(OCc2ccc(Cl)cc2)ccc(F)c1Cc1c[nH]c2ncc(Cl)cc12]
P-2082 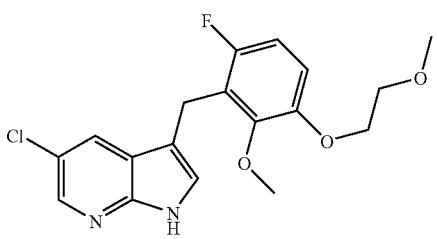 [SMILES: COCCOc1ccc(F)c(Cc2c[nH]c3ncc(Cl)cc23)c1OC]
P-2083 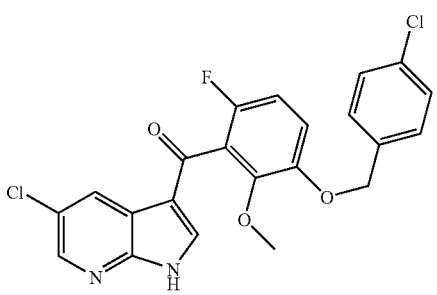 [SMILES: COc1c(OCc2ccc(Cl)cc2)ccc(F)c1C(=O)c1c[nH]c2ncc(Cl)cc12]
P-2084 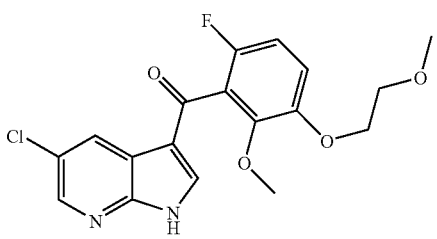 [SMILES: COCCOc1ccc(F)c(C(=O)c2c[nH]c3ncc(Cl)cc23)c1OC]

TABLE 1-continued
Additional compounds of the invention
P-2087
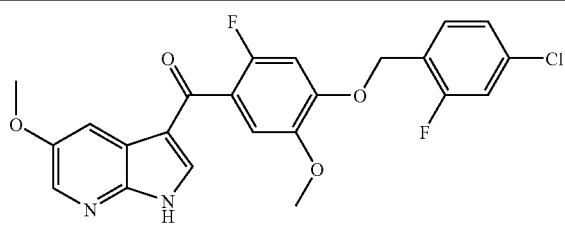
P-2088
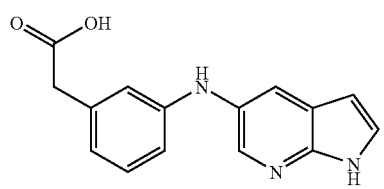 [SMILES: O=C(O)Cc1cccc(Nc2cnc3[nH]ccc3c2)c1]
P-2089
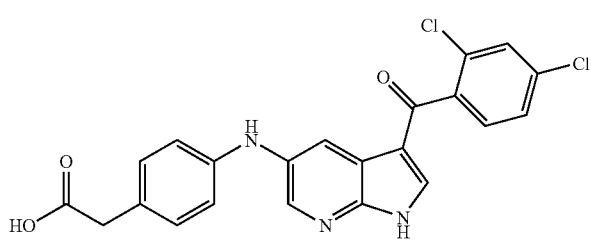 [SMILES: O=C(O)Cc1ccc(Nc2cnc3[nH]cc(C(=O)c4ccc(Cl)cc4Cl)c3c2)cc1]
P-2090
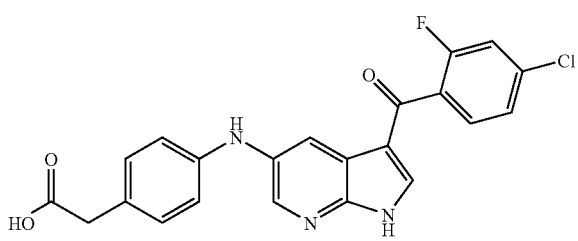 [SMILES: O=C(O)Cc1ccc(Nc2cnc3[nH]cc(C(=O)c4ccc(Cl)cc4F)c3c2)cc1]
P-2091
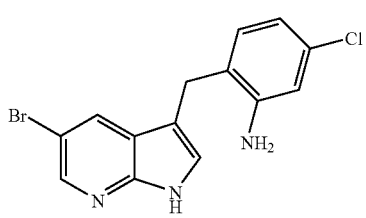
P-2092
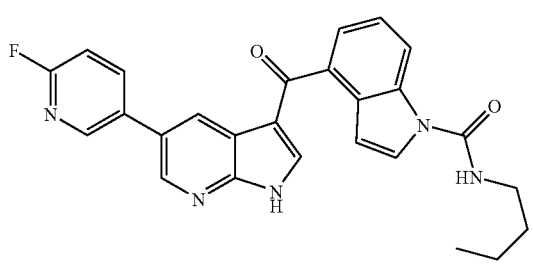 [SMILES: CCCCNC(=O)n1ccc2c(C(=O)c3c[nH]c4ncc(-c5ccc(F)nc5)cc34)cccc21]
P-2093
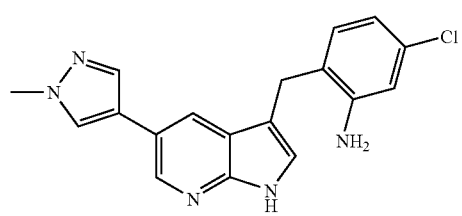 [SMILES: Cn1cc(-c2cnc3[nH]cc(Cc4ccc(Cl)cc4N)c3c2)cn1]

TABLE 1-continued

Additional compounds of the invention

P-2095
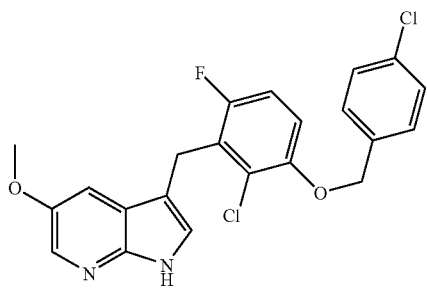 [SMILES: COc1cnc2[nH]cc(Cc3c(F)ccc(OCc4ccc(Cl)cc4)c3Cl)c2c1]

P-2096
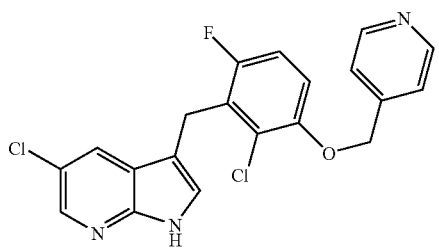 [SMILES: Fc1ccc(OCc2ccncc2)c(Cl)c1Cc1c[nH]c2ncc(Cl)cc12]

P-2097
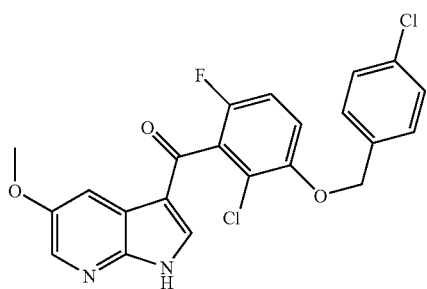 [SMILES: COc1cnc2[nH]cc(C(=O)c3c(F)ccc(OCc4ccc(Cl)cc4)c3Cl)c2c1]

P-2098
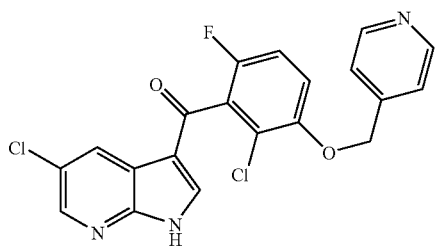 [SMILES: O=C(c1c(F)ccc(OCc2ccncc2)c1Cl)c1c[nH]c2ncc(Cl)cc12]

Example 75

Kinase Activity Assays

The effect of potential modulators of kinase activity can be measured in a variety of different assays known in the art. For example, direct radiometric, indirect FRET or AlphaScreen assays may be used to assess the level of phosphorylation of a substrate in the presence of test compounds in order to determine the inhibitory affect of the compound on the kinase. Invitrogen (Carlsbad, Calif.) uses a FRET based assay for Btk, EGFR, EphB2, Flt3, lrak4, Kdr, MAP2K1, MAPKAPK2, PDGFRB, PKC theta, Stk6 and Yes. For these assays, compounds of the invention were screened by Invitrogen using Z'-Lyte™ kinase assay.

Briefly, the Invitrogen kinase assay involves use of a specific peptide substrate optimized for each kinase, containing a fluorophore at each end that make up the FRET pair. The peptide sensitivity to proteolytic cleavage depends on phosphorylation of the peptide. Non-phosphorylated peptide is cleaved by a protease while peptide phosphorylated by the kinase is not cleaved. Cleavage of the peptide disrupts the FRET between the donor (coumarin) and acceptor (fluorescein) fluorophores, resulting in an increase in the ratio of donor emission to acceptor emission. The emission ratio of coumarin to fluorescein is used to assess the reaction progress. The extent of phosphorylation is determined from the emission ratio, which is low when the kinase is active (phosphorylated peptide is not cleaved, FRET pair connected) or higher for inhibited kinase (non-phosphorylated peptide is cleaved, FRET pair separated). Thus, the assay involves a kinase reaction in the presence of varying concentrations of a given compound, a development reaction with site specific protease, and detection of the fluorescent emission ratio of coumarin and fluorscein. The emission ratio as a function of compound concentration was used to determine the $IC_{50}$ value. Reaction conditions for each kinase are determined to provide optimal reaction times, incubation temperature, kinase and ATP concentrations. Test samples are made up in 1× kinase buffer (50 mM HEPES pH 7.5, 50 mM MgCl$_2$, 5 mM EGTA, 0.05% BRIJ-35) and compound at desired concentration prepared in DMSO such that the final DMSO is 1%. Assay controls include 0% phosphorylation, which contains no ATP, 100% phosphorylation control, which consists of a synthetically phosphorylated peptide, and 0% inhibition control, which contains active kinase conditions without compound. Typically, assay plates are prepared to 10 µl final volume per sample, adding 2.5 µl of compound at 4× the desired concentration in 4% DMSO (serial dilution of compound provides concentration curve), 5 µl of the desired kinase mixed with Z'-LYTE™ peptide substrate (2× in 2× kinase buffer, final peptide at 2 µM), and 2.5 µl of 4×ATP solution. All kinase except for MAP2K1 were at 10 µM ATP in the kinase reaction, while MAP2K1 was at 100 µM. Samples are mixed and the kinase reaction is incubated 1 hour at room temperature, after which 5 µl of development solution is added and mixed. After incubation for another 1 hour at room temperature, 5 µl of stop reagent is added to each sample and mixed. The fluorescence signals are measured to determine the emission ratio.

AlphaScreen assay was used to screen additional kinases. The assay is similarly dependent on the phosphorylation of a peptide substrate. In this assay, an antibody that recognizes phosphorylated substrate is bound to an acceptor bead. The peptide substrate is attached to biotin, which binds to a donor head that contains streptavidin. Thus phosphorylated substrate is bound by antibody and streptavidin, bringing the donor and acceptor heads into close proximity when kinase is not inhibited. The donor produces singlet oxygen which results in emission from the acceptor when they are in close proximity. Conversely, when kinase is inhibited, the donor and acceptor beads are not associated and the emission from the acceptor is reduced. The fluorescence signal vs. compound concentration was used to determine the IC$_{50}$ values.

Genetic Engineering

For some of the kinase screens, preparation of the kinase was required. Plasmids encoding a selection of kinase enzymes were engineered using common polymerase chain reaction (PCR) methods. The relevant DNA sequences and encoded protein sequences used in the assay are shown for each (see below). Complementary DNA cloned from various human tissues were purchased from Invitrogen, and these were used as substrates in the PCR reactions. Specific custom synthetic oligonucleotide primers (Invitrogen see below) were designed to initiate the PCR product, and also to provide the appropriate restriction enzyme cleavage sites for ligation with the plasmids. In selected cases additional pairs of oligonucleotides (see below) were used to introduce mutations into the coding sequence to alter the sequence for enzyme activation (BRAF), for removing problematic surface Cys residues (FGFR1), or for disabling the capacity to bind ATP (MEK1 substrate).

In the case of KIT, the entire sequence encoding the enzyme was made through a gene synthesis procedure, using custom synthetic oligonucleotides covering the entire coding sequence (Invitrogen).

The plasmids used for ligation with the kinase-encoding inserts were derivatives of either pET (Novagen) for expression using E. coli, or pFastBac (Invitrogen) for expression using baculovirus infection of insect cell cultures. In each of these cases the kinase was engineered to include a Histidine tag for purification using metal affinity chromatography.

In some cases the kinase-encoding plasmids were engineered as bicistronic mRNA to co-express a second protein that modifies the kinase protein during its expression in the host cell. In the cases of Abl, FGFR1, Flt1, Kdr, Kit, Met, Ret, and Src protein tyrosine phosphatase 1B (PTP), was co-expressed for dephosphorylation of the phospho-Tyrosines. In the case of ERK2, an activated form of MEK1 (MEK1DD), was co-expressed for phosphorylation and activation of the ERK2. In the case of p38a, an activated form of MEK6 (MKK6) was co-expressed for phosphorylation and activation of the p38a. In the case of BRAF, the chaperone CDC37, was co-expressed for more efficient protein folding of the BRAF.

Plasmids encoding phosphorylation substrate proteins were expressed as N-terminal GST fusions and C-terminal biotinylation fusions, using pGEX vectors (Amersham) modified to include sequences encoding a C-terminal biotinylation tag. These substrates include MEK1, a substrate for BRAF, and BAD, a substrate for Pim1.

Protein Expression in E. coli and Purification.

For protein expression, plasmids containing genes of interest were transformed into E. coli strains BL21(DE3)RIL or pLyS (Invitrogen) and transformants selected for growth on LB agar plates containing appropriate antibiotics. Single colonies were grown overnight at 37° C. in 200 ml TB (Terrific broth) media. 16×1 L of fresh TB media in 2.8 L flasks were inoculated with 10 ml of overnight culture and grown with constant shaking at 37° C. Once cultures reached an absorbance of 1.0 at 600 nm, IPTG was added and cultures were allowed to grow for a further 12 to 18 hrs at temperatures ranging from 12-30° C. Cells were harvested by centrifugation and pellets frozen at −80° C. until ready for lysis.

For protein Purification; frozen E. coli cell pellets were resuspended in lysis buffer and lysed using standard mechanical methods. Soluble proteins were purified via poly-Histidine tags using immobilized metal affinity purification IMAC. In the case of all kinases described here all have been purified using a 3 step purification process utilizing; IMAC, size exclusion chromatography and ion exchange chromatography. In most cases the poly-Histidine tag was removed using Thrombin (Calbiochem).

In some cases the purification protocol required modifications in order to stabilize soluble protein during purification and concentration. In the case of BRaf 5 mM MgCl$_2$ was required throughout purification. In the case of Ret a combination of 1 mM ATP and 5 mM MgCl$_2$ was required during cell lysis and throughout purification. In the case of Zap70 a 5M excess of AMP-PCP over protein was required as well as 5 mM MgCl$_2$.

Baculovirus Expression Vector System

Virus Production:

The transfection of a monolayer of Spodoptera frugiperda (Sf9) cells was performed utilizing a bacmid containing the gene of interest and Cellfectin (Invitrogen) transfection reagent in antibiotic-free, serum-free Grace's complete media (Invitrogen). After a five hour incubation, the transfection media was removed, and the monolayer was fed with Grace's media containing 10% FBS and antibiotics. After a 72 to 96 hr incubation, the cell supernatant containing the virus was harvested. The titer of the virus stock was then determined using a baculovirus titer kit (BD). The virus stock was then expanded using low Multiplicity of Infection (MOI of 0.1) cultures and harvested 48 hrs post-infection. The titer of the expanded virus stock was then determined for use in recombinant protein production.

Protein Production:

The protein expression level was optimized by varying the MOI (1-10) and time of harvest (48-72 hrs). Sf9 cells were adapted to SF-900 II serum-free media and grown in suspension in spinner flasks. The cell suspension was then used to inoculate a Wave bioreactor for 25 L production scale. Cells were harvested 48-72 hrs post-infection and stored at −80° C.

until ready for lysis. Proteins were purified similarly to those expressed in E. coli.

Kinase Assay

AlphaScreen assays were done using compounds dissolved in DMSO to a concentration of 20 mM. The compounds were diluted accordingly to the desired final concentrations in each sample well, using 1:3 serial dilution for a total of 8 concentration points. Plates were prepared such that each kinase reaction is 20 µl in 1× kinase buffer, 5% DMSO and 10 µM ATP. Kinase and assay conditions (defined below) used for each kinase are shown in Table 3. After incubation of the kinase reaction for 1 hour at room temperature, 5 µl of donor beads in stop buffer (50 mM EDTA in 1× kinase buffer) was added, the sample was mixed and incubated for 20 minutes at room temperature before adding 5 µl of acceptor beads in stop buffer. The samples were incubated for 60 minutes at room temperature and the signal per well was read on AlphaQuest reader. Phosphorylated substrate results in binding of the antibody and association of the donor and acceptor beads such that signal correlates with kinase activity. The signal vs. compound concentration was used to determine the $IC_{50}$.

Assay Condition A:

| | |
|---|---|
| Kinase buffer | HEPES 50 mM, pH 7.2, 5 mM $MgCl_2$, 5 mM $MnCl_2$, 0.2% BSA, 0.01% NP-40 |
| Substrate | 100 nM biotin-(E4Y)3 (Open Source Biotech, Inc.) |
| Donor bead | 1 µg/ml Streptavidin coated bead (Perkin Elmer Life Science). |
| Acceptor bead | 1 µg/ml PY20 coated bead (Perkin Elmer Life Science) |

Assay Condition B:

| | |
|---|---|
| Kinase buffer | 50 mM HEPES pH 7.0, 50 mM NaCl, 2 mM $MgCl_2$, 1 mM $MnCl_2$, 1 mM DTT, 0.01% Tween-20. |
| Substrate | 100 nM biotin-MEK1 (prepared as described above). |
| Donor bead | 10 µg/ml Streptavidin coated bead (Perkin Elmer Life Science). |
| Acceptor bead | 10 µg/ml Protein A coated, bound to anti phospho MEK1/2 antibody (CellSignal) |

Assay Condition C:

| | |
|---|---|
| Kinase buffer | 8 mM HEPES pH 7.0, 4 mM $MgCl_2$, 1 mM DTT, 0.01% Tween-20. |
| Substrate | 100 nM biotin-MBP (Upstate Biotechnology, Waltham, MA). |
| Donor bead | 10 µg/ml Streptavidin coated bead (Perkin Elmer Life Science). |
| Acceptor bead | 10 µg/ml Protein A coated, bound to anti phospho MBP antibody (CellSignal) |

Assay Condition D:

| | |
|---|---|
| Kinase buffer | 8 mM MOPS pH 7.4, 2 mM $MgCl_2$, 8 mM $MnCl_2$, 2 mM DTT, 0.01% Tween-20. |
| Substrate | 30 nM biotin-(E4Y)10 (Upstate Biotechnology). |
| Donor bead | 20 µg/ml Streptavidin coated bead (Perkin Elmer Life Science). |
| Acceptor bead | 20 µg/ml PY20 antibody coated (Perkin Elmer Life Science) |

Assay Condition E:

| | |
|---|---|
| Kinase buffer | 20 mM HEPES pH 7.0, 10 mM $MgCl_2$, 1 mM DTT, 0.01% Tween-20. |
| Substrate | 30 nM biotin-ATF2 (Upstate Biotechnology). |
| Donor bead | 10 µg/ml Streptavidin coated bead (Perkin Elmer Life Science). |
| Acceptor bead | 10 µg/ml Protein A coated, bound to anti phospho ATF2 antibody (CellSignal) |

Assay Condition F:

| | |
|---|---|
| Kinase buffer | 8 mM HEPES pH 7.0, 4 mM $MgCl_2$, 1 mM DTT, 0.01% Tween-20. |
| Substrate | 100 nM biotin-BAD (prepared as described above). |
| Donor bead | 10 µg/ml Streptavidin coated bead (Perkin Elmer Life Science). |
| Acceptor bead | 10 µg/ml Protein A coated, bound to anti phospho BAD (Ser112) antibody (CellSignal) |

Assay Condition G:

| | |
|---|---|
| Kinase buffer | MOPS 25 mM, pH 7.1, 0.1 mM $MgCl_2$, 5 mM $MnCl_2$, 0.2% BSA, 1 mM DTT, 0.01% Tween-20. |
| Substrate | 100 nM biotin-(E4Y)3 (Open Source Biotech, Inc.) |
| Donor bead | 1 µg/ml Streptavidin coated bead (Perkin Elmer Life Science). |
| Acceptor bead | 1 µg/ml PY20 coated bead (Perkin Elmer Life Science) |

TABLE 3

Kinase reaction conditions (20 µl reaction volume) for kinase screens.

| Kinase | Vendor* | Plasmid Number | Expression Host | Assay Condition |
|---|---|---|---|---|
| Abl | | P1121 | E. coli | A (1 ng kinase) |
| B-Raf | Upstate | | | B (0.1 ng kinase) |
| B-Raf V600E | | P4254 | Sf9 | B (0.1 ng kinase) |
| c-Raf-1 | Upstate | | | B (0.1 ng kinase) |
| Erk2 | | P4227 | E. coli | C (4 ng kinase) |
| Fak | | P1358 | Sf9 | A (0.1 ng kinase) |
| FGFR1 | | P1351 | E. coli | A (0.1 ng kinase) |
| Flt1 | | P1826 | E. coli | A (0.1 ng kinase) |
| Flt4 | ProQinase | | | A (0.1 ng kinase) |
| Fms | Upstate | | | D (0.5 ng kinase) |
| Jnk1 | Upstate | | | E (0.1 ng kinase) |
| Jnk2 | Roche | | | E (0.05 ng kinase) |
| Jnk3 | Upstate | | | E (0.1 ng kinase) |
| Kit | | P1332 | E. coli | A (0.1 ng kinase) |
| Met | | P1818 | E. coli | A (0.1 ng kinase) |
| p38 | | P4292 | E. coli | E (6 ng kinase) |
| Pim1 | | P1215 | E. coli | F (0.01 ng kinase) |
| Pyk2 | Upstate | | | D (1 ng kinase) |
| Ret | | P1378 | E. coli | A (0.01 ng kinase) |
| Src | | P1144 | E. coli | A (0.01 ng kinase) |
| Zap70 | | P1868 | Sf9 | G (0.1 ng kinase) |

*Upstate = Upstate Biotechnology
Roche = Roche Protein Expression Group (Indianapolis, IN)
ProQinase = ProQinase GmbH (Freiburg, Germany)

Kit was alternatively purchased from Cell Signalling Technology. Kit and Fms assays were also run at 100 µM ATP, where for Fms the 1× buffer was 8 mM MOPS pH7.0, 2 mM $MgCl_2$, 8 mM $MnCl_2$, 2 mM DTT, 50 mM NaCl, 0.01% BSA and 0.01% Tween-20 and stop buffer was 8 mM MOPS, pH 7.0, 100 mM EDTA, 0.01% BSA and for kit, 1 ng kinase was used and the 1× buffer was 8 mM MOPS pH 7.0, 1 mM MgCl$_2$, 2 mM MnCl$_2$, 1 mM DTT, 0.001% BSA and 0.01% Tween-20, with substrate of 30 nM biotin-(E4Y)$_{10}$ (Upstate Biotechnology) and beads were at 10 μg/ml in stop buffer of 8 mM MOPS, pH 7.0, 100 mM EDTA, 0.3% BSA.

Compounds screened by at least one of the methods described above, or by similar methods, having IC$_{50}$ of less than 10 μM are shown in tables 2a (Abl), 2b (B-Raf), 2c (B-Raf V600E), 2 d (Btk), 2e (c-Raf-1), 2f (EGFR), 2g (EphB2), 2h (Erk2), 2i (Fak), 2j (FGFR1), 2k (Flt1), 2l (Flt3), 2m (Flt4), 2n (Fms), 2o (Irak4), 2p (Jnk1), 2q (Jnk2), 2r (Jnk3), 2s (Kdr), 2t (Kit), 2u (MAP2K1), 2v (MAPKAPK2), 2w (Met), 2x (p38), 2y (PDGFRB), 2z (Pim1), 2aa (PKC theta), 2bb (Pyk2), 2cc (Ret), 2dd (Src), 2ee (Stk6), and 2ff (Yes), 2gg (Zap70), 2hh (Akt3), 2ii (ALK), 2jj (Cdk2), 2kk (Csk), 2ll (EphA2), 2mm (EphB4), 2nn (Frk), 2oo (Gskβ), 2pp (Hck), 2qq (MAP4K4), 2rr (IGFIR), 2ss (IKK beta), 2tt (Itk), 2uu (Jak3), 2vv (MLK1), 2ww (TrkA), 2xx (PDGFRA), 2yy (Plk1), 2zz (Brk), 2ab (ROCK1), 2ac (Syk), 2ad (TEC), and 2ac (Tie2).

TABLE 2a

Compounds with activity toward kinase Abl with IC$_{50}$ ≦ 10 μM.

| | |
|---|---|
| Abl | P-0001, P-0002, P-0003, P-0005, P-0007, P-0010, P-0011, P-0012, P-0019, P-0025, P-0028, P-0032, P-0033, P-0040, P-0041, P-0045, P-0047, P-0048, P-0050, P-0054, P-0056, P-0058, P-0068, P-0072, P-0074, P-0090, P-0093, P-0134, P-0140, P-0142, P-0167, P-0169, P-0196, P-0218, P-0224, P-0244, P-0316, P-0320, P-0448, P-0453, P-0501, P-0521, P-0529, P-0550, P-0559, P-0562, P-0579, P-0594, P-0599, P-0604, P-0611, P-0623, P-0624, P-0645, P-0656, P-0671, P-0675, P-0691, P-0693, P-0708, P-0738, P-0751, P-0762, P-0781, P-0794, P-0800, P-0806, P-0885, P-1011, P-1012, P-1115, P-1127, P-1318, P-1336, P-1394, P-1426 |

TABLE 2b

Compounds with activity toward kinase B-Raf with IC$_{50}$ ≦ 10 μM.

| | |
|---|---|
| B-Raf | P-0001, P-0002, P-0003, P-0004, P-0005, P-0006, P-0007, P-0008, P-0009, P-0010, P-0016, P-0019, P-0021, P-0024, P-0025, P-0026, P-0027, P-0032, P-0034, P-0035, P-0036, P-0037, P-0038, P-0041, P-0042, P-0045, P-0050, P-0052, P-0054, P-0055, P-0056, P-0059, P-0060, P-0065, P-0066, P-0067, P-0068, P-0078, P-0079, P-0082, P-0088, P-0090, P-0093, P-0095, P-0102, P-0112, P-0114, P-0122, P-0126, P-0140, P-0143, P-0162, P-0165, P-0166, P-0171, P-0178, P-0180, P-0184, P-0188, P-0192, P-0196, P-0200, P-0210, P-0228, P-0257, P-0262, P-0265, P-0269, P-0271, P-0284, P-0293, P-0297, P-0302, P-0307, P-0310, P-0351, P-0356, P-0369, P-0382, P-0396, P-0414, P-0448, P-0486, P-0521, P-0550, P-0556, P-0559, P-0579, P-0594, P-0599, P-0604, P-0613, P-0636, P-0683, P-0685, P-0693, P-0697, P-0700, P-0716, P-0721, P-0728, P-0734, P-0744, P-0745, P-0746, P-0753, P-0763, P-0773, P-0774, P-0776, P-0778, P-0779, P-0794, P-0798, P-0805, P-0806, P-0807, P-0818, P-0837, P-0841, P-0842, P-0848, P-0850, P-0851, P-0853, P-0857, P-0860, P-0861, P-0863, P-0866, P-0867, P-0868, P-0874, P-0876, P-0877, P-0883, P-0885, P-0889, P-0894, P-0896, P-0897, P-0898, P-0902, P-0904, P-0907, P-0909, P-0910, P-0911, P-0912, P-0913, P-0919, P-0924, P-0928, P-0931, P-0932, P-0933, P-0937, P-0939, P-0941, P-0944, P-0946, P-0947, P-0952, P-0954, P-0955, P-0956, P-0958, P-0959, P-0973, P-0975, P-0978, P-0980, P-0983, P-0984, P-0987, P-0991, P-0997, P-0998, P-1003, P-1004, P-1006, P-1009, P-1013, P-1014, P-1020, P-1027, P-1028, P-1056, P-1076, P-1080, P-1110, P-1116, P-1243, P-1244, P-1246, P-1247, P-1249, P-1250, P-1251, P-1252, P-1253, P-1254, P-1255, P-1256, P-1257, P-1258, P-1259, P-1260, P-1261, P-1262, P-1263, P-1264, P-1265, P-1266, P-1267, P-1268, P-1269, P-1270, P-1279, P-1280, P-1281, P-1282, P-1288, P-1289, P-1317, P-1318, P-1336, P-1338, P-1341, P-1343, P-1346, P-1347, P-1348, P-1349, P-1365, P-1383, P-1384, P-1385, P-1386, P-1387, P-1388, P-1389, P-1390, P-1391, P-1395, P-1397, P-1419, P-1420, P-1429, P-1430, P-1431, P-1432, P-1433, P-1445, P-1446, P-1447, P-1451, P-1452, P-1453, P-1454, P-1455, P-1456, P-1457, P-1458, P-1459, P-1467, P-1469, P-1472, P-1473, P-1475, P-1477, P-1479, P-1480, P-1481, P-1485, P-1486, P-1526, P-1527, P-1528, P-1529, P-1532, P-1534, P-1539, P-1541, P-1542, P-1544, P-1546, P-1547, P-1548, P-1549, P-1552, P-1553, P-1554, P-1555, P-1556, P-1559, P-1566, P-1567, P-1568, P-1569, P-1570, P-1576, P-1577, P-1580, P-1581, P-1582, P-1583, P-1584, P-1585, P-1586, P-1589, P-1590, P-1591, P-1592, P-1593, P-1596, P-1597, P-1598, P-1599, P-1600, P-1602, P-1605, P-1608, P-1609, P-1610, P-1612, P-1613, P-1616, P-1621, P-1627, P-1630, P-1631, P-1636, P-1637, P-1638, P-1639, P-1656, P-1660, P-1663, P-1664, P-1665, P-1670, P-1671, P-1687, P-1700, P-1701, P-1702, P-1703, P-1704, P-1705, P-1706, P-1707, P-1708, P-1709, P-1710, P-1711, P-1712, P-1713, P-1714, P-1715, P-1716, P-1717, P-1718, P-1719, P-1720, P-1721, P-1722, P-1723, P-1724, P-1725, P-1726, P-1727, P-1728, P-1729, P-1730, P-1731, P-1732, P-1733, P-1734, P-1735, P-1736, P-1737, P-1738, P-1739, P-1740, P-1741, P-1742, P-1746, P-1747, P-1748, P-1749, P-1750, P-1751, P-1752, P-1753, P-1755, P-1756, P-1757, P-1758, P-1759, P-1760, P-1762, P-1763, P-1764, P-1765, P-1766, P-1767, P-1768, P-1769, P-1770, P-1771, P-1772, P-1773, P-1774, P-1775, P-1776, P-1777, P-1778, P-1779, P-1780, P-1781, P-1782, P-1783, P-1784, P-1798, P-1799, P-1800, P-1802, P-1804, P-1816, P-1817, P-1818, P-1819, P-1822, P-1823, P-1825, P-1827, P-1828, P-1839, P-1840, P-1841, P-1842, P-1864, P-1865, P-1871, P-1872, P-1873, P-1878, P-1879, P-1881, P-1882, P-1907, P-1912, P-1916, P-1980, P-1996, P-1997, P-1998, P-2005, P-2006, P-2007, P-2012, P-2013 |

TABLE 2c

Compounds with activity toward kinase B-Raf V600E with IC$_{50}$ ≦ 10 μM.

| | |
|---|---|
| B-Raf V600E | P-0001, P-0002, P-0003, P-0004, P-0005, P-0006, P-0007, P-0008, P-0009, P-0010, P-0011, P-0012, P-0013, P-0014, P-0015, P-0016, P-0017, P-0019, P-0021, P-0022, P-0024, P-0025, P-0026, P-0027, P-0028, P-0032, P-0033, P-0034, P-0035, P-0036, P-0037, P-0038, P-0039, P-0040, P-0041, P-0042, P-0043, P-0044, P-0045, P-0046, P-0047, P-0048, P-0049, P-0050, P-0051, P-0052, P-0053, P-0054, P-0055, P-0056, P-0059, P-0060, P-0062, P-0063, P-0066, P-0067, P-0068, P-0070, P-0071, P-0072, P-0073, P-0074, P-0075, P-0078, P-0079, P-0082, P-0085, P-0088, P-0089, P-0090, P-0092, P-0093, P-0095, P-0097, P-0099, P-0100, P-0102, P-0107, P-0108, P-0109, P-0110, P-0112, P-0114, P-0118, P-0119, P-0121, P-0122, P-0124, P-0126, P-0129, P-0134, P-0135, P-0137, P-0139, P-0140, P-0141, P-0146, P-0147, P-0148, P-0152, P-0153, P-0156, P-0160, P-0162, P-0165, P-0166, P-0170, P-0171, P-0174, P-0175, P-0178, P-0180, P-0181, P-0184, P-0185, P-0186, P-0187, P-0188, P-0191, P-0192, P-0196, P-0199, P-0200, P-0205, P-0208, P-0210, P-0211, P-0215, P-0228, P-0231, P-0237, P-0242, P-0243, P-0244, P-0246, P-0248, P-0252, P-0255, P-0257, P-0261, P-0262, P-0265, P-0269, P-0271, P-0274, P-0284, P-0287, P-0293, P-0295, P-0297, P-0302, P-0307, P-0308, P-0311, P-0318, P-0320, P-0325, P-0333, P-0344, P-0347, P-0351, P-0352, P-0355, P-0356, P-0358, P-0369, P-0373, P-0381, P-0382, P-0386, P-0388, P-0396, P-0409, P-0414, P-0418, P-0420, P-0421, P-0434, P-0441, P-0447, P-0448, P-0453, P-0472, P-0483, P-0486, P-0493, P-0515, P-0521, P-0535, P-0550, P-0552, P-0559, P-0573, P-0579, P-0592, P-0594, P-0599, P-0600, P-0603, P-0604, P-0613, P-0623, P-0624, P-0636, P-0638, P-0645, P-0646, P-0647, P-0651, P-0656, P-0668, P-0671, P-0679, P-0683, P-0685, P-0691, P-0693, P-0696, P-0698, P-0700, P-0710, P-0713, P-0716, P-0721, P-0728, P-0730, P-0734, P-0744, P-0745, P-0746, P-0751, P-0753, P-0762, P-0763, P-0771, P-0773, P-0774, P-0776, P-0777, P-0778, P-0779, P-0794, P-0798, P-0803, P-0805, P-0806, P-0807, P-0810, P-0811, P-0816, P-0818, P-0819, P-0833, P-0837, P-0841, P-0842, P-0848, P-0850, P-0851, P-0853, P-0857, P-0860, P-0861, P-0863, P-0866, P-0867, P-0868, P-0874, P-0876, P-0877, P-0885, P-0886, P-0889, P-0893, P-0894, P-0896, P-0897, P-0898, P-0902, P-0904, P-0905, P-0907, P-0910, P-0911, P-0912, P-0913, P-0919, P-0927, P-0928, P-0931, P-0933, P-0937, P-0939, P-0944, P-0946, P-0947, P-0950, P-0951, P-0952, P-0954, P-0955, P-0956, P-0957, P-0958, P-0959, P-0962, P-0964, P-0971, P-0976, P-0980, P-0981, P-0983, P-0984, P-0991, P-0997, P-0998, P-1000, P-1002, P-1003, P-1004, P-1006, P-1007, P-1008, P-1009, P-1010, P-1013, P-1014, P-1015, P-1016, P-1018, P-1020, P-1021, P-1022, P-1024, P-1025, P-1026, P-1028, P-1029, P-1030, P-1031, P-1035, P-1043, P-1049, P-1056, P-1061, P-1063, P-1064, P-1065, P-1067, P-1069, P-1070, P-1071, P-1074, P-1082, P-1085, P-1090, P-1091, P-1112, P-1113, P-1116, P-1117, P-1120, P-1123, P-1128, P-1131, P-1138, P-1139, P-1140, P-1160, P-1177, P-1179, P-1180, P-1181, P-1183, P-1187, P-1194, P-1195, P-1199, P-1243, P-1244, P-1246, P-1247, P-1249, P-1250, P-1251, P-1252, P-1253, P-1254, P-1255, P-1256, P-1257, P-1258, P-1259, P-1260, P-1261, P-1262, P-1263, P-1264, P-1265, P-1266, P-1267, P-1269, P-1270, P-1279, P-1280, P-1281, P-1282, P-1283, P-1288, P-1289, P-1316, P-1317, P-1318, P-1323, P-1329, P-1336, P-1341, P-1343, P-1345, P-1346, P-1347, P-1348, P-1349, P-1365, P-1366, P-1368, P-1369, P-1370, P-1381, P-1383, P-1384, P-1385, P-1386, P-1387, P-1388, P-1389, P-1390, P-1391, P-1392, P-1394, P-1395, P-1396, P-1397, P-1398, P-1399, P-1402, P-1403, P-1409, P-1411, P-1413, P-1414, P-1415, P-1416, P-1417, P-1418, P-1419, P-1420, P-1423, P-1425, P-1426, P-1429, P-1430, P-1431, P-1432, P-1433, P-1444, P-1445, P-1446, P-1447, P-1448, P-1449, P-1450, P-1451, P-1452, P-1453, P-1454, P-1455, P-1456, P-1457, P-1458, P-1459, P-1462, P-1465, P-1466, P-1467, P-1469, P-1470, P-1471, P-1472, P-1473, P-1474, P-1475, P-1477, P-1478, P-1479, P-1480, P-1481, P-1485, P-1486, P-1495, P-1505, P-1506, P-1516, P-1526, P-1527, P-1528, P-1529, P-1530, P-1531, P-1532, P-1534, P-1539, P-1540, P-1541, P-1542, P-1544, P-1545, P-1546, P-1547, P-1548, P-1549, P-1550, P-1552, P-1553, P-1554, P-1556, P-1558, P-1559, P-1561, P-1564, P-1566, P-1567, P-1568, P-1569, P-1570, P-1572, P-1575, P-1576, P-1577, P-1578, P-1579, P-1581, P-1582, P-1583, P-1584, P-1585, P-1586, P-1589, P-1590, P-1591, P-1592, P-1594, P-1596, P-1597, P-1598, P-1599, P-1600, P-1601, P-1602, P-1605, P-1606, P-1607, P-1608, P-1609, P-1610, P-1611, P-1612, P-1613, P-1614, P-1621, P-1627, P-1630, P-1631, P-1636, P-1637, P-1638, P-1639, P-1656, P-1660, P-1663, P-1664, P-1665, P-1666, P-1670, P-1671, P-1687, P-1698, P-1700, P-1701, P-1702, P-1703, P-1704, P-1705, P-1706, P-1707, P-1708, P-1709, P-1710, P-1711, P-1712, P-1713, P-1714, P-1715, P-1716, P-1717, P-1718, P-1719, P-1720, P-1721, P-1722, P-1723, P-1724, P-1725, P-1726, P-1727, P-1728, P-1729, P-1730, P-1731, P-1732, P-1733, P-1734, P-1735, P-1736, P-1737, P-1738, P-1739, P-1740, P-1741, P-1742, P-1746, P-1747, P-1748, P-1749, P-1750, P-1751, P-1752, P-1753, P-1755, P-1756, P-1757, P-1758, P-1759, P-1760, P-1762, P-1763, P-1764, P-1765, P-1766, P-1767, P-1768, P-1769, P-1770, P-1771, P-1772, P-1773, P-1774, P-1775, P-1776, P-1777, P-1778, P-1779, P-1780, P-1781, P-1782, P-1783, P-1784, P-1797, P-1798, P-1799, P-1800, P-1802, P-1804, P-1816, P-1817, P-1818, P-1819, P-1822, P-1823, P-1828, P-1839, P-1840, P-1841, P-1842, P-1843, P-1864, P-1865, P-1871, P-1872, P-1873, P-1878, P-1879, P-1881, P-1882, P-1907, P-1912, P-1916, P-1980, P-1996, P-1997, P-1998, P-2005, P-2006, P-2007, P-2012, P-2013 |

TABLE 2d

Compounds with activity toward kinase Btk with $IC_{50} \leq 10 \mu M$.

Btk: P-0005, P-0006, P-0007, P-0009, P-0010, P-0011, P-0012, P-0013, P-0014, P-0015, P-0016, P-0017, P-0019, P-0020, P-0021, P-0022, P-0024, P-0025, P-0026, P-0027, P-0028, P-0029, P-0031, P-0033, P-0040, P-0041, P-0042, P-0043, P-0044, P-0045, P-0046, P-0047, P-0048, P-0049, P-0050, P-0051, P-0052, P-0053, P-0054, P-0055, P-0059, P-0060, P-0061, P-0062, P-0063, P-0067, P-0068, P-0070, P-0072, P-0073, P-0074, P-0075, P-0079, P-0081, P-0082, P-0083, P-0085, P-0088, P-0089, P-0090, P-0093, P-0094, P-0097, P-0102, P-0107, P-0108, P-0109, P-0112, P-0113, P-0125, P-0134, P-0135, P-0138, P-0139, P-0145, P-0148, P-0152, P-0156, P-0166, P-0171, P-0217, P-0228, P-0257, P-0280, P-0297, P-0302, P-0304, P-0314, P-0321, P-0325, P-0351, P-0418, P-0429, P-0763, P-0806, P-0807, P-0885, P-0897, P-0991, P-0997, P-1020, P-1262, P-1266, P-1267, P-1269, P-1317, P-1336, P-1343, P-1346, P-1388, P-1389, P-1390, P-1420, P-1426, P-1459, P-1473, P-1475, P-1479, P-1480, P-1481, P-1485, P-1486

TABLE 2e

Compounds with activity toward kinase c-Raf-1 with $IC_{50} \leq 10 \mu M$ c-Raf-1: P-0001, P-0002, P-0004, P-0005, P-0006, P-0007, P-0008, P-0009, P-0010, P-0015, P-0016, P-0021, P-0024, P-0025, P-0026, P-0027, P-0032, P-0034, P-0035, P-0036, P-0037, P-0038, P-0042, P-0045, P-0052, P-0055, P-0066, P-0078, P-0079, P-0082, P-0088, P-0090, P-0102, P-0112, P-0114, P-0121, P-0122, P-0137, P-0156, P-0162, P-0165, P-0166, P-0170, P-0178, P-0180, P-0184, P-0188, P-0210, P-0228, P-0257, P-0262, P-0265, P-0269, P-0297, P-0302, P-0307, P-0356, P-0369, P-0382, P-0396, P-0418, P-0486, P-0521, P-0535, P-0542, P-0559, P-0604, P-0613, P-0636, P-0656, P-0685, P-0700, P-0716, P-0721, P-0728, P-0734, P-0744, P-0745, P-0746, P-0753, P-0763, P-0773, P-0774, P-0776, P-0778, P-0779, P-0794, P-0798, P-0805, P-0806, P-0807, P-0811, P-0818, P-0837, P-0841, P-0842, P-0848, P-0850, P-0851, P-0853, P-0857, P-0860, P-0861, P-0863, P-0866, P-0867, P-0868, P-0874, P-0876, P-0877, P-0883, P-0885, P-0889, P-0890, P-0894, P-0896, P-0897, P-0898, P-0902, P-0904, P-0907, P-0909, P-0910, P-0911, P-0912, P-0913, P-0919, P-0924, P-0928, P-0931, P-0933, P-0937, P-0939, P-0941, P-0944, P-0946, P-0947, P-0950, P-0952, P-0954, P-0955, P-0956, P-0957, P-0958, P-0959, P-0964, P-0971, P-0973, P-0974, P-0975, P-0978, P-0983, P-0987, P-0991, P-0997, P-0998, P-1002, P-1003, P-1004, P-1006, P-1009, P-1013, P-1014, P-1015, P-1017, P-1020, P-1027, P-1028, P-1047, P-1056, P-1061, P-1063, P-1064, P-1065, P-1070, P-1071, P-1076, P-1077, P-1078, P-1079, P-1118, P-1122, P-1145, P-1243, P-1244, P-1246, P-1247, P-1249, P-1250, P-1251, P-1253, P-1254, P-1255, P-1256, P-1257, P-1258, P-1260, P-1261, P-1262, P-1265, P-1279, P-1283, P-1288, P-1289, P-1316, P-1317, P-1318, P-1336, P-1338, P-1365, P-1386, P-1387, P-1388, P-1389, P-1390, P-1391, P-1395, P-1396, P-1397, P-1398, P-1403, P-1413, P-1419, P-1431, P-1432, P-1433, P-1448, P-1451, P-1452, P-1453, P-1454, P-1455, P-1456, P-1458, P-1541, P-1542, P-1546, P-1547, P-1581, P-1583, P-1630, P-1671, P-1712, P-1713, P-1714, P-1733, P-1737, P-1738, P-1739, P-1740, P-1783, P-1839, P-1864, P-1871, P-1873, P-1878, P-1879, P-1881, P-1882

TABLE 2f

Compounds with activity toward kinase EGFR with $IC_{50} \leq 10 \mu M$

EGFR: P-0001, P-0002, P-0003, P-0004, P-0025, P-0095, P-0153, P-0877

TABLE 2h

Compounds with activity toward kinase Erk2 with $IC_{50} \leq 10 \mu M$

Erk2: P-0031, P-0041, P-0058, P-0154, P-0550, P-0611, P-1336

TABLE 2g

Compounds with activity toward kinase EphB2 with $IC_{50} \leq 10 \mu M$

EphB2: P-0001, P-0003, P-0005, P-0006, P-0007, P-0009, P-0010, P-0011, P-0012, P-0013, P-0014, P-0015, P-0016, P-0017, P-0019, P-0020, P-0021, P-0022, P-0025, P-0027, P-0028, P-0029, P-0032, P-0033, P-0034, P-0035, P-0036, P-0038, P-0040, P-0041, P-0042, P-0043, P-0044, P-0045, P-0048, P-0050, P-0052, P-0053, P-0055, P-0056, P-0059, P-0062, P-0067, P-0068, P-0070, P-0072, P-0074, P-0075, P-0078, P-0083, P-0088, P-0090, P-0093, P-0102, P-0107, P-0109, P-0114, P-0124, P-0125, P-0126, P-0139, P-0145, P-0186

TABLE 2i

Compounds with activity toward kinase Fak with $IC_{50} \leq 10\ \mu M$

Fak: P-0001, P-0002, P-0003, P-0004, P-0006, P-0007, P-0008, P-0009, P-0016, P-0018, P-0024, P-0025, P-0026, P-0027, P-0032, P-0034, P-0035, P-0036, P-0037, P-0045, P-0054, P-0055, P-0067, P-0078, P-0088, P-0102, P-0112, P-0114, P-0166, P-0196, P-0209, P-0210, P-0211, P-0224, P-0257, P-0269, P-0276, P-0293, P-0298, P-0302, P-0310, P-0333, P-0391, P-0396, P-0437, P-0486, P-0494, P-0501, P-0611, P-0668, P-0675, P-0685, P-0691, P-0700, P-0721, P-0774, P-0795, P-0797, P-0806, P-0811, P-0818, P-0837, P-0850, P-0851, P-0867, P-0885, P-0889, P-0910, P-0911, P-0933, P-0951, P-0955, P-0956, P-0986, P-0992, P-1002, P-1009, P-1013, P-1020, P-1054, P-1083, P-1114, P-1146, P-1190, P-1247, P-1249, P-1250, P-1253, P-1255, P-1256, P-1263, P-1264, P-1266, P-1267, P-1269, P-1279, P-1280, P-1281, P-1282, P-1288, P-1289, P-1316, P-1318, P-1321, P-1323, P-1329, P-1336, P-1341, P-1346, P-1347, P-1348, P-1349, P-1359, P-1365, P-1383, P-1384, P-1385, P-1387, P-1388, P-1389, P-1390, P-1391, P-1392, P-1394, P-1396, P-1397, P-1400, P-1401, P-1402, P-1403, P-1411, P-1431, P-1432, P-1433, P-1445, P-1446, P-1447, P-1449, P-1450, P-1451, P-1452, P-1453, P-1455, P-1456, P-1457, P-1458, P-1459, P-1473, P-1474, P-1475, P-1477, P-1478, P-1479, P-1480, P-1481, P-1482, P-1485, P-1486, P-1492, P-1495, P-1500, P-1502, P-1685

TABLE 2j

Compounds with activity toward kinase FGFR with $IC_{50} \leq 10\ \mu M$

FGFR: P-0001, P-0002, P-0003, P-0004, P-0005, P-0006, P-0007, P-0008, P-0009, P-0010, P-0011, P-0012, P-0013, P-0015, P-0016, P-0017, P-0019, P-0020, P-0021, P-0024, P-0025, P-0026, P-0027, P-0028, P-0029, P-0032, P-0033, P-0034, P-0035, P-0036, P-0037, P-0038, P-0039, P-0040, P-0041, P-0042, P-0043, P-0045, P-0050, P-0052, P-0054, P-0055, P-0056, P-0058, P-0059, P-0066, P-0067, P-0068, P-0072, P-0073, P-0078, P-0079, P-0082, P-0088, P-0089, P-0090, P-0093, P-0096, P-0097, P-0099, P-0101, P-0102, P-0103, P-0112, P-0114, P-0119, P-0121, P-0129, P-0132, P-0134, P-0137, P-0140, P-0142, P-0149, P-0150, P-0152, P-0156, P-0158, P-0165, P-0166, P-0167, P-0168, P-0170, P-0171, P-0175, P-0178, P-0180, P-0184, P-0189, P-0192, P-0196, P-0198, P-0204, P-0205, P-0206, P-0210, P-0211, P-0215, P-0217, P-0218, P-0219, P-0220, P-0227, P-0228, P-0232, P-0233, P-0239, P-0242, P-0244, P-0246, P-0248, P-0257, P-0262, P-0265, P-0267, P-0269, P-0271, P-0274, P-0284, P-0287, P-0289, P-0293, P-0294, P-0297, P-0298, P-0302, P-0304, P-0308, P-0309, P-0316, P-0320, P-0321, P-0325, P-0326, P-0329, P-0335, P-0339, P-0341, P-0344, P-0346, P-0351, P-0363, P-0368, P-0369, P-0371, P-0373, P-0374, P-0379, P-0383, P-0385, P-0391, P-0392, P-0396, P-0400, P-0404, P-0409, P-0411, P-0418, P-0420, P-0421, P-0424, P-0426, P-0442, P-0447, P-0448, P-0452, P-0453, P-0459, P-0473, P-0474, P-0479, P-0483, P-0486, P-0489, P-0493, P-0495, P-0501, P-0507, P-0510, P-0515, P-0520, P-0521, P-0535, P-0550, P-0556, P-0559, P-0561, P-0562, P-0563, P-0575, P-0579, P-0594, P-0599, P-0611, P-0613, P-0615, P-0623, P-0624, P-0632, P-0636, P-0640, P-0645, P-0647, P-0656, P-0658, P-0668, P-0671, P-0679, P-0683, P-0685, P-0691, P-0693, P-0697, P-0698, P-0699, P-0700, P-0708, P-0710, P-0721, P-0728, P-0730, P-0734, P-0737, P-0744, P-0745, P-0746, P-0749, P-0751, P-0753, P-0763, P-0771, P-0773, P-0774, P-0776, P-0798, P-0805, P-0806, P-0807, P-0811, P-0818, P-0819, P-0826, P-0828, P-0835, P-0837, P-0841, P-0848, P-0850, P-0851, P-0853, P-0854, P-0857, P-0860, P-0865, P-0867, P-0868, P-0874, P-0876, P-0877, P-0885, P-0889, P-0894, P-0896, P-0897, P-0898, P-0902, P-0904, P-0907, P-0910, P-0911, P-0912, P-0913, P-0919, P-0927, P-0933, P-0935, P-0937, P-0944, P-0947, P-0950, P-0951, P-0952, P-0954, P-0955, P-0956, P-0958, P-0964, P-0974, P-0976, P-0977, P-0979, P-0983, P-0991, P-0997, P-1002, P-1004, P-1008, P-1009, P-1015, P-1017, P-1018, P-1020, P-1021, P-1027, P-1066, P-1074, P-1078, P-1110, P-1111, P-1116, P-1120, P-1123, P-1125, P-1142, P-1181, P-1182, P-1188, P-1194, P-1246, P-1249, P-1250, P-1251, P-1252, P-1253, P-1254, P-1255, P-1256, P-1257, P-1258, P-1259, P-1260, P-1261, P-1262, P-1263, P-1264, P-1265, P-1266, P-1267, P-1269, P-1270, P-1272, P-1273, P-1274, P-1279, P-1280, P-1281, P-1282, P-1283, P-1287, P-1288, P-1289, P-1316, P-1317, P-1318, P-1321, P-1322, P-1323, P-1325, P-1326, P-1327, P-1328, P-1329, P-1330, P-1331, P-1332, P-1333, P-1334, P-1335, P-1336, P-1337, P-1338, P-1339, P-1340, P-1341, P-1342, P-1343, P-1344, P-1345, P-1346, P-1347, P-1348, P-1349, P-1365, P-1366, P-1367, P-1369, P-1377, P-1380, P-1381, P-1382, P-1383, P-1384, P-1385, P-1386, P-1387, P-1388, P-1389, P-1390, P-1391, P-1392, P-1393, P-1394, P-1395, P-1396, P-1397, P-1398, P-1399, P-1402, P-1403, P-1404, P-1406, P-1407, P-1409, P-1411, P-1415, P-1416, P-1418, P-1419, P-1420, P-1423, P-1424, P-1426, P-1428, P-1429, P-1430, P-1431, P-1433, P-1445, P-1446, P-1447, P-1448, P-1451, P-1452, P-1453, P-1454, P-1455, P-1456, P-1458, P-1459, P-1460, P-1461, P-1463, P-1464, P-1465, P-1467, P-1468, P-1469, P-1472, P-1473, P-1474, P-1475, P-1476, P-1477, P-1478, P-1479, P-1480, P-1481, P-1482, P-1485, P-1486, P-1512, P-1516, P-1522, P-1524, P-1525, P-1526, P-1527, P-1528, P-1529, P-1530, P-1534, P-1538, P-1539, P-1542, P-1545, P-1546, P-1547, P-1548, P-1549, P-1550, P-1554, P-1555, P-1556, P-1561, P-1564, P-1577, P-1581, P-1582, P-1583, P-1584, P-1585, P-1589, P-1591, P-1592, P-1593, P-1595, P-1597, P-1603, P-1605, P-1608, P-1609, P-1610, P-1614, P-1621, P-1622, P-1624, P-1625, P-1685

TABLE 2k

Compounds with activity toward kinase Flt1 with IC$_{50}$ ≦ 10 μM

Flt1:  P-0001, P-0002, P-0003, P-0004, P-0005, P-0008, P-0009, P-0011, P-0012, P-0013,
P-0016, P-0017, P-0018, P-0019, P-0020, P-0021, P-0024, P-0026, P-0027, P-0032,
P-0033, P-0034, P-0036, P-0037, P-0038, P-0039, P-0041, P-0054, P-0055, P-0056,
P-0067, P-0068, P-0072, P-0078, P-0082, P-0088, P-0090, P-0091, P-0101, P-0103,
P-0112, P-0114, P-0127, P-0134, P-0150, P-0154, P-0166, P-0177, P-0180, P-0184,
P-0194, P-0196, P-0206, P-0211, P-0214, P-0224, P-0244, P-0269, P-0274, P-0278,
P-0287, P-0298, P-0302, P-0315, P-0320, P-0325, P-0326, P-0337, P-0371, P-0373,
P-0383, P-0404, P-0409, P-0421, P-0448, P-0455, P-0461, P-0470, P-0477, P-0483,
P-0486, P-0491, P-0514, P-0515, P-0521, P-0550, P-0559, P-0579, P-0603, P-0624,
P-0629, P-0632, P-0636, P-0640, P-0656, P-0668, P-0679, P-0683, P-0685, P-0691,
P-0700, P-0708, P-0721, P-0733, P-0737, P-0749, P-0751, P-0757, P-0768, P-0771,
P-0773, P-0774, P-0777, P-0805, P-0866, P-0868, P-0951, P-0958, P-0962, P-1002,
P-1008, P-1010, P-1018, P-1021, P-1027, P-1082, P-1110, P-1112, P-1147, P-1160,
P-1181, P-1194, P-1246, P-1247, P-1250, P-1251, P-1255, P-1256, P-1259, P-1260,
P-1261, P-1262, P-1266, P-1269, P-1279, P-1289, P-1317, P-1318, P-1365, P-1366,
P-1370, P-1372, P-1373, P-1383, P-1393, P-1395, P-1403, P-1404, P-1406, P-1411,
P-1415, P-1416, P-1417, P-1418, P-1420, P-1422, P-1423, P-1424, P-1425, P-1426,
P-1427, P-1428, P-1429, P-1430, P-1431, P-1432, P-1433, P-1445, P-1446, P-1447,
P-1457, P-1460, P-1461, P-1462, P-1463, P-1464, P-1465, P-1467, P-1468, P-1469,
P-1472, P-1475, P-1486, P-1491, P-1492, P-1495, P-1497, P-1499, P-1502, P-1505,
P-1523, P-1526, P-1527, P-1528, P-1529, P-1530, P-1531, P-1532, P-1533, P-1534,
P-1541, P-1542, P-1544, P-1546, P-1547, P-1548, P-1549, P-1552, P-1553, P-1554,
P-1556, P-1557, P-1559, P-1564, P-1566, P-1567, P-1569, P-1570, P-1571, P-1572,
P-1575, P-1576, P-1577, P-1580, P-1581, P-1582, P-1583, P-1584, P-1585, P-1586,
P-1587, P-1589, P-1590, P-1591, P-1592, P-1593, P-1594, P-1595, P-1596, P-1597,
P-1598, P-1599, P-1600, P-1601, P-1602, P-1603, P-1605, P-1606, P-1608, P-1609,
P-1610, P-1612, P-1613, P-1614, P-1615, P-1618, P-1619, P-1621, P-1622, P-1624,
P-1625, P-1686

TABLE 2l

Compounds with activity toward kinase Flt3 with IC$_{50}$ ≦ 10 μM

Flt3:  P-0088, P-0262, P-0409, P-0636, P-0806, P-1244,
P-1280, P-1318, P-1336, P-1394, P-1426

TABLE 2m

Compounds with activity toward kinase Flt4 with IC$_{50}$ ≦ 10 μM

Flt4:  P-0001, P-0003, P-0005, P-0011, P-0012, P-0019, P-0024, P-0029, P-0032, P-0039,
P-0040, P-0041, P-0090, P-0093, P-0097, P-0117, P-0142, P-0167, P-0190, P-0196,
P-0204, P-0205, P-0206, P-0211, P-0215, P-0218, P-0224, P-0265, P-0316, P-0325,
P-0335, P-0352, P-0418, P-0448, P-0452, P-0453, P-0495, P-0521, P-0544, P-0550,
P-0559, P-0579, P-0594, P-0599, P-0617, P-0624, P-0632, P-0645, P-0656, P-0668,
P-0679, P-0691, P-0703, P-0708, P-0737, P-0738, P-0751, P-0762, P-0771, P-0813

TABLE 2n

Compounds with activity toward kinase Fms with IC$_{50}$ ≦ 10 μM

Fms:  P-0001, P-0002, P-0003, P-0004, P-0005, P-0006, P-0007, P-0008, P-0009, P-0010,
P-0012, P-0016, P-0019, P-0020, P-0021, P-0025, P-0026, P-0027, P-0032, P-0033,
P-0034, P-0035, P-0036, P-0037, P-0038, P-0042, P-0045, P-0048, P-0054, P-0067,
P-0068, P-0072, P-0078, P-0079, P-0082, P-0088, P-0090, P-0093, P-0101, P-0102,
P-0103, P-0112, P-0114, P-0121, P-0129, P-0134, P-0145, P-0152, P-0166, P-0170,
P-0175, P-0180, P-0184, P-0189, P-0196, P-0210, P-0211, P-0228, P-0233, P-0237,
P-0239, P-0244, P-0257, P-0262, P-0269, P-0274, P-0284, P-0291, P-0293,
P-0297, P-0298, P-0302, P-0317, P-0325, P-0327, P-0333, P-0351, P-0369, P-0373,
P-0383, P-0391, P-0396, P-0409, P-0418, P-0420, P-0421, P-0461, P-0483, P-0486,
P-0491, P-0501, P-0515, P-0535, P-0559, P-0563, P-0613, P-0636, P-0656, P-0685,
P-0721, P-0733, P-0753, P-0763, P-0771, P-0773, P-0774, P-0778, P-0798, P-0805,
P-0806, P-0807, P-0811, P-0818, P-0835, P-0837, P-0848, P-0850, P-0851, P-0853,
P-0854, P-0857, P-0867, P-0874, P-0876, P-0883, P-0885, P-0898, P-0911, P-0913,
P-0919, P-0927, P-0931, P-0933, P-0952, P-0954, P-0955, P-0956, P-0958, P-1002,
P-1008, P-1009, P-1013, P-1110, P-1112, P-1124, P-1194, P-1246, P-1247, P-1249,
P-1250, P-1251, P-1252, P-1253, P-1255, P-1259, P-1260, P-1262, P-1263, P-1264,
P-1265, P-1266, P-1267, P-1269, P-1279, P-1280, P-1281, P-1282, P-1289, P-1316,
P-1317, P-1318, P-1321, P-1323, P-1324, P-1325, P-1326, P-1327, P-1328, P-1329,
P-1330, P-1331, P-1332, P-1333, P-1334, P-1335, P-1336, P-1337, P-1338, P-1339,
P-1340, P-1341, P-1342, P-1343, P-1344, P-1346, P-1365, P-1366, P-1368, P-1369,

TABLE 2n-continued

Compounds with activity toward kinase Fms with IC$_{50}$ ≦ 10 μM

P-1370, P-1372, P-1376, P-1380, P-1381, P-1384, P-1385, P-1386, P-1387, P-1388,
P-1389, P-1390, P-1391, P-1392, P-1393, P-1394, P-1395, P-1397, P-1399, P-1400,
P-1402, P-1403, P-1404, P-1405, P-1406, P-1409, P-1410, P-1411, P-1415, P-1416,
P-1419, P-1420, P-1421, P-1423, P-1425, P-1426, P-1427, P-1428, P-1429, P-1430,
P-1431, P-1432, P-1433, P-1445, P-1447, P-1448, P-1449, P-1450, P-1451, P-1452,
P-1453, P-1454, P-1455, P-1456, P-1457, P-1458, P-1459, P-1460, P-1461, P-1462,
P-1463, P-1464, P-1465, P-1466, P-1467, P-1468, P-1469, P-1470, P-1471, P-1472,
P-1473, P-1474, P-1475, P-1476, P-1477, P-1478, P-1479, P-1480, P-1481, P-1482,
P-1483, P-1485, P-1486, P-1488, P-1489, P-1490, P-1491, P-1492, P-1493, P-1494,
P-1495, P-1496, P-1497, P-1498, P-1499, P-1500, P-1501, P-1502, P-1503, P-1504,
P-1505, P-1506, P-1511, P-1522, P-1525, P-1526, P-1527, P-1528, P-1529, P-1530,
P-1532, P-1534, P-1541, P-1542, P-1544, P-1545, P-1546, P-1547, P-1548, P-1549,
P-1552, P-1553, P-1554, P-1555, P-1556, P-1558, P-1559, P-1564, P-1566, P-1567,
P-1568, P-1569, P-1570, P-1571, P-1572, P-1575, P-1576, P-1580, P-1581, P-1583,
P-1586, P-1587, P-1589, P-1591, P-1594, P-1595, P-1596, P-1597, P-1598, P-1599,
P-1602, P-1606, P-1608, P-1609, P-1610, P-1611, P-1612, P-1613, P-1615, P-1616,
P-1618, P-1621, P-1625, P-1627, P-1630, P-1631, P-1636, P-1637, P-1638, P-1639,
P-1652, P-1653, P-1654, P-1656, P-1657, P-1660, P-1663, P-1664, P-1665, P-1670,
P-1671, P-1685, P-1687, P-1700, P-1701, P-1702, P-1703, P-1704, P-1705, P-1706,
P-1707, P-1708, P-1709, P-1710, P-1711, P-1712, P-1713, P-1714, P-1715, P-1716,
P-1717, P-1718, P-1719, P-1720, P-1721, P-1722, P-1723, P-1724, P-1725, P-1726,
P-1727, P-1728, P-1729, P-1730, P-1731, P-1732, P-1733, P-1734, P-1735, P-1736,
P-1737, P-1738, P-1739, P-1740, P-1741, P-1742, P-1746, P-1747, P-1748, P-1749,
P-1750, P-1751, P-1753, P-1754, P-1755, P-1756, P-1757, P-1758, P-1759, P-1760,
P-1761, P-1762, P-1763, P-1764, P-1765, P-1766, P-1767, P-1768, P-1769, P-1771,
P-1772, P-1773, P-1774, P-1775, P-1776, P-1778, P-1779, P-1780, P-1781, P-1782,
P-1783, P-1784, P-1796, P-1798, P-1799, P-1800, P-1802, P-1803, P-1804, P-1816,
P-1817, P-1818, P-1819, P-1821, P-1822, P-1827, P-1828, P-1839, P-1840, P-1864,
P-1871, P-1872, P-1873, P-1878, P-1879, P-1881, P-1882, P-1907, P-1912, P-1916,
P-1980, P-1996, P-1997, P-1998, P-2005, P-2006, P-2007, P-2012, P-2013

TABLE 2o

Compounds with activity toward kinase Irak4 with IC$_{50}$ ≦ 10 μM

Irak4: P-0002, P-0020, P-0076, P-0087, P-0091, P-0130

TABLE 2p

Compounds with activity toward kinase Jnk1 with IC$_{50}$ ≦ 10 μM

Jnk1: P-0001, P-0002, P-0003, P-0004, P-0006, P-0008, P-0009, P-0010, P-0015, P-0016,
P-0021, P-0025, P-0026, P-0027, P-0032, P-0033, P-0034, P-0035, P-0036, P-0037,
P-0038, P-0040, P-0042, P-0045, P-0052, P-0054, P-0056, P-0066, P-0078, P-0079,
P-0082, P-0088, P-0090, P-0102, P-0112, P-0114, P-0121, P-0134, P-0140, P-0156,
P-0184, P-0196, P-0204, P-0228, P-0244, P-0257, P-0269, P-0285, P-0297, P-0302,
P-0308, P-0431, P-0448, P-0486, P-0521, P-0559, P-0579, P-0599, P-0624, P-0636,
P-0668, P-0685, P-0691, P-0700, P-0721, P-0728, P-0734, P-0745, P-0753, P-0763,
P-0774, P-0807, P-0848, P-0850, P-0851, P-0853, P-0860, P-0876, P-0897, P-0956,
P-0958, P-0991, P-0997, P-1002, P-1008, P-1009, P-1021, P-1251, P-1253, P-1256,
P-1260, P-1262, P-1266, P-1279, P-1280, P-1281, P-1288, P-1289, P-1317, P-1318,
P-1336, P-1338, P-1343, P-1346, P-1347, P-1348, P-1349, P-1356, P-1359, P-1365,
P-1366, P-1370, P-1384, P-1385, P-1390, P-1394, P-1400, P-1402, P-1432, P-1433,
P-1445, P-1446, P-1447, P-1456, P-1458, P-1459, P-1465, P-1468, P-1473, P-1475,
P-1486, P-1523, P-1534, P-1546, P-1547, P-1548, P-1549, P-1553, P-1554, P-1556,
P-1566, P-1567, P-1570, P-1576, P-1577, P-1585, P-1589, P-1591, P-1592, P-1596,
P-1602, P-1610, P-1611, P-1618, P-1621, P-1627, P-1631, P-1636, P-1637, P-1638,
P-1639, P-1656, P-1660, P-1687, P-1702, P-1706, P-1707, P-1708, P-1720, P-1722,
P-1723, P-1724, P-1725, P-1727, P-1730, P-1731, P-1742, P-1748, P-1749, P-1750,
P-1751, P-1755, P-1756, P-1757, P-1759, P-1760, P-1764, P-1765, P-1767, P-1770,
P-1775, P-1776, P-1777, P-1778, P-1779, P-1827, P-1828, P-1839, P-1842, P-1864,
P-1873, P-1878, P-1879, P-1896, P-1897, P-1898, P-2007

TABLE 2q

Compounds with activity toward kinase Jnk2 with $IC_{50} \leq 10\ \mu M$

Jnk2: P-0001, P-0005, P-0006, P-0009, P-0013, P-0015, P-0016, P-0025, P-0027, P-0033, P-0034, P-0035, P-0040, P-0042, P-0052, P-0054, P-0056, P-0066, P-0069, P-0079, P-0082, P-0088, P-0090, P-0121, P-0140, P-0142, P-0156, P-0184, P-0196, P-0204, P-0228, P-0238, P-0269, P-0285, P-0297, P-0308, P-0448, P-0486, P-0521, P-0579, P-0594, P-0599, P-0623, P-0685, P-0700, P-0721, P-0734, P-0744, P-0746, P-0774, P-1253, P-1318, P-1445, P-1447, P-1486, P-1547, P-1548, P-1554, P-1566, P-1567, P-1570, P-1575, P-1576, P-1589, P-1591, P-1602, P-1611, P-1621, P-1627, P-1656, P-1671, P-1687, P-1700, P-1702, P-1711, P-1720, P-1722, P-1723, P-1724, P-1727, P-1728, P-1729, P-1730, P-1731, P-1732, P-1737, P-1742, P-1748, P-1749, P-1750, P-1751, P-1753, P-1755, P-1756, P-1757, P-1759, P-1760, P-1764, P-1765, P-1767, P-1770, P-1776, P-1777, P-1778, P-1779, P-1827, P-1828, P-1864, P-2007

TABLE 2r

Compounds with activity toward kinase Jnk3 with $IC_{50} \leq 10\ \mu M$

Jnk3: P-0001, P-0002, P-0003, P-0004, P-0006, P-0008, P-0009, P-0010, P-0015, P-0016, P-0024, P-0025, P-0026, P-0027, P-0031, P-0032, P-0033, P-0034, P-0035, P-0036, P-0037, P-0038, P-0040, P-0041, P-0045, P-0047, P-0052, P-0054, P-0056, P-0058, P-0059, P-0066, P-0078, P-0079, P-0080, P-0088, P-0089, P-0090, P-0093, P-0102, P-0112, P-0114, P-0115, P-0117, P-0122, P-0132, P-0133, P-0134, P-0165, P-0166, P-0167, P-0176, P-0179, P-0184, P-0189, P-0190, P-0196, P-0204, P-0211, P-0213, P-0218, P-0228, P-0238, P-0244, P-0257, P-0263, P-0269, P-0279, P-0285, P-0300, P-0308, P-0313, P-0320, P-0371, P-0378, P-0448, P-0483, P-0521, P-0550, P-0559, P-0562, P-0579, P-0594, P-0599, P-0604, P-0624, P-0625, P-0632, P-0636, P-0640, P-0645, P-0656, P-0659, P-0668, P-0671, P-0675, P-0682, P-0683, P-0691, P-0697, P-0698, P-0703, P-0710, P-0716, P-0734, P-0738, P-0753, P-0755, P-0757, P-0763, P-0774, P-0778, P-0807, P-0822, P-0851, P-0951, P-0962, P-0991, P-1002, P-1005, P-1008, P-1010, P-1011, P-1016, P-1018, P-1021, P-1022, P-1032, P-1082, P-1087, P-1088, P-1253, P-1279, P-1280, P-1289, P-1317, P-1318, P-1346, P-1347, P-1348, P-1349, P-1355, P-1356, P-1359, P-1372, P-1375, P-1384, P-1385, P-1394, P-1400, P-1445, P-1447, P-1458, P-1465, P-1468, P-1473, P-1475, P-1477, P-1485, P-1486, P-1489, P-1490, P-1505, P-1529, P-1534, P-1546, P-1547, P-1548, P-1554, P-1561, P-1566, P-1567, P-1570, P-1576, P-1577, P-1585, P-1589, P-1591, P-1592, P-1610, P-1611, P-1618, P-1621, P-1636, P-1687, P-1702, P-1703, P-1704, P-1706, P-1707, P-1713, P-1716, P-1720, P-1722, P-1724, P-1742, P-1748, P-1749, P-1750, P-1753, P-1756, P-1757, P-1759, P-1764, P-1765, P-1767, P-1770, P-1775, P-1776, P-1777, P-1827, P-1828, P-1864, P-2007

TABLE 2s

Compounds with activity toward kinase Kdr with $IC_{50} \leq 10\ \mu M$

Kdr: P-0001, P-0003, P-0005, P-0006, P-0007, P-0009, P-0011, P-0012, P-0013, P-0014, P-0015, P-0016, P-0017, P-0018, P-0019, P-0020, P-0021, P-0022, P-0023, P-0024, P-0025, P-0027, P-0028, P-0029, P-0030, P-0031, P-0032, P-0033, P-0039, P-0040, P-0041, P-0042, P-0043, P-0044, P-0045, P-0046, P-0048, P-0049, P-0050, P-0051, P-0052, P-0053, P-0054, P-0055, P-0056, P-0057, P-0059, P-0060, P-0061, P-0063, P-0064, P-0065, P-0067, P-0068, P-0069, P-0070, P-0071, P-0073, P-0074, P-0075, P-0076, P-0077, P-0078, P-0080, P-0081, P-0082, P-0084, P-0085, P-0086, P-0087, P-0088, P-0089, P-0090, P-0091, P-0092, P-0093, P-0096, P-0097, P-0098, P-0100, P-0101, P-0102, P-0103, P-0105, P-0106, P-0107, P-0108, P-0110, P-0111, P-0112, P-0113, P-0114, P-0115, P-0117, P-0120, P-0122, P-0125, P-0126, P-0127, P-0128, P-0129, P-0130, P-0131, P-0133, P-0134, P-0135, P-0136, P-0137, P-0139, P-0140, P-0141, P-0142, P-0143, P-0144, P-0145, P-0147, P-0149, P-0152, P-0157, P-0158, P-0161, P-0162, P-0163, P-0164, P-0165, P-0167, P-0168, P-0169, P-0170, P-0172, P-0173, P-0174, P-0175, P-0176, P-0177, P-0179, P-0180, P-0182, P-0184, P-0189, P-0190, P-0192, P-0194, P-0195, P-0196, P-0197, P-0198, P-0199, P-0202, P-0203, P-0204, P-0206, P-0212, P-0213, P-0216, P-0218, P-0224, P-0225, P-0226, P-0230, P-0234, P-0242, P-0243, P-0260, P-0261, P-0262, P-0267, P-0268, P-0269, P-0270, P-0274, P-0279, P-0287, P-0288, P-0289, P-0293, P-0295, P-0296, P-0299, P-0308, P-0316, P-0319, P-0320, P-0321, P-0322, P-0326, P-0337, P-0339, P-0369, P-0376, P-0379, P-0391, P-0409, P-0418, P-0427, P-0448, P-0455, P-0458, P-0473, P-0482, P-0495, P-0521, P-0550, P-0559, P-0562, P-0579, P-0611, P-0623, P-0624, P-0632, P-0640, P-0645, P-0668, P-0679, P-0683, P-0691, P-0703, P-0708, P-0730, P-0737, P-0738, P-0751, P-0762, P-0771, P-0777, P-0796, P-0806, P-0813, P-0933, P-0951, P-0956, P-0962, P-0981, P-1023, P-1244, P-1280, P-1318, P-1394, P-1426

TABLE 2t

Compounds with activity toward kinase Kit with IC$_{50}$ ≦ 10 μM

Kit: P-0001, P-0002, P-0003, P-0004, P-0005, P-0006, P-0007, P-0008, P-0009, P-0011, P-0012, P-0013, P-0016, P-0017, P-0018, P-0019, P-0020, P-0021, P-0024, P-0026, P-0027, P-0028, P-0029, P-0030, P-0031, P-0032, P-0033, P-0034, P-0035, P-0036, P-0037, P-0038, P-0039, P-0040, P-0041, P-0042, P-0050, P-0054, P-0056, P-0059, P-0064, P-0067, P-0069, P-0072, P-0078, P-0079, P-0080, P-0082, P-0086, P-0088, P-0090, P-0093, P-0097, P-0101, P-0102, P-0103, P-0112, P-0114, P-0115, P-0117, P-0120, P-0121, P-0122, P-0123, P-0127, P-0129, P-0132, P-0133, P-0134, P-0136, P-0140, P-0142, P-0152, P-0154, P-0157, P-0166, P-0167, P-0168, P-0171, P-0175, P-0176, P-0179, P-0180, P-0184, P-0189, P-0190, P-0195, P-0196, P-0204, P-0205, P-0206, P-0210, P-0211, P-0213, P-0216, P-0217, P-0218, P-0224, P-0233, P-0235, P-0237, P-0244, P-0248, P-0253, P-0257, P-0262, P-0263, P-0265, P-0269, P-0274, P-0279, P-0284, P-0287, P-0289, P-0293, P-0298, P-0300, P-0302, P-0304, P-0315, P-0316, P-0321, P-0323, P-0325, P-0326, P-0333, P-0341, P-0346, P-0352, P-0367, P-0369, P-0371, P-0373, P-0378, P-0384, P-0385, P-0391, P-0392, P-0396, P-0402, P-0404, P-0409, P-0411, P-0418, P-0420, P-0421, P-0427, P-0447, P-0448, P-0450, P-0453, P-0459, P-0461, P-0473, P-0483, P-0491, P-0495, P-0499, P-0501, P-0511, P-0519, P-0521, P-0535, P-0550, P-0554, P-0556, P-0559, P-0561, P-0562, P-0563, P-0579, P-0594, P-0599, P-0604, P-0611, P-0613, P-0617, P-0623, P-0624, P-0625, P-0626, P-0632, P-0636, P-0640, P-0644, P-0645, P-0647, P-0656, P-0658, P-0659, P-0668, P-0671, P-0679, P-0682, P-0683, P-0685, P-0690, P-0691, P-0693, P-0697, P-0699, P-0700, P-0703, P-0708, P-0721, P-0733, P-0736, P-0737, P-0738, P-0749, P-0751, P-0753, P-0755, P-0757, P-0762, P-0763, P-0771, P-0773, P-0774, P-0776, P-0778, P-0794, P-0796, P-0798, P-0800, P-0806, P-0810, P-0813, P-0815, P-0818, P-0825, P-0835, P-0837, P-0848, P-0850, P-0851, P-0853, P-0854, P-0857, P-0860, P-0861, P-0865, P-0866, P-0867, P-0874, P-0876, P-0877, P-0885, P-0889, P-0898, P-0905, P-0907, P-0910, P-0911, P-0913, P-0919, P-0924, P-0927, P-0931, P-0933, P-0935, P-0937, P-0951, P-0952, P-0954, P-0955, P-0956, P-0958, P-0962, P-0964, P-0978, P-0983, P-1002, P-1008, P-1009, P-1010, P-1013, P-1016, P-1018, P-1021, P-1033, P-1082, P-1084, P-1096, P-1110, P-1112, P-1160, P-1181, P-1194, P-1246, P-1247, P-1249, P-1250, P-1251, P-1252, P-1253, P-1254, P-1255, P-1256, P-1257, P-1259, P-1260, P-1261, P-1262, P-1263, P-1264, P-1266, P-1267, P-1268, P-1269, P-1275, P-1279, P-1280, P-1281, P-1289, P-1316, P-1317, P-1318, P-1320, P-1321, P-1323, P-1329, P-1336, P-1338, P-1341, P-1343, P-1346, P-1347, P-1348, P-1349, P-1365, P-1366, P-1367, P-1368, P-1369, P-1370, P-1372, P-1376, P-1380, P-1382, P-1383, P-1384, P-1385, P-1386, P-1387, P-1388, P-1389, P-1390, P-1391, P-1392, P-1393, P-1394, P-1395, P-1396, P-1397, P-1399, P-1400, P-1402, P-1403, P-1404, P-1406, P-1407, P-1408, P-1409, P-1410, P-1411, P-1413, P-1414, P-1415, P-1416, P-1417, P-1419, P-1420, P-1422, P-1423, P-1424, P-1425, P-1426, P-1427, P-1428, P-1429, P-1430, P-1431, P-1432, P-1433, P-1445, P-1446, P-1447, P-1449, P-1450, P-1451, P-1452, P-1453, P-1454, P-1455, P-1456, P-1457, P-1458, P-1460, P-1461, P-1462, P-1463, P-1464, P-1465, P-1466, P-1467, P-1468, P-1469, P-1470, P-1471, P-1472, P-1474, P-1475, P-1476, P-1478, P-1479, P-1480, P-1481, P-1482, P-1483, P-1484, P-1486, P-1488, P-1489, P-1490, P-1493, P-1495, P-1497, P-1498, P-1499, P-1500, P-1501, P-1502, P-1503, P-1505, P-1506, P-1514, P-1521, P-1522, P-1525, P-1526, P-1527, P-1528, P-1529, P-1530, P-1531, P-1532, P-1534, P-1538, P-1541, P-1542, P-1543, P-1544, P-1545, P-1546, P-1547, P-1548, P-1549, P-1550, P-1551, P-1552, P-1553, P-1554, P-1557, P-1559, P-1562, P-1564, P-1565, P-1566, P-1567, P-1568, P-1569, P-1574, P-1575, P-1576, P-1578, P-1580, P-1581, P-1582, P-1583, P-1590, P-1591, P-1593, P-1598, P-1599, P-1605, P-1630, P-1671, P-1685, P-1700, P-1703, P-1704, P-1705, P-1706, P-1707, P-1708, P-1709, P-1711, P-1712, P-1713, P-1714, P-1718, P-1719, P-1720, P-1733, P-1737, P-1739, P-1740, P-1767, P-1776, P-1783, P-1798, P-1822, P-1839, P-1840, P-1864, P-1865, P-1871, P-1872, P-1873, P-1878, P-1879, P-1881, P-1882, P-1980, P-1996, P-1997, P-1998

TABLE 2u

Compounds with activity toward kinase MAP2K1 with IC$_{50}$ ≦ 10 μM

MAP2K1: P-0001, P-0002, P-0003, P-0005, P-0006, P-0008, P-0010, P-0011, P-0012, P-0014, P-0015, P-0017, P-0018, P-0022, P-0023, P-0029, P-0031, P-0041, P-0046, P-0051, P-0057, P-0058, P-0061, P-0076, P-0079, P-0081, P-0087, P-0098, P-0099, P-0105, P-0108, P-0111, P-0120, P-0149, P-0152, P-0158, P-0167, P-0170, P-0177, P-0194, P-0198, P-0331, P-0337, P-0568, P-0806

TABLE 2v

Compounds with activity toward kinase MAPKAPK2 with IC$_{50}$ ≦ 10 μM

MAPKAPK2: P-0007, P-0041, P-0057, P-0058, P-0077, P-0086, P-0104, P-0106, P-0151, P-0226

TABLE 2w

Compounds with activity toward kinase Met with IC$_{50}$ ≦ 10 μM

Met: P-0001, P-0002, P-0004, P-0006, P-0008, P-0009, P-0015, P-0016, P-0020, P-0026, P-0027, P-0028, P-0034, P-0035, P-0037, P-0038, P-0041, P-0052, P-0054, P-0058, P-0066, P-0076, P-0078, P-0082, P-0101, P-0114, P-0117, P-0140, P-0146, P-0149, P-0156, P-0165, P-0184, P-0228, P-0262, P-0269, P-0320, P-0325, P-0369, P-0419, P-0542, P-0550, P-0675, P-0685, P-0700, P-0716, P-0721, P-0746, P-0761, P-0763, P-0773, P-0778, P-0781, P-0811, P-0822, P-0842, P-0951, P-0962, P-1008, P-1012, P-1023, P-1037, P-1068, P-1092, P-1114, P-1132, P-1280, P-1394, P-1465, P-1527

TABLE 2x

Compounds with activity toward kinase p38 with IC$_{50}$ ≦ 10 μM p38: P-0001, P-0002, P-0003, P-0004, P-0005, P-0006, P-0008, P-0010, P-0016, P-0019, P-0025, P-0026, P-0027, P-0028, P-0032, P-0034, P-0035, P-0036, P-0037, P-0038, P-0041, P-0045, P-0050, P-0056, P-0058, P-0059, P-0066, P-0068, P-0079, P-0082, P-0088, P-0090, P-0093, P-0112, P-0114, P-0122, P-0134, P-0155, P-0156, P-0158, P-0163, P-0167, P-0170, P-0184, P-0190, P-0196, P-0204, P-0205, P-0210, P-0228, P-0244, P-0257, P-0262, P-0267, P-0297, P-0302, P-0308, P-0369, P-0442, P-0448, P-0511, P-0519, P-0521, P-0550, P-0559, P-0579, P-0594, P-0599, P-0604, P-0611, P-0624, P-0636, P-0645, P-0668, P-0671, P-0679, P-0685, P-0691, P-0699, P-0700, P-0703, P-0708, P-0716, P-0721, P-0728, P-0734, P-0738, P-0744, P-0745, P-0746, P-0751, P-0753, P-0757, P-0763, P-0773, P-0774, P-0776, P-0798, P-0806, P-0807, P-0841, P-0842, P-0868, P-0884, P-0887, P-0933, P-1042, P-1046

TABLE 2y

Compounds with activity toward kinase PDGFRB with IC$_{50}$ ≦ 10 μM

PDGFRB: P-0088, P-0262

TABLE 2z

Compounds with activity toward kinase Pim1 with IC$_{50}$ ≦ 10 μM

Pim1: P-0024, P-0090

TABLE 2aa

Compounds with activity toward kinase PKC theta with IC$_{50}$ ≦ 10 μM

PKC theta: P-0001, P-0002, P-0003, P-0004, P-0006, P-0008, P-0011, P-0012, P-0013, P-0014, P-0017, P-0019, P-0020, P-0021, P-0022, P-0024, P-0025, P-0026, P-0030, P-0031, P-0039, P-0044, P-0046, P-0049, P-0051, P-0055, P-0057, P-0060, P-0063, P-0069, P-0070, P-0109, P-0112, P-0238, P-0270

TABLE 2bb

Compounds with activity toward kinase Pyk2 with IC$_{50}$ ≦ 10 μM

Pyk2: P-0001, P-0010, P-0015, P-0018, P-0021, P-0024, P-0032, P-0041, P-0052, P-0056, P-0058, P-0069, P-0078, P-0086, P-0088, P-0095, P-0112, P-0116, P-0122, P-0137, P-0142, P-0166, P-0178, P-0188, P-0257, P-0262, P-0269, P-0287, P-0318, P-0320, P-0356, P-0369, P-0396, P-0486, P-0501, P-0521, P-0529, P-0550, P-0559, P-0562, P-0611, P-0636, P-0685, P-0697, P-0700, P-0728, P-0753, P-0806, P-0818, P-0837, P-0848, P-0850, P-0851, P-0857, P-0861, P-0866, P-0867, P-0874, P-0883, P-0897, P-0898, P-0910, P-0911, P-0912, P-0919, P-0924, P-0928, P-0944, P-0946, P-0947, P-0957, P-0964, P-0978, P-0991, P-0997, P-1002, P-1010, P-1018, P-1069, P-1280, P-1281, P-1282, P-1288, P-1316, P-1349, P-1365, P-1367, P-1368, P-1370, P-1372, P-1373, P-1375, P-1376, P-1377, P-1379, P-1380, P-1381

TABLE 2cc

Compounds with activity toward kinase Ret with IC$_{50}$ ≦ 10 μM

Ret: P-0001, P-0001, P-0002, P-0003, P-0003, P-0004, P-0005, P-0005, P-0006, P-0008, P-0009, P-0010, P-0011, P-0012, P-0013, P-0014, P-0015, P-0016, P-0017, P-0019, P-0020, P-0022, P-0024, P-0025, P-0026, P-0027, P-0028, P-0028, P-0029, P-0032, P-0032, P-0033, P-0034, P-0035, P-0036, P-0037, P-0038, P-0039, P-0040, P-0040, P-0041, P-0041, P-0042, P-0043, P-0044, P-0045, P-0046, P-0047, P-0048, P-0049, P-0050, P-0051, P-0052, P-0053, P-0054, P-0055, P-0056, P-0058, P-0059, P-0060, P-0061, P-0062, P-0063, P-0064, P-0065, P-0066, P-0069, P-0070, P-0071, P-0072, P-0073, P-0075, P-0078, P-0079, P-0082, P-0083, P-0085, P-0088, P-0089, P-0090, P-0094, P-0095, P-0096, P-0097, P-0099, P-0100, P-0101, P-0102, P-0103, P-0107, P-0108, P-0109, P-0110, P-0113, P-0114, P-0115, P-0116, P-0117, P-0119, P-0121, P-0122, P-0123, P-0124, P-0134, P-0135, P-0137, P-0138, P-0139, P-0140, P-0141, P-0142, P-0148, P-0152, P-0156, P-0158, P-0159, P-0165, P-0167, P-0171, P-0175, P-0179, P-0181, P-0184, P-0186, P-0190, P-0196, P-0196, P-0204, P-0205, P-0206, P-0210, P-0211, P-0215, P-0218, P-0224, P-0228, P-0231, P-0232, P-0236, P-0244, P-0244, P-0245, P-0246, P-0248, P-0250, P-0257, P-0262, P-0265, P-0269, P-0280, P-0286, P-0289, P-0293, P-0297, P-0302, P-0304, P-0307, P-0308, P-0314, P-0316, P-0316, P-0320, P-0320, P-0321, P-0325, P-0329, P-0339, P-0341, P-0344, P-0347, P-0351, P-0352, P-0363, P-0367, P-0369, P-0371, P-0378, P-0385, P-0392, P-0396, P-0412, P-0418, P-0434, P-0448, P-0448, P-0452, P-0453, P-0453, P-0469, P-0472, P-0486, P-0495, P-0501, P-0501, P-0517, P-0520, P-0521, P-0521, P-0533, P-0536, P-0542, P-0550, P-0550, P-0559, P-0559, P-0561, P-0579, P-0594, P-0596, P-0599, P-0599, P-0604, P-0608, P-0611, P-0623, P-0623, P-0624, P-0624, P-0632, P-0636, P-0638, P-0640, P-0644, P-0645, P-0645, P-0647, P-0656, P-0659, P-0668, P-0668, P-0671, P-0675, P-0678, P-0679, P-0682, P-0683, P-0691, P-0693, P-0697, P-0698, P-0699, P-0700, P-0703, P-0708, P-0710, P-0716, P-0721, P-0726, P-0728, P-0730, P-0734, P-0735, P-0736, P-0737, P-0738, P-0744, P-0745, P-0746, P-0749, P-0751, P-0753, P-0757, P-0761, P-0762, P-0763, P-0771, P-0778, P-0794, P-0795, P-0796, P-0807, P-0810, P-0811, P-0813, P-0822, P-0825, P-0826, P-0835, P-0841, P-0863, P-0865, P-0881, P-0939, P-0976, P-0977, P-0985, P-0998, P-1000, P-1005, P-1007, P-1011, P-1019, P-1024, P-1025, P-1026, P-1029, P-1031, P-1033, P-1036, P-1066, P-1072, P-1073, P-1075, P-1081, P-1085, P-1089, P-1097, P-1111, P-1113, P-1115, P-1117, P-1119, P-1121, P-1125, P-1126, P-1129, P-1130, P-1133, P-1134, P-1135, P-1137, P-1178, P-1181, P-1185, P-1188, P-1189, P-1191, P-1192, P-1193, P-1196, P-1198, P-1200, P-1201

TABLE 2dd

Compounds with activity toward kinase Src with IC$_{50}$ ≦ 10 μM

Src: P-0001, P-0002, P-0003, P-0004, P-0005, P-0006, P-0007, P-0008, P-0009, P-0010, P-0016, P-0017, P-0021, P-0025, P-0026, P-0027, P-0028, P-0032, P-0034, P-0035, P-0036, P-0037, P-0038, P-0040, P-0041, P-0045, P-0055, P-0067, P-0068, P-0072, P-0078, P-0079, P-0082, P-0088, P-0090, P-0102, P-0112, P-0114, P-0134, P-0152, P-0166, P-0171, P-0196, P-0209, P-0210, P-0237, P-0244, P-0269, P-0302, P-0316, P-0320, P-0373, P-0396, P-0448, P-0453, P-0483, P-0501, P-0515, P-0521, P-0550, P-0559, P-0562, P-0599, P-0623, P-0624, P-0645, P-0647, P-0668, P-0685, P-0700, P-0721, P-0753, P-0763, P-0771, P-0774, P-0805, P-0806, P-0807, P-0818, P-0837, P-0848, P-0850, P-0851, P-0853, P-0857, P-0866, P-0874, P-0876, P-0877, P-0885, P-0889, P-0898, P-0907, P-0910, P-0933, P-0950, P-0952, P-0955, P-0956, P-0958, P-0997, P-1009, P-1010, P-1013, P-1020, P-1021, P-1181, P-1247, P-1249, P-1250, P-1251, P-1252, P-1253, P-1254, P-1255, P-1256, P-1257, P-1258, P-1261, P-1262, P-1263, P-1264, P-1265, P-1266, P-1267, P-1269, P-1280, P-1281, P-1288, P-1289, P-1316, P-1317, P-1318, P-1336, P-1338, P-1343, P-1345, P-1346, P-1347, P-1348, P-1349, P-1366, P-1383, P-1384, P-1385, P-1387, P-1388, P-1390, P-1391, P-1394, P-1396, P-1397, P-1398, P-1399, P-1403, P-1416, P-1417, P-1431, P-1432, P-1433, p-1445, p-1446, P-1447, P-1448, P-1451, P-1457, P-1459, P-1469, P-1472, P-1473, P-1475, P-1476, P-1477, P-1478, P-1479, P-1480, P-1481, P-1484, P-1485, P-1486, P-1495, P-1496, P-1506, P-1527, P-1530

TABLE 2ee

Compounds with activity toward kinase Stk6 with IC$_{50}$ ≦ 10 μM

Stk6: P-0001, P-0002, P-0003, P-0007, P-0008, P-0009, P-0010, P-0011, P-0013, P-0014, P-0015, P-0018, P-0020, P-0022, P-0023, P-0029, P-0030, P-0031, P-0032, P-0033, P-0035, P-0040, P-0041, P-0042, P-0043, P-0044, P-0045, P-0046, P-0049, P-0051, P-0052, P-0054, P-0056, P-0057, P-0058, P-0060, P-0061, P-0063, P-0064, P-0065, P-0069, P-0070, P-0071, P-0076, P-0077, P-0080, P-0081, P-0082, P-0086, P-0087, P-0088, P-0091, P-0092, P-0093, P-0094, P-0098, P-0099, P-0100, P-0101, P-0104,

TABLE 2ee-continued

Compounds with activity toward kinase Stk6 with IC$_{50}$ ≦ 10 μM

P-0105, P-0106, P-0110, P-0111, P-0115, P-0117, P-0118, P-0119, P-0120, P-0123, P-0127, P-0128, P-0129, P-0131, P-0132, P-0133, P-0136, P-0140, P-0143, P-0146, P-0147, P-0148, P-0153, P-0154, P-0155, P-0157, P-0160, P-0162, P-0163, P-0164, P-0169, P-0172, P-0173, P-0174, P-0176, P-0177, P-0179, P-0181, P-0185, P-0187, P-0188, P-0189, P-0191, P-0193, P-0199, P-0201, P-0202, P-0203, P-0206, P-0207, P-0208, P-0212, P-0213, P-0214, P-0221, P-0225, P-0235, P-0237, P-0249, P-0250, P-0251, P-0253, P-0260, P-0261, P-0269, P-0272, P-0276, P-0279, P-0281, P-0283, P-0287, P-0290, P-0295, P-0300, P-0313, P-0317, P-0319, P-0322, P-0345, P-0348, P-0355, P-0370, P-0372, P-0406, P-0407, P-0417, P-0419, P-0426, P-0436, P-0441, P-0445, P-0469, P-0471, P-0489, P-0546, P-0806, P-0885, P-0933, P-0955, P-1013, P-1280, P-1336, P-1394, P-1426

TABLE 2ff

Compounds with activity toward kinase Yes with IC$_{50}$ ≦ 10 μM

Yes: P-0005, P-0007, P-0010, P-0011, P-0012, P-0013, P-0014, P-0015, P-0016, P-0017, P-0019, P-0020, P-0021, P-0022, P-0024, P-0027, P-0028, P-0029, P-0031, P-0033, P-0036, P-0040, P-0042, P-0043, P-0044, P-0045, P-0046, P-0047, P-0048, P-0049, P-0050, P-0051, P-0052, P-0053, P-0055, P-0056, P-0059, P-0060, P-0061, P-0062, P-0063, P-0065, P-0067, P-0068, P-0070, P-0072, P-0074, P-0075, P-0081, P-0082, P-0083, P-0088, P-0090, P-0093, P-0095, P-0097, P-0101, P-0102, P-0107, P-0109, P-0112, P-0122, P-0124, P-0125, P-0126, P-0129, P-0134, P-0138, P-0139, P-0145, P-0152, P-0153, P-0161, P-0162, P-0166, P-0171, P-0175, P-0188, P-0202, P-0209, P-0210, P-0230, P-0237, P-0271, P-0283, P-0310, P-0327, P-0483, P-0636

TABLE 2gg

Compounds with activity toward kinase Zap70 with IC$_{50}$ ≦ 10 μM

Zap70: P-0001, P-0004, P-0015, P-0030, P-0032, P-0033, P-0034, P-0035, P-0037, P-0038, P-0040, P-0041, P-0047, P-0058, P-0123, P-0193, P-0195, P-0205, P-0218, P-0228, P-0249, P-0275, P-0296, P-0310, P-0320, P-0342, P-0348, P-0359, P-0360, P-0378, P-0379, P-0387, P-0394, P-0434, P-0442, P-0456, P-0476, P-0484, P-0495, P-0500, P-0507, P-0523, P-0550, P-0586, P-0602, P-0607, P-0611, P-0624, P-0642, P-0649, P-0675, P-0676, P-0694, P-0698, P-0703, P-0716, P-0724, P-0727, P-0755, P-0795, P-0808, P-0836, P-0842, P-0856, P-0859, P-0865, P-0875, P-0878, P-0880, P-0888, P-0929, P-0930, P-0953, P-0982, P-0996, P-1000, P-1005, P-1019, P-1051, P-1073, P-1081, P-1089, P-1119, P-1184, P-1197

TABLE 2hh

Compounds with activity toward kinase Akt3 with IC$_{50}$ ≦ 10 μM

Akt3: P-0001, P-0002, P-0003, P-0004, P-0005, P-0006, P-0008, P-0019, P-0021, P-0024, P-0025, P-0026, P-0027, P-0034, P-0035, P-0036, P-0037, P-0038, P-0041, P-0048, P-0055, P-0057, P-0058, P-0060, P-0067, P-0099, P-0112, P-0114, P-0122, P-0127, P-0154, P-0196, P-0270, P-0278, P-0307, P-0329, P-0404, P-0436, P-0573, P-0861, P-0866, P-0883, P-0890, P-0924, P-0936, P-0940, P-0951, P-0952, P-0958, P-0962, P-0978, P-0990, P-0995, P-1010, P-1016, P-1018, P-1021, P-1022, P-1027, P-1034, P-1039, P-1040, P-1043, P-1047, P-1060, P-1062, P-1082, P-1095, P-1139, P-1145, P-1147, P-1150, P-1155, P-1158, P-1172, P-1224, P-1288, P-1459

TABLE 2ii

Compounds with activity toward kinase ALK with IC$_{50}$ ≦ 10 μM

ALK: P-0806, P-1280, P-1244, P-1336, P-1394, P-1426

TABLE 2jj

Compounds with activity toward kinase Cdk2 with IC$_{50}$ ≦ 10 μM

Cdk2: P-0806, P-1280, P-1244, P-1394

TABLE 2kk

Compounds with activity toward kinase Csk with $IC_{50} \leq 10\ \mu M$

| | |
|---|---|
| Csk: | P-0007, P-0805, P-0806, P-0885, P-0933, P-0955, P-0956, P-1013, P-1020, P-1336, P-1394, P-1426 |

TABLE 2ll

Compounds with activity toward kinase EphA2 with $IC_{50} \leq 10\ \mu M$

| | |
|---|---|
| EphA2: | P-1336, P-1394 |

TABLE 2mm

Compounds with activity toward kinase EphB4 with $IC_{50} \leq 10\ \mu M$

| | |
|---|---|
| EphB4: | P-0806, P-1336 |

TABLE 2nn

Compounds with activity toward kinase Frk with $IC_{50} \leq 10\ \mu M$

| | |
|---|---|
| Frk: | P-0007, P-0805, P-0885, P-0933, P-0955, P-0956, P-1013, P-1020, P-1244, P-1318, P-1336, P-1394 |

TABLE 2oo

Compounds with activity toward kinase Gsk3β with $IC_{50} \leq 10\ \mu M$

| | |
|---|---|
| Gsk3β: | P-0007, P-0015, P-0017, P-0053, P-0057, P-0079, P-0081, P-0085, P-0086, P-0094, P-0104, P-0106, P-0109, P-0123, P-0135, P-0148, P-0154, P-0159, P-0169, P-0180, P-0207, P-0226, P-0236, P-0252, P-0273, P-0462, P-0700, P-0728, P-0763, P-0850, P-0902, P-0913, P-0969, P-1002, P-1142, P-1181, P-1252, P-1317, P-1336, P-1372, P-1426 |

TABLE 2pp

Compounds with activity toward kinase Hck with $IC_{50} \leq 10\ \mu M$

| | |
|---|---|
| Hck: | P-0007, P-0806, P-0885, P-0933, P-1318, P-1336, P-1394, P-1426 |

TABLE 2qq

Compounds with activity toward kinase MAP4K4 with $IC_{50} \leq 10\ \mu M$

| | |
|---|---|
| MAP4K4: | P-0007, P-0057, P-0069, P-0079, P-0082, P-0088, P-0130, P-0131, P-0152, P-0174, P-0176, P-0198, P-0202, P-0214, P-0220, P-0256, P-0269, P-0287, P-0300, P-0317, P-0357, P-0367, P-0369, P-0391, P-0402, P-0442, P-0449, P-0477, P-0488, P-0495, P-0518, P-0527, P-0537, P-0573, P-0601, P-0685, P-0695, P-0700, P-0728, P-0734, P-0753, P-0800, P-0806, P-0811, P-0850, P-0851, P-0853, P-0862, P-0885, P-0896, P-0902, P-0904, P-0909, P-0913, P-0931, P-0933, P-0937, P-0954, P-0958, P-0971, P-0986, P-1017, P-1042, P-1056, P-1252, P-1253, P-1279, P-1280, P-1289, P-1317, P-1318, P-1336, P-1372, P-1383, P-1394, P-1406, P-1411, P-1414, P-1415, P-1417, P-1418, P-1426, P-1429, P-1685 |

TABLE 2rr

Compounds with activity toward kinase IGF1R with $IC_{50} \leq 10\ \mu M$

| | |
|---|---|
| IGF1R: | P-0002, P-0003, P-0004, P-0009, P-0031, P-0079, P-0080, P-0084, P-0115, P-0136, P-0154, P-0157, P-0212, P-0213, P-0700, P-0716, P-0746, P-0850, P-1336, P-1337, P-1390, P-1394 |

TABLE 2ss

Compounds with activity toward kinase IKK beta with $IC_{50} \leq 10\ \mu M$

| | |
|---|---|
| IKK beta: | P-0007, P-0013, P-0014, P-0029, P-0057, P-0073, P-0084, P-0085, P-0086, P-0087, P-0096, P-0098, P-0106, P-0111, P-0115, P-0120, P-0127, P-0128, P-0133, P-0135, P-0163, P-0164, P-0172, P-0177, P-0179, P-0216, P-0270, P-0272, P-0315, P-0376, P-0404, P-0410, P-0436, P-0629, P-0682, P-0690, P-0790, P-0896, P-0920, P-0962, P-1223 |

TABLE 2tt

Compounds with activity toward kinase Itk with $IC_{50} \leq 10\ \mu M$

| | |
|---|---|
| Itk: | P-0002, P-0003, P-0004, P-0006, P-0008, P-0009, P-0013, P-0016, P-0019, P-0020, P-0024, P-0025, P-0027, P-0031, P-0034, P-0035, P-0036, P-0038, P-0067, P-0173, P-0196, P-0521, P-0579, P-0716, P-0778, P-0883, P-0951, P-1016, P-1067, P-1337, P-1385 |

TABLE 2uu

Compounds with activity toward kinase Jak3 with $IC_{50} \leq 10\ \mu M$

| | |
|---|---|
| Jak3: | P-0003, P-0004, P-0009, P-0013, P-0014, P-0019, P-0020, P-0022, P-0024, P-0034, P-0039, P-0044, P-0046, P-0049, P-0051, P-0060, P-0061, P-0063, P-0070, P-0084, P-0101, P-0106, P-0108, P-0109, P-0119, P-0122, P-0124, P-0138, P-0141, P-0146, P-0171, P-0178, P-0187, P-0215, P-0318, P-0521, P-0730, P-0863, P-01367, P-01385 |

TABLE 2vv

Compounds with activity toward kinase MLK1 with $IC_{50} \leq 10\ \mu M$

| | |
|---|---|
| MLK1: | P-1336, P-1426 |

TABLE 2ww

Compounds with activity toward kinase TrkA with $IC_{50} \leq 10\ \mu M$

| | |
|---|---|
| TrkA: | P-0409, P-0806, P-1244, P-1426 |

TABLE 2xx

Compounds with activity toward kinase PDGFRA with $IC_{50} \leq 10\ \mu M$

PDGFRA: P-0007, P-0409, P-0806, P-0885, P-0933, P-1280, P-1336, P-1394, P-1426

TABLE 2yy

Compounds with activity toward kinase Plk1 with $IC_{50} \leq 10\ \mu M$

Plk1: P-0018, P-0022, P-0031, P-0044, P-0046, P-0067, P-0075, P-0083, P-0085, P-0099, P-0113, P-0123, P-0128, P-0135, P-0146, P-0148, P-0154, P-0178, P-0286, P-0332, P-0345, P-0366, P-0480, P-0490, P-0581, P-0863, P-0954, P-1138

TABLE 2zz

Compounds with activity toward kinase Brk with $IC_{50} \leq 10\ \mu M$

Brk: P-0007, P-0805, P-0806, P-0885, P-0933, P-0955, P-0956, P-1013, P-1020, P-1244, P-1318, P-1336, P-1394

TABLE 2ab

Compounds with activity toward kinase ROCK1 with $IC_{50} \leq 10\ \mu M$

ROCK1: P-0057

TABLE 2ac

Compounds with activity toward kinase Syk with $IC_{50} \leq 10\ \mu M$

Syk: P-0002, P-0010, P-0033, P-0054, P-0056, P-0057, P-0089, P-0196, P-0448, P-0521, P-0599, P-1336

TABLE 2ad

Compounds with activity toward kinase TEC with $IC_{50} \leq 10\ \mu M$

TEC: P-0017, P-0033, P-0044, P-0088, P-0156, P-0166, P-0228, P-0257, P-0297, P-0429, P-0897, P-0954, P-0983, P-0991, P-0997, P-1020, P-1317

TABLE 2ae

Compounds with activity toward kinase Tie2 with $IC_{50} \leq 10\ \mu M$

Tie2: P-0806, P-1280, P-1336, P-1394, P-1426

Plasmid Sequence and PCR Primer Information:

```
Abl
PCR primers
Abl      ABL-227       CACCACGGTGTGTCCCCCAACTACGA              1424
                       (SEQ ID NO: ___)

CABL-A        GTCACGTCGACTCAGACGCCTTGTTTCCCCAGCT        736
                       (SEQ ID NO: ___)

P1121. pET-SPEC BI-PTP Abl G227-V515-X
taatacgactcactatagggggaattgtgagcggataacaattcccctctagaaataattt    (SEQ ID NO: ___)
tgtttaactttaagaaggagatataccatgggtcaccaccatcaccaccacggtgtgtcc
                         M  G  H  H  H  H  H  H  G  V  S        (SEQ ID NO: ___)

cccaactacgacaagtgggagatggaacgcacggacatcaccatgaagcacaagctgggc
 P  N  Y  D  K  W  E  M  E  R  T  D  I  T  M  K  H  K  L  G gggggccagtacggggaggtgtacgagggcgtgtggaagaaatacagcctgacggtggcc
 G  G  Q  Y  G  E  V  Y  E  G  V  W  K  K  Y  S  L  T  V  A gtgaagaccttgaaggaggacaccatggaggtggaagagttcttgaaagaagctgcagtc
 V  K  T  L  K  E  D  T  M  E  V  E  E  F  L  K  E  A  A  V atgaaagagatcaaacaccctaacctggtgcagctccttggggtctgcacccgggagccc
 M  K  E  I  K  H  P  N  L  V  Q  L  L  G  V  C  T  R  E  P ccgttctatatcatcactgagttcatgacctacgggaacctcctggactacctgagggag
 P  F  Y  I  I  T  E  F  M  T  Y  G  N  L  L  D  Y  L  R  E tgcaaccggcaggaggtgaacgccgtggtgctgctgtacatggccactcagatctcgtca
 C  N  R  Q  E  V  N  A  V  V  L  L  Y  M  A  T  Q  I  S  S gccatggagtacctggagaagaaaaacttcatccacagagatcttgctgcccgaaactgc
 A  M  E  Y  L  E  K  K  N  F  I  H  R  D  L  A  A  R  N  C ctggtaggggagaaccacttggtgaaggtagctgattttggcctgagcaggttgatgaca
 L  V  G  E  N  H  L  V  K  V  A  D  F  G  L  S  R  L  M  T ggggacacctacacagcccatgctggagccaagttccccatcaaatggactgcacccgag
 G  D  T  Y  T  A  H  A  G  A  K  F  P  I  K  W  T  A  P  E agcctggcctacaacaagttctccatcaagtccgacgtctgggcatttggagtattgctt
 S  L  A  Y  N  K  F  S  I  K  S  D  V  W  A  F  G  V  L  L
```

-continued

```
tgggaaattgctacctatggcatgtccccttacccgggaattgacctgtcccaggtgtat
 W  E  I  A  T  Y  G  M  S  P  Y  P  G  I  D  L  S  Q  V  Y gagctgctagagaaggactaccgcatggagcgcccagaaggctgcccagagaaggtctat
 E  L  L  E  K  D  Y  R  M  E  R  P  E  G  C  P  E  K  V  Y gaactcatgcgagcatgttggcagtggaatccctctgaccggccctcctttgctgaaatc
 E  L  M  R  A  C  W  Q  W  N  P  S  D  R  P  S  F  A  E  I caccaagcctttgaaacaatgttccaggaatccagtatctcagacgaagtggaaaaggag
 H  Q  A  F  E  T  M  F  Q  E  S  S  I  S  D  E  V  E  K  E ctggggaaacaaggcgtctgagtcgac
 L  G  K  Q  G  V  -
```

B-Raf V600E
PCR primers

| BRAF | BRAF437D-2 | ACGGGACCATATGGATGATTGGGAGATTCCTGA (SEQ ID NO: ___) | 4783 |
| | BRAF722K-A | CACTGGTCGACTATTTTGGCAATGAGCGGGCCA (SEQ ID NO: ___) | 4784 |
| | BRAFV599E-S | GGTCTAGCTACAGAAAAATCTCGATGGAG (SEQ ID NO: ___) | 893 |
| | BRAFV599E-A | CTCCATCGAGATTTTTCTGTAGCTAGACC (SEQ ID NO: ___) | 894 |

P4254. pFastBacBD-CDC37 BRAF D437-K722-X, V600E

```
     tattccggattattcataccgtcccaccatcgggcgcggatctcggtccgaaacc    (SEQ ID NO: ___)
atgtcgtactaccatcaccatcaccatcacgattacgatatcccaacgaccgaaaacctg
 M  S  Y  Y  H  H  H  H  H  H  D  Y  D  I  P  T  T  E  N  L   (SEQ ID NO: ___)

tattttcagggccatatggatgattgggagattcctgatgggcagattacagtgggacaa
 Y  F  Q  G  H  M  D  D  W  E  I  P  D  G  Q  I  T  V  G  Q agaattggatctggatcatttggaacagtctacaagggaaagtggcatggtgatgtggca
 R  I  G  S  G  S  F  G  T  V  Y  K  G  K  W  H  G  D  V  A gtgaaaatgttgaatgtgacagcacctacacctcagcagttacaagccttcaaaaatgaa
 V  K  M  L  N  V  T  A  P  T  P  Q  Q  L  Q  A  F  K  N  E gtaggagtactcaggaaaacacgacatgtgaatatcctactcttcatgggctattccaca
 V  G  V  L  R  K  T  R  H  V  N  I  L  L  F  M  G  Y  S  T aagccacaactggctattgttacccagtggtgtgagggctccagcttgtatcaccatctc
 K  P  Q  L  A  I  V  T  Q  W  C  E  G  S  S  L  Y  H  H  L catatcattgagaccaaatttgagatgatcaaacttatagatattgcacgacagactgca
 H  I  I  E  T  K  F  E  M  I  K  L  I  D  I  A  R  Q  T  A cagggcatggattacttacacgccaagtcaatcatccacagagacctcaagagtaataat
 Q  G  M  D  Y  L  H  A  K  S  I  I  H  R  D  L  K  S  N  N atatttcttcatgaagacctcacagtaaaaataggtgattttggtctagctacagaaaaa
 I  F  L  H  E  D  L  T  V  K  I  G  D  F  G  L  A  T  E  K tctcgatggagtgggtcccatcagtttgaacagttgtctggatccattttgtggatggca
 S  R  W  S  G  S  H  Q  F  E  Q  L  S  G  S  I  L  W  M  A ccagaagtcatcagaatgcaagataaaaatccatacagctttcagtcagatgtatatgca
 P  E  V  I  R  M  Q  D  K  N  P  Y  S  F  Q  S  D  V  Y  A tttggaattgttcLgtatgaattgatgactggacagttaccttattcaaacatcaacaac
 F  G  I  V  L  Y  E  L  M  T  G  Q  L  P  Y  S  N  I  N  N agggaccagataatttttatggtgggacgaggatacctgtctccagatctcagtaaggta
 R  D  Q  I  I  F  M  V  G  R  G  Y  L  S  P  D  L  S  K  V cggagtaactgtccaaaagccatgaagagattaatggcagagtgcctcaaaaagaaaga
 R  S  N  C  P  K  A  M  K  R  L  M  A  E  C  L  K  K  R gatgagagaccactctttccccaaattctcgcctctattgagctgctggcccgctcattg
 D  E  R  P  L  F  P  Q  I  L  A  S  I  E  L  L  A  R  S  L ccaaaatagtcgactagagcctgcagtctcgaggcatgcggtaccaagctt
 P  K  -
```

```
Erk2
PCR primers
ERK2      ERK2-S          GGCAGCCCATATGGCGGCGGCGGCGGC                748
                          (SEQ ID NO: ___)

ERK2-A          TGTCCGTCGACATTTAAGATCTGTATCCTGG            749
                          (SEQ ID NO: ___)

P4227.pET15S ERK2/MEK1DD
taatacgactcactatagggaattgtgagcggataacaattcccctctagaaataatttt     (SEQ ID NO: ___)
tgtttaactttaagaaggagatataccatgggcagcagccatcatcatcatcatcacagc
                          M  G  S  S  H  H  H  H  H  H  S         (SEQ ID NO: ___)

agcggcctggtgccgcgcggcagccatatggcggcggcggcgggcgcgggccccggagatg
 S  G  L  V  P  R  G  S  H  M  A  A  A  A  G  A  G  P  E  M gtccgcgggcaggtgttcgacgtggggccgcgctacaccaacctctcgtacatcggcgag
 V  R  G  Q  V  F  D  V  G  P  R  Y  T  N  L  S  Y  I  G  E ggcgcctacggcatggtgtgctctgcttatgataatgtcaacaaagttcgagtagctatc
 G  A  Y  G  M  V  C  S  A  Y  D  N  V  N  K  V  R  V  A  I aagaaaatcagccccttTgagcaccagacctactgccagagaaaccctgagggagataaaa
 K  K  I  S  P  F  E  H  Q  T  Y  C  Q  R  T  L  R  E  I  K atcttactgcgcttcagacatgagaacatcattggaatcaatgacattattcgagcacca
 I  L  L  R  F  R  H  E  N  I  I  G  I  N  D  I  I  R  A  P accatcgagcaaatgaaagatgtatatatagtacaggacctcatggaaacagatctttac
 T  I  E  Q  M  K  D  V  Y  I  V  Q  D  L  M  E  T  D  L  Y aagctcttgaagacacaacacctcagcaatgaccatatctgctattttctctaccagatc
 K  L  L  K  T  Q  H  L  S  N  D  H  I  C  Y  F  L  Y  Q  I ctcagagggttaaaatatatccattcagctaacgttctgcaccgtgacctcaagccttcc
 L  R  G  L  K  Y  I  H  S  A  N  V  L  H  R  D  L  K  P  S aacctgctgctcaacaccaccTgtgatctcaagatctgtgactttggcctggcccgtgtt
 N  L  L  L  N  T  T  C  D  L  K  I  C  D  F  G  L  A  R  V gcagatccagaccatgatcacacagggttcctgacagaatatgtggccacacgttggtac
 A  D  P  D  H  D  H  T  G  F  L  T  E  Y  V  A  T  R  W  Y agggctccagaaattatgttgaattccaagggctacaccaagtccattgatatttggtct
 R  A  P  E  I  M  L  N  S  K  G  Y  T  K  S  I  D  I  W  S gtaggctgcattctggcagaaatgctttctaacaggcccatcttTccagggaagcattat
 V  G  C  I  L  A  E  M  L  S  N  R  P  I  F  P  G  K  H  Y cttgaccagctgaaccacattttgggtattcttggatccccatcacaagaagacctgaat
 L  D  Q  L  N  H  I  L  G  I  L  G  S  P  S  Q  E  D  L  N tgtataataaatttaaaagctaggaactatttgctttctcttccacacaaaaataaggtg
 C  I  I  N  L  K  A  R  N  Y  L  L  S  L  P  H  K  N  K  V ccatggaacaggctgttcccaaatgctgactccaaagctctggacttattggacaaaatg
 P  W  N  R  L  F  P  N  A  D  S  K  A  L  D  L  L  D  K  M ttgacattcaacccacacaagagattgaagtagaacaggctctggcccacccatatctg
 L  T  F  N  P  H  K  R  I  E  V  E  Q  A  L  A  H  P  Y  L gagcagtattacgacccgagtgacgagcccatcgccgaagcaccattcaagttcgacatg
 E  Q  Y  Y  D  P  S  D  E  P  I  A  E  A  P  F  K  F  D  M gaattggatgacttgcctaaggaaaagctcaaagaactaattttTgaagagactgctaga
 E  L  D  D  L  P  K  E  K  L  K  E  L  I  F  E  E  T  A  R ttccagccaggatacagatcttaaatgtcgac
 F  Q  P  G  Y  R  S  -

Fak
PCR primers
FAK       FAK411          GCTGGATCCACCAGGGATTATCAAAG                 2156
                          (SEQ ID NO: ___)

FAK686          GTTCTTGTCGACTACTGAGCCTTCTCTTCCTCCA         2157
                          (SEQ ID NO: ___)

P1358.pFastBacHtb FAK S411-Q686-X
     tattccggattattcataccgtcccaccatcgggcgcggatctcggtccgaaacc       (SEQ ID NO: ___)
atgtcgtactaccatcaccatcaccatcacgattacgatatcccaacgaccgaaaacctg
```

-continued

```
                    M  S  Y  Y  H  H  H  H  H  H  D  Y  D  I  P  T  T  E  N  L      (SEQ ID NO: ___)

tattttcagggcgccatgggatccaccagggattatgagattcaaagagaaagaatagaa
 Y  F  Q  G  A  M  G  S  T  R  D  Y  E  I  Q  R  E  R  I  E cttggacgatgtattggagaaggccaatttggagatgtacatcaaggcatttatatgagt
 L  G  R  C  I  G  E  G  Q  F  G  D  V  H  Q  G  I  Y  M  S ccagagaatccagctttggcggttgcaattaaaacatgtaaaaactgtacttcggacagc
 P  E  N  P  A  L  A  V  A  I  K  T  C  K  N  C  T  S  D  S gtgagagagaaattcttcaagaagccttaacaatgcgtcagtttgaccatcctcatatt
 V  R  E  K  F  L  Q  E  A  L  T  M  R  Q  F  D  H  P  H  I gtgaagctgattggagtcatcacagagaatcctgtctggataatCatggagctgtgcaca
 V  K  L  I  G  V  I  T  E  N  P  V  W  I  I  M  E  L  C  T cttggagagctgaggtcatttttgcaagtaaggaaatacagtttggatctagcatctttg
 L  G  E  L  R  S  F  L  Q  V  R  K  Y  S  L  D  L  A  S  L atcctgtatgcctatcagcttagtacagctcttgcatatctagagagcaaaagatttgta
 I  L  Y  A  Y  Q  L  S  T  A  L  A  Y  L  E  S  K  R  F  V cacagggacattgctgctcggaatgttctggtgtcctcaaatgattgtgtaaaattagga
 H  R  D  I  A  A  R  N  V  L  V  S  S  N  D  C  V  K  L  G gactttggattatcccgatatatggaagatagtacttactacaaagcttccaaaggaaaa
 D  F  G  L  S  R  Y  M  E  D  S  T  Y  Y  K  A  S  K  G  K ttgcctattaaatggatggctccagagtcaatCaattttCgacgttttacCtcagctagt
 L  P  I  K  W  M  A  P  E  S  I  N  F  R  R  F  T  S  A  S gacgtatggatgtttggtgtgtgtatgtgggagatactgatgcatggtgtgaagcctttt
 D  V  W  M  F  G  V  C  M  W  E  I  L  M  H  G  V  K  P  F caaggagtgaagaacaatgatgtaatcggtcgaattgaaaatggggaaagattaccaatg
 Q  G  V  K  N  N  D  V  I  G  R  I  E  N  G  E  R  L  P  M cctccaaattgtcctcctaccctctacagcctttatgacgaaatgctgggcctatgacccc
 P  P  N  C  P  P  T  L  Y  S  L  M  T  K  C  W  A  Y  D  P agcaggcggcccaggtttactgaacttaaagctcagctcagcacaatcctggaggaagag
 S  R  R  P  R  F  T  E  L  K  A  Q  L  S  T  I  L  E  E  E aaggctcagtagtcgacgagctcactagtcgcggccgctttcgaatctagagcctgcagt
 K  A  Q  -  S  T  S  S  L  V  A  A  A  F  E  S  R  A  C  S ctcgaggcatgcggtaccaagcttgtcgagaagtactagaggatcataatc
 L  E  A  C  G  T  K  L  V  E  K  Y  -
```

FGFR1
PCR primers

| FGFR1 | FGFR1-S | GACTCCTCATATGGCAGGGGTCTCTGAGTATGA (SEQ ID NO: ___) | 1237 |
|---|---|---|---|
|  | FGFR-SAL | CAGGTCGTCGACTACTCCTGGTTGGAGGTCAGG (SEQ ID NO: ___) | 1611 |
|  | C488A-1 | CTGGGAGAGGGCGCGTTTGGGCAGGTGG (SEQ ID NO: ___) | 2038 |
|  | C488A-2 | CCACCTGCCCAAACGCGCCCTCTCCCAG (SEQ ID NO: ___) | 2039 |
|  | C584S-1 | CAGGGCTGGAATACAGCTACAACCCCAGC (SEQ ID NO: ___) | 2041 |
|  | C584S-2 | GCTGGGGTTGTAGCTGTATTCCAGCCCTG (SEQ ID NO: ___) | 2042 |

```
P1351.pET N6 BI-PTP FGFR A458-E765-X C488A, C584S
taatacgactcactatagggggaattgtgagcggataacaattcccctctagaaataattt    (SEQ ID NO: ___)
tgtttaactttaagaaggagatataccatgggtcaccaccatcaccatcatatggcaggg
                                M  G  H  H  H  H  H  H  M  A  G    (SEQ ID NO: ___)

gtctctgagtatgagcttcccgaagaccctcgctgggagctgcctcgggacagactggtc
 V  S  E  Y  E  L  P  E  D  P  R  W  E  L  P  R  D  R  L  V ttaggcaaacccctgggagagggcgcgtttgggcaggtggtgttggcagaggctatcggg
 L  G  K  P  L  G  E  G  A  F  G  Q  V  V  L  A  E  A  I  G
```

-continued

```
ctggacaaggacaaacccaaccgtgtgaccaaagtggctgtgaagatgttgaagtcggac
 L   D   K   D   K   P   N   R   V   T   K   V   A   V   K   M   L   K   S   D gcaacagagaaagacttgtcagacctgatctcagaaatggagatgatgaagatgatcggg
 A   T   E   K   D   L   S   D   L   I   S   E   M   E   M   M   K   M   I   G aagcataagaatatcatcaacctgctggggggcctgcacgcaggatggtccttgtatgtc
 K   H   K   N   I   I   N   L   L   G   A   C   T   Q   D   G   P   L   Y   V atcgtggagtatgcctccaagggcaacctgcgggagtacctgcaggcccggaggccccca
 I   V   E   Y   A   S   K   G   N   L   R   E   Y   L   Q   A   R   R   P   P gggctggaatacagctacaaccccagccacaacccagaggagcagctctcctccaaggac
 G   L   E   Y   S   Y   N   P   S   H   N   P   E   E   Q   L   S   S   K   D ctggtgtcctgcgcctaccaggtggcccgaggcatggagtatctggcctccaagaagtgc
 L   V   S   C   A   Y   Q   V   A   R   G   M   E   Y   L   A   S   K   K   C atacaccgagacctggcagccaggaatgtcctggtgacagaggacaatgtgatgaagata
 I   H   R   D   L   A   A   R   N   V   L   V   T   E   D   N   V   M   K   I gcagactttggcctcgcacgggacattcaccacatcgactactataaaaagacaaccaac
 A   D   F   G   L   A   R   D   I   H   H   I   D   Y   Y   K   K   T   T   N ggccgactgcctgtgaagtggatggcacccgaggcattatttgaccggatctacacccac
 G   R   L   P   V   K   W   M   A   P   E   A   L   F   D   R   I   Y   T   H cagagtgatgtgtggtctttcggggtgctcctgtgggagatcttcactctgggcggctcc
 Q   S   D   V   W   S   F   G   V   L   L   W   E   I   F   T   L   G   G   S ccataccccggtgtgcctgtggaggaacttttcaagctgctgaaggagggtcaccgcatg
 P   Y   P   G   V   P   V   E   E   L   F   K   L   L   K   E   G   H   R   M gacaagcccagtaactgcaccaacgagctgtacatgatgatgcgggactgctggcatgca
 D   K   P   S   N   C   T   N   E   L   Y   M   M   M   R   D   C   W   H   A gtgccctcacagagacccaccttcaagcagctggtggaagacctggaccgcatcgtggcc
 V   P   S   Q   R   P   T   F   K   Q   L   V   E   D   L   D   R   I   V   A ttgacctccaaccaggagtagtcgacgaaggagatatatcc
 L   T   S   N   Q   E   -
```

Flt1
PCR primers
| FLT1 | FLT1-S | ATCAATTCATATGGACCCAGATGAAGTTCC (SEQ ID NO: ___) | 737 |
|---|---|---|---|
| | FLT1-A | ATGTAGTCGACCTAATCCTGTTGTACATTTGCTT (SEQ ID NO: ___) | 738 |

P1826.pETN6 BI-PTP FLT1 M799-D1165-X WT

```
taatacgactcactatagggggaattgtgagcggataacaattcccctctagaaataattt    (SEQ ID NO: ___)
tgtttaactttaagaaggagatataccatgggtcaccaccatcaccatcatatggaccca
                              M   G   H   H   H   H   H   H   M   D   P    (SEQ ID NO: ___)

gatgaagttcctttggatgagcagtgtgagcggctcccttatgatgccagcaagtgggag
 D   E   V   P   L   D   E   Q   C   E   R   L   P   Y   D   A   S   K   W   E tttgcccggggagagacttaaactgggcaaatcacttggaagaggggcttttggaaaagtg
 F   A   R   E   R   L   K   L   G   K   S   L   G   R   G   A   F   G   K   V gttcaagcatcagcatttggcattaagaaatcacctacgtgccggactgtggctgtgaaa
 V   Q   A   S   A   F   G   I   K   K   S   P   T   C   R   T   V   A   V   K atgctgaaagagggggccacggccagcgagtacaaagctcLgatgactgagctaaaaatc
 M   L   K   E   G   A   T   A   S   E   Y   K   A   L   M   T   E   L   K   I ttgacccacattggccaccatctgaacgtggttaacctgctgggagcctgcaccaagcaa
 L   T   H   I   G   H   H   L   N   V   V   N   L   L   G   A   C   T   K   Q ggagggcctctgatggtgattgttgaatactgcaaatatggaaatctctccaactacctc
 G   G   P   L   M   V   I   V   E   Y   C   K   Y   G   N   L   S   N   Y   L aagagcaaacgtgacttatttttttctcaacaaggatgcagcactacacatggagcctaag
 K   S   K   R   D   L   F   F   L   N   K   D   A   A   L   H   M   E   P   K aaagaaaaaatggagccaggcctggaacaaggcaagaaaccaagactagatagcgtcacc
 K   E   K   M   E   P   G   L   E   Q   G   K   K   P   R   L   D   S   V   T agcagcgaaagctttgcgagctccggctttcaggaagataaaagtctgagtgatgttgag
 S   S   E   S   F   A   S   S   G   F   Q   E   D   K   S   L   S   D   V   E
```

```
gaagaggaggattctgacggtttctacaaggagcccatcactatggaagatctgatttct
 E  E  E  D  S  D  G  F  Y  K  E  P  I  T  M  E  D  L  I  S tacagttttcaagtggccagaggcatggagttcctgtcttccagaaagtgcattcatcgg
 Y  S  F  Q  V  A  R  G  M  E  F  L  S  S  R  K  C  I  H  R gacctggcagcgagaaacattcttttatctgagaacaacgtggtgaagatttgtgattt
 D  L  A  A  R  N  I  L  L  S  E  N  N  V  V  K  I  C  D  F ggccttgcccgggatatttataagaaccccgattatgtgagaaaaggagatactcgactt
 G  L  A  R  D  I  Y  K  N  P  D  Y  V  R  K  G  D  T  R  L cctctgaaatggatggctcccgaatctatctttgacaaaatctacagcaccaagagcgac
 P  L  K  W  M  A  P  E  S  I  F  D  K  I  Y  S  T  K  S  D gtgtggtcttacggagtattgctgtgggaaatcttctccttaggtgggtctccatcccca
 V  W  S  Y  G  V  L  L  W  E  I  F  S  L  G  G  S  P  Y  P ggagtacaaatggatgaggactttgcagtcgcctgagggaaggcatgaggatgagagct
 G  V  Q  M  D  E  D  F  C  S  R  L  R  E  G  M  R  M  R  A cctgagtactctactcctgaaatctatcagatcatgctggactgctggcacagagaccca
 P  E  Y  S  T  P  E  I  Y  Q  T  M  L  D  C  W  H  R  D  P aaagaaaggccaagatttgcagaacttgtggaaaaactaggtgatttgcttcaagcaaat
 K  E  R  P  R  F  A  E  L  V  E  K  L  G  D  L  L  Q  A  N gtacaacaggattaggtcgaccaccaccaccaccactgagatccggctggccctact
 V  Q  Q  D  - ggccgaaaggaattcgaggccagcagggccaccgctgagcaataactagcataacccctt
ggggcctctaaacgggtcttgagggggttttttg
```

Kit
PCR primers

| KIT | 8K1A | ATGTACGAAGTTCAGTGGAAAGTTGTTGAAGAAATCAACGG (SEQ ID NO: ___) | 1775 |
| --- | --- | --- | --- |
| | 8K1B | GGTCGATGTAAACGTAGTTGTTACCGTTGATTTCTTCAACAACTTT (SEQ ID NO: ___) | 1777 |
| | 8K2A | AACAACTACGTTTACATCGACCCGACCCAGCTGCCGTACGAC (SEQ ID NO: ___) | 1779 |
| | 8K2B | GTTACGCGGGAACTCCCATTTGTGGTCGTACGGCAGCTGGGTC (SEQ ID NO: ___) | 1781 |
| | 8K3A | AAATGGGAGTTCCCGCGTAACCGTCTGTCTTTCGGTAAAACCC (SEQ ID NO: ___) | 1782 |
| | 8K3B | ACCGAACGCACCCGCACCCAGGGTTTTACCGAAAGACAGAC (SEQ ID NO: ___) | 1783 |
| | 8K4A | GGTGCGGGTGCGTTCGGTAAAGTTGTTGAAGCGACCGCGTACG (SEQ ID NO: ___) | 1784 |
| | 8K4B | GCCGCGTCAGATTTGATCAGACCGTACGCGGTCGCTTCAAC (SEQ ID NO: ___) | 1735 |
| | 8K5A | CTGATCAAATCTGACGCGGCGATGACCGTTGCGGTTAAAATGC (SEQ ID NO: ___) | 1736 |
| | 8K5B | GTCAGGTGCGCAGACGGTTTCAGCATTTTAACCGCAACGGTCA (SEQ ID NO: ___) | 1787 |
| | 8K6A | AAACCGTCTGCGCACCTGACCGAACGTGAAGCGCTGATGTCTG (SEQ ID NO: ___) | 1788 |
| | 8K6B | CCAGGTAAGACAGAACTTTCAGTTCAGACATCAGCGCTTCACGT (SEQ ID NO: ___) | 1789 |
| | 8K7A | CTGAAAGTTCTGTCTTACCTGGGTAACCACATGAACATCGTTAA (SEQ ID NO: ___) | 1791 |
| | 8K7B | GGTGCACGCACCCAGCAGGTTAACGATGTTCATGTGGTTAC (SEQ ID NO: ___) | 1792 |
| | 8K8A | CTGCTGGGTGCGTGCACCATCGGTGGTCCGACCCTGGTTATCA (SEQ ID NO: ___) | 1793 |

-continued

| | | |
|---|---|---|
| 8K8B | GTCACCGTAGCAGCAGTATTCGGTGATAACCAGGGTCGGACCA (SEQ ID NO: ___) | 1794 |
| 8K9A | GAATACTGCTGCTACGGTGACCTGCTGAACTTCCTGCGTCGTA (SEQ ID NO: ___) | 1795 |
| 8K9B | AGAGCAGATGAAAGAGTCACGTTTACGACGCAGGAAGTTCAGC (SEQ ID NO: ___) | 1796 |
| 8K10A | CGTGACTCTTTCATCTGCTCTAAACAGGAAGACCACGCGGAAG (SEQ ID NO: ___) | 1797 |
| 8K10B | CAGCAGGTTTTTGTACAGCGCCGCTTCCGCGTGGTCTTCCTGT (SEQ ID NO: ___) | 1798 |
| 8K11A | GCGCTGTACAAAAACCTGCTGCACTCTAAAGAATCTTCTTGCTC (SEQ ID NO: ___) | 1799 |
| 8K11B | CCATGTATTCGTTGGTAGAGTCAGAGCAAGAAGATTCTTTAGAGT (SEQ ID NO: ___) | 1811 |
| 8K11A | GACTCTACCAACGAATACATGGACATGAAACCGGGTGTTTCTTA (SEQ ID NO: ___) | 1812 |
| 8K11B | TCCGCTTTGGTCGGAACAACGTAAGAAACACCCGGTTTCATGT (SEQ ID NO: ___) | 1813 |
| 8K12A | GTTGTTCCGACCAAAGCGGACAAACGTCGTTCTGTTCGTATCG (SEQ ID NO: ___) | 1814 |
| 8K12B | TAACGTCACGTTCGATGTAAGAACCGATACGAACAGAACGACGTTT (SEQ ID NO: ___) | 1815 |
| 8K13A | TCTTACATCGAACGTGACGTTACCCCGGCGATCATGGAAGACG (SEQ ID NO: ___) | 1816 |
| 8K13B | CCAGGTCCAGCGCCAGTTCGTCGTCTTCCATGATCGCCGG (SEQ ID NO: ___) | 1817 |
| 8K14A | GAACTGGCGCTGGACCTGGAAGACCTGCTGTCTTTCTCTTACC (SEQ ID NO: ___) | 1818 |
| 8K14B | GAACGCCATACCTTTCGCAACCTGGTAAGAGAAAGACAGCAGGT (SEQ ID NO: ___) | 1819 |
| 8K15A | GTTGCGAAAGGTATGGCGTTCCTGGCGTCTAAAAACTGCATCCA (SEQ ID NO: ___) | 1821 |
| 8K15B | CGCGCCGCCAGGTCACGGTGGATGCAGTTTTTAGACGCC (SEQ ID NO: ___) | 1822 |
| 8K16A | CGTGACCTGGCGGCGCGTAACATCCTGCTGACCCACGGTCG (SEQ ID NO: ___) | 1823 |
| 8K16B | ACCGAAGTCGCAGATTTTGGTGATACGACCGTGGGTCAGCAGG (SEQ ID NO: ___) | 1824 |
| 8K17A | ACCAAAATCTGCGACTTCGGTCTGGCGCGTGACATCAAAAACG (SEQ ID NO: ___) | 1825 |
| 8K17B | GTTACCTTTAACAACGTAGTTAGAGTCGTTTTTGATGTCACGCGCC (SEQ ID NO: ___) | 1826 |
| 8K18A | TCTAACTACGTTGTTAAAGGTAACGCGCGTCTGCCGGTTAAATG (SEQ ID NO: ___) | 1827 |
| 8K18B | GAAGATAGATTCCGGCGCCATCCATTTAACCGGCAGACGCGC (SEQ ID NO: ___) | 1829 |
| 8K19A | ATGGCGCCGGAATCTATCTTCAACTGCGTTTACACCTTCGAATC (SEQ ID NO: ___) | 1831 |
| 8K19B | GATACCGTAAGACCAAACGTCAGATTCGAAGGTGTAAACGCAG (SEQ ID NO: ___) | 1832 |
| BK20A | GACGTTTGGTCTTACGGTATCTTCCTGTGGGAACTGTTCTCTC (SEQ ID NO: ___) | 1833 |
| 8K20B | CCTGTGGGAACTGTTCTCTCTGGGTTCTTCTCCGTACCCGG (SEQ ID NO: ___) | 1834 |

-continued

| | | |
|---|---|---|
| 8K21A | GGTTCTTCTCCGTACCCGGGTATGCCGGTTGACTCTAAATTCTAT (SEQ ID NO: ___) | 1835 |
| 8K21B | CGGAAACCTTCTTTGATCATTTTGTAGAATTTAGAGTCAACCGGC (SEQ ID NO: ___) | 1836 |
| 8K22A | AAAATGATCAAAGAAGGTTTCCGTATGCTGTCTCCGGAACACG (SEQ ID NO: ___) | 1837 |
| 8K22B | ATGTCGTACATTTCCGCCGGCGCGTGTTCCGGAGACAGCATA (SEQ ID NO: ___) | 1838 |
| 8K23A | CCGGCGGAAATGTACGACATCATGAAAACCTGCTGGGACGCG (SEQ ID NO: ___) | 1839 |
| 8K23B | AAGGTCGGACGTTTCAGCGGGTCCGCGTCCCAGCAGGTTTTC (SEQ ID NO: ___) | 1841 |
| 8K24A | CCGCTGAAACGTCCGACCTTCAACAGATCGTTCAGCTGATCG (SEQ ID NO: ___) | 1842 |
| 8K24B | TTGGTAGATTCAGAGATCTGTTTTTCGATCAGCTGAACGATCTGTT (SEQ ID NO: ___) | 1843 |
| 8K25A | AAACAGATCTCTGAATCTACCAACCACATCTACTCTAACCTGGC (SEQ ID NO: ___) | 1844 |
| 8K25B | TGACGGTTCGGAGAGCAGTTCGCCAGGTTAGAGTAGATGTGC (SEQ ID NO: ___) | 1845 |
| 8K26A | AACTGCTCTCCGAACCGTCAGAAACCGGTTGTTGACCACTCTC (SEQ ID NO: ___) | 1846 |
| 8K26B | GTAGAACCAACAGAGTTGATACGAACAGAGTGGTCAACAACCGGT (SEQ ID NO: ___) | 1847 |
| 8K27A | CGTATCAACTCTGTTGGTTCTACCGCGTCTTCTTCTCAGCCG (SEQ ID NO: ___) | 1848 |
| 8K27B | AACGTCGTCGTGAACCAGCAGCGGCTGAGAAGAAGACGCG (SEQ ID NO: ___) | 1849 |
| 8K-F | GTTGTTTCATATGTACGAAGTTCAGTGGAAAG (SEQ ID NO: ___) | 1851 |
| 8K-R | GTTGTTTGTCGACTAAACGTCGTCGTGAACCAGCAG (SEQ ID NO: ___) | 1852 |
| KIT COD-K948X | GTTCTTGTCGACTATTTCTGACGGTTCGGAGAGC | 3411 |

P1332.N6 BI PTP KIT M552-K948-X COD
```
taatacgactcactataggggaattgtgagcggataacaattcccctctagaaataattt    (SEQ ID NO: ___)
tgtttaactttaagaaggagatataccatgggtcaccaccatcaccatcatatgtacgaa
                        M  G  H  H  H  H  H  H  M  Y  E        (SEQ ID NO: ___)

gttcagtggaaagttgttgaagaaatcaacggtaacaactacgtttacatcgacccgacc
 V  Q  W  K  V  V  E  E  I  N  G  N  N  Y  V  Y  I  D  P  T cagctgccgtacgaccacaaatgggagttcccgcgtaaccgtctgtctttcggtaaaacc
 Q  L  P  Y  D  H  K  W  E  F  P  R  N  R  L  S  F  G  K  T ctgggtgcgggtgcgttcggtaaagttgttgaagcgaccgcgtacggtctgatcaaatct
 L  G  A  G  A  F  G  K  V  V  E  A  T  A  Y  G  L  I  K  S gacgcggcgatgaccgttgcggttaaaatgctgaaaccgtctgcgcacctgaccgaacgt
 D  A  A  M  T  V  A  V  K  M  L  K  P  S  A  H  L  T  E  R gaagcgctgatgtctgaactgaaagttctgtcttacctgggtaaccacatgaacatcgtt
 E  A  L  M  S  E  L  K  V  L  S  Y  L  G  N  H  M  N  I  V aacctgctgggtgcgtgcaccatcggtggtccgaccctggttatcaccgaatactgctgc
 N  L  L  G  A  C  T  I  G  G  P  T  L  V  I  T  E  Y  C  C tacggtgacctgctgaacttcctgcgtcgtaaacgtgactcttttcatctgctctaaacag
 Y  G  D  L  L  N  F  L  R  R  K  R  D  S  F  I  C  S  K  Q gaagaccacgcggaagcggcgctgtacaaaaaacctgctgcactctaaagaatcttcttgc
 E  D  H  A  E  A  A  L  Y  K  N  L  L  H  S  K  E  S  S  C tctgactctaccaacgaatacatggacatgaaaccgggtgtttcttacgttgttccgacc
 S  D  S  T  N  E  Y  M  D  M  K  P  G  V  S  Y  V  V  P  T
```

```
aaagcggacaaacgtcgttctgttcgtatcggttcttacatcgaacgtgacgttaccccg
 K  A  D  K  R  R  S  V  R  I  G  S  Y  I  E  R  D  V  T  P gcgatcatggaagacgacgaactggcgctggacctggaagacctgctgtctttctcttac
 A  I  M  E  D  D  E  L  A  L  D  L  E  D  L  L  S  F  S  Y caggttgcgaaaggtatggcgttcctggcgtctaaaaactgcatccaccgtgacctggcg
 Q  V  A  K  G  M  A  F  L  A  S  K  N  C  I  H  R  D  L  A gcgcgtaacatcctgctgacccacggtcgtatcaccaaaatctgcgacttcggtctggcg
 A  R  N  I  L  L  T  H  G  R  I  T  K  I  C  D  F  G  L  A cgtgacatcaaaaacgactctaactacgttgttaaaggtaacgcgcgtctgccggttaaa
 R  D  I  K  N  D  S  N  Y  V  V  K  G  N  A  R  L  P  V  K tggatggcgccggaatctatcttcaactgcgtttacaccttcgaatctgacgtttggtct
 W  M  A  P  E  S  I  F  N  C  V  Y  T  F  E  S  D  V  W  S tacggtatcttcctgtgggaactgttctctctgggttcttctccgtacccgggtatgccg
 Y  G  I  F  L  W  E  L  F  S  L  G  S  S  P  Y  P  G  M  P gttgactctaaattctacaaaatgatcaaagaaggtttccgtatgctgtctccggaacac
 V  D  S  K  F  Y  K  M  I  K  E  G  F  R  M  L  S  P  E  H gcgccggcggaaatgtacgacatcatgaaaacctgctgggacgcggacccgctgaaacgt
 A  P  A  E  M  Y  D  I  M  K  T  C  W  D  A  D  P  L  K  R ccgaccttcaaacagatcgttcagctgatcgaaaaacagatctctgaatctaccaaccac
 P  T  F  K  Q  I  V  Q  L  I  E  K  Q  I  S  E  S  T  N  H atctactctaacctggcgaactgctctccgaaccgtcagaaatagtcgactgaaaaagga
 I  Y  S  N  L  A  N  C  S  P  N  R  Q  K  - agagt

MET
PCR primers
MET    G1056         CATCCTACATATGGGGGACTCTGATATATCCAGTC            1223
                     (SEQ ID NO: ___)

G-1364        CTAGCAGGTCGACTACCCAATGAAAGTAGAGAAGATCGC        1318
                     (SEQ ID NO: ___)

P1818.pETN6 BI-PTP MET G1056-G1364-X WT
taatacgactcactatagggaattgtgagcggataacaattcccctctagaaataattt     (SEQ ID NO: ___)
tgtttaactttaagaaggagatataccatgggtcaccaccatcaccatcatatgggggac
                           M  G  H  H  H  H  H  H  M  G  D    (SEQ ID NO: ___)

tctgatatatccagtccattactgcaaaatactgtccacattgacctcagtgctctaaat
 S  D  I  S  S  P  L  L  Q  N  T  V  H  I  D  L  S  A  L  N ccagagctggtccaggcagtgpagcatgtagtgattgggcccagtagcctgattgtgcat
 P  E  L  V  Q  A  V  Q  H  V  V  I  G  P  S  S  L  I  V  H ttcaatgaagtcataggaagagggcattttggttgtgtatatcatgggactttgttggac
 F  N  E  V  I  G  R  G  H  F  G  C  V  Y  H  G  T  L  L  D aatgatggcaagaaaattcactgtgctgtgaaatccttgaacagaatcactgacatagga
 N  D  G  K  K  I  H  C  A  V  K  S  L  N  R  I  T  D  I  G gaagtttcccaatttctgaccgagggaatcatcatgaaagattttagtcatcccaatgtc
 E  V  S  Q  F  L  T  E  G  I  I  M  K  D  F  S  H  P  N  V ctctcgctcctgggaatctgcctgcgaagtgaagggtctccgctggtggtcctaccatac
 L  S  L  L  G  I  C  L  R  S  E  G  S  P  L  V  V  L  P  Y atgaaacatggagatcttcgaaatttcattcgaaatgagactcataatccaactgtaaaa
 M  K  H  G  D  L  R  N  F  I  R  N  E  T  H  N  P  T  V  K gatcttattggctttggtcttcaagtagccaaaggcatgaaatatcttgcaagcaaaaag
 D  L  I  G  F  G  L  Q  V  A  K  G  M  K  Y  L  A  S  K  K tttgtccacagagacttggctgcaagaaactgtatgctggatgaaaaattcacagtcaag
 F  V  H  R  D  L  A  A  R  N  C  M  L  D  E  K  F  T  V  K gttgctgattttggtcttgccagagacatgtatgataaagaatactatagtgtacacaac
 V  A  D  F  G  L  A  R  D  M  Y  D  K  E  Y  Y  S  V  H  N aaaacaggtgcaaagctgccagtgaagtggatggctttggaaagtctgcaaactcaaaag
 K  T  G  A  K  L  P  V  K  W  M  A  L  E  S  L  Q  T  Q  K
```

```
tttaccaccaagtcagatgtgtggtcctttggcgtgctcctctgggagctgatgacaaga
 F  T  T  K  S  D  V  W  S  F  G  V  L  L  W  E  L  M  T  R ggagcccccaccttatcctgatgtaaacacctttgatataactgtttacttgttgcaaggg
 G  A  P  P  Y  P  D  V  N  T  F  D  I  T  V  Y  L  L  Q  G agaagactcctacaacccgaatactgcccagaccccttatatgaagtaatgctaaaatgc
 R  R  L  L  Q  P  E  Y  C  P  D  P  L  Y  E  V  M  L  K  C tggcacccta aagccgaaatgcgcccatccttttctgaactggtgtcccggatatcagcg
 W  H  P  K  A  E  M  R  P  S  F  S  E  L  V  S  R  I  S  A atcttctctactttcattgggtagtcgac
 I  F  S  T  F  I  G  - p38
PCR primers
p38A     P38A-2          CCGGATCCATATGTCTCAGGAGAGGCCCAC               253
                         (SEQ ID NO: ___)

P38A-A          GAAACCCTCGAGTCAGGACTCCATCTCTTCTTG            254
                         (SEQ ID NO: ___)

P4292.pET15S P38A M1-S360-X MKK6DD
taatacgactcactatagggggaattgtgagcggataacaattcccctctagaaataattt   (SEQ ID NO: ___)
tgtttaactttaagaaggagatataccatgggcagcagccatcatcatcatcatcacagc   (SEQ ID NO: ___)
                          M  G  S  S  H  H  H  H  H  H  S agcggcctggtgccgcgcggcagccatatgtctcaggagaggcccacgttctaccggcag
 S  G  L  V  P  R  G  S  H  M  S  Q  E  R  P  T  F  Y  R  Q gagctgaacaagacaatctgggaggtgcccgagcgttaccagaacctgtctccagtgggc
 E  L  N  K  T  I  W  E  V  P  E  R  Y  Q  N  L  S  P  V  G tctggcgcctatggctctgtgtgtgctgcttttgacacaaaaacgggggttacgtgtggca
 S  G  A  Y  G  S  V  C  A  A  F  D  T  K  T  G  L  R  V  A gtgaagaagctctccagacccatttcagtccatcattcatgcgaaaagaacctacagagaa
 V  K  K  L  S  R  P  F  Q  S  I  I  H  A  K  R  T  Y  R  E ctgcggttacttaaacacatgaaacatgaaaatgtgattggtctgttggacgttttaca
 L  R  L  L  K  H  M  K  H  E  N  V  I  G  L  L  D  V  F  T cctgcaaggtctctggaggaattcaatgatgtgtatctggtgaccccatctcatggggca
 P  A  R  S  L  E  E  F  N  D  V  Y  L  V  T  H  L  M  G  A gatctgaacaacattgtgaaatgtcagaagcttacagatgaccatgttcagttccttatc
 D  L  N  N  I  V  K  C  Q  K  L  T  D  D  H  V  Q  F  L  I taccaaaattctccgaggtctaaagtatatacattcagctgacataattcacagggaccta
 Y  Q  I  L  R  G  L  K  Y  I  H  S  A  D  I  I  H  R  D  L aaacctagtaatctagctgtgaatgaagactgtgagctgaagattctggattttggactg
 K  P  S  N  L  A  V  N  E  D  C  E  L  K  I  L  D  F  G  L gctcggcacacagatgatgaaatgacaggctacgtggccactaggtggtacagggctcct
 A  R  H  T  D  D  E  M  T  G  Y  V  A  T  R  W  Y  R  A  P gagatcatgctgaactggatgcattacaaccagacagttgatatttggtcagtgggatgc
 E  I  M  L  N  W  M  H  Y  N  Q  T  V  D  I  W  S  V  G  C ataatggccgagctgttgactggaagaacattgtttcctggtacagaccatattgatcag
 I  M  A  E  L  L  T  G  R  T  L  F  P  G  T  D  H  I  D  Q ttgaagctcattttaagactcgttggaaccccaggggctgagcttttgaagaaaatctcc
 L  K  L  I  L  R  L  V  G  T  P  G  A  E  L  L  K  K  I  S tcagagtctgcaagaaactatattcagtctttgactcagatgccgaagatgaactttgcg
 S  E  S  A  R  N  Y  I  Q  S  L  T  Q  M  P  K  M  N  F  A aatgtatttattggtgccaatcccctggctgtcgacttgctggagaagatgcttgtattg
 N  V  F  I  G  A  N  P  L  A  V  D  L  L  E  K  M  L  V  L gactcagataagagaattacagcggcccaagcccttgcacatgcctactttgctcagtac
 D  S  D  K  R  I  T  A  A  Q  A  L  A  H  A  Y  F  A  Q  Y cacgatcctgatgatgaaccagtggccgatccttatgatcagtcctttgaaagcagggac
 H  D  P  D  D  E  P  V  A  D  P  Y  D  Q  S  F  E  S  R  D
```

-continued

```
ctccttatagatgagtggaaaagcctgacctatgatgaagtcatcagctttgtgccacca
 L  L  I  D  E  W  K  S  L  T  Y  D  E  V  I  S  F  V  P  P ccccttgaccaagaagagatggagtcctgactcgac
 P  L  D  Q  E  E  M  E  S  -
```

Pim1
PCR primers

| PIM1 | PIM-1S | GCTGGCGCATATGAAGGAGAAGGAGCCCCTGGAG | 233 |
|------|--------|-------------------------------------|-----|
|      |        | (SEQ ID NO: ___)                    |     |
|      | PIM-1A | GAAAGGGTCGACTTTGCTGGGCCCCGGCGACAG   | 234 |
|      |        | (SEQ ID NO: ___)                    |     |

P1215.pET29SRI PIM1 E29-K313 HIS WT

```
agatcgatctcgatcccgcgaaattaatacgactcactatagggggaattgtgagcggataa    (SEQ ID NO: ___)
caattcccctctagaaataattttgtttaactttaagaaggagatatacatatgaaggag
                                                    M  K  E       (SEQ ID NO: ___)

aaggagcccctggagtcgcagtaccaggtgggcccgctactgggcagcggcggcttcggc
 K  E  P  L  E  S  Q  Y  Q  V  G  P  L  L  G  S  G  G  F  G tcggtctactcaggcatccgcgtctccgacaacttgccggtggccatcaaacacgtggag
 S  V  Y  S  G  I  R  V  S  D  N  L  P  V  A  I  K  H  V  E aaggaccggatttccgactggggagagctgcctaatggcactcgagtgcccatggaagtg
 K  D  R  I  S  D  W  G  E  L  P  N  G  T  R  V  P  M  E  V gtcctgctgaagaaggtgagctcgggtttctccggcgtcattaggctcctggactggttc
 V  L  L  K  K  V  S  S  G  F  S  G  V  I  R  L  L  D  W  F gagaggcccgacagtttcgtcctgatcctggagaggcccgagccggtgcaagatctcttc
 E  R  P  D  S  F  V  L  I  L  E  R  P  E  P  V  Q  D  L  F gacttcatcacggaaaggggagccctgcaagaggagctggcccgcagcttcttctggcag
 D  F  I  T  E  R  G  A  L  Q  E  E  L  A  R  S  F  F  W  Q gtgctggaggccgtgcggcactgccacaactgcggggtgctccaccgcgacatcaaggac
 V  L  E  A  V  R  H  C  H  N  C  G  V  L  H  R  D  I  K  D gaaaacatccttatcgacctcaatcgcggcgagctcaagctcatcgacttcgggtcgggg
 E  N  I  L  I  D  L  N  R  G  E  L  K  L  I  D  E  G  S  G gcgctgctcaaggacaccgtctacacggacttcgatgggacccgagtgtatagccctcca
 A  L  L  K  D  T  V  Y  T  D  F  D  G  T  R  V  Y  S  P  P gagtggatccgctaccatcgctaccatggcaggtcggcggcagtctggtccctggggatc
 E  W  I  R  Y  H  R  Y  H  G  R  S  A  A  V  W  S  L  G  I ctgctgtatgatatggtgtgtggagatattccttttcgagcatgacgaagagatcatcagg
 L  L  Y  D  M  V  C  G  D  I  P  F  E  H  D  E  E  I  I  R ggccaggttttcttcaggcagagggtctcttcagaatgtcagcatctcattagatggtgc
 G  Q  V  F  F  R  Q  R  V  S  S  E  C  Q  H  L  I  R  W  C ttggcccctgagaccatcagataggccaaccttcgaagaaatccagaaccatccatggatg
 L  A  L  R  P  S  D  R  P  T  F  E  E  I  Q  N  H  P  W  M caagatgttctcctgccccaggaaactgctgagatccacctccacagcctgtcgccgggg
 Q  D  V  L  L  P  Q  E  T  A  E  I  H  L  H  S  L  S  P  G cccagcaaagtcgaccaccaccaccaccaccactgagatccggctgctaacaaagcccga
 P  S  K  V  D  H  H  H  H  H  H  - aaggaattcgagttggctgctgccaccgctgagcaataactagcataacccccttggggcc
tctaaacgggtcttgaggggttttttg
```

Ret
PCR primers

| RET | RETH661 | GTTCTTCATATGCACAAGTTTGCCCACAAGCCA | 2184 |
|-----|---------|------------------------------------|------|
|     |         | (SEQ ID NO: ___)                   |      |
|     | RE-1012-HIS | GTTCTTGTCGACCCTCTTAACCATCATCTTCTCCAGGTCT | 2431 |
|     |         | (SEQ ID NO: ___)                   |      |

P1378.pET-SF BI-PTP RET H661-R1012 HIS

```
taatacgactcactatagggggaattgtgagcggataacaattcccctctagaaataatttt    (SEQ ID NO: ___)
gtttaactttaagaaggagatatacatatgcacaagtttgcccacaagccacccatctcc
                              M  H  K  F  A  H  K  P  P  I  S    (SEQ ID NO: ___)
```

-continued

```
tcagctgagatgaccttccggaggcccgcccaggcctcccggtcagctactcctcttcc
 S  A  E  M  T  F  R  R  P  A  Q  A  F  P  V  S  Y  S  S  S ggtgcccgccggccctcgctggactccatggagaaccaggtctccgtggatgccttcaag
 G  A  R  R  P  S  L  D  S  M  E  N  Q  V  S  V  D  A  F  K atcctggaggatccaaagtgggaatttccctcggaagaacttggttcttggaaaaactcta
 I  L  E  D  P  K  W  E  F  P  R  K  N  L  V  L  G  K  T  L ggagaaggcgaatttggaaaagtggtcaaggcaacggccttccatctgaaaggcagagca
 G  E  G  E  F  G  K  V  V  K  A  T  A  F  H  L  K  G  R  A gggtacaccacggtggccgtgaagatgctgaaagagaacgcctcccgagtgagcttcga
 G  Y  T  T  V  A  V  K  M  L  K  E  N  A  S  P  S  E  L  R gacctgctgtcagagttcaacgtcctgaagcaggtcaaccacccacatgtcatcaaattg
 D  L  L  S  E  F  N  V  L  K  Q  V  N  H  P  H  V  I  K  L tatggggcctgcagccaggatggcccgctcctcctcatcgtggagtacgccaaatacggc
 Y  G  A  C  S  Q  D  G  P  L  L  L  I  V  E  Y  A  K  Y  G tccctgcggggcttcctccgcgagagccgcaaagtggggcctggctacctgggcagtgga
 S  L  R  G  F  L  R  E  S  R  K  V  G  P  G  Y  L  G  S  G ggcagccgcaactccagctccctggaccaccggatgagcgggccctcaccatgggcgac
 G  S  R  N  S  S  S  L  D  H  P  D  E  R  A  L  T  M  G  D ctcatctcatttgcctggcagatctcacaggggatgcagtatctggccgagatgaagctc
 L  I  S  F  A  W  Q  I  S  Q  G  M  Q  Y  L  A  E  M  K  L gttcatcgggacttggcagccagaaacatcctggtagctgagggcggaagatgaagatt
 V  H  R  D  L  A  A  R  N  I  L  V  A  E  G  R  K  M  K  I tcggatttcggcttgtcccgagatgtttatgaagaggattcctacgtgaagaggagccag
 S  D  F  G  L  S  R  D  V  Y  E  E  D  S  Y  V  K  R  S  Q ggtcggattccagttaaatggatggcaattgaatccctttttgatcatatctacaccacg
 G  R  I  P  V  K  W  M  A  I  E  S  L  F  D  H  I  Y  T  T caaagtgatgtatggtcttttggtgtcctgctgtgggagatcgtgaccctaggggggaaac
 Q  S  D  V  W  S  F  G  V  L  L  W  E  I  V  T  L  G  G  N ccctatcctgggattcctcctgagcggCtcttcaaccttctgaagaccggccaccggatg
 P  Y  P  G  I  P  P  E  R  L  F  N  L  L  K  T  G  H  R  M gagaggccagacaactgcagcgaggagatgtaCcgcctgatgctgcaatgctggaagcag
 E  R  P  D  N  C  S  E  E  M  Y  R  L  M  L  Q  C  W  K  Q gagccggacaaaaggccggtgtttgcggacatcagcaaagacctggagaagatgatggtt
 E  P  D  K  R  P  V  F  A  D  I  S  K  D  L  E  K  M  M  V aagagggtcgaccaccaccaccaccaccactgagatccggctggccctactggccgaaag
 K  R  V  D  H  H  H  H  H  H  - gaattcgaggccagcagggccaccgctgagcaataactagcataaccccttggggcctct
aaacgggtcttgagggggttttttg
```

Src
PCR primers

SRC-86                    GCTGGCCCATATGGTGACCACCTTTGTGGCCCT         1452
                             (SEQ ID NO: ___)

SRC-452 (L536)          GCTACTAGTCGACCTAGAGGTTCTCCCCGGGCT         1453
                             (SEQ ID NO: ___)

P1144. pET-N6 BI-PTP SRC V86-L536-X

```
taatacgactcactatagggaattgtgagcggataacaattcccctctagaaataattt              (SEQ ID NO: ___)
tgtttaactttaagaaggagatataccatgggtcaccaccatcaccatcatggtgacc
                             M  G  H  H  H  H  H  H  M  V  T              (SEQ ID NO: ___)

acctttgtggccctctatgactatgagtctaggacggagacagacctgtccttcaagaaa
 T  F  V  A  L  Y  D  Y  E  S  R  T  E  T  D  L  S  F  K  K ggcgagcggctccagattgtcaacaacacagagggagactggtggctggcccactcgctc
 G  E  R  L  Q  I  V  N  N  T  E  G  D  W  W  L  A  H  S  L agcacaggacagacaggctacatccccagcaactacgtggcgccctccgactccatccag
 S  T  G  Q  T  G  Y  I  P  S  N  Y  V  A  P  S  D  S  I  Q gctgaggagtggtattttggcaagatcaccagacgggagtcagagcggttactgctcaat
 A  E  E  W  Y  F  G  K  I  T  R  R  E  S  E  R  L  L  L  N
```

```
gcagagaacccgagagggaccttcctcgtgcgagaaagtgagaccacgaaaggtgcctac
 A  E  N  P  R  G  T  F  L  V  R  E  S  E  T  T  K  G  A  Y tgcctctcagtgtctgacttcgacaacgccaagggcctcaacgtgaagcactacaagatc
 C  L  S  V  S  D  F  D  N  A  K  G  L  N  V  K  H  Y  K  I cgcaagctggacagcggcggcttctacatcacctcccgcacccagttcaacagcctgcag
 R  K  L  D  S  G  G  F  Y  I  T  S  R  T  Q  F  N  S  L  Q cagctggtggcctactactccaaacacgccgatggcctgtgccaccgcctcaccaccgtg
 Q  L  V  A  Y  Y  S  K  H  A  D  G  L  C  H  R  L  T  T  V tgccccacgtccaagccgcagactcagggcctggccaaggatgcctgggagatccctcgg
 C  P  T  S  K  P  Q  T  Q  G  L  A  K  D  A  W  E  I  P  R gagtcgctgcggctggaggtcaagctgggccagggctgctttggcgaggtgtggatgggg
 E  S  L  R  L  E  V  K  L  G  Q  G  C  F  G  E  V  W  M  G acctggaacggtaccaccagggtggccatcaaaaccctgaagcctggcacgatgtctcca
 T  W  N  G  T  T  R  V  A  I  K  T  L  K  P  G  T  M  S  P gaggccttcctgcaggaggcccaggtcatgaagaagctgaggcatgagaagctggtgcag
 E  A  F  L  Q  E  A  Q  V  M  K  K  L  R  H  E  K  L  V  Q ttgtatgctgtggtttcagaggagcccatttacatcgtcacggagtacatgagcaagggg
 L  Y  A  V  V  S  E  E  P  I  Y  I  V  T  E  Y  M  S  K  G agtttgctggactttctcaaggggggagacaggcaagtacctgcggctgcctcagctggtg
 S  L  L  D  F  L  K  G  E  T  G  K  Y  L  R  L  P  Q  L  V gacatggctgctcagatcgcctcaggcatggcgtacgtggagcggatgaactacgtccac
 D  M  A  A  Q  I  A  S  G  M  A  Y  V  E  R  M  N  Y  V  H cgggaccttcgtgcagccaacatcctggtgggagagaacctggtgtgcaaagtggccgac
 R  D  L  R  A  A  N  I  L  V  G  E  N  L  V  C  K  V  A  D tttgggctggctcggctcattgaagacaatgagtacacggcgcggcaaggtgccaaattc
 F  G  L  A  R  L  I  E  D  N  E  Y  T  A  R  Q  G  A  K  F cccatcaagtggacggctccagaagctgccctctatggccgcttcaccatcaagtcggac
 P  I  K  W  T  A  P  E  A  A  L  Y  G  R  F  T  I  K  S  D gtgtggtccttcgggatcctgctgactgagctcaccacaaagggacgggtgccctaccct
 V  W  S  F  G  I  L  L  T  E  L  T  T  K  G  R  V  P  Y  P gggatggtgaaccgcgaggtgctggaccaggtggagcggggctaccggatgccctgcccg
 G  M  V  N  R  E  V  L  D  Q  V  E  R  G  Y  R  M  P  C  P ccggagtgtcccgagtccctgcacgacctcatgtgccagtgctggcggaaggagcctgag
 P  E  C  P  E  S  L  H  D  L  M  C  Q  C  W  R  K  E  P  E gagcggcccaccttcgagtacctgcaggccttcctggaggactacttcacgtccaccgag
 E  R  P  T  F  E  Y  L  Q  A  F  L  E  D  Y  F  T  S  T  E ccccagtaccagcccggggagaacctctaggtcgacgaaggagatatatcc
 P  Q  Y  Q  P  G  E  N  L  -

Zap70
PCR primers
ZAP70     ZAP70-D327-BAMHI-N      AGAGGGATCCGCCACCATGGACAAGAAGCTCTTCCTGAA        5172
                                  (SEQ ID NO: ___)

ZAP70-G606-HIS          ACGAATTCTAGTGGTGGTGGTGGTGGTGCCCTTCCACCT        5171
                                  TGCTG
                                  (SEQ ID NO: ___)

P1868.pFastBac1 ZAP70 D327-G606 HIS, WT
agatcatggagataattaaaatgataaccatctcgcaaataaataagtattttactgtttt     (SEQ ID NO: ___)
cgtaacagtttttgtaataaaaaaaacctataaatattccggattattcataccgtcccacc
atcgggcgcggatccgccaccatggacaagaagctcttcctgaagcgcgataacctcctc
                M  D  K  K  L  F  L  K  R  D  N  L  L           (SEQ ID NO: ___)

atagctgacattgaacttggctgcggcaactttggctcagtgcgccaggcgtgtaccgc
 I  A  D  I  E  L  G  C  G  N  F  G  S  V  R  Q  G  V  Y  R atgcgcaagaagcagatcgacgtggccatcaaggtgctgaagcagggcacggagaaggca
 M  R  K  K  Q  I  D  V  A  I  K  V  L  K  Q  G  T  E  K  A gacacggaagagatgatgcgcgaggcgcagatcatgcaccagctggacaaccccctacatc
 D  T  E  E  M  M  R  E  A  Q  I  M  H  Q  L  D  N  P  Y  I
```

```
gtgcggctcattggcgtctgccaggccgaggccctcatgctggtcatggagatggctggg
 V  R  L  I  G  V  C  Q  A  E  A  L  M  L  V  M  E  M  A  G ggcgggccgctgcacaagttcctggtcggcaagagggaggagatccctgtgagcaatgtg
 G  G  P  L  H  K  F  L  V  G  K  R  E  E  I  P  V  S  N  V gccgagctgctgcaccaggtgtccatgggatgaagtacctggaggagaagaactttgtg
 A  E  L  L  H  Q  V  S  M  G  M  K  Y  L  E  E  K  N  F  V caccgtgacctggcggcccgcaacgtcctgctggttaaccggcactacgccaagatcagc
 H  R  D  L  A  A  R  N  V  L  L  V  N  R  H  Y  A  K  I  S gactttggcctctccaaagcactgggtgccgacgacagctactacactgcccgctcagca
 D  F  G  L  S  K  A  L  G  A  D  D  S  Y  Y  T  A  R  S  A gggaagtggccgctcaagtggtacgcacccgaatgcatcaacttccgcaagttctccagc
 G  K  W  P  L  K  W  Y  A  P  E  C  I  N  F  R  K  F  S  S cgcagcgatgtctggagctatggggtcaccatgtgggaggccttgtcctacggccagaag
 R  S  D  V  W  S  Y  G  V  T  M  W  E  A  L  S  Y  G  Q  K ccctacaagaagatgaaagggccggaggtcatggccttcatcgagcagggcaagcggatg
 P  Y  K  K  M  K  G  P  E  V  M  A  F  I  E  Q  G  K  R  M gaatgcccaccagagtgtccaccgaactgtacgcactcatgagtgactgctggatctac
 E  C  P  P  E  C  P  P  E  L  Y  A  L  M  S  D  C  W  I  Y aagtgggaggatcgccccgacttcctgaccgtggagcagcgcatgcgagcctgttactac
 K  W  E  D  R  P  D  F  L  T  V  E  Q  R  M  R  A  C  Y  Y agcctggccagcaaggtggaagggcaccaccaccaccaccactagaattc
 S  L  A  S  K  V  E  G  H  H  H  H  H  H  -

BAD substrate
PCR primers
BAD       BAD-N          GTTGTGACATATGTTCCAGATCCCAGAGTTTG                 1613
                         (SEQ ID NO: ___)

BAD-S          GTTGTGAGTCGACTCACTGGGAGGGGGCGGA                  1614
                         (SEQ ID NO: ___)

P963.pET-BH BAD M1-Q168-X
tacgactcactatagggaattgtgagcggataacaattcccctctagaaataattttgt       (SEQ ID NO: ___)
ttaactttaagaaggagatataccatggctggttgcctgaacgacatcttcgaagctcag
                         M  A  G  C  L  N  D  I  F  E  A  Q     (polypeptide SEQ ID NO: ___)

aaaatcgaatggcaccatcaccatcaccatatgttccagatcccagagtttgagccgagt
 K  I  E  W  H  H  H  H  H  H  M  F  Q  I  P  E  F  E  P  S gagcaggaagactccagctctgcagagaggggcctgggccccagccccgcagggacggg
 E  Q  E  D  S  S  S  A  E  R  G  L  G  P  S  P  A  G  D  G ccctcaggctccggcaagcatcatcgccaggcccaggcctcctgtgggacgccagtcac
 P  S  G  S  G  K  H  H  R  Q  A  P  G  L  L  W  D  A  S  H cagcaggagcagccaaccagcagcagccatcatggaggcgctggggctgtggagatccgg
 Q  Q  E  Q  P  T  S  S  S  H  H  G  G  A  G  A  V  E  I  R agtcgcacagctcctaccccgcggggacggaggacgacgaagggatgggggaggagccc
 S  R  H  S  S  Y  P  A  G  T  E  D  D  E  G  M  G  E  E  P agccccttcggggccgctcgcgctcggcgccccccaacctctgggcagcacagcgctat
 S  P  F  R  G  R  S  R  S  A  P  P  N  L  W  A  A  Q  R  Y ggccgcgagctccggaggatgagtgacgagtttgtggactccttttaagaagggacttcct
 G  R  E  L  R  R  M  S  D  E  F  V  D  S  F  K  K  G  L  P cgcccgaagagcgcgggcacagcaacgcagatgcggcaaagctccagctggacgcgagtc
 R  P  K  S  A  G  T  A  T  Q  M  R  Q  S  S  S  W  T  R  V ttccagtcctggtgggatcggaacttgggcaggggaagctccgcccctcccagtgagtc
 F  Q  S  W  W  D  R  N  L  G  R  G  S  S  A  P  S  Q  - gaccaccaccaccaccaccactgagatccggctgccctactggccgaaaggaattcgag
gccagcagggccaccgctgagcaataactagcataaccccttggggcctctaaacgggtc
ttgagggggtttttg
```

-continued

MEK1 substrate
PCR primers

| MEK1 | MEK1-S | CGGGTCCCATATGCCCAAGAAGAAGCCGAC (SEQ ID NO: ___) | 755 |
| --- | --- | --- | --- |
| | MEK-HIS | GTTCGTTGTCGACGACGCCAGCAGCATGGGTTG (SEQ ID NO: ___) | 2127 |
| | K97A-1 (K104A) | CTAATTCATCTGGAGATCGCGCCCGCAATCCGG (SEQ ID NO: ___) | 2023 |
| | K97A-2 (K104A) | CCGGATTGCGGGCGCGATCTCCAGATGAATTAG (SEQ ID NO: ___) | 2024 |

P1277.pGEX-BIO MEK1 K97A

```
atgtcccctatactaggttattggaaaattaagggccttgtgcaacccactcgacttctt    (SEQ ID NO: ___)
 M  S  P  I  L  G  Y  W  K  I  K  G  L  V  Q  P  T  R  L  L     (nucleic acid SEQ ID NO: )

ttggaatatcttgaagaaaaatatgaagagcatttgtatgagcgcgatgaaggtgataaa
 L  E  Y  L  E  E  K  Y  E  E  H  L  Y  E  R  D  E  G  D  K tggcgaaacaaaaagtttgaattgggtttggagtttcccaatcttccttattatattgat
 W  R  N  K  K  F  E  L  G  L  E  F  P  N  L  P  Y  Y  I  D ggtgatgttaaattaacacagtctatggccatcatacgttatatagctgacaagcacaac
 G  D  V  K  L  T  Q  S  M  A  I  I  R  Y  I  A  D  K  H  N atgttgggtggttgtccaaaagagcgtgcagagatttcaatgcttgaaggagcggttttg
 M  L  G  G  C  P  K  E  R  A  E  I  S  M  L  E  G  A  V  L gatattagatacggtgtttcgagaattgcatatagtaaagactttgaaactctcaaagtt
 D  I  R  Y  G  V  S  R  I  A  Y  S  K  D  F  E  T  L  K  V gattttcttagcaagctacctgaaatgctgaaaatgttcgaagatcgtttatgtcataaa
 D  F  L  S  K  L  P  E  M  L  K  M  F  E  D  R  L  C  H  K acatatttaaatggtgatcatgtaacccatcctgacttcatgttgtatgacgctcttgat
 T  Y  L  N  G  D  H  V  T  H  P  D  F  M  L  Y  D  A  L  D gttgttttatacatggaccccaatgtgcctggatgcgttcccaaaattagtttgttttaaa
 V  V  L  Y  M  D  P  M  C  L  D  A  F  P  K  L  V  C  F  K aaacgtattgaagctatcccacaaattgataagtacttgaaatccagcaagtatatagca
 K  R  I  E  A  I  P  Q  I  D  K  Y  L  K  S  S  K  Y  I  A tggcctttgcagggctggcaagccacgtttggtggtggcgaccatcctccaaaatcggat
 W  P  L  Q  G  W  Q  A  T  F  G  G  G  D  H  P  P  K  S  D ctggttccgcgtggatctcatatgcccaagaagaagccgacgcccatccagctgaacccg
 L  V  P  R  G  S  H  M  P  K  K  K  P  T  P  I  Q  L  N  P gcccccgacggctctgcagttaacgggaccagctctgcggagaccaacttggaggcttg
 A  P  D  G  S  A  V  N  G  T  S  S  A  E  T  N  L  E  A  L cagaagaagctggaggagctagagcttgatgagcagcagcgaaagcgccttgaggccttt
 Q  K  K  L  E  E  L  E  L  D  E  Q  Q  R  K  R  L  E  A  F cttacccagaagcagaaggtgggagaactgaaggatgacgactttgagaagatcagtgag
 L  T  Q  K  Q  K  V  G  E  L  K  D  D  D  F  E  K  I  S  E ctgggggctggcaatggcggtgtggtgttcaaggtctcccacaagccttctggcctggtc
 L  G  A  G  N  G  G  V  V  F  K  V  S  H  K  P  S  G  L  V atggccagagcgctaattcatctggagatcaaacccgcaatccggaaccagatcataagg
 M  A  R  A  L  I  H  L  E  I  K  P  A  I  R  N  Q  I  I  R gagctgcaggttctgcatgagtgcaactctccgtacatcgtgggcttctatggtgcgttc
 E  L  Q  V  L  H  E  C  N  S  P  Y  I  V  G  F  Y  G  A  F tacagcgatggcgagatcagtatctgcatggagcacatggatggaggttctctggatcaa
 Y  S  D  G  E  I  S  I  C  M  E  H  M  D  G  G  S  L  D  Q gtcctgaagaaagctggaagaattcctgaacaaattttaggaaaagttagcattgctgta
 V  L  K  K  A  G  R  I  P  E  Q  I  L  G  K  V  S  I  A  V ataaaaggcctgacatatctgagggagaagcacaagatcatgcacagagatgtcaagccc
 I  K  G  L  T  Y  L  R  E  K  H  K  I  M  H  R  D  V  K  P tccaacatcctagtcaactcccgtggggagatcaagctctgtgactttggggtcagcggg
 S  N  I  L  V  N  S  R  G  E  I  K  L  C  D  F  G  V  S  G
```

-continued
```
cagctcatcgactccatggccaactccttcgtgggcacaaggtcctacatgtcgccagaa
 Q   L   I   D   S   M   A   N   S   F   V   G   T   R   S   Y   M   S   P   E agactccaggggactcattactctgtgcagtcagacatctggagcatgggactgtctctg
 R   L   Q   G   T   H   Y   S   V   Q   S   D   I   W   S   M   G   L   S   L gtagagatggcggttggaggtatccatccctcctccagatgccaaggagctggagctg
 V   E   M   A   V   G   R   Y   P   I   P   P   P   D   A   K   E   L   E   L atgtttgggtgccaggtggaaggagatgcggctgagaccccacccaggccaaggaccccc
 M   F   G   C   Q   V   E   G   D   A   A   E   T   P   P   R   P   R   T   P gggaggcccctttagctcatacggaatggacagccgacctcccatggcaatttttgagttg
 G   R   P   L   S   S   Y   G   M   D   S   R   P   P   M   A   I   F   E   L ttggattacatagtcaacgagcctcctccaaaactgcccagtggagtgttcagtctggaa
 L   D   Y   I   V   N   E   P   P   P   K   L   P   S   G   V   F   S   L   E tttcaagattttgtgaataaatgcttaataaaaaacccgcagagagagcagatttgaag
 F   Q   D   F   V   N   K   C   L   I   K   N   P   A   E   R   A   D   L   K caactcatggttcatgcttttatcaagagatctgatgctgaggaagtggattttgcaggt
 Q   L   M   V   H   A   F   I   K   R   S   D   A   E   E   V   D   F   A   G tggctctgctccaccatcggccttaaccagcccagcacaccaacccatgctgctggcgtc
 W   L   C   S   T   I   G   L   N   Q   P   S   T   P   T   H   A   A   G   V gtcgacctgaacgacatcttcgaagctcagaaaatcgaatggcaccgttagaattc
 V   D   L   N   D   I   F   E   A   Q   K   I   E   W   H   R   -
+PS
```

Example 76

Efficacy of Compounds in Combination with Standard-of-Care Chemotherapeutic Agents in Four Human Cancer Cell Lines Compounds of the invention, such as compounds of Formula III, in combination with a standard chemotherapeutic agent, such as 5-fluorouracil, carboplatin, dacarbazine, gefitinib, oxaliplatin, paclitaxel, SN-38, tcmozolomide, or vinblastine, can be assessed for their effectiveness in killing human tumor cells. Human tumor cell lines, such as A-375 (malignant melanoma), SK-MEL-2 (malignant melanoma, skin metastasis), COLO 205 (colorectal adenocarcinoma, ascites metastasis) or SW-620 (colorectal adenocarcinoma, lymph node metastasis) can be treated with a compound of Formula III alone, or in combination with one of the above-mentioned chemotherapeutic agents.

Tumor cells are grown as a monolayer at 37° C. in a humidified atmosphere (5% $CO_2$, 95% air). Cells are grown in a suitable culture medium, e.g. RPMI 1640 (Ref BE12-702F, Cambrex, Verviers, Belgium) containing 2 mM L-glutamine and supplemented with 10% fetal bovine serum (Ref DE14-801E, Cambrex). For experimental use, the tumor cells are detached from the culture flask by a 5-minute treatment with trypsin-verscne (Ref 02-007E, Cambrex), diluted in Hanks' medium without calcium or magnesium (Ref BE10-543F, Cambrex). Trypsin treatment is neutralized by culture medium addition. The cells are counted in a hemocytometer and their viability assessed by 0.25% trypan blue exclusion.

The cell lines are checked for mycoplasma contamination with the Mycotect assay kit (Ref 15672-017, Invitrogen, Cergy-Pontoise, France) in accordance with the manufacturer's instructions. The mycoplasma test is assayed from the culture supernatants of the cell lines and compared to negative and positive controls.

The tumor cells (10,000 per well) are plated in 96-well flat-bottom microtitration plates (Ref 055260, Nunc, Dutscher, Brumath, France) and incubated at 37° C. for 24 hours before treatment in 100 µl of drug-free culture medium supplemented with 10% FBS. In order to assess the $IC_{50}$ of each compound to be used for each cell line, the tumor cells are incubated in a 200 µl final volume of RPMI 1640 supplemented with 10% FBS and containing either a compound of Formula III or one of 5-fluorouracil, carboplatin, dacarbazine, gefitinib, oxaliplatin, paclitaxel, SN-38, temozolomide, or vinblastine. The compounds are tested in a suitable concentration range, such as $10^{-8}$ to $10^{-3}$ M for a compound of Formula III, 5-fluorouracil, dacarbazine or gefitinib, $10^{-9}$ to $10^{-4}$ M for carboplatin, oxaliplatin, or temozolomide, $10^{-11}$ to $10^{-6}$ M for paclitaxel or SN-38, and $10^{-15}$ to $10^{-10}$ M for vinblastine. Compounds of Formula III are dissolved in DMSO and diluted with culture medium to the desired concentrations. 5-fluorouracil (50 mg/ml, Dakota Pharm, LePlessis Robinson, France), carboplatin (10 mg/ml, Aguettant, Lyon, France), and paclitaxel (6 mg/ml, Bristol-Myers Squibb SpA, Rueil Malmaison, France), are diluted with culture medium to the desired concentrations. Dacarbazine (Sigma, Saint Quentin Fallavier, France) and vinblastine (Lilly France S.A., Saint Cloud, France) are dissolved in NaCl 0.9% and diluted with culture medium to the desired concentrations. Gefitinib is dissolved in a mixed solution of RPMI 1640 and DMSO and diluted with culture medium to the desired concentrations (maximum final DMSO of 0.1% v/v). SN-38 (LKT Laboratories, Inc., St. Paul, Minn.) is dissolved in DMSO and diluted with culture medium to the desired concentrations (maximum final DMSO of 0.1% v/v). Temozolomide (LKT Laboratories, Inc., St. Paul, Minn.) is dissolved in water for injection and diluted with culture medium to the desired concentrations. Cells are incubated for 96 hours in the presence of test substances at 37° C. under 5% $CO_2$. At the end of treatments, the cytotoxic activity is evaluated by an MTT assay.

For the MTT assay, at the end of the cells treatment, 20 µl of a 5 mg/ml solution 0.22 µm filtered tetrazolium reagent (MTT, Ref M2128, Sigma) in Phosphate Buffered Saline (PBS, Ref BE17-517Q, Cambrex), is added in each well. Culture plates are incubated for 2 h at 37° C. The resulting supernatant is removed and formazan crystals dissolved with 200 µl of DMSO per well. Absorbency (OD) is measured at 570 nm in each well using VICTOR³™ 1420 multilabeled counter (Wallac, PerkinElmer, Courtaboeuf, France).

The $IC_{50}$ for each compound on each cell line is determined from the OD measurements of each sample. The dose response inhibition of cell proliferation is expressed as:

IC=(OD of drug exposed cells/OD of drug free wells)×100.

The mean of multiple measurements for each concentration is plotted vs. the drug concentration. The dose-response curves are plotted using XLFit 3 (IDBS, United Kingdom). The $IC_{50}$ (drug concentration to obtain 50% inhibition of cell proliferation) determination values are calculated using the XLFit 3 from semi-log curves. The $IC_{50}$ value determined for each compound in each cell line is used to determine the concentration of a compound of Formula III and of the standard chemotherapeutic to be used in combination.

The cells are treated with a combination of five concentrations of a compound of Formula III and five concentrations of one of 5-fluorouracil, carboplatin, dacarbazine, gefitinib, oxaliplatin, paclitaxel, SN-38, temozolomide, or vinblastine, based on the $IC_{50}$ results. The compounds and cells are treated per the IC50 determination described above and assayed by the MTT assay.

The results are assessed to determine whether the combination is synergistic or antagonistic. The compound interactions are calculated by multiple drug effect analysis and are performed by the median equation principle according to the methodology described by Chou and Talalay (Adv. Enzyme Regul. 1984, 22: 27-55).

The combination index (CI) will be calculated by the Chou et al, equation (Adv. Enzyme Regul. 1984, 22: 27-55; Encyclopaedia of human biology, Academic Press, 1991, 2: 371-9; Synergism and Antagonism in Chemotherapy, Academic Press, 1991, 61-102) which takes into account both the potency ($D_m$ or $IC_{50}$) and the shape of the dose-effect curve (the m value). The general equation for the CI of the two compounds is given by:

$$CI = \frac{(D)_1}{(D_x)_1} + \frac{(D)_2}{(D_x)_2} + \frac{(D)_1(D)_2}{(D_x)_1(D_x)_2}$$

where:

$(D_x)_1$ and $(D_x)_2$ in the denominators are the doses (or concentrations) for compound 1 and compound 2 alone which demonstrate x % of inhibition, whereas $(D)_1$ and $(D)_2$ in the numerators are doses of both compounds (1 and 2) in combination thet also inhibit x % (iso-effective). CI<1, =1, and >1 indicate synergism, additive effect and antagonism, respectively.

The $(D_x)_1$ and $(D_x)_2$ can be calculated from the median-effect equation of Chou et al. (J. Natl. Cancer Inst. 1994, 86: 1517-24):

$$D_x = D_m \left(\frac{f_a}{1 - f_a}\right)^{1/m}$$

where:

$D_m$ is the median-effect dose that is obtained from the anti-log of x-intercept of the median-effect plot, x=log(D) versus y=log $\{f_a/(1-f_n)\}$, or $D_m = 10^{-(y-intercept)/m}$; and m is the slope of the median-effect plot and $f_a$ is the fraction of cells affected by the treatment.

Each CI will be calculated with CalcuSyn software (Biosoft, UK) from the mean affected fraction at each drug ratio concentration.

Additional examples. Unless specifically indicated otherwise, the Formula enumeration and R group enumeration used in the following examples is not related to such enumeration in other sections of this application. The reagents and solvents used in these examples can be readily substituted with appropriate alternatives as are known in the art and isolation of products is readily achieved by methods known in the art, including, but not limited to, extraction, crystallization, and chromatographic methods. For the following examples, the following formulae are defined:

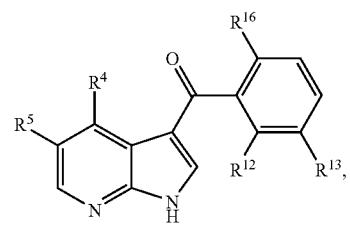

Formula I

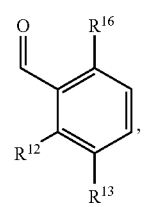

Formula II

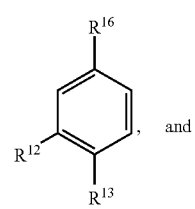

and

Formula III

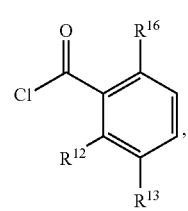

Formula XV wherein:

$R^4$ and $R^5$ are independently selected from the group consisting of hydrogen, halogen, optionally substituted lower alkyl, optionally substituted lower alkenyl, optionally substituted lower alkynyl, optionally substituted cycloalkyl, optionally substituted heterocycloalkyl, optionally substituted aryl, optionally substituted heteroaryl, —CN, —NO$_2$, —CR$^a$R$^b$R$^{26'}$, and —LR$^{26'}$;

L at each occurrence is independently selected from the group consisting of -(alk)$_a$-S-(alk)$_b$-, -(alk)$_a$-O-(alk)$_b$-, -(alk)$_a$-NR$^{25'}$-(alk)$_b$-, -(alk)$_a$-C(O)-(O)-(alk)$_b$-, -(alk)$_a$-C(S)-(alk)$_b$-, -(alk)$_a$-S(O)-(alk)$_b$-, -(alk)$_a$-S(O)$_2$-(alk)$_b$-, -(alk)$_a$-OC(O)-(alk)$_b$-, -(alk)$_a$-C(O)O-(alk)$_b$-, -(alk)$_a$-OC(S)-(alk)$_b$-, -(alk)$_a$-C(S)O-(alk)$_b$-, -(alk)$_a$-C(O)NR$^{25'}$-(alk)$_b$-, -(alk)$_a$-C(S)NR$^{25'}$-(alk)$_b$-, -(alk)$_a$-S(O)$_2$NR$^{25'}$-(alk)$_b$-, -(alk)$_a$-NR$^{25'}$C(O)-(alk)$_b$, -(alk)$_a$-NR$^{25'}$C (S)-(alk)$_b$-, -(alk)$_a$-NR$^{25'}$S(O)$_2$-(alk)$_b$-, -(alk)$_a$-NR$^{25'}$C(O)O-(alk)$_b$-, -(alk)$_a$-NR$^{25'}$C(S)O-(alk)$_b$-, -(alk)$_a$-OC(O)NR$^{25'}$-(alk)$_b$-, -(alk)$_a$-OC(S)NR$^{25'}$-(alk)$_b$-, -(alk)$_a$-NR$^{25'}$C(O)NR$^{25'}$-(alk)$_b$-, -(alk)$_a$-NR$^{25'}$C(S)NR$^{25'}$-(alk)$_b$-, and -(alk)$_a$-NR$^{25'}$S(O)$_2$NR$^{25'}$-(alk)$_b$-;

a and b are independently 0 or 1;

alk is C$_{1-3}$ alkylene or C$_{1-3}$ alkylene substituted with one or more substituents selected from the group consisting of fluoro, —OH, —NH$_2$, lower alkyl, lower alkoxy, lower alkylthio, mono-alkylamino, di-alkylamino, and —NR$^8$R$^9$, wherein lower alkyl or the alkyl chain(s) of lower alkoxy, lower alkylthio, mono-alkylamino or di-alkylamino are optionally subsituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino and cycloalkylamino, provided however, that any substitution of the alkyl chain carbon bound to O of alkoxy, S of thioalkyl or N of mono- or di-alkylamino is fluoro;

wherein R$^a$ and R$^b$ at each occurrence are independently selected from the group consisting of hydrogen, fluoro, —OH, —NH$_2$, lower alkyl, lower alkoxy, lower alkylthio, mono-alkylamino, di-alkylamino, and —NR$^8$R$^9$, wherein the alkyl chain(s) of lower alkyl, lower alkoxy, lower alkylthio, mono-alkylamino, or di-alkylamino are optionally substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino, and cycloalkylamino, provided, however, that any substitution of the alkyl chain carbon bound to O of alkoxy, S of thioalkyl or N of mono- or di-alkylamino is fluoro; or any two of R$^a$ and R$^b$ on the same or different carbons combine to form a 3-7 membered monocyclic cycloalkyl or 5-7 membered monocyclic heterocycloalkyl and any others of R$^a$ and R$^b$ are independently selected from the group consisting of hydrogen, fluoro, —OH, —NH$_2$, lower alkyl, lower alkoxy, lower alkylthio, mono-alkylamino, di-alkylamino, and —NR$^8$R$^9$, wherein the alkyl chain(s) of lower alkyl, lower alkoxy, lower alkylthio, mono-alkylamino, or di-alkylamino are optionally subsituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino, and cycloalkylamino, provided, however, that any substitution of the alkyl chain carbon bound to O of alkoxy, S of thioalkyl or N of mono- or di-alkylamino is fluoro, and wherein the 3-7 membered monocyclic cycloalkyl or 5-7 membered monocyclic heterocycloalkyl are optionally substituted with one or more substituents selected from the group consisting of halogen, —OH, —NH$_2$, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino;

R$^8$ and R$^9$ combine with the nitrogen to which they are attached to form a 5-7 membered heterocycloalkyl optionally substituted with one or more substituents selected from the group consisting of fluoro, —OH, —NH$_2$, lower alkyl, fluoro substituted lower alkyl, lower alkoxy, fluoro substituted lower alkoxy, lower alkylthio, and fluoro substituted lower alkylthio;

R$^{25'}$ at each occurrence is independently selected from the group consisting of hydrogen, optionally substituted lower alkyl, optionally substituted cycloalkyl, optionally substituted heterocycloalkyl, optionally substituted aryl, and optionally substituted heteroaryl; and R$^{26'}$ at each occurrence are independently selected from the group consisting of hydrogen, provided, however, that hydrogen is not bound to any of S(O), S(O)$_2$, C(O) or C(S) of L, optionally substituted lower alkyl, optionally substituted lower alkenyl, provided, however, that when R$^{26'}$ is optionally substituted lower alkenyl, no alkene carbon thereof is bound to N, S, O, S(O), S(O)$_2$, C(O) or C(S) of L or L$_1$, optionally substituted lower alkynyl, provided, however, that when R$^{26'}$ is optionally substituted lower alkynyl, no alkyne carbon thereof is bound to N, S, O, S(O), S(O)$_2$, C(O) or C(S) of L, optionally substituted cycloalkyl, optionally substituted heterocycloalkyl, optionally substituted aryl, and optionally substituted heteroaryl;

R$^{12}$, R$^{13}$ and R$^{16}$ independently selected from the group consisting of hydrogen, halogen, optionally substituted lower alkyl, optionally substituted lower alkenyl, optionally substituted lower alkynyl, optionally substituted cycloalkyl, optionally substituted heterocycloalkyl, optionally substituted aryl, optionally substituted heteroaryl, —CN, —NO$_2$, —CR$^a$R$^b$R$^{24}$, and —LR$^{24}$, where L and R$^{24}$ are as defined for Formula I;

R$^{28}$ is —SO$_2$R$^{25}$, —C(=O)R$^{25}$, —C(=O)NR$^{25}$, —C(=O)OR$^2$, —C(=S)R$^{25}$, —C(=S)NR$^{25}$, —C(=S)OR$^{25}$, or —SO$_2$NR$^{25}$R$^{26}$; wherein R$^{25}$ and R$^{26}$ are hydrogen, optionally substituted lower alkyl, optionally substituted lower alkenyl, optionally substituted lower alkynyl, optionally substituted cycloalkyl, optionally substituted heterocycloalkyl, optionally substituted aryl, or optionally substituted heteroaryl, or R$^{25}$ and R$^{26}$ together with the nitrogen form optionally substituted 5-7 membered heterocycloalkyl or optionally substituted 5 or 7 membered nitrogen containing heteroaryl.

R$^{29}$ is hydrogen or optionally substituted lower alkyl; and

R$^{30}$ is optionally substituted lower alkyl or optionally substituted benzyl, wherein optionally substituted benzyl refers to an optionally substituted aralkyl with unsubstituted structure —CH$_2$-phenyl.

Example 77

Synthesis of Compound of Formula II, Where R$^{12}$ and R$^{16}$ are Independently Fluoro or Chloro

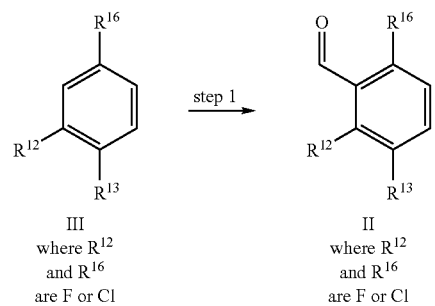

Step 1—Synthesis of Compound of Formula II

Compound of Formula II, where R$^{12}$ and R$^{16}$ are fluoro or chloro, may be synthesized by reacting a compound of Formula III with an organolithium reagent (e.g. n-butyllithium, lithium diisopropylamine) in an inert solvent (e.g. THF), followed by the addition of a formylating reagent (e.g. DMF). The reaction is allowed to proceed, typically at −78° C., for 1-2 hours and the desired product is isolated by standard procedures (e.g. extraction, silica gel chromatography).

Example 78

Synthesis of Compound of Formula III, Where $R^{13}$ is $NR^{28}R^{29}$

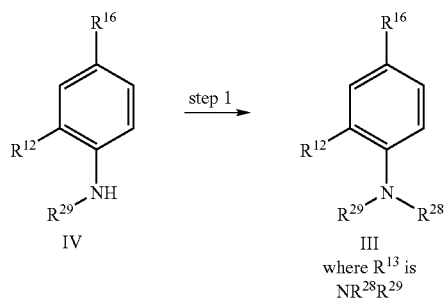

Step—1—Synthesis of Compound of Formula III Where $R^{13}$ is $NR^{28}R^{29}$

Compound of Formula III, where $R^{13}$ is $NR^{28}R^{29}$, may be synthesized by reacting a compound of Formula IV with a base (e.g. pyridine, sodium hydride) in an inert solvent (e.g. DMF, $CH_2Cl_2$), followed by an appropriate reagent ($R^{25}SO_2Cl$, e.g. propane-1-sulfonyl chloride; $R^{25}C(\!=\!O)Cl$, e.g. acetyl chloride; $R^{25}NCO$, e.g. propyl isocyanate: $R^{23}OC(\!=\!O)Cl$, e.g. benzyl chloroformate; $R^{26}R^{25}NSO_2Cl$, e.g. dimethylsulfamoyl chloride.) The reaction is allowed to proceed, typically at room temperature, for 8-12 hours and the desired product is isolated by standard procedures (e.g. extraction and silica gel chromatography).

Example 79

Synthesis of Compound of Formula III, Where $R^{13}$ is $CONR^{25}R^{26}$

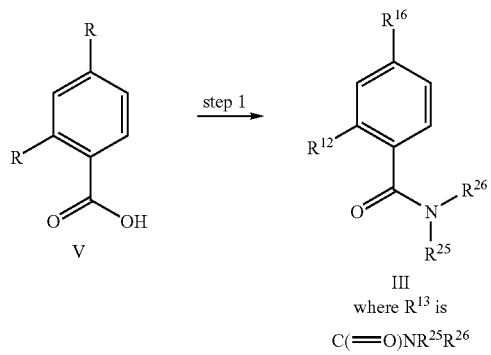

Step—1—Synthesis of Compound of Formula III, Where $R^{13}$ is $C(\!=\!O)NR^{25}R^{26}$ Compound of Formula III, where $R^{13}$ is $C(\!=\!O)NR^{25}R^{26}$, may be synthesized by reacting a compound of Formula V with a base (e.g. N,N-diisopropylethylamine) and condensing reagents (e.g. N-(3-dimethylaminopropyl)-N'-ethylcarbodiimide hydrochloride and 1-hydroxybenzotriazole) in all inert solvent (e.g. tetrahydrofuran), followed by an amine ($R^{25}R^{26}NH$, e.g. 1-propanamine). The reaction is allowed to proceed, typically at room temperature, for 8-12 hours and the desired product is isolated by standard procedures (e.g. extraction, silica gel chromatography).

Example 80

Synthesis of Compound of Formula III, Where $R^{13}$ is $SO_2NR^{25}R^{26}$

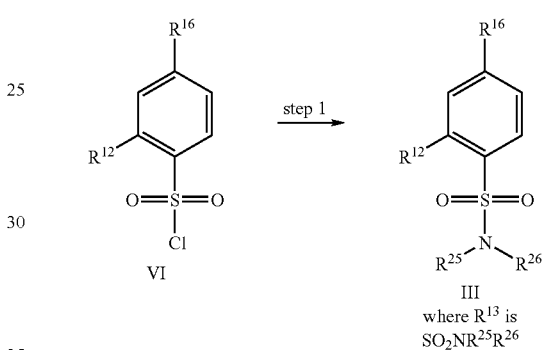

Step—1—Synthesis of Compound of Formula III

Compound of Formula III, where $R^{13}$ is $-SO_2NR^{25}R^{26}$, is synthesized by reacting a compound of Formula VI with a base (e.g. triethylamine) in an inert solvent (e.g. $CH_2Cl_2$), followed by an appropriate reagent ($R^{25}R^{25}NH_2$, e.g. 1-propanamine). The reaction is allowed to proceed, typically at room temperature, for 2-5 hours and the desired product is isolated by standard procedures (e.g. extraction, silica gel chromatography).

Example 81

Synthesis of Compound of Formula III, Where $R^{13}$ is OP Where P is a Protecting Group

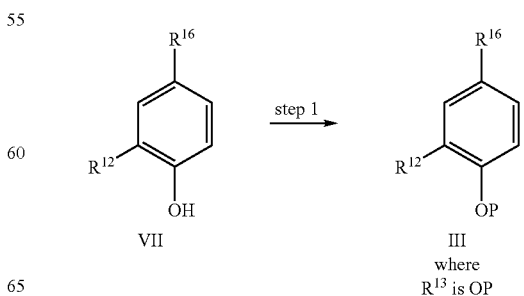

Step—1—Synthesis of Compound of Formula III, Where R¹³ is OP and P is a Protecting Group Compound of Formula III, where $R^{13}$ is —OP and P is a protecting group, is synthesized by reacting a compound of Formula VII with a base (e.g. imidazole) in a polar solvent (e.g. DMF), followed by an appropriate reagent (e.g. tert-butyl-chloro-dimethyl-silane) to introduce the protecting group. The reaction is allowed to proceed, typically at room temperature, for 8-12 hours, and the desired product is isolated by standard procedures (e.g. extraction, silica gel chromatography).

Example 82

Synthesis of Compound of Formula VIII

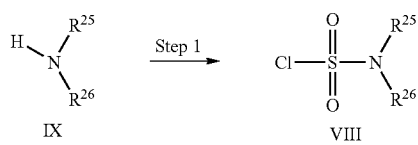

Step—1—Synthesis of Compound of Formula VIII

Compound of Formula VIII is synthesized by reacting a compound of Formula IX with a base (e.g. pyridine) in an inert solvent (e.g. $CR_2Cl_2$), followed by sulfuryl chloride. The reaction is allowed to proceed, typically under reflux, for 8-12 hours and the desired product is isolated by standard procedures (e.g. evaporation).

Example 83

Synthesis of Compounds of Formula X

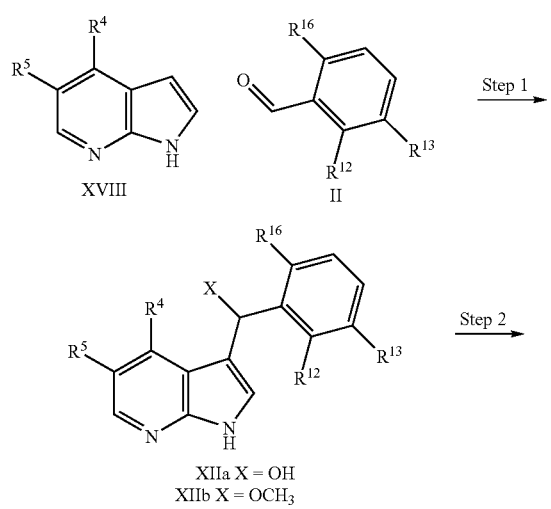

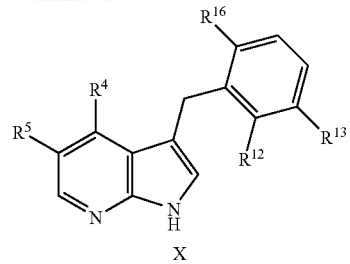

Step 1—Preparation of Compounds of Formula XIIa and XIIb

To a compound of Formula XVIII and a compound of Formula II is added an appropriate solvent (e.g. methanol) followed by an appropriate base (e.g. potassium hydroxide, sodium methoxide). The reaction is typically allowed to stir at room temperature overnight. Isolation by convention means (e.g. extraction, washing and filtering) affords a mixture of compounds of Formula XIIa and XIIb which may be separated by silica gel chromatography if desired.

Step 2—Preparation of Compounds of Formula X

To a compound of Formula XIIa or XIIb in an appropriate solvent (e.g. acetonitrile) is added a reducing agent (e.g. trifluoroacetic acid and triethylsilane). Typically, the reaction is allowed to stir at room temperature overnight. Isolation by conventional means (e.g. extraction and silica gel column chromatography) affords compounds of Formula X.

Example 84

Synthesis of Compounds of Formula I

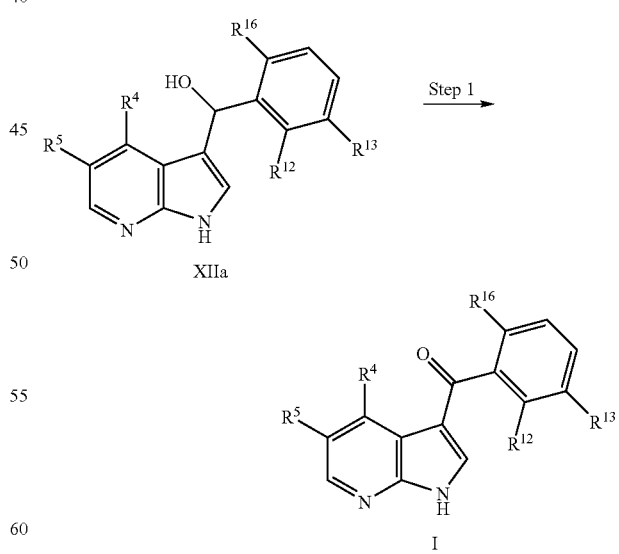

Step 1—Preparation of Compounds of Formula I

To a compound of Formula XIIa in an appropriate solvent (e.g. THF) is added an oxidizing agent (e.g. Dess-Martin periodane, TEMPO, DDQ). Typically, the reaction is allowed to stir at room temperature for 20 minutes. Isolation by conventional means (e.g. extraction and silica gel column chromatography) affords compounds of Formula I.

Example 85

Synthesis of Compounds of Formula XIII Where $R^{12}$ and $R^{16}$ are Independently Chloro or Fluoro

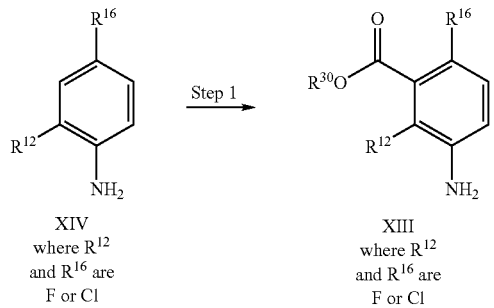

Step—1—Synthesis of Compound of Formula XIII, Where $R^{12}$ and $R^{16}$ are Chloro or Fluoro Compound of Formula XIII, where $R^{12}$ and $R^{16}$ are chloro or fluoro, is synthesized by reacting a compound of Formula XIV with an organolithium reagent (e.g. n-butyllithium) and a temporary protecting group (e.g. 1,2-Bis-(chloro-dimethylsilanyl)-ethane) and DMF in a inert solvent (e.g. THF) under inert atmosphere (e.g. argon) at −78° C. for 2-4 hours, followed by removal of the temporary protecting group using an acid (e.g. 1N HCl). The product is isolated by extraction and silica gel column chromatography.

Example 86

Synthesis of Compounds of Formula XV, Where $R^{13}$ is $NHR^{28}$

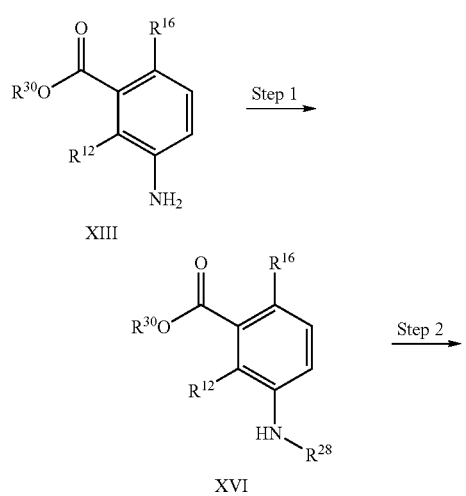

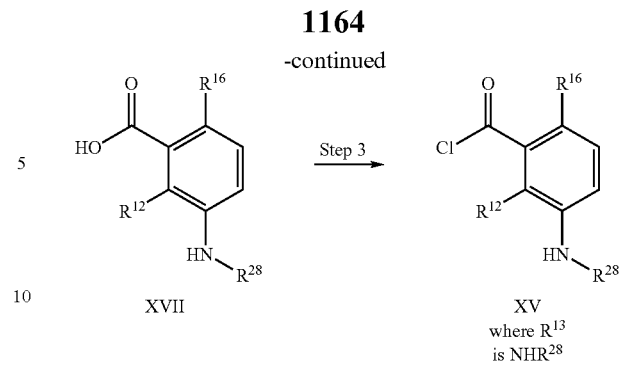

Step 1—Synthesis of Compound of Formula XVI

Compound of Formula XVI may be synthesized by reacting a compound of Formula XIII with a base (e.g. pyridine, sodium hydride) in an inert solvent (e.g. DMF, $CH_2Cl_2$), followed by an appropriate reagent ($R^{25}SO_2Cl$, e.g., propane-1-sulfonyl chloride: $R^{25}C(=O)Cl$, e.g. acetyl chloride; $R^{25}NCO$, e.g., propyl isocyanate; $R^{25}OC(=O)Cl$, benzyl chloroformate; $R^{26}R^{25}NSO_2Cl$, e.g., dimethylsulfamoyl chloride). The reaction is allowed to proceed, typically at room temperature, for 8-12 hours and the desired product is isolated by standard procedures (e.g. extraction and silica gel chromatography).

Step 2—Synthesis of Compound of Formula XVII

Compound of Formula XVII, may be synthesized by hydrolyzing a compound of Formula XVI with an aqueous base solution (e.g. sodium hydroxide). The reaction is allowed to proceed, typically under reflux, for 8-12 hours and the desired product is isolated by standard procedures (e.g. extraction).

Step 3—Synthesis of Compound of Formula XV, Where $R^{13}$ is $NHR^{28}$

Compound of Formula XV, where $R^{13}$ is $NHR^{28}$, may be synthesized by reacting a compound of Formula XVII with thionyl chloride. The reaction is allowed to proceed, typically under reflux, for 3 hours and the desired product is isolated by standard procedures (e.g. evaporation).

Example 87

Synthesis of Compounds of Formula XV

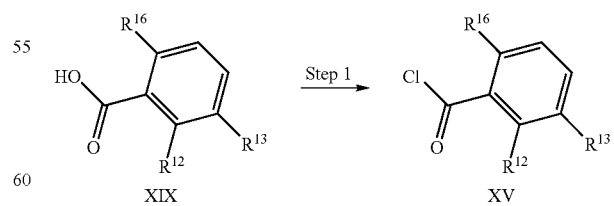

Step 1—Synthesis of Compound of Formula XV

Compound of Formula XV may be synthesized by reacting a compound of Formula XIX with thionyl chloride. The reac-

Example 88

Synthesis of Compounds of Formula I

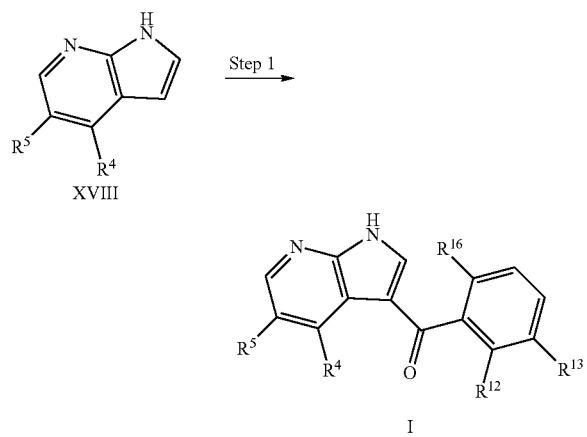

Step—1—Synthesis of compound of Formula I

Compound of Formula I is synthesized by reacting a compound of Formula XVIII with a compound of Formula XV (Example 83, e.g. benzoyl chloride) in the presence of a Lewis acid (e.g. aluminum trichloride) in an inert solvent (e.g. methylene chloride) under an inert atmosphere (e.g. argon) at room temperature or with heating up to reflux for 1-18 hours. The product is isolated by extraction and silica gel column chromatography.

Example 89

Synthesis of Compounds of Formula I where $R^5$ is Aryl or Heteroaryl

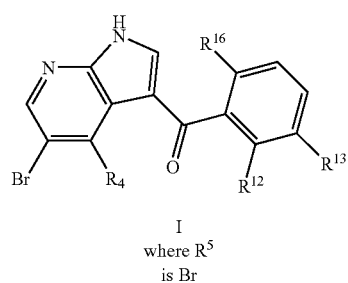

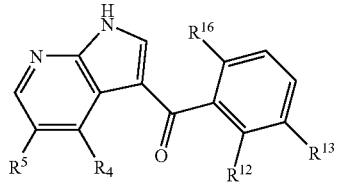

Step 1: Synthesis of Compound of Formula I, Where $R^5$ is Aryl or Heteraryl

Compound of the Formula I, where $R^5$ is aryl or heteroaryl, is prepared by reacting a compound of Formula I, where $R^5$ is bromo, under Suzuki coupling conditions, with boronic acid (e.g. phenyl boronic acid) in the presence of a base (e.g., potassium carbonate) and catalyst (e.g., Pd(Ph$_3$P)$_4$) in aqueous/THF solvent system. After 4-12 hours with heating to 80° C. or heating in a microwave instrument at 120° C. for 15 minutes, the product is isolated by standard workup procedures (e.g. silica gel column chromatography).

Example 90

Synthesis of Compounds of Formula I

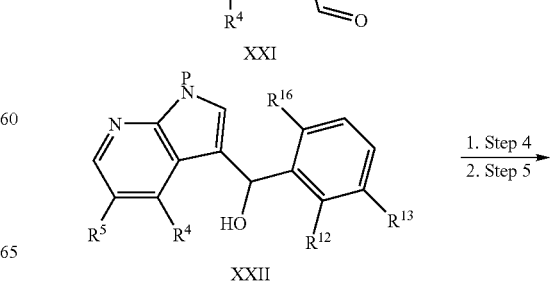

tion is allowed to proceed, typically under reflux, for 3 hours and the desired product is isolated by standard procedures (e.g. evaporation).

-continued

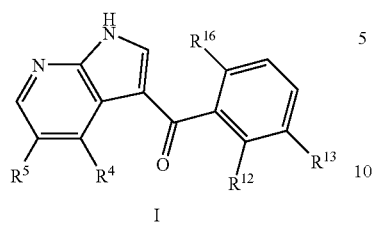

I

Step—1—Synthesis of compound XX

Compound of Formula XX can be synthesized by reacting a compound of Formula XVIII with hexamothyltetramine and acetic acid in water with heating to reflux for two hours. After cooling, the desired product precipitates and may be collected by filtration.

Step—2—Synthesis of Compound of Formula XXI

Compound of Formula XXI, where P is a protecting group, is synthesized by reacting a compound XX with an appropriate reagent to introduce a protecting group (P—X, e.g. triisopropylsilylchloride) and a base (e.g. sodium hydride) in a solvent (e.g. THF) typically at room temperature for 8-12 hours. The product is isolated by conventional means (e.g. extraction).

Step—3—Synthesis of Compound of Formula XXII

Compound of Formula XXII is synthesized by reacting a compound of Formula XXI in a solvent (e.g. THF) with an organolithium reagent (e.g. phenyl lithium) in a solvent (e.g. THF) under an inert atmosphere, cooled to −78° C. An appropriate organolithium reagent can also be prepared by reacting compounds of Formula III, where $R^{12}$ and $R^{16}$ are independently fluoro or chloro, with an organolithium reagent (e.g. butyllithium) in a solvent (e.g. THF) under an inert atmosphere, cooled to −78° C. The reaction is typically allowed to warm to room temperature and stirred for 30 minutes. The product is isolated by conventional means (e.g. extraction).

Step—4—Synthesis of an Intermediate of Compound of Formula I

An intermediate of compound of Formula I is synthesized by reacting a compound of Formula XXII with an appropriate reagent to remove the protecting group, P, (e.g. tetra-n-butyl ammonium fluoride) in an appropriate solvent (e.g. THF). The final product is isolated by standard procedures (e.g. extraction).

Step—5—Synthesis of Compound of Formula I

Compound of Formula I is synthesized by reacting the intermediate from Step 4 with an oxidizing agent (e.g. Dess-Martin periodane, TEMPO) in an aprotic solvent (e.g. THF) typically at room temperature for 20 minutes. The product is isolated by conventional means (e.g. extraction and silica gel chromatography).

Example 91

Synthesis of Compounds of Formula I, Where $R^{13}$ is $NHC(=O)NR^{25}R^{26}$

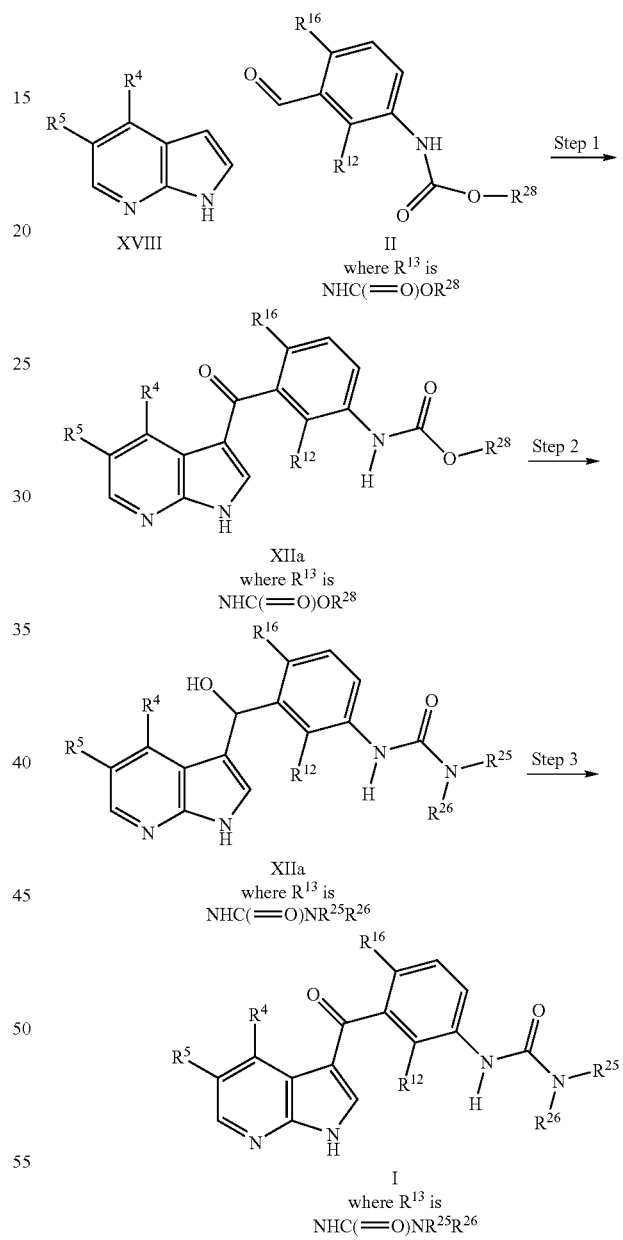

Step 1—Preparation of Compounds of Formula XIIa Where $R^{13}$ is $NHC(=O)OR^{28}$ To a compound of Formula XVIII and a compound of Formula II, where $R^{13}$ is $NHC(=O)OR^{28}$, is added an appropriate solvent (e.g. methanol) followed by an appropriate base (e.g. potassium hydroxide). The reaction is typically allowed to stir at room temperature overnight. Isolation by convention means (e.g. extraction, washing and filtering) affords compound of Formula XIIa where $R^{13}$ is NHC(=O)OR$^{28}$.

Step 2—Preparation of Compounds of Formula XIIa, where $R^{13}$ is NHC(=O)NR$^{25}$R$^{26}$ Compound of Formula XIIa, where $R^{13}$ is NHC(=O)NR$^{25}$R$^{26}$, is synthesized by reacting a compound of Formula XIIa, where $R^{13}$ is NHC(=O)OR$^{28}$, with an amine of the formula NHR$^{25}$R$^{26}$ (e.g. propylamine) in an appropriate solvent (e.g. dioxane) followed by an appropriate base (e.g. triethylamine). The reaction is typically heated at 140° C. for 15 minutes in a CEM Discover microwave instrument. Isolation by convention means (e.g. extraction, washing and filtering) affords compounds of Formula XIIa, where $R^{13}$ is NHC(=O)NR$^{25}$R$^{26}$.

Step 3—Preparation of Compounds of Formula I, Where $R^{13}$ is NHC(=O)NR$^{25}$R$^{26}$ Compound of Formula I, where $R^{13}$ is NHC(=O)NR$^{25}$R$^{26}$, is synthesized by reacting a compound of Formula XIIa, where $R^{13}$ is NHC(=O)NR$^{25}$R$^{26}$, with an oxidizing agent (e.g. Dess-Martin periodane, TEMPO) in an appropriate solvent (e.g. THF). The reaction is typically stirred at room temperature for 15 minutes. Isolation by convention means (e.g. extraction, washing and filtering) affords compounds of Formula I, where $R^{13}$ is NHC(=O)NR$^{25}$R$^{26}$.

Example 92

Synthesis of Compounds of Formula I, Where $R^{13}$ is NHC(=O)OR$^{25}$

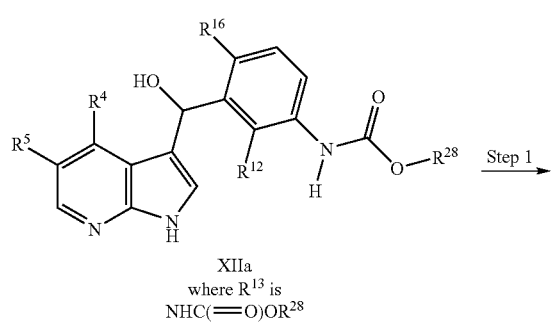

XIIa
where $R^{13}$ is
NHC(=O)OR$^{28}$

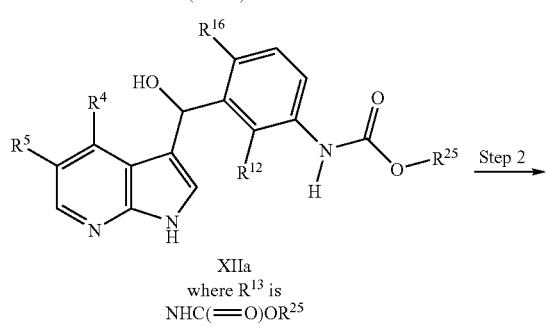

XIIa
where $R^{13}$ is
NHC(=O)OR$^{25}$

-continued

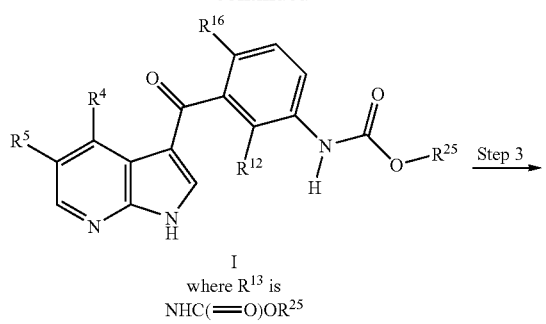

I
where $R^{13}$ is
NHC(=O)OR$^{25}$

Step 1—Preparation of Compounds of Formula XIIa, Where $R^{13}$ is NHC(=O)OR$^{25}$ Compound of Formula XIIa, where $R^{13}$ is NHC(=O)OR$^{25}$, is synthesized by reacting a compound of Formula XIIa, where $R^{13}$ is NHC(=O)OR$^{28}$, with an alcohol of the formula R$^{25}$OH (e.g. methanol) in an appropriate solvent (e.g. dioxane) followed by an appropriate base (e.g. triethylamine). The reaction is typically heated at 140° C. for 15 minutes in a CEM Discover microwave instrument. Isolation by convention means (e.g. extraction, washing and filtering) affords compounds of Formula XIIa, where $R^{13}$ is NHC(=O)OR$^{25}$.

Step 2—Preparation of Compounds of Formula I, Where $R^{13}$ is NHC(=O)OR$^{25}$ Compound of Formula I, where $R^{13}$ is NHC(=O)OR$^{25}$, is synthesized by reacting a compound of Formula XIIa, where $R^{13}$ is NHC(=O)OR$^{25}$, with an oxidizing agent (e.g. Dess-Martin periodane, TEMPO) in an appropriate solvent (e.g. THF). The reaction is typically stirred at room temperature for 15 minutes. Isolation by convention means (e.g. extraction, washing and filtering) affords compounds of Formula I, where $R^{13}$ is NHC(=O)OR$^{25}$.

lp;&1pExample 93

Synthesis of Compounds of Formula I, Where $R^4$ and $R^5$ are Hydrogen

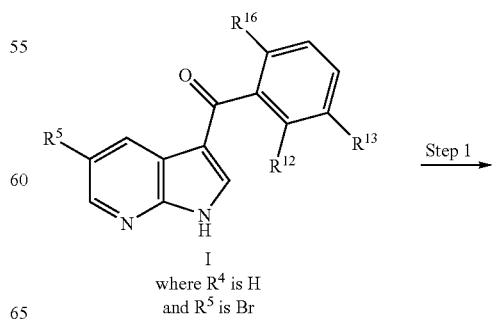

I
where $R^4$ is H
and $R^5$ is Br

1171

-continued

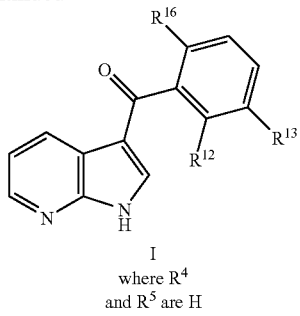

I
where R⁴
and R⁵ are H

Step 1—Preparation of Compounds of Formula I Where R⁴ and R⁵ are Hydrogen

Compound of Formula I, where R⁴ and R⁵ are hydrogen, is synthesized by hydrogenating compound of Formula I, where R⁴ is hydrogen and R⁵ is bromo, in the presence of an appropriate solvent (e.g methanol) and catalyst (e.g. 10% Pd/C), under an atmosphere of hydrogen gas. The reaction is typically allowed to stir at room temperature for 8-12 hours. Isolation by convention means (e.g. extraction, washing and filtering) affords compounds of Formula I, where R⁴ and R⁵ are hydrogen.

Synthesis of Compound of Formula Ia

Compounds of Formula Ia are compounds of Formula XVIII in which R⁴ is hydrogen and R⁵ is the only substituent on the core structure. Exemplary synthetic schemes for groups of compounds within Formula Ia are shown in Examples 91 to 99 for different selections of R⁵.

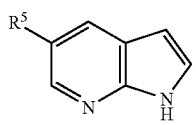

Formula Ia

Example 94

Synthesis of Compounds of Formula Ia Where R⁵ is Aryl or Heteroaryl

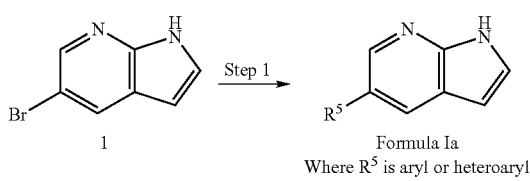

Compound of Formula Ia, where R⁵ is aryl or heteroaryl, is synthesized from compound 1 under Suzuki reaction conditions using aryl or heteroaryl bornonic acids (e.g. phenyl bornonic acid) in the presence of a base (e.g. potassium carbonate) and a catalyst (e.g. Pd(PPh₃)₄) in aqueous/THF system with thermal heating (e.g. 80° C. for 12 hours) or microwave heating (e.g. 120° C. for 15 minutes). The product is isolated by conventional means (e.g. silica gel column chromatography).

1172

Example 95

Synthesis of Compounds of Formula Ia Where R⁵ is Alkyl or Cycloalkyl

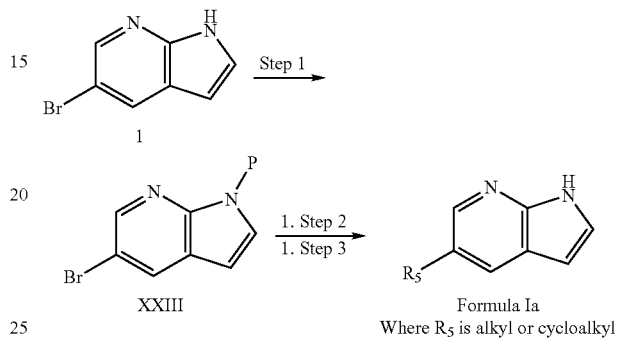

Step—1—Synthesis of Compound of Formula XXIII

Compound of Formula XXIII, where P is a protecting group, is synthesized by reacting compound 1 with a base (e.g. sodium hydride) in an inert solvent (e.g. THF), followed by an appropriate reagent (P—X, e.g., triisopropylsilylchloride) for introduction of a protecting group. The reaction is allowed to proceed, typically at room temperature, for 8-12 hours and the desired product is isolated by standard procedures (e.g. extraction) (Greene, T. W.; Wuts, P. G. M, *Protective Groups in Organic Synthesis I*, 3rd ed.; John Wiley & Sons: New York, 1981).

Step—1—Synthesis of an Intermediate of Compound of Formula Ia, Where R⁵ is Alkyl and Cycloalkyl An intermediate of compound of Formula Ia, where R⁵ is alkyl or cycloalkyl, is synthesized by reacting a compound of Formula XXIII with an alkyl or cycloalkyl Grignard reagent (e.g. ethyl magnesium bromide) in the presence of catalyst (e.g. [1,1'-bis(diphenylphosphino)ferrocene]dichloropalladium(II)) in an inert solvent (e.g. toluene) at low temperature (e.g. −78° C.) or under reflux for 2-8 hours. The product is isolated by standard procedures (e.g. extraction and silica gel column chromatography) as described by literature. (T. Hayashi, M. Konishi, Y. Kobori, M. Kumada, T. Iliguchi, K. Hirotsu; *J. Am. Chem. Soc.* 1984, 106, 158-163).

Step—3—Synthesis of Compound of Formula Ia, Where R⁵ is Alkyl and Cycloalkyl Compound of Formula Ia, where R⁵ is alkyl or cycloalkyl, is synthesized by reacting an intermediate of compound Formula Ia from Step 2 with an appropriate reagent to remove the protecting group (e.g. tetrabutylammonium fluoride) in an appropriate solvent (e.g. tetrahydrofuran). The product is isolated by standard procedures (e.g. extraction and silica gel column chromatography).

Example 96

Synthesis of Compounds of Formula Ia Where $R^5$ is $NR^{22}R^{23}$

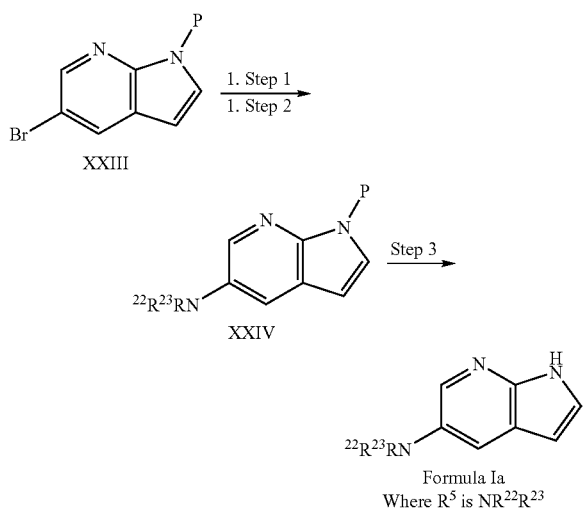

Step—1—Synthesis of an Intermediate of Compound of Formula XXIV

An intermediate of compound of Formula XXIV, is synthesized by reacting a compound of Formula XXIII, with an amine of the formula $NHR^{22}R^{23}$ (e.g. aniline) in a solvent (e.g. toluene), in the presence of a base (e.g. sodium tert-butoxide) and a catalyst composed of a metal (e.g., Tris (dibenzylideneacetone)dipalladium(0)) and a ligand (e.g., tri-tert-hutylphosphine) with heating, typically to 95° C., for 8-12 hours as described (Thomas, et. al., J. Am. Chem. Soc., 2001, 123, 9404) by substituting a compound of Formula XXIII for the N-substituted-3,6-dibromocarbazole. The desired compound is purified by silica gel column chromatography. This intermediate is used directly in Step 3 to provide compound of Formula Ia where $R^5$ is $NR^{22}R^{23}$ and $R^{22}$ and $R^{23}$ are not —$C(X)R^{20}$, —$C(X)NR^{17}R^{18}$, —$S(O)_2R^{21}$, or $S(O)_2NR^{17}R^{13}$ or alternatively, it can be additionally substituted as described in Step 2.

Step—2—Synthesis of Compound of Formula XXIV

The intermediate from Step 1 can be further modified when $R^{23}$ or $R^{23}$ is hydrogen. In this case, the intermediate from Step 1 can be reacted with a base (e.g. sodium hydride) in a solvent (e.g. N,N-dimethylformamide), followed by reaction with an alkylating reagent (e.g. benzyl bromide) or an acylating reagent (e.g. benzoyl chloride, phenyl isocyanate, phenyl isothiocyanate, phenylsulfonyl chloride) typically at room temperature or with heating up to 80° C. for 1-12 hours. The desired product can be purified by conventional means (e.g. silica gel column chromatography). Alternatively, when $R^{22}$ or $R^{23}$ is a suitable protecting group (e.g. benzyl), it may be removed by appropriate treatment (e.g. hydrogenation) to provide a compound where $R^{22}$ and/or $R^{23}$ are hydrogen, which is suitable for further modification with an alkylating reagent or acylating reagent as described herein.

Step—3—Synthesis of Compound of Formula Ia, Where $R^5$ is —$NR^{22}R^{23}$

Compound of Formula Ia, where $R^5$ is —$NR^{22}R^{23}$, is synthesized by reacting a compound of Formula XXIV with an appropriate reagent to remove the protecting group (e.g. tetra-n-butylammonium fluoride) in an appropriate solvent (e.g. methanol). The final product can be isolated by standard procedures (e.g. extraction).

Example 97

Synthesis of Compounds of Formula Ia Where $R^5$ is $C(O)NR^{25}R^{26}$

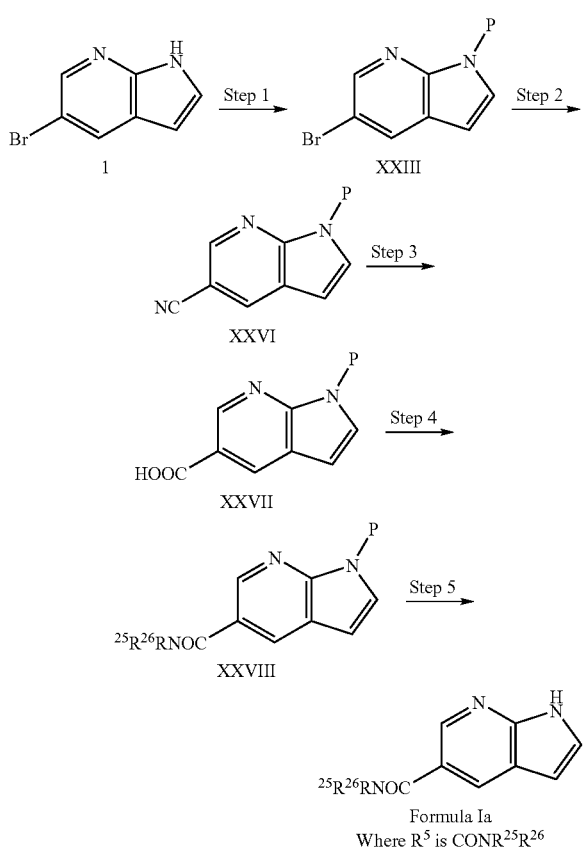

Step—1—Synthesis of Compound of Formula XXIII

Compound of Formula XIII, where P is a protecting group, is synthesized by reacting compound 1 with a base (e.g. sodium hydride) in a solvent (e.g. THF), followed by an appropriate reagent (P—X, e.g. triisopropylsilylchloride) for introduction of a protecting group. The reaction is allowed to proceed, typically at room temperature for 8-12 hours, and the desired product is isolated by standard procedures (e.g. extraction and silica gel column chromatography) (Greene, T.

W.; Wuts, P. G. M. *Protective Groups in Organic Synthesis I*, 3rd ed.; John Wiley & Sons: New York, 1981).

Step—2—Synthesis of Compound of Formula XXVI

Compound of Formula XXVI may be synthesized by reacting a compound of Formula XXIII with sodium cyanide in a polar aprotic solvent (e.g. DMF) in an inert atmosphere (e.g. argon), in the presence of a catalyst (e.g. cuprous iodide or Tris(dibenzylidencacctonc)dipalladium(0)) following the procedure described by Buchwald et. al., J. Am. Chem. Soc., 2003, 125, 2890-2891, by substituting 5-bromo-7-azaindole for 5-bromo-indole.

Step—3—Synthesis of Compound of Formula XXVII

Compound of Formula XXVII may be synthesized by heating a compound of Formula XXVI with aqueous base (e.g. aq. KOH) in the presence of an alcohol (e.g. ethanol) at higher temperatures (e.g. 90° C.) for required time, typically 24 h, as described in Org. Syn. Collective Volume 2, 292 (1943). Alternatively, compounds of Formula XXVII may be synthesized directly from a compound of Formula XXIII by reacting a compound of Formula XXIII with a strong base (e.g. n-hutyllithium) and benzyl chloroformate in an inert solvent (e.g. THF), and further debenzylation by hydrogenating the obtained benzyl ester with hydrogen, in the presence of a catalyst (e.g. 20% Pd(OH)$_2$/C) at room temperature. The product may be isolated by filtration and evaporation.

Step—4—Synthesis of Compound of Formula XXVIII

Compound of Formula XXVIII may be synthesized by reacting a compound of Formula XXVII with an amine (e.g. benzylamine) in a polar aprotic solvent (e.g. DMF) in an inert atmosphere, in presence of an activating agent (e.g. PyBroP (Bromotri(pyrrolidino)phosphonium hexafluorophosphate) following the procedure described by Coste et. al., J. Org. Chem., 1994, 59, 2437.

Step—5—Synthesis of Compound of Formula Ia

Compound of Formula Ia, where $R^5$ is C(O)NR$^{25}$R$^{26}$, may be synthesized by cleaving the protective group (e.g. TIPS) of a compound of Formula XXVIII with appropriate reagents (e.g. TBAF) and isolating the product (e.g. extraction and silica gel column chromatography).

Example 98

Synthesis of Compounds of Formula Ia where $R^5$ is CH$_2$NHR$^{25}$R$^{26}$

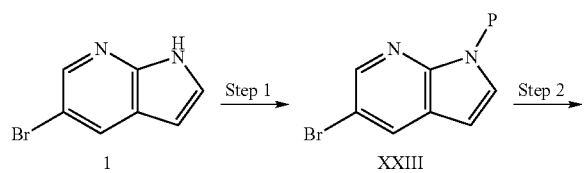

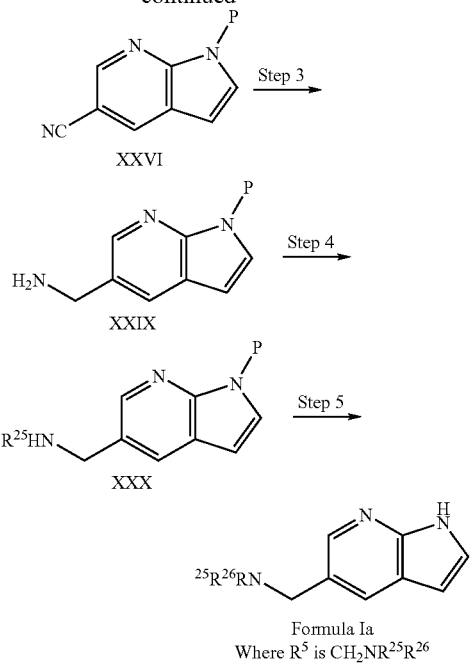

Formula Ia
Where $R^5$ is CH$_2$NR$^{25}$R$^{26}$

Step—1—Synthesis of Compound of Formula XXIII

Compound of Formula XXIII, where P is a protecting group, is synthesized by reacting compound 1 with a base (e.g. sodium hydride) in a solvent (e.g. THF), followed by an appropriate reagent (P—X, e.g. triisopropylsilylchloride) for introduction of a protecting group. The reaction is allowed to proceed, typically at room temperature, for 8-12 hours and the desired product is isolated by standard procedures (e.g. extraction and silica gel column chromatography) (Greene, T. W.; Wuts, P. G. M. *Protective Groups in Organic Synthesis I*, 3rd ed.; John Wiley & Sons: New York, 1981).

Step—2 Synthesis of Compound of Formula XXVI

Compound of Formula XXVI may be synthesized by reacting a compound of Formula XXIII with sodium cyanide in a polar aprotic solvent (e.g. DMF) in an inert atmosphere, in presence of a catalyst (e.g. Tris(dibenzylideneacetone)dipalladium(0) or cuprous iodide) following the procedure described by Buchwald et, al., J Am. Chem. Soc., 2003, 125, 2890-2891, by substituting 5-bromo-7-azaindole for 5-bromo-indole.

Step—3—Synthesis of Compound of Formula XXIX

Compound of Formula XXIX can be synthesized from a compound of Formula XXVI under hydrogenation conditions using a catalyst (e.g. PtO$_2$) in an atmosphere of H$_2$ as described by Secrist III et. al., J Org. Chem., 1972, 37, 335-336.

Step—4—Synthesis of Compound of Formula XXX

Compound of Formula XXX can be synthesized from a compound of Formula XXIX with an electrophilic reagent (e.g. benzyl bromide, benzenesulfonyl chloride, benzoyl chloride, phenyl isocyanate, phenyl isothiocyanate) in a polar aprotic solvent (e.g. DMF) in an inert atmosphere, in the presence of a base (e.g. K$_2$CO$_3$, Et$_3$N). The product can be isolated by standard methods (e.g. aqueous work up and silica gel column chromatography).

Step—5—Synthesis of Compound of Formula Ia

Compound of Formula Ia, where R$^5$ is CH$_2$NHR$^{25}$R$^{26}$, can be synthesized from a compound of Formula XXX with an electrophilic reagent (e.g. benzyl bromide, benzenesulfonyl chloride, benzoyl chloride, phenyl isocyanate, phenyl isothiocyanate) in a polar aprotic solvent (e.g. DMF) in an inert atmosphere, in the presence of a base (e.g. K$_2$CO$_3$, Et$_3$N), followed by &protection of the protecting group with appropriate conditions (e.g. tetra-n-butylammonium fluoride) and purification by conventional meand (e.g. silica gel chromatography).

Example 99

Synthesis of Compounds of Formula Ia Where R$^5$ is OR$^{25}$

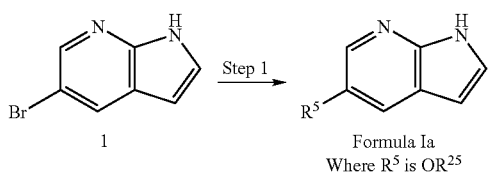

Step—1—Synthesis of Compound of Formula Ia, Where R$^5$ is OR$^{25}$

A compound of Formula Ia, where R$^5$ is OR$^{25}$, is synthesized by reacting compound 1 with a reagent of formula R$^{25}$OH (e.g. methanol) in the presence of base (e.g. sodium methoxide) and copper (I) bromide in a solvent (e.g. N,N-dimethylformamide) typically with heating to reflux for 2-8 hours as described by Mazeas, et. al. in *Heterocycles*, 1999, 50:1065. The desired intermediate is purified by conventional means (e.g. silica gel column chromatography).

Example 100

Synthesis of Compounds of Formula Ia Where R$^5$ is SR$^{25}$

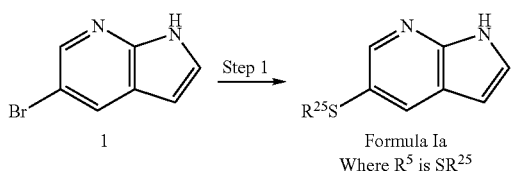

Compound of Formula Ia, where R$^5$ is SR$^{25}$, can be prepared by reacting compound 1 with a strong base (e.g. potassium hydride or t-butyl lithium) and dialkyldisulfides (e.g. dimethyldisulfane) or thiophenols (e.g. 4-methoxythiophenol) in a polar aprotic solvent (e.g. N,N-dimethylformamide) in an inert atmosphere following the procedure described by Yang et. al., Heterocycles, 1992, 34, 1169, by substituting 5-bromo-7-azaindole for 5-bromo-indole.

Example 101

Synthesis of Compounds of Formula Ia Where R$^5$ is S(O)R$^{25}$ or S(O)$_2$R$^{25}$

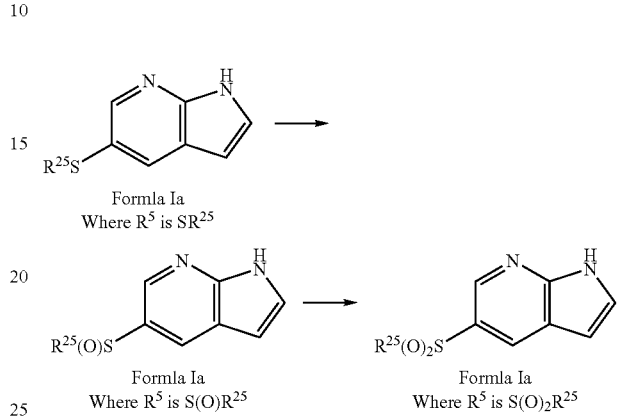

Compounds of Formula Ia, where R$^5$ is S(O)R$^{25}$, or S(O)$_2$R$^{25}$ can be prepared by reacting compound of Formula Ia, where R$^5$ is SR$^{25}$, with 1 or 2 equivalents of oxidizing agent (e.g. Oxone), respectively, in a polar solvent (e.g. DMF), using standard procedures.

Example 102

Synthesis of Compound of Formula Ic, Where Y$^3$ is C(O) or CH$_2$; Y$^6$ is NH; and R$^{27}$ is Independently Halogen

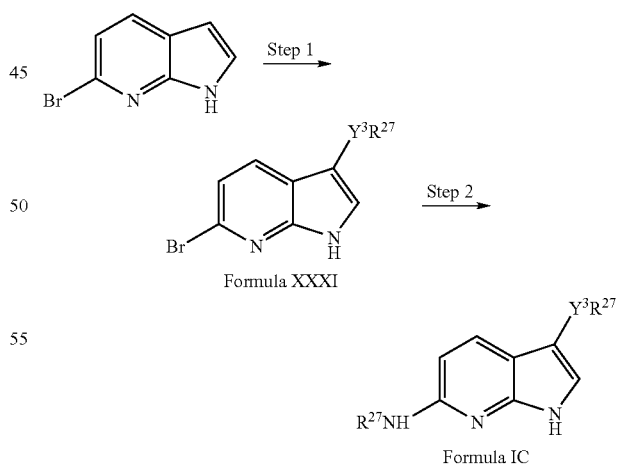

Step—1 Synthesis of Compound of Formula XXXI

Compound of Formula XXXI in turn can be prepared by reacting 6-bromo-7-azaindole (Minakata, S., et al, Synthesis, 1992, p 661-663) with an appropriate nucleophile (e.g. acid chlorides, alkyl halides, and the like) in polar aprotic solvents (e.g. THF, DMF) in the presence of a Lewis acid (e.g. $AlCl_3$, $InCl_3$ etc.). The product may be isolated by following standard procedures (work up and silica gel column chromatography).

Step—2 Synthesis of Compound of Formula Ic

Compound of Formula Ic can be prepared by reacting compound of Formula XXXI with $R^{27}NH_2$ under Buckwald reaction conditions (Palladium tetrakis trialkylphosphine and a base). The product may be isolated by following standard procedures (work up and silica gel column chromatography).

Example 103

Synthesis of Compound of Formula Id, Where $Y^3$ is C(O) or $CH_2$; $Y^2$ is $CH_2$; and $R^{27}$ is Independently Halogen

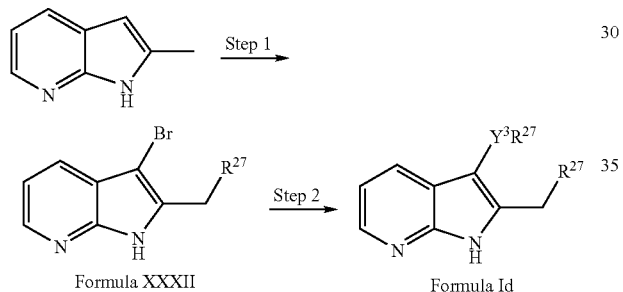

Step—1 Synthesis of Compound of Formula XXXII

Compound of Formula XXXII can be prepared from 2-methyl-7-azaindole (Clemo, S; *J. Chem. Soc.*, 1945, p 603-607) by reacting with N-bromosuccinimide in carbon tetrachloride followed by the reaction of the di bromo compound with a nucleophile (e.g. amine, alkoxy, phenoxy, etc). The product may be isolated by following standard procedures (work up and silica gel column chromatography).

Step—2 Synthesis of Compound of Formula Id

Compound of Formula XXXII can be reacted with a lithium reagent (e.g. butyl lithium) followed by the reaction with an aldehyde to provide the key intermediate to compound of Formula Id. This intermediate can be reacted with a reducing agent (e.g. trifluoroacetic acid and triethylsilane) at room temperature overnight to provide a compound of Formula Id where $Y^3$ is $CH_2$ as described in Example 79 step—2, or with an oxidizing agent (e.g. Dess-Martin periodane, TEMPO) at room temperature for 20 minutes to provide a compound of Formula Id where $Y^3$ is C(O) as described in Example 80.

Example 104

Synthesis of Compound of Formula Ie, Where $Y^4$ is NH; $Y^2$ is $CH_2$; and $R^{27}$ is Independently Halogen

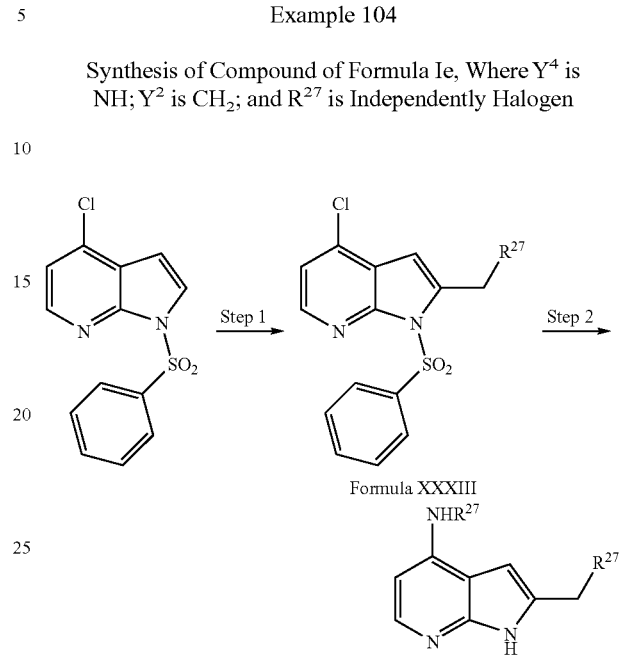

Step—1 Synthesis of Compound of Formula XXXIII

Compound of Formula XXXIII can be prepared by reacting 4-chloro-1-phenylsulfonyl-7-azaindole (Mendiola, J., et al.; *J. Org. Chem,* 2004, p 4974-4983) with lithium reagent (e.g. LDA) at low temperature (e.g. −40° C.) followed by the addition of an alkyl halide (e.g. benzyl bromide). The product may be isolated by following standard procedures (work up and silica gel column chromatography).

Step—2 Synthesis of Compound of Formula Ie

Compound of Formula Ie can be prepared by reacting a compound of Formula XXXIII with an amine of formula $R^{27}NH_2$ under Buckwald reaction conditions followed by deprotection and isolating the product by following standard procedures (work up and silica gel column chromatography).

Example 105

Synthesis of Compound of Formula $I_f$, Where $Y^5$ is NH; $Y^2$ is $CH_2$; $R^{27}$ is Independently Halogen

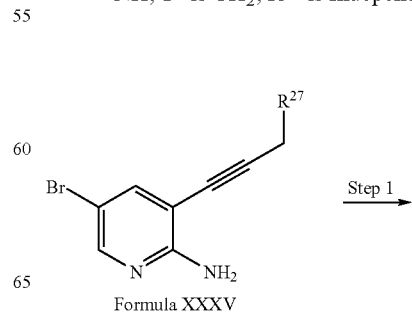

-continued

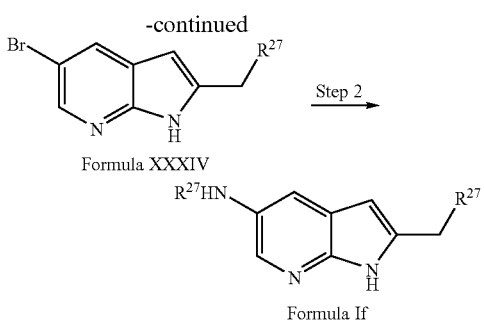

Step—1 Synthesis of Compound of Formula XXXIV

Compound of Formula XXXIV can be prepared by reacting a compound of Formula XXXV with a strong base (e.g. KH, potassium tert-butoxide) in a suitable solvent (e.g. NMP) at ambient temperature (Koradin, C., et.al.; *Tetrahedron*, 2003, p 1571-1588). The product may be isolated by following standard procedures (work up and silica gel column chromatography).

Step—2 Synthesis of Compound of Formula $I_f$

Compound of Formula $I_f$ can be prepared by reacting a compound of Formula XXXIV with an amine of formula $R^{27}NH_2$ under Buckwald reaction conditions followed by deprotection and isolating the product by following standard procedures (work up and silica gel column chromatography).

Example 106

Synthesis of Compound of Formula Ij, Where $Y^4$ is NH; $Y^5$ is O; and $R^{27}$ is Independently Halogen

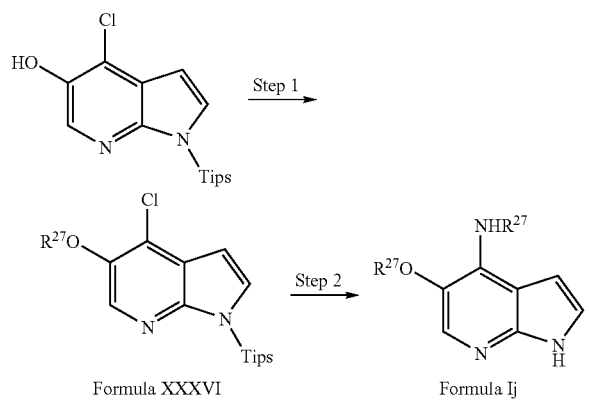

Step—1 Synthesis of Compound of Formula XXXVI

Compound of Formula XXXVI can be synthesized by reacting N-triisopopylsilyl-4-chloro-5-hydroxy-7-azaindole (L'Heureux, A., Thibault, C., and Ruel, R.; *Tetrahedron Letters*, 2004, p 2317-2319) with an alcohol (e.g. benzyl alcohol) under Mitsunobu reaction conditions and isolating the product by following standard procedures (work up and silica gel column chromatography).

Step—2 Synthesis of Compound of Formula Ij

Compound of Formula Ij can be prepared by reacting a compound of Formula XXXVI with an amine of formula $R^{27}NH_2$ under Buckwald reaction conditions followed by deprotection and isolating the product by following standard procedures (work up and silica gel column chromatography).

Additional examples of certain methods contemplated by the present invention may be found in the following applications: U.S. Prov. App. No, 60/580,898, filed Jun. 17, 2004; U.S. Prov. App. No. 60/682,076, filed May 17, 2005; U.S. Prov. App. No. 60/682,058, filed May 17, 2005; U.S. Prov. App. No. 60/682,063, filed May 17, 2005: U.S. Prov. App. No. 60/682,051, filed May 17, 2005; U.S. Prov. App. No. 60/682,042, filed May 17, 2005; U.S. Prov. App. No. 60/692,750, filed Jun. 22, 2005; and U.S. Prov. App. No. 60/692,960, filed Jun. 22, 2005; each of which are hereby incorporated by reference herein in their entireties including all specifications, figures, and tables, and for all purposes.

All patents and other references cited in the specification are indicative of the level of skill of those skilled in the art to which the invention pertains, and are incorporated by reference in their entireties, including any tables and figures, to the same extent as if each reference had beer incorporated by reference in its entirety individually.

One skilled in the art would readily appreciate that the present invention is well adapted to obtain the ends and advantages mentioned, as well as those inherent therein. The methods, variances, and compositions described herein as presently representative of preferred embodiments are exemplary and are not intended as limitations on the scope of the invention. Changes therein and other uses will occur to those skilled in the art, which are encompassed within the spirit of the invention, are defined by the scope of the claims.

It will be readily apparent to one skilled in the art that varying substitutions and modifications may be made to the invention disclosed herein without departing from the scope and spirit of the invention. For example, variations can be made to crystallization or co-crystallization conditions for Ret and Ret surrogate proteins and/or various kinase domain sequences can be used. Thus, such additional embodiments are within the scope of the present invention and the following claims.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood thet although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

Also, unless indicated to the contrary, where various numerical values are provided for embodiments, additional embodiments are described by taking any 2 different values as the endpoints of a range. Such ranges are also within the scope of the described invention.

Thus, additional embodiments are within the scope of the invention and within the following claims.

That which is claimed is:

1. A compound having the structure of Formula VIIa:

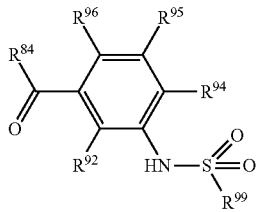

Formula VIIa wherein:
- $R^{84}$ is selected from the group consisting of hydrogen, lower alkoxy, and —Cl;
- $R^{94}$, $R^{95}$, and $R^{96}$ are independently selected from the group consisting of hydrogen, halogen, lower alkyl, fluoro substituted lower alkyl, lower alkoxy, and fluoro substituted lower alkoxy;
- $R^{92}$ is fluoro;
- $R^{99}$ is selected from the group consisting of optionally substituted $C_{2-6}$ alkyl and —$NR^{79}R^{80}$; wherein, when $R^{99}$ is substituted $C_{2-6}$alkyl, $R^{84}$ is hydrogen or —Cl; and
- $R^{79}$ and $R^{80}$ combine with the nitrogen to which they are attached to form optionally substituted 5-7 membered heterocycloalkyl.

2. The compound of claim 1 wherein $R^{94}$ and $R^{95}$ are hydrogen.

3. The compound of claim 1 wherein $R^{96}$ is selected from the group consisting of hydrogen, fluoro and chloro.

4. The compound of claim 3 wherein $R^{96}$ is hydrogen.

5. The compound of claim 3 wherein $R^{96}$ is fluoro.

6. The compound of claim 3 wherein $R^{96}$ is chloro.

7. The compound of claim 1 wherein $R^{99}$ is optionally substituted $C_{2-6}$alkyl.

8. The compound of claim 1 wherein $R^{99}$ is n-propyl.

9. The compound of claim 1 wherein $R^{99}$ is optionally substituted aryl.

10. The compound of claim 1 wherein $R^{99}$ is optionally substituted heteroaryl.

11. The compound of claim 1 wherein $R^{99}$ is —$NR^{79}R^{80}$.

12. The compound of claim 11 wherein $R^{79}$ and $R^{80}$ are independently hydrogen or optionally substituted lower alkyl.

13. The compound of claim 11 wherein $R^{79}$ and $R^{80}$ combine with the nitrogen to which they are attached to form optionally substituted 5-7 membered heterocycloalkyl.

14. The compound of claim 1 wherein $R^{92}$ and $R^{96}$ are fluoro, $R^{94}$ and $R^{95}$ are hydrogen, and $R^{99}$ is n-propyl.

15. The compound of claim 14 wherein $R^{84}$ is hydrogen.

16. The compound of claim 14 wherein $R^{84}$ is —Cl.

17. The compound of claim 13, wherein $R^{92}$ and $R^{96}$ are fluoro and $R^{94}$ and $R^{95}$ are hydrogen.

18. The compound of claim 17, wherein $R^{84}$ is hydrogen or —Cl.

* * * * *

SEQUENCE LISTING

```
<160> NUMBER OF SEQ ID NOS: 125

<210> SEQ ID NO 1
<211> LENGTH: 26
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 1
caccacggtg tgtcccccaa ctacga                                          26

<210> SEQ ID NO 2
<211> LENGTH: 34
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 2
gtcacgtcga ctcagacgcc ttgtttcccc agct                                 34

<210> SEQ ID NO 3
<211> LENGTH: 987
<212> TYPE: DNA
<213> ORGANISM: Artificial Sequence
<220> FEATURE:
<223> OTHER INFORMATION: Description of Artificial Sequence: Synthetic
      Plasmid
<220> FEATURE:
<221> NAME/KEY: CDS
<222> LOCATION: (88)..(978)

<400> SEQUENCE: 3
taatacgact cactataggg gaattgtgag cggataacaa ttcccctcta gaaataattt     60
tgtttaactt taagaaggag atatacc atg ggt cac cac cat cac cac cac ggt   114
                               Met Gly His His His His His His Gly
                                 1               5 gtg tcc ccc aac tac gac aag tgg gag atg gaa cgc acg gac atc acc    162
Val Ser Pro Asn Tyr Asp Lys Trp Glu Met Glu Arg Thr Asp Ile Thr
 10              15                  20                  25 atg aag cac aag ctg ggc ggg ggc cag tac ggg gag gtg tac gag ggc    210
Met Lys His Lys Leu Gly Gly Gly Gln Tyr Gly Glu Val Tyr Glu Gly
             30                  35                  40 gtg tgg aag aaa tac agc ctg acg gtg gcc gtg aag acc ttg aag gag    258
Val Trp Lys Lys Tyr Ser Leu Thr Val Ala Val Lys Thr Leu Lys Glu
         45                  50                  55 gac acc atg gag gtg gaa gag ttc ttg aaa gaa gct gca gtc atg aaa    306
Asp Thr Met Glu Val Glu Glu Phe Leu Lys Glu Ala Ala Val Met Lys
     60                  65                  70 gag atc aaa cac cct aac ctg gtg cag ctc ctt ggg gtc tgc acc cgg    354
Glu Ile Lys His Pro Asn Leu Val Gln Leu Leu Gly Val Cys Thr Arg
 75                  80                  85 gag ccc ccg ttc tat atc atc act gag ttc atg acc tac ggg aac ctc    402
Glu Pro Pro Phe Tyr Ile Ile Thr Glu Phe Met Thr Tyr Gly Asn Leu
             90                  95                 100                 105
```

```
ctg gac tac ctg agg gag tgc aac cgg cag gag gtg aac gcc gtg gtg        450
Leu Asp Tyr Leu Arg Glu Cys Asn Arg Gln Glu Val Asn Ala Val Val
            110                 115                 120 ctg ctg tac atg gcc act cag atc tcg tca gcc atg gag tac ctg gag        498
Leu Leu Tyr Met Ala Thr Gln Ile Ser Ser Ala Met Glu Tyr Leu Glu
        125                 130                 135 aag aaa aac ttc atc cac aga gat ctt gct gcc cga aac tgc ctg gta        546
Lys Lys Asn Phe Ile His Arg Asp Leu Ala Ala Arg Asn Cys Leu Val
        140                 145                 150 ggg gag aac cac ttg gtg aag gta gct gat ttt ggc ctg agc agg ttg        594
Gly Glu Asn His Leu Val Lys Val Ala Asp Phe Gly Leu Ser Arg Leu
    155                 160                 165 atg aca ggg gac acc tac aca gcc cat gct gga gcc aag ttc ccc atc        642
Met Thr Gly Asp Thr Tyr Thr Ala His Ala Gly Ala Lys Phe Pro Ile
170             175                 180                 185 aaa tgg act gca ccc gag agc ctg gcc tac aac aag ttc tcc atc aag        690
Lys Trp Thr Ala Pro Glu Ser Leu Ala Tyr Asn Lys Phe Ser Ile Lys
                190                 195                 200 tcc gac gtc tgg gca ttt gga gta ttg ctt tgg gaa att gct acc tat        738
Ser Asp Val Trp Ala Phe Gly Val Leu Leu Trp Glu Ile Ala Thr Tyr
            205                 210                 215 ggc atg tcc cct tac ccg gga att gac ctg tcc cag gtg tat gag ctg        786
Gly Met Ser Pro Tyr Pro Gly Ile Asp Leu Ser Gln Val Tyr Glu Leu
        220                 225                 230 cta gag aag gac tac cgc atg gag cgc cca gaa ggc tgc cca gag aag        834
Leu Glu Lys Asp Tyr Arg Met Glu Arg Pro Glu Gly Cys Pro Glu Lys
    235                 240                 245 gtc tat gaa ctc atg cga gca tgt tgg cag tgg aat ccc tct gac cgg        882
Val Tyr Glu Leu Met Arg Ala Cys Trp Gln Trp Asn Pro Ser Asp Arg
250             255                 260                 265 ccc tcc ttt gct gaa atc cac caa gcc ttt gaa aca atg ttc cag gaa        930
Pro Ser Phe Ala Glu Ile His Gln Ala Phe Glu Thr Met Phe Gln Glu
                270                 275                 280 tcc agt atc tca gac gaa gtg gaa aag gag ctg ggg aaa caa ggc gtc        978
Ser Ser Ile Ser Asp Glu Val Glu Lys Glu Leu Gly Lys Gln Gly Val
            285                 290                 295 tgagtcgac                                                              987
```

<210> SEQ ID NO 4
<211> LENGTH: 297
<212> TYPE: PRT
<213> ORGANISM: Artificial Sequence
<220> FEATURE:
<223> OTHER INFORMATION: Description of Artificial Sequence: Synthetic
      Plasmid

<400> SEQUENCE: 4

```
Met Gly His His His His His Gly Val Ser Pro Asn Tyr Asp Lys
 1               5                  10                  15

Trp Glu Met Glu Arg Thr Asp Ile Thr Met Lys His Lys Leu Gly Gly
            20                  25                  30

Gly Gln Tyr Gly Glu Val Tyr Glu Gly Val Trp Lys Lys Tyr Ser Leu
        35                  40                  45

Thr Val Ala Val Lys Thr Leu Lys Glu Asp Thr Met Glu Val Glu Glu
    50                  55                  60

Phe Leu Lys Glu Ala Ala Val Met Lys Glu Ile Lys His Pro Asn Leu
65                  70                  75                  80

Val Gln Leu Leu Gly Val Cys Thr Arg Glu Pro Pro Phe Tyr Ile Ile
                85                  90                  95
```

-continued

```
Thr Glu Phe Met Thr Tyr Gly Asn Leu Leu Asp Tyr Leu Arg Glu Cys
            100                 105                 110
Asn Arg Gln Glu Val Asn Ala Val Leu Leu Tyr Met Ala Thr Gln
        115                 120                 125
Ile Ser Ser Ala Met Glu Tyr Leu Glu Lys Lys Asn Phe Ile His Arg
130                 135                 140
Asp Leu Ala Ala Arg Asn Cys Leu Val Gly Glu Asn His Leu Val Lys
145                 150                 155                 160
Val Ala Asp Phe Gly Leu Ser Arg Leu Met Thr Gly Asp Thr Tyr Thr
                165                 170                 175
Ala His Ala Gly Ala Lys Phe Pro Ile Lys Trp Thr Ala Pro Glu Ser
            180                 185                 190
Leu Ala Tyr Asn Lys Phe Ser Ile Lys Ser Asp Val Trp Ala Phe Gly
        195                 200                 205
Val Leu Leu Trp Glu Ile Ala Thr Tyr Gly Met Ser Pro Tyr Pro Gly
    210                 215                 220
Ile Asp Leu Ser Gln Val Tyr Glu Leu Leu Glu Lys Asp Tyr Arg Met
225                 230                 235                 240
Glu Arg Pro Glu Gly Cys Pro Glu Lys Val Tyr Glu Leu Met Arg Ala
                245                 250                 255
Cys Trp Gln Trp Asn Pro Ser Asp Arg Pro Ser Phe Ala Glu Ile His
            260                 265                 270
Gln Ala Phe Glu Thr Met Phe Gln Glu Ser Ser Ile Ser Asp Glu Val
        275                 280                 285
Glu Lys Glu Leu Gly Lys Gln Gly Val
    290                 295
```

<210> SEQ ID NO 5
<211> LENGTH: 33
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 5
acgggaccat atggatgatt gggagattcc tga                                  33

<210> SEQ ID NO 6
<211> LENGTH: 33
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 6
cactggtcga ctattttggc aatgagcggg cca                                  33

<210> SEQ ID NO 7
<211> LENGTH: 29
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 7
ggtctagcta cagaaaaatc tcgatggag                                       29

```
<210> SEQ ID NO 8
<211> LENGTH: 29
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 8
ctccatcgag attttctgt agctagacc                                              29

<210> SEQ ID NO 9
<211> LENGTH: 1006
<212> TYPE: DNA
<213> ORGANISM: Artificial Sequence
<220> FEATURE:
<223> OTHER INFORMATION: Description of Artificial Sequence: Synthetic
      Plasmid
<220> FEATURE:
<221> NAME/KEY: CDS
<222> LOCATION: (56)..(961)

<400> SEQUENCE: 9
tattccggat tattcatacc gtcccaccat cgggcgcgga tctcggtccg aaacc atg          58
                                                                Met
                                                                  1 tcg tac tac cat cac cat cac cat cac gat tac gat atc cca acg acc         106
Ser Tyr Tyr His His His His His His Asp Tyr Asp Ile Pro Thr Thr
              5                  10                  15 gaa aac ctg tat ttt cag ggc cat atg gat gat tgg gag att cct gat         154
Glu Asn Leu Tyr Phe Gln Gly His Met Asp Asp Trp Glu Ile Pro Asp
         20                  25                  30 ggg cag att aca gtg gga caa aga att gga tct gga tca ttt gga aca         202
Gly Gln Ile Thr Val Gly Gln Arg Ile Gly Ser Gly Ser Phe Gly Thr
     35                  40                  45 gtc tac aag gga aag tgg cat ggt gat gtg gca gtg aaa atg ttg aat         250
Val Tyr Lys Gly Lys Trp His Gly Asp Val Ala Val Lys Met Leu Asn
 50                  55                  60                  65 gtg aca gca cct aca cct cag cag tta caa gcc ttc aaa aat gaa gta         298
Val Thr Ala Pro Thr Pro Gln Gln Leu Gln Ala Phe Lys Asn Glu Val
                 70                  75                  80 gga gta ctc agg aaa aca cga cat gtg aat atc cta ctc ttc atg ggc         346
Gly Val Leu Arg Lys Thr Arg His Val Asn Ile Leu Leu Phe Met Gly
             85                  90                  95 tat tcc aca aag cca caa ctg gct att gtt acc cag tgg tgt gag ggc         394
Tyr Ser Thr Lys Pro Gln Leu Ala Ile Val Thr Gln Trp Cys Glu Gly
        100                 105                 110 tcc agc ttg tat cac cat ctc cat atc att gag acc aaa ttt gag atg         442
Ser Ser Leu Tyr His His Leu His Ile Ile Glu Thr Lys Phe Glu Met
    115                 120                 125 atc aaa ctt ata gat att gca cga cag act gca cag ggc atg gat tac         490
Ile Lys Leu Ile Asp Ile Ala Arg Gln Thr Ala Gln Gly Met Asp Tyr
130                 135                 140                 145 tta cac gcc aag tca atc atc cac aga gac ctc aag agt aat aat ata         538
Leu His Ala Lys Ser Ile Ile His Arg Asp Leu Lys Ser Asn Asn Ile
                150                 155                 160 ttt ctt cat gaa gac ctc aca gta aaa ata ggt gat ttt ggt cta gct         586
Phe Leu His Glu Asp Leu Thr Val Lys Ile Gly Asp Phe Gly Leu Ala
            165                 170                 175 aca gaa aaa tct cga tgg agt ggg tcc cat cag ttt gaa cag ttg tct         634
Thr Glu Lys Ser Arg Trp Ser Gly Ser His Gln Phe Glu Gln Leu Ser
        180                 185                 190 gga tcc att ttg tgg atg gca cca gaa gtc atc aga atg caa gat aaa         682
Gly Ser Ile Leu Trp Met Ala Pro Glu Val Ile Arg Met Gln Asp Lys
```

-continued

```
                      195                 200                 205
aat cca tac agc ttt cag tca gat gta tat gca ttt gga att gtt ctg     730
Asn Pro Tyr Ser Phe Gln Ser Asp Val Tyr Ala Phe Gly Ile Val Leu
210                 215                 220                 225 tat gaa ttg atg act gga cag tta cct tat tca aac atc aac aac agg     778
Tyr Glu Leu Met Thr Gly Gln Leu Pro Tyr Ser Asn Ile Asn Asn Arg
                230                 235                 240 gac cag ata att ttt atg gtg gga cga gga tac ctg tct cca gat ctc     826
Asp Gln Ile Ile Phe Met Val Gly Arg Gly Tyr Leu Ser Pro Asp Leu
            245                 250                 255 agt aag gta cgg agt aac tgt cca aaa gcc atg aag aga tta atg gca     874
Ser Lys Val Arg Ser Asn Cys Pro Lys Ala Met Lys Arg Leu Met Ala
        260                 265                 270 gag tgc ctc aaa aag aaa aga gat gag aga cca ctc ttt ccc caa att     922
Glu Cys Leu Lys Lys Lys Arg Asp Glu Arg Pro Leu Phe Pro Gln Ile
275                 280                 285 ctc gcc tct att gag ctg ctg gcc cgc tca ttg cca aaa tagtcgacta      971
Leu Ala Ser Ile Glu Leu Leu Ala Arg Ser Leu Pro Lys
290                 295                 300 gagcctgcag tctcgaggca tgcggtacca agctt                              1006
```

<210> SEQ ID NO 10
<211> LENGTH: 302
<212> TYPE: PRT
<213> ORGANISM: Artificial Sequence
<220> FEATURE:
<223> OTHER INFORMATION: Description of Artificial Sequence: Synthetic
      Plasmid

<400> SEQUENCE: 10

```
Met Ser Tyr Tyr His His His His His His Asp Tyr Asp Ile Pro Thr
 1               5                   10                  15

Thr Glu Asn Leu Tyr Phe Gln Gly His Met Asp Asp Trp Glu Ile Pro
                20                  25                  30

Asp Gly Gln Ile Thr Val Gly Gln Arg Ile Gly Ser Gly Ser Phe Gly
            35                  40                  45

Thr Val Tyr Lys Gly Lys Trp His Gly Asp Val Ala Val Lys Met Leu
        50                  55                  60

Asn Val Thr Ala Pro Thr Pro Gln Gln Leu Gln Ala Phe Lys Asn Glu
65                  70                  75                  80

Val Gly Val Leu Arg Lys Thr Arg His Val Asn Ile Leu Leu Phe Met
                85                  90                  95

Gly Tyr Ser Thr Lys Pro Gln Leu Ala Ile Val Thr Gln Trp Cys Glu
            100                 105                 110

Gly Ser Ser Leu Tyr His His Leu His Ile Ile Glu Thr Lys Phe Glu
        115                 120                 125

Met Ile Lys Leu Ile Asp Ile Ala Arg Gln Thr Ala Gln Gly Met Asp
130                 135                 140

Tyr Leu His Ala Lys Ser Ile Ile His Arg Asp Leu Lys Ser Asn Asn
145                 150                 155                 160

Ile Phe Leu His Glu Asp Leu Thr Val Lys Ile Gly Asp Phe Gly Leu
                165                 170                 175

Ala Thr Glu Lys Ser Arg Trp Ser Gly Ser His Gln Phe Glu Gln Leu
            180                 185                 190

Ser Gly Ser Ile Leu Trp Met Ala Pro Glu Val Ile Arg Met Gln Asp
        195                 200                 205

Lys Asn Pro Tyr Ser Phe Gln Ser Asp Val Tyr Ala Phe Gly Ile Val
210                 215                 220
```

```
Leu Tyr Glu Leu Met Thr Gly Gln Leu Pro Tyr Ser Asn Ile Asn Asn
225                 230                 235                 240

Arg Asp Gln Ile Ile Phe Met Val Gly Arg Gly Tyr Leu Ser Pro Asp
            245                 250                 255

Leu Ser Lys Val Arg Ser Asn Cys Pro Lys Ala Met Lys Arg Leu Met
        260                 265                 270

Ala Glu Cys Leu Lys Lys Lys Arg Asp Glu Arg Pro Leu Phe Pro Gln
    275                 280                 285

Ile Leu Ala Ser Ile Glu Leu Leu Ala Arg Ser Leu Pro Lys
    290                 295                 300

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 11
ggcagcccat atggcggcgg cggcggcggc                                             30

<210> SEQ ID NO 12
<211> LENGTH: 31
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 12
tgtccgtcga catttaagat ctgtatcctg g                                           31

<210> SEQ ID NO 13
<211> LENGTH: 1232
<212> TYPE: DNA
<213> ORGANISM: Artificial Sequence
<220> FEATURE:
<223> OTHER INFORMATION: Description of Artificial Sequence: Synthetic
      Plasmid
<220> FEATURE:
<221> NAME/KEY: CDS
<222> LOCATION: (88)..(1221)

<400> SEQUENCE: 13
taatacgact cactataggg gaattgtgag cggataacaa ttcccctcta gaaataattt            60
tgtttaactt taagaaggag atatacc atg ggc agc agc cat cat cat cat cat          114
                              Met Gly Ser Ser His His His His His
                                1               5 cac agc agc ggc ctg gtg ccg cgc ggc agc cat atg gcg gcg gcg gcg            162
His Ser Ser Gly Leu Val Pro Arg Gly Ser His Met Ala Ala Ala Ala
 10                  15                  20                  25 ggc gcg ggc ccg gag atg gtc cgc ggg cag gtg ttc gac gtg ggg ccg            210
Gly Ala Gly Pro Glu Met Val Arg Gly Gln Val Phe Asp Val Gly Pro
                 30                  35                  40 cgc tac acc aac ctc tcg tac atc ggc gag ggc gcc tac ggc atg gtg            258
Arg Tyr Thr Asn Leu Ser Tyr Ile Gly Glu Gly Ala Tyr Gly Met Val
             45                  50                  55 tgc tct gct tat gat aat gtc aac aaa gtt cga gta gct atc aag aaa            306
Cys Ser Ala Tyr Asp Asn Val Asn Lys Val Arg Val Ala Ile Lys Lys
         60                  65                  70 atc agc ccc ttt gag cac cag acc tac tgc cag aga acc ctg agg gag            354
Ile Ser Pro Phe Glu His Gln Thr Tyr Cys Gln Arg Thr Leu Arg Glu
```

```
                75                  80                  85
ata aaa atc tta ctg cgc ttc aga cat gag aac atc att gga atc aat      402
Ile Lys Ile Leu Leu Arg Phe Arg His Glu Asn Ile Ile Gly Ile Asn
 90                  95                 100                 105 gac att att cga gca cca acc atc gag caa atg aaa gat gta tat ata      450
Asp Ile Ile Arg Ala Pro Thr Ile Glu Gln Met Lys Asp Val Tyr Ile
                110                 115                 120 gta cag gac ctc atg gaa aca gat ctt tac aag ctc ttg aag aca caa      498
Val Gln Asp Leu Met Glu Thr Asp Leu Tyr Lys Leu Leu Lys Thr Gln
            125                 130                 135 cac ctc agc aat gac cat atc tgc tat ttt ctc tac cag atc ctc aga      546
His Leu Ser Asn Asp His Ile Cys Tyr Phe Leu Tyr Gln Ile Leu Arg
        140                 145                 150 ggg tta aaa tat atc cat tca gct aac gtt ctg cac cgt gac ctc aag      594
Gly Leu Lys Tyr Ile His Ser Ala Asn Val Leu His Arg Asp Leu Lys
    155                 160                 165 cct tcc aac ctg ctg ctc aac acc acc tgt gat ctc aag atc tgt gac      642
Pro Ser Asn Leu Leu Leu Asn Thr Thr Cys Asp Leu Lys Ile Cys Asp
170                 175                 180                 185 ttt ggc ctg gcc cgt gtt gca gat cca gac cat gat cac aca ggg ttc      690
Phe Gly Leu Ala Arg Val Ala Asp Pro Asp His Asp His Thr Gly Phe
                190                 195                 200 ctg aca gaa tat gtg gcc aca cgt tgg tac agg gct cca gaa att atg      738
Leu Thr Glu Tyr Val Ala Thr Arg Trp Tyr Arg Ala Pro Glu Ile Met
            205                 210                 215 ttg aat tcc aag ggc tac acc aag tcc att gat att tgg tct gta ggc      786
Leu Asn Ser Lys Gly Tyr Thr Lys Ser Ile Asp Ile Trp Ser Val Gly
        220                 225                 230 tgc att ctg gca gaa atg ctt tct aac agg ccc atc ttt cca ggg aag      834
Cys Ile Leu Ala Glu Met Leu Ser Asn Arg Pro Ile Phe Pro Gly Lys
    235                 240                 245 cat tat ctt gac cag ctg aac cac att ttg ggt att ctt gga tcc cca      882
His Tyr Leu Asp Gln Leu Asn His Ile Leu Gly Ile Leu Gly Ser Pro
250                 255                 260                 265 tca caa gaa gac ctg aat tgt ata ata aat tta aaa gct agg aac tat      930
Ser Gln Glu Asp Leu Asn Cys Ile Ile Asn Leu Lys Ala Arg Asn Tyr
                270                 275                 280 ttg ctt tct ctt cca cac aaa aat aag gtg cca tgg aac agg ctg ttc      978
Leu Leu Ser Leu Pro His Lys Asn Lys Val Pro Trp Asn Arg Leu Phe
            285                 290                 295 cca aat gct gac tcc aaa gct ctg gac tta ttg gac aaa atg ttg aca     1026
Pro Asn Ala Asp Ser Lys Ala Leu Asp Leu Leu Asp Lys Met Leu Thr
        300                 305                 310 ttc aac cca cac aag agg att gaa gta gaa cag gct ctg gcc cac cca     1074
Phe Asn Pro His Lys Arg Ile Glu Val Glu Gln Ala Leu Ala His Pro
    315                 320                 325 tat ctg gag cag tat tac gac ccg agt gac gag ccc atc gcc gaa gca     1122
Tyr Leu Glu Gln Tyr Tyr Asp Pro Ser Asp Glu Pro Ile Ala Glu Ala
330                 335                 340                 345 cca ttc aag ttc gac atg gaa ttg gat gac ttg cct aag gaa aag ctc     1170
Pro Phe Lys Phe Asp Met Glu Leu Asp Asp Leu Pro Lys Glu Lys Leu
                350                 355                 360 aaa gaa cta att ttt gaa gag act gct aga ttc cag cca gga tac aga     1218
Lys Glu Leu Ile Phe Glu Glu Thr Ala Arg Phe Gln Pro Gly Tyr Arg
            365                 370                 375 tct taaatgtcga c                                                    1232
Ser

<210> SEQ ID NO 14
<211> LENGTH: 378
```

```
<212> TYPE: PRT
<213> ORGANISM: Artificial Sequence
<220> FEATURE:
<223> OTHER INFORMATION: Description of Artificial Sequence: Synthetic
      Plasmid

<400> SEQUENCE: 14

Met Gly Ser Ser His His His His His His Ser Ser Gly Leu Val Pro
1               5                   10                  15

Arg Gly Ser His Met Ala Ala Ala Gly Ala Gly Pro Glu Met Val
            20                  25                  30

Arg Gly Gln Val Phe Asp Val Gly Pro Arg Tyr Thr Asn Leu Ser Tyr
        35                  40                  45

Ile Gly Glu Gly Ala Tyr Gly Met Val Cys Ser Ala Tyr Asp Asn Val
    50                  55                  60

Asn Lys Val Arg Val Ala Ile Lys Lys Ile Ser Pro Phe Glu His Gln
65                  70                  75                  80

Thr Tyr Cys Gln Arg Thr Leu Arg Glu Ile Lys Ile Leu Leu Arg Phe
            85                  90                  95

Arg His Glu Asn Ile Ile Gly Ile Asn Asp Ile Ile Arg Ala Pro Thr
        100                 105                 110

Ile Glu Gln Met Lys Asp Val Tyr Ile Val Gln Asp Leu Met Glu Thr
    115                 120                 125

Asp Leu Tyr Lys Leu Leu Lys Thr Gln His Leu Ser Asn Asp His Ile
130                 135                 140

Cys Tyr Phe Leu Tyr Gln Ile Leu Arg Gly Leu Lys Tyr Ile His Ser
145                 150                 155                 160

Ala Asn Val Leu His Arg Asp Leu Lys Pro Ser Asn Leu Leu Leu Asn
            165                 170                 175

Thr Thr Cys Asp Leu Lys Ile Cys Asp Phe Gly Leu Ala Arg Val Ala
        180                 185                 190

Asp Pro Asp His Asp His Thr Gly Phe Leu Thr Glu Tyr Val Ala Thr
    195                 200                 205

Arg Trp Tyr Arg Ala Pro Glu Ile Met Leu Asn Ser Lys Gly Tyr Thr
210                 215                 220

Lys Ser Ile Asp Ile Trp Ser Val Gly Cys Ile Leu Ala Glu Met Leu
225                 230                 235                 240

Ser Asn Arg Pro Ile Phe Pro Gly Lys His Tyr Leu Asp Gln Leu Asn
            245                 250                 255

His Ile Leu Gly Ile Leu Gly Ser Pro Ser Gln Glu Asp Leu Asn Cys
        260                 265                 270

Ile Ile Asn Leu Lys Ala Arg Asn Tyr Leu Leu Ser Leu Pro His Lys
    275                 280                 285

Asn Lys Val Pro Trp Asn Arg Leu Phe Pro Asn Ala Asp Ser Lys Ala
290                 295                 300

Leu Asp Leu Leu Asp Lys Met Leu Thr Phe Asn Pro His Lys Arg Ile
305                 310                 315                 320

Glu Val Glu Gln Ala Leu Ala His Pro Tyr Leu Glu Gln Tyr Tyr Asp
            325                 330                 335

Pro Ser Asp Glu Pro Ile Ala Glu Ala Pro Phe Lys Phe Asp Met Glu
        340                 345                 350

Leu Asp Asp Leu Pro Lys Glu Lys Leu Lys Glu Leu Ile Phe Glu Glu
    355                 360                 365

Thr Ala Arg Phe Gln Pro Gly Tyr Arg Ser
370                 375
```

-continued

<210> SEQ ID NO 15
<211> LENGTH: 32
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 15
gctggatcca ccagggatta tgagattcaa ag                                    32

<210> SEQ ID NO 16
<211> LENGTH: 34
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 16
gttcttgtcg actactgagc cttctcttcc tcca                                  34

<210> SEQ ID NO 17
<211> LENGTH: 1066
<212> TYPE: DNA
<213> ORGANISM: Artificial Sequence
<220> FEATURE:
<223> OTHER INFORMATION: Description of Artificial Sequence: Synthetic
      Plasmid
<220> FEATURE:
<221> NAME/KEY: CDS
<222> LOCATION: (56)..(964)
<220> FEATURE:
<221> NAME/KEY: CDS
<222> LOCATION: (968)..(1051)

<400> SEQUENCE: 17

```
tattccggat tattcatacc gtcccaccat cgggcgcgga tctcggtccg aaacc atg        58
                                                              Met
                                                                1 tcg tac tac cat cac cat cac cat cac gat tac gat atc cca acg acc       106
Ser Tyr Tyr His His His His His His Asp Tyr Asp Ile Pro Thr Thr
          5                  10                  15 gaa aac ctg tat ttt cag ggc gcc atg gga tcc acc agg gat tat gag       154
Glu Asn Leu Tyr Phe Gln Gly Ala Met Gly Ser Thr Arg Asp Tyr Glu
     20                  25                  30 att caa aga gaa aga ata gaa ctt gga cga tgt att gga gaa ggc caa       202
Ile Gln Arg Glu Arg Ile Glu Leu Gly Arg Cys Ile Gly Glu Gly Gln
 35                  40                  45 ttt gga gat gta cat caa ggc att tat atg agt cca gag aat cca gct       250
Phe Gly Asp Val His Gln Gly Ile Tyr Met Ser Pro Glu Asn Pro Ala
 50                  55                  60                  65 ttg gcg gtt gca att aaa aca tgt aaa aac tgt act tcg gac agc gtg       298
Leu Ala Val Ala Ile Lys Thr Cys Lys Asn Cys Thr Ser Asp Ser Val
                 70                  75                  80 aga gag aaa ttt ctt caa gaa gcc tta aca atg cgt cag ttt gac cat       346
Arg Glu Lys Phe Leu Gln Glu Ala Leu Thr Met Arg Gln Phe Asp His
             85                  90                  95 cct cat att gtg aag ctg att gga gtc atc aca gag aat cct gtc tgg       394
Pro His Ile Val Lys Leu Ile Gly Val Ile Thr Glu Asn Pro Val Trp
        100                 105                 110 ata atc atg gag ctg tgc aca ctt gga gag ctg agg tca ttt ctg caa       442
Ile Ile Met Glu Leu Cys Thr Leu Gly Glu Leu Arg Ser Phe Leu Gln
    115                 120                 125 gta agg aaa tac agt ttg gat cta gca tct ttg atc ctg tat gcc tat       490
```

| | | | | | | | | | | | | | | |
|---|---|---|---|---|---|---|---|---|---|---|---|---|---|---|
|Val|Arg|Lys|Tyr|Ser|Leu|Asp|Leu|Ala|Ser|Leu|Ile|Leu|Tyr|Ala|Tyr|
|130| | | | |135| | | | |140| | | |145|

```
cag ctt agt aca gct ctt gca tat cta gag agc aaa aga ttt gta cac      538
Gln Leu Ser Thr Ala Leu Ala Tyr Leu Glu Ser Lys Arg Phe Val His
            150                 155                 160 agg gac att gct gct cgg aat gtt ctg gtg tcc tca aat gat tgt gta      586
Arg Asp Ile Ala Ala Arg Asn Val Leu Val Ser Ser Asn Asp Cys Val
            165                 170                 175 aaa tta gga gac ttt gga tta tcc cga tat atg gaa gat agt act tac      634
Lys Leu Gly Asp Phe Gly Leu Ser Arg Tyr Met Glu Asp Ser Thr Tyr
            180                 185                 190 tac aaa gct tcc aaa gga aaa ttg cct att aaa tgg atg gct cca gag      682
Tyr Lys Ala Ser Lys Gly Lys Leu Pro Ile Lys Trp Met Ala Pro Glu
195                 200                 205 tca atc aat ttt cga cgt ttt acc tca gct agt gac gta tgg atg ttt      730
Ser Ile Asn Phe Arg Arg Phe Thr Ser Ala Ser Asp Val Trp Met Phe
210                 215                 220                 225 ggt gtg tgt atg tgg gag ata ctg atg cat ggt gtg aag cct ttt caa      778
Gly Val Cys Met Trp Glu Ile Leu Met His Gly Val Lys Pro Phe Gln
            230                 235                 240 gga gtg aag aac aat gat gta atc ggt cga att gaa aat ggg gaa aga      826
Gly Val Lys Asn Asn Asp Val Ile Gly Arg Ile Glu Asn Gly Glu Arg
            245                 250                 255 tta cca atg cct cca aat tgt cct cct acc ctc tac agc ctt atg acg      874
Leu Pro Met Pro Pro Asn Cys Pro Pro Thr Leu Tyr Ser Leu Met Thr
            260                 265                 270 aaa tgc tgg gcc tat gac ccc agc agg cgg ccc agg ttt act gaa ctt      922
Lys Cys Trp Ala Tyr Asp Pro Ser Arg Arg Pro Arg Phe Thr Glu Leu
275                 280                 285 aaa gct cag ctc agc aca atc ctg gag gaa gag aag gct cag tag tcg      970
Lys Ala Gln Leu Ser Thr Ile Leu Glu Glu Glu Lys Ala Gln     Ser
290                 295                 300 acg agc tca cta gtc gcg gcc gct ttc gaa tct aga gcc tgc agt ctc     1018
Thr Ser Ser Leu Val Ala Ala Ala Phe Glu Ser Arg Ala Cys Ser Leu
305                 310                 315                 320 gag gca tgc ggt acc aag ctt gtc gag aag tac tagaggatca taatc        1066
Glu Ala Cys Gly Thr Lys Leu Val Glu Lys Tyr
            325                 330

<210> SEQ ID NO 18
<211> LENGTH: 331
<212> TYPE: PRT
<213> ORGANISM: Artificial Sequence
<220> FEATURE:
<223> OTHER INFORMATION: Description of Artificial Sequence: Synthetic
      Plasmid

<400> SEQUENCE: 18

Met Ser Tyr Tyr His His His His His His Asp Tyr Asp Ile Pro Thr
 1                   5                  10                  15

Thr Glu Asn Leu Tyr Phe Gln Gly Ala Met Gly Ser Thr Arg Asp Tyr
                20                  25                  30

Glu Ile Gln Arg Glu Arg Ile Glu Leu Gly Arg Cys Ile Gly Glu Gly
            35                  40                  45

Gln Phe Gly Asp Val His Gln Gly Ile Tyr Met Ser Pro Glu Asn Pro
        50                  55                  60

Ala Leu Ala Val Ala Ile Lys Thr Cys Lys Asn Cys Thr Ser Asp Ser
65                  70                  75                  80

Val Arg Glu Lys Phe Leu Gln Glu Ala Leu Thr Met Arg Gln Phe Asp
                85                  90                  95
```

His Pro His Ile Val Lys Leu Ile Gly Val Ile Thr Glu Asn Pro Val
                100                 105                 110

Trp Ile Ile Met Glu Leu Cys Thr Leu Gly Glu Leu Arg Ser Phe Leu
            115                 120                 125

Gln Val Arg Lys Tyr Ser Leu Asp Leu Ala Ser Leu Ile Leu Tyr Ala
    130                 135                 140

Tyr Gln Leu Ser Thr Ala Leu Ala Tyr Leu Glu Ser Lys Arg Phe Val
145                 150                 155                 160

His Arg Asp Ile Ala Ala Arg Asn Val Leu Val Ser Ser Asn Asp Cys
                165                 170                 175

Val Lys Leu Gly Asp Phe Gly Leu Ser Arg Tyr Met Glu Asp Ser Thr
            180                 185                 190

Tyr Tyr Lys Ala Ser Lys Gly Lys Leu Pro Ile Lys Trp Met Ala Pro
    195                 200                 205

Glu Ser Ile Asn Phe Arg Arg Phe Thr Ser Ala Ser Asp Val Trp Met
210                 215                 220

Phe Gly Val Cys Met Trp Glu Ile Leu Met His Gly Val Lys Pro Phe
225                 230                 235                 240

Gln Gly Val Lys Asn Asn Asp Val Ile Gly Arg Ile Glu Asn Gly Glu
            245                 250                 255

Arg Leu Pro Met Pro Pro Asn Cys Pro Pro Thr Leu Tyr Ser Leu Met
                260                 265                 270

Thr Lys Cys Trp Ala Tyr Asp Pro Ser Arg Arg Pro Arg Phe Thr Glu
            275                 280                 285

Leu Lys Ala Gln Leu Ser Thr Ile Leu Glu Glu Glu Lys Ala Gln Ser
    290                 295                 300

Thr Ser Ser Leu Val Ala Ala Phe Glu Ser Arg Ala Cys Ser Leu
305                 310                 315                 320

Glu Ala Cys Gly Thr Lys Leu Val Glu Lys Tyr
                325                 330

<210> SEQ ID NO 19
<211> LENGTH: 33
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 19
gactcctcat atggcagggg tctctgagta tga                                33

<210> SEQ ID NO 20
<211> LENGTH: 34
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 20
caggtcgtcg actactcctg gttggaggtc aagg                               34

<210> SEQ ID NO 21
<211> LENGTH: 28
<212> TYPE: DNA
<213> ORGANISM: Artificial Sequence
<220> FEATURE:
<223> OTHER INFORMATION: Description of Artificial Sequence: Synthetic
      Primer -continued

```
<400> SEQUENCE: 21
ctgggagagg gcgcgtttgg gcaggtgg                                              28

<210> SEQ ID NO 22
<211> LENGTH: 28
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 22
ccacctgccc aaacgcgccc tctcccag                                              28

<210> SEQ ID NO 23
<211> LENGTH: 29
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 23
cagggctgga atacagctac aaccccagc                                             29

<210> SEQ ID NO 24
<211> LENGTH: 29
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 24
gctggggttg tagctgtatt ccagccctg                                             29

<210> SEQ ID NO 25
<211> LENGTH: 1061
<212> TYPE: DNA
<213> ORGANISM: Artificial Sequence
<220> FEATURE:
<223> OTHER INFORMATION: Description of Artificial Sequence: Synthetic
      Plasmid
<220> FEATURE:
<221> NAME/KEY: CDS
<222> LOCATION: (88)..(1038)

<400> SEQUENCE: 25
taatacgact cactataggg gaattgtgag cggataacaa ttcccctcta gaaataattt           60
tgtttaactt taagaaggag atatacc atg ggt cac cac cat cac cat cat atg          114
                                Met Gly His His His His His His Met
                                  1               5 gca ggg gtc tct gag tat gag ctt ccc gaa gac cct cgc tgg gag ctg            162
Ala Gly Val Ser Glu Tyr Glu Leu Pro Glu Asp Pro Arg Trp Glu Leu
 10                  15                  20                  25 cct cgg gac aga ctg gtc tta ggc aaa ccc ctg gga gag ggc gcg ttt            210
Pro Arg Asp Arg Leu Val Leu Gly Lys Pro Leu Gly Glu Gly Ala Phe
                 30                  35                  40 ggg cag gtg gtg ttg gca gag gct atc ggg ctg gac aag gac aaa ccc            258
Gly Gln Val Val Leu Ala Glu Ala Ile Gly Leu Asp Lys Asp Lys Pro
             45                  50                  55 aac cgt gtg acc aaa gtg gct gtg aag atg ttg aag tcg gac gca aca            306
Asn Arg Val Thr Lys Val Ala Val Lys Met Leu Lys Ser Asp Ala Thr
         60                  65                  70 gag aaa gac ttg tca gac ctg atc tca gaa atg gag atg atg aag atg            354
```

```
Glu Lys Asp Leu Ser Asp Leu Ile Ser Glu Met Glu Met Met Lys Met
 75                  80                  85 atc ggg aag cat aag aat atc atc aac ctg ctg ggg gcc tgc acg cag      402
Ile Gly Lys His Lys Asn Ile Ile Asn Leu Leu Gly Ala Cys Thr Gln
 90                  95                 100                 105 gat ggt ccc ttg tat gtc atc gtg gag tat gcc tcc aag ggc aac ctg      450
Asp Gly Pro Leu Tyr Val Ile Val Glu Tyr Ala Ser Lys Gly Asn Leu
                    110                 115                 120 cgg gag tac ctg cag gcc cgg agg ccc cca ggg ctg gaa tac agc tac      498
Arg Glu Tyr Leu Gln Ala Arg Arg Pro Pro Gly Leu Glu Tyr Ser Tyr
                125                 130                 135 aac ccc agc cac aac cca gag gag cag ctc tcc tcc aag gac ctg gtg      546
Asn Pro Ser His Asn Pro Glu Glu Gln Leu Ser Ser Lys Asp Leu Val
            140                 145                 150 tcc tgc gcc tac cag gtg gcc cga ggc atg gag tat ctg gcc tcc aag      594
Ser Cys Ala Tyr Gln Val Ala Arg Gly Met Glu Tyr Leu Ala Ser Lys
        155                 160                 165 aag tgc ata cac cga gac ctg gca gcc agg aat gtc ctg gtg aca gag      642
Lys Cys Ile His Arg Asp Leu Ala Ala Arg Asn Val Leu Val Thr Glu
170                 175                 180                 185 gac aat gtg atg aag ata gca gac ttt ggc ctc gca cgg gac att cac      690
Asp Asn Val Met Lys Ile Ala Asp Phe Gly Leu Ala Arg Asp Ile His
                190                 195                 200 cac atc gac tac tat aaa aag aca acc aac ggc cga ctg cct gtg aag      738
His Ile Asp Tyr Tyr Lys Lys Thr Thr Asn Gly Arg Leu Pro Val Lys
            205                 210                 215 tgg atg gca ccc gag gca tta ttt gac cgg atc tac acc cac cag agt      786
Trp Met Ala Pro Glu Ala Leu Phe Asp Arg Ile Tyr Thr His Gln Ser
        220                 225                 230 gat gtg tgg tct ttc ggg gtg ctc ctg tgg gag atc ttc act ctg ggc      834
Asp Val Trp Ser Phe Gly Val Leu Leu Trp Glu Ile Phe Thr Leu Gly
235                 240                 245 ggc tcc cca tac ccc ggt gtg cct gtg gag gaa ctt ttc aag ctg ctg      882
Gly Ser Pro Tyr Pro Gly Val Pro Val Glu Glu Leu Phe Lys Leu Leu
250                 255                 260                 265 aag gag ggt cac cgc atg gac aag ccc agt aac tgc acc aac gag ctg      930
Lys Glu Gly His Arg Met Asp Lys Pro Ser Asn Cys Thr Asn Glu Leu
                270                 275                 280 tac atg atg atg cgg gac tgc tgg cat gca gtg ccc tca cag aga ccc      978
Tyr Met Met Met Arg Asp Cys Trp His Ala Val Pro Ser Gln Arg Pro
            285                 290                 295 acc ttc aag cag ctg gtg gaa gac ctg gac cgc atc gtg gcc ttg acc     1026
Thr Phe Lys Gln Leu Val Glu Asp Leu Asp Arg Ile Val Ala Leu Thr
        300                 305                 310 tcc aac cag gag tagtcgacga aggagatata tcc                          1061
Ser Asn Gln Glu
    315

<210> SEQ ID NO 26
<211> LENGTH: 317
<212> TYPE: PRT
<213> ORGANISM: Artificial Sequence
<220> FEATURE:
<223> OTHER INFORMATION: Description of Artificial Sequence: Synthetic
      Plasmid

<400> SEQUENCE: 26

Met Gly His His His His His His Met Ala Gly Val Ser Glu Tyr Glu
 1               5                  10                  15

Leu Pro Glu Asp Pro Arg Trp Glu Leu Pro Arg Asp Arg Leu Val Leu
            20                  25                  30
```

```
Gly Lys Pro Leu Gly Glu Gly Ala Phe Gly Gln Val Val Leu Ala Glu
         35                  40                  45
Ala Ile Gly Leu Asp Lys Asp Lys Pro Asn Arg Val Thr Lys Val Ala
     50                  55                  60
Val Lys Met Leu Lys Ser Asp Ala Thr Glu Lys Asp Leu Ser Asp Leu
 65                  70                  75                  80
Ile Ser Glu Met Glu Met Met Lys Met Ile Gly Lys His Lys Asn Ile
                 85                  90                  95
Ile Asn Leu Leu Gly Ala Cys Thr Gln Asp Gly Pro Leu Tyr Val Ile
            100                 105                 110
Val Glu Tyr Ala Ser Lys Gly Asn Leu Arg Glu Tyr Leu Gln Ala Arg
        115                 120                 125
Arg Pro Pro Gly Leu Glu Tyr Ser Tyr Asn Pro Ser His Asn Pro Glu
    130                 135                 140
Glu Gln Leu Ser Ser Lys Asp Leu Val Ser Cys Ala Tyr Gln Val Ala
145                 150                 155                 160
Arg Gly Met Glu Tyr Leu Ala Ser Lys Lys Cys Ile His Arg Asp Leu
                165                 170                 175
Ala Ala Arg Asn Val Leu Val Thr Glu Asp Asn Val Met Lys Ile Ala
            180                 185                 190
Asp Phe Gly Leu Ala Arg Asp Ile His His Ile Asp Tyr Tyr Lys Lys
        195                 200                 205
Thr Thr Asn Gly Arg Leu Pro Val Lys Trp Met Ala Pro Glu Ala Leu
    210                 215                 220
Phe Asp Arg Ile Tyr Thr His Gln Ser Asp Val Trp Ser Phe Gly Val
225                 230                 235                 240
Leu Leu Trp Glu Ile Phe Thr Leu Gly Gly Ser Pro Tyr Pro Gly Val
                245                 250                 255
Pro Val Glu Glu Leu Phe Lys Leu Leu Lys Glu Gly His Arg Met Asp
            260                 265                 270
Lys Pro Ser Asn Cys Thr Asn Glu Leu Tyr Met Met Met Arg Asp Cys
        275                 280                 285
Trp His Ala Val Pro Ser Gln Arg Pro Thr Phe Lys Gln Leu Val Glu
    290                 295                 300
Asp Leu Asp Arg Ile Val Ala Leu Thr Ser Asn Gln Glu
305                 310                 315

<210> SEQ ID NO 27
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 27
atcaattcat atggacccag atgaagttcc                                       30

<210> SEQ ID NO 28
<211> LENGTH: 34
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 28
atgtagtcga cctaatcctg ttgtacattt gctt                                  34
```

```
<210> SEQ ID NO 29
<211> LENGTH: 1353
<212> TYPE: DNA
<213> ORGANISM: Artificial Sequence
<220> FEATURE:
<223> OTHER INFORMATION: Description of Artificial Sequence: Synthetic
      Plasmid
<220> FEATURE:
<221> NAME/KEY: CDS
<222> LOCATION: (88)..(1212)

<400> SEQUENCE: 29
taatacgact cactataggg gaattgtgag cggataacaa ttcccctcta gaaataattt      60
tgtttaactt taagaaggag atatacc atg ggt cac cac cat cac cat cat atg    114
                                Met Gly His His His His His His Met
                                 1               5 gac cca gat gaa gtt cct ttg gat gag cag tgt gag cgg ctc cct tat      162
Asp Pro Asp Glu Val Pro Leu Asp Glu Gln Cys Glu Arg Leu Pro Tyr
 10              15                  20                  25 gat gcc agc aag tgg gag ttt gcc cgg gag aga ctt aaa ctg ggc aaa      210
Asp Ala Ser Lys Trp Glu Phe Ala Arg Glu Arg Leu Lys Leu Gly Lys
             30                  35                  40 tca ctt gga aga ggg gct ttt gga aaa gtg gtt caa gca tca gca ttt      258
Ser Leu Gly Arg Gly Ala Phe Gly Lys Val Val Gln Ala Ser Ala Phe
         45                  50                  55 ggc att aag aaa tca cct acg tgc cgg act gtg gct gtg aaa atg ctg      306
Gly Ile Lys Lys Ser Pro Thr Cys Arg Thr Val Ala Val Lys Met Leu
     60                  65                  70 aaa gag ggg gcc acg gcc agc gag tac aaa gct ctg atg act gag cta      354
Lys Glu Gly Ala Thr Ala Ser Glu Tyr Lys Ala Leu Met Thr Glu Leu
 75                  80                  85 aaa atc ttg acc cac att ggc cac cat ctg aac gtg gtt aac ctg ctg      402
Lys Ile Leu Thr His Ile Gly His His Leu Asn Val Val Asn Leu Leu
 90                  95                 100                 105 gga gcc tgc acc aag caa gga ggg cct ctg atg gtg att gtt gaa tac      450
Gly Ala Cys Thr Lys Gln Gly Gly Pro Leu Met Val Ile Val Glu Tyr
             110                 115                 120 tgc aaa tat gga aat ctc tcc aac tac ctc aag agc aaa cgt gac tta      498
Cys Lys Tyr Gly Asn Leu Ser Asn Tyr Leu Lys Ser Lys Arg Asp Leu
         125                 130                 135 ttt ttt ctc aac aag gat gca gca cta cac atg gag cct aag aaa gaa      546
Phe Phe Leu Asn Lys Asp Ala Ala Leu His Met Glu Pro Lys Lys Glu
     140                 145                 150 aaa atg gag cca ggc ctg gaa caa ggc aag aaa cca aga cta gat agc      594
Lys Met Glu Pro Gly Leu Glu Gln Gly Lys Lys Pro Arg Leu Asp Ser
155                 160                 165 gtc acc agc agc gaa agc ttt gcg agc tcc ggc ttt cag gaa gat aaa      642
Val Thr Ser Ser Glu Ser Phe Ala Ser Ser Gly Phe Gln Glu Asp Lys
170                 175                 180                 185 agt ctg agt gat gtt gag gaa gag gag gat tct gac ggt ttc tac aag      690
Ser Leu Ser Asp Val Glu Glu Glu Glu Asp Ser Asp Gly Phe Tyr Lys
                 190                 195                 200 gag ccc atc act atg gaa gat ctg att tct tac agt ttt caa gtg gcc      738
Glu Pro Ile Thr Met Glu Asp Leu Ile Ser Tyr Ser Phe Gln Val Ala
             205                 210                 215 aga ggc atg gag ttc ctg tct tcc aga aag tgc att cat cgg gac ctg      786
Arg Gly Met Glu Phe Leu Ser Ser Arg Lys Cys Ile His Arg Asp Leu
         220                 225                 230 gca gcg aga aac att ctt tta tct gag aac aac gtg gtg aag att tgt      834
Ala Ala Arg Asn Ile Leu Leu Ser Glu Asn Asn Val Val Lys Ile Cys
     235                 240                 245
```

```
gat ttt ggc ctt gcc cgg gat att tat aag aac ccc gat tat gtg aga       882
Asp Phe Gly Leu Ala Arg Asp Ile Tyr Lys Asn Pro Asp Tyr Val Arg
250                 255                 260                 265 aaa gga gat act cga ctt cct ctg aaa tgg atg gct ccc gaa tct atc       930
Lys Gly Asp Thr Arg Leu Pro Leu Lys Trp Met Ala Pro Glu Ser Ile
            270                 275                 280 ttt gac aaa atc tac agc acc aag agc gac gtg tgg tct tac gga gta       978
Phe Asp Lys Ile Tyr Ser Thr Lys Ser Asp Val Trp Ser Tyr Gly Val
                285                 290                 295 ttg ctg tgg gaa atc ttc tcc tta ggt ggg tct cca tac cca gga gta      1026
Leu Leu Trp Glu Ile Phe Ser Leu Gly Gly Ser Pro Tyr Pro Gly Val
            300                 305                 310 caa atg gat gag gac ttt tgc agt cgc ctg agg gaa ggc atg agg atg      1074
Gln Met Asp Glu Asp Phe Cys Ser Arg Leu Arg Glu Gly Met Arg Met
        315                 320                 325 aga gct cct gag tac tct act cct gaa atc tat cag atc atg ctg gac      1122
Arg Ala Pro Glu Tyr Ser Thr Pro Glu Ile Tyr Gln Ile Met Leu Asp
330                 335                 340                 345 tgc tgg cac aga gac cca aaa gaa agg cca aga ttt gca gaa ctt gtg      1170
Cys Trp His Arg Asp Pro Lys Glu Arg Pro Arg Phe Ala Glu Leu Val
                350                 355                 360 gaa aaa cta ggt gat ttg ctt caa gca aat gta caa cag gat              1212
Glu Lys Leu Gly Asp Leu Leu Gln Ala Asn Val Gln Gln Asp
            365                 370                 375 taggtcgacc accaccacca ccaccactga gatccggctg ccctactgg ccgaaaggaa     1272 ttcgaggcca gcagggccac cgctgagcaa taactagcat aacccctggg ggcctctaaa    1332
cgggtcttga ggggtttttt g                                              1353

<210> SEQ ID NO 30
<211> LENGTH: 375
<212> TYPE: PRT
<213> ORGANISM: Artificial Sequence
<220> FEATURE:
<223> OTHER INFORMATION: Description of Artificial Sequence: Synthetic
      Plasmid

<400> SEQUENCE: 30

Met Gly His His His His His His Met Asp Pro Asp Glu Val Pro Leu
 1               5                  10                  15

Asp Glu Gln Cys Glu Arg Leu Pro Tyr Asp Ala Ser Lys Trp Glu Phe
            20                  25                  30

Ala Arg Glu Arg Leu Lys Leu Gly Lys Ser Leu Gly Arg Gly Ala Phe
        35                  40                  45

Gly Lys Val Val Gln Ala Ser Ala Phe Gly Ile Lys Lys Ser Pro Thr
    50                  55                  60

Cys Arg Thr Val Ala Val Lys Met Leu Lys Glu Gly Ala Thr Ala Ser
65                  70                  75                  80

Glu Tyr Lys Ala Leu Met Thr Glu Leu Lys Ile Leu Thr His Ile Gly
                85                  90                  95

His His Leu Asn Val Val Asn Leu Leu Gly Ala Cys Thr Lys Gln Gly
            100                 105                 110

Gly Pro Leu Met Val Ile Val Glu Tyr Cys Lys Tyr Gly Asn Leu Ser
        115                 120                 125

Asn Tyr Leu Lys Ser Lys Arg Asp Leu Phe Phe Leu Asn Lys Asp Ala
    130                 135                 140

Ala Leu His Met Glu Pro Lys Lys Glu Lys Met Glu Pro Gly Leu Glu
145                 150                 155                 160

Gln Gly Lys Lys Pro Arg Leu Asp Ser Val Thr Ser Ser Glu Ser Phe
```

```
                    165                 170                 175
Ala Ser Ser Gly Phe Gln Glu Asp Lys Ser Leu Ser Asp Val Glu Glu
            180                 185                 190

Glu Glu Asp Ser Asp Gly Phe Tyr Lys Glu Pro Ile Thr Met Glu Asp
            195                 200                 205

Leu Ile Ser Tyr Ser Phe Gln Val Ala Arg Gly Met Glu Phe Leu Ser
            210                 215                 220

Ser Arg Lys Cys Ile His Arg Asp Leu Ala Ala Arg Asn Ile Leu Leu
225                 230                 235                 240

Ser Glu Asn Asn Val Val Lys Ile Cys Asp Phe Gly Leu Ala Arg Asp
                245                 250                 255

Ile Tyr Lys Asn Pro Asp Tyr Val Arg Lys Gly Asp Thr Arg Leu Pro
            260                 265                 270

Leu Lys Trp Met Ala Pro Glu Ser Ile Phe Asp Lys Ile Tyr Ser Thr
            275                 280                 285

Lys Ser Asp Val Trp Ser Tyr Gly Val Leu Leu Trp Glu Ile Phe Ser
290                 295                 300

Leu Gly Gly Ser Pro Tyr Pro Gly Val Gln Met Asp Glu Asp Phe Cys
305                 310                 315                 320

Ser Arg Leu Arg Glu Gly Met Arg Met Arg Ala Pro Glu Tyr Ser Thr
                325                 330                 335

Pro Glu Ile Tyr Gln Ile Met Leu Asp Cys Trp His Arg Asp Pro Lys
            340                 345                 350

Glu Arg Pro Arg Phe Ala Glu Leu Val Glu Lys Leu Gly Asp Leu Leu
            355                 360                 365

Gln Ala Asn Val Gln Gln Asp
            370                 375

<210> SEQ ID NO 31
<211> LENGTH: 41
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 31
atgtacgaag ttcagtggaa agttgttgaa gaaatcaacg g                   41

<210> SEQ ID NO 32
<211> LENGTH: 46
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 32
ggtcgatgta aacgtagttg ttaccgttga tttcttcaac aacttt             46

<210> SEQ ID NO 33
<211> LENGTH: 42
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 33
aacaactacg tttacatcga cccgacccag ctgccgtacg ac                  42
```

```
<210> SEQ ID NO 34
<211> LENGTH: 43
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 34
gttacgcggg aactcccatt tgtggtcgta cggcagctgg gtc                    43

<210> SEQ ID NO 35
<211> LENGTH: 43
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 35
aaatgggagt tcccgcgtaa ccgtctgtct ttcggtaaaa ccc                    43

<210> SEQ ID NO 36
<211> LENGTH: 41
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 36
accgaacgca cccgcaccca gggttttacc gaaagacaga c                      41

<210> SEQ ID NO 37
<211> LENGTH: 43
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 37
ggtgcgggtg cgttcggtaa agttgttgaa gcgaccgcgt acg                    43

<210> SEQ ID NO 38
<211> LENGTH: 41
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 38
gccgcgtcag atttgatcag accgtacgcg gtcgcttcaa c                      41

<210> SEQ ID NO 39
<211> LENGTH: 43
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 39
ctgatcaaat ctgacgcggc gatgaccgtt gcggttaaaa tgc                    43

<210> SEQ ID NO 40
```

```
<211> LENGTH: 43
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 40
gtcaggtgcg cagacggttt cagcatttta accgcaacgg tca                43

<210> SEQ ID NO 41
<211> LENGTH: 43
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 41
aaaccgtctg cgcacctgac cgaacgtgaa gcgctgatgt ctg                43

<210> SEQ ID NO 42
<211> LENGTH: 44
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 42
ccaggtaaga cagaactttc agttcagaca tcagcgcttc acgt               44

<210> SEQ ID NO 43
<211> LENGTH: 44
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 43
ctgaaagttc tgtcttacct gggtaaccac atgaacatcg ttaa               44

<210> SEQ ID NO 44
<211> LENGTH: 41
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 44
ggtgcacgca cccagcaggt taacgatgtt catgtggtta c                  41

<210> SEQ ID NO 45
<211> LENGTH: 43
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 45
ctgctgggtg cgtgcaccat cggtggtccg accctggtta tca                43

<210> SEQ ID NO 46
<211> LENGTH: 43
<212> TYPE: DNA
```

```
<213> ORGANISM: Artificial Sequence
<220> FEATURE:
<223> OTHER INFORMATION: Description of Artificial Sequence: Synthetic
      Primer

<400> SEQUENCE: 46
gtcaccgtag cagcagtatt cggtgataac cagggtcgga cca                    43

<210> SEQ ID NO 47
<211> LENGTH: 43
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 47
gaatactgct gctacggtga cctgctgaac ttcctgcgtc gta                    43

<210> SEQ ID NO 48
<211> LENGTH: 43
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 48
agagcagatg aaagagtcac gtttacgacg caggaagttc agc                    43

<210> SEQ ID NO 49
<211> LENGTH: 43
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 49
cgtgactctt tcatctgctc taaacaggaa gaccacgcgg aag                    43

<210> SEQ ID NO 50
<211> LENGTH: 43
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 50
cagcaggttt ttgtacagcg ccgcttccgc gtggtcttcc tgt                    43

<210> SEQ ID NO 51
<211> LENGTH: 44
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 51
gcgctgtaca aaaacctgct gcactctaaa gaatcttctt gctc                   44

<210> SEQ ID NO 52
<211> LENGTH: 45
<212> TYPE: DNA
<213> ORGANISM: Artificial Sequence
<220> FEATURE:
```

-continued

<223> OTHER INFORMATION: Description of Artificial Sequence: Synthetic
      Primer

<400> SEQUENCE: 52
ccatgtattc gttggtagag tcagagcaag aagattcttt agagt                45

<210> SEQ ID NO 53
<211> LENGTH: 44
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 53
gactctacca acgaatacat ggacatgaaa ccgggtgttt ctta                 44

<210> SEQ ID NO 54
<211> LENGTH: 43
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 54
tccgctttgg tcggaacaac gtaagaaaca cccggtttca tgt                  43

<210> SEQ ID NO 55
<211> LENGTH: 43
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 55
gttgttccga ccaaagcgga caaacgtcgt tctgttcgta tcg                  43

<210> SEQ ID NO 56
<211> LENGTH: 46
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 56
taacgtcacg ttcgatgtaa gaaccgatac gaacagaacg acgttt               46

<210> SEQ ID NO 57
<211> LENGTH: 43
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 57
tcttacatcg aacgtgacgt taccccggcg atcatggaag acg                  43

<210> SEQ ID NO 58
<211> LENGTH: 40
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 58
ccaggtccag cgccagttcg tcgtcttcca tgatcgccgg         40

<210> SEQ ID NO 59
<211> LENGTH: 43
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 59
gaactggcgc tggacctgga agacctgctg tctttctctt acc     43

<210> SEQ ID NO 60
<211> LENGTH: 44
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 60
gaacgccata cctttcgcaa cctggtaaga gaaagacagc aggt    44

<210> SEQ ID NO 61
<211> LENGTH: 44
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 61
gttgcgaaag gtatggcgtt cctggcgtct aaaaactgca tcca    44

<210> SEQ ID NO 62
<211> LENGTH: 39
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 62
cgcgccgcca ggtcacggtg gatgcagttt ttagacgcc          39

<210> SEQ ID NO 63
<211> LENGTH: 41
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 63
cgtgacctgg cggcgcgtaa catcctgctg acccacggtc g       41

<210> SEQ ID NO 64
<211> LENGTH: 43
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 64
accgaagtcg cagattttgg tgatacgacc gtgggtcagc agg    43

<210> SEQ ID NO 65
<211> LENGTH: 43
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 65
accaaaatct gcgacttcgg tctggcgcgt gacatcaaaa acg    43

<210> SEQ ID NO 66
<211> LENGTH: 46
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 66
gttaccttta acaacgtagt tagagtcgtt tttgatgtca cgcgcc    46

<210> SEQ ID NO 67
<211> LENGTH: 44
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 67
tctaactacg ttgttaaagg taacgcgcgt ctgccggtta aatg    44

<210> SEQ ID NO 68
<211> LENGTH: 42
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 68
gaagatagat tccggcgcca tccatttaac cggcagacgc gc    42

<210> SEQ ID NO 69
<211> LENGTH: 44
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 69
atggcgccgg aatctatctt caactgcgtt tacaccttcg aatc    44

<210> SEQ ID NO 70
<211> LENGTH: 43
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 70
gataccgtaa gaccaaacgt cagattcgaa ggtgtaaacg cag    43

<210> SEQ ID NO 71
<211> LENGTH: 43
<212> TYPE: DNA
<213> ORGANISM: Artificial Sequence
<220> FEATURE:
<223> OTHER INFORMATION: Description of Artificial Sequence: Synthetic
    Primer

<400> SEQUENCE: 71
gacgtttggt cttacggtat cttcctgtgg gaactgttct ctc          43

<210> SEQ ID NO 72
<211> LENGTH: 41
<212> TYPE: DNA
<213> ORGANISM: Artificial Sequence
<220> FEATURE:
<223> OTHER INFORMATION: Description of Artificial Sequence: Synthetic
    Primer

<400> SEQUENCE: 72
cctgtgggaa ctgttctctc tgggttcttc tccgtacccg g            41

<210> SEQ ID NO 73
<211> LENGTH: 45
<212> TYPE: DNA
<213> ORGANISM: Artificial Sequence
<220> FEATURE:
<223> OTHER INFORMATION: Description of Artificial Sequence: Synthetic
    Primer

<400> SEQUENCE: 73
ggttcttctc cgtacccggg tatgccggtt gactctaaat tctat        45

<210> SEQ ID NO 74
<211> LENGTH: 45
<212> TYPE: DNA
<213> ORGANISM: Artificial Sequence
<220> FEATURE:
<223> OTHER INFORMATION: Description of Artificial Sequence: Synthetic
    Primer

<400> SEQUENCE: 74
cggaaacctt ctttgatcat tttgtagaat ttagagtcaa ccggc        45

<210> SEQ ID NO 75
<211> LENGTH: 43
<212> TYPE: DNA
<213> ORGANISM: Artificial Sequence
<220> FEATURE:
<223> OTHER INFORMATION: Description of Artificial Sequence: Synthetic
    Primer

<400> SEQUENCE: 75
aaaatgatca agaaggttt ccgtatgctg tctccggaac acg           43

<210> SEQ ID NO 76
<211> LENGTH: 42
<212> TYPE: DNA
<213> ORGANISM: Artificial Sequence
<220> FEATURE:
<223> OTHER INFORMATION: Description of Artificial Sequence: Synthetic
    Primer

<400> SEQUENCE: 76
atgtcgtaca tttccgccgg cgcgtgttcc ggagacagca ta           42

```
<210> SEQ ID NO 77
<211> LENGTH: 42
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 77
ccggcggaaa tgtacgacat catgaaaacc tgctgggacg cg                         42

<210> SEQ ID NO 78
<211> LENGTH: 42
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 78
aaggtcggac gtttcagcgg gtccgcgtcc cagcaggttt tc                         42

<210> SEQ ID NO 79
<211> LENGTH: 43
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 79
ccgctgaaac gtccgacctt caaacagatc gttcagctga tcg                        43

<210> SEQ ID NO 80
<211> LENGTH: 46
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 80
ttggtagatt cagagatctg tttttcgatc agctgaacga tctgtt                     46

<210> SEQ ID NO 81
<211> LENGTH: 44
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 81
aaacagatct ctgaatctac caaccacatc tactctaacc tggc                       44

<210> SEQ ID NO 82
<211> LENGTH: 42
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 82
tgacggttcg gagagcagtt cgccaggtta gagtagatgt gg                         42

<210> SEQ ID NO 83
<211> LENGTH: 43
```

```
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 83
aactgctctc cgaaccgtca gaaaccggtt gttgaccact ctg                    43

<210> SEQ ID NO 84
<211> LENGTH: 45
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 84
gtagaaccaa cagagttgat acgaacagag tggtcaacaa ccggt                  45

<210> SEQ ID NO 85
<211> LENGTH: 42
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 85
cgtatcaact ctgttggttc taccgcgtct tcttctcagc cg                     42

<210> SEQ ID NO 86
<211> LENGTH: 40
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 86
aacgtcgtcg tgaaccagca gcggctgaga agaagacgcg                        40

<210> SEQ ID NO 87
<211> LENGTH: 32
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 87
gttgtttcat atgtacgaag ttcagtggaa ag                                32

<210> SEQ ID NO 88
<211> LENGTH: 36
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 88
gttgtttgtc gactaaacgt cgtcgtgaac cagcag                            36

<210> SEQ ID NO 89
<211> LENGTH: 34
<212> TYPE: DNA
<213> ORGANISM: Artificial Sequence
```

```
<220> FEATURE:
<223> OTHER INFORMATION: Description of Artificial Sequence: Synthetic
      Primer

<400> SEQUENCE: 89
gttcttgtcg actatttctg acggttcgga gagc                                    34

<210> SEQ ID NO 90
<211> LENGTH: 1325
<212> TYPE: DNA
<213> ORGANISM: Artificial Sequence
<220> FEATURE:
<223> OTHER INFORMATION: Description of Artificial Sequence: Synthetic
      Plasmid
<220> FEATURE:
<221> NAME/KEY: CDS
<222> LOCATION: (88)..(1302)

<400> SEQUENCE: 90
taatacgact cactataggg gaattgtgag cggataacaa ttcccctcta gaaataattt        60
tgtttaactt taagaaggag atatacc atg ggt cac cac cat cac cat cat atg      114
                                Met Gly His His His His His His Met
                                  1               5 tac gaa gtt cag tgg aaa gtt gtt gaa gaa atc aac ggt aac aac tac        162
Tyr Glu Val Gln Trp Lys Val Val Glu Glu Ile Asn Gly Asn Asn Tyr
 10                  15                  20                  25 gtt tac atc gac ccg acc cag ctg ccg tac gac cac aaa tgg gag ttc        210
Val Tyr Ile Asp Pro Thr Gln Leu Pro Tyr Asp His Lys Trp Glu Phe
                 30                  35                  40 ccg cgt aac cgt ctg tct ttc ggt aaa acc ctg ggt gcg ggt gcg ttc        258
Pro Arg Asn Arg Leu Ser Phe Gly Lys Thr Leu Gly Ala Gly Ala Phe
             45                  50                  55 ggt aaa gtt gtt gaa gcg acc gcg tac ggt ctg atc aaa tct gac gcg        306
Gly Lys Val Val Glu Ala Thr Ala Tyr Gly Leu Ile Lys Ser Asp Ala
         60                  65                  70 gcg atg acc gtt gcg gtt aaa atg ctg aaa ccg tct gcg cac ctg acc        354
Ala Met Thr Val Ala Val Lys Met Leu Lys Pro Ser Ala His Leu Thr
     75                  80                  85 gaa cgt gaa gcg ctg atg tct gaa ctg aaa gtt ctg tct tac ctg ggt        402
Glu Arg Glu Ala Leu Met Ser Glu Leu Lys Val Leu Ser Tyr Leu Gly
 90                  95                 100                 105 aac cac atg aac atc gtt aac ctg ctg ggt gcg tgc acc atc ggt ggt        450
Asn His Met Asn Ile Val Asn Leu Leu Gly Ala Cys Thr Ile Gly Gly
                110                 115                 120 ccg acc ctg gtt atc acc gaa tac tgc tgc tac ggt gac ctg ctg aac        498
Pro Thr Leu Val Ile Thr Glu Tyr Cys Cys Tyr Gly Asp Leu Leu Asn
            125                 130                 135 ttc ctg cgt cgt aaa cgt gac tct ttc atc tgc tct aaa cag gaa gac        546
Phe Leu Arg Arg Lys Arg Asp Ser Phe Ile Cys Ser Lys Gln Glu Asp
        140                 145                 150 cac gcg gaa gcg gcg ctg tac aaa aac ctg ctg cac tct aaa gaa tct        594
His Ala Glu Ala Ala Leu Tyr Lys Asn Leu Leu His Ser Lys Glu Ser
    155                 160                 165 tct tgc tct gac tct acc aac gaa tac atg gac atg aaa ccg ggt gtt        642
Ser Cys Ser Asp Ser Thr Asn Glu Tyr Met Asp Met Lys Pro Gly Val
170                 175                 180                 185 tct tac gtt gtt ccg acc aaa gcg gac aaa cgt cgt tct gtt cgt atc        690
Ser Tyr Val Val Pro Thr Lys Ala Asp Lys Arg Arg Ser Val Arg Ile
                190                 195                 200 ggt tct tac atc gaa cgt gac gtt acc ccg gcg atc atg gaa gac gac        738
Gly Ser Tyr Ile Glu Arg Asp Val Thr Pro Ala Ile Met Glu Asp Asp
            205                 210                 215
```

```
gaa ctg gcg ctg gac ctg gaa gac ctg ctg tct ttc tct tac cag gtt    786
Glu Leu Ala Leu Asp Leu Glu Asp Leu Leu Ser Phe Ser Tyr Gln Val
        220                 225                 230 gcg aaa ggt atg gcg ttc ctg gcg tct aaa aac tgc atc cac cgt gac    834
Ala Lys Gly Met Ala Phe Leu Ala Ser Lys Asn Cys Ile His Arg Asp
235                 240                 245 ctg gcg gcg cgt aac atc ctg ctg acc cac ggt cgt atc acc aaa atc    882
Leu Ala Ala Arg Asn Ile Leu Leu Thr His Gly Arg Ile Thr Lys Ile
250                 255                 260                 265 tgc gac ttc ggt ctg gcg cgt gac atc aaa aac gac tct aac tac gtt    930
Cys Asp Phe Gly Leu Ala Arg Asp Ile Lys Asn Asp Ser Asn Tyr Val
                270                 275                 280 gtt aaa ggt aac gcg cgt ctg ccg gtt aaa tgg atg gcg ccg gaa tct    978
Val Lys Gly Asn Ala Arg Leu Pro Val Lys Trp Met Ala Pro Glu Ser
            285                 290                 295 atc ttc aac tgc gtt tac acc ttc gaa tct gac gtt tgg tct tac ggt   1026
Ile Phe Asn Cys Val Tyr Thr Phe Glu Ser Asp Val Trp Ser Tyr Gly
        300                 305                 310 atc ttc ctg tgg gaa ctg ttc tct ctg ggt tct tct ccg tac ccg ggt   1074
Ile Phe Leu Trp Glu Leu Phe Ser Leu Gly Ser Ser Pro Tyr Pro Gly
315                 320                 325 atg ccg gtt gac tct aaa ttc tac aaa atg atc aaa gaa ggt ttc cgt   1122
Met Pro Val Asp Ser Lys Phe Tyr Lys Met Ile Lys Glu Gly Phe Arg
330                 335                 340                 345 atg ctg tct ccg gaa cac gcg ccg gcg gaa atg tac gac atc atg aaa   1170
Met Leu Ser Pro Glu His Ala Pro Ala Glu Met Tyr Asp Ile Met Lys
                350                 355                 360 acc tgc tgg gac gcg gac ccg ctg aaa cgt ccg acc ttc aaa cag atc   1218
Thr Cys Trp Asp Ala Asp Pro Leu Lys Arg Pro Thr Phe Lys Gln Ile
            365                 370                 375 gtt cag ctg atc gaa aaa cag atc tct gaa tct acc aac cac atc tac   1266
Val Gln Leu Ile Glu Lys Gln Ile Ser Glu Ser Thr Asn His Ile Tyr
        380                 385                 390 tct aac ctg gcg aac tgc tct ccg aac cgt cag aaa tagtcgactg         1312
Ser Asn Leu Ala Asn Cys Ser Pro Asn Arg Gln Lys
395                 400                 405 aaaaaggaag agt                                                    1325

<210> SEQ ID NO 91
<211> LENGTH: 405
<212> TYPE: PRT
<213> ORGANISM: Artificial Sequence
<220> FEATURE:
<223> OTHER INFORMATION: Description of Artificial Sequence: Synthetic
      Plasmid

<400> SEQUENCE: 91

Met Gly His His His His His His Met Tyr Glu Val Gln Trp Lys Val
1               5                   10                  15

Val Glu Glu Ile Asn Gly Asn Asn Tyr Val Tyr Ile Asp Pro Thr Gln
            20                  25                  30

Leu Pro Tyr Asp His Lys Trp Glu Phe Pro Arg Asn Arg Leu Ser Phe
        35                  40                  45

Gly Lys Thr Leu Gly Ala Gly Ala Phe Gly Lys Val Val Glu Ala Thr
    50                  55                  60

Ala Tyr Gly Leu Ile Lys Ser Asp Ala Ala Met Thr Val Ala Val Lys
65                  70                  75                  80

Met Leu Lys Pro Ser Ala His Leu Thr Glu Arg Glu Ala Leu Met Ser
                85                  90                  95

Glu Leu Lys Val Leu Ser Tyr Leu Gly Asn His Met Asn Ile Val Asn
```

```
              100                 105                 110
Leu Leu Gly Ala Cys Thr Ile Gly Gly Pro Thr Leu Val Ile Thr Glu
        115                 120                 125

Tyr Cys Cys Tyr Gly Asp Leu Leu Asn Phe Leu Arg Arg Lys Arg Asp
130                 135                 140

Ser Phe Ile Cys Ser Lys Gln Glu Asp His Ala Glu Ala Ala Leu Tyr
145                 150                 155                 160

Lys Asn Leu Leu His Ser Lys Glu Ser Ser Cys Ser Asp Ser Thr Asn
                165                 170                 175

Glu Tyr Met Asp Met Lys Pro Gly Val Ser Tyr Val Val Pro Thr Lys
            180                 185                 190

Ala Asp Lys Arg Arg Ser Val Arg Ile Gly Ser Tyr Ile Glu Arg Asp
        195                 200                 205

Val Thr Pro Ala Ile Met Glu Asp Asp Glu Leu Ala Leu Asp Leu Glu
    210                 215                 220

Asp Leu Leu Ser Phe Ser Tyr Gln Val Ala Lys Gly Met Ala Phe Leu
225                 230                 235                 240

Ala Ser Lys Asn Cys Ile His Arg Asp Leu Ala Ala Arg Asn Ile Leu
                245                 250                 255

Leu Thr His Gly Arg Ile Thr Lys Ile Cys Asp Phe Gly Leu Ala Arg
            260                 265                 270

Asp Ile Lys Asn Asp Ser Asn Tyr Val Val Lys Gly Asn Ala Arg Leu
        275                 280                 285

Pro Val Lys Trp Met Ala Pro Glu Ser Ile Phe Asn Cys Val Tyr Thr
    290                 295                 300

Phe Glu Ser Asp Val Trp Ser Tyr Gly Ile Phe Leu Trp Glu Leu Phe
305                 310                 315                 320

Ser Leu Gly Ser Ser Pro Tyr Pro Gly Met Pro Val Asp Ser Lys Phe
                325                 330                 335

Tyr Lys Met Ile Lys Glu Gly Phe Arg Met Leu Ser Pro Glu His Ala
            340                 345                 350

Pro Ala Glu Met Tyr Asp Ile Met Lys Thr Cys Trp Asp Ala Asp Pro
        355                 360                 365

Leu Lys Arg Pro Thr Phe Lys Gln Ile Val Gln Leu Ile Glu Lys Gln
    370                 375                 380

Ile Ser Glu Ser Thr Asn His Ile Tyr Ser Asn Leu Ala Asn Cys Ser
385                 390                 395                 400

Pro Asn Arg Gln Lys
            405

<210> SEQ ID NO 92
<211> LENGTH: 35
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 92
catcctacat atgggggact ctgatatatc cagtc                              35

<210> SEQ ID NO 93
<211> LENGTH: 39
<212> TYPE: DNA
<213> ORGANISM: Artificial Sequence
<220> FEATURE:
<223> OTHER INFORMATION: Description of Artificial Sequence: Synthetic
      Primer
```

```
<400> SEQUENCE: 93
ctagcaggtc gactacccaa tgaaagtaga aagatcgc                                39

<210> SEQ ID NO 94
<211> LENGTH: 1049
<212> TYPE: DNA
<213> ORGANISM: Artificial Sequence
<220> FEATURE:
<223> OTHER INFORMATION: Description of Artificial Sequence: Synthetic
      Plasmid
<220> FEATURE:
<221> NAME/KEY: CDS
<222> LOCATION: (88)..(1041)

<400> SEQUENCE: 94
taatacgact cactataggg gaattgtgag cggataacaa ttcccctcta gaaataattt        60
tgtttaactt taagaaggag atatacc atg ggt cac cac cat cac cat cat atg      114
                               Met Gly His His His His His His Met
                                 1               5 ggg gac tct gat ata tcc agt cca tta ctg caa aat act gtc cac att        162
Gly Asp Ser Asp Ile Ser Ser Pro Leu Leu Gln Asn Thr Val His Ile
 10              15                  20                  25 gac ctc agt gct cta aat cca gag ctg gtc cag gca gtg cag cat gta        210
Asp Leu Ser Ala Leu Asn Pro Glu Leu Val Gln Ala Val Gln His Val
             30                  35                  40 gtg att ggg ccc agt agc ctg att gtg cat ttc aat gaa gtc ata gga        258
Val Ile Gly Pro Ser Ser Leu Ile Val His Phe Asn Glu Val Ile Gly
         45                  50                  55 aga ggg cat ttt ggt tgt gta tat cat ggg act ttg ttg gac aat gat        306
Arg Gly His Phe Gly Cys Val Tyr His Gly Thr Leu Leu Asp Asn Asp
     60                  65                  70 ggc aag aaa att cac tgt gct gtg aaa tcc ttg aac aga atc act gac        354
Gly Lys Lys Ile His Cys Ala Val Lys Ser Leu Asn Arg Ile Thr Asp
 75                  80                  85 ata gga gaa gtt tcc caa ttt ctg acc gag gga atc atc atg aaa gat        402
Ile Gly Glu Val Ser Gln Phe Leu Thr Glu Gly Ile Ile Met Lys Asp
 90                  95                 100                 105 ttt agt cat ccc aat gtc ctc tcg ctc ctg gga atc tgc ctg cga agt        450
Phe Ser His Pro Asn Val Leu Ser Leu Leu Gly Ile Cys Leu Arg Ser
            110                 115                 120 gaa ggg tct ccg ctg gtg gtc cta cca tac atg aaa cat gga gat ctt        498
Glu Gly Ser Pro Leu Val Val Leu Pro Tyr Met Lys His Gly Asp Leu
        125                 130                 135 cga aat ttc att cga aat gag act cat aat cca act gta aaa gat ctt        546
Arg Asn Phe Ile Arg Asn Glu Thr His Asn Pro Thr Val Lys Asp Leu
    140                 145                 150 att ggc ttt ggt ctt caa gta gcc aaa ggc atg aaa tat ctt gca agc        594
Ile Gly Phe Gly Leu Gln Val Ala Lys Gly Met Lys Tyr Leu Ala Ser
155                 160                 165 aaa aag ttt gtc cac aga gac ttg gct gca aga aac tgt atg ctg gat        642
Lys Lys Phe Val His Arg Asp Leu Ala Ala Arg Asn Cys Met Leu Asp
170                 175                 180                 185 gaa aaa ttc aca gtc aag gtt gct gat ttt ggt ctt gcc aga gac atg        690
Glu Lys Phe Thr Val Lys Val Ala Asp Phe Gly Leu Ala Arg Asp Met
            190                 195                 200 tat gat aaa gaa tac tat agt gta cac aac aaa aca ggt gca aag ctg        738
Tyr Asp Lys Glu Tyr Tyr Ser Val His Asn Lys Thr Gly Ala Lys Leu
        205                 210                 215 cca gtg aag tgg atg gct ttg gaa agt ctg caa act caa aag ttt acc        786
Pro Val Lys Trp Met Ala Leu Glu Ser Leu Gln Thr Gln Lys Phe Thr
    220                 225                 230
```

```
acc aag tca gat gtg tgg tcc ttt ggc gtg ctc ctc tgg gag ctg atg      834
Thr Lys Ser Asp Val Trp Ser Phe Gly Val Leu Leu Trp Glu Leu Met
235                 240                 245 aca aga gga gcc cca cct tat cct gat gta aac acc ttt gat ata act      882
Thr Arg Gly Ala Pro Pro Tyr Pro Asp Val Asn Thr Phe Asp Ile Thr
250                 255                 260                 265 gtt tac ttg ttg caa ggg aga aga ctc cta caa ccc gaa tac tgc cca      930
Val Tyr Leu Leu Gln Gly Arg Arg Leu Leu Gln Pro Glu Tyr Cys Pro
            270                 275                 280 gac ccc tta tat gaa gta atg cta aaa tgc tgg cac cct aaa gcc gaa      978
Asp Pro Leu Tyr Glu Val Met Leu Lys Cys Trp His Pro Lys Ala Glu
        285                 290                 295 atg cgc cca tcc ttt tct gaa ctg gtg tcc cgg ata tca gcg atc ttc     1026
Met Arg Pro Ser Phe Ser Glu Leu Val Ser Arg Ile Ser Ala Ile Phe
    300                 305                 310 tct act ttc att ggg tagtcgac                                        1049
Ser Thr Phe Ile Gly
    315

<210> SEQ ID NO 95
<211> LENGTH: 318
<212> TYPE: PRT
<213> ORGANISM: Artificial Sequence
<220> FEATURE:
<223> OTHER INFORMATION: Description of Artificial Sequence: Synthetic
      Plasmid

<400> SEQUENCE: 95

Met Gly His His His His His His Met Gly Asp Ser Asp Ile Ser Ser
1               5                   10                  15

Pro Leu Gln Asn Thr Val His Ile Asp Leu Ser Ala Leu Asn Pro
            20                  25                  30

Glu Leu Val Gln Ala Val Gln His Val Val Ile Gly Pro Ser Ser Leu
        35                  40                  45

Ile Val His Phe Asn Glu Val Ile Gly Arg Gly His Phe Gly Cys Val
    50                  55                  60

Tyr His Gly Thr Leu Leu Asp Asn Asp Gly Lys Lys Ile His Cys Ala
65                  70                  75                  80

Val Lys Ser Leu Asn Arg Ile Thr Asp Ile Gly Glu Val Ser Gln Phe
                85                  90                  95

Leu Thr Glu Gly Ile Ile Met Lys Asp Phe Ser His Pro Asn Val Leu
            100                 105                 110

Ser Leu Leu Gly Ile Cys Leu Arg Ser Glu Gly Ser Pro Leu Val Val
        115                 120                 125

Leu Pro Tyr Met Lys His Gly Asp Leu Arg Asn Phe Ile Arg Asn Glu
    130                 135                 140

Thr His Asn Pro Thr Val Lys Asp Leu Ile Gly Phe Gly Leu Gln Val
145                 150                 155                 160

Ala Lys Gly Met Lys Tyr Leu Ala Ser Lys Lys Phe Val His Arg Asp
                165                 170                 175

Leu Ala Ala Arg Asn Cys Met Leu Asp Glu Lys Phe Thr Val Lys Val
            180                 185                 190

Ala Asp Phe Gly Leu Ala Arg Asp Met Tyr Asp Lys Glu Tyr Tyr Ser
        195                 200                 205

Val His Asn Lys Thr Gly Ala Lys Leu Pro Val Lys Trp Met Ala Leu
    210                 215                 220

Glu Ser Leu Gln Thr Gln Lys Phe Thr Thr Lys Ser Asp Val Trp Ser
225                 230                 235                 240
```

```
Phe Gly Val Leu Leu Trp Glu Leu Met Thr Arg Gly Ala Pro Pro Tyr
                245                 250                 255

Pro Asp Val Asn Thr Phe Asp Ile Thr Val Tyr Leu Leu Gln Gly Arg
            260                 265                 270

Arg Leu Leu Gln Pro Glu Tyr Cys Pro Asp Pro Leu Tyr Glu Val Met
        275                 280                 285

Leu Lys Cys Trp His Pro Lys Ala Glu Met Arg Pro Ser Phe Ser Glu
    290                 295                 300

Leu Val Ser Arg Ile Ser Ala Ile Phe Ser Thr Phe Ile Gly
305                 310                 315

<210> SEQ ID NO 96
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 96
ccggatccat atgtctcagg agaggcccac                                       30

<210> SEQ ID NO 97
<211> LENGTH: 33
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 97
gaaaccctcg agtcaggact ccatctcttc ttg                                   33

<210> SEQ ID NO 98
<211> LENGTH: 1236
<212> TYPE: DNA
<213> ORGANISM: Artificial Sequence
<220> FEATURE:
<223> OTHER INFORMATION: Description of Artificial Sequence: Synthetic
      Plasmid
<220> FEATURE:
<221> NAME/KEY: CDS
<222> LOCATION: (88)..(1227)

<400> SEQUENCE: 98
taatacgact cactataggg gaattgtgag cggataacaa ttcccctcta gaaataattt      60
tgtttaactt taagaaggag atatacc atg ggc agc agc cat cat cat cat cat    114
                             Met Gly Ser Ser His His His His His
                              1               5 cac agc agc ggc ctg gtg ccg cgc ggc agc cat atg tct cag gag agg      162
His Ser Ser Gly Leu Val Pro Arg Gly Ser His Met Ser Gln Glu Arg
 10                  15                  20                  25 ccc acg ttc tac cgg cag gag ctg aac aag aca atc tgg gag gtg ccc      210
Pro Thr Phe Tyr Arg Gln Glu Leu Asn Lys Thr Ile Trp Glu Val Pro
                 30                  35                  40 gag cgt tac cag aac ctg tct cca gtg ggc tct ggc gcc tat ggc tct      258
Glu Arg Tyr Gln Asn Leu Ser Pro Val Gly Ser Gly Ala Tyr Gly Ser
             45                  50                  55 gtg tgt gct gct ttt gac aca aaa acg ggg tta cgt gtg gca gtg aag      306
Val Cys Ala Ala Phe Asp Thr Lys Thr Gly Leu Arg Val Ala Val Lys
         60                  65                  70 aag ctc tcc aga cca ttt cag tcc atc att cat gcg aaa aga acc tac      354
Lys Leu Ser Arg Pro Phe Gln Ser Ile Ile His Ala Lys Arg Thr Tyr
```

```
                 75                  80                  85 aga gaa ctg cgg tta ctt aaa cac atg aaa cat gaa aat gtg att ggt      402
Arg Glu Leu Arg Leu Leu Lys His Met Lys His Glu Asn Val Ile Gly
 90                  95                 100                 105 ctg ttg gac gtt ttt aca cct gca agg tct ctg gag gaa ttc aat gat      450
Leu Leu Asp Val Phe Thr Pro Ala Arg Ser Leu Glu Glu Phe Asn Asp
                110                 115                 120 gtg tat ctg gtg acc cat ctc atg ggg gca gat ctg aac aac att gtg      498
Val Tyr Leu Val Thr His Leu Met Gly Ala Asp Leu Asn Asn Ile Val
            125                 130                 135 aaa tgt cag aag ctt aca gat gac cat gtt cag ttc ctt atc tac caa      546
Lys Cys Gln Lys Leu Thr Asp Asp His Val Gln Phe Leu Ile Tyr Gln
        140                 145                 150 att ctc cga ggt cta aag tat ata cat tca gct gac ata att cac agg      594
Ile Leu Arg Gly Leu Lys Tyr Ile His Ser Ala Asp Ile Ile His Arg
    155                 160                 165 gac cta aaa cct agt aat cta gct gtg aat gaa gac tgt gag ctg aag      642
Asp Leu Lys Pro Ser Asn Leu Ala Val Asn Glu Asp Cys Glu Leu Lys
170                 175                 180                 185 att ctg gat ttt gga ctg gct cgg cac aca gat gat gaa atg aca ggc      690
Ile Leu Asp Phe Gly Leu Ala Arg His Thr Asp Asp Glu Met Thr Gly
                190                 195                 200 tac gtg gcc act agg tgg tac agg gct cct gag atc atg ctg aac tgg      738
Tyr Val Ala Thr Arg Trp Tyr Arg Ala Pro Glu Ile Met Leu Asn Trp
            205                 210                 215 atg cat tac aac cag aca gtt gat att tgg tca gtg gga tgc ata atg      786
Met His Tyr Asn Gln Thr Val Asp Ile Trp Ser Val Gly Cys Ile Met
        220                 225                 230 gcc gag ctg ttg act gga aga aca ttg ttt cct ggt aca gac cat att      834
Ala Glu Leu Leu Thr Gly Arg Thr Leu Phe Pro Gly Thr Asp His Ile
    235                 240                 245 gat cag ttg aag ctc att tta aga ctc gtt gga acc cca ggg gct gag      882
Asp Gln Leu Lys Leu Ile Leu Arg Leu Val Gly Thr Pro Gly Ala Glu
250                 255                 260                 265 ctt ttg aag aaa atc tcc tca gag tct gca aga aac tat att cag tct      930
Leu Leu Lys Lys Ile Ser Ser Glu Ser Ala Arg Asn Tyr Ile Gln Ser
                270                 275                 280 ttg act cag atg ccg aag atg aac ttt gcg aat gta ttt att ggt gcc      978
Leu Thr Gln Met Pro Lys Met Asn Phe Ala Asn Val Phe Ile Gly Ala
            285                 290                 295 aat ccc ctg gct gtc gac ttg ctg gag aag atg ctt gta ttg gac tca     1026
Asn Pro Leu Ala Val Asp Leu Leu Glu Lys Met Leu Val Leu Asp Ser
        300                 305                 310 gat aag aga att aca gcg gcc caa gcc ctt gca cat gcc tac ttt gct     1074
Asp Lys Arg Ile Thr Ala Ala Gln Ala Leu Ala His Ala Tyr Phe Ala
    315                 320                 325 cag tac cac gat cct gat gat gaa cca gtg gcc gat cct tat gat cag     1122
Gln Tyr His Asp Pro Asp Asp Glu Pro Val Ala Asp Pro Tyr Asp Gln
330                 335                 340                 345 tcc ttt gaa agc agg gac ctc ctt ata gat gag tgg aaa agc ctg acc     1170
Ser Phe Glu Ser Arg Asp Leu Leu Ile Asp Glu Trp Lys Ser Leu Thr
                350                 355                 360 tat gat gaa gtc atc agc ttt gtg cca cca ccc ctt gac caa gaa gag     1218
Tyr Asp Glu Val Ile Ser Phe Val Pro Pro Pro Leu Asp Gln Glu Glu
            365                 370                 375 atg gag tcc tgactcgac                                               1236
Met Glu Ser
        380

<210> SEQ ID NO 99
```

```
<211> LENGTH: 380
<212> TYPE: PRT
<213> ORGANISM: Artificial Sequence
<220> FEATURE:
<223> OTHER INFORMATION: Description of Artificial Sequence: Synthetic
      Plasmid

<400> SEQUENCE: 99

Met Gly Ser Ser His His His His His His Ser Ser Gly Leu Val Pro
 1               5                  10                  15

Arg Gly Ser His Met Ser Gln Glu Arg Pro Thr Phe Tyr Arg Gln Glu
            20                  25                  30

Leu Asn Lys Thr Ile Trp Glu Val Pro Glu Arg Tyr Gln Asn Leu Ser
        35                  40                  45

Pro Val Gly Ser Gly Ala Tyr Gly Ser Val Cys Ala Ala Phe Asp Thr
    50                  55                  60

Lys Thr Gly Leu Arg Val Ala Val Lys Lys Leu Ser Arg Pro Phe Gln
65                  70                  75                  80

Ser Ile Ile His Ala Lys Arg Thr Tyr Arg Glu Leu Arg Leu Leu Lys
                85                  90                  95

His Met Lys His Glu Asn Val Ile Gly Leu Leu Asp Val Phe Thr Pro
            100                 105                 110

Ala Arg Ser Leu Glu Glu Phe Asn Asp Val Tyr Leu Val Thr His Leu
        115                 120                 125

Met Gly Ala Asp Leu Asn Asn Ile Val Lys Cys Gln Lys Leu Thr Asp
    130                 135                 140

Asp His Val Gln Phe Leu Ile Tyr Gln Ile Leu Arg Gly Leu Lys Tyr
145                 150                 155                 160

Ile His Ser Ala Asp Ile Ile His Arg Asp Leu Lys Pro Ser Asn Leu
                165                 170                 175

Ala Val Asn Glu Asp Cys Glu Leu Lys Ile Leu Asp Phe Gly Leu Ala
            180                 185                 190

Arg His Thr Asp Asp Glu Met Thr Gly Tyr Val Ala Thr Arg Trp Tyr
        195                 200                 205

Arg Ala Pro Glu Ile Met Leu Asn Trp Met His Tyr Asn Gln Thr Val
    210                 215                 220

Asp Ile Trp Ser Val Gly Cys Ile Met Ala Glu Leu Leu Thr Gly Arg
225                 230                 235                 240

Thr Leu Phe Pro Gly Thr Asp His Ile Asp Gln Leu Lys Leu Ile Leu
                245                 250                 255

Arg Leu Val Gly Thr Pro Gly Ala Glu Leu Leu Lys Lys Ile Ser Ser
            260                 265                 270

Glu Ser Ala Arg Asn Tyr Ile Gln Ser Leu Thr Gln Met Pro Lys Met
        275                 280                 285

Asn Phe Ala Asn Val Phe Ile Gly Ala Asn Pro Leu Ala Val Asp Leu
    290                 295                 300

Leu Glu Lys Met Leu Val Leu Asp Ser Asp Lys Arg Ile Thr Ala Ala
305                 310                 315                 320

Gln Ala Leu Ala His Ala Tyr Phe Ala Gln Tyr His Asp Pro Asp Asp
                325                 330                 335

Glu Pro Val Ala Asp Pro Tyr Asp Gln Ser Phe Glu Ser Arg Asp Leu
            340                 345                 350

Leu Ile Asp Glu Trp Lys Ser Leu Thr Tyr Asp Glu Val Ile Ser Phe
        355                 360                 365

Val Pro Pro Pro Leu Asp Gln Glu Glu Met Glu Ser
    370                 375                 380
```

<210> SEQ ID NO 100
<211> LENGTH: 34
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 100
gctggcgcat atgaaggaga aggagccccct ggag                                 34

<210> SEQ ID NO 101
<211> LENGTH: 33
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 101
gaaagggtcg actttgctgg gccccggcga cag                                   33

<210> SEQ ID NO 102
<211> LENGTH: 1108
<212> TYPE: DNA
<213> ORGANISM: Artificial Sequence
<220> FEATURE:
<223> OTHER INFORMATION: Description of Artificial Sequence: Synthetic
      Plasmid
<220> FEATURE:
<221> NAME/KEY: CDS
<222> LOCATION: (113)..(994)

<400> SEQUENCE: 102
agatcgatct cgatcccgcg aaattaatac gactcactat agggggaattg tgagcggata    60 acaattcccc tctagaaata attttgttta actttaagaa ggagatatac at atg aag    118
                                                           Met Lys
                                                             1 gag aag gag ccc ctg gag tcg cag tac cag gtg ggc ccg cta ctg ggc       166
Glu Lys Glu Pro Leu Glu Ser Gln Tyr Gln Val Gly Pro Leu Leu Gly
          5                   10                  15 agc ggc ggc ttc ggc tcg gtc tac tca ggc atc cgc gtc tcc gac aac       214
Ser Gly Gly Phe Gly Ser Val Tyr Ser Gly Ile Arg Val Ser Asp Asn
     20                  25                  30 ttg ccg gtg gcc atc aaa cac gtg gag aag gac cgg att tcc gac tgg       262
Leu Pro Val Ala Ile Lys His Val Glu Lys Asp Arg Ile Ser Asp Trp
 35                  40                  45                  50 gga gag ctg cct aat ggc act cga gtg ccc atg gaa gtg gtc ctg ctg       310
Gly Glu Leu Pro Asn Gly Thr Arg Val Pro Met Glu Val Val Leu Leu
                 55                  60                  65 aag aag gtg agc tcg ggt ttc tcc ggc gtc att agg ctc ctg gac tgg       358
Lys Lys Val Ser Ser Gly Phe Ser Gly Val Ile Arg Leu Leu Asp Trp
             70                  75                  80 ttc gag agg ccc gac agt ttc gtc ctg atc ctg gag agg ccc gag ccg       406
Phe Glu Arg Pro Asp Ser Phe Val Leu Ile Leu Glu Arg Pro Glu Pro
         85                  90                  95 gtg caa gat ctc ttc gac ttc atc acg gaa agg gga gcc ctg caa gag       454
Val Gln Asp Leu Phe Asp Phe Ile Thr Glu Arg Gly Ala Leu Gln Glu
     100                 105                 110 gag ctg gcc cgc agc ttc ttc tgg cag gtg ctg gag gcc gtg cgg cac       502
Glu Leu Ala Arg Ser Phe Phe Trp Gln Val Leu Glu Ala Val Arg His
115                 120                 125                 130 tgc cac aac tgc ggg gtg ctc cac cgc gac atc aag gac gaa aac atc       550

```
                                                                                           -continued Cys His Asn Cys Gly Val Leu His Arg Asp Ile Lys Asp Glu Asn Ile
            135                 140                 145 ctt atc gac ctc aat cgc ggc gag ctc aag ctc atc gac ttc ggg tcg           598
Leu Ile Asp Leu Asn Arg Gly Glu Leu Lys Leu Ile Asp Phe Gly Ser
        150                 155                 160 ggg gcg ctg ctc aag gac acc gtc tac acg gac ttc gat ggg acc cga           646
Gly Ala Leu Leu Lys Asp Thr Val Tyr Thr Asp Phe Asp Gly Thr Arg
165                 170                 175 gtg tat agc cct cca gag tgg atc cgc tac cat cgc tac cat ggc agg           694
Val Tyr Ser Pro Pro Glu Trp Ile Arg Tyr His Arg Tyr His Gly Arg
        180                 185                 190 tcg gcg gca gtc tgg tcc ctg ggg atc ctg ctg tat gat atg gtg tgt           742
Ser Ala Ala Val Trp Ser Leu Gly Ile Leu Leu Tyr Asp Met Val Cys
195                 200                 205                 210 gga gat att cct ttc gag cat gac gaa gag atc atc agg ggc cag gtt           790
Gly Asp Ile Pro Phe Glu His Asp Glu Glu Ile Ile Arg Gly Gln Val
            215                 220                 225 ttc ttc agg cag agg gtc tct tca gaa tgt cag cat ctc att aga tgg           838
Phe Phe Arg Gln Arg Val Ser Ser Glu Cys Gln His Leu Ile Arg Trp
        230                 235                 240 tgc ttg gcc ctg aga cca tca gat agg cca acc ttc gaa gaa atc cag           886
Cys Leu Ala Leu Arg Pro Ser Asp Arg Pro Thr Phe Glu Glu Ile Gln
    245                 250                 255 aac cat cca tgg atg caa gat gtt ctc ctg ccc cag gaa act gct gag           934
Asn His Pro Trp Met Gln Asp Val Leu Leu Pro Gln Glu Thr Ala Glu
260                 265                 270 atc cac ctc cac agc ctg tcg ccg ggg ccc agc aaa gtc gac cac cac           982
Ile His Leu His Ser Leu Ser Pro Gly Pro Ser Lys Val Asp His His
275                 280                 285                 290 cac cac cac cac tgagatccgg ctgctaacaa agcccgaaag gaattcgagt              1034
His His His His tggctgctgc caccgctgag caataactag cataaccct tggggcctct aaacgggtct         1094 tgagggggttt tttg                                                          1108

<210> SEQ ID NO 103
<211> LENGTH: 294
<212> TYPE: PRT
<213> ORGANISM: Artificial Sequence
<220> FEATURE:
<223> OTHER INFORMATION: Description of Artificial Sequence: Synthetic
      Plasmid

<400> SEQUENCE: 103

Met Lys Glu Lys Glu Pro Leu Glu Ser Gln Tyr Gln Val Gly Pro Leu
 1               5                  10                  15

Leu Gly Ser Gly Gly Phe Gly Ser Val Tyr Ser Gly Ile Arg Val Ser
            20                  25                  30

Asp Asn Leu Pro Val Ala Ile Lys His Val Glu Lys Asp Arg Ile Ser
        35                  40                  45

Asp Trp Gly Glu Leu Pro Asn Gly Thr Arg Val Pro Met Glu Val Val
    50                  55                  60

Leu Leu Lys Lys Val Ser Ser Gly Phe Ser Gly Val Ile Arg Leu Leu
65                  70                  75                  80

Asp Trp Phe Glu Arg Pro Asp Ser Phe Val Leu Ile Leu Glu Arg Pro
                85                  90                  95

Glu Pro Val Gln Asp Leu Phe Asp Phe Ile Thr Glu Arg Gly Ala Leu
            100                 105                 110

Gln Glu Glu Leu Ala Arg Ser Phe Phe Trp Gln Val Leu Glu Ala Val
        115                 120                 125
```

```
Arg His Cys His Asn Cys Gly Val Leu His Arg Asp Ile Lys Asp Glu
    130                 135                 140

Asn Ile Leu Ile Asp Leu Asn Arg Gly Glu Leu Lys Leu Ile Asp Phe
145                 150                 155                 160

Gly Ser Gly Ala Leu Leu Lys Asp Thr Val Tyr Thr Asp Phe Asp Gly
                165                 170                 175

Thr Arg Val Tyr Ser Pro Pro Glu Trp Ile Arg Tyr His Arg Tyr His
            180                 185                 190

Gly Arg Ser Ala Ala Val Trp Ser Leu Gly Ile Leu Leu Tyr Asp Met
        195                 200                 205

Val Cys Gly Asp Ile Pro Phe Glu His Asp Glu Glu Ile Ile Arg Gly
    210                 215                 220

Gln Val Phe Phe Arg Gln Arg Val Ser Ser Glu Cys Gln His Leu Ile
225                 230                 235                 240

Arg Trp Cys Leu Ala Leu Arg Pro Ser Asp Arg Pro Thr Phe Glu Glu
                245                 250                 255

Ile Gln Asn His Pro Trp Met Gln Asp Val Leu Leu Pro Gln Glu Thr
            260                 265                 270

Ala Glu Ile His Leu His Ser Leu Ser Pro Gly Pro Ser Lys Val Asp
        275                 280                 285

His His His His His His
    290

<210> SEQ ID NO 104
<211> LENGTH: 33
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 104
gttcttcata tgcacaagtt tgcccacaag cca                                33

<210> SEQ ID NO 105
<211> LENGTH: 40
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 105
gttcttgtcg accctcttaa ccatcatctt ctccaggtct                         40

<210> SEQ ID NO 106
<211> LENGTH: 1285
<212> TYPE: DNA
<213> ORGANISM: Artificial Sequence
<220> FEATURE:
<223> OTHER INFORMATION: Description of Artificial Sequence: Synthetic
      Plasmid
<220> FEATURE:
<221> NAME/KEY: CDS
<222> LOCATION: (89)..(1171)

<400> SEQUENCE: 106
taatacgact cactataggg gaattgtgag cggataacaa ttcccctcta gaaataattt    60
tgtttaactt taagaaggag atatacat atg cac aag ttt gcc cac aag cca      112
                                Met His Lys Phe Ala His Lys Pro
                                 1               5
```

```
ccc atc tcc tca gct gag atg acc ttc cgg agg ccc gcc cag gcc ttc      160
Pro Ile Ser Ser Ala Glu Met Thr Phe Arg Arg Pro Ala Gln Ala Phe
    10              15                  20 ccg gtc agc tac tcc tct tcc ggt gcc cgc cgg ccc tcg ctg gac tcc      208
Pro Val Ser Tyr Ser Ser Ser Gly Ala Arg Arg Pro Ser Leu Asp Ser
 25              30                  35                  40 atg gag aac cag gtc tcc gtg gat gcc ttc aag atc ctg gag gat cca      256
Met Glu Asn Gln Val Ser Val Asp Ala Phe Lys Ile Leu Glu Asp Pro
            45                  50                  55 aag tgg gaa ttc cct cgg aag aac ttg gtt ctt gga aaa act cta gga      304
Lys Trp Glu Phe Pro Arg Lys Asn Leu Val Leu Gly Lys Thr Leu Gly
                60                  65                  70 gaa ggc gaa ttt gga aaa gtg gtc aag gca acg gcc ttc cat ctg aaa      352
Glu Gly Glu Phe Gly Lys Val Val Lys Ala Thr Ala Phe His Leu Lys
     75                  80                  85 ggc aga gca ggg tac acc acg gtg gcc gtg aag atg ctg aaa gag aac      400
Gly Arg Ala Gly Tyr Thr Thr Val Ala Val Lys Met Leu Lys Glu Asn
 90                  95                 100 gcc tcc ccg agt gag ctt cga gac ctg ctg tca gag ttc aac gtc ctg      448
Ala Ser Pro Ser Glu Leu Arg Asp Leu Leu Ser Glu Phe Asn Val Leu
105                 110                 115                 120 aag cag gtc aac cac cca cat gtc atc aaa ttg tat ggg gcc tgc agc      496
Lys Gln Val Asn His Pro His Val Ile Lys Leu Tyr Gly Ala Cys Ser
                125                 130                 135 cag gat ggc ccg ctc ctc ctc atc gtg gag tac gcc aaa tac ggc tcc      544
Gln Asp Gly Pro Leu Leu Leu Ile Val Glu Tyr Ala Lys Tyr Gly Ser
            140                 145                 150 ctg cgg ggc ttc ctc cgc gag agc cgc aaa gtg ggg cct ggc tac ctg      592
Leu Arg Gly Phe Leu Arg Glu Ser Arg Lys Val Gly Pro Gly Tyr Leu
                155                 160                 165 ggc agt gga ggc agc cgc aac tcc agc tcc ctg gac cac ccg gat gag      640
Gly Ser Gly Gly Ser Arg Asn Ser Ser Ser Leu Asp His Pro Asp Glu
170                 175                 180 cgg gcc ctc acc atg ggc gac ctc atc tca ttt gcc tgg cag atc tca      688
Arg Ala Leu Thr Met Gly Asp Leu Ile Ser Phe Ala Trp Gln Ile Ser
185                 190                 195                 200 cag ggg atg cag tat ctg gcc gag atg aag ctc gtt cat cgg gac ttg      736
Gln Gly Met Gln Tyr Leu Ala Glu Met Lys Leu Val His Arg Asp Leu
            205                 210                 215 gca gcc aga aac atc ctg gta gct gag ggg cgg aag atg aag att tcg      784
Ala Ala Arg Asn Ile Leu Val Ala Glu Gly Arg Lys Met Lys Ile Ser
                220                 225                 230 gat ttc ggc ttg tcc cga gat gtt tat gaa gag gat tcc tac gtg aag      832
Asp Phe Gly Leu Ser Arg Asp Val Tyr Glu Glu Asp Ser Tyr Val Lys
235                 240                 245 agg agc cag ggt cgg att cca gtt aaa tgg atg gca att gaa tcc ctt      880
Arg Ser Gln Gly Arg Ile Pro Val Lys Trp Met Ala Ile Glu Ser Leu
            250                 255                 260 ttt gat cat atc tac acc acg caa agt gat gta tgg tct ttt ggt gtc      928
Phe Asp His Ile Tyr Thr Thr Gln Ser Asp Val Trp Ser Phe Gly Val
265                 270                 275                 280 ctg ctg tgg gag atc gtg acc cta ggg gga aac ccc tat cct ggg att      976
Leu Leu Trp Glu Ile Val Thr Leu Gly Gly Asn Pro Tyr Pro Gly Ile
                285                 290                 295 cct cct gag cgg ctc ttc aac ctt ctg aag acc ggc cac cgg atg gag     1024
Pro Pro Glu Arg Leu Phe Asn Leu Leu Lys Thr Gly His Arg Met Glu
                300                 305                 310 agg cca gac aac tgc agc gag gag atg tac cgc ctg atg ctg caa tgc     1072
Arg Pro Asp Asn Cys Ser Glu Glu Met Tyr Arg Leu Met Leu Gln Cys
            315                 320                 325
```

-continued

```
tgg aag cag gag ccg gac aaa agg ccg gtg ttt gcg gac atc agc aaa    1120
Trp Lys Gln Glu Pro Asp Lys Arg Pro Val Phe Ala Asp Ile Ser Lys
    330                 335                 340 gac ctg gag aag atg atg gtt aag agg gtc gac cac cac cac cac cac    1168
Asp Leu Glu Lys Met Met Val Lys Arg Val Asp His His His His His
345                 350                 355                 360 cac tgagatccgg ctggccctac tggccgaaag gaattcgagg ccagcagggc         1221
His caccgctgag caataactag cataacccct tggggcctct aaacgggtct tgaggggttt  1281
tttg                                                               1285

<210> SEQ ID NO 107
<211> LENGTH: 361
<212> TYPE: PRT
<213> ORGANISM: Artificial Sequence
<220> FEATURE:
<223> OTHER INFORMATION: Description of Artificial Sequence: Synthetic
      Plasmid

<400> SEQUENCE: 107

Met His Lys Phe Ala His Lys Pro Pro Ile Ser Ser Ala Glu Met Thr
1               5                   10                  15

Phe Arg Arg Pro Ala Gln Ala Phe Pro Val Ser Tyr Ser Ser Ser Gly
            20                  25                  30

Ala Arg Arg Pro Ser Leu Asp Ser Met Glu Asn Gln Val Ser Val Asp
        35                  40                  45

Ala Phe Lys Ile Leu Glu Asp Pro Lys Trp Glu Phe Pro Arg Lys Asn
    50                  55                  60

Leu Val Leu Gly Lys Thr Leu Gly Glu Gly Glu Phe Gly Lys Val Val
65                  70                  75                  80

Lys Ala Thr Ala Phe His Leu Lys Gly Arg Ala Gly Tyr Thr Thr Val
                85                  90                  95

Ala Val Lys Met Leu Lys Glu Asn Ala Ser Pro Ser Glu Leu Arg Asp
            100                 105                 110

Leu Leu Ser Glu Phe Asn Val Leu Lys Gln Val Asn His Pro His Val
        115                 120                 125

Ile Lys Leu Tyr Gly Ala Cys Ser Gln Asp Gly Pro Leu Leu Leu Ile
    130                 135                 140

Val Glu Tyr Ala Lys Tyr Gly Ser Leu Arg Gly Phe Leu Arg Glu Ser
145                 150                 155                 160

Arg Lys Val Gly Pro Gly Tyr Leu Gly Ser Gly Gly Ser Arg Asn Ser
                165                 170                 175

Ser Ser Leu Asp His Pro Asp Glu Arg Ala Leu Thr Met Gly Asp Leu
            180                 185                 190

Ile Ser Phe Ala Trp Gln Ile Ser Gln Gly Met Gln Tyr Leu Ala Glu
        195                 200                 205

Met Lys Leu Val His Arg Asp Leu Ala Ala Arg Asn Ile Leu Val Ala
    210                 215                 220

Glu Gly Arg Lys Met Lys Ile Ser Asp Phe Gly Leu Ser Arg Asp Val
225                 230                 235                 240

Tyr Glu Glu Asp Ser Tyr Val Lys Arg Ser Gln Gly Arg Ile Pro Val
                245                 250                 255

Lys Trp Met Ala Ile Glu Ser Leu Phe Asp His Ile Tyr Thr Thr Gln
            260                 265                 270

Ser Asp Val Trp Ser Phe Gly Val Leu Leu Trp Glu Ile Val Thr Leu
        275                 280                 285
```

-continued

```
Gly Gly Asn Pro Tyr Pro Gly Ile Pro Pro Glu Arg Leu Phe Asn Leu
    290                 295                 300

Leu Lys Thr Gly His Arg Met Glu Arg Pro Asp Asn Cys Ser Glu Glu
305                 310                 315                 320

Met Tyr Arg Leu Met Leu Gln Cys Trp Lys Gln Glu Pro Asp Lys Arg
                325                 330                 335

Pro Val Phe Ala Asp Ile Ser Lys Asp Leu Glu Lys Met Met Val Lys
            340                 345                 350

Arg Val Asp His His His His His His
            355                 360

<210> SEQ ID NO 108
<211> LENGTH: 33
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 108
gctggcccat atggtgacca cctttgtggc cct                                33

<210> SEQ ID NO 109
<211> LENGTH: 33
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 109
gctactagtc gacctagagg ttctccccgg gct                                33

<210> SEQ ID NO 110
<211> LENGTH: 1491
<212> TYPE: DNA
<213> ORGANISM: Artificial Sequence
<220> FEATURE:
<223> OTHER INFORMATION: Description of Artificial Sequence: Synthetic
      Plasmid
<220> FEATURE:
<221> NAME/KEY: CDS
<222> LOCATION: (88)..(1467)

<400> SEQUENCE: 110
taatacgact cactataggg gaattgtgag cggataacaa ttcccctcta gaaataattt    60
tgtttaactt taagaaggag atatacc atg ggt cac cac cat cac cat cat atg   114
                              Met Gly His His His His His His Met
                                1               5 gtg acc acc ttt gtg gcc ctc tat gac tat gag tct agg acg gag aca   162
Val Thr Thr Phe Val Ala Leu Tyr Asp Tyr Glu Ser Arg Thr Glu Thr
 10                  15                  20                  25 gac ctg tcc ttc aag aaa ggc gag cgg ctc cag att gtc aac aac aca   210
Asp Leu Ser Phe Lys Lys Gly Glu Arg Leu Gln Ile Val Asn Asn Thr
                 30                  35                  40 gag gga gac tgg tgg ctg gcc cac tcg ctc agc aca gga cag aca ggc   258
Glu Gly Asp Trp Trp Leu Ala His Ser Leu Ser Thr Gly Gln Thr Gly
             45                  50                  55 tac atc ccc agc aac tac gtg gcg ccc tcc gac tcc atc cag gct gag   306
Tyr Ile Pro Ser Asn Tyr Val Ala Pro Ser Asp Ser Ile Gln Ala Glu
         60                  65                  70 gag tgg tat ttt ggc aag atc acc aga cgg gag tca gag cgg tta ctg   354
Glu Trp Tyr Phe Gly Lys Ile Thr Arg Arg Glu Ser Glu Arg Leu Leu
     75                  80                  85
```

-continued

| | | | | | | | | | | | | | | | | |
|---|---|---|---|---|---|---|---|---|---|---|---|---|---|---|---|---|
| ctc | aat | gca | gag | aac | ccg | aga | ggg | acc | ttc | ctc | gtg | cga | gaa | agt | gag | 402 |
| Leu | Asn | Ala | Glu | Asn | Pro | Arg | Gly | Thr | Phe | Leu | Val | Arg | Glu | Ser | Glu | |
| 90 | | | | 95 | | | | | 100 | | | | | 105 | | |
| acc | acg | aaa | ggt | gcc | tac | tgc | ctc | tca | gtg | tct | gac | ttc | gac | aac | gcc | 450 |
| Thr | Thr | Lys | Gly | Ala | Tyr | Cys | Leu | Ser | Val | Ser | Asp | Phe | Asp | Asn | Ala | |
| | | | 110 | | | | | 115 | | | | | 120 | | | |
| aag | ggc | ctc | aac | gtg | aag | cac | tac | aag | atc | cgc | aag | ctg | gac | agc | ggc | 498 |
| Lys | Gly | Leu | Asn | Val | Lys | His | Tyr | Lys | Ile | Arg | Lys | Leu | Asp | Ser | Gly | |
| | 125 | | | | | 130 | | | | | 135 | | | | | |
| ggc | ttc | tac | atc | acc | tcc | cgc | acc | cag | ttc | aac | agc | ctg | cag | cag | ctg | 546 |
| Gly | Phe | Tyr | Ile | Thr | Ser | Arg | Thr | Gln | Phe | Asn | Ser | Leu | Gln | Gln | Leu | |
| 140 | | | | | 145 | | | | | 150 | | | | | | |
| gtg | gcc | tac | tac | tcc | aaa | cac | gcc | gat | ggc | ctg | tgc | cac | cgc | ctc | acc | 594 |
| Val | Ala | Tyr | Tyr | Ser | Lys | His | Ala | Asp | Gly | Leu | Cys | His | Arg | Leu | Thr | |
| | 155 | | | | | 160 | | | | | 165 | | | | | |
| acc | gtg | tgc | ccc | acg | tcc | aag | ccg | cag | act | cag | ggc | ctg | gcc | aag | gat | 642 |
| Thr | Val | Cys | Pro | Thr | Ser | Lys | Pro | Gln | Thr | Gln | Gly | Leu | Ala | Lys | Asp | |
| 170 | | | | 175 | | | | | 180 | | | | | 185 | | |
| gcc | tgg | gag | atc | cct | cgg | gag | tcg | ctg | cgg | ctg | gag | gtc | aag | ctg | ggc | 690 |
| Ala | Trp | Glu | Ile | Pro | Arg | Glu | Ser | Leu | Arg | Leu | Glu | Val | Lys | Leu | Gly | |
| | | | 190 | | | | | 195 | | | | | 200 | | | |
| cag | ggc | tgc | ttt | ggc | gag | gtg | tgg | atg | ggg | acc | tgg | aac | ggt | acc | acc | 738 |
| Gln | Gly | Cys | Phe | Gly | Glu | Val | Trp | Met | Gly | Thr | Trp | Asn | Gly | Thr | Thr | |
| | | 205 | | | | | 210 | | | | | 215 | | | | |
| agg | gtg | gcc | atc | aaa | acc | ctg | aag | cct | ggc | acg | atg | tct | cca | gag | gcc | 786 |
| Arg | Val | Ala | Ile | Lys | Thr | Leu | Lys | Pro | Gly | Thr | Met | Ser | Pro | Glu | Ala | |
| | | 220 | | | | | 225 | | | | | 230 | | | | |
| ttc | ctg | cag | gag | gcc | cag | gtc | atg | aag | aag | ctg | agg | cat | gag | aag | ctg | 834 |
| Phe | Leu | Gln | Glu | Ala | Gln | Val | Met | Lys | Lys | Leu | Arg | His | Glu | Lys | Leu | |
| | 235 | | | | | 240 | | | | | 245 | | | | | |
| gtg | cag | ttg | tat | gct | gtg | gtt | tca | gag | gag | ccc | att | tac | atc | gtc | acg | 882 |
| Val | Gln | Leu | Tyr | Ala | Val | Val | Ser | Glu | Glu | Pro | Ile | Tyr | Ile | Val | Thr | |
| 250 | | | | | 255 | | | | | 260 | | | | | 265 | |
| gag | tac | atg | agc | aag | ggg | agt | ttg | ctg | gac | ttt | ctc | aag | ggg | gag | aca | 930 |
| Glu | Tyr | Met | Ser | Lys | Gly | Ser | Leu | Leu | Asp | Phe | Leu | Lys | Gly | Glu | Thr | |
| | | | 270 | | | | | 275 | | | | | 280 | | | |
| ggc | aag | tac | ctg | cgg | ctg | cct | cag | ctg | gtg | gac | atg | gct | gct | cag | atc | 978 |
| Gly | Lys | Tyr | Leu | Arg | Leu | Pro | Gln | Leu | Val | Asp | Met | Ala | Ala | Gln | Ile | |
| | | 285 | | | | | 290 | | | | | 295 | | | | |
| gcc | tca | ggc | atg | gcg | tac | gtg | gag | cgg | atg | aac | tac | gtc | cac | cgg | gac | 1026 |
| Ala | Ser | Gly | Met | Ala | Tyr | Val | Glu | Arg | Met | Asn | Tyr | Val | His | Arg | Asp | |
| | | 300 | | | | | 305 | | | | | 310 | | | | |
| ctt | cgt | gca | gcc | aac | atc | ctg | gtg | gga | gag | aac | ctg | gtg | tgc | aaa | gtg | 1074 |
| Leu | Arg | Ala | Ala | Asn | Ile | Leu | Val | Gly | Glu | Asn | Leu | Val | Cys | Lys | Val | |
| | 315 | | | | | 320 | | | | | 325 | | | | | |
| gcc | gac | ttt | ggg | ctg | gct | cgg | ctc | att | gaa | gac | aat | gag | tac | acg | gcg | 1122 |
| Ala | Asp | Phe | Gly | Leu | Ala | Arg | Leu | Ile | Glu | Asp | Asn | Glu | Tyr | Thr | Ala | |
| 330 | | | | | 335 | | | | | 340 | | | | | 345 | |
| cgg | caa | ggt | gcc | aaa | ttc | ccc | atc | aag | tgg | acg | gct | cca | gaa | gct | gcc | 1170 |
| Arg | Gln | Gly | Ala | Lys | Phe | Pro | Ile | Lys | Trp | Thr | Ala | Pro | Glu | Ala | Ala | |
| | | | | 350 | | | | | 355 | | | | | 360 | | |
| ctc | tat | ggc | cgc | ttc | acc | atc | aag | tcg | gac | gtg | tgg | tcc | ttc | ggg | atc | 1218 |
| Leu | Tyr | Gly | Arg | Phe | Thr | Ile | Lys | Ser | Asp | Val | Trp | Ser | Phe | Gly | Ile | |
| | | 365 | | | | | 370 | | | | | 375 | | | | |
| ctg | ctg | act | gag | ctc | acc | aca | aag | gga | cgg | gtg | ccc | tac | cct | ggg | atg | 1266 |
| Leu | Leu | Thr | Glu | Leu | Thr | Thr | Lys | Gly | Arg | Val | Pro | Tyr | Pro | Gly | Met | |
| | | | 380 | | | | | 385 | | | | | 390 | | | |
| gtg | aac | cgc | gag | gtg | ctg | gac | cag | gtg | gag | cgg | ggc | tac | cgg | atg | ccc | 1314 |
| Val | Asn | Arg | Glu | Val | Leu | Asp | Gln | Val | Glu | Arg | Gly | Tyr | Arg | Met | Pro | |
| | 395 | | | | | 400 | | | | | 405 | | | | | |

```
tgc ccg ccg gag tgt ccc gag tcc ctg cac gac ctc atg tgc cag tgc       1362
Cys Pro Pro Glu Cys Pro Glu Ser Leu His Asp Leu Met Cys Gln Cys
410             415                 420                 425 tgg cgg aag gag cct gag gag cgg ccc acc ttc gag tac ctg cag gcc       1410
Trp Arg Lys Glu Pro Glu Glu Arg Pro Thr Phe Glu Tyr Leu Gln Ala
            430                 435                 440 ttc ctg gag gac tac ttc acg tcc acc gag ccc cag tac cag ccc ggg       1458
Phe Leu Glu Asp Tyr Phe Thr Ser Thr Glu Pro Gln Tyr Gln Pro Gly
        445                 450                 455 gag aac ctc taggtcgacg aaggagatat atcc                                 1491
Glu Asn Leu
        460

<210> SEQ ID NO 111
<211> LENGTH: 460
<212> TYPE: PRT
<213> ORGANISM: Artificial Sequence
<220> FEATURE:
<223> OTHER INFORMATION: Description of Artificial Sequence: Synthetic
      Plasmid

<400> SEQUENCE: 111

Met Gly His His His His His His Met Val Thr Thr Phe Val Ala Leu
1               5                   10                  15

Tyr Asp Tyr Glu Ser Arg Thr Glu Thr Asp Leu Ser Phe Lys Lys Gly
            20                  25                  30

Glu Arg Leu Gln Ile Val Asn Asn Thr Glu Gly Asp Trp Trp Leu Ala
        35                  40                  45

His Ser Leu Ser Thr Gly Gln Thr Gly Tyr Ile Pro Ser Asn Tyr Val
    50                  55                  60

Ala Pro Ser Asp Ser Ile Gln Ala Glu Glu Trp Tyr Phe Gly Lys Ile
65                  70                  75                  80

Thr Arg Arg Glu Ser Glu Arg Leu Leu Leu Asn Ala Glu Asn Pro Arg
                85                  90                  95

Gly Thr Phe Leu Val Arg Glu Ser Glu Thr Thr Lys Gly Ala Tyr Cys
            100                 105                 110

Leu Ser Val Ser Asp Phe Asp Asn Ala Lys Gly Leu Asn Val Lys His
        115                 120                 125

Tyr Lys Ile Arg Lys Leu Asp Ser Gly Gly Phe Tyr Ile Thr Ser Arg
    130                 135                 140

Thr Gln Phe Asn Ser Leu Gln Gln Leu Val Ala Tyr Tyr Ser Lys His
145                 150                 155                 160

Ala Asp Gly Leu Cys His Arg Leu Thr Thr Val Cys Pro Thr Ser Lys
                165                 170                 175

Pro Gln Thr Gln Gly Leu Ala Lys Asp Ala Trp Glu Ile Pro Arg Glu
            180                 185                 190

Ser Leu Arg Leu Glu Val Lys Leu Gly Gln Gly Cys Phe Gly Glu Val
        195                 200                 205

Trp Met Gly Thr Trp Asn Gly Thr Thr Arg Val Ala Ile Lys Thr Leu
    210                 215                 220

Lys Pro Gly Thr Met Ser Pro Glu Ala Phe Leu Gln Glu Ala Gln Val
225                 230                 235                 240

Met Lys Lys Leu Arg His Glu Lys Leu Val Gln Leu Tyr Ala Val Val
                245                 250                 255

Ser Glu Glu Pro Ile Tyr Ile Val Thr Glu Tyr Met Ser Lys Gly Ser
            260                 265                 270

Leu Leu Asp Phe Leu Lys Gly Glu Thr Gly Lys Tyr Leu Arg Leu Pro
```

```
               275                 280                 285
Gln Leu Val Asp Met Ala Ala Gln Ile Ala Ser Gly Met Ala Tyr Val
        290                 295                 300
Glu Arg Met Asn Tyr Val His Arg Asp Leu Arg Ala Ala Asn Ile Leu
305                 310                 315                 320
Val Gly Glu Asn Leu Val Cys Lys Val Ala Asp Phe Gly Leu Ala Arg
                325                 330                 335
Leu Ile Glu Asp Asn Glu Tyr Thr Ala Arg Gln Gly Ala Lys Phe Pro
            340                 345                 350
Ile Lys Trp Thr Ala Pro Glu Ala Ala Leu Tyr Gly Arg Phe Thr Ile
        355                 360                 365
Lys Ser Asp Val Trp Ser Phe Gly Ile Leu Leu Thr Glu Leu Thr Thr
    370                 375                 380
Lys Gly Arg Val Pro Tyr Pro Gly Met Val Asn Arg Glu Val Leu Asp
385                 390                 395                 400
Gln Val Glu Arg Gly Tyr Arg Met Pro Cys Pro Pro Glu Cys Pro Glu
                405                 410                 415
Ser Leu His Asp Leu Met Cys Gln Cys Trp Arg Lys Glu Pro Glu Glu
            420                 425                 430
Arg Pro Thr Phe Glu Tyr Leu Gln Ala Phe Leu Glu Asp Tyr Phe Thr
        435                 440                 445
Ser Thr Glu Pro Gln Tyr Gln Pro Gly Glu Asn Leu
    450                 455                 460

<210> SEQ ID NO 112
<211> LENGTH: 39
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 112
agagggatcc gccaccatgg acaagaagct cttcctgaa                          39

<210> SEQ ID NO 113
<211> LENGTH: 47
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 113
acgaattcta gtggtggtgg tggtggtggt gcccttccac cttgctg                 47

<210> SEQ ID NO 114
<211> LENGTH: 1014
<212> TYPE: DNA
<213> ORGANISM: Artificial Sequence
<220> FEATURE:
<223> OTHER INFORMATION: Description of Artificial Sequence: Synthetic
      Plasmid
<220> FEATURE:
<221> NAME/KEY: CDS
<222> LOCATION: (143)..(1006)

<400> SEQUENCE: 114
agatcatgga gataattaaa atgataacca tctcgcaaat aaataagtat tttactgttt    60
tcgtaacagt tttgtaataa aaaaacctat aaatattccg gattattcat accgtcccac   120
catcgggcgc ggatccgcca cc atg gac aag aag ctc ttc ctg aag cgc gat   172
```

```
                Met Asp Lys Lys Leu Phe Leu Lys Arg Asp
                 1               5                   10 aac ctc ctc ata gct gac att gaa ctt ggc tgc ggc aac ttt ggc tca         220
Asn Leu Leu Ile Ala Asp Ile Glu Leu Gly Cys Gly Asn Phe Gly Ser
             15                  20                  25 gtg cgc cag ggc gtg tac cgc atg cgc aag aag cag atc gac gtg gcc        268
Val Arg Gln Gly Val Tyr Arg Met Arg Lys Lys Gln Ile Asp Val Ala
             30                  35                  40 atc aag gtg ctg aag cag ggc acg gag aag gca gac acg gaa gag atg        316
Ile Lys Val Leu Lys Gln Gly Thr Glu Lys Ala Asp Thr Glu Glu Met
             45                  50                  55 atg cgc gag gcg cag atc atg cac cag ctg gac aac ccc tac atc gtg        364
Met Arg Glu Ala Gln Ile Met His Gln Leu Asp Asn Pro Tyr Ile Val
 60              65                  70 cgg ctc att ggc gtc tgc cag gcc gag gcc ctc atg ctg gtc atg gag        412
Arg Leu Ile Gly Val Cys Gln Ala Glu Ala Leu Met Leu Val Met Glu
 75              80                  85                  90 atg gct ggg ggg ccg ctg cac aag ttc ctg gtc ggc aag agg gag            460
Met Ala Gly Gly Gly Pro Leu His Lys Phe Leu Val Gly Lys Arg Glu
                 95                 100                 105 gag atc cct gtg agc aat gtg gcc gag ctg ctg cac cag gtg tcc atg        508
Glu Ile Pro Val Ser Asn Val Ala Glu Leu Leu His Gln Val Ser Met
                110                 115                 120 ggg atg aag tac ctg gag gag aag aac ttt gtg cac cgt gac ctg gcg        556
Gly Met Lys Tyr Leu Glu Glu Lys Asn Phe Val His Arg Asp Leu Ala
            125                 130                 135 gcc cgc aac gtc ctg ctg gtt aac cgg cac tac gcc aag atc agc gac        604
Ala Arg Asn Val Leu Leu Val Asn Arg His Tyr Ala Lys Ile Ser Asp
140                 145                 150 ttt ggc ctc tcc aaa gca ctg ggt gcc gac gac agc tac tac act gcc        652
Phe Gly Leu Ser Lys Ala Leu Gly Ala Asp Asp Ser Tyr Tyr Thr Ala
155                 160                 165                 170 cgc tca gca ggg aag tgg ccg ctc aag tgg tac gca ccc gaa tgc atc        700
Arg Ser Ala Gly Lys Trp Pro Leu Lys Trp Tyr Ala Pro Glu Cys Ile
                175                 180                 185 aac ttc cgc aag ttc tcc agc cgc agc gat gtc tgg agc tat ggg gtc        748
Asn Phe Arg Lys Phe Ser Ser Arg Ser Asp Val Trp Ser Tyr Gly Val
                190                 195                 200 acc atg tgg gag gcc ttg tcc tac ggc cag aag ccc tac aag aag atg        796
Thr Met Trp Glu Ala Leu Ser Tyr Gly Gln Lys Pro Tyr Lys Lys Met
            205                 210                 215 aaa ggg ccg gag gtc atg gcc ttc atc gag cag ggc aag cgg atg gaa        844
Lys Gly Pro Glu Val Met Ala Phe Ile Glu Gln Gly Lys Arg Met Glu
220                 225                 230 tgc cca cca gag tgt cca ccc gaa ctg tac gca ctc atg agt gac tgc        892
Cys Pro Pro Glu Cys Pro Pro Glu Leu Tyr Ala Leu Met Ser Asp Cys
235                 240                 245                 250 tgg atc tac aag tgg gag gat cgc ccc gac ttc ctg acc gtg gag cag        940
Trp Ile Tyr Lys Trp Glu Asp Arg Pro Asp Phe Leu Thr Val Glu Gln
                255                 260                 265 cgc atg cga gcc tgt tac tac agc ctg gcc agc aag gtg gaa ggg cac        988
Arg Met Arg Ala Cys Tyr Tyr Ser Leu Ala Ser Lys Val Glu Gly His
                270                 275                 280 cac cac cac cac cac cac tagaattc                                      1014
His His His His His His
            285

<210> SEQ ID NO 115
<211> LENGTH: 288
<212> TYPE: PRT
<213> ORGANISM: Artificial Sequence
```

```
<220> FEATURE:
<223> OTHER INFORMATION: Description of Artificial Sequence: Synthetic
      Plasmid

<400> SEQUENCE: 115

Met Asp Lys Lys Leu Phe Leu Lys Arg Asp Asn Leu Leu Ile Ala Asp
  1               5                  10                  15

Ile Glu Leu Gly Cys Gly Asn Phe Gly Ser Val Arg Gln Gly Val Tyr
                 20                  25                  30

Arg Met Arg Lys Lys Gln Ile Asp Val Ala Ile Lys Val Leu Lys Gln
             35                  40                  45

Gly Thr Glu Lys Ala Asp Thr Glu Glu Met Met Arg Glu Ala Gln Ile
 50                  55                  60

Met His Gln Leu Asp Asn Pro Tyr Ile Val Arg Leu Ile Gly Val Cys
 65                  70                  75                  80

Gln Ala Glu Ala Leu Met Leu Val Met Glu Met Ala Gly Gly Pro
                 85                  90                  95

Leu His Lys Phe Leu Val Gly Lys Arg Glu Glu Ile Pro Val Ser Asn
                100                 105                 110

Val Ala Glu Leu Leu His Gln Val Ser Met Gly Met Lys Tyr Leu Glu
                115                 120                 125

Glu Lys Asn Phe Val His Arg Asp Leu Ala Ala Arg Asn Val Leu Leu
            130                 135                 140

Val Asn Arg His Tyr Ala Lys Ile Ser Asp Phe Gly Leu Ser Lys Ala
145                 150                 155                 160

Leu Gly Ala Asp Asp Ser Tyr Tyr Thr Ala Arg Ser Ala Gly Lys Trp
                165                 170                 175

Pro Leu Lys Trp Tyr Ala Pro Glu Cys Ile Asn Phe Arg Lys Phe Ser
                180                 185                 190

Ser Arg Ser Asp Val Trp Ser Tyr Gly Val Thr Met Trp Glu Ala Leu
            195                 200                 205

Ser Tyr Gly Gln Lys Pro Tyr Lys Lys Met Lys Gly Pro Glu Val Met
            210                 215                 220

Ala Phe Ile Glu Gln Gly Lys Arg Met Glu Cys Pro Pro Glu Cys Pro
225                 230                 235                 240

Pro Glu Leu Tyr Ala Leu Met Ser Asp Cys Trp Ile Tyr Lys Trp Glu
                245                 250                 255

Asp Arg Pro Asp Phe Leu Thr Val Glu Gln Arg Met Arg Ala Cys Tyr
                260                 265                 270

Tyr Ser Leu Ala Ser Lys Val Glu Gly His His His His His His
                275                 280                 285

<210> SEQ ID NO 116
<211> LENGTH: 32
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 116
gttgtgacat atgttccaga tcccagagtt tg                                 32

<210> SEQ ID NO 117
<211> LENGTH: 31
<212> TYPE: DNA
<213> ORGANISM: Artificial Sequence
<220> FEATURE:
<223> OTHER INFORMATION: Description of Artificial Sequence: Synthetic
```

```
                Primer

<400> SEQUENCE: 117
gttgtgagtc gactcactgg gagggggcgg a                                      31

<210> SEQ ID NO 118
<211> LENGTH: 795
<212> TYPE: DNA
<213> ORGANISM: Artificial Sequence
<220> FEATURE:
<223> OTHER INFORMATION: Description of Artificial Sequence: Synthetic
      Plasmid
<220> FEATURE:
<221> NAME/KEY: CDS
<222> LOCATION: (85)..(654)

<400> SEQUENCE: 118
tacgactcac tatagggga ttgtgagcgg ataacaattc ccctctagaa ataattttgt         60
ttaactttaa gaaggagata tacc atg gct ggt tgc ctg aac gac atc ttc         111
                              Met Ala Gly Cys Leu Asn Asp Ile Phe
                                1               5 gaa gct cag aaa atc gaa tgg cac cat cac cat cac cat atg ttc cag         159
Glu Ala Gln Lys Ile Glu Trp His His His His His His Met Phe Gln
 10              15                  20                  25 atc cca gag ttt gag ccg agt gag cag gaa gac tcc agc tct gca gag         207
Ile Pro Glu Phe Glu Pro Ser Glu Gln Glu Asp Ser Ser Ser Ala Glu
             30                  35                  40 agg ggc ctg ggc ccc agc ccc gca ggg gac ggg ccc tca ggc tcc ggc         255
Arg Gly Leu Gly Pro Ser Pro Ala Gly Asp Gly Pro Ser Gly Ser Gly
         45                  50                  55 aag cat cat cgc cag gcc cca ggc ctc ctg tgg gac gcc agt cac cag         303
Lys His His Arg Gln Ala Pro Gly Leu Leu Trp Asp Ala Ser His Gln
     60                  65                  70 cag gag cag cca acc agc agc agc cat cat gga ggc gct ggg gct gtg         351
Gln Glu Gln Pro Thr Ser Ser Ser His His Gly Gly Ala Gly Ala Val
 75                  80                  85 gag atc cgg agt cgc cac agc tcc tac ccc gcg ggg acg gag gac gac         399
Glu Ile Arg Ser Arg His Ser Ser Tyr Pro Ala Gly Thr Glu Asp Asp
             90                  95                 100                 105 gaa ggg atg ggg gag gag ccc agc ccc ttt cgg ggc cgc tcg cgc tcg         447
Glu Gly Met Gly Glu Glu Pro Ser Pro Phe Arg Gly Arg Ser Arg Ser
                110                 115                 120 gcg ccc ccc aac ctc tgg gca gca cag cgc tat ggc cgc gag ctc cgg         495
Ala Pro Pro Asn Leu Trp Ala Ala Gln Arg Tyr Gly Arg Glu Leu Arg
            125                 130                 135 agg atg agt gac gag ttt gtg gac tcc ttt aag aag gga ctt cct cgc         543
Arg Met Ser Asp Glu Phe Val Asp Ser Phe Lys Lys Gly Leu Pro Arg
        140                 145                 150 ccg aag agc gcg ggc aca gca acg cag atg cgg caa agc tcc agc tgg         591
Pro Lys Ser Ala Gly Thr Ala Thr Gln Met Arg Gln Ser Ser Ser Trp
    155                 160                 165 acg cga gtc ttc cag tcc tgg tgg gat cgg aac ttg ggc agg gga agc         639
Thr Arg Val Phe Gln Ser Trp Trp Asp Arg Asn Leu Gly Arg Gly Ser
170                 175                 180                 185 tcc gcc ccc tcc cag tgagtcgacc accaccacca ccaccactga gatccggctg         694
Ser Ala Pro Ser Gln
                190 gccctactgg ccgaaaggaa ttcgaggcca gcagggccac cgctgagcaa taactagcat       754 aaccccttgg ggcctctaaa cgggtcttga ggggttttt g                            795

<210> SEQ ID NO 119
```

-continued

```
<211> LENGTH: 190
<212> TYPE: PRT
<213> ORGANISM: Artificial Sequence
<220> FEATURE:
<223> OTHER INFORMATION: Description of Artificial Sequence: Synthetic
      Plasmid

<400> SEQUENCE: 119
```

Met Ala Gly Cys Leu Asn Asp Ile Phe Glu Ala Gln Lys Ile Glu Trp
 1               5                  10                  15

His His His His His His Met Phe Gln Ile Pro Glu Phe Glu Pro Ser
             20                  25                  30

Glu Gln Glu Asp Ser Ser Ala Glu Arg Gly Leu Gly Pro Ser Pro
         35                  40                  45

Ala Gly Asp Gly Pro Ser Gly Ser Gly Lys His His Arg Gln Ala Pro
 50                  55                  60

Gly Leu Leu Trp Asp Ala Ser His Gln Gln Glu Gln Pro Thr Ser Ser
 65                  70                  75                  80

Ser His His Gly Gly Ala Gly Ala Val Glu Ile Arg Ser Arg His Ser
                 85                  90                  95

Ser Tyr Pro Ala Gly Thr Glu Asp Asp Glu Met Gly Glu Glu Pro
            100                 105                 110

Ser Pro Phe Arg Gly Arg Ser Arg Ser Ala Pro Pro Asn Leu Trp Ala
        115                 120                 125

Ala Gln Arg Tyr Gly Arg Glu Leu Arg Arg Met Ser Asp Glu Phe Val
130                 135                 140

Asp Ser Phe Lys Lys Gly Leu Pro Arg Pro Lys Ser Ala Gly Thr Ala
145                 150                 155                 160

Thr Gln Met Arg Gln Ser Ser Ser Trp Thr Arg Val Phe Gln Ser Trp
                165                 170                 175

Trp Asp Arg Asn Leu Gly Arg Gly Ser Ser Ala Pro Ser Gln
            180                 185                 190

```
<210> SEQ ID NO 120
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 120
cgggtcccat atgcccaaga agaagccgac                                        30

<210> SEQ ID NO 121
<211> LENGTH: 33
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 121
gttcgttgtc gacgacgcca gcagcatggg ttg                                    33

<210> SEQ ID NO 122
<211> LENGTH: 33
<212> TYPE: DNA
<213> ORGANISM: Artificial Sequence
<220> FEATURE:
<223> OTHER INFORMATION: Description of Artificial Sequence: Synthetic
      Primer
```

-continued

<400> SEQUENCE: 122
ctaattcatc tggagatcgc gcccgcaatc cgg                                33

<210> SEQ ID NO 123
<211> LENGTH: 33
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 123
ccggattgcg ggcgcgatct ccagatgaat tag                                33

<210> SEQ ID NO 124
<211> LENGTH: 1916
<212> TYPE: DNA
<213> ORGANISM: Artificial Sequence
<220> FEATURE:
<223> OTHER INFORMATION: Description of Artificial Sequence: Synthetic
      Plasmid
<220> FEATURE:
<221> NAME/KEY: CDS
<222> LOCATION: (1)..(1908)

<400> SEQUENCE: 124

```
atg tcc cct ata cta ggt tat tgg aaa att aag ggc ctt gtg caa ccc      48
Met Ser Pro Ile Leu Gly Tyr Trp Lys Ile Lys Gly Leu Val Gln Pro
  1               5                  10                  15 act cga ctt ctt ttg gaa tat ctt gaa gaa aaa tat gaa gag cat ttg      96
Thr Arg Leu Leu Leu Glu Tyr Leu Glu Glu Lys Tyr Glu Glu His Leu
             20                  25                  30 tat gag cgc gat gaa ggt gat aaa tgg cga aac aaa aag ttt gaa ttg     144
Tyr Glu Arg Asp Glu Gly Asp Lys Trp Arg Asn Lys Lys Phe Glu Leu
         35                  40                  45 ggt ttg gag ttt ccc aat ctt cct tat tat att gat ggt gat gtt aaa     192
Gly Leu Glu Phe Pro Asn Leu Pro Tyr Tyr Ile Asp Gly Asp Val Lys
     50                  55                  60 tta aca cag tct atg gcc atc ata cgt tat ata gct gac aag cac aac     240
Leu Thr Gln Ser Met Ala Ile Ile Arg Tyr Ile Ala Asp Lys His Asn
 65                  70                  75                  80 atg ttg ggt ggt tgt cca aaa gag cgt gca gag att tca atg ctt gaa     288
Met Leu Gly Gly Cys Pro Lys Glu Arg Ala Glu Ile Ser Met Leu Glu
                 85                  90                  95 gga gcg gtt ttg gat att aga tac ggt gtt tcg aga att gca tat agt     336
Gly Ala Val Leu Asp Ile Arg Tyr Gly Val Ser Arg Ile Ala Tyr Ser
            100                 105                 110 aaa gac ttt gaa act ctc aaa gtt gat ttt ctt agc aag cta cct gaa     384
Lys Asp Phe Glu Thr Leu Lys Val Asp Phe Leu Ser Lys Leu Pro Glu
        115                 120                 125 atg ctg aaa atg ttc gaa gat cgt tta tgt cat aaa aca tat tta aat     432
Met Leu Lys Met Phe Glu Asp Arg Leu Cys His Lys Thr Tyr Leu Asn
    130                 135                 140 ggt gat cat gta acc cat cct gac ttc atg ttg tat gac gct ctt gat     480
Gly Asp His Val Thr His Pro Asp Phe Met Leu Tyr Asp Ala Leu Asp
145                 150                 155                 160 gtt gtt tta tac atg gac cca atg tgc ctg gat gcg ttc cca aaa tta     528
Val Val Leu Tyr Met Asp Pro Met Cys Leu Asp Ala Phe Pro Lys Leu
                165                 170                 175 gtt tgt ttt aaa aaa cgt att gaa gct atc cca caa att gat aag tac     576
Val Cys Phe Lys Lys Arg Ile Glu Ala Ile Pro Gln Ile Asp Lys Tyr
            180                 185                 190 ttg aaa tcc agc aag tat ata gca tgg cct ttg cag ggc tgg caa gcc     624
```

```
Leu Lys Ser Ser Lys Tyr Ile Ala Trp Pro Leu Gln Gly Trp Gln Ala
        195                 200                 205 acg ttt ggt ggt ggc gac cat cct cca aaa tcg gat ctg gtt ccg cgt    672
Thr Phe Gly Gly Gly Asp His Pro Pro Lys Ser Asp Leu Val Pro Arg
    210                 215                 220 gga tct cat atg ccc aag aag aag ccg acg ccc atc cag ctg aac ccg    720
Gly Ser His Met Pro Lys Lys Lys Pro Thr Pro Ile Gln Leu Asn Pro
225             230                 235                 240 gcc ccc gac ggc tct gca gtt aac ggg acc agc tct gcg gag acc aac    768
Ala Pro Asp Gly Ser Ala Val Asn Gly Thr Ser Ser Ala Glu Thr Asn
                245                 250                 255 ttg gag gcc ttg cag aag aag ctg gag gag cta gag ctt gat gag cag    816
Leu Glu Ala Leu Gln Lys Lys Leu Glu Glu Leu Glu Leu Asp Glu Gln
            260                 265                 270 cag cga aag cgc ctt gag gcc ttt ctt acc cag aag cag aag gtg gga    864
Gln Arg Lys Arg Leu Glu Ala Phe Leu Thr Gln Lys Gln Lys Val Gly
        275                 280                 285 gaa ctg aag gat gac gac ttt gag aag atc agt gag ctg ggc gct ggc    912
Glu Leu Lys Asp Asp Asp Phe Glu Lys Ile Ser Glu Leu Gly Ala Gly
    290                 295                 300 aat ggc ggt gtg gtg ttc aag gtc tcc cac aag cct tct ggc ctg gtc    960
Asn Gly Gly Val Val Phe Lys Val Ser His Lys Pro Ser Gly Leu Val
305                 310                 315                 320 atg gcc aga gcg cta att cat ctg gag atc aaa ccc gca atc cgg aac    1008
Met Ala Arg Ala Leu Ile His Leu Glu Ile Lys Pro Ala Ile Arg Asn
                325                 330                 335 cag atc ata agg gag ctg cag gtt ctg cat gag tgc aac tct ccg tac    1056
Gln Ile Ile Arg Glu Leu Gln Val Leu His Glu Cys Asn Ser Pro Tyr
            340                 345                 350 atc gtg ggc ttc tat ggt gcg ttc tac agc gat ggc gag atc agt atc    1104
Ile Val Gly Phe Tyr Gly Ala Phe Tyr Ser Asp Gly Glu Ile Ser Ile
        355                 360                 365 tgc atg gag cac atg gat gga ggt tct ctg gat caa gtc ctg aag aaa    1152
Cys Met Glu His Met Asp Gly Gly Ser Leu Asp Gln Val Leu Lys Lys
    370                 375                 380 gct gga aga att cct gaa caa att tta gga aaa gtt agc att gct gta    1200
Ala Gly Arg Ile Pro Glu Gln Ile Leu Gly Lys Val Ser Ile Ala Val
385                 390                 395                 400 ata aaa ggc ctg aca tat ctg agg gag aag cac aag atc atg cac aga    1248
Ile Lys Gly Leu Thr Tyr Leu Arg Glu Lys His Lys Ile Met His Arg
                405                 410                 415 gat gtc aag ccc tcc aac atc cta gtc aac tcc cgt ggg gag atc aag    1296
Asp Val Lys Pro Ser Asn Ile Leu Val Asn Ser Arg Gly Glu Ile Lys
            420                 425                 430 ctc tgt gac ttt ggg gtc agc ggg cag ctc atc gac tcc atg gcc aac    1344
Leu Cys Asp Phe Gly Val Ser Gly Gln Leu Ile Asp Ser Met Ala Asn
        435                 440                 445 tcc ttc gtg ggc aca agg tcc tac atg tcg cca gaa aga ctc cag ggg    1392
Ser Phe Val Gly Thr Arg Ser Tyr Met Ser Pro Glu Arg Leu Gln Gly
    450                 455                 460 act cat tac tct gtg cag tca gac atc tgg agc atg gga ctg tct ctg    1440
Thr His Tyr Ser Val Gln Ser Asp Ile Trp Ser Met Gly Leu Ser Leu
465                 470                 475                 480 gta gag atg gcg gtt ggg agg tat ccc atc cct cct cca gat gcc aag    1488
Val Glu Met Ala Val Gly Arg Tyr Pro Ile Pro Pro Pro Asp Ala Lys
                485                 490                 495 gag ctg gag ctg atg ttt ggg tgc cag gtg gaa gga gat gcg gct gag    1536
Glu Leu Glu Leu Met Phe Gly Cys Gln Val Glu Gly Asp Ala Ala Glu
            500                 505                 510 acc cca ccc agg cca agg acc ccc ggg agg ccc ctt agc tca tac gga    1584
```

```
Thr Pro Pro Arg Pro Arg Thr Pro Gly Arg Pro Leu Ser Ser Tyr Gly
        515                 520                 525 atg gac agc cga cct ccc atg gca att ttt gag ttg ttg gat tac ata    1632
Met Asp Ser Arg Pro Pro Met Ala Ile Phe Glu Leu Leu Asp Tyr Ile
530                 535                 540 gtc aac gag cct cct cca aaa ctg ccc agt gga gtg ttc agt ctg gaa    1680
Val Asn Glu Pro Pro Pro Lys Leu Pro Ser Gly Val Phe Ser Leu Glu
545                 550                 555                 560 ttt caa gat ttt gtg aat aaa tgc tta ata aaa aac ccc gca gag aga    1728
Phe Gln Asp Phe Val Asn Lys Cys Leu Ile Lys Asn Pro Ala Glu Arg
                565                 570                 575 gca gat ttg aag caa ctc atg gtt cat gct ttt atc aag aga tct gat    1776
Ala Asp Leu Lys Gln Leu Met Val His Ala Phe Ile Lys Arg Ser Asp
            580                 585                 590 gct gag gaa gtg gat ttt gca ggt tgg ctc tgc tcc acc atc ggc ctt    1824
Ala Glu Glu Val Asp Phe Ala Gly Trp Leu Cys Ser Thr Ile Gly Leu
        595                 600                 605 aac cag ccc agc aca cca acc cat gct gct ggc gtc gtc gac ctg aac    1872
Asn Gln Pro Ser Thr Pro Thr His Ala Ala Gly Val Val Asp Leu Asn
    610                 615                 620 gac atc ttc gaa gct cag aaa atc gaa tgg cac cgt tagaattc           1916
Asp Ile Phe Glu Ala Gln Lys Ile Glu Trp His Arg
625                 630                 635

<210> SEQ ID NO 125
<211> LENGTH: 636
<212> TYPE: PRT
<213> ORGANISM: Artificial Sequence
<220> FEATURE:
<223> OTHER INFORMATION: Description of Artificial Sequence: Synthetic
      Plasmid

<400> SEQUENCE: 125

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190
```

-continued

Leu Lys Ser Ser Lys Tyr Ile Ala Trp Pro Leu Gln Gly Trp Gln Ala
         195                 200                 205

Thr Phe Gly Gly Gly Asp His Pro Pro Lys Ser Asp Leu Val Pro Arg
    210                 215                 220

Gly Ser His Met Pro Lys Lys Pro Thr Pro Ile Gln Leu Asn Pro
225                 230                 235                 240

Ala Pro Asp Gly Ser Ala Val Asn Gly Thr Ser Ser Ala Glu Thr Asn
                245                 250                 255

Leu Glu Ala Leu Gln Lys Lys Leu Glu Glu Leu Glu Leu Asp Glu Gln
                260                 265                 270

Gln Arg Lys Arg Leu Glu Ala Phe Leu Thr Gln Lys Gln Lys Val Gly
        275                 280                 285

Glu Leu Lys Asp Asp Asp Phe Glu Lys Ile Ser Glu Leu Gly Ala Gly
    290                 295                 300

Asn Gly Gly Val Val Phe Lys Val Ser His Lys Pro Ser Gly Leu Val
305                 310                 315                 320

Met Ala Arg Ala Leu Ile His Leu Glu Ile Lys Pro Ala Ile Arg Asn
                325                 330                 335

Gln Ile Ile Arg Glu Leu Gln Val Leu His Glu Cys Asn Ser Pro Tyr
                340                 345                 350

Ile Val Gly Phe Tyr Gly Ala Phe Tyr Ser Asp Gly Glu Ile Ser Ile
                355                 360                 365

Cys Met Glu His Met Asp Gly Gly Ser Leu Asp Gln Val Leu Lys Lys
        370                 375                 380

Ala Gly Arg Ile Pro Glu Gln Ile Leu Gly Lys Val Ser Ile Ala Val
385                 390                 395                 400

Ile Lys Gly Leu Thr Tyr Leu Arg Glu Lys His Lys Ile Met His Arg
                405                 410                 415

Asp Val Lys Pro Ser Asn Ile Leu Val Asn Ser Arg Gly Glu Ile Lys
                420                 425                 430

Leu Cys Asp Phe Gly Val Ser Gly Gln Leu Ile Asp Ser Met Ala Asn
        435                 440                 445

Ser Phe Val Gly Thr Arg Ser Tyr Met Ser Pro Glu Arg Leu Gln Gly
    450                 455                 460

Thr His Tyr Ser Val Gln Ser Asp Ile Trp Ser Met Gly Leu Ser Leu
465                 470                 475                 480

Val Glu Met Ala Val Gly Arg Tyr Pro Ile Pro Pro Pro Asp Ala Lys
                485                 490                 495

Glu Leu Glu Leu Met Phe Gly Cys Gln Val Glu Gly Asp Ala Ala Glu
                500                 505                 510

Thr Pro Pro Arg Pro Arg Thr Pro Gly Arg Pro Leu Ser Ser Tyr Gly
        515                 520                 525

Met Asp Ser Arg Pro Pro Met Ala Ile Phe Glu Leu Leu Asp Tyr Ile
    530                 535                 540

Val Asn Glu Pro Pro Pro Lys Leu Pro Ser Gly Val Phe Ser Leu Glu
545                 550                 555                 560

Phe Gln Asp Phe Val Asn Lys Cys Leu Ile Lys Asn Pro Ala Glu Arg
                565                 570                 575

Ala Asp Leu Lys Gln Leu Met Val His Ala Phe Ile Lys Arg Ser Asp
                580                 585                 590

Ala Glu Glu Val Asp Phe Ala Gly Trp Leu Cys Ser Thr Ile Gly Leu
        595                 600                 605

```
Asn Gln Pro Ser Thr Pro Thr His Ala Ala Gly Val Val Asp Leu Asn
        610             615             620

Asp Ile Phe Glu Ala Gln Lys Ile Glu Trp His Arg
625                 630             635
```